US012480163B2

(12) United States Patent
Stegmaier

(10) Patent No.: US 12,480,163 B2
(45) Date of Patent: Nov. 25, 2025

(54) COMPOSITIONS AND METHODS FOR IDENTIFICATION ASSESSMENT, PREVENTION, AND TREATMENT OF EWING SARCOMA USING TP53 DEPENDENCY BIOMARKERS AND MODULATORS

(71) Applicant: Dana-Farber Cancer Institute, Inc., Boston, MA (US)

(72) Inventor: Kimberly Stegmaier, Jamaica Plain, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 839 days.

(21) Appl. No.: 17/260,824

(22) PCT Filed: Jul. 17, 2019

(86) PCT No.: PCT/US2019/042110

§ 371 (c)(1),
(2) Date: Jan. 15, 2021

(87) PCT Pub. No.: WO2020/018611

PCT Pub. Date: Jan. 23, 2020

(65) Prior Publication Data

US 2021/0324478 A1 Oct. 21, 2021

Related U.S. Application Data

(60) Provisional application No. 62/699,970, filed on Jul. 18, 2018.

(51) Int. Cl.

| | |
|---|---|
| ***C12Q 1/6886*** | (2018.01) |
| ***A61K 38/12*** | (2006.01) |
| ***A61K 45/06*** | (2006.01) |
| ***A61P 35/00*** | (2006.01) |
| ***G01N 33/50*** | (2006.01) |

(52) U.S. Cl.

CPC ............ *C12Q 1/6886* (2013.01); *A61K 38/12* (2013.01); *A61K 45/06* (2013.01); *A61P 35/00* (2018.01); *G01N 33/5011* (2013.01); *C12Q 2600/112* (2013.01); *C12Q 2600/158* (2013.01)

(58) Field of Classification Search

CPC ........ C12Q 1/6886; A61P 35/00; A61K 38/12
See application file for complete search history.

(56) References Cited

U.S. PATENT DOCUMENTS

| | | | | |
|---|---|---|---|---|
| 2004/0265931 A1* | 12/2004 | Gu | A61P 43/00 435/7.23 |
| 2015/0291611 A1* | 10/2015 | Gollner | A61P 35/00 548/410 |
| 2015/0320754 A1* | 11/2015 | Kutok | A61K 45/06 424/278.1 |
| 2016/0000764 A1* | 1/2016 | Weinstabl | A61P 43/00 548/410 |
| 2017/0174695 A1* | 6/2017 | Gollner | A61P 31/00 |
| 2017/0218457 A1 | 8/2017 | Zhu | |
| 2017/0348266 A1 | 12/2017 | Scott et al. | |
| 2020/0069818 A1* | 3/2020 | Jaskula-Ranga | A61K 35/761 |

FOREIGN PATENT DOCUMENTS

| | | | |
|---|---|---|---|
| WO | WO-2015/000945 A1 | 1/2015 | |
| WO | WO-2016/081897 A1 | 5/2016 | |
| WO | WO-2017/165617 A1 | 9/2017 | |
| WO | WO-2018009525 A1 * | 1/2018 | A61K 35/761 |
| WO | WO-2020/018611 A1 | 1/2020 | |

OTHER PUBLICATIONS

Sonnemann et al., 2011, Anticancer effects of the p53 activator nutlin-3 in Ewing's sarcoma cells, European Journal of Cancer 47:1432-1441.*

Neilsen et al., 2010, Targeting the p53 Pathway in Ewing Sarcoma, Sarcoma, 2011 (17 pages).*

Wachter et al., Apr. 2017, Mechanistic Validation of a Clinical Lead Stapled Peptide that Reactivates p53 by Dual HDM2 and HDMX Targeting, Oncogene, 36(15): 2184-2190.*

Stolte et al., 2018, Genome-scale CRISPR-Cas9 screen identifies druggable dependencies in TP53 wild-type Ewing sarcoma, J Exp Med, 215(8): 2137-2155.*

Schauer et al., 2020, Selective USP7 inhibition elicits cancer cell killing through a p53-dependent mechanism, Nature Scientific Reports, 10: 5324 (15 pages).*

Malapelle et al., 2017, USP7 inhibitors, downregulating CCDC6, sensitize lung neuroendocrine cancer cells to PARP-inhibitor drugs, Lung Cancer, 107: 41-49.*

Carra et al., 2017, Therapeutic inhibition of USP7-PTEN network in chronic lymphocytic leukemia: a strategy to overcome TP53 mutates/deleted clones, Oncotarget, 8(22): 35508-35522.*

Wang et al., 2017, The USP7 Inhibitor P5091 Induces Cell Death in Ovarian Cancers with Different P53 Status, Cellular Physiology and Biochemistry, 43: 1755-1766.*

Tavana et al., 2018, Targeting HAUSP in both p53 wildtype and p53-mutant tumors, Cell Cycle, 17(7): 823-828.*

Chen et al., 2016, Wip1 inhibitor GSK2830371 inhibits neuroblastoma growth by inducing Chk2/p53-mediated apoptosis, Scientific Reports, 6: 38011 (12 pages).*

Richter et al., 2015, WIP1 Phosphatase as a Potential Therapeutic Target in Neuroblastoma, PLoS One, 10(2): e0115635 (15 pages).*

Kojima et al., 2016, The pathophysiological significance of PPM1D and therapeutic targeting of PPM1D-mediated signaling by GSK2830371 in mantle cell lymphoma, Oncotarget, 7(43): 69625-69637.*

Pechackova et al., 2016, Inhibition of WIP1 phosphatase sensitizes breast cancer cells to genotoxic stress and to MDM2 antagonist nutlin-3, Oncotarget, 7(12): 14458-14475.*

(Continued)

*Primary Examiner* — Amber D Steele
(74) *Attorney, Agent, or Firm* — Foley Hoag LLP; DeAnn F. Smith

(57) ABSTRACT

The present invention is based, in part, on the identification of TP53 dependency biomarkers, including MDM2, MDM4, USP7, and Wipl/PPM1D, as well as modulators and methods of use thereof, for identifying, assessing, preventing, and treating Ewing sarcoma.

18 Claims, 24 Drawing Sheets

Specification includes a Sequence Listing.

(56) References Cited

OTHER PUBLICATIONS

Sriraman et al., 2016, Cooperation of Nutlin-3a and a Wip1 inhibitor to induce p53 activity, Oncotarget, 7(22): 31623-31638.*
Wu et al., 2018, Targeting negative regulation of p53 by MDM2 and WIP1 as a therapeutic strategy in cutaneous melanoma, British Journal of Cancer, 118: 495-508.*
Chang et al., 2013, Stapled alpha-helical peptide drug development: A potent dual inhibitor of MDM2 and MDMX for p53-dependent cancer therapy, PNAS, E3445-E3454.*
An et al., 2017, USP7 inhibitorP5091 inhibits Wnt signaling and colorectal tumor growth, Biochemical Pharmacology, 131: 29-39.*
Esfandiari et al., 2016, Chemical inhibition of wild-type p53 induced phosphatase 1 (WIP1/PPM1D) by GSK2830371 potentiates the sensitivity to MDM2 inhibitors in a p53-dependent manner, Mol Cancer Ther, 15(3): 379-391.*
Crane et al., "Nutlin-3a: A Potential Therapeutic Opportunity for TP53 Wild-Type Ovarian Carcinomas," PLoS One 10(8):1-13 (2015).
International Search Report and Written Opinion for International Application No. PCT/US2019/042110 dated Sep. 30, 2019.

* cited by examiner

FIG. 1A
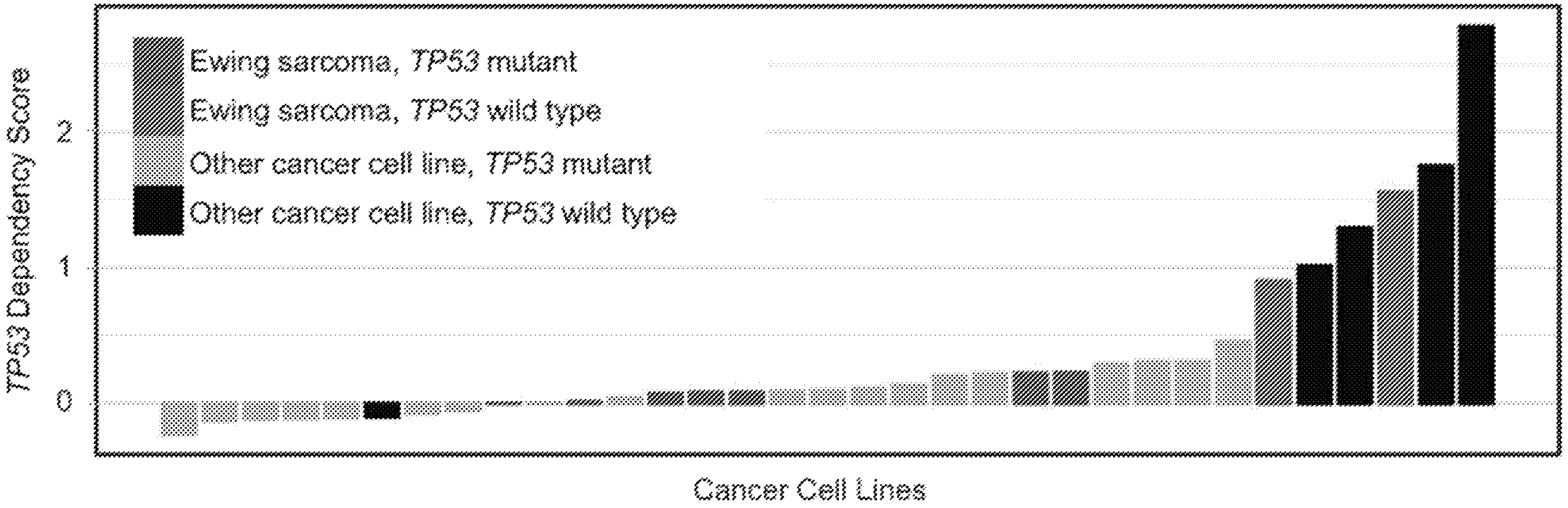
FIG. 1B
| Gene | Pearson Correlation to TP53 Dependency Score | Known Interaction with p53 |
|---|---|---|
| *MDM4* | -0.79 | Yes |
| *PPM1D* | -0.76 | Yes |
| *MDM2* | -0.66 | Yes |
| *PPM1G* | -0.65 | Yes |
| *LIG4* | -0.61 | Yes |
| *PUM3* | -0.59 | Unknown |
| *USP7* | -0.55 | Yes |
| *UBE2D3* | -0.54 | Yes |
FIG. 1C
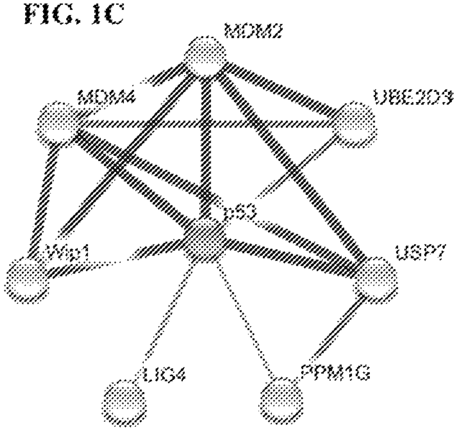

FIG. 11

| CELL LINE | p53 STATUS | CCLE | CCLE |
|---|---|---|---|
| A375_SKIN | mut | Intron | chr17 7578555 T>A |
| A673_BONE | mut | | |
| BXPC3_PANCREAS | mut | Missense Mutation | chr17 7578190 T>C p.Y220C |
| CADOES1_BONE | wt | | |
| CAL120_BREAST | mut | Splice Site SNP | chr17 7578176 A>C p.E224_splice |
| COLO741_SKIN | mut | Frame Shift Ins | chr17 7579882-7579883 ins TT p.K32fs |
| CORL105_LUNG | wt | | |
| EW8_BONE | mut | | |
| EWS502_BONE | mut | | |
| G402_SOFT_TISSUE | wt | | |
| HCC44_LUNG | mut | Missense Mutation | chr17 7578406 C>A p.R175L |
| HS294T_SKIN | wt | | |
| HT29_LARGE_INTESTINE | mut | | |
| K562_HAEMATOPOIETIC_AND_LYMPHOID_TISSUE | mut | Frame Shift Ins | chr17 7578523-7578524 ins G p.Q136fs |
| L33_PANCREAS | mut | | |
| LNCAPCLONEFGC_PROSTATE | wt | | |
| MEWO_SKIN | mut | Intron, Missense Mutation<br>Nonsense Mutation | chr17 7579786 G>A, chr17 7577509 C>T p.E258K<br>chr17 7576897 G>A p.Q317* |
| MHHES1_BONE | mut | In Frame Del | chr17 7578204-7578206 Del ACT p.S215del |
| NCIH1373_LUNG | mut | Nonsense Mutation | chr17 7574012 C>A p.E339* |
| NCIH2009_LUNG | mut | Missense Mutation | chr17 7577120 C>A p.R273L |
| PANC0327_PANCREAS | mut | | |
| PANC0813_PANCREAS | wt | | |
| PANC1_PANCREAS | mut | | |
| PATU8902_PANCREAS | mut | Missense Mutation | chr17 7578404 A>T p.C176S |
| PATU8988T_PANCREAS | mut | | |
| PC3_PROSTATE | mut | Frame Shift Del | chr17 7578516 Del G p.A138fs |
| RDES_BONE | mut | | |
| SKES1_BONE | mut | Missense Mutation | chr17 7578403 C>A p.C176F |
| SU8686_PANCREAS | mut | Missense Mutation | chr17 7577548 C>T p.G245S |
| T47D_BREAST | mut | Missense Mutation | chr17 7578268 G>A p.L194F |
| TC32_BONE | wt | | |
| TC71_BONE | mut | Nonsense Mutation | chr17 7578212 G>A p.R213* |
| TOV112D_OVARY | mut | | |

FIG. 11 (cont.)

| p53.free.fr | 10.1038/nbt.3080 | 10.1158/2159-8290.CD-16-0154 |
|---|---|---|
| p.Thr118delinsThrfsX5 | | p.A119fs, CCLE/COSMIC |
| p.Tyr220Cys | chr17 7578190 T->C 220Y/C | p.Y220C, CCLE/COSMIC |
| | | |
| | | p.?_splice, CCLE/COSMIC |
| p.Lys320_Lys321delinsLysfsX24 | | p.K321fs,p.F322fs* CCLE/COSMIC |
| | | |
| | | p.Y220C, COSMIC |
| | | p.C135F, PMID: 17425403 |
| | | |
| | chr17 7579406 G->C 94S/*; chr17 7578406 C->A 175R/L | p.R175L,p.S94*, CCLE/COSMIC |
| | | |
| p.Arg273His | chr17 7577120 C->T 273R/H | p.R273H, CCLE/COSMIC |
| p.Cys135_Gln136delinsGlnfsX12 | | p.Q136fs, CCLE/COSMIC |
| | | p.P89fs, CCLE |
| | | |
| p.Glu258Lys; p.Phe341Phe; p.Arg342X;<br>p.Glu258Lys; p.Gln317X | chr17 7577509 C->T 258E/K | p.E258K,p.Q317*, CCLE/COSMIC |
| p.Ser215del | | p.S215del, CCLE/COSMIC |
| p.Pro47Leu | | p.E339*, CCLE |
| p.Arg273Leu | chr17 7577120 C->A 273R/L | p.R273L, CCLE/COSMIC |
| | | p.?_splice, COSMIC |
| | | |
| p.Arg273Cys; p.Arg273His | chr17 7577120 C->T 273R/H | p.R273H, PMID: 20418756 |
| | chr17 7578404 A->T 176C/S | p.C176S, CCLE/COSMIC |
| | chr17 7577094 G->A 282R/W | p.R282W, COSMIC |
| p.Ala138fsX31; p.Arg282Trp | | p.K139f, CCLE/COSMIC |
| p.Arg273Cys | | p.R273C, PMID: 25223734 |
| p.Cys176Phe | | p.C176F, CCLE/COSMIC |
| p.Gly245Ser | chr17 7577548 C->T 245G/S | p.G245S,p.G360V CCLE/COSMIC |
| p.Leu194Phe | chr17 7578269 G->A 194L/F | p.L194F, CCLE/COSMIC |
| | | |
| | chr17 7578212 G->A 213R/* | p.R213*, CCLE/COSMIC |
| p.Arg175His | chr17 7578406 C->T 175R/H | p.R175H, COSMIC |

SEQUENCE LISTING

```
<160> NUMBER OF SEQ ID NOS: 137

<210> SEQ ID NO 1
<211> LENGTH: 7495
<212> TYPE: DNA
<213> ORGANISM: Homo sapiens

<400> SEQUENCE: 1

gtagggggcg cgcaccgagg caccgcggcg agcttggctg cttctggggc ctgtgtggcc     60

ctgtgtgtcg gaaagatgga gcaagaagcc gagcccgagg ggcggccgcg acccctctga    120

ccgagatcct gctgctttcg cagccaggag caccgtccct ccccggatta gtgcgtacga    180

gcgcccagtg ccctggcccg gagagtggaa tgatccccga ggcccagggc gtcgtgcttc    240

cgcgcgcccc gtgaaggaaa ctggggagtc ttgagggacc cccgactcca agcgcgaaaa    300

ccccggatgg tgaggagcag gcaaatgtgc aataccaaca tgtctgtacc tactgatggt    360

gctgtaacca cctcacagat tccagcttcg gaacaagaga ccctggttag accaaagcca    420

ttgcttttga agttattaaa gtctgttggt gcacaaaaag acacttatac tatgaaagag    480
```

-continued

```
gttctttttt atcttggcca gtatattatg actaaacgat tatatgatga gaagcaacaa    540
catattgtat attgttcaaa tgatcttcta ggagatttgt ttggcgtgcc aagcttctct    600
gtgaaagagc acaggaaaat atataccatg atctacagga acttggtagt agtcaatcag    660
caggaatcat cggactcagg tacatctgtg agtgagaaca ggtgtcacct tgaaggtggg    720
agtgatcaaa aggaccttgt acaagagctt caggaagaga aaccttcatc ttcacatttg    780
gtttctagac catctacctc atctagaagg agagcaatta gtgagacaga agaaaattca    840
gatgaattat ctggtgaacg acaaagaaaa cgccacaaat ctgatagtat ttccctttcc    900
tttgatgaaa gcctggctct gtgtgtaata agggagatat gttgtgaaag aagcagtagc    960
agtgaatcta cagggacgcc atcgaatccg gatcttgatg ctggtgtaag tgaacattca   1020
ggtgattggt tggatcagga ttcagtttca gatcagttta gtgtagaatt tgaagttgaa   1080
tctctcgact cagaagatta tagccttagt gaagaaggac aagaactctc agatgaagat   1140
gatgaggtat atcaagttac tgtgtatcag gcaggggaga gtgatacaga ttcatttgaa   1200
gaagatcctg aaatttcctt agctgactat tggaaatgca cttcatgcaa tgaaatgaat   1260
cccccccttc catcacattg caacagatgt tgggcccttc gtgagaattg gcttcctgaa   1320
gataaaggga aagataaagg ggaaatctct gagaaagcca aactggaaaa ctcaacacaa   1380
gctgaagagg gctttgatgt tcctgattgt aaaaaaacta tagtgaatga ttccagagag   1440
tcatgtgttg aggaaaatga tgataaaatt acacaagctt cacaatcaca agaaagtgaa   1500
gactattctc agccatcaac ttctagtagc attatttata gcagccaaga agatgtgaaa   1560
gagtttgaaa gggaagaaac ccaagacaaa gaagagagtg tggaatctag tttgcccctt   1620
aatgccattg aaccttgtgt gatttgtcaa ggtcgaccta aaaatggttg cattgtccat   1680
ggcaaaacag gacatcttat ggcctgcttt acatgtgcaa agaagctaaa gaaaaggaat   1740
aagccctgcc cagtatgtag acaaccaatt caaatgattg tgctaactta tttcccctag   1800
ttgacctgtc tataagagaa ttatatattt ctaactatat aaccctagga atttagacaa   1860
cctgaaattt attcacatat atcaaagtga gaaaatgcct caattcacat agatttcttc   1920
tctttagtat aattgaccta ctttggtagt ggaatagtga atacttacta taatttgact   1980
tgaatatgta gctcatcctt tacaccaact cctaatttta aataatttct actctgtctt   2040
aaatgagaag tacttggttt tttttttct taaatatgta tatgacattt aaatgtaact   2100
tattattttt tttgagaccg agtcttgctc tgttacccag gctggagtgc agtggcgtga   2160
tcttggctca ctgcaagctc tgcctcccgg gttcgcacca ttctcctgcc tcagcctccc   2220
aattagcttg gcctacagtc atctgccacc acacctggct aattttttgt acttttagta   2280
gagacagggt ttcaccgtgt tagccaggat ggtctcgatc tcctgacctc gtgatccgcc   2340
cacctcggcc tcccaaagtg ctgggattac aggcatgagc caccgcgtcc ggcctaaatg   2400
tcacttagta cctttgatat aaagagaaaa tgtgtgaaag atttagtttt ttgttttttt   2460
gtttgtttgt ttgtttgttt gttttgagat gagtctctct gtcgcccagg ctggagtgca   2520
gtgtcatgat ctagcagtct ccgcttcccg ggttcaagcc attctcctgg ctcagcctct   2580
ggagcagctg ggattacagg catgcaccac catgcccagc taatttttgt atttttagta   2640
gagatagggt ttcaccatgt tggccaggct ggtcacgaac tcctgacctc aagtgaggtc   2700
acccgcctcg gcctcccgaa gtgctgggat tgcagatgtg agccaccatg tccagccaag   2760
aattagtatt taaattttag atactctttt tttttttttt tttttttttt tttgagacag   2820
agtcttgctc catcacccat gctagagtgc agtggagtga tctcggctca ctgcaacttc   2880
```

-continued cgccttctgg gttcaagcta ttctcctgcc tcagccttcc aagtaactgg gattacaggc 2940
atgtaccacc ataccagctg attttttgt atttttagta aagacagggt ttcaccatgt 3000
tagccaggct gatcttgaac tcctaaactc aagtgatcta ctcacctcag cctcccaaaa 3060
tgctgggatt acagatgtga ggcacctggc ctcagatttt tgatactctt aaaccttctg 3120
atccttagtt tctctctcca aaatactctt tctaggttaa aaaaaaaaag gctcttatat 3180
ttggtgctat gtaaatgaaa atgtttttta ggttttcttg atttaacaat agagacaggg 3240
tctccctgtg ttgcccaggc tggtctcgaa ctcctgggct caagagatcc tcctgtcttg 3300
gcctcgcaaa gtgctaagta ggattacagg cgttagccac cacacccggc tgtaaaaatg 3360
tacttattct ccagcctctt ttgtataaac catagtaagg gatgggagta atgatgttat 3420
ctgtgaaaat agccaccatt tacccgtaag acaaaacttg ttaaagcctc ctgagtctaa 3480
cctagattac atcaggccct ttttcacaca caaaaaaatc ctttatggga tttaatggaa 3540
tctgttgttt ccccctaagt tgaaaaacaa ctctaagaca ctttaaagta ccttcttggc 3600
ctgggttaca tggttcccag cctaggtttc agacttttgc ttaaggccag ttttagaaac 3660
ccgtgaattc agaaaagtta attcagaaat ttgataaaca gaattgttat ttaaaaacta 3720
actggaaaga ttgttaagtt ctttctgaat tattcagaaa ttatgcatca ttttccttca 3780
agaatgacag ggtcagcatg tggaattcca agatacctct tgacttcctc tcaagctccg 3840
tgtttggtca gtggaggccc atccgagctc agcactgaga agtgttagtt tctttgggac 3900
ccatctaccc tgaccacatc atgatgttca tctgcagctg ttgcaaggtg ttcagattgt 3960
ataaacataa atgtcacaaa aactttaaaa gaagtgcaat tctcaaaagg ttaggtggac 4020
taaagcattc tgtaaagcaa ctgctaataa tgagcttaca gtggatttga atttgaaaaa 4080
tatagtaaca agcctgtcaa atatctgcaa gaactatgga ataaaactac tgatgcagtg 4140
aagacagttg aaaagatcaa acaaatgcca agctatattt ataatgaaca aattcaagaa 4200
aaaggactac ggaaagttca ggacatcaaa gaagtcaggc aaaactcatc ttgacccctg 4260
ttgcaggcaa aggaacgcag ctggaagaaa agatgatata acagttaaca ggatgcagac 4320
atggcagagg tttcctaaaa atctcattat ctataaccat ttctatattt acatttgaaa 4380
atctcctttg gagacttaga acctctaaat tattgactta tttttatat aaggtcactc 4440 cgatgaaagg tgattacaaa atcatctaca ttgctgtcta caaaacagat aatatggatg 4500
tttgatcgca tctcattgtt aactctttac tgatatgttt gtaaatacag aagtgaaatg 4560
tggacataaa atagttacgc tatttggtta atggtactag acaacatgta attaatgaca 4620
ttcaaaaatt tatggctagt gatatatata aagtaaaatt ttctttgcag taaaatatgc 4680
cctttattat agaagggagg atataaggaa ccaacagttt gtatgaaaat agctcaaata 4740
atatctttta ttttgatttt aatatttctt attttggttt attagtgtct tagaacaaaa 4800
tggccttata taatgaagcc tagttatgct ggactgtttt gatctctttt aattgttctg 4860
acagatagtt ggggatgaga gccgaataag gtttgcctga aataactgac actatataat 4920
ttctgctttg gcaaatacta agttctaact tgtcattcct ggtagaacaa gctttatttt 4980
tcgagcctag caatgatcta gaagcagatg ttatctcagt gccttttgca atttgttgtg 5040
tgggtttttt tttttttaaa gccacacaat aattttggaa aacaatgtat gggtagaaca 5100
tgtgtctgtt aattgcacac aaaaccactt ttaatgggta cagagttaaa tttgaaggaa 5160
taagttctag ctgaagtatt atgaactcca aataatgctt tgaggacctc caaaggtaaa 5220

```
agtactaatc cctttggcca tttattgaga gagagagaga gagagagtag ggtgactata   5280
gttaatgtat tgaatgttct tgctacaaat aaatgatatt tgagctgatg ggtgtgctaa   5340
ttacactgat ttgatcaata cccattgtat gtgaaacagt acatacacca tatttacaat   5400
tatgtattta acatttaaaa tttctaatat aagtatctct caaactgtgg attaacttct   5460
tgatttatat ttaaatatga atcttaagca aaacagtgaa aataaccatc ttgatttagt   5520
gtttttctcc catatgtgaa ttgtatatac ttaggtgaag acaataaaat caactgaact   5580
gtaagcttag aataggactg aggtaattct gcacagcaac tttactaatg gtacattgtt   5640
gcttcaaaac tctctctctc tctctctgtc tgtctcaata aatggccaaa gggattagta   5700
gtttacctgt ggaggtcctc caagcattat ttggagttga taatacttca gctacaacca   5760
agcagaatct cttttttttg gaggtcctcg aagcattatt tggagttgat aatacttcag   5820
cttcaatttg gagttgataa tatttcagct agaacctagt agaatctgtt tttttccttt   5880
ggaggtcctc aaagcattat tggagttcat aatactgaag ctagaaccaa gcagaatctg   5940
tttttttctg aggagtatcg gtagcataaa tgtgattata aacatagtac acttgatata   6000
tggaggcagt gacagctatt tttacaaaat ttaaatctgc aaatggattc aacatgttta   6060
tgggttatta aaattgtctg atttcttagg ttctttatag tacacgtgtt gaaaataaat   6120
gattaagaat tgtttcaaga atgcaattat ttgatcttaa atttttatga gttgttaaaa   6180
tagaaattat ttgaatatca tatatttggg taacaaaagg cacaagtctg aatgtgtttc   6240
tttttctgga atggccatgc ctgcccactt tagaaataca aatatcactg ggcagcttga   6300
agcagttggg agcctccaat gagagcaact tgagagaatg atgttgcaag ttagtaggag   6360
taagaaatgc tgtgttctcc ctgtcttctc ttaggtcaca tggcagcctg gcctaagtga   6420
tcgtgaatgg tctataaggg aggtagctgg gacagggagg ggagtttggg ctagccaccg   6480
taccacttgt cagcgtgaaa agtaagattg taattgcctg tttagttttc tgcctcatct   6540
ttgaaagttc caccaagctg ggaacctctt gattgtgagg cacaaatgta agtacatcag   6600
aaaaaaacaa aaaaactggc tttaaagcag gagcttgtgg gcccctaagc cagacgggga   6660
ctagcttttg gcattatata attaagattt tttaaatcct taataagggt tttattttat   6720
ttttatttat tttttgagac ggagtcttgc tctgtggctc aggctggagt acagtggtgc   6780
aatcttggct cactgcaacc tctgcctcct ggctgtgttc aagtggttct gcttcagcct   6840
cccaagtagc tggggttaga gcaccctgtc accacgcccc gctaattttt gtatttctag   6900
cagagatgaa gtttcactat gttggccagg ctgggctcaa actcctgacc tcaagtgatc   6960
tgcccgcctt ggcccccaa agtgctgtga ttacaggcgt gagccgccac gcccagccta   7020
ataagggttt taaagataat tagtgtgtag gtctgtaggc ttatgatggt aaccacaagt   7080
tgttaatggc attgtgaaaa gtttttagtt gcgctttatg ggtggatgct gaattacatt   7140
ttgatttgat acttataaaa agaaaaagta tttcttcagc ttaaaaaatt gtttaaaagt   7200
ttgtgatcat attgtctacc atgtagccag ctttcaatta tatgtaagag ggactttttg   7260
acatttacaa ataatacttt gaggtagata tctgaaagca ccagcacttg gaaggtgttc   7320
agaagtaaca aattataaaa tgagctaaca aacgaaaggc aaaataaaac cgtaaagcaa   7380
gcagatggga ggcgtgttca gtaacttatt cataatgcat ctgaaatgat tgctgtactc   7440
aaatatttaa cgttagagta atagtatttt gaatgaaaac catagttgat tgtct        7495
```

<210> SEQ ID NO 2
<211> LENGTH: 497

<212> TYPE: PRT
<213> ORGANISM: Homo sapiens

<400> SEQUENCE: 2

Met Val Arg Ser Arg Gln Met Cys Asn Thr Asn Met Ser Val Pro Thr
1               5                   10                  15

Asp Gly Ala Val Thr Thr Ser Gln Ile Pro Ala Ser Glu Gln Glu Thr
            20                  25                  30

Leu Val Arg Pro Lys Pro Leu Leu Leu Lys Leu Leu Lys Ser Val Gly
        35                  40                  45

Ala Gln Lys Asp Thr Tyr Thr Met Lys Glu Val Leu Phe Tyr Leu Gly
    50                  55                  60

Gln Tyr Ile Met Thr Lys Arg Leu Tyr Asp Glu Lys Gln Gln His Ile
65                  70                  75                  80

Val Tyr Cys Ser Asn Asp Leu Leu Gly Asp Leu Phe Gly Val Pro Ser
                85                  90                  95

Phe Ser Val Lys Glu His Arg Lys Ile Tyr Thr Met Ile Tyr Arg Asn
            100                 105                 110

Leu Val Val Val Asn Gln Gln Glu Ser Ser Asp Ser Gly Thr Ser Val
        115                 120                 125

Ser Glu Asn Arg Cys His Leu Glu Gly Gly Ser Asp Gln Lys Asp Leu
    130                 135                 140

Val Gln Glu Leu Gln Glu Glu Lys Pro Ser Ser Ser His Leu Val Ser
145                 150                 155                 160

Arg Pro Ser Thr Ser Ser Arg Arg Arg Ala Ile Ser Glu Thr Glu Glu
                165                 170                 175

Asn Ser Asp Glu Leu Ser Gly Glu Arg Gln Arg Lys Arg His Lys Ser
            180                 185                 190

Asp Ser Ile Ser Leu Ser Phe Asp Glu Ser Leu Ala Leu Cys Val Ile
        195                 200                 205

Arg Glu Ile Cys Cys Glu Arg Ser Ser Ser Ser Glu Ser Thr Gly Thr
    210                 215                 220

Pro Ser Asn Pro Asp Leu Asp Ala Gly Val Ser Glu His Ser Gly Asp
225                 230                 235                 240

Trp Leu Asp Gln Asp Ser Val Ser Asp Gln Phe Ser Val Glu Phe Glu
                245                 250                 255

Val Glu Ser Leu Asp Ser Glu Asp Tyr Ser Leu Ser Glu Glu Gly Gln
            260                 265                 270

Glu Leu Ser Asp Glu Asp Asp Glu Val Tyr Gln Val Thr Val Tyr Gln
        275                 280                 285

Ala Gly Glu Ser Asp Thr Asp Ser Phe Glu Glu Asp Pro Glu Ile Ser
    290                 295                 300

Leu Ala Asp Tyr Trp Lys Cys Thr Ser Cys Asn Glu Met Asn Pro Pro
305                 310                 315                 320

Leu Pro Ser His Cys Asn Arg Cys Trp Ala Leu Arg Glu Asn Trp Leu
                325                 330                 335

Pro Glu Asp Lys Gly Lys Asp Lys Gly Glu Ile Ser Glu Lys Ala Lys
            340                 345                 350

Leu Glu Asn Ser Thr Gln Ala Glu Glu Gly Phe Asp Val Pro Asp Cys
        355                 360                 365

Lys Lys Thr Ile Val Asn Asp Ser Arg Glu Ser Cys Val Glu Glu Asn
    370                 375                 380

Asp Asp Lys Ile Thr Gln Ala Ser Gln Ser Gln Glu Ser Glu Asp Tyr
385                 390                 395                 400

```
Ser Gln Pro Ser Thr Ser Ser Ser Ile Ile Tyr Ser Ser Gln Glu Asp
                405                 410                 415

Val Lys Glu Phe Glu Arg Glu Glu Thr Gln Asp Lys Glu Glu Ser Val
            420                 425                 430

Glu Ser Ser Leu Pro Leu Asn Ala Ile Glu Pro Cys Val Ile Cys Gln
        435                 440                 445

Gly Arg Pro Lys Asn Gly Cys Ile Val His Gly Lys Thr Gly His Leu
    450                 455                 460

Met Ala Cys Phe Thr Cys Ala Lys Lys Leu Lys Lys Arg Asn Lys Pro
465                 470                 475                 480

Cys Pro Val Cys Arg Gln Pro Ile Gln Met Ile Val Leu Thr Tyr Phe
                485                 490                 495

Pro


<210> SEQ ID NO 3
<211> LENGTH: 7330
<212> TYPE: DNA
<213> ORGANISM: Homo sapiens

<400> SEQUENCE: 3

gtagggggcg cgcaccgagg caccgcggcg agcttggctg cttctggggc ctgtgtggcc     60

ctgtgtgtcg gaaagatgga gcaagaagcc gagcccgagg ggcggccgcg acccctctga    120

ccgagatcct gctgctttcg cagccaggag caccgtccct ccccggatta gtgcgtacga    180

gcgcccagtg ccctggcccg gagagtggaa tgatccccga ggcccagggc gtcgtgcttc    240

cgcgcgcccc gtgaaggaaa ctggggagtc ttgagggacc cccgactcca agcgcgaaaa    300

ccccggatgg tgaggagcag gcaaatgtgc aataccaaca tgtctgtacc tactgatggt    360

gctgtaacca cctcacagat tccagcttcg gaacaagaga ccctggttag accaaagcca    420

ttgcttttga agttattaaa gtctgttggt gcacaaaaag acacttatac tatgaaagag    480

gttctttttt atcttggcca gtatattatg actaaacgat tatatgatga gaagcaacaa    540

catattgtat attgttcaaa tgatcttcta ggagatttgt ttggcgtgcc aagcttctct    600

gtgaaagagc acaggaaaat atataccatg atctacagga acttggtagt agtcaatcag    660

caggaagaaa attcagatga attatctggt gaacgacaaa gaaaacgcca caaatctgat    720

agtatttccc tttcctttga tgaaagcctg gctctgtgtg taataaggga gatatgttgt    780

gaaagaagca gtagcagtga atctacaggg acgccatcga atccggatct tgatgctggt    840

gtaagtgaac attcaggtga ttggttggat caggattcag tttcagatca gtttagtgta    900

gaatttgaag ttgaatctct cgactcagaa gattatagcc ttagtgaaga aggacaagaa    960

ctctcagatg aagatgatga ggtatatcaa gttactgtgt atcaggcagg ggagagtgat   1020

acagattcat ttgaagaaga tcctgaaatt tccttagctg actattggaa atgcacttca   1080

tgcaatgaaa tgaatccccc ccttccatca cattgcaaca gatgttgggc ccttcgtgag   1140

aattggcttc ctgaagataa agggaaagat aaaggggaaa tctctgagaa agccaaactg   1200

gaaaactcaa cacaagctga agagggcttt gatgttcctg attgtaaaaa aactatagtg   1260

aatgattcca gagagtcatg tgttgaggaa aatgatgata aaattacaca agcttcacaa   1320

tcacaagaaa gtgaagacta ttctcagcca tcaacttcta gtagcattat ttatagcagc   1380

caagaagatg tgaaagagtt tgaaagggaa gaaacccaag acaaagaaga gagtgtggaa   1440

tctagtttgc cccttaatgc cattgaacct tgtgtgattt gtcaaggtcg acctaaaaat   1500
```

-continued

```
ggttgcattg tccatggcaa aacaggacat cttatggcct gctttacatg tgcaaagaag   1560
ctaaagaaaa ggaataagcc ctgcccagta tgtagacaac caattcaaat gattgtgcta   1620
acttatttcc cctagttgac ctgtctataa gagaattata tatttctaac tatataaccc   1680
taggaattta gacaacctga aatttattca catatatcaa agtgagaaaa tgcctcaatt   1740
cacatagatt tcttctcttt agtataattg acctactttg gtagtggaat agtgaatact   1800
tactataatt tgacttgaat atgtagctca tcctttacac caactcctaa ttttaaataa   1860
tttctactct gtcttaaatg agaagtactt ggtttttttt tttcttaaat atgtatatga   1920
catttaaatg taacttatta tttttttga gaccgagtct tgctctgtta cccaggctgg   1980
agtgcagtgg cgtgatcttg gctcactgca agctctgcct cccgggttcg caccattctc   2040
ctgcctcagc ctcccaatta gcttggccta cagtcatctg ccaccacacc tggctaattt   2100
tttgtacttt tagtagagac agggtttcac cgtgttagcc aggatggtct cgatctcctg   2160
acctcgtgat ccgcccacct cggcctccca aagtgctggg attacaggca tgagccaccg   2220
cgtccggcct aaatgtcact tagtaccttt gatataaaga gaaaatgtgt gaaagattta   2280
gtttttgtt tttttgtttg tttgtttgtt tgtttgtttt gagatgagtc tctctgtcgc   2340
ccaggctgga gtgcagtgtc atgatctagc agtctccgct tcccgggttc aagccattct   2400
cctggctcag cctctggagc agctgggatt acaggcatgc accaccatgc ccagctaatt   2460
tttgtatttt tagtagagat agggtttcac catgttggcc aggctggtca cgaactcctg   2520
acctcaagtg aggtcacccg cctcggcctc ccgaagtgct gggattgcag atgtgagcca   2580
ccatgtccag ccaagaatta gtatttaaat tttagatact cttttttttt tttttttttt   2640
tttttttga gacagagtct tgctccatca cccatgctag agtgcagtgg agtgatctcg   2700
gctcactgca acttccgcct tctgggttca agctattctc ctgcctcagc cttccaagta   2760
actgggatta caggcatgta ccaccatacc agctgatttt tttgtatttt tagtaaagac   2820
agggtttcac catgttagcc aggctgatct tgaactccta aactcaagtg atctactcac   2880
ctcagcctcc caaaatgctg ggattacaga tgtgaggcac ctggcctcag atttttgata   2940
ctcttaaacc ttctgatcct tagtttctct ctccaaaata ctctttctag gttaaaaaaa   3000
aaaaggctct tatatttggt gctatgtaaa tgaaaatgtt ttttaggttt tcttgattta   3060
acaatagaga cagggtctcc ctgtgttgcc caggctggtc tcgaactcct gggctcaaga   3120
gatcctcctg tcttggcctc gcaaagtgct aagtaggatt acaggcgtta gccaccacac   3180
ccggctgtaa aaatgtactt attctccagc ctcttttgta taaaccatag taagggatgg   3240
gagtaatgat gttatctgtg aaaatagcca ccatttaccc gtaagacaaa acttgttaaa   3300
gcctcctgag tctaacctag attacatcag gccctttttc acacacaaaa aaatccttta   3360
tgggatttaa tggaatctgt tgtttccccc taagttgaaa aacaactcta agacacttta   3420
aagtaccttc ttggcctggg ttacatggtt cccagcctag gtttcagact tttgcttaag   3480
gccagtttta gaaacccgtg aattcagaaa agttaattca gaaatttgat aaacagaatt   3540
gttatttaaa aactaactgg aaagattgtt aagttctttc tgaattattc agaaattatg   3600
catcattttc cttcaagaat gacagggtca gcatgtggaa ttccaagata cctcttgact   3660
tcctctcaag ctccgtgttt ggtcagtgga ggcccatccg agctcagcac tgagaagtgt   3720
tagtttcttt gggacccatc taccctgacc acatcatgat gttcatctgc agctgttgca   3780
aggtgttcag attgtataaa cataaatgtc acaaaaactt taaaagaagt gcaattctca   3840
aaaggttagg tggactaaag cattctgtaa agcaactgct aataatgagc ttacagtgga   3900
```

```
tttgaatttg aaaaatatag taacaagcct gtcaaatatc tgcaagaact atggaataaa   3960
actactgatg cagtgaagac agttgaaaag atcaaacaaa tgccaagcta tatttataat   4020
gaacaaattc aagaaaaagg actacggaaa gttcaggaca tcaaagaagt caggcaaaac   4080
tcatcttgac ccctgttgca ggcaaaggaa cgcagctgga agaaaagatg atataacagt   4140
taacaggatg cagacatggc agaggtttcc taaaaatctc attatctata accatttcta   4200
tatttacatt tgaaaatctc ctttggagac ttagaacctc taaattattg acttattttt   4260
tatataaggt cactccgatg aaaggtgatt acaaaatcat ctacattgct gtctacaaaa   4320
cagataatat ggatgtttga tcgcatctca ttgttaactc tttactgata tgtttgtaaa   4380
tacagaagtg aaatgtggac ataaaatagt tacgctattt ggttaatggt actagacaac   4440
atgtaattaa tgacattcaa aaatttatgg ctagtgatat atataaagta aaattttctt   4500
tgcagtaaaa tatgcccttt attatagaag ggaggatata aggaaccaac agtttgtatg   4560
aaaatagctc aaataatatc ttttattttg attttaatat ttcttatttt ggtttattag   4620
tgtcttagaa caaaatggcc ttatataatg aagcctagtt atgctggact gttttgatct   4680
cttttaattg ttctgacaga tagttgggga tgagagccga ataaggtttg cctgaaataa   4740
ctgacactat ataatttctg ctttggcaaa tactaagttc taacttgtca ttcctggtag   4800
aacaagcttt atttttcgag cctagcaatg atctagaagc agatgttatc tcagtgcctt   4860
ttgcaatttg ttgtgtgggt tttttttttt ttaaagccac acaataattt tggaaaacaa   4920
tgtatgggta gaacatgtgt ctgttaattg cacacaaaac cacttttaat gggtacagag   4980
ttaaatttga aggaataagt tctagctgaa gtattatgaa ctccaaataa tgctttgagg   5040
acctccaaag gtaaaagtac taatcccttt ggccatttat tgagagagag agagagagag   5100
agtagggtga ctatagttaa tgtattgaat gttcttgcta caaataaatg atatttgagc   5160
tgatgggtgt gctaattaca ctgatttgat caatacccat tgtatgtgaa acagtacata   5220
caccatattt acaattatgt atttaacatt taaaatttct aatataagta tctctcaaac   5280
tgtggattaa cttcttgatt tatatttaaa tatgaatctt aagcaaaaca gtgaaaataa   5340
ccatcttgat ttagtgtttt tctcccatat gtgaattgta tatacttagg tgaagacaat   5400
aaaatcaact gaactgtaag cttagaatag gactgaggta attctgcaca gcaactttac   5460
taatggtaca ttgttgcttc aaaactctct ctctctctct ctgtctgtct caataaatgg   5520
ccaaagggat tagtagttta cctgtggagg tcctccaagc attatttgga gttgataata   5580
cttcagctac aaccaagcag aatctctttt ttttggaggt cctcgaagca ttatttggag   5640
ttgataatac ttcagcttca atttggagtt gataatattt cagctagaac ctagtagaat   5700
ctgttttttt cctttggagg tcctcaaagc attattggag ttcataatac tgaagctaga   5760
accaagcaga atctgttttt ttctgaggag tatcggtagc ataaatgtga ttataaacat   5820
agtacacttg atatatggag gcagtgacag ctatttttac aaaatttaaa tctgcaaatg   5880
gattcaacat gtttatgggt tattaaaatt gtctgatttc ttaggttctt tatagtacac   5940
gtgttgaaaa taaatgatta agaattgttt caagaatgca attatttgat cttaaatttt   6000
tatgagttgt taaaatagaa attatttgaa tatcatatat ttgggtaaca aaaggcacaa   6060
gtctgaatgt gtttcttttt ctggaatggc catgcctgcc cactttagaa atacaaatat   6120
cactgggcag cttgaagcag ttgggagcct ccaatgagag caacttgaga gaatgatgtt   6180
gcaagttagt aggagtaaga aatgctgtgt tctccctgtc ttctcttagg tcacatggca   6240
```

-continued

```
gcctggccta agtgatcgtg aatggtctat aagggaggta gctgggacag ggaggggagt   6300

ttgggctagc caccgtacca cttgtcagcg tgaaaagtaa gattgtaatt gcctgtttag   6360

ttttctgcct catctttgaa agttccacca agctgggaac ctcttgattg tgaggcacaa   6420

atgtaagtac atcagaaaaa aacaaaaaaa ctggctttaa agcaggagct tgtgggcccc   6480

taagccagac ggggactagc ttttggcatt atataattaa gatttttttaa atccttaata   6540

agggttttat tttattttta tttatttttt gagacggagt cttgctctgt ggctcaggct   6600

ggagtacagt ggtgcaatct tggctcactg caacctctgc ctcctggctg tgttcaagtg   6660

gttctgcttc agcctcccaa gtagctgggg ttagagcacc ctgtcaccac gccccgctaa   6720

tttttgtatt tctagcagag atgaagtttc actatgttgg ccaggctggg ctcaaactcc   6780

tgacctcaag tgatctgccc gccttggccc cccaaagtgc tgtgattaca ggcgtgagcc   6840

gccacgccca gcctaataag ggttttaaag ataattagtg tgtaggtctg taggcttatg   6900

atggtaacca caagttgtta atggcattgt gaaaagtttt tagttgcgct ttatgggtgg   6960

atgctgaatt acattttgat ttgatactta taaaaagaaa aagtatttct tcagcttaaa   7020

aaattgttta aaagtttgtg atcatattgt ctaccatgta gccagctttc aattatatgt   7080

aagagggact ttttgacatt tacaaataat actttgaggt agatatctga aagcaccagc   7140

acttggaagg tgttcagaag taacaaatta taaaatgagc taacaaacga aaggcaaaat   7200

aaaaccgtaa agcaagcaga tgggaggcgt gttcagtaac ttattcataa tgcatctgaa   7260

atgattgctg tactcaaata tttaacgtta gagtaatagt attttgaatg aaaaccatag   7320

ttgattgtct                                                          7330
```

<210> SEQ ID NO 4
<211> LENGTH: 442
<212> TYPE: PRT
<213> ORGANISM: Homo sapiens

<400> SEQUENCE: 4

```
Met Val Arg Ser Arg Gln Met Cys Asn Thr Asn Met Ser Val Pro Thr
1               5                   10                  15

Asp Gly Ala Val Thr Thr Ser Gln Ile Pro Ala Ser Glu Gln Glu Thr
            20                  25                  30

Leu Val Arg Pro Lys Pro Leu Leu Leu Lys Leu Leu Lys Ser Val Gly
        35                  40                  45

Ala Gln Lys Asp Thr Tyr Thr Met Lys Glu Val Leu Phe Tyr Leu Gly
    50                  55                  60

Gln Tyr Ile Met Thr Lys Arg Leu Tyr Asp Glu Lys Gln Gln His Ile
65                  70                  75                  80

Val Tyr Cys Ser Asn Asp Leu Leu Gly Asp Leu Phe Gly Val Pro Ser
                85                  90                  95

Phe Ser Val Lys Glu His Arg Lys Ile Tyr Thr Met Ile Tyr Arg Asn
            100                 105                 110

Leu Val Val Val Asn Gln Gln Glu Glu Asn Ser Asp Glu Leu Ser Gly
        115                 120                 125

Glu Arg Gln Arg Lys Arg His Lys Ser Asp Ser Ile Ser Leu Ser Phe
    130                 135                 140

Asp Glu Ser Leu Ala Leu Cys Val Ile Arg Glu Ile Cys Cys Glu Arg
145                 150                 155                 160

Ser Ser Ser Ser Glu Ser Thr Gly Thr Pro Ser Asn Pro Asp Leu Asp
                165                 170                 175
```

-continued

```
Ala Gly Val Ser Glu His Ser Gly Asp Trp Leu Asp Gln Asp Ser Val
            180                 185                 190

Ser Asp Gln Phe Ser Val Glu Phe Glu Val Glu Ser Leu Asp Ser Glu
        195                 200                 205

Asp Tyr Ser Leu Ser Glu Glu Gly Gln Glu Leu Ser Asp Glu Asp Asp
    210                 215                 220

Glu Val Tyr Gln Val Thr Val Tyr Gln Ala Gly Glu Ser Asp Thr Asp
225                 230                 235                 240

Ser Phe Glu Glu Asp Pro Glu Ile Ser Leu Ala Asp Tyr Trp Lys Cys
                245                 250                 255

Thr Ser Cys Asn Glu Met Asn Pro Pro Leu Pro Ser His Cys Asn Arg
            260                 265                 270

Cys Trp Ala Leu Arg Glu Asn Trp Leu Pro Glu Asp Lys Gly Lys Asp
        275                 280                 285

Lys Gly Glu Ile Ser Glu Lys Ala Lys Leu Glu Asn Ser Thr Gln Ala
    290                 295                 300

Glu Glu Gly Phe Asp Val Pro Asp Cys Lys Lys Thr Ile Val Asn Asp
305                 310                 315                 320

Ser Arg Glu Ser Cys Val Glu Glu Asn Asp Asp Lys Ile Thr Gln Ala
                325                 330                 335

Ser Gln Ser Gln Glu Ser Glu Asp Tyr Ser Gln Pro Ser Thr Ser Ser
            340                 345                 350

Ser Ile Ile Tyr Ser Ser Gln Glu Asp Val Lys Glu Phe Glu Arg Glu
        355                 360                 365

Glu Thr Gln Asp Lys Glu Glu Ser Val Glu Ser Ser Leu Pro Leu Asn
    370                 375                 380

Ala Ile Glu Pro Cys Val Ile Cys Gln Gly Arg Pro Lys Asn Gly Cys
385                 390                 395                 400

Ile Val His Gly Lys Thr Gly His Leu Met Ala Cys Phe Thr Cys Ala
                405                 410                 415

Lys Lys Leu Lys Lys Arg Asn Lys Pro Cys Pro Val Cys Arg Gln Pro
            420                 425                 430

Ile Gln Met Ile Val Leu Thr Tyr Phe Pro
        435                 440
```

<210> SEQ ID NO 5
<211> LENGTH: 7104
<212> TYPE: DNA
<213> ORGANISM: Homo sapiens

<400> SEQUENCE: 5

```
tgtgttcagt ggcgattgga gggtagacct gtgggcacgg acgcacgcca ctttttctct      60

gctgatccag gcaaatgtgc aataccaaca tgtctgtacc tactgatggt gctgtaacca     120

cctcacagat tccagcttcg gaacaagaga ccctggttag accaaagcca ttgcttttga     180

agttattaaa gtctgttggt gcacaaaaag acacttatac tatgaaagag gttctttttt     240

atcttggcca gtatattatg actaaacgat tatatgatga gaagcaacaa catattgtat     300

attgttcaaa tgatcttcta ggagatttgt ttggcgtgcc aagcttctct gtgaaagagc     360

acaggaaaat atataccatg atctacagga acttggtagt agtcaatcag caggaatcat     420

cggactcagg tacatctgtg agtgagaaca ggtgtcacct tgaaggtggg agtgatcaaa     480

aggaccttgt acaagagctt caggaagaga aaccttcatc ttcacatttg gtttctagac     540

catctacctc atctagaagg agagcaatta gtgagacaga agaaaattca gatgaattat     600
```

-continued

```
ctggtgaacg acaaagaaaa cgccacaaat ctgatagtat ttccctttcc tttgatgaaa    660
gcctggctct gtgtgtaata agggagatat gttgtgaaag aagcagtagc agtgaatcta    720
cagggacgcc atcgaatccg gatcttgatg ctggtgtata tcaagttact gtgtatcagg    780
caggggagag tgatacagat tcatttgaag aagatcctga aatttcctta gctgactatt    840
ggaaatgcac ttcatgcaat gaaatgaatc ccccccttcc atcacattgc aacagatgtt    900
gggcccttcg tgagaattgg cttcctgaag ataaagggaa agataaaggg gaaatctctg    960
agaaagccaa actggaaaac tcaacacaag ctgaagaggg ctttgatgtt cctgattgta   1020
aaaaaactat agtgaatgat tccagagagt catgtgttga ggaaaatgat gataaaatta   1080
cacaagcttc acaatcacaa gaaagtgaag actattctca gccatcaact tctagtagca   1140
ttatttatag cagccaagaa gatgtgaaag agtttgaaag ggaagaaacc caagacaaag   1200
aagagagtgt ggaatctagt ttgcccctta atgccattga accttgtgtg atttgtcaag   1260
gtcgacctaa aaatggttgc attgtccatg gcaaaacagg acatcttatg gcctgcttta   1320
catgtgcaaa gaagctaaag aaaaggaata agccctgccc agtatgtaga caaccaattc   1380
aaatgattgt gctaacttat ttcccctagt tgacctgtct ataagagaat tatatatttc   1440
taactatata accctaggaa tttagacaac ctgaaattta ttcacatata tcaaagtgag   1500
aaaatgcctc aattcacata gatttcttct ctttagtata attgacctac tttggtagtg   1560
gaatagtgaa tacttactat aatttgactt gaatatgtag ctcatccttt acaccaactc   1620
ctaattttaa ataatttcta ctctgtctta aatgagaagt acttggtttt tttttttctt   1680
aaatatgtat atgacattta aatgtaactt attatttttt ttgagaccga gtcttgctct   1740
gttacccagg ctggagtgca gtggcgtgat cttggctcac tgcaagctct gcctcccggg   1800
ttcgcaccat tctcctgcct cagcctccca attagcttgg cctacagtca tctgccacca   1860
cacctggcta atttttgta ctttagtag agacagggtt tcaccgtgtt agccaggatg   1920
gtctcgatct cctgacctcg tgatccgccc acctcggcct cccaaagtgc tgggattaca   1980
ggcatgagcc accgcgtccg gcctaaatgt cacttagtac ctttgatata aagagaaaat   2040
gtgtgaaaga tttagttttt tgtttttttg tttgtttgtt tgtttgtttg ttttgagatg   2100
agtctctctg tcgcccaggc tggagtgcag tgtcatgatc tagcagtctc cgcttcccgg   2160
gttcaagcca ttctcctggc tcagcctctg gagcagctgg gattacaggc atgcaccacc   2220
atgcccagct aatttttgta tttttagtag agatagggtt tcaccatgtt ggccaggctg   2280
gtcacgaact cctgacctca agtgaggtca cccgcctcgg cctcccgaag tgctgggatt   2340
gcagatgtga gccaccatgt ccagccaaga attagtattt aaattttaga tactcttttt   2400
tttttttttt tttttttttt ttgagacaga gtcttgctcc atcacccatg ctagagtgca   2460
gtggagtgat ctcggctcac tgcaacttcc gccttctggg ttcaagctat tctcctgcct   2520
cagccttcca agtaactggg attacaggca tgtaccacca taccagctga ttttttttgta   2580
tttttagtaa agacagggtt tcaccatgtt agccaggctg atcttgaact cctaaactca   2640
agtgatctac tcacctcagc ctcccaaaat gctgggatta cagatgtgag gcacctggcc   2700
tcagattttt gatactctta aaccttctga tccttagttt ctctctccaa aatactcttt   2760
ctaggttaaa aaaaaaaagg ctcttatatt tggtgctatg taaatgaaaa tgttttttag   2820
gttttcttga tttaacaata gagacagggt ctccctgtgt tgcccaggct ggtctcgaac   2880
tcctgggctc aagagatcct cctgtcttgg cctcgcaaag tgctaagtag gattacaggc   2940
gttagccacc acacccggct gtaaaaatgt acttattctc cagcctcttt tgtataaacc   3000
```

atagtaaggg atgggagtaa tgatgttatc tgtgaaaata gccaccattt acccgtaaga 3060
caaaacttgt taaagcctcc tgagtctaac ctagattaca tcaggcccttt tttcacacac 3120
aaaaaaatcc tttatgggat ttaatggaat ctgttgtttc cccctaagtt gaaaaacaac 3180
tctaagacac tttaaagtac cttcttggcc tgggttacat ggttcccagc ctaggtttca 3240
gacttttgct taaggccagt tttagaaacc cgtgaattca gaaaagttaa ttcagaaatt 3300
tgataaacag aattgttatt taaaaactaa ctggaaagat tgttaagttc tttctgaatt 3360
attcagaaat tatgcatcat tttccttcaa gaatgacagg gtcagcatgt ggaattccaa 3420
gatacctctt gacttcctct caagctccgt gtttggtcag tggaggccca tccgagctca 3480
gcactgagaa gtgttagttt ctttgggacc catctaccct gaccacatca tgatgttcat 3540
ctgcagctgt tgcaaggtgt tcagattgta taaacataaa tgtcacaaaa actttaaaag 3600
aagtgcaatt ctcaaaaggt taggtggact aaagcattct gtaaagcaac tgctaataat 3660
gagcttacag tggatttgaa tttgaaaaat atagtaacaa gcctgtcaaa tatctgcaag 3720
aactatggaa taaaactact gatgcagtga agacagttga aaagatcaaa caaatgccaa 3780
gctatattta taatgaacaa attcaagaaa aaggactacg gaaagttcag gacatcaaag 3840
aagtcaggca aaactcatct tgacccctgt tgcaggcaaa ggaacgcagc tggaagaaaa 3900
gatgatataa cagttaacag gatgcagaca tggcagaggt ttcctaaaaa tctcattatc 3960
tataaccatt tctatattta catttgaaaa tctcctttgg agacttagaa cctctaaatt 4020
attgacttat tttttatata aggtcactcc gatgaaaggt gattacaaaa tcatctacat 4080
tgctgtctac aaaacagata atatggatgt ttgatcgcat ctcattgtta actctttact 4140
gatatgtttg taaatacaga agtgaaatgt ggacataaaa tagttacgct atttggttaa 4200
tggtactaga caacatgtaa ttaatgacat tcaaaaattt atggctagtg atatatataa 4260
agtaaaattt tctttgcagt aaaatatgcc ctttattata gaagggagga tataaggaac 4320
caacagtttg tatgaaaata gctcaaataa tatcttttat tttgatttta atatttctta 4380
ttttggttta ttagtgtctt agaacaaaat ggccttatat aatgaagcct agttatgctg 4440
gactgttttg atctctttta attgttctga cagatagttg gggatgagag ccgaataagg 4500
tttgcctgaa ataactgaca ctatataatt tctgctttgg caaatactaa gttctaactt 4560
gtcattcctg gtagaacaag ctttattttt cgagcctagc aatgatctag aagcagatgt 4620
tatctcagtg ccttttgcaa tttgttgtgt gggttttttt ttttttaaag ccacacaata 4680
attttggaaa acaatgtatg ggtagaacat gtgtctgtta attgcacaca aaaccacttt 4740
taatgggtac agagttaaat ttgaaggaat aagttctagc tgaagtatta tgaactccaa 4800
ataatgcttt gaggacctcc aaaggtaaaa gtactaatcc ctttggccat tttattgagag 4860
agagagagag agagagtagg gtgactatag ttaatgtatt gaatgttctt gctacaaata 4920
aatgatattt gagctgatgg gtgtgctaat tacactgatt tgatcaatac ccattgtatg 4980
tgaaacagta catacaccat atttacaatt atgtatttaa catttaaaat ttctaatata 5040
agtatctctc aaactgtgga ttaacttctt gatttatatt taaatatgaa tcttaagcaa 5100
aacagtgaaa ataaccatct tgatttagtg tttttctccc atatgtgaat tgtatatact 5160
taggtgaaga caataaaatc aactgaactg taagcttaga ataggactga ggtaattctg 5220
cacagcaact ttactaatgg tacattgttg cttcaaaact ctctctctct ctctctgtct 5280
gtctcaataa atggccaaag ggattagtag tttacctgtg gaggtcctcc aagcattatt 5340

-continued

```
tggagttgat aatacttcag ctacaaccaa gcagaatctc tttttttgg aggtcctcga   5400

agcattattt ggagttgata atacttcagc ttcaatttgg agttgataat atttcagcta   5460

gaacctagta gaatctgttt ttttcctttg gaggtcctca aagcattatt ggagttcata   5520

atactgaagc tagaaccaag cagaatctgt ttttttctga ggagtatcgg tagcataaat   5580

gtgattataa acatagtaca cttgatatat ggaggcagtg acagctattt ttacaaaatt   5640

taaatctgca aatggattca acatgtttat gggttattaa aattgtctga tttcttaggt   5700

tctttatagt acacgtgttg aaaataaatg attaagaatt gtttcaagaa tgcaattatt   5760

tgatcttaaa tttttatgag ttgttaaaat agaaattatt tgaatatcat atatttgggt   5820

aacaaaaggc acaagtctga atgtgtttct ttttctggaa tggccatgcc tgcccacttt   5880

agaaatacaa atatcactgg gcagcttgaa gcagttggga gcctccaatg agagcaactt   5940

gagagaatga tgttgcaagt tagtaggagt aagaaatgct gtgttctccc tgtcttctct   6000

taggtcacat ggcagcctgg cctaagtgat cgtgaatggt ctataaggga ggtagctggg   6060

acagggaggg gagtttgggc tagccaccgt accacttgtc agcgtgaaaa gtaagattgt   6120

aattgcctgt ttagttttct gcctcatctt tgaaagttcc accaagctgg gaacctcttg   6180

attgtgaggc acaaatgtaa gtacatcaga aaaaaacaaa aaaactggct ttaaagcagg   6240

agcttgtggg cccctaagcc agacggggac tagcttttgg cattatataa ttaagatttt   6300

ttaaatcctt aataagggtt ttattttatt tttatttatt ttttgagacg gagtcttgct   6360

ctgtggctca ggctggagta cagtggtgca atcttggctc actgcaacct ctgcctcctg   6420

gctgtgttca agtggttctg cttcagcctc ccaagtagct ggggttagag caccctgtca   6480

ccacgccccg ctaattttg tatttctagc agagatgaag tttcactatg ttggccaggc   6540

tgggctcaaa ctcctgacct caagtgatct gcccgccttg gccccccaaa gtgctgtgat   6600

tacaggcgtg agccgccacg cccagcctaa taagggtttt aaagataatt agtgtgtagg   6660

tctgtaggct tatgatggta accacaagtt gttaatggca ttgtgaaaag tttttagttg   6720

cgctttatgg gtggatgctg aattacattt tgatttgata cttataaaaa gaaaaagtat   6780

ttcttcagct taaaaaattg tttaaaagtt tgtgatcata ttgtctacca tgtagccagc   6840

tttcaattat atgtaagagg gactttttga catttacaaa taatactttg aggtagatat   6900

ctgaaagcac cagcacttgg aaggtgttca gaagtaacaa attataaaat gagctaacaa   6960

acgaaaggca aaataaaacc gtaaagcaag cagatgggag gcgtgttcag taacttattc   7020

ataatgcatc tgaaatgatt gctgtactca aatatttaac gttagagtaa tagtattttg   7080

aatgaaaacc atagttgatt gtct                                         7104
```

<210> SEQ ID NO 6
<211> LENGTH: 444
<212> TYPE: PRT
<213> ORGANISM: Homo sapiens

<400> SEQUENCE: 6

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60
```

```
Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
    210                 215                 220

Asp Ala Gly Val Tyr Gln Val Thr Val Tyr Gln Ala Gly Glu Ser Asp
225                 230                 235                 240

Thr Asp Ser Phe Glu Glu Asp Pro Glu Ile Ser Leu Ala Asp Tyr Trp
                245                 250                 255

Lys Cys Thr Ser Cys Asn Glu Met Asn Pro Pro Leu Pro Ser His Cys
            260                 265                 270

Asn Arg Cys Trp Ala Leu Arg Glu Asn Trp Leu Pro Glu Asp Lys Gly
        275                 280                 285

Lys Asp Lys Gly Glu Ile Ser Glu Lys Ala Lys Leu Glu Asn Ser Thr
    290                 295                 300

Gln Ala Glu Glu Gly Phe Asp Val Pro Asp Cys Lys Lys Thr Ile Val
305                 310                 315                 320

Asn Asp Ser Arg Glu Ser Cys Val Glu Glu Asn Asp Asp Lys Ile Thr
                325                 330                 335

Gln Ala Ser Gln Ser Gln Glu Ser Glu Asp Tyr Ser Gln Pro Ser Thr
            340                 345                 350

Ser Ser Ser Ile Ile Tyr Ser Ser Gln Glu Asp Val Lys Glu Phe Glu
        355                 360                 365

Arg Glu Glu Thr Gln Asp Lys Glu Glu Ser Val Glu Ser Ser Leu Pro
    370                 375                 380

Leu Asn Ala Ile Glu Pro Cys Val Ile Cys Gln Gly Arg Pro Lys Asn
385                 390                 395                 400

Gly Cys Ile Val His Gly Lys Thr Gly His Leu Met Ala Cys Phe Thr
                405                 410                 415

Cys Ala Lys Lys Leu Lys Lys Arg Asn Lys Pro Cys Pro Val Cys Arg
            420                 425                 430

Gln Pro Ile Gln Met Ile Val Leu Thr Tyr Phe Pro
        435                 440
```

<210> SEQ ID NO 7
<211> LENGTH: 6657
<212> TYPE: DNA
<213> ORGANISM: Homo sapiens -continued

<400> SEQUENCE: 7
tgtgttcagt ggcgattgga gggtagacct gtgggcacgg acgcacgcca ctttttctct 60
gctgatccag gcaaatgtgc aataccaaca tgtctgtacc tactgatggt gctgtaacca 120
cctcacagat tccagcttcg gaacaagaga ccctggttag accaaagcca ttgcttttga 180
agttattaaa gtctgttggt gcacaaaaag acacttatac tatgaaagag gatcttgatg 240
ctggtgtaag tgaacattca ggtgattggt tggatcagga ttcagtttca gatcagttta 300
gtgtagaatt tgaagttgaa tctctcgact cagaagatta tagccttagt gaagaaggac 360
aagaactctc agatgaagat gatgaggact attggaaatg cacttcatgc aatgaaatga 420
atccccccct tccatcacat tgcaacagat gttgggccct tcgtgagaat tggcttcctg 480
aagataaagg gaaagataaa ggggaaatct ctgagaaagc caaactggaa aactcaacac 540
aagctgaaga gggctttgat gttcctgatt gtaaaaaaac tatagtgaat gattccagag 600
agtcatgtgt tgaggaaaat gatgataaaa ttacacaagc ttcacaatca caagaaagtg 660
aagactattc tcagccatca acttctagta gcattattta tagcagccaa gaagatgtga 720
aagagtttga aagggaagaa acccaagaca aagaagagag tgtggaatct agtttgcccc 780
ttaatgccat tgaaccttgt gtgatttgtc aaggtcgacc taaaaatggt tgcattgtcc 840
atggcaaaac aggacatctt atggcctgct ttacatgtgc aaagaagcta aagaaaagga 900
ataagccctg cccagtatgt agacaaccaa ttcaaatgat tgtgctaact tatttcccct 960
agttgacctg tctataagag aattatatat ttctaactat ataaccctag gaatttagac 1020
aacctgaaat ttattcacat atatcaaagt gagaaaatgc ctcaattcac atagatttct 1080
tctctttagt ataattgacc tactttggta gtggaatagt gaatacttac tataatttga 1140
cttgaatatg tagctcatcc tttacaccaa ctcctaattt taaataattt ctactctgtc 1200
ttaaatgaga agtacttggt ttttttttt cttaaatatg tatatgacat ttaaatgtaa 1260
cttattattt tttttgagac cgagtcttgc tctgttaccc aggctggagt gcagtggcgt 1320
gatcttggct cactgcaagc tctgcctccc gggttcgcac cattctcctg cctcagcctc 1380
ccaattagct tggcctacag tcatctgcca ccacacctgg ctaatttttt gtacttttag 1440
tagagacagg gtttcaccgt gttagccagg atggtctcga tctcctgacc tcgtgatccg 1500
cccacctcgg cctcccaaag tgctgggatt acaggcatga gccaccgcgt ccggcctaaa 1560
tgtcacttag tacctttgat ataaagagaa aatgtgtgaa agatttagtt ttttgttttt 1620
ttgtttgttt gtttgtttgt ttgttttgag atgagtctct ctgtcgccca ggctggagtg 1680
cagtgtcatg atctagcagt ctccgcttcc cgggttcaag ccattctcct ggctcagcct 1740
ctggagcagc tgggattaca ggcatgcacc accatgccca gctaattttt gtatttttag 1800
tagagatagg gtttcaccat gttggccagg ctggtcacga actcctgacc tcaagtgagg 1860
tcacccgcct cggcctcccg aagtgctggg attgcagatg tgagccacca tgtccagcca 1920
agaattagta tttaaatttt agatactctt tttttttttt tttttttttt tttttgagac 1980
agagtcttgc tccatcaccc atgctagagt gcagtggagt gatctcggct cactgcaact 2040
tccgccttct gggttcaagc tattctcctg cctcagcctt ccaagtaact gggattacag 2100
gcatgtacca ccataccagc tgattttttt gtatttttag taaagacagg gtttcaccat 2160
gttagccagg ctgatcttga actcctaaac tcaagtgatc tactcacctc agcctcccaa 2220
aatgctggga ttacagatgt gaggcacctg gcctcagatt tttgatactc ttaaaccttc 2280
tgatccttag tttctctctc caaaatactc tttctaggtt aaaaaaaaaa aggctcttat 2340

-continued

```
atttggtgct atgtaaatga aaatgttttt taggttttct tgatttaaca atagagacag   2400
ggtctccctg tgttgcccag gctggtctcg aactcctggg ctcaagagat cctcctgtct   2460
tggcctcgca aagtgctaag taggattaca ggcgttagcc accacacccg gctgtaaaaa   2520
tgtacttatt ctccagcctc ttttgtataa accatagtaa gggatgggag taatgatgtt   2580
atctgtgaaa atagccacca tttacccgta agacaaaact tgttaaagcc tcctgagtct   2640
aacctagatt acatcaggcc ctttttcaca cacaaaaaaa tcctttatgg gatttaatgg   2700
aatctgttgt ttccccctaa gttgaaaaac aactctaaga cactttaaag taccttcttg   2760
gcctgggtta catggttccc agcctaggtt tcagactttt gcttaaggcc agttttagaa   2820
acccgtgaat tcagaaaagt taattcagaa atttgataaa cagaattgtt atttaaaaac   2880
taactggaaa gattgttaag ttctttctga attattcaga aattatgcat cattttcctt   2940
caagaatgac agggtcagca tgtggaattc caagatacct cttgacttcc tctcaagctc   3000
cgtgtttggt cagtggaggc ccatccgagc tcagcactga gaagtgttag tttctttggg   3060
acccatctac cctgaccaca tcatgatgtt catctgcagc tgttgcaagg tgttcagatt   3120
gtataaacat aaatgtcaca aaaactttaa aagaagtgca attctcaaaa ggttaggtgg   3180
actaaagcat tctgtaaagc aactgctaat aatgagctta cagtggattt gaatttgaaa   3240
aatatagtaa caagcctgtc aaatatctgc aagaactatg gaataaaact actgatgcag   3300
tgaagacagt tgaaaagatc aaacaaatgc caagctatat ttataatgaa caaattcaag   3360
aaaaaggact acggaaagtt caggacatca aagaagtcag gcaaaactca tcttgacccc   3420
tgttgcaggc aaaggaacgc agctggaaga aaagatgata taacagttaa caggatgcag   3480
acatggcaga ggtttcctaa aaatctcatt atctataacc atttctatat ttacatttga   3540
aaatctcctt tggagactta gaacctctaa attattgact tattttttat ataaggtcac   3600
tccgatgaaa ggtgattaca aaatcatcta cattgctgtc tacaaaacag ataatatgga   3660
tgtttgatcg catctcattg ttaactcttt actgatatgt ttgtaaatac agaagtgaaa   3720
tgtggacata aaatagttac gctatttggt taatggtact agacaacatg taattaatga   3780
cattcaaaaa tttatggcta gtgatatata taaagtaaaa ttttctttgc agtaaaatat   3840
gccctttatt atagaaggga ggatataagg aaccaacagt ttgtatgaaa atagctcaaa   3900
taatatcttt tattttgatt ttaatatttc ttattttggt ttattagtgt cttagaacaa   3960
aatggcctta tataatgaag cctagttatg ctggactgtt ttgatctctt ttaattgttc   4020
tgacagatag ttggggatga gagccgaata aggtttgcct gaaataactg acactatata   4080
atttctgctt tggcaaatac taagttctaa cttgtcattc ctggtagaac aagctttatt   4140
tttcgagcct agcaatgatc tagaagcaga tgttatctca gtgccttttg caatttgttg   4200
tgtgggtttt ttttttttta aagccacaca ataattttgg aaaacaatgt atgggtagaa   4260
catgtgtctg ttaattgcac acaaaaccac ttttaatggg tacagagtta aatttgaagg   4320
aataagttct agctgaagta ttatgaactc caaataatgc tttgaggacc tccaaaggta   4380
aaagtactaa tccctttggc catttattga gagagagaga gagagagagt agggtgacta   4440
tagttaatgt attgaatgtt cttgctacaa ataaatgata tttgagctga tgggtgtgct   4500
aattacactg atttgatcaa tacccattgt atgtgaaaca gtacatacac catatttaca   4560
attatgtatt taacatttaa aatttctaat ataagtatct ctcaaactgt ggattaactt   4620
cttgatttat atttaaatat gaatcttaag caaaacagtg aaaataacca tcttgattta   4680
```

-continued gtgtttttct cccatatgtg aattgtatat acttaggtga agacaataaa atcaactgaa 4740
ctgtaagctt agaataggac tgaggtaatt ctgcacagca actttactaa tggtacattg 4800
ttgcttcaaa actctctctc tctctctctg tctgtctcaa taaatggcca aagggattag 4860
tagtttacct gtggaggtcc tccaagcatt atttggagtt gataatactt cagctacaac 4920
caagcagaat ctcttttttt tggaggtcct cgaagcatta tttggagttg ataatacttc 4980
agcttcaatt tggagttgat aatatttcag ctagaaccta gtagaatctg tttttttcct 5040
ttggaggtcc tcaaagcatt attggagttc ataatactga agctagaacc aagcagaatc 5100
tgtttttttc tgaggagtat cggtagcata aatgtgatta taaacatagt acacttgata 5160
tatggaggca gtgacagcta tttttacaaa atttaaatct gcaaatggat tcaacatgtt 5220
tatgggttat taaaattgtc tgatttctta ggttctttat agtacacgtg ttgaaaataa 5280
atgattaaga attgtttcaa gaatgcaatt atttgatctt aaatttttat gagttgttaa 5340
aatagaaatt atttgaatat catatatttg ggtaacaaaa ggcacaagtc tgaatgtgtt 5400
tctttttctg gaatggccat gcctgcccac tttagaaata caaatatcac tgggcagctt 5460
gaagcagttg ggagcctcca atgagagcaa cttgagagaa tgatgttgca agttagtagg 5520
agtaagaaat gctgtgttct ccctgtcttc tcttaggtca catggcagcc tggcctaagt 5580
gatcgtgaat ggtctataag ggaggtagct gggacaggga ggggagtttg ggctagccac 5640
cgtaccactt gtcagcgtga aaagtaagat tgtaattgcc tgtttagttt tctgcctcat 5700
ctttgaaagt tccaccaagc tgggaacctc ttgattgtga ggcacaaatg taagtacatc 5760
agaaaaaaac aaaaaaactg gctttaaagc aggagcttgt gggcccctaa gccagacggg 5820
gactagcttt tggcattata taattaagat tttttaaatc cttaataagg gttttatttt 5880
atttttattt attttttgag acggagtctt gctctgtggc tcaggctgga gtacagtggt 5940
gcaatcttgg ctcactgcaa cctctgcctc ctggctgtgt tcaagtggtt ctgcttcagc 6000
ctcccaagta gctggggtta gagcaccctg tcaccacgcc ccgctaattt ttgtatttct 6060
agcagagatg aagtttcact atgttggcca ggctgggctc aaactcctga cctcaagtga 6120
tctgcccgcc ttggcccccc aaagtgctgt gattacaggc gtgagccgcc acgcccagcc 6180
taataagggt tttaaagata attagtgtgt aggtctgtag gcttatgatg gtaaccacaa 6240
gttgttaatg gcattgtgaa aagtttttag ttgcgcttta tgggtggatg ctgaattaca 6300
ttttgatttg atacttataa aaagaaaaag tatttcttca gcttaaaaaa ttgtttaaaa 6360
gtttgtgatc atattgtcta ccatgtagcc agctttcaat tatatgtaag agggactttt 6420
tgacatttac aaataatact ttgaggtaga tatctgaaag caccagcact tggaaggtgt 6480
tcagaagtaa caaattataa aatgagctaa caaacgaaag gcaaaataaa accgtaaagc 6540
aagcagatgg gaggcgtgtt cagtaactta ttcataatgc atctgaaatg attgctgtac 6600
tcaaatattt aacgttagag taatagtatt ttgaatgaaa accatagttg attgtct 6657

<210> SEQ ID NO 8
<211> LENGTH: 295
<212> TYPE: PRT
<213> ORGANISM: Homo sapiens

<400> SEQUENCE: 8

Met Cys Asn Thr Asn Met Ser Val Pro Thr Asp Gly Ala Val Thr Thr
1 5 10 15

Ser Gln Ile Pro Ala Ser Glu Gln Glu Thr Leu Val Arg Pro Lys Pro
20 25 30

-continued

```
Leu Leu Leu Lys Leu Leu Lys Ser Val Gly Ala Gln Lys Asp Thr Tyr
        35                  40                  45

Thr Met Lys Glu Asp Leu Asp Ala Gly Val Ser Glu His Ser Gly Asp
    50                  55                  60

Trp Leu Asp Gln Asp Ser Val Ser Asp Gln Phe Ser Val Glu Phe Glu
65                  70                  75                  80

Val Glu Ser Leu Asp Ser Glu Asp Tyr Ser Leu Ser Glu Glu Gly Gln
                85                  90                  95

Glu Leu Ser Asp Glu Asp Asp Glu Asp Tyr Trp Lys Cys Thr Ser Cys
            100                 105                 110

Asn Glu Met Asn Pro Pro Leu Pro Ser His Cys Asn Arg Cys Trp Ala
        115                 120                 125

Leu Arg Glu Asn Trp Leu Pro Glu Asp Lys Gly Lys Asp Lys Gly Glu
    130                 135                 140

Ile Ser Glu Lys Ala Lys Leu Glu Asn Ser Thr Gln Ala Glu Glu Gly
145                 150                 155                 160

Phe Asp Val Pro Asp Cys Lys Lys Thr Ile Val Asn Asp Ser Arg Glu
                165                 170                 175

Ser Cys Val Glu Glu Asn Asp Asp Lys Ile Thr Gln Ala Ser Gln Ser
            180                 185                 190

Gln Glu Ser Glu Asp Tyr Ser Gln Pro Ser Thr Ser Ser Ser Ile Ile
        195                 200                 205

Tyr Ser Ser Gln Glu Asp Val Lys Glu Phe Glu Arg Glu Glu Thr Gln
    210                 215                 220

Asp Lys Glu Glu Ser Val Glu Ser Ser Leu Pro Leu Asn Ala Ile Glu
225                 230                 235                 240

Pro Cys Val Ile Cys Gln Gly Arg Pro Lys Asn Gly Cys Ile Val His
                245                 250                 255

Gly Lys Thr Gly His Leu Met Ala Cys Phe Thr Cys Ala Lys Lys Leu
            260                 265                 270

Lys Lys Arg Asn Lys Pro Cys Pro Val Cys Arg Gln Pro Ile Gln Met
        275                 280                 285

Ile Val Leu Thr Tyr Phe Pro
    290                 295
```

<210> SEQ ID NO 9
<211> LENGTH: 6735
<212> TYPE: DNA
<213> ORGANISM: Homo sapiens

<400> SEQUENCE: 9

```
tgtgttcagt ggcgattgga gggtagacct gtgggcacgg acgcacgcca ctttttctct      60

gctgatccag gcaaatgtgc aataccaaca tgtctgtacc tactgatggt gctgtaacca     120

cctcacagat tccagcttcg gaacaagaga ccctggttag accaaagcca ttgcttttga     180

agttattaaa gtctgttggt gcacaaaaag acacttatac tatgaaagag gatcttgatg     240

ctggtgtaag tgaacattca ggtgattggt tggatcagga ttcagtttca gatcagttta     300

gtgtagaatt tgaagttgaa tctctcgact cagaagatta tagccttagt gaagaaggac     360

aagaactctc agatgaagat gatgaggtat atcaagttac tgtgtatcag gcaggggaga     420

gtgatacaga ttcatttgaa gaagatcctg aaatttcctt agctgactat tggaaatgca     480

cttcatgcaa tgaaatgaat ccccccctt c catcacattg caacagatgt tgggcccttc     540

gtgagaattg gcttcctgaa gataaaggga aagataaagg ggaaatctct gagaaagcca     600
```

```
aactggaaaa ctcaacacaa gctgaagagg gctttgatgt tcctgattgt aaaaaaacta    660
tagtgaatga ttccagagag tcatgtgttg aggaaaatga tgataaaatt acacaagctt    720
cacaatcaca agaaagtgaa gactattctc agccatcaac ttctagtagc attatttata    780
gcagccaaga agatgtgaaa gagtttgaaa gggaagaaac ccaagacaaa gaagagagtg    840
tggaatctag tttgcccctt aatgccattg aaccttgtgt gatttgtcaa ggtcgaccta    900
aaaatggttg cattgtccat ggcaaaacag gacatcttat ggcctgcttt acatgtgcaa    960
agaagctaaa gaaaaggaat aagccctgcc cagtatgtag acaaccaatt caaatgattg   1020
tgctaactta tttcccctag ttgacctgtc tataagagaa ttatatattt ctaactatat   1080
aaccctagga atttagacaa cctgaaattt attcacatat atcaaagtga gaaaatgcct   1140
caattcacat agatttcttc tctttagtat aattgaccta ctttggtagt ggaatagtga   1200
atacttacta taatttgact tgaatatgta gctcatcctt tacaccaact cctaatttta   1260
aataatttct actctgtctt aaatgagaag tacttggttt tttttttct taaatatgta   1320
tatgacattt aaatgtaact tattattttt tttgagaccg agtcttgctc tgttacccag   1380
gctggagtgc agtggcgtga tcttggctca ctgcaagctc tgcctcccgg gttcgcacca   1440
ttctcctgcc tcagcctccc aattagcttg gcctacagtc atctgccacc acacctggct   1500
aattttttgt acttttagta gagacagggt ttcaccgtgt tagccaggat ggtctcgatc   1560
tcctgacctc gtgatccgcc cacctcggcc tcccaaagtg ctgggattac aggcatgagc   1620
caccgcgtcc ggcctaaatg tcacttagta cctttgatat aaagagaaaa tgtgtgaaag   1680
atttagtttt ttgttttttt gtttgtttgt ttgtttgttt gttttgagat gagtctctct   1740
gtcgcccagg ctggagtgca gtgtcatgat ctagcagtct ccgcttcccg ggttcaagcc   1800
attctcctgg ctcagcctct ggagcagctg ggattacagg catgcaccac catgcccagc   1860
taatttttgt atttttagta gagatagggt ttcaccatgt tggccaggct ggtcacgaac   1920
tcctgacctc aagtgaggtc acccgcctcg gcctcccgaa gtgctgggat tgcagatgtg   1980
agccaccatg tccagccaag aattagtatt taaattttag atactctttt tttttttttt   2040
tttttttttt tttgagacag agtcttgctc catcacccat gctagagtgc agtggagtga   2100
tctcggctca ctgcaacttc cgccttctgg gttcaagcta ttctcctgcc tcagccttcc   2160
aagtaactgg gattacaggc atgtaccacc ataccagctg atttttttgt atttttagta   2220
aagacagggt ttcaccatgt tagccaggct gatcttgaac tcctaaactc aagtgatcta   2280
ctcacctcag cctcccaaaa tgctgggatt acagatgtga ggcacctggc ctcagatttt   2340
tgatactctt aaaccttctg atccttagtt tctctctcca aaatactctt tctaggttaa   2400
aaaaaaaaag gctcttatat ttggtgctat gtaaatgaaa atgtttttta ggttttcttg   2460
atttaacaat agagacaggg tctccctgtg ttgcccaggc tggtctcgaa ctcctgggct   2520
caagagatcc tcctgtcttg gcctcgcaaa gtgctaagta ggattacagg cgttagccac   2580
cacacccggc tgtaaaaatg tacttattct ccagcctctt ttgtataaac catagtaagg   2640
gatgggagta atgatgttat ctgtgaaaat agccaccatt tacccgtaag acaaaacttg   2700
ttaaagcctc ctgagtctaa cctagattac atcaggccct ttttcacaca caaaaaaatc   2760
ctttatggga tttaatggaa tctgttgttt ccccctaagt tgaaaaacaa ctctaagaca   2820
ctttaaagta ccttcttggc ctgggttaca tggttcccag cctaggtttc agacttttgc   2880
ttaaggccag ttttagaaac ccgtgaattc agaaaagtta attcagaaat ttgataaaca   2940
```

-continued

```
gaattgttat ttaaaaacta actggaaaga ttgttaagtt ctttctgaat tattcagaaa   3000
ttatgcatca ttttccttca agaatgacag ggtcagcatg tggaattcca agatacctct   3060
tgacttcctc tcaagctccg tgtttggtca gtggaggccc atccgagctc agcactgaga   3120
agtgttagtt tctttgggac ccatctaccc tgaccacatc atgatgttca tctgcagctg   3180
ttgcaaggtg ttcagattgt ataaacataa atgtcacaaa aactttaaaa gaagtgcaat   3240
tctcaaaagg ttaggtggac taaagcattc tgtaaagcaa ctgctaataa tgagcttaca   3300
gtggatttga atttgaaaaa tatagtaaca agcctgtcaa atatctgcaa gaactatgga   3360
ataaaactac tgatgcagtg aagacagttg aaaagatcaa acaaatgcca agctatattt   3420
ataatgaaca aattcaagaa aaaggactac ggaaagttca ggacatcaaa gaagtcaggc   3480
aaaactcatc ttgacccctg ttgcaggcaa aggaacgcag ctggaagaaa agatgatata   3540
acagttaaca ggatgcagac atggcagagg tttcctaaaa atctcattat ctataaccat   3600
ttctatattt acatttgaaa atctcctttg gagacttaga acctctaaat tattgactta   3660
ttttttatat aaggtcactc cgatgaaagg tgattacaaa atcatctaca ttgctgtcta   3720
caaaacagat aatatggatg tttgatcgca tctcattgtt aactctttac tgatatgttt   3780
gtaaatacag aagtgaaatg tggacataaa atagttacgc tatttggtta atggtactag   3840
acaacatgta attaatgaca ttcaaaaatt tatggctagt gatatatata aagtaaaatt   3900
ttctttgcag taaaatatgc cctttattat agaagggagg atataaggaa ccaacagttt   3960
gtatgaaaat agctcaaata atatctttta ttttgatttt aatatttctt attttggttt   4020
attagtgtct tagaacaaaa tggccttata taatgaagcc tagttatgct ggactgtttt   4080
gatctctttt aattgttctg acagatagtt ggggatgaga gccgaataag gtttgcctga   4140
aataactgac actatataat ttctgctttg gcaaatacta agttctaact tgtcattcct   4200
ggtagaacaa gctttatttt tcgagcctag caatgatcta gaagcagatg ttatctcagt   4260
gccttttgca atttgttgtg tgggtttttt tttttttaaa gccacacaat aattttggaa   4320
aacaatgtat gggtagaaca tgtgtctgtt aattgcacac aaaaccactt ttaatgggta   4380
cagagttaaa tttgaaggaa taagttctag ctgaagtatt atgaactcca aataatgctt   4440
tgaggacctc caaaggtaaa agtactaatc cctttggcca tttattgaga gagagagaga   4500
gagagagtag ggtgactata gttaatgtat tgaatgttct tgctacaaat aaatgatatt   4560
tgagctgatg ggtgtgctaa ttacactgat ttgatcaata cccattgtat gtgaaacagt   4620
acatacacca tatttacaat tatgtattta acatttaaaa tttctaatat aagtatctct   4680
caaactgtgg attaacttct tgatttatat ttaaatatga atcttaagca aaacagtgaa   4740
aataaccatc ttgatttagt gtttttctcc catatgtgaa ttgtatatac ttaggtgaag   4800
acaataaaat caactgaact gtaagcttag aataggactg aggtaattct gcacagcaac   4860
tttactaatg gtacattgtt gcttcaaaac tctctctctc tctctctgtc tgtctcaata   4920
aatggccaaa gggattagta gtttacctgt ggaggtcctc caagcattat ttggagttga   4980
taatacttca gctacaacca agcagaatct cttttttttg gaggtcctcg aagcattatt   5040
tggagttgat aatacttcag cttcaatttg gagttgataa tatttcagct agaacctagt   5100
agaatctgtt tttttccttt ggaggtcctc aaagcattat tggagttcat aatactgaag   5160
ctagaaccaa gcagaatctg ttttttttctg aggagtatcg gtagcataaa tgtgattata   5220
aacatagtac acttgatata tggaggcagt gacagctatt tttacaaaat ttaaatctgc   5280
aaatggattc aacatgttta tgggttatta aaattgtctg atttcttagg ttctttatag   5340
```

```
tacacgtgtt gaaaataaat gattaagaat tgtttcaaga atgcaattat ttgatcttaa   5400
atttttatga gttgttaaaa tagaaattat ttgaatatca tatatttggg taacaaaagg   5460
cacaagtctg aatgtgtttc tttttctgga atggccatgc ctgcccactt tagaaataca   5520
aatatcactg ggcagcttga agcagttggg agcctccaat gagagcaact tgagagaatg   5580
atgttgcaag ttagtaggag taagaaatgc tgtgttctcc ctgtcttctc ttaggtcaca   5640
tggcagcctg gcctaagtga tcgtgaatgg tctataaggg aggtagctgg gacagggagg   5700
ggagtttggg ctagccaccg taccacttgt cagcgtgaaa agtaagattg taattgcctg   5760
tttagttttc tgcctcatct ttgaaagttc caccaagctg ggaacctctt gattgtgagg   5820
cacaaatgta agtacatcag aaaaaaacaa aaaaactggc tttaaagcag gagcttgtgg   5880
gcccctaagc cagacgggga ctagcttttg gcattatata attaagattt tttaaatcct   5940
taataagggt tttattttat ttttatttat tttttgagac ggagtcttgc tctgtggctc   6000
aggctggagt acagtggtgc aatcttggct cactgcaacc tctgcctcct ggctgtgttc   6060
aagtggttct gcttcagcct cccaagtagc tggggttaga gcaccctgtc accacgcccc   6120
gctaattttt gtatttctag cagagatgaa gtttcactat gttggccagg ctgggctcaa   6180
actcctgacc tcaagtgatc tgcccgcctt ggccccccaa agtgctgtga ttacaggcgt   6240
gagccgccac gcccagccta ataagggttt taaagataat tagtgtgtag gtctgtaggc   6300
ttatgatggt aaccacaagt tgttaatggc attgtgaaaa gtttttagtt gcgctttatg   6360
ggtggatgct gaattacatt ttgatttgat acttataaaa agaaaaagta tttcttcagc   6420
ttaaaaaatt gtttaaaagt ttgtgatcat attgtctacc atgtagccag ctttcaatta   6480
tatgtaagag ggactttttg acatttacaa ataatacttt gaggtagata tctgaaagca   6540
ccagcacttg gaaggtgttc agaagtaaca aattataaaa tgagctaaca aacgaaaggc   6600
aaaataaaac cgtaaagcaa gcagatggga ggcgtgttca gtaacttatt cataatgcat   6660
ctgaaatgat tgctgtactc aaatatttaa cgttagagta atagtatttt gaatgaaaac   6720
catagttgat tgtct                                                    6735
```

```
<210> SEQ ID NO 10
<211> LENGTH: 321
<212> TYPE: PRT
<213> ORGANISM: Homo sapiens

<400> SEQUENCE: 10

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Asp Leu Asp Ala Gly Val Ser Glu His Ser Gly Asp
    50                  55                  60

Trp Leu Asp Gln Asp Ser Val Ser Asp Gln Phe Ser Val Glu Phe Glu
65                  70                  75                  80

Val Glu Ser Leu Asp Ser Glu Asp Tyr Ser Leu Ser Glu Glu Gly Gln
                85                  90                  95

Glu Leu Ser Asp Glu Asp Asp Glu Val Tyr Gln Val Thr Val Tyr Gln
            100                 105                 110
```

```
Ala Gly Glu Ser Asp Thr Asp Ser Phe Glu Glu Asp Pro Glu Ile Ser
        115                 120                 125

Leu Ala Asp Tyr Trp Lys Cys Thr Ser Cys Asn Glu Met Asn Pro Pro
    130                 135                 140

Leu Pro Ser His Cys Asn Arg Cys Trp Ala Leu Arg Glu Asn Trp Leu
145                 150                 155                 160

Pro Glu Asp Lys Gly Lys Asp Lys Gly Glu Ile Ser Glu Lys Ala Lys
                165                 170                 175

Leu Glu Asn Ser Thr Gln Ala Glu Glu Gly Phe Asp Val Pro Asp Cys
            180                 185                 190

Lys Lys Thr Ile Val Asn Asp Ser Arg Glu Ser Cys Val Glu Glu Asn
        195                 200                 205

Asp Asp Lys Ile Thr Gln Ala Ser Gln Ser Gln Glu Ser Glu Asp Tyr
    210                 215                 220

Ser Gln Pro Ser Thr Ser Ser Ser Ile Ile Tyr Ser Ser Gln Glu Asp
225                 230                 235                 240

Val Lys Glu Phe Glu Arg Glu Glu Thr Gln Asp Lys Glu Glu Ser Val
                245                 250                 255

Glu Ser Ser Leu Pro Leu Asn Ala Ile Glu Pro Cys Val Ile Cys Gln
            260                 265                 270

Gly Arg Pro Lys Asn Gly Cys Ile Val His Gly Lys Thr Gly His Leu
        275                 280                 285

Met Ala Cys Phe Thr Cys Ala Lys Lys Leu Lys Lys Arg Asn Lys Pro
    290                 295                 300

Cys Pro Val Cys Arg Gln Pro Ile Gln Met Ile Val Leu Thr Tyr Phe
305                 310                 315                 320

Pro
```

<210> SEQ ID NO 11
<211> LENGTH: 3124
<212> TYPE: DNA
<213> ORGANISM: Mus musculus

<400> SEQUENCE: 11

```
gttctctccg cggacggtag gggcgctcg tcacagaact ctgctttgtt aacggggcct      60

ccggggccag cgtagcctag gagcggccgg tgaggagccg ccgccttctc gtcgctcgag     120

ctctggagcg accatggtcg ctcaggcccc ggccgcgggg cctccgcgct ccccgtgaag     180

ggtcggaaga tgcgcgggaa gtagcagccg tctgctgggc gagcgggaga ccgaccggac     240

acccctgggg gaccctctcg gatcaccgcg cttctcctgc gggcctccag gccaatgtgc     300

aataccaaca tgtctgtgtc taccgagggt gctgcaagca cctcacagat tccagcttcg     360

gaacaagaga ctctggttag accaaaacca ttgcttttga agttgttaaa gtccgttgga     420

gcgcaaaacg acacttacac tatgaaagag attatatttt atattggcca gtatattatg     480

actaagaggt tatatgacga gaagcagcag cacattgtgt attgttcaaa tgatctccta     540

ggagatgtgt ttggagtccc gagtttctct gtgaaggagc acaggaaaat atatgcaatg     600

atctacagaa atttagtggc tgtaagtcag caagactctg gcacatcgct gagtgagagc     660

agacgtcagc ctgaaggtgg gagtgatctg aaggatcctt tgcaagcgcc accagaagag     720

aaaccttcat cttctgattt aatttctaga ctgtctacct catctagaag gagatccatt     780

agtgagacag aagagaacac agatgagcta cctggggagc ggcaccggaa gcgccgcagg     840

tccctgtcct ttgatccgag cctgggtctg tgtgagctga gggagatgtg cagcggcggc     900
```

-continued

```
agcagcagca gtagcagcag cagcagcgag tccacagaga cgccctcgca tcaggatctt    960
gacgatggcg taagtgagca ttctggtgat tgcctggatc aggattcagt ttctgatcag   1020
tttagcgtgg aatttgaagt tgagtctctg gactcggaag attacagcct gagtgacgaa   1080
gggcacgagc tctcagatga ggatgatgag gtctatcggg tcacagtcta tcagacagga   1140
gaaagcgata cagactcttt tgaaggagat cctgagattt ccttagctga ctattggaag   1200
tgtacctcat gcaatgaaat gaatcctccc cttccatcac actgcaaaag atgctggacc   1260
cttcgtgaga actggcttcc agacgataag gggaaagata aagtggaaat ctctgaaaaa   1320
gccaaactgg aaaactcagc tcaggcagaa gaaggcttgg atgtgcctga tggcaaaaag   1380
ctgacagaga atgatgctaa agagccatgt gctgaggagg acagcgagga gaaggccgaa   1440
cagacgcccc tgtcccagga gagtgacgac tattcccaac catcgacttc cagcagcatt   1500
gtttatagca gccaagaaag cgtgaaagag ttgaaggagg aaacgcagga caaagacgag   1560
agtgtggaat ctagcttctc cctgaatgcc atcgaaccat gtgtgatctg ccaggggcgg   1620
cctaaaaatg gctgcattgt tcacggcaag actggacacc tcatgtcatg tttcacgtgt   1680
gcaaagaagc taaaaaaaag aaacaagccc tgcccagtgt gcagacagcc aatccaaatg   1740
attgtgctaa cttacttcaa ctagctgacc tgctcacaaa aatagaattt tatatttcta   1800
actatatgac cccaaatta gacaacatgg gtattatttt tatacattaa agccagaaaa   1860
ctgtcttagt ccacataaaa ttcacttata atttatcctg gagagtaaat atggtgaata   1920
ttttcttcct ttttagggaa atttcacttg tttattttat atttgtgttt taagtaattt   1980
gcattggctg tttatatttt ccttatattt taaataatct ccgcttggaa ggactttgga   2040
agtgtatgtg agaagtcctt tccatctcct gcagatgatg gtggaccttc ctcatcaagg   2100
gctacagaag tacttgattt ctgttttttt tgttaataat aagaacattt aatttattta   2160
gtgtctttca tgtaaagagt taaagactat gtgaaggatt gtatatttaa gttattgaaa   2220
ttctgaaact gtagtaatct aaaatgtgtg agttgtgggc tgcagagaag actcagccag   2280
taaaggcacc tgctgtgtac acccactgac acacatttga tccttggaac cccaggaag    2340
agtgaaccag ttccacaaag ttgttccctg atcttcaaat ggatgcacgc atgcacgcac   2400
acacacgcgc gcgtgcgcac acacacacac acacacacac acacacacac acacacacac   2460
acacacacag ttttaaaggc atgaattgca tctggtggta tgtaagtgaa aacacacgcc   2520
ttattttcca gcattttcag ctttttgtca taggggtgtg gcacaagtgt tgcagtttgt   2580
cccaggttga aaagcctgag gctggtagaa gcgccttttt gcctcagctc cgtggttcct   2640
ggtggttgcc tatgtttcag gcctgtactt aggctaggtt tagaaaccag cccattcaga   2700
aagactgaat cagaacatgg ataaagtgaa ctcattctaa gatgactcgt ctatccatgt   2760
agattaatct cctggttcat aataggcctc ttccctttga ttgaagggtc acgtctaagt   2820
atagaaaaca taaaactgta aggtagagga agcgaaggat agctttgtat taatgttgcg   2880
ttaaagcttc agagacaaga acaagaacac tcctcccacg tgacagcatt tgaataggag   2940
gcggtgggtg cggcagcctg ggcagcttca gtcccgattt acaataaagt accttgtgtg   3000
ttattagttc ttaaatgttt atttagaaat ggcattgatg ttatttattt gcaaataaat   3060
ggtttattga agaattgtga aagagatttg tcttacacaa aaaaaaaaaa aaaaaaaaaa   3120
aaaa                                                                3124
```

<210> SEQ ID NO 12
<211> LENGTH: 489
<212> TYPE: PRT
<213> ORGANISM: Mus musculus

<400> SEQUENCE: 12

```
Met Cys Asn Thr Asn Met Ser Val Ser Thr Glu Gly Ala Ala Ser Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Asn Asp Thr Tyr
        35                  40                  45

Thr Met Lys Glu Ile Ile Phe Tyr Ile Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Val Phe Gly Val Pro Ser Phe Ser Val Lys Glu His
                85                  90                  95

Arg Lys Ile Tyr Ala Met Ile Tyr Arg Asn Leu Val Ala Val Ser Gln
            100                 105                 110

Gln Asp Ser Gly Thr Ser Leu Ser Glu Ser Arg Arg Gln Pro Glu Gly
        115                 120                 125

Gly Ser Asp Leu Lys Asp Pro Leu Gln Ala Pro Pro Glu Glu Lys Pro
    130                 135                 140

Ser Ser Ser Asp Leu Ile Ser Arg Leu Ser Thr Ser Ser Arg Arg Arg
145                 150                 155                 160

Ser Ile Ser Glu Thr Glu Glu Asn Thr Asp Glu Leu Pro Gly Glu Arg
                165                 170                 175

His Arg Lys Arg Arg Arg Ser Leu Ser Phe Asp Pro Ser Leu Gly Leu
            180                 185                 190

Cys Glu Leu Arg Glu Met Cys Ser Gly Gly Ser Ser Ser Ser Ser Ser
        195                 200                 205

Ser Ser Ser Glu Ser Thr Glu Thr Pro Ser His Gln Asp Leu Asp Asp
    210                 215                 220

Gly Val Ser Glu His Ser Gly Asp Cys Leu Asp Gln Asp Ser Val Ser
225                 230                 235                 240

Asp Gln Phe Ser Val Glu Phe Glu Val Glu Ser Leu Asp Ser Glu Asp
                245                 250                 255

Tyr Ser Leu Ser Asp Glu Gly His Glu Leu Ser Asp Glu Asp Asp Glu
            260                 265                 270

Val Tyr Arg Val Thr Val Tyr Gln Thr Gly Glu Ser Asp Thr Asp Ser
        275                 280                 285

Phe Glu Gly Asp Pro Glu Ile Ser Leu Ala Asp Tyr Trp Lys Cys Thr
    290                 295                 300

Ser Cys Asn Glu Met Asn Pro Pro Leu Pro Ser His Cys Lys Arg Cys
305                 310                 315                 320

Trp Thr Leu Arg Glu Asn Trp Leu Pro Asp Asp Lys Gly Lys Asp Lys
                325                 330                 335

Val Glu Ile Ser Glu Lys Ala Lys Leu Glu Asn Ser Ala Gln Ala Glu
            340                 345                 350

Glu Gly Leu Asp Val Pro Asp Gly Lys Lys Leu Thr Glu Asn Asp Ala
        355                 360                 365
```

```
Lys Glu Pro Cys Ala Glu Glu Asp Ser Glu Glu Lys Ala Glu Gln Thr
    370                 375                 380

Pro Leu Ser Gln Glu Ser Asp Asp Tyr Ser Gln Pro Ser Thr Ser Ser
385                 390                 395                 400

Ser Ile Val Tyr Ser Ser Gln Glu Ser Val Lys Glu Leu Lys Glu Glu
                405                 410                 415

Thr Gln Asp Lys Asp Glu Ser Val Glu Ser Ser Phe Ser Leu Asn Ala
            420                 425                 430

Ile Glu Pro Cys Val Ile Cys Gln Gly Arg Pro Lys Asn Gly Cys Ile
        435                 440                 445

Val His Gly Lys Thr Gly His Leu Met Ser Cys Phe Thr Cys Ala Lys
    450                 455                 460

Lys Leu Lys Lys Arg Asn Lys Pro Cys Pro Val Cys Arg Gln Pro Ile
465                 470                 475                 480

Gln Met Ile Val Leu Thr Tyr Phe Asn
                485


<210> SEQ ID NO 13
<211> LENGTH: 3039
<212> TYPE: DNA
<213> ORGANISM: Mus musculus

<400> SEQUENCE: 13

gttctctccg cggacggtag ggggcgctcg tcacagaact ctgctttgtt aacggggcct     60

ccggggccag cgtagcctag gagcggccgg tgaggagccg ccgccttctc gtcgctcgag    120

ctctggagcg accatggtcg ctcaggcccc ggccgcgggg cctccgcgct ccccgtgaag    180

ggtcggaaga tgcgcgggaa gtagcagccg tctgctgggc gagcgggaga ccgaccggac    240

acccctgggg gaccctctcg gatcaccgcg cttctcctgc gggcctccag gttagaccaa    300

aaccattgct tttgaagttg ttaaagtccg ttggagcgca aaacgacact tacactatga    360

aagagattat attttatatt ggccagtata ttatgactaa gaggttatat gacgagaagc    420

agcagcacat tgtgtattgt tcaaatgatc tcctaggaga tgtgtttgga gtcccgagtt    480

tctctgtgaa ggagcacagg aaaatatatg caatgatcta cagaaattta gtggctgtaa    540

gtcagcaaga ctctggcaca tcgctgagtg agagcagacg tcagcctgaa ggtgggagtg    600

atctgaagga tcctttgcaa gcgccaccag aagagaaacc ttcatcttct gatttaattt    660

ctagactgtc tacctcatct agaaggagat ccattagtga gacagaagag aacacagatg    720

agctacctgg ggagcggcac cggaagcgcc gcaggtccct gtcctttgat ccgagcctgg    780

gtctgtgtga gctgagggag atgtgcagcg gcggcagcag cagcagtagc agcagcagca    840

gcgagtccac agagacgccc tcgcatcagg atcttgacga tggcgtaagt gagcattctg    900

gtgattgcct ggatcaggat tcagtttctg atcagtttag cgtggaattt gaagttgagt    960

ctctggactc ggaagattac agcctgagtg acgaagggca cgagctctca gatgaggatg   1020

atgaggtcta tcgggtcaca gtctatcaga caggagaaag cgatacagac tcttttgaag   1080

gagatcctga gatttcctta gctgactatt ggaagtgtac ctcatgcaat gaaatgaatc   1140

ctccccttcc atcacactgc aaaagatgct ggacccttcg tgagaactgg cttccagacg   1200

ataaggggaa agataaagtg gaaatctctg aaaaagccaa actggaaaac tcagctcagg   1260

cagaagaagg cttggatgtg cctgatggca aaaagctgac agagaatgat gctaaagagc   1320

catgtgctga ggaggacagc gaggagaagg ccgaacagac gcccctgtcc caggagagtg   1380
```

```
acgactattc ccaaccatcg acttccagca gcattgttta tagcagccaa gaaagcgtga   1440
aagagttgaa ggaggaaacg caggacaaag acgagagtgt ggaatctagc ttctccctga   1500
atgccatcga accatgtgtg atctgccagg ggcggcctaa aaatggctgc attgttcacg   1560
gcaagactgg acacctcatg tcatgtttca cgtgtgcaaa gaagctaaaa aaaagaaaca   1620
agccctgccc agtgtgcaga cagccaatcc aaatgattgt gctaacttac ttcaactagc   1680
tgacctgctc acaaaaatag aattttatat ttctaactat atgacccccca aattagacaa   1740
catgggtatt atttttatac attaaagcca gaaaactgtc ttagtccaca taaaattcac   1800
ttataattta tcctggagag taaatatggt gaatattttc ttccttttta gggaaatttc   1860
acttgtttat tttatatttg tgttttaagt aatttgcatt ggctgtttat attttcctta   1920
tattttaaat aatctccgct tggaaggact ttggaagtgt atgtgagaag tcctttccat   1980
ctcctgcaga tgatggtgga ccttcctcat caagggctac agaagtactt gatttctgtt   2040
tttttgtta ataataagaa catttaattt atttagtgtc tttcatgtaa agagttaaag   2100
actatgtgaa ggattgtata tttaagttat tgaaattctg aaactgtagt aatctaaaat   2160
gtgtgagttg tgggctgcag agaagactca gccagtaaag gcacctgctg tgtacaccca   2220
ctgacacaca tttgatcctt ggaaccccca ggaagagtga accagttcca caaagttgtt   2280
ccctgatctt caaatggatg cacgcatgca cgcacacaca cgcgcgcgtg cgcacacaca   2340
cacacacaca cacacacaca cacacacaca cacacacaca cacagtttta aaggcatgaa   2400
ttgcatctgg tggtatgtaa gtgaaaacac acgccttatt ttccagcatt ttcagctttt   2460
tgtcataggg gtgtggcaca agtgttgcag tttgtcccag gttgaaaagc ctgaggctgg   2520
tagaagcgcc tttttgcctc agctccgtgg ttcctggtgg ttgcctatgt ttcaggcctg   2580
tacttaggct aggtttagaa accagcccat tcagaaagac tgaatcagaa catggataaa   2640
gtgaactcat tctaagatga ctcgtctatc catgtagatt aatctcctgg ttcataatag   2700
gcctcttccc tttgattgaa gggtcacgtc taagtataga aaacataaaa ctgtaaggta   2760
gaggaagcga aggatagctt tgtattaatg ttgcgttaaa gcttcagaga caagaacaag   2820
aacactcctc ccacgtgaca gcatttgaat aggaggcggt gggtgcggca gcctgggcag   2880
cttcagtccc gatttacaat aaagtacctt gtgtgttatt agttcttaaa tgtttattta   2940
gaaatggcat tgatgttatt tatttgcaaa taaatggttt attgaagaat tgtgaaagag   3000
atttgtctta cacaaaaaaa aaaaaaaaaa aaaaaaaaa                          3039
```

<210> SEQ ID NO 14
<211> LENGTH: 440
<212> TYPE: PRT
<213> ORGANISM: Mus musculus

<400> SEQUENCE: 14

```
Met Lys Glu Ile Ile Phe Tyr Ile Gly Gln Tyr Ile Met Thr Lys Arg
1               5                   10                  15

Leu Tyr Asp Glu Lys Gln Gln His Ile Val Tyr Cys Ser Asn Asp Leu
            20                  25                  30

Leu Gly Asp Val Phe Gly Val Pro Ser Phe Ser Val Lys Glu His Arg
        35                  40                  45

Lys Ile Tyr Ala Met Ile Tyr Arg Asn Leu Val Ala Val Ser Gln Gln
    50                  55                  60

Asp Ser Gly Thr Ser Leu Ser Glu Ser Arg Arg Gln Pro Glu Gly Gly
65                  70                  75                  80
```

```
Ser Asp Leu Lys Asp Pro Leu Gln Ala Pro Pro Glu Glu Lys Pro Ser
                85                  90                  95

Ser Ser Asp Leu Ile Ser Arg Leu Ser Thr Ser Ser Arg Arg Arg Ser
            100                 105                 110

Ile Ser Glu Thr Glu Glu Asn Thr Asp Glu Leu Pro Gly Glu Arg His
        115                 120                 125

Arg Lys Arg Arg Arg Ser Leu Ser Phe Asp Pro Ser Leu Gly Leu Cys
    130                 135                 140

Glu Leu Arg Glu Met Cys Ser Gly Gly Ser Ser Ser Ser Ser Ser Ser
145                 150                 155                 160

Ser Ser Glu Ser Thr Glu Thr Pro Ser His Gln Asp Leu Asp Asp Gly
                165                 170                 175

Val Ser Glu His Ser Gly Asp Cys Leu Asp Gln Asp Ser Val Ser Asp
            180                 185                 190

Gln Phe Ser Val Glu Phe Glu Val Glu Ser Leu Asp Ser Glu Asp Tyr
        195                 200                 205

Ser Leu Ser Asp Glu Gly His Glu Leu Ser Asp Glu Asp Asp Glu Val
    210                 215                 220

Tyr Arg Val Thr Val Tyr Gln Thr Gly Glu Ser Asp Thr Asp Ser Phe
225                 230                 235                 240

Glu Gly Asp Pro Glu Ile Ser Leu Ala Asp Tyr Trp Lys Cys Thr Ser
                245                 250                 255

Cys Asn Glu Met Asn Pro Pro Leu Pro Ser His Cys Lys Arg Cys Trp
            260                 265                 270

Thr Leu Arg Glu Asn Trp Leu Pro Asp Asp Lys Gly Lys Asp Lys Val
        275                 280                 285

Glu Ile Ser Glu Lys Ala Lys Leu Glu Asn Ser Ala Gln Ala Glu Glu
    290                 295                 300

Gly Leu Asp Val Pro Asp Gly Lys Lys Leu Thr Glu Asn Asp Ala Lys
305                 310                 315                 320

Glu Pro Cys Ala Glu Glu Asp Ser Glu Glu Lys Ala Glu Gln Thr Pro
                325                 330                 335

Leu Ser Gln Glu Ser Asp Asp Tyr Ser Gln Pro Ser Thr Ser Ser Ser
            340                 345                 350

Ile Val Tyr Ser Ser Gln Glu Ser Val Lys Glu Leu Lys Glu Glu Thr
        355                 360                 365

Gln Asp Lys Asp Glu Ser Val Glu Ser Ser Phe Ser Leu Asn Ala Ile
    370                 375                 380

Glu Pro Cys Val Ile Cys Gln Gly Arg Pro Lys Asn Gly Cys Ile Val
385                 390                 395                 400

His Gly Lys Thr Gly His Leu Met Ser Cys Phe Thr Cys Ala Lys Lys
                405                 410                 415

Leu Lys Lys Arg Asn Lys Pro Cys Pro Val Cys Arg Gln Pro Ile Gln
            420                 425                 430

Met Ile Val Leu Thr Tyr Phe Asn
        435                 440
```

<210> SEQ ID NO 15
<211> LENGTH: 10090
<212> TYPE: DNA
<213> ORGANISM: Homo sapiens -continued

<400> SEQUENCE: 15

```
gtgtgggagg ccggaagttg cggcttcatt actcgccatt tcaaaatgct gccgaggccc     60
taggatctgt gactgccacc cctcccccca cccgggctcg gcgggggagc gactcatgga    120
gctgccgtaa gttttaccaa cagactgcag tttcttcact accaaaatga catcattttc    180
cacctctgct cagtgttcaa catctgacag tgcttgcagg atctctcctg gacaaatcaa    240
tcaggtacga ccaaaactgc cgcttttgaa gattttgcat gcagcaggtg cgcaaggtga    300
aatgttcact gttaaagagg tcatgcacta tttaggtcag tacataatgg tgaagcaact    360
ttatgatcag caggagcagc atatggtata ttgtggtgga gatcttttgg gagaactact    420
gggacgtcag agcttctccg tgaaagaccc aagccctctc tatgatatgc taagaaagaa    480
tcttgtcact ttagccactg ctactacaga tgctgctcag actctcgctc tcgcacagga    540
tcacagtatg gatattccaa gtcaagacca actgaagcaa agtgcagagg aaagttccac    600
ttccagaaaa agaactacag aagacgatat ccccacactg cctacctcag agcataaatg    660
catacattct agagaagatg aagacttaat tgaaaattta gcccaagatg aaacatctag    720
gctggacctt ggatttgagg agtgggatgt agctggcctg ccttggtggt ttttaggaaa    780
cttgagaagc aactatacac ctagaagtaa tggctcaact gatttacaga caaatcagga    840
tgtgggtact gccattgttt cagatactac agatgacttg tggtttttga atgagtcagt    900
atcagagcag ttaggtgttg gaataaaagt tgaagctgct gatactgaac aaacaagtga    960
agaagtaggg aaagtaagtg acaaaaaggt gattgaagtg ggaaaaaatg atgacctgga   1020
ggactctaag tccttaagtg atgataccga tgtagaggtt acctctgagg atgagtggca   1080
gtgtactgaa tgcaagaaat ttaactctcc aagcaagagg tactgttttc gttgttgggc   1140
cttgaggaag gattggtatt cagattgttc aaagttaacc cattctctct ccacgtctga   1200
tatcactgcc atacctgaaa aggaaaatga aggaaatgat gtccctgatt gtcgaagaac   1260
catttcggct cctgtcgtta gacctaaaga tgcgtatata aagaaagaaa actccaaact   1320
ttttgatccc tgcaactcag tggaattctt ggatttggct cacagttctg aaagccaaga   1380
gaccatctca agcatgggag aacagttaga taacctttct gaacagagaa cagatacaga   1440
aaacatggag gattgccaga atctcttgaa gccatgtagc ttatgtgaga aaagaccacg   1500
agacgggaac attattcatg gaaggacggg ccatcttgtc acttgttttc actgtgccag   1560
aagactaaag aaggctgggg cttcatgccc tatttgcaag aaagagattc agctggttat   1620
taaggttttt atagcataat ggtagtacga acataaaaat gcatttattc cgttcactta   1680
ccacattatt tgaaaatcaa tcctttattt aattttattt ccaacctgtc agagaatgtt   1740
cttaggcatc aaaatccaag gtagctgtaa gaaaaatact ggagctaaca atgaagaaca   1800
gaagtaatct gattagtcaa attattaagt gccatggatt actttatgca gcagtcaggt   1860
acatagttag gtgaacccaa aagaaaaact cttgaaaaca agagatttct tccatgcaca   1920
tttacaatat tgaggtataa ttaacatgat aaagtgtttc cttctaacga gttgtagaaa   1980
tctgagtaac cacccaaaaa agcaatagaa tgtttctgtc accccaaaac actcccttct   2040
gcccctcttc agacagtcct tcagctattt catggctctc accctagttt tttttttttt   2100
tgcacttttt tttttccggg ggtatagggg aggtgtgggg cgacagggtc tgtcttgttc   2160
tgtctcccag gctgaagtgc agtgcagtgg tatgatcatg gctcactgca gccttggttt   2220
cctgggcata agtggtcttc ccacttcagc ctcctgagta gctgagacta tagactagca   2280
```

-continued taaccacact ggctaatttt ttgtggagat gaagtctcac tatgttgccc aggctggtct 2340
cgaactcctg ggctcaaaca atcctcccgc ctcagccttc caaattgctg ggattatagt 2400
catgaggcac ctagtctggc ccttttgcaa gactttaatc tgaaatctaa atttttaaaa 2460
tttaagtact tacaaaggat atactatcca acatattgca tattatatat gtgctttaaa 2520
gttttttttt ttttttgaga gacggtctca ctttgtcatc caagctggag tgcagtggtg 2580
caaacacggc ccacctcctg ggctcaagtg atcctccagc ctcagcttcc ctcacaggca 2640
ttcactatca ctcccagcta attaaaataa tttgtagacg gtgtctcgtt atgttgccca 2700
ggctggtctc gaactcctgg gtttaagtga ttccccccgcc tcagcctccc aaagtgttgg 2760
gcttacagcc ttgagccact atgcttggct caaagatatt tttatgaaag ccctgggact 2820
atagatttag ctgattaaat ttatagaaaa agtcctgtca tataaactgg caaagtctgt 2880
tcttaattta attagccaaa tcagacttaa cttccgtcag aacatgtctt ggttttaatt 2940
cagataaaca cacaaacata cttctctggc acagccttca gaagcatcag tttttgtttt 3000
gttttgtttt gtttttttgag acagggtctt gctctgtcgc ccaggctgga gtgcactggc 3060
acaatcacag ttcactgcag cctcgacctc ccagatccaa gcaatcctcc cacctaagcc 3120
tcccaagtag ctgggtctat aggcgcgtgc caccaccatg cccagctgaa ttttgtattt 3180
tttgtacaga cagcattttg ccatgttgcc caggctggtc ccaaacttct agcctcaagc 3240
aaccctcctg cctcagcctc tcaaagtgct aggattgcag tcctgagcta ctgcccccta 3300
ccctctttgc gtcttaggag tcatttagat ttttttttgat ccttttgttt agtgcctctg 3360
gagctgctta caccaaggca atacgccttg atatactgga tggttgagag gcagcctctt 3420
ttttttttt ttttttttt ttttttgga ggatagggag tatggctgtt gtgaaaaggg 3480
aggtaaagag aaatggtaga tctgaagagg cctcatcaga gcacatattt taggacaaca 3540
catatggaaa ttggacatct ttaagttggt ttccatagag ctatgcatgt atccttaccc 3600
ccatgggaaa atgttggtgt gttctcaagg gtatgcatgt gtcattttga agaccaaggc 3660
cctagaattg tcaaacttaa ggatcataaa aatcatgagg gttgcttgtt aaaaatgtcc 3720
aaacgtgcag agactgatct ttgagatctg gaccaggaat ttgcatttga acaagtgttc 3780
ctggaatctc tatgcaagtt ttatacagaa catacttttg gaatccttgc cctagacagg 3840
ggtgtccaat cttttggctt ccctggtcca caatggaaga agaattgtct tggaccacac 3900
ataaaataca ctaacactaa caatagctga tgagctaaaa aaaaaaaaaa aaaaaaatcgt 3960
ggaccgggcg tagtggctca cgcctgtaat cccaacactt tgggagatca cctaggtcgg 4020
gagtttgaga ccagcctgac cgacatggag aaaccccatt tttactaaaa atacaaaaaa 4080
ttagctgggc atggtggtgc atgcctgtag tcccagctac tcaggaggct gaggcaggag 4140
aatcgcttga acctgagagg gggagattgc ggtgagctga gattgcgcca ttgcacccca 4200
gcctgggcaa caatagcgaa actgtctcag aaaaaagaaa aaaaaaatcg caaaaagaaa 4260
aatctcataa tgtcgttgtt ggtttttttt ttttttttg agacagtctc actctgttgc 4320
ccaggctgga gtgcaatggc atgatctctg ctcaccgcaa cctctgcctc ccgggttcag 4380
gtgattctcc tgcctcagcc tcccagatag ctgggactac aggcacatac caccatgcct 4440
ggctaatttt tgtattttta gtagagatgg gggtttcact gtgttggcca ggctggtctc 4500
gaactcctga cctcatgatc cacacacctc ggcctcccaa agtcctgcga ttacaggcgt 4560
gagctaccgc acccagccaa gttgtaattt ttaataaaac ttaagaagta aacattttac 4620
ttatgtttat aggtatttga tcctaaattt gacacatcat tgcccatgaa agaatcctct 4680

-continued

```
taggctgctc agcttcactc ttcctgcttg cccaccgggg tttttcactg cttctgttag   4740
cactaagtac ttagacgatc ctaagatatg tgcttgagcc gaatttcatc tttacttgta   4800
ggaaacttta aactatttct tttcttttct tttttttttt tttttacttg agatggagtt   4860
ttgctcttgt cgcccaggct ggagtgcagt ggagtgatct cggctcactg caacctctgc   4920
ctcccgggtt caaatgattc tcctgcctca gcctcccaag tagctgggat tacaggtgtg   4980
caccaccatg tctggctaat tttgtatttt tagtagagat ggtttcacca tgttggtcag   5040
gctggtctcg aactcctgac ctcaggtcat ccacccacct cagcctcgca aagtgctgag   5100
attacaggca tgagccacag cgcccagctt aaactatttt cttggtctgt ttttgatttt   5160
ctttttttcct tgccactgcg gtacagattt tttttactca ctgccactaa actaaagcaa   5220
ggcatagttt atatgtgaag tgttcagagt ttactgctat aaggaaactt ccaaatactg   5280
acatttacct tttagctgta gttattggga ccatgtgctc tggttttctg gagactgcca   5340
aattgctccc atttttctgc atcccacctg gtttctttct gcatgtcccc tttcactttc   5400
aaacctcttc atttggatgt taaattatat ggtcacctag ttataggtaa gccttgttcg   5460
agttgatatc ttgattgtga ggaaggatct gtgtcattgg agcttgtttc tgctgcaacg   5520
tgctgtagac tatgaataat gaaatcacac cacattacca tcagatttct tgttttagtt   5580
gtcaaattaa tatttatgat tgttatcttg ggcgaaaagt tcagagcaga gatgacaaat   5640
cattagaaca acgatgaatt tcagtattac ggctaaaaag ttcttctgtc tgaatattaa   5700
ctcactctcc ttccagtgta cttcacagta attggtatgc tttttttattt aatgcttaaa   5760
tcaaacttta taaaaatctt agaccagatc tttaatatgg tatgccattt ccccagtcta   5820
ccaatggaat agtatgggtt tctaatccta ggcttgtaca atggattgga gttgagccat   5880
gccagcctcc acactgccac taacttctgt aatgtaagat tgagtcactg ccaagcattt   5940
gaaatatgca gttgtgtttt aattataatt tatgtatagt tagatgtatg tagtgcattg   6000
tgtggtatta tttggtttgt aagaatttat ttttaagggt caaggtcatt tgtaacattt   6060
tgtgtgtgtc aattcaatgc aatgttggct gccttttgaa gtctttgata tattggtgaa   6120
tattcttctg atctataata caaagctatg taatgttacc tcttgactcg cttttgaaag   6180
gaagacaatt gttaactaga tatttgagtt ttttcccctc agaattatgt gaatttctga   6240
tatatggctt tagatactgt gaatctgttt tccatttagt cagttatctg cttaaattgt   6300
tcagaactat atcctaacga gcaattagtt ctgatggttc tcccagtcat gagtgtgcat   6360
gtgtgcaagc atgttttgat cctgatgcta cctttgctaa aaatggccat agattaggaa   6420
ctagctatgt ttttagaatc aaagatgaac cggtaagctg tctcatgtac caaacgtgaa   6480
atttacagtg tttacaaatg tctggaattt tgcactgcca tagggaatgt taaggttact   6540
tggctggaat ttatcagact tgtgagtaaa caagttgaag tttagcagat gagggggaat   6600
attgaggccc ctaaggctaa acaaaataat cagtatctga gatagtggct aatgtggctc   6660
cccaggccta atttgggaac agtttttcct gattgctttg agaagtactt tcttttgaca   6720
gaaattttca ttctgcttgc cattgctata ttctcccttt ataggagcca ttggatttct   6780
ttccttttgt gggaaatgtc ccattagcat tttcagatct tttgatgtgc actaatgcca   6840
ttattggtaa tgccgttatt ggtgaataca gcatagttaa ataaactgtt acagtaaatc   6900
tacacttgga tttgctgcac ctctaccaat agccttttga atgactgaaa gtgttaacag   6960
agaaagaggc atgtctgcag aaagagatag ctaatatttt ttggtacttt atctgaaatc   7020
```

-continued

```
caagatgctg cttcccctgc aggttgtttt ccttcttacg atcctcattg aatcccctct   7080
gggagcacag gacagttagt agaactctcc atttcttttt ttttttttt agacggagtc   7140
tctctctgtc gccccggctg gagtgcagtg gcgcgatctc ggctcactgc aacctccgcc   7200
tcccgggttc accccattct cctgcctcag cctccctagt agctgggact ataggcgccc   7260
gccaccacgc ctggctaatt tttgtatttt tattggagac ggggtttcac cgtcttagcc   7320
aggatggtct tgatctcctg acctcgtgat ctgcccacct cagcctccca aagtactggg   7380
attacaggcg tgagccaccg cgcccggccg gaactctcca tttcttaagg taaagagggt   7440
caaggatacc taaaaagggt caaataatgc tagaagagca attcctcttt cagagcagtt   7500
gctgtaattt ggcaaatgct ttatcgaaga ttgatattag gctaggggcg gtggcttacg   7560
cctgtaatcc cagcactttg ggaggccgag gtgggtggat tgcctgagct caggagttcg   7620
agaccagtct gaccagtatg gtgaaaccct gtctctacta aaaatacaaa aattagccgg   7680
tcgtggtggc gtgcacctgt agtcccagct acttggcagg ttgagacagg agaatcgctt   7740
gaacctggga ggtggaggtt gcagtgagcc gagactgcac cactgcgctc ccacctgggt   7800
gacagagact ctgtctcaaa aaaaaggaca tttatcatta taacatctta ttagagcccc   7860
taatttctta tctgaaggca ctgttttttt ttttaaacag ttaagtactg atgtcaacag   7920
acaaatattt ctgatcagat agtcccctgt caacagtagc aaatgtggtt tcataaagtg   7980
ggaagaaaac agcattttaa agtaactttt tgggagactg atttgagtaa taataaaact   8040
ctggtctccc ttaagaaaaa aaaacccttc cacctttact gtgtcattta tatcccctta   8100
gttccaaagt taattatctt atttctggat attgctttta taccaaagac ccttatcagc   8160
ccttgtaact acagtatctt tagataagat tcctctttcc agtcagtcct gggaaatgtt   8220
tctgttgcag agttaggcgg tagatgggaa gctgtgatgg cagagctact atctaataaa   8280
gtaacaactc gtagttgagg cttcctttct gtgtgtgatg ggggataggg agttagctcc   8340
cctgttgtct cagcactaag aaattgaggt caggccaggc gcggtggttc actcctgtta   8400
ttccagcact ggggtggcca aagtgggcag attgcttgcg ctctggagct cgagaccagc   8460
ctgggcaaca tggtgaaacc ctgtctctac caaaaataca aaaaaaaagc tgggcatggt   8520
gggtgcatgc ttgtcccagc tactgaggag gctgaggtgg gaggatcgct tgagcctggg   8580
aggtggaggt tgcagtgagc tgagatggca ccactgcaat ccaaggtggg tgacagagac   8640
gctgtctcaa agaaattgag gtcaggcttc cttcttacag aattattttt ttctctgtag   8700
tttgcctcat tttttcactt tcttttcaat gagaatcgaa gtgtttcttt tgggtttttt   8760
tttcccccctt ttaaaatcaa caggaaatgt ttcaaaggag ggatgaaatg cttcttggct   8820
tcctcagcac ttggcaaggt agacctcata gcaaccttga atatgacttt ctttagtctc   8880
tagctatgca ctattaagtg cctcttgggt agaggtagag ttaagtattg agtgccagtc   8940
ttgacgtccg tatgcctcag tttttctcat atataaaaag cagtatacat acctaccctt   9000
ttctacctca tcatttgttg tagggattaa atccgggaga gcaattctga agcctataaa   9060
tttccttgaa gagatctaag aacctattat gctcttggtg taccaagctc tggggtatat   9120
attcagaata cctcatgttc tggaagctga gcactagctc ccctttattg cctgcctggc   9180
agagcctgtt tgattactgc aggccctttt acccatgctt ctagtttagg tattctttct   9240
ttgatatgag gctcttgacc agaaaagagt tctttctcta ggtgttctga gagaagtttg   9300
taaatttgga tagtacattc tatcctgata aaaccacctt gctgtggtct tgatgtacaa   9360
aaaaaaattt tttttttgag acagagtctt actctgtcac ccaggctgga atgcagtggc   9420
```

```
gcaatcttgg ttcactgcaa cccccgcctc ctgggttcaa gcgatcctcc tgcctcaacc   9480

tctcaagtag ctgggactac aggcgtgcac caccacacct ggctaatttt gtatttttag   9540

tagagacagg gtttcaccat gttggccagg ctggtcttga actcctgacc tcaggcgatc   9600

tgcccgcctt ggcctcccaa agtactggga ttacaggcgt gagcaactgc tcctggccca   9660

aaacatctct ttctacatac acttgagtag gtggcataaa atgcactgtc aatatataga   9720

aaacatgaaa ttttccaaat atttccgatc agagaatcac aagagcagca aatgtggttt   9780

catcaagtgg gaagaaagca gcaatttaaa ataacttttt gggagactga attgagtaat   9840

aataaaactt cagtctttcg ctaataataa taataataat aataataaca acaacttatt   9900

gaatgtggcc agctcactag atgaggaaag aggaaggcat tttctgcatt cttgcctagt   9960

tttccttata agcaccacta agttaatagc tctgtctttt tggtgtttgc actatgtaat  10020

gcttttaata ctttttaatt gtgctttttt atgtattaaa tgtttttcct tttgccaaaa  10080

aaaaaaaaaa                                                          10090


<210> SEQ ID NO 16
<211> LENGTH: 490
<212> TYPE: PRT
<213> ORGANISM: Homo sapiens

<400> SEQUENCE: 16

Met Thr Ser Phe Ser Thr Ser Ala Gln Cys Ser Thr Ser Asp Ser Ala
1               5                   10                  15

Cys Arg Ile Ser Pro Gly Gln Ile Asn Gln Val Arg Pro Lys Leu Pro
            20                  25                  30

Leu Leu Lys Ile Leu His Ala Ala Gly Ala Gln Gly Glu Met Phe Thr
        35                  40                  45

Val Lys Glu Val Met His Tyr Leu Gly Gln Tyr Ile Met Val Lys Gln
    50                  55                  60

Leu Tyr Asp Gln Gln Glu Gln His Met Val Tyr Cys Gly Gly Asp Leu
65                  70                  75                  80

Leu Gly Glu Leu Leu Gly Arg Gln Ser Phe Ser Val Lys Asp Pro Ser
                85                  90                  95

Pro Leu Tyr Asp Met Leu Arg Lys Asn Leu Val Thr Leu Ala Thr Ala
            100                 105                 110

Thr Thr Asp Ala Ala Gln Thr Leu Ala Leu Ala Gln Asp His Ser Met
        115                 120                 125

Asp Ile Pro Ser Gln Asp Gln Leu Lys Gln Ser Ala Glu Glu Ser Ser
    130                 135                 140

Thr Ser Arg Lys Arg Thr Thr Glu Asp Asp Ile Pro Thr Leu Pro Thr
145                 150                 155                 160

Ser Glu His Lys Cys Ile His Ser Arg Glu Asp Glu Asp Leu Ile Glu
                165                 170                 175

Asn Leu Ala Gln Asp Glu Thr Ser Arg Leu Asp Leu Gly Phe Glu Glu
            180                 185                 190

Trp Asp Val Ala Gly Leu Pro Trp Trp Phe Leu Gly Asn Leu Arg Ser
        195                 200                 205

Asn Tyr Thr Pro Arg Ser Asn Gly Ser Thr Asp Leu Gln Thr Asn Gln
    210                 215                 220

Asp Val Gly Thr Ala Ile Val Ser Asp Thr Thr Asp Asp Leu Trp Phe
225                 230                 235                 240
```

```
Leu Asn Glu Ser Val Ser Glu Gln Leu Gly Val Gly Ile Lys Val Glu
                245                 250                 255

Ala Ala Asp Thr Glu Gln Thr Ser Glu Glu Val Gly Lys Val Ser Asp
            260                 265                 270

Lys Lys Val Ile Glu Val Gly Lys Asn Asp Asp Leu Glu Asp Ser Lys
        275                 280                 285

Ser Leu Ser Asp Asp Thr Asp Val Glu Val Thr Ser Glu Asp Glu Trp
    290                 295                 300

Gln Cys Thr Glu Cys Lys Lys Phe Asn Ser Pro Ser Lys Arg Tyr Cys
305                 310                 315                 320

Phe Arg Cys Trp Ala Leu Arg Lys Asp Trp Tyr Ser Asp Cys Ser Lys
                325                 330                 335

Leu Thr His Ser Leu Ser Thr Ser Asp Ile Thr Ala Ile Pro Glu Lys
            340                 345                 350

Glu Asn Glu Gly Asn Asp Val Pro Asp Cys Arg Arg Thr Ile Ser Ala
        355                 360                 365

Pro Val Val Arg Pro Lys Asp Ala Tyr Ile Lys Lys Glu Asn Ser Lys
    370                 375                 380

Leu Phe Asp Pro Cys Asn Ser Val Glu Phe Leu Asp Leu Ala His Ser
385                 390                 395                 400

Ser Glu Ser Gln Glu Thr Ile Ser Ser Met Gly Glu Gln Leu Asp Asn
                405                 410                 415

Leu Ser Glu Gln Arg Thr Asp Thr Glu Asn Met Glu Asp Cys Gln Asn
            420                 425                 430

Leu Leu Lys Pro Cys Ser Leu Cys Glu Lys Arg Pro Arg Asp Gly Asn
        435                 440                 445

Ile Ile His Gly Arg Thr Gly His Leu Val Thr Cys Phe His Cys Ala
    450                 455                 460

Arg Arg Leu Lys Lys Ala Gly Ala Ser Cys Pro Ile Cys Lys Lys Glu
465                 470                 475                 480

Ile Gln Leu Val Ile Lys Val Phe Ile Ala
                485                 490


<210> SEQ ID NO 17
<211> LENGTH: 9940
<212> TYPE: DNA
<213> ORGANISM: Homo sapiens

<400> SEQUENCE: 17

gtgtgggagg ccggaagttg cggcttcatt actcgccatt tcaaaatgct gccgaggccc      60

taggatctgt gactgccacc cctcccccca cccgggctcg gcgggggagc gactcatgga     120

gctgccgtaa gttttaccaa cagactgcag tttcttcact accaaaatga catcattttc     180

cacctctgct cagtgttcaa catctgacag tgcttgcagg atctctcctg gacaaatcaa     240

tcaggtacga ccaaaactgc cgcttttgaa gattttgcat gcagcaggtg cgcaaggtga     300

aatgttcact gttaaagagg tcatgcacta tttaggtcag tacataatgg tgaagcaact     360

ttatgatcag caggagcagc atatggtata ttgtggtgga gatcttttgg gagaactact     420

gggacgtcag agcttctccg tgaaagaccc aagccctctc tatgatatgc taagaaagaa     480

tcttgtcact ttagccactg ctactacaga tgctgctcag actctcgctc tcgcacagga     540

tcacagtatg gatattccaa gtcaagacca actgaagcaa agtgcagagg aaagttccac     600

ttccagaaaa agaactacag aagacgatat ccccacactg cctacctcag agcataaatg     660
```

-continued

```
catacattct agagaagatg aagacttaat tgaaaattta gcccaagatg aaacatctag    720
gctggacctt ggatttgagg agtgggatgt agctggcctg ccttggtggt ttttaggaaa    780
cttgagaagc aactatacac ctagaagtaa tggctcaact gatttacaga caaatcaggt    840
gattgaagtg ggaaaaaatg atgacctgga ggactctaag tccttaagtg atgataccga    900
tgtagaggtt acctctgagg atgagtggca gtgtactgaa tgcaagaaat ttaactctcc    960
aagcaagagg tactgttttc gttgttgggc cttgaggaag gattggtatt cagattgttc   1020
aaagttaacc cattctctct ccacgtctga tatcactgcc atacctgaaa aggaaaatga   1080
aggaaatgat gtccctgatt gtcgaagaac catttcggct cctgtcgtta gacctaaaga   1140
tgcgtatata aagaaagaaa actccaaact ttttgatccc tgcaactcag tggaattctt   1200
ggatttggct cacagttctg aaagccaaga gaccatctca agcatgggag aacagttaga   1260
taacctttct gaacagagaa cagatacaga aaacatggag gattgccaga atctcttgaa   1320
gccatgtagc ttatgtgaga aaagaccacg agacgggaac attattcatg gaaggacggg   1380
ccatcttgtc acttgttttc actgtgccag aagactaaag aaggctgggg cttcatgccc   1440
tatttgcaag aaagagattc agctggttat taaggttttt atagcataat ggtagtacga   1500
acataaaaat gcatttattc cgttcactta ccacattatt tgaaaatcaa tcctttattt   1560
aattttattt ccaacctgtc agagaatgtt cttaggcatc aaaatccaag gtagctgtaa   1620
gaaaaatact ggagctaaca atgaagaaca gaagtaatct gattagtcaa attattaagt   1680
gccatggatt actttatgca gcagtcaggt acatagttag gtgaacccaa aagaaaaact   1740
cttgaaaaca agagatttct tccatgcaca tttacaatat tgaggtataa ttaacatgat   1800
aaagtgtttc cttctaacga gttgtagaaa tctgagtaac cacccaaaaa agcaatagaa   1860
tgtttctgtc accccaaaac actcccttct gcccctcttc agacagtcct tcagctattt   1920
catggctctc accctagttt tttttttttt tgcacttttt tttttccggg ggtatagggg   1980
aggtgtgggg cgacagggtc tgtcttgttc tgtctcccag gctgaagtgc agtgcagtgg   2040
tatgatcatg gctcactgca gccttggttt cctgggcata agtggtcttc ccacttcagc   2100
ctcctgagta gctgagacta tagactagca taaccacact ggctaatttt ttgtggagat   2160
gaagtctcac tatgttgccc aggctggtct cgaactcctg ggctcaaaca atcctcccgc   2220
ctcagccttc caaattgctg ggattatagt catgaggcac ctagtctggc ccttttgcaa   2280
gactttaatc tgaaatctaa atttttaaaa tttaagtact tacaaaggat atactatcca   2340
acatattgca tattatatat gtgctttaaa gttttttttt ttttttgaga gacggtctca   2400
ctttgtcatc caagctggag tgcagtggtg caaacacggc ccacctcctg ggctcaagtg   2460
atcctccagc ctcagcttcc ctcacaggca ttcactatca ctcccagcta attaaaataa   2520
tttgtagacg gtgtctcgtt atgttgccca ggctggtctc gaactcctgg gtttaagtga   2580
ttcccccgcc tcagcctccc aaagtgttgg gcttacagcc ttgagccact atgcttggct   2640
caaagatatt tttatgaaag ccctgggact atagatttag ctgattaaat ttatagaaaa   2700
agtcctgtca tataaactgg caaagtctgt tcttaattta attagccaaa tcagacttaa   2760
cttccgtcag aacatgtctt ggttttaatt cagataaaca cacaaacata cttctctggc   2820
acagccttca gaagcatcag tttttgtttt gttttgtttt gtttttgag acagggtctt    2880
gctctgtcgc ccaggctgga gtgcactggc acaatcacag ttcactgcag cctcgacctc   2940
ccagatccaa gcaatcctcc cacctaagcc tcccaagtag ctgggtctat aggcgcgtgc   3000
caccaccatg cccagctgaa ttttgtattt tttgtacaga cagcattttg ccatgttgcc   3060
```

-continued caggctggtc ccaaacttct agcctcaagc aaccctcctg cctcagcctc tcaaagtgct 3120
aggattgcag tcctgagcta ctgcccccta ccctctttgc gtcttaggag tcatttagat 3180
tttttttgat ccttttgttt agtgcctctg gagctgctta caccaaggca atacgccttg 3240
atatactgga tggttgagag gcagcctctt tttttttttt tttttttttt tttttttgga 3300
ggatagggag tatggctgtt gtgaaaaggg aggtaaagag aaatggtaga tctgaagagg 3360
cctcatcaga gcacatattt taggacaaca catatggaaa ttggacatct ttaagttggt 3420
ttccatagag ctatgcatgt atccttaccc ccatgggaaa atgttggtgt gttctcaagg 3480
gtatgcatgt gtcattttga agaccaaggc cctagaattg tcaaacttaa ggatcataaa 3540
aatcatgagg gttgcttgtt aaaaatgtcc aaacgtgcag agactgatct ttgagatctg 3600
gaccaggaat ttgcatttga acaagtgttc ctggaatctc tatgcaagtt ttatacagaa 3660
catacttttg gaatccttgc cctagacagg ggtgtccaat cttttggctt ccctggtcca 3720
caatggaaga agaattgtct tggaccacac ataaaataca ctaacactaa caatagctga 3780
tgagctaaaa aaaaaaaaaa aaaaaatcgt ggaccgggcg tagtggctca cgcctgtaat 3840
cccaacactt tgggagatca cctaggtcgg gagtttgaga ccagcctgac cgacatggag 3900
aaaccccatt tttactaaaa atacaaaaaa ttagctgggc atggtggtgc atgcctgtag 3960
tcccagctac tcaggaggct gaggcaggag aatcgcttga acctgagagg gggagattgc 4020
ggtgagctga gattgcgcca ttgcacccca gcctgggcaa caatagcgaa actgtctcag 4080
aaaaaagaaa aaaaaaatcg caaaaagaaa aatctcataa tgtcgttgtt ggtttttttt 4140
tttttttttg agacagtctc actctgttgc ccaggctgga gtgcaatggc atgatctctg 4200
ctcaccgcaa cctctgcctc ccgggttcag gtgattctcc tgcctcagcc tcccagatag 4260
ctgggactac aggcacatac caccatgcct ggctaatttt tgtattttta gtagagatgg 4320
gggtttcact gtgttggcca ggctggtctc gaactcctga cctcatgatc cacacacctc 4380
ggcctcccaa agtcctgcga ttacaggcgt gagctaccgc acccagccaa gttgtaattt 4440
ttaataaaac ttaagaagta aacattttac ttatgtttat aggtatttga tcctaaattt 4500
gacacatcat tgcccatgaa agaatcctct taggctgctc agcttcactc ttcctgcttg 4560
cccaccgggg tttttcactg cttctgttag cactaagtac ttagacgatc ctaagatatg 4620
tgcttgagcc gaatttcatc tttacttgta ggaaacttta aactatttct tttcttttct 4680
tttttttttt tttttacttg agatggagtt ttgctcttgt cgcccaggct ggagtgcagt 4740
ggagtgatct cggctcactg caacctctgc ctcccgggtt caaatgattc tcctgcctca 4800
gcctcccaag tagctgggat tacaggtgtg caccaccatg tctggctaat tttgtatttt 4860
tagtagagat ggtttcacca tgttggtcag gctggtctcg aactcctgac ctcaggtcat 4920
ccacccacct cagcctcgca aagtgctgag attacaggca tgagccacag cgcccagctt 4980
aaactatttt cttggtctgt ttttgatttt cttttttcct tgccactgcg gtacagattt 5040
tttttactca ctgccactaa actaaagcaa ggcatagttt atatgtgaag tgttcagagt 5100
ttactgctat aaggaaactt ccaaatactg acatttacct tttagctgta gttattggga 5160
ccatgtgctc tggttttctg gagactgcca aattgctccc atttttctgc atcccacctg 5220
gtttctttct gcatgtcccc tttcactttc aaacctcttc atttggatgt taaattatat 5280
ggtcacctag ttataggtaa gccttgttcg agttgatatc ttgattgtga ggaaggatct 5340
gtgtcattgg agcttgtttc tgctgcaacg tgctgtagac tatgaataat gaaatcacac 5400
cacattacca tcagatttct tgttttagtt gtcaaattaa tatttatgat tgttatcttg 5460
ggcgaaaagt tcagagcaga gatgacaaat cattagaaca acgatgaatt tcagtattac 5520
ggctaaaaag ttcttctgtc tgaatattaa ctcactctcc ttccagtgta cttcacagta 5580
attggtatgc ttttttattt aatgcttaaa tcaaacttta taaaaatctt agaccagatc 5640
tttaatatgg tatgccattt ccccagtcta ccaatggaat agtatgggtt tctaatccta 5700
ggcttgtaca atggattgga gttgagccat gccagcctcc acactgccac taacttctgt 5760
aatgtaagat tgagtcactg ccaagcattt gaaatatgca gttgtgtttt aattataatt 5820
tatgtatagt tagatgtatg tagtgcattg tgtggtatta tttggtttgt aagaatttat 5880
ttttaagggt caaggtcatt tgtaacattt tgtgtgtgtc aattcaatgc aatgttggct 5940
gccttttgaa gtctttgata tattggtgaa tattcttctg atctataata caaagctatg 6000
taatgttacc tcttgactcg cttttgaaag gaagacaatt gttaactaga tatttgagtt 6060
ttttcccctc agaattatgt gaatttctga tatatggctt tagatactgt gaatctgttt 6120
tccatttagt cagttatctg cttaaattgt tcagaactat atcctaacga gcaattagtt 6180
ctgatggttc tcccagtcat gagtgtgcat gtgtgcaagc atgttttgat cctgatgcta 6240
cctttgctaa aaatggccat agattaggaa ctagctatgt ttttagaatc aaagatgaac 6300
cggtaagctg tctcatgtac caaacgtgaa atttacagtg tttacaaatg tctggaattt 6360
tgcactgcca tagggaatgt taaggttact tggctggaat ttatcagact tgtgagtaaa 6420
caagttgaag tttagcagat gagggggaat attgaggccc ctaaggctaa acaaaataat 6480
cagtatctga gatagtggct aatgtggctc cccaggccta atttgggaac agtttttcct 6540
gattgctttg agaagtactt tcttttgaca gaaattttca ttctgcttgc cattgctata 6600
ttctcccttt ataggagcca ttggatttct ttccttttgt gggaaatgtc ccattagcat 6660
tttcagatct tttgatgtgc actaatgcca ttattggtaa tgccgttatt ggtgaataca 6720
gcatagttaa ataaactgtt acagtaaatc tacacttgga tttgctgcac ctctaccaat 6780
agccttttga atgactgaaa gtgttaacag agaaagaggc atgtctgcag aaagagatag 6840
ctaatatttt ttggtacttt atctgaaatc caagatgctg cttcccctgc aggttgtttt 6900
ccttcttacg atcctcattg aatcccctct gggagcacag gacagttagt agaactctcc 6960
atttcttttt tttttttttt agacggagtc tctctctgtc gccccggctg gagtgcagtg 7020
gcgcgatctc ggctcactgc aacctccgcc tcccgggttc accccattct cctgcctcag 7080
cctccctagt agctgggact ataggcgccc gccaccacgc ctggctaatt tttgtatttt 7140
tattggagac ggggtttcac cgtcttagcc aggatggtct tgatctcctg acctcgtgat 7200
ctgcccacct cagcctccca aagtactggg attacaggcg tgagccaccg cgcccggccg 7260
gaactctcca tttcttaagg taaagagggt caaggatacc taaaaagggt caaataatgc 7320
tagaagagca attcctcttt cagagcagtt gctgtaattt ggcaaatgct ttatcgaaga 7380
ttgatattag gctaggggcg gtggcttacg cctgtaatcc cagcactttg ggaggccgag 7440
gtgggtggat tgcctgagct caggagttcg agaccagtct gaccagtatg gtgaaaccct 7500
gtctctacta aaaatacaaa aattagccgg tcgtggtggc gtgcacctgt agtcccagct 7560
acttggcagg ttgagacagg agaatcgctt gaacctggga ggtggaggtt gcagtgagcc 7620
gagactgcac cactgcgctc ccacctgggt gacagagact ctgtctcaaa aaaaaggaca 7680
tttatcatta taacatctta ttagagcccc taatttctta tctgaaggca ctgttttttt 7740
ttttaaacag ttaagtactg atgtcaacag acaaatattt ctgatcagat agtcccctgt 7800

-continued

```
caacagtagc aaatgtggtt tcataaagtg ggaagaaaac agcattttaa agtaactttt   7860
tgggagactg atttgagtaa taataaaact ctggtctccc ttaagaaaaa aaaacccttc   7920
cacctttact gtgtcattta tatcccctta gttccaaagt taattatctt atttctggat   7980
attgctttta taccaaagac ccttatcagc ccttgtaact acagtatctt tagataagat   8040
tcctctttcc agtcagtcct gggaaatgtt tctgttgcag agttaggcgg tagatgggaa   8100
gctgtgatgg cagagctact atctaataaa gtaacaactc gtagttgagg cttcctttct   8160
gtgtgtgatg ggggataggg agttagctcc cctgttgtct cagcactaag aaattgaggt   8220
caggccaggc gcggtggttc actcctgtta ttccagcact ggggtggcca aagtgggcag   8280
attgcttgcg ctctggagct cgagaccagc ctgggcaaca tggtgaaacc ctgtctctac   8340
caaaaataca aaaaaaaagc tgggcatggt gggtgcatgc ttgtcccagc tactgaggag   8400
gctgaggtgg gaggatcgct tgagcctggg aggtggaggt tgcagtgagc tgagatggca   8460
ccactgcaat ccaaggtggg tgacagagac gctgtctcaa agaaattgag gtcaggcttc   8520
cttcttacag aattattttt ttctctgtag tttgcctcat tttttcactt tcttttcaat   8580
gagaatcgaa gtgtttcttt tggtttttt tttcccctt ttaaaatcaa caggaaatgt   8640
ttcaaaggag ggatgaaatg cttcttggct tcctcagcac ttggcaaggt agacctcata   8700
gcaaccttga atatgacttt ctttagtctc tagctatgca ctattaagtg cctcttgggt   8760
agaggtagag ttaagtattg agtgccagtc ttgacgtccg tatgcctcag tttttctcat   8820
atataaaaag cagtatacat acctaccctt ttctacctca tcatttgttg tagggattaa   8880
atccgggaga gcaattctga agcctataaa tttccttgaa gagatctaag aacctattat   8940
gctcttggtg taccaagctc tggggtatat attcagaata cctcatgttc tggaagctga   9000
gcactagctc ccctttattg cctgcctggc agagcctgtt tgattactgc aggccctttt   9060
acccatgctt ctagtttagg tattctttct ttgatatgag gctcttgacc agaaaagagt   9120
tctttctcta ggtgttctga gagaagtttg taaatttgga tagtacattc tatcctgata   9180
aaaccacctt gctgtggtct tgatgtacaa aaaaaaattt ttttttgag acagagtctt   9240
actctgtcac ccaggctgga atgcagtggc gcaatcttgg ttcactgcaa cccccgcctc   9300
ctgggttcaa gcgatcctcc tgcctcaacc tctcaagtag ctgggactac aggcgtgcac   9360
caccacacct ggctaatttt gtatttttag tagagacagg gtttcaccat gttggccagg   9420
ctggtcttga actcctgacc tcaggcgatc tgcccgcctt ggcctcccaa agtactggga   9480
ttacaggcgt gagcaactgc tcctggccca aaacatctct ttctacatac acttgagtag   9540
gtggcataaa atgcactgtc aatatataga aaacatgaaa ttttccaaat atttccgatc   9600
agagaatcac aagagcagca aatgtggttt catcaagtgg gaagaaagca gcaatttaaa   9660
ataacttttt gggagactga attgagtaat aataaaactt cagtctttcg ctaataataa   9720
taataataat aataataaca acaacttatt gaatgtggcc agctcactag atgaggaaag   9780
aggaaggcat tttctgcatt cttgcctagt tttccttata agcaccacta agttaatagc   9840
tctgtctttt tggtgtttgc actatgtaat gcttttaata ctttttaatt gtgctttttt   9900
atgtattaaa tgtttttcct tttgccaaaa aaaaaaaaaa                         9940
```

<210> SEQ ID NO 18
<211> LENGTH: 440
<212> TYPE: PRT
<213> ORGANISM: Homo sapiens

<400> SEQUENCE: 18

Met Thr Ser Phe Ser Thr Ser Ala Gln Cys Ser Thr Ser Asp Ser Ala
1               5                   10                  15

Cys Arg Ile Ser Pro Gly Gln Ile Asn Gln Val Arg Pro Lys Leu Pro
            20                  25                  30

Leu Leu Lys Ile Leu His Ala Ala Gly Ala Gln Gly Glu Met Phe Thr
        35                  40                  45

Val Lys Glu Val Met His Tyr Leu Gly Gln Tyr Ile Met Val Lys Gln
    50                  55                  60

Leu Tyr Asp Gln Gln Glu Gln His Met Val Tyr Cys Gly Gly Asp Leu
65                  70                  75                  80

Leu Gly Glu Leu Leu Gly Arg Gln Ser Phe Ser Val Lys Asp Pro Ser
                85                  90                  95

Pro Leu Tyr Asp Met Leu Arg Lys Asn Leu Val Thr Leu Ala Thr Ala
            100                 105                 110

Thr Thr Asp Ala Ala Gln Thr Leu Ala Leu Ala Gln Asp His Ser Met
        115                 120                 125

Asp Ile Pro Ser Gln Asp Gln Leu Lys Gln Ser Ala Glu Glu Ser Ser
    130                 135                 140

Thr Ser Arg Lys Arg Thr Thr Glu Asp Asp Ile Pro Thr Leu Pro Thr
145                 150                 155                 160

Ser Glu His Lys Cys Ile His Ser Arg Glu Asp Glu Asp Leu Ile Glu
                165                 170                 175

Asn Leu Ala Gln Asp Glu Thr Ser Arg Leu Asp Leu Gly Phe Glu Glu
            180                 185                 190

Trp Asp Val Ala Gly Leu Pro Trp Trp Phe Leu Gly Asn Leu Arg Ser
        195                 200                 205

Asn Tyr Thr Pro Arg Ser Asn Gly Ser Thr Asp Leu Gln Thr Asn Gln
    210                 215                 220

Val Ile Glu Val Gly Lys Asn Asp Asp Leu Glu Asp Ser Lys Ser Leu
225                 230                 235                 240

Ser Asp Asp Thr Asp Val Glu Val Thr Ser Glu Asp Glu Trp Gln Cys
                245                 250                 255

Thr Glu Cys Lys Lys Phe Asn Ser Pro Ser Lys Arg Tyr Cys Phe Arg
            260                 265                 270

Cys Trp Ala Leu Arg Lys Asp Trp Tyr Ser Asp Cys Ser Lys Leu Thr
        275                 280                 285

His Ser Leu Ser Thr Ser Asp Ile Thr Ala Ile Pro Glu Lys Glu Asn
    290                 295                 300

Glu Gly Asn Asp Val Pro Asp Cys Arg Arg Thr Ile Ser Ala Pro Val
305                 310                 315                 320

Val Arg Pro Lys Asp Ala Tyr Ile Lys Lys Glu Asn Ser Lys Leu Phe
                325                 330                 335

Asp Pro Cys Asn Ser Val Glu Phe Leu Asp Leu Ala His Ser Ser Glu
            340                 345                 350

Ser Gln Glu Thr Ile Ser Ser Met Gly Glu Gln Leu Asp Asn Leu Ser
        355                 360                 365

Glu Gln Arg Thr Asp Thr Glu Asn Met Glu Asp Cys Gln Asn Leu Leu
    370                 375                 380

Lys Pro Cys Ser Leu Cys Glu Lys Arg Pro Arg Asp Gly Asn Ile Ile
385                 390                 395                 400

His Gly Arg Thr Gly His Leu Val Thr Cys Phe His Cys Ala Arg Arg
                405                 410                 415

```
Leu Lys Lys Ala Gly Ala Ser Cys Pro Ile Cys Lys Lys Glu Ile Gln
            420                 425                 430

Leu Val Ile Lys Val Phe Ile Ala
        435                 440


<210> SEQ ID NO 19
<211> LENGTH: 9112
<212> TYPE: DNA
<213> ORGANISM: Homo sapiens

<400> SEQUENCE: 19

gtgtgggagg ccggaagttg cggcttcatt actcgccatt tcaaaatgct gccgaggccc     60

taggatctgt gactgccacc cctccccca cccgggctcg gcgggggagc gactcatgga    120

gctgccgtaa gttttaccaa cagactgcag tttcttcact accaaaatga catcattttc    180

cacctctgct cagtgttcaa catctgacag tgcttgcagg atctctcctg gacaaatcaa    240

tcaggaaaat gaaggaaatg atgtccctga ttgtcgaaga accatttcgg ctcctgtcgt    300

tagacctaaa gatgcgtata taaagaaaga aaactccaaa ctttttgatc cctgcaactc    360

agtggaattc ttggatttgg ctcacagttc tgaaagccaa gagaccatct caagcatggg    420

agaacagtta gataaccttt ctgaacagag aacagataca gaaaacatgg aggattgcca    480

gaatctcttg aagccatgta gcttatgtga gaaaagacca cgagacggga acattattca    540

tggaaggacg ggccatcttg tcacttgttt tcactgtgcc agaagactaa agaaggctgg    600

ggcttcatgc cctatttgca agaaagagat tcagctggtt attaaggttt ttatagcata    660

atggtagtac gaacataaaa atgcatttat tccgttcact taccacatta tttgaaaatc    720

aatcctttat ttaattttat ttccaacctg tcagagaatg ttcttaggca tcaaaatcca    780

aggtagctgt aagaaaaata ctggagctaa caatgaagaa cagaagtaat ctgattagtc    840

aaattattaa gtgccatgga ttactttatg cagcagtcag gtacatagtt aggtgaaccc    900

aaaagaaaaa ctcttgaaaa caagagattt cttccatgca catttacaat attgaggtat    960

aattaacatg ataaagtgtt tccttctaac gagttgtaga aatctgagta accacccaaa   1020

aaagcaatag aatgtttctg tcaccccaaa acactccctt ctgcccctct tcagacagtc   1080

cttcagctat ttcatggctc tcaccctagt tttttttttt tttgcacttt tttttttccg   1140

ggggtatagg ggaggtgtgg ggcgacaggg tctgtcttgt tctgtctccc aggctgaagt   1200

gcagtgcagt ggtatgatca tggctcactg cagccttggt ttcctgggca taagtggtct   1260

tcccacttca gcctcctgag tagctgagac tatagactag cataaccaca ctggctaatt   1320

ttttgtggag atgaagtctc actatgttgc ccaggctggt ctcgaactcc tgggctcaaa   1380

caatcctccc gcctcagcct tccaaattgc tgggattata gtcatgaggc acctagtctg   1440

gcccttttgc aagactttaa tctgaaatct aaatttttaa aatttaagta cttacaaagg   1500

atatactatc caacatattg catattatat atgtgcttta aagttttttt ttttttttga   1560

gagacggtct cactttgtca tccaagctgg agtgcagtgg tgcaaacacg gcccacctcc   1620

tgggctcaag tgatcctcca gcctcagctt ccctcacagg cattcactat cactcccagc   1680

taattaaaat aatttgtaga cggtgtctcg ttatgttgcc caggctggtc tcgaactcct   1740

gggtttaagt gattcccccg cctcagcctc ccaaagtgtt gggcttacag ccttgagcca   1800

ctatgcttgg ctcaaagata tttttatgaa agccctggga ctatagattt agctgattaa   1860

atttatagaa aaagtcctgt catataaact ggcaaagtct gttcttaatt taattagcca   1920
```

-continued

```
aatcagactt aacttccgtc agaacatgtc ttggttttaa ttcagataaa cacacaaaca   1980
tacttctctg gcacagcctt cagaagcatc agtttttgtt ttgttttgtt ttgtttttttg  2040
agacagggtc ttgctctgtc gcccaggctg gagtgcactg gcacaatcac agttcactgc   2100
agcctcgacc tcccagatcc aagcaatcct cccacctaag cctcccaagt agctgggtct   2160
ataggcgcgt gccaccacca tgcccagctg aattttgtat tttttgtaca gacagcattt   2220
tgccatgttg cccaggctgg tcccaaactt ctagcctcaa gcaaccctcc tgcctcagcc   2280
tctcaaagtg ctaggattgc agtcctgagc tactgccccc taccctcttt gcgtcttagg   2340
agtcatttag attttttttg atccttttgt ttagtgcctc tggagctgct tacaccaagg   2400
caatacgcct tgatatactg gatggttgag aggcagcctc tttttttttt tttttttttt   2460
tttttttttg gaggataggg agtatggctg ttgtgaaaag ggaggtaaag agaaatggta   2520
gatctgaaga ggcctcatca gagcacatat tttaggacaa cacatatgga aattggacat   2580
ctttaagttg gtttccatag agctatgcat gtatccttac ccccatggga aaatgttggt   2640
gtgttctcaa gggtatgcat gtgtcatttt gaagaccaag gccctagaat tgtcaaactt   2700
aaggatcata aaaatcatga gggttgcttg ttaaaaatgt ccaaacgtgc agagactgat   2760
ctttgagatc tggaccagga atttgcattt gaacaagtgt tcctggaatc tctatgcaag   2820
ttttatacag aacatacttt tggaatcctt gccctagaca ggggtgtcca atcttttggc   2880
ttccctggtc cacaatggaa gaagaattgt cttggaccac acataaaata cactaacact   2940
aacaatagct gatgagctaa aaaaaaaaaa aaaaaaaatc gtggaccggg cgtagtggct   3000
cacgcctgta atcccaacac tttgggagat cacctaggtc gggagtttga gaccagcctg   3060
accgacatgg agaaacccca tttttactaa aaatacaaaa aattagctgg gcatggtggt   3120
gcatgcctgt agtcccagct actcaggagg ctgaggcagg agaatcgctt gaacctgaga   3180
gggggagatt gcggtgagct gagattgcgc cattgcaccc cagcctgggc aacaatagcg   3240
aaactgtctc agaaaaaaga aaaaaaaaat cgcaaaaaga aaaatctcat aatgtcgttg   3300
ttggtttttt tttttttttt tgagacagtc tcactctgtt gcccaggctg gagtgcaatg   3360
gcatgatctc tgctcaccgc aacctctgcc tcccgggttc aggtgattct cctgcctcag   3420
cctcccagat agctgggact acaggcacat accaccatgc ctggctaatt tttgtatttt   3480
tagtagagat gggggtttca ctgtgttggc caggctggtc tcgaactcct gacctcatga   3540
tccacacacc tcggcctccc aaagtcctgc gattacaggc gtgagctacc gcacccagcc   3600
aagttgtaat ttttaataaa acttaagaag taaacatttt acttatgttt ataggtattt   3660
gatcctaaat ttgacacatc attgcccatg aaagaatcct cttaggctgc tcagcttcac   3720
tcttcctgct tgcccaccgg ggtttttcac tgcttctgtt agcactaagt acttagacga   3780
tcctaagata tgtgcttgag ccgaatttca tctttacttg taggaaactt taaactattt   3840
cttttctttt cttttttttt ttttttttact tgagatggag ttttgctctt gtcgcccagg   3900
ctggagtgca gtggagtgat ctcggctcac tgcaacctct gcctcccggg ttcaaatgat   3960
tctcctgcct cagcctccca agtagctggg attacaggtg tgcaccacca tgtctggcta   4020
attttgtatt tttagtagag atggtttcac catgttggtc aggctggtct cgaactcctg   4080
acctcaggtc atccacccac ctcagcctcg caaagtgctg agattacagg catgagccac   4140
agcgcccagc ttaaactatt ttcttggtct gtttttgatt ttcttttttc cttgccactg   4200
cggtacagat tttttttact cactgccact aaactaaagc aaggcatagt ttatatgtga   4260
agtgttcaga gtttactgct ataaggaaac ttccaaatac tgacatttac cttttagctg   4320
```

```
tagttattgg gaccatgtgc tctggttttc tggagactgc caaattgctc ccatttttct   4380
gcatcccacc tggtttcttt ctgcatgtcc cctttcactt tcaaacctct tcatttggat   4440
gttaaattat atggtcacct agttataggt aagccttgtt cgagttgata tcttgattgt   4500
gaggaaggat ctgtgtcatt ggagcttgtt tctgctgcaa cgtgctgtag actatgaata   4560
atgaaatcac accacattac catcagattt cttgttttag ttgtcaaatt aatatttatg   4620
attgttatct tgggcgaaaa gttcagagca gagatgacaa atcattagaa caacgatgaa   4680
tttcagtatt acggctaaaa agttcttctg tctgaatatt aactcactct ccttccagtg   4740
tacttcacag taattggtat gctttttat ttaatgctta aatcaaactt tataaaaatc   4800
ttagaccaga tctttaatat ggtatgccat ttccccagtc taccaatgga atagtatggg   4860
tttctaatcc taggcttgta caatggattg gagttgagcc atgccagcct ccacactgcc   4920
actaacttct gtaatgtaag attgagtcac tgccaagcat ttgaaatatg cagttgtgtt   4980
ttaattataa tttatgtata gttagatgta tgtagtgcat tgtgtggtat tatttggttt   5040
gtaagaattt atttttaagg gtcaaggtca tttgtaacat tttgtgtgtg tcaattcaat   5100
gcaatgttgg ctgccttttg aagtctttga tatattggtg aatattcttc tgatctataa   5160
tacaaagcta tgtaatgtta cctcttgact cgcttttgaa aggaagacaa ttgttaacta   5220
gatatttgag tttttcccc tcagaattat gtgaatttct gatatatggc tttagatact   5280
gtgaatctgt tttccattta gtcagttatc tgcttaaatt gttcagaact atatcctaac   5340
gagcaattag ttctgatggt tctcccagtc atgagtgtgc atgtgtgcaa gcatgttttg   5400
atcctgatgc taccttgct aaaaatggcc atagattagg aactagctat gtttttagaa   5460
tcaaagatga accggtaagc tgtctcatgt accaaacgtg aaatttacag tgtttacaaa   5520
tgtctggaat tttgcactgc catagggaat gttaaggtta cttggctgga atttatcaga   5580
cttgtgagta aacaagttga agtttagcag atgaggggga atattgaggc ccctaaggct   5640
aaacaaaata atcagtatct gagatagtgg ctaatgtggc tccccaggcc taatttggga   5700
acagtttttc ctgattgctt tgagaagtac tttcttttga cagaaatttt cattctgctt   5760
gccattgcta tattctccct ttataggagc cattggattt ctttcctttt gtgggaaatg   5820
tcccattagc attttcagat cttttgatgt gcactaatgc cattattggt aatgccgtta   5880
ttggtgaata cagcatagtt aaataaactg ttacagtaaa tctacacttg gatttgctgc   5940
acctctacca atagcctttt gaatgactga aagtgttaac agagaaagag gcatgtctgc   6000
agaaagagat agctaatatt ttttggtact ttatctgaaa tccaagatgc tgcttcccct   6060
gcaggttgtt ttccttctta cgatcctcat tgaatcccct ctgggagcac aggacagtta   6120
gtagaactct ccatttcttt ttttttttt ttagacggag tctctctctg tcgccccggc   6180
tggagtgcag tggcgcgatc tcggctcact gcaacctccg cctcccgggt tcaccccatt   6240
ctcctgcctc agcctcccta gtagctggga ctataggcgc ccgccaccac gcctggctaa   6300
tttttgtatt tttattggag acggggtttc accgtcttag ccaggatggt cttgatctcc   6360
tgacctcgtg atctgcccac ctcagcctcc caaagtactg ggattacagg cgtgagccac   6420
cgcgcccggc cggaactctc catttcttaa ggtaaagagg gtcaaggata cctaaaaagg   6480
gtcaaataat gctagaagag caattcctct ttcagagcag ttgctgtaat ttggcaaatg   6540
ctttatcgaa gattgatatt aggctagggg cggtggctta cgcctgtaat cccagcactt   6600
tgggaggccg aggtgggtgg attgcctgag ctcaggagtt cgagaccagt ctgaccagta   6660
```

-continued

```
tggtgaaacc ctgtctctac taaaaataca aaaattagcc ggtcgtggtg gcgtgcacct   6720
gtagtcccag ctacttggca ggttgagaca ggagaatcgc ttgaacctgg gaggtggagg   6780
ttgcagtgag ccgagactgc accactgcgc tcccacctgg gtgacagaga ctctgtctca   6840
aaaaaaagga catttatcat tataacatct tattagagcc cctaatttct tatctgaagg   6900
cactgttttt ttttttaaac agttaagtac tgatgtcaac agacaaatat ttctgatcag   6960
atagtcccct gtcaacagta gcaaatgtgg tttcataaag tgggaagaaa acagcatttt   7020
aaagtaactt tttgggagac tgatttgagt aataataaaa ctctggtctc ccttaagaaa   7080
aaaaaaccct tccaccttta ctgtgtcatt tatatcccct tagttccaaa gttaattatc   7140
ttatttctgg atattgcttt tataccaaag acccttatca gcccttgtaa ctacagtatc   7200
tttagataag attcctcttt ccagtcagtc ctgggaaatg tttctgttgc agagttaggc   7260
ggtagatggg aagctgtgat ggcagagcta ctatctaata aagtaacaac tcgtagttga   7320
ggcttccttt ctgtgtgtga tgggggatag ggagttagct cccctgttgt ctcagcacta   7380
agaaattgag gtcaggccag gcgcggtggt tcactcctgt tattccagca ctggggtggc   7440
caaagtgggc agattgcttg cgctctggag ctcgagacca gcctgggcaa catggtgaaa   7500
ccctgtctct accaaaaata caaaaaaaaa gctgggcatg gtgggtgcat gcttgtccca   7560
gctactgagg aggctgaggt gggaggatcg cttgagcctg ggaggtggag gttgcagtga   7620
gctgagatgg caccactgca atccaaggtg ggtgacagag acgctgtctc aaagaaattg   7680
aggtcaggct tccttcttac agaattattt ttttctctgt agtttgcctc attttttcac   7740
tttcttttca atgagaatcg aagtgtttct tttgggtttt tttttccccc ttttaaaatc   7800
aacaggaaat gtttcaaagg agggatgaaa tgcttcttgg cttcctcagc acttggcaag   7860
gtagacctca tagcaacctt gaatatgact ttctttagtc tctagctatg cactattaag   7920
tgcctcttgg gtagaggtag agttaagtat tgagtgccag tcttgacgtc cgtatgcctc   7980
agtttttctc atatataaaa agcagtatac atacctaccc ttttctacct catcatttgt   8040
tgtagggatt aaatccggga gagcaattct gaagcctata aatttccttg aagagatcta   8100
agaacctatt atgctcttgg tgtaccaagc tctggggtat atattcagaa tacctcatgt   8160
tctggaagct gagcactagc tccccttttat tgcctgcctg gcagagcctg tttgattact   8220
gcaggccctt ttacccatgc ttctagttta ggtattcttt ctttgatatg aggctcttga   8280
ccagaaaaga gttctttctc taggtgttct gagagaagtt tgtaaatttg gatagtacat   8340
tctatcctga taaaaccacc ttgctgtggt cttgatgtac aaaaaaaaat ttttttttttg   8400
agacagagtc ttactctgtc acccaggctg gaatgcagtg gcgcaatctt ggttcactgc   8460
aacccccgcc tcctgggttc aagcgatcct cctgcctcaa cctctcaagt agctgggact   8520
acaggcgtgc accaccacac ctggctaatt ttgtattttt agtagagaca gggtttcacc   8580
atgttggcca ggctggtctt gaactcctga cctcaggcga tctgcccgcc ttggcctccc   8640
aaagtactgg gattacaggc gtgagcaact gctcctggcc caaaacatct ctttctacat   8700
acacttgagt aggtggcata aaatgcactg tcaatatata gaaaacatga aattttccaa   8760
atatttccga tcagagaatc acaagagcag caaatgtggt ttcatcaagt gggaagaaag   8820
cagcaattta aaataacttt ttgggagact gaattgagta ataataaaac ttcagtcttt   8880
cgctaataat aataataata ataataataa caacaactta ttgaatgtgg ccagctcact   8940
agatgaggaa agaggaaggc attttctgca ttcttgccta gttttcctta taagcaccac   9000
```

taagttaata gctctgtctt tttggtgttt gcactatgta atgcttttaa tactttttaa 9060
ttgtgctttt ttatgtatta aatgtttttc cttttgccaa aaaaaaaaaa aa 9112

<210> SEQ ID NO 20
<211> LENGTH: 164
<212> TYPE: PRT
<213> ORGANISM: Homo sapiens

<400> SEQUENCE: 20

Met Thr Ser Phe Ser Thr Ser Ala Gln Cys Ser Thr Ser Asp Ser Ala
1 5 10 15

Cys Arg Ile Ser Pro Gly Gln Ile Asn Gln Glu Asn Glu Gly Asn Asp
20 25 30

Val Pro Asp Cys Arg Arg Thr Ile Ser Ala Pro Val Val Arg Pro Lys
35 40 45

Asp Ala Tyr Ile Lys Lys Glu Asn Ser Lys Leu Phe Asp Pro Cys Asn
50 55 60

Ser Val Glu Phe Leu Asp Leu Ala His Ser Ser Glu Ser Gln Glu Thr
65 70 75 80

Ile Ser Ser Met Gly Glu Gln Leu Asp Asn Leu Ser Glu Gln Arg Thr
85 90 95

Asp Thr Glu Asn Met Glu Asp Cys Gln Asn Leu Leu Lys Pro Cys Ser
100 105 110

Leu Cys Glu Lys Arg Pro Arg Asp Gly Asn Ile Ile His Gly Arg Thr
115 120 125

Gly His Leu Val Thr Cys Phe His Cys Ala Arg Arg Leu Lys Lys Ala
130 135 140

Gly Ala Ser Cys Pro Ile Cys Lys Lys Glu Ile Gln Leu Val Ile Lys
145 150 155 160

Val Phe Ile Ala

<210> SEQ ID NO 21
<211> LENGTH: 10022
<212> TYPE: DNA
<213> ORGANISM: Homo sapiens

<400> SEQUENCE: 21
gtgtgggagg ccggaagttg cggcttcatt actcgccatt tcaaaatgct gccgaggccc 60
taggatctgt gactgccacc cctcccccca cccgggctcg gcgggggagc gactcatgga 120
gctgccgtaa gttttaccaa cagactgcag tttcttcact accaaaatga catcattttc 180
cacctctgct cagtgttcaa catctgacag tgcttgcagg atctctcctg gacaaatcaa 240
tcaggtacga ccaaaactgc cgcttttgaa gattttgcat gcagcaggtg cgcaaggtga 300
aatgttcact gttaaagagg tcatgcacta tttaggtcag tacataatgg tgaagcaact 360
ttatgatcag caggagcagc atatggtata ttgtggtgga gatcttttgg gagaactact 420
gggacgtcag agcttctccg tgaaagaccc aagccctctc tatgatatgc taagaaagaa 480
tcttgtcact ttagccactg ctactacagc aaagtgcaga ggaaagttcc acttccagaa 540
aaagaactac agaagacgat atccccacac tgcctacctc agagcataaa tgcatacatt 600
ctagagaaga tgaagactta attgaaaatt tagcccaaga tgaaacatct aggctggacc 660
ttggatttga ggagtgggat gtagctggcc tgccttggtg gtttttagga aacttgagaa 720
gcaactatac acctagaagt aatggctcaa ctgatttaca gacaaatcag gatgtgggta 780

-continued

```
ctgccattgt ttcagatact acagatgact tgtggttttt gaatgagtca gtatcagagc    840
agttaggtgt tggaataaaa gttgaagctg ctgatactga acaaacaagt gaagaagtag    900
ggaaagtaag tgacaaaaag gtgattgaag tgggaaaaaa tgatgacctg gaggactcta    960
agtccttaag tgatgatacc gatgtagagg ttacctctga ggatgagtgg cagtgtactg   1020
aatgcaagaa atttaactct ccaagcaaga ggtactgttt tcgttgttgg gccttgagga   1080
aggattggta ttcagattgt tcaaagttaa cccattctct ctccacgtct gatatcactg   1140
ccatacctga aaaggaaaat gaaggaaatg atgtccctga ttgtcgaaga accatttcgg   1200
ctcctgtcgt tagacctaaa gatgcgtata taaagaaaga aaactccaaa ctttttgatc   1260
cctgcaactc agtggaattc ttggatttgg ctcacagttc tgaaagccaa gagaccatct   1320
caagcatggg agaacagtta gataaccttt ctgaacagag aacagataca gaaaacatgg   1380
aggattgcca gaatctcttg aagccatgta gcttatgtga gaaaagacca cgagacggga   1440
acattattca tggaaggacg ggccatcttg tcacttgttt tcactgtgcc agaagactaa   1500
agaaggctgg ggcttcatgc cctatttgca agaaagagat tcagctggtt attaaggttt   1560
ttatagcata atggtagtac gaacataaaa atgcatttat tccgttcact taccacatta   1620
tttgaaaatc aatcctttat ttaattttat ttccaacctg tcagagaatg ttcttaggca   1680
tcaaaatcca aggtagctgt aagaaaaata ctggagctaa caatgaagaa cagaagtaat   1740
ctgattagtc aaattattaa gtgccatgga ttactttatg cagcagtcag gtacatagtt   1800
aggtgaaccc aaaagaaaaa ctcttgaaaa caagagattt cttccatgca catttacaat   1860
attgaggtat aattaacatg ataaagtgtt tccttctaac gagttgtaga aatctgagta   1920
accacccaaa aaagcaatag aatgtttctg tcaccccaaa acactccctt ctgcccctct   1980
tcagacagtc cttcagctat ttcatggctc tcaccctagt tttttttttt tttgcacttt   2040
tttttttccg gggtatagg ggaggtgtgg ggcgacaggg tctgtcttgt tctgtctccc   2100
aggctgaagt gcagtgcagt ggtatgatca tggctcactg cagccttggt ttcctgggca   2160
taagtggtct tcccacttca gcctcctgag tagctgagac tatagactag cataaccaca   2220
ctggctaatt ttttgtggag atgaagtctc actatgttgc ccaggctggt ctcgaactcc   2280
tgggctcaaa caatcctccc gcctcagcct tccaaattgc tgggattata gtcatgaggc   2340
acctagtctg gccctttttgc aagactttaa tctgaaatct aaatttttaa aatttaagta   2400
cttacaaagg atatactatc caacatattg catattatat atgtgcttta aagttttttt   2460
tttttttga gagacggtct cactttgtca tccaagctgg agtgcagtgg tgcaaacacg   2520
gcccacctcc tgggctcaag tgatcctcca gcctcagctt ccctcacagg cattcactat   2580
cactcccagc taattaaaat aatttgtaga cggtgtctcg ttatgttgcc caggctggtc   2640
tcgaactcct gggtttaagt gattcccccg cctcagcctc ccaaagtgtt gggcttacag   2700
ccttgagcca ctatgcttgg ctcaaagata tttttatgaa agccctggga ctatagattt   2760
agctgattaa atttatagaa aaagtcctgt catataaact ggcaaagtct gttcttaatt   2820
taattagcca aatcagactt aacttccgtc agaacatgtc ttggttttaa ttcagataaa   2880
cacacaaaca tacttctctg gcacagcctt cagaagcatc agtttttgtt ttgttttgtt   2940
ttgtttttg agacagggtc ttgctctgtc gcccaggctg gagtgcactg gcacaatcac   3000
agttcactgc agcctcgacc tcccagatcc aagcaatcct cccacctaag cctcccaagt   3060
agctgggtct ataggcgcgt gccaccacca tgcccagctg aattttgtat tttttgtaca   3120
gacagcattt tgccatgttg cccaggctgg tcccaaactt ctagcctcaa gcaaccctcc   3180
```

-continued

```
tgcctcagcc tctcaaagtg ctaggattgc agtcctgagc tactgccccc taccctcttt   3240
gcgtcttagg agtcatttag attttttttg atccttttgt ttagtgcctc tggagctgct   3300
tacaccaagg caatacgcct tgatatactg gatggttgag aggcagcctc tttttttttt   3360
tttttttttt tttttttttg gaggataggg agtatggctg ttgtgaaaag ggaggtaaag   3420
agaaatggta gatctgaaga ggcctcatca gagcacatat tttaggacaa cacatatgga   3480
aattggacat ctttaagttg gtttccatag agctatgcat gtatccttac cccatggga   3540
aaatgttggt gtgttctcaa gggtatgcat gtgtcatttt gaagaccaag gccctagaat   3600
tgtcaaactt aaggatcata aaaatcatga gggttgcttg ttaaaaatgt ccaaacgtgc   3660
agagactgat ctttgagatc tggaccagga atttgcattt gaacaagtgt tcctggaatc   3720
tctatgcaag ttttatacag aacatacttt tggaatcctt gccctagaca ggggtgtcca   3780
atcttttggc ttccctggtc cacaatggaa gaagaattgt cttggaccac acataaaata   3840
cactaacact aacaatagct gatgagctaa aaaaaaaaaa aaaaaaaatc gtggaccggg   3900
cgtagtggct cacgcctgta atcccaacac tttgggagat cacctaggtc gggagtttga   3960
gaccagcctg accgacatgg agaaacccca tttttactaa aaatacaaaa aattagctgg   4020
gcatggtggt gcatgcctgt agtcccagct actcaggagg ctgaggcagg agaatcgctt   4080
gaacctgaga gggggagatt gcggtgagct gagattgcgc cattgcaccc cagcctgggc   4140
aacaatagcg aaactgtctc agaaaaaaga aaaaaaaaat cgcaaaaaga aaaatctcat   4200
aatgtcgttg ttggtttttt tttttttttt tgagacagtc tcactctgtt gcccaggctg   4260
gagtgcaatg gcatgatctc tgctcaccgc aacctctgcc tcccgggttc aggtgattct   4320
cctgcctcag cctcccagat agctgggact acaggcacat accaccatgc ctggctaatt   4380
tttgtatttt tagtagagat gggggtttca ctgtgttggc caggctggtc tcgaactcct   4440
gacctcatga tccacacacc tcggcctccc aaagtcctgc gattacaggc gtgagctacc   4500
gcacccagcc aagttgtaat ttttaataaa acttaagaag taaacatttt acttatgttt   4560
ataggtattt gatcctaaat ttgacacatc attgcccatg aaagaatcct cttaggctgc   4620
tcagcttcac tcttcctgct tgcccaccgg ggtttttcac tgcttctgtt agcactaagt   4680
acttagacga tcctaagata tgtgcttgag ccgaatttca tctttacttg taggaaactt   4740
taaactattt cttttctttt cttttttttt tttttttact tgagatggag ttttgctctt   4800
gtcgcccagg ctggagtgca gtggagtgat ctcggctcac tgcaacctct gcctcccggg   4860
ttcaaatgat tctcctgcct cagcctccca agtagctggg attacaggtg tgcaccacca   4920
tgtctggcta attttgtatt tttagtagag atggtttcac catgttggtc aggctggtct   4980
cgaactcctg acctcaggtc atccacccac ctcagcctcg caaagtgctg agattacagg   5040
catgagccac agcgcccagc ttaaactatt ttcttggtct gtttttgatt ttcttttttc   5100
cttgccactg cggtacagat ttttttttact cactgccact aaactaaagc aaggcatagt   5160
ttatatgtga agtgttcaga gtttactgct ataaggaaac ttccaaatac tgacatttac   5220
cttttagctg tagttattgg gaccatgtgc tctggttttc tggagactgc caaattgctc   5280
ccatttttct gcatcccacc tggtttcttt ctgcatgtcc cctttcactt tcaaacctct   5340
tcatttggat gttaaattat atggtcacct agttataggt aagccttgtt cgagttgata   5400
tcttgattgt gaggaaggat ctgtgtcatt ggagcttgtt tctgctgcaa cgtgctgtag   5460
actatgaata atgaaatcac accacattac catcagattt cttgttttag ttgtcaaatt   5520
```

-continued

```
aatatttatg attgttatct tgggcgaaaa gttcagagca gagatgacaa atcattagaa   5580
caacgatgaa tttcagtatt acggctaaaa agttcttctg tctgaatatt aactcactct   5640
ccttccagtg tacttcacag taattggtat gctttttat ttaatgctta aatcaaactt    5700
tataaaaatc ttagaccaga tctttaatat ggtatgccat ttccccagtc taccaatgga   5760
atagtatggg tttctaatcc taggcttgta caatggattg gagttgagcc atgccagcct   5820
ccacactgcc actaacttct gtaatgtaag attgagtcac tgccaagcat ttgaaatatg   5880
cagttgtgtt ttaattataa tttatgtata gttagatgta tgtagtgcat tgtgtggtat   5940
tatttggttt gtaagaattt atttttaagg gtcaaggtca tttgtaacat tttgtgtgtg   6000
tcaattcaat gcaatgttgg ctgccttttg aagtctttga tatattggtg aatattcttc   6060
tgatctataa tacaaagcta tgtaatgtta cctcttgact cgcttttgaa aggaagacaa   6120
ttgttaacta gatatttgag tttttcccc tcagaattat gtgaatttct gatatatggc    6180
tttagatact gtgaatctgt tttccattta gtcagttatc tgcttaaatt gttcagaact   6240
atatcctaac gagcaattag ttctgatggt tctcccagtc atgagtgtgc atgtgtgcaa   6300
gcatgttttg atcctgatgc tacctttgct aaaaatggcc atagattagg aactagctat   6360
gtttttagaa tcaaagatga accggtaagc tgtctcatgt accaaacgtg aaatttacag   6420
tgtttacaaa tgtctggaat tttgcactgc catagggaat gttaaggtta cttggctgga   6480
atttatcaga cttgtgagta aacaagttga agtttagcag atgaggggga atattgaggc   6540
ccctaaggct aaacaaaata atcagtatct gagatagtgg ctaatgtggc tccccaggcc   6600
taatttggga acagtttttc ctgattgctt tgagaagtac tttcttttga cagaaatttt   6660
cattctgctt gccattgcta tattctccct ttataggagc cattggattt ctttcctttt   6720
gtgggaaatg tcccattagc attttcagat cttttgatgt gcactaatgc cattattggt   6780
aatgccgtta ttggtgaata cagcatagtt aaataaactg ttacagtaaa tctacacttg   6840
gatttgctgc acctctacca atagcctttt gaatgactga aagtgttaac agagaaagag   6900
gcatgtctgc agaaagagat agctaatatt ttttggtact ttatctgaaa tccaagatgc   6960
tgcttcccct gcaggttgtt ttccttctta cgatcctcat tgaatcccct ctgggagcac   7020
aggacagtta gtagaactct ccatttcttt tttttttttt ttagacggag tctctctctg   7080
tcgccccggc tggagtgcag tggcgcgatc tcggctcact gcaacctccg cctcccgggt   7140
tcaccccatt ctcctgcctc agcctcccta gtagctggga ctataggcgc ccgccaccac   7200
gcctggctaa tttttgtatt tttattggag acggggtttc accgtcttag ccaggatggt   7260
cttgatctcc tgacctcgtg atctgcccac ctcagcctcc caaagtactg ggattacagg   7320
cgtgagccac cgcgcccggc cggaactctc catttcttaa ggtaaagagg gtcaaggata   7380
cctaaaaagg gtcaaataat gctagaagag caattcctct ttcagagcag ttgctgtaat   7440
ttggcaaatg ctttatcgaa gattgatatt aggctagggg cggtggctta cgcctgtaat   7500
cccagcactt tgggaggccg aggtgggtgg attgcctgag ctcaggagtt cgagaccagt   7560
ctgaccagta tggtgaaacc ctgtctctac taaaaataca aaaattagcc ggtcgtggtg   7620
gcgtgcacct gtagtcccag ctacttggca ggttgagaca ggagaatcgc ttgaacctgg   7680
gaggtggagg ttgcagtgag ccgagactgc accactgcgc tcccacctgg gtgacagaga   7740
ctctgtctca aaaaaaagga catttatcat tataacatct tattagagcc cctaatttct   7800
tatctgaagg cactgttttt ttttttaaac agttaagtac tgatgtcaac agacaaatat   7860
ttctgatcag atagtcccct gtcaacagta gcaaatgtgg tttcataaag tgggaagaaa   7920
```

-continued

```
acagcatttt aaagtaactt tttgggagac tgatttgagt aataataaaa ctctggtctc   7980
ccttaagaaa aaaaaaccct tccaccttta ctgtgtcatt tatatcccct tagttccaaa   8040
gttaattatc ttatttctgg atattgcttt tataccaaag acccttatca gcccttgtaa   8100
ctacagtatc tttagataag attcctcttt ccagtcagtc ctgggaaatg tttctgttgc   8160
agagttaggc ggtagatggg aagctgtgat ggcagagcta ctatctaata aagtaacaac   8220
tcgtagttga ggcttccttt ctgtgtgtga tgggggatag ggagttagct cccctgttgt   8280
ctcagcacta agaaattgag gtcaggccag gcgcggtggt tcactcctgt tattccagca   8340
ctggggtggc caaagtgggc agattgcttg cgctctggag ctcgagacca gcctgggcaa   8400
catggtgaaa ccctgtctct accaaaaata caaaaaaaaa gctgggcatg gtgggtgcat   8460
gcttgtccca gctactgagg aggctgaggt gggaggatcg cttgagcctg ggaggtggag   8520
gttgcagtga gctgagatgg caccactgca atccaaggtg ggtgacagag acgctgtctc   8580
aaagaaattg aggtcaggct tccttcttac agaattattt ttttctctgt agtttgcctc   8640
attttttcac tttcttttca atgagaatcg aagtgtttct tttgggtttt tttttccccc   8700
ttttaaaatc aacaggaaat gtttcaaagg agggatgaaa tgcttcttgg cttcctcagc   8760
acttggcaag gtagacctca tagcaacctt gaatatgact ttctttagtc tctagctatg   8820
cactattaag tgcctcttgg gtagaggtag agttaagtat tgagtgccag tcttgacgtc   8880
cgtatgcctc agtttttctc atatataaaa agcagtatac atacctaccc ttttctacct   8940
catcatttgt tgtagggatt aaatccggga gagcaattct gaagcctata aatttccttg   9000
aagagatcta agaacctatt atgctcttgg tgtaccaagc tctggggtat atattcagaa   9060
tacctcatgt tctggaagct gagcactagc tccccttatt tgcctgcctg gcagagcctg   9120
tttgattact gcaggccctt ttacccatgc ttctagttta ggtattcttt ctttgatatg   9180
aggctcttga ccagaaaaga gttctttctc taggtgttct gagagaagtt tgtaaatttg   9240
gatagtacat tctatcctga taaaaccacc ttgctgtggt cttgatgtac aaaaaaaaat   9300
tttttttttg agacagagtc ttactctgtc acccaggctg gaatgcagtg gcgcaatctt   9360
ggttcactgc aacccccgcc tcctgggttc aagcgatcct cctgcctcaa cctctcaagt   9420
agctgggact acaggcgtgc accaccacac ctggctaatt ttgtattttt agtagagaca   9480
gggtttcacc atgttggcca ggctggtctt gaactcctga cctcaggcga tctgcccgcc   9540
ttggcctccc aaagtactgg gattacaggc gtgagcaact gctcctggcc caaaacatct   9600
ctttctacat acacttgagt aggtggcata aaatgcactg tcaatatata gaaaacatga   9660
aattttccaa atatttccga tcagagaatc acaagagcag caaatgtggt ttcatcaagt   9720
gggaagaaag cagcaattta aaataacttt ttgggagact gaattgagta ataataaaac   9780
ttcagtcttt cgctaataat aataataata ataataataa caacaactta ttgaatgtgg   9840
ccagctcact agatgaggaa agaggaaggc attttctgca ttcttgccta gttttcctta   9900
taagcaccac taagttaata gctctgtctt tttggtgttt gcactatgta atgcttttaa   9960
tactttttaa ttgtgctttt ttatgtatta aatgtttttc cttttgccaa aaaaaaaaaa  10020
aa                                                                10022
```

<210> SEQ ID NO 22
<211> LENGTH: 140
<212> TYPE: PRT
<213> ORGANISM: Homo sapiens

<400> SEQUENCE: 22

```
Met Thr Ser Phe Ser Thr Ser Ala Gln Cys Ser Thr Ser Asp Ser Ala
1               5                   10                  15

Cys Arg Ile Ser Pro Gly Gln Ile Asn Gln Val Arg Pro Lys Leu Pro
            20                  25                  30

Leu Leu Lys Ile Leu His Ala Ala Gly Ala Gln Gly Glu Met Phe Thr
        35                  40                  45

Val Lys Glu Val Met His Tyr Leu Gly Gln Tyr Ile Met Val Lys Gln
    50                  55                  60

Leu Tyr Asp Gln Gln Glu Gln His Met Val Tyr Cys Gly Gly Asp Leu
65                  70                  75                  80

Leu Gly Glu Leu Leu Gly Arg Gln Ser Phe Ser Val Lys Asp Pro Ser
                85                  90                  95

Pro Leu Tyr Asp Met Leu Arg Lys Asn Leu Val Thr Leu Ala Thr Ala
            100                 105                 110

Thr Thr Ala Lys Cys Arg Gly Lys Phe His Phe Gln Lys Lys Asn Tyr
        115                 120                 125

Arg Arg Arg Tyr Pro His Thr Ala Tyr Leu Arg Ala
    130                 135                 140
```

<210> SEQ ID NO 23
<211> LENGTH: 9796
<212> TYPE: DNA
<213> ORGANISM: Homo sapiens

<400> SEQUENCE: 23

```
gtgtgggagg ccggaagttg cggcttcatt actcgccatt tcaaaatgct gccgaggccc     60

taggatctgt gactgccacc cctcccccca cccgggctcg gcgggggagc gactcatgga    120

gctgccgtaa gttttaccaa cagactgcag tttcttcact accaaaatga catcattttc    180

cacctctgct cagtgttcaa catctgacag tgcttgcagg atctctcctg gacaaatcaa    240

tcaggatcac agtatggata ttccaagtca agaccaactg aagcaaagtg cagaggaaag    300

ttccacttcc agaaaaagaa ctacagaaga cgatatcccc acactgccta cctcagagca    360

taaatgcata cattctagag aagatgaaga cttaattgaa aatttagccc aagatgaaac    420

atctaggctg gaccttggat ttgaggagtg ggatgtagct ggcctgcctt ggtggttttt    480

aggaaacttg agaagcaact atacacctag aagtaatggc tcaactgatt tacagacaaa    540

tcaggatgtg ggtactgcca ttgtttcaga tactacagat gacttgtggt tttgaatga     600

gtcagtatca gagcagttag gtgttggaat aaaagttgaa gctgctgata ctgaacaaac    660

aagtgaagaa gtagggaaag taagtgacaa aaaggtgatt gaagtgggaa aaaatgatga    720

cctggaggac tctaagtcct taagtgatga taccgatgta gaggttacct ctgaggatga    780

gtggcagtgt actgaatgca agaaatttaa ctctccaagc aagaggtact gttttcgttg    840

ttgggccttg aggaaggatt ggtattcaga ttgttcaaag ttaacccatt ctctctccac    900

gtctgatatc actgccatac ctgaaaagga aaatgaagga aatgatgtcc ctgattgtcg    960

aagaaccatt tcggctcctg tcgttagacc taaagatgcg tatataaaga aagaaaactc   1020

caaacttttt gatccctgca actcagtgga attcttggat ttggctcaca gttctgaaag   1080

ccaagagacc atctcaagca tgggagaaca gttagataac ctttctgaac agagaacaga   1140

tacagaaaac atggaggatt gccagaatct cttgaagcca tgtagcttat gtgagaaaag   1200

accacgagac gggaacatta ttcatggaag gacgggccat cttgtcactt gttttcactg   1260
```

-continued

```
tgccagaaga ctaaagaagg ctggggcttc atgccctatt tgcaagaaag agattcagct   1320
ggttattaag gtttttatag cataatggta gtacgaacat aaaaatgcat ttattccgtt   1380
cacttaccac attatttgaa aatcaatcct ttatttaatt ttatttccaa cctgtcagag   1440
aatgttctta ggcatcaaaa tccaaggtag ctgtaagaaa aatactggag ctaacaatga   1500
agaacagaag taatctgatt agtcaaatta ttaagtgcca tggattactt tatgcagcag   1560
tcaggtacat agttaggtga acccaaaaga aaaactcttg aaaacaagag atttcttcca   1620
tgcacattta caatattgag gtataattaa catgataaag tgtttccttc taacgagttg   1680
tagaaatctg agtaaccacc caaaaaagca atagaatgtt tctgtcaccc caaaacactc   1740
ccttctgccc ctcttcagac agtccttcag ctatttcatg gctctcaccc tagttttttt   1800
tttttttgca cttttttttt tccgggggta taggggaggt gtggggcgac agggtctgtc   1860
ttgttctgtc tcccaggctg aagtgcagtg cagtggtatg atcatggctc actgcagcct   1920
tggtttcctg ggcataagtg gtcttcccac ttcagcctcc tgagtagctg agactataga   1980
ctagcataac cacactggct aatttttttgt ggagatgaag tctcactatg ttgcccaggc   2040
tggtctcgaa ctcctgggct caaacaatcc tcccgcctca gccttccaaa ttgctgggat   2100
tatagtcatg aggcacctag tctggccctt ttgcaagact ttaatctgaa atctaaattt   2160
ttaaaattta agtacttaca aaggatatac tatccaacat attgcatatt atatatgtgc   2220
tttaaagttt tttttttttt ttgagagacg gtctcacttt gtcatccaag ctggagtgca   2280
gtggtgcaaa cacggcccac ctcctgggct caagtgatcc tccagcctca gcttccctca   2340
caggcattca ctatcactcc cagctaatta aaataatttg tagacggtgt ctcgttatgt   2400
tgcccaggct ggtctcgaac tcctgggttt aagtgattcc cccgcctcag cctcccaaag   2460
tgttgggctt acagccttga gccactatgc ttggctcaaa gatattttta tgaaagccct   2520
gggactatag atttagctga ttaaatttat agaaaaagtc ctgtcatata aactggcaaa   2580
gtctgttctt aatttaatta gccaaatcag acttaacttc cgtcagaaca tgtcttggtt   2640
ttaattcaga taaacacaca aacatacttc tctggcacag ccttcagaag catcagtttt   2700
tgttttgttt tgttttgttt tttgagacag ggtcttgctc tgtcgcccag gctggagtgc   2760
actggcacaa tcacagttca ctgcagcctc gacctcccag atccaagcaa tcctcccacc   2820
taagcctccc aagtagctgg gtctataggc gcgtgccacc accatgccca gctgaatttt   2880
gtattttttg tacagacagc attttgccat gttgcccagg ctggtcccaa acttctagcc   2940
tcaagcaacc ctcctgcctc agcctctcaa agtgctagga ttgcagtcct gagctactgc   3000
cccctaccct ctttgcgtct taggagtcat ttagattttt tttgatcctt ttgtttagtg   3060
cctctggagc tgcttacacc aaggcaatac gccttgatat actggatggt tgagaggcag   3120
cctctttttt tttttttttt tttttttttt tttggaggat agggagtatg gctgttgtga   3180
aaagggaggt aaagagaaat ggtagatctg aagaggcctc atcagagcac atattttagg   3240
acaacacata tggaaattgg acatctttaa gttggtttcc atagagctat gcatgtatcc   3300
ttaccccccat gggaaaatgt tggtgtgttc tcaagggtat gcatgtgtca ttttgaagac   3360
caaggcccta gaattgtcaa acttaaggat cataaaaatc atgagggttg cttgttaaaa   3420
atgtccaaac gtgcagagac tgatctttga gatctggacc aggaatttgc atttgaacaa   3480
gtgttcctgg aatctctatg caagttttat acagaacata cttttggaat ccttgcccta   3540
gacaggggtg tccaatcttt tggcttccct ggtccacaat ggaagaagaa ttgtcttgga   3600
ccacacataa aatacactaa cactaacaat agctgatgag ctaaaaaaaa aaaaaaaaaa   3660
```

aatcgtggac cgggcgtagt ggctcacgcc tgtaatccca acactttggg agatcaccta 3720
ggtcgggagt ttgagaccag cctgaccgac atggagaaac cccattttta ctaaaaatac 3780
aaaaaattag ctgggcatgg tggtgcatgc ctgtagtccc agctactcag gaggctgagg 3840
caggagaatc gcttgaacct gagaggggga gattgcggtg agctgagatt gcgccattgc 3900
accccagcct gggcaacaat agcgaaactg tctcagaaaa aagaaaaaaa aaatcgcaaa 3960
aagaaaaatc tcataatgtc gttgttggtt tttttttttt tttttgagac agtctcactc 4020
tgttgcccag gctggagtgc aatggcatga tctctgctca ccgcaacctc tgcctcccgg 4080
gttcaggtga ttctcctgcc tcagcctccc agatagctgg gactacaggc acataccacc 4140
atgcctggct aatttttgta tttttagtag agatgggggt ttcactgtgt tggccaggct 4200
ggtctcgaac tcctgacctc atgatccaca cacctcggcc tcccaaagtc ctgcgattac 4260
aggcgtgagc taccgcaccc agccaagttg taatttttaa taaaacttaa gaagtaaaca 4320
ttttacttat gtttataggt atttgatcct aaatttgaca catcattgcc catgaaagaa 4380
tcctcttagg ctgctcagct tcactcttcc tgcttgccca ccggggtttt tcactgcttc 4440
tgttagcact aagtacttag acgatcctaa gatatgtgct tgagccgaat ttcatcttta 4500
cttgtaggaa actttaaact atttcttttc ttttcttttt tttttttttt tacttgagat 4560
ggagttttgc tcttgtcgcc caggctggag tgcagtggag tgatctcggc tcactgcaac 4620
ctctgcctcc cgggttcaaa tgattctcct gcctcagcct cccaagtagc tgggattaca 4680
ggtgtgcacc accatgtctg gctaattttg tatttttagt agagatggtt tcaccatgtt 4740
ggtcaggctg gtctcgaact cctgacctca ggtcatccac ccacctcagc ctcgcaaagt 4800
gctgagatta caggcatgag ccacagcgcc cagcttaaac tattttcttg gtctgttttt 4860
gattttcttt tttccttgcc actgcggtac agattttttt tactcactgc cactaaacta 4920
aagcaaggca tagtttatat gtgaagtgtt cagagtttac tgctataagg aaacttccaa 4980
atactgacat ttacctttta gctgtagtta ttgggaccat gtgctctggt tttctggaga 5040
ctgccaaatt gctcccattt ttctgcatcc cacctggttt ctttctgcat gtcccctttc 5100
actttcaaac ctcttcattt ggatgttaaa ttatatggtc acctagttat aggtaagcct 5160
tgttcgagtt gatatcttga ttgtgaggaa ggatctgtgt cattggagct tgtttctgct 5220
gcaacgtgct gtagactatg aataatgaaa tcacaccaca ttaccatcag atttcttgtt 5280
ttagttgtca aattaatatt tatgattgtt atcttgggcg aaaagttcag agcagagatg 5340
acaaatcatt agaacaacga tgaatttcag tattacggct aaaaagttct tctgtctgaa 5400
tattaactca ctctccttcc agtgtacttc acagtaattg gtatgctttt ttatttaatg 5460
cttaaatcaa actttataaa aatcttagac cagatcttta atatggtatg ccatttcccc 5520
agtctaccaa tggaatagta tgggtttcta atcctaggct tgtacaatgg attggagttg 5580
agccatgcca gcctccacac tgccactaac ttctgtaatg taagattgag tcactgccaa 5640
gcatttgaaa tatgcagttg tgttttaatt ataatttatg tatagttaga tgtatgtagt 5700
gcattgtgtg gtattatttg gtttgtaaga atttattttt aagggtcaag gtcatttgta 5760
acattttgtg tgtgtcaatt caatgcaatg ttggctgcct tttgaagtct ttgatatatt 5820
ggtgaatatt cttctgatct ataatacaaa gctatgtaat gttacctctt gactcgcttt 5880
tgaaaggaag acaattgtta actagatatt tgagtttttt cccctcagaa ttatgtgaat 5940
ttctgatata tggctttaga tactgtgaat ctgttttcca tttagtcagt tatctgctta 6000

-continued

```
aattgttcag aactatatcc taacgagcaa ttagttctga tggttctccc agtcatgagt   6060
gtgcatgtgt gcaagcatgt tttgatcctg atgctacctt tgctaaaaat ggccatagat   6120
taggaactag ctatgttttt agaatcaaag atgaaccggt aagctgtctc atgtaccaaa   6180
cgtgaaattt acagtgttta caaatgtctg gaattttgca ctgccatagg gaatgttaag   6240
gttacttggc tggaatttat cagacttgtg agtaaacaag ttgaagttta gcagatgagg   6300
gggaatattg aggcccctaa ggctaaacaa aataatcagt atctgagata gtggctaatg   6360
tggctcccca ggcctaattt gggaacagtt tttcctgatt gctttgagaa gtactttctt   6420
ttgacagaaa ttttcattct gcttgccatt gctatattct ccctttatag gagccattgg   6480
atttctttcc ttttgtggga aatgtcccat tagcattttc agatcttttg atgtgcacta   6540
atgccattat tggtaatgcc gttattggtg aatacagcat agttaaataa actgttacag   6600
taaatctaca cttggatttg ctgcacctct accaatagcc ttttgaatga ctgaaagtgt   6660
taacagagaa agaggcatgt ctgcagaaag agatagctaa tattttttgg tactttatct   6720
gaaatccaag atgctgcttc ccctgcaggt tgttttcctt cttacgatcc tcattgaatc   6780
ccctctggga gcacaggaca gttagtagaa ctctccattt cttttttttt ttttttagac   6840
ggagtctctc tctgtcgccc cggctggagt gcagtggcgc gatctcggct cactgcaacc   6900
tccgcctccc gggttcaccc cattctcctg cctcagcctc cctagtagct gggactatag   6960
gcgcccgcca ccacgcctgg ctaatttttg tatttttatt ggagacgggg tttcaccgtc   7020
ttagccagga tggtcttgat ctcctgacct cgtgatctgc ccacctcagc ctcccaaagt   7080
actgggatta caggcgtgag ccaccgcgcc cggccggaac tctccatttc ttaaggtaaa   7140
gagggtcaag gatacctaaa aagggtcaaa taatgctaga agagcaattc ctctttcaga   7200
gcagttgctg taatttggca aatgctttat cgaagattga tattaggcta ggggcggtgg   7260
cttacgcctg taatcccagc actttgggag gccgaggtgg gtggattgcc tgagctcagg   7320
agttcgagac cagtctgacc agtatggtga aaccctgtct ctactaaaaa tacaaaaatt   7380
agccggtcgt ggtggcgtgc acctgtagtc ccagctactt ggcaggttga gacaggagaa   7440
tcgcttgaac ctgggaggtg gaggttgcag tgagccgaga ctgcaccact gcgctcccac   7500
ctgggtgaca gagactctgt ctcaaaaaaa aggacattta tcattataac atcttattag   7560
agcccctaat ttcttatctg aaggcactgt tttttttttt aaacagttaa gtactgatgt   7620
caacagacaa atatttctga tcagatagtc ccctgtcaac agtagcaaat gtggtttcat   7680
aaagtgggaa gaaaacagca ttttaaagta actttttggg agactgattt gagtaataat   7740
aaaactctgg tctcccttaa gaaaaaaaaa cccttccacc tttactgtgt catttatatc   7800
cccttagttc caaagttaat tatcttattt ctggatattg cttttatacc aaagaccctt   7860
atcagccctt gtaactacag tatctttaga taagattcct ctttccagtc agtcctggga   7920
aatgtttctg ttgcagagtt aggcggtaga tgggaagctg tgatggcaga gctactatct   7980
aataaagtaa caactcgtag ttgaggcttc ctttctgtgt gtgatggggg atagggagtt   8040
agctcccctg ttgtctcagc actaagaaat tgaggtcagg ccaggcgcgg tggttcactc   8100
ctgttattcc agcactgggg tggccaaagt gggcagattg cttgcgctct ggagctcgag   8160
accagcctgg gcaacatggt gaaaccctgt ctctaccaaa aatacaaaaa aaaagctggg   8220
catggtgggt gcatgcttgt cccagctact gaggaggctg aggtgggagg atcgcttgag   8280
cctgggaggt ggaggttgca gtgagctgag atggcaccac tgcaatccaa ggtgggtgac   8340
agagacgctg tctcaaagaa attgaggtca ggcttccttc ttacagaatt atttttttct   8400
```

```
ctgtagtttg cctcattttt tcactttctt ttcaatgaga atcgaagtgt ttcttttggg   8460

ttttttttc cccctttaa aatcaacagg aaatgtttca aaggagggat gaaatgcttc   8520

ttggcttcct cagcacttgg caaggtagac ctcatagcaa ccttgaatat gactttcttt   8580

agtctctagc tatgcactat taagtgcctc ttgggtagag gtagagttaa gtattgagtg   8640

ccagtcttga cgtccgtatg cctcagtttt tctcatatat aaaaagcagt atacatacct   8700

acccttttct acctcatcat ttgttgtagg gattaaatcc gggagagcaa ttctgaagcc   8760

tataaatttc cttgaagaga tctaagaacc tattatgctc ttggtgtacc aagctctggg   8820

gtatatattc agaatacctc atgttctgga agctgagcac tagctcccct ttattgcctg   8880

cctggcagag cctgtttgat tactgcaggc ccttttaccc atgcttctag tttaggtatt   8940

ctttctttga tatgaggctc ttgaccagaa aagagttctt tctctaggtg ttctgagaga   9000

agtttgtaaa tttggatagt acattctatc ctgataaaac caccttgctg tggtcttgat   9060

gtacaaaaaa aaattttttt tttgagacag agtcttactc tgtcacccag gctggaatgc   9120

agtggcgcaa tcttggttca ctgcaacccc cgcctcctgg gttcaagcga tcctcctgcc   9180

tcaacctctc aagtagctgg gactacaggc gtgcaccacc acacctggct aattttgtat   9240

ttttagtaga gacagggttt caccatgttg gccaggctgg tcttgaactc ctgacctcag   9300

gcgatctgcc cgccttggcc tcccaaagta ctgggattac aggcgtgagc aactgctcct   9360

ggcccaaaac atctctttct acatacactt gagtaggtgg cataaaatgc actgtcaata   9420

tatagaaaac atgaaatttt ccaaatattt ccgatcagag aatcacaaga gcagcaaatg   9480

tggtttcatc aagtgggaag aaagcagcaa tttaaaataa ctttttggga gactgaattg   9540

agtaataata aaacttcagt ctttcgctaa taataataat aataataata ataacaacaa   9600

cttattgaat gtggccagct cactagatga ggaaagagga aggcattttc tgcattcttg   9660

cctagtttc cttataagca ccactaagtt aatagctctg tctttttggt gtttgcacta   9720

tgtaatgctt ttaatacttt ttaattgtgc ttttttatgt attaaatgtt tttccttttg   9780

ccaaaaaaaa aaaaaa                                                   9796
```

<210> SEQ ID NO 24
<211> LENGTH: 392
<212> TYPE: PRT
<213> ORGANISM: Homo sapiens

<400> SEQUENCE: 24

```
Met Thr Ser Phe Ser Thr Ser Ala Gln Cys Ser Thr Ser Asp Ser Ala
1               5                   10                  15

Cys Arg Ile Ser Pro Gly Gln Ile Asn Gln Asp His Ser Met Asp Ile
            20                  25                  30

Pro Ser Gln Asp Gln Leu Lys Gln Ser Ala Glu Glu Ser Ser Thr Ser
        35                  40                  45

Arg Lys Arg Thr Thr Glu Asp Asp Ile Pro Thr Leu Pro Thr Ser Glu
    50                  55                  60

His Lys Cys Ile His Ser Arg Glu Asp Glu Asp Leu Ile Glu Asn Leu
65                  70                  75                  80

Ala Gln Asp Glu Thr Ser Arg Leu Asp Leu Gly Phe Glu Glu Trp Asp
                85                  90                  95

Val Ala Gly Leu Pro Trp Trp Phe Leu Gly Asn Leu Arg Ser Asn Tyr
            100                 105                 110
```

-continued

Thr Pro Arg Ser Asn Gly Ser Thr Asp Leu Gln Thr Asn Gln Asp Val
115 120 125

Gly Thr Ala Ile Val Ser Asp Thr Thr Asp Asp Leu Trp Phe Leu Asn
130 135 140

Glu Ser Val Ser Glu Gln Leu Gly Val Gly Ile Lys Val Glu Ala Ala
145 150 155 160

Asp Thr Glu Gln Thr Ser Glu Glu Val Gly Lys Val Ser Asp Lys Lys
165 170 175

Val Ile Glu Val Gly Lys Asn Asp Asp Leu Glu Asp Ser Lys Ser Leu
180 185 190

Ser Asp Asp Thr Asp Val Glu Val Thr Ser Glu Asp Glu Trp Gln Cys
195 200 205

Thr Glu Cys Lys Lys Phe Asn Ser Pro Ser Lys Arg Tyr Cys Phe Arg
210 215 220

Cys Trp Ala Leu Arg Lys Asp Trp Tyr Ser Asp Cys Ser Lys Leu Thr
225 230 235 240

His Ser Leu Ser Thr Ser Asp Ile Thr Ala Ile Pro Glu Lys Glu Asn
245 250 255

Glu Gly Asn Asp Val Pro Asp Cys Arg Arg Thr Ile Ser Ala Pro Val
260 265 270

Val Arg Pro Lys Asp Ala Tyr Ile Lys Lys Glu Asn Ser Lys Leu Phe
275 280 285

Asp Pro Cys Asn Ser Val Glu Phe Leu Asp Leu Ala His Ser Ser Glu
290 295 300

Ser Gln Glu Thr Ile Ser Ser Met Gly Glu Gln Leu Asp Asn Leu Ser
305 310 315 320

Glu Gln Arg Thr Asp Thr Glu Asn Met Glu Asp Cys Gln Asn Leu Leu
325 330 335

Lys Pro Cys Ser Leu Cys Glu Lys Arg Pro Arg Asp Gly Asn Ile Ile
340 345 350

His Gly Arg Thr Gly His Leu Val Thr Cys Phe His Cys Ala Arg Arg
355 360 365

Leu Lys Lys Ala Gly Ala Ser Cys Pro Ile Cys Lys Lys Glu Ile Gln
370 375 380

Leu Val Ile Lys Val Phe Ile Ala
385 390

<210> SEQ ID NO 25
<211> LENGTH: 9611
<212> TYPE: DNA
<213> ORGANISM: Homo sapiens

<400> SEQUENCE: 25
gtgtgggagg ccggaagttg cggcttcatt actcgccatt tcaaaatgct gccgaggccc 60
taggatctgt gactgccacc cctccccccca cccgggctcg gcgggggagc gactcatgga 120
gctgccgtaa gttttaccaa cagactgcag tttcttcact accaaaatga catcattttc 180
cacctctgct cagtgttcaa catctgacag tgcttgcagg atctctcctg gacaaatcaa 240
tcaggtacga ccaaaactgc cgcttttgaa gattttgcat gcagcaggtg cgcaaggtga 300
aatgttcact gttaaagagg tcatgcacta tttaggtcag tacataatgg tgaagcaact 360
ttatgatcag caggagcagc atatggtata ttgtggtgga gatcttttgg gagaactact 420
gggacgtcag agcttctccg tgaaagaccc aagccctctc tatgatatgc taagaaagaa 480

-continued

```
tcttgtcact ttagccactg ctactacagg tgattgaagt gggaaaaaat gatgacctgg    540
aggactctaa gtccttaagt gatgataccg atgtagaggt tacctctgag gatgagtggc    600
agtgtactga atgcaagaaa tttaactctc caagcaagag gtactgtttt cgttgttggg    660
ccttgaggaa ggattggtat tcagattgtt caaagttaac ccattctctc tccacgtctg    720
atatcactgc catacctgaa aaggaaaatg aaggaaatga tgtccctgat tgtcgaagaa    780
ccatttcggc tcctgtcgtt agacctaaag atgcgtatat aaagaaagaa aactccaaac    840
tttttgatcc ctgcaactca gtggaattct tggatttggc tcacagttct gaaagccaag    900
agaccatctc aagcatggga gaacagttag ataacctttc tgaacagaga acagatacag    960
aaaacatgga ggattgccag aatctcttga agccatgtag cttatgtgag aaaagaccac   1020
gagacgggaa cattattcat ggaaggacgg gccatcttgt cacttgtttt cactgtgcca   1080
gaagactaaa gaaggctggg gcttcatgcc ctatttgcaa gaaagagatt cagctggtta   1140
ttaaggtttt tatagcataa tggtagtacg aacataaaaa tgcatttatt ccgttcactt   1200
accacattat ttgaaaatca atcctttatt taattttatt tccaacctgt cagagaatgt   1260
tcttaggcat caaaatccaa ggtagctgta agaaaaatac tggagctaac aatgaagaac   1320
agaagtaatc tgattagtca aattattaag tgccatggat tactttatgc agcagtcagg   1380
tacatagtta ggtgaaccca aaagaaaaac tcttgaaaac aagagatttc ttccatgcac   1440
atttacaata ttgaggtata attaacatga taaagtgttt ccttctaacg agttgtagaa   1500
atctgagtaa ccacccaaaa aagcaataga atgtttctgt caccccaaaa cactcccttc   1560
tgcccctctt cagacagtcc ttcagctatt tcatggctct caccctagtt tttttttttt   1620
ttgcactttt ttttttccgg gggtataggg gaggtgtggg gcgacagggt ctgtcttgtt   1680
ctgtctccca ggctgaagtg cagtgcagtg gtatgatcat ggctcactgc agccttggtt   1740
tcctgggcat aagtggtctt cccacttcag cctcctgagt agctgagact atagactagc   1800
ataaccacac tggctaattt tttgtggaga tgaagtctca ctatgttgcc caggctggtc   1860
tcgaactcct gggctcaaac aatcctcccg cctcagcctt ccaaattgct gggattatag   1920
tcatgaggca cctagtctgg cccttttgca agactttaat ctgaaatcta aatttttaaa   1980
atttaagtac ttacaaagga tatactatcc aacatattgc atattatata tgtgctttaa   2040
agtttttttt tttttttgag agacggtctc actttgtcat ccaagctgga gtgcagtggt   2100
gcaaacacgg cccacctcct gggctcaagt gatcctccag cctcagcttc cctcacaggc   2160
attcactatc actcccagct aattaaaata atttgtagac ggtgtctcgt tatgttgccc   2220
aggctggtct cgaactcctg ggtttaagtg attcccccgc ctcagcctcc caaagtgttg   2280
ggcttacagc cttgagccac tatgcttggc tcaaagatat ttttatgaaa gccctgggac   2340
tatagattta gctgattaaa tttatagaaa aagtcctgtc atataaactg gcaaagtctg   2400
ttcttaattt aattagccaa atcagactta acttccgtca gaacatgtct tggttttaat   2460
tcagataaac acacaaacat acttctctgg cacagccttc agaagcatca gtttttgttt   2520
tgttttgttt tgttttttga gacagggtct tgctctgtcg cccaggctgg agtgcactgg   2580
cacaatcaca gttcactgca gcctcgacct cccagatcca agcaatcctc ccacctaagc   2640
ctcccaagta gctgggtcta taggcgcgtg ccaccaccat gcccagctga attttgtatt   2700
ttttgtacag acagcatttt gccatgttgc ccaggctggt cccaaacttc tagcctcaag   2760
caaccctcct gcctcagcct ctcaaagtgc taggattgca gtcctgagct actgcccccct   2820
accctctttg cgtcttagga gtcatttaga tttttttga tccttttgtt tagtgcctct   2880
```

-continued

```
ggagctgctt acaccaaggc aatacgcctt gatatactgg atggttgaga ggcagcctct   2940
tttttttttt tttttttttt ttttttttgg aggataggga gtatggctgt tgtgaaaagg   3000
gaggtaaaga gaaatggtag atctgaagag gcctcatcag agcacatatt ttaggacaac   3060
acatatggaa attggacatc tttaagttgg tttccataga gctatgcatg tatccttacc   3120
cccatgggaa aatgttggtg tgttctcaag ggtatgcatg tgtcattttg aagaccaagg   3180
ccctagaatt gtcaaactta aggatcataa aaatcatgag ggttgcttgt taaaaatgtc   3240
caaacgtgca gagactgatc tttgagatct ggaccaggaa tttgcatttg aacaagtgtt   3300
cctggaatct ctatgcaagt tttatacaga acatactttt ggaatccttg ccctagacag   3360
gggtgtccaa tcttttggct tccctggtcc acaatggaag aagaattgtc ttggaccaca   3420
cataaaatac actaacacta acaatagctg atgagctaaa aaaaaaaaaa aaaaaaatcg   3480
tggaccgggc gtagtggctc acgcctgtaa tcccaacact ttgggagatc acctaggtcg   3540
ggagtttgag accagcctga ccgacatgga gaaaccccat ttttactaaa aatacaaaaa   3600
attagctggg catggtggtg catgcctgta gtcccagcta ctcaggaggc tgaggcagga   3660
gaatcgcttg aacctgagag gggagattg cggtgagctg agattgcgcc attgcacccc   3720
agcctgggca acaatagcga aactgtctca gaaaaaagaa aaaaaaaatc gcaaaaagaa   3780
aaatctcata atgtcgttgt tggttttttt tttttttttt gagacagtct cactctgttg   3840
cccaggctgg agtgcaatgg catgatctct gctcaccgca acctctgcct cccgggttca   3900
ggtgattctc ctgcctcagc ctcccagata gctgggacta caggcacata ccaccatgcc   3960
tggctaattt ttgtattttt agtagagatg gggtttcac tgtgttggcc aggctggtct   4020
cgaactcctg acctcatgat ccacacacct cggcctccca aagtcctgcg attacaggcg   4080
tgagctaccg cacccagcca agttgtaatt tttaataaaa cttaagaagt aaacatttta   4140
cttatgttta taggtatttg atcctaaatt tgacacatca ttgcccatga aagaatcctc   4200
ttaggctgct cagcttcact cttcctgctt gcccaccggg gtttttcact gcttctgtta   4260
gcactaagta cttagacgat cctaagatat gtgcttgagc cgaatttcat ctttacttgt   4320
aggaaacttt aaactatttc ttttcttttc tttttttttt ttttttactt gagatggagt   4380
tttgctcttg tcgcccaggc tggagtgcag tggagtgatc tcggctcact gcaacctctg   4440
cctcccgggt tcaaatgatt ctcctgcctc agcctcccaa gtagctggga ttacaggtgt   4500
gcaccaccat gtctggctaa ttttgtattt ttagtagaga tggtttcacc atgttggtca   4560
ggctggtctc gaactcctga cctcaggtca tccacccacc tcagcctcgc aaagtgctga   4620
gattacaggc atgagccaca gcgcccagct taaactattt tcttggtctg tttttgattt   4680
tctttttcc ttgccactgc ggtacagatt tttttactc actgccacta aactaaagca   4740
aggcatagtt tatatgtgaa gtgttcagag tttactgcta taaggaaact tccaaatact   4800
gacatttacc ttttagctgt agttattggg accatgtgct ctggttttct ggagactgcc   4860
aaattgctcc catttttctg catcccacct ggtttctttc tgcatgtccc ctttcacttt   4920
caaacctctt catttggatg ttaaattata tggtcaccta gttataggta agccttgttc   4980
gagttgatat cttgattgtg aggaaggatc tgtgtcattg gagcttgttt ctgctgcaac   5040
gtgctgtaga ctatgaataa tgaaatcaca ccacattacc atcagatttc ttgttttagt   5100
tgtcaaatta atatttatga ttgttatctt gggcgaaaag ttcagagcag agatgacaaa   5160
tcattagaac aacgatgaat ttcagtatta cggctaaaaa gttcttctgt ctgaatatta   5220
```

-continued actcactctc cttccagtgt acttcacagt aattggtatg ctttttttatt taatgcttaa 5280 atcaaacttt ataaaaatct tagaccagat ctttaatatg gtatgccatt tccccagtct 5340
accaatggaa tagtatgggt ttctaatcct aggcttgtac aatggattgg agttgagcca 5400
tgccagcctc cacactgcca ctaacttctg taatgtaaga ttgagtcact gccaagcatt 5460
tgaaatatgc agttgtgttt taattataat ttatgtatag ttagatgtat gtagtgcatt 5520
gtgtggtatt atttggtttg taagaattta tttttaaggg tcaaggtcat ttgtaacatt 5580
ttgtgtgtgt caattcaatg caatgttggc tgccttttga agtctttgat atattggtga 5640
atattcttct gatctataat acaaagctat gtaatgttac ctcttgactc gcttttgaaa 5700
ggaagacaat tgttaactag atatttgagt tttttcccct cagaattatg tgaatttctg 5760
atatatggct ttagatactg tgaatctgtt ttccatttag tcagttatct gcttaaattg 5820
ttcagaacta tatcctaacg agcaattagt tctgatggtt ctcccagtca tgagtgtgca 5880
tgtgtgcaag catgttttga tcctgatgct acctttgcta aaaatggcca tagattagga 5940
actagctatg tttttagaat caaagatgaa ccggtaagct gtctcatgta ccaaacgtga 6000
aatttacagt gtttacaaat gtctggaatt ttgcactgcc atagggaatg ttaaggttac 6060
ttggctggaa tttatcagac ttgtgagtaa acaagttgaa gtttagcaga tgagggggaa 6120
tattgaggcc cctaaggcta aacaaaataa tcagtatctg agatagtggc taatgtggct 6180
ccccaggcct aatttgggaa cagtttttcc tgattgcttt gagaagtact ttcttttgac 6240
agaaattttc attctgcttg ccattgctat attctccctt tataggagcc attggatttc 6300
tttccttttg tgggaaatgt cccattagca ttttcagatc ttttgatgtg cactaatgcc 6360
attattggta atgccgttat tggtgaatac agcatagtta aataaactgt tacagtaaat 6420
ctacacttgg atttgctgca cctctaccaa tagccttttg aatgactgaa agtgttaaca 6480
gagaaagagg catgtctgca gaaagagata gctaatattt tttggtactt tatctgaaat 6540
ccaagatgct gcttcccctg caggttgttt tccttcttac gatcctcatt gaatcccctc 6600
tgggagcaca ggacagttag tagaactctc catttctttt tttttttttt tagacggagt 6660
ctctctctgt cgccccggct ggagtgcagt ggcgcgatct cggctcactg caacctccgc 6720
ctcccgggtt caccccattc tcctgcctca gcctccctag tagctgggac tataggcgcc 6780
cgccaccacg cctggctaat ttttgtattt ttattggaga cggggtttca ccgtcttagc 6840
caggatggtc ttgatctcct gacctcgtga tctgcccacc tcagcctccc aaagtactgg 6900
gattacaggc gtgagccacc gcgcccggcc ggaactctcc atttcttaag gtaaagaggg 6960
tcaaggatac ctaaaaaggg tcaaataatg ctagaagagc aattcctctt tcagagcagt 7020
tgctgtaatt tggcaaatgc tttatcgaag attgatatta ggctaggggc ggtggcttac 7080
gcctgtaatc ccagcacttt gggaggccga ggtgggtgga ttgcctgagc tcaggagttc 7140
gagaccagtc tgaccagtat ggtgaaaccc tgtctctact aaaaatacaa aaattagccg 7200
gtcgtggtgg cgtgcacctg tagtcccagc tacttggcag gttgagacag gagaatcgct 7260
tgaacctggg aggtggaggt tgcagtgagc cgagactgca ccactgcgct cccacctggg 7320
tgacagagac tctgtctcaa aaaaaaggac atttatcatt ataacatctt attagagccc 7380
ctaatttctt atctgaaggc actgtttttt tttttaaaca gttaagtact gatgtcaaca 7440
gacaaatatt tctgatcaga tagtcccctg tcaacagtag caaatgtggt ttcataaagt 7500
gggaagaaaa cagcatttta aagtaacttt ttgggagact gatttgagta ataataaaac 7560
tctggtctcc cttaagaaaa aaaaaccctt ccacctttac tgtgtcattt atatcccctt 7620

```
agttccaaag ttaattatct tatttctgga tattgctttt ataccaaaga cccttatcag   7680
cccttgtaac tacagtatct ttagataaga ttcctctttc cagtcagtcc tgggaaatgt   7740
ttctgttgca gagttaggcg gtagatggga agctgtgatg gcagagctac tatctaataa   7800
agtaacaact cgtagttgag gcttcctttc tgtgtgtgat gggggatagg gagttagctc   7860
ccctgttgtc tcagcactaa gaaattgagg tcaggccagg cgcggtggtt cactcctgtt   7920
attccagcac tggggtggcc aaagtgggca gattgcttgc gctctggagc tcgagaccag   7980
cctgggcaac atggtgaaac cctgtctcta ccaaaaatac aaaaaaaaag ctgggcatgg   8040
tgggtgcatg cttgtcccag ctactgagga ggctgaggtg ggaggatcgc ttgagcctgg   8100
gaggtggagg ttgcagtgag ctgagatggc accactgcaa tccaaggtgg gtgacagaga   8160
cgctgtctca aagaaattga ggtcaggctt ccttcttaca gaattatttt tttctctgta   8220
gtttgcctca ttttttcact ttcttttcaa tgagaatcga agtgtttctt ttgggttttt   8280
ttttccccct tttaaaatca acaggaaatg tttcaaagga gggatgaaat gcttcttggc   8340
ttcctcagca cttggcaagg tagacctcat agcaaccttg aatatgactt tctttagtct   8400
ctagctatgc actattaagt gcctcttggg tagaggtaga gttaagtatt gagtgccagt   8460
cttgacgtcc gtatgcctca gtttttctca tatataaaaa gcagtataca tacctaccct   8520
tttctacctc atcatttgtt gtagggatta aatccgggag agcaattctg aagcctataa   8580
atttccttga agagatctaa gaacctatta tgctcttggt gtaccaagct ctggggtata   8640
tattcagaat acctcatgtt ctggaagctg agcactagct cccctttatt gcctgcctgg   8700
cagagcctgt ttgattactg caggcccttt tacccatgct tctagtttag gtattctttc   8760
tttgatatga ggctcttgac cagaaaagag ttctttctct aggtgttctg agagaagttt   8820
gtaaatttgg atagtacatt ctatcctgat aaaaccacct tgctgtggtc ttgatgtaca   8880
aaaaaaaatt tttttttga gacagagtct tactctgtca cccaggctgg aatgcagtgg    8940
cgcaatcttg gttcactgca acccccgcct cctgggttca agcgatcctc ctgcctcaac   9000
ctctcaagta gctgggacta caggcgtgca ccaccacacc tggctaattt tgtattttta   9060
gtagagacag ggtttcacca tgttggccag gctggtcttg aactcctgac ctcaggcgat   9120
ctgcccgcct tggcctccca aagtactggg attacaggcg tgagcaactg ctcctggccc   9180
aaaacatctc tttctacata cacttgagta ggtggcataa aatgcactgt caatatatag   9240
aaaacatgaa attttccaaa tatttccgat cagagaatca caagagcagc aaatgtggtt   9300
tcatcaagtg ggaagaaagc agcaatttaa aataactttt tgggagactg aattgagtaa   9360
taataaaact tcagtctttc gctaataata ataataataa taataataac aacaacttat   9420
tgaatgtggc cagctcacta gatgaggaaa gaggaaggca ttttctgcat tcttgcctag   9480
ttttccttat aagcaccact aagttaatag ctctgtcttt ttggtgtttg cactatgtaa   9540
tgcttttaat actttttaat tgtgcttttt tatgtattaa atgtttttcc ttttgccaaa   9600
aaaaaaaaaa a                                                         9611
```

<210> SEQ ID NO 26
<211> LENGTH: 116
<212> TYPE: PRT
<213> ORGANISM: Homo sapiens

<400> SEQUENCE: 26

```
Met Thr Ser Phe Ser Thr Ser Ala Gln Cys Ser Thr Ser Asp Ser Ala
1               5                   10                  15
```

```
Cys Arg Ile Ser Pro Gly Gln Ile Asn Gln Val Arg Pro Lys Leu Pro
            20                  25                  30

Leu Leu Lys Ile Leu His Ala Ala Gly Ala Gln Gly Glu Met Phe Thr
        35                  40                  45

Val Lys Glu Val Met His Tyr Leu Gly Gln Tyr Ile Met Val Lys Gln
    50                  55                  60

Leu Tyr Asp Gln Gln Glu Gln His Met Val Tyr Cys Gly Gly Asp Leu
65                  70                  75                  80

Leu Gly Glu Leu Leu Gly Arg Gln Ser Phe Ser Val Lys Asp Pro Ser
                85                  90                  95

Pro Leu Tyr Asp Met Leu Arg Lys Asn Leu Val Thr Leu Ala Thr Ala
            100                 105                 110

Thr Thr Gly Asp
        115


<210> SEQ ID NO 27
<211> LENGTH: 9421
<212> TYPE: DNA
<213> ORGANISM: Homo sapiens

<400> SEQUENCE: 27

gtgtgggagg ccggaagttg cggcttcatt actcgccatt tcaaaatgct gccgaggccc      60

taggatctgt gactgccacc cctccccccca cccgggctcg gcgggggagc gactcatgga     120

gctgccgtaa gttttaccaa cagactgcag tttcttcact accaaaatga catcattttc     180

cacctctgct cagtgttcaa catctgacag tgcttgcagg atctctcctg gacaaatcaa     240

tcaggtacga ccaaaactgc cgcttttgaa gattttgcat gcagcaggtg cgcaaggtga     300

aatgttcact gttaaagagg tgattgaagt gggaaaaaat gatgacctgg aggactctaa     360

gtccttaagt gatgataccg atgtagaggt tacctctgag gatgagtggc agtgtactga     420

atgcaagaaa tttaactctc caagcaagag gtactgtttt cgttgttggg ccttgaggaa     480

ggattggtat tcagattgtt caaagttaac ccattctctc tccacgtctg atatcactgc     540

catacctgaa aaggaaaatg aaggaaatga tgtccctgat tgtcgaagaa ccatttcggc     600

tcctgtcgtt agacctaaag atgcgtatat aaagaaagaa aactccaaac tttttgatcc     660

ctgcaactca gtggaattct tggatttggc tcacagttct gaaagccaag agaccatctc     720

aagcatggga gaacagttag ataacctttc tgaacagaga acagatacag aaaacatgga     780

ggattgccag aatctcttga agccatgtag cttatgtgag aaaagaccac gagacgggaa     840

cattattcat ggaaggacgg gccatcttgt cacttgtttt cactgtgcca gaagactaaa     900

gaaggctggg gcttcatgcc ctatttgcaa gaaagagatt cagctggtta ttaaggtttt     960

tatagcataa tggtagtacg aacataaaaa tgcatttatt ccgttcactt accacattat    1020

ttgaaaatca atcctttatt taattttatt tccaacctgt cagagaatgt tcttaggcat    1080

caaaatccaa ggtagctgta agaaaaatac tggagctaac aatgaagaac agaagtaatc    1140

tgattagtca aattattaag tgccatggat tactttatgc agcagtcagg tacatagtta    1200

ggtgaaccca aaagaaaaac tcttgaaaac aagagatttc ttccatgcac atttacaata    1260

ttgaggtata attaacatga taaagtgttt ccttctaacg agttgtagaa atctgagtaa    1320

ccacccaaaa aagcaataga atgtttctgt caccccaaaa cactcccttc tgcccctctt    1380

cagacagtcc ttcagctatt tcatggctct caccctagtt tttttttttt ttgcactttt    1440

ttttttccgg gggtataggg gaggtgtggg gcgacagggt ctgtcttgtt ctgtctccca    1500
```

-continued

```
ggctgaagtg cagtgcagtg gtatgatcat ggctcactgc agccttggtt tcctgggcat   1560
aagtggtctt cccacttcag cctcctgagt agctgagact atagactagc ataaccacac   1620
tggctaattt tttgtggaga tgaagtctca ctatgttgcc caggctggtc tcgaactcct   1680
gggctcaaac aatcctcccg cctcagcctt ccaaattgct gggattatag tcatgaggca   1740
cctagtctgg ccctttttgca agactttaat ctgaaatcta aatttttaaa atttaagtac   1800
ttacaaagga tatactatcc aacatattgc atattatata tgtgctttaa agtttttttt   1860
tttttttgag agacggtctc actttgtcat ccaagctgga gtgcagtggt gcaaacacgg   1920
cccacctcct gggctcaagt gatcctccag cctcagcttc cctcacaggc attcactatc   1980
actcccagct aattaaaata atttgtagac ggtgtctcgt tatgttgccc aggctggtct   2040
cgaactcctg ggtttaagtg attcccccgc ctcagcctcc caaagtgttg ggcttacagc   2100
cttgagccac tatgcttggc tcaaagatat ttttatgaaa gccctgggac tatagattta   2160
gctgattaaa tttatagaaa aagtcctgtc atataaactg gcaaagtctg ttcttaattt   2220
aattagccaa atcagactta acttccgtca gaacatgtct tggttttaat tcagataaac   2280
acacaaacat acttctctgg cacagccttc agaagcatca gtttttgttt tgttttgttt   2340
tgtttttttga gacagggtct tgctctgtcg cccaggctgg agtgcactgg cacaatcaca   2400
gttcactgca gcctcgacct cccagatcca agcaatcctc ccacctaagc ctcccaagta   2460
gctgggtcta taggcgcgtg ccaccaccat gcccagctga attttgtatt ttttgtacag   2520
acagcatttt gccatgttgc ccaggctggt cccaaacttc tagcctcaag caaccctcct   2580
gcctcagcct ctcaaagtgc taggattgca gtcctgagct actgcccccct accctctttg   2640
cgtcttagga gtcatttaga tttttttttga tccttttgtt tagtgcctct ggagctgctt   2700
acaccaaggc aatacgcctt gatatactgg atggttgaga ggcagcctct tttttttttt   2760
tttttttttt tttttttttgg aggataggga gtatggctgt tgtgaaaagg gaggtaaaga   2820
gaaatggtag atctgaagag gcctcatcag agcacatatt ttaggacaac acatatggaa   2880
attggacatc tttaagttgg tttccataga gctatgcatg tatccttacc cccatgggaa   2940
aatgttggtg tgttctcaag ggtatgcatg tgtcattttg aagaccaagg ccctagaatt   3000
gtcaaactta aggatcataa aaatcatgag ggttgcttgt taaaaatgtc caaacgtgca   3060
gagactgatc tttgagatct ggaccaggaa tttgcatttg aacaagtgtt cctggaatct   3120
ctatgcaagt tttatacaga acatactttt ggaatccttg ccctagacag gggtgtccaa   3180
tcttttggct tccctggtcc acaatggaag aagaattgtc ttggaccaca cataaaatac   3240
actaacacta acaatagctg atgagctaaa aaaaaaaaaa aaaaaaatcg tggaccgggc   3300
gtagtggctc acgcctgtaa tcccaacact ttgggagatc acctaggtcg ggagtttgag   3360
accagcctga ccgacatgga gaaaccccat ttttactaaa aatacaaaaa attagctggg   3420
catggtggtg catgcctgta gtcccagcta ctcaggaggc tgaggcagga gaatcgcttg   3480
aacctgagag ggggagattg cggtgagctg agattgcgcc attgcacccc agcctgggca   3540
acaatagcga aactgtctca gaaaaaagaa aaaaaaaatc gcaaaaagaa aaatctcata   3600
atgtcgttgt tggttttttt tttttttttt gagacagtct cactctgttg cccaggctgg   3660
agtgcaatgg catgatctct gctcaccgca acctctgcct cccgggttca ggtgattctc   3720
ctgcctcagc ctcccagata gctgggacta caggcacata ccaccatgcc tggctaattt   3780
ttgtattttt agtagagatg gggggtttcac tgtgttggcc aggctggtct cgaactcctg   3840
```

-continued

```
acctcatgat ccacacacct cggcctccca aagtcctgcg attacaggcg tgagctaccg   3900
cacccagcca agttgtaatt tttaataaaa cttaagaagt aaacatttta cttatgttta   3960
taggtatttg atcctaaatt tgacacatca ttgcccatga aagaatcctc ttaggctgct   4020
cagcttcact cttcctgctt gcccaccggg gtttttcact gcttctgtta gcactaagta   4080
cttagacgat cctaagatat gtgcttgagc cgaatttcat ctttacttgt aggaaacttt   4140
aaactatttc ttttcttttc tttttttttt ttttttactt gagatggagt tttgctcttg   4200
tcgcccaggc tggagtgcag tggagtgatc tcggctcact gcaacctctg cctcccgggt   4260
tcaaatgatt ctcctgcctc agcctcccaa gtagctggga ttacaggtgt gcaccaccat   4320
gtctggctaa ttttgtattt ttagtagaga tggtttcacc atgttggtca ggctggtctc   4380
gaactcctga cctcaggtca tccacccacc tcagcctcgc aaagtgctga gattacaggc   4440
atgagccaca gcgcccagct taaactattt tcttggtctg tttttgattt tctttttttcc   4500
ttgccactgc ggtacagatt tttttactc actgccacta aactaaagca aggcatagtt   4560
tatatgtgaa gtgttcagag tttactgcta taaggaaact tccaaatact gacatttacc   4620
ttttagctgt agttattggg accatgtgct ctggttttct ggagactgcc aaattgctcc   4680
catttttctg catcccacct ggtttctttc tgcatgtccc ctttcacttt caaacctctt   4740
catttggatg ttaaattata tggtcaccta gttataggta agccttgttc gagttgatat   4800
cttgattgtg aggaaggatc tgtgtcattg gagcttgttt ctgctgcaac gtgctgtaga   4860
ctatgaataa tgaaatcaca ccacattacc atcagatttc ttgttttagt tgtcaaatta   4920
atatttatga ttgttatctt gggcgaaaag ttcagagcag agatgacaaa tcattagaac   4980
aacgatgaat ttcagtatta cggctaaaaa gttcttctgt ctgaatatta actcactctc   5040
cttccagtgt acttcacagt aattggtatg ctttttttatt taatgcttaa atcaaacttt   5100
ataaaaatct tagaccagat ctttaatatg gtatgccatt tccccagtct accaatggaa   5160
tagtatgggt ttctaatcct aggcttgtac aatggattgg agttgagcca tgccagcctc   5220
cacactgcca ctaacttctg taatgtaaga ttgagtcact gccaagcatt tgaaatatgc   5280
agttgtgttt taattataat ttatgtatag ttagatgtat gtagtgcatt gtgtggtatt   5340
atttggtttg taagaattta tttttaaggg tcaaggtcat ttgtaacatt ttgtgtgtgt   5400
caattcaatg caatgttggc tgccttttga agtctttgat atattggtga atattcttct   5460
gatctataat acaaagctat gtaatgttac ctcttgactc gcttttgaaa ggaagacaat   5520
tgttaactag atatttgagt tttttcccct cagaattatg tgaatttctg atatatggct   5580
ttagatactg tgaatctgtt ttccatttag tcagttatct gcttaaattg ttcagaacta   5640
tatcctaacg agcaattagt tctgatggtt ctcccagtca tgagtgtgca tgtgtgcaag   5700
catgttttga tcctgatgct acctttgcta aaaatggcca tagattagga actagctatg   5760
tttttagaat caaagatgaa ccggtaagct gtctcatgta ccaaacgtga aatttacagt   5820
gtttacaaat gtctggaatt ttgcactgcc atagggaatg ttaaggttac ttggctggaa   5880
tttatcagac ttgtgagtaa acaagttgaa gtttagcaga tgagggggaa tattgaggcc   5940
cctaaggcta aacaaaataa tcagtatctg agatagtggc taatgtggct ccccaggcct   6000
aatttgggaa cagtttttcc tgattgcttt gagaagtact ttcttttgac agaaattttc   6060
attctgcttg ccattgctat attctccctt tataggagcc attggatttc tttccttttg   6120
tgggaaatgt cccattagca ttttcagatc ttttgatgtg cactaatgcc attattggta   6180
atgccgttat tggtgaatac agcatagtta aataaactgt tacagtaaat ctacacttgg   6240
```

-continued atttgctgca cctctaccaa tagccttttg aatgactgaa agtgttaaca gagaaagagg 6300
catgtctgca gaaagagata gctaatattt tttggtactt tatctgaaat ccaagatgct 6360
gcttcccctg caggttgttt tccttcttac gatcctcatt gaatcccctc tgggagcaca 6420
ggacagttag tagaactctc catttctttt tttttttttt tagacggagt ctctctctgt 6480
cgccccggct ggagtgcagt ggcgcgatct cggctcactg caacctccgc ctcccgggtt 6540
caccccattc tcctgcctca gcctccctag tagctgggac tataggcgcc cgccaccacg 6600
cctggctaat tttgtatttt ttattggaga cggggtttca ccgtcttagc caggatggtc 6660
ttgatctcct gacctcgtga tctgcccacc tcagcctccc aaagtactgg gattacaggc 6720
gtgagccacc gcgcccggcc ggaactctcc atttcttaag gtaaagaggg tcaaggatac 6780
ctaaaaaggg tcaaataatg ctagaagagc aattcctctt tcagagcagt tgctgtaatt 6840
tggcaaatgc tttatcgaag attgatatta ggctaggggc ggtggcttac gcctgtaatc 6900
ccagcacttt gggaggccga ggtgggtgga ttgcctgagc tcaggagttc gagaccagtc 6960
tgaccagtat ggtgaaaccc tgtctctact aaaaatacaa aaattagccg gtcgtggtgg 7020
cgtgcacctg tagtcccagc tacttggcag gttgagacag gagaatcgct tgaacctggg 7080
aggtggaggt tgcagtgagc cgagactgca ccactgcgct cccacctggg tgacagagac 7140
tctgtctcaa aaaaaaggac atttatcatt ataacatctt attagagccc ctaatttctt 7200
atctgaaggc actgtttttt tttttaaaca gttaagtact gatgtcaaca gacaaatatt 7260
tctgatcaga tagtcccctg tcaacagtag caaatgtggt ttcataaagt gggaagaaaa 7320
cagcatttta aagtaacttt ttgggagact gatttgagta ataataaaac tctggtctcc 7380
cttaagaaaa aaaaaccctt ccacctttac tgtgtcattt atatcccctt agttccaaag 7440
ttaattatct tatttctgga tattgctttt ataccaaaga cccttatcag cccttgtaac 7500
tacagtatct ttagataaga ttcctctttc cagtcagtcc tgggaaatgt ttctgttgca 7560
gagttaggcg gtagatggga agctgtgatg gcagagctac tatctaataa agtaacaact 7620
cgtagttgag gcttcctttc tgtgtgtgat gggggatagg gagttagctc ccctgttgtc 7680
tcagcactaa gaaattgagg tcaggccagg cgcggtggtt cactcctgtt attccagcac 7740
tggggtggcc aaagtgggca gattgcttgc gctctggagc tcgagaccag cctgggcaac 7800
atggtgaaac cctgtctcta ccaaaaatac aaaaaaaaag ctgggcatgg tgggtgcatg 7860
cttgtcccag ctactgagga ggctgaggtg ggaggatcgc ttgagcctgg gaggtggagg 7920
ttgcagtgag ctgagatggc accactgcaa tccaaggtgg gtgacagaga cgctgtctca 7980
aagaaattga ggtcaggctt ccttcttaca gaattatttt tttctctgta gtttgcctca 8040
ttttttcact ttcttttcaa tgagaatcga agtgtttctt ttgggttttt ttttccccct 8100
tttaaaatca acaggaaatg tttcaaagga gggatgaaat gcttcttggc ttcctcagca 8160
cttggcaagg tagacctcat agcaaccttg aatatgactt tctttagtct ctagctatgc 8220
actattaagt gcctcttggg tagaggtaga gttaagtatt gagtgccagt cttgacgtcc 8280
gtatgcctca gtttttctca tatataaaaa gcagtataca tacctaccct tttctacctc 8340
atcatttgtt gtagggatta aatccgggag agcaattctg aagcctataa atttccttga 8400
agagatctaa gaacctatta tgctcttggt gtaccaagct ctggggtata tattcagaat 8460
acctcatgtt ctggaagctg agcactagct ccccttatt gcctgcctgg cagagcctgt 8520
ttgattactg caggcccttt tacccatgct tctagtttag gtattctttc tttgatatga 8580

```
ggctcttgac cagaaaagag ttctttctct aggtgttctg agagaagttt gtaaatttgg   8640

atagtacatt ctatcctgat aaaaccacct tgctgtggtc ttgatgtaca aaaaaaaatt   8700

ttttttttga gacagagtct tactctgtca cccaggctgg aatgcagtgg cgcaatcttg   8760

gttcactgca acccccgcct cctgggttca agcgatcctc ctgcctcaac ctctcaagta   8820

gctgggacta caggcgtgca ccaccacacc tggctaattt tgtattttta gtagagacag   8880

ggtttcacca tgttggccag gctggtcttg aactcctgac ctcaggcgat ctgcccgcct   8940

tggcctccca aagtactggg attacaggcg tgagcaactg ctcctggccc aaaacatctc   9000

tttctacata cacttgagta ggtggcataa aatgcactgt caatatatag aaaacatgaa   9060

attttccaaa tatttccgat cagagaatca caagagcagc aaatgtggtt tcatcaagtg   9120

ggaagaaagc agcaatttaa aataactttt tgggagactg aattgagtaa taataaaact   9180

tcagtctttc gctaataata ataataataa taataataac aacaacttat tgaatgtggc   9240

cagctcacta gatgaggaaa gaggaaggca ttttctgcat tcttgcctag ttttccttat   9300

aagcaccact aagttaatag ctctgtcttt ttggtgtttg cactatgtaa tgcttttaat   9360

actttttaat tgtgcttttt tatgtattaa atgtttttcc ttttgccaaa aaaaaaaaaa   9420

a                                                                   9421
```

<210> SEQ ID NO 28
<211> LENGTH: 267
<212> TYPE: PRT
<213> ORGANISM: Homo sapiens

<400> SEQUENCE: 28

```
Met Thr Ser Phe Ser Thr Ser Ala Gln Cys Ser Thr Ser Asp Ser Ala
1               5                   10                  15

Cys Arg Ile Ser Pro Gly Gln Ile Asn Gln Val Arg Pro Lys Leu Pro
            20                  25                  30

Leu Leu Lys Ile Leu His Ala Ala Gly Ala Gln Gly Glu Met Phe Thr
        35                  40                  45

Val Lys Glu Val Ile Glu Val Gly Lys Asn Asp Asp Leu Glu Asp Ser
    50                  55                  60

Lys Ser Leu Ser Asp Asp Thr Asp Val Glu Val Thr Ser Glu Asp Glu
65                  70                  75                  80

Trp Gln Cys Thr Glu Cys Lys Lys Phe Asn Ser Pro Ser Lys Arg Tyr
                85                  90                  95

Cys Phe Arg Cys Trp Ala Leu Arg Lys Asp Trp Tyr Ser Asp Cys Ser
            100                 105                 110

Lys Leu Thr His Ser Leu Ser Thr Ser Asp Ile Thr Ala Ile Pro Glu
        115                 120                 125

Lys Glu Asn Glu Gly Asn Asp Val Pro Asp Cys Arg Arg Thr Ile Ser
    130                 135                 140

Ala Pro Val Val Arg Pro Lys Asp Ala Tyr Ile Lys Lys Glu Asn Ser
145                 150                 155                 160

Lys Leu Phe Asp Pro Cys Asn Ser Val Glu Phe Leu Asp Leu Ala His
                165                 170                 175

Ser Ser Glu Ser Gln Glu Thr Ile Ser Ser Met Gly Glu Gln Leu Asp
            180                 185                 190

Asn Leu Ser Glu Gln Arg Thr Asp Thr Glu Asn Met Glu Asp Cys Gln
        195                 200                 205

Asn Leu Leu Lys Pro Cys Ser Leu Cys Glu Lys Arg Pro Arg Asp Gly
    210                 215                 220
```

-continued

Asn Ile Ile His Gly Arg Thr Gly His Leu Val Thr Cys Phe His Cys
225 230 235 240

Ala Arg Arg Leu Lys Lys Ala Gly Ala Ser Cys Pro Ile Cys Lys Lys
245 250 255

Glu Ile Gln Leu Val Ile Lys Val Phe Ile Ala
260 265

<210> SEQ ID NO 29
<211> LENGTH: 7223
<212> TYPE: DNA
<213> ORGANISM: Mus musculus

<400> SEQUENCE: 29
tctatggttc ccccggcctc cccggaagct cttgcgaacg ctgggtttga gaggccggaa 60
gtggtgctgc cgttgctcgc agtttcaaaa tgcagtgcag gccttagggt ctccggctgc 120
cacccctccc ccagctagga gggggagcga ctcatggagc ggccgtaagt ttgctaactg 180
tggagtcttc actgccaaaa tgacatcaca ttccacctcg gcccagtgtt cagcatctga 240
cagtgcttgc agaatttctt cggaacaaat tagtcagcag gtgcggccaa aactgcagct 300
tttgaagatt ttgcatgcag caggtgcgca gggggaagta ttcaccatga aagaggtaat 360
gcactatcta ggccagtata taatggtgaa gcagctctat gatcaacagg agcaacatat 420
ggtatactgt ggtggagatc ttttgggaga tctacttgga tgtcagagct tttctgtgaa 480
agatccaagc cctctctatg acatgctaag aaagaatctt gttacatcag cttctattaa 540
cacagatgct gctcagactc tcgctctcgc acaggatcac actatggatt ttccaagtca 600
agaccgactg aagcacggtg caacagaata ctccaatccc agaaaaagaa ctgaagaaga 660
ggatactcac acactgccta cctcacgaca taaatgcaga gactccagag cagatgaaga 720
cttgatagaa catttatctc aagatgagac atctaggctt gaccttgatt ttgaggagtg 780
ggacgttgct ggcctgcctt ggtggtttct agggaatttg agaaacaact gtattcctaa 840
aagtaatggc tcaactgatt tacagacaaa tcaggatata ggtactgcca ttgtttcaga 900
cactacggat gatttgtggt ttttaaatga gaccgtgtca gagcaattag gtgttggaat 960
aaaagttgaa gctgctaatt ctgagcaaac aagtgaagta gggaaaacaa gtaacaagaa 1020
gacggtggag gtgggaaagg atgatgatct tgaggactcc aggtccttga gcgatgatac 1080
tgacgtggaa cttacctctg aggatgagtg gcagtgtacg gaatgcaaga agtttaattc 1140
tccaagcaag aggtactgtt ttcgttgctg ggccttgaga aaggattggt attcggattg 1200
ttctaaatta actcattccc tatctacatc taatattact gccatacctg aaaagaagga 1260
caatgaagga attgatgttc ccgattgtag gagaaccatt tcagctcctg ttgttaggcc 1320
taaagatgga tatttaaagg aggaaaagcc caggtttgac ccttgcaact cagtgggatt 1380
tttggatttg gctcatagtt ctgaaagcca ggagatcatc tcaagcgcga gagaacaaac 1440
agatattttt tctgagcaga aagctgaaac agaaagtatg gaagatttcc agaatgtctt 1500
gaagccgtgt agcttatgtg aaaaaaggcc tcgggatggg aacattattc atgggaagac 1560
gagccatctg acgacatgtt tccactgtgc caggagactg aagaagtctg gggcttcgtg 1620
tcctgcttgt aagaaagaga ttcagttggt tattaaagtt tttatagcat agttgagtca 1680
gtcacagaga aatactagga ggaccaggtc atttatcaaa aaaatcagta ttcttagagg 1740
caggggcaga agatcaccaa ttttgatgcc agtctgggcc atataatgag atcttagtct 1800
taaaaggatc agtattgagc atcttttata aatgtgaccc attgcatatg tttatttgta 1860
taagcatata tgaactttta gctaagtttt gagggtttca ttagtgagaa gatactttgt 1920
tcttccaaat tgtgaaccca gagggaataa tatcaataca aacatagcaa tgcattcttt 1980
tattcacttc caaattattg caagaataat acattagttg atttattctc taccctggtg 2040
ttatgtaatg ttcttgaggc atcaaaatct aaagcattta ttaaatactg gggctaacac 2100
tgaagaggac atatccagtc agtcgctcat tgtgtagtca aggatgacct taaattcctg 2160
atagctgtct ctaccaccta tgtgctcata ggctcatagg ccgcccact agcccatctg 2220
aaatctctta gttttaggtc aggtaacaca ggtgtacatc tctccacagc cttattatca 2280
gttccaaaaa ggaaaggcac agactttgtt gcccacactt tgcatttgtc tctcaagctg 2340
gctgggtgtt ttgtgtttg tgctctgcag ctgttcacat tctgaggcag tggcctatga 2400
taaggcttga acagtagaga ggaggaatgt agcagctgtg aaaggagggg aacaaattga 2460
tctcttcaat tctgcttagt cattttagac cacatcaact tagtataata tcaatatatg 2520
aactgaagat cttcacgctg aatcccgtat gcctgttctg tgtccactga acacatggcc 2580
atcttgatgt ttccccaggg acatgagaac atcattttaa agaccaagtc cctagaacta 2640
ttgagcttga gggcaatcta gctgtcttgg cttttcctat ggctcctgct gttagaaagg 2700
gggagatgca tggtatccag tcccccttaat gtcattatgt ccctgctgga ctgggaccac 2760
tggggctcct ctaattacta ctaagaggag ctatgttagc tttatcttgc attgatccca 2820
tgttccctgt ctgtcccatg ctctaccatt agacccaact ttaccaaatt ctcactggat 2880
cagttatcat agttactctt taattttgat gacaaagcac caatgcaaaa tataaaagaa 2940
agcatttaat ggggtttgct tttgagaggg ttagaatcca tgatggcagg cagggacagc 3000
tgagagctca catcttgatc tgcaagtaga atgcagagaa aaagagagcc ctggaaaacc 3060
ccagggcctg ccccccagt gtcgtaattg gtctaccttt tccaccgact ggggtccaag 3120
tattcaaact taagagcctg tggtttatat tctcatgtaa accaccacat tccatgaaaa 3180
gaattactaa ttactgtgct gcagaaccag tattaggcgt tctggacacc tcttctatca 3240
aagaaattac ttttcactcc aggcttaggc aaattcttag gacaagggta gaaggcagcc 3300
acattctttg tcaaacataa ccagaataag tctttagcca gttgttaata gttgttctac 3360
cctgcagcct cttgatctag gcttcctctc agtactaact gtcttttagg ctccaactgg 3420
acccattaag ctctgtttac agccttgaac cctttcttag tccaaagtct tacacattcc 3480
tccaaaaaaa ccacatggtc aggtctttca cagcaaagat ccacttcctg gtagtagctt 3540
ctgtgtcttg gctactctaa aattgctatg acaaaacatc ccgaccaagg cagaatgtac 3600
aagaaagcat tgagtttatg gtttcagagg tatttagttc atgatagaac agttgagagc 3660
ttacatcttg atctgtaagt aggaggcaga gagagaaccc aggggatggc atggactttt 3720
gaaacctcca agccttcacc ttgtgacaga cctccccaac agagccacat ctcctaatcc 3780
tttccaagta gttcctccaa ctggggacca aatactccag catgagcata ggggagcatt 3840
ctcattcaca ccaccagttt gccgaggaac tttcctagcc atggcttgtc attcattgct 3900
cccagttgat aatttcacta tttgtagcaa actcagtggc caagtccttg ctattatggg 3960
tcttctgctt gtattgaaaa tactgcagct cctgttgggg ttgctgtgca gtctctctga 4020
gggactgata acagacttgt atatccatat ctccatggca gtgagaaacg gtagcttaga 4080
ggtaatccta gaagccatca ctcacagtcc ctgcttgaga ataggctatg atatgtctag 4140
ccctggactt tagtcatttc ctagacatgg acctgctggg tggaattggg tcattatgat 4200

-continued gtttaattcc aagcactgca ttcaaaatag gatacatgat atagtatgtc agcttcattc 4260
taacgtttct cctaatcttt tggggcagag tcttgctgtt tcaccatgac tggcctgggc 4320
cttaccctac atctcaggct ggcctcagct ttgcagtgac cttcctgctt ttgcctctcg 4380
agtgctggaa ttctaggcat gtaatgacta aatttcttat tttgcttttt atttaagttt 4440
ttgttactct atcttggaca aaaagtgcag agcagaggtg tcggattact aggaaagtct 4500
ccagggcttc gctgttactg tgttccccac agggacttcc tggttgttga cgtgcttctg 4560
tttactactg tgtcagatga gcgactcaga gctcggcttc agataggtgt gactgccgcc 4620
ctcgcccatt taggatgtag tagatttatg attgagggct ggaacgggta gattacattg 4680
taccgccaag catttgtgac tgtgtggata tatattcatt atttatgtat atttaggtgt 4740
gtgtgatact ttgcatggtt tgaaagaatc tattctgaaa gccaggatca tttgtaacct 4800
ttgtgtgtca gttcaatgta atgttggggc ctttgaaaag ttgattgaga aattggggat 4860
cattcccagt tctccgatgt tacttgttta gtcctcttta gaaagaaaga cacttttgga 4920
ccagctgttt cgctgttttg ttctgtttcc atgatattct gtgaacctcc atggctttag 4980
atactgtgac tgttattttc ctttttgccc aaattgttga ttcagtctaa agaatactat 5040
tttttgatgc ctcttacaat tcatgcatgt gcacactata gattgatgct acctttgcta 5100
aaaatgtctt aagataaaga actagctctt tagaacctgc acttcaaaga taaacctgga 5160
agctgtcctg tgccaaaagt aaagtgtaca atgtttacag atgggtggaa ttttgcactg 5220
ccatagggaa cggtgagctc gcatcacggg gttccttaga tgtatgggta gatagttgca 5280
gttgagctta tgagaggaac tgtggagccc tctaaggcta agctgctaat gagtatccaa 5340
gacaggtggt tggtgaacgt gactccctag acctagctgg ggtcttctgt tgacagctct 5400
tcatggtttg cagacactat atgttttctt tagaggagct gccagctctc ccctcttgtg 5460
aaagactgtc ttgtagacat tttgagatct tttgatgtaa tgtgcaatcc caagtaatgc 5520
cattattggt gaatgtagca ttgttaaact tttattgtaa attatctctg atcttacctt 5580
gatagcctta gggtttttttg tttttgtttt tttttgttat gttttcagag acagagtctc 5640
gctatttggt ttacctagaa tttgctttat gattaggctg tccccaaact cacagatgtc 5700
tgcctttcta ccaccacgcc catgtaactg atgttaccaa aaatgatctc atatccatgg 5760
tgttgcttat gtgtctttgc ataggcgcct ccttcagtcc catctaggag cacagcacag 5820
tagaagtcca tttcttaagt gggcagagtc agagataagc taagagggca agtagttgct 5880
tcagtggttt ttagagcttg gcaaacgctt tactgaagat tagcattgtg ttgtgacact 5940
tgagggccaa tacgagcatt taatttgtta cctaaaggtg ctttgtgttc ttaaacagca 6000
agtatttgat gtgtgtaaac atttcccttc attctccctc cctcctcacc gtttttatgg 6060
tctcctattt ctgagttagc tgcatttgga cattgctttt atgccagagg ccatctgtca 6120
ccttggatgt ttagaagtac agtgtactta tgtagggtcc tccttgagcc tgtcctgagc 6180
agtgttgtgg ttacagaatt gcctacgagc tccaacagag aggtggggaa gctgggaggg 6240
cacagctgtc tggcttcctt tgtggaggtg ttggtttgtt tgaacactaa ggaatttgag 6300
gttaatcttc cccctcttcc tgcccatagt tttcacttcc ctttcagtaa gaacgacccc 6360
ctaaaagaaa acaggaggag atgcagcgct ttaggccgcc ttagccagca gcttgtgtcc 6420
tactctggaa gttgtaacct acagtttttc tcacctgtaa agccaacaca cacagctacc 6480
cgtttctacc tcagtttgat gtggcgacta tggaggaaca actcttaaaa gctctgactg 6540
ccttgaagat ggaggaagct agtggtcttg gtcgactgtg ctctgaggtt tatattgaga 6600

```
atcctttatt ctggaagtga gtgcggttct cctgaccgcc tgctcagtag aacctgtgtt   6660

gcctgcttta agtctctgcc cacctgcctg tcctttcctt gacactaggc tcttgattag   6720

gaagagttgt ctccagatgc tttgagaagc acatgtaaat ctagatagca cattctaccc   6780

tgatggaact tccttgcttg tcttgctgta taggaattca ttctgtatac acttgagtgg   6840

gtggcatgag atgctcgact tgtgtgtcga gaggcagtgt catgacattc ccagtctggt   6900

acttgccagt gcagaagcaa atgaggggta ataaactgag aagaagggca gcttactaac   6960

gaggccagag ggaaatgttt ccgtgtgtcc ttatgtaact ttttacagtg ccactaagtt   7020

aatagccctg tacatgggtg tttgcactat gtaatgcttt taatgcggtt ttattgtgtt   7080

tttgtgtgat taaacagttt tcatttcatt gtgttttgtc attattggaa ataggtaatt   7140

ttgcttatgt acagctaacc cattttctgt tatctttggc atgatttggg gaagtgatta   7200

aaagtcattg gcagcttttc cct                                          7223
```

<210> SEQ ID NO 30
<211> LENGTH: 490
<212> TYPE: PRT
<213> ORGANISM: Mus musculus

<400> SEQUENCE: 30

```
Met Thr Ser His Ser Thr Ser Ala Gln Cys Ser Ala Ser Asp Ser Ala
1               5                   10                  15

Cys Arg Ile Ser Ser Glu Gln Ile Ser Gln Gln Val Arg Pro Lys Leu
            20                  25                  30

Gln Leu Leu Lys Ile Leu His Ala Ala Gly Ala Gln Gly Glu Val Phe
        35                  40                  45

Thr Met Lys Glu Val Met His Tyr Leu Gly Gln Tyr Ile Met Val Lys
    50                  55                  60

Gln Leu Tyr Asp Gln Gln Glu Gln His Met Val Tyr Cys Gly Gly Asp
65                  70                  75                  80

Leu Leu Gly Asp Leu Leu Gly Cys Gln Ser Phe Ser Val Lys Asp Pro
                85                  90                  95

Ser Pro Leu Tyr Asp Met Leu Arg Lys Asn Leu Val Thr Ser Ala Ser
            100                 105                 110

Ile Asn Thr Asp Ala Ala Gln Thr Leu Ala Leu Ala Gln Asp His Thr
        115                 120                 125

Met Asp Phe Pro Ser Gln Asp Arg Leu Lys His Gly Ala Thr Glu Tyr
    130                 135                 140

Ser Asn Pro Arg Lys Arg Thr Glu Glu Glu Asp Thr His Thr Leu Pro
145                 150                 155                 160

Thr Ser Arg His Lys Cys Arg Asp Ser Arg Ala Asp Glu Asp Leu Ile
                165                 170                 175

Glu His Leu Ser Gln Asp Glu Thr Ser Arg Leu Asp Leu Asp Phe Glu
            180                 185                 190

Glu Trp Asp Val Ala Gly Leu Pro Trp Trp Phe Leu Gly Asn Leu Arg
        195                 200                 205

Asn Asn Cys Ile Pro Lys Ser Asn Gly Ser Thr Asp Leu Gln Thr Asn
    210                 215                 220

Gln Asp Ile Gly Thr Ala Ile Val Ser Asp Thr Thr Asp Asp Leu Trp
225                 230                 235                 240

Phe Leu Asn Glu Thr Val Ser Glu Gln Leu Gly Val Gly Ile Lys Val
                245                 250                 255
```

```
Glu Ala Ala Asn Ser Glu Gln Thr Ser Glu Val Gly Lys Thr Ser Asn
            260                 265                 270

Lys Lys Thr Val Glu Val Gly Lys Asp Asp Asp Leu Glu Asp Ser Arg
        275                 280                 285

Ser Leu Ser Asp Asp Thr Asp Val Glu Leu Thr Ser Glu Asp Glu Trp
    290                 295                 300

Gln Cys Thr Glu Cys Lys Lys Phe Asn Ser Pro Ser Lys Arg Tyr Cys
305                 310                 315                 320

Phe Arg Cys Trp Ala Leu Arg Lys Asp Trp Tyr Ser Asp Cys Ser Lys
                325                 330                 335

Leu Thr His Ser Leu Ser Thr Ser Asn Ile Thr Ala Ile Pro Glu Lys
            340                 345                 350

Lys Asp Asn Glu Gly Ile Asp Val Pro Asp Cys Arg Arg Thr Ile Ser
        355                 360                 365

Ala Pro Val Val Arg Pro Lys Asp Gly Tyr Leu Lys Glu Glu Lys Pro
    370                 375                 380

Arg Phe Asp Pro Cys Asn Ser Val Gly Phe Leu Asp Leu Ala His Ser
385                 390                 395                 400

Ser Glu Ser Gln Glu Ile Ile Ser Ser Ala Arg Glu Gln Thr Asp Ile
                405                 410                 415

Phe Ser Glu Gln Lys Ala Glu Thr Glu Ser Met Glu Asp Phe Gln Asn
            420                 425                 430

Val Leu Lys Pro Cys Ser Leu Cys Glu Lys Arg Pro Arg Asp Gly Asn
        435                 440                 445

Ile Ile His Gly Lys Thr Ser His Leu Thr Thr Cys Phe His Cys Ala
    450                 455                 460

Arg Arg Leu Lys Lys Ser Gly Ala Ser Cys Pro Ala Cys Lys Lys Glu
465                 470                 475                 480

Ile Gln Leu Val Ile Lys Val Phe Ile Ala
                485                 490
```

<210> SEQ ID NO 31
<211> LENGTH: 7107
<212> TYPE: DNA
<213> ORGANISM: Mus musculus

<400> SEQUENCE: 31

```
gggtgggttt gtggtggtgg tttaaggcag cagtggtcaa agaagaaaca aagtttgcta      60

actgtggagt cttcactgcc aaaatgacat cacattccac ctcggcccag tgttcagcat     120

ctgacagtgc ttgcagaatt tcttcggaac aaattagtca gcaggtgcgg ccaaaactgc     180

agcttttgaa gattttgcat gcagcaggtg cgcaggggga agtattcacc atgaaagagg     240

taatgcacta tctaggccag tatataatgg tgaagcagct ctatgatcaa caggagcaac     300

atatggtata ctgtggtgga gatcttttgg gagatctact tggatgtcag agcttttctg     360

tgaaagatcc aagccctctc tatgacatgc taagaaagaa tcttgttaca tcagcttcta     420

ttaacacaga tgctgctcag actctcgctc tcgcacagga tcacactatg gattttccaa     480

gtcaagaccg actgaagcac ggtgcaacag aatactccaa tcccagaaaa agaactgaag     540

aagaggatac tcacacactg cctacctcac gacataaatg cagagactcc agagcagatg     600

aagacttgat agaacattta tctcaagatg agacatctag gcttgacctt gattttgagg     660

agtgggacgt tgctggcctg ccttggtggt ttctagggaa tttgagaaac aactgtattc     720

ctaaaagtaa tggctcaact gatttacaga caaatcagga tataggtact gccattgttt     780
```

-continued

```
cagacactac ggatgatttg tggtttttaa atgagaccgt gtcagagcaa ttaggtgttg    840
gaataaaagt tgaagctgct aattctgagc aaacaagtga agtagggaaa acaagtaaca    900
agaagacggt ggaggtggga aaggatgatg atcttgagga ctccaggtcc ttgagcgatg    960
atactgacgt ggaacttacc tctgaggatg agtggcagtg tacggaatgc aagaagttta   1020
attctccaag caagaggtac tgttttcgtt gctgggcctt gagaaaggat tggtattcgg   1080
attgttctaa attaactcat tccctatcta catctaatat tactgccata cctgaaaaga   1140
aggacaatga aggaattgat gttcccgatt gtaggagaac catttcagct cctgttgtta   1200
ggcctaaaga tggatattta aaggaggaaa agcccaggtt tgacccttgc aactcagtgg   1260
gatttttgga tttggctcat agttctgaaa gccaggagat catctcaagc gcgagagaac   1320
aaacagatat tttttctgag cagaaagctg aaacagaaag tatggaagat ttccagaatg   1380
tcttgaagcc gtgtagctta tgtgaaaaaa ggcctcggga tgggaacatt attcatggga   1440
agacgagcca tctgacgaca tgtttccact gtgccaggag actgaagaag tctggggctt   1500
cgtgtcctgc ttgtaagaaa gagattcagt tggttattaa agtttttata gcatagttga   1560
gtcagtcaca gagaaatact aggaggacca ggtcatttat caaaaaaatc agtattctta   1620
gaggcagggg cagaagatca ccaattttga tgccagtctg ggccatataa tgagatctta   1680
gtcttaaaag gatcagtatt gagcatcttt tataaatgtg acccattgca tatgtttatt   1740
tgtataagca tatatgaact tttagctaag ttttgagggt ttcattagtg agaagatact   1800
ttgttcttcc aaattgtgaa cccagaggga ataatatcaa tacaaacata gcaatgcatt   1860
cttttattca cttccaaatt attgcaagaa taatacatta gttgatttat tctctaccct   1920
ggtgttatgt aatgttcttg aggcatcaaa atctaaagca tttattaaat actggggcta   1980
acactgaaga ggacatatcc agtcagtcgc tcattgtgta gtcaaggatg accttaaatt   2040
cctgatagct gtctctacca cctatgtgct cataggctca taggccgccc cactagccca   2100
tctgaaatct cttagtttta ggtcaggtaa cacaggtgta catctctcca cagccttatt   2160
atcagttcca aaaaggaaag gcacagactt tgttgcccac actttgcatt tgtctctcaa   2220
gctggctggg tgttttgtgt tttgtgctct gcagctgttc acattctgag gcagtggcct   2280
atgataaggc ttgaacagta gagaggagga atgtagcagc tgtgaaagga ggggaacaaa   2340
ttgatctctt caattctgct tagtcatttt agaccacatc aacttagtat aatatcaata   2400
tatgaactga agatcttcac gctgaatccc gtatgcctgt tctgtgtcca ctgaacacat   2460
ggccatcttg atgtttcccc agggacatga gaacatcatt ttaaagacca agtccctaga   2520
actattgagc ttgagggcaa tctagctgtc ttggcttttc ctatggctcc tgctgttaga   2580
aagggggaga tgcatggtat ccagtcccct taatgtcatt atgtccctgc tggactggga   2640
ccactggggc tcctctaatt actactaaga ggagctatgt tagctttatc ttgcattgat   2700
cccatgttcc ctgtctgtcc catgctctac cattagaccc aactttacca aattctcact   2760
ggatcagtta tcatagttac tctttaattt tgatgacaaa gcaccaatgc aaaatataaa   2820
agaaagcatt taatggggtt tgcttttgag agggttagaa tccatgatgg caggcaggga   2880
cagctgagag ctcacatctt gatctgcaag tagaatgcag agaaaaagag agccctggaa   2940
aaccccaggg cctgcccccc cagtgtcgta attggtctac cttttccacc gactggggtc   3000
caagtattca aacttaagag cctgtggttt atattctcat gtaaaccacc acattccatg   3060
aaaagaatta ctaattactg tgctgcagaa ccagtattag gcgttctgga cacctcttct   3120
atcaaagaaa ttacttttca ctccaggctt aggcaaattc ttaggacaag ggtagaaggc   3180
```

agccacattc tttgtcaaac ataaccagaa taagtcttta gccagttgtt aatagttgtt 3240
ctaccctgca gcctcttgat ctaggcttcc tctcagtact aactgtcttt taggctccaa 3300
ctggacccat taagctctgt ttacagcctt gaaccctttc ttagtccaaa gtcttacaca 3360
ttcctccaaa aaaaccacat ggtcaggtct ttcacagcaa agatccactt cctggtagta 3420
gcttctgtgt cttggctact ctaaaattgc tatgacaaaa catcccgacc aaggcagaat 3480
gtacaagaaa gcattgagtt tatggtttca gaggtattta gttcatgata gaacagttga 3540
gagcttacat cttgatctgt aagtaggagg cagagagaga acccagggga tggcatggac 3600
ttttgaaacc tccaagcctt caccttgtga cagacctccc caacagagcc acatctccta 3660
atcctttcca agtagttcct ccaactgggg accaaatact ccagcatgag catagggggag 3720 cattctcatt cacaccacca gtttgccgag gaactttcct agccatggct tgtcattcat 3780
tgctcccagt tgataatttc actatttgta gcaaactcag tggccaagtc cttgctatta 3840
tgggtcttct gcttgtattg aaaatactgc agctcctgtt ggggttgctg tgcagtctct 3900
ctgagggact gataacagac ttgtatatcc atatctccat ggcagtgaga aacggtagct 3960
tagaggtaat cctagaagcc atcactcaca gtccctgctt gagaataggc tatgatatgt 4020
ctagccctgg actttagtca tttcctagac atggacctgc tgggtggaat tgggtcatta 4080
tgatgtttaa ttccaagcac tgcattcaaa ataggataca tgatatagta tgtcagcttc 4140
attctaacgt ttctcctaat cttttggggc agagtcttgc tgtttcacca tgactggcct 4200
gggccttacc ctacatctca ggctggcctc agctttgcag tgaccttcct gcttttgcct 4260
ctcgagtgct ggaattctag gcatgtaatg actaaatttc ttattttgct ttttatttaa 4320
gtttttgtta ctctatcttg gacaaaaagt gcagagcaga ggtgtcggat tactaggaaa 4380
gtctccaggg cttcgctgtt actgtgttcc ccacagggac ttcctggttg ttgacgtgct 4440
tctgtttact actgtgtcag atgagcgact cagagctcgg cttcagatag gtgtgactgc 4500
cgccctcgcc catttaggat gtagtagatt tatgattgag ggctggaacg ggtagattac 4560
attgtaccgc caagcatttg tgactgtgtg gatatatatt cattatttat gtatatttag 4620
gtgtgtgtga tactttgcat ggtttgaaag aatctattct gaaagccagg atcatttgta 4680
acctttgtgt gtcagttcaa tgtaatgttg gggcctttga aaagttgatt gagaaattgg 4740
ggatcattcc cagttctccg atgttacttg tttagtcctc tttagaaaga aagacacttt 4800
tggaccagct gtttcgctgt tttgttctgt ttccatgata ttctgtgaac ctccatggct 4860
ttagatactg tgactgttat tttcctttt gcccaaattg ttgattcagt ctaaagaata 4920
ctattttttg atgcctctta caattcatgc atgtgcacac tatagattga tgctaccttt 4980
gctaaaaatg tcttaagata aagaactagc tctttagaac ctgcacttca aagataaacc 5040
tggaagctgt cctgtgccaa aagtaaagtg tacaatgttt acagatgggt ggaattttgc 5100
actgccatag ggaacggtga gctcgcatca cggggttcct tagatgtatg ggtagatagt 5160
tgcagttgag cttatgagag gaactgtgga gccctctaag gctaagctgc taatgagtat 5220
ccaagacagg tggttggtga acgtgactcc ctagacctag ctggggtctt ctgttgacag 5280
ctcttcatgg tttgcagaca ctatatgttt tctttagagg agctgccagc tctcccctct 5340
tgtgaaagac tgtcttgtag acattttgag atcttttgat gtaatgtgca atcccaagta 5400
atgccattat tggtgaatgt agcattgtta aacttttatt gtaaattatc tctgatctta 5460
ccttgatagc cttagggttt tttgtttttg ttttttttg ttatgttttc agagacagag 5520

-continued

```
tctcgctatt tggtttacct agaatttgct ttatgattag gctgtcccca aactcacaga   5580

tgtctgcctt tctaccacca cgcccatgta actgatgtta ccaaaaatga tctcatatcc   5640

atggtgttgc ttatgtgtct ttgcataggc gcctccttca gtcccatcta ggagcacagc   5700

acagtagaag tccatttctt aagtgggcag agtcagagat aagctaagag ggcaagtagt   5760

tgcttcagtg gtttttagag cttggcaaac gctttactga agattagcat tgtgttgtga   5820

cacttgaggg ccaatacgag catttaattt gttacctaaa ggtgctttgt gttcttaaac   5880

agcaagtatt tgatgtgtgt aaacatttcc cttcattctc cctccctcct caccgttttt   5940

atggtctcct atttctgagt tagctgcatt tggacattgc ttttatgcca gaggccatct   6000

gtcaccttgg atgtttagaa gtacagtgta cttatgtagg gtcctccttg agcctgtcct   6060

gagcagtgtt gtggttacag aattgcctac gagctccaac agagaggtgg ggaagctggg   6120

agggcacagc tgtctggctt cctttgtgga ggtgttggtt tgtttgaaca ctaaggaatt   6180

tgaggttaat cttcccctc ttcctgccca tagttttcac ttccctttca gtaagaacga   6240

ccccctaaaa gaaaacagga ggagatgcag cgctttaggc cgccttagcc agcagcttgt   6300

gtcctactct ggaagttgta acctacagtt tttctcacct gtaaagccaa cacacacagc   6360

tacccgtttc tacctcagtt tgatgtggcg actatggagg aacaactctt aaaagctctg   6420

actgccttga agatggagga agctagtggt cttggtcgac tgtgctctga ggtttatatt   6480

gagaatcctt tattctggaa gtgagtgcgg ttctcctgac cgcctgctca gtagaacctg   6540

tgttgcctgc tttaagtctc tgcccacctg cctgtccttt ccttgacact aggctcttga   6600

ttaggaagag ttgtctccag atgctttgag aagcacatgt aaatctagat agcacattct   6660

accctgatgg aacttccttg cttgtcttgc tgtataggaa ttcattctgt atacacttga   6720

gtgggtggca tgagatgctc gacttgtgtg tcgagaggca gtgtcatgac attcccagtc   6780

tggtacttgc cagtgcagaa gcaaatgagg ggtaataaac tgagaagaag ggcagcttac   6840

taacgaggcc agagggaaat gtttccgtgt gtccttatgt aactttttac agtgccacta   6900

agttaatagc cctgtacatg ggtgtttgca ctatgtaatg cttttaatgc ggttttattg   6960

tgtttttgtg tgattaaaca gttttcattt cattgtgttt tgtcattatt ggaaataggt   7020

aattttgctt atgtacagct aacccatttt ctgttatctt tggcatgatt tggggaagtg   7080

attaaaagtc attggcagct tttccct                                       7107
```

<210> SEQ ID NO 32
<211> LENGTH: 490
<212> TYPE: PRT
<213> ORGANISM: Mus musculus

<400> SEQUENCE: 32

```
Met Thr Ser His Ser Thr Ser Ala Gln Cys Ser Ala Ser Asp Ser Ala
1               5                   10                  15

Cys Arg Ile Ser Ser Glu Gln Ile Ser Gln Gln Val Arg Pro Lys Leu
            20                  25                  30

Gln Leu Leu Lys Ile Leu His Ala Ala Gly Ala Gln Gly Glu Val Phe
        35                  40                  45

Thr Met Lys Glu Val Met His Tyr Leu Gly Gln Tyr Ile Met Val Lys
    50                  55                  60

Gln Leu Tyr Asp Gln Gln Glu Gln His Met Val Tyr Cys Gly Gly Asp
65                  70                  75                  80

Leu Leu Gly Asp Leu Leu Gly Cys Gln Ser Phe Ser Val Lys Asp Pro
                85                  90                  95
```

```
Ser Pro Leu Tyr Asp Met Leu Arg Lys Asn Leu Val Thr Ser Ala Ser
            100                 105                 110

Ile Asn Thr Asp Ala Ala Gln Thr Leu Ala Leu Ala Gln Asp His Thr
        115                 120                 125

Met Asp Phe Pro Ser Gln Asp Arg Leu Lys His Gly Ala Thr Glu Tyr
    130                 135                 140

Ser Asn Pro Arg Lys Arg Thr Glu Glu Glu Asp Thr His Thr Leu Pro
145                 150                 155                 160

Thr Ser Arg His Lys Cys Arg Asp Ser Arg Ala Asp Glu Asp Leu Ile
                165                 170                 175

Glu His Leu Ser Gln Asp Glu Thr Ser Arg Leu Asp Leu Asp Phe Glu
            180                 185                 190

Glu Trp Asp Val Ala Gly Leu Pro Trp Trp Phe Leu Gly Asn Leu Arg
        195                 200                 205

Asn Asn Cys Ile Pro Lys Ser Asn Gly Ser Thr Asp Leu Gln Thr Asn
    210                 215                 220

Gln Asp Ile Gly Thr Ala Ile Val Ser Asp Thr Thr Asp Asp Leu Trp
225                 230                 235                 240

Phe Leu Asn Glu Thr Val Ser Glu Gln Leu Gly Val Gly Ile Lys Val
                245                 250                 255

Glu Ala Ala Asn Ser Glu Gln Thr Ser Glu Val Gly Lys Thr Ser Asn
            260                 265                 270

Lys Lys Thr Val Glu Val Gly Lys Asp Asp Asp Leu Glu Asp Ser Arg
        275                 280                 285

Ser Leu Ser Asp Asp Thr Asp Val Glu Leu Thr Ser Glu Asp Glu Trp
    290                 295                 300

Gln Cys Thr Glu Cys Lys Lys Phe Asn Ser Pro Ser Lys Arg Tyr Cys
305                 310                 315                 320

Phe Arg Cys Trp Ala Leu Arg Lys Asp Trp Tyr Ser Asp Cys Ser Lys
                325                 330                 335

Leu Thr His Ser Leu Ser Thr Ser Asn Ile Thr Ala Ile Pro Glu Lys
            340                 345                 350

Lys Asp Asn Glu Gly Ile Asp Val Pro Asp Cys Arg Arg Thr Ile Ser
        355                 360                 365

Ala Pro Val Val Arg Pro Lys Asp Gly Tyr Leu Lys Glu Glu Lys Pro
    370                 375                 380

Arg Phe Asp Pro Cys Asn Ser Val Gly Phe Leu Asp Leu Ala His Ser
385                 390                 395                 400

Ser Glu Ser Gln Glu Ile Ile Ser Ser Ala Arg Glu Gln Thr Asp Ile
                405                 410                 415

Phe Ser Glu Gln Lys Ala Glu Thr Glu Ser Met Glu Asp Phe Gln Asn
            420                 425                 430

Val Leu Lys Pro Cys Ser Leu Cys Glu Lys Arg Pro Arg Asp Gly Asn
        435                 440                 445

Ile Ile His Gly Lys Thr Ser His Leu Thr Thr Cys Phe His Cys Ala
    450                 455                 460

Arg Arg Leu Lys Lys Ser Gly Ala Ser Cys Pro Ala Cys Lys Lys Glu
465                 470                 475                 480

Ile Gln Leu Val Ile Lys Val Phe Ile Ala
                485                 490
```

<210> SEQ ID NO 33
<211> LENGTH: 7220

<212> TYPE: DNA
<213> ORGANISM: Mus musculus

<400> SEQUENCE: 33
tctatggttc cccggcctcc cccggaagct cttgcgaacg ctgggtttga gaggccggaa 60
gtggtgctgc cgttgctcgc agtttcaaaa tgcagtgcag gccttagggt ctccggctgc 120
cacccctccc ccagctagga gggggagcga ctcatggagc ggccgtaagt ttgctaactg 180
tggagtcttc actgccaaaa tgacatcaca ttccacctcg gcccagtgtt cagcatctga 240
cagtgcttgc agaatttctt cggaacaaat tagtcaggtg cggccaaaac tgcagctttt 300
gaagattttg catgcagcag gtgcgcaggg ggaagtattc accatgaaag aggtaatgca 360
ctatctaggc cagtatataa tggtgaagca gctctatgat caacaggagc aacatatggt 420
atactgtggt ggagatcttt tgggagatct acttggatgt cagagctttt ctgtgaaaga 480
tccaagccct ctctatgaca tgctaagaaa gaatcttgtt acatcagctt ctattaacac 540
agatgctgct cagactctcg ctctcgcaca ggatcacact atggattttc caagtcaaga 600
ccgactgaag cacggtgcaa cagaatactc caatcccaga aaaagaactg aagaagagga 660
tactcacaca ctgcctacct cacgacataa atgcagagac tccagagcag atgaagactt 720
gatagaacat ttatctcaag atgagacatc taggcttgac cttgattttg aggagtggga 780
cgttgctggc ctgccttggt ggtttctagg gaatttgaga aacaactgta ttcctaaaag 840
taatggctca actgatttac agacaaatca ggatataggt actgccattg tttcagacac 900
tacggatgat ttgtggtttt taaatgagac cgtgtcagag caattaggtg ttggaataaa 960
agttgaagct gctaattctg agcaaacaag tgaagtaggg aaaacaagta acaagaagac 1020
ggtggaggtg ggaaaggatg atgatcttga ggactccagg tccttgagcg atgatactga 1080
cgtggaactt acctctgagg atgagtggca gtgtacggaa tgcaagaagt ttaattctcc 1140
aagcaagagg tactgttttc gttgctgggc cttgagaaag gattggtatt cggattgttc 1200
taaattaact cattccctat ctacatctaa tattactgcc atacctgaaa agaaggacaa 1260
tgaaggaatt gatgttcccg attgtaggag aaccatttca gctcctgttg ttaggcctaa 1320
agatggatat ttaaaggagg aaaagcccag gtttgaccct tgcaactcag tgggattttt 1380
ggatttggct catagttctg aaagccagga gatcatctca agcgcgagag aacaaacaga 1440 tatttttttct gagcagaaag ctgaaacaga aagtatggaa gatttccaga atgtcttgaa 1500
gccgtgtagc ttatgtgaaa aaaggcctcg ggatgggaac attattcatg ggaagacgag 1560
ccatctgacg acatgtttcc actgtgccag gagactgaag aagtctgggg cttcgtgtcc 1620
tgcttgtaag aaagagattc agttggttat taaagttttt atagcatagt tgagtcagtc 1680
acagagaaat actaggagga ccaggtcatt tatcaaaaaa atcagtattc ttagaggcag 1740
gggcagaaga tcaccaattt tgatgccagt ctgggccata taatgagatc ttagtcttaa 1800
aaggatcagt attgagcatc ttttataaat gtgacccatt gcatatgttt atttgtataa 1860
gcatatatga acttttagct aagttttgag ggtttcatta gtgagaagat actttgttct 1920
tccaaattgt gaacccagag ggaataatat caatacaaac atagcaatgc attcttttat 1980
tcacttccaa attattgcaa gaataataca ttagttgatt tattctctac cctggtgtta 2040
tgtaatgttc ttgaggcatc aaaatctaaa gcatttatta aatactgggg ctaacactga 2100
agaggacata tccagtcagt cgctcattgt gtagtcaagg atgaccttaa attcctgata 2160
gctgtctcta ccacctatgt gctcataggc tcataggccg ccccactagc ccatctgaaa 2220

-continued

```
tctcttagtt ttaggtcagg taacacaggt gtacatctct ccacagcctt attatcagtt   2280
ccaaaaagga aaggcacaga ctttgttgcc cacactttgc atttgtctct caagctggct   2340
gggtgttttg tgttttgtgc tctgcagctg ttcacattct gaggcagtgg cctatgataa   2400
ggcttgaaca gtagagagga ggaatgtagc agctgtgaaa ggaggggaac aaattgatct   2460
cttcaattct gcttagtcat tttagaccac atcaacttag tataatatca atatatgaac   2520
tgaagatctt cacgctgaat cccgtatgcc tgttctgtgt ccactgaaca catggccatc   2580
ttgatgtttc cccagggaca tgagaacatc attttaaaga ccaagtccct agaactattg   2640
agcttgaggg caatctagct gtcttggctt ttcctatggc tcctgctgtt agaaaggggg   2700
agatgcatgg tatccagtcc ccttaatgtc attatgtccc tgctggactg ggaccactgg   2760
ggctcctcta attactacta agaggagcta tgttagcttt atcttgcatt gatcccatgt   2820
tccctgtctg tcccatgctc taccattaga cccaacttta ccaaattctc actggatcag   2880
ttatcatagt tactctttaa ttttgatgac aaagcaccaa tgcaaaatat aaaagaaagc   2940
atttaatggg gtttgctttt gagagggtta gaatccatga tggcaggcag ggacagctga   3000
gagctcacat cttgatctgc aagtagaatg cagagaaaaa gagagccctg gaaaacccca   3060
gggcctgccc ccccagtgtc gtaattggtc taccttttcc accgactggg gtccaagtat   3120
tcaaacttaa gagcctgtgg tttatattct catgtaaacc accacattcc atgaaaagaa   3180
ttactaatta ctgtgctgca gaaccagtat taggcgttct ggacacctct tctatcaaag   3240
aaattacttt tcactccagg cttaggcaaa ttcttaggac aagggtagaa ggcagccaca   3300
ttctttgtca aacataacca gaataagtct ttagccagtt gttaatagtt gttctaccct   3360
gcagcctctt gatctaggct tcctctcagt actaactgtc ttttaggctc caactggacc   3420
cattaagctc tgtttacagc cttgaaccct ttcttagtcc aaagtcttac acattcctcc   3480
aaaaaaacca catggtcagg tctttcacag caaagatcca cttcctggta gtagcttctg   3540
tgtcttggct actctaaaat tgctatgaca aaacatcccg accaaggcag aatgtacaag   3600
aaagcattga gtttatggtt tcagaggtat ttagttcatg atagaacagt tgagagctta   3660
catcttgatc tgtaagtagg aggcagagag agaacccagg ggatggcatg gacttttgaa   3720
acctccaagc cttcaccttg tgacagacct ccccaacaga gccacatctc ctaatccttt   3780
ccaagtagtt cctccaactg gggaccaaat actccagcat gagcataggg gagcattctc   3840
attcacacca ccagtttgcc gaggaacttt cctagccatg gcttgtcatt cattgctccc   3900
agttgataat ttcactattt gtagcaaact cagtggccaa gtccttgcta ttatgggtct   3960
tctgcttgta ttgaaaatac tgcagctcct gttggggttg ctgtgcagtc tctctgaggg   4020
actgataaca gacttgtata tccatatctc catggcagtg agaaacggta gcttagaggt   4080
aatcctagaa gccatcactc acagtccctg cttgagaata ggctatgata tgtctagccc   4140
tggactttag tcatttccta gacatggacc tgctgggtgg aattgggtca ttatgatgtt   4200
taattccaag cactgcattc aaaataggat acatgatata gtatgtcagc ttcattctaa   4260
cgtttctcct aatcttttgg ggcagagtct tgctgtttca ccatgactgg cctgggcctt   4320
accctacatc tcaggctggc ctcagctttg cagtgacctt cctgcttttg cctctcgagt   4380
gctggaattc taggcatgta atgactaaat ttcttatttt gctttttatt taagtttttg   4440
ttactctatc ttggacaaaa agtgcagagc agaggtgtcg gattactagg aaagtctcca   4500
gggcttcgct gttactgtgt tccccacagg gacttcctgg ttgttgacgt gcttctgttt   4560
actactgtgt cagatgagcg actcagagct cggcttcaga taggtgtgac tgccgccctc   4620
```

-continued

```
gcccatttag gatgtagtag atttatgatt gagggctgga acgggtagat tacattgtac   4680
cgccaagcat ttgtgactgt gtggatatat attcattatt tatgtatatt taggtgtgtg   4740
tgatactttg catggtttga aagaatctat tctgaaagcc aggatcattt gtaacctttg   4800
tgtgtcagtt caatgtaatg ttggggcctt tgaaaagttg attgagaaat tggggatcat   4860
tcccagttct ccgatgttac ttgtttagtc ctctttagaa agaaagacac ttttggacca   4920
gctgtttcgc tgttttgttc tgtttccatg atattctgtg aacctccatg gctttagata   4980
ctgtgactgt tattttcctt tttgcccaaa ttgttgattc agtctaaaga atactatttt   5040
ttgatgcctc ttacaattca tgcatgtgca cactatagat tgatgctacc tttgctaaaa   5100
atgtcttaag ataaagaact agctctttag aacctgcact tcaaagataa acctggaagc   5160
tgtcctgtgc caaaagtaaa gtgtacaatg tttacagatg ggtggaattt tgcactgcca   5220
tagggaacgg tgagctcgca tcacggggtt ccttagatgt atgggtagat agttgcagtt   5280
gagcttatga gaggaactgt ggagccctct aaggctaagc tgctaatgag tatccaagac   5340
aggtggttgg tgaacgtgac tccctagacc tagctggggt cttctgttga cagctcttca   5400
tggtttgcag acactatatg ttttctttag aggagctgcc agctctcccc tcttgtgaaa   5460
gactgtcttg tagacatttt gagatctttt gatgtaatgt gcaatcccaa gtaatgccat   5520
tattggtgaa tgtagcattg ttaaactttt attgtaaatt atctctgatc ttaccttgat   5580
agccttaggg tttttgtttt ttgttttttt ttgttatgtt ttcagagaca gagtctcgct   5640
atttggttta cctagaattt gctttatgat taggctgtcc ccaaactcac agatgtctgc   5700
ctttctacca ccacgcccat gtaactgatg ttaccaaaaa tgatctcata tccatggtgt   5760
tgcttatgtg tctttgcata ggcgcctcct tcagtcccat ctaggagcac agcacagtag   5820
aagtccattt cttaagtggg cagagtcaga gataagctaa gagggcaagt agttgcttca   5880
gtggttttta gagcttggca aacgctttac tgaagattag cattgtgttg tgacacttga   5940
gggccaatac gagcatttaa tttgttacct aaaggtgctt tgtgttctta aacagcaagt   6000
atttgatgtg tgtaaacatt tcccttcatt ctccctccct cctcaccgtt tttatggtct   6060
cctatttctg agttagctgc atttggacat tgcttttatg ccagaggcca tctgtcacct   6120
tggatgttta gaagtacagt gtacttatgt agggtcctcc ttgagcctgt cctgagcagt   6180
gttgtggtta cagaattgcc tacgagctcc aacagagagg tggggaagct gggagggcac   6240
agctgtctgg cttcctttgt ggaggtgttg gtttgtttga acactaagga atttgaggtt   6300
aatcttcccc ctcttcctgc ccatagtttt cacttccctt tcagtaagaa cgacccccta   6360
aaagaaaaca ggaggagatg cagcgcttta ggccgcctta gccagcagct tgtgtcctac   6420
tctggaagtt gtaacctaca gtttttctca cctgtaaagc caacacacac agctacccgt   6480
ttctacctca gtttgatgtg gcgactatgg aggaacaact cttaaaagct ctgactgcct   6540
tgaagatgga ggaagctagt ggtcttggtc gactgtgctc tgaggtttat attgagaatc   6600
ctttattctg gaagtgagtg cggttctcct gaccgcctgc tcagtagaac ctgtgttgcc   6660
tgctttaagt ctctgcccac ctgcctgtcc tttccttgac actaggctct tgattaggaa   6720
gagttgtctc cagatgcttt gagaagcaca tgtaaatcta gatagcacat tctaccctga   6780
tggaacttcc ttgcttgtct tgctgtatag gaattcattc tgtatacact tgagtgggtg   6840
gcatgagatg ctcgacttgt gtgtcgagag gcagtgtcat gacattccca gtctggtact   6900
tgccagtgca gaagcaaatg aggggtaata aactgagaag aagggcagct tactaacgag   6960
```

```
gccagaggga aatgtttccg tgtgtcctta tgtaactttt tacagtgcca ctaagttaat   7020

agccctgtac atgggtgttt gcactatgta atgcttttaa tgcggtttta ttgtgttttt   7080

gtgtgattaa acagttttca tttcattgtg ttttgtcatt attggaaata ggtaattttg   7140

cttatgtaca gctaacccat tttctgttat ctttggcatg atttggggaa gtgattaaaa   7200

gtcattggca gcttttccct                                               7220
```

<210> SEQ ID NO 34
<211> LENGTH: 489
<212> TYPE: PRT
<213> ORGANISM: Mus musculus

<400> SEQUENCE: 34

```
Met Thr Ser His Ser Thr Ser Ala Gln Cys Ser Ala Ser Asp Ser Ala
1               5                   10                  15

Cys Arg Ile Ser Ser Glu Gln Ile Ser Gln Val Arg Pro Lys Leu Gln
            20                  25                  30

Leu Leu Lys Ile Leu His Ala Ala Gly Ala Gln Gly Glu Val Phe Thr
        35                  40                  45

Met Lys Glu Val Met His Tyr Leu Gly Gln Tyr Ile Met Val Lys Gln
    50                  55                  60

Leu Tyr Asp Gln Gln Glu Gln His Met Val Tyr Cys Gly Gly Asp Leu
65                  70                  75                  80

Leu Gly Asp Leu Leu Gly Cys Gln Ser Phe Ser Val Lys Asp Pro Ser
                85                  90                  95

Pro Leu Tyr Asp Met Leu Arg Lys Asn Leu Val Thr Ser Ala Ser Ile
            100                 105                 110

Asn Thr Asp Ala Ala Gln Thr Leu Ala Leu Ala Gln Asp His Thr Met
        115                 120                 125

Asp Phe Pro Ser Gln Asp Arg Leu Lys His Gly Ala Thr Glu Tyr Ser
    130                 135                 140

Asn Pro Arg Lys Arg Thr Glu Glu Glu Asp Thr His Thr Leu Pro Thr
145                 150                 155                 160

Ser Arg His Lys Cys Arg Asp Ser Arg Ala Asp Glu Asp Leu Ile Glu
                165                 170                 175

His Leu Ser Gln Asp Glu Thr Ser Arg Leu Asp Leu Asp Phe Glu Glu
            180                 185                 190

Trp Asp Val Ala Gly Leu Pro Trp Trp Phe Leu Gly Asn Leu Arg Asn
        195                 200                 205

Asn Cys Ile Pro Lys Ser Asn Gly Ser Thr Asp Leu Gln Thr Asn Gln
    210                 215                 220

Asp Ile Gly Thr Ala Ile Val Ser Asp Thr Thr Asp Asp Leu Trp Phe
225                 230                 235                 240

Leu Asn Glu Thr Val Ser Glu Gln Leu Gly Val Gly Ile Lys Val Glu
                245                 250                 255

Ala Ala Asn Ser Glu Gln Thr Ser Glu Val Gly Lys Thr Ser Asn Lys
            260                 265                 270

Lys Thr Val Glu Val Gly Lys Asp Asp Asp Leu Glu Asp Ser Arg Ser
        275                 280                 285

Leu Ser Asp Asp Thr Asp Val Glu Leu Thr Ser Glu Asp Glu Trp Gln
    290                 295                 300

Cys Thr Glu Cys Lys Lys Phe Asn Ser Pro Ser Lys Arg Tyr Cys Phe
305                 310                 315                 320
```

```
Arg Cys Trp Ala Leu Arg Lys Asp Trp Tyr Ser Asp Cys Ser Lys Leu
                325                 330                 335

Thr His Ser Leu Ser Thr Ser Asn Ile Thr Ala Ile Pro Glu Lys Lys
            340                 345                 350

Asp Asn Glu Gly Ile Asp Val Pro Asp Cys Arg Arg Thr Ile Ser Ala
        355                 360                 365

Pro Val Val Arg Pro Lys Asp Gly Tyr Leu Lys Glu Glu Lys Pro Arg
    370                 375                 380

Phe Asp Pro Cys Asn Ser Val Gly Phe Leu Asp Leu Ala His Ser Ser
385                 390                 395                 400

Glu Ser Gln Glu Ile Ile Ser Ser Ala Arg Glu Gln Thr Asp Ile Phe
                405                 410                 415

Ser Glu Gln Lys Ala Glu Thr Glu Ser Met Glu Asp Phe Gln Asn Val
            420                 425                 430

Leu Lys Pro Cys Ser Leu Cys Glu Lys Arg Pro Arg Asp Gly Asn Ile
        435                 440                 445

Ile His Gly Lys Thr Ser His Leu Thr Thr Cys Phe His Cys Ala Arg
    450                 455                 460

Arg Leu Lys Lys Ser Gly Ala Ser Cys Pro Ala Cys Lys Lys Glu Ile
465                 470                 475                 480

Gln Leu Val Ile Lys Val Phe Ile Ala
                485
```

<210> SEQ ID NO 35
<211> LENGTH: 7194
<212> TYPE: DNA
<213> ORGANISM: Mus musculus

<400> SEQUENCE: 35

```
tctatggttc cccggcctc cccggaagct cttgcgaacg ctgggtttga gaggccggaa      60

gtggtgctgc cgttgctcgc agtttcaaaa tgcagtgcag gccttagggt ctccggctgc    120

cacccctccc ccagctagga gggggagcga ctcatggagc ggccgtaagt ttgctaactg    180

tggagtcttc actgccaaaa tgacatcaca ttccacctcg gcccagtgtt cagcatctga    240

cagtgcttgc agaatttctt cggaacaaat tagtcagcag gtgcggccaa aactgcagct    300

tttgaagatt ttgcatgcag caggtgcgca gggggaagta ttcaccatga aagaggtaat    360

gcactatcta ggccagtata taatggtgaa gcagctctat gatcaacagg agcaacatat    420

ggtatactgt ggtggagatc ttttgggaga tctacttgga tgtcagagct ttttctgtgaa    480

agatccaagc cctctctatg acatgctaag aaagaatctt gttacatcag cttctattaa    540

cacaggatca cactatggat tttccaagtc aagaccgact gaagcacggt gcaacagaat    600

actccaatcc cagaaaaaga actgaagaag aggatactca cacactgcct acctcacgac    660

ataaatgcag agactccaga gcagatgaag acttgataga acatttatct caagatgaga    720

catctaggct tgaccttgat tttgaggagt gggacgttgc tggcctgcct tggtggtttc    780

tagggaattt gagaaacaac tgtattccta aaagtaatgg ctcaactgat ttacagacaa    840

atcaggatat aggtactgcc attgtttcag acactacgga tgatttgtgg tttttaaatg    900

agaccgtgtc agagcaatta ggtgttggaa taaaagttga agctgctaat tctgagcaaa    960

caagtgaagt agggaaaaca agtaacaaga agacggtgga ggtgggaaag gatgatgatc   1020

ttgaggactc caggtccttg agcgatgata ctgacgtgga acttacctct gaggatgagt   1080

ggcagtgtac ggaatgcaag aagtttaatt ctccaagcaa gaggtactgt tttcgttgct   1140
```

```
gggccttgag aaaggattgg tattcggatt gttctaaatt aactcattcc ctatctacat   1200
ctaatattac tgccatacct gaaaagaagg acaatgaagg aattgatgtt cccgattgta   1260
ggagaaccat ttcagctcct gttgttaggc ctaaagatgg atatttaaag gaggaaaagc   1320
ccaggtttga cccttgcaac tcagtgggat ttttggattt ggctcatagt tctgaaagcc   1380
aggagatcat ctcaagcgcg agagaacaaa cagatatttt ttctgagcag aaagctgaaa   1440
cagaaagtat ggaagatttc cagaatgtct tgaagccgtg tagcttatgt gaaaaaaggc   1500
ctcgggatgg gaacattatt catgggaaga cgagccatct gacgacatgt ttccactgtg   1560
ccaggagact gaagaagtct ggggcttcgt gtcctgcttg taagaaagag attcagttgg   1620
ttattaaagt ttttatagca tagttgagtc agtcacagag aaatactagg aggaccaggt   1680
catttatcaa aaaaatcagt attcttagag gcaggggcag aagatcacca attttgatgc   1740
cagtctgggc catataatga gatcttagtc ttaaaaggat cagtattgag catcttttat   1800
aaatgtgacc cattgcatat gtttatttgt ataagcatat atgaactttt agctaagttt   1860
tgagggtttc attagtgaga agatactttg ttcttccaaa ttgtgaaccc agagggaata   1920
atatcaatac aaacatagca atgcattctt ttattcactt ccaaattatt gcaagaataa   1980
tacattagtt gatttattct ctaccctggt gttatgtaat gttcttgagg catcaaaatc   2040
taaagcattt attaaatact ggggctaaca ctgaagagga catatccagt cagtcgctca   2100
ttgtgtagtc aaggatgacc ttaaattcct gatagctgtc tctaccacct atgtgctcat   2160
aggctcatag gccgccccac tagcccatct gaaatctctt agttttaggt caggtaacac   2220
aggtgtacat ctctccacag ccttattatc agttccaaaa aggaaaggca cagactttgt   2280
tgcccacact ttgcatttgt ctctcaagct ggctgggtgt tttgtgtttt gtgctctgca   2340
gctgttcaca ttctgaggca gtggcctatg ataaggcttg aacagtagag aggaggaatg   2400
tagcagctgt gaaaggaggg gaacaaattg atctcttcaa ttctgcttag tcattttaga   2460
ccacatcaac ttagtataat atcaatatat gaactgaaga tcttcacgct gaatcccgta   2520
tgcctgttct gtgtccactg aacacatggc catcttgatg tttccccagg gacatgagaa   2580
catcatttta aagaccaagt ccctagaact attgagcttg agggcaatct agctgtcttg   2640
gcttttccta tggctcctgc tgttagaaag gggagagatgc atggtatcca gtccccttaa   2700
tgtcattatg tccctgctgg actgggacca ctggggctcc tctaattact actaagagga   2760
gctatgttag ctttatcttg cattgatccc atgttccctg tctgtcccat gctctaccat   2820
tagacccaac tttaccaaat tctcactgga tcagttatca tagttactct ttaattttga   2880
tgacaaagca ccaatgcaaa atataaaaga aagcatttaa tggggtttgc ttttgagagg   2940
gttagaatcc atgatggcag gcagggacag ctgagagctc acatcttgat ctgcaagtag   3000
aatgcagaga aaaagagagc cctggaaaac cccagggcct gcccccccag tgtcgtaatt   3060
ggtctacctt ttccaccgac tggggtccaa gtattcaaac ttaagagcct gtggtttata   3120
ttctcatgta aaccaccaca ttccatgaaa agaattacta attactgtgc tgcagaacca   3180
gtattaggcg ttctggacac ctcttctatc aaagaaatta cttttcactc caggcttagg   3240
caaattctta ggacaagggt agaaggcagc cacattcttt gtcaaacata accagaataa   3300
gtctttagcc agttgttaat agttgttcta ccctgcagcc tcttgatcta ggcttcctct   3360
cagtactaac tgtcttttag gctccaactg gacccattaa gctctgttta cagccttgaa   3420
ccctttctta gtccaaagtc ttacacattc ctccaaaaaa accacatggt caggtctttc   3480
```

acagcaaaga tccacttcct ggtagtagct tctgtgtctt ggctactcta aaattgctat 3540
gacaaaacat cccgaccaag gcagaatgta caagaaagca ttgagtttat ggtttcagag 3600
gtatttagtt catgatagaa cagttgagag cttacatctt gatctgtaag taggaggcag 3660
agagagaacc caggggatgg catggacttt tgaaacctcc aagccttcac cttgtgacag 3720
acctccccaa cagagccaca tctcctaatc ctttccaagt agttcctcca actggggacc 3780
aaatactcca gcatgagcat aggggagcat tctcattcac accaccagtt tgccgaggaa 3840
ctttcctagc catggcttgt cattcattgc tcccagttga taatttcact atttgtagca 3900
aactcagtgg ccaagtcctt gctattatgg gtcttctgct tgtattgaaa atactgcagc 3960
tcctgttggg gttgctgtgc agtctctctg agggactgat aacagacttg tatatccata 4020
tctccatggc agtgagaaac ggtagcttag aggtaatcct agaagccatc actcacagtc 4080
cctgcttgag aataggctat gatatgtcta gccctggact ttagtcattt cctagacatg 4140
gacctgctgg gtggaattgg gtcattatga tgtttaattc caagcactgc attcaaaata 4200
ggatacatga tatagtatgt cagcttcatt ctaacgtttc tcctaatctt ttggggcaga 4260
gtcttgctgt ttcaccatga ctggcctggg ccttacccta catctcaggc tggcctcagc 4320
tttgcagtga ccttcctgct tttgcctctc gagtgctgga attctaggca tgtaatgact 4380
aaatttctta ttttgctttt tatttaagtt tttgttactc tatcttggac aaaaagtgca 4440
gagcagaggt gtcggattac taggaaagtc tccagggctt cgctgttact gtgttcccca 4500
cagggacttc ctggttgttg acgtgcttct gtttactact gtgtcagatg agcgactcag 4560
agctcggctt cagataggtg tgactgccgc cctcgcccat ttaggatgta gtagatttat 4620
gattgagggc tggaacgggt agattacatt gtaccgccaa gcatttgtga ctgtgtggat 4680
atatattcat tatttatgta tatttaggtg tgtgtgatac tttgcatggt ttgaaagaat 4740
ctattctgaa agccaggatc atttgtaacc tttgtgtgtc agttcaatgt aatgttgggg 4800
cctttgaaaa gttgattgag aaattgggga tcattcccag ttctccgatg ttacttgttt 4860
agtcctcttt agaaagaaag acacttttgg accagctgtt tcgctgtttt gttctgtttc 4920
catgatattc tgtgaacctc catggcttta gatactgtga ctgttatttt cctttttgcc 4980
caaattgttg attcagtcta aagaatacta ttttttgatg cctcttacaa ttcatgcatg 5040
tgcacactat agattgatgc tacctttgct aaaaatgtct taagataaag aactagctct 5100
ttagaacctg cacttcaaag ataaacctgg aagctgtcct gtgccaaaag taaagtgtac 5160
aatgtttaca gatgggtgga attttgcact gccataggga acggtgagct cgcatcacgg 5220
ggttccttag atgtatgggt agatagttgc agttgagctt atgagaggaa ctgtggagcc 5280
ctctaaggct aagctgctaa tgagtatcca agacaggtgg ttggtgaacg tgactcccta 5340
gacctagctg gggtcttctg ttgacagctc ttcatggttt gcagacacta tatgttttct 5400
ttagaggagc tgccagctct cccctcttgt gaaagactgt cttgtagaca ttttgagatc 5460
ttttgatgta atgtgcaatc ccaagtaatg ccattattgg tgaatgtagc attgttaaac 5520
ttttattgta aattatctct gatcttacct tgatagcctt agggtttttt gtttttgttt 5580
ttttttgtta tgttttcaga gacagagtct cgctatttgg tttacctaga atttgcttta 5640
tgattaggct gtccccaaac tcacagatgt ctgcctttct accaccacgc ccatgtaact 5700
gatgttacca aaaatgatct catatccatg gtgttgctta tgtgtctttg cataggcgcc 5760
tccttcagtc ccatctagga gcacagcaca gtagaagtcc atttcttaag tgggcagagt 5820
cagagataag ctaagagggc aagtagttgc ttcagtggtt tttagagctt ggcaaacgct 5880

```
ttactgaaga ttagcattgt gttgtgacac ttgagggcca atacgagcat ttaatttgtt   5940

acctaaaggt gctttgtgtt cttaaacagc aagtatttga tgtgtgtaaa catttccctt   6000

cattctccct ccctcctcac cgtttttatg gtctcctatt tctgagttag ctgcatttgg   6060

acattgcttt tatgccagag gccatctgtc accttggatg tttagaagta cagtgtactt   6120

atgtagggtc ctccttgagc ctgtcctgag cagtgttgtg gttacagaat tgcctacgag   6180

ctccaacaga gaggtgggga agctgggagg gcacagctgt ctggcttcct ttgtggaggt   6240

gttggtttgt ttgaacacta aggaatttga ggttaatctt ccccctcttc ctgcccatag   6300

ttttcacttc cctttcagta agaacgaccc cctaaaagaa aacaggagga gatgcagcgc   6360

tttaggccgc cttagccagc agcttgtgtc ctactctgga agttgtaacc tacagttttt   6420

ctcacctgta aagccaacac acacagctac ccgtttctac ctcagtttga tgtggcgact   6480

atggaggaac aactcttaaa agctctgact gccttgaaga tggaggaagc tagtggtctt   6540

ggtcgactgt gctctgaggt ttatattgag aatcctttat tctggaagtg agtgcggttc   6600

tcctgaccgc ctgctcagta gaacctgtgt tgcctgcttt aagtctctgc ccacctgcct   6660

gtcctttcct tgacactagg ctcttgatta ggaagagttg tctccagatg ctttgagaag   6720

cacatgtaaa tctagatagc acattctacc ctgatggaac ttccttgctt gtcttgctgt   6780

ataggaattc attctgtata cacttgagtg ggtggcatga gatgctcgac ttgtgtgtcg   6840

agaggcagtg tcatgacatt cccagtctgg tacttgccag tgcagaagca aatgaggggt   6900

aataaactga gaagaagggc agcttactaa cgaggccaga gggaaatgtt tccgtgtgtc   6960

cttatgtaac tttttacagt gccactaagt taatagccct gtacatgggt gtttgcacta   7020

tgtaatgctt ttaatgcggt tttattgtgt ttttgtgtga ttaaacagtt ttcatttcat   7080

tgtgttttgt cattattgga aataggtaat tttgcttatg tacagctaac ccatttctg    7140

ttatctttgg catgatttgg ggaagtgatt aaaagtcatt ggcagctttt ccct         7194
```

<210> SEQ ID NO 36
<211> LENGTH: 362
<212> TYPE: PRT
<213> ORGANISM: Mus musculus

<400> SEQUENCE: 36

```
Met Asp Phe Pro Ser Gln Asp Arg Leu Lys His Gly Ala Thr Glu Tyr
1               5                   10                  15

Ser Asn Pro Arg Lys Arg Thr Glu Glu Glu Asp Thr His Thr Leu Pro
            20                  25                  30

Thr Ser Arg His Lys Cys Arg Asp Ser Arg Ala Asp Glu Asp Leu Ile
        35                  40                  45

Glu His Leu Ser Gln Asp Glu Thr Ser Arg Leu Asp Leu Asp Phe Glu
    50                  55                  60

Glu Trp Asp Val Ala Gly Leu Pro Trp Trp Phe Leu Gly Asn Leu Arg
65                  70                  75                  80

Asn Asn Cys Ile Pro Lys Ser Asn Gly Ser Thr Asp Leu Gln Thr Asn
                85                  90                  95

Gln Asp Ile Gly Thr Ala Ile Val Ser Asp Thr Thr Asp Asp Leu Trp
            100                 105                 110

Phe Leu Asn Glu Thr Val Ser Glu Gln Leu Gly Val Gly Ile Lys Val
        115                 120                 125

Glu Ala Ala Asn Ser Glu Gln Thr Ser Glu Val Gly Lys Thr Ser Asn
    130                 135                 140
```

```
Lys Lys Thr Val Glu Val Gly Lys Asp Asp Asp Leu Glu Asp Ser Arg
145                 150                 155                 160

Ser Leu Ser Asp Asp Thr Asp Val Glu Leu Thr Ser Glu Asp Glu Trp
                165                 170                 175

Gln Cys Thr Glu Cys Lys Lys Phe Asn Ser Pro Ser Lys Arg Tyr Cys
            180                 185                 190

Phe Arg Cys Trp Ala Leu Arg Lys Asp Trp Tyr Ser Asp Cys Ser Lys
        195                 200                 205

Leu Thr His Ser Leu Ser Thr Ser Asn Ile Thr Ala Ile Pro Glu Lys
    210                 215                 220

Lys Asp Asn Glu Gly Ile Asp Val Pro Asp Cys Arg Arg Thr Ile Ser
225                 230                 235                 240

Ala Pro Val Val Arg Pro Lys Asp Gly Tyr Leu Lys Glu Glu Lys Pro
                245                 250                 255

Arg Phe Asp Pro Cys Asn Ser Val Gly Phe Leu Asp Leu Ala His Ser
            260                 265                 270

Ser Glu Ser Gln Glu Ile Ile Ser Ser Ala Arg Glu Gln Thr Asp Ile
        275                 280                 285

Phe Ser Glu Gln Lys Ala Glu Thr Glu Ser Met Glu Asp Phe Gln Asn
    290                 295                 300

Val Leu Lys Pro Cys Ser Leu Cys Glu Lys Arg Pro Arg Asp Gly Asn
305                 310                 315                 320

Ile Ile His Gly Lys Thr Ser His Leu Thr Thr Cys Phe His Cys Ala
                325                 330                 335

Arg Arg Leu Lys Lys Ser Gly Ala Ser Cys Pro Ala Cys Lys Lys Glu
            340                 345                 350

Ile Gln Leu Val Ile Lys Val Phe Ile Ala
        355                 360
```

```
<210> SEQ ID NO 37
<211> LENGTH: 7298
<212> TYPE: DNA
<213> ORGANISM: Mus musculus

<400> SEQUENCE: 37

tctatggttc ccccggcctc cccggaagct cttgcgaacg ctgggtttga gaggccggaa      60

gtggtgctgc cgttgctcgc agtttcaaaa tgcagtgcag gccttagggt ctccggctgc     120

cacccctccc ccagctagga gggggagcga ctcatggagc ggccgtaagg attcacctga     180

gggacacttg gctggtttag tttttagctt ctgtgctgga tttgagaatt gagaatttca     240

gttcagtttt gctaactgtg gagtcttcac tgccaaaatg acatcacatt ccacctcggc     300

ccagtgttca gcatctgaca gtgcttgcag aatttcttcg gaacaaatta gtcaggtgcg     360

gccaaaactg cagcttttga agattttgca tgcagcaggt gcgcaggggg aagtattcac     420

catgaaagag gtaatgcact atctaggcca gtatataatg gtgaagcagc tctatgatca     480

acaggagcaa catatggtat actgtggtgg agatcttttg ggagatctac ttggatgtca     540

gagcttttct gtgaaagatc caagccctct ctatgacatg ctaagaaaga atcttgttac     600

atcagcttct attaacacag atgctgctca gactctcgct ctcgcacagg atcacactat     660

ggattttcca agtcaagacc gactgaagca cggtgcaaca gaatactcca atcccagaaa     720

aagaactgaa gaagaggata ctcacacact gcctacctca cgacataaat gcagagactc     780

cagagcagat gaagacttga tagaacattt atctcaagat gagacatcta ggcttgacct     840
```

-continued

```
tgattttgag gagtgggacg ttgctggcct gccttggtgg tttctaggga atttgagaaa    900
caactgtatt cctaaaagta atggctcaac tgatttacag acaaatcagg atataggtac    960
tgccattgtt tcagacacta cggatgattt gtggttttta aatgagaccg tgtcagagca   1020
attaggtgtt ggaataaaag ttgaagctgc taattctgag caaacaagtg aagtagggaa   1080
aacaagtaac aagaagacgg tggaggtggg aaaggatgat gatcttgagg actccaggtc   1140
cttgagcgat gatactgacg tggaacttac ctctgaggat gagtggcagt gtacggaatg   1200
caagaagttt aattctccaa gcaagaggta ctgttttcgt tgctgggcct tgagaaagga   1260
ttggtattcg gattgttcta aattaactca ttccctatct acatctaata ttactgccat   1320
acctgaaaag aaggacaatg aaggaattga tgttcccgat tgtaggagaa ccatttcagc   1380
tcctgttgtt aggcctaaag atggatattt aaaggaggaa aagcccaggt ttgacccttg   1440
caactcagtg ggatttttgg atttggctca tagttctgaa agccaggaga tcatctcaag   1500
cgcgagagaa caaacagata tttttctga gcagaaagct gaaacagaaa gtatggaaga   1560
tttccagaat gtcttgaagc cgtgtagctt atgtgaaaaa aggcctcggg atgggaacat   1620
tattcatggg aagacgagcc atctgacgac atgtttccac tgtgccagga gactgaagaa   1680
gtctggggct tcgtgtcctg cttgtaagaa agagattcag ttggttatta aagtttttat   1740
agcatagttg agtcagtcac agagaaatac taggaggacc aggtcattta tcaaaaaaat   1800
cagtattctt agaggcaggg gcagaagatc accaattttg atgccagtct gggccatata   1860
atgagatctt agtcttaaaa ggatcagtat tgagcatctt ttataaatgt gacccattgc   1920
atatgtttat ttgtataagc atatatgaac ttttagctaa gttttgaggg tttcattagt   1980
gagaagatac tttgttcttc caaattgtga acccagaggg aataatatca atacaaacat   2040
agcaatgcat tcttttattc acttccaaat tattgcaaga ataatacatt agttgattta   2100
ttctctaccc tggtgttatg taatgttctt gaggcatcaa aatctaaagc atttattaaa   2160
tactggggct aacactgaag aggacatatc cagtcagtcg ctcattgtgt agtcaaggat   2220
gaccttaaat tcctgatagc tgtctctacc acctatgtgc tcataggctc ataggccgcc   2280
ccactagccc atctgaaatc tcttagtttt aggtcaggta acacaggtgt acatctctcc   2340
acagccttat tatcagttcc aaaaaggaaa ggcacagact ttgttgccca cactttgcat   2400
ttgtctctca agctggctgg gtgttttgtg ttttgtgctc tgcagctgtt cacattctga   2460
ggcagtggcc tatgataagg cttgaacagt agagaggagg aatgtagcag ctgtgaaagg   2520
aggggaacaa attgatctct tcaattctgc ttagtcattt tagaccacat caacttagta   2580
taatatcaat atatgaactg aagatcttca cgctgaatcc cgtatgcctg ttctgtgtcc   2640
actgaacaca tggccatctt gatgtttccc cagggacatg agaacatcat tttaaagacc   2700
aagtccctag aactattgag cttgagggca atctagctgt cttggctttt cctatggctc   2760
ctgctgttag aaagggggag atgcatggta tccagtcccc ttaatgtcat tatgtccctg   2820
ctggactggg accactgggg ctcctctaat tactactaag aggagctatg ttagctttat   2880
cttgcattga tcccatgttc cctgtctgtc ccatgctcta ccattagacc caactttacc   2940
aaattctcac tggatcagtt atcatagtta ctctttaatt ttgatgacaa agcaccaatg   3000
caaaatataa aagaaagcat ttaatggggt ttgcttttga gagggttaga atccatgatg   3060
gcaggcaggg acagctgaga gctcacatct tgatctgcaa gtagaatgca gagaaaaaga   3120
gagccctgga aaaccccagg gcctgccccc ccagtgtcgt aattggtcta ccttttccac   3180
cgactggggt ccaagtattc aaacttaaga gcctgtggtt tatattctca tgtaaaccac   3240
```

```
cacattccat gaaaagaatt actaattact gtgctgcaga accagtatta ggcgttctgg   3300
acacctcttc tatcaaagaa attacttttc actccaggct taggcaaatt cttaggacaa   3360
gggtagaagg cagccacatt ctttgtcaaa cataaccaga ataagtcttt agccagttgt   3420
taatagttgt tctaccctgc agcctcttga tctaggcttc ctctcagtac taactgtctt   3480
ttaggctcca actggaccca ttaagctctg tttacagcct tgaacccttt cttagtccaa   3540
agtcttacac attcctccaa aaaaaccaca tggtcaggtc tttcacagca aagatccact   3600
tcctggtagt agcttctgtg tcttggctac tctaaaattg ctatgacaaa acatcccgac   3660
caaggcagaa tgtacaagaa agcattgagt ttatggtttc agaggtattt agttcatgat   3720
agaacagttg agagcttaca tcttgatctg taagtaggag gcagagagag aacccagggg   3780
atggcatgga cttttgaaac ctccaagcct tcaccttgtg acagacctcc ccaacagagc   3840
cacatctcct aatcctttcc aagtagttcc tccaactggg gaccaaatac tccagcatga   3900
gcatagggga gcattctcat tcacaccacc agtttgccga ggaactttcc tagccatggc   3960
ttgtcattca ttgctcccag ttgataattt cactatttgt agcaaactca gtggccaagt   4020
ccttgctatt atgggtcttc tgcttgtatt gaaaatactg cagctcctgt tggggttgct   4080
gtgcagtctc tctgagggac tgataacaga cttgtatatc catatctcca tggcagtgag   4140
aaacggtagc ttagaggtaa tcctagaagc catcactcac agtccctgct tgagaatagg   4200
ctatgatatg tctagccctg gactttagtc atttcctaga catggacctg ctgggtggaa   4260
ttgggtcatt atgatgttta attccaagca ctgcattcaa aataggatac atgatatagt   4320
atgtcagctt cattctaacg tttctcctaa tcttttgggg cagagtcttg ctgtttcacc   4380
atgactggcc tgggccttac cctacatctc aggctggcct cagctttgca gtgaccttcc   4440
tgcttttgcc tctcgagtgc tggaattcta ggcatgtaat gactaaattt cttattttgc   4500
tttttattta agtttttgtt actctatctt ggacaaaaag tgcagagcag aggtgtcgga   4560
ttactaggaa agtctccagg gcttcgctgt tactgtgttc cccacaggga cttcctggtt   4620
gttgacgtgc ttctgtttac tactgtgtca gatgagcgac tcagagctcg gcttcagata   4680
ggtgtgactg ccgccctcgc ccatttagga tgtagtagat ttatgattga gggctggaac   4740
gggtagatta cattgtaccg ccaagcattt gtgactgtgt ggatatatat tcattattta   4800
tgtatattta ggtgtgtgtg atactttgca tggtttgaaa gaatctattc tgaaagccag   4860
gatcatttgt aacctttgtg tgtcagttca atgtaatgtt ggggcctttg aaaagttgat   4920
tgagaaattg gggatcattc ccagttctcc gatgttactt gtttagtcct ctttagaaag   4980
aaagacactt ttggaccagc tgtttcgctg ttttgttctg tttccatgat attctgtgaa   5040
cctccatggc tttagatact gtgactgtta ttttcctttt tgcccaaatt gttgattcag   5100
tctaaagaat actatttttt gatgcctctt acaattcatg catgtgcaca ctatagattg   5160
atgctacctt tgctaaaaat gtcttaagat aaagaactag ctctttagaa cctgcacttc   5220
aaagataaac ctggaagctg tcctgtgcca aaagtaaagt gtacaatgtt tacagatggg   5280
tggaattttg cactgccata gggaacggtg agctcgcatc acggggttcc ttagatgtat   5340
gggtagatag ttgcagttga gcttatgaga ggaactgtgg agccctctaa ggctaagctg   5400
ctaatgagta tccaagacag gtggttggtg aacgtgactc cctagaccta gctggggtct   5460
tctgttgaca gctcttcatg gtttgcagac actatatgtt ttctttagag gagctgccag   5520
ctctcccctc ttgtgaaaga ctgtcttgta gacattttga gatcttttga tgtaatgtgc   5580
```

-continued aatcccaagt aatgccatta ttggtgaatg tagcattgtt aaacttttat tgtaaattat 5640
ctctgatctt accttgatag ccttagggtt ttttgttttt gttttttttt gttatgtttt 5700
cagagacaga gtctcgctat ttggtttacc tagaatttgc tttatgatta ggctgtcccc 5760
aaactcacag atgtctgcct ttctaccacc acgcccatgt aactgatgtt accaaaaatg 5820
atctcatatc catggtgttg cttatgtgtc tttgcatagg cgcctccttc agtcccatct 5880
aggagcacag cacagtagaa gtccatttct taagtgggca gagtcagaga taagctaaga 5940
gggcaagtag ttgcttcagt ggtttttaga gcttggcaaa cgctttactg aagattagca 6000
ttgtgttgtg acacttgagg gccaatacga gcatttaatt tgttacctaa aggtgctttg 6060
tgttcttaaa cagcaagtat ttgatgtgtg taaacatttc ccttcattct ccctccctcc 6120
tcaccgtttt tatggtctcc tatttctgag ttagctgcat ttggacattg cttttatgcc 6180
agaggccatc tgtcaccttg gatgtttaga agtacagtgt acttatgtag ggtcctcctt 6240
gagcctgtcc tgagcagtgt tgtggttaca gaattgccta cgagctccaa cagagaggtg 6300
gggaagctgg gagggcacag ctgtctggct tcctttgtgg aggtgttggt ttgtttgaac 6360
actaaggaat ttgaggttaa tcttcccccct cttcctgccc atagttttca cttccctttc 6420
agtaagaacg accccctaaa agaaaacagg aggagatgca gcgctttagg ccgccttagc 6480
cagcagcttg tgtcctactc tggaagttgt aacctacagt ttttctcacc tgtaaagcca 6540
acacacacag ctacccgttt ctacctcagt ttgatgtggc gactatggag gaacaactct 6600
taaaagctct gactgccttg aagatggagg aagctagtgg tcttggtcga ctgtgctctg 6660
aggtttatat tgagaatcct ttattctgga agtgagtgcg gttctcctga ccgcctgctc 6720
agtagaacct gtgttgcctg ctttaagtct ctgcccacct gcctgtcctt tccttgacac 6780
taggctcttg attaggaaga gttgtctcca gatgctttga gaagcacatg taaatctaga 6840
tagcacattc taccctgatg gaacttcctt gcttgtcttg ctgtatagga attcattctg 6900
tatacacttg agtgggtggc atgagatgct cgacttgtgt gtcgagaggc agtgtcatga 6960
cattcccagt ctggtacttg ccagtgcaga agcaaatgag ggtaataaaa ctgagaagaa 7020
gggcagctta ctaacgaggc cagagggaaa tgtttccgtg tgtccttatg taacttttta 7080
cagtgccact aagttaatag ccctgtacat gggtgtttgc actatgtaat gcttttaatg 7140
cggttttatt gtgtttttgt gtgattaaac agttttcatt tcattgtgtt ttgtcattat 7200
tggaaatagg taattttgct tatgtacagc taacccattt tctgttatct ttggcatgat 7260
ttggggaagt gattaaaagt cattggcagc ttttccct 7298

<210> SEQ ID NO 38
<211> LENGTH: 489
<212> TYPE: PRT
<213> ORGANISM: Mus musculus

<400> SEQUENCE: 38

Met Thr Ser His Ser Thr Ser Ala Gln Cys Ser Ala Ser Asp Ser Ala
1               5                   10                  15

Cys Arg Ile Ser Ser Glu Gln Ile Ser Gln Val Arg Pro Lys Leu Gln
            20                  25                  30

Leu Leu Lys Ile Leu His Ala Ala Gly Ala Gln Gly Glu Val Phe Thr
        35                  40                  45

Met Lys Glu Val Met His Tyr Leu Gly Gln Tyr Ile Met Val Lys Gln
    50                  55                  60

```
Leu Tyr Asp Gln Gln Glu Gln His Met Val Tyr Cys Gly Gly Asp Leu
65                  70                  75                  80

Leu Gly Asp Leu Leu Gly Cys Gln Ser Phe Ser Val Lys Asp Pro Ser
                85                  90                  95

Pro Leu Tyr Asp Met Leu Arg Lys Asn Leu Val Thr Ser Ala Ser Ile
            100                 105                 110

Asn Thr Asp Ala Ala Gln Thr Leu Ala Leu Ala Gln Asp His Thr Met
        115                 120                 125

Asp Phe Pro Ser Gln Asp Arg Leu Lys His Gly Ala Thr Glu Tyr Ser
    130                 135                 140

Asn Pro Arg Lys Arg Thr Glu Glu Glu Asp Thr His Thr Leu Pro Thr
145                 150                 155                 160

Ser Arg His Lys Cys Arg Asp Ser Arg Ala Asp Glu Asp Leu Ile Glu
                165                 170                 175

His Leu Ser Gln Asp Glu Thr Ser Arg Leu Asp Leu Asp Phe Glu Glu
            180                 185                 190

Trp Asp Val Ala Gly Leu Pro Trp Trp Phe Leu Gly Asn Leu Arg Asn
        195                 200                 205

Asn Cys Ile Pro Lys Ser Asn Gly Ser Thr Asp Leu Gln Thr Asn Gln
    210                 215                 220

Asp Ile Gly Thr Ala Ile Val Ser Asp Thr Thr Asp Asp Leu Trp Phe
225                 230                 235                 240

Leu Asn Glu Thr Val Ser Glu Gln Leu Gly Val Gly Ile Lys Val Glu
                245                 250                 255

Ala Ala Asn Ser Glu Gln Thr Ser Glu Val Gly Lys Thr Ser Asn Lys
            260                 265                 270

Lys Thr Val Glu Val Gly Lys Asp Asp Asp Leu Glu Asp Ser Arg Ser
        275                 280                 285

Leu Ser Asp Asp Thr Asp Val Glu Leu Thr Ser Glu Asp Glu Trp Gln
    290                 295                 300

Cys Thr Glu Cys Lys Lys Phe Asn Ser Pro Ser Lys Arg Tyr Cys Phe
305                 310                 315                 320

Arg Cys Trp Ala Leu Arg Lys Asp Trp Tyr Ser Asp Cys Ser Lys Leu
                325                 330                 335

Thr His Ser Leu Ser Thr Ser Asn Ile Thr Ala Ile Pro Glu Lys Lys
            340                 345                 350

Asp Asn Glu Gly Ile Asp Val Pro Asp Cys Arg Arg Thr Ile Ser Ala
        355                 360                 365

Pro Val Val Arg Pro Lys Asp Gly Tyr Leu Lys Glu Glu Lys Pro Arg
    370                 375                 380

Phe Asp Pro Cys Asn Ser Val Gly Phe Leu Asp Leu Ala His Ser Ser
385                 390                 395                 400

Glu Ser Gln Glu Ile Ile Ser Ser Ala Arg Glu Gln Thr Asp Ile Phe
                405                 410                 415

Ser Glu Gln Lys Ala Glu Thr Glu Ser Met Glu Asp Phe Gln Asn Val
            420                 425                 430

Leu Lys Pro Cys Ser Leu Cys Glu Lys Arg Pro Arg Asp Gly Asn Ile
        435                 440                 445

Ile His Gly Lys Thr Ser His Leu Thr Thr Cys Phe His Cys Ala Arg
    450                 455                 460

Arg Leu Lys Lys Ser Gly Ala Ser Cys Pro Ala Cys Lys Lys Glu Ile
465                 470                 475                 480
```

```
Gln Leu Val Ile Lys Val Phe Ile Ala
                485


<210> SEQ ID NO 39
<211> LENGTH: 911
<212> TYPE: PRT
<213> ORGANISM: Homo sapiens

<400> SEQUENCE: 39

Met Ala Ala Ser Gln Thr Ser Gln Thr Val Ala Ser His Val Pro Phe
1               5                   10                  15

Ala Asp Leu Cys Ser Thr Leu Glu Arg Ile Gln Lys Ser Lys Gly Arg
            20                  25                  30

Ala Glu Lys Ile Arg His Phe Arg Glu Phe Leu Asp Ser Trp Arg Lys
        35                  40                  45

Phe His Asp Ala Leu His Lys Asn His Lys Asp Val Thr Asp Ser Phe
    50                  55                  60

Tyr Pro Ala Met Arg Leu Ile Leu Pro Gln Leu Glu Arg Glu Arg Met
65                  70                  75                  80

Ala Tyr Gly Ile Lys Glu Thr Met Leu Ala Lys Leu Tyr Ile Glu Leu
                85                  90                  95

Leu Asn Leu Pro Arg Asp Gly Lys Asp Ala Leu Lys Leu Leu Asn Tyr
            100                 105                 110

Arg Thr Pro Thr Gly Thr His Gly Asp Ala Gly Asp Phe Ala Met Ile
        115                 120                 125

Ala Tyr Phe Val Leu Lys Pro Arg Cys Leu Gln Lys Gly Ser Leu Thr
    130                 135                 140

Ile Gln Gln Val Asn Asp Leu Leu Asp Ser Ile Ala Ser Asn Asn Ser
145                 150                 155                 160

Ala Lys Arg Lys Asp Leu Ile Lys Lys Ser Leu Leu Gln Leu Ile Thr
                165                 170                 175

Gln Ser Ser Ala Leu Glu Gln Lys Trp Leu Ile Arg Met Ile Ile Lys
            180                 185                 190

Asp Leu Lys Leu Gly Val Ser Gln Gln Thr Ile Phe Ser Val Phe His
        195                 200                 205

Asn Asp Ala Ala Glu Leu His Asn Val Thr Thr Asp Leu Glu Lys Val
    210                 215                 220

Cys Arg Gln Leu His Asp Pro Ser Val Gly Leu Ser Asp Ile Ser Ile
225                 230                 235                 240

Thr Leu Phe Ser Ala Phe Lys Pro Met Leu Ala Ala Ile Ala Asp Ile
                245                 250                 255

Glu His Ile Glu Lys Asp Met Lys His Gln Ser Phe Tyr Ile Glu Thr
            260                 265                 270

Lys Leu Asp Gly Glu Arg Met Gln Met His Lys Asp Gly Asp Val Tyr
        275                 280                 285

Lys Tyr Phe Ser Arg Asn Gly Tyr Asn Tyr Thr Asp Gln Phe Gly Ala
    290                 295                 300

Ser Pro Thr Glu Gly Ser Leu Thr Pro Phe Ile His Asn Ala Phe Lys
305                 310                 315                 320

Ala Asp Ile Gln Ile Cys Ile Leu Asp Gly Glu Met Met Ala Tyr Asn
                325                 330                 335

Pro Asn Thr Gln Thr Phe Met Gln Lys Gly Thr Lys Phe Asp Ile Lys
            340                 345                 350

Arg Met Val Glu Asp Ser Asp Leu Gln Thr Cys Tyr Cys Val Phe Asp
        355                 360                 365
```

-continued

```
Val Leu Met Val Asn Asn Lys Lys Leu Gly His Glu Thr Leu Arg Lys
    370                 375                 380

Arg Tyr Glu Ile Leu Ser Ser Ile Phe Thr Pro Ile Pro Gly Arg Ile
385                 390                 395                 400

Glu Ile Val Gln Lys Thr Gln Ala His Thr Lys Asn Glu Val Ile Asp
                405                 410                 415

Ala Leu Asn Glu Ala Ile Asp Lys Arg Glu Glu Gly Ile Met Val Lys
            420                 425                 430

Gln Pro Leu Ser Ile Tyr Lys Pro Asp Lys Arg Gly Glu Gly Trp Leu
        435                 440                 445

Lys Ile Lys Pro Glu Tyr Val Ser Gly Leu Met Asp Glu Leu Asp Ile
    450                 455                 460

Leu Ile Val Gly Gly Tyr Trp Gly Lys Gly Ser Arg Gly Gly Met Met
465                 470                 475                 480

Ser His Phe Leu Cys Ala Val Ala Glu Lys Pro Pro Pro Gly Glu Lys
                485                 490                 495

Pro Ser Val Phe His Thr Leu Ser Arg Val Gly Ser Gly Cys Thr Met
            500                 505                 510

Lys Glu Leu Tyr Asp Leu Gly Leu Lys Leu Ala Lys Tyr Trp Lys Pro
        515                 520                 525

Phe His Arg Lys Ala Pro Pro Ser Ser Ile Leu Cys Gly Thr Glu Lys
    530                 535                 540

Pro Glu Val Tyr Ile Glu Pro Cys Asn Ser Val Ile Val Gln Ile Lys
545                 550                 555                 560

Ala Ala Glu Ile Val Pro Ser Asp Met Tyr Lys Thr Gly Cys Thr Leu
                565                 570                 575

Arg Phe Pro Arg Ile Glu Lys Ile Arg Asp Asp Lys Glu Trp His Glu
            580                 585                 590

Cys Met Thr Leu Asp Asp Leu Glu Gln Leu Arg Gly Lys Ala Ser Gly
        595                 600                 605

Lys Leu Ala Ser Lys His Leu Tyr Ile Gly Gly Asp Asp Glu Pro Gln
    610                 615                 620

Glu Lys Lys Arg Lys Ala Ala Pro Lys Met Lys Lys Val Ile Gly Ile
625                 630                 635                 640

Ile Glu His Leu Lys Ala Pro Asn Leu Thr Asn Val Asn Lys Ile Ser
                645                 650                 655

Asn Ile Phe Glu Asp Val Glu Phe Cys Val Met Ser Gly Thr Asp Ser
            660                 665                 670

Gln Pro Lys Pro Asp Leu Glu Asn Arg Ile Ala Glu Phe Gly Gly Tyr
        675                 680                 685

Ile Val Gln Asn Pro Gly Pro Asp Thr Tyr Cys Val Ile Ala Gly Ser
    690                 695                 700

Glu Asn Ile Arg Val Lys Asn Ile Ile Leu Ser Asn Lys His Asp Val
705                 710                 715                 720

Val Lys Pro Ala Trp Leu Leu Glu Cys Phe Lys Thr Lys Ser Phe Val
                725                 730                 735

Pro Trp Gln Pro Arg Phe Met Ile His Met Cys Pro Ser Thr Lys Glu
            740                 745                 750

His Phe Ala Arg Glu Tyr Asp Cys Tyr Gly Asp Ser Tyr Phe Ile Asp
        755                 760                 765

Thr Asp Leu Asn Gln Leu Lys Glu Val Phe Ser Gly Ile Lys Asn Ser
    770                 775                 780
```

-continued

```
Asn Glu Gln Thr Pro Glu Glu Met Ala Ser Leu Ile Ala Asp Leu Glu
785                 790                 795                 800

Tyr Arg Tyr Ser Trp Asp Cys Ser Pro Leu Ser Met Phe Arg Arg His
                805                 810                 815

Thr Val Tyr Leu Asp Ser Tyr Ala Val Ile Asn Asp Leu Ser Thr Lys
            820                 825                 830

Asn Glu Gly Thr Arg Leu Ala Ile Lys Ala Leu Glu Leu Arg Phe His
        835                 840                 845

Gly Ala Lys Val Val Ser Cys Leu Ala Glu Gly Val Ser His Val Ile
    850                 855                 860

Ile Gly Glu Asp His Ser Arg Val Ala Asp Phe Lys Ala Phe Arg Arg
865                 870                 875                 880

Thr Phe Lys Arg Lys Phe Lys Ile Leu Lys Glu Ser Trp Val Thr Asp
                885                 890                 895

Ser Ile Asp Lys Cys Glu Leu Gln Glu Glu Asn Gln Tyr Leu Ile
            900                 905                 910


<210> SEQ ID NO 40
<211> LENGTH: 844
<212> TYPE: PRT
<213> ORGANISM: Homo sapiens

<400> SEQUENCE: 40

Met Arg Leu Ile Leu Pro Gln Leu Glu Arg Glu Arg Met Ala Tyr Gly
1               5                   10                  15

Ile Lys Glu Thr Met Leu Ala Lys Leu Tyr Ile Glu Leu Leu Asn Leu
            20                  25                  30

Pro Arg Asp Gly Lys Asp Ala Leu Lys Leu Leu Asn Tyr Arg Thr Pro
        35                  40                  45

Thr Gly Thr His Gly Asp Ala Gly Asp Phe Ala Met Ile Ala Tyr Phe
    50                  55                  60

Val Leu Lys Pro Arg Cys Leu Gln Lys Gly Ser Leu Thr Ile Gln Gln
65                  70                  75                  80

Val Asn Asp Leu Leu Asp Ser Ile Ala Ser Asn Asn Ser Ala Lys Arg
                85                  90                  95

Lys Asp Leu Ile Lys Lys Ser Leu Leu Gln Leu Ile Thr Gln Ser Ser
            100                 105                 110

Ala Leu Glu Gln Lys Trp Leu Ile Arg Met Ile Ile Lys Asp Leu Lys
        115                 120                 125

Leu Gly Val Ser Gln Gln Thr Ile Phe Ser Val Phe His Asn Asp Ala
    130                 135                 140

Ala Glu Leu His Asn Val Thr Thr Asp Leu Glu Lys Val Cys Arg Gln
145                 150                 155                 160

Leu His Asp Pro Ser Val Gly Leu Ser Asp Ile Ser Ile Thr Leu Phe
                165                 170                 175

Ser Ala Phe Lys Pro Met Leu Ala Ala Ile Ala Asp Ile Glu His Ile
            180                 185                 190

Glu Lys Asp Met Lys His Gln Ser Phe Tyr Ile Glu Thr Lys Leu Asp
        195                 200                 205

Gly Glu Arg Met Gln Met His Lys Asp Gly Asp Val Tyr Lys Tyr Phe
    210                 215                 220

Ser Arg Asn Gly Tyr Asn Tyr Thr Asp Gln Phe Gly Ala Ser Pro Thr
225                 230                 235                 240

Glu Gly Ser Leu Thr Pro Phe Ile His Asn Ala Phe Lys Ala Asp Ile
                245                 250                 255
```

```
Gln Ile Cys Ile Leu Asp Gly Glu Met Met Ala Tyr Asn Pro Asn Thr
            260                 265                 270

Gln Thr Phe Met Gln Lys Gly Thr Lys Phe Asp Ile Lys Arg Met Val
        275                 280                 285

Glu Asp Ser Asp Leu Gln Thr Cys Tyr Cys Val Phe Asp Val Leu Met
    290                 295                 300

Val Asn Asn Lys Lys Leu Gly His Glu Thr Leu Arg Lys Arg Tyr Glu
305                 310                 315                 320

Ile Leu Ser Ser Ile Phe Thr Pro Ile Pro Gly Arg Ile Glu Ile Val
                325                 330                 335

Gln Lys Thr Gln Ala His Thr Lys Asn Glu Val Ile Asp Ala Leu Asn
            340                 345                 350

Glu Ala Ile Asp Lys Arg Glu Glu Gly Ile Met Val Lys Gln Pro Leu
        355                 360                 365

Ser Ile Tyr Lys Pro Asp Lys Arg Gly Glu Gly Trp Leu Lys Ile Lys
    370                 375                 380

Pro Glu Tyr Val Ser Gly Leu Met Asp Glu Leu Asp Ile Leu Ile Val
385                 390                 395                 400

Gly Gly Tyr Trp Gly Lys Gly Ser Arg Gly Gly Met Met Ser His Phe
                405                 410                 415

Leu Cys Ala Val Ala Glu Lys Pro Pro Pro Gly Glu Lys Pro Ser Val
            420                 425                 430

Phe His Thr Leu Ser Arg Val Gly Ser Gly Cys Thr Met Lys Glu Leu
        435                 440                 445

Tyr Asp Leu Gly Leu Lys Leu Ala Lys Tyr Trp Lys Pro Phe His Arg
    450                 455                 460

Lys Ala Pro Pro Ser Ser Ile Leu Cys Gly Thr Glu Lys Pro Glu Val
465                 470                 475                 480

Tyr Ile Glu Pro Cys Asn Ser Val Ile Val Gln Ile Lys Ala Ala Glu
                485                 490                 495

Ile Val Pro Ser Asp Met Tyr Lys Thr Gly Cys Thr Leu Arg Phe Pro
            500                 505                 510

Arg Ile Glu Lys Ile Arg Asp Asp Lys Glu Trp His Glu Cys Met Thr
        515                 520                 525

Leu Asp Asp Leu Glu Gln Leu Arg Gly Lys Ala Ser Gly Lys Leu Ala
    530                 535                 540

Ser Lys His Leu Tyr Ile Gly Gly Asp Asp Glu Pro Gln Glu Lys Lys
545                 550                 555                 560

Arg Lys Ala Ala Pro Lys Met Lys Lys Val Ile Gly Ile Ile Glu His
                565                 570                 575

Leu Lys Ala Pro Asn Leu Thr Asn Val Asn Lys Ile Ser Asn Ile Phe
            580                 585                 590

Glu Asp Val Glu Phe Cys Val Met Ser Gly Thr Asp Ser Gln Pro Lys
        595                 600                 605

Pro Asp Leu Glu Asn Arg Ile Ala Glu Phe Gly Gly Tyr Ile Val Gln
    610                 615                 620

Asn Pro Gly Pro Asp Thr Tyr Cys Val Ile Ala Gly Ser Glu Asn Ile
625                 630                 635                 640

Arg Val Lys Asn Ile Ile Leu Ser Asn Lys His Asp Val Val Lys Pro
                645                 650                 655

Ala Trp Leu Leu Glu Cys Phe Lys Thr Lys Ser Phe Val Pro Trp Gln
            660                 665                 670
```

```
Pro Arg Phe Met Ile His Met Cys Pro Ser Thr Lys Glu His Phe Ala
        675                 680                 685

Arg Glu Tyr Asp Cys Tyr Gly Asp Ser Tyr Phe Ile Asp Thr Asp Leu
    690                 695                 700

Asn Gln Leu Lys Glu Val Phe Ser Gly Ile Lys Asn Ser Asn Glu Gln
705                 710                 715                 720

Thr Pro Glu Glu Met Ala Ser Leu Ile Ala Asp Leu Glu Tyr Arg Tyr
                725                 730                 735

Ser Trp Asp Cys Ser Pro Leu Ser Met Phe Arg Arg His Thr Val Tyr
            740                 745                 750

Leu Asp Ser Tyr Ala Val Ile Asn Asp Leu Ser Thr Lys Asn Glu Gly
        755                 760                 765

Thr Arg Leu Ala Ile Lys Ala Leu Glu Leu Arg Phe His Gly Ala Lys
    770                 775                 780

Val Val Ser Cys Leu Ala Glu Gly Val Ser His Val Ile Ile Gly Glu
785                 790                 795                 800

Asp His Ser Arg Val Ala Asp Phe Lys Ala Phe Arg Arg Thr Phe Lys
                805                 810                 815

Arg Lys Phe Lys Ile Leu Lys Glu Ser Trp Val Thr Asp Ser Ile Asp
            820                 825                 830

Lys Cys Glu Leu Gln Glu Glu Asn Gln Tyr Leu Ile
        835                 840


<210> SEQ ID NO 41
<211> LENGTH: 923
<212> TYPE: PRT
<213> ORGANISM: Homo sapiens

<400> SEQUENCE: 41

Met Ala Thr Pro Gln Glu Thr Ile Lys Ile Ser Phe Tyr Ser Trp Asp
1               5                   10                  15

Ser Leu Val His Arg Gly Asn Gly Ala Cys Pro Arg Pro Asp Leu Cys
            20                  25                  30

Ser Thr Leu Glu Arg Ile Gln Lys Ser Lys Gly Arg Ala Glu Lys Ile
        35                  40                  45

Arg His Phe Arg Glu Phe Leu Asp Ser Trp Arg Lys Phe His Asp Ala
    50                  55                  60

Leu His Lys Asn His Lys Asp Val Thr Asp Ser Phe Tyr Pro Ala Met
65                  70                  75                  80

Arg Leu Ile Leu Pro Gln Leu Glu Arg Glu Arg Met Ala Tyr Gly Ile
                85                  90                  95

Lys Glu Thr Met Leu Ala Lys Leu Tyr Ile Glu Leu Leu Asn Leu Pro
            100                 105                 110

Arg Asp Gly Lys Asp Ala Leu Lys Leu Leu Asn Tyr Arg Thr Pro Thr
        115                 120                 125

Gly Thr His Gly Asp Ala Gly Asp Phe Ala Met Ile Ala Tyr Phe Val
    130                 135                 140

Leu Lys Pro Arg Cys Leu Gln Lys Gly Ser Leu Thr Ile Gln Gln Val
145                 150                 155                 160

Asn Asp Leu Leu Asp Ser Ile Ala Ser Asn Asn Ser Ala Lys Arg Lys
                165                 170                 175

Asp Leu Ile Lys Lys Ser Leu Leu Gln Leu Ile Thr Gln Ser Ser Ala
            180                 185                 190

Leu Glu Gln Lys Trp Leu Ile Arg Met Ile Ile Lys Asp Leu Lys Leu
        195                 200                 205
```

-continued

```
Gly Val Ser Gln Gln Thr Ile Phe Ser Val Phe His Asn Asp Ala Ala
    210                 215                 220

Glu Leu His Asn Val Thr Thr Asp Leu Glu Lys Val Cys Arg Gln Leu
225                 230                 235                 240

His Asp Pro Ser Val Gly Leu Ser Asp Ile Ser Ile Thr Leu Phe Ser
                245                 250                 255

Ala Phe Lys Pro Met Leu Ala Ala Ile Ala Asp Ile Glu His Ile Glu
            260                 265                 270

Lys Asp Met Lys His Gln Ser Phe Tyr Ile Glu Thr Lys Leu Asp Gly
        275                 280                 285

Glu Arg Met Gln Met His Lys Asp Gly Asp Val Tyr Lys Tyr Phe Ser
    290                 295                 300

Arg Asn Gly Tyr Asn Tyr Thr Asp Gln Phe Gly Ala Ser Pro Thr Glu
305                 310                 315                 320

Gly Ser Leu Thr Pro Phe Ile His Asn Ala Phe Lys Ala Asp Ile Gln
                325                 330                 335

Ile Cys Ile Leu Asp Gly Glu Met Met Ala Tyr Asn Pro Asn Thr Gln
            340                 345                 350

Thr Phe Met Gln Lys Gly Thr Lys Phe Asp Ile Lys Arg Met Val Glu
        355                 360                 365

Asp Ser Asp Leu Gln Thr Cys Tyr Cys Val Phe Asp Val Leu Met Val
    370                 375                 380

Asn Asn Lys Lys Leu Gly His Glu Thr Leu Arg Lys Arg Tyr Glu Ile
385                 390                 395                 400

Leu Ser Ser Ile Phe Thr Pro Ile Pro Gly Arg Ile Glu Ile Val Gln
                405                 410                 415

Lys Thr Gln Ala His Thr Lys Asn Glu Val Ile Asp Ala Leu Asn Glu
            420                 425                 430

Ala Ile Asp Lys Arg Glu Glu Gly Ile Met Val Lys Gln Pro Leu Ser
        435                 440                 445

Ile Tyr Lys Pro Asp Lys Arg Gly Glu Gly Trp Leu Lys Ile Lys Pro
    450                 455                 460

Glu Tyr Val Ser Gly Leu Met Asp Glu Leu Asp Ile Leu Ile Val Gly
465                 470                 475                 480

Gly Tyr Trp Gly Lys Gly Ser Arg Gly Gly Met Met Ser His Phe Leu
                485                 490                 495

Cys Ala Val Ala Glu Lys Pro Pro Pro Gly Glu Lys Pro Ser Val Phe
            500                 505                 510

His Thr Leu Ser Arg Val Gly Ser Gly Cys Thr Met Lys Glu Leu Tyr
        515                 520                 525

Asp Leu Gly Leu Lys Leu Ala Lys Tyr Trp Lys Pro Phe His Arg Lys
    530                 535                 540

Ala Pro Pro Ser Ser Ile Leu Cys Gly Thr Glu Lys Pro Glu Val Tyr
545                 550                 555                 560

Ile Glu Pro Cys Asn Ser Val Ile Val Gln Ile Lys Ala Ala Glu Ile
                565                 570                 575

Val Pro Ser Asp Met Tyr Lys Thr Gly Cys Thr Leu Arg Phe Pro Arg
            580                 585                 590

Ile Glu Lys Ile Arg Asp Asp Lys Glu Trp His Glu Cys Met Thr Leu
        595                 600                 605

Asp Asp Leu Glu Gln Leu Arg Gly Lys Ala Ser Gly Lys Leu Ala Ser
    610                 615                 620
```

```
Lys His Leu Tyr Ile Gly Gly Asp Asp Glu Pro Gln Glu Lys Lys Arg
625                 630                 635                 640

Lys Ala Ala Pro Lys Met Lys Lys Val Ile Gly Ile Ile Glu His Leu
                645                 650                 655

Lys Ala Pro Asn Leu Thr Asn Val Asn Lys Ile Ser Asn Ile Phe Glu
            660                 665                 670

Asp Val Glu Phe Cys Val Met Ser Gly Thr Asp Ser Gln Pro Lys Pro
        675                 680                 685

Asp Leu Glu Asn Arg Ile Ala Glu Phe Gly Gly Tyr Ile Val Gln Asn
    690                 695                 700

Pro Gly Pro Asp Thr Tyr Cys Val Ile Ala Gly Ser Glu Asn Ile Arg
705                 710                 715                 720

Val Lys Asn Ile Ile Leu Ser Asn Lys His Asp Val Val Lys Pro Ala
                725                 730                 735

Trp Leu Leu Glu Cys Phe Lys Thr Lys Ser Phe Val Pro Trp Gln Pro
            740                 745                 750

Arg Phe Met Ile His Met Cys Pro Ser Thr Lys Glu His Phe Ala Arg
        755                 760                 765

Glu Tyr Asp Cys Tyr Gly Asp Ser Tyr Phe Ile Asp Thr Asp Leu Asn
    770                 775                 780

Gln Leu Lys Glu Val Phe Ser Gly Ile Lys Asn Ser Asn Glu Gln Thr
785                 790                 795                 800

Pro Glu Glu Met Ala Ser Leu Ile Ala Asp Leu Glu Tyr Arg Tyr Ser
                805                 810                 815

Trp Asp Cys Ser Pro Leu Ser Met Phe Arg Arg His Thr Val Tyr Leu
            820                 825                 830

Asp Ser Tyr Ala Val Ile Asn Asp Leu Ser Thr Lys Asn Glu Gly Thr
        835                 840                 845

Arg Leu Ala Ile Lys Ala Leu Glu Leu Arg Phe His Gly Ala Lys Val
    850                 855                 860

Val Ser Cys Leu Ala Glu Gly Val Ser His Val Ile Ile Gly Glu Asp
865                 870                 875                 880

His Ser Arg Val Ala Asp Phe Lys Ala Phe Arg Arg Thr Phe Lys Arg
                885                 890                 895

Lys Phe Lys Ile Leu Lys Glu Ser Trp Val Thr Asp Ser Ile Asp Lys
            900                 905                 910

Cys Glu Leu Gln Glu Glu Asn Gln Tyr Leu Ile
        915                 920
```

<210> SEQ ID NO 42
<211> LENGTH: 4115
<212> TYPE: DNA
<213> ORGANISM: Homo sapiens

<400> SEQUENCE: 42

```
ccacagcgct gtagactgcg ccgcattaga agcctggcct cctgatgctg tgctcttcat      60

ctagacccaa gccccaggtc gtgggacgat ttctcccgtt tttgactccc tggaactgta     120

ttgcctgctt tacctgcgta catgttgatt ctttctcatg gcaaccccgc aggaaaccat     180

caagatctca ttttacagct gggattctct ggttcacaga ggtaacggag cttgcccgag     240

gccagttaaa cgagaagatt catcaccgct ttgatggctg cctcacaaac ttcacaaact     300

gttgcatctc acgttccttt tgcagatttg tgttcaactt tagaacgaat acagaaaagt     360

aaaggacgtg cagaaaaaat cagacacttc agggaatttt tagattcttg gagaaaattt     420
```

-continued

```
catgatgctc ttcataagaa ccacaaagat gtcacagact ctttttatcc agcaatgaga    480
ctaattcttc ctcagctaga aagagagaga atggcctatg gaattaaaga aactatgctt    540
gctaagcttt atattgagtt gcttaattta cctagagatg gaaaagatgc cctcaaactt    600
ttaaactaca gaacacccac tggaactcat ggagatgctg gagactttgc aatgattgca    660
tattttgtgt tgaagccaag atgtttacag aaaggaagtt taaccataca gcaagtaaac    720
gacctttttag actcaattgc cagcaataat tctgctaaaa gaaaagacct aataaaaaag    780
agccttcttc aacttataac tcagagttca gcacttgagc aaaagtggct tatacggatg    840
atcataaagg atttaaagct tggtgttagt cagcaaacta tcttttctgt ttttcataat    900
gatgctgctg agttgcataa tgtcactaca gatctggaaa aagtctgtag gcaactgcat    960
gatccttctg taggactcag tgatatttct atcactttat tttctgcatt taaaccaatg   1020
ctagctgcta ttgcagatat tgagcacatt gagaaggata tgaaacatca gagtttctac   1080
atagaaacca agctagatgg tgaacgtatg caaatgcaca aagatggaga tgtatataaa   1140
tacttctctc gaaatggata taactacact gatcagtttg gtgcttctcc tactgaaggt   1200
tctcttaccc cattcattca taatgcattc aaagcagata tacaaatctg tattcttgat   1260
ggtgagatga tggcctataa tcctaataca caaactttca tgcaaaaggg aactaagttt   1320
gatattaaaa gaatggtaga ggattctgat ctgcaaactt gttattgtgt ttttgatgta   1380
ttgatggtta ataataaaaa gctagggcat gagactctga gaaagaggta tgagattctt   1440
agtagtattt ttacaccaat tccaggtaga atagaaatag tgcagaaaac acaagctcat   1500
actaagaatg aagtaattga tgcattgaat gaagcaatag ataaaagaga agagggaatt   1560
atggtaaaac aacctctatc catctacaag ccagacaaaa gaggtgaagg gtggttaaaa   1620
attaaaccag agtatgtcag tggactaatg gatgaattgg acattttaat tgttggagga   1680
tattggggta aaggatcacg ggtggaatg atgtctcatt ttctgtgtgc agtagcagag   1740
aagcccccctc ctggtgagaa gccatctgtg tttcatactc tctctcgtgt tgggtctggc   1800
tgcaccatga aagaactgta tgatctgggt ttgaaattgg ccaagtattg gaagcctttt   1860
catagaaaag ctccaccaag cagcatttta tgtggaacag agaagccaga agtatacatt   1920
gaaccttgta attctgtcat tgttcagatt aaagcagcag agatcgtacc cagtgatatg   1980
tataaaactg gctgcacctt gcgttttcca cgaattgaaa agataagaga tgacaaggag   2040
tggcatgagt gcatgaccct ggacgaccta gaacaactta gggggaaggc atctggtaag   2100
ctcgcatcta aacaccttta tataggtggt gatgatgaac cacaagaaaa aaagcggaaa   2160
gctgccccaa agatgaagaa agttattgga attattgagc acttaaaagc acctaacctt   2220
actaacgtta acaaaatttc taatatattt gaagatgtag agttttgtgt tatgagtgga   2280
acagatagcc agccaaagcc tgacctggag aacagaattg cagaatttgg tggttatata   2340
gtacaaaatc caggcccaga cacgtactgt gtaattgcag ggtctgagaa catcagagtg   2400
aaaaacataa ttttgtcaaa taaacatgat gttgtcaagc ctgcatggct tttagaatgt   2460
tttaagacca aaagctttgt accatggcag cctcgcttta tgattcatat gtgcccatca   2520
accaaagaac attttgcccg tgaatatgat tgctatggtg atagttattt cattgataca   2580
gacttgaacc aactgaagga agtattctca ggaattaaaa attctaacga gcagactcct   2640
gaagaaatgg cttctctgat tgctgattta gaatatcggt attcctggga ttgctctcct   2700
ctcagtatgt ttcgacgcca caccgtttat ttggactcgt atgctgttat taatgacctg   2760
agtaccaaaa atgaggggac aaggttagct attaaagcct tggagcttcg gtttcatgga   2820
```

gcaaaagtag tttcttgttt agctgaggga gtgtctcatg taataattgg ggaagatcat 2880
agtcgtgttg cagattttaa agcttttaga agaactttta agagaaagtt taaaatccta 2940
aaagaaagtt gggtaactga ttcaatagac aagtgtgaat tacaagaaga aaaccagtat 3000
ttgatttaaa gctaggtttc ctagtgagga aagcctctga tctggcagac tcattgcagc 3060
aggtggtaat gataaaatac taaactacat tttatttttg tatcttaaaa atctatgcct 3120
aaaaagtatc attacatata ggaaaacaat aattttaact tttaaggttg aaaagacaat 3180
agcccaaagc caagaaagaa aaattatctt gaatgtagta ttcaatgatt ttttatgatc 3240
aaggtgaaat aaacagtcta aagaagaggt gtttttataa tatccatata gaaatctaga 3300
atttttactt agatactaat aaaatacatt tagaaacttt taaagtcatg aaaaagcatt 3360
aaccttctaa acagtatatt ctaaaaagtc aaaacgttaa caatagtttt tatctaataa 3420
aagcactgca agaaaatagg gtagaattgt tacagctgga cttgtaaaaa tatgtctttt 3480
tactcagggt ttaaaatgtc ccatttaaat atgaaatgta aacaaatttg tttttttaagg 3540 ttaaggccaa atgtaacaat aaaaccctgt cgatggtttt agctaaatta gaggaagttg 3600
tatgagactt aatgatctaa aaacttaaaa ttgaattggt ttgattaaaa ataaagcttg 3660
caattttaaa agtagctcac atttaatttc ttgtgtgaaa tagaacatgc tttaaaggaa 3720
gtatttttat gtgaatttgc attccagtat aaatagtatt cacaaaaaag attttcctag 3780
attttatcta ttgaataggt gtcaatatgg catgcatatt gtaactttca ttagaaataa 3840
gttgctttga cttttaaaaa tgacatagtt agattattta aagtcaatgt atatagtata 3900
tattatgtat ggatttatat accaaatttt ggaatacagc ctatctcatg accatattga 3960
aatgtacgga atttgatcca tgcgatacta tgtgtgcatt atttgaaagt tattggaaat 4020
tttattcaaa ccgtggaaca aatgtatgtg attttgttat acttcttaat ttaaataaaa 4080
tatttaatgc actattaaaa aaaaaaaaaa aaaaa 4115

<210> SEQ ID NO 43
<211> LENGTH: 3994
<212> TYPE: DNA
<213> ORGANISM: Homo sapiens

<400> SEQUENCE: 43
cttctggcgc cagcttccgg cttagcggct gagcttcagg cttgacgtca ggaaaccatc 60
aagatctcat tttacagctg ggattctctg gttcacagag gtaacggagc ttgcccgagg 120
ccagttaaac gagaagattc atcaccgctt tgatggctgc ctcacaaact tcacaaactg 180
ttgcatctca cgttcctttt gcagatttgt gttcaacttt agaacgaata cagaaaagta 240
aaggacgtgc agaaaaaatc agacacttca gggaattttt agattcttgg agaaaatttc 300
atgatgctct tcataagaac cacaaagatg tcacagactc tttttatcca gcaatgagac 360
taattcttcc tcagctagaa agagagagaa tggcctatgg aattaaagaa actatgcttg 420
ctaagcttta tattgagttg cttaatttac ctagagatgg aaaagatgcc ctcaaacttt 480
taaactacag aacacccact ggaactcatg gagatgctgg agactttgca atgattgcat 540
attttgtgtt gaagccaaga tgtttacaga aaggaagttt aaccatacag caagtaaacg 600
accttttaga ctcaattgcc agcaataatt ctgctaaaag aaaagaccta ataaaaaaga 660
gccttcttca acttataact cagagttcag cacttgagca aaagtggctt atacggatga 720
tcataaagga tttaaagctt ggtgttagtc agcaaactat cttttctgtt tttcataatg 780

-continued

```
atgctgctga gttgcataat gtcactacag atctggaaaa agtctgtagg caactgcatg    840
atccttctgt aggactcagt gatatttcta tcactttatt ttctgcattt aaaccaatgc    900
tagctgctat tgcagatatt gagcacattg agaaggatat gaaacatcag agtttctaca    960
tagaaaccaa gctagatggt gaacgtatgc aaatgcacaa agatggagat gtatataaat   1020
acttctctcg aaatggatat aactacactg atcagtttgg tgcttctcct actgaaggtt   1080
ctcttacccc attcattcat aatgcattca aagcagatat acaaatctgt attcttgatg   1140
gtgagatgat ggcctataat cctaatacac aaactttcat gcaaaaggga actaagtttg   1200
atattaaaag aatggtagag gattctgatc tgcaaacttg ttattgtgtt tttgatgtat   1260
tgatggttaa taataaaaag ctagggcatg agactctgag aaagaggtat gagattctta   1320
gtagtatttt tacaccaatt ccaggtagaa tagaaatagt gcagaaaaca caagctcata   1380
ctaagaatga agtaattgat gcattgaatg aagcaataga taaaagagaa gagggaatta   1440
tggtaaaaca acctctatcc atctacaagc cagacaaaag aggtgaaggg tggttaaaaa   1500
ttaaaccaga gtatgtcagt ggactaatgg atgaattgga cattttaatt gttggaggat   1560
attggggtaa aggatcacgg ggtggaatga tgtctcattt tctgtgtgca gtagcagaga   1620
agccccctcc tggtgagaag ccatctgtgt ttcatactct ctctcgtgtt gggtctggct   1680
gcaccatgaa agaactgtat gatctgggtt tgaaattggc caagtattgg aagccttttc   1740
atagaaaagc tccaccaagc agcattttat gtggaacaga gaagccagaa gtatacattg   1800
aaccttgtaa ttctgtcatt gttcagatta aagcagcaga gatcgtaccc agtgatatgt   1860
ataaaactgg ctgcaccttg cgttttccac gaattgaaaa gataagagat gacaaggagt   1920
ggcatgagtg catgaccctg gacgacctag aacaacttag gggaaggca tctggtaagc    1980
tcgcatctaa acacctttat ataggtggtg atgatgaacc acaagaaaaa aagcggaaag   2040
ctgccccaaa gatgaagaaa gttattggaa ttattgagca cttaaaagca cctaacctta   2100
ctaacgttaa caaaatttct aatatatttg aagatgtaga gttttgtgtt atgagtggaa   2160
cagatagcca gccaaagcct gacctggaga acagaattgc agaatttggt ggttatatag   2220
tacaaaatcc aggcccagac acgtactgtg taattgcagg gtctgagaac atcagagtga   2280
aaaacataat tttgtcaaat aaacatgatg ttgtcaagcc tgcatggctt ttagaatgtt   2340
ttaagaccaa aagctttgta ccatggcagc ctcgctttat gattcatatg tgcccatcaa   2400
ccaaagaaca ttttgcccgt gaatatgatt gctatggtga tagttatttc attgatacag   2460
acttgaacca actgaaggaa gtattctcag gaattaaaaa ttctaacgag cagactcctg   2520
aagaaatggc ttctctgatt gctgatttag aatatcggta ttcctgggat tgctctcctc   2580
tcagtatgtt tcgacgccac accgtttatt tggactcgta tgctgttatt aatgacctga   2640
gtaccaaaaa tgaggggaca aggttagcta ttaaagcctt ggagcttcgg tttcatggag   2700
caaaagtagt ttcttgttta gctgagggag tgtctcatgt aataattggg gaagatcata   2760
gtcgtgttgc agattttaaa gcttttagaa gaacttttaa gagaaagttt aaaatcctaa   2820
aagaaagttg ggtaactgat tcaatagaca agtgtgaatt acaagaagaa aaccagtatt   2880
tgatttaaag ctaggtttcc tagtgaggaa agcctctgat ctggcagact cattgcagca   2940
ggtggtaatg ataaaatact aaactacatt ttatttttgt atcttaaaaa tctatgccta   3000
aaaagtatca ttacatatag gaaaacaata attttaactt ttaaggttga aaagacaata   3060
gcccaaagcc aagaaagaaa aattatcttg aatgtagtat tcaatgattt tttatgatca   3120
aggtgaaata aacagtctaa agaagaggtg tttttataat atccatatag aaatctagaa   3180
```

tttttactta gatactaata aaatacattt agaaactttt aaagtcatga aaaagcatta 3240
accttctaaa cagtatattc taaaaagtca aaacgttaac aatagttttt atctaataaa 3300
agcactgcaa gaaaataggg tagaattgtt acagctggac ttgtaaaaat atgtcttttt 3360
actcagggtt taaaatgtcc catttaaata tgaaatgtaa acaaatttgt tttttaaggt 3420
taaggccaaa tgtaacaata aaaccctgtc gatggtttta gctaaattag aggaagttgt 3480
atgagactta atgatctaaa aacttaaaat tgaattggtt tgattaaaaa taaagcttgc 3540
aattttaaaa gtagctcaca tttaatttct tgtgtgaaat agaacatgct ttaaaggaag 3600
tatttttatg tgaatttgca ttccagtata aatagtattc acaaaaaaga ttttcctaga 3660
ttttatctat tgaataggtg tcaatatggc atgcatattg taactttcat tagaaataag 3720
ttgctttgac ttttaaaaat gacatagtta gattatttaa agtcaatgta tatagtatat 3780
attatgtatg gatttatata ccaaattttg gaatacagcc tatctcatga ccatattgaa 3840
atgtacggaa tttgatccat gcgatactat gtgtgcatta tttgaaagtt attggaaatt 3900
ttattcaaac cgtggaacaa atgtatgtga ttttgttata cttcttaatt taaataaaat 3960
atttaatgca ctattaaaaa aaaaaaaaaa aaaa 3994

<210> SEQ ID NO 44
<211> LENGTH: 3914
<212> TYPE: DNA
<213> ORGANISM: Homo sapiens

<400> SEQUENCE: 44
cttctggcgc cagcttccgg cttagcggct gagcttcagg cttgacgtca ggaaaccatc 60
aagatctcat tttacagctg ggattctctg gttcacagag gtaacggagc ttgcccgagg 120
ccagatttgt gttcaacttt agaacgaata cagaaaagta aaggacgtgc agaaaaaatc 180
agacacttca gggaattttt agattcttgg agaaaatttc atgatgctct tcataagaac 240
cacaaagatg tcacagactc tttttatcca gcaatgagac taattcttcc tcagctagaa 300
agagagagaa tggcctatgg aattaaagaa actatgcttg ctaagcttta tattgagttg 360
cttaatttac ctagagatgg aaaagatgcc ctcaaacttt taaactacag aacacccact 420
ggaactcatg gagatgctgg agactttgca atgattgcat attttgtgtt gaagccaaga 480
tgtttacaga aaggaagttt aaccatacag caagtaaacg accttttaga ctcaattgcc 540
agcaataatt ctgctaaaag aaaagaccta ataaaaaaga gccttcttca acttataact 600
cagagttcag cacttgagca aaagtggctt atacggatga tcataaagga tttaaagctt 660
ggtgttagtc agcaaactat cttttctgtt tttcataatg atgctgctga gttgcataat 720
gtcactacag atctggaaaa agtctgtagg caactgcatg atccttctgt aggactcagt 780
gatatttcta tcactttatt ttctgcattt aaaccaatgc tagctgctat tgcagatatt 840
gagcacattg agaaggatat gaaacatcag agtttctaca tagaaaccaa gctagatggt 900
gaacgtatgc aaatgcacaa agatggagat gtatataaat acttctctcg aaatggatat 960
aactacactg atcagtttgg tgcttctcct actgaaggtt ctcttacccc attcattcat 1020
aatgcattca aagcagatat acaaatctgt attcttgatg gtgagatgat ggcctataat 1080
cctaatacac aaactttcat gcaaaaggga actaagtttg atattaaaag aatggtagag 1140
gattctgatc tgcaaacttg ttattgtgtt tttgatgtat tgatggttaa taataaaaag 1200
ctagggcatg agactctgag aaagaggtat gagattctta gtagtatttt tacaccaatt 1260

-continued

```
ccaggtagaa tagaaatagt gcagaaaaca caagctcata ctaagaatga agtaattgat   1320
gcattgaatg aagcaataga taaaagagaa gagggaatta tggtaaaaca acctctatcc   1380
atctacaagc cagacaaaag aggtgaaggg tggttaaaaa ttaaaccaga gtatgtcagt   1440
ggactaatgg atgaattgga cattttaatt gttggaggat attggggtaa aggatcacgg   1500
ggtggaatga tgtctcattt tctgtgtgca gtagcagaga agccccctcc tggtgagaag   1560
ccatctgtgt ttcatactct ctctcgtgtt gggtctggct gcaccatgaa agaactgtat   1620
gatctgggtt tgaaattggc caagtattgg aagccttttc atagaaaagc tccaccaagc   1680
agcattttat gtggaacaga gaagccagaa gtatacattg aaccttgtaa ttctgtcatt   1740
gttcagatta aagcagcaga gatcgtaccc agtgatatgt ataaaactgg ctgcaccttg   1800
cgttttccac gaattgaaaa gataagagat gacaaggagt ggcatgagtg catgaccctg   1860
gacgacctag aacaacttag gggaaggca tctggtaagc tcgcatctaa acacctttat   1920
ataggtggtg atgatgaacc acaagaaaaa aagcggaaag ctgccccaaa gatgaagaaa   1980
gttattggaa ttattgagca cttaaaagca cctaacctta ctaacgttaa caaaatttct   2040
aatatatttg aagatgtaga gttttgtgtt atgagtggaa cagatagcca gccaaagcct   2100
gacctggaga acagaattgc agaatttggt ggttatatag tacaaaatcc aggcccagac   2160
acgtactgtg taattgcagg gtctgagaac atcagagtga aaaacataat tttgtcaaat   2220
aaacatgatg ttgtcaagcc tgcatggctt ttagaatgtt ttaagaccaa aagctttgta   2280
ccatggcagc ctcgctttat gattcatatg tgcccatcaa ccaaagaaca ttttgcccgt   2340
gaatatgatt gctatggtga tagttatttc attgatacag acttgaacca actgaaggaa   2400
gtattctcag gaattaaaaa ttctaacgag cagactcctg aagaaatggc ttctctgatt   2460
gctgatttag aatatcggta ttcctgggat tgctctcctc tcagtatgtt tcgacgccac   2520
accgtttatt tggactcgta tgctgttatt aatgacctga gtaccaaaaa tgaggggaca   2580
aggttagcta ttaaagcctt ggagcttcgg tttcatggag caaaagtagt ttcttgttta   2640
gctgagggag tgtctcatgt aataattggg gaagatcata gtcgtgttgc agattttaaa   2700
gcttttagaa gaacttttaa gagaaagttt aaaatcctaa aagaaagttg ggtaactgat   2760
tcaatagaca agtgtgaatt acaagaagaa aaccagtatt tgatttaaag ctaggtttcc   2820
tagtgaggaa agcctctgat ctggcagact cattgcagca ggtggtaatg ataaaatact   2880
aaactacatt ttatttttgt atcttaaaaa tctatgccta aaaagtatca ttacatatag   2940
gaaaacaata attttaactt ttaaggttga aaagacaata gcccaaagcc aagaaagaaa   3000
aattatcttg aatgtagtat tcaatgattt tttatgatca aggtgaaata aacagtctaa   3060
agaagaggtg tttttataat atccatatag aaatctagaa tttttactta gatactaata   3120
aaatacattt agaaactttt aaagtcatga aaaagcatta accttctaaa cagtatattc   3180
taaaaagtca aaacgttaac aatagttttt atctaataaa agcactgcaa gaaaataggg   3240
tagaattgtt acagctggac ttgtaaaaat atgtcttttt actcagggtt taaaatgtcc   3300
catttaaata tgaaatgtaa acaaatttgt tttttaaggt taaggccaaa tgtaacaata   3360
aaaccctgtc gatggtttta gctaaattag aggaagttgt atgagactta atgatctaaa   3420
aacttaaaat tgaattggtt tgattaaaaa taaagcttgc aattttaaaa gtagctcaca   3480
tttaatttct tgtgtgaaat agaacatgct ttaaaggaag tatttttatg tgaatttgca   3540
ttccagtata aatagtattc acaaaaaaga ttttcctaga ttttatctat tgaataggtg   3600
tcaatatggc atgcatattg taactttcat tagaaataag ttgctttgac ttttaaaaat   3660
```

gacatagtta gattatttaa agtcaatgta tatagtatat attatgtatg gatttatata 3720
ccaaattttg gaatacagcc tatctcatga ccatattgaa atgtacggaa tttgatccat 3780
gcgatactat gtgtgcatta tttgaaagtt attggaaatt ttattcaaac cgtggaacaa 3840
atgtatgtga ttttgttata cttcttaatt taaataaaat atttaatgca ctattaaaaa 3900
aaaaaaaaaa aaaa 3914

<210> SEQ ID NO 45
<211> LENGTH: 4479
<212> TYPE: DNA
<213> ORGANISM: Homo sapiens

<400> SEQUENCE: 45
gccagtgagc ccccgcgacg gtggcccgga cggaaaagat acctcggcgg cgtgggcccg 60
gctccctgct ccaggaccta gggatcttgg ccttccaccc tcctccgagc accaggactc 120
cctccagttc cgtacccgag gcctccgtgg tgaagaggtg ccggacccga tgagctcggg 180
agtccaccat cgctctgcaa gccgcagaga gcatctgctg ccgaggccaa taggagccgt 240
gtgtactcaa gaccctaacc aggatcctgc aggtcccgcc tccgcagccc cacggggctg 300
ccggcccccc cacctcccat cgcgagcctg gctgcgccgg cgtgcttgag cccggtgact 360
gcaaggcccc gggtctcccc tgcgcctgcg cggcgagcag ctggcggaac cggcatcttc 420
tggcgccagc ttccggctta gcggctgagc ttcaggcttg acgtcagacc caagccccag 480
gtcgtgggac gatttctccc gtttttgact ccctggaact gtattgcctg ctttacctgc 540
gtacatgttg attctttctc atggcaaccc cgcaggaaac catcaagatc tcattttaca 600
gctgggattc tctggttcac agagttaaac gagaagattc atcaccgctt tgatggctgc 660
ctcacaaact tcacaaactg ttgcatctca cgttcctttt gcagatttgt gttcaacttt 720
agaacgaata cagaaaagta aaggacgtgc agaaaaaatc agacacttca gggaattttt 780
agattcttgg agaaaatttc atgatgctct tcataagaac cacaaagatg tcacagactc 840
tttttatcca gcaatgagac taattcttcc tcagctagaa agagagagaa tggcctatgg 900
aattaaagaa actatgcttg ctaagcttta tattgagttg cttaatttac ctagagatgg 960
aaaagatgcc ctcaaacttt taaactacag aacacccact ggaactcatg gagatgctgg 1020
agactttgca atgattgcat attttgtgtt gaagccaaga tgtttacaga aaggaagttt 1080
aaccatacag caagtaaacg accttttaga ctcaattgcc agcaataatt ctgctaaaag 1140
aaaagaccta ataaaaaaga gccttcttca acttataact cagagttcag cacttgagca 1200
aaagtggctt atacggatga tcataaagga tttaaagctt ggtgttagtc agcaaactat 1260
cttttctgtt tttcataatg atgctgctga gttgcataat gtcactacag atctggaaaa 1320
agtctgtagg caactgcatg atccttctgt aggactcagt gatatttcta tcactttatt 1380
ttctgcattt aaaccaatgc tagctgctat tgcagatatt gagcacattg agaaggatat 1440
gaaacatcag agtttctaca tagaaaccaa gctagatggt gaacgtatgc aaatgcacaa 1500
agatggagat gtatataaat acttctctcg aaatggatat aactacactg atcagtttgg 1560
tgcttctcct actgaaggtt ctcttacccc attcattcat aatgcattca aagcagatat 1620
acaaatctgt attcttgatg gtgagatgat ggcctataat cctaatacac aaactttcat 1680
gcaaaaggga actaagtttg atattaaaag aatggtagag gattctgatc tgcaaacttg 1740
ttattgtgtt tttgatgtat tgatggttaa taataaaaag ctagggcatg agactctgag 1800

-continued

```
aaagaggtat gagattctta gtagtatttt tacaccaatt ccaggtagaa tagaaatagt   1860
gcagaaaaca caagctcata ctaagaatga agtaattgat gcattgaatg aagcaataga   1920
taaaagagaa gagggaatta tggtaaaaca acctctatcc atctacaagc cagacaaaag   1980
aggtgaaggg tggttaaaaa ttaaaccaga gtatgtcagt ggactaatgg atgaattgga   2040
cattttaatt gttggaggat attggggtaa aggatcacgg ggtggaatga tgtctcattt   2100
tctgtgtgca gtagcagaga agccccctcc tggtgagaag ccatctgtgt ttcatactct   2160
ctctcgtgtt gggtctggct gcaccatgaa agaactgtat gatctgggtt tgaaattggc   2220
caagtattgg aagccttttc atagaaaagc tccaccaagc agcattttat gtggaacaga   2280
gaagccagaa gtatacattg aaccttgtaa ttctgtcatt gttcagatta aagcagcaga   2340
gatcgtaccc agtgatatgt ataaaactgg ctgcaccttg cgttttccac gaattgaaaa   2400
gataagagat gacaaggagt ggcatgagtg catgaccctg gacgacctag aacaacttag   2460
ggggaaggca tctggtaagc tcgcatctaa acacctttat ataggtggtg atgatgaacc   2520
acaagaaaaa aagcggaaag ctgccccaaa gatgaagaaa gttattggaa ttattgagca   2580
cttaaaagca cctaacctta ctaacgttaa caaaatttct aatatatttg aagatgtaga   2640
gttttgtgtt atgagtggaa cagatagcca gccaaagcct gacctggaga acagaattgc   2700
agaatttggt ggttatatag tacaaaatcc aggcccagac acgtactgtg taattgcagg   2760
gtctgagaac atcagagtga aaaacataat tttgtcaaat aaacatgatg ttgtcaagcc   2820
tgcatggctt ttagaatgtt ttaagaccaa aagctttgta ccatggcagc ctcgctttat   2880
gattcatatg tgcccatcaa ccaaagaaca ttttgcccgt gaatatgatt gctatggtga   2940
tagttatttc attgatacag acttgaacca actgaaggaa gtattctcag gaattaaaaa   3000
ttctaacgag cagactcctg aagaaatggc ttctctgatt gctgatttag aatatcggta   3060
ttcctgggat tgctctcctc tcagtatgtt tcgacgccac accgtttatt tggactcgta   3120
tgctgttatt aatgacctga gtaccaaaaa tgaggggaca aggttagcta ttaaagcctt   3180
ggagcttcgg tttcatggag caaaagtagt ttcttgttta gctgagggag tgtctcatgt   3240
aataattggg gaagatcata gtcgtgttgc agattttaaa gcttttagaa gaacttttaa   3300
gagaaagttt aaaatcctaa aagaaagttg ggtaactgat tcaatagaca agtgtgaatt   3360
acaagaagaa aaccagtatt tgatttaaag ctaggtttcc tagtgaggaa agcctctgat   3420
ctggcagact cattgcagca ggtggtaatg ataaaatact aaactacatt ttatttttgt   3480
atcttaaaaa tctatgccta aaaagtatca ttacatatag gaaaacaata attttaactt   3540
ttaaggttga aaagacaata gcccaaagcc aagaaagaaa aattatcttg aatgtagtat   3600
tcaatgattt tttatgatca aggtgaaata aacagtctaa agaagaggtg tttttataat   3660
atccatatag aaatctagaa tttttactta gatactaata aaatacattt agaaactttt   3720
aaagtcatga aaaagcatta accttctaaa cagtatattc taaaaagtca aaacgttaac   3780
aatagttttt atctaataaa agcactgcaa gaaaataggg tagaattgtt acagctggac   3840
ttgtaaaaat atgtcttttt actcagggtt taaaatgtcc catttaaata tgaaatgtaa   3900
acaaatttgt tttttaaggt taaggccaaa tgtaacaata aaaccctgtc gatggtttta   3960
gctaaattag aggaagttgt atgagactta atgatctaaa aacttaaaat tgaattggtt   4020
tgattaaaaa taaagcttgc aattttaaaa gtagctcaca tttaatttct tgtgtgaaat   4080
agaacatgct ttaaaggaag tatttttatg tgaatttgca ttccagtata aatagtattc   4140
acaaaaaaga ttttcctaga ttttatctat tgaataggtg tcaatatggc atgcatattg   4200
```

```
taactttcat tagaaataag ttgctttgac ttttaaaaat gacatagtta gattatttaa   4260

agtcaatgta tatagtatat attatgtatg gatttatata ccaaattttg gaatacagcc   4320

tatctcatga ccatattgaa atgtacggaa tttgatccat gcgatactat gtgtgcatta   4380

tttgaaagtt attggaaatt ttattcaaac cgtggaacaa atgtatgtga ttttgttata   4440

cttcttaatt taaataaaat atttaatgca ctattaaaa                          4479


<210> SEQ ID NO 46
<211> LENGTH: 4503
<212> TYPE: DNA
<213> ORGANISM: Homo sapiens

<400> SEQUENCE: 46

gccagtgagc ccccgcgacg gtggcccgga cggaaaagat acctcggcgg cgtgggcccg     60

gctccctgct ccaggaccta gggatcttgg ccttccaccc tcctccgagc accaggactc    120

cctccagttc cgtacccgag gcctccgtgg tgaagaggtg ccggacccga tgagctcggg    180

agtccaccat cgctctgcaa gccgcagaga gcatctgctg ccgaggccaa taggagccgt    240

gtgtactcaa gaccctaacc aggatcctgc aggtcccgcc tccgcagccc cacggggctg    300

ccggcccccc cacctcccat cgcgagcctg gctgcgccgg cgtgcttgag cccggtgact    360

gcaaggcccc gggtctcccc tgcgcctgcg cggcgagcag ctggcggaac cggcatcttc    420

tggcgccagc ttccggctta gcggctgagc ttcaggcttg acgtcagacc caagccccag    480

gtcgtgggac gatttctccc gtttttgact ccctggaact gtattgcctg ctttacctgc    540

gtacatgttg attctttctc atggcaaccc cgcaggaaac catcaagatc tcattttaca    600

gctgggattc tctggttcac agaggtaacg gagcttgccc gaggccagtt aaacgagaag    660

attcatcacc gctttgatgg ctgcctcaca aacttcacaa actgttgcat ctcacgttcc    720

ttttgcagat ttgtgttcaa ctttagaacg aatacagaaa agtaaaggac gtgcagaaaa    780

aatcagacac ttcagggaat ttttagattc ttggagaaaa tttcatgatg ctcttcataa    840

gaaccacaaa gatgtcacag actcttttta tccagcaatg agactaattc ttcctcagct    900

agaaagagag agaatggcct atggaattaa agaaactatg cttgctaagc tttatattga    960

gttgcttaat ttacctagag atggaaaaga tgccctcaaa cttttaaact acagaacacc   1020

cactggaact catggagatg ctggagactt tgcaatgatt gcatattttg tgttgaagcc   1080

aagatgttta cagaaaggaa gtttaaccat acagcaagta aacgaccttt tagactcaat   1140

tgccagcaat aattctgcta aaagaaaaga cctaataaaa aagagccttc ttcaacttat   1200

aactcagagt tcagcacttg agcaaaagtg gcttatacgg atgatcataa aggatttaaa   1260

gcttggtgtt agtcagcaaa ctatcttttc tgtttttcat aatgatgctg ctgagttgca   1320

taatgtcact acagatctgg aaaaagtctg taggcaactg catgatcctt ctgtaggact   1380

cagtgatatt tctatcactt tattttctgc atttaaacca atgctagctg ctattgcaga   1440

tattgagcac attgagaagg atatgaaaca tcagagtttc tacatagaaa ccaagctaga   1500

tggtgaacgt atgcaaatgc acaaagatgg agatgtatat aaatacttct ctcgaaatgg   1560

atataactac actgatcagt ttggtgcttc tcctactgaa ggttctctta ccccattcat   1620

tcataatgca ttcaaagcag atatacaaat ctgtattctt gatggtgaga tgatggccta   1680

taatcctaat acacaaactt tcatgcaaaa gggaactaag tttgatatta aaagaatggt   1740

agaggattct gatctgcaaa cttgttattg tgtttttgat gtattgatgg ttaataataa   1800
```

-continued aaagctaggg catgagactc tgagaaagag gtatgagatt cttagtagta tttttacacc 1860
aattccaggt agaatagaaa tagtgcagaa aacacaagct catactaaga atgaagtaat 1920
tgatgcattg aatgaagcaa tagataaaag agaagaggga attatggtaa aacaacctct 1980
atccatctac aagccagaca aaagaggtga agggtggtta aaaattaaac cagagtatgt 2040
cagtggacta atggatgaat tggacatttt aattgttgga ggatattggg gtaaaggatc 2100
acggggtgga atgatgtctc attttctgtg tgcagtagca gagaagcccc ctcctggtga 2160
gaagccatct gtgtttcata ctctctctcg tgttgggtct ggctgcacca tgaaagaact 2220
gtatgatctg ggtttgaaat tggccaagta ttggaagcct tttcatagaa aagctccacc 2280
aagcagcatt ttatgtggaa cagagaagcc agaagtatac attgaacctt gtaattctgt 2340
cattgttcag attaaagcag cagagatcgt acccagtgat atgtataaaa ctggctgcac 2400
cttgcgtttt ccacgaattg aaaagataag agatgacaag gagtggcatg agtgcatgac 2460
cctggacgac ctagaacaac ttagggggaa ggcatctggt aagctcgcat ctaaacacct 2520
ttatataggt ggtgatgatg aaccacaaga aaaaaagcgg aaagctgccc caaagatgaa 2580
gaaagttatt ggaattattg agcacttaaa agcacctaac cttactaacg ttaacaaaat 2640
ttctaatata tttgaagatg tagagttttg tgttatgagt ggaacagata gccagccaaa 2700
gcctgacctg gagaacagaa ttgcagaatt tggtggttat atagtacaaa atccaggccc 2760
agacacgtac tgtgtaattg cagggtctga gaacatcaga gtgaaaaaca taattttgtc 2820
aaataaacat gatgttgtca agcctgcatg gcttttagaa tgttttaaga ccaaaagctt 2880
tgtaccatgg cagcctcgct ttatgattca tatgtgccca tcaaccaaag aacattttgc 2940
ccgtgaatat gattgctatg gtgatagtta tttcattgat acagacttga accaactgaa 3000
ggaagtattc tcaggaatta aaaattctaa cgagcagact cctgaagaaa tggcttctct 3060
gattgctgat ttagaatatc ggtattcctg ggattgctct cctctcagta tgtttcgacg 3120
ccacaccgtt tatttggact cgtatgctgt tattaatgac ctgagtacca aaaatgaggg 3180
gacaaggtta gctattaaag ccttggagct tcggtttcat ggagcaaaag tagtttcttg 3240
tttagctgag ggagtgtctc atgtaataat tggggaagat catagtcgtg ttgcagattt 3300
taaagctttt agaagaactt ttaagagaaa gtttaaaatc ctaaaagaaa gttgggtaac 3360
tgattcaata gacaagtgtg aattacaaga agaaaaccag tatttgattt aaagctaggt 3420
ttcctagtga ggaaagcctc tgatctggca gactcattgc agcaggtggt aatgataaaa 3480
tactaaacta cattttattt ttgtatctta aaaatctatg cctaaaaagt atcattacat 3540
ataggaaaac aataatttta acttttaagg ttgaaaagac aatagcccaa agccaagaaa 3600
gaaaaattat cttgaatgta gtattcaatg attttttatg atcaaggtga aataaacagt 3660
ctaaagaaga ggtgttttta taatatccat atagaaatct agaattttta cttagatact 3720
aataaaatac atttagaaac ttttaaagtc atgaaaaagc attaaccttc taaacagtat 3780
attctaaaaa gtcaaaacgt taacaatagt ttttatctaa taaaagcact gcaagaaaat 3840
agggtagaat tgttacagct ggacttgtaa aaatatgtct ttttactcag ggtttaaaat 3900
gtcccattta aatatgaaat gtaaacaaat ttgtttttta aggttaaggc caaatgtaac 3960
aataaaaccc tgtcgatggt tttagctaaa ttagaggaag ttgtatgaga cttaatgatc 4020
taaaaactta aaattgaatt ggtttgatta aaaataaagc ttgcaatttt aaaagtagct 4080
cacatttaat ttcttgtgtg aaatagaaca tgctttaaag gaagtatttt tatgtgaatt 4140
tgcattccag tataaatagt attcacaaaa aagattttcc tagattttat ctattgaata 4200

```
ggtgtcaata tggcatgcat attgtaactt tcattagaaa taagttgctt tgacttttaa   4260

aaatgacata gttagattat ttaaagtcaa tgtatatagt atatattatg tatggattta   4320

tataccaaat tttggaatac agcctatctc atgaccatat tgaaatgtac ggaatttgat   4380

ccatgcgata ctatgtgtgc attatttgaa agttattgga aattttattc aaaccgtgga   4440

acaaatgtat gtgattttgt tatacttctt aatttaaata aaatatttaa tgcactatta   4500

aaa                                                                 4503


<210> SEQ ID NO 47
<211> LENGTH: 4395
<212> TYPE: DNA
<213> ORGANISM: Homo sapiens

<400> SEQUENCE: 47

gccagtgagc ccccgcgacg gtggcccgga cggaaaagat acctcggcgg cgtgggcccg     60

gctccctgct ccaggaccta gggatcttgg ccttccaccc tcctccgagc accaggactc    120

cctccagttc cgtacccgag gcctccgtgg tgaagaggtg ccggacccga tgagctcggg    180

agtccaccat cgctctgcaa gccgcagaga gcatctgctg ccgaggccaa taggagccgt    240

gtgtactcaa gaccctaacc aggatcctgc aggtcccgcc tccgcagccc cacggggctg    300

ccggcccccc cacctcccat cgcgagcctg gctgcgccgg cgtgcttgag cccggtgact    360

gcaaggcccc gggtctcccc tgcgcctgcg cggcgagcag ctggcggaac cggcatcttc    420

tggcgccagc ttccggctta gcggctgagc ttcaggcttg acgtcaggaa accatcaaga    480

tctcatttta cagctgggat tctctggttc acagaggtaa cggagcttgc ccgaggccag    540

ttaaacgaga agattcatca ccgctttgat ggctgcctca caaacttcac aaactgttgc    600

atctcacgtt ccttttgcag atttgtgttc aactttagaa cgaatacaga aaagtaaagg    660

acgtgcagaa aaaatcagac acttcaggga atttttagat tcttggagaa aatttcatga    720

tgctcttcat aagaaccaca aagatgtcac agactctttt tatccagcaa tgagactaat    780

tcttcctcag ctagaaagag agagaatggc ctatggaatt aaagaaacta tgcttgctaa    840

gctttatatt gagttgctta atttacctag agatggaaaa gatgccctca aacttttaaa    900

ctacagaaca cccactggaa ctcatggaga tgctggagac tttgcaatga ttgcatattt    960

tgtgttgaag ccaagatgtt tacagaaagg aagtttaacc atacagcaag taaacgacct   1020

tttagactca attgccagca ataattctgc taaaagaaaa gacctaataa aaaagagcct   1080

tcttcaactt ataactcaga gttcagcact tgagcaaaag tggcttatac ggatgatcat   1140

aaaggattta aagcttggtg ttagtcagca aactatcttt tctgtttttc ataatgatgc   1200

tgctgagttg cataatgtca ctacagatct ggaaaaagtc tgtaggcaac tgcatgatcc   1260

ttctgtagga ctcagtgata tttctatcac tttattttct gcatttaaac caatgctagc   1320

tgctattgca gatattgagc acattgagaa ggatatgaaa catcagagtt tctacataga   1380

aaccaagcta gatggtgaac gtatgcaaat gcacaaagat ggagatgtat ataaatactt   1440

ctctcgaaat ggatataact acactgatca gtttggtgct tctcctactg aaggttctct   1500

taccccattc attcataatg cattcaaagc agatatacaa atctgtattc ttgatggtga   1560

gatgatggcc tataatccta atacacaaac tttcatgcaa aagggaacta agtttgatat   1620

taaaagaatg gtagaggatt ctgatctgca aacttgttat tgtgtttttg atgtattgat   1680

ggttaataat aaaaagctag ggcatgagac tctgagaaag aggtatgaga ttcttagtag   1740
```

```
tatttttaca ccaattccag gtagaataga aatagtgcag aaaacacaag ctcatactaa   1800
gaatgaagta attgatgcat tgaatgaagc aatagataaa agagaagagg gaattatggt   1860
aaaacaacct ctatccatct acaagccaga caaaagaggt gaagggtggt taaaaattaa   1920
accagagtat gtcagtggac taatggatga attggacatt ttaattgttg gaggatattg   1980
gggtaaagga tcacggggtg gaatgatgtc tcattttctg tgtgcagtag cagagaagcc   2040
ccctcctggt gagaagccat ctgtgtttca tactctctct cgtgttgggt ctggctgcac   2100
catgaaagaa ctgtatgatc tgggtttgaa attggccaag tattggaagc cttttcatag   2160
aaaagctcca ccaagcagca ttttatgtgg aacagagaag ccagaagtat acattgaacc   2220
ttgtaattct gtcattgttc agattaaagc agcagagatc gtacccagtg atatgtataa   2280
aactggctgc accttgcgtt ttccacgaat tgaaaagata agagatgaca aggagtggca   2340
tgagtgcatg accctggacg acctagaaca acttaggggg aaggcatctg gtaagctcgc   2400
atctaaacac ctttatatag gtggtgatga tgaaccacaa gaaaaaaagc ggaaagctgc   2460
cccaaagatg aagaaagtta ttggaattat tgagcactta aaagcaccta accttactaa   2520
cgttaacaaa atttctaata tatttgaaga tgtagagttt tgtgttatga gtggaacaga   2580
tagccagcca aagcctgacc tggagaacag aattgcagaa tttggtggtt atatagtaca   2640
aaatccaggc ccagacacgt actgtgtaat tgcagggtct gagaacatca gagtgaaaaa   2700
cataattttg tcaaataaac atgatgttgt caagcctgca tggcttttag aatgttttaa   2760
gaccaaaagc tttgtaccat ggcagcctcg ctttatgatt catatgtgcc catcaaccaa   2820
agaacatttt gcccgtgaat atgattgcta tggtgatagt tatttcattg atacagactt   2880
gaaccaactg aaggaagtat tctcaggaat taaaaattct aacgagcaga ctcctgaaga   2940
aatggcttct ctgattgctg atttagaata tcggtattcc tgggattgct ctcctctcag   3000
tatgtttcga cgccacaccg tttatttgga ctcgtatgct gttattaatg acctgagtac   3060
caaaaatgag ggacaaggt tagctattaa agccttggag cttcggtttc atggagcaaa   3120
agtagtttct tgtttagctg agggagtgtc tcatgtaata attggggaag atcatagtcg   3180
tgttgcagat tttaaagctt ttagaagaac ttttaagaga aagtttaaaa tcctaaaaga   3240
aagttgggta actgattcaa tagacaagtg tgaattacaa gaagaaaacc agtatttgat   3300
ttaaagctag gtttcctagt gaggaaagcc tctgatctgg cagactcatt gcagcaggtg   3360
gtaatgataa aatactaaac tacattttat ttttgtatct taaaaatcta tgcctaaaaa   3420
gtatcattac atataggaaa acaataattt taacttttaa ggttgaaaag acaatagccc   3480
aaagccaaga aagaaaaatt atcttgaatg tagtattcaa tgattttta tgatcaaggt   3540
gaaataaaca gtctaaagaa gaggtgtttt tataatatcc atatagaaat ctagaatttt   3600
tacttagata ctaataaaat acatttagaa acttttaaag tcatgaaaaa gcattaacct   3660
tctaaacagt atattctaaa aagtcaaaac gttaacaata gtttttatct aataaaagca   3720
ctgcaagaaa atagggtaga attgttacag ctggacttgt aaaaatatgt ctttttactc   3780
agggtttaaa atgtcccatt taaatatgaa atgtaaacaa atttgttttt taaggttaag   3840
gccaaatgta acaataaaac cctgtcgatg gttttagcta aattagagga agttgtatga   3900
gacttaatga tctaaaaact taaaattgaa ttggtttgat taaaaataaa gcttgcaatt   3960
ttaaaagtag ctcacattta atttcttgtg tgaaatagaa catgctttaa aggaagtatt   4020
tttatgtgaa tttgcattcc agtataaata gtattcacaa aaaagatttt cctagatttt   4080
atctattgaa taggtgtcaa tatggcatgc atattgtaac tttcattaga aataagttgc   4140
```

tttgactttt aaaaatgaca tagttagatt atttaaagtc aatgtatata gtatatatta 4200
tgtatggatt tatataccaa attttggaat acagcctatc tcatgaccat attgaaatgt 4260
acggaatttg atccatgcga tactatgtgt gcattatttg aaagttattg gaaattttat 4320
tcaaaccgtg gaacaaatgt atgtgatttt gttatacttc ttaatttaaa taaaatattt 4380
aatgcactat taaaa 4395

<210> SEQ ID NO 48
<211> LENGTH: 4114
<212> TYPE: DNA
<213> ORGANISM: Homo sapiens

<400> SEQUENCE: 48
gacggtgtgg ggggagtcaa gtggaaggtg tggtccagca ggcggcgaga agtctgtggg 60
gcaacagacc gggggaagac ccaagcccca ggtcgtggga cgatttctcc cgtttttgac 120
tccctggaac tgtattgcct gctttacctg cgtacatgtt gattctttct catggcaacc 180
ccgcaggaaa ccatcaagat ctcattttac agctgggatt ctctggttca cagaggtaac 240
ggagcttgcc cgaggccagt taaacgagaa gattcatcac cgctttgatg gctgcctcac 300
aaacttcaca aactgttgca tctcacgttc cttttgcaga tttgtgttca actttagaac 360
gaatacagaa aagtaaagga cgtgcagaaa aaatcagaca cttcagggaa tttttagatt 420
cttggagaaa atttcatgat gctcttcata agaaccacaa agatgtcaca gactcttttt 480
atccagcaat gagactaatt cttcctcagc tagaaagaga gagaatggcc tatggaatta 540
aagaaactat gcttgctaag ctttatattg agttgcttaa tttacctaga gatggaaaag 600
atgccctcaa acttttaaac tacagaacac ccactggaac tcatggagat gctggagact 660
ttgcaatgat tgcatatttt gtgttgaagc caagatgttt acagaaagga agtttaacca 720
tacagcaagt aaacgacctt ttagactcaa ttgccagcaa taattctgct aaaagaaaag 780
acctaataaa aaagagcctt cttcaactta taactcagag ttcagcactt gagcaaaagt 840
ggcttatacg gatgatcata aaggatttaa agcttggtgt tagtcagcaa actatctttt 900
ctgtttttca taatgatgct gctgagttgc ataatgtcac tacagatctg gaaaaagtct 960
gtaggcaact gcatgatcct tctgtaggac tcagtgatat ttctatcact ttattttctg 1020
catttaaacc aatgctagct gctattgcag atattgagca cattgagaag gatatgaaac 1080
atcagagttt ctacatagaa accaagctag atggtgaacg tatgcaaatg cacaaagatg 1140
gagatgtata taaatacttc tctcgaaatg gatataacta cactgatcag tttggtgctt 1200
ctcctactga aggttctctt accccattca ttcataatgc attcaaagca gatatacaaa 1260
tctgtattct tgatggtgag atgatggcct ataatcctaa tacacaaact ttcatgcaaa 1320
agggaactaa gtttgatatt aaaagaatgg tagaggattc tgatctgcaa acttgttatt 1380
gtgtttttga tgtattgatg gttaataata aaaagctagg gcatgagact ctgagaaaga 1440
ggtatgagat tcttagtagt atttttacac caattccagg tagaatagaa atagtgcaga 1500
aaacacaagc tcatactaag aatgaagtaa ttgatgcatt gaatgaagca atagataaaa 1560
gagaagaggg aattatggta aaacaacctc tatccatcta caagccagac aaaagaggtg 1620
aagggtggtt aaaaattaaa ccagagtatg tcagtggact aatggatgaa ttggacattt 1680
taattgttgg aggatattgg ggtaaaggat cacggggtgg aatgatgtct cattttctgt 1740
gtgcagtagc agagaagccc cctcctggtg agaagccatc tgtgtttcat actctctctc 1800

-continued

```
gtgttgggtc tggctgcacc atgaaagaac tgtatgatct gggtttgaaa ttggccaagt   1860
attggaagcc ttttcataga aaagctccac caagcagcat tttatgtgga acagagaagc   1920
cagaagtata cattgaacct tgtaattctg tcattgttca gattaaagca gcagagatcg   1980
tacccagtga tatgtataaa actggctgca ccttgcgttt tccacgaatt gaaaagataa   2040
gagatgacaa ggagtggcat gagtgcatga ccctggacga cctagaacaa cttaggggga   2100
aggcatctgg taagctcgca tctaaacacc tttatatagg tggtgatgat gaaccacaag   2160
aaaaaaagcg gaaagctgcc ccaaagatga agaaagttat tggaattatt gagcacttaa   2220
aagcacctaa ccttactaac gttaacaaaa tttctaatat atttgaagat gtagagtttt   2280
gtgttatgag tggaacagat agccagccaa agcctgacct ggagaacaga attgcagaat   2340
ttggtggtta tatagtacaa aatccaggcc cagacacgta ctgtgtaatt gcagggtctg   2400
agaacatcag agtgaaaaac ataattttgt caaataaaca tgatgttgtc aagcctgcat   2460
ggcttttaga atgttttaag accaaaagct ttgtaccatg gcagcctcgc tttatgattc   2520
atatgtgccc atcaaccaaa gaacattttg cccgtgaata tgattgctat ggtgatagtt   2580
atttcattga tacagacttg aaccaactga aggaagtatt ctcaggaatt aaaaattcta   2640
acgagcagac tcctgaagaa atggcttctc tgattgctga tttagaatat cggtattcct   2700
gggattgctc tcctctcagt atgtttcgac gccacaccgt ttatttggac tcgtatgctg   2760
ttattaatga cctgagtacc aaaaatgagg ggacaaggtt agctattaaa gccttggagc   2820
ttcggtttca tggagcaaaa gtagtttctt gtttagctga gggagtgtct catgtaataa   2880
ttggggaaga tcatagtcgt gttgcagatt ttaaagcttt tagaagaact tttaagagaa   2940
agtttaaaat cctaaaagaa agttgggtaa ctgattcaat agacaagtgt gaattacaag   3000
aagaaaacca gtatttgatt taaagctagg tttcctagtg aggaaagcct ctgatctggc   3060
agactcattg cagcaggtgg taatgataaa atactaaact acattttatt tttgtatctt   3120
aaaaatctat gcctaaaaag tatcattaca tataggaaaa caataatttt aacttttaag   3180
gttgaaaaga caatagccca aagccaagaa agaaaaatta tcttgaatgt agtattcaat   3240
gattttttat gatcaaggtg aaataaacag tctaaagaag aggtgttttt ataatatcca   3300
tatagaaatc tagaattttt acttagatac taataaaata catttagaaa cttttaaagt   3360
catgaaaaag cattaacctt ctaaacagta tattctaaaa agtcaaaacg ttaacaatag   3420
tttttatcta ataaaagcac tgcaagaaaa tagggtagaa ttgttacagc tggacttgta   3480
aaaatatgtc tttttactca gggtttaaaa tgtcccattt aaatatgaaa tgtaaacaaa   3540
tttgtttttt aaggttaagg ccaaatgtaa caataaaacc ctgtcgatgg ttttagctaa   3600
attagaggaa gttgtatgag acttaatgat ctaaaaactt aaaattgaat tggtttgatt   3660
aaaaataaag cttgcaattt taaaagtagc tcacatttaa tttcttgtgt gaaatagaac   3720
atgctttaaa ggaagtattt ttatgtgaat ttgcattcca gtataaatag tattcacaaa   3780
aaagatttc ctagatttta tctattgaat aggtgtcaat atggcatgca tattgtaact   3840
ttcattagaa ataagttgct ttgactttta aaaatgacat agttagatta tttaaagtca   3900
atgtatatag tatatattat gtatggattt atataccaaa ttttggaata cagcctatct   3960
catgaccata ttgaaatgta cggaatttga tccatgcgat actatgtgtg cattatttga   4020
aagttattgg aaattttatt caaaccgtgg aacaaatgta tgtgattttg ttatacttct   4080
taatttaaat aaaatattta atgcactatt aaaa                               4114
```

-continued

<210> SEQ ID NO 49
<211> LENGTH: 4006
<212> TYPE: DNA
<213> ORGANISM: Homo sapiens

<400> SEQUENCE: 49
gacggtgtgg ggggagtcaa gtggaaggtg tggtccagca ggcggcgaga agtctgtggg 60
gcaacagacc gggggaagga aaccatcaag atctcatttt acagctggga ttctctggtt 120
cacagaggta acggagcttg cccgaggcca gttaaacgag aagattcatc accgctttga 180
tggctgcctc acaaacttca caaactgttg catctcacgt tccttttgca gatttgtgtt 240
caactttaga acgaatacag aaaagtaaag gacgtgcaga aaaaatcaga cacttcaggg 300
aatttttaga ttcttggaga aaatttcatg atgctcttca taagaaccac aaagatgtca 360
cagactcttt ttatccagca atgagactaa ttcttcctca gctagaaaga gagagaatgg 420
cctatggaat taaagaaact atgcttgcta agctttatat tgagttgctt aatttaccta 480
gagatggaaa agatgccctc aaacttttaa actacagaac acccactgga actcatggag 540
atgctggaga ctttgcaatg attgcatatt ttgtgttgaa gccaagatgt ttacagaaag 600
gaagtttaac catacagcaa gtaaacgacc ttttagactc aattgccagc aataattctg 660
ctaaaagaaa agacctaata aaaaagagcc ttcttcaact tataactcag agttcagcac 720
ttgagcaaaa gtggcttata cggatgatca taaaggattt aaagcttggt gttagtcagc 780
aaactatctt ttctgttttt cataatgatg ctgctgagtt gcataatgtc actacagatc 840
tggaaaaagt ctgtaggcaa ctgcatgatc cttctgtagg actcagtgat atttctatca 900
ctttattttc tgcatttaaa ccaatgctag ctgctattgc agatattgag cacattgaga 960
aggatatgaa acatcagagt ttctacatag aaaccaagct agatggtgaa cgtatgcaaa 1020
tgcacaaaga tggagatgta tataaatact tctctcgaaa tggatataac tacactgatc 1080
agtttggtgc ttctcctact gaaggttctc ttaccccatt cattcataat gcattcaaag 1140
cagatataca aatctgtatt cttgatggtg agatgatggc ctataatcct aatacacaaa 1200
ctttcatgca aaagggaact aagtttgata ttaaaagaat ggtagaggat tctgatctgc 1260
aaacttgtta ttgtgttttt gatgtattga tggttaataa taaaaagcta gggcatgaga 1320
ctctgagaaa gaggtatgag attcttagta gtatttttac accaattcca ggtagaatag 1380
aaatagtgca gaaaacacaa gctcatacta agaatgaagt aattgatgca ttgaatgaag 1440
caatagataa aagagaagag ggaattatgg taaaacaacc tctatccatc tacaagccag 1500
acaaaagagg tgaagggtgg ttaaaaatta aaccagagta tgtcagtgga ctaatggatg 1560
aattggacat tttaattgtt ggaggatatt ggggtaaagg atcacggggt ggaatgatgt 1620
ctcattttct gtgtgcagta gcagagaagc cccctcctgg tgagaagcca tctgtgtttc 1680
atactctctc tcgtgttggg tctggctgca ccatgaaaga actgtatgat ctgggtttga 1740
aattggccaa gtattggaag ccttttcata gaaaagctcc accaagcagc attttatgtg 1800
gaacagagaa gccagaagta tacattgaac cttgtaattc tgtcattgtt cagattaaag 1860
cagcagagat cgtacccagt gatatgtata aaactggctg caccttgcgt tttccacgaa 1920
ttgaaaagat aagagatgac aaggagtggc atgagtgcat gaccctggac gacctagaac 1980
aacttagggg gaaggcatct ggtaagctcg catctaaaca cctttatata ggtggtgatg 2040
atgaaccaca agaaaaaaag cggaaagctg ccccaaagat gaagaaagtt attggaatta 2100
ttgagcactt aaaagcacct aaccttacta acgttaacaa aatttctaat atatttgaag 2160

```
atgtagagtt ttgtgttatg agtggaacag atagccagcc aaagcctgac ctggagaaca   2220

gaattgcaga atttggtggt tatatagtac aaaatccagg cccagacacg tactgtgtaa   2280

ttgcagggtc tgagaacatc agagtgaaaa acataatttt gtcaaataaa catgatgttg   2340

tcaagcctgc atggctttta gaatgtttta agaccaaaag ctttgtacca tggcagcctc   2400

gctttatgat tcatatgtgc ccatcaacca aagaacattt tgcccgtgaa tatgattgct   2460

atggtgatag ttatttcatt gatacagact tgaaccaact gaaggaagta ttctcaggaa   2520

ttaaaaattc taacgagcag actcctgaag aaatggcttc tctgattgct gatttagaat   2580

atcggtattc ctgggattgc tctcctctca gtatgtttcg acgccacacc gtttatttgg   2640

actcgtatgc tgttattaat gacctgagta ccaaaaatga ggggacaagg ttagctatta   2700

aagccttgga gcttcggttt catggagcaa aagtagtttc ttgtttagct gagggagtgt   2760

ctcatgtaat aattggggaa gatcatagtc gtgttgcaga ttttaaagct tttagaagaa   2820

cttttaagag aaagtttaaa atcctaaaag aaagttgggt aactgattca atagacaagt   2880

gtgaattaca agaagaaaac cagtatttga tttaaagcta ggtttcctag tgaggaaagc   2940

ctctgatctg gcagactcat tgcagcaggt ggtaatgata aaatactaaa ctacatttta   3000

tttttgtatc ttaaaaatct atgcctaaaa agtatcatta catataggaa aacaataatt   3060

ttaactttta aggttgaaaa gacaatagcc caaagccaag aaagaaaaat tatcttgaat   3120

gtagtattca atgatttttt atgatcaagg tgaaataaac agtctaaaga agaggtgttt   3180

ttataatatc catatagaaa tctagaattt ttacttagat actaataaaa tacatttaga   3240

aacttttaaa gtcatgaaaa agcattaacc ttctaaacag tatattctaa aaagtcaaaa   3300

cgttaacaat agtttttatc taataaaagc actgcaagaa aatagggtag aattgttaca   3360

gctggacttg taaaaatatg tctttttact cagggtttaa aatgtcccat ttaaatatga   3420

aatgtaaaca aatttgtttt ttaaggttaa ggccaaatgt aacaataaaa ccctgtcgat   3480

ggttttagct aaattagagg aagttgtatg agacttaatg atctaaaaac ttaaaattga   3540

attggtttga ttaaaaataa agcttgcaat tttaaaagta gctcacattt aatttcttgt   3600

gtgaaataga acatgcttta aaggaagtat ttttatgtga atttgcattc cagtataaat   3660

agtattcaca aaaaagattt tcctagattt tatctattga ataggtgtca atatggcatg   3720

catattgtaa ctttcattag aaataagttg ctttgacttt taaaaatgac atagttagat   3780

tatttaaagt caatgtatat agtatatatt atgtatggat ttatatacca aattttggaa   3840

tacagcctat ctcatgacca tattgaaatg tacggaattt gatccatgcg atactatgtg   3900

tgcattattt gaaagttatt ggaaatttta ttcaaaccgt ggaacaaatg tatgtgattt   3960

tgttatactt cttaatttaa ataaaatatt taatgcacta ttaaaa                4006
```

<210> SEQ ID NO 50
<211> LENGTH: 3955
<212> TYPE: DNA
<213> ORGANISM: Homo sapiens

<400> SEQUENCE: 50

```
ggggtatctg tgggacgtca ggttggggaa accatcaaga tctcatttta cagctgggat     60

tctctggttc acagaggtaa cggagcttgc ccgaggccag ttaaacgaga agattcatca    120

ccgctttgat ggctgcctca caaacttcac aaactgttgc atctcacgtt ccttttgcag    180

atttgtgttc aactttagaa cgaatacaga aaagtaaagg acgtgcagaa aaaatcagac    240

acttcaggga atttttagat tcttggagaa aatttcatga tgctcttcat aagaaccaca    300
```

-continued

```
aagatgtcac agactctttt tatccagcaa tgagactaat tcttcctcag ctagaaagag    360
agagaatggc ctatggaatt aaagaaacta tgcttgctaa gctttatatt gagttgctta    420
atttacctag agatggaaaa gatgccctca aacttttaaa ctacagaaca cccactggaa    480
ctcatggaga tgctggagac tttgcaatga ttgcatattt tgtgttgaag ccaagatgtt    540
tacagaaagg aagtttaacc atacagcaag taaacgacct tttagactca attgccagca    600
ataattctgc taaaagaaaa gacctaataa aaaagagcct tcttcaactt ataactcaga    660
gttcagcact tgagcaaaag tggcttatac ggatgatcat aaaggattta aagcttggtg    720
ttagtcagca aactatcttt tctgtttttc ataatgatgc tgctgagttg cataatgtca    780
ctacagatct ggaaaaagtc tgtaggcaac tgcatgatcc ttctgtagga ctcagtgata    840
tttctatcac tttattttct gcatttaaac caatgctagc tgctattgca gatattgagc    900
acattgagaa ggatatgaaa catcagagtt tctacataga aaccaagcta gatggtgaac    960
gtatgcaaat gcacaaagat ggagatgtat ataaatactt ctctcgaaat ggatataact   1020
acactgatca gtttggtgct tctcctactg aaggttctct taccccattc attcataatg   1080
cattcaaagc agatatacaa atctgtattc ttgatggtga gatgatggcc tataatccta   1140
atacacaaac tttcatgcaa aagggaacta agtttgatat taaaagaatg gtagaggatt   1200
ctgatctgca aacttgttat tgtgtttttg atgtattgat ggttaataat aaaaagctag   1260
ggcatgagac tctgagaaag aggtatgaga ttcttagtag tatttttaca ccaattccag   1320
gtagaataga aatagtgcag aaaacacaag ctcatactaa gaatgaagta attgatgcat   1380
tgaatgaagc aatagataaa agagaagagg gaattatggt aaaacaacct ctatccatct   1440
acaagccaga caaaagaggt gaagggtggt taaaaattaa accagagtat gtcagtggac   1500
taatggatga attggacatt ttaattgttg gaggatattg ggtaaagga tcacggggtg   1560
gaatgatgtc tcattttctg tgtgcagtag cagagaagcc ccctcctggt gagaagccat   1620
ctgtgtttca tactctctct cgtgttgggt ctggctgcac catgaaagaa ctgtatgatc   1680
tgggtttgaa attggccaag tattggaagc cttttcatag aaaagctcca ccaagcagca   1740
ttttatgtgg aacagagaag ccagaagtat acattgaacc ttgtaattct gtcattgttc   1800
agattaaagc agcagagatc gtacccagtg atatgtataa aactggctgc accttgcgtt   1860
ttccacgaat tgaaaagata agagatgaca aggagtggca tgagtgcatg accctggacg   1920
acctagaaca acttaggggg aaggcatctg gtaagctcgc atctaaacac ctttatatag   1980
gtggtgatga tgaaccacaa gaaaaaaagc ggaaagctgc cccaaagatg aagaaagtta   2040
ttggaattat tgagcactta aaagcaccta accttactaa cgttaacaaa atttctaata   2100
tatttgaaga tgtagagttt tgtgttatga gtggaacaga tagccagcca aagcctgacc   2160
tggagaacag aattgcagaa tttggtggtt atatagtaca aaatccaggc ccagacacgt   2220
actgtgtaat tgcagggtct gagaacatca gagtgaaaaa cataattttg tcaaataaac   2280
atgatgttgt caagcctgca tggcttttag aatgttttaa gaccaaaagc tttgtaccat   2340
ggcagcctcg ctttatgatt catatgtgcc catcaaccaa agaacatttt gcccgtgaat   2400
atgattgcta tggtgatagt tatttcattg atacagactt gaaccaactg aaggaagtat   2460
tctcaggaat taaaaattct aacgagcaga ctcctgaaga aatggcttct ctgattgctg   2520
atttagaata tcggtattcc tgggattgct ctcctctcag tatgtttcga cgccacaccg   2580
tttatttgga ctcgtatgct gttattaatg acctgagtac caaaaatgag gggacaaggt   2640
```

```
tagctattaa agccttggag cttcggtttc atggagcaaa agtagtttct tgtttagctg   2700
agggagtgtc tcatgtaata attggggaag atcatagtcg tgttgcagat tttaaagctt   2760
ttagaagaac ttttaagaga aagtttaaaa tcctaaaaga aagttgggta actgattcaa   2820
tagacaagtg tgaattacaa gaagaaaacc agtatttgat ttaaagctag gtttcctagt   2880
gaggaaagcc tctgatctgg cagactcatt gcagcaggtg gtaatgataa aatactaaac   2940
tacattttat ttttgtatct taaaaatcta tgcctaaaaa gtatcattac atataggaaa   3000
acaataattt taacttttaa ggttgaaaag acaatagccc aaagccaaga aagaaaaatt   3060
atcttgaatg tagtattcaa tgattttta tgatcaaggt gaaataaaca gtctaaagaa   3120
gaggtgtttt tataatatcc atatagaaat ctagaatttt tacttagata ctaataaaat   3180
acatttagaa acttttaaag tcatgaaaaa gcattaacct tctaaacagt atattctaaa   3240
aagtcaaaac gttaacaata gtttttatct aataaaagca ctgcaagaaa atagggtaga   3300
attgttacag ctggacttgt aaaaatatgt ctttttactc agggtttaaa atgtcccatt   3360
taaatatgaa atgtaaacaa atttgttttt taaggttaag gccaaatgta acaataaaac   3420
cctgtcgatg gttttagcta aattagagga agttgtatga gacttaatga tctaaaaact   3480
taaaattgaa ttggtttgat taaaaataaa gcttgcaatt ttaaaagtag ctcacattta   3540
atttcttgtg tgaaatagaa catgctttaa aggaagtatt tttatgtgaa tttgcattcc   3600
agtataaata gtattcacaa aaaagatttt cctagatttt atctattgaa taggtgtcaa   3660
tatggcatgc atattgtaac tttcattaga aataagttgc tttgactttt aaaaatgaca   3720
tagttagatt atttaaagtc aatgtatata gtatatatta tgtatggatt tatataccaa   3780
attttggaat acagcctatc tcatgaccat attgaaatgt acggaatttg atccatgcga   3840
tactatgtgt gcattatttg aaagttattg gaaattttat tcaaaccgtg gaacaaatgt   3900
atgtgatttt gttatacttc ttaatttaaa taaaatattt aatgcactat taaaa        3955
```

<210> SEQ ID NO 51
<211> LENGTH: 4034
<212> TYPE: DNA
<213> ORGANISM: Homo sapiens

<400> SEQUENCE: 51

```
gacggtgtgg ggggagtcaa gtggaaggtg tggtccagca ggcggcgaga agtctgtggg     60
gcaacagacc gggggaagac ccaagcccca ggtcgtggga cgatttctcc cgtttttgac    120
tccctggaac tgtattgcct gctttacctg cgtacatgtt gattctttct catggcaacc    180
ccgcaggaaa ccatcaagat ctcattttac agctgggatt ctctggttca cagaggtaac    240
ggagcttgcc cgaggccaga tttgtgttca actttagaac gaatacagaa aagtaaagga    300
cgtgcagaaa aaatcagaca cttcagggaa tttttagatt cttggagaaa atttcatgat    360
gctcttcata agaaccacaa agatgtcaca gactcttttt atccagcaat gagactaatt    420
cttcctcagc tagaaagaga gagaatggcc tatggaatta aagaaactat gcttgctaag    480
ctttatattg agttgcttaa tttacctaga gatggaaaag atgccctcaa acttttaaac    540
tacagaacac ccactggaac tcatggagat gctggagact ttgcaatgat tgcatatttt    600
gtgttgaagc caagatgttt acagaaagga agtttaacca tacagcaagt aaacgacctt    660
ttagactcaa ttgccagcaa taattctgct aaaagaaaag acctaataaa aaagagcctt    720
cttcaactta taactcagag ttcagcactt gagcaaaagt ggcttatacg gatgatcata    780
aaggatttaa agcttggtgt tagtcagcaa actatctttt ctgtttttca taatgatgct    840
```

```
gctgagttgc ataatgtcac tacagatctg gaaaaagtct gtaggcaact gcatgatcct    900
tctgtaggac tcagtgatat ttctatcact ttattttctg catttaaacc aatgctagct    960
gctattgcag atattgagca cattgagaag gatatgaaac atcagagttt ctacatagaa   1020
accaagctag atggtgaacg tatgcaaatg cacaaagatg gagatgtata taaatacttc   1080
tctcgaaatg gatataacta cactgatcag tttggtgctt ctcctactga aggttctctt   1140
accccattca ttcataatgc attcaaagca gatatacaaa tctgtattct tgatggtgag   1200
atgatggcct ataatcctaa tacacaaact ttcatgcaaa agggaactaa gtttgatatt   1260
aaaagaatgg tagaggattc tgatctgcaa acttgttatt gtgtttttga tgtattgatg   1320
gttaataata aaaagctagg gcatgagact ctgagaaaga ggtatgagat tcttagtagt   1380
atttttacac caattccagg tagaatagaa atagtgcaga aacacaagc tcatactaag   1440
aatgaagtaa ttgatgcatt gaatgaagca atagataaaa gagaagaggg aattatggta   1500
aaacaacctc tatccatcta caagccagac aaaagaggtg aagggtggtt aaaaattaaa   1560
ccagagtatg tcagtggact aatggatgaa ttggacattt taattgttgg aggatattgg   1620
ggtaaaggat cacggggtgg aatgatgtct catttttctgt gtgcagtagc agagaagccc   1680
cctcctggtg agaagccatc tgtgtttcat actctctctc gtgttgggtc tggctgcacc   1740
atgaaagaac tgtatgatct gggtttgaaa ttggccaagt attggaagcc ttttcataga   1800
aaagctccac caagcagcat tttatgtgga acagagaagc cagaagtata cattgaacct   1860
tgtaattctg tcattgttca gattaaagca gcagagatcg tacccagtga tatgtataaa   1920
actggctgca ccttgcgttt tccacgaatt gaaaagataa gagatgacaa ggagtggcat   1980
gagtgcatga ccctggacga cctagaacaa cttagggggga aggcatctgg taagctcgca   2040
tctaaacacc tttatatagg tggtgatgat gaaccacaag aaaaaaagcg gaaagctgcc   2100
ccaaagatga agaaagttat tggaattatt gagcacttaa aagcacctaa ccttactaac   2160
gttaacaaaa tttctaatat atttgaagat gtagagtttt gtgttatgag tggaacagat   2220
agccagccaa agcctgacct ggagaacaga attgcagaat ttggtggtta tatagtacaa   2280
aatccaggcc cagacacgta ctgtgtaatt gcagggtctg agaacatcag agtgaaaaac   2340
ataattttgt caaataaaca tgatgttgtc aagcctgcat ggcttttaga atgttttaag   2400
accaaaagct ttgtaccatg gcagcctcgc tttatgattc atatgtgccc atcaaccaaa   2460
gaacattttg cccgtgaata tgattgctat ggtgatagtt atttcattga tacagacttg   2520
aaccaactga aggaagtatt ctcaggaatt aaaaattcta acgagcagac tcctgaagaa   2580
atggcttctc tgattgctga tttagaatat cggtattcct gggattgctc tcctctcagt   2640
atgtttcgac gccacaccgt ttatttggac tcgtatgctg ttattaatga cctgagtacc   2700
aaaaatgagg ggacaaggtt agctattaaa gccttggagc ttcggtttca tggagcaaaa   2760
gtagtttctt gtttagctga gggagtgtct catgtaataa ttggggaaga tcatagtcgt   2820
gttgcagatt ttaaagcttt tagaagaact tttaagagaa agtttaaaat cctaaaagaa   2880
agttgggtaa ctgattcaat agacaagtgt gaattacaag aagaaaacca gtatttgatt   2940
taaagctagg tttcctagtg aggaaagcct ctgatctggc agactcattg cagcaggtgg   3000
taatgataaa atactaaact acattttatt tttgtatctt aaaaatctat gcctaaaaag   3060
tatcattaca tataggaaaa caataatttt aacttttaag gttgaaaaga caatagccca   3120
aagccaagaa agaaaaatta tcttgaatgt agtattcaat gattttttat gatcaaggtg   3180
```

```
aaataaacag tctaaagaag aggtgttttt ataatatcca tatagaaatc tagaattttt   3240
acttagatac taataaaata catttagaaa cttttaaagt catgaaaaag cattaacctt   3300
ctaaacagta tattctaaaa agtcaaaacg ttaacaatag tttttatcta ataaaagcac   3360
tgcaagaaaa tagggtagaa ttgttacagc tggacttgta aaaatatgtc tttttactca   3420
gggtttaaaa tgtcccattt aaatatgaaa tgtaaacaaa tttgtttttt aaggttaagg   3480
ccaaatgtaa caataaaacc ctgtcgatgg ttttagctaa attagaggaa gttgtatgag   3540
acttaatgat ctaaaaactt aaaattgaat tggtttgatt aaaaataaag cttgcaattt   3600
taaaagtagc tcacatttaa tttcttgtgt gaaatagaac atgctttaaa ggaagtattt   3660
ttatgtgaat ttgcattcca gtataaatag tattcacaaa aaagattttc ctagatttta   3720
tctattgaat aggtgtcaat atggcatgca tattgtaact ttcattagaa ataagttgct   3780
ttgactttta aaaatgacat agttagatta tttaaagtca atgtatatag tatatattat   3840
gtatggattt atataccaaa ttttggaata cagcctatct catgaccata ttgaaatgta   3900
cggaatttga tccatgcgat actatgtgtg cattatttga aagttattgg aaattttatt   3960
caaaccgtgg aacaaatgta tgtgattttg ttatacttct taatttaaat aaaatattta   4020
atgcactatt aaaa                                                     4034
```

<210> SEQ ID NO 52
<211> LENGTH: 4081
<212> TYPE: DNA
<213> ORGANISM: Mus musculus

<400> SEQUENCE: 52

```
ggggcaacct ctgctaagca agtggtgtgg cgggttggag gaggcaggga ggttcttggt     60
cctagggagg ctgcgtcctt cccgtgcttt gtcccagcgt caccacccgc cttccacggt    120
gcagccggct cgctggggac tgatttcagg tggcagccac cgggtgaaga aatcgtgtcc    180
tgatgcttag ttgtatccgc acgctgccct gccccctgcc acctagctac ctgggacctg    240
cgcgctcccc cagctccttc attcggcagg gttggggttc acgggctgct tagttcaaac    300
cggaggattt gttgtcgctt ctatggcttc ctcacaaact tcacaaactg ttgcagctca    360
tgtccccttt gcagacttat gttccacact agaacggata cagaaaggta aagaccgtgc    420
agaaaaaatc aggcacttca aggagttttt ggattcgtgg agaaaatttc atgatgccct    480
tcataagaac agaaaggacg ttacagactc tttttaccct gcaatgagac tcattctccc    540
ccagttagaa agagagagga tggcttatgg aatcaaagaa accatgctcg ctaagctcta    600
catcgaattg ctgaacttac cacgagaagg caaggatgcc cagaagctcc tcaattaccg    660
aacccccagt ggagctcgca cggatgctgg ggactttgcc atgattgcat actttgtttt    720
gaagccaagg tgcttacaga aaggaagctt aaccatacag caggtaaatg aactcttaga    780
cttagttgcc agcaataact ctggcaaaaa aaaagaccta gtgaaaaaga gccttcttca    840
gttaataacc cagagttcag cactggagca aaaatggctg attcgcatga ttatcaaaga    900
cttaaagctt ggcatcagtc agcaaacaat attttccatt ttccacaatg atgcagttga    960
gttgcacaac gtcaccacag atctggaaaa ggtctgcagg cagctgcatg acccctctgt   1020
agggcttagt gacatctcta tcactctgtt ttctgccttt aagccaatgc tagctgctgt   1080
agcagacgtg gagcgtgtgg agaaggacat gaagcagcag agtttctaca tcgaaactaa   1140
gcttgatggt gagcgcatgc agatgcacaa agatggcgcg ctgtaccggt acttctccag   1200
aaacggttac aactataccg accagtttgg tgaatctcca caggaaggct ctctcacccc   1260
```

-continued

```
atttattcac aatgcgttcg ggacagatgt gcaagcgtgc atccttgacg gtgagatgat   1320
ggcctacaac ccaacaacac agactttcat gcagaagggg gtcaagtttg atatcaaaag   1380
gatggtggaa gattctggcc tacagacttg ttactctgtt tttgacgtac tgatggttaa   1440
taagaagaag ctagggcgcg agactcttag gaagaggtat gagatcctta gtagcacttt   1500
cacacccata caaggccgca tagaaatagt gcagaaaact caagctcata caaagaagga   1560
agtagtggat gcattaaatg atgccataga caagagagaa gaggggatca tggttaaaca   1620
ccctctgtcc atttacaagc cagacaaaag aggtgaaggg tggctaaaga ttaaaccaga   1680
gtacgtcagt ggactaatgg atgaattaga cgtcctaatt gtgggggggct actggggtaa   1740
aggttcacga ggtggcatga tgtctcactt tttgtgtgca gtggcagaga caccacctcc   1800
tggtgacagg ccatctgtat tccacactct gtgccgtgtt gggtctggtt acaccatgaa   1860
agaactctat gacctgggct tgaaattggc aaaatactgg aagccttttc ataagaaatc   1920
tccaccaagt agcattctgt gtggtacaga gaagccggaa gtgtacatag agcctcagaa   1980
ctctgtcatt gttcagatca aggcagctga gatcgtcccc agtgacatgt acaagactgg   2040
ctccaccctg cgcttcccac gcatcgaaaa gatcagagat gacaaagagt ggcacgaatg   2100
tatgacactg ggtgacttgg agcagctgag ggggaaagca tctgggaagc ttgccacgaa   2160
acaccttcat gtaggtgatg atgatgaacc tagagaaaaa aggcggaagc ccatctccaa   2220
gacgaagaaa gccattagaa tcattgaaca cttaaaagca cccaaccttt ctaacgtaaa   2280
caaagtttcc aatgtatttg aagatgttga gttttgtgtt atgagtggat tagatggtta   2340
tccaaaggct gacctagaga acagaattgc agaattcggt ggttatatag tacagaatcc   2400
aggcccggat acatactgtg ttattgcagg ttctgagaac gttagagtga aaaacattat   2460
ttcttcagat aaaaatgatg ttgtcaagcc cgagtggctt ttagagtgtt ttaagacaaa   2520
aacatgcgtg ccgtggcaac ctcgctttat gattcacatg tgcccgtcga caaagcagca   2580
ttttgcccgt gagtatgact gctatggtga tagctatttt gttgacacag atttggatca   2640
attgaaagaa gtgtttctag gaattaaacc cagtgagcag cagactcctg aagaaatggc   2700
ccctgtgatt gctgacttag aatgtcgtta ttcctgggac cactctcctc tcagtatgtt   2760
tcgacattac accatttatt tggacttgta tgctgttatt aatgacttga gttccagaat   2820
tgaagccacg agattaggta ttacagccct tgagctgcgg tttcatggag caaaggtggt   2880
ttcctgctta tctgaagggg tatctcatgt tatcattggg gaggatcaga gacgagttac   2940
tgactttaaa atattcagaa gaatgcttaa gaaaaagttt aaaatcctgc aagaaagttg   3000
ggtgtccgat tcagtagaca agggcgaact gcaggaggaa aaccagtatt tgctttagag   3060
cttgctggcc cggcgggggg gggggaagaa gaagtgttat tgtcagacaa cagcagacag   3120
tgatgatgaa atagccagta gccttcattg tatctcctaa tacttcaaaa ggattattga   3180
tcagaacgca ataattttca agtagaaagg aaactaaatg ggccaaagca aaaaaaaaaa   3240
aaccaaaaaa aataaaacaa acaaaaaaaa ccaacccttt tcctaacacg acttataact   3300
atggcttcaa gaagtgcttg tatggtatcc atactgaagc tatccatact taaagtgtat   3360
ttgaaacctt ttagaaacat caccactatt gactttctag acaaaatttt ccagacttaa   3420
aaattaaagt ttttagctaa taaaagtatt ataccaataa aaaaaatcag aattgttaaa   3480
gttagactta taaaaataag catttttatt tgcgggctca aatacccccct ataagcatga   3540
catattaagc ataaagagtt tttaaggttc atcaaatgtt ttttgataat gtgggggaag   3600
```

```
ttgagagaga atcatctaaa caccaaacac ttaagatatt aattttattg aaaaaaatcc   3660

ttgcaacttt taagttagct gagacttaat tttggtgaag actttaatgt ttcatggaga   3720

aatgtttgag tgaatttaca ctccagcatt gacagtgttt acagaacttg tctcctatcg   3780

atgatccatt gcgtagctgt ccatacagtg aacactttca ttagagactg ggtgctctgg   3840

cttttagaga tggcttttat gactatgttg aagtcacagt catgtgtgga ttgtatctgt   3900

tgagaattgt acttccatgg cagtactgaa atggagggat gtgggacctt aagtgatggg   3960

tataaactat ttaagtaatt agacttgttg aagtgattga agaaacattt gtgattattg   4020

taacttaaat aaaattatta aatattgtaa cttaaataaa attattgaat atttaatgta   4080

a                                                                   4081
```

<210> SEQ ID NO 53
<211> LENGTH: 911
<212> TYPE: PRT
<213> ORGANISM: Mus musculus

<400> SEQUENCE: 53

```
Met Ala Ser Ser Gln Thr Ser Gln Thr Val Ala Ala His Val Pro Phe
1               5                   10                  15

Ala Asp Leu Cys Ser Thr Leu Glu Arg Ile Gln Lys Gly Lys Asp Arg
            20                  25                  30

Ala Glu Lys Ile Arg His Phe Lys Glu Phe Leu Asp Ser Trp Arg Lys
        35                  40                  45

Phe His Asp Ala Leu His Lys Asn Arg Lys Asp Val Thr Asp Ser Phe
    50                  55                  60

Tyr Pro Ala Met Arg Leu Ile Leu Pro Gln Leu Glu Arg Glu Arg Met
65                  70                  75                  80

Ala Tyr Gly Ile Lys Glu Thr Met Leu Ala Lys Leu Tyr Ile Glu Leu
                85                  90                  95

Leu Asn Leu Pro Arg Glu Gly Lys Asp Ala Gln Lys Leu Leu Asn Tyr
            100                 105                 110

Arg Thr Pro Ser Gly Ala Arg Thr Asp Ala Gly Asp Phe Ala Met Ile
        115                 120                 125

Ala Tyr Phe Val Leu Lys Pro Arg Cys Leu Gln Lys Gly Ser Leu Thr
    130                 135                 140

Ile Gln Gln Val Asn Glu Leu Leu Asp Leu Val Ala Ser Asn Asn Ser
145                 150                 155                 160

Gly Lys Lys Lys Asp Leu Val Lys Lys Ser Leu Leu Gln Leu Ile Thr
                165                 170                 175

Gln Ser Ser Ala Leu Glu Gln Lys Trp Leu Ile Arg Met Ile Ile Lys
            180                 185                 190

Asp Leu Lys Leu Gly Ile Ser Gln Gln Thr Ile Phe Ser Ile Phe His
        195                 200                 205

Asn Asp Ala Val Glu Leu His Asn Val Thr Thr Asp Leu Glu Lys Val
    210                 215                 220

Cys Arg Gln Leu His Asp Pro Ser Val Gly Leu Ser Asp Ile Ser Ile
225                 230                 235                 240

Thr Leu Phe Ser Ala Phe Lys Pro Met Leu Ala Ala Val Ala Asp Val
                245                 250                 255

Glu Arg Val Glu Lys Asp Met Lys Gln Gln Ser Phe Tyr Ile Glu Thr
            260                 265                 270

Lys Leu Asp Gly Glu Arg Met Gln Met His Lys Asp Gly Ala Leu Tyr
        275                 280                 285
```

```
Arg Tyr Phe Ser Arg Asn Gly Tyr Asn Tyr Thr Asp Gln Phe Gly Glu
    290                 295                 300

Ser Pro Gln Glu Gly Ser Leu Thr Pro Phe Ile His Asn Ala Phe Gly
305                 310                 315                 320

Thr Asp Val Gln Ala Cys Ile Leu Asp Gly Glu Met Met Ala Tyr Asn
                325                 330                 335

Pro Thr Thr Gln Thr Phe Met Gln Lys Gly Val Lys Phe Asp Ile Lys
            340                 345                 350

Arg Met Val Glu Asp Ser Gly Leu Gln Thr Cys Tyr Ser Val Phe Asp
        355                 360                 365

Val Leu Met Val Asn Lys Lys Lys Leu Gly Arg Glu Thr Leu Arg Lys
    370                 375                 380

Arg Tyr Glu Ile Leu Ser Ser Thr Phe Thr Pro Ile Gln Gly Arg Ile
385                 390                 395                 400

Glu Ile Val Gln Lys Thr Gln Ala His Thr Lys Lys Glu Val Val Asp
                405                 410                 415

Ala Leu Asn Asp Ala Ile Asp Lys Arg Glu Glu Gly Ile Met Val Lys
            420                 425                 430

His Pro Leu Ser Ile Tyr Lys Pro Asp Lys Arg Gly Glu Gly Trp Leu
        435                 440                 445

Lys Ile Lys Pro Glu Tyr Val Ser Gly Leu Met Asp Glu Leu Asp Val
    450                 455                 460

Leu Ile Val Gly Gly Tyr Trp Gly Lys Gly Ser Arg Gly Gly Met Met
465                 470                 475                 480

Ser His Phe Leu Cys Ala Val Ala Glu Thr Pro Pro Pro Gly Asp Arg
                485                 490                 495

Pro Ser Val Phe His Thr Leu Cys Arg Val Gly Ser Gly Tyr Thr Met
            500                 505                 510

Lys Glu Leu Tyr Asp Leu Gly Leu Lys Leu Ala Lys Tyr Trp Lys Pro
        515                 520                 525

Phe His Lys Lys Ser Pro Pro Ser Ser Ile Leu Cys Gly Thr Glu Lys
    530                 535                 540

Pro Glu Val Tyr Ile Glu Pro Gln Asn Ser Val Ile Val Gln Ile Lys
545                 550                 555                 560

Ala Ala Glu Ile Val Pro Ser Asp Met Tyr Lys Thr Gly Ser Thr Leu
                565                 570                 575

Arg Phe Pro Arg Ile Glu Lys Ile Arg Asp Asp Lys Glu Trp His Glu
            580                 585                 590

Cys Met Thr Leu Gly Asp Leu Glu Gln Leu Arg Gly Lys Ala Ser Gly
        595                 600                 605

Lys Leu Ala Thr Lys His Leu His Val Gly Asp Asp Asp Glu Pro Arg
    610                 615                 620

Glu Lys Arg Arg Lys Pro Ile Ser Lys Thr Lys Lys Ala Ile Arg Ile
625                 630                 635                 640

Ile Glu His Leu Lys Ala Pro Asn Leu Ser Asn Val Asn Lys Val Ser
                645                 650                 655

Asn Val Phe Glu Asp Val Glu Phe Cys Val Met Ser Gly Leu Asp Gly
            660                 665                 670

Tyr Pro Lys Ala Asp Leu Glu Asn Arg Ile Ala Glu Phe Gly Gly Tyr
        675                 680                 685

Ile Val Gln Asn Pro Gly Pro Asp Thr Tyr Cys Val Ile Ala Gly Ser
    690                 695                 700
```

-continued

```
Glu Asn Val Arg Val Lys Asn Ile Ile Ser Ser Asp Lys Asn Asp Val
705                 710                 715                 720

Val Lys Pro Glu Trp Leu Leu Glu Cys Phe Lys Thr Lys Thr Cys Val
                725                 730                 735

Pro Trp Gln Pro Arg Phe Met Ile His Met Cys Pro Ser Thr Lys Gln
            740                 745                 750

His Phe Ala Arg Glu Tyr Asp Cys Tyr Gly Asp Ser Tyr Phe Val Asp
        755                 760                 765

Thr Asp Leu Asp Gln Leu Lys Glu Val Phe Leu Gly Ile Lys Pro Ser
    770                 775                 780

Glu Gln Gln Thr Pro Glu Glu Met Ala Pro Val Ile Ala Asp Leu Glu
785                 790                 795                 800

Cys Arg Tyr Ser Trp Asp His Ser Pro Leu Ser Met Phe Arg His Tyr
                805                 810                 815

Thr Ile Tyr Leu Asp Leu Tyr Ala Val Ile Asn Asp Leu Ser Ser Arg
            820                 825                 830

Ile Glu Ala Thr Arg Leu Gly Ile Thr Ala Leu Glu Leu Arg Phe His
        835                 840                 845

Gly Ala Lys Val Val Ser Cys Leu Ser Glu Gly Val Ser His Val Ile
    850                 855                 860

Ile Gly Glu Asp Gln Arg Arg Val Thr Asp Phe Lys Ile Phe Arg Arg
865                 870                 875                 880

Met Leu Lys Lys Lys Phe Lys Ile Leu Gln Glu Ser Trp Val Ser Asp
                885                 890                 895

Ser Val Asp Lys Gly Glu Leu Gln Glu Glu Asn Gln Tyr Leu Leu
            900                 905                 910
```

<210> SEQ ID NO 54
<211> LENGTH: 2232
<212> TYPE: DNA
<213> ORGANISM: Homo sapiens

<400> SEQUENCE: 54

```
ggcccggggg cggagcaagg caaggaagcg gaagcggaga ggcggtcggg atccgctgcg     60

cgagctgtct cggtcccacg tgtgcgagtt gctacgatgg aagttaaagg gaaaaagcaa    120

ttcacaggaa agagtacaaa gacagcacaa gaaaaaaaca gatttcataa aaatagtgat    180

tctggttctt caaagacatt tccaacaagg aaagttgcta aagaaggtgg acctaaagtc    240

acatctagga actttgagaa aagtatcaca aaacttggga aaaagggtgt aaagcagttc    300

aagaataagc agcaagggga caaatcacca aagaacaaat tccagccggc aaataaattc    360

aacaagaaga gaaaattcca gccagatggt agaagcgatg aatcagcagc caagaagccc    420

aaatgggatg acttcaaaaa gaagaagaaa gaactgaagc aaagcagaca actcagtgat    480

aaaaccaact atgacattgt tgttcgggca aagcagatgt gggagatttt aagaagaaaa    540

gactgtgaca aagaaaaaag agtaaagtta atgagtgatt tgcagaagtt gattcaaggg    600

aaaattaaaa ctattgcatt tgcacacgat tcaactcgtg tgatccagtg ttacattcag    660

tatggtaatg aagaacagag aaaacaggct tttgaagaat tgcgagatga tttggttgag    720

ttaagtaaag ccaaatattc gagaaatatt gttaagaaat ttctcatgta tggaagtaaa    780

ccacagattg cagagataat cagaagtttt aaaggccacg tgaggaagat gctgcggcat    840

gcggaagcat cagccatcgt ggagtacgca tacaatgaca aagccatttt ggagcagagg    900

aacatgctga cggaagagct ctatgggaac acatttcagc tttacaagtc agcagatcac    960
```

```
cgaactctgg acaaagtgtt agaggtacag ccagaaaaat tagaacttat tatggatgaa   1020

atgaaacaga ttctaactcc aatggcccaa aaggaagctg tgattaagca ctcattggtg   1080

cataaagtat tcttggactt ttttacctat gcacccccca aactcagatc agaaatgatt   1140

gaagccatcc gcgaagcggt ggtctacctg gcacacacac acgatggcgc cagagtggcc   1200

atgcactgcc tgtggcatgg cacgcccaag gacaggaaag tgattgtgaa aacaatgaag   1260

acttatgttg aaaaggtggc taatggccaa tactcccatt tggttttact ggcggcattt   1320

gattgtattg atgatactaa gcttgtgaag cagataatca tatcagaaat tatcagttca   1380

ttgcctagca tagtaaatga caaatatgga aggaaggtcc tattgtactt actaagcccc   1440

agagatcctg cacatacagt acgagaaatc attgaagttc tgcaaaaagg agatggaaat   1500

gcacacagta agaaagatac agaggtccgc agacgggagc tcctagaatc catttctcca   1560

gctttgttaa gctacctgca agaacacgcc caagaagtgg tgctagataa gtctgcgtgt   1620

gtgttggtgt ctgacattct gggatctgcc actggagacg ttcagcctac catgaatgcc   1680

atcgccagct tggcagcaac aggactgcat cctggtggca aggacggaga gcttcacatt   1740

gcagaacatc ctgcaggaca tctagttctg aagtggttaa tagagcaaga taaaaagatg   1800

aaagaaaatg ggagagaagg ttgttttgca aaaacacttg tagagcatgt tggtatgaag   1860

aacctgaagt cctgggctag tgtaaatcga ggtgccatta ttctttctag cctcctccag   1920

agttgtgacc tggaagttgc aaacaaagtc aaagctgcac tgaaaagctt gattcctaca   1980

ttggaaaaaa ccaaaagcac cagcaaagga atagaaattc tacttgaaaa actgagcaca   2040

taggtggaaa gagttaagag caagatggaa tgatttttc tgttctctgt tctgtttccc    2100

aatgcagaaa agaaggggta gggtccacca tactggtaat tggggtactc tgtatatgtg   2160

tttcttcttt gtatacgaat ctatttatat aaattgtttt tttaaatggt ctttttttaaa  2220

aaaaaaaaaa aa                                                        2232
```

<210> SEQ ID NO 55
<211> LENGTH: 648
<212> TYPE: PRT
<213> ORGANISM: Homo sapiens

<400> SEQUENCE: 55

```
Met Glu Val Lys Gly Lys Lys Gln Phe Thr Gly Lys Ser Thr Lys Thr
1               5                   10                  15

Ala Gln Glu Lys Asn Arg Phe His Lys Asn Ser Asp Ser Gly Ser Ser
            20                  25                  30

Lys Thr Phe Pro Thr Arg Lys Val Ala Lys Glu Gly Gly Pro Lys Val
        35                  40                  45

Thr Ser Arg Asn Phe Glu Lys Ser Ile Thr Lys Leu Gly Lys Lys Gly
    50                  55                  60

Val Lys Gln Phe Lys Asn Lys Gln Gln Gly Asp Lys Ser Pro Lys Asn
65                  70                  75                  80

Lys Phe Gln Pro Ala Asn Lys Phe Asn Lys Lys Arg Lys Phe Gln Pro
                85                  90                  95

Asp Gly Arg Ser Asp Glu Ser Ala Ala Lys Lys Pro Lys Trp Asp Asp
            100                 105                 110

Phe Lys Lys Lys Lys Lys Glu Leu Lys Gln Ser Arg Gln Leu Ser Asp
        115                 120                 125

Lys Thr Asn Tyr Asp Ile Val Val Arg Ala Lys Gln Met Trp Glu Ile
    130                 135                 140
```

-continued

```
Leu Arg Arg Lys Asp Cys Asp Lys Glu Lys Arg Val Lys Leu Met Ser
145                 150                 155                 160

Asp Leu Gln Lys Leu Ile Gln Gly Lys Ile Lys Thr Ile Ala Phe Ala
                165                 170                 175

His Asp Ser Thr Arg Val Ile Gln Cys Tyr Ile Gln Tyr Gly Asn Glu
            180                 185                 190

Glu Gln Arg Lys Gln Ala Phe Glu Glu Leu Arg Asp Asp Leu Val Glu
        195                 200                 205

Leu Ser Lys Ala Lys Tyr Ser Arg Asn Ile Val Lys Lys Phe Leu Met
    210                 215                 220

Tyr Gly Ser Lys Pro Gln Ile Ala Glu Ile Ile Arg Ser Phe Lys Gly
225                 230                 235                 240

His Val Arg Lys Met Leu Arg His Ala Glu Ala Ser Ala Ile Val Glu
                245                 250                 255

Tyr Ala Tyr Asn Asp Lys Ala Ile Leu Glu Gln Arg Asn Met Leu Thr
            260                 265                 270

Glu Glu Leu Tyr Gly Asn Thr Phe Gln Leu Tyr Lys Ser Ala Asp His
        275                 280                 285

Arg Thr Leu Asp Lys Val Leu Glu Val Gln Pro Glu Lys Leu Glu Leu
    290                 295                 300

Ile Met Asp Glu Met Lys Gln Ile Leu Thr Pro Met Ala Gln Lys Glu
305                 310                 315                 320

Ala Val Ile Lys His Ser Leu Val His Lys Val Phe Leu Asp Phe Phe
                325                 330                 335

Thr Tyr Ala Pro Pro Lys Leu Arg Ser Glu Met Ile Glu Ala Ile Arg
            340                 345                 350

Glu Ala Val Val Tyr Leu Ala His Thr His Asp Gly Ala Arg Val Ala
        355                 360                 365

Met His Cys Leu Trp His Gly Thr Pro Lys Asp Arg Lys Val Ile Val
    370                 375                 380

Lys Thr Met Lys Thr Tyr Val Glu Lys Val Ala Asn Gly Gln Tyr Ser
385                 390                 395                 400

His Leu Val Leu Leu Ala Ala Phe Asp Cys Ile Asp Asp Thr Lys Leu
                405                 410                 415

Val Lys Gln Ile Ile Ile Ser Glu Ile Ile Ser Ser Leu Pro Ser Ile
            420                 425                 430

Val Asn Asp Lys Tyr Gly Arg Lys Val Leu Leu Tyr Leu Leu Ser Pro
        435                 440                 445

Arg Asp Pro Ala His Thr Val Arg Glu Ile Ile Glu Val Leu Gln Lys
    450                 455                 460

Gly Asp Gly Asn Ala His Ser Lys Lys Asp Thr Glu Val Arg Arg Arg
465                 470                 475                 480

Glu Leu Leu Glu Ser Ile Ser Pro Ala Leu Leu Ser Tyr Leu Gln Glu
                485                 490                 495

His Ala Gln Glu Val Val Leu Asp Lys Ser Ala Cys Val Leu Val Ser
            500                 505                 510

Asp Ile Leu Gly Ser Ala Thr Gly Asp Val Gln Pro Thr Met Asn Ala
        515                 520                 525

Ile Ala Ser Leu Ala Ala Thr Gly Leu His Pro Gly Gly Lys Asp Gly
    530                 535                 540

Glu Leu His Ile Ala Glu His Pro Ala Gly His Leu Val Leu Lys Trp
545                 550                 555                 560
```

```
Leu Ile Glu Gln Asp Lys Lys Met Lys Glu Asn Gly Arg Glu Gly Cys
                565                 570                 575

Phe Ala Lys Thr Leu Val Glu His Val Gly Met Lys Asn Leu Lys Ser
            580                 585                 590

Trp Ala Ser Val Asn Arg Gly Ala Ile Ile Leu Ser Ser Leu Leu Gln
        595                 600                 605

Ser Cys Asp Leu Glu Val Ala Asn Lys Val Lys Ala Ala Leu Lys Ser
    610                 615                 620

Leu Ile Pro Thr Leu Glu Lys Thr Lys Ser Thr Ser Lys Gly Ile Glu
625                 630                 635                 640

Ile Leu Leu Glu Lys Leu Ser Thr
                645
```

<210> SEQ ID NO 56
<211> LENGTH: 3596
<212> TYPE: DNA
<213> ORGANISM: Mus musculus

<400> SEQUENCE: 56

```
agtaccagga cgtaacgcta caatcagcgg atccggggcg gggcagaacg cggaagcgga     60

agcggaagcg gcggggggtg gtggcggaac tctgcgagtt tctgccccac gtgtgcgaag    120

tactatgatg gaagtcaaag ggaagaaaaa gtttacagga aagagtccac agacatcaca    180

aggaaagaat aaatttcata agaacagtga gtctagttct tcaaagacat tcccaaggaa    240

agctgttaag gaaggcggac ctaaagtcac atctaagaac tttgagaaag gtgccacaaa    300

acctggcaag aaaggtgtga agcagttcaa gaacaagcca caaggggggca aaggaccgaa    360

ggacaaattt cagaaggcaa ataaattcag caagaagcgg aaattccagc cagatggtga    420

aagtgatgaa tcaggagcca agaaacccaa gtgggatgac ttcaaaaaga agaagaaaga    480

gctgaagcag agcaggcagc tcagtgacaa gaccaactat gacatcgtgg ttcgagcaaa    540

gcacatttgg gagagcttga gaagaaaaga ttgtgacaag gaaaaacggg tgaagctcat    600

gagtgatttg cagaagttga ttcaagggaa aattaaaact atcgcctttg cacatgactc    660

gacgcgcgtg atccagtgct tcattcagta tgggaacgag gagcagagga agcaggcttt    720

ccaagagttg caaggcgact tggttgaatt aagtaaagcc aaatattcca ggaatatcgt    780

taagaaattt ctcatgtatg gaagtaagcc acaagttgcg gagataatca gaagttttaa    840

aggtcatgtg aggaagatgc tgcggcattc ggaggcatcg gccattgtgg agtacgcata    900

caacgacaaa gccattttgg aacagaggaa catgctgaca gaggagctct atggaacac     960

gtttcagctt tacaagtcag cagatcaccc aacgctggac aaggtgctgg agctgcagcc   1020

agcaaagcta gagcttatca tggacgagat gaagcagatt ctgacaccga tggcccaaaa   1080

ggaagctgtg attaagcact cactcgttca taaagtattc ttggactttt ttacctacgc   1140

accccccaaaa cctcgatcag aactaattga agccatccgg gaagcagtgg tgtacctggc   1200

ccacacacac gatggcgcca gagtggccat gcactgcctg tggcacggca cacccaagga   1260

caggaaagtg atcgtgaaaa cgatgaagac gtatgtggag aaggttgcca atggccagta   1320

ctctcacttg gttctcctgg cagcgtttga ctgtattgat gatactaagc ttgtgaagca   1380

gataatcata tcagaaatca tcagttcctt gcccagcata gttaatgaca aatacggaag   1440

gaaagtcctc ttgtacttga tgagccccag agaccccgcc cacacggtgc ccgagctcat   1500

cgagcttctg cagaagggtg atggcaacgc gcacagcaag aaggacactg caatccgccg   1560
```

-continued gcgtgagctc ttggagtcca tctctccagc tttgctgagc tacctgcaag gacacactca 1620
agaggtggtg ctggataagt ctgcatgtgt gctggtgtct gacatgctgg gatctgctac 1680
tggagatgtt cagcctgcta tggatgccat cgccagtttg gcagcagcag aactgcatcc 1740
tggtggcaag gacggagagc ttcatgttgc tgagcatcct gcaggacatc tggttctcaa 1800
atggttacta gagcaagata aaaagatgaa agaaagcgga aaggaaggtt gttttgcaaa 1860
aacccttgta gagcgtgttg gtatgaagaa cctcaagtcc tgggccagca tcaaccgagg 1920
tgccattatt ctttccagcc ttcttcagag ttgtgaccaa gaagttgtaa acaaagtcaa 1980
aggtggactg aaacccctga ttcctacctt ggaaaaaaac aaaagcagca gcagaggcat 2040
ccagaccctg cttgagaagc tgactgcgta ggcagcagga tgagcaagcg ggaacccgct 2100
tcccagagga gaaggtggaa tctctcatac tcacaactgg acgctctgtg catgcatttg 2160
ttaaaggacc tatttatata aaattgtttc taaaagagac ctttggttta atgtcaactg 2220
tctgatctgt gagactgagt actacacagt atggcagtga tctgtgggcc caggtgtgtg 2280
ctctgtggtt gaatggctta atttaggaaa ggagacagct atgatctgag aaggtttcct 2340
ggtgtaggtg aactttagag ggatgttata acaaaagaat taaggacatg aagttcaaac 2400
agagtgtgta tagtggagca ggaaagtggt ctgaactccg ggaagcctgt ggccagggca 2460
gcctgcactg gggacagctg cttcctcagc tgccgtgcag actgagttcc atcaggtttg 2520
tttggaagct gctctggtca gtccagcaca tggagggaag tgtgctagag gaatcaggag 2580
atgatgggtc ctcgcttgaa gtcagcgttg ctgggaaagt ctgatctttg tatttgggcc 2640
ttcagggtaa ataccttcca aggagaatga ggacattgtc ccatgaacaa tccctaaaat 2700
agtcagagcc catagtgtga ctaaaagggg gaactgtaga ggattgagtg taggtagtat 2760
gtttggactt taaaaataca gctggctttc agcggcaaaa ctggagatct gtagaccatg 2820
agaacttgtg tagcaggcgt ttttagtaca gaggcctgtc cttgctgctc tgcatgtctg 2880
atatatacta aggcggccat ctgaccctct gaggaattgt ctgtgcctta cctgtcccaa 2940
cttaaggttc caggactact aatgcagctt ctaggactct cctgccctct cgtgctgggg 3000
tgtagtaagc cctttcccag gcatgacacc tgccactgtt ggctggatcc tctaggcatg 3060
gagtgaggag gagagtgggg aaagacagtt tgatttgctt ctgtgtggct aacataccat 3120
gactcgagtt ttcgttctcc gtataaagga ccgtttagag agatgagagt cgggtgctaa 3180
catgtttaat ctttaaaagt gaaaaacacg tacataactt gaaaggtgct tttgtgcagc 3240
ttgtagaaaa agcagctgtt tcctctgtag ttctaattca cgctctccat aatgacttga 3300
gttcttagct ctggtgaatt tctaaacatg tagtatgaag tcccgagtac ctaaaacgta 3360
tatattcaaa tacacaataa agagcatgtt tatttttttgt tttttaaggc aggatcttgc 3420
tatgtagctc tgactgtttt gaaatttatt gtgtagacca aactggcctc aaactcacag 3480
agatctgcct gcctctgtct ccctggtgct gcgattaaag atgtgggcca ccacatccag 3540
ctgaggacac agttaaaaaa aaaaaaaaaa aaaaaaaaaa aaaaaaaaaa aaaaaa 3596

<210> SEQ ID NO 57
<211> LENGTH: 648
<212> TYPE: PRT
<213> ORGANISM: Mus musculus

<400> SEQUENCE: 57

Met Met Glu Val Lys Gly Lys Lys Lys Phe Thr Gly Lys Ser Pro Gln
1 5 10 15

-continued

```
Thr Ser Gln Gly Lys Asn Lys Phe His Lys Asn Ser Glu Ser Ser Ser
            20                  25                  30

Ser Lys Thr Phe Pro Arg Lys Ala Val Lys Glu Gly Gly Pro Lys Val
        35                  40                  45

Thr Ser Lys Asn Phe Glu Lys Gly Ala Thr Lys Pro Gly Lys Lys Gly
    50                  55                  60

Val Lys Gln Phe Lys Asn Lys Pro Gln Gly Gly Lys Gly Pro Lys Asp
65                  70                  75                  80

Lys Phe Gln Lys Ala Asn Lys Phe Ser Lys Lys Arg Lys Phe Gln Pro
                85                  90                  95

Asp Gly Glu Ser Asp Glu Ser Gly Ala Lys Lys Pro Lys Trp Asp Asp
            100                 105                 110

Phe Lys Lys Lys Lys Lys Glu Leu Lys Gln Ser Arg Gln Leu Ser Asp
        115                 120                 125

Lys Thr Asn Tyr Asp Ile Val Val Arg Ala Lys His Ile Trp Glu Ser
    130                 135                 140

Leu Arg Arg Lys Asp Cys Asp Lys Glu Lys Arg Val Lys Leu Met Ser
145                 150                 155                 160

Asp Leu Gln Lys Leu Ile Gln Gly Lys Ile Lys Thr Ile Ala Phe Ala
                165                 170                 175

His Asp Ser Thr Arg Val Ile Gln Cys Phe Ile Gln Tyr Gly Asn Glu
            180                 185                 190

Glu Gln Arg Lys Gln Ala Phe Gln Glu Leu Gln Gly Asp Leu Val Glu
        195                 200                 205

Leu Ser Lys Ala Lys Tyr Ser Arg Asn Ile Val Lys Lys Phe Leu Met
    210                 215                 220

Tyr Gly Ser Lys Pro Gln Val Ala Glu Ile Ile Arg Ser Phe Lys Gly
225                 230                 235                 240

His Val Arg Lys Met Leu Arg His Ser Glu Ala Ser Ala Ile Val Glu
                245                 250                 255

Tyr Ala Tyr Asn Asp Lys Ala Ile Leu Glu Gln Arg Asn Met Leu Thr
            260                 265                 270

Glu Glu Leu Tyr Gly Asn Thr Phe Gln Leu Tyr Lys Ser Ala Asp His
        275                 280                 285

Pro Thr Leu Asp Lys Val Leu Glu Leu Gln Pro Ala Lys Leu Glu Leu
    290                 295                 300

Ile Met Asp Glu Met Lys Gln Ile Leu Thr Pro Met Ala Gln Lys Glu
305                 310                 315                 320

Ala Val Ile Lys His Ser Leu Val His Lys Val Phe Leu Asp Phe Phe
                325                 330                 335

Thr Tyr Ala Pro Pro Lys Pro Arg Ser Glu Leu Ile Glu Ala Ile Arg
            340                 345                 350

Glu Ala Val Val Tyr Leu Ala His Thr His Asp Gly Ala Arg Val Ala
        355                 360                 365

Met His Cys Leu Trp His Gly Thr Pro Lys Asp Arg Lys Val Ile Val
    370                 375                 380

Lys Thr Met Lys Thr Tyr Val Glu Lys Val Ala Asn Gly Gln Tyr Ser
385                 390                 395                 400

His Leu Val Leu Leu Ala Ala Phe Asp Cys Ile Asp Asp Thr Lys Leu
                405                 410                 415

Val Lys Gln Ile Ile Ile Ser Glu Ile Ile Ser Ser Leu Pro Ser Ile
            420                 425                 430
```

Val Asn Asp Lys Tyr Gly Arg Lys Val Leu Leu Tyr Leu Met Ser Pro
435 440 445

Arg Asp Pro Ala His Thr Val Pro Glu Leu Ile Glu Leu Leu Gln Lys
450 455 460

Gly Asp Gly Asn Ala His Ser Lys Lys Asp Thr Ala Ile Arg Arg Arg
465 470 475 480

Glu Leu Leu Glu Ser Ile Ser Pro Ala Leu Leu Ser Tyr Leu Gln Gly
485 490 495

His Thr Gln Glu Val Val Leu Asp Lys Ser Ala Cys Val Leu Val Ser
500 505 510

Asp Met Leu Gly Ser Ala Thr Gly Asp Val Gln Pro Ala Met Asp Ala
515 520 525

Ile Ala Ser Leu Ala Ala Ala Glu Leu His Pro Gly Gly Lys Asp Gly
530 535 540

Glu Leu His Val Ala Glu His Pro Ala Gly His Leu Val Leu Lys Trp
545 550 555 560

Leu Leu Glu Gln Asp Lys Lys Met Lys Glu Ser Gly Lys Glu Gly Cys
565 570 575

Phe Ala Lys Thr Leu Val Glu Arg Val Gly Met Lys Asn Leu Lys Ser
580 585 590

Trp Ala Ser Ile Asn Arg Gly Ala Ile Ile Leu Ser Ser Leu Leu Gln
595 600 605

Ser Cys Asp Gln Glu Val Val Asn Lys Val Lys Gly Gly Leu Lys Pro
610 615 620

Leu Ile Pro Thr Leu Glu Lys Asn Lys Ser Ser Ser Arg Gly Ile Gln
625 630 635 640

Thr Leu Leu Glu Lys Leu Thr Ala
645

<210> SEQ ID NO 58
<211> LENGTH: 147
<212> TYPE: PRT
<213> ORGANISM: Homo sapiens

<400> SEQUENCE: 58

Met Ala Leu Lys Arg Ile Asn Lys Glu Leu Ser Asp Leu Ala Arg Asp
1 5 10 15

Pro Pro Ala Gln Cys Ser Ala Gly Pro Val Gly Asp Asp Met Phe His
20 25 30

Trp Gln Ala Thr Ile Met Gly Pro Asn Asp Ser Pro Tyr Gln Gly Gly
35 40 45

Val Phe Phe Leu Thr Ile His Phe Pro Thr Asp Tyr Pro Phe Lys Pro
50 55 60

Pro Lys Val Ala Phe Thr Thr Arg Ile Tyr His Pro Asn Ile Asn Ser
65 70 75 80

Asn Gly Ser Ile Cys Leu Asp Ile Leu Arg Ser Gln Trp Ser Pro Ala
85 90 95

Leu Thr Ile Ser Lys Val Leu Leu Ser Ile Cys Ser Leu Leu Cys Asp
100 105 110

Pro Asn Pro Asp Asp Pro Leu Val Pro Glu Ile Ala Arg Ile Tyr Lys
115 120 125

```
Thr Asp Arg Asp Lys Tyr Asn Arg Ile Ser Arg Glu Trp Thr Gln Lys
    130                 135                 140

Tyr Ala Met
145


<210> SEQ ID NO 59
<211> LENGTH: 148
<212> TYPE: PRT
<213> ORGANISM: Homo sapiens

<400> SEQUENCE: 59

Met Ala Leu Lys Arg Ile Asn Lys Glu Leu Ser Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Phe Leu Thr Ile His Phe Pro Thr Asp Tyr Pro Phe Lys Pro
    50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Lys
        115                 120                 125

Thr Asp Arg Asp Lys Tyr Asn Arg Leu Ala Arg Glu Trp Thr Glu Lys
    130                 135                 140

Tyr Ala Met Leu
145


<210> SEQ ID NO 60
<211> LENGTH: 149
<212> TYPE: PRT
<213> ORGANISM: Homo sapiens

<400> SEQUENCE: 60

Met Leu Ser Asn Arg Lys Cys Leu Ser Lys Glu Leu Ser Asp Leu Ala
1               5                   10                  15

Arg Asp Pro Pro Ala Gln Cys Ser Ala Gly Pro Val Gly Asp Asp Met
            20                  25                  30

Phe His Trp Gln Ala Thr Ile Met Gly Pro Asn Asp Ser Pro Tyr Gln
        35                  40                  45

Gly Gly Val Phe Phe Leu Thr Ile His Phe Pro Thr Asp Tyr Pro Phe
    50                  55                  60

Lys Pro Pro Lys Val Ala Phe Thr Thr Arg Ile Tyr His Pro Asn Ile
65                  70                  75                  80

Asn Ser Asn Gly Ser Ile Cys Leu Asp Ile Leu Arg Ser Gln Trp Ser
                85                  90                  95

Pro Ala Leu Thr Ile Ser Lys Val Leu Leu Ser Ile Cys Ser Leu Leu
            100                 105                 110

Cys Asp Pro Asn Pro Asp Asp Pro Leu Val Pro Glu Ile Ala Arg Ile
        115                 120                 125

Tyr Lys Thr Asp Arg Asp Lys Tyr Asn Arg Ile Ser Arg Glu Trp Thr
    130                 135                 140
```

Gln Lys Tyr Ala Met
145

<210> SEQ ID NO 61
<211> LENGTH: 118
<212> TYPE: PRT
<213> ORGANISM: Homo sapiens

<400> SEQUENCE: 61

Met Phe His Trp Gln Ala Thr Ile Met Gly Pro Asn Asp Ser Pro Tyr
1 5 10 15

Gln Gly Gly Val Phe Phe Leu Thr Ile His Phe Pro Thr Asp Tyr Pro
20 25 30

Phe Lys Pro Pro Lys Val Ala Phe Thr Thr Arg Ile Tyr His Pro Asn
35 40 45

Ile Asn Ser Asn Gly Ser Ile Cys Leu Asp Ile Leu Arg Ser Gln Trp
50 55 60

Ser Pro Ala Leu Thr Ile Ser Lys Val Leu Leu Ser Ile Cys Ser Leu
65 70 75 80

Leu Cys Asp Pro Asn Pro Asp Asp Pro Leu Val Pro Glu Ile Ala Arg
85 90 95

Ile Tyr Lys Thr Asp Arg Asp Lys Tyr Asn Arg Ile Ser Arg Glu Trp
100 105 110

Thr Gln Lys Tyr Ala Met
115

<210> SEQ ID NO 62
<211> LENGTH: 3976
<212> TYPE: DNA
<213> ORGANISM: Homo sapiens

<400> SEQUENCE: 62
accaagtgag gaaactgggg gacgctgtgg ggaggggcgt ggggctggat cgcgcagcgg 60
ctgcttcctt taccttcctc ccatggtctc cttccggttc tcgatgcttc tctgagccta 120
agggtttccg ccactcgttc accctccccc cagctcatga tcctcctccc tcccccgccc 180
tcctggtcca atctccgatc tgtttagtaa gaaggtgctg ttccgagaag aaggaaaagg 240
gcttgacacg tattcactcg gccccggacg tgggaagcaa gccgtctggc ttcggcctca 300
catcggtctt gtgctcggga cggcggcgtt ggcggactga tccgcggcgg tgaagaggcg 360
cctgtgtctg gcagagctgg tgtgagacga gacaatcctg ccccgccgcc gggataatca 420
agagttttgg ccggaccttt gagcatacac cgagagagtg aggagccaga cgacaagcac 480
acactatggc gctgaaacgg attaataagg aacttagtga tttggcccgt gaccctccag 540
cacaatgttc tgcaggtcca gttggggatg atatgtttca ttggcaagcc acaattatgg 600
gacctaatga cagcccatat caaggcggtg tattcttttt gacaattcat ttccctacag 660
actacccctt caaaccacct aaggttgcat ttacaacaag aatttatcat ccaaatatta 720
acagtaatgg cagcatttgt ctcgatattc taagatcaca gtggtcgcct gctttaacaa 780
tttctaaagt tcttttatcc atttgttcac tgctatgtga tccaaaccca gatgaccccc 840
tagtgccaga gattgcacgg atctataaaa cagacagaga taagtacaac agaatatctc 900
gggaatggac tcagaagtat gccatgtgat gctaccttaa agtcagaata acctgcatta 960
tagctggaat aaactttaaa ttactgttcc ttttttgatt ttcttatccg gctgctcccc 1020
tatcagacct catctttttt aattttattt tttgtttacc tccctccatt cattcacatg 1080

```
ctcatctgag aagacttaag ttcttccagc tttggacaat aactgctttt agaaactgta   1140
aagtagttac aagagaacag ttgcccaaga ctcagaattt ttaaaaaaaa aaatggagca   1200
tgtgtattat gtggccaatg tcttcactct aacttggtta tgagactaaa accattcctc   1260
actgctctaa catgctgaag aaatcatctg agggggaggg agatggatgc tcagttgtca   1320
catcaaagga tacagcatta ttctagcagc atccattctt gtttaagcct tccactgtta   1380
gagatttgag gttacatgat atgctttatg ctcataactg atgtggctgg agaattggta   1440
ttgaatttat agcatcagca gaacagaaaa tgtgatgtat tttatgcatg tcaataaagg   1500
aatgacctgt tcttgttcta cagagaatgg aaattggaag tcaaacaccc tttgtattcc   1560
aaaatagggt ctcaaacatt ttgtaatttt catttaaatt gttaggaggc ttggagctat   1620
tagttaatct atcttccaat acactgttta atatagcact gaataaatga tgcaagttgt   1680
caatggatga gtgatcaact aatagctctg ctagtaattg atttattttt cttcaataaa   1740
gttgcataaa ccaatgagtt agctgcctgg attaatcagt atgggaaaca atcttttgta   1800
aatgcaaagc tgttttttgt atatactgtt gggatttgct tcattgtttg acatcaaatg   1860
atgatgtaaa gttcgaaaga gtgaatattt tgccatgttc agttaaagtg cacagtctgt   1920
tacaggttga cacattgctt gacctgattt atgcagaatt aataagctat ttggatagtg   1980
tagctttaat gtgctgcaca tgatactggc agccctagag ttcatagatg gacttttggg   2040
acccagcagt tttgaaatgt gtttatggag tttaagaaat ttattttcca ggtgcagccc   2100
ctgtctaact gaaatttctc ttcaccttgt acacttgaca gctgaaaaaa aacaacatgg   2160
gagtaataat gggtcaaaat ttgcaaaata aagtactgtt ttggtgtggg agttgtcatg   2220
aggctgtgtt gaagtgactt atctatgtgg gatattgagt atccattgaa atggatttgt   2280
tcagccattt acattaatga gcatttaaat gcaacagata tcatttcagg tgacttaaca   2340
tgaatgaata aaagtcaatg ctattggatt gttttttgtt tgacaagtgc tatctgtgcc   2400
actgatttaa cttctgtagt aacaagggca ttaccattct tcacctttcc taattctgat   2460
cccatagttt tacatttttc ctgtttattt tgattttgtt cactgcttta tttcttaaag   2520
ttctagcaca tctgtgactc ctccacttcc acatttttgc actgcttaca cttacgtgca   2580
atcttattcc ttgtctgcac acacatgtgg aaagctagaa ataaatgtta aaacttactt   2640
tttataaaca ttttaatatg tagtttggac atgatttatt gacttaaggt tcttctctaa   2700
actggaagtg aaatgcatgc cttctgaaga tgttctggct ttgttaattc tgtaatcatt   2760
tcattgggga aaaaaccagc tacgcagttt ttccaatgag tgaatttttt catttttgtgt  2820
tttgcttaaa acggctcctt cagggtagat gtcatactgc ataacttttt tggattcaaa   2880
ttatgaatga gaaattagtt aacattctgc tccacaaggt aagaaaaact gctctttggc   2940
tctattttca aaattacttc tgagatgcat atagtctcaa aataacagct ttagtaggca   3000
tatcacttct tgaaagccaa acatgagtgt aagacacttt tatgaaacac ggtggatccc   3060
taactggctt tcaaattgac ctttatagcc ttagacaacc cttaggtatt tacggagatg   3120
acttctttga ttgtcataac aattagtgga tgtgtccagt tctctgtatc tttgacttga   3180
tgctttatac atcatttcat ttgttgcttc taagggaata agccatagag gcttctccag   3240
gtttaaaaga acagtaaagt acctggaaaa ccaacatttt tgaatgtatg gacactggac   3300
atgagatatg tacaatgaaa tcttaaaaga atctaagaat ttgccctctt tgccccactc   3360
cacccagtaa tttgacatta ctagtgccat gtataggacc caactgagta ttagaatcag   3420
```

-continued

```
ttttgactat gtctttgtat ttcctaaatc ttttaatgca taaaccgaat tagggtccag   3480

ttggcctgtt aatggtaaat ttacatttta aatgactcag tttgtttttc ctgggcgagt   3540

ttgcaatgtg ataatcagat tttttaaaac tgattaattt gctttcttgt gtgggtgtac   3600

tcacatttta aagtatgaac cacagttaac tagtggtctc aggggtagtg aaacactcac   3660

ttttttttt gtttgtttt ttttgtttgt tgaaatggct tagttgaagt atacttaagg   3720

tactgatcat gctgtgttag taatttgggc ggggaggggg gtaactcagc catgttttgt   3780

gttggcataa caaaactgtt aatgattgtt gattacactt ttaagtgaat ttgtctttta   3840

tgaggaaccc agtgcaagtc actaaatatt gtctaatagt gacatctgca taagacttgt   3900

aatagctgaa gttaattgag cttaaaggaa ttgttaccat taaagtctgt gtttaaagac   3960

aaaaaaaaaa aaaaaa                                                   3976
```

<210> SEQ ID NO 63
<211> LENGTH: 4184
<212> TYPE: DNA
<213> ORGANISM: Homo sapiens

<400> SEQUENCE: 63

```
accaagtgag gaaactgggg gacgctgtgg ggaggggcgt ggggctggat cgcgcagcgg     60

ctgcttcctt taccttcctc ccatggtctc cttccggttc tcgatgcttc tctgagccta    120

agggtttccg ccactcgttc accctccccc cagctcatga tcctcctccc tcccccgccc    180

tcctggtcca atctccgatc tgtttagtaa gaaggtgctg ttccgagaag aaggaaaagg    240

gcttgacacg tattcactcg gccccggacg tgggaagcaa gccgtctggc ttcggcctca    300

catcggtctt gtgctcggga cggcggcgtt ggcggactga tccgcggcgg tgaagagagg    360

ccgggaagtt aaacttgtag ccaccacctc cgctcttccc gtcaccctcg cccccacttc    420

gggccgaaag cacggtacag aggctgttgg tggctttgcc acgccacccc acccaccccg    480

gatcgcggct gtcttaaggg acctggattc atcaggggct cttcggggcc tgtgcgagtg    540

ctgatctgct ccgtttttgc aaaaggcgcc tgtgtctggc agagctggtg tgagacgaga    600

caatcctgcc ccgccgccgg gataatcaag agttttggcc ggacctttga gcatacaccg    660

agagagtgag gagccagacg acaagcacac actatggcgc tgaaacggat taataaggaa    720

cttagtgatt tggcccgtga ccctccagca caatgttctg caggtccagt tggggatgat    780

atgtttcatt ggcaagccac aattatggga cctaatgaca gcccatatca aggcggtgta    840

ttctttttga caattcattt tcctacagac taccccttca aaccacctaa ggttgcattt    900

acaacaagaa tttatcatcc aaatattaac agtaatggca gcatttgtct cgatattcta    960

agatcacagt ggtcgcctgc tttaacaatt tctaaagttc ttttatccat ttgttcactg   1020

ctatgtgatc caaacccaga tgacccccta gtgccagaga ttgcacggat ctataaaaca   1080

gacagagata agtacaacag aatatctcgg gaatggactc agaagtatgc catgtgatgc   1140

taccttaaag tcagaataac ctgcattata gctggaataa actttaaatt actgttcctt   1200

ttttgatttt cttatccggc tgctccccta tcagacctca tctttttttaa ttttattttt   1260

tgtttacctc cctccattca ttcacatgct catctgagaa gacttaagtt cttccagctt   1320

tggacaataa ctgcttttag aaactgtaaa gtagttacaa gagaacagtt gcccaagact   1380

cagaattttt aaaaaaaaaa atggagcatg tgtattatgt ggccaatgtc ttcactctaa   1440

cttggttatg agactaaaac cattcctcac tgctctaaca tgctgaagaa atcatctgag   1500

ggggagggag atggatgctc agttgtcaca tcaaaggata cagcattatt ctagcagcat   1560
```

-continued ccattcttgt ttaagccttc cactgttaga gatttgaggt tacatgatat gctttatgct 1620
cataactgat gtggctggag aattggtatt gaatttatag catcagcaga acagaaaatg 1680
tgatgtattt tatgcatgtc aataaaggaa tgacctgttc ttgttctaca gagaatggaa 1740
attggaagtc aaacaccctt tgtattccaa aatagggtct caaacatttt gtaattttca 1800
tttaaattgt taggaggctt ggagctatta gttaatctat cttccaatac actgtttaat 1860
atagcactga ataaatgatg caagttgtca atggatgagt gatcaactaa tagctctgct 1920
agtaattgat ttatttttct tcaataaagt tgcataaacc aatgagttag ctgcctggat 1980
taatcagtat gggaaacaat cttttgtaaa tgcaaagctg ttttttgtat atactgttgg 2040
gatttgcttc attgtttgac atcaaatgat gatgtaaagt tcgaaagagt gaatattttg 2100
ccatgttcag ttaaagtgca cagtctgtta caggttgaca cattgcttga cctgatttat 2160
gcagaattaa taagctattt ggatagtgta gctttaatgt gctgcacatg atactggcag 2220
ccctagagtt catagatgga cttttgggac ccagcagttt tgaaatgtgt ttatggagtt 2280
taagaaattt attttccagg tgcagcccct gtctaactga aatttctctt caccttgtac 2340
acttgacagc tgaaaaaaaa caacatggga gtaataatgg gtcaaaattt gcaaaataaa 2400
gtactgtttt ggtgtgggag ttgtcatgag gctgtgttga agtgacttat ctatgtggga 2460
tattgagtat ccattgaaat ggatttgttc agccatttac attaatgagc atttaaatgc 2520
aacagatatc atttcaggtg acttaacatg aatgaataaa agtcaatgct attggattgt 2580
tttttgtttg acaagtgcta tctgtgccac tgatttaact tctgtagtaa caagggcatt 2640
accattcttc acctttccta attctgatcc catagtttta cattttttcct gtttattttg 2700
attttgttca ctgctttatt tcttaaagtt ctagcacatc tgtgactcct ccacttccac 2760
atttttgcac tgcttacact tacgtgcaat cttattcctt gtctgcacac acatgtggaa 2820
agctagaaat aaatgttaaa acttactttt tataaacatt ttaatatgta gtttggacat 2880
gatttattga cttaaggttc ttctctaaac tggaagtgaa atgcatgcct tctgaagatg 2940
ttctggcttt gttaattctg taatcatttc attggggaaa aaaccagcta cgcagttttt 3000
ccaatgagtg aattttttca ttttgtgttt tgcttaaaac ggctccttca gggtagatgt 3060
catactgcat aactttttg gattcaaatt atgaatgaga aattagttaa cattctgctc 3120
cacaaggtaa gaaaaactgc tctttggctc tattttcaaa attacttctg agatgcatat 3180
agtctcaaaa taacagcttt agtaggcata tcacttcttg aaagccaaac atgagtgtaa 3240
gacactttta tgaaacacgg tggatcccta actggctttc aaattgacct ttatagcctt 3300
agacaaccct taggtattta cggagatgac ttctttgatt gtcataacaa ttagtggatg 3360
tgtccagttc tctgtatctt tgacttgatg ctttatacat catttcattt gttgcttcta 3420
agggaataag ccatagaggc ttctccaggt ttaaaagaac agtaaagtac ctggaaaacc 3480
aacattttg aatgtatgga cactggacat gagatatgta caatgaaatc ttaaaagaat 3540
ctaagaattt gccctctttg ccccactcca cccagtaatt tgacattact agtgccatgt 3600
ataggaccca actgagtatt agaatcagtt ttgactatgt ctttgtattt cctaaatctt 3660
ttaatgcata aaccgaatta gggtccagtt ggcctgttaa tggtaaattt acattttaaa 3720
tgactcagtt tgtttttcct gggcgagttt gcaatgtgat aatcagattt tttaaaactg 3780
attaatttgc tttcttgtgt gggtgtactc acattttaaa gtatgaacca cagttaacta 3840
gtggtctcag ggtagtgaa acactcactt ttttttttgt ttgttttttt ttgtttgttg 3900
aaatggctta gttgaagtat acttaaggta ctgatcatgc tgtgttagta atttgggcgg 3960
ggaggggggt aactcagcca tgttttgtgt tggcataaca aaactgttaa tgattgttga 4020
ttacactttt aagtgaattt gtcttttatg aggaacccag tgcaagtcac taaatattgt 4080
ctaatagtga catctgcata agacttgtaa tagctgaagt taattgagct taaaggaatt 4140
gttaccatta aagtctgtgt ttaaagacaa aaaaaaaaaa aaaa 4184

<210> SEQ ID NO 64
<211> LENGTH: 3954
<212> TYPE: DNA
<213> ORGANISM: Homo sapiens

<400> SEQUENCE: 64
gtagttccgt cagagcggac atcttgtggc tgtgtcgtgc gcgtgagccc cgtagggccg 60
gggaggcacc agctgccgcg cggggaggag gccgaggccg cagcttgagg gaggccccgg 120
cccctctagg ccgggaagtt aaacttgtag ccaccacctc cgctcttccc gtcaccctcg 180
cccccacttc gggccgaaag cacggtacag aggctgttgg tggctttgcc acgccacccc 240
acccaccccg gatcgcggct gtcttaaggg acctggattc atcaggggct cttcggggcc 300
tgtgcgagtg ctgatctgct ccgtttttgc aaaaggcgcc tgtgtctggc agagctggtg 360
tgagacgaga caatcctgcc ccgccgccgg gataatcaag agttttggcc ggacctttga 420
gcatacaccg agagagtgag gagccagacg acaagcacac actatggcgc tgaaacggat 480
taataaggaa cttagtgatt tggcccgtga ccctccagca caatgttctg caggtccagt 540
tggggatgat atgtttcatt ggcaagccac aattatggga cctaatgaca gcccatatca 600
aggcggtgta ttctttttga caattcattt tcctacagac taccccttca aaccacctaa 660
ggttgcattt acaacaagaa tttatcatcc aaatattaac agtaatggca gcatttgtct 720
cgatattcta agatcacagt ggtcgcctgc tttaacaatt tctaaagttc ttttatccat 780
ttgttcactg ctatgtgatc caaacccaga tgacccccta gtgccagaga ttgcacggat 840
ctataaaaca gacagagata agtacaacag aatatctcgg gaatggactc agaagtatgc 900
catgtgatgc taccttaaag tcagaataac ctgcattata gctggaataa actttaaatt 960
actgttcctt ttttgatttt cttatccggc tgctccccta tcagacctca tctttttttaa 1020 ttttattttt tgtttacctc cctccattca ttcacatgct catctgagaa gacttaagtt 1080
cttccagctt tggacaataa ctgcttttag aaactgtaaa gtagttacaa gagaacagtt 1140
gcccaagact cagaattttt aaaaaaaaaa atggagcatg tgtattatgt ggccaatgtc 1200
ttcactctaa cttggttatg agactaaaac cattcctcac tgctctaaca tgctgaagaa 1260
atcatctgag gggggaggga gatggatgctc agttgtcaca tcaaaggata cagcattatt 1320
ctagcagcat ccattcttgt ttaagccttc cactgttaga gatttgaggt tacatgatat 1380
gctttatgct cataactgat gtggctggag aattggtatt gaatttatag catcagcaga 1440
acagaaaatg tgatgtattt tatgcatgtc aataaaggaa tgacctgttc ttgttctaca 1500
gagaatggaa attggaagtc aaacaccctt tgtattccaa aatagggtct caaacatttt 1560
gtaattttca tttaaattgt taggaggctt ggagctatta gttaatctat cttccaatac 1620
actgtttaat atagcactga ataaatgatg caagttgtca atggatgagt gatcaactaa 1680
tagctctgct agtaattgat ttattttttct tcaataaagt tgcataaacc aatgagttag 1740
ctgcctggat taatcagtat gggaaacaat cttttgtaaa tgcaaagctg ttttttgtat 1800
atactgttgg gatttgcttc attgtttgac atcaaatgat gatgtaaagt tcgaaagagt 1860

-continued

```
gaatattttg ccatgttcag ttaaagtgca cagtctgtta caggttgaca cattgcttga   1920
cctgatttat gcagaattaa taagctattt ggatagtgta gctttaatgt gctgcacatg   1980
atactggcag ccctagagtt catagatgga cttttgggac ccagcagttt tgaaatgtgt   2040
ttatggagtt taagaaattt attttccagg tgcagcccct gtctaactga aatttctctt   2100
caccttgtac acttgacagc tgaaaaaaaa caacatggga gtaataatgg gtcaaaattt   2160
gcaaaataaa gtactgtttt ggtgtgggag ttgtcatgag gctgtgttga agtgacttat   2220
ctatgtggga tattgagtat ccattgaaat ggatttgttc agccatttac attaatgagc   2280
atttaaatgc aacagatatc atttcaggtg acttaacatg aatgaataaa agtcaatgct   2340
attggattgt tttttgtttg acaagtgcta tctgtgccac tgatttaact tctgtagtaa   2400
caagggcatt accattcttc acctttccta attctgatcc catagtttta catttttcct   2460
gtttattttg attttgttca ctgctttatt tcttaaagtt ctagcacatc tgtgactcct   2520
ccacttccac atttttgcac tgcttacact tacgtgcaat cttattcctt gtctgcacac   2580
acatgtggaa agctagaaat aaatgttaaa acttactttt tataaacatt ttaatatgta   2640
gtttggacat gatttattga cttaaggttc ttctctaaac tggaagtgaa atgcatgcct   2700
tctgaagatg ttctggcttt gttaattctg taatcatttc attggggaaa aaaccagcta   2760
cgcagttttt ccaatgagtg aattttttca ttttgtgttt tgcttaaaac ggctccttca   2820
gggtagatgt catactgcat aactttttg gattcaaatt atgaatgaga aattagttaa    2880
cattctgctc cacaaggtaa gaaaaactgc tctttggctc tattttcaaa attacttctg   2940
agatgcatat agtctcaaaa taacagcttt agtaggcata tcacttcttg aaagccaaac   3000
atgagtgtaa gacactttta tgaaacacgg tggatcccta actggctttc aaattgacct   3060
ttatagcctt agacaaccct taggtattta cggagatgac ttctttgatt gtcataacaa   3120
ttagtggatg tgtccagttc tctgtatctt tgacttgatg ctttatacat catttcattt   3180
gttgcttcta agggaataag ccatagaggc ttctccaggt ttaaaagaac agtaaagtac   3240
ctggaaaacc aacattttg aatgtatgga cactggacat gagatatgta caatgaaatc    3300
ttaaaagaat ctaagaattt gccctctttg ccccactcca cccagtaatt tgacattact   3360
agtgccatgt ataggaccca actgagtatt agaatcagtt ttgactatgt ctttgtattt   3420
cctaaatctt ttaatgcata aaccgaatta gggtccagtt ggcctgttaa tggtaaattt   3480
acattttaaa tgactcagtt tgtttttcct gggcgagttt gcaatgtgat aatcagattt   3540
tttaaaactg attaatttgc tttcttgtgt gggtgtactc acattttaaa gtatgaacca   3600
cagttaacta gtggtctcag gggtagtgaa acactcactt tttttttgt ttgtttttt     3660
ttgtttgttg aaatggctta gttgaagtat acttaaggta ctgatcatgc tgtgttagta   3720
atttgggcgg ggaggggggt aactcagcca tgttttgtgt tggcataaca aaactgttaa   3780
tgattgttga ttacactttt aagtgaattt gtcttttatg aggaacccag tgcaagtcac   3840
taaatattgt ctaatagtga catctgcata agacttgtaa tagctgaagt taattgagct   3900
taaaggaatt gttaccatta aagtctgtgt ttaaagacaa aaaaaaaaaa aaaa         3954
```

<210> SEQ ID NO 65
<211> LENGTH: 3833
<212> TYPE: DNA
<213> ORGANISM: Homo sapiens

<400> SEQUENCE: 65

```
accaagtgag gaaactgggg gacgctgtgg ggaggggcgt ggggctggat cgcgcagcgg     60
ctgcttcctt taccttcctc ccatggtctc cttccggttc tcgatgcttc tctgagccta    120
agggtttccg ccactcgttc accctccccc cagctcatga tcctcctccc tcccccgccc    180
tcctggtcca atctccgatc tgtttagtaa gaaggcgcct gtgtctggca gagctggtgt    240
gagacgagac aatcctgccc cgccgccggg ataatcaaga gttttggccg gacctttgag    300
catacaccga gagagtgagg agccagacga caagcacaca ctatggcgct gaaacggatt    360
aataaggaac ttagtgattt ggcccgtgac cctccagcac aatgttctgc aggtccagtt    420
ggggatgata tgtttcattg gcaagccaca attatgggac ctaatgacag cccatatcaa    480
ggcggtgtat tctttttgac aattcatttt cctacagact accccttcaa accacctaag    540
gttgcattta caacaagaat ttatcatcca aatattaaca gtaatggcag catttgtctc    600
gatattctaa gatcacagtg gtcgcctgct ttaacaattt ctaaagttct tttatccatt    660
tgttcactgc tatgtgatcc aaacccagat gaccccctag tgccagagat tgcacggatc    720
tataaaacag acagagataa gtacaacaga atatctcggg aatggactca gaagtatgcc    780
atgtgatgct accttaaagt cagaataacc tgcattatag ctggaataaa ctttaaatta    840
ctgttccttt tttgattttc ttatccggct gctcccctat cagacctcat ctttttttaat    900
tttatttttt gtttacctcc ctccattcat tcacatgctc atctgagaag acttaagttc    960
ttccagcttt ggacaataac tgcttttaga aactgtaaag tagttacaag agaacagttg   1020
cccaagactc agaattttta aaaaaaaaaa tggagcatgt gtattatgtg gccaatgtct   1080
tcactctaac ttggttatga gactaaaacc attcctcact gctctaacat gctgaagaaa   1140
tcatctgagg gggagggaga tggatgctca gttgtcacat caaaggatac agcattattc   1200
tagcagcatc cattcttgtt taagccttcc actgttagag atttgaggtt acatgatatg   1260
ctttatgctc ataactgatg tggctggaga attggtattg aatttatagc atcagcagaa   1320
cagaaaatgt gatgtatttt atgcatgtca ataaaggaat gacctgttct tgttctacag   1380
agaatggaaa ttggaagtca aacacccttt gtattccaaa atagggtctc aaacattttg   1440
taattttcat ttaaattgtt aggaggcttg gagctattag ttaatctatc ttccaataca   1500
ctgtttaata tagcactgaa taaatgatgc aagttgtcaa tggatgagtg atcaactaat   1560
agctctgcta gtaattgatt tatttttctt caataaagtt gcataaacca atgagttagc   1620
tgcctggatt aatcagtatg ggaaacaatc ttttgtaaat gcaaagctgt tttttgtata   1680
tactgttggg atttgcttca ttgtttgaca tcaaatgatg atgtaaagtt cgaaagagtg   1740
aatattttgc catgttcagt taaagtgcac agtctgttac aggttgacac attgcttgac   1800
ctgatttatg cagaattaat aagctatttg gatagtgtag ctttaatgtg ctgcacatga   1860
tactggcagc cctagagttc atagatggac ttttgggacc cagcagtttt gaaatgtgtt   1920
tatggagttt aagaaattta ttttccaggt gcagcccctg tctaactgaa atttctcttc   1980
accttgtaca cttgacagct gaaaaaaaac aacatgggag taataatggg tcaaaatttg   2040
caaaataaag tactgttttg gtgtgggagt tgtcatgagg ctgtgttgaa gtgacttatc   2100
tatgtgggat attgagtatc cattgaaatg gatttgttca gccatttaca ttaatgagca   2160
tttaaatgca acagatatca tttcaggtga cttaacatga atgaataaaa gtcaatgcta   2220
ttggattgtt ttttgtttga caagtgctat ctgtgccact gatttaactt ctgtagtaac   2280
```

-continued

```
aagggcatta ccattcttca cctttcctaa ttctgatccc atagttttac atttttcctg   2340

tttattttga ttttgttcac tgctttattt cttaaagttc tagcacatct gtgactcctc   2400

cacttccaca tttttgcact gcttacactt acgtgcaatc ttattccttg tctgcacaca   2460

catgtggaaa gctagaaata aatgttaaaa cttacttttt ataaacattt taatatgtag   2520

tttggacatg atttattgac ttaaggttct tctctaaact ggaagtgaaa tgcatgcctt   2580

ctgaagatgt tctggctttg ttaattctgt aatcatttca ttggggaaaa aaccagctac   2640

gcagtttttc caatgagtga attttttcat tttgtgtttt gcttaaaacg gctccttcag   2700

ggtagatgtc atactgcata actttttttgg attcaaatta tgaatgagaa attagttaac   2760

attctgctcc acaaggtaag aaaaactgct ctttggctct attttcaaaa ttacttctga   2820

gatgcatata gtctcaaaat aacagcttta gtaggcatat cacttcttga aagccaaaca   2880

tgagtgtaag acacttttat gaaacacggt ggatccctaa ctggctttca aattgacctt   2940

tatagcctta gacaaccctt aggtatttac ggagatgact tctttgattg tcataacaat   3000

tagtggatgt gtccagttct ctgtatcttt gacttgatgc tttatacatc atttcatttg   3060

ttgcttctaa gggaataagc catagaggct tctccaggtt taaaagaaca gtaaagtacc   3120

tggaaaacca acatttttga atgtatggac actggacatg agatatgtac aatgaaatct   3180

taaaagaatc taagaatttg ccctctttgc cccactccac ccagtaattt gacattacta   3240

gtgccatgta taggacccaa ctgagtatta gaatcagttt tgactatgtc tttgtatttc   3300

ctaaatcttt taatgcataa accgaattag ggtccagttg gcctgttaat ggtaaattta   3360

cattttaaat gactcagttt gtttttcctg ggcgagtttg caatgtgata atcagatttt   3420

ttaaaactga ttaatttgct ttcttgtgtg ggtgtactca cattttaaag tatgaaccac   3480

agttaactag tggtctcagg ggtagtgaaa cactcacttt tttttttgtt tgtttttttt   3540

tgtttgttga aatggcttag ttgaagtata cttaaggtac tgatcatgct gtgttagtaa   3600

tttgggcggg gagggggggta actcagccat gttttgtgtt ggcataacaa aactgttaat   3660

gattgttgat tacactttta agtgaatttg tcttttatga ggaacccagt gcaagtcact   3720

aaatattgtc taatagtgac atctgcataa gacttgtaat agctgaagtt aattgagctt   3780

aaaggaattg ttaccattaa agtctgtgtt taaagacaaa aaaaaaaaaa aaa          3833
```

```
<210> SEQ ID NO 66
<211> LENGTH: 3856
<212> TYPE: DNA
<213> ORGANISM: Homo sapiens

<400> SEQUENCE: 66
```

```
tggggaattc catttcctct accaaccacc ggcataagca ttcaggggcg ttgctttcct     60

ggcagtggcc cgccccagtt cgagccggtg ccttactgcg tctcgcgaga acttatgcat    120

tttggaggcg gaaccccgtc aggaaaagcg cacaaaactg ctcttaagtc attgcagagc    180

taccgcttcg gttagccagc cacgaagttc tcgcgagagt cgtctcctcg ataccaagcg    240

cctgtgtctg gcagagctgg tgtgagacga gacaatcctg ccccgccgcc gggataatca    300

agagttttgg ccggaccttt gagcatacac cgagagagtg aggagccaga cgacaagcac    360

acactatggc gctgaaacgg attaataagg aacttagtga tttggcccgt gaccctccag    420

cacaatgttc tgcaggtcca gttggggatg atatgtttca ttggcaagcc acaattatgg    480

gacctaatga cagcccatat caaggcggtg tattcttttt gacaattcat tttcctacag    540

actacccctt caaaccacct aaggttgcat ttacaacaag aatttatcat ccaaatatta    600
```

-continued

```
acagtaatgg cagcatttgt ctcgatattc taagatcaca gtggtcgcct gctttaacaa    660
tttctaaagt tcttttatcc atttgttcac tgctatgtga tccaaaccca gatgaccccc    720
tagtgccaga gattgcacgg atctataaaa cagacagaga taagtacaac agaatatctc    780
gggaatggac tcagaagtat gccatgtgat gctaccttaa agtcagaata acctgcatta    840
tagctggaat aaactttaaa ttactgttcc ttttttgatt ttcttatccg gctgctcccc    900
tatcagacct catctttttt aattttattt tttgtttacc tccctccatt cattcacatg    960
ctcatctgag aagacttaag ttcttccagc tttggacaat aactgctttt agaaactgta   1020
aagtagttac aagagaacag ttgcccaaga ctcagaattt ttaaaaaaaa aaatggagca   1080
tgtgtattat gtggccaatg tcttcactct aacttggtta tgagactaaa accattcctc   1140
actgctctaa catgctgaag aaatcatctg agggggaggg agatggatgc tcagttgtca   1200
catcaaagga tacagcatta ttctagcagc atccattctt gtttaagcct tccactgtta   1260
gagatttgag gttacatgat atgctttatg ctcataactg atgtggctgg agaattggta   1320
ttgaatttat agcatcagca gaacagaaaa tgtgatgtat tttatgcatg tcaataaagg   1380
aatgacctgt tcttgttcta cagagaatgg aaattggaag tcaaacaccc tttgtattcc   1440
aaaatagggt ctcaaacatt ttgtaatttt catttaaatt gttaggaggc ttggagctat   1500
tagttaatct atcttccaat acactgttta atatagcact gaataaatga tgcaagttgt   1560
caatggatga gtgatcaact aatagctctg ctagtaattg atttattttt cttcaataaa   1620
gttgcataaa ccaatgagtt agctgcctgg attaatcagt atgggaaaca atcttttgta   1680
aatgcaaagc tgtttttttgt atatactgtt gggatttgct tcattgtttg acatcaaatg   1740
atgatgtaaa gttcgaaaga gtgaatattt tgccatgttc agttaaagtg cacagtctgt   1800
tacaggttga cacattgctt gacctgattt atgcagaatt aataagctat ttggatagtg   1860
tagctttaat gtgctgcaca tgatactggc agccctagag ttcatagatg gacttttggg   1920
acccagcagt tttgaaatgt gtttatggag tttaagaaat ttattttcca ggtgcagccc   1980
ctgtctaact gaaatttctc ttcaccttgt acacttgaca gctgaaaaaa aacaacatgg   2040
gagtaataat gggtcaaaat ttgcaaaata aagtactgtt ttggtgtggg agttgtcatg   2100
aggctgtgtt gaagtgactt atctatgtgg gatattgagt atccattgaa atggatttgt   2160
tcagccattt acattaatga gcatttaaat gcaacagata tcatttcagg tgacttaaca   2220
tgaatgaata aaagtcaatg ctattggatt gttttttgtt tgacaagtgc tatctgtgcc   2280
actgatttaa cttctgtagt aacaagggca ttaccattct tcacctttcc taattctgat   2340
cccatagttt tacatttttc ctgtttattt tgattttgtt cactgcttta tttcttaaag   2400
ttctagcaca tctgtgactc ctccacttcc acatttttgc actgcttaca cttacgtgca   2460
atcttattcc ttgtctgcac acacatgtgg aaagctagaa ataaatgtta aaacttactt   2520
tttataaaca ttttaatatg tagtttggac atgatttatt gacttaaggt tcttctctaa   2580
actggaagtg aaatgcatgc cttctgaaga tgttctggct ttgttaattc tgtaatcatt   2640
tcattgggga aaaaaccagc tacgcagttt ttccaatgag tgaatttttt cattttgtgt   2700
tttgcttaaa acggctcctt cagggtagat gtcatactgc ataacttttt tggattcaaa   2760
ttatgaatga gaaattagtt aacattctgc tccacaaggt aagaaaaact gctctttggc   2820
tctattttca aaattacttc tgagatgcat atagtctcaa aataacagct ttagtaggca   2880
tatcacttct tgaaagccaa acatgagtgt aagacacttt tatgaaacac ggtggatccc   2940
```

taactggctt tcaaattgac ctttatagcc ttagacaacc cttaggtatt tacggagatg 3000
acttctttga ttgtcataac aattagtgga tgtgtccagt tctctgtatc tttgacttga 3060
tgctttatac atcatttcat ttgttgcttc taagggaata agccatagag gcttctccag 3120
gtttaaaaga acagtaaagt acctggaaaa ccaacatttt tgaatgtatg gacactggac 3180
atgagatatg tacaatgaaa tcttaaaaga atctaagaat ttgccctctt tgccccactc 3240
cacccagtaa tttgacatta ctagtgccat gtataggacc caactgagta ttagaatcag 3300
ttttgactat gtctttgtat ttcctaaatc ttttaatgca taaaccgaat tagggtccag 3360
ttggcctgtt aatggtaaat ttacatttta aatgactcag tttgttttc ctgggcgagt 3420 ttgcaatgtg ataatcagat tttttaaaac tgattaattt gctttcttgt gtgggtgtac 3480
tcacatttta aagtatgaac cacagttaac tagtggtctc aggggtagtg aaacactcac 3540 ttttttttt gtttgtttt ttttgtttgt tgaaatggct tagttgaagt atacttaagg 3600
tactgatcat gctgtgttag taatttgggc ggggaggggg gtaactcagc catgttttgt 3660
gttggcataa caaaactgtt aatgattgtt gattacactt ttaagtgaat ttgtctttta 3720
tgaggaaccc agtgcaagtc actaaatatt gtctaatagt gacatctgca taagacttgt 3780
aatagctgaa gttaattgag cttaaaggaa ttgttaccat taaagtctgt gtttaaagac 3840
aaaaaaaaaa aaaaaa 3856

<210> SEQ ID NO 67
<211> LENGTH: 3798
<212> TYPE: DNA
<213> ORGANISM: Homo sapiens

<400> SEQUENCE: 67
ggcggactgc cgaggcgcgg gaactggcgg gtagcgaggc cctcctcgga atctcgtgtg 60
aaggtggccc tcctcttggg cctttaacgt ctgtagatgc tggagaccag cagaaaggat 120
actgtgtgcg atgagataag catgtgagaa tgctttctaa ccgaaagtgc ctttcaaaag 180
cgcctgtgtc tggcagagct ggtgtgagac gagacaatcc tgccccgccg ccgggataat 240
caagagtttt ggccggacct ttgagcatac accgagagag tgaggagcca gacgacaagc 300
acacactatg gcgctgaaac ggattaataa ggaacttagt gatttggccc gtgaccctcc 360
agcacaatgt tctgcaggtc cagttgggga tgatatgttt cattggcaag ccacaattat 420
gggacctaat gacagcccat atcaaggcgg tgtattcttt ttgacaattc attttcctac 480
agactacccc ttcaaaccac ctaaggttgc atttacaaca agaatttatc atccaaatat 540
taacagtaat ggcagcattt gtctcgatat tctaagatca cagtggtcgc ctgctttaac 600
aatttctaaa gttcttttat ccatttgttc actgctatgt gatccaaacc cagatgaccc 660
cctagtgcca gagattgcac ggatctataa aacagacaga gataagtaca acagaatatc 720
tcgggaatgg actcagaagt atgccatgtg atgctacctt aaagtcagaa taacctgcat 780
tatagctgga ataaacttta aattactgtt cctttttga ttttcttatc cggctgctcc 840
cctatcagac ctcatctttt ttaattttat tttttgttta cctccctcca ttcattcaca 900
tgctcatctg agaagactta agttcttcca gctttggaca ataactgctt ttagaaactg 960
taaagtagtt acaagagaac agttgcccaa gactcagaat ttttaaaaaa aaaaatggag 1020
catgtgtatt atgtggccaa tgtcttcact ctaacttggt tatgagacta aaaccattcc 1080
tcactgctct aacatgctga agaaatcatc tgagggggag ggagatggat gctcagttgt 1140
cacatcaaag gatacagcat tattctagca gcatccattc ttgtttaagc cttccactgt 1200
tagagatttg aggttacatg atatgcttta tgctcataac tgatgtggct ggagaattgg 1260
tattgaattt atagcatcag cagaacagaa aatgtgatgt attttatgca tgtcaataaa 1320
ggaatgacct gttcttgttc tacagagaat ggaaattgga agtcaaacac cctttgtatt 1380
ccaaaatagg gtctcaaaca ttttgtaatt ttcatttaaa ttgttaggag gcttggagct 1440
attagttaat ctatcttcca atacactgtt taatatagca ctgaataaat gatgcaagtt 1500
gtcaatggat gagtgatcaa ctaatagctc tgctagtaat tgatttattt ttcttcaata 1560
aagttgcata aaccaatgag ttagctgcct ggattaatca gtatgggaaa caatcttttg 1620
taaatgcaaa gctgtttttt gtatatactg ttgggatttg cttcattgtt tgacatcaaa 1680
tgatgatgta aagttcgaaa gagtgaatat tttgccatgt tcagttaaag tgcacagtct 1740
gttacaggtt gacacattgc ttgacctgat ttatgcagaa ttaataagct atttggatag 1800
tgtagcttta atgtgctgca catgatactg gcagccctag agttcataga tggacttttg 1860
ggacccagca gttttgaaat gtgtttatgg agtttaagaa atttattttc caggtgcagc 1920
ccctgtctaa ctgaaatttc tcttcacctt gtacacttga cagctgaaaa aaaacaacat 1980
gggagtaata atgggtcaaa atttgcaaaa taaagtactg ttttggtgtg ggagttgtca 2040
tgaggctgtg ttgaagtgac ttatctatgt gggatattga gtatccattg aaatggattt 2100
gttcagccat ttacattaat gagcatttaa atgcaacaga tatcatttca ggtgacttaa 2160
catgaatgaa taaaagtcaa tgctattgga ttgtttttg tttgacaagt gctatctgtg 2220
ccactgattt aacttctgta gtaacaaggg cattaccatt cttcaccttt cctaattctg 2280
atcccatagt tttacatttt tcctgtttat tttgattttg ttcactgctt tatttcttaa 2340
agttctagca catctgtgac tcctccactt ccacattttt gcactgctta cacttacgtg 2400
caatcttatt ccttgtctgc acacacatgt ggaaagctag aaataaatgt taaaacttac 2460
tttttataaa cattttaata tgtagtttgg acatgattta ttgacttaag gttcttctct 2520
aaactggaag tgaaatgcat gccttctgaa gatgttctgg ctttgttaat tctgtaatca 2580
tttcattggg gaaaaaacca gctacgcagt ttttccaatg agtgaatttt ttcattttgt 2640
gttttgctta aaacggctcc ttcagggtag atgtcatact gcataacttt tttggattca 2700
aattatgaat gagaaattag ttaacattct gctccacaag gtaagaaaaa ctgctctttg 2760
gctctatttt caaaattact tctgagatgc atatagtctc aaaataacag ctttagtagg 2820
catatcactt cttgaaagcc aaacatgagt gtaagacact tttatgaaac acggtggatc 2880
cctaactggc tttcaaattg acctttatag ccttagacaa cccttaggta tttacggaga 2940
tgacttcttt gattgtcata acaattagtg gatgtgtcca gttctctgta tctttgactt 3000
gatgctttat acatcatttc atttgttgct tctaagggaa taagccatag aggcttctcc 3060
aggtttaaaa gaacagtaaa gtacctggaa aaccaacatt tttgaatgta tggacactgg 3120
acatgagata tgtacaatga aatcttaaaa gaatctaaga atttgccctc tttgccccac 3180
tccacccagt aatttgacat tactagtgcc atgtatagga cccaactgag tattagaatc 3240
agttttgact atgtctttgt atttcctaaa tcttttaatg cataaaccga attagggtcc 3300
agttggcctg ttaatggtaa atttacattt taaatgactc agtttgtttt tcctgggcga 3360
gtttgcaatg tgataatcag attttttaaa actgattaat ttgctttctt gtgtgggtgt 3420
actcacattt taaagtatga accacagtta actagtggtc tcaggggtag tgaaacactc 3480
actttttttt ttgtttgttt ttttttgttt gttgaaatgg cttagttgaa gtatacttaa 3540
ggtactgatc atgctgtgtt agtaatttgg gcggggaggg gggtaactca gccatgtttt 3600
gtgttggcat aacaaaactg ttaatgattg ttgattacac ttttaagtga atttgtcttt 3660
tatgaggaac ccagtgcaag tcactaaata ttgtctaata gtgacatctg cataagactt 3720
gtaatagctg aagttaattg agcttaaagg aattgttacc attaaagtct gtgtttaaag 3780
acaaaaaaaa aaaaaaaa 3798

<210> SEQ ID NO 68
<211> LENGTH: 4141
<212> TYPE: DNA
<213> ORGANISM: Homo sapiens

<400> SEQUENCE: 68
accaagtgag gaaactgggg gacgctgtgg ggaggggcgt ggggctggat cgcgcagcgg 60
ctgcttcctt taccttcctc ccatggtctc cttccggttc tcgatgcttc tctgagccta 120
agggtttccg ccactcgttc accctccccc cagctcatga tcctcctccc tcccccgccc 180
tcctggtcca atctccgatc tgtttagtaa gaaggtgctg ttccgagaag aaggaaaagg 240
gcttgacacg tattcactcg gccccggacg tgggaagcaa gccgtctggc ttcggcctca 300
catcggtctt gtgctcggga cggcggcgtt ggcggactga tccgcggcgg tgaagaggca 360
ggaggagggg gaggggcgga gcgtggcagc tggcagtagt tccgtcagag cggacatctt 420
gtggctgtgt cgtgcgcgtg agccccgtag ggccggggag gcaccagctg ccgcgcgggg 480
aggaggccga ggccgcagct tgagggaggc cccggcccct ctgcgcctgt gtctggcaga 540
gctggtgtga gacgagacaa tcctgccccg ccgccgggat aatcaagagt tttggccgga 600
cctttgagca tacaccgaga gagtgaggag ccagacgaca agcacacact atggcgctga 660
aacggattaa taaggaactt agtgatttgg cccgtgaccc tccagcacaa tgttctgcag 720
gtccagttgg ggatgatatg tttcattggc aagccacaat tatgggacct aatgacagcc 780
catatcaagg cggtgtattc tttttgacaa ttcattttcc tacagactac cccttcaaac 840
cacctaaggt tgcatttaca acaagaattt atcatccaaa tattaacagt aatggcagca 900
tttgtctcga tattctaaga tcacagtggt cgcctgcttt aacaatttct aaagttcttt 960
tatccatttg ttcactgcta tgtgatccaa acccagatga ccccctagtg ccagagattg 1020
cacggatcta taaaacagac agagataagt acaacagaat atctcgggaa tggactcaga 1080
agtatgccat gtgatgctac cttaaagtca gaataacctg cattatagct ggaataaact 1140
ttaaattact gttccttttt tgattttctt atccggctgc tcccctatca gacctcatct 1200
tttttaattt tatttttttgt ttacctccct ccattcattc acatgctcat ctgagaagac 1260
ttaagttctt ccagctttgg acaataactg cttttagaaa ctgtaaagta gttacaagag 1320
aacagttgcc caagactcag aatttttaaa aaaaaaaatg gagcatgtgt attatgtggc 1380
caatgtcttc actctaactt ggttatgaga ctaaaaccat tcctcactgc tctaacatgc 1440
tgaagaaatc atctgagggg gagggagatg gatgctcagt tgtcacatca aaggatacag 1500
cattattcta gcagcatcca ttcttgttta agccttccac tgttagagat ttgaggttac 1560
atgatatgct ttatgctcat aactgatgtg gctggagaat tggtattgaa tttatagcat 1620
cagcagaaca gaaaatgtga tgtattttat gcatgtcaat aaaggaatga cctgttcttg 1680
ttctacagag aatggaaatt ggaagtcaaa caccctttgt attccaaaat agggtctcaa 1740
acattttgta attttcattt aaattgttag gaggcttgga gctattagtt aatctatctt 1800
ccaatacact gtttaatata gcactgaata aatgatgcaa gttgtcaatg gatgagtgat 1860

-continued

```
caactaatag ctctgctagt aattgattta tttttcttca ataaagttgc ataaaccaat   1920
gagttagctg cctggattaa tcagtatggg aaacaatctt ttgtaaatgc aaagctgttt   1980
tttgtatata ctgttgggat ttgcttcatt gtttgacatc aaatgatgat gtaaagttcg   2040
aaagagtgaa tattttgcca tgttcagtta aagtgcacag tctgttacag gttgacacat   2100
tgcttgacct gatttatgca gaattaataa gctatttgga tagtgtagct ttaatgtgct   2160
gcacatgata ctggcagccc tagagttcat agatggactt ttgggaccca gcagttttga   2220
aatgtgttta tggagtttaa gaaatttatt ttccaggtgc agcccctgtc taactgaaat   2280
ttctcttcac cttgtacact tgacagctga aaaaaaacaa catgggagta ataatgggtc   2340
aaaatttgca aaataaagta ctgttttggt gtgggagttg tcatgaggct gtgttgaagt   2400
gacttatcta tgtgggatat tgagtatcca ttgaaatgga tttgttcagc catttacatt   2460
aatgagcatt taaatgcaac agatatcatt tcaggtgact taacatgaat gaataaaagt   2520
caatgctatt ggattgtttt ttgtttgaca agtgctatct gtgccactga tttaacttct   2580
gtagtaacaa gggcattacc attcttcacc tttcctaatt ctgatcccat agttttacat   2640
ttttcctgtt tattttgatt ttgttcactg ctttatttct taaagttcta gcacatctgt   2700
gactcctcca cttccacatt tttgcactgc ttacacttac gtgcaatctt attccttgtc   2760
tgcacacaca tgtggaaagc tagaaataaa tgttaaaact tactttttat aaacatttta   2820
atatgtagtt tggacatgat ttattgactt aaggttcttc tctaaactgg aagtgaaatg   2880
catgccttct gaagatgttc tggctttgtt aattctgtaa tcatttcatt ggggaaaaaa   2940
ccagctacgc agtttttcca atgagtgaat tttttcattt tgtgttttgc ttaaaacggc   3000
tccttcaggg tagatgtcat actgcataac ttttttggat tcaaattatg aatgagaaat   3060
tagttaacat tctgctccac aaggtaagaa aaactgctct ttggctctat tttcaaaatt   3120
acttctgaga tgcatatagt ctcaaaataa cagctttagt aggcatatca cttcttgaaa   3180
gccaaacatg agtgtaagac acttttatga aacacggtgg atccctaact ggctttcaaa   3240
ttgaccttta tagccttaga caacccttag gtatttacgg agatgacttc tttgattgtc   3300
ataacaatta gtggatgtgt ccagttctct gtatctttga cttgatgctt tatacatcat   3360
ttcatttgtt gcttctaagg gaataagcca tagaggcttc tccaggttta aaagaacagt   3420
aaagtacctg gaaaaccaac atttttgaat gtatggacac tggacatgag atatgtacaa   3480
tgaaatctta aaagaatcta agaatttgcc ctctttgccc cactccaccc agtaatttga   3540
cattactagt gccatgtata ggacccaact gagtattaga atcagttttg actatgtctt   3600
tgtatttcct aaatctttta atgcataaac cgaattaggg tccagttggc ctgttaatgg   3660
taaatttaca ttttaaatga ctcagtttgt ttttcctggg cgagtttgca atgtgataat   3720
cagattttttt aaaactgatt aatttgcttt cttgtgtggg tgtactcaca ttttaaagta   3780
tgaaccacag ttaactagtg gtctcagggg tagtgaaaca ctcacttttt tttttgtttg   3840
tttttttttg tttgttgaaa tggcttagtt gaagtatact taaggtactg atcatgctgt   3900
gttagtaatt tgggcgggga ggggggtaac tcagccatgt tttgtgttgg cataacaaaa   3960
ctgttaatga ttgttgatta cacttttaag tgaatttgtc ttttatgagg aacccagtgc   4020
aagtcactaa atattgtcta atagtgacat ctgcataaga cttgtaatag ctgaagttaa   4080
ttgagcttaa aggaattgtt accattaaag tctgtgttta aagacaaaaa aaaaaaaaaa   4140
a                                                                   4141
```

<210> SEQ ID NO 69
<211> LENGTH: 4216
<212> TYPE: DNA
<213> ORGANISM: Homo sapiens

<400> SEQUENCE: 69
gggcgcgcgc gggagcgcgc tggaaggcgg agtgagtgta cggtggcgtc aggggtgaca 60
cagaatagct cgctgcgagg atagcaatac acatcaagtc tcccttcctt tatttccttc 120
cttttcccgg ccgcaccttt ggacagaaac cgaaagcagc ccggcgtccg tccggagtct 180
tatgcttccc cctcccccct tgcctttctt tgccctagtg acgccggtat agcgccgact 240
aggccccggc tcctcctctg ctgggctccg gaccctgccc cgcacccacc cctttctcct 300
acgcctcttc ctctcccacc cgggtctctt cctttctaga ggccgggaag ttaaacttgt 360
agccaccacc tccgctcttc ccgtcaccct cgccccccact tcgggccgaa agcacggtac 420
agaggctgtt ggtggctttg ccacgccacc ccacccaccc cggatcgcgg ctgtcttaag 480
ggacctggat tcatcagggg ctcttcgggg cctgtgcgag tgctgatctg ctccgttttt 540
gcaaaaggcg cctgtgtctg gcagagctgg tgtgagacga gacaatcctg ccccgccgcc 600
gggataatca agagttttgg ccggaccttt gagcatacac cgagagagtg aggagccaga 660
cgacaagcac acactatggc gctgaaacgg attaataagg aacttagtga tttggcccgt 720
gaccctccag cacaatgttc tgcaggtcca gttggggatg atatgtttca ttggcaagcc 780
acaattatgg gacctaatga cagcccatat caaggcggtg tattcttttt gacaattcat 840
tttcctacag actacccctt caaaccacct aaggttgcat ttacaacaag aatttatcat 900
ccaaatatta acagtaatgg cagcatttgt ctcgatattc taagatcaca gtggtcgcct 960
gctttaacaa tttctaaagt tcttttatcc atttgttcac tgctatgtga tccaaaccca 1020
gatgaccccc tagtgccaga gattgcacgg atctataaaa cagacagaga taagtacaat 1080
aggttagcaa gagagtggac agagaaatac gctatgttgt agggtacaac agaatatctc 1140
gggaatggac tcagaagtat gccatgtgat gctaccttaa agtcagaata acctgcatta 1200
tagctggaat aaactttaaa ttactgttcc tttttttgatt ttcttatccg gctgctcccc 1260
tatcagacct catctttttt aattttattt tttgtttacc tccctccatt cattcacatg 1320
ctcatctgag aagacttaag ttcttccagc tttggacaat aactgctttt agaaactgta 1380
aagtagttac aagagaacag ttgcccaaga ctcagaattt ttaaaaaaaa aaatggagca 1440
tgtgtattat gtggccaatg tcttcactct aacttggtta tgagactaaa accattcctc 1500
actgctctaa catgctgaag aaatcatctg agggggaggg agatggatgc tcagttgtca 1560
catcaaagga tacagcatta ttctagcagc atccattctt gtttaagcct tccactgtta 1620
gagatttgag gttacatgat atgctttatg ctcataactg atgtggctgg agaattggta 1680
ttgaatttat agcatcagca gaacagaaaa tgtgatgtat tttatgcatg tcaataaagg 1740
aatgacctgt tcttgttcta cagagaatgg aaattggaag tcaaacaccc tttgtattcc 1800
aaaatagggt ctcaaacatt ttgtaatttt catttaaatt gttaggaggc ttggagctat 1860
tagttaatct atcttccaat acactgttta atatagcact gaataaatga tgcaagttgt 1920
caatggatga gtgatcaact aatagctctg ctagtaattg atttattttt cttcaataaa 1980
gttgcataaa ccaatgagtt agctgcctgg attaatcagt atgggaaaca atcttttgta 2040
aatgcaaagc tgttttttgt atatactgtt gggatttgct tcattgtttg acatcaaatg 2100
atgatgtaaa gttcgaaaga gtgaatattt tgccatgttc agttaaagtg cacagtctgt 2160
tacaggttga cacattgctt gacctgattt atgcagaatt aataagctat ttggatagtg 2220
tagctttaat gtgctgcaca tgatactggc agccctagag ttcatagatg gacttttggg 2280
acccagcagt tttgaaatgt gtttatggag tttaagaaat ttattttcca ggtgcagccc 2340
ctgtctaact gaaatttctc ttcaccttgt acacttgaca gctgaaaaaa aacaacatgg 2400
gagtaataat gggtcaaaat ttgcaaaata aagtactgtt ttggtgtggg agttgtcatg 2460
aggctgtgtt gaagtgactt atctatgtgg gatattgagt atccattgaa atggatttgt 2520
tcagccattt acattaatga gcatttaaat gcaacagata tcatttcagg tgacttaaca 2580
tgaatgaata aaagtcaatg ctattggatt gtttttttgtt tgacaagtgc tatctgtgcc 2640
actgatttaa cttctgtagt aacaagggca ttaccattct tcacctttcc taattctgat 2700
cccatagttt tacatttttc ctgtttattt tgattttgtt cactgcttta tttcttaaag 2760
ttctagcaca tctgtgactc ctccacttcc acatttttgc actgcttaca cttacgtgca 2820
atcttattcc ttgtctgcac acacatgtgg aaagctagaa ataaatgtta aaacttactt 2880
tttataaaca ttttaatatg tagtttggac atgatttatt gacttaaggt tcttctctaa 2940
actggaagtg aaatgcatgc cttctgaaga tgttctggct ttgttaattc tgtaatcatt 3000
tcattgggga aaaaaccagc tacgcagttt ttccaatgag tgaatttttt cattttgtgt 3060
tttgcttaaa acggctcctt cagggtagat gtcatactgc ataacttttt tggattcaaa 3120
ttatgaatga gaaattagtt aacattctgc tccacaaggt aagaaaaact gctctttggc 3180
tctattttca aaattacttc tgagatgcat atagtctcaa aataacagct ttagtaggca 3240
tatcacttct tgaaagccaa acatgagtgt aagacacttt tatgaaacac ggtggatccc 3300
taactggctt tcaaattgac ctttatagcc ttagacaacc cttaggtatt tacggagatg 3360
acttctttga ttgtcataac aattagtgga tgtgtccagt tctctgtatc tttgacttga 3420
tgctttatac atcatttcat ttgttgcttc taagggaata agccatagag gcttctccag 3480
gtttaaaaga acagtaaagt acctggaaaa ccaacatttt tgaatgtatg gacactggac 3540
atgagatatg tacaatgaaa tcttaaaaga atctaagaat ttgccctctt tgccccactc 3600
cacccagtaa tttgacatta ctagtgccat gtataggacc caactgagta ttagaatcag 3660
ttttgactat gtctttgtat ttcctaaatc ttttaatgca taaaccgaat tagggtccag 3720
ttggcctgtt aatggtaaat ttacatttta aatgactcag tttgtttttc ctgggcgagt 3780
ttgcaatgtg ataatcagat tttttaaaac tgattaattt gctttcttgt gtgggtgtac 3840
tcacatttta aagtatgaac cacagttaac tagtggtctc aggggtagtg aaacactcac 3900 ttttttttt gtttgtttt ttttgtttgt tgaaatggct tagttgaagt atacttaagg 3960
tactgatcat gctgtgttag taatttgggc ggggaggggg gtaactcagc catgttttgt 4020
gttggcataa caaaactgtt aatgattgtt gattacactt ttaagtgaat ttgtctttta 4080
tgaggaaccc agtgcaagtc actaaatatt gtctaatagt gacatctgca taagacttgt 4140
aatagctgaa gttaattgag cttaaaggaa ttgttaccat taaagtctgt gtttaaagac 4200
aaaaaaaaaa aaaaaa 4216

<210> SEQ ID NO 70
<211> LENGTH: 3646
<212> TYPE: DNA
<213> ORGANISM: Homo sapiens

<400> SEQUENCE: 70

```
ggcggactgc cgaggcgcgg gaactggcgg gtagcgaggc cctcctcgga atctcgtgtg     60
aaggtggccc tcctcttggg cctttaacgt ctgtagatgc tggagaccag cagaaaggat    120
actgtgtgcg atgagataag catgtgagaa tgctttctaa ccgaaagtgc ctttcaaaag    180
aacttagtga tttggcccgt gaccctccag cacaatgttc tgcaggtcca gttggggatg    240
atatgtttca ttggcaagcc acaattatgg gacctaatga cagcccatat caaggcggtg    300
tattcttttt gacaattcat ttcctacag actacccctt caaaccacct aaggttgcat    360
ttacaacaag aatttatcat ccaaatatta acagtaatgg cagcatttgt ctcgatattc    420
taagatcaca gtggtcgcct gctttaacaa tttctaaagt tcttttatcc atttgttcac    480
tgctatgtga tccaaaccca gatgaccccc tagtgccaga gattgcacgg atctataaaa    540
cagacagaga taagtacaac agaatatctc gggaatggac tcagaagtat gccatgtgat    600
gctaccttaa agtcagaata acctgcatta tagctggaat aaactttaaa ttactgttcc    660
ttttttgatt ttcttatccg gctgctcccc tatcagacct catctttttt aattttattt    720
tttgtttacc tccctccatt cattcacatg ctcatctgag aagacttaag ttcttccagc    780
tttggacaat aactgctttt agaaactgta aagtagttac aagagaacag ttgcccaaga    840
ctcagaattt ttaaaaaaaa aaatggagca tgtgtattat gtggccaatg tcttcactct    900
aacttggtta tgagactaaa accattcctc actgctctaa catgctgaag aaatcatctg    960
agggggaggg agatggatgc tcagttgtca catcaaagga tacagcatta ttctagcagc   1020
atccattctt gtttaagcct tccactgtta gagatttgag gttacatgat atgctttatg   1080
ctcataactg atgtggctgg agaattggta ttgaatttat agcatcagca gaacagaaaa   1140
tgtgatgtat tttatgcatg tcaataaagg aatgacctgt tcttgttcta cagagaatgg   1200
aaattggaag tcaaacaccc tttgtattcc aaaatagggt ctcaaacatt ttgtaatttt   1260
catttaaatt gttaggaggc ttggagctat tagttaatct atcttccaat acactgttta   1320
atatagcact gaataaatga tgcaagttgt caatggatga gtgatcaact aatagctctg   1380
ctagtaattg atttattttt cttcaataaa gttgcataaa ccaatgagtt agctgcctgg   1440
attaatcagt atgggaaaca atctttttgta aatgcaaagc tgtttttttgt atatactgtt   1500
gggatttgct tcattgtttg acatcaaatg atgatgtaaa gttcgaaaga gtgaatattt   1560
tgccatgttc agttaaagtg cacagtctgt tacaggttga cacattgctt gacctgattt   1620
atgcagaatt aataagctat ttggatagtg tagctttaat gtgctgcaca tgatactggc   1680
agccctagag ttcatagatg gacttttggg acccagcagt tttgaaatgt gtttatggag   1740
tttaagaaat ttattttcca ggtgcagccc ctgtctaact gaaatttctc ttcaccttgt   1800
acacttgaca gctgaaaaaa aacaacatgg gagtaataat gggtcaaaat ttgcaaaata   1860
aagtactgtt ttggtgtggg agttgtcatg aggctgtgtt gaagtgactt atctatgtgg   1920
gatattgagt atccattgaa atggatttgt tcagccattt acattaatga gcatttaaat   1980
gcaacagata tcatttcagg tgacttaaca tgaatgaata aaagtcaatg ctattggatt   2040
gttttttgtt tgacaagtgc tatctgtgcc actgatttaa cttctgtagt aacaagggca   2100
ttaccattct tcacctttcc taattctgat cccatagttt tacatttttc ctgtttattt   2160
tgattttgtt cactgcttta tttcttaaag ttctagcaca tctgtgactc ctccacttcc   2220
acatttttgc actgcttaca cttacgtgca atcttattcc ttgtctgcac acacatgtgg   2280
```

```
aaagctagaa ataaatgtta aaacttactt tttataaaca ttttaatatg tagtttggac   2340
atgatttatt gacttaaggt tcttctctaa actggaagtg aaatgcatgc cttctgaaga   2400
tgttctggct ttgttaattc tgtaatcatt tcattgggga aaaaaccagc tacgcagttt   2460
ttccaatgag tgaatttttt cattttgtgt tttgcttaaa acggctcctt cagggtagat   2520
gtcatactgc ataacttttt tggattcaaa ttatgaatga gaaattagtt aacattctgc   2580
tccacaaggt aagaaaaact gctctttggc tctattttca aaattacttc tgagatgcat   2640
atagtctcaa aataacagct ttagtaggca tatcacttct tgaaagccaa acatgagtgt   2700
aagacacttt tatgaaacac ggtggatccc taactggctt tcaaattgac ctttatagcc   2760
ttagacaacc cttaggtatt tacggagatg acttctttga ttgtcataac aattagtgga   2820
tgtgtccagt tctctgtatc tttgacttga tgctttatac atcatttcat ttgttgcttc   2880
taagggaata agccatagag gcttctccag gtttaaaaga acagtaaagt acctggaaaa   2940
ccaacatttt tgaatgtatg gacactggac atgagatatg tacaatgaaa tcttaaaaga   3000
atctaagaat ttgccctctt tgccccactc cacccagtaa tttgacatta ctagtgccat   3060
gtataggacc caactgagta ttagaatcag ttttgactat gtctttgtat ttcctaaatc   3120
ttttaatgca taaaccgaat tagggtccag ttggcctgtt aatggtaaat ttacatttta   3180
aatgactcag tttgtttttc ctgggcgagt ttgcaatgtg ataatcagat tttttaaaac   3240
tgattaattt gctttcttgt gtgggtgtac tcacatttta aagtatgaac cacagttaac   3300
tagtggtctc aggggtagtg aaacactcac tttttttttt gtttgttttt ttttgtttgt   3360
tgaaatggct tagttgaagt atacttaagg tactgatcat gctgtgttag taatttgggc   3420
ggggaggggg gtaactcagc catgttttgt gttggcataa caaaactgtt aatgattgtt   3480
gattacactt ttaagtgaat ttgtctttta tgaggaaccc agtgcaagtc actaaatatt   3540
gtctaatagt gacatctgca taagacttgt aatagctgaa gttaattgag cttaaaggaa   3600
ttgttaccat taaagtctgt gtttaaagac aaaaaaaaaa aaaaaa                  3646
```

<210> SEQ ID NO 71
<211> LENGTH: 3669
<212> TYPE: DNA
<213> ORGANISM: Homo sapiens

<400> SEQUENCE: 71

```
agttgcagct tttcacccga agctatttat ccgagggaca ccgggaactg atgtaaaagg     60
cattctggaa gctccctttt ccttttggct ggagagtggg ggtggataag ggtgcgatg    120
gcaagggtgg agtgtttaca gctaacttga aaaaaatgtc atggaataaa ttcagcctta    180
ctagaaaaat tgtggagtgt cggaacttag tgatttggcc cgtgaccctc cagcacaatg    240
ttctgcaggt ccagttgggg atgatatgtt tcattggcaa gccacaatta tgggacctaa    300
tgacagccca tatcaaggcg gtgtattctt tttgacaatt cattttccta cagactaccc    360
cttcaaacca cctaaggttg catttacaac aagaatttat catccaaata ttaacagtaa    420
tggcagcatt tgtctcgata ttctaagatc acagtggtcg cctgctttaa caatttctaa    480
agttctttta tccatttgtt cactgctatg tgatccaaac ccagatgacc ccctagtgcc    540
agagattgca cggatctata aaacagacag agataagtac aacagaatat ctcgggaatg    600
gactcagaag tatgccatgt gatgctacct taaagtcaga ataacctgca ttatagctgg    660
aataaacttt aaattactgt tcctttttttg attttcttat ccggctgctc ccctatcaga    720
cctcatcttt tttaatttta ttttttgttt acctccctcc attcattcac atgctcatct    780
```

```
gagaagactt aagttcttcc agctttggac aataactgct tttagaaact gtaaagtagt    840
tacaagagaa cagttgccca agactcagaa tttttaaaaa aaaaaatgga gcatgtgtat    900
tatgtggcca atgtcttcac tctaacttgg ttatgagact aaaaccattc ctcactgctc    960
taacatgctg aagaaatcat ctgaggggga gggagatgga tgctcagttg tcacatcaaa   1020
ggatacagca ttattctagc agcatccatt cttgtttaag ccttccactg ttagagattt   1080
gaggttacat gatatgcttt atgctcataa ctgatgtggc tggagaattg gtattgaatt   1140
tatagcatca gcagaacaga aaatgtgatg tattttatgc atgtcaataa aggaatgacc   1200
tgttcttgtt ctacagagaa tggaaattgg aagtcaaaca ccctttgtat tccaaaatag   1260
ggtctcaaac attttgtaat tttcatttaa attgttagga ggcttggagc tattagttaa   1320
tctatcttcc aatacactgt ttaatatagc actgaataaa tgatgcaagt tgtcaatgga   1380
tgagtgatca actaatagct ctgctagtaa ttgatttatt tttcttcaat aaagttgcat   1440
aaaccaatga gttagctgcc tggattaatc agtatgggaa acaatctttt gtaaatgcaa   1500
agctgttttt tgtatatact gttgggattt gcttcattgt ttgacatcaa atgatgatgt   1560
aaagttcgaa agagtgaata ttttgccatg ttcagttaaa gtgcacagtc tgttacaggt   1620
tgacacattg cttgacctga tttatgcaga attaataagc tatttggata gtgtagcttt   1680
aatgtgctgc acatgatact ggcagcccta gagttcatag atggactttt gggacccagc   1740
agttttgaaa tgtgtttatg gagtttaaga aatttatttt ccaggtgcag cccctgtcta   1800
actgaaattt ctcttcacct tgtacacttg acagctgaaa aaaaacaaca tgggagtaat   1860
aatgggtcaa aatttgcaaa ataaagtact gttttggtgt gggagttgtc atgaggctgt   1920
gttgaagtga cttatctatg tgggatattg agtatccatt gaaatggatt tgttcagcca   1980
tttacattaa tgagcattta aatgcaacag atatcatttc aggtgactta acatgaatga   2040
ataaaagtca atgctattgg attgtttttt gtttgacaag tgctatctgt gccactgatt   2100
taacttctgt agtaacaagg gcattaccat tcttcacctt tcctaattct gatcccatag   2160
ttttacattt ttcctgttta ttttgatttt gttcactgct ttatttctta aagttctagc   2220
acatctgtga ctcctccact tccacatttt tgcactgctt acacttacgt gcaatcttat   2280
tccttgtctg cacacacatg tggaaagcta gaaataaatg ttaaaactta ctttttataa   2340
acattttaat atgtagtttg gacatgattt attgacttaa ggttcttctc taaactggaa   2400
gtgaaatgca tgccttctga agatgttctg gctttgttaa ttctgtaatc atttcattgg   2460
ggaaaaaacc agctacgcag tttttccaat gagtgaattt tttcattttg tgttttgctt   2520
aaaacggctc cttcagggta gatgtcatac tgcataactt ttttggattc aaattatgaa   2580
tgagaaatta gttaacattc tgctccacaa ggtaagaaaa actgctcttt ggctctattt   2640
tcaaaattac ttctgagatg catatagtct caaaataaca gctttagtag gcatatcact   2700
tcttgaaagc caaacatgag tgtaagacac ttttatgaaa cacggtggat ccctaactgg   2760
ctttcaaatt gacctttata gccttagaca acccttaggt atttacggag atgacttctt   2820
tgattgtcat aacaattagt ggatgtgtcc agttctctgt atctttgact tgatgcttta   2880
tacatcattt catttgttgc ttctaaggga ataagccata gaggcttctc caggtttaaa   2940
agaacagtaa agtacctgga aaaccaacat ttttgaatgt atggacactg gacatgagat   3000
atgtacaatg aaatcttaaa agaatctaag aatttgccct ctttgcccca ctccacccag   3060
taatttgaca ttactagtgc catgtatagg acccaactga gtattagaat cagttttgac   3120
```

```
tatgtctttg tatttcctaa atcttttaat gcataaaccg aattagggtc cagttggcct   3180

gttaatggta aatttacatt ttaaatgact cagtttgttt ttcctgggcg agtttgcaat   3240

gtgataatca gattttttaa aactgattaa tttgctttct tgtgtgggtg tactcacatt   3300

ttaaagtatg aaccacagtt aactagtggt ctcaggggta gtgaaacact cacttttttt   3360

tttgtttgtt ttttttgtt tgttgaaatg gcttagttga agtatactta aggtactgat   3420

catgctgtgt tagtaatttg ggcggggagg ggggtaactc agccatgttt tgtgttggca   3480

taacaaaact gttaatgatt gttgattaca cttttaagtg aatttgtctt ttatgaggaa   3540

cccagtgcaa gtcactaaat attgtctaat agtgacatct gcataagact tgtaatagct   3600

gaagttaatt gagcttaaag gaattgttac cattaaagtc tgtgtttaaa gacaaaaaaa   3660

aaaaaaaaa                                                           3669
```

<210> SEQ ID NO 72
<211> LENGTH: 3670
<212> TYPE: DNA
<213> ORGANISM: Mus musculus

<400> SEQUENCE: 72

```
ggatttgggg gcgggtcccg agccaggaag agagcacaaa actgccctta agtcattgca     60

gacccggagc tgctgcgagc ctgccacgag gttctcgcga gatccgccac ctccatccca    120

agcgcctgtg tctggcagag ccggtgtgag aagaagagac aacccttccc cgccgccggg    180

ataatcaaga attttggccg gacctttgag tacacctcgg gatagtgagg agcccggcga    240

aaagcacaga ctatggcgct gaaacggatt aataaggaac ttagtgattt ggcccgtgac    300

cctccagcac aatgttctgc aggtccagtt ggagatgaca tgtttcattg gcaagccaca    360

attatgggac ctaatgacag cccatatcaa ggtggtgtat tctttttgac aattcatttt    420

cctacagact accccttcaa accacctaag gttgcattta caacaagaat ttatcatcca    480

aatattaaca gtaatggcag catttgtctt gatattctaa gatcacagtg gtctcctgct    540

ttaactattt ctaaagttct tttatccatt tgttcactgc tatgtgatcc aaacccagac    600

gaccccctag tgccagagat tgcacggatc tataaaacag acagagataa gtacaacaga    660

atatctcggg aatggactca gaagtatgcc atgtgatgct accttacagt cagaataacc    720

tgcattatag ctggaataaa ctttaaatta ctgttccttt tttgattttc ttatccggct    780

gctcccctat cagacctcat cttttttaat tttatttttt gtttacctcc ctccattcat    840

tcacatgctc atctgagaag acttaagttc ttccagcttt ggacaataac tgcttttaga    900

aactgtaaag tagttacacg agaacagttg cccaagattc agaaattttt ttaaaaactg    960

gagcatgtgt attatgtggc caatgtcttc actctaactt ggttatgaga ctaaaccaat   1020

cctcactgct ctaacatgct gaagaagcca tctgaggggg agggagatgg atgctcagct   1080

gtcacatcaa aggaagcagc attattctag cagcatccgt tcttgtttaa accttccact   1140

gttagaggtt tgaggttaca tgatatactt tatgctcata actgatgtgg ctggagaatt   1200

ggtattgaat tatagcatca gcagaacaga aaatgtgatg tattttatgc atgtcaataa   1260

aggaatgacc tgttcttgtt ctacagagaa tggaaattgg aagtcaaaca ccctttgtat   1320

tccaaaatag ggtctcaaaa cattttgtaa ttttcattta aattgttagg aggcttggag   1380

ctattagtta atctatcttc caatactgtt taatatagca ctgaataaat gatgcgagtt   1440

gtcaatggat gagtgatcaa ctaatagctc tcctagtaat tgatttattt ttcttcaata   1500

aagttgcata aaccaatgag ttagctgcct ggattaatca gtatgggaaa caatcctttg   1560
```

-continued

```
taaatgcaaa gctgtttttg tatatactgt tgggatttgc ttcattgttt gacatcaaat   1620
gatgatgtaa agttcaaaag agtgaatata ttgccatgtt cagttaaaat gcacagtctg   1680
ttacaggttg acacattgct tgacctgatt tatgcagaat taataagcta ttcaaatagt   1740
gtagctttaa tacgctgcac atgattctgg cagccctaga gttcataaat ggacttggga   1800
ctcagcagtt ttgaaacgtg tatatggagt ttaagaaatt tattttccag gtgcatcccc   1860
ttctaactaa aattttcttc atcttgtaca cttaacagct gaaaaagata tatatatata   1920
taaaacttgg gagtaataat gggtcaaaat ttacaaaata aagtactgtt ttggtgtggg   1980
agttgtcatg aggctgtgtt gaagtgactt aactgtggga tattgactat ccattgagat   2040
ggatttgttc agccatttac attaatgagc atttaaatgc aacagatcat ttcgggtgac   2100
ttaacatgaa tgaataaaaa agtcaatgct attggattgt ttgacaagtg ctatctgtgc   2160
cactaaatct tatgtagtaa taagggcatt accatttttc acccaagttc tgaacctgta   2220
gtttgacacc tttttctagc tttgatttct ccattgcttt cttagtcttg tatttgattt   2280
ctagcacatg tgatgttcac ttccatattt tgcactgctt atatttacgt gcaatcttat   2340
tccttgtccg cacacagatg tggaaagcta gaaataaatg taaaagctta atttttttata   2400
aacatttaaa tatgtaattt ggacatgatt tgttacttaa ggttctttaa actggaagtg   2460
aagtgcatgc cttctgaaga tgttctggct ttattctgta ataagtattt acattggaaa   2520
ataccaattt cgctatacag tttttttttcc acacacccat tttacctttt gcttaaattg   2580
tgggttcttc agggttaatg tcacgctaat taataaaact tttgggttca aatcaagtgt   2640
tcccacaagg gtaagaacag tattctttga ctcttaaaaa gtcctttctg agacctgtac   2700
tcaaaacagc tttattaggc ctgtgtcgtg aaagccagat atgacaaaca tttttacaaa   2760
gcagtggatc tctagttggc tttcaaattc ctcccatcta ccacctttgg tatttacaga   2820
gatgacgtcc ttaaaccatt gtcagaatta atgggtatgt ccagttctct ttatctttga   2880
cttgatgctt tatacaacat ttcatatgtc gcttctaagg gaataagcca tagaggcttc   2940
tccaggttta agagaacaga gtacctggaa aaccaacatt ctgaatgtat agacactgga   3000
ctggacttga ggtcacctat gatgaggttt ttaaaagaat ctaagaattt gctctctacc   3060
cttcccagta gtgtgtggca tcactagtgc tgggtatagg actaaagtga gtattaggtt   3120
gaatattgtt gtagagtatt tgtgtgtcct atacctctta atgcataaat tcctaaattt   3180
aaacatgtct ttagagtcca gttggcctgt caatggtgaa tttcctttttg atttttttctt   3240
gggcaggttt gcaatgtgat aatcagattt ttttttaact gattatagat tgtttccttg   3300
tgtgggtgta ctcacattta aaagtatgaa ccacggttaa ctagtggtct caggggtagt   3360
gaaacactca ctttttattt actgggttag ttgaagtatt cttaagacac tgatcatgct   3420
gtgttcgtga tttgggggggt gggtaatact aaaattagtc atgttttgtg ttcacataac   3480
aaaactgttc aatgactgtt ggttacactt ttaagtgaat ttgtctccta ttttatgagg   3540
aacccaatgc aagtcactaa atgtcttaat agtgacatct gcataagact tgtaatagct   3600
aaagttaatt gagcttaaag gaattgttac cattaaagtc tgtgtttaaa cacactttgg   3660
tcttactcag                                                          3670
```

<210> SEQ ID NO 73
<211> LENGTH: 147
<212> TYPE: PRT
<213> ORGANISM: Mus musculus

<400> SEQUENCE: 73

Met Ala Leu Lys Arg Ile Asn Lys Glu Leu Ser Asp Leu Ala Arg Asp
1 5 10 15

Pro Pro Ala Gln Cys Ser Ala Gly Pro Val Gly Asp Asp Met Phe His
20 25 30

Trp Gln Ala Thr Ile Met Gly Pro Asn Asp Ser Pro Tyr Gln Gly Gly
35 40 45

Val Phe Phe Leu Thr Ile His Phe Pro Thr Asp Tyr Pro Phe Lys Pro
50 55 60

Pro Lys Val Ala Phe Thr Thr Arg Ile Tyr His Pro Asn Ile Asn Ser
65 70 75 80

Asn Gly Ser Ile Cys Leu Asp Ile Leu Arg Ser Gln Trp Ser Pro Ala
85 90 95

Leu Thr Ile Ser Lys Val Leu Leu Ser Ile Cys Ser Leu Leu Cys Asp
100 105 110

Pro Asn Pro Asp Asp Pro Leu Val Pro Glu Ile Ala Arg Ile Tyr Lys
115 120 125

Thr Asp Arg Asp Lys Tyr Asn Arg Ile Ser Arg Glu Trp Thr Gln Lys
130 135 140

Tyr Ala Met
145

<210> SEQ ID NO 74
<211> LENGTH: 3666
<212> TYPE: DNA
<213> ORGANISM: Mus musculus

<400> SEQUENCE: 74
cacgaggttc tcgcgagatc cgccacctcc atcccaagtg aggaaacggg gggccactca 60
gggaggggcg tggggcctcg accgcgcagc tgccgcttcc attaccttcc tcctaaggcg 120
cctgtgtctg gcagagccgg tgtgagaaga agagacaacc cttccccgcc gccgggataa 180
tcaagaattt tggccggacc tttgagtaca cctcgggata gtgaggagcc cggcgaaaag 240
cacagactat ggcgctgaaa cggattaata aggaacttag tgatttggcc cgtgaccctc 300
cagcacaatg ttctgcaggt ccagttggag atgacatgtt tcattggcaa gccacaatta 360
tgggacctaa tgacagccca tatcaaggtg gtgtattctt tttgacaatt cattttccta 420
cagactaccc cttcaaacca cctaaggttg catttacaac aagaatttat catccaaata 480
ttaacagtaa tggcagcatt tgtcttgata ttctaagatc acagtggtct cctgctttaa 540
ctatttctaa agttctttta tccatttgtt cactgctatg tgatccaaac ccagacgacc 600
ccctagtgcc agagattgca cggatctata aaacagacag agataagtac aacagaatat 660
ctcgggaatg gactcagaag tatgccatgt gatgctacct tacagtcaga ataacctgca 720
ttatagctgg aataaacttt aaattactgt tcctttttg atttcttat ccggctgctc 780 ccctatcaga cctcatcttt tttaatttta tttttgttt acctccctcc attcattcac 840
atgctcatct gagaagactt aagttcttcc agctttggac aataactgct tttagaaact 900
gtaaagtagt tacacgagaa cagttgccca agattcagaa attttttaa aaactggagc 960 atgtgtatta tgtggccaat gtcttcactc taacttggtt atgagactaa accaatcctc 1020
actgctctaa catgctgaag aagccatctg agggggaggg agatggatgc tcagctgtca 1080
catcaaagga agcagcatta ttctagcagc atccgttctt gtttaaacct tccactgtta 1140
gaggtttgag gttacatgat atactttatg ctcataactg atgtggctgg agaattggta 1200
ttgaattata gcatcagcag aacagaaaat gtgatgtatt ttatgcatgt caataaagga 1260
atgacctgtt cttgttctac agagaatgga aattggaagt caaacaccct ttgtattcca 1320
aaatagggtc tcaaaacatt ttgtaatttt catttaaatt gttaggaggc ttggagctat 1380
tagttaatct atcttccaat actgtttaat atagcactga ataaatgatg cgagttgtca 1440
atggatgagt gatcaactaa tagctctcct agtaattgat ttatttttct tcaataaagt 1500
tgcataaacc aatgagttag ctgcctggat taatcagtat gggaaacaat cctttgtaaa 1560
tgcaaagctg tttttgtata tactgttggg atttgcttca ttgtttgaca tcaaatgatg 1620
atgtaaagtt caaaagagtg aatatattgc catgttcagt taaaatgcac agtctgttac 1680
aggttgacac attgcttgac ctgatttatg cagaattaat aagctattca aatagtgtag 1740
ctttaatacg ctgcacatga ttctggcagc cctagagttc ataaatggac ttgggactca 1800
gcagttttga aacgtgtata tggagtttaa gaaatttatt ttccaggtgc atccccttct 1860
aactaaaatt ttcttcatct tgtacactta acagctgaaa aagatatata tatatataaa 1920
acttgggagt aataatgggt caaaatttac aaaataaagt actgttttgg tgtgggagtt 1980
gtcatgaggc tgtgttgaag tgacttaact gtgggatatt gactatccat tgagatggat 2040
ttgttcagcc atttacatta atgagcattt aaatgcaaca gatcatttcg ggtgacttaa 2100
catgaatgaa taaaaaagtc aatgctattg gattgtttga caagtgctat ctgtgccact 2160
aaatcttatg tagtaataag ggcattacca tttttcaccc aagttctgaa cctgtagttt 2220
gacacctttt tctagctttg atttctccat tgctttctta gtcttgtatt tgatttctag 2280
cacatgtgat gttcacttcc atattttgca ctgcttatat ttacgtgcaa tcttattcct 2340
tgtccgcaca cagatgtgga aagctagaaa taaatgtaaa agcttaattt tttataaaca 2400
tttaaatatg taatttggac atgatttgtt acttaaggtt ctttaaactg gaagtgaagt 2460
gcatgccttc tgaagatgtt ctggctttat tctgtaataa gtatttacat tggaaaatac 2520
caatttcgct atacagtttt ttttccacac acccatttta ccttttgctt aaattgtggg 2580
ttcttcaggg ttaatgtcac gctaattaat aaaacttttg ggttcaaatc aagtgttccc 2640
acaagggtaa gaacagtatt ctttgactct taaaaagtcc tttctgagac ctgtactcaa 2700
aacagcttta ttaggcctgt gtcgtgaaag ccagatatga caaacatttt tacaaagcag 2760
tggatctcta gttggctttc aaattcctcc catctaccac ctttggtatt tacagagatg 2820
acgtccttaa accattgtca gaattaatgg gtatgtccag ttctctttat ctttgacttg 2880
atgctttata caacatttca tatgtcgctt ctaagggaat aagccataga ggcttctcca 2940
ggtttaagag aacagagtac ctggaaaacc aacattctga atgtatagac actggactgg 3000
acttgaggtc acctatgatg aggtttttaa aagaatctaa gaatttgctc tctacccttc 3060
ccagtagtgt gtggcatcac tagtgctggg tataggacta aagtgagtat taggttgaat 3120
attgttgtag agtatttgtg tgtcctatac ctcttaatgc ataaattcct aaatttaaac 3180
atgtctttag agtccagttg gcctgtcaat ggtgaatttc cttttgattt tttcttgggc 3240
aggtttgcaa tgtgataatc agattttttt ttaactgatt atagattgtt tccttgtgtg 3300
ggtgtactca catttaaaag tatgaaccac ggttaactag tggtctcagg ggtagtgaaa 3360
cactcacttt ttatttactg ggttagttga agtattctta agacactgat catgctgtgt 3420
tcgtgatttg gggggtgggt aatactaaaa ttagtcatgt tttgtgttca cataacaaaa 3480
ctgttcaatg actgttggtt acacttttaa gtgaatttgt ctcctatttt atgaggaacc 3540
caatgcaagt cactaaatgt cttaatagtg acatctgcat aagacttgta atagctaaag 3600
ttaattgagc ttaaaggaat tgttaccatt aaagtctgtg tttaaacaca ctttggtctt 3660
actcag 3666

<210> SEQ ID NO 75
<211> LENGTH: 147
<212> TYPE: PRT
<213> ORGANISM: Mus musculus

<400> SEQUENCE: 75

Met Ala Leu Lys Arg Ile Asn Lys Glu Leu Ser Asp Leu Ala Arg Asp
1 5 10 15

Pro Pro Ala Gln Cys Ser Ala Gly Pro Val Gly Asp Asp Met Phe His
20 25 30

Trp Gln Ala Thr Ile Met Gly Pro Asn Asp Ser Pro Tyr Gln Gly Gly
35 40 45

Val Phe Phe Leu Thr Ile His Phe Pro Thr Asp Tyr Pro Phe Lys Pro
50 55 60

Pro Lys Val Ala Phe Thr Thr Arg Ile Tyr His Pro Asn Ile Asn Ser
65 70 75 80

Asn Gly Ser Ile Cys Leu Asp Ile Leu Arg Ser Gln Trp Ser Pro Ala
85 90 95

Leu Thr Ile Ser Lys Val Leu Leu Ser Ile Cys Ser Leu Leu Cys Asp
100 105 110

Pro Asn Pro Asp Asp Pro Leu Val Pro Glu Ile Ala Arg Ile Tyr Lys
115 120 125

Thr Asp Arg Asp Lys Tyr Asn Arg Ile Ser Arg Glu Trp Thr Gln Lys
130 135 140

Tyr Ala Met
145

<210> SEQ ID NO 76
<211> LENGTH: 3768
<212> TYPE: DNA
<213> ORGANISM: Mus musculus

<400> SEQUENCE: 76
actcgcctac cctccccctc agcccatgac ccgcctccgt cccccgccct cccggcccga 60
cctccgatcg ctttagcgag aaggtgctgt tccgacaggg agacggcaag cgggcggcac 120
gtccactcgg cccgagcgag ggaagcaaac cgctccccc tgaacccctc ggctcgcccc 180
gcgctcgcga cggcggcgtt ggcggacgga tacgcggcgg cgcctgtgtc tggcagagcc 240
ggtgtgagaa gaagagacaa cccttccccg ccgccgggat aatcaagaat tttggccgga 300
cctttgagta cacctcggga tagtgaggag cccggcgaaa agcacagact atggcgctga 360
aacggattaa taaggaactt agtgatttgg cccgtgaccc tccagcacaa tgttctgcag 420
gtccagttgg agatgacatg tttcattggc aagccacaat tatgggacct aatgacagcc 480
catatcaagg tggtgtattc tttttgacaa ttcattttcc tacagactac cccttcaaac 540
cacctaaggt tgcatttaca acaagaattt atcatccaaa tattaacagt aatggcagca 600
tttgtcttga tattctaaga tcacagtggt ctcctgcttt aactatttct aaagttcttt 660
tatccatttg ttcactgcta tgtgatccaa acccagacga ccccctagtg ccagagattg 720
cacggatcta taaaacagac agagataagt acaacagaat atctcgggaa tggactcaga 780
agtatgccat gtgatgctac cttacagtca gaataacctg cattatagct ggaataaact 840

-continued

```
ttaaattact gttccttttt tgattttctt atccggctgc tcccctatca gacctcatct    900
tttttaattt tattttttgt ttacctccct ccattcattc acatgctcat ctgagaagac    960
ttaagttctt ccagctttgg acaataactg cttttagaaa ctgtaaagta gttacacgag   1020
aacagttgcc caagattcag aaattttttt aaaaactgga gcatgtgtat tatgtggcca   1080
atgtcttcac tctaacttgg ttatgagact aaaccaatcc tcactgctct aacatgctga   1140
agaagccatc tgagggggag ggagatggat gctcagctgt cacatcaaag gaagcagcat   1200
tattctagca gcatccgttc ttgtttaaac cttccactgt tagaggtttg aggttacatg   1260
atatacttta tgctcataac tgatgtggct ggagaattgg tattgaatta tagcatcagc   1320
agaacagaaa atgtgatgta ttttatgcat gtcaataaag gaatgacctg ttcttgttct   1380
acagagaatg gaaattggaa gtcaaacacc ctttgtattc caaaataggg tctcaaaaca   1440
ttttgtaatt ttcatttaaa ttgttaggag gcttggagct attagttaat ctatcttcca   1500
atactgttta atatagcact gaataaatga tgcgagttgt caatggatga gtgatcaact   1560
aatagctctc ctagtaattg atttattttt cttcaataaa gttgcataaa ccaatgagtt   1620
agctgcctgg attaatcagt atgggaaaca atcctttgta aatgcaaagc tgtttttgta   1680
tatactgttg ggatttgctt cattgtttga catcaaatga tgatgtaaag ttcaaaagag   1740
tgaatatatt gccatgttca gttaaaatgc acagtctgtt acaggttgac acattgcttg   1800
acctgattta tgcagaatta ataagctatt caaatagtgt agctttaata cgctgcacat   1860
gattctggca gccctagagt tcataaatgg acttgggact cagcagtttt gaaacgtgta   1920
tatggagttt aagaaattta ttttccaggt gcatcccctt ctaactaaaa ttttcttcat   1980
cttgtacact taacagctga aaaagatata tatatatata aaacttggga gtaataatgg   2040
gtcaaaattt acaaaataaa gtactgtttt ggtgtgggag ttgtcatgag gctgtgttga   2100
agtgacttaa ctgtgggata ttgactatcc attgagatgg atttgttcag ccatttacat   2160
taatgagcat ttaaatgcaa cagatcattt cgggtgactt aacatgaatg aataaaaaag   2220
tcaatgctat tggattgttt gacaagtgct atctgtgcca ctaaatctta tgtagtaata   2280
agggcattac catttttcac ccaagttctg aacctgtagt ttgacacctt tttctagctt   2340
tgatttctcc attgctttct tagtcttgta tttgatttct agcacatgtg atgttcactt   2400
ccatattttg cactgcttat atttacgtgc aatcttattc cttgtccgca cacagatgtg   2460
gaaagctaga aataaatgta aaagcttaat tttttataaa catttaaata tgtaatttgg   2520
acatgatttg ttacttaagg ttctttaaac tggaagtgaa gtgcatgcct tctgaagatg   2580
ttctggcttt attctgtaat aagtatttac attggaaaat accaatttcg ctatacagtt   2640
ttttttccac acacccattt taccttttgc ttaaattgtg ggttcttcag ggttaatgtc   2700
acgctaatta ataaaacttt tgggttcaaa tcaagtgttc ccacaagggt aagaacagta   2760
ttctttgact cttaaaaagt cctttctgag acctgtactc aaaacagctt tattaggcct   2820
gtgtcgtgaa agccagatat gacaaacatt tttacaaagc agtggatctc tagttggctt   2880
tcaaattcct cccatctacc acctttggta tttacagaga tgacgtcctt aaaccattgt   2940
cagaattaat gggtatgtcc agttctcttt atctttgact tgatgcttta tacaacattt   3000
catatgtcgc ttctaaggga ataagccata gaggcttctc caggtttaag agaacagagt   3060
acctggaaaa ccaacattct gaatgtatag acactggact ggacttgagg tcacctatga   3120
tgaggttttt aaaagaatct aagaatttgc tctctaccct tcccagtagt gtgtggcatc   3180
```

-continued

```
actagtgctg ggtataggac taaagtgagt attaggttga atattgttgt agagtatttg   3240

tgtgtcctat acctcttaat gcataaattc ctaaatttaa acatgtcttt agagtccagt   3300

tggcctgtca atggtgaatt tccttttgat tttttcttgg gcaggtttgc aatgtgataa   3360

tcagattttt ttttaactga ttatagattg tttccttgtg tgggtgtact cacatttaaa   3420

agtatgaacc acggttaact agtggtctca ggggtagtga aacactcact ttttatttac   3480

tgggttagtt gaagtattct taagacactg atcatgctgt gttcgtgatt tggggggtgg   3540

gtaatactaa aattagtcat gttttgtgtt cacataacaa aactgttcaa tgactgttgg   3600

ttacactttt aagtgaattt gtctcctatt ttatgaggaa cccaatgcaa gtcactaaat   3660

gtcttaatag tgacatctgc ataagacttg taatagctaa agttaattga gcttaaagga   3720

attgttacca ttaaagtctg tgtttaaaca cactttggtc ttactcag              3768
```

<210> SEQ ID NO 77
<211> LENGTH: 147
<212> TYPE: PRT
<213> ORGANISM: Mus musculus

<400> SEQUENCE: 77

```
Met Ala Leu Lys Arg Ile Asn Lys Glu Leu Ser Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Phe Leu Thr Ile His Phe Pro Thr Asp Tyr Pro Phe Lys Pro
    50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Lys
        115                 120                 125

Thr Asp Arg Asp Lys Tyr Asn Arg Ile Ser Arg Glu Trp Thr Gln Lys
    130                 135                 140

Tyr Ala Met
145
```

<210> SEQ ID NO 78
<211> LENGTH: 4067
<212> TYPE: DNA
<213> ORGANISM: Mus musculus

<400> SEQUENCE: 78

```
gcgctgcgag gcggagagta cggtggtgtc aggggcgacc cagaacagcc ctcgccgtgg     60

ggacgggagc gcacccgggg cccattgcct tgtgctggct cgctgtccct tggagccgaa    120

accgaaagga gcccggcgtc ggtccggagc cgcccgctcc cctccccctt gcctttctct    180

gcccgagtga cgccggccta gcgccgacta ggccccggct cctcctctgc ccggctctgg    240

accctgcccc gcacccaccc ctttctcctc cgcctcttcc tctcccaccc ggggctcgtc    300

ttcctttcaa gaggccggga agttaaactt gtaaccacct ctcggcgctt cccgtcaccc    360

tctcgccctc tctggggcga agcgcggatc tcggtagctg gtggctccgc caccccgccc    420
```

cgccctgccg ggatcgcggc ggttttcagg gttctggagt cagcagggtt tctccgaggc 480
cctggcgagt cgctgacctg ctccgttttt gcaaaaaggc gcctgtgtct ggcagagccg 540
gtgtgagaag aagagacaac ccttccccgc cgccgggata atcaagaatt ttggccggac 600
ctttgagtac acctcgggat agtgaggagc ccggcgaaaa gcacagacta tggcgctgaa 660
acggattaat aaggaactta gtgatttggc ccgtgaccct ccagcacaat gttctgcagg 720
tccagttgga gatgacatgt ttcattggca agccacaatt atgggaccta atgacagccc 780
atatcaaggt ggtgtattct tttgacaat tcattttcct acagactacc ccttcaaacc 840
acctaaggtt gcatttacaa caagaattta tcatccaaat attaacagta atggcagcat 900
ttgtcttgat attctaagat cacagtggtc tcctgcttta actatttcta aagttctttt 960
atccatttgt tcactgctat gtgatccaaa cccagacgac cccctagtgc cagagattgc 1020
acggatctat aaaacagaca gagataagta caacagaata tctcgggaat ggactcagaa 1080
gtatgccatg tgatgctacc ttacagtcag aataacctgc attatagctg gaataaactt 1140
taaattactg ttccttttt gattttctta tccggctgct cccctatcag acctcatctt 1200
ttttaatttt attttttgtt tacctccctc cattcattca catgctcatc tgagaagact 1260
taagttcttc cagctttgga caataactgc ttttagaaac tgtaaagtag ttacacgaga 1320
acagttgccc aagattcaga aatttttta aaaactggag catgtgtatt atgtggccaa 1380
tgtcttcact ctaacttggt tatgagacta aaccaatcct cactgctcta acatgctgaa 1440
gaagccatct gagggggagg gagatggatg ctcagctgtc acatcaaagg aagcagcatt 1500
attctagcag catccgttct tgtttaaacc ttccactgtt agaggtttga ggttacatga 1560
tatactttat gctcataact gatgtggctg gagaattggt attgaattat agcatcagca 1620
gaacagaaaa tgtgatgtat tttatgcatg tcaataaagg aatgacctgt tcttgttcta 1680
cagagaatgg aaattggaag tcaaacaccc tttgtattcc aaaatagggt ctcaaaacat 1740
tttgtaattt tcatttaaat tgttaggagg cttggagcta ttagttaatc tatcttccaa 1800
tactgtttaa tatagcactg aataaatgat gcgagttgtc aatggatgag tgatcaacta 1860
atagctctcc tagtaattga tttattttc ttcaataaag ttgcataaac caatgagtta 1920
gctgcctgga ttaatcagta tgggaaacaa tcctttgtaa atgcaaagct gtttttgtat 1980
atactgttgg gatttgcttc attgtttgac atcaaatgat gatgtaaagt tcaaaagagt 2040
gaatatattg ccatgttcag ttaaaatgca cagtctgtta caggttgaca cattgcttga 2100
cctgatttat gcagaattaa taagctattc aaatagtgta gctttaatac gctgcacatg 2160
attctggcag ccctagagtt cataaatgga cttgggactc agcagttttg aaacgtgtat 2220
atggagttta agaaatttat tttccaggtg catccccttc taactaaaat tttcttcatc 2280
ttgtacactt aacagctgaa aaagatatat atatatataa aacttgggag taataatggg 2340
tcaaaattta caaaataaag tactgttttg gtgtgggagt tgtcatgagg ctgtgttgaa 2400
gtgacttaac tgtgggatat tgactatcca ttgagatgga tttgttcagc catttacatt 2460
aatgagcatt taaatgcaac agatcatttc gggtgactta acatgaatga ataaaaaagt 2520
caatgctatt ggattgtttg acaagtgcta tctgtgccac taaatcttat gtagtaataa 2580
gggcattacc atttttcacc caagttctga acctgtagtt tgacaccttt ttctagcttt 2640
gatttctcca ttgctttctt agtcttgtat ttgatttcta gcacatgtga tgttcacttc 2700
catattttgc actgcttata tttacgtgca atcttattcc ttgtccgcac acagatgtgg 2760

-continued

```
aaagctagaa ataaatgtaa aagcttaatt ttttataaac atttaaatat gtaatttgga   2820
catgatttgt tacttaaggt tctttaaact ggaagtgaag tgcatgcctt ctgaagatgt   2880
tctggcttta ttctgtaata agtatttaca ttggaaaata ccaatttcgc tatacagttt   2940
tttttccaca cacccatttt accttttgct taaattgtgg gttcttcagg gttaatgtca   3000
cgctaattaa taaaactttt gggttcaaat caagtgttcc cacaagggta agaacagtat   3060
tctttgactc ttaaaaagtc ctttctgaga cctgtactca aaacagcttt attaggcctg   3120
tgtcgtgaaa gccagatatg acaaacattt ttacaaagca gtggatctct agttggcttt   3180
caaattcctc ccatctacca cctttggtat ttacagagat gacgtcctta aaccattgtc   3240
agaattaatg ggtatgtcca gttctcttta tctttgactt gatgctttat acaacatttc   3300
atatgtcgct tctaagggaa taagccatag aggcttctcc aggtttaaga gaacagagta   3360
cctggaaaac caacattctg aatgtataga cactggactg gacttgaggt cacctatgat   3420
gaggttttta aaagaatcta agaatttgct ctctaccctt cccagtagtg tgtggcatca   3480
ctagtgctgg gtataggact aaagtgagta ttaggttgaa tattgttgta gagtatttgt   3540
gtgtcctata cctcttaatg cataaattcc taaatttaaa catgtcttta gagtccagtt   3600
ggcctgtcaa tggtgaattt ccttttgatt ttttcttggg caggtttgca atgtgataat   3660
cagatttttt tttaactgat tatagattgt ttccttgtgt gggtgtactc acatttaaaa   3720
gtatgaacca cggttaacta gtggtctcag gggtagtgaa acactcactt tttatttact   3780
gggttagttg aagtattctt aagacactga tcatgctgtg ttcgtgattt ggggggtggg   3840
taatactaaa attagtcatg ttttgtgttc acataacaaa actgttcaat gactgttggt   3900
tacactttta agtgaatttg tctcctattt tatgaggaac ccaatgcaag tcactaaatg   3960
tcttaatagt gacatctgca taagacttgt aatagctaaa gttaattgag cttaaaggaa   4020
ttgttaccat taaagtctgt gtttaaacac actttggtct tactcag                 4067
```

```
<210> SEQ ID NO 79
<211> LENGTH: 147
<212> TYPE: PRT
<213> ORGANISM: Mus musculus

<400> SEQUENCE: 79

Met Ala Leu Lys Arg Ile Asn Lys Glu Leu Ser Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Phe Leu Thr Ile His Phe Pro Thr Asp Tyr Pro Phe Lys Pro
    50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Lys
        115                 120                 125

Thr Asp Arg Asp Lys Tyr Asn Arg Ile Ser Arg Glu Trp Thr Gln Lys
    130                 135                 140
```

Tyr Ala Met
145

<210> SEQ ID NO 80
<211> LENGTH: 3757
<212> TYPE: DNA
<213> ORGANISM: Mus musculus

<400> SEQUENCE: 80
gaataggcgg ggggaggggc ggagcgtggc agctggcagt agttccgtca gagcggacat 60
cttgtggctg tgccgtgcgc gtgagccccg tagggccggg gaggcaccag ctgccgcgcg 120
gggaggaggc cgaggccgca gctcgaggga ggccccggcc ctctgcgcct gtgtctggca 180
gagccggtgt gagaagaaga gacaaccctt ccccgccgcc gggataatca agaattttgg 240
ccggaccttt gagtacacct cgggatagtg aggagcccgg cgaaaagcac agactatggc 300
gctgaaacgg attaataagg aacttagtga tttggcccgt gaccctccag cacaatgttc 360
tgcaggtcca gttggagatg acatgtttca ttggcaagcc acaattatgg gacctctcaa 420
tgaaagtgag caagcacctg ctgtgtgatg aggataaaga atgacagccc atatcaaggt 480
ggtgtattct ttttgacaat tcattttcct acagactacc ccttcaaacc acctaaggtt 540
gcatttacaa caagaattta tcatccaaat attaacagta atggcagcat ttgtcttgat 600
attctaagat cacagtggtc tcctgcttta actatttcta aagttctttt atccatttgt 660
tcactgctat gtgatccaaa cccagacgac cccctagtgc cagagattgc acggatctat 720
aaaacagaca gagataagta caacagaata tctcgggaat ggactcagaa gtatgccatg 780
tgatgctacc ttacagtcag aataacctgc attatagctg gaataaactt taaattactg 840
ttcctttttt gattttctta tccggctgct cccctatcag acctcatctt ttttaatttt 900
attttttgtt tacctccctc cattcattca catgctcatc tgagaagact taagttcttc 960
cagctttgga caataactgc ttttagaaac tgtaaagtag ttacacgaga acagttgccc 1020
aagattcaga aattttttta aaaactggag catgtgtatt atgtggccaa tgtcttcact 1080
ctaacttggt tatgagacta aaccaatcct cactgctcta acatgctgaa gaagccatct 1140
gagggggagg gagatggatg ctcagctgtc acatcaaagg aagcagcatt attctagcag 1200
catccgttct tgtttaaacc ttccactgtt agaggtttga ggttacatga tatactttat 1260
gctcataact gatgtggctg gagaattggt attgaattat agcatcagca gaacagaaaa 1320
tgtgatgtat tttatgcatg tcaataaagg aatgacctgt tcttgttcta cagagaatgg 1380
aaattggaag tcaaacaccc tttgtattcc aaaatagggt ctcaaaacat tttgtaattt 1440
tcatttaaat tgttaggagg cttggagcta ttagttaatc tatcttccaa tactgtttaa 1500
tatagcactg aataaatgat gcgagttgtc aatggatgag tgatcaacta atagctctcc 1560
tagtaattga tttatttttc ttcaataaag ttgcataaac caatgagtta gctgcctgga 1620
ttaatcagta tgggaaacaa tcctttgtaa atgcaaagct gtttttgtat atactgttgg 1680
gatttgcttc attgtttgac atcaaatgat gatgtaaagt tcaaaagagt gaatatattg 1740
ccatgttcag ttaaaatgca cagtctgtta caggttgaca cattgcttga cctgatttat 1800
gcagaattaa taagctattc aaatagtgta gctttaatac gctgcacatg attctggcag 1860
ccctagagtt cataaatgga cttgggactc agcagttttg aaacgtgtat atggagttta 1920
agaaatttat tttccaggtg catccccttc taactaaaat tttcttcatc ttgtacactt 1980
aacagctgaa aaagatatat atatatataa aacttgggag taataatggg tcaaaattta 2040

```
caaaataaag tactgttttg gtgtgggagt tgtcatgagg ctgtgttgaa gtgacttaac   2100
tgtgggatat tgactatcca ttgagatgga tttgttcagc catttacatt aatgagcatt   2160
taaatgcaac agatcatttc gggtgactta acatgaatga ataaaaaagt caatgctatt   2220
ggattgtttg acaagtgcta tctgtgccac taaatcttat gtagtaataa gggcattacc   2280
atttttcacc caagttctga acctgtagtt tgacaccttt ttctagcttt gatttctcca   2340
ttgctttctt agtcttgtat ttgatttcta gcacatgtga tgttcacttc catattttgc   2400
actgcttata tttacgtgca atcttattcc ttgtccgcac acagatgtgg aaagctagaa   2460
ataaatgtaa aagcttaatt ttttataaac atttaaatat gtaatttgga catgatttgt   2520
tacttaaggt tctttaaact ggaagtgaag tgcatgcctt ctgaagatgt tctggcttta   2580
ttctgtaata agtatttaca ttggaaaata ccaatttcgc tatacagttt tttttccaca   2640
cacccatttt accttttgct taaattgtgg gttcttcagg gttaatgtca cgctaattaa   2700
taaaactttt gggttcaaat caagtgttcc cacaagggta agaacagtat tctttgactc   2760
ttaaaaagtc ctttctgaga cctgtactca aaacagcttt attaggcctg tgtcgtgaaa   2820
gccagatatg acaaacattt ttacaaagca gtggatctct agttggcttt caaattcctc   2880
ccatctacca cctttggtat ttacagagat gacgtcctta aaccattgtc agaattaatg   2940
ggtatgtcca gttctcttta tctttgactt gatgctttat acaacatttc atatgtcgct   3000
tctaagggaa taagccatag aggcttctcc aggtttaaga gaacagagta cctggaaaac   3060
caacattctg aatgtataga cactggactg gacttgaggt cacctatgat gaggttttta   3120
aaagaatcta agaatttgct ctctaccctt cccagtagtg tgtggcatca ctagtgctgg   3180
gtataggact aaagtgagta ttaggttgaa tattgttgta gagtatttgt gtgtcctata   3240
cctcttaatg cataaattcc taaatttaaa catgtcttta gagtccagtt ggcctgtcaa   3300
tggtgaattt ccttttgatt ttttcttggg caggtttgca atgtgataat cagatttttt   3360
tttaactgat tatagattgt ttccttgtgt gggtgtactc acatttaaaa gtatgaacca   3420
cggttaacta gtggtctcag gggtagtgaa acactcactt tttatttact gggttagttg   3480
aagtattctt aagacactga tcatgctgtg ttcgtgattt ggggggtggg taatactaaa   3540
attagtcatg ttttgtgttc acataacaaa actgttcaat gactgttggt tacactttta   3600
agtgaatttg tctcctattt tatgaggaac ccaatgcaag tcactaaatg tcttaatagt   3660
gacatctgca taagacttgt aatagctaaa gttaattgag cttaaaggaa ttgttaccat   3720
taaagtctgt gtttaaacac actttggtct tactcag                             3757
```

<210> SEQ ID NO 81
<211> LENGTH: 111
<212> TYPE: PRT
<213> ORGANISM: Mus musculus

<400> SEQUENCE: 81

```
Met Arg Ile Lys Asn Asp Ser Pro Tyr Gln Gly Gly Val Phe Phe Leu
1               5                   10                  15

Thr Ile His Phe Pro Thr Asp Tyr Pro Phe Lys Pro Pro Lys Val Ala
            20                  25                  30

Phe Thr Thr Arg Ile Tyr His Pro Asn Ile Asn Ser Asn Gly Ser Ile
        35                  40                  45

Cys Leu Asp Ile Leu Arg Ser Gln Trp Ser Pro Ala Leu Thr Ile Ser
    50                  55                  60
```

-continued

Lys Val Leu Leu Ser Ile Cys Ser Leu Leu Cys Asp Pro Asn Pro Asp
65 70 75 80

Asp Pro Leu Val Pro Glu Ile Ala Arg Ile Tyr Lys Thr Asp Arg Asp
85 90 95

Lys Tyr Asn Arg Ile Ser Arg Glu Trp Thr Gln Lys Tyr Ala Met
100 105 110

<210> SEQ ID NO 82
<211> LENGTH: 3713
<212> TYPE: DNA
<213> ORGANISM: Mus musculus

<400> SEQUENCE: 82
gaataggcgg ggggaggggc ggagcgtggc agctggcagt agttccgtca gagcggacat 60
cttgtggctg tgccgtgcgc gtgagccccg tagggccggg gaggcaccag ctgccgcgcg 120
gggaggaggc cgaggccgca gctcgaggga ggccccggcc ctctgcgcct gtgtctggca 180
gagccggtgt gagaagaaga gacaaccctt ccccgccgcc gggataatca agaattttgg 240
ccggaccttt gagtacacct cgggatagtg aggagcccgg cgaaaagcac agactatggc 300
gctgaaacgg attaataagg aacttagtga tttggcccgt gaccctccag cacaatgttc 360
tgcaggtcca gttggagatg acatgtttca ttggcaagcc acaattatgg gacctaatga 420
cagcccatat caaggtggtg tattcttttt gacaattcat tttcctacag actacccctt 480
caaaccacct aaggttgcat ttacaacaag aatttatcat ccaaatatta acagtaatgg 540
cagcatttgt cttgatattc taagatcaca gtggtctcct gctttaacta tttctaaagt 600
tcttttatcc atttgttcac tgctatgtga tccaaaccca gacgaccccc tagtgccaga 660
gattgcacgg atctataaaa cagacagaga taagtacaac agaatatctc gggaatggac 720
tcagaagtat gccatgtgat gctaccttac agtcagaata acctgcatta tagctggaat 780
aaactttaaa ttactgttcc ttttttgatt ttcttatccg gctgctcccc tatcagacct 840
catctttttt aattttattt tttgtttacc tccctccatt cattcacatg ctcatctgag 900
aagacttaag ttcttccagc tttggacaat aactgctttt agaaactgta aagtagttac 960
acgagaacag ttgcccaaga ttcagaaatt tttttaaaaa ctggagcatg tgtattatgt 1020
ggccaatgtc ttcactctaa cttggttatg agactaaacc aatcctcact gctctaacat 1080
gctgaagaag ccatctgagg gggagggaga tggatgctca gctgtcacat caaaggaagc 1140
agcattattc tagcagcatc cgttcttgtt taaaccttcc actgttagag gtttgaggtt 1200
acatgatata ctttatgctc ataactgatg tggctggaga attggtattg aattatagca 1260
tcagcagaac agaaaatgtg atgtatttta tgcatgtcaa taaaggaatg acctgttctt 1320
gttctacaga gaatggaaat tggaagtcaa acaccctttg tattccaaaa tagggtctca 1380
aaacattttg taattttcat ttaaattgtt aggaggcttg gagctattag ttaatctatc 1440
ttccaatact gtttaatata gcactgaata aatgatgcga gttgtcaatg gatgagtgat 1500
caactaatag ctctcctagt aattgattta tttttcttca ataaagttgc ataaaccaat 1560
gagttagctg cctggattaa tcagtatggg aaacaatcct ttgtaaatgc aaagctgttt 1620
ttgtatatac tgttgggatt tgcttcattg tttgacatca aatgatgatg taaagttcaa 1680
aagagtgaat atattgccat gttcagttaa aatgcacagt ctgttacagg ttgacacatt 1740
gcttgacctg atttatgcag aattaataag ctattcaaat agtgtagctt taatacgctg 1800
cacatgattc tggcagccct agagttcata aatggacttg ggactcagca gttttgaaac 1860

```
gtgtatatgg agtttaagaa atttattttc caggtgcatc cccttctaac taaaattttc   1920
ttcatcttgt acacttaaca gctgaaaaag atatatatat atataaaact tgggagtaat   1980
aatgggtcaa aatttacaaa ataaagtact gttttggtgt gggagttgtc atgaggctgt   2040
gttgaagtga cttaactgtg ggatattgac tatccattga gatggatttg ttcagccatt   2100
tacattaatg agcatttaaa tgcaacagat catttcgggt gacttaacat gaatgaataa   2160
aaaagtcaat gctattggat tgtttgacaa gtgctatctg tgccactaaa tcttatgtag   2220
taataagggc attaccattt ttcacccaag ttctgaacct gtagtttgac accttttttct   2280
agctttgatt tctccattgc tttcttagtc ttgtatttga tttctagcac atgtgatgtt   2340
cacttccata ttttgcactg cttatattta cgtgcaatct tattccttgt ccgcacacag   2400
atgtggaaag ctagaaataa atgtaaaagc ttaatttttt ataaacattt aaatatgtaa   2460
tttggacatg atttgttact taaggttctt taaactggaa gtgaagtgca tgccttctga   2520
agatgttctg gctttattct gtaataagta tttacattgg aaaataccaa tttcgctata   2580
cagttttttt tccacacacc cattttacct tttgcttaaa ttgtgggttc ttcagggtta   2640
atgtcacgct aattaataaa acttttgggt tcaaatcaag tgttcccaca agggtaagaa   2700
cagtattctt tgactcttaa aaagtccttt ctgagacctg tactcaaaac agctttatta   2760
ggcctgtgtc gtgaaagcca gatatgacaa acatttttac aaagcagtgg atctctagtt   2820
ggctttcaaa ttcctcccat ctaccacctt tggtatttac agagatgacg tccttaaacc   2880
attgtcagaa ttaatgggta tgtccagttc tctttatctt tgacttgatg ctttatacaa   2940
catttcatat gtcgcttcta agggaataag ccatagaggc ttctccaggt ttaagagaac   3000
agagtacctg gaaaaccaac attctgaatg tatagacact ggactggact tgaggtcacc   3060
tatgatgagg tttttaaaag aatctaagaa tttgctctct acccttccca gtagtgtgtg   3120
gcatcactag tgctgggtat aggactaaag tgagtattag gttgaatatt gttgtagagt   3180
atttgtgtgt cctatacctc ttaatgcata aattcctaaa tttaaacatg tctttagagt   3240
ccagttggcc tgtcaatggt gaatttcctt ttgatttttt cttgggcagg tttgcaatgt   3300
gataatcaga ttttttttta actgattata gattgtttcc ttgtgtgggt gtactcacat   3360
ttaaaagtat gaaccacggt taactagtgg tctcaggggt agtgaaacac tcacttttta   3420
tttactgggt tagttgaagt attcttaaga cactgatcat gctgtgttcg tgatttgggg   3480
ggtgggtaat actaaaatta gtcatgtttt gtgttcacat aacaaaactg ttcaatgact   3540
gttggttaca cttttaagtg aatttgtctc ctattttatg aggaacccaa tgcaagtcac   3600
taaatgtctt aatagtgaca tctgcataag acttgtaata gctaaagtta attgagctta   3660
aaggaattgt taccattaaa gtctgtgttt aaacacactt tggtcttact cag          3713
```

<210> SEQ ID NO 83
<211> LENGTH: 111
<212> TYPE: PRT
<213> ORGANISM: Mus musculus

<400> SEQUENCE: 83

```
Met Arg Ile Lys Asn Asp Ser Pro Tyr Gln Gly Gly Val Phe Phe Leu
1               5                   10                  15

Thr Ile His Phe Pro Thr Asp Tyr Pro Phe Lys Pro Pro Lys Val Ala
            20                  25                  30

Phe Thr Thr Arg Ile Tyr His Pro Asn Ile Asn Ser Asn Gly Ser Ile
        35                  40                  45
```

```
Cys Leu Asp Ile Leu Arg Ser Gln Trp Ser Pro Ala Leu Thr Ile Ser
    50                  55                  60

Lys Val Leu Leu Ser Ile Cys Ser Leu Leu Cys Asp Pro Asn Pro Asp
65                  70                  75                  80

Asp Pro Leu Val Pro Glu Ile Ala Arg Ile Tyr Lys Thr Asp Arg Asp
                85                  90                  95

Lys Tyr Asn Arg Ile Ser Arg Glu Trp Thr Gln Lys Tyr Ala Met
            100                 105                 110


<210> SEQ ID NO 84
<211> LENGTH: 4790
<212> TYPE: DNA
<213> ORGANISM: Homo sapiens

<400> SEQUENCE: 84

ggggaagcgc agtgcgcagg cgcaactgcc tggctctgct cgctccggcg ctccggccca     60

gctctcgcgg acaagtccag acatcgcgcg cccccccttc tccgggtccg ccccctcccc    120

cttctcggcg tcgtcgaaga taaacaatag ttggccggcg agcgcctagt gtgtctcccg    180

ccgccggatt cggcgggctg cgtgggaccg gcgggatccc ggccagccgg ccatggcggg    240

gctgtactcg ctgggagtga gcgtcttctc cgaccagggc gggaggaagt acatggagga    300

cgttactcaa atcgttgtgg agcccgaacc gacggctgaa gaaaagccct cgccgcggcg    360

gtcgctgtct cagccgttgc ctccgcggcc gtcgccggcc gcccttcccg gcggcgaagt    420

ctcggggaaa ggcccagcgg tggcagcccg agaggctcgc gaccctctcc cggacgccgg    480

ggcctcgccg gcacctagcc gctgctgccg ccgccgttcc tccgtggcct tttcgccgt     540

gtgcgacggg cacggcgggc gggaggcggc acagtttgcc cgggagcact tgtggggttt    600

catcaagaag cagaagggtt tcacctcgtc cgagccggct aaggtttgcg ctgccatccg    660

caaaggcttt ctcgcttgtc accttgccat gtggaagaaa ctggcggaat ggccaaagac    720

tatgacgggt cttcctagca catcagggac aactgccagt gtggtcatca ttcggggcat    780

gaagatgtat gtagctcacg taggtgactc aggggtggtt cttggaattc aggatgaccc    840

gaaggatgac tttgtcagag ctgtggaggt gacacaggac cataagccag aacttcccaa    900

ggaaagagaa cgaatcgaag gacttggtgg gagtgtaatg aacaagtctg ggtgaatcg     960

tgtagtttgg aaacgacctc gactcactca caatggacct gttagaagga gcacagttat   1020

tgaccagatt ccttttctgg cagtagcaag agcacttggt gatttgtgga gctatgattt   1080

cttcagtggt gaatttgtgg tgtcacctga accagacaca agtgtccaca ctcttgaccc   1140

tcagaagcac aagtatatta tattggggag tgatggactt tggaatatga ttccaccaca   1200

agatgccatc tcaatgtgcc aggaccaaga ggagaaaaaa tacctgatgg gtgagcatgg   1260

acaatcttgt gccaaaatgc ttgtgaatcg agcattgggc cgctggaggc agcgtatgct   1320

ccgagcagat aacactagtg ccatagtaat ctgcatctct ccagaagtgg acaatcaggg   1380

aaactttacc aatgaagatg agttatacct gaacctgact gacagccctt cctataatag   1440

tcaagaaacc tgtgtgatga ctccttcccc atgttctaca ccaccagtca agtcactgga   1500

ggaggatcca tggccaaggg tgaattctaa ggaccatata cctgccctgg ttcgtagcaa   1560

tgccttctca gagaattttt tagaggtttc agctgagata gctcgagaga atgtccaagg   1620

tgtagtcata ccctcaaaag atccagaacc acttgaagaa aattgcgcta aagccctgac   1680

tttaaggata catgattctt tgaataatag ccttccaatt ggccttgtgc ctactaattc   1740
```

-continued

```
aacaaacact gtcatggacc aaaaaaattt gaagatgtca actcctggcc aaatgaaagc   1800
ccaagaaatt gaaagaaccc ctccaacaaa ctttaaaagg acattagaag agtccaattc   1860
tggcccccctg atgaagaagc atagacgaaa tggcttaagt cgaagtagtg gtgctcagcc   1920
tgcaagtctc cccacaacct cacagcgaaa gaactctgtt aaactcacca tgcgacgcag   1980
acttaggggc cagaagaaaa ttggaaatcc tttacttcat caacacagga aaactgtttg   2040
tgtttgctga aatgcatctg ggaaatgagg tttttccaaa cttaggatat aagagggctt   2100
tttaaatttg gtgccgatgt tgaacttttt ttaaggggag aaaattaaaa gaaatataca   2160
gtttgacttt ttggaattca gcagttttat cctggccttg tacttgcttg tattgtaaat   2220
gtggattttg tagatgttag ggtataagtt gctgtaaaat ttgtgtaaat ttgtatccac   2280
acaaattcag tctctgaata cacagtattc agagtctctg atacacagta attgtgacaa   2340
tagggctaaa tgtttaaaga aatcaaaaga atctattaga ttttagaaaa acatttaaac   2400
tttttaaaat acttattaaa aaatttgtat aagccacttg tcttgaaaac tgtgcaactt   2460
tttaaagtaa attattaagc agactggaaa agtgatgtat tttcatagtg acctgtgttt   2520
cacttaatgt ttcttagagc caagtgtctt ttaaacatta tttttttattt ctgatttcat   2580
aattcagaac taaatttttc atagaagtgt tgagccatgc tacagttagt cttgtcccaa   2640
ttaaaatact atgcagtatc tcttacatca gtagcatttt tctaaaacct tagtcatcag   2700
atatgcttac taaatcttca gcatagaagg aagtgtgttt gcctaaaaca atctaaaaca   2760
attcccttct ttttcatccc agaccaatgg cattattagg tcttaaagta gttactccct   2820
tctcgtgttt gcttaaaata tgtgaagttt tccttgctat ttcaataaca gatggtgctg   2880
ctaattccca acatttctta aattatttta tatcatacag ttttcattga ttatatgggt   2940
atatattcat ctaataaatc agtgaactgt tcctcatgtt gctgaatttg tagttgttgg   3000
tttattttaa tggtatgtac aagttgagta tcccttatcc aaaatgcttg ggaccagaag   3060
tgtttcagat tttttaaaat tttggaatat ttgctttata ctgagctttt gagtgttccc   3120
aatctgaaat tcaaaatgct ctaatgagca tttcctttga gcatcatgcc tgctctgaaa   3180
aagtttctga ttctggagca ttttggattt tggattttca gattagggat gcttaacctg   3240
gattaacatt ctgttgtgcc atgatcatgc tttacagtga gtgtatttta tttatttatt   3300
attttgtttg tttgtttgag atggagtctc actctgtcat ccaggctaga gtgcagtggc   3360
gtgatctcgg ctgactgcaa cctctgcctc ccgggttcaa gtgattctcc tgcctcaatc   3420
tctctcccca gaagctggga ttacaggtgt gtgccaccac acccggctaa tttttttttt   3480
ttttttgag atggagtcta gctctgtcat ccaggctgga gtgcagtggt gtgatctcgg   3540
ctccctgcaa cctctgcctt ctgggttcct gcgattctcc tgcctcagcc tcctgagtag   3600
ctgagattac aggcacgcgc cactgtgccc agccaatttt tgtattttta gtagagatgg   3660
ggtttcacat gtcagtcatg ctggtcttga tctcctgacc tcgtgatcca cccgcctcga   3720
cctcccaaag tactgggatt acaggcgtga gccaccgcat ccggcctgag ttttatgctt   3780
tcaatgtatt tcttacattt cagttcaagt gattttcatg tctcagcctc ctgagtagct   3840
ggaactacag gtgcgtgcca ccatgcctgg ctaagttttg tatttttagt agagatgggt   3900
tttcatcatg ttggccaaga tggtcttgat ctcttgacct catgatccac cagcctaggc   3960
ctcccaaagt gctgggatta caggtgtgag ccaccgtgcc cagccaacta tgccattatt   4020
taaccatgtc cacacattct ggttattttc aatattttgc agaagataat tcttgatcgg   4080
tgtgtcttat gccacaagga ttaaaatatg tattcattgc tacaaaacaa tatctcgaaa   4140
```

```
tttagcagtt taaaacaaca aatattatct ccagtttctg agcctcagaa atctgagagt   4200

ggtttagctg ggtgatagtc tcgtggtttt ggtcaagcta ccaaccaggg ctacaatctt   4260

tcgaaggtgt cattggggct agaagatctg cttcccgcaa gactcacagc tgttggcagg   4320

agacctcagt ttgttgccac atgttcccct ccagagggcc tctcacaaca tggcagttat   4380

ttgtccccag agcaagcaac accggagggc aaggaagaag ccatgatgtt ttttgtaacc   4440

tagcctctga aagtgtcata ccaattctgt attttgttgg tcacacagac caagtcaact   4500

acaacgtggg agactcctac acaaggcatg aattctagga ggtgggcatt tttaagtgtc   4560

atctggaagg aggctgtcac aacctggaag ttaaaagcat tgatattctg aaatacagcg   4620

tgtataacat tgttttagta gggtgtgcaa tagttatgtt ttggtaatag cattaatgaa   4680

caatgttatt ttcatcttcc agacatctgg aagattgctc tagtggagta aaacatctta   4740

atgtattttg tccctaaata aactatctca ctaacaaaaa aaaaaaaaaa              4790
```

```
<210> SEQ ID NO 85
<211> LENGTH: 605
<212> TYPE: PRT
<213> ORGANISM: Homo sapiens

<400> SEQUENCE: 85

Met Ala Gly Leu Tyr Ser Leu Gly Val Ser Val Phe Ser Asp Gln Gly
1               5                   10                  15

Gly Arg Lys Tyr Met Glu Asp Val Thr Gln Ile Val Val Glu Pro Glu
            20                  25                  30

Pro Thr Ala Glu Glu Lys Pro Ser Pro Arg Arg Ser Leu Ser Gln Pro
        35                  40                  45

Leu Pro Pro Arg Pro Ser Pro Ala Ala Leu Pro Gly Gly Glu Val Ser
    50                  55                  60

Gly Lys Gly Pro Ala Val Ala Ala Arg Glu Ala Arg Asp Pro Leu Pro
65                  70                  75                  80

Asp Ala Gly Ala Ser Pro Ala Pro Ser Arg Cys Cys Arg Arg Arg Ser
                85                  90                  95

Ser Val Ala Phe Phe Ala Val Cys Asp Gly His Gly Gly Arg Glu Ala
            100                 105                 110

Ala Gln Phe Ala Arg Glu His Leu Trp Gly Phe Ile Lys Lys Gln Lys
        115                 120                 125

Gly Phe Thr Ser Ser Glu Pro Ala Lys Val Cys Ala Ala Ile Arg Lys
    130                 135                 140

Gly Phe Leu Ala Cys His Leu Ala Met Trp Lys Lys Leu Ala Glu Trp
145                 150                 155                 160

Pro Lys Thr Met Thr Gly Leu Pro Ser Thr Ser Gly Thr Thr Ala Ser
                165                 170                 175

Val Val Ile Ile Arg Gly Met Lys Met Tyr Val Ala His Val Gly Asp
            180                 185                 190

Ser Gly Val Val Leu Gly Ile Gln Asp Asp Pro Lys Asp Asp Phe Val
        195                 200                 205

Arg Ala Val Glu Val Thr Gln Asp His Lys Pro Glu Leu Pro Lys Glu
    210                 215                 220

Arg Glu Arg Ile Glu Gly Leu Gly Gly Ser Val Met Asn Lys Ser Gly
225                 230                 235                 240

Val Asn Arg Val Val Trp Lys Arg Pro Arg Leu Thr His Asn Gly Pro
                245                 250                 255
```

-continued

```
Val Arg Arg Ser Thr Val Ile Asp Gln Ile Pro Phe Leu Ala Val Ala
            260                 265                 270

Arg Ala Leu Gly Asp Leu Trp Ser Tyr Asp Phe Phe Ser Gly Glu Phe
        275                 280                 285

Val Val Ser Pro Glu Pro Asp Thr Ser Val His Thr Leu Asp Pro Gln
    290                 295                 300

Lys His Lys Tyr Ile Ile Leu Gly Ser Asp Gly Leu Trp Asn Met Ile
305                 310                 315                 320

Pro Pro Gln Asp Ala Ile Ser Met Cys Gln Asp Gln Glu Glu Lys Lys
                325                 330                 335

Tyr Leu Met Gly Glu His Gly Gln Ser Cys Ala Lys Met Leu Val Asn
            340                 345                 350

Arg Ala Leu Gly Arg Trp Arg Gln Arg Met Leu Arg Ala Asp Asn Thr
        355                 360                 365

Ser Ala Ile Val Ile Cys Ile Ser Pro Glu Val Asp Asn Gln Gly Asn
    370                 375                 380

Phe Thr Asn Glu Asp Glu Leu Tyr Leu Asn Leu Thr Asp Ser Pro Ser
385                 390                 395                 400

Tyr Asn Ser Gln Glu Thr Cys Val Met Thr Pro Ser Pro Cys Ser Thr
                405                 410                 415

Pro Pro Val Lys Ser Leu Glu Glu Asp Pro Trp Pro Arg Val Asn Ser
            420                 425                 430

Lys Asp His Ile Pro Ala Leu Val Arg Ser Asn Ala Phe Ser Glu Asn
        435                 440                 445

Phe Leu Glu Val Ser Ala Glu Ile Ala Arg Glu Asn Val Gln Gly Val
    450                 455                 460

Val Ile Pro Ser Lys Asp Pro Glu Pro Leu Glu Glu Asn Cys Ala Lys
465                 470                 475                 480

Ala Leu Thr Leu Arg Ile His Asp Ser Leu Asn Asn Ser Leu Pro Ile
                485                 490                 495

Gly Leu Val Pro Thr Asn Ser Thr Asn Thr Val Met Asp Gln Lys Asn
            500                 505                 510

Leu Lys Met Ser Thr Pro Gly Gln Met Lys Ala Gln Glu Ile Glu Arg
        515                 520                 525

Thr Pro Pro Thr Asn Phe Lys Arg Thr Leu Glu Glu Ser Asn Ser Gly
    530                 535                 540

Pro Leu Met Lys Lys His Arg Arg Asn Gly Leu Ser Arg Ser Ser Gly
545                 550                 555                 560

Ala Gln Pro Ala Ser Leu Pro Thr Thr Ser Gln Arg Lys Asn Ser Val
                565                 570                 575

Lys Leu Thr Met Arg Arg Arg Leu Arg Gly Gln Lys Lys Ile Gly Asn
            580                 585                 590

Pro Leu Leu His Gln His Arg Lys Thr Val Cys Val Cys
        595                 600                 605
```

<210> SEQ ID NO 86
<211> LENGTH: 2911
<212> TYPE: DNA
<213> ORGANISM: Mus musculus

<400> SEQUENCE: 86

```
cgcagctgct cggctcctct cgcccgcgac tcgaccggcc cagctctcgc ggacaagtcc      60

cgacatcacg cgcccccccc caccgccgcg gggaccgcct cctcttcact ctcggcttcg     120

tcgaagataa acaatagttg gccggcgagc ggcgagtgtg tctcccgcct cggaattcgg     180
```

-continued

```
cgggctgcgt gggaacggcg ggatcccggg cagccggcca tggcggggct gtactcgctg    240
ggagtgagcg tcttctcgga ccagggcggg aggaagtaca tggaggacgt aactcagatc    300
gtggtggagc ccgagccggc tgcggaggac aagccggcgc cggtaccgcg gcgggcgctc    360
gggttgccgg cgacccccac tctcgccggc gtcgggccat cggaaaaagg cccggcggcg    420
gcccgcgacc ctgccccgga cgccgcggcc tcgctacccg ctggccgctg ctgtcgccgc    480
cgctcttcgg tggccttctt tgcagtgtgc gacgggcacg gcggtcggga ggcggcacag    540
tttgcccggg agcacttgtg ggtttcatc aagaagcaga aaggcttcac ctcgtccgag    600
cccgccaagg tgtgcgctgc catccgcaaa ggtttcctcg cctgtcacct cgccatgtgg    660
aagaaactgg cagaatggcc aaagactatg acaggtcttc ccagcacgtc cgggacaact    720
gccagtgtgg ttataatacg gggcatgaag atgtatgtag cgcatgtagg tgactctggg    780
gtggtccttg gaattcagga tgacccaaag gatgattttg tgagagctgt ggaggtgaca    840
caagatcaca agccagaact tcccaaggaa agagaaagaa tcgaaggact tggcggcagt    900
gtgatgaaca agtctggagt gaaccgagta gtttggaaaa ggccccggct cactcacagt    960
ggacctgtca gaaggagcac agtcattgac cagattcctt ttctggctgt agcaagagcg   1020
cttggtgact tgtggagcta tgatttcttc agtggtaagt ttgtggtgtc acctgaacca   1080
gacaccagtg tccacactct tgacccccgg aagcacaagt atattatcct gggaagtgat   1140
ggactttgga atatggttcc acctcaagat gccatctcca tgtgccaaga ccaagaggag   1200
aaaaaatact tgatgggtga gcaaggacag tcctgtgcca aaatgcttgt gaatcgagca   1260
cttggccgct ggaggcagcg tatgcttcgg gcagataaca caagtgccat cgtaatctgc   1320
atctctccag aagtagacaa ccaagggaac ttcaccaatg aagatgagct ctttctgaac   1380
ctgactgata gccctactta caacagccag gagacctgtg tgatgacttc ttctccaagt   1440
tctacaccac caatcaagtc accggaagaa gatgcatggc caaggctgag ctctaaggac   1500
catatacctg cccttgttcg cagtaatgcc ttctcagaga agtttttaga ggtcccagct   1560
gagatagcta gagggaatat ccagactgta gtgatgacct caaaagactc agagacactt   1620
gaagaaaatt gccccaaagc cctgacttta aggattcatg attctttgaa taatactctg   1680
tcagttggcc tcattccaac caattcaaca aatactatca tggaccaaaa aaacttaaag   1740
atgtcaactc caggtcaaat gaaagctcaa gaagttgaaa gaacccctcc agccaatttt   1800
aaaaggacat tagaagaatc caactctggc ccccttatga agaagcaccg acgaaatggc   1860
ttaagtcgaa gtagcggggc ccaggcttcc agtctcccta cagcatccca gcgcaggcac   1920
tctgtcaaac tgaccctgag gcgcagactc aggggccaga ggaagatggg aaatcctctt   1980
ctccaccagc accggaaaac agtgtgtgtg tgctgagatg ggcctgggaa gtgggggtct   2040
ccctacctac gactgagggc tttttaaact tggtgcgaag ttgaactttt ttaaggggat   2100
aaaataaaga gaatacagtt tgactttttg gaatttaaca gttttatttt ggccttgtac   2160
ttgcctgtat tataatgtga attttgtaga tgtagggaat aagttgctgt aaaatgtgtg   2220
taaatttgta tcctttacac aagtttagtc tcttactctg acacatagta attgtgacag   2280
cagggctaat gttgaagaaa agtcagaaga atctttaaga ttttaaaaat gtctttaaag   2340
tttttaaaat gcttactaca tacttatata cacccttgt gaagaacaca tgacttttta    2400
aagaaaatta ctaagcaaac tggaaaagtg aagtattttc atagtgatct gtgctccact   2460
taatgtttcc cagggaccat tagtgtcttt ttaaaattac attttatttc acatttcata   2520
```

```
attcagaagt aaacctttca taggaaaaat actgagctgt gctaatgtag ctgattttag   2580

tctccttgtc ccacttacac tatgcagtat ctcctaactt cagtgcactc tgctagaaca   2640

gtacatttgc tgtatttact gaaatctctg gcacagaagg aagtgtgttt gcctcacaca   2700

ccatttgtcc cagaccagtg gcattaggcc atatattctc ttctagtgtt tgcttaaaat   2760

atgtgaagtt tttcttgcta tttcaataac aaatggtgct gctaacaccc aacatttcct   2820

aaattatttt ctatcataca gttttcattg gttatatgag tatgtctacc caataaatca   2880

ctgaatttat gttgaaaaaa aaaaaaaaaa a                                   2911


<210> SEQ ID NO 87
<211> LENGTH: 598
<212> TYPE: PRT
<213> ORGANISM: Mus musculus

<400> SEQUENCE: 87

Met Ala Gly Leu Tyr Ser Leu Gly Val Ser Val Phe Ser Asp Gln Gly
1               5                   10                  15

Gly Arg Lys Tyr Met Glu Asp Val Thr Gln Ile Val Val Glu Pro Glu
            20                  25                  30

Pro Ala Ala Glu Asp Lys Pro Ala Pro Val Pro Arg Arg Ala Leu Gly
        35                  40                  45

Leu Pro Ala Thr Pro Thr Leu Ala Gly Val Gly Pro Ser Glu Lys Gly
    50                  55                  60

Pro Ala Ala Ala Arg Asp Pro Ala Pro Asp Ala Ala Ala Ser Leu Pro
65                  70                  75                  80

Ala Gly Arg Cys Cys Arg Arg Arg Ser Ser Val Ala Phe Phe Ala Val
                85                  90                  95

Cys Asp Gly His Gly Gly Arg Glu Ala Ala Gln Phe Ala Arg Glu His
            100                 105                 110

Leu Trp Gly Phe Ile Lys Lys Gln Lys Gly Phe Thr Ser Ser Glu Pro
        115                 120                 125

Ala Lys Val Cys Ala Ala Ile Arg Lys Gly Phe Leu Ala Cys His Leu
    130                 135                 140

Ala Met Trp Lys Lys Leu Ala Glu Trp Pro Lys Thr Met Thr Gly Leu
145                 150                 155                 160

Pro Ser Thr Ser Gly Thr Thr Ala Ser Val Val Ile Ile Arg Gly Met
                165                 170                 175

Lys Met Tyr Val Ala His Val Gly Asp Ser Gly Val Val Leu Gly Ile
            180                 185                 190

Gln Asp Asp Pro Lys Asp Asp Phe Val Arg Ala Val Glu Val Thr Gln
        195                 200                 205

Asp His Lys Pro Glu Leu Pro Lys Glu Arg Glu Arg Ile Glu Gly Leu
    210                 215                 220

Gly Gly Ser Val Met Asn Lys Ser Gly Val Asn Arg Val Val Trp Lys
225                 230                 235                 240

Arg Pro Arg Leu Thr His Ser Gly Pro Val Arg Arg Ser Thr Val Ile
                245                 250                 255

Asp Gln Ile Pro Phe Leu Ala Val Ala Arg Ala Leu Gly Asp Leu Trp
            260                 265                 270

Ser Tyr Asp Phe Phe Ser Gly Lys Phe Val Val Ser Pro Glu Pro Asp
        275                 280                 285

Thr Ser Val His Thr Leu Asp Pro Arg Lys His Lys Tyr Ile Ile Leu
    290                 295                 300
```

-continued

```
Gly Ser Asp Gly Leu Trp Asn Met Val Pro Pro Gln Asp Ala Ile Ser
305                 310                 315                 320

Met Cys Gln Asp Gln Glu Glu Lys Lys Tyr Leu Met Gly Glu Gln Gly
                325                 330                 335

Gln Ser Cys Ala Lys Met Leu Val Asn Arg Ala Leu Gly Arg Trp Arg
            340                 345                 350

Gln Arg Met Leu Arg Ala Asp Asn Thr Ser Ala Ile Val Ile Cys Ile
        355                 360                 365

Ser Pro Glu Val Asp Asn Gln Gly Asn Phe Thr Asn Glu Asp Glu Leu
    370                 375                 380

Phe Leu Asn Leu Thr Asp Ser Pro Thr Tyr Asn Ser Gln Glu Thr Cys
385                 390                 395                 400

Val Met Thr Ser Ser Pro Ser Ser Thr Pro Pro Ile Lys Ser Pro Glu
                405                 410                 415

Glu Asp Ala Trp Pro Arg Leu Ser Ser Lys Asp His Ile Pro Ala Leu
            420                 425                 430

Val Arg Ser Asn Ala Phe Ser Glu Lys Phe Leu Glu Val Pro Ala Glu
        435                 440                 445

Ile Ala Arg Gly Asn Ile Gln Thr Val Val Met Thr Ser Lys Asp Ser
    450                 455                 460

Glu Thr Leu Glu Glu Asn Cys Pro Lys Ala Leu Thr Leu Arg Ile His
465                 470                 475                 480

Asp Ser Leu Asn Asn Thr Leu Ser Val Gly Leu Ile Pro Thr Asn Ser
                485                 490                 495

Thr Asn Thr Ile Met Asp Gln Lys Asn Leu Lys Met Ser Thr Pro Gly
            500                 505                 510

Gln Met Lys Ala Gln Glu Val Glu Arg Thr Pro Pro Ala Asn Phe Lys
        515                 520                 525

Arg Thr Leu Glu Glu Ser Asn Ser Gly Pro Leu Met Lys Lys His Arg
    530                 535                 540

Arg Asn Gly Leu Ser Arg Ser Ser Gly Ala Gln Ala Ser Ser Leu Pro
545                 550                 555                 560

Thr Ala Ser Gln Arg Arg His Ser Val Lys Leu Thr Leu Arg Arg Arg
                565                 570                 575

Leu Arg Gly Gln Arg Lys Met Gly Asn Pro Leu Leu His Gln His Arg
            580                 585                 590

Lys Thr Val Cys Val Cys
        595
```

<210> SEQ ID NO 88
<211> LENGTH: 2302
<212> TYPE: DNA
<213> ORGANISM: Homo sapiens

<400> SEQUENCE: 88

```
agttgctaag gaaatgactg cccgcagcgc ctggccccgc cgcgcaggcc gggcggggtc      60

tggagcggcg ccgtttccgc ttccgctccc tcacagctcc cgtcccgtta ccgcctcctg     120

gccggcctcg cgcctttcac cggcaccttg cgtcggtcgc gccgcggggc ctgctcctgc     180

cgcgcgcacc cccggggctt cggctccggc acgggtcgcg cccagctttc ctgcacctga     240

ggccgccggc cagccgccgc catgggtgcc tacctctccc agcccaacac ggtgaagtgc     300

tccggggacg gggtcggcgc cccgcgcctg ccgctgccct acggcttctc cgccatgcaa     360

ggctggcgcg tctccatgga ggatgctcac aactgtattc ctgagctgga cagtgagaca     420
```

-continued

```
gccatgtttt ctgtctacga tggacatgga ggggaggaag ttgccttgta ctgtgccaaa    480
tatcttcctg atatcatcaa agatcagaag gcctacaagg aaggcaagct acagaaggct    540
ttagaagatg ccttcttggc tattgacgcc aaattgacca ctgaagaagt cattaaagag    600
ctggcacaga ttgcagggcg acccactgag gatgaagatg aaaaagaaaa agtagctgat    660
gaagatgatg tggacaatga ggaggctgca ctgctgcatg aagaggctac catgactatt    720
gaagagctgc tgacacgcta cggggcagaac tgtcacaagg gccctcccca cagcaaatct    780
ggaggtggga caggcgagga accagggtcc cagggcctca atggggaggc aggacctgag    840
gactcaacta gggaaactcc ttcacaagaa aatggcccca cagccaaggc ctacacaggc    900
ttttcctcca actcggaacg tgggactgag gcaggccaag ttggtgagcc tggcattccc    960
actggtgagg ctgggccttc ctgctcttca gcctctgaca agctgcctcg agttgctaag   1020
tccaagttct ttgaggacag tgaggatgag tcagatgagg cggaggaaga agaggaagac   1080
agtgaggaat gcagcgagga agaggatggc tacagcagtg aggaggcaga gaatgaggaa   1140
gatgaggatg acaccgagga ggctgaagag gacgatgaag aagaagaaga agagatgatg   1200
gtgccaggga tggaaggcaa agaggagcct ggctctgaca gtggtacaac agcggtggtg   1260
gccctgatac gagggaagca gttgattgta gccaacgcag gagactctcg ctgtgtggta   1320
tctgaggctg gcaaagcttt agacatgtcc tatgatcaca aaccagagga tgaagtagaa   1380
ctagcacgca tcaagaatgc tggtggcaag gtcaccatgg atgggcgagt caacgggggc   1440
ctcaacctct ccagagccat tggggaccac ttctataaga gaaacaagaa cctgccacct   1500
gaggaacaga tgatttcagc ccttcctgac atcaaggtgc tgactctcac tgacgaccat   1560
gaattcatgg tcattgcctg tgatggcatc tggaatgtga tgagcagcca ggaagttgta   1620
gatttcattc aatcaaagat cagccagcgt gatgaaaatg gggagcttcg gttattgtca   1680
tccattgtgg aagagctgct ggatcagtgc ctggcaccag acacttctgg ggatggtaca   1740
gggtgtgaca acatgacctg catcatcatt tgcttcaagc cccgaaacac agcagagctc   1800
cagccagaga gtggcaagcg aaaactagag gaggtgctct ctactgaggg ggctgaagaa   1860
aatggcaaca gcgacaagaa gaagaaggcc aagcgagact agcagtcatc cagacccctg   1920
cccacctaga ctgttttctg agccctccgg acctgagact gagttttgtc tttttccttt   1980
agccttagca gtgggtatga ggtgtgcagg gggagctggg tggcttcact ccgcccattc   2040
caaagagggc tctccctcca cactgcagcc gggagcctct gctgtccttc ccagccgcct   2100
ctgctcctcg ggctcatcac cggttctgtg cctgtgctct gttgtgttgg agggaaggac   2160
tggcggttct ggtttttact ctgtgaactt tatttaagga cattcttttt tattggcggc   2220
tccatggccc tcggccgctt gcacccgctc tctgttgtac actttcaatc aacacttttt   2280
cagactaaag gccaaaacct aa                                             2302
```

<210> SEQ ID NO 89
<211> LENGTH: 546
<212> TYPE: PRT
<213> ORGANISM: Homo sapiens

<400> SEQUENCE: 89

```
Met Gly Ala Tyr Leu Ser Gln Pro Asn Thr Val Lys Cys Ser Gly Asp
1               5                   10                  15

Gly Val Gly Ala Pro Arg Leu Pro Leu Pro Tyr Gly Phe Ser Ala Met
            20                  25                  30
```

-continued

```
Gln Gly Trp Arg Val Ser Met Glu Asp Ala His Asn Cys Ile Pro Glu
        35                  40                  45

Leu Asp Ser Glu Thr Ala Met Phe Ser Val Tyr Asp Gly His Gly Gly
    50                  55                  60

Glu Glu Val Ala Leu Tyr Cys Ala Lys Tyr Leu Pro Asp Ile Ile Lys
65                  70                  75                  80

Asp Gln Lys Ala Tyr Lys Glu Gly Lys Leu Gln Lys Ala Leu Glu Asp
                85                  90                  95

Ala Phe Leu Ala Ile Asp Ala Lys Leu Thr Thr Glu Glu Val Ile Lys
            100                 105                 110

Glu Leu Ala Gln Ile Ala Gly Arg Pro Thr Glu Asp Glu Asp Glu Lys
        115                 120                 125

Glu Lys Val Ala Asp Glu Asp Asp Val Asp Asn Glu Glu Ala Ala Leu
    130                 135                 140

Leu His Glu Glu Ala Thr Met Thr Ile Glu Glu Leu Leu Thr Arg Tyr
145                 150                 155                 160

Gly Gln Asn Cys His Lys Gly Pro Pro His Ser Lys Ser Gly Gly Gly
                165                 170                 175

Thr Gly Glu Glu Pro Gly Ser Gln Gly Leu Asn Gly Glu Ala Gly Pro
            180                 185                 190

Glu Asp Ser Thr Arg Glu Thr Pro Ser Gln Glu Asn Gly Pro Thr Ala
        195                 200                 205

Lys Ala Tyr Thr Gly Phe Ser Ser Asn Ser Glu Arg Gly Thr Glu Ala
    210                 215                 220

Gly Gln Val Gly Glu Pro Gly Ile Pro Thr Gly Glu Ala Gly Pro Ser
225                 230                 235                 240

Cys Ser Ser Ala Ser Asp Lys Leu Pro Arg Val Ala Lys Ser Lys Phe
                245                 250                 255

Phe Glu Asp Ser Glu Asp Glu Ser Asp Glu Ala Glu Glu Glu Glu Glu
            260                 265                 270

Asp Ser Glu Glu Cys Ser Glu Glu Glu Asp Gly Tyr Ser Ser Glu Glu
        275                 280                 285

Ala Glu Asn Glu Glu Asp Glu Asp Asp Thr Glu Glu Ala Glu Glu Asp
    290                 295                 300

Asp Glu Glu Glu Glu Glu Glu Met Met Val Pro Gly Met Glu Gly Lys
305                 310                 315                 320

Glu Glu Pro Gly Ser Asp Ser Gly Thr Thr Ala Val Val Ala Leu Ile
                325                 330                 335

Arg Gly Lys Gln Leu Ile Val Ala Asn Ala Gly Asp Ser Arg Cys Val
            340                 345                 350

Val Ser Glu Ala Gly Lys Ala Leu Asp Met Ser Tyr Asp His Lys Pro
        355                 360                 365

Glu Asp Glu Val Glu Leu Ala Arg Ile Lys Asn Ala Gly Gly Lys Val
    370                 375                 380

Thr Met Asp Gly Arg Val Asn Gly Gly Leu Asn Leu Ser Arg Ala Ile
385                 390                 395                 400

Gly Asp His Phe Tyr Lys Arg Asn Lys Asn Leu Pro Pro Glu Glu Gln
                405                 410                 415

Met Ile Ser Ala Leu Pro Asp Ile Lys Val Leu Thr Leu Thr Asp Asp
            420                 425                 430

His Glu Phe Met Val Ile Ala Cys Asp Gly Ile Trp Asn Val Met Ser
        435                 440                 445
```

```
Ser Gln Glu Val Val Asp Phe Ile Gln Ser Lys Ile Ser Gln Arg Asp
    450                 455                 460

Glu Asn Gly Glu Leu Arg Leu Leu Ser Ser Ile Val Glu Glu Leu Leu
465                 470                 475                 480

Asp Gln Cys Leu Ala Pro Asp Thr Ser Gly Asp Gly Thr Gly Cys Asp
                485                 490                 495

Asn Met Thr Cys Ile Ile Ile Cys Phe Lys Pro Arg Asn Thr Ala Glu
            500                 505                 510

Leu Gln Pro Glu Ser Gly Lys Arg Lys Leu Glu Glu Val Leu Ser Thr
        515                 520                 525

Glu Gly Ala Glu Glu Asn Gly Asn Ser Asp Lys Lys Lys Lys Ala Lys
    530                 535                 540

Arg Asp
545


<210> SEQ ID NO 90
<211> LENGTH: 2165
<212> TYPE: DNA
<213> ORGANISM: Mus musculus

<400> SEQUENCE: 90

cttgcgtcga ctgcgcagcc gggcccgctc cttgccacgc gcgcccccag gggccccggc     60

tccggcgccg gcaagggtcg cgtcccgctt acctgttcct caggtagcca gccatccgcc    120

gccatgggtg cctacctctc tcagcccaac acggtgaagt gctccgggga cggggttggc    180

gccccgcggc tcccgctgcc ctacggcttc tccgccatgc aaggctggcg cgtctccatg    240

gaggatgctc acaactgtat tcctgagctg gacaatgaga cagccatgtt ttctgtctac    300

gatggacatg gaggggaaga ggttgccttg tactgtgcca aatatcttcc tgatattatc    360

aaagatcaga aggcctacaa ggaaggcaag cttcagaagg ctttacaaga tgccttcttg    420

gctattgatg ccaagctgac cacagaggaa gtcattaagg aactggccca gattgcaggg    480

agacccactg aagatgagga tgataaagac aaagtagcag atgaggatga tgtggacaat    540

gaggaggctg cattgttgca tgaagaggct accatgacta ttgaagagct gctgacgcga    600

tatgggcaga actgtcagaa ggtccctccc cacaccaaat ctggaattgg gacaggcgat    660

gaaccagggc cccagggcct caatggggag gctggacctg aggacccatc tagggaaact    720

ccttcccagg aaaatggccc cacagccaaa ggccacacag gcttttcctc caactcggaa    780

catgggactg aggcaggcca aattagtgag cccggtactg ctaccggtga ggctggacct    840

tcctgctctt cagcctctga caagctgcct cgagttgcta agtccaagtt ctttgaggac    900

agtgaagatg aatcagatga ggtggaggaa gaggaggatg acagtgagga atgtagtgag    960

gacgaggacg gctacagcag tgaggaggca gagaacgagg aagacgagga tgacacggag   1020

gaggctgaag aggatgatga tgaagagatg atggtccctg gaatggaagg caaagaagag   1080

cctggttctg acagtggcac aacagcggtg gtggctctga tcagagggaa gcagttgatt   1140

gtggccaatg caggagactc tcgctgtgtg gtgtccgagg ctggcaaagc tttagatatg   1200

tcctatgacc acaaaccaga ggatgaagtg gagctggcac gcatcaagaa tgctggtggc   1260

aaggtcacca tggatggacg agtcaatgga ggcctcaacc tctccagggc cattggagac   1320

cacttctaca agagaaacaa aaacttgcca ccccaggaac agatgatttc tgcccttcct   1380

gacatcaagg tgctgactct cactgatgac catgaattca tggtcattgc ttgtgacggc   1440

atctggaatg tgatgagcag ccaggaggtt gtagacttta ttcaatcaaa gatcagtcaa   1500
```

```
cgtgatgaaa acggggagct tcggttattg tcatccattg tggaagagct gctggatcag   1560

tgcctggcgc cagacacttc tggggatggt acagggtgtg acaacatgac gtgcatcatc   1620

atttgcttca agccccgaaa cacagtagag cttcaggcag agagtggcaa gaggaaactg   1680

gaggaggcac tgtccacgga gggggctgaa gacaccggca acagtgacaa aaagaaggcc   1740

aagagggact agtggtcaac cggaccctgc ccatgtggac tgttttctga gcccttggac   1800

ccgagactga gttttgtcct tgtcctttag ccttagcagt gggtatgagg tgtgcagggg   1860

gctgggtggc tttcctcagc ccattacaaa gagggccccc caccccccc acgcggcagc   1920

ctgggaggct ctgctgtcct cttaagcctc cttactctcc ttgggctcat cgactatcgg   1980

ttctgtgcct gtgctctgtt gtgttggagg gaaggactgg tagttctgat ttttactctg   2040

tgaacacttt atttaaggac attctttttt attggcggct ctgtgacccc tagccgcttg   2100

cacccgctct ctgttgtaca ctttcaagca acactttttc agactaaagg ccaaacaaaa   2160

gctaa                                                               2165


<210> SEQ ID NO 91
<211> LENGTH: 542
<212> TYPE: PRT
<213> ORGANISM: Mus musculus

<400> SEQUENCE: 91

Met Gly Ala Tyr Leu Ser Gln Pro Asn Thr Val Lys Cys Ser Gly Asp
1               5                   10                  15

Gly Val Gly Ala Pro Arg Leu Pro Leu Pro Tyr Gly Phe Ser Ala Met
            20                  25                  30

Gln Gly Trp Arg Val Ser Met Glu Asp Ala His Asn Cys Ile Pro Glu
        35                  40                  45

Leu Asp Asn Glu Thr Ala Met Phe Ser Val Tyr Asp Gly His Gly Gly
    50                  55                  60

Glu Glu Val Ala Leu Tyr Cys Ala Lys Tyr Leu Pro Asp Ile Ile Lys
65                  70                  75                  80

Asp Gln Lys Ala Tyr Lys Glu Gly Lys Leu Gln Lys Ala Leu Gln Asp
                85                  90                  95

Ala Phe Leu Ala Ile Asp Ala Lys Leu Thr Thr Glu Glu Val Ile Lys
            100                 105                 110

Glu Leu Ala Gln Ile Ala Gly Arg Pro Thr Glu Asp Glu Asp Asp Lys
        115                 120                 125

Asp Lys Val Ala Asp Glu Asp Asp Val Asp Asn Glu Glu Ala Ala Leu
    130                 135                 140

Leu His Glu Glu Ala Thr Met Thr Ile Glu Glu Leu Leu Thr Arg Tyr
145                 150                 155                 160

Gly Gln Asn Cys Gln Lys Val Pro Pro His Thr Lys Ser Gly Ile Gly
                165                 170                 175

Thr Gly Asp Glu Pro Gly Pro Gln Gly Leu Asn Gly Glu Ala Gly Pro
            180                 185                 190

Glu Asp Pro Ser Arg Glu Thr Pro Ser Gln Glu Asn Gly Pro Thr Ala
        195                 200                 205

Lys Gly His Thr Gly Phe Ser Ser Asn Ser Glu His Gly Thr Glu Ala
    210                 215                 220

Gly Gln Ile Ser Glu Pro Gly Thr Ala Thr Gly Glu Ala Gly Pro Ser
225                 230                 235                 240

Cys Ser Ser Ala Ser Asp Lys Leu Pro Arg Val Ala Lys Ser Lys Phe
                245                 250                 255
```

```
Phe Glu Asp Ser Glu Asp Glu Ser Asp Glu Val Glu Glu Glu Glu Asp
            260                 265                 270

Asp Ser Glu Glu Cys Ser Glu Asp Glu Asp Gly Tyr Ser Ser Glu Glu
        275                 280                 285

Ala Glu Asn Glu Glu Asp Glu Asp Asp Thr Glu Glu Ala Glu Glu Asp
    290                 295                 300

Asp Asp Glu Glu Met Met Val Pro Gly Met Glu Gly Lys Glu Glu Pro
305                 310                 315                 320

Gly Ser Asp Ser Gly Thr Thr Ala Val Val Ala Leu Ile Arg Gly Lys
                325                 330                 335

Gln Leu Ile Val Ala Asn Ala Gly Asp Ser Arg Cys Val Val Ser Glu
            340                 345                 350

Ala Gly Lys Ala Leu Asp Met Ser Tyr Asp His Lys Pro Glu Asp Glu
        355                 360                 365

Val Glu Leu Ala Arg Ile Lys Asn Ala Gly Gly Lys Val Thr Met Asp
    370                 375                 380

Gly Arg Val Asn Gly Gly Leu Asn Leu Ser Arg Ala Ile Gly Asp His
385                 390                 395                 400

Phe Tyr Lys Arg Asn Lys Asn Leu Pro Pro Gln Glu Gln Met Ile Ser
                405                 410                 415

Ala Leu Pro Asp Ile Lys Val Leu Thr Leu Thr Asp Asp His Glu Phe
            420                 425                 430

Met Val Ile Ala Cys Asp Gly Ile Trp Asn Val Met Ser Ser Gln Glu
        435                 440                 445

Val Val Asp Phe Ile Gln Ser Lys Ile Ser Gln Arg Asp Glu Asn Gly
    450                 455                 460

Glu Leu Arg Leu Leu Ser Ser Ile Val Glu Glu Leu Leu Asp Gln Cys
465                 470                 475                 480

Leu Ala Pro Asp Thr Ser Gly Asp Gly Thr Gly Cys Asp Asn Met Thr
                485                 490                 495

Cys Ile Ile Ile Cys Phe Lys Pro Arg Asn Thr Val Glu Leu Gln Ala
            500                 505                 510

Glu Ser Gly Lys Arg Lys Leu Glu Glu Ala Leu Ser Thr Glu Gly Ala
        515                 520                 525

Glu Asp Thr Gly Asn Ser Asp Lys Lys Lys Ala Lys Arg Asp
    530                 535                 540


<210> SEQ ID NO 92
<211> LENGTH: 393
<212> TYPE: PRT
<213> ORGANISM: Homo sapiens

<400> SEQUENCE: 92

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80
```

```
Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

<210> SEQ ID NO 93
<211> LENGTH: 2591
<212> TYPE: DNA
<213> ORGANISM: Homo sapiens

<400> SEQUENCE: 93

```
gatgggattg gggttttccc ctcccatgtg ctcaagactg gcgctaaaag ttttgagctt      60

ctcaaaagtc tagagccacc gtccagggag caggtagctg ctgggctccg ggacactttt     120

gcgttcgggc tgggagcgtg ctttccacga cggtgacacg cttccctgga ttggcagcca     180

gactgccttc cgggtcactg ccatggagga gccgcagtca gatcctagcg tcgagccccc     240

tctgagtcag gaaacatttt cagacctatg gaaactactt cctgaaaaca acgttctgtc     300
```

-continued

```
ccccttgccg tcccaagcaa tggatgattt gatgctgtcc ccggacgata ttgaacaatg    360
gttcactgaa gacccaggtc cagatgaagc tcccagaatg ccagaggctg ctccccccgt    420
ggcccctgca ccagcagctc ctacaccggc ggcccctgca ccagccccct cctggcccct    480
gtcatcttct gtcccttccc agaaaaccta ccagggcagc tacggtttcc gtctgggctt    540
cttgcattct gggacagcca agtctgtgac ttgcacgtac tcccctgccc tcaacaagat    600
gttttgccaa ctggccaaga cctgccctgt gcagctgtgg gttgattcca caccccccgcc    660
cggcacccgc gtccgcgcca tggccatcta caagcagtca cagcacatga cggaggttgt    720
gaggcgctgc ccccaccatg agcgctgctc agatagcgat ggtctggccc ctcctcagca    780
tcttatccga gtggaaggaa atttgcgtgt ggagtatttg gatgacagaa acacttttcg    840
acatagtgtg gtggtgccct atgagccgcc tgaggttggc tctgactgta ccaccatcca    900
ctacaactac atgtgtaaca gttcctgcat gggcggcatg aaccggaggc ccatcctcac    960
catcatcaca ctggaagact ccagtggtaa tctactggga cggaacagct ttgaggtgcg   1020
tgtttgtgcc tgtcctggga gagaccggcg cacagaggaa gagaatctcc gcaagaaagg   1080
ggagcctcac cacgagctgc ccccagggag cactaagcga gcactgccca acaacaccag   1140
ctcctctccc cagccaaaga agaaaccact ggatggagaa tatttcaccc ttcagatccg   1200
tgggcgtgag cgcttcgaga tgttccgaga gctgaatgag gccttggaac tcaaggatgc   1260
ccaggctggg aaggagccag gggggagcag ggctcactcc agccacctga agtccaaaaa   1320
gggtcagtct acctcccgcc ataaaaaact catgttcaag acagaagggc ctgactcaga   1380
ctgacattct ccacttcttg ttccccactg acagcctccc acccccatct ctccctcccc   1440
tgccattttg ggttttgggt ctttgaaccc ttgcttgcaa taggtgtgcg tcagaagcac   1500
ccaggacttc catttgcttt gtcccggggc tccactgaac aagttggcct gcactggtgt   1560
tttgttgtgg ggaggaggat ggggagtagg acataccagc ttagatttta aggtttttac   1620
tgtgagggat gtttgggaga tgtaagaaat gttcttgcag ttaagggtta gtttacaatc   1680
agccacattc taggtagggg cccacttcac cgtactaacc agggaagctg tccctcactg   1740
ttgaattttc tctaacttca aggcccatat ctgtgaaatg ctggcatttg cacctacctc   1800
acagagtgca ttgtgagggt taatgaaata atgtacatct ggccttgaaa ccacctttta   1860
ttacatgggg tctagaactt gaccccccttg agggtgcttg ttccctctcc ctgttggtcg   1920
gtgggttggt agtttctaca gttgggcagc tggttaggta gagggagttg tcaagtctct   1980
gctggcccag ccaaaccctg tctgacaacc tcttggtgaa ccttagtacc taaaaggaaa   2040
tctcacccca tcccacaccc tggaggattt catctcttgt atatgatgat ctggatccac   2100
caagacttgt tttatgctca gggtcaattt cttttttctt tttttttttt tttttttcttt   2160
ttctttgaga ctgggtctcg ctttgttgcc caggctggag tggagtggcg tgatcttggc   2220
ttactgcagc ctttgcctcc ccggctcgag cagtcctgcc tcagcctccg gagtagctgg   2280
gaccacaggt tcatgccacc atggccagcc aacttttgca tgttttgtag agatggggtc   2340
tcacagtgtt gcccaggctg gtctcaaact cctgggctca ggcgatccac ctgtctcagc   2400
ctcccagagt gctgggatta caattgtgag ccaccacgtc cagctggaag ggtcaacatc   2460
ttttacattc tgcaagcaca tctgcatttt caccccaccc ttcccctcct tctccctttt   2520
tatatcccat ttttatatcg atctcttatt ttacaataaa actttgctgc cacctgtgtg   2580
tctgaggggt g                                                         2591
```

<210> SEQ ID NO 94
<211> LENGTH: 2588
<212> TYPE: DNA
<213> ORGANISM: Homo sapiens

<400> SEQUENCE: 94
gatgggattg gggttttccc ctcccatgtg ctcaagactg gcgctaaaag ttttgagctt 60
ctcaaaagtc tagagccacc gtccagggag caggtagctg ctgggctccg gggacacttt 120
gcgttcgggc tgggagcgtg ctttccacga cggtgacacg cttccctgga ttggccagac 180
tgccttccgg gtcactgcca tggaggagcc gcagtcagat cctagcgtcg agccccctct 240
gagtcaggaa acattttcag acctatggaa actacttcct gaaaacaacg ttctgtcccc 300
cttgccgtcc caagcaatgg atgatttgat gctgtccccg gacgatattg aacaatggtt 360
cactgaagac ccaggtccag atgaagctcc cagaatgcca gaggctgctc cccccgtggc 420
ccctgcacca gcagctccta caccggcggc ccctgcacca gccccctcct ggcccctgtc 480
atcttctgtc ccttcccaga aaacctacca gggcagctac ggtttccgtc tgggcttctt 540
gcattctggg acagccaagt ctgtgacttg cacgtactcc cctgccctca acaagatgtt 600
ttgccaactg gccaagacct gccctgtgca gctgtgggtt gattccacac ccccgcccgg 660
cacccgcgtc cgcgccatgg ccatctacaa gcagtcacag cacatgacgg aggttgtgag 720
gcgctgcccc caccatgagc gctgctcaga tagcgatggt ctggcccctc ctcagcatct 780
tatccgagtg gaaggaaatt tgcgtgtgga gtatttggat gacagaaaca cttttcgaca 840
tagtgtggtg gtgccctatg agccgcctga ggttggctct gactgtacca ccatccacta 900
caactacatg tgtaacagtt cctgcatggg cggcatgaac cggaggccca tcctcaccat 960
catcacactg gaagactcca gtggtaatct actgggacgg aacagctttg aggtgcgtgt 1020
ttgtgcctgt cctgggagag accggcgcac agaggaagag aatctccgca agaaagggga 1080
gcctcaccac gagctgcccc cagggagcac taagcgagca ctgcccaaca acaccagctc 1140
ctctccccag ccaaagaaga aaccactgga tggagaatat ttcacccttc agatccgtgg 1200
gcgtgagcgc ttcgagatgt tccgagagct gaatgaggcc ttggaactca aggatgccca 1260
ggctgggaag gagccagggg ggagcagggc tcactccagc cacctgaagt ccaaaaaggg 1320
tcagtctacc tcccgccata aaaaactcat gttcaagaca gaagggcctg actcagactg 1380
acattctcca cttcttgttc cccactgaca gcctcccacc cccatctctc cctcccctgc 1440
cattttgggt tttgggtctt tgaacccttg cttgcaatag gtgtgcgtca gaagcaccca 1500
ggacttccat ttgctttgtc ccggggctcc actgaacaag ttggcctgca ctggtgtttt 1560
gttgtgggga ggaggatggg gagtaggaca taccagctta gattttaagg tttttactgt 1620
gagggatgtt tgggagatgt aagaaatgtt cttgcagtta agggttagtt tacaatcagc 1680
cacattctag gtaggggccc acttcaccgt actaaccagg gaagctgtcc ctcactgttg 1740
aattttctct aacttcaagg cccatatctg tgaaatgctg gcatttgcac ctacctcaca 1800
gagtgcattg tgagggttaa tgaaataatg tacatctggc cttgaaacca ccttttatta 1860
catggggtct agaacttgac ccccttgagg gtgcttgttc cctctccctg ttggtcggtg 1920
ggttggtagt ttctacagtt gggcagctgg ttaggtagag ggagttgtca agtctctgct 1980
ggcccagcca aaccctgtct gacaacctct tggtgaacct tagtacctaa aaggaaatct 2040
caccccatcc cacaccctgg aggatttcat ctcttgtata tgatgatctg gatccaccaa 2100
gacttgtttt atgctcaggg tcaatttctt ttttcttttt tttttttttt tttcttttc 2160

```
tttgagactg ggtctcgctt tgttgcccag gctggagtgg agtggcgtga tcttggctta   2220

ctgcagcctt tgcctccccg gctcgagcag tcctgcctca gcctccggag tagctgggac   2280

cacaggttca tgccaccatg gccagccaac ttttgcatgt tttgtagaga tggggtctca   2340

cagtgttgcc caggctggtc tcaaactcct gggctcaggc gatccacctg tctcagcctc   2400

ccagagtgct gggattacaa ttgtgagcca ccacgtccag ctggaagggt caacatcttt   2460

tacattctgc aagcacatct gcattttcac cccacccttc ccctccttct cccttttat   2520

atcccatttt tatatcgatc tcttatttta caataaaact ttgctgccac ctgtgtgtct   2580

gaggggtg                                                            2588
```

<210> SEQ ID NO 95
<211> LENGTH: 341
<212> TYPE: PRT
<213> ORGANISM: Homo sapiens

<400> SEQUENCE: 95

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285
```

-continued

```
Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Asp Gln Thr Ser Phe
                325                 330                 335

Gln Lys Glu Asn Cys
            340
```

<210> SEQ ID NO 96
<211> LENGTH: 2724
<212> TYPE: DNA
<213> ORGANISM: Homo sapiens

<400> SEQUENCE: 96

```
gatgggattg gggttttccc ctcccatgtg ctcaagactg gcgctaaaag ttttgagctt     60

ctcaaaagtc tagagccacc gtccagggag caggtagctg ctgggctccg gggacacttt    120

gcgttcgggc tgggagcgtg ctttccacga cggtgacacg cttccctgga ttggcagcca    180

gactgccttc cgggtcactg ccatggagga gccgcagtca gatcctagcg tcgagccccc    240

tctgagtcag gaaacatttt cagacctatg gaaactactt cctgaaaaca acgttctgtc    300

ccccttgccg tcccaagcaa tggatgattt gatgctgtcc ccggacgata ttgaacaatg    360

gttcactgaa gacccaggtc cagatgaagc tcccagaatg ccagaggctg ctccccccgt    420

ggcccctgca ccagcagctc ctacaccggc ggcccctgca ccagccccct cctggcccct    480

gtcatcttct gtcccttccc agaaaaccta ccagggcagc tacggtttcc gtctgggctt    540

cttgcattct gggacagcca agtctgtgac ttgcacgtac tcccctgccc tcaacaagat    600

gttttgccaa ctggccaaga cctgccctgt gcagctgtgg gttgattcca caccccgccc    660

cggcacccgc gtccgcgcca tggccatcta caagcagtca cagcacatga cggaggttgt    720

gaggcgctgc ccccaccatg agcgctgctc agatagcgat ggtctggccc ctcctcagca    780

tcttatccga gtggaaggaa atttgcgtgt ggagtatttg gatgacagaa acacttttcg    840

acatagtgtg gtggtgccct atgagccgcc tgaggttggc tctgactgta ccaccatcca    900

ctacaactac atgtgtaaca gttcctgcat gggcggcatg aaccggaggc ccatcctcac    960

catcatcaca ctggaagact ccagtggtaa tctactggga cggaacagct ttgaggtgcg   1020

tgtttgtgcc tgtcctggga gagaccggcg cacagaggaa gagaatctcc gcaagaaagg   1080

ggagcctcac cacgagctgc ccccagggag cactaagcga gcactgccca acaacaccag   1140

ctcctctccc cagccaaaga agaaaccact ggatggagaa tatttcaccc ttcaggacca   1200

gaccagcttt caaaaagaaa attgttaaag agagcatgaa aatggttcta tgactttgcc   1260

tgatacagat gctacttgac ttacgatggt gttacttcct gataaactcg tcgtaagttg   1320

aaaatattat ccgtgggcgt gagcgcttcg agatgttccg agagctgaat gaggccttgg   1380

aactcaagga tgcccaggct gggaaggagc caggggggag cagggctcac tccagccacc   1440

tgaagtccaa aaagggtcag tctacctccc gccataaaaa actcatgttc aagacagaag   1500

ggcctgactc agactgacat tctccacttc ttgttcccca ctgacagcct cccaccccca   1560

tctctccctc ccctgccatt ttgggttttg ggtctttgaa cccttgcttg caataggtgt   1620

gcgtcagaag cacccaggac ttccatttgc tttgtcccgg ggctccactg aacaagttgg   1680

cctgcactgg tgttttgttg tggggaggag gatggggagt aggacatacc agcttagatt   1740
```

```
ttaaggtttt tactgtgagg gatgtttggg agatgtaaga aatgttcttg cagttaaggg   1800

ttagtttaca atcagccaca ttctaggtag gggcccactt caccgtacta accagggaag   1860

ctgtccctca ctgttgaatt ttctctaact tcaaggccca tatctgtgaa atgctggcat   1920

ttgcacctac ctcacagagt gcattgtgag ggttaatgaa ataatgtaca tctggccttg   1980

aaaccacctt ttattacatg gggtctagaa cttgaccccc ttgagggtgc ttgttccctc   2040

tccctgttgg tcggtgggtt ggtagtttct acagttgggc agctggttag gtagagggag   2100

ttgtcaagtc tctgctggcc cagccaaacc ctgtctgaca acctcttggt gaaccttagt   2160

acctaaaagg aaatctcacc ccatcccaca ccctggagga tttcatctct tgtatatgat   2220

gatctggatc caccaagact tgttttatgc tcagggtcaa tttctttttt cttttttttt   2280

tttttttttc tttttctttg agactgggtc tcgctttgtt gcccaggctg gagtggagtg   2340

gcgtgatctt ggcttactgc agcctttgcc tccccggctc gagcagtcct gcctcagcct   2400

ccggagtagc tgggaccaca ggttcatgcc accatggcca gccaactttt gcatgttttg   2460

tagagatggg gtctcacagt gttgcccagg ctggtctcaa actcctgggc tcaggcgatc   2520

cacctgtctc agcctcccag agtgctggga ttacaattgt gagccaccac gtccagctgg   2580

aagggtcaac atcttttaca ttctgcaagc acatctgcat tttcacccca cccttcccct   2640

ccttctccct ttttatatcc catttttata tcgatctctt attttacaat aaaactttgc   2700

tgccacctgt gtgtctgagg ggtg                                          2724
```

<210> SEQ ID NO 97
<211> LENGTH: 346
<212> TYPE: PRT
<213> ORGANISM: Homo sapiens

<400> SEQUENCE: 97

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190
```

-continued

```
His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Met Leu Leu Asp Leu
                325                 330                 335

Arg Trp Cys Tyr Phe Leu Ile Asn Ser Ser
            340                 345
```

<210> SEQ ID NO 98
<211> LENGTH: 2651
<212> TYPE: DNA
<213> ORGANISM: Homo sapiens

<400> SEQUENCE: 98

```
gatgggattg gggttttccc ctcccatgtg ctcaagactg gcgctaaaag ttttgagctt     60

ctcaaaagtc tagagccacc gtccagggag caggtagctg ctgggctccg gggacacttt    120

gcgttcgggc tgggagcgtg ctttccacga cggtgacacg cttccctgga ttggcagcca    180

gactgccttc cgggtcactg ccatggagga gccgcagtca gatcctagcg tcgagccccc    240

tctgagtcag gaaacatttt cagacctatg gaaactactt cctgaaaaca acgttctgtc    300

cccettgccg tcccaagcaa tggatgattt gatgctgtcc ccggacgata ttgaacaatg    360

gttcactgaa gacccaggtc cagatgaagc tcccagaatg ccagaggctg ctccccccgt    420

ggcccctgca ccagcagctc ctacaccggc ggcccctgca ccagcccect cctggcccct    480

gtcatcttct gtcccttccc agaaaaccta ccagggcagc tacggtttcc gtctgggctt    540

cttgcattct gggacagcca agtctgtgac ttgcacgtac tcccctgccc tcaacaagat    600

gttttgccaa ctggccaaga cctgccctgt gcagctgtgg gttgattcca cacccccgcc    660

cggcacccgc gtccgcgcca tggccatcta caagcagtca cagcacatga cggaggttgt    720

gaggcgctgc ccccaccatg agcgctgctc agatagcgat ggtctggccc ctcctcagca    780

tcttatccga gtggaaggaa atttgcgtgt ggagtatttg gatgacagaa acacttttcg    840

acatagtgtg gtggtgccct atgagccgcc tgaggttggc tctgactgta ccaccatcca    900

ctacaactac atgtgtaaca gttcctgcat gggcggcatg aaccggaggc ccatcctcac    960

catcatcaca ctggaagact ccagtggtaa tctactggga cggaacagct ttgaggtgcg   1020

tgtttgtgcc tgtcctggga gagaccggcg cacagaggaa gagaatctcc gcaagaaagg   1080

ggagcctcac cacgagctgc ccccagggag cactaagcga gcactgccca acaacaccag   1140

ctcctctccc cagccaaaga agaaaccact ggatggagaa tatttcaccc ttcagatgct   1200
```

-continued

```
acttgactta cgatggtgtt acttcctgat aaactcgtcg taagttgaaa atattatccg   1260

tgggcgtgag cgcttcgaga tgttccgaga gctgaatgag gccttggaac tcaaggatgc   1320

ccaggctggg aaggagccag gggggagcag ggctcactcc agccacctga agtccaaaaa   1380

gggtcagtct acctcccgcc ataaaaaact catgttcaag acagaagggc ctgactcaga   1440

ctgacattct ccacttcttg ttccccactg acagcctccc acccccatct ctccctcccc   1500

tgccattttg ggttttgggt ctttgaaccc ttgcttgcaa taggtgtgcg tcagaagcac   1560

ccaggacttc catttgcttt gtcccggggc tccactgaac aagttggcct gcactggtgt   1620

tttgttgtgg ggaggaggat ggggagtagg acataccagc ttagatttta aggtttttac   1680

tgtgagggat gtttgggaga tgtaagaaat gttcttgcag ttaagggtta gtttacaatc   1740

agccacattc taggtagggg cccacttcac cgtactaacc agggaagctg tccctcactg   1800

ttgaattttc tctaacttca aggcccatat ctgtgaaatg ctggcatttg cacctacctc   1860

acagagtgca ttgtgagggt taatgaaata atgtacatct ggccttgaaa ccacctttta   1920

ttacatgggg tctagaactt gaccccettg agggtgcttg ttccctctcc ctgttggtcg   1980

gtgggttggt agtttctaca gttgggcagc tggttaggta gagggagttg tcaagtctct   2040

gctggcccag ccaaaccctg tctgacaacc tcttggtgaa ccttagtacc taaaaggaaa   2100

tctcacccca tcccacaccc tggaggattt catctcttgt atatgatgat ctggatccac   2160

caagacttgt tttatgctca gggtcaattt ctttttctt ttttttttt tttttcttt   2220

ttctttgaga ctgggtctcg ctttgttgcc caggctggag tggagtggcg tgatcttggc   2280

ttactgcagc ctttgcctcc ccggctcgag cagtcctgcc tcagcctccg gagtagctgg   2340

gaccacaggt tcatgccacc atggccagcc aacttttgca tgttttgtag agatggggtc   2400

tcacagtgtt gcccaggctg gtctcaaact cctgggctca ggcgatccac ctgtctcagc   2460

ctcccagagt gctgggatta caattgtgag ccaccacgtc cagctggaag ggtcaacatc   2520

ttttacattc tgcaagcaca tctgcatttt caccccaccc ttcccctcct tctccctttt   2580

tatatcccat ttttatatcg atctcttatt ttacaataaa actttgctgc cacctgtgtg   2640

tctgaggggt g                                                         2651
```

<210> SEQ ID NO 99
<211> LENGTH: 261
<212> TYPE: PRT
<213> ORGANISM: Homo sapiens

<400> SEQUENCE: 99

```
Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110
```

-continued

```
Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Ile Arg Gly Arg Glu Arg Phe Glu Met
        195                 200                 205

Phe Arg Glu Leu Asn Glu Ala Leu Glu Leu Lys Asp Ala Gln Ala Gly
    210                 215                 220

Lys Glu Pro Gly Gly Ser Arg Ala His Ser Ser His Leu Lys Ser Lys
225                 230                 235                 240

Lys Gly Gln Ser Thr Ser Arg His Lys Lys Leu Met Phe Lys Thr Glu
                245                 250                 255

Gly Pro Asp Ser Asp
            260


<210> SEQ ID NO 100
<211> LENGTH: 2271
<212> TYPE: DNA
<213> ORGANISM: Homo sapiens

<400> SEQUENCE: 100

tgaggccagg agatggaggc tgcagtgagc tgtgatcaca ccactgtgct ccagcctgag      60

tgacagagca agaccctatc tcaaaaaaaa aaaaaaaaaa gaaaagctcc tgaggtgtag     120

acgccaactc tctctagctc gctagtgggt tgcaggaggt gcttacgcat gtttgtttct     180

ttgctgccgt cttccagttg ctttatctgt tcacttgtgc cctgactttc aactctgtct     240

ccttcctctt cctacagtac tcccctgccc tcaacaagat gttttgccaa ctggccaaga     300

cctgccctgt gcagctgtgg gttgattcca cacccccgcc cggcacccgc gtccgcgcca     360

tggccatcta caagcagtca cagcacatga cggaggttgt gaggcgctgc ccccaccatg     420

agcgctgctc agatagcgat ggtctggccc ctcctcagca tcttatccga gtggaaggaa     480

atttgcgtgt ggagtatttg gatgacagaa acacttttcg acatagtgtg gtggtgccct     540

atgagccgcc tgaggttggc tctgactgta ccaccatcca ctacaactac atgtgtaaca     600

gttcctgcat gggcggcatg aaccggaggc ccatcctcac catcatcaca ctggaagact     660

ccagtggtaa tctactggga cggaacagct ttgaggtgcg tgtttgtgcc tgtcctggga     720

gagaccggcg cacagaggaa gagaatctcc gcaagaaagg ggagcctcac cacgagctgc     780

ccccagggag cactaagcga gcactgccca acaacaccag ctcctctccc cagccaaaga     840

agaaaccact ggatggagaa tatttcaccc ttcagatccg tgggcgtgag cgcttcgaga     900

tgttccgaga gctgaatgag gccttggaac tcaaggatgc ccaggctggg aaggagccag     960

gggggagcag ggctcactcc agccacctga agtccaaaaa gggtcagtct acctcccgcc    1020

ataaaaaact catgttcaag acagaagggc ctgactcaga ctgacattct ccacttcttg    1080

ttccccactg acagcctccc acccccatct ctccctcccc tgccattttg ggttttgggt    1140

ctttgaaccc ttgcttgcaa taggtgtgcg tcagaagcac ccaggacttc catttgcttt    1200

gtcccggggc tccactgaac aagttggcct gcactggtgt tttgttgtgg ggaggaggat    1260
```

```
ggggagtagg acataccagc ttagatttta aggtttttac tgtgagggat gtttgggaga   1320

tgtaagaaat gttcttgcag ttaagggtta gtttacaatc agccacattc taggtagggg   1380

cccacttcac cgtactaacc agggaagctg tccctcactg ttgaattttc tctaacttca   1440

aggcccatat ctgtgaaatg ctggcatttg cacctacctc acagagtgca ttgtgagggt   1500

taatgaaata atgtacatct ggccttgaaa ccacctttta ttacatgggg tctagaactt   1560

gaccccccttg agggtgcttg ttccctctcc ctgttggtcg gtgggttggt agtttctaca   1620

gttgggcagc tggttaggta gagggagttg tcaagtctct gctggcccag ccaaaccctg   1680

tctgacaacc tcttggtgaa ccttagtacc taaaaggaaa tctcacccca tcccacaccc   1740

tggaggattt catctcttgt atatgatgat ctggatccac caagacttgt tttatgctca   1800

gggtcaattt ctttttcttt tttttttttt ttttttcttt ttctttgaga ctgggtctcg   1860

ctttgttgcc caggctggag tggagtggcg tgatcttggc ttactgcagc ctttgcctcc   1920

ccggctcgag cagtcctgcc tcagcctccg gagtagctgg gaccacaggt tcatgccacc   1980

atggccagcc aacttttgca tgttttgtag agatggggtc tcacagtgtt gcccaggctg   2040

gtctcaaact cctgggctca ggcgatccac ctgtctcagc ctcccagagt gctgggatta   2100

caattgtgag ccaccacgtc cagctggaag ggtcaacatc ttttacattc tgcaagcaca   2160

tctgcatttt caccccaccc ttcccctcct tctccctttt tatatcccat ttttatatcg   2220

atctcttatt ttacaataaa actttgctgc cacctgtgtg tctgaggggt g            2271
```

<210> SEQ ID NO 101
<211> LENGTH: 209
<212> TYPE: PRT
<213> ORGANISM: Homo sapiens

<400> SEQUENCE: 101

```
Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190
```

```
Gly Glu Tyr Phe Thr Leu Gln Asp Gln Thr Ser Phe Gln Lys Glu Asn
        195                 200                 205

Cys


<210> SEQ ID NO 102
<211> LENGTH: 2404
<212> TYPE: DNA
<213> ORGANISM: Homo sapiens

<400> SEQUENCE: 102

tgaggccagg agatggaggc tgcagtgagc tgtgatcaca ccactgtgct ccagcctgag     60

tgacagagca agaccctatc tcaaaaaaaa aaaaaaaaaa gaaaagctcc tgaggtgtag    120

acgccaactc tctctagctc gctagtgggt tgcaggaggt gcttacgcat gtttgtttct    180

ttgctgccgt cttccagttg ctttatctgt tcacttgtgc cctgactttc aactctgtct    240

ccttcctctt cctacagtac tcccctgccc tcaacaagat gttttgccaa ctggccaaga    300

cctgccctgt gcagctgtgg gttgattcca cacccccgcc cggcacccgc gtccgcgcca    360

tggccatcta caagcagtca cagcacatga cggaggttgt gaggcgctgc ccccaccatg    420

agcgctgctc agatagcgat ggtctggccc ctcctcagca tcttatccga gtggaaggaa    480

atttgcgtgt ggagtatttg gatgacagaa acacttttcg acatagtgtg gtggtgccct    540

atgagccgcc tgaggttggc tctgactgta ccaccatcca ctacaactac atgtgtaaca    600

gttcctgcat gggcggcatg aaccggaggc ccatcctcac catcatcaca ctggaagact    660

ccagtggtaa tctactggga cggaacagct ttgaggtgcg tgtttgtgcc tgtcctggga    720

gagaccggcg cacagaggaa gagaatctcc gcaagaaagg ggagcctcac cacgagctgc    780

ccccagggag cactaagcga gcactgccca acaacaccag ctcctctccc cagccaaaga    840

agaaaccact ggatggagaa tatttcaccc ttcaggacca gaccagcttt caaaaagaaa    900

attgttaaag agagcatgaa aatggttcta tgactttgcc tgatacagat gctacttgac    960

ttacgatggt gttacttcct gataaactcg tcgtaagttg aaaatattat ccgtgggcgt   1020

gagcgcttcg agatgttccg agagctgaat gaggccttgg aactcaagga tgcccaggct   1080

gggaaggagc caggggggag cagggctcac tccagccacc tgaagtccaa aaagggtcag   1140

tctacctccc gccataaaaa actcatgttc aagacagaag ggcctgactc agactgacat   1200

tctccacttc ttgttcccca ctgacagcct cccaccccca tctctccctc ccctgccatt   1260

ttgggttttg ggtctttgaa cccttgcttg caataggtgt gcgtcagaag cacccaggac   1320

ttccatttgc tttgtcccgg ggctccactg aacaagttgg cctgcactgg tgttttgttg   1380

tggggaggag gatggggagt aggacatacc agcttagatt ttaaggtttt tactgtgagg   1440

gatgtttggg agatgtaaga aatgttcttg cagttaaggg ttagtttaca atcagccaca   1500

ttctaggtag ggcccactt caccgtacta accagggaag ctgtccctca ctgttgaatt   1560

ttctctaact tcaaggccca tatctgtgaa atgctggcat ttgcacctac ctcacagagt   1620

gcattgtgag ggttaatgaa ataatgtaca tctggccttg aaaccacctt ttattacatg   1680

gggtctagaa cttgaccccc ttgagggtgc ttgttccctc tccctgttgg tcggtgggtt   1740

ggtagtttct acagttgggc agctggttag gtagagggag ttgtcaagtc tctgctggcc   1800

cagccaaacc ctgtctgaca acctcttggt gaaccttagt acctaaaagg aaatctcacc   1860

ccatcccaca ccctggagga tttcatctct tgtatatgat gatctggatc caccaagact   1920

tgttttatgc tcagggtcaa tttctttttt cttttttttt tttttttttc tttttctttg   1980
```

agactgggtc tcgctttgtt gcccaggctg gagtggagtg gcgtgatctt ggcttactgc 2040
agcctttgcc tccccggctc gagcagtcct gcctcagcct ccggagtagc tgggaccaca 2100
ggttcatgcc accatggcca gccaactttt gcatgttttg tagagatggg gtctcacagt 2160
gttgcccagg ctggtctcaa actcctgggc tcaggcgatc cacctgtctc agcctcccag 2220
agtgctggga ttacaattgt gagccaccac gtccagctgg aagggtcaac atcttttaca 2280
ttctgcaagc acatctgcat tttcacccca cccttcccct ccttctccct ttttatatcc 2340
catttttata tcgatctctt attttacaat aaaactttgc tgccacctgt gtgtctgagg 2400
ggtg 2404

<210> SEQ ID NO 103
<211> LENGTH: 214
<212> TYPE: PRT
<213> ORGANISM: Homo sapiens

<400> SEQUENCE: 103

Met Phe Cys Gln Leu Ala Lys Thr Cys Pro Val Gln Leu Trp Val Asp
1 5 10 15

Ser Thr Pro Pro Pro Gly Thr Arg Val Arg Ala Met Ala Ile Tyr Lys
20 25 30

Gln Ser Gln His Met Thr Glu Val Val Arg Arg Cys Pro His His Glu
35 40 45

Arg Cys Ser Asp Ser Asp Gly Leu Ala Pro Pro Gln His Leu Ile Arg
50 55 60

Val Glu Gly Asn Leu Arg Val Glu Tyr Leu Asp Asp Arg Asn Thr Phe
65 70 75 80

Arg His Ser Val Val Val Pro Tyr Glu Pro Pro Glu Val Gly Ser Asp
85 90 95

Cys Thr Thr Ile His Tyr Asn Tyr Met Cys Asn Ser Ser Cys Met Gly
100 105 110

Gly Met Asn Arg Arg Pro Ile Leu Thr Ile Ile Thr Leu Glu Asp Ser
115 120 125

Ser Gly Asn Leu Leu Gly Arg Asn Ser Phe Glu Val Arg Val Cys Ala
130 135 140

Cys Pro Gly Arg Asp Arg Arg Thr Glu Glu Glu Asn Leu Arg Lys Lys
145 150 155 160

Gly Glu Pro His His Glu Leu Pro Pro Gly Ser Thr Lys Arg Ala Leu
165 170 175

Pro Asn Asn Thr Ser Ser Ser Pro Gln Pro Lys Lys Lys Pro Leu Asp
180 185 190

Gly Glu Tyr Phe Thr Leu Gln Met Leu Leu Asp Leu Arg Trp Cys Tyr
195 200 205

Phe Leu Ile Asn Ser Ser
210

<210> SEQ ID NO 104
<211> LENGTH: 2331
<212> TYPE: DNA
<213> ORGANISM: Homo sapiens

<400> SEQUENCE: 104
tgaggccagg agatggaggc tgcagtgagc tgtgatcaca ccactgtgct ccagcctgag 60
tgacagagca agaccctatc tcaaaaaaaa aaaaaaaaaa gaaaagctcc tgaggtgtag 120
acgccaactc tctctagctc gctagtgggt tgcaggaggt gcttacgcat gtttgtttct 180

```
ttgctgccgt cttccagttg ctttatctgt tcacttgtgc cctgactttc aactctgtct    240
ccttcctctt cctacagtac tcccctgccc tcaacaagat gttttgccaa ctggccaaga    300
cctgccctgt gcagctgtgg gttgattcca cacccccgcc cggcacccgc gtccgcgcca    360
tggccatcta caagcagtca cagcacatga cggaggttgt gaggcgctgc ccccaccatg    420
agcgctgctc agatagcgat ggtctggccc ctcctcagca tcttatccga gtggaaggaa    480
atttgcgtgt ggagtatttg gatgacagaa acacttttcg acatagtgtg gtggtgccct    540
atgagccgcc tgaggttggc tctgactgta ccaccatcca ctacaactac atgtgtaaca    600
gttcctgcat gggcggcatg aaccggaggc ccatcctcac catcatcaca ctggaagact    660
ccagtggtaa tctactggga cggaacagct ttgaggtgcg tgtttgtgcc tgtcctggga    720
gagaccggcg cacagaggaa gagaatctcc gcaagaaagg ggagcctcac cacgagctgc    780
ccccagggag cactaagcga gcactgccca acaacaccag ctcctctccc cagccaaaga    840
agaaaccact ggatggagaa tatttcaccc ttcagatgct acttgactta cgatggtgtt    900
acttcctgat aaactcgtcg taagttgaaa atattatccg tgggcgtgag cgcttcgaga    960
tgttccgaga gctgaatgag gccttggaac tcaaggatgc ccaggctggg aaggagccag   1020
gggggagcag ggctcactcc agccacctga agtccaaaaa gggtcagtct acctcccgcc   1080
ataaaaaact catgttcaag acagaagggc ctgactcaga ctgacattct ccacttcttg   1140
ttccccactg acagcctccc acccccatct ctccctcccc tgccattttg ggttttgggt   1200
ctttgaaccc ttgcttgcaa taggtgtgcg tcagaagcac ccaggacttc catttgcttt   1260
gtcccggggc tccactgaac aagttggcct gcactggtgt tttgttgtgg ggaggaggat   1320
ggggagtagg acataccagc ttagatttta aggtttttac tgtgagggat gtttgggaga   1380
tgtaagaaat gttcttgcag ttaagggtta gtttacaatc agccacattc taggtagggg   1440
cccacttcac cgtactaacc agggaagctg tccctcactg ttgaattttc tctaacttca   1500
aggcccatat ctgtgaaatg ctggcatttg cacctacctc acagagtgca ttgtgagggt   1560
taatgaaata atgtacatct ggccttgaaa ccacctttta ttacatgggg tctagaactt   1620
gaccccccttg agggtgcttg ttccctctcc ctgttggtcg gtgggttggt agtttctaca   1680
gttgggcagc tggttaggta gagggagttg tcaagtctct gctggcccag ccaaaccctg   1740
tctgacaacc tcttggtgaa ccttagtacc taaaaggaaa tctcacccca tcccacaccc   1800
tggaggattt catctcttgt atatgatgat ctggatccac caagacttgt tttatgctca   1860
gggtcaattt ctttttcttt ttttttttt ttttttcttt ttctttgaga ctgggtctcg   1920
ctttgttgcc caggctggag tggagtggcg tgatcttggc ttactgcagc ctttgcctcc   1980
ccggctcgag cagtcctgcc tcagcctccg gagtagctgg gaccacaggt tcatgccacc   2040
atggccagcc aacttttgca tgttttgtag agatggggtc tcacagtgtt gcccaggctg   2100
gtctcaaact cctgggctca ggcgatccac ctgtctcagc ctcccagagt gctgggatta   2160
caattgtgag ccaccacgtc cagctggaag ggtcaacatc ttttacattc tgcaagcaca   2220
tctgcatttt caccccaccc ttcccctcct tctccctttt tatatcccat ttttatatcg   2280
atctcttatt ttacaataaa actttgctgc cacctgtgtg tctgaggggt g            2331
```

<210> SEQ ID NO 105
<211> LENGTH: 354
<212> TYPE: PRT
<213> ORGANISM: Homo sapiens -continued

<400> SEQUENCE: 105

```
Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
            20                  25                  30

Pro Val Ala Pro Ala Pro Ala Ala Pro Thr Pro Ala Ala Pro Ala Pro
        35                  40                  45

Ala Pro Ser Trp Pro Leu Ser Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
        275                 280                 285

Phe Thr Leu Gln Ile Arg Gly Arg Glu Arg Phe Glu Met Phe Arg Glu
    290                 295                 300

Leu Asn Glu Ala Leu Glu Leu Lys Asp Ala Gln Ala Gly Lys Glu Pro
305                 310                 315                 320

Gly Gly Ser Arg Ala His Ser Ser His Leu Lys Ser Lys Lys Gly Gln
                325                 330                 335

Ser Thr Ser Arg His Lys Lys Leu Met Phe Lys Thr Glu Gly Pro Asp
            340                 345                 350

Ser Asp
```

<210> SEQ ID NO 106
<211> LENGTH: 2708
<212> TYPE: DNA
<213> ORGANISM: Homo sapiens

<400> SEQUENCE: 106

```
gatgggattg ggttttccc ctcccatgtg ctcaagactg gcgctaaaag ttttgagctt     60
ctcaaaagtc tagagccacc gtccagggag caggtagctg ctgggctccg gggacacttt    120
gcgttcgggc tgggagcgtg ctttccacga cggtgacacg cttccctgga ttggcagcca    180
gactgccttc cgggtcactg ccatggagga gccgcagtca gatcctagcg tcgagccccc    240
tctgagtcag gaaacatttt cagacctatg gaaactgtga gtggatccat tggaagggca    300
ggcccaccac ccccacccca accccagccc cctagcagag acctgtggga agcgaaaatt    360
ccatgggact gactttctgc tcttgtcttt cagacttcct gaaaacaacg ttctgtcccc    420
cttgccgtcc caagcaatgg atgatttgat gctgtccccg gacgatattg aacaatggtt    480
cactgaagac ccaggtccag atgaagctcc cagaatgcca gaggctgctc cccccgtggc    540
ccctgcacca gcagctccta caccggcggc ccctgcacca gccccctcct ggcccctgtc    600
atcttctgtc ccttcccaga aaacctacca gggcagctac ggtttccgtc tgggcttctt    660
gcattctggg acagccaagt ctgtgacttg cacgtactcc cctgccctca acaagatgtt    720
ttgccaactg gccaagacct gccctgtgca gctgtgggtt gattccacac ccccgcccgg    780
cacccgcgtc cgcgccatgg ccatctacaa gcagtcacag cacatgacgg aggttgtgag    840
gcgctgcccc caccatgagc gctgctcaga tagcgatggt ctggcccctc ctcagcatct    900
tatccgagtg gaaggaaatt tgcgtgtgga gtatttggat gacagaaaca cttttcgaca    960
tagtgtggtg gtgccctatg agccgcctga ggttggctct gactgtacca ccatccacta   1020
caactacatg tgtaacagtt cctgcatggg cggcatgaac cggaggccca tcctcaccat   1080
catcacactg gaagactcca gtggtaatct actgggacgg aacagctttg aggtgcgtgt   1140
ttgtgcctgt cctgggagag accggcgcac agaggaagag aatctccgca agaaagggga   1200
gcctcaccac gagctgcccc cagggagcac taagcgagca ctgcccaaca acaccagctc   1260
ctctccccag ccaaagaaga aaccactgga tggagaatat ttcacccttc agatccgtgg   1320
gcgtgagcgc ttcgagatgt tccgagagct gaatgaggcc ttggaactca aggatgccca   1380
ggctgggaag gagccagggg ggagcagggc tcactccagc cacctgaagt ccaaaaaggg   1440
tcagtctacc tcccgccata aaaaactcat gttcaagaca gaagggcctg actcagactg   1500
acattctcca cttcttgttc cccactgaca gcctcccacc cccatctctc cctcccctgc   1560
cattttgggt tttgggtctt tgaacccttg cttgcaatag gtgtgcgtca gaagcaccca   1620
ggacttccat ttgctttgtc ccggggctcc actgaacaag ttggcctgca ctggtgtttt   1680
gttgtgggga ggaggatggg gagtaggaca taccagctta gattttaagg tttttactgt   1740
gagggatgtt tgggagatgt aagaaatgtt cttgcagtta agggttagtt tacaatcagc   1800
cacattctag gtaggggccc acttcaccgt actaaccagg gaagctgtcc ctcactgttg   1860
aattttctct aacttcaagg cccatatctg tgaaatgctg gcatttgcac ctacctcaca   1920
gagtgcattg tgagggttaa tgaaataatg tacatctggc cttgaaacca ccttttatta   1980
catggggtct agaacttgac cccccttgagg gtgcttgttc cctctccctg ttggtcggtg   2040
ggttggtagt ttctacagtt gggcagctgg ttaggtagag ggagttgtca agtctctgct   2100
ggcccagcca aaccctgtct gacaacctct tggtgaacct tagtacctaa aaggaaatct   2160
caccccatcc cacaccctgg aggatttcat ctcttgtata tgatgatctg gatccaccaa   2220
gacttgtttt atgctcaggg tcaatttctt ttttcttttt tttttttttt tttcttttttc  2280
```

-continued

```
tttgagactg ggtctcgctt tgttgcccag gctggagtgg agtggcgtga tcttggctta   2340
ctgcagcctt tgcctccccg gctcgagcag tcctgcctca gcctccggag tagctgggac   2400
cacaggttca tgccaccatg gccagccaac ttttgcatgt tttgtagaga tggggtctca   2460
cagtgttgcc caggctggtc tcaaactcct gggctcaggc gatccacctg tctcagcctc   2520
ccagagtgct gggattacaa ttgtgagcca ccacgtccag ctggaagggt caacatcttt   2580
tacattctgc aagcacatct gcattttcac cccacccttc ccctccttct ccctttttat   2640
atcccatttt tatatcgatc tcttatttta caataaaact ttgctgccac ctgtgtgtct   2700
gaggggtg                                                            2708
```

<210> SEQ ID NO 107
<211> LENGTH: 2591
<212> TYPE: DNA
<213> ORGANISM: Homo sapiens

<400> SEQUENCE: 107

```
gatgggattg gggttttccc ctcccatgtg ctcaagactg gcgctaaaag ttttgagctt     60
ctcaaaagtc tagagccacc gtccagggag caggtagctg ctgggctccg gggacacttt    120
gcgttcgggc tgggagcgtg ctttccacga cggtgacacg cttccctgga ttggcagcca    180
gactgccttc cgggtcactg ccatggagga gccgcagtca gatcctagcg tcgagccccc    240
tctgagtcag gaaacatttt cagacctatg gaaactactt cctgaaaaca acgttctgtc    300
cccottgccg tcccaagcaa tggatgattt gatgctgtcc ccggacgata ttgaacaatg    360
gttcactgaa gacccaggtc cagatgaagc tcccagaatg ccagaggctg ctccccccgt    420
ggcccctgca ccagcagctc ctacaccggc ggcccctgca ccagccccct cctggcccct    480
gtcatcttct gtcccttccc agaaaaccta ccagggcagc tacggtttcc gtctgggctt    540
cttgcattct gggacagcca agtctgtgac ttgcacgtac tcccctgccc tcaacaagat    600
gttttgccaa ctggccaaga cctgccctgt gcagctgtgg gttgattcca caccccgcc     660
cggcacccgc gtccgcgcca tggccatcta caagcagtca cagcacatga cggaggttgt    720
gaggcgctgc ccccaccatg agcgctgctc agatagcgat ggtctggccc ctcctcagca    780
tcttatccga gtggaaggaa atttgcgtgt ggagtatttg gatgacagaa acacttttcg    840
acatagtgtg gtggtgccct atgagccgcc tgaggttggc tctgactgta ccaccatcca    900
ctacaactac atgtgtaaca gttcctgcat gggcggcatg aaccggaggc ccatcctcac    960
catcatcaca ctggaagact ccagtggtaa tctactggga cggaacagct ttgaggtgcg   1020
tgtttgtgcc tgtcctggga gagaccggcg cacagaggaa gagaatctcc gcaagaaagg   1080
ggagcctcac cacgagctgc ccccagggag cactaagcga gcactgccca acaacaccag   1140
ctcctctccc cagccaaaga agaaaccact ggatggagaa tatttcaccc ttcagatccg   1200
tgggcgtgag cgcttcgaga tgttccgaga gctgaatgag gccttggaac tcaaggatgc   1260
ccaggctggg aaggagccag gggggagcag ggctcactcc agccacctga agtccaaaaa   1320
gggtcagtct acctcccgcc ataaaaaact catgttcaag acagaagggc ctgactcaga   1380
ctgacattct ccacttcttg ttccccactg acagcctccc acccccatct ctccctcccc   1440
tgccattttg ggttttgggt ctttgaaccc ttgcttgcaa taggtgtgcg tcagaagcac   1500
ccaggacttc catttgcttt gtcccggggc tccactgaac aagttggcct gcactggtgt   1560
tttgttgtgg ggaggaggat ggggagtagg acataccagc ttagatttta aggtttttac   1620
tgtgagggat gtttgggaga tgtaagaaat gttcttgcag ttaagggtta gtttacaatc   1680
```

-continued

```
agccacattc taggtagggg cccacttcac cgtactaacc agggaagctg tccctcactg   1740

ttgaattttc tctaacttca aggcccatat ctgtgaaatg ctggcatttg cacctacctc   1800

acagagtgca ttgtgagggt taatgaaata atgtacatct ggccttgaaa ccacctttta   1860

ttacatgggg tctagaactt gaccccccttg agggtgcttg ttccctctcc ctgttggtcg   1920

gtgggttggt agtttctaca gttgggcagc tggttaggta gagggagttg tcaagtctct   1980

gctggcccag ccaaaccctg tctgacaacc tcttggtgaa ccttagtacc taaaaggaaa   2040

tctcacccca tcccacaccc tggaggattt catctcttgt atatgatgat ctggatccac   2100

caagacttgt tttatgctca gggtcaattt ctttttttctt ttttttttt ttttttcttt   2160

ttctttgaga ctgggtctcg ctttgttgcc caggctggag tggagtggcg tgatcttggc   2220

ttactgcagc ctttgcctcc ccggctcgag cagtcctgcc tcagcctccg gagtagctgg   2280

gaccacaggt tcatgccacc atggccagcc aacttttgca tgttttgtag agatggggtc   2340

tcacagtgtt gcccaggctg gtctcaaact cctgggctca ggcgatccac ctgtctcagc   2400

ctcccagagt gctgggatta caattgtgag ccaccacgtc cagctggaag ggtcaacatc   2460

ttttacattc tgcaagcaca tctgcatttt caccccaccc ttcccctcct tctccctttt   2520

tatatcccat ttttatatcg atctcttatt ttacaataaa actttgctgc cacctgtgtg   2580

tctgaggggt g                                                          2591
```

```
<210> SEQ ID NO 108
<211> LENGTH: 2588
<212> TYPE: DNA
<213> ORGANISM: Homo sapiens

<400> SEQUENCE: 108

gatgggattg gggttttccc ctcccatgtg ctcaagactg gcgctaaaag ttttgagctt     60

ctcaaaagtc tagagccacc gtccagggag caggtagctg ctgggctccg gggacacttt    120

gcgttcgggc tgggagcgtg ctttccacga cggtgacacg cttccctgga ttggccagac    180

tgccttccgg gtcactgcca tggaggagcc gcagtcagat cctagcgtcg agcccccctct    240

gagtcaggaa acattttcag acctatggaa actacttcct gaaaacaacg ttctgtcccc    300

cttgccgtcc caagcaatgg atgatttgat gctgtccccg gacgatattg aacaatggtt    360

cactgaagac ccaggtccag atgaagctcc cagaatgcca gaggctgctc cccccgtggc    420

ccctgcacca gcagctccta caccggcggc ccctgcacca gccccctcct ggcccctgtc    480

atcttctgtc ccttcccaga aaacctacca gggcagctac ggtttccgtc tgggcttctt    540

gcattctggg acagccaagt ctgtgacttg cacgtactcc cctgccctca acaagatgtt    600

ttgccaactg gccaagacct gccctgtgca gctgtgggtt gattccacac ccccgcccgg    660

cacccgcgtc cgcgccatgg ccatctacaa gcagtcacag cacatgacgg aggttgtgag    720

gcgctgcccc caccatgagc gctgctcaga tagcgatggt ctggcccctc ctcagcatct    780

tatccgagtg gaaggaaatt tgcgtgtgga gtatttggat gacagaaaca cttttcgaca    840

tagtgtggtg gtgccctatg agccgcctga ggttggctct gactgtacca ccatccacta    900

caactacatg tgtaacagtt cctgcatggg cggcatgaac cggaggccca tcctcaccat    960

catcacactg gaagactcca gtggtaatct actgggacgg aacagctttg aggtgcgtgt   1020

ttgtgcctgt cctgggagag accggcgcac agaggaagag aatctccgca agaaagggga   1080

gcctcaccac gagctgcccc cagggagcac taagcgagca ctgcccaaca acaccagctc   1140
```

```
ctctccccag ccaaagaaga aaccactgga tggagaatat ttcacccttc agatccgtgg   1200

gcgtgagcgc ttcgagatgt tccgagagct gaatgaggcc ttggaactca aggatgccca   1260

ggctgggaag gagccagggg ggagcagggc tcactccagc cacctgaagt ccaaaaaggg   1320

tcagtctacc tcccgccata aaaaactcat gttcaagaca gaagggcctg actcagactg   1380

acattctcca cttcttgttc cccactgaca gcctcccacc cccatctctc cctcccctgc   1440

cattttgggt tttgggtctt tgaacccttg cttgcaatag gtgtgcgtca gaagcaccca   1500

ggacttccat ttgctttgtc ccggggctcc actgaacaag ttggcctgca ctggtgtttt   1560

gttgtgggga ggaggatggg gagtaggaca taccagctta gattttaagg tttttactgt   1620

gagggatgtt tgggagatgt aagaaatgtt cttgcagtta agggttagtt tacaatcagc   1680

cacattctag gtaggggccc acttcaccgt actaaccagg gaagctgtcc ctcactgttg   1740

aattttctct aacttcaagg cccatatctg tgaaatgctg gcatttgcac ctacctcaca   1800

gagtgcattg tgagggttaa tgaaataatg tacatctggc cttgaaacca ccttttatta   1860

catggggtct agaacttgac cccettgagg gtgcttgttc cctctccctg ttggtcggtg   1920

ggttggtagt ttctacagtt gggcagctgg ttaggtagag ggagttgtca agtctctgct   1980

ggcccagcca aaccctgtct gacaacctct tggtgaacct tagtacctaa aaggaaatct   2040

caccccatcc cacaccctgg aggatttcat ctcttgtata tgatgatctg gatccaccaa   2100

gacttgtttt atgctcaggg tcaatttctt ttttcttttt tttttttttt tttctttttc   2160

tttgagactg ggtctcgctt tgttgcccag gctggagtgg agtggcgtga tcttggctta   2220

ctgcagcctt tgcctccccg gctcgagcag tcctgcctca gcctccggag tagctgggac   2280

cacaggttca tgccaccatg gccagccaac ttttgcatgt tttgtagaga tggggtctca   2340

cagtgttgcc caggctggtc tcaaactcct gggctcaggc gatccacctg tctcagcctc   2400

ccagagtgct gggattacaa ttgtgagcca ccacgtccag ctggaagggt caacatcttt   2460

tacattctgc aagcacatct gcattttcac ccccacccttc ccctccttct cccttttat   2520

atcccatttt tatatcgatc tcttatttta caataaaact ttgctgccac ctgtgtgtct   2580

gaggggtg                                                            2588
```

<210> SEQ ID NO 109
<211> LENGTH: 307
<212> TYPE: PRT
<213> ORGANISM: Homo sapiens

<400> SEQUENCE: 109

```
Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
            20                  25                  30

Pro Val Ala Pro Ala Pro Ala Ala Pro Thr Pro Ala Ala Pro Ala Pro
        35                  40                  45

Ala Pro Ser Trp Pro Leu Ser Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
            100                 105                 110
```

-continued

```
Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
        275                 280                 285

Phe Thr Leu Gln Met Leu Leu Asp Leu Arg Trp Cys Tyr Phe Leu Ile
    290                 295                 300

Asn Ser Ser
305
```

<210> SEQ ID NO 110
<211> LENGTH: 2651
<212> TYPE: DNA
<213> ORGANISM: Homo sapiens

<400> SEQUENCE: 110

```
gatgggattg gggttttccc ctcccatgtg ctcaagactg gcgctaaaag ttttgagctt      60

ctcaaaagtc tagagccacc gtccagggag caggtagctg ctgggctccg gggacacttt     120

gcgttcgggc tgggagcgtg ctttccacga cggtgacacg cttccctgga ttggcagcca     180

gactgccttc cgggtcactg ccatggagga gccgcagtca gatcctagcg tcgagccccc     240

tctgagtcag gaaacatttt cagacctatg gaaactactt cctgaaaaca acgttctgtc     300

cccottgccg tcccaagcaa tggatgattt gatgctgtcc ccggacgata ttgaacaatg     360

gttcactgaa gacccaggtc cagatgaagc tcccagaatg ccagaggctg ctccccccgt     420

ggcccctgca ccagcagctc ctacaccggc ggcccctgca ccagccccct cctggcccct     480

gtcatcttct gtcccttccc agaaaaccta ccagggcagc tacggtttcc gtctgggctt     540

cttgcattct gggacagcca agtctgtgac ttgcacgtac tcccctgccc tcaacaagat     600

gttttgccaa ctggccaaga cctgccctgt gcagctgtgg gttgattcca caccccccgcc    660

cggcacccgc gtccgcgcca tggccatcta caagcagtca cagcacatga cggaggttgt     720

gaggcgctgc ccccaccatg agcgctgctc agatagcgat ggtctggccc ctcctcagca     780

tcttatccga gtggaaggaa atttgcgtgt ggagtatttg gatgacagaa acacttttcg     840

acatagtgtg gtggtgccct atgagccgcc tgaggttggc tctgactgta ccaccatcca     900

ctacaactac atgtgtaaca gttcctgcat gggcggcatg aaccggaggc ccatcctcac     960
```

-continued

```
catcatcaca ctggaagact ccagtggtaa tctactggga cggaacagct ttgaggtgcg   1020

tgtttgtgcc tgtcctggga gagaccggcg cacagaggaa gagaatctcc gcaagaaagg   1080

ggagcctcac cacgagctgc ccccagggag cactaagcga gcactgccca acaacaccag   1140

ctcctctccc cagccaaaga agaaaccact ggatggagaa tatttcaccc ttcagatgct   1200

acttgactta cgatggtgtt acttcctgat aaactcgtcg taagttgaaa atattatccg   1260

tgggcgtgag cgcttcgaga tgttccgaga gctgaatgag gccttggaac tcaaggatgc   1320

ccaggctggg aaggagccag gggggagcag ggctcactcc agccacctga agtccaaaaa   1380

gggtcagtct acctcccgcc ataaaaaact catgttcaag acagaagggc ctgactcaga   1440

ctgacattct ccacttcttg ttccccactg acagcctccc acccccatct ctccctcccc   1500

tgccattttg ggttttgggt ctttgaaccc ttgcttgcaa taggtgtgcg tcagaagcac   1560

ccaggacttc catttgcttt gtcccggggc tccactgaac aagttggcct gcactggtgt   1620

tttgttgtgg ggaggaggat ggggagtagg acataccagc ttagatttta aggtttttac   1680

tgtgagggat gtttgggaga tgtaagaaat gttcttgcag ttaagggtta gtttacaatc   1740

agccacattc taggtagggg cccacttcac cgtactaacc agggaagctg tccctcactg   1800

ttgaatttc tctaacttca aggcccatat ctgtgaaatg ctggcatttg cacctacctc   1860

acagagtgca ttgtgagggt taatgaaata atgtacatct ggccttgaaa ccacctttta   1920

ttacatgggg tctagaactt gaccccttg agggtgcttg ttccctctcc ctgttggtcg   1980

gtgggttggt agtttctaca gttgggcagc tggttaggta gagggagttg tcaagtctct   2040

gctggcccag ccaaaccctg tctgacaacc tcttggtgaa ccttagtacc taaaaggaaa   2100

tctcacccca tcccacaccc tggaggattt catctcttgt atatgatgat ctggatccac   2160

caagacttgt tttatgctca gggtcaattt ctttttttctt ttttttttt tttttctttt   2220

ttctttgaga ctgggtctcg ctttgttgcc caggctggag tggagtggcg tgatcttggc   2280

ttactgcagc ctttgcctcc ccggctcgag cagtcctgcc tcagcctccg gagtagctgg   2340

gaccacaggt tcatgccacc atggccagcc aacttttgca tgttttgtag agatggggtc   2400

tcacagtgtt gcccaggctg gtctcaaact cctgggctca ggcgatccac ctgtctcagc   2460

ctcccagagt gctgggatta caattgtgag ccaccacgtc cagctggaag ggtcaacatc   2520

ttttacattc tgcaagcaca tctgcatttt caccccaccc ttcccctcct tctccctttt   2580

tatatcccat ttttatatcg atctcttatt ttacaataaa actttgctgc cacctgtgtg   2640

tctgaggggt g                                                         2651
```

<210> SEQ ID NO 111
<211> LENGTH: 302
<212> TYPE: PRT
<213> ORGANISM: Homo sapiens

<400> SEQUENCE: 111

```
Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
            20                  25                  30

Pro Val Ala Pro Ala Pro Ala Ala Pro Thr Pro Ala Ala Pro Ala Pro
        35                  40                  45

Ala Pro Ser Trp Pro Leu Ser Ser Ser Val Pro Ser Gln Lys Thr Tyr
    50                  55                  60
```

```
Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
        275                 280                 285

Phe Thr Leu Gln Asp Gln Thr Ser Phe Gln Lys Glu Asn Cys
    290                 295                 300
```

<210> SEQ ID NO 112
<211> LENGTH: 2724
<212> TYPE: DNA
<213> ORGANISM: Homo sapiens

<400> SEQUENCE: 112

```
gatgggattg gggttttccc ctcccatgtg ctcaagactg gcgctaaaag ttttgagctt      60

ctcaaaagtc tagagccacc gtccagggag caggtagctg ctgggctccg gggacacttt     120

gcgttcgggc tgggagcgtg ctttccacga cggtgacacg cttccctgga ttggcagcca     180

gactgccttc cgggtcactg ccatggagga gccgcagtca gatcctagcg tcgagccccc     240

tctgagtcag gaaacatttt cagacctatg gaaactactt cctgaaaaca acgttctgtc     300

cccctttgccg tcccaagcaa tggatgattt gatgctgtcc ccggacgata ttgaacaatg     360

gttcactgaa gacccaggtc cagatgaagc tcccagaatg ccagaggctg ctccccccgt     420

ggcccctgca ccagcagctc ctacaccggc ggcccctgca ccagcccccct cctggcccct     480

gtcatcttct gtcccttccc agaaaaccta ccagggcagc tacggtttcc gtctgggctt     540

cttgcattct gggacagcca agtctgtgac ttgcacgtac tcccctgccc tcaacaagat     600

gttttgccaa ctggccaaga cctgccctgt gcagctgtgg gttgattcca caccccccgcc     660

cggcacccgc gtccgcgcca tggccatcta caagcagtca cagcacatga cggaggttgt     720

gaggcgctgc ccccaccatg agcgctgctc agatagcgat ggtctggccc ctcctcagca     780
```

-continued

```
tcttatccga gtggaaggaa atttgcgtgt ggagtatttg gatgacagaa acacttttcg    840

acatagtgtg gtggtgccct atgagccgcc tgaggttggc tctgactgta ccaccatcca    900

ctacaactac atgtgtaaca gttcctgcat gggcggcatg aaccggaggc ccatcctcac    960

catcatcaca ctggaagact ccagtggtaa tctactggga cggaacagct ttgaggtgcg   1020

tgtttgtgcc tgtcctggga gagaccggcg cacagaggaa gagaatctcc gcaagaaagg   1080

ggagcctcac cacgagctgc ccccagggag cactaagcga gcactgccca acaacaccag   1140

ctcctctccc cagccaaaga agaaaccact ggatggagaa tatttcaccc ttcaggacca   1200

gaccagcttt caaaaagaaa attgttaaag agagcatgaa aatggttcta tgactttgcc   1260

tgatacagat gctacttgac ttacgatggt gttacttcct gataaactcg tcgtaagttg   1320

aaaatattat ccgtgggcgt gagcgcttcg agatgttccg agagctgaat gaggccttgg   1380

aactcaagga tgcccaggct gggaaggagc caggggggag cagggctcac tccagccacc   1440

tgaagtccaa aaagggtcag tctacctccc gccataaaaa actcatgttc aagacagaag   1500

ggcctgactc agactgacat tctccacttc ttgttcccca ctgacagcct cccaccccca   1560

tctctccctc ccctgccatt ttgggttttg ggtctttgaa cccttgcttg caataggtgt   1620

gcgtcagaag cacccaggac ttccatttgc tttgtcccgg ggctccactg aacaagttgg   1680

cctgcactgg tgttttgttg tggggaggag gatggggagt aggacatacc agcttagatt   1740

ttaaggtttt tactgtgagg gatgtttggg agatgtaaga aatgttcttg cagttaaggg   1800

ttagtttaca atcagccaca ttctaggtag gggcccactt caccgtacta accagggaag   1860

ctgtccctca ctgttgaatt ttctctaact tcaaggccca tatctgtgaa atgctggcat   1920

ttgcacctac ctcacagagt gcattgtgag ggttaatgaa ataatgtaca tctggccttg   1980

aaaccacctt ttattacatg gggtctagaa cttgaccccc ttgagggtgc ttgttccctc   2040

tccctgttgg tcggtgggtt ggtagtttct acagttgggc agctggttag gtagagggag   2100

ttgtcaagtc tctgctggcc cagccaaacc ctgtctgaca acctcttggt gaaccttagt   2160

acctaaaagg aaatctcacc ccatcccaca ccctggagga tttcatctct tgtatatgat   2220

gatctggatc caccaagact tgttttatgc tcagggtcaa tttctttttt cttttttttt   2280

ttttttttc tttttctttg agactgggtc tcgctttgtt gcccaggctg gagtggagtg   2340

gcgtgatctt ggcttactgc agcctttgcc tccccggctc gagcagtcct gcctcagcct   2400

ccggagtagc tgggaccaca ggttcatgcc accatggcca gccaactttt gcatgttttg   2460

tagagatggg gtctcacagt gttgcccagg ctggtctcaa actcctgggc tcaggcgatc   2520

cacctgtctc agcctcccag agtgctggga ttacaattgt gagccaccac gtccagctgg   2580

aagggtcaac atcttttaca ttctgcaagc acatctgcat tttcacccca cccttcccct   2640

ccttctccct ttttatatcc catttttata tcgatctctt attttacaat aaaactttgc   2700

tgccacctgt gtgtctgagg ggtg                                          2724
```

<210> SEQ ID NO 113
<211> LENGTH: 234
<212> TYPE: PRT
<213> ORGANISM: Homo sapiens

<400> SEQUENCE: 113

```
Met Ala Ile Tyr Lys Gln Ser Gln His Met Thr Glu Val Val Arg Arg
1               5                   10                  15
```

```
Cys Pro His His Glu Arg Cys Ser Asp Ser Asp Gly Leu Ala Pro Pro
            20                  25                  30

Gln His Leu Ile Arg Val Glu Gly Asn Leu Arg Val Glu Tyr Leu Asp
        35                  40                  45

Asp Arg Asn Thr Phe Arg His Ser Val Val Val Pro Tyr Glu Pro Pro
    50                  55                  60

Glu Val Gly Ser Asp Cys Thr Thr Ile His Tyr Asn Tyr Met Cys Asn
65                  70                  75                  80

Ser Ser Cys Met Gly Gly Met Asn Arg Arg Pro Ile Leu Thr Ile Ile
                85                  90                  95

Thr Leu Glu Asp Ser Ser Gly Asn Leu Leu Gly Arg Asn Ser Phe Glu
            100                 105                 110

Val Arg Val Cys Ala Cys Pro Gly Arg Asp Arg Arg Thr Glu Glu Glu
        115                 120                 125

Asn Leu Arg Lys Lys Gly Glu Pro His His Glu Leu Pro Pro Gly Ser
    130                 135                 140

Thr Lys Arg Ala Leu Pro Asn Asn Thr Ser Ser Ser Pro Gln Pro Lys
145                 150                 155                 160

Lys Lys Pro Leu Asp Gly Glu Tyr Phe Thr Leu Gln Ile Arg Gly Arg
                165                 170                 175

Glu Arg Phe Glu Met Phe Arg Glu Leu Asn Glu Ala Leu Glu Leu Lys
            180                 185                 190

Asp Ala Gln Ala Gly Lys Glu Pro Gly Gly Ser Arg Ala His Ser Ser
        195                 200                 205

His Leu Lys Ser Lys Lys Gly Gln Ser Thr Ser Arg His Lys Lys Leu
    210                 215                 220

Met Phe Lys Thr Glu Gly Pro Asp Ser Asp
225                 230
```

<210> SEQ ID NO 114
<211> LENGTH: 2271
<212> TYPE: DNA
<213> ORGANISM: Homo sapiens

<400> SEQUENCE: 114

```
tgaggccagg agatggaggc tgcagtgagc tgtgatcaca ccactgtgct ccagcctgag      60

tgacagagca agaccctatc tcaaaaaaaa aaaaaaaaaa gaaaagctcc tgaggtgtag     120

acgccaactc tctctagctc gctagtgggt tgcaggaggt gcttacgcat gtttgtttct     180

ttgctgccgt cttccagttg ctttatctgt tcacttgtgc cctgactttc aactctgtct     240

ccttcctctt cctacagtac tcccctgccc tcaacaagat gttttgccaa ctggccaaga     300

cctgccctgt gcagctgtgg gttgattcca cacccccgcc cggcacccgc gtccgcgcca     360

tggccatcta caagcagtca cagcacatga cggaggttgt gaggcgctgc ccccaccatg     420

agcgctgctc agatagcgat ggtctggccc ctcctcagca tcttatccga gtggaaggaa     480

atttgcgtgt ggagtatttg gatgacagaa acacttttcg acatagtgtg gtggtgccct     540

atgagccgcc tgaggttggc tctgactgta ccaccatcca ctacaactac atgtgtaaca     600

gttcctgcat gggcggcatg aaccggaggc ccatcctcac catcatcaca ctggaagact     660

ccagtggtaa tctactggga cggaacagct ttgaggtgcg tgtttgtgcc tgtcctggga     720

gagaccggcg cacagaggaa gagaatctcc gcaagaaagg ggagcctcac cacgagctgc     780

ccccagggag cactaagcga gcactgccca acaacaccag ctcctctccc cagccaaaga     840
```

-continued

```
agaaaccact ggatggagaa tatttcaccc ttcagatccg tgggcgtgag cgcttcgaga    900

tgttccgaga gctgaatgag gccttggaac tcaaggatgc ccaggctggg aaggagccag    960

gggggagcag ggctcactcc agccacctga agtccaaaaa gggtcagtct acctcccgcc   1020

ataaaaaact catgttcaag acagaagggc ctgactcaga ctgacattct ccacttcttg   1080

ttccccactg acagcctccc acccccatct ctccctcccc tgccattttg ggttttgggt   1140

ctttgaaccc ttgcttgcaa taggtgtgcg tcagaagcac ccaggacttc catttgcttt   1200

gtcccggggc tccactgaac aagttggcct gcactggtgt tttgttgtgg ggaggaggat   1260

ggggagtagg acataccagc ttagatttta aggtttttac tgtgagggat gtttgggaga   1320

tgtaagaaat gttcttgcag ttaagggtta gtttacaatc agccacattc taggtagggg   1380

cccacttcac cgtactaacc agggaagctg tccctcactg ttgaattttc tctaacttca   1440

aggcccatat ctgtgaaatg ctggcatttg cacctacctc acagagtgca ttgtgagggt   1500

taatgaaata atgtacatct ggccttgaaa ccacctttta ttacatgggg tctagaactt   1560

gaccccccttg agggtgcttg ttccctctcc ctgttggtcg gtgggttggt agtttctaca  1620

gttgggcagc tggttaggta gagggagttg tcaagtctct gctggcccag ccaaaccctg   1680

tctgacaacc tcttggtgaa ccttagtacc taaaaggaaa tctcacccca tcccacaccc   1740

tggaggattt catctcttgt atatgatgat ctggatccac caagacttgt tttatgctca   1800

gggtcaattt ctttttcttt tttttttttt ttttttcttt ttctttgaga ctgggtctcg   1860

ctttgttgcc caggctggag tggagtggcg tgatcttggc ttactgcagc ctttgcctcc   1920

ccggctcgag cagtcctgcc tcagcctccg gagtagctgg gaccacaggt tcatgccacc   1980

atggccagcc aacttttgca tgttttgtag agatggggtc tcacagtgtt gcccaggctg   2040

gtctcaaact cctgggctca ggcgatccac ctgtctcagc ctcccagagt gctgggatta   2100

caattgtgag ccaccacgtc cagctggaag ggtcaacatc ttttacattc tgcaagcaca   2160

tctgcatttt caccccaccc ttcccctcct tctccctttt tatatcccat ttttatatcg   2220

atctcttatt ttacaataaa actttgctgc cacctgtgtg tctgaggggt g            2271
```

```
<210> SEQ ID NO 115
<211> LENGTH: 182
<212> TYPE: PRT
<213> ORGANISM: Homo sapiens

<400> SEQUENCE: 115

Met Ala Ile Tyr Lys Gln Ser Gln His Met Thr Glu Val Val Arg Arg
1               5                   10                  15

Cys Pro His His Glu Arg Cys Ser Asp Ser Asp Gly Leu Ala Pro Pro
            20                  25                  30

Gln His Leu Ile Arg Val Glu Gly Asn Leu Arg Val Glu Tyr Leu Asp
        35                  40                  45

Asp Arg Asn Thr Phe Arg His Ser Val Val Val Pro Tyr Glu Pro Pro
    50                  55                  60

Glu Val Gly Ser Asp Cys Thr Thr Ile His Tyr Asn Tyr Met Cys Asn
65                  70                  75                  80

Ser Ser Cys Met Gly Gly Met Asn Arg Arg Pro Ile Leu Thr Ile Ile
                85                  90                  95

Thr Leu Glu Asp Ser Ser Gly Asn Leu Leu Gly Arg Asn Ser Phe Glu
            100                 105                 110

Val Arg Val Cys Ala Cys Pro Gly Arg Asp Arg Arg Thr Glu Glu Glu
        115                 120                 125
```

```
Asn Leu Arg Lys Lys Gly Glu Pro His His Glu Leu Pro Pro Gly Ser
    130                 135                 140

Thr Lys Arg Ala Leu Pro Asn Asn Thr Ser Ser Ser Pro Gln Pro Lys
145                 150                 155                 160

Lys Lys Pro Leu Asp Gly Glu Tyr Phe Thr Leu Gln Asp Gln Thr Ser
                165                 170                 175

Phe Gln Lys Glu Asn Cys
            180


<210> SEQ ID NO 116
<211> LENGTH: 2404
<212> TYPE: DNA
<213> ORGANISM: Homo sapiens

<400> SEQUENCE: 116

tgaggccagg agatggaggc tgcagtgagc tgtgatcaca ccactgtgct ccagcctgag     60

tgacagagca agaccctatc tcaaaaaaaa aaaaaaaaaa gaaaagctcc tgaggtgtag    120

acgccaactc tctctagctc gctagtgggt tgcaggaggt gcttacgcat gtttgtttct    180

ttgctgccgt cttccagttg ctttatctgt tcacttgtgc cctgactttc aactctgtct    240

ccttcctctt cctacagtac tcccctgccc tcaacaagat gttttgccaa ctggccaaga    300

cctgccctgt gcagctgtgg gttgattcca cacccccgcc cggcacccgc gtccgcgcca    360

tggccatcta caagcagtca cagcacatga cggaggttgt gaggcgctgc ccccaccatg    420

agcgctgctc agatagcgat ggtctggccc ctcctcagca tcttatccga gtggaaggaa    480

atttgcgtgt ggagtatttg gatgacagaa acacttttcg acatagtgtg gtggtgccct    540

atgagccgcc tgaggttggc tctgactgta ccaccatcca ctacaactac atgtgtaaca    600

gttcctgcat gggcggcatg aaccggaggc ccatcctcac catcatcaca ctggaagact    660

ccagtggtaa tctactggga cggaacagct ttgaggtgcg tgtttgtgcc tgtcctggga    720

gagaccggcg cacagaggaa gagaatctcc gcaagaaagg ggagcctcac cacgagctgc    780

ccccagggag cactaagcga gcactgccca acaacaccag ctcctctccc cagccaaaga    840

agaaaccact ggatggagaa tatttcaccc ttcaggacca gaccagcttt caaaaagaaa    900

attgttaaag agagcatgaa aatggttcta tgactttgcc tgatacagat gctacttgac    960

ttacgatggt gttacttcct gataaactcg tcgtaagttg aaaatattat ccgtgggcgt   1020

gagcgcttcg agatgttccg agagctgaat gaggccttgg aactcaagga tgcccaggct   1080

gggaaggagc caggggggag cagggctcac tccagccacc tgaagtccaa aaagggtcag   1140

tctacctccc gccataaaaa actcatgttc aagacagaag ggcctgactc agactgacat   1200

tctccacttc ttgttcccca ctgacagcct cccaccccca tctctccctc ccctgccatt   1260

ttgggttttg ggtctttgaa cccttgcttg caataggtgt gcgtcagaag cacccaggac   1320

ttccatttgc tttgtcccgg ggctccactg aacaagttgg cctgcactgg tgttttgttg   1380

tggggaggag gatggggagt aggacatacc agcttagatt ttaaggtttt tactgtgagg   1440

gatgtttggg agatgtaaga aatgttcttg cagttaaggg ttagtttaca atcagccaca   1500

ttctaggtag ggcccactt caccgtacta accagggaag ctgtccctca ctgttgaatt   1560

ttctctaact tcaaggccca tatctgtgaa atgctggcat ttgcacctac ctcacagagt   1620

gcattgtgag ggttaatgaa ataatgtaca tctggccttg aaaccacctt ttattacatg   1680

gggtctagaa cttgaccccc ttgagggtgc ttgttccctc tccctgttgg tcggtgggtt   1740
```

ggtagtttct acagttgggc agctggttag gtagagggag ttgtcaagtc tctgctggcc 1800
cagccaaacc ctgtctgaca acctcttggt gaaccttagt acctaaaagg aaatctcacc 1860
ccatcccaca ccctggagga tttcatctct tgtatatgat gatctggatc caccaagact 1920
tgttttatgc tcagggtcaa tttctttttt cttttttttt ttttttttc tttttctttg 1980 agactgggtc tcgctttgtt gcccaggctg gagtggagtg gcgtgatctt ggcttactgc 2040
agcctttgcc tccccggctc gagcagtcct gcctcagcct ccggagtagc tgggaccaca 2100
ggttcatgcc accatggcca gccaactttt gcatgttttg tagagatggg gtctcacagt 2160
gttgcccagg ctggtctcaa actcctgggc tcaggcgatc cacctgtctc agcctcccag 2220
agtgctggga ttacaattgt gagccaccac gtccagctgg aagggtcaac atcttttaca 2280
ttctgcaagc acatctgcat tttcacccca cccttcccct ccttctccct ttttatatcc 2340
catttttata tcgatctctt attttacaat aaaactttgc tgccacctgt gtgtctgagg 2400
ggtg 2404

<210> SEQ ID NO 117
<211> LENGTH: 187
<212> TYPE: PRT
<213> ORGANISM: Homo sapiens

<400> SEQUENCE: 117

Met Ala Ile Tyr Lys Gln Ser Gln His Met Thr Glu Val Val Arg Arg
1               5                   10                  15

Cys Pro His His Glu Arg Cys Ser Asp Ser Asp Gly Leu Ala Pro Pro
            20                  25                  30

Gln His Leu Ile Arg Val Glu Gly Asn Leu Arg Val Glu Tyr Leu Asp
        35                  40                  45

Asp Arg Asn Thr Phe Arg His Ser Val Val Val Pro Tyr Glu Pro Pro
    50                  55                  60

Glu Val Gly Ser Asp Cys Thr Thr Ile His Tyr Asn Tyr Met Cys Asn
65                  70                  75                  80

Ser Ser Cys Met Gly Gly Met Asn Arg Arg Pro Ile Leu Thr Ile Ile
                85                  90                  95

Thr Leu Glu Asp Ser Ser Gly Asn Leu Leu Gly Arg Asn Ser Phe Glu
            100                 105                 110

Val Arg Val Cys Ala Cys Pro Gly Arg Asp Arg Arg Thr Glu Glu Glu
        115                 120                 125

Asn Leu Arg Lys Lys Gly Glu Pro His His Glu Leu Pro Pro Gly Ser
    130                 135                 140

Thr Lys Arg Ala Leu Pro Asn Asn Thr Ser Ser Ser Pro Gln Pro Lys
145                 150                 155                 160

Lys Lys Pro Leu Asp Gly Glu Tyr Phe Thr Leu Gln Met Leu Leu Asp
                165                 170                 175

Leu Arg Trp Cys Tyr Phe Leu Ile Asn Ser Ser
            180                 185

<210> SEQ ID NO 118
<211> LENGTH: 2331
<212> TYPE: DNA
<213> ORGANISM: Homo sapiens

<400> SEQUENCE: 118
tgaggccagg agatggaggc tgcagtgagc tgtgatcaca ccactgtgct ccagcctgag 60
tgacagagca agaccctatc tcaaaaaaaa aaaaaaaaaa gaaaagctcc tgaggtgtag 120

-continued

```
acgccaactc tctctagctc gctagtgggt tgcaggaggt gcttacgcat gtttgtttct    180
ttgctgccgt cttccagttg ctttatctgt tcacttgtgc cctgactttc aactctgtct    240
ccttcctctt cctacagtac tcccctgccc tcaacaagat gttttgccaa ctggccaaga    300
cctgccctgt gcagctgtgg gttgattcca cacccccgcc cggcacccgc gtccgcgcca    360
tggccatcta caagcagtca cagcacatga cggaggttgt gaggcgctgc ccccaccatg    420
agcgctgctc agatagcgat ggtctggccc ctcctcagca tcttatccga gtggaaggaa    480
atttgcgtgt ggagtatttg gatgacagaa acacttttcg acatagtgtg gtggtgccct    540
atgagccgcc tgaggttggc tctgactgta ccaccatcca ctacaactac atgtgtaaca    600
gttcctgcat gggcggcatg aaccggaggc ccatcctcac catcatcaca ctggaagact    660
ccagtggtaa tctactggga cggaacagct ttgaggtgcg tgtttgtgcc tgtcctggga    720
gagaccggcg cacagaggaa gagaatctcc gcaagaaagg ggagcctcac cacgagctgc    780
ccccagggag cactaagcga gcactgccca acaacaccag ctcctctccc cagccaaaga    840
agaaaccact ggatggagaa tatttcaccc ttcagatgct acttgactta cgatggtgtt    900
acttcctgat aaactcgtcg taagttgaaa atattatccg tgggcgtgag cgcttcgaga    960
tgttccgaga gctgaatgag gccttggaac tcaaggatgc ccaggctggg aaggagccag   1020
gggggagcag ggctcactcc agccacctga agtccaaaaa gggtcagtct acctcccgcc   1080
ataaaaaact catgttcaag acagaagggc ctgactcaga ctgacattct ccacttcttg   1140
ttccccactg acagcctccc acccccatct ctccctcccc tgccattttg ggttttgggt   1200
ctttgaaccc ttgcttgcaa taggtgtgcg tcagaagcac ccaggacttc catttgcttt   1260
gtcccggggc tccactgaac aagttggcct gcactggtgt tttgttgtgg ggaggaggat   1320
ggggagtagg acataccagc ttagatttta aggtttttac tgtgagggat gtttgggaga   1380
tgtaagaaat gttcttgcag ttaagggtta gtttacaatc agccacattc taggtagggg   1440
cccacttcac cgtactaacc agggaagctg tccctcactg ttgaattttc tctaacttca   1500
aggcccatat ctgtgaaatg ctggcatttg cacctacctc acagagtgca ttgtgagggt   1560
taatgaaata atgtacatct ggccttgaaa ccacctttta ttacatgggg tctagaactt   1620
gacccccttg agggtgcttg ttccctctcc ctgttggtcg gtgggttggt agtttctaca   1680
gttgggcagc tggttaggta gagggagttg tcaagtctct gctggcccag ccaaaccctg   1740
tctgacaacc tcttggtgaa ccttagtacc taaaaggaaa tctcacccca tcccacaccc   1800
tggaggattt catctcttgt atatgatgat ctggatccac caagacttgt tttatgctca   1860
gggtcaattt ctttttttctt ttttttttt tttttctttt ttctttgaga ctgggtctcg   1920
ctttgttgcc caggctggag tggagtggcg tgatcttggc ttactgcagc ctttgcctcc   1980
ccggctcgag cagtcctgcc tcagcctccg gagtagctgg gaccacaggt tcatgccacc   2040
atggccagcc aacttttgca tgttttgtag agatggggtc tcacagtgtt gcccaggctg   2100
gtctcaaact cctgggctca ggcgatccac ctgtctcagc ctcccagagt gctgggatta   2160
caattgtgag ccaccacgtc cagctggaag ggtcaacatc ttttacattc tgcaagcaca   2220
tctgcatttt caccccaccc ttcccctcct tctccctttt tatatcccat ttttatatcg   2280
atctcttatt ttacaataaa actttgctgc cacctgtgtg tctgaggggt g             2331
```

<210> SEQ ID NO 119
<211> LENGTH: 381
<212> TYPE: PRT

<213> ORGANISM: Mus musculus

<400> SEQUENCE: 119

```
Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
            20                  25                  30

Asp Ile Leu Pro Ser Pro His Cys Met Asp Asp Leu Leu Leu Pro Gln
        35                  40                  45

Asp Val Glu Glu Phe Phe Glu Gly Pro Ser Glu Ala Leu Arg Val Ser
    50                  55                  60

Gly Ala Pro Ala Ala Gln Asp Pro Val Thr Glu Thr Pro Gly Pro Val
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
            100                 105                 110

Ser Gly Thr Ala Lys Ser Val Met Cys Thr Tyr Ser Pro Pro Leu Asn
        115                 120                 125

Lys Leu Phe Cys Gln Leu Ala Lys Thr Cys Pro Val Gln Leu Trp Val
    130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
    210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Glu Asn Phe Arg Lys
        275                 280                 285

Lys Glu Val Leu Cys Pro Glu Leu Pro Pro Gly Ser Ala Lys Arg Ala
    290                 295                 300

Leu Pro Thr Cys Thr Ser Ala Ser Pro Pro Gln Lys Lys Lys Pro Leu
305                 310                 315                 320

Asp Gly Glu Tyr Phe Thr Leu Lys Ile Arg Gly Arg Lys Arg Phe Glu
                325                 330                 335

Met Phe Arg Glu Leu Asn Glu Ala Leu Glu Leu Lys Asp Ala His Ala
            340                 345                 350

Thr Glu Glu Ser Gly Asp Ser Arg Ala His Ser Ser Leu Gln Pro Arg
        355                 360                 365

Ala Phe Gln Ala Leu Ile Lys Glu Glu Ser Pro Asn Cys
    370                 375                 380
```

<210> SEQ ID NO 120
<211> LENGTH: 1877

<212> TYPE: DNA
<213> ORGANISM: Mus musculus

<400> SEQUENCE: 120

```
tttcccctcc cacgtgctca ccctggctaa agttctgtag cttcagttca ttgggaccat     60

cctggctgta ggtagcgact acagttaggg ggcacctagc attcaggccc tcatcctcct    120

ccttcccagc agggtgtcac gcttctccga agactggatg actgccatgg aggagtcaca    180

gtcggatatc agcctcgagc tccctctgag ccaggagaca ttttcaggct tatggaaact    240

acttcctcca gaagatatcc tgccatcacc tcactgcatg gacgatctgt tgctgcccca    300

ggatgttgag gagtttttg aaggcccaag tgaagccctc cgagtgtcag gagctcctgc    360

agcacaggac cctgtcaccg agacccctgg gccagtggcc cctgccccag ccactccatg    420

gcccctgtca tcttttgtcc cttctcaaaa aacttaccag ggcaactatg gcttccacct    480

gggcttcctg cagtctggga cagccaagtc tgttatgtgc acgtactctc ctcccctcaa    540

taagctattc tgccagctgg cgaagacgtg ccctgtgcag ttgtgggtca gcgccacacc    600

tccagctggg agccgtgtcc gcgccatggc catctacaag aagtcacagc acatgacgga    660

ggtcgtgaga cgctgccccc accatgagcg ctgctccgat ggtgatggcc tggctcctcc    720

ccagcatctt atccgggtgg aaggaaattt gtatcccgag tatctggaag acaggcagac    780

ttttcgccac agcgtggtgg taccttatga gccacccgag gccggctctg agtataccac    840

catccactac aagtacatgt gtaatagctc ctgcatgggg ggcatgaacc gccgacctat    900

ccttaccatc atcacactgg aagactccag tgggaacctt ctgggacggg acagctttga    960

ggttcgtgtt tgtgcctgcc ctgggagaga ccgccgtaca gaagaagaaa atttccgcaa   1020

aaaggaagtc ctttgccctg aactgccccc agggagcgca aagagagcgc tgcccacctg   1080

cacaagcgcc tctcccccgc aaaagaaaaa accacttgat ggagagtatt tcaccctcaa   1140

gatccgcggg cgtaaacgct tcgagatgtt ccgggagctg aatgaggcct tagagttaaa   1200

ggatgcccat gctacagagg agtctggaga cagcagggct cactccagcc tccagcctag   1260

agccttccaa gccttgatca aggaggaaag cccaaactgc tagctcccat cacttcatcc   1320

ctcccctttt ctgtcttcct atagctacct gaagaccaag aagggccagt ctacttcccg   1380

ccataaaaaa acaatggtca agaaagtggg gcctgactca gactgactgc ctctgcatcc   1440

cgtccccatc accagcctcc ccctctcctt gctgtcttat gacttcaggg ctgagacaca   1500

atcctcccgg tcccttctgc tgcctttttt accttgtagc tagggctcag ccccctctct   1560

gagtagtggt tcctggccca agttggggaa taggttgata gttgtcaggt ctctgctggc   1620

ccagcgaaat tctatccagc cagttgttgg accctggcac ctacaatgaa atctcaccct   1680

accccacacc ctgtaagatt ctatcttggg ccctcatagg gtccatatcc tccagggcct   1740

actttccttc cattctgcaa agcctgtctg catttatcca ccccccaccc tgtctccctc   1800

ttttttttt ttttacccct ttttatatat caatttccta ttttacaata aaattttgtt   1860

atcacttaaa aaaaaaa                                                  1877
```

<210> SEQ ID NO 121
<211> LENGTH: 390
<212> TYPE: PRT
<213> ORGANISM: Mus musculus

<400> SEQUENCE: 121

```
Met Thr Ala Met Glu Glu Ser Gln Ser Asp Ile Ser Leu Glu Leu Pro
1               5                   10                  15
```

```
Leu Ser Gln Glu Thr Phe Ser Gly Leu Trp Lys Leu Leu Pro Pro Glu
            20                  25                  30

Asp Ile Leu Pro Ser Pro His Cys Met Asp Asp Leu Leu Leu Pro Gln
        35                  40                  45

Asp Val Glu Glu Phe Phe Glu Gly Pro Ser Glu Ala Leu Arg Val Ser
    50                  55                  60

Gly Ala Pro Ala Ala Gln Asp Pro Val Thr Glu Thr Pro Gly Pro Val
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
            100                 105                 110

Ser Gly Thr Ala Lys Ser Val Met Cys Thr Tyr Ser Pro Pro Leu Asn
        115                 120                 125

Lys Leu Phe Cys Gln Leu Ala Lys Thr Cys Pro Val Gln Leu Trp Val
    130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
    210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Glu Asn Phe Arg Lys
        275                 280                 285

Lys Glu Val Leu Cys Pro Glu Leu Pro Pro Gly Ser Ala Lys Arg Ala
    290                 295                 300

Leu Pro Thr Cys Thr Ser Ala Ser Pro Pro Gln Lys Lys Lys Pro Leu
305                 310                 315                 320

Asp Gly Glu Tyr Phe Thr Leu Lys Ile Arg Gly Arg Lys Arg Phe Glu
                325                 330                 335

Met Phe Arg Glu Leu Asn Glu Ala Leu Glu Leu Lys Asp Ala His Ala
            340                 345                 350

Thr Glu Glu Ser Gly Asp Ser Arg Ala His Ser Ser Tyr Leu Lys Thr
        355                 360                 365

Lys Lys Gly Gln Ser Thr Ser Arg His Lys Lys Thr Met Val Lys Lys
    370                 375                 380

Val Gly Pro Asp Ser Asp
385                 390
```

<210> SEQ ID NO 122
<211> LENGTH: 1781
<212> TYPE: DNA
<213> ORGANISM: Mus musculus

<400> SEQUENCE: 122
tttcccctcc cacgtgctca ccctggctaa agttctgtag cttcagttca ttgggaccat 60
cctggctgta ggtagcgact acagttaggg ggcacctagc attcaggccc tcatcctcct 120
ccttcccagc agggtgtcac gcttctccga agactggatg actgccatgg aggagtcaca 180
gtcggatatc agcctcgagc tccctctgag ccaggagaca ttttcaggct tatggaaact 240
acttcctcca gaagatatcc tgccatcacc tcactgcatg gacgatctgt tgctgcccca 300
ggatgttgag gagttttttg aaggcccaag tgaagccctc cgagtgtcag gagctcctgc 360
agcacaggac cctgtcaccg agacccctgg gccagtggcc cctgccccag ccactccatg 420
gcccctgtca tcttttgtcc cttctcaaaa aacttaccag ggcaactatg gcttccacct 480
gggcttcctg cagtctggga cagccaagtc tgttatgtgc acgtactctc ctcccctcaa 540
taagctattc tgccagctgg cgaagacgtg ccctgtgcag ttgtgggtca gcgccacacc 600
tccagctggg agccgtgtcc gcgccatggc catctacaag aagtcacagc acatgacgga 660
ggtcgtgaga cgctgccccc accatgagcg ctgctccgat ggtgatggcc tggctcctcc 720
ccagcatctt atccgggtgg aaggaaattt gtatcccgag tatctggaag acaggcagac 780
ttttcgccac agcgtggtgg taccttatga gccacccgag gccggctctg agtataccac 840
catccactac aagtacatgt gtaatagctc ctgcatgggg ggcatgaacc gccgacctat 900
ccttaccatc atcacactgg aagactccag tgggaacctt ctgggacggg acagctttga 960
ggttcgtgtt tgtgcctgcc ctgggagaga ccgccgtaca gaagaagaaa atttccgcaa 1020
aaaggaagtc ctttgccctg aactgccccc agggagcgca aagagagcgc tgcccacctg 1080
cacaagcgcc tctcccccgc aaaagaaaaa accacttgat ggagagtatt tcaccctcaa 1140
gatccgcggg cgtaaacgct tcgagatgtt ccgggagctg aatgaggcct tagagttaaa 1200
ggatgcccat gctacagagg agtctggaga cagcagggct cactccagct acctgaagac 1260
caagaagggc cagtctactt cccgccataa aaaaacaatg gtcaagaaag tggggcctga 1320
ctcagactga ctgcctctgc atcccgtccc catcaccagc ctcccccctct ccttgctgtc 1380
ttatgacttc agggctgaga cacaatcctc ccggtccctt ctgctgcctt ttttaccttg 1440
tagctagggc tcagcccccct ctctgagtag tggttcctgg cccaagttgg ggaataggtt 1500
gatagttgtc aggtctctgc tggcccagcg aaattctatc cagccagttg ttggaccctg 1560
gcacctacaa tgaaatctca ccctacccca caccctgtaa gattctatct tgggccctca 1620
tagggtccat atcctccagg gcctactttc cttccattct gcaaagcctg tctgcattta 1680
tccacccccc accctgtctc cctctttttt tttttttac cccttttat atatcaattt 1740
cctattttac aataaaattt tgttatcact taaaaaaaaa a 1781

<210> SEQ ID NO 123
<211> LENGTH: 4077
<212> TYPE: DNA
<213> ORGANISM: Homo sapiens

<400> SEQUENCE: 123
gccagtgagc ccccgcgacg gtggcccgga cggaaaagat acctcggcgg cgtgggcccg 60
gctccctgct ccaggaccta gggatcttgg ccttccaccc tcctccgagc accaggactc 120
cctccagttc cgtacccgag gcctccgtgg tgaagaggtg ccggacccga tgagctcggg 180
agtccaccat cgctctgcaa gccgcagtta aacgagaaga ttcatcaccg ctttgatggc 240
tgcctcacaa acttcacaaa ctgttgcatc tcacgttcct tttgcagatt tgtgttcaac 300

-continued

```
tttagaacga atacagaaaa gtaaaggacg tgcagaaaaa atcagacact tcagggaatt    360
tttagattct tggagaaaat ttcatgatgc tcttcataag aaccacaaag atgtcacaga    420
ctctttttat ccagcaatga gactaattct tcctcagcta gaaagagaga gaatggccta    480
tggaattaaa gaaactatgc ttgctaagct ttatattgag ttgcttaatt tacctagaga    540
tggaaaagat gccctcaaac ttttaaacta cagaacaccc actggaactc atggagatgc    600
tggagacttt gcaatgattg catattttgt gttgaagcca agatgtttac agaaaggaag    660
tttaaccata cagcaagtaa acgacctttt agactcaatt gccagcaata attctgctaa    720
aagaaaagac ctaataaaaa agagccttct tcaacttata actcagagtt cagcacttga    780
gcaaaagtgg cttatacgga tgatcataaa ggatttaaag cttggtgtta gtcagcaaac    840
tatcttttct gtttttcata atgatgctgc tgagttgcat aatgtcacta cagatctgga    900
aaaagtctgt aggcaactgc atgatccttc tgtaggactc agtgatattt ctatcacttt    960
attttctgca tttaaaccaa tgctagctgc tattgcagat attgagcaca ttgagaagga   1020
tatgaaacat cagagtttct acatagaaac caagctagat ggtgaacgta tgcaaatgca   1080
caaagatgga gatgtatata aatacttctc tcgaaatgga tataactaca ctgatcagtt   1140
tggtgcttct cctactgaag gttctcttac cccattcatt cataatgcat tcaaagcaga   1200
tatacaaatc tgtattcttg atggtgagat gatggcctat aatcctaata cacaaacttt   1260
catgcaaaag ggaactaagt ttgatattaa aagaatggta gaggattctg atctgcaaac   1320
ttgttattgt gtttttgatg tattgatggt taataataaa aagctagggc atgagactct   1380
gagaaagagg tatgagattc ttagtagtat ttttacacca attccaggta gaatagaaat   1440
agtgcagaaa acacaagctc atactaagaa tgaagtaatt gatgcattga atgaagcaat   1500
agataaaaga gaagagggaa ttatggtaaa acaacctcta tccatctaca agccagacaa   1560
aagaggtgaa gggtggttaa aaattaaacc agagtatgtc agtggactaa tggatgaatt   1620
ggacatttta attgttggag gatattgggg taaaggatca cggggtggaa tgatgtctca   1680
ttttctgtgt gcagtagcag agaagccccc tcctggtgag aagccatctg tgtttcatac   1740
tctctctcgt gttgggtctg gctgcaccat gaaagaactg tatgatctgg gtttgaaatt   1800
ggccaagtat tggaagcctt ttcatagaaa agctccacca agcagcattt tatgtggaac   1860
agagaagcca gaagtataca ttgaaccttg taattctgtc attgttcaga ttaaagcagc   1920
agagatcgta cccagtgata tgtataaaac tggctgcacc ttgcgttttc cacgaattga   1980
aaagataaga gatgacaagg agtggcatga gtgcatgacc ctggacgacc tagaacaact   2040
tagggggaag gcatctggta agctcgcatc taaacacctt tatataggtg gtgatgatga   2100
accacaagaa aaaaagcgga aagctgcccc aaagatgaag aaagttattg gaattattga   2160
gcacttaaaa gcacctaacc ttactaacgt taacaaaatt tctaatatat ttgaagatgt   2220
agagttttgt gttatgagtg gaacagatag ccagccaaag cctgacctgg agaacagaat   2280
tgcagaattt ggtggttata tagtacaaaa tccaggccca gacacgtact gtgtaattgc   2340
agggtctgag aacatcagag tgaaaaacat aattttgtca aataaacatg atgttgtcaa   2400
gcctgcatgg cttttagaat gttttaagac caaaagcttt gtaccatggc agcctcgctt   2460
tatgattcat atgtgcccat caaccaaaga acattttgcc cgtgaatatg attgctatgg   2520
tgatagttat ttcattgata cagacttgaa ccaactgaag gaagtattct caggaattaa   2580
aaattctaac gagcagactc ctgaagaaat ggcttctctg attgctgatt tagaatatcg   2640
```

```
gtattcctgg gattgctctc ctctcagtat gtttcgacgc cacaccgttt atttggactc   2700

gtatgctgtt attaatgacc tgagtaccaa aaatgagggg acaaggttag ctattaaagc   2760

cttggagctt cggtttcatg gagcaaaagt agtttcttgt ttagctgagg gagtgtctca   2820

tgtaataatt ggggaagatc atagtcgtgt tgcagatttt aaagctttta gaagaacttt   2880

taagagaaag tttaaaatcc taaaagaaag ttgggtaact gattcaatag acaagtgtga   2940

attacaagaa gaaaaccagt atttgattta aagctaggtt tcctagtgag gaaagcctct   3000

gatctggcag actcattgca gcaggtggta atgataaaat actaaactac attttatttt   3060

tgtatcttaa aaatctatgc ctaaaaagta tcattacata taggaaaaca ataattttaa   3120

cttttaaggt tgaaaagaca atagcccaaa gccaagaaag aaaaattatc ttgaatgtag   3180

tattcaatga ttttttatga tcaaggtgaa ataaacagtc taaagaagag gtgtttttat   3240

aatatccata tagaaatcta gaatttttac ttagatacta ataaaataca tttagaaact   3300

tttaaagtca tgaaaaagca ttaaccttct aaacagtata ttctaaaaag tcaaaacgtt   3360

aacaatagtt tttatctaat aaaagcactg caagaaaata gggtagaatt gttacagctg   3420

gacttgtaaa aatatgtctt tttactcagg gtttaaaatg tcccatttaa atatgaaatg   3480

taaacaaatt tgtttttttaa ggttaaggcc aaatgtaaca ataaaaccct gtcgatggtt   3540

ttagctaaat tagaggaagt tgtatgagac ttaatgatct aaaaacttaa aattgaattg   3600

gtttgattaa aaataaagct tgcaatttta aaagtagctc acatttaatt tcttgtgtga   3660

aatagaacat gctttaaagg aagtattttt atgtgaattt gcattccagt ataaatagta   3720

ttcacaaaaa agattttcct agattttatc tattgaatag gtgtcaatat ggcatgcata   3780

ttgtaacttt cattagaaat aagttgcttt gacttttaaa aatgacatag ttagattatt   3840

taaagtcaat gtatatagta tatattatgt atggatttat ataccaaatt ttggaataca   3900

gcctatctca tgaccatatt gaaatgtacg gaatttgatc catgcgatac tatgtgtgca   3960

ttatttgaaa gttattggaa attttattca aaccgtggaa caaatgtatg tgattttgtt   4020

atacttctta atttaaataa aatatttaat gcactattaa aaaaaaaaaa aaaaaaa      4077
```

```
<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: MOD_RES
<222> LOCATION: (1)..(1)
<223> OTHER INFORMATION: Acetylated leucine
<220> FEATURE:
<221> NAME/KEY: MOD_RES
<222> LOCATION: (4)..(4)
<223> OTHER INFORMATION: R-2-(7'-octenyl) alanine
<220> FEATURE:
<221> NAME/KEY: SITE
<222> LOCATION: (4)..(11)
<223> OTHER INFORMATION: Cyclic stapled peptide
<220> FEATURE:
<221> NAME/KEY: MOD_RES
<222> LOCATION: (10)..(10)
<223> OTHER INFORMATION: 2-amino-4-cyanobutyric acid
<220> FEATURE:
<221> NAME/KEY: MOD_RES
<222> LOCATION: (11)..(11)
<223> OTHER INFORMATION: S-2-(4'-pentenyl) alanine
<220> FEATURE:
<221> NAME/KEY: MOD_RES
<222> LOCATION: (14)..(14)
```

-continued

<223> OTHER INFORMATION: Amidated alanine

<400> SEQUENCE: 124

Leu Thr Phe Ala Glu Tyr Trp Ala Gln Xaa Ala Ser Ala Ala
1 5 10

<210> SEQ ID NO 125
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 125
guagcgaacg uguccggcgu 20

<210> SEQ ID NO 126
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 126
aguuacugug uaucaggcag 20

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 127
agacacuuau acuaugaaag 20

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 128
agauguugaa cacugagcag 20

<210> SEQ ID NO 129
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 129
aagaauucca cugaguugca 20

<210> SEQ ID NO 130
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 130
agauguauga ucccaaaacg 20

<210> SEQ ID NO 131
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 131
accauaccca aauuauuccg 20

<210> SEQ ID NO 132
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 132
cugaagaaaa gcccucgccg 20

<210> SEQ ID NO 133
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 133
caggugauuu guggagcuau 20

<210> SEQ ID NO 134
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 134
gcuuguagau ggccauggcg 20

<210> SEQ ID NO 135
<211> LENGTH: 20
<212> TYPE: RNA
<213> ORGANISM: Artificial Sequence
<220> FEATURE:
<223> OTHER INFORMATION: Description of Artificial Sequence:
Synthetic polynucleotide

<400> SEQUENCE: 135
uccucagcau cuuauccgag 20

<210> SEQ ID NO 136
<211> LENGTH: 20
<212> TYPE: RNA
<213> ORGANISM: Artificial Sequence
<220> FEATURE:

-continued

```
<223> OTHER INFORMATION: Description of Artificial Sequence:
      Synthetic polynucleotide

<400> SEQUENCE: 136

gcagucacag cacaugacgg                                         20


<210> SEQ ID NO 137
<211> LENGTH: 20
<212> TYPE: RNA
<213> ORGANISM: Artificial Sequence
<220> FEATURE:
<223> OTHER INFORMATION: Description of Artificial Sequence:
      Synthetic polynucleotide

<400> SEQUENCE: 137

guagugguaa ucuacuggga                                         20
```

COMPOSITIONS AND METHODS FOR IDENTIFICATION ASSESSMENT, PREVENTION, AND TREATMENT OF EWING SARCOMA USING TP53 DEPENDENCY BIOMARKERS AND MODULATORS

CROSS-REFERENCE TO RELATED APPLICATIONS

This application is the U.S. national phase of International Patent Application Serial No. PCT/US2019/042110, filed Jul. 17, 2019, which claims the benefit of priority from U.S. Provisioanl Application Ser. No. 62/699,970, filed on Jul. 18, 2018, the entire content of each of said applications are incorporated herein in their entirety by this reference.

STATEMENT OF RIGHTS

This invention was made with government support under grant number R01 CA211681 and R35 CA210030 awarded by The National Institutes of Health. The government has certain rights in the present invention.

SEQUENCE LISTING

This application contains a Sequence Listing in computer readable form. The computer readable form is incorporated herein by reference. Said ASCII copy, created on Apr. 18, 2024, is named DFS-26201_SL.txt and is 596,338 bytes in size.

BACKGROUND OF THE INVENTION

Ewing sarcoma is a small round blue cell tumor affecting children and adolescents that is treated with a combination of interval compressed chemotherapy, radiation, and surgery. While outcomes have improved over the last several decades for patients with localized disease, little progress has been made in the treatment of patients with newly diagnosed metastatic or relapsed disease. Moreover, treatment-related toxicity is significant, and currently, there are no targeted therapies for Ewing sarcoma approved by the United States Food and Drug Administration (Balamuth and Womer (2010) *Lancet Oncol.* 11:184-192; Gaspar et al. (2015) *J. Clin. Oncol.* 33:3036-3046).

The defining event in Ewing sarcoma is a somatic chromosomal translocation, most commonly between chromosomes 11 and 22, causing a fusion between the EWSR1 (Ewing sarcoma breakpoint region 1) gene and an ETS family gene FLI1 (Friend leukemia virus integration 1). The resulting fusion protein, EWS/FLI, is an aberrant oncogenic transcription factor (Riggi et al. (2008) *Cancer Res.* 68:2176-2185). Efforts to directly inhibit EWS/FLI have been largely unsuccessful (Gaspar et al. (2015) *J. Clin. Oncol.* 33:3036-3046). Several recent massively parallel sequencing efforts revealed that Ewing sarcoma tumors possess remarkably quiet genomes, with few recurrent genetic events and no immediately druggable mutated kinases (Brohl et al. (2014) *PLOS Genet.* 10: e1004475; Crompton et al. (2014) *Cancer Discov.* 4:1326-1341; Tirode et al. (2014) *Cancer Discov.* 4:1342-1353). While the paucity of genetic events is a challenge for the development of precision medicine approaches using kinase inhibitors, the genomic simplicity may enable other treatment strategies. Up to 90% of Ewing sarcoma tumors present with wild-type TP53 (Tumor protein 53), allowing for new therapeutic strategies involving p53 activation.

Although the majority of patient tumors retain wild-type TP53, there has been a historic bias against studying p53 dependent genes in this disease. The vast majority of Ewing sarcoma cell lines harbor TP53 mutations (Brohl et al. (2014) *PLOS Genet.* 10: e1004475; Crompton et al. (2014) *Cancer Discov.* 4:1326-1341; Tirode et al. (2014) *Cancer Discov.* 4:1342-1353), and patient-derived Ewing sarcoma xenografts have only recently been established (Ordonez et al. (2015) *Oncotarget* 6:18875-18890). Consequently, models with TP53 mutations have been overrepresented in Ewing sarcoma studies in the past.

Accordingly, there is a great need to identify new Ewing sarcoma-related targets and biomarkers useful for the identification, assessment, prevention, and treatment of this disease.

SUMMARY OF THE INVENTION

The present invention is based, at least in part, on the discovery of targets influencing hyperproliferative cell growth in Ewing sarcoma characterized as having an intact TP53 tumor suppressor (e.g., encoding TP53 that is wild-type and/or encoding an intact TP53 protein such as one that lacks a missense, nonsense, insertion, deletion, frameshift, repeat expansion, and/or other TP53 function disrupting mutation). Modulating one or more of the targets (e.g., inhibiting the function of one or more such targets) can inhibit such hyperproliferative cell growth to thereby treat Ewing sarcoma. In addition, the targets are biomarkers that are useful for identifying and assessing modulation of such hyperproliferative cell growth.

For example, in one aspect, a method of treating a subject afflicted with Ewing sarcoma, wherein cancer cells of the Ewing sarcoma encode intact tumor protein 53 (TP53), comprising administering to the subject at least one agent that inhibits the copy number, amount, and/or activity of at least one biomarker listed in Table 1, thereby treating the subject afflicted with Ewing sarcoma, is provided.

Numerous embodiments are further provided that can be applied to any aspect of the present invention and/or combined with any other embodiment described herein. For example, in one embodiment, the at least one agent is administered in a pharmaceutically acceptable formulation. In another embodiment, the at least one agent directly binds the at least one biomarker listed in Table 1. In still another embodiment, the at least one biomarker listed in Table 1 is selected from the group consisting of human MDM2, human MDM4, human USP7, human PPM1D, and orthologs thereof. In yet another embodiment, the method further comprises administering one or more additional anti-cancer agents, optionally wherein the additional anti-cancer agent comprises chemotherapy.

In another aspect, a method of inhibiting hyperproliferative growth of a Ewing sarcoma cancer cell(s) that encodes intact tumor protein 53 (TP53), the method comprising contacting the Ewing sarcoma cancer cell(s) with at least one agent that inhibits the copy number, amount, and/or activity of at least one biomarker listed in Table 1, thereby inhibiting hyperproliferative growth of the Ewing sarcoma cancer cell(s), is provided.

As described above, numerous embodiments are further provided that can be applied to any aspect of the present invention and/or combined with any other embodiment described herein. For example, in one embodiment, the step of contacting occurs in vivo, ex vivo, or in vitro. In another embodiment, the at least one agent is administered in a pharmaceutically acceptable formulation. In still another embodiment, the at least one agent directly binds the at least one biomarker listed in Table 1. In yet another embodiment, the at least one biomarker listed in Table 1 is selected from the group consisting of human MDM2, human MDM4, human USP7, human PPM1D, and orthologs thereof. In another embodiment, the method further comprises administering one or more additional anti-cancer agents, optionally wherein the additional anti-cancer agent comprises chemotherapy.

In still another aspect, a method of determining whether a subject afflicted with Ewing sarcoma or at risk for developing Ewing sarcoma would benefit from therapy with at least one agent that inhibits the copy number, amount, and/or activity of at least one biomarker listed in Table 1, the method comprising a) obtaining a biological sample from the subject; b) determining the copy number, amount, and/or activity of at least one biomarker listed in Tables 1-2 in the subject's Ewing sarcoma cancer cells; c) determining the copy number, amount, and/or activity of the at least one biomarker in a control; and d) comparing the copy number, amount, and/or activity of the at least one biomarker detected in steps b) and c); wherein the presence of or an increase in the copy number, amount, and/or activity of the at least one biomarker in the subject sample relative to the control copy number, amount, and/or activity of the at least one biomarker indicates that the subject afflicted with Ewing sarcoma or at risk for developing Ewing sarcoma would benefit from therapy with the at least one agent that inhibits the copy number, amount, and/or activity of the at least one biomarker listed in Tables 1-2, and wherein the absence of or a decrease in the copy number, amount, and/or activity of the at least one biomarker in the subject sample relative to the control copy number, amount, and/or activity of the at least one biomarker indicates that the subject afflicted with Ewing sarcoma or at risk for developing Ewing sarcoma would not benefit from therapy with the at least one agent that inhibits the copy number, amount, and/or activity of the at least one biomarker listed in Tables 1-2, is provided.

As described above, numerous embodiments are further provided that can be applied to any aspect of the present invention and/or combined with any other embodiment described herein. For example, in one embodiment, the method urther comprises recommending, prescribing, or administering the therapy comprising the at least one agent if the Ewing sarcoma is determined to benefit from the therapy comprising the at least one agent. In another embodiment, the method further comprises recommending, prescribing, or administering anti-cancer therapy other than therapy comprising the at least one agent if the Ewing sarcoma is determined not to benefit from the therapy comprising the at least one agent. In still another embodiment, the anti-cancer therapy is selected from the group consisting of targeted therapy, chemotherapy, radiation therapy, and/or hormonal therapy. In yet another embodiment, the control is determined from a cancerous or non-cancerous sample from either the patient or a member of the same species to which the patient belongs. In another embodiment, the control comprises cells. In still another embodiment, the method further comprises determining responsiveness to the therapy comprising the at least one agent measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In yet another aspect, a method of assessing the efficacy of an agent for treating Ewing sarcoma in a subject, wherein the Ewing sarcoma cancer cells encode intact tumor protein 53 (TP53), comprising a) detecting in a first subject sample and maintained in the presence of the agent the copy number, amount, or activity of at least one biomarker listed in Table 1; b) detecting the copy number, amount, and/or activity of the at least one biomarker listed in Table 1 in a second subject sample and maintained in the absence of the test compound; and c) comparing the copy number, amount, and/or activity of the at least one biomarker listed in Table 1 from steps a) and b), wherein the presence or an increased copy number, amount, and/or activity of the at least one biomarker listed in Table 1 in the first subject sample relative to the second subject sample, indicates that the agent treats the Ewing sarcoma in the subject, is provided.

In another aspect, a method of monitoring the progression of Ewing sarcoma in a subject, wherein cancer cells of the Ewing sarcoma encode intact tumor protein 53 (TP53), comprising a) detecting in a subject sample at a first point in time the copy number, amount, and/or activity of at least one biomarker listed in Table 1; b) repeating step a) during at least one subsequent point in time after administration of a therapeutic agent; and c) comparing the copy number, amount, and/or activity detected in steps a) and b), wherein an increased copy number, amount, and/or activity of the at least one biomarker listed in Table 1 in the first subject sample relative to at least one subsequent subject sample, indicates that the agent treats the Ewing sarcoma in the subject, is provided.

As described above, numerous embodiments are further provided that can be applied to any aspect of the present invention and/or combined with any other embodiment described herein. For example, in one embodiment, the subject has undergone treatment, completed treatment, and/or is in remission for the Ewing sarcoma between the first point in time and the subsequent point in time. In another embodiment, the subject has undergone therapy with at least one inhibitor of at least one biomarker listed in Table 1 between the first point in time and the subsequent point in time. In still another embodiment, the first and/or at least one subsequent sample is selected from the group consisting of ex vivo and in vivo samples. In yet another embodiment, the first and/or at least one subsequent sample is obtained from an animal model of Ewing sarcoma. In another embodiment, the first and/or at least one subsequent sample is a portion of a single sample or pooled samples obtained from the subject.

In still another aspect, a cell-based method for identifying an agent which inhibits a Ewing sarcoma cancer cell(s), wherein the cancer cell(s) encode intact tumor protein 53 (TP53), comprising a) contacting the Ewing sarcoma cancer cell(s) expressing at least one biomarker listed in Table 1 with a test agent; and b) determining the effect of the test agent on the copy number, level of expression, or level of activity of the at least one biomarker listed in Table 1 to thereby identify an agent that inhibits the Ewing sarcoma cancer cell(s), is provided.

As described above, numerous embodiments are further provided that can be applied to any aspect of the present invention and/or combined with any other embodiment described herein. For example, in one embodiment, said cells are isolated from an animal model of Ewing sarcoma. In another embodiment, said cells are from a subject afflicted with Ewing sarcoma. In still another embodiment, said cells are unresponsive to therapy with at least one agent that inhibits the copy number, amount, and/or activity of at least one biomarker listed in Table 1. In yet another embodiment, the step of contacting occurs in vivo, ex vivo, or in vitro. In another embodiment, the method further comprises determining the ability of the test agent to bind to the at least one biomarker listed in Table 1 before or after determining the effect of the test agent on the copy number, level of expression, or level of activity of the at least one biomarker listed in Table 1. In still another embodiment, the sample comprises cells, cell lines, histological slides, paraffin embedded tissue, fresh frozen tissue, fresh tissue, biopsies, blood, plasma, serum, buccal scrape, saliva, cerebrospinal fluid, urine, stool, mucus, or bone marrow, obtained from the subject. In yet another embodiment, the copy number is assessed by microarray, quantitative PCR (qPCR), high-throughput sequencing, comparative genomic hybridization (CGH), or fluorescent in situ hybridization (FISH). In another embodiment, the amount of the at least one biomarker is assessed by detecting the presence in the samples of a polynucleotide molecule encoding the biomarker or a portion of said polynucleotide molecule. In still another embodiment, the polynucleotide molecule is a mRNA, cDNA, or functional variants or fragments thereof. In yet another embodiment, the step of detecting further comprises amplifying the polynucleotide molecule. In another embodiment, the amount of the at least one biomarker is assessed by annealing a nucleic acid probe with the sample of the polynucleotide encoding the one or more biomarkers or a portion of said polynucleotide molecule under stringent hybridization conditions. In still another embodiment, the amount of the at least one biomarker is assessed by detecting the presence a polypeptide of the at least one biomarker. In yet another embodiment, the presence of said polypeptide is detected using a reagent which specifically binds with said polypeptide. In another embodiment, the reagent is selected from the group consisting of an antibody, an antibody derivative, and an antibody fragment. In still another embodiment, the activity of the at least one biomarker is assessed by determining the magnitude of modulation of at least one biomarker listed in Table 1 or Table 2. In yet another embodiment, the activity of the at least one biomarker is assessed by determining the magnitude of modulation of the activity or expression level of at least one downstream target of the at least one biomarker. In another embodiment, the agent or test agent inhibits at least one biomarker selected from the group consisting of human MDM2, human MDM4, human USP7, human PPM1D, and orthologs of said biomarkers thereof. In still another embodiment, the inhibitor agent or test agent is an inhibitor selected from the group consisting of a small molecule, antisense nucleic acid, interfering RNA, shRNA, siRNA, aptamer, ribozyme, dominant-negative protein binding partner, peptide, stapled peptide, and combinations thereof. In yet another embodiment, the at least one biomarker is selected from the group consisting of 2, 3, 4, 5, 6, 7, 8, or more biomarkers. In another embodiment, the TP53 is wildtype TP53. In still another embodiment, the Ewing sarcoma is metastatic and/or relapsed. In yet another ermbodiment, the Ewing sarcoma comprises intact TP53. In another embodiment, the TP53 is wildtype TP53. In still another embodiment, the subject is a mammal. In yet another embodiment, the mammal is an animal model of Ewing sarcoma. In another embodiment, the mammal is a human.

BRIEF DESCRIPTION OF THE DRAWINGS

FIG. 1A-FIG. 1D show the results of a genome-scale CRISPR-Cas9 screen of 33 cancer cell lines that identifies genetic vulnerabilities negatively correlated with TP53 dependency in TP53 wild-type lines. FIG. 1A shows a waterfall plot of TP53 dependency in 33 cancer cell lines shows positive dependency score in known TP53 wild-type cell lines consistent with the hypothesis that disruption of TP53 in these lines would lead to a proliferation advantage. Based on these data, 6 of 33 lines are believed to have a functional p53 pathway. A single cell line for which there is no documented TP53 mutation, PANC08.13, behaves like a TP53 mutant line, suggesting it has a nonfunctional p53 pathway. FIG. 1B shows the top eight anti-correlated genetic dependencies to TP53 dependency. FIG. 1C shows seven of the top eight anti-correlated genes are connected to TP53 in the STRING database indicating putative protein-protein interactions. The widths of the edges correspond to the level of confidence in interactions (medium confidence STRING score of 0.4; high confidence STRING score of 0.7; highest confidence STRING score of 0.9). FIG. 1D whos MDM4, PPM1D, MDM2, and USP7 dependency scores in Ewing sarcoma cell lines in the CRI SPR-Cas9 screen stratified by TP53 mutational status (mut, mutant; wt, wild type).

FIG. 2A shows the correlation of TP53 dependency scores with dependency scores of MDM4, PPM1D, MDM2, PPMIG (protein phosphatase, Mg2+/Mn2+ dependent 1G), LIG4 (DNA Ligase 4), PUM (*pumilio* RNA binding family member 3), USP7, and UBE2D3 (ubiquitin conjugating enzyme E2 D3). FIG. 2B shows a comparison of dependency scores of MDM4, PPM1D, MDM2, PPMIG, LIG4, PUM3, USP7, and UBE2D3 in TP53 wild-type versus TP53 mutated Ewing sarcoma cell lines (mut, mutant; wt, wild type).

FIG. 3C shows the relative viability of Ewing sarcoma and SJSA-X cells infected with sgRNAs targeting MDM2 compared with control sgRNAs 14 d after infection. Each data point shows the mean of eight replicates, data are plotted as mean values+/−standard deviation. The experiment was performed twice and data points of one representative experiment are shown. Western blots (FIG. 3D) show decreased protein levels of MDM4 after infection with sgRNAs targeting MDM4 compared with control sgRNAs. Western blots (FIG. 3) demonstrate decreased protein levels of MDM4 with sgRNAs targeting MDM4 compared with control guides in the SJSA-X cell line. FIG. 3F show relative viability of Ewing sarcoma and SJSA-X cells infected with sgRNAs targeting MDM4 or control sgRNAs 14 d after infection. Each data point shows the mean of eight replicates, data are plotted as mean values+/−standard deviation. The experiment was performed twice and data points of one representative experiment are shown. Significance was calculated by paired, two-tailed t test: n.s, not significant for $P>0.05$; *, $P\leq0.05$; , for $P\leq0.01$; *, $P\leq0.001$).

FIG. 4B shows the results of immunoprecipitation experiments demonstrating partial disruption of p53-MDM4 complex after treating cellular lysates with ATSP-7041, while RG7388 does not interrupt binding. TC32 cells were treated with RG7388 (last four lanes) to increase p53 protein levels. FIG. 4C shows the results of Ewing sarcoma cells treated with ATSP-7041 for 3 d. TP53 wild-type Ewing sarcoma cell lines are shown in red color (i.e., lighter color with connected lines). TP53 mutated Ewing sarcoma cell lines are shown in black (i.e., darker color marks unconnected by lines). Values are normalized to vehicle control. E ach data point shows the mean of eight replicates; error bars are mean values+/−standard deviation. The experiment was performed twice and data points of one representative experiment are shown. FIG. 4D shows the results of Ewing sarcoma cells treated with negative control peptide ATSP-7342 for 3 d. TP53 wild-type Ewing sarcoma cell lines are shown in red (i.e., lighter color with connected lines). TP53 mutant Ewing sarcoma cell lines are shown in black (i.e., darker color marks unconnected by lines). Values are normalized to vehicle control. Each data point shows the mean of eight replicates; error bars are mean values+/−standard deviation. The experiment was performed twice and data points of one representative experiment are shown. FIG. 4E shows that 2-d treatment with ATSP-7041 triggers cell death in TC32 (treated with 2 μM) and CHLA258 (treated with 4 μM) cell lines, as measured by Annexin V staining. Data points represent the mean of five replicates of two experiments and error bars are mean+/−standard deviation. FIG. 4F shows the viability effect of dual CRISPR-Cas9 knockout of MDM2 and MDM4 in TC32 cells. Cells were infected with sgRNAs targeting MDM2 and selected with puromycin and sgRNAs targeting MDM4 and selected with blasticidin. The relative viability of eight replicates are shown 11 d post-infection. The experiment was performed twice and data points of one representative experiment are shown. Significance was calculated by paired, two-tailed t test: , P≤0.01; *, P≤0.001.

FIG. 5B provides quantitative PCR results showing an increase of MDM2 mRNA levels with vehicle (black) or ATSP-7041 (gray) treatment of TC32 xenograft cells in vivo. Values were normalized to the first vehicle-treated sample. Each bar represents an individual mouse tumor; error bars represent standard deviation of three technical replicates. Significance was calculated by paired, two-tailed t test: *, P≤0.001. FIG. 5C provides quantitative PCR results showing an increase of p21 mRNA levels with vehicle (black) or ATSP-7041 (gray) treatment of TC32 xenograft cells in vivo. Values were normalized to the first vehicle-treated sample. Each bar represents an individual mouse tumor; error bars represent standard deviation of three technical replicates. Significance was calculated by paired, two-tailed t test: *, P≤0.001. FIG. 5D shows normalized average tumor volume from mice bearing TC32 xenograft tumors treated with 30 mg/kg ATSP-7041 q.o.d. (red (i.e., the lower line), n=8), or vehicle q.o.d. (black (i.e., the upper line), n=7). Mice were treated with 10 doses. Tumor volume from each mouse was normalized to the tumor volume at the day of enrollment. Error bars represent standard deviation. Significance was calculated by two-way ANOVA analysis: , P≤0.01. Western blot (FIG. 5E) results show an increase of MDM2, p53, and p21 protein levels in PDX tumor tissues after ATSP-7041 treatment in vivo. After tumor engraftment, mice were treated with three doses of 30 mg/kg q.o.d. ATSP-7041 or vehicle and sacrificed 8 h after the last dose. Each lane represents an individual mouse tumor. FIG. 5F provides quantitative PCR results showing an increase of MDM2 mRNA levels with vehicle (black) or ATSP-7041 (gray) treatment of PDX cells in vivo. Values were normalized to the first vehicle-treated sample. Each bar represents an individual mouse tumor; error bars represent standard deviation of three technical replicates. Significance was calculated by paired, two-tailed t test: *, P≤0.001. FIG. 5G provides quantitative PCR results showing an increase of p21 mRNA levels with vehicle (black) or ATSP-7041 (gray) treatment of PDX cells in vivo. Values were normalized to the first vehicle-treated sample. Each bar represents an individual mouse tumor; error bars represent standard deviation of three technical replicates. Significance was calculated by paired, two-tailed t test: *, P≤0.001. FIG. 5H shows normalized average tumor volumes from mice bearing PDX tumors treated with 30 mg/kg ATSP-7041 q.o.d. (red (i.e., the lower line), n=8), or vehicle q.o.d. (black (i.e., the upper line), n=7). Mice were treated with 10 doses. Tumor volume for each mouse was normalized to the tumor volume at the day of enrollment. Error bars represent standard deviation. Significance was calculated by two-way ANOVA analysis: *, P≤0.001. FIG. 5I shows survival of mice bearing PDX tumors. One mouse treated with ATSP-7041 had complete tumor regression without recurrence over the observed time frame. Significance was calculated by Log-rank (Mantel-Cox) test: **, P≤0.01.

FIG. 6B shows the relative viability of Ewing sarcoma cells infected with sgRNAs targeting USP7 or control sgRNAs 14 d after infection. Each data point shows the mean of eight replicates; data are plotted as mean values+/−standard deviation. The experiment was performed twice and data points of one representative experiment are shown. Western blots (FIG. 6C) show decreased protein levels of Wip1 after infection with sgRNAs targeting PPM1D compared with control sgRNAs. FIG. 6D show the relative viability of Ewing sarcoma cells infected with sgRNAs targeting PPM1D or control sgRNAs 14 d after infection. Each data point shows the mean of eight replicates, data are plotted as mean values+/−standard deviation. The experiment was performed twice and data points of one representative experiment are shown. Significance was calculated by paired, two-tailed t test: not significant (n.s.) for P>0.05; *, P≤0.05; , P≤0.01; *, P≤0.001.

FIG. 7B shows the results of Ewing sarcoma cells treated with P5091 for 3 d. TP53 wild-type Ewing sarcoma cell lines are shown in red (i.e., generally the lower left lines); TP53 mutant Ewing sarcoma cell lines are shown in black (i.e., generally the upper right lines). Values were normalized to vehicle controls. Each data point shows the mean of eight replicates;

error bars are mean values+/−standard deviation. The experiment was performed twice and data points of one representative experiment are shown. FIG. 7C shows that 2-d treatment with P5091 triggers cell death in TC32 (treated with 6.5 μM) and CHLA258 cells (treated with 8 μM) as measured by Annexin V staining. Data points represent the mean of five replicates of two experiments, and error bars are mean+/−standard deviation. Western blots (FIG. 7D) show decreased protein levels of Wip1 and increased pSer15-p53 upon GSK2830371 treatment at the indicated time and concentration. FIG. 7E shows results of Ewing sarcoma cells treated with GSK2830371 for 3 d. TP53 wild-type Ewing sarcoma cell lines are shown in red (i.e., generally the lower left lines); TP53 mutated Ewing sarcoma cell lines are shown in black (i.e., the upper right lines). Values were normalized to vehicle controls. Each data point shows the mean of eight replicates; error bars are mean values+/−standard deviation. The experiment was performed twice, and data points of one representative experiment are shown. FIG. 7F shows that 3-d treatment with GSK2830371 triggers cell death in TC32 and CHLA258 (both treated with 15 μM) cell lines, as measured by Annexin V staining. Data points represent the mean of five replicates of two experiments, and error bars are mean values+/−standard deviation. Significance was calculated by paired, two-tailed t test: *, P≤0.05; , P≤0.01; *, P≤0.001.

FIG. 8A shows CI plots for the combination of ATSP-7041 with P5091 in TC32, TC138, and CHLA258 cells after 5 d of treatment. Western blots (FIG. 8B) shows decreased MDM2 protein levels in TC32 and TC138 cells treated with a combination of ATSP-7041 and P5091 compared with treatment with ATSP-7041 alone. Cells were treated at the indicated concentrations for 2 d (ATSP, ATSP-7041). FIG. 8C shows CI plots for the combination of ATSP-7041 with GSK2830371 in TC32, TC138, and CHLA258 cells after 3 d of treatment. Western blots (FIG. 8D) show increased phospho-Serine15-p53 protein levels with combination treatment of ATSP-7041 and GSK2830371 in TC32 and CHLA258 cells. Cells were treated at indicated concentrations for 2 d (ATSP, ATSP-7041; GSK, GSK2830371).

FIG. 9A-FIG. 9C show CI plots for the combination of ATSP-7041 with doxorubicin, etoposide, and vincristine after 3 d of treatment in TC32 (FIG. 9A), TC138 (FIG. 9B), and CHLA258 (FIG. 9C) cells. Western blots (FIG. 9D) show increased p53 protein levels in TC32 cells treat with combinations of ATSP-7041 and doxorubicin. Cells were treated at indicated concentrations for 2 d (ATSP, ATSP-7041; Doxo, doxorubicin). Western blots (FIG. 9E) show increased p53 protein levels in TC32 cells treat with combinations of ATSP-7041 and etoposide. Cells were treated at indicated concentrations for 2 d (ATSP, ATSP-7041; Eto, etoposide). Western blots (FIG. 9F) show increased p53 protein levels in TC32 cells treat with combinations of ATSP-7041 and vincristine. Cells were treated at indicated concentrations for 2 d (ATSP, ATSP-7041; Vinc, vincristine).

FIG. 10B show the results of TP53 knockout cells treated with ATSP-7041 for 3 d. Values were normalized to vehicle controls. Each data point shows the mean of eight replicates; error bars are mean values+/−standard deviation. The experiment was performed twice and data points of one representative experiment are shown. FIG. 10C show the results of TP53 knockout cells treated with GSK2830371 for 3 d. Values were normalized to vehicle controls. Each data point shows the mean of eight replicates; error bars are mean values+/−standard deviation. The experiment was performed twice, and data points of one representative experiment are shown. FIG. 10D shows the results of TP53 knockout cells treated with P5091 for 3 d. Values were normalized to vehicle controls. Each data point shows the mean of eight replicates; error bars are mean values+/−standard deviation. The experiment was performed twice, and data points of one representative experiment are shown. Western blots (FIG. 10E) show decreased protein levels of USP7 after infection with sgRNAs targeting USP7 in TC32 TP53 knockout cells. Western blots (FIG. 10F) show decreased protein levels of Wip1 after infection with sgRNAs targeting PPM1D in TC32 TP53 knockout cells. FIG. 10G show the relative viability of TC32 TP53 knockout cells infected with sgRNAs targeting USP7 or PPM1D or control sgRNAs 14 d after infection. Each data point shows the mean of eight replicates, data are plotted as mean values+/−standard deviation. The experiment was performed twice and data points of one representative experiment are shown. Significance was calculated by paired, two-tailed t test: not significant (n.s.) for P>0.05; *, P≤0.05; , P<0.01; *, P≤0.001. FIG. 10H show the results of Ewing sarcoma cells treated with XL-188 for 3 d. TP53 wild-type Ewing sarcoma cell lines are shown in red (i.e., generally the lower lines); TP53 mutated Ewing sarcoma cell lines are shown in black (i.e., generally the upper lines). Values were normalized to vehicle controls. Each data point shows the mean of eight replicates; error bars are mean values+/−standard deviation. The experiment was performed twice, and data points of one representative experiment are shown. FIG. 10I shows the results of TP53 knockout cells treated with XL-188 for 3 d. Values were normalized to vehicle controls. Each data point shows the mean of eight replicates; error bars are mean values+/−standard deviation. The experiment was performed twice and data points of one representative experiment are shown.

FIG. 11 shows p53 mutation status of cancer cell lines, including Ewing sarcoma cell lines.

Figure 1D:
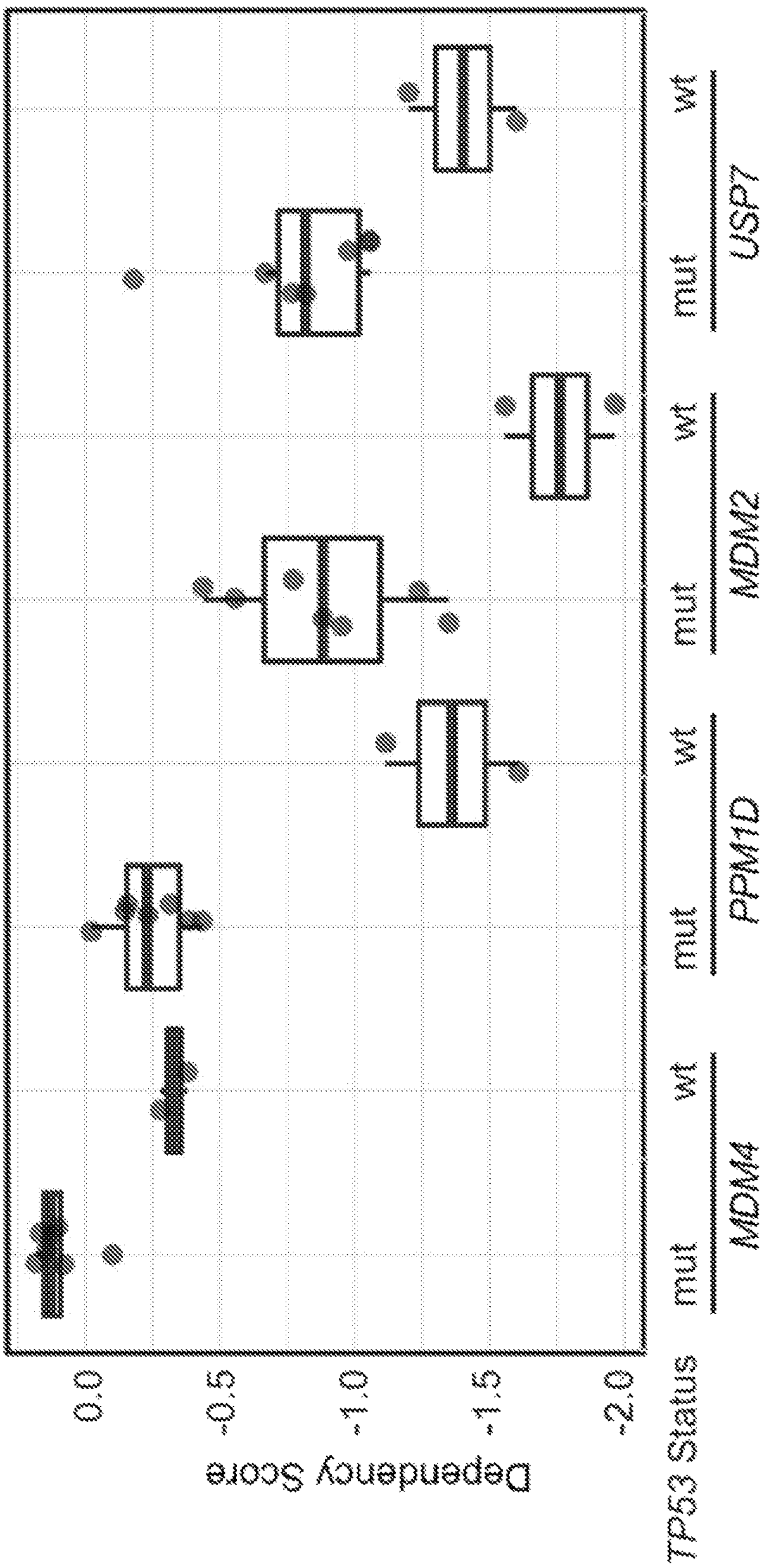

Note that for every figure containing a histogram, the bars from left to right for each discreet measurement correspond to the figure boxes from top to bottom in the figure legend as indicated, unless otherwise defined such as in FIG. 1A.

DETAILED DESCRIPTION OF THE INVENTION

It has been determined herein that certain targets influence hyperproliferative cell growth in Ewing sarcoma characterized as having an intact TP53 tumor suppressor (e.g., encoding TP53 that is wild-type and/or encoding a functional TP53 protein such as one that lacks a missense, nonsense, insertion, deletion, frameshift, repeat expansion, and/or other TP53 function disrupting mutation). The presence, absence, amount (e.g., copy number or level of expression), and/or activity of certain TP53 pathway components and dependencies are biomarkers for the diagnosis, prognosis, and treatment of Ewing sarcoma. In particular, the identification of druggable dependencies in Ewing sarcoma models with intact p53, which better recapitulates the more common disease biology, was performed using genome-scale clustered regularly interspaced short palindromic repeats (CRISPR) paired with the CRISPR-associated nuclease 9 (Cas9) for screening purposes (Cong et al. (2013) *Science* 339:819-823; Mali et al. (2013) *Science* 339:823-826; Shalem et al. (2014) *Science* 343:84-87; Aguirre et al. (2016) *Cancer Discov.* 6:914-929). It was hypothesized that deletion of TP53 by single guide RNA (sgRNA)-guided CRISPR-Cas9 constructs would give a proliferative advantage exclusively in TP53 wild-type cell lines and, therefore, leveraged the data to identify genetic dependencies anti-correlated with TP53 dependency scores. The p53 regulators murine double minute 2 (MDM2), murine double minute 4 (MDM4), ubiquitin specific peptidase 7 (USP7), and protein phosphatase, Mg2+/Mn2+-dependent 1D (PPM1D) were among the top druggable dependencies with strong anti-correlation to TP53 dependency scores. All four were validated in secondary assays to be essential for proliferation of TP53 wild-type Ewing sarcoma cells. Moreover, chemical inhibitors of these targets, including a stapled peptide dual inhibitor of MDM2 and MDM4 (ATSP-7041), an USP7 inhibitor (P5091), and a wild-type p53-induced phosphatase 1 (Wip1; encoded by the PPM1D gene) inhibitor (GSK2830371) reduced the viability of Ewing sarcoma cell lines as single agents and were highly synergistic in combination. ATSP-7041 showed anti-tumor efficacy in vivo in several Ewing sarcoma models. Consistent with all four targets being highly correlated dependencies in the screening data, combinatorial targeting with pharmacologic inhibitors showed synergistic activity. Furthermore, ATSP-7041 synergized with standard-of-care Ewing sarcoma chemotherapeutic agents. To further demonstrate that these treatment strategies depended on functional p53, TP53 knockout cell lines were generated. TP53 knockout rescued CRISPR-Cas9-mediated or inhibitor-mediated anti-viability effects of target deletion/inhibition of all four targets.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 10%, 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal amount if the amount is at least about two, and preferably at least about three, four, or five times, higher or lower, respectively, than the normal amount of the biomarker.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CHI domains; (ii) a $F(ab')_2$ fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of tbhe Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies encompassed by the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies encompassed by the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the predictive score."

The term "biomarker" refers to a measurable entity encompassed by the present invention that has been determined to be predictive of anti-cancer therapy (e.g., at least one inhibitor of at least one biomarker listed in Table 1) effects on a cancer. Biomarkers can include, without limitation, nucleic acids (e.g., genomic nucleic acids and/or transcribed nucleic acids) and proteins, particularly those involved shown in Table 1. The biomarkers listed in Table 1 are also useful as therapeutic targets.

For example, the term "MDM2" refers to MDM2 proto-oncogene, a nuclear-localized E3 ubiquitin ligase. MDM2 protein can promote tumor formation by targeting tumor suppressor proteins, such as p53, for proteasomal degradation. MDM2 gene is itself transcriptionally-regulated by p53. Overexpression or amplification of MDM2 locus is detected in a variety of different cancers. MDM2 is an E3 ubiquitin-protein ligase that mediates ubiquitination of p53/TP53, leading to its degradation by the proteasome. It inhibits p53/TP53- and p73/TP73-mediated cell cycle arrest and apoptosis by binding its transcriptional activation domain. MDM2 also acts as an ubiquitin ligase E3 toward itself and ARRB1. MDM2 permits the nuclear export of p53/TP53. MDM2 promotes proteasome-dependent ubiquitin-independent degradation of retinoblastoma RB1 protein. MDM2 inhibits DAXX-mediated apoptosis by inducing its ubiquitination and degradation. MDM2 is a component of the TRIM28/KAP1-MDM2-p53/TP53 complex involved in stabilizing p53/TP53. MDM2 is also a component of the TRIM28/KAP1-ERBB4-MDM2 complex which links growth factor and DNA damage response pathways. MDM2 mediates ubiquitination and subsequent proteasome degradation of DYRK2 in nucleus. MDM2 also ubiquitinates IGF1R and SNAIL and promotes them to proteasomal degradation. MDM2 ubiquitinates DCX, leading to DCX degradation and reduction of the dendritic spine density of olfactory bulb granule cells. MDM2 ubiquitinates DLG4, leading to proteasomal degradation of DLG4 which is required for AMPA receptor endocytosis. In some embodiments, human MDM2 protein has 491 amino acids and a molecular mass of 55233 Da. The known binding partners of MDM2 include, e.g., USP2, MDM4, DAXX, USP7, PASSF1, RB1, EP300, E2F1, RYBP, APEX1, PML, RFFL, RNF34, CDK5RAP3, CDKN2A/ARF, MTA1, AARB2, TBRG1, MTBP, ADGRB1, PSMA3, ARRB1, ARRB2, CDKN2AIP, RFWD3, USP7, PYHIN1, p53/TP53, TP73/p73, RBL5 and RP11.

The term "MDM2" is intended to include fragments, variants (e.g., allelic variants), and derivatives thereof. Representative human MDM2 cDNA and human MDM2 protein sequences are well-known in the art and are publicly available from the National Center for Biotechnology Information (NCBI). For example, at least five different human MDM2 isoforms are known. Human MDM2 isoform a (NP_002383.2) is encodable by the transcript variant 1 (NM_002392.5). Human MDM2 isoform h (NP_001138811.1) is encodable by the transcript variant 2 (NM_001145339.2). Human MDM2 isoform g (NP_001138809.1) is encodable by the transcript variant 3 (NM_001145337.2). Human MDM2 isoform i (NP_001138812.1) is encodable by the transcript variant 4 (NM_001145340.2). Human MDM2 isoform 1 (NP_001265391.1) is encodable by the transcript variant 5 (NM_001278462.1). Nucleic acid and polypeptide sequences of MDM2 orthologs in organisms other than humans are well known and include, for example, chimpanzee MDM2 (XM_024347943.1 and XP_024203711.1, XM_024347942.1 and XP_024203710.1, XM_016923838.2 and XP_016779327.1, XM_009425800.3 and XP_009424075.1, XM_001155208.6 and XP_001155208.1, XM_009425803.3 and XP_009424078.1, and XM_016923839.1 and XP_016779328.1), monkey MDM2 (NM_001266402.1 and NP_001253331.1), dog MDM2 (NM_001003103.2 and NP_001003103.1), cattle MDM2 (NM_001099107.1 and NP_001092577.1), mouse MDM2 (NM_001288586.2 and NP_001275515.1, and NM_010786.4 and NP_034916.1), rat MDM2 (NM_001108099.1 and NP_001101569.1), chicken MDM2 (NM_001199384.1 and NP_001186313.1), tropical clawed frog MDM2 (NM_001244760.1 and NP_001231689.1, and NM_203912.2 and NP_989243.1), and zebrafish MDM2 (NM_131364.2 and NP_571439.2). Representative sequences of MDM2 orthologs are presented below in Table 1.

Anti-MDM2 antibodies suitable for detecting MDM2 protein are well-known in the art and include, for example, antibodies CF804750 and TA804750 (Origene), antibodies NB100-2736 and AF1244 (Novus Biologicals, Littleton, CO), antibodies ab38618 and ab 16895 (AbCam, Cambridge, MA), antibody MA1-113 (ThermoFisher Scientific), antibody 45-878 (ProSci), etc. In addition, reagents are well-known for detecting MDM2. Multiple clinical tests of MDM2 are available in NIH Genetic Testing Registry (GTR®) (e.g., GTR Test ID: GTR000518111.2, offered by Fulgent Clinical Diagnostics Lab (Temple City, CA)). Moreover, multiple siRNA, shRNA, CRISPR constructs for reducing MDM2 expression can be found in the commercial product lists of the above-referenced companies, such as siRNA products #sc-29394 and sc-37263, and CRISPR products #sc-400045-KO-2 and #sc-400045 from Santa Cruz Biotechnology, RNAi products SR302849 and TL311529V, and CRISPR product KN219518 (Origene), and multiple CRISPR products from GenScript (Piscataway, NJ). Chemical inhibitors of MDM2 are also available, including, e.g., SP 141, Nutlin-3, Nutlin 3a, NSC 66811, RITA (TOCRIS, Minneapolis, MN), and ATSP-7041 (Ac-Leu17-Thr-Phe-cyclo(R8-Glu-Tyr-Trp-Ala-Gln-Cba-S5)-Ser-Ala-Ala30—NH2 (SEQ ID NO: 124): Chang et al., (2013) Proc Natl Acad Sci U SA, 110: E3445-E3454). It is to be noted that the term can further be used to refer to any combination of features described herein regarding MDM2 molecules. For example, any combination of sequence composition, percentage identify, sequence length, domain structure, functional activity, etc. can be used to describe a MDM2 molecule encompassed by the present invention.

The term "MDM4" refers to MDM4, p53 regulator, a nuclear protein that contains a p53 binding domain at the N-terminus and a RING finger domain at the C-terminus, and shows structural similarity to p53-binding protein MDM2. Both proteins bind the p53 tumor suppressor protein and inhibit its activity, and have been shown to be overexpressed in a variety of human cancers. However, unlike MDM2 which degrades p53, MDM4 protein inhibits p53 by binding its transcriptional activation domain. MDM4 protein also interacts with MDM2 protein via the RING finger domain, and inhibits the latter's degradation. MDM4 protein can reverse MDM2-targeted degradation of p53, while maintaining suppression of p53 transactivation and apoptotic functions. MDM4 inhibits p53/TP53- and TP73/p73-mediated cell cycle arrest and apoptosis by binding its transcriptional activation domain. MDM4 inhibits degradation of MDM2. MDM4 can reverse MDM2-targeted degradation of TP53 while maintaining suppression of TP53 transactivation and apoptotic functions. Diseases associated with MDM4 include intraocular retinoblastoma and familial retinoblastoma. Among its related pathways are cdk-mediated phosphorylation and removal of cdc6 and metabolism of proteins. In some embodiments, human MDM4 protein has 490 amino acids and/or a molecular mass of 54864 Da. The known binding partners of MDM4 include, e.g., YWHAG, MDM2, TP53, TP73 and USP2.

The term "MDM4" is intended to include fragments, variants (e.g., allelic variants), and derivatives thereof. Representative human MDM4 cDNA and human MDM4 protein sequences are well-known in the art and are publicly available from the National Center for Biotechnology Information (NCBI). For example, seven different human MDM4 isoforms are known. Human MDM4 isoform 1 (NP_002384.2) is encodable by the transcript variant 1 (NM_002393.4). Human MDM4 isoform 2 (NP_001191100.1) is encodable by the transcript variant 2 (NM_001204171.1). Human MDM4 isoform 3 (NP_001191101.1) is encodable by the transcript variant 3 (NM_001204172.1). Human MDM4 isoform 4 (NP_001265445.1) is encodable by the transcript variant 4 (NM_001278516.1). Human MDM4 isoform 5 (NP_001265446.1) is encodable by the transcript variant 5 (NM_001278517.1). Human MDM4 isoform 6 (NP_001265447.1) is encodable by the transcript variant 6 (NM_001278518.1). Human MDM4 isoform 7 (NP_001265448.1) is encodable by the transcript variant 7 (NM_001278519.1). Nucleic acid and polypeptide sequences of MDM4 orthologs in organisms other than humans are well known and include, for example, chimpanzee MDM4 (NM_001280376.1 and NP_001267305.1), monkey MDM4 (XM_015119513.1 and XP_014974999.1), dog MDM4 (XM_536098.6 and XP_536098.3, XM_022415425.1 and XP_022271133.1, XM_022415426.1 and XP_022271134.1, XM_022415421.1 and XP_022271129.1, XM_022415422.1 and XP_022271130.1, XM_022415420.1 and XP_022271128.1, XM_022415424.1 and XP_022271132.1, and XM_022415423.1 and XP_022271131.1), cattle MDM4 (NM_001046169.1 and NP_001039634.1), mouse MDM4 (NM_001302801.1 and NP_001289730.1, NM_001302802.1 and NP_001289731.1, NM_001302803.1 and NP_001289732.1, NM_001302804.1 and NP_001289733.1, and NM_008575.4 and NP_032601.2), rat MDM4 (NM_001012026.1 and NP_001012026.1), chicken MDM4 (XM_417957.6 and XP_417957.3, XM_015299095.2 and XP_015154581.1, XM_004934926.3 and XP_004934983.1, XM_004934924.3 and XP_004934981.1, XM_004934925.2 and XP_004934982.2, and XM_015299096.2 and XP_015154582.1), tropical clawed frog MDM4 (NM_001142245.1 and NP_001135717.1), and zebrafish MDM4 (NM_001328581.1 and NP_001315510.1, and NM_212732.2 and NP_997897.2). Representative sequences of MDM4 orthologs are presented below in Table 1.

Anti-MDM4 antibodies suitable for detecting MDM4 protein are well-known in the art and include, for example, antibodies CF505750 and TA505750 (Origene), antibodies NB100-556 and NBP1-28862 (Novus Biologicals, Littleton, CO), antibodies ab49993 and ab 16058 (AbCam, Cambridge, MA), antibody MA5-26198 (ThermoFisher Scientific), antibody 57-314 (ProSci), etc. In addition, reagents are well-known for detecting MDM4. Multiple clinical tests of MDM4 are available in NIH Genetic Testing Registry (GTR®) (e.g., GTR Test ID: GTR000540743.2, offered by Fulgent Clinical Diagnostics Lab (Temple City, CA)). Moreover, mutilple siRNA, shRNA, CRISPR constructs for reducing MDM4 expression can be found in the commercial product lists of the above-referenced companies, such as siRNA products #sc-37448 and sc-37449, and CRISPR product #sc-417855 from Santa Cruz Biotechnology, RNAi products SR302850 and TL311528V, and CRISPR product KN209620 (Origene), and multiple CRISPR products from GenScript (Piscataway, NJ). Chemical inhibitors of MDM4 are also available, including, e.g., NSC207895 (Millipore Sigma), SAH-p53-8, SJ-172550, CTX-1, XI-006, XI-011, ALRN-6924, and ATSP-7041 (Ac-Leu17-Thr-Phe-cyclo (R8-Glu-Tyr-Trp-Ala-Gln-Cba-S5)-Ser-Ala-Ala30-NH2 (SEQ ID NO: 124); Chang et al., (2013) Proc Natl Acad Sci USA, 110: E3445-E3454). It is to be noted that the term can further be used to refer to any combination of features described herein regarding MDM4 molecules. For example, any combination of sequence composition, percentage identify, sequence length, domain structure, functional activity, etc. can be used to describe a MDM4 molecule encompassed by the present invention.

The term "LIG4" refers to DNA Ligase 4, a DNA ligase that joins single-strand breaks in a double-stranded polydeoxynucleotide in an ATP-dependent reaction. LIG4 protein is essential for V (D) J recombination and DNA double-strand break (DSB) repair through nonhomologous end joining (NHEJ). LIG4 protein forms a complex with the X-ray repair cross complementing protein 4 (XRCC4), and further interacts with the DNA-dependent protein kinase (DNA-PK). Both XRCC4 and DNA-PK are known to be required for NHEJ. The crystal structure of the complex formed by LIG4 protein and XRCC4 has been resolved. Defects in LIG4 are the cause of LIG4 syndrome. LIG4 efficiently joins single-strand breaks in a double-stranded polydeoxynucleotide in an ATP-dependent reaction. LIG4 is involved in DNA non-homologous end joining (NHEJ) required for double-strand break repair and V (D) J recombination. The LIG4-XRCC4 complex is responsible for the NHEJ ligation step, and XRCC4 enhances the joining activity of LIG4. Binding of the LIG4-XRCC4 complex to DNA ends is dependent on the assembly of the DNA-dependent protein kinase complex DNA-PK to these DNA ends. In some embodiments, human LIG4 protein has 911 amino acids and a molecular mass of 103971 Da. The known binding partners of LIG4 include, e.g., XRCC4 and APLF.

The term "LIG4" is intended to include fragments, variants (e.g., allelic variants), and derivatives thereof. Representative human LIG4 cDNA and human LIG4 protein sequences are well-known in the art and are publicly available from the National Center for Biotechnology Information (NCBI). For example, at least three different human LIG4 isoforms are known. Human LIG4 isoform 1 (NP_002303.2, NP_996820.1, NP_001091738.1, NP_001339527.1, NP_001339528.1, NP_001339529.1, NP_001339530.1, NP_001339531.1, NP_001339532.1) is encodable by the transcript variant 1 (NM_002312.3), the transcript variant 2 (NM_206937.1), the transcript variant 3 (NM_001098268.1), the transcript variant 5 (NM_001352598.1), the transcript variant 6 (NM_001352599.1), the transcript variant 7 (NM_001352600.1), the transcript variant 8 (NM_001352601.1), the transcirpt variant 9 (NM_001352602.1), the transcirpt variant 10 (NM_001352603.1). Human LIG4 isoform 2 (NP_001317524.1) is encodable by the transcript variant 4 (NM_001330595.1). Human LIG4 isoform 3 (NP_001339533.1) is encodable by the transcript variant 11 (NM_001352604.1). Nucleic acid and polypeptide sequences of LIG4 orthologs in organisms other than humans are well known and include, for example, dog LIG4 (XM_022408151.1 and XP_022263859.1, XM_022408150.1 and XP_022263858.1, XM_005634097.3 and XP_005634154.1, XM_542663.5 and XP_542663.2, and XM_005634098.3 and XP_005634155.1), cattle LIG4 (NM_001191126.1 and NP_001178055.1), mouse LIG4 (NM_176953.3 and NP_795927.2), rat LIG4 (NM_001106095.1 and NP_001099565.1), chicken LIG4 (NM_001030816.1 and NP_001025987.1), tropical clawed frog LIG4 (NM_001016981.2 and NP_001016981.1), and zebrafish LIG4 (NM_001103123.1 and NP_001096593.1). Representative sequences of LIG4 orthologs are presented below in Table 1.

Anti-LIG4 antibodies suitable for detecting LIG4 protein are well-known in the art and include, for example, antibodies TA334753 and TA323263 (Origene), antibodies NBP2-16182 and NBP1-87405 (Novus Biologicals, Littleton, CO), antibodies ab26039 and ab 193353 (AbCam, Cambridge, MA), antibody PA5-51562 (ThermoFisher Scientific), antibody TX108820 (GeneTex), etc. In addition, reagents are well-known for detecting LIG4. Multiple clinical tests of LIG4 are available in NIH Genetic Testing Registry (GTR®) (e.g., GTR Test ID: GTR000518133.2, offered by Fulgent Clinical Diagnostics Lab (Temple City, CA)). Moreover, mutilple siRNA, shRNA, CRISPR constructs for reducing LIG4 expression can be found in the commercial product lists of the above-referenced companies, such as siRNA products #sc-37394 and sc-72113, and CRISPR product #sc-401372 from Santa Cruz Biotechnology, RNAi products SR302689 and TL303530V, and CRISPR product KN206295 (Origene), and multiple CRISPR products from GenScript (Piscataway, NJ). Chemical inhibitors of LIG4 are also available, including, e.g., L189 (Tocris Bioscience, MN). It is to be noted that the term can further be used to refer to any combination of features described herein regarding LIG4 molecules. For example, any combination of sequence composition, percentage identify, sequence length, domain structure, functional activity, etc. can be used to describe a LIG4 molecule encompassed by the present invention.

The term "PUM3" refers to *Pumilio* RNA Binding Family Member 3. PUM3 inhibits the poly(ADP-ribosyl) ation activity of PARP1 and the degradation of PARPI by CASP3 following genotoxic stress (Chang et al., (2011) Cancer Res 71:1126-1134). PUM3 binds to double-stranded RNA or DNA without sequence specificity (Qiu et al., (2014) Proc Natl Acad Sci USA 111:18554-18559). PUM3 is involved in development of the eye and of primordial germ cells. Diseases associated with PUM3 include teeth hard tissue disease. In some embodiments, human PUM3 protein has 648 amino acids and/or a molecular mass of 73584 Da. The known binding partners of PUM3 include, e.g., PARP1.

The term "PUM3" is intended to include fragments, variants (e.g., allelic variants), and derivatives thereof. Representative human PUM3 cDNA and human PUM3 protein sequences are well-known in the art and are publicly available from the National Center for Biotechnology Information (NCBI). For example, at least one human PUM3 isoform is known. Human PUM3 (NP_055693.4) is encodable by the transcript (NM_014878.4). Nucleic acid and polypeptide sequences of PUM3 orthologs in organisms other than humans are well known and include, for example, chimpanzee PUM3 (XM_009456263.2 and XP_009454538.1), monkey PUM3 (XM_015117807.1 and XP_014973293.1, XM_015117806.1 and XP_014973292.1), dog PUM3 (XM_533539.5 and XP_533539.4), cattle PUM3 (NM_001098030.1 and NP_001091499.1), mouse PUM3 (NM_177474.5 and NP_803425.1), chicken PUM3 (NM_001031437.1 and NP_001026608.1), tropical clawed frog PUM3 (NM_001122795.1 and NP_001116267.1), and zebrafish PUM3 (NM_001353848.1 and NP_001340777.1). Representative sequences of PUM3 orthologs are presented below in Table 1.

Anti-PUM3 antibodies suitable for detecting PUM3 protein are well-known in the art and include, for example, antibodies TA339320 and TA345757 (Origene), antibodies NBP1-57531 and H00009933-B01 (Novus Biologicals, Littleton, CO), antibodies ab156692 and ab228003 (AbCam, Cambridge, MA), etc. In addition, reagents are well-known for detecting PUM3. Multiple clinical tests of PUM3 are available in NIH Genetic Testing Registry (GTR®) (e.g., GTR Test ID: GTR000548219.2, offered by Fulgent Clinical Diagnostics Lab (Temple City, CA)). Moreover, mutilple siRNA, shRNA, CRISPR constructs for reducing PUM3 expression can be found in the commercial product lists of the above-referenced companies, such as RNAi products SR306674 and TL316891V, and CRISPR product KN201875 (Origene), and multiple CRISPR products from GenScript (Piscataway, NJ). It is to be noted that the term can further be used to refer to any combination of features described herein regarding PUM3 molecules. For example, any combination of sequence composition, percentage identify, sequence length, domain structure, functional activity, etc. can be used to describe a PUM3 molecule encompassed by the present invention.

The term "UBE2D3" refers to Ubiquitin Conjugating Enzyme E2 D3, which is a member of the E2 ubiquitin-conjugating enzyme family. UBE2D3 functions in the ubiquitination of the tumor-suppressor protein p53, which is induced by an E3 ubiquitin-protein ligase. UBE2D3 accepts ubiquitin from the E1 complex and catalyzes its covalent attachment to other proteins. UBE2D3 in vitro catalyzes Lys-11-, as well as Lys-48-linked polyubiquitination. UBE2D3 cooperates with the E2 CDC34 and the SCF (FBXW11) E3 ligase complex for the polyubiquitination of NFKBIA leading to its subsequent proteasomal degradation. UBE2D3 acts as an initiator E2, priming the phosphorylated NFKBIA target at positions Lys-21 and/or Lys-22 with a monoubiquitin. Ubiquitin chain elongation is then performed by CDC34, building ubiquitin chains from the UBE2D3-primed NFKBIA-linked ubiquitin. UBE2D3 acts also as an initiator E2, in conjunction with RNF8, for the priming of PCNA. UBE2D3 induces monoubiquitination of PCNA, and its subsequent polyubiquitination, which are essential events in the operation of the DNA damage tolerance (DDT) pathway that is activated after DNA damage caused by UV or chemical agents during S-phase. UBE2D3 associates with the BRCA1/BARD1 E3 ligase complex to perform ubiquitination at DNA damage sites following ionizing radiation leading to DNA repair. UBE2D3 also targets DAPK3 for ubiquitination, which influences promyelocytic leukemia protein nuclear body (PML-NB) formation in the nucleus. In conjunction with the MDM2 and TOPORS E3 ligases, UBE2D3 induces ubiquitination of p53/TP53. UBE2D3 supports NRDP1-mediated ubiquitination and degradation of ERBB3 and of BRUCE, which triggers apoptosis. In conjunction with the CBL E3 ligase, UBE2D3 targets EGFR for polyubiquitination at the plasma membrane as well as during its internalization and transport on endosomes. In conjunction with the STUB1 E3 quality control E3 ligase, UBE2D3 ubiquitinates unfolded proteins to catalyze their immediate destruction. In some embodiments, human UBE2D3 protein has 147 amino acids and/or a molecular mass of 16687 Da. The known binding partners of UBE2D3 include, e.g., SCF, BRCA1, DAPK3, CBLC, and UBTD1.

The term "UBE2D3" is intended to include fragments, variants (e.g., allelic variants), and derivatives thereof. Representative human UBE2D3 cDNA and human UBE2D3 protein sequences are well-known in the art and are publicly available from the National Center for Biotechnology Information (NCBI). For example, at least four different human UBE2D3 isoforms are known. Human UBE2D3 isoform 1 (NP_003331.1, NP_871615.1, NP_871616.1, NP_871617.1, NP_871618.1, NP_871619.1, NP_871620.1) is encodable by the transcript variant 1 (NM_003340.6), the transcript variant 2 (NM_181886.3), the transcript variant 3 (NM_181887.2), the transcript variant 4 (NM_181888.3), the transcript variant 5 (NM_181889.2), the transcript variant 6 (NM_181890.2), and the transcript variant 7 (NM_181891.2). Human UBE2D3 isoform 2 (NP_871621.1) is encodable by the transcript variant 8 (NM_181892.3). Human UBE2D3 isoform 3 (NP_871622.1) is encodable by the transcript variant 9 (NM_181893.2). Human UBE2D3 isoform 4 (NP_001287724.1) is encodable by the transcript variant 10 (NM_001300795.1). Nucleic acid and polypeptide sequences of UBE2D3 orthologs in organisms other than humans are well known and include, for example, monkey UBE2D3 (NM_001261204.1 and NP_001248133.1), dog UBE2D3 (XM_005642458.3 and XP_005642515.1), cattle UBE2D3 (NM_001075135.1 and NP_001068603.1), mouse UBE2D3 (NM_001356594.1 and NP_001343523.1, NM_001356595.1 and NP_001343524.1, NM_001356596.1 and NP_001343525.1, NM_001356597.1 and NP_001343526.1, NM_001356598.1 and NP_001343527.1, and NM_025356.5 and NP_079632.1), rat UBE2D3 (NM_031237.1 and NP_112516.1), chicken UBE2D3 (NM_001031153.1 and NP_001026324.1), and zebrafish UBE2D3 (NM_199571.1 and NP_955865.1). Representative sequences of UBE2D3 orthologs are presented below in Table 1.

Anti-UBE2D3 antibodies suitable for detecting UBE2D3 protein are well-known in the art and include, for example, antibody AP54438PU-N(Origene), antibodies NBP1-55276 and H00007323-M01 (Novus Biologicals, Littleton, CO), antibodies ab 176568 and ab 106315 (AbCam, Cambridge, MA), antibody PA5-42280 (ThermoFisher Scientific), antibodies 25-815 and 58-731 (ProSci), etc. In addition, reagents are well-known for detecting UBE2D3. Multiple clinical tests of UBE2D3 are available in NIH Genetic Testing Registry (GTR®) (e.g., GTR Test ID: GTR000544717.2, offered by Fulgent Clinical Diagnostics Lab (Temple City, CA)). Moreover, mutilple siRNA, shRNA, CRISPR constructs for reducing UBE2D3 expression can be found in the commercial product lists of the above-referenced companies, such as siRNA products #sc-41681 and sc-41682, and CRISPR product #sc-405029 from Santa Cruz Biotechnology, RNAi products SR3304999 and TL300702V, and CRISPR product KN207371 (Origene), and multiple CRISPR products from GenScript (Piscataway, NJ). It is to be noted that the term can further be used to refer to any combination of features described herein regarding UBE2D3 molecules. For example, any combination of sequence composition, percentage identify, sequence length, domain structure, functional activity, etc. can be used to describe a UBE2D3 molecule encompassed by the present invention.

The term "PPM1D" or "Wip1" refers to protein phosphatase, Mg2+/Mn2+ dependent 1D, a member of the PP2C family of Ser/Thr protein phosphatases. PP2C family members are known to be negative regulators of cell stress response pathways. The expression of PPM1D is induced in a p53-dependent manner in response to various environmental stresses. While being induced by tumor suppressor protein TP53/p53, this phosphatase negatively regulates the activity of p38 MAP kinase, MAPK/p38, through which it reduces the phosphorylation of p53, and in turn suppresses p53-mediated transcription and apoptosis. This phosphatase thus mediates a feedback regulation of p38-p53 signaling that contributes to growth inhibition and the suppression of stress induced apoptosis. PPM1D is located in a chromosomal region known to be amplified in breast cancer. The amplification of PPM1D has been detected in both breast cancer cell line and primary breast tumors, which suggests a role of this gene in cancer development. PPM1D is required for the relief of p53-dependent checkpoint mediated cell cycle arrest. PPM1D binds to and dephosphorylates Ser-15 of TP53 and Ser-345 of CHEKI which contributes to the functional inactivation of these proteins. PPM1D mediates MAPK14 dephosphorylation and inactivation (An et al., (2011) *Plos One* 6: e16427). In some embodiments, human PPM1D protein has 605 amino acids and/or a molecular mass of 66675 Da. The known binding partners of PPM1D include, e.g., CHEKI, CHEK2, and MAPK14.

The term "PPM1D" is intended to include fragments, variants (e.g., allelic variants), and derivatives thereof. Representative human PPM1D cDNA and human PPM1D protein sequences are well-known in the art and are publicly available from the National Center for Biotechnology Information (NCBI). For example, at least one human PPM1D isoform is known. Human PPM1D (NP_003611.1) is encodable by the transcript variant 1 (NM_003620.3). Nucleic acid and polypeptide sequences of PPM1D orthologs in organisms other than humans are well known and include, for example, chimpanzee PPM1D (NM_001246550.1 and NP_001233479.1), monkey PPM1D (NM_001260836.2 and NP_001247765.1), dog PPM1D (XM_022423258.1 and XP_022278966.1, and XM_847666.5 and XP_852759.2), cattle PPM1D (NM_001191444.2 and NP_001178373.1), mouse PPM1D (NM_016910.3 and NP_058606.3), rat PPM1D (NM_001105825.2 and NP_001099295.2), chicken PPM1D (XM_415890.5 and XP_415890.4), tropical clawed frog PPM1D (XM_002933837.4 and XP_002933883.2), and zebrafish PPM1D (NM_001007340.1 and NP_001007341.1, and NM_201090.2 and NP_957384.2). Representative sequences of PPM1D orthologs are presented below in Table 1.

Anti-PPM1D antibodies suitable for detecting PPM1D protein are well-known in the art and include, for example, antibodies TA811187 and TA811157 (Origene), antibodies NBP1-87249 and 28930002 (Novus Biologicals, Littleton, CO), antibodies ab31270 and ab236515 (AbCam, Cambridge, MA), antibody PA5-72839 (ThermoFisher Scientific), antibody 8043 (ProSci), etc. In addition, reagents are well-known for detecting PPM1D. Multiple clinical tests of PPM1D are available in NIH Genetic Testing Registry (GTR®) (e.g., GTR Test ID: GTR000518437.2, offered by Fulgent Clinical Diagnostics Lab (Temple City, CA)). Moreover, mutilple siRNA, shRNA, CRISPR constructs for reducing PPM1D expression can be found in the commercial product lists of the above-referenced companies, such as siRNA products #sc-39205 and sc-39206, and CRISPR product #sc-400980 from Santa Cruz Biotechnology, RNAi products SR305566 and TL310245V, and CRISPR product KN209328 (Origene), and multiple CRISPR products from GenScript (Piscataway, NJ). Chemical inhibitors of PPM1D are also available, including, e.g., GSK2830371 ($C_{23}H_{29}ClN_4O_2S$, chemical name: 5-[[(5-Chloro-2-methyl-3-pyridinyl)amino]methyl]-N-[(1S)-1-(cyclopentylmethyl)-2-(cycloprpylamino)-2-oxoethyl]-2-thiophenecarboxamide; TOCRIS cat #: 5140). It is to be noted that the term can further be used to refer to any combination of features described herein regarding PPM1D molecules. For example, any combination of sequence composition, percentage identify, sequence length, domain structure, functional activity, etc. can be used to describe a PPM1D molecule encompassed by the present invention.

The term "PPM1G" refers to Protein Phosphatase, Mg2+/Mn2+ Dependent 1G, a member of the PP2C family of Ser/Thr protein phosphatases. PP2C family members are known to be negative regulators of cell stress response pathways. This phosphatase is found to be responsible for the dephosphorylation of Pre-mRNA splicing factors, which is important for the formation of functional spliceosome. Studies of a similar gene in mice suggested a role of this phosphatase in regulating cell cycle progression. Among its related pathways are mRNA splicing major pathway and development dopamine D2 receptor transactivation of EGFR. In some embodiments, human PPM1G protein has 546 amino acids and/or a molecular mass of 59272 Da. The known binding partners of PPM1G include, e.g., NOL3.

The term "PPM1G" is intended to include fragments, variants (e.g., allelic variants), and derivatives thereof. Representative human PPM1G cDNA and human PPM1G protein sequences are well-known in the art and are publicly available from the National Center for Biotechnology Information (NCBI). For example, at least one human PPM1G isoform is known. Human PPM1G (NP_817092.1) is encodable by the transcript variant 1 (NM_177983.2). Nucleic acid and polypeptide sequences of PPM1G orthologs in organisms other than humans are well known and include, for example, chimpanzee PPM1G (NM_001246455.1 and NP_001233384.1), monkey PPM1G (NM_001257613.2 and NP_001244542.1), dog PPM1G (XM_532910.6 and XP_532910.2, and XM_005630263.2 and XP_005630320.1), cattle PPM1G (NM_174801.4 and NP_777226.2), mouse PPM1G (NM_008014.3 and NP_032040.1), rat PPM1G (NM_147209.2 and NP_671742.1), chicken PPM1G (XM_003641050.4 and XP_003641098.1), tropical clawed frog PPM1G (NM_001015840.1 and NP_001015840.1), and zebrafish PPM1G (NM_201488.1 and NP_958896.1). Representative sequences of PPM1G orthologs are presented below in Table 1.

Anti-PPM1G antibodies suitable for detecting PPM1G protein are well-known in the art and include, for example, antibodies AM09028PU-N and AM09028PU-S(Origene), antibodies NBP1-87246 and NBP1-87245 (Novus Biologicals, Littleton, CO), antibodies ab186423 and ab70794 (AbCam, Cambridge, MA), antibody PA5-57308 (ThermoFisher Scientific), antibody 48-080 (ProSci), etc. In addition, reagents are well-known for detecting PPM1G. Multiple clinical tests of PPM1G are available in NIH Genetic Testing Registry (GTR®) (e.g., GTR Test ID: GTR000543617.2, offered by Fulgent Clinical Diagnostics Lab (Temple City, CA)). Moreover, mutilple siRNA, shRNA, CRISPR constructs for reducing PPM1G expression can be found in the commercial product lists of the above-referenced companies, such as siRNA products #sc-61388 and sc-61390, and CRISPR product #sc-404206 from Santa Cruz Biotechnology, RNAi products SR303669 and TL310243V, and CRISPR product KN200439 (Origene), and multiple CRISPR products from GenScript (Piscataway, NJ). It is to be noted that the term can further be used to refer to any combination of features described herein regarding PPM1G molecules. For example, any combination of sequence composition, percentage identify, sequence length, domain structure, functional activity, etc. can be used to describe a PPM1G molecule encompassed by the present invention.

USP7/HAUSP (herpes virus-associated USP) is well known in the art (Reverdy et al. (2012) *Chem. Biol.* 19:567-477) as a 135 kDa protein in the USP family of DUB enzymes. In addition to a DUB domain, USP7 also contains an N-terminal TRAF-like MATH domain (Zapata et al. (2001) *J. Biol. Chem.* 276:24242-24252) and a C-terminal domain that contains at least five ubiquitin-like domains (Faesen et al. (2011) *Mol. Cell* 44:147-159). This protein is produced ubiquitously and is highly conserved in eukaryotes (see, for example, human USP7 nucleic acid and protein sequences well-known in the art and publicly available under accession numbers NM_001286457.1 and NP_001273386.1; NM_001286458.1 and NP_001273387.1; NM_001321858.1 and NP_001308787.1; and NM_003470.2 and NP_003461.2). Nucleic acid and polypeptide sequences of USP7 orthologs in organisms other than humans are well known and include, for example, chimpanzee USP7 (XM_024349753.1 and XP_024205521.1, XM_016929384.2 and XP_016784873.1, XM_016929385.2 and XP_016784874.1, and XM_016929388.2 and XP_016784877.1), monkey USP7 (XM_015125591.1 and XP_014981077.1, XM_002802389.2 and XP_002802435.1, XM_002802388.2 and XP_002802434.1, and XM_015125592.1 and XP_014981078.1), dog USP7 (XM_005621558.3 and XP_005621615.1, and XM_005621559.3 and XP_005621616.1), cattle USP7 (XM_024985414.1 and XP_024841182.1, and XM_005224667.4 and XP_005224724.1), mouse USP7 (NM_001003918.2 and NP_001003918.2), rat USP7 (NM_001024790.1 and NP_001019961.1), chicken USP7 (NM_001348012.1 and NP_001334941.1, and NM_204471.2 and NP_989802.2), tropical clawed frog USP7 (XM_012970920.2 and XP_012826374.1, and XM_002939449.4 and XP_002939495.2), and zebrafish USP7 (XM_005163957.3 and XP_005164014.1, and XM_686123.9 and XP_691215.4). Representative sequences of USP7 orthologs are presented below in Table 1.

USP7 is primarily a nuclear protein and localizes to a subset of PML bodies (Everett et al. (1999) *J. Virol.* 73:417-426; Muratani et al. (2002) *Nat. Cell Biol.* 4:106-110). At the molecular level, by virtue of its deubiquitinating activity, USP7 has been shown to regulate the steady-state level of several poly-ubiquitinated substrates. For example, USP7 alters the level of the p53 and p16INK4a tumor suppressors through LIG4 stabilization and Bmil/Mel18 stabilization, respectively (Cummins et al. (2004) Nature 428; Li et al. (2004) *Mol. Cell* 13:8790-896; Maertens et al. (2010) *EMBO J.* 29:2553-2565). USP7 binding to p53 was recently shown to be regulated by TSPYL5, a protein potentially involved in breast oncogenesis through its competition with p53 for binding to the same region of USP7 (Epping et al. (2011) *Nat. Cell Biol.* 13:102-108). Additional proteins involved in genomic integrity and regulation, such as the DNMT1 DNA methylase and the claspin adaptor, are also stabilized by USP7 (Du et al. (2010) *Sci. Signal.* 3: ra80; Faustrup et al. (2009) *J. Cell Biol.* 184:13-19). USP7 has also been shown to regulate the cellular compartmentalization of several mono-ubiquitinated substrates by deubiquitination. In this respect, the PTEN and FOXO4 tumor suppressors are inactivated by USP7-induced nuclear export (Song et al. (2008) *Nature* 455:813-817; van der Horst et al. (2006) *Nat. Cell Biol.* 8:1064-1073). USP7 overexpression has also been reported in human prostate cancer and was directly associated with tumor aggressiveness (Song et al. (2008) *Nature* 455:813-817). Previous in vivo data also underlined the involvement of USP7 in cancer cell proliferation (Becker et al. (2008) *Cell Cycle* 7:7-10).

Anti-USP7 antibodies suitable for detecting USP7 protein are well-known in the art and include, for example, antibodies CF504064 and TA504064 (Origene), antibodies NB100-513 and NBP2-24641 (Novus Biologicals, Littleton, CO), antibodies ab4080 and ab 108931 (AbCam, Cambridge, MA), antibody 712032 (ThermoFisher Scientific), antibody 58-667 (ProSci), etc. In addition, reagents are well-known for detecting USP7. Multiple clinical tests of USP7 are available in NIH Genetic Testing Registry (GTR®) (e.g., GTR Test ID: GTR000544219.2, offered by Fulgent Clinical Diagnostics Lab (Temple City, CA)). Moreover, mutilple siRNA, shRNA, CRISPR constructs for reducing USP7 expression can be found in the commercial product lists of the above-referenced companies, such as siRNA products #sc-41521 and sc-77373, and CRISPR product #sc-402013-KO-2 from Santa Cruz Biotechnology, RNAi products SR305301 and TL308454V, and CRISPR product KN213986 (Origene), and multiple CRISPR products from GenScript (Piscataway, NJ). USP7-selective agents are known (see, for example, XL-188 ($C_{32}H_{42}N_6O_4$, chemical name: (R)—N-(3-((4-hydroxy-1-(3-phenylbutanoyl) piperidin-4-yl)methyl)-4-oxo-3,4-dihydroquinazolin-7-yl)-3-(4-methylpiperazin-1-yl) propanamide;

ProbeChem) and other exemplary agents listed in Table 3, D'Arcy et al. (2015) *Pharmacol. Ther.* 147:32-54, and others described herein).

The term "TP53" refers to Tumor Protein P53, a tumor suppressor protein containing transcriptional activation, DNA binding, and oligomerization domains. The encoded protein responds to diverse cellular stresses to regulate expression of target genes, thereby inducing cell cycle arrest, apoptosis, senescence, DNA repair, or changes in metabolism. Mutations in this gene are associated with a variety of human cancers, including hereditary cancers such as Li-Fraumeni syndrome. TP53 mutations are universal across cancer types. The loss of a tumor suppressor is most often through large deleterious events, such as frameshift mutations, or premature stop codons. In TP53 however, many of the observed mutations in cancer are found to be single nucleotide missense variants. These variants are broadly distributed throughout the gene, but with the majority localizing in the DNA binding domain. There is no single hotspot in the DNA binding domain, but a majority of mutations occur in amino acid positions 175, 245, 248, 273, and 282 (NM_000546). While a large proportion of cancer genomics research is focused on somatic variants, TP53 is also of note in the germline. Germline TP53 mutations are the hallmark of Li-Fraumeni syndrome, and many (both germline and somatic) variants have been found to have a prognostic impact on patient outcomes. TP53 acts as a tumor suppressor in many tumor types by inducing growth arrest or apoptosis depending on the physiological circumstances and cell type. TP53 is involved in cell cycle regulation as a trans-activator that acts to negatively regulate cell division by controlling a set of genes required for this process. One of the activated genes is an inhibitor of cyclin-dependent kinases. Apoptosis induction seems to be mediated either by stimulation of BAX and FAS antigen expression, or by repression of Bcl-2 expression. In cooperation with mitochondrial PPIF, TP53 is involved in activating oxidative stress-induced necrosis, and the function is largely independent of transcription. TP53 induces the transcription of long intergenic non-coding RNA p21 (lincRNA-p21) and lincRNA-Mkln1. LincRNA-p21 participates in TP53-dependent transcriptional repression leading to apoptosis and seem to have to effect on cell-cycle regulation. TP53 is implicated in Notch signaling cross-over. TP53 prevents CDK7 kinase activity when associated to CAK complex in response to DNA damage, thus stopping cell cycle progression. Isoform 2 of TP53 enhances the transactivation activity of isoform 1 from some but not all TP53-inducible promoters. Isoform 4 of TP53 suppresses transactivation activity and impairs growth suppression mediated by isoform 1. Isoform 7 of TP53 inhibits isoform 1-mediated apoptosis. TP53 regulates the circadian clock by repressing CLOCK-ARNTL/BMAL1-mediated transcriptional activation of PER2 (Miki et al., (2013) *Nat Commun* 4:2444). In some embodiments, human TP53 protein has 393 amino acids and a molecular mass of 43653 Da. The known binding partners of TP53 include, e.g., AXIN1, ING4, YWHAZ, HIPK1, HIPK2, WWOX, GRK5, ANKRD2, RFFL, RNF 34, and TP53INP1.

The term "TP53" is intended to include fragments, variants (e.g., allelic variants), and derivatives thereof. Representative human TP53 cDNA and human TP53 protein sequences are well-known in the art and are publicly available from the National Center for Biotechnology Information (NCBI). For example, at least 12 different human TP53 isoforms are known. Human TP53 isoform a (NP_000537.3, NP_001119584.1) is encodable by the transcript variant 1 (NM_000546.5) and the trancript vairant 2 (NM_001126112.2). Human TP53 isoform b (NP_001119586.1) is encodable by the transcript variant 3 (NM_001126114.2). Human TP53 isoform c (NP_001119585.1) is encodable by the transcript variant 4 (NM_001126113.2). Human TP53 isoform d (NP_001119587.1) is encodable by the transcript variant 5 (NM_001126115.1). Human TP53 isoform e (NP_001119588.1) is encodable by the transcript variant 6 (NM_001126116.1). Human TP53 isoform f (NP_001119589.1) is encodable by the transcript variant 7 (NM_001126117.1). Human TP53 isoform g (NP_001119590.1, NP_001263689.1, and NP_001263690.1) is encodable by the transcript variant 8 (NM_001126118.1), the transcript variant 1 (NM_001276760.1), and the transcript variant 2 (NM_001276761.1). Human TP53 isoform h (NP_001263624.1) is encodable by the transcript variant 4 (NM_001276695.1). Human TP53 isoform i (NP_001263625.1) is encodable by the transcript variant 3 (NM_001276696.1). Human TP53 isoform j (NP_001263626.1) is encodable by the transcript variant 5 (NM_001276697.1). Human TP53 isoform k (NP_001263627.1) is encodable by the transcript variant 6 (NM_001276698.1). Human TP53 isoform 1 (NP_001263628.1) is encodable by the transcript variant 7 (NM_001276699.1). Nucleic acid and polypeptide sequences of TP53 orthologs in organisms other than humans are well known and include, for example, chimpanzee TP53 (XM_001172077.5 and XP_001172077.2, and XM_016931470.2 and XP_016786959.2), monkey TP53 (NM_001047151.2 and NP_001040616.1), dog TP53 (NM_001003210.1 and NP_001003210.1), cattle TP53 (NM_174201.2 and NP_776626.1), mouse TP53 (NM_001127233.1 and NP_001120705.1, and NM_011640.3 and NP_035770.2), rat TP53 (NM_030989.3 and NP_112251.2), tropical clawed frog TP53 (NM_001001903.1 and NP_001001903.1), and zebrafish TP53 (NM_001271820.1 and NP_001258749.1, NM_001328587.1 and NP_001315516.1, NM_001328588.1 and NP_001315517.1, and NM_131327.2 and NP_571402.1). Representative sequences of TP53 orthologs are presented below in Table 2.

Anti-TP53 antibodies suitable for detecting TP53 protein are well-known in the art and include, for example, antibodies TA502925 and CF502924 (Origene), antibodies NB200-103 and NB200-171 (Novus Biologicals, Littleton, CO), antibodies ab26 and ab1101 (AbCam, Cambridge, MA), antibody 700439 (ThermoFisher Scientific), antibody 33-856 (ProSci), etc. In addition, reagents are well-known for detecting TP53. Multiple clinical tests of TP53 are available in NIH Genetic Testing Registry (GTR®) (e.g., GTR Test ID: GTR000517320.2, offered by Fulgent Clinical Diagnostics Lab (Temple City, CA)). Moreover, mutilple siRNA, shRNA, CRISPR constructs for reducing TP53 expression can be found in the commercial product lists of the above-referenced companies, such as siRNA products #sc-29435 and sc-44218, and CRISPR product #sc-416469 from Santa Cruz Biotechnology, RNAi products SR322075 and TL320558V, and CRISPR product KN200003 (Origene), and multiple CRISPR products from GenScript (Piscataway, NJ). Chemical inhibitors of TP53 are also available, including, e.g., Cyclic Pifithrin-a hydrobromide, RITA (TOCRIS, MN). It is to be noted that the term can further be used to refer to any combination of features described herein regarding TP53 molecules. For example, any combination of sequence composition, percentage identify, sequence length, domain structure, functional activity, etc. can be used to describe a TP53 molecule encompassed by the present invention.

The term "intact TP53" refers to a nucleic acid encoding a TP53 protein having a function of wildtype TP53, as well as the encoded protein thereof. While "wildtype TP53" refers to naturally occurring nucleic acid encoding a functional TP53 protein or the protein itself, intact TP53 can further encompass recombinantly designed nucleic acids that still encode a protein having a tumor suppressor function of wildtype TP53. The term also includes the encoded protein. Generally, wildtype and intact TP53 encompass nucleic acids that lack a mutation that would disrupt tumor suppressor ability of the encoded protein, such as missense, nonsense, insertion, deletion, frameshift, repeat expansion, and/or other TP53 function disrupting mutations. Mutations disrupting TP53 tumor suppressor activity are well-known in the art and are compiled in various publicly available genetic sequence databases (see for example the IARC TP53 database available on the World Wide Web at p53.iarc.fr; Leroy et al. (2014) *Hum. Mutat.* 35:756-765; Bouaoun et al. (2016) *Hum. Mutat.* 37:865-876). In addition, assays for determining TP53 function, including tumor suppressor ability, are well-known in the art and include those performed and described in the Examples below.

The term "TP53-dependent cancer" refers to cancer that is functionally dependent on TP53. For instance, even if the expression level of TP53 (e.g., TP53 mRNA, TP53 protein, newly synthesized TP53 protein, etc.) in a tumor tissue is comparable to its expression level in normal tissue, a cancer is TP53-dependent if inhibition of the TP53 mRNA and/or protein, directly or indirectly, such as by using RNAi or any other means, or deletion of the TP53 gene (e.g., by knockout or clutsered regularly interspaced short palindromic repeates (CRISPR) technology) leads to inhibition of oncogenesis, tumor cell proliferation, tumor metastasis or induces tumor cell differentiation. Because TP53 is a tumor suppressor, TP53 that has an activity of wildtype TP53 need only be present in small amounts in some embodiments, such as expressed from a single allele and/or copy. The term "TP53-depdendent cancer" also refers to a cancer in which TP53 is expressed (e.g., TP53 mRNA, TP53 protein, newly synthesized TP53 protein, etc.) at a significantly higher level than the normal amount of TP53 expressed in a non-cancerous cell of the same cell type as the TP53-dependent cancer. A significantly higher amount of TP53 relative to the normal amount of TP53 is an amount greater than the standard error of the assay employed to assess amount, and preferably at least 5%, 10%, 20%, 30%, 40%, 50%, 60%, 70%, 80%, 90%, 100%, 150%, 200%, 300%, 350%, 400%, 500%, 600%, 700%, 800%, 900%, 1000% or more than the normal amount. Alternately, the amount of the biomarker in the subject can be considered "significantly" higher or lower than the normal amount if the amount is at least about two, and preferably at least about three, four, or five times, higher or lower, respectively, than the normal amount of TP53.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of oncogenes, such as c-MYC. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer.

In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In some embodiments, the cancer is Ewing's sarcoma (EWS). Ewing's sarcoma usually occurs in bone and the most common sites for the primary lesion are the pelvic bones, femur, humerus, and ribs. Ewing's sarcoma occurs less commonly at non-bone primary sites, a presentation that has historically been termed extraosseous Ewing's sarcoma. However, the morphological and biological characteristics of Ewing's tumors developing in soft tissues appear to be indistinguishable from those of tumors developing at bone sites. Delattre et al., 1994, New Engl. J. Med. 331:294-299; Llombart-Bosch et al., 1990, Cancer 66:2589-2601. Ewing's sarcoma is more common in males (1.6 male: 1 female) and usually presents in childhood or early adulthood, with a peak between 10 and 20 years of age. Most cases of Ewing's sarcoma are the result of a translocation between chromosomes 11 and 22, which fuses the EWSR1 gene of chromosome 22 to the FLI1 gene of chromosome 11 to generate the aberrant transcription factor EWS-FLI1. Other translocations are at t(21;22) and t(7;22).

The diagnosis of Ewing's sarcoma is based on histomorphologic findings, immunohistochemistry and molecular pathology. Ewing's sarcoma is a small-blue-round-cell tumor that typically has a clear cytoplasm on H&E staining, due to glycogen. The presence of the glycogen can be demonstrated with positive PAS staining and negative PAS diastase staining. The characteristic immunostain is CD99, which diffusely marks the cell membrane. Morphologic and immunohistochemical findings are corroborated with an associated chromosomal translocation.

Surgery of Ewing's sarcoma is usually limited to the initial diagnostic biopsy of the primary tumor. Patients usually underwent induction chemotherapy followed by radiation therapy for local control. The successful treatment of patients with Ewing's sarcoma requires the use of multidrug chemotherapy. Combination chemotherapy for Ewing's sarcoma has traditionally included vincristine, doxorubicin, cyclophosphamide, and dactinomycin (VAdriaC or VAC). The importance of doxorubicin has been demonstrated in randomized comparative trials with increased doxorubicin dose intensity during the early months of therapy resulting in improved event-free survival. See, e.g., Nesbit et al., 1990, J. Clin. Oncol. 8:1664-1674; Kinsella et al., 1991, Int. J. Radiat. Oncol. Biol. Phy. 20:389-395; Smith et al., 1991, J. Natl. Cancer Inst. 83:1460-1470.

The term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The terms "conjoint therapy" and "combination therapy," as used herein, refer to the administration of two or more therapeutic substances, e.g., combinations of agents that target different biomarkers, multiple agents that target the same biomarker, combination of anti-biomarker agents and additional anti-cancer agents like chemotherapy, and the like, and combinations thereof. The different agents comprising the combination therapy can be administered concomitant with, prior to, or following the administration of one or more therapeutic agents.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods encompassed by the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods encompassed by the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide anti-cancer therapy (e.g., therapy with at least one agent that inhibits at least one biomarker listed in Table 1). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "expression signature" or "signature" refers to a group of two or more coordinately expressed biomarkers. For example, the genes, proteins, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker encompassed by the present invention. The kit may be promoted, distributed, or sold as a unit for performing the methods encompassed by the present invention. The kit may comprise one or more reagents necessary to express a composition useful in the methods encompassed by the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression and/or activity of a biomarker is the level of expression and/or activity of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. The same determination can be made to determine overactivity or underactivity. Such "significance" levels can also be applied to any other measured parameter described herein, such as for expression, inhibition, cytotoxicity, cell growth, and the like.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to anti-cancer therapy, such as therapy with at least one agent that inhibits at least one biomarker listed in Table 1. Such predictive use of the biomarker may be confirmed by, e.g., (1) increased or decreased copy number (e.g., by FISH, FISH plus SKY, single-molecule sequencing, e.g., as described in the art at least at *J. Biotechnol.,* 86:289-301, or qPCR), overexpression or underexpression of a biomarker nucleic acid (e.g., by ISH, Northern Blot, or qPCR), increased or decreased biomarker protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular anti-cancer therapy (e.g., therapy with at least one agent that inhibits at least one biomarker listed in Table 1) or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The term "response to anti-cancer therapy" (e.g., therapy with at least one agent that inhibits at least one biomarker listed in Table 1) relates to any response of the hyperproliferative disorder (e.g., cancer) to an anti-cancer therapy, such as therapy with at least one agent that inhibits at least one biomarker listed in Table 1, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section. Thus, the terms "response" or "responsiveness" can refer to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene encompassed by the present invention, or a fragment thereof, short interfering RNA (siRNA), and small molecules which interfere with or inhibit expression of a target biomarker nucleic acid by RNA interference (RNAi).

"RNA interference (RNAi)" is an evolutionally conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76 (18): 9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method encompassed by the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., biomarker inhibitor, chemotherapeutic, and/or radiation therapy). In some embodiments, normal cells are not affected to an extent that causes the normal cells to be unduly injured by the anti-cancer therapy (e.g., therapy with at least one agent that inhibits at least one biomarker listed in Table 1). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42:2159-2164), cell death assays (Weisenthal L M, Shoemaker R H, Marsden J A, Dill P L, Baker J A, Moran E M, Cancer Res 1984; 94:161-173; Weisenthal L M, Lippman M E, Cancer Treat Rep 1985; 69:615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993:415-432; Weisenthal L M, Contrib Gynecol Obstet 1994; 19:82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA Apr.; 9 (4): 493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

The term "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "synergistic effect" refers to the combined effect of two or more agents, such as therapy with at least two agents that inhibit at least two biomarker slisted in Table 1, can be greater than the sum of the separate effects of the anticancer agents alone.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods encompassed by the present invention may be administered in a sufficient amount to produce a reasonable benefit/risk ratio applicable to such treatment.

The terms "therapeutically-effective amount" and "effective amount" as used herein means that amount of a compound, material, or composition comprising a compound encompassed by the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the LD50 and the ED50.

Compositions that exhibit large therapeutic indices are preferred. In some embodiments, the LD50 (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the ED50 (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |

-continued

| GENETIC CODE | |
|---|---|
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers encompassed by the present invention and related biomarkers (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below.

Representative sequences of the biomarkers described above are presented below in Table 1. It is to be noted that the terms described above can further be used to refer to any combination of features described herein regarding the biomarkers. For example, any combination of sequence composition, percentage identify, sequence length, domain structure, functional activity, etc. can be used to describe a biomarker encompassed by the present invention.

TABLE 1

```
MDM4
PPM1D/Wip1
MDM2
PPM1G
LIG4
PUM3
USP7
UBE2D3

SEQ ID NO: 1 Human MDM2 Transcript Variant 1 cDNA Sequence
(NM_002392.5; CDS: 307-1800)
   1 gtagggggcg cgcaccgagg caccgcggcg agcttggctg cttctggggc ctgtgtggcc
  61 ctgtgtgtcg gaaagatgga gcaagaagcc gagcccgagg ggcggccgcg acccctctga
 121 ccgagatcct gctgctttcg cagccaggag caccgtccct ccccggatta gtgcgtacga
 181 gcgcccagtg ccctggcccg gagagtggaa tgatccccga ggcccagggc gtcgtgcttc
 241 cgcgcgcccc gtgaaggaaa ctggggagtc ttgagggacc cccgactcca agcgcgaaaa
 301 ccccggatgg tgaggagcag gcaaatgtgc aataccaaca tgtctgtacc tactgatggt
 361 gctgtaacca cctcacagat tccagcttcg gaacaagaga ccctggttag accaaagcca
 421 ttgcttttga agttattaaa gtctgttggt gcacaaaaag acacttatac tatgaaagag
 481 gttctttttt atcttggcca gtatattatg actaaacgat tatatgatga gaagcaacaa
 541 catattgtat attgttcaaa tgatcttcta ggagatttgt ttggcgtgcc aagcttctct
 601 gtgaaagagc acaggaaaat atataccatg atctacagga acttggtagt agtcaatcag
 661 caggaatcat cggactcagg tacatctgtg agtgagaaca ggtgtcacct tgaaggtggg
 721 agtgatcaaa aggaccttgt acaagagctt caggaagaga aaccttcatc ttcacatttg
 781 gtttctagac catctacctc atctagaagg agagcaatta gtgagacaga agaaaattca
 841 gatgaattat ctggtgaacg acaaagaaaa cgccacaaat ctgatagtat ttccctttcc
 901 tttgatgaaa gcctggctct gtgtgtaata agggagatat gttgtgaaag aagcagtagc
 961 agtgaatcta cagggacgcc atcgaatccg gatcttgatg ctggtgtaag tgaacattca
1021 ggtgattggt tggatcagga ttcagtttca gatcagttta gtgtagaatt tgaagttgaa
1081 tctctcgact cagaagatta tagccttagt gaagaaggac aagaactctc agatgaagat
1141 gatgaggtat atcaagttac tgtgtatcag gcaggggaga gtgatacaga ttcatttgaa
1201 gaagatcctg aaatttcctt agctgactat tggaaatgca cttcatgcaa tgaaatgaat
1261 cccccccttc catcacattg caacagatgt tgggcccttc gtgagaattg gcttcctgaa
1321 gataaaggga aagataaagg ggaaatctct gagaaagcca aactggaaaa ctcaacacaa
1381 gctgaagagg gctttgatgt tcctgattgt aaaaaaacta tagtgaatga ttccagagag
1441 tcatgtgttg aggaaaatga tgataaaatt acacaagctt cacaatcaca agaaagtgaa
1501 gactattctc agccatcaac ttctagtagc attatttata gcagccaaga agatgtgaaa
1561 gagtttgaaa gggaagaaac ccaagacaaa gaagagagtg tggaatctag tttgcccctt
1621 aatgccattg aaccttgtgt gatttgtcaa ggtcgaccta aaaatggttg cattgtccat
1681 ggcaaaacag gacatcttat ggcctgcttt acatgtgcaa agaagctaaa gaaaaggaat
1741 aagccctgcc cagtatgtag acaaccaatt caaatgattg tgctaactta tttcccctag
```

TABLE 1-continued

| | | | | | | |
|---|---|---|---|---|---|---|
| 1801 | ttgacctgtc | tataagagaa | ttatatattt | ctaactatat | aaccctagga | atttagacaa |
| 1861 | cctgaaattt | attcacatat | atcaaagtga | gaaaatgcct | caattcacat | agatttcttc |
| 1921 | tctttagtat | aattgaccta | ctttggtagt | ggaatagtga | atacttacta | taatttgact |
| 1981 | tgaatatgta | gctcatcctt | tacaccaact | cctaatttta | aataatttct | actctgtctt |
| 2041 | aaatgagaag | tacttggttt | tttttttct | taaatatgta | tatgacattt | aaatgtaact |
| 2101 | tattattttt | tttgagaccg | agtcttgctc | tgttacccag | gctggagtgc | agtggcgtga |
| 2161 | tcttggctca | ctgcaagctc | tgcctcccgg | gttcgcacca | ttctcctgcc | tcagcctccc |
| 2221 | aattagcttg | gcctacagtc | atctgccacc | acacctggct | aatttttgt | acttttagta |
| 2281 | gagacagggt | ttcaccgtgt | tagccaggat | ggtctcgatc | tcctgacctc | gtgatccgcc |
| 2341 | cacctcggcc | tcccaaagtg | ctgggattac | aggcatgagc | caccgcgtcc | ggcctaaatg |
| 2401 | tcacttagta | cctttgatat | aaagagaaaa | tgtgtgaaag | atttagtttt | ttgtttttt |
| 2461 | gtttgtttgt | ttgtttgttt | gttttgagat | gagtctctct | gtcgcccagg | ctggagtgca |
| 2521 | gtgtcatgat | ctagcagtct | ccgcttcccg | ggttcaagcc | attctcctgg | ctcagcctct |
| 2581 | ggagcagctg | ggattacagg | catgcaccac | catgcccagc | taatttttgt | atttttagta |
| 2641 | gagatagggt | ttcaccatgt | tggccaggct | ggtcacgaac | tcctgacctc | aagtgaggtc |
| 2701 | acccgcctcg | gcctcccgaa | gtgctgggat | tgcagatgtg | agccaccatg | tccagccaag |
| 2761 | aattagtatt | taaattttag | atactctttt | tttttttt | tttttttt | tttgagacag |
| 2821 | agtcttgctc | catcacccat | gctagagtgc | agtggagtga | tctcggctca | ctgcaacttc |
| 2881 | cgccttctgg | gttcaagcta | ttctcctgcc | tcagccttcc | aagtaactgg | gattacaggc |
| 2941 | atgtaccacc | ataccagctg | atttttttgt | atttttagta | aagacagggt | ttcaccatgt |
| 3001 | tagccaggct | gatcttgaac | tcctaaactc | aagtgatcta | ctcacctcag | cctcccaaaa |
| 3061 | tgctgggatt | acagatgtga | ggcacctggc | ctcagatttt | tgatactctt | aaaccttctg |
| 3121 | atccttagtt | tctctctcca | aaatactctt | tctaggttaa | aaaaaaaaag | gctcttatat |
| 3181 | ttggtgctat | gtaaatgaaa | atgtttttta | ggttttcttg | atttaacaat | agagacaggg |
| 3241 | tctccctgtg | ttgcccaggc | tggtctcgaa | ctcctgggct | caagagatcc | tcctgtcttg |
| 3301 | gcctcgcaaa | gtgctaagta | ggattacagg | cgttagccac | cacacccggc | tgtaaaaatg |
| 3361 | tacttattct | ccagcctctt | ttgtataaac | catagtaagg | gatgggagta | atgatgttat |
| 3421 | ctgtgaaaat | agccaccatt | tacccgtaag | acaaaacttg | ttaaagcctc | ctgagtctaa |
| 3481 | cctagattac | atcaggccct | ttttcacaca | caaaaaaatc | ctttatggga | tttaatggaa |
| 3541 | tctgttgttt | ccccctaagt | tgaaaaacaa | ctctaagaca | ctttaaagta | ccttcttggc |
| 3601 | ctgggttaca | tggttcccag | cctaggtttc | agacttttgc | ttaaggccag | ttttagaaac |
| 3661 | ccgtgaattc | agaaaagtta | attcagaaat | ttgataaaca | gaattgttat | ttaaaaacta |
| 3721 | actggaaaga | ttgttaagtt | ctttctgaat | tattcagaaa | ttatgcatca | ttttccttca |
| 3781 | agaatgacag | ggtcagcatg | tggaattcca | agatacctct | tgacttcctc | tcaagctccg |
| 3841 | tgtttggtca | gtggaggccc | atccgagctc | agcactgaga | agtgttagtt | tctttgggac |
| 3901 | ccatctaccc | tgaccacatc | atgatgttca | tctgcagctg | ttgcaaggtg | ttcagattgt |
| 3961 | ataaacataa | atgtcacaaa | aactttaaaa | gaagtgcaat | tctcaaaagg | ttaggtggac |
| 4021 | taaagcattc | tgtaaagcaa | ctgctaataa | tgagcttaca | gtggatttga | atttgaaaaa |
| 4081 | tatagtaaca | agcctgtcaa | atatctgcaa | gaactatgga | ataaaactac | tgatgcagtg |
| 4141 | aagacagttg | aaaagatcaa | acaaatgcca | agctatattt | ataatgaaca | aattcaagaa |
| 4201 | aaaggactac | ggaaagttca | ggacatcaaa | gaagtcaggc | aaaactcatc | ttgacccctg |
| 4261 | ttgcaggcaa | aggaacgcag | ctggaagaaa | agatgatata | acagttaaca | ggatgcagac |
| 4321 | atggcagagg | tttcctaaaa | atctcattat | ctataaccat | ttctatattt | acatttgaaa |
| 4381 | atctcctttg | gagacttaga | acctctaaat | tattgactta | tttttttatat | aaggtcactc |
| 4441 | cgatgaaagg | tgattacaaa | atcatctaca | ttgctgtcta | caaaacagat | aatatggatg |
| 4501 | tttgatcgca | tctcattgtt | aactctttac | tgatatgttt | gtaaatacag | aagtgaaatg |
| 4561 | tggacataaa | atagttacgc | tatttggtta | atggtactag | acaacatgta | attaatgaca |
| 4621 | ttcaaaaatt | tatggctagt | gatatatata | aagtaaaatt | ttctttgcag | taaaatatgc |
| 4681 | cctttattat | agaagggagg | atataaggaa | ccaacagttt | gtatgaaaat | agctcaaata |
| 4741 | atatctttta | ttttgatttt | aatatttctt | attttggttt | attagtgtct | tagaacaaaa |
| 4801 | tggccttata | taatgaagcc | tagttatgct | ggactgtttt | gatctctttt | aattgttctg |
| 4861 | acagatagtt | ggggatgaga | gccgaataag | gtttgcctga | aataactgac | actatataat |
| 4921 | ttctgctttg | gcaaatacta | agttctaact | tgtcattcct | ggtagaacaa | gctttatttt |
| 4981 | tcgagcctag | caatgatcta | gaagcagatg | ttatctcagt | gccttttgca | atttgttgtg |
| 5041 | tgggtttttt | ttttttaaa | gccacacaat | aattttggaa | aacaatgtat | gggtagaaca |
| 5101 | tgtgtctgtt | aattgcacac | aaaaccactt | ttaatgggta | cagagttaaa | tttgaaggaa |
| 5161 | taagttctag | ctgaagtatt | atgaactcca | aataatgctt | tgaggacctc | caaaggtaaa |
| 5221 | agtactaatc | cctttggcca | tttattgaga | gagagagaga | gagagagtag | ggtgactata |
| 5281 | gttaatgtat | tgaatgttct | tgctacaaat | aaatgatatt | tgagctgatg | ggtgtgctaa |
| 5341 | ttacactgat | ttgatcaata | cccattgtat | gtgaaacagt | acatacacca | tatttacaat |
| 5401 | tatgtattta | acatttaaaa | tttctaatat | aagtatctct | caaactgtgg | attaacttct |
| 5461 | tgatttatat | ttaaatatga | atcttaagca | aaacagtgaa | aataaccatc | ttgatttagt |
| 5521 | gtttttctcc | catatgtgaa | ttgtatatac | ttaggtgaag | acaataaaat | caactgaact |
| 5581 | gtaagcttag | aataggactg | aggtaattct | gcacagcaac | tttactaatg | gtacattgtt |
| 5641 | gcttcaaaac | tctctctctc | tctctctgtc | tgtctcaata | aatggccaaa | gggattagta |
| 5701 | gtttacctgt | ggaggtcctc | caagcattat | ttggagttga | taatacttca | gctacaacca |
| 5761 | agcagaatct | cttttttttg | gaggtcctcg | aagcattatt | tggagttgat | aatacttcag |
| 5821 | cttcaatttg | gagttgataa | tatttcagct | agaacctagt | agaatctgtt | tttttccttt |
| 5881 | ggaggtcctc | aaagcattat | tggagttcat | aatactgaag | ctagaaccaa | gcagaatctg |
| 5941 | ttttttttctg | aggagtatcg | gtagcataaa | tgtgattata | aacatagtac | acttgatata |
| 6001 | tggaggcagt | gacagctatt | tttacaaaat | ttaaatctgc | aaatggattc | aacatgttta |
| 6061 | tgggttatta | aaattgtctg | atttcttagg | ttctttatag | tacacgtgtt | gaaaataaat |
| 6121 | gattaagaat | tgtttcaaga | atgcaattat | ttgatcttaa | atttttatga | gttgttaaaa |
| 6181 | tagaaattat | ttgaatatca | tatatttggg | taacaaaagg | cacaagtctg | aatgtgtttc |
| 6241 | tttttctgga | atggccatgc | ctgcccactt | tagaaataca | aatatcactg | ggcagcttga |
| 6301 | agcagttggg | agcctccaat | gagagcaact | tgagagaatg | atgttgcaag | ttagtaggag |
| 6361 | taagaaatgc | tgtgttctcc | ctgtcttctc | ttaggtcaca | tggcagcctg | gcctaagtga |
| 6421 | tcgtgaatgg | tctataaggg | aggtagctgg | gacagggagg | ggagtttggg | ctagccaccg |
| 6481 | taccacttgt | cagcgtgaaa | agtaagattg | taattgcctg | tttagttttc | tgcctcatct |
| 6541 | ttgaaagttc | caccaagctg | ggaacctctt | gattgtgagg | cacaaatgta | agtacatcag |

TABLE 1-continued 6601 aaaaaaacaa aaaaactggc tttaaagcag gagcttgtgg gcccctaagc cagacgggga
6661 ctagcttttg gcattatata attaagattt tttaaatcct taataagggt tttattttat
6721 ttttatttat tttttgagac ggagtcttgc tctgtggctc aggctggagt acagtggtgc
6781 aatcttggct cactgcaacc tctgcctcct ggctgtgttc aagtggttct gcttcagcct
6841 cccaagtagc tggggttaga gcaccctgtc accacgcccc gctaattttt gtatttctag
6901 cagagatgaa gtttcactat gttggccagg ctgggctcaa actcctgacc tcaagtgatc
6961 tgcccgcctt ggccccccaa agtgctgtga ttacaggcgt gagccgccac gcccagccta
7021 ataagggttt taaagataat tagtgtgtag gtctgtaggc ttatgatggt aaccacaagt
7081 tgttaatggc attgtgaaaa gtttttagtt gcgctttatg ggtggatgct gaattacatt
7141 ttgatttgat acttataaaa agaaaaagta tttcttcagc ttaaaaaatt gtttaaaagt
7201 ttgtgatcat attgtctacc atgtagccag ctttcaatta tatgtaagag ggactttttg
7261 acatttacaa ataatacttt gaggtagata tctgaaagca ccagcacttg gaaggtgttc
7321 agaagtaaca aattataaaa tgagctaaca aacgaaaggc aaaataaaac cgtaaagcaa
7381 gcagatggga ggcgtgttca gtaacttatt cataatgcat ctgaaatgat tgctgtactc
7441 aaatatttaa cgttagagta atagtatttt gaatgaaaac catagttgat tgtct SEQ ID NO: 2 Human MDM2 Isoform a Amino Acid Sequence (NP_002383.2)
1 MVRSRQMCNT NMSVPTDGAV TTSQIPASEQ ETLVRPKPLL LKLLKSVGAQ KDTYTMKEVL
61 FYLGQYIMTK RLYDEKQQHI VYCSNDLLGD LFGVPSFSVK EHRKIYTMIY RNLVVVNQQE
121 SSDSGTSVSE NRCHLEGGSD QKDLVQELQE EKPSSSHLVS RPSTSSRRRA ISETEENSDE
181 LSGERQRKRH KSDSISLSFD ESLALCVIRE ICCERSSSSE STGTPSNPDL DAGVSEHSGD
241 WLDQDSYSDQ FSVEFEVESL DSEDYSLSEE GQELSDEDDE VYQVTVYQAG ESDTDSFEED
301 PEISLADYWK CTSCNEMNPP LPSHCNRCWA LRENWLPEDK GKDKGEISEK AKLENSTQAE
361 EGFDVPDCKK TIVNDSRESC VEENDDKITQ ASQSQESEDY SQPSTSSSII YSSQEDVKEF
421 EREETQDKEE SVESSLPINA IEPCVICQGR PKNGCIVHGK TGHLMACFTC AKKLKKRNKP
481 CPVCRQPIQM IVLTYFP SEQ ID NO: 3 Human MDM2 Transcript Variant 2 cDNA Sequence
(NM_001145339.2; CDS: 307-1635)
1 gtagggggcg cgcaccgagg caccgcggcg agcttggctg cttctggggc ctgtgtggcc
61 ctgtgtgtcg gaaagatgga gcaagaagcc gagcccgagg ggcggccgcg acccctctga
121 ccgagatcct gctgctttcg cagccaggag caccgtccct ccccggatta gtgcgtacga
181 gcgcccagtg ccctggcccg gagagtggaa tgatccccga ggcccagggc gtcgtgcttc
241 cgcgcgcccc gtgaaggaaa ctggggagtc ttgagggacc cccgactcca agcgcgaaaa
301 ccccggatgg tgaggagcag gcaaatgtgc aataccaaca tgtctgtacc tactgatggt
361 gctgtaacca cctcacagat tccagcttcg gaacaagaga ccctggttag accaaagcca
421 ttgcttttga agttattaaa gtctgttggt gcacaaaaag acacttatac tatgaaagag
481 gttctttttt atcttggcca gtatattatg actaaacgat tatatgatga gaagcaacaa
541 catattgtat attgttcaaa tgatcttcta ggagatttgt ttggcgtgcc aagcttctct
601 gtgaaagagc acaggaaaat atataccatg atctacagga acttggtagt agtcaatcag
661 caggaagaaa attcagatga attatctggt gaacgacaaa gaaaacgcca caaatctgat
721 agtatttccc tttcctttga tgaaagcctg gctctgtgtg taataaggga gatatgttgt
781 gaaagaagca gtagcagtga atctacaggg acgccatcga atccggatct tgatgctggt
841 gtaagtgaac attcaggtga ttggttggat caggattcag tttcagatca gtttagtgta
901 gaatttgaag ttgaatctct cgactcagaa gattatagcc ttagtgaaga aggacaagaa
961 ctctcagatg aagatgatga ggtatatcaa gttactgtgt atcaggcagg ggagagtgat
1021 acagattcat ttgaagaaga tcctgaaatt tccttagctg actattggaa atgcacttca
1081 tgcaatgaaa tgaatccccc ccttccatca cattgcaaca gatgttgggc ccttcgtgag
1141 aattggcttc ctgaagataa agggaaagat aaaggggaaa tctctgagaa agccaaactg
1201 gaaaactcaa cacaagctga agagggcttt gatgttcctg attgtaaaaa aactatagtg
1261 aatgattcca gagagtcatg tgttgaggaa aatgatgata aaattacaca agcttcacaa
1321 tcacaagaaa gtgaagacta ttctcagcca tcaacttcta gtagcattat ttatagcagc
1381 caagaagatg tgaaagagtt tgaaagggaa gaaacccaag acaaagaaga gagtgtggaa
1441 tctagtttgc cccttaatgc cattgaacct tgtgtgattt gtcaaggtcg acctaaaaat
1501 ggttgcattg tccatggcaa aacaggacat cttatggcct gctttacatg tgcaaagaag
1561 ctaaagaaaa ggaataagcc ctgcccagta tgtagacaac caattcaaat gattgtgcta
1621 acttatttcc cctagttgac ctgtctataa gagaattata tatttctaac tatataaccc
1681 taggaattta gacaacctga aatttattca catatatcaa agtgagaaaa tgcctcaatt
1741 cacatagatt tcttctcttt agtataattg acctactttg gtagtggaat agtgaatact
1801 tactataatt tgacttgaat atgtagctca tcctttacac caactcctaa ttttaaataa
1861 tttctactct gtcttaaatg agaagtactt ggtttttttt tttcttaaat atgtatatga
1921 catttaaatg taacttatta ttttttttga gaccgagtct tgctctgtta cccaggctgg
1981 agtgcagtgg cgtgatcttg gctcactgca agctctgcct cccgggttcg caccattctc
2041 ctgcctcagc ctcccaatta gcttggccta cagtcatctg ccaccacacc tggctaattt
2101 tttgtacttt tagtagagac agggtttcac cgtgttagcc aggatggtct cgatctcctg
2161 acctcgtgat ccgcccacct cggcctccca aagtgctggg attacaggca tgagccaccg
2221 cgtccggcct aaatgtcact tagtaccttt gatataaaga gaaaatgtgt gaaagattta
2281 gtttttttgtt tttttgtttg tttgtttgtt tgtttgtttt gagatgagtc tctctgtcgc
2341 ccaggctgga gtgcagtgtc atgatctagc agtctccgct tcccgggttc aagccattct
2401 cctggctcag cctctggagc agctgggatt acaggcatgc accaccatgc ccagctaatt
2461 tttgtatttt tagtagagat agggtttcac catgttggcc aggctggtca cgaactcctg
2521 acctcaagtg aggtcacccg cctcggcctc ccgaagtgct gggattgcag atgtgagcca
2581 ccatgtccag ccaagaatta gtatttaaat tttagatact cttttttttt tttttttttt
2641 tttttttga gacagagtct tgctccatca cccatgctag agtgcagtgg agtgatctcg
2701 gctcactgca acttccgcct tctgggttca agctattctc ctgcctcagc cttccaagta
2761 actgggatta caggcatgta ccaccatacc agctgatttt tttgtatttt tagtaaagac
2821 agggtttcac catgttagcc aggctgatct tgaactccta aactcaagtg atctactcac
2881 ctcagcctcc caaaatgctg ggattacaga tgtgaggcac ctggcctcag atttttgata
2941 ctcttaaacc ttctgatcct tagtttctct ctccaaaata ctctttctag gttaaaaaaa
3001 aaaaggctct tatatttggt gctatgtaaa tgaaaatgtt ttttaggttt tcttgattta TABLE 1-continued 3061 acaatagaga cagggtctcc ctgtgttgcc caggctggtc tcgaactcct gggctcaaga
3121 gatcctcctg tcttggcctc gcaaagtgct aagtaggatt acaggcgtta gccaccacac
3181 ccggctgtaa aaatgtactt attctccagc ctcttttgta taaaccatag taagggatgg
3241 gagtaatgat gttatctgtg aaaatagcca ccatttaccc gtaagacaaa acttgttaaa
3301 gcctcctgag tctaacctag attacatcag gcccttttc acacacaaaa aaatccttta
3361 tgggatttaa tggaatctgt tgtttccccc taagttgaaa aacaactcta agacacttta
3421 aagtaccttc ttggcctggg ttacatggtt cccagcctag gtttcagact tttgcttaag
3481 gccagtttta gaaacccgtg aattcagaaa agttaattca gaaatttgat aaacagaatt
3541 gttatttaaa aactaactgg aaagattgtt aagttctttc tgaattattc agaaattatg
3601 catcattttc cttcaagaat gacagggtca gcatgtggaa ttccaagata cctcttgact
3661 tcctctcaag ctccgtgttt ggtcagtgga ggcccatccg agctcagcac tgagaagtgt
3721 tagtttcttt gggacccatc taccctgacc acatcatgat gttcatctgc agctgttgca
3781 aggtgttcag attgtataaa cataaatgtc acaaaaactt taaaagaagt gcaattctca
3841 aaaggttagg tggactaaag cattctgtaa agcaactgct aataatgagc ttacagtgga
3901 tttgaatttg aaaaatatag taacaagcct gtcaaatatc tgcaagaact atggaataaa
3961 actactgatg cagtgaagac agttgaaaag atcaaacaaa tgccaagcta tatttataat
4021 gaacaaattc aagaaaaagg actacggaaa gttcaggaca tcaaagaagt caggcaaaac
4081 tcatcttgac ccctgttgca ggcaaaggaa cgcagctgga agaaaagatg atataacagt
4141 taacaggatg cagacatggc agaggtttcc taaaaatctc attatctata accatttcta
4201 tatttacatt tgaaaatctc ctttggagac ttagaacctc taaattattg acttattttt
4261 tatataaggt cactccgatg aaaggtgatt acaaaatcat ctacattgct gtctacaaaa
4321 cagataatat ggatgtttga tcgcatctca ttgttaactc tttactgata tgtttgtaaa
4381 tacagaagtg aaatgtggac ataaaatagt tacgctattt ggttaatggt actagacaac
4441 atgtaattaa tgacattcaa aaatttatgg ctagtgatat atataaagta aaattttctt
4501 tgcagtaaaa tatgcccttt attatagaag ggaggatata aggaaccaac agtttgtatg
4561 aaaatagctc aaataatatc ttttattttg attttaatat ttcttatttt ggtttattag
4621 tgtcttagaa caaaatggcc ttatataatg aagcctagtt atgctggact gttttgatct
4681 cttttaattg ttctgacaga tagttgggga tgagagccga ataaggtttg cctgaaataa
4741 ctgacactat ataatttctg ctttggcaaa tactaagttc taacttgtca ttcctggtag
4801 aacaagcttt atttttcgag cctagcaatg atctagaagc agatgttatc tcagtgcctt
4861 ttgcaatttg ttgtgtgggt tttttttttt ttaaagccac acaataattt tggaaaacaa
4921 tgtatgggta gaacatgtgt ctgttaattg cacacaaaac cacttttaat gggtacagag
4981 ttaaatttga aggaataagt tctagctgaa gtattatgaa ctccaaataa tgctttgagg
5041 acctccaaag gtaaaagtac taatcccttt ggccatttat tgagagagag agagagagag
5101 agtagggtga ctatagttaa tgtattgaat gttcttgcta caaataaatg atatttgagc
5161 tgatgggtgt gctaattaca ctgatttgat caatacccat tgtatgtgaa acagtacata
5221 caccatattt acaattatgt atttaacatt taaaatttct aatataagta tctctcaaac
5281 tgtggattaa cttcttgatt tatatttaaa tatgaatctt aagcaaaaca gtgaaaataa
5341 ccatcttgat ttagtgtttt tctcccatat gtgaattgta tatacttagg tgaagacaat
5401 aaaatcaact gaactgtaag cttagaatag gactgaggta attctgcaca gcaactttac
5461 taatggtaca ttgttgcttc aaaactctct ctctctctct ctgtctgtct caataaatgg
5521 ccaaagggat tagtagttta cctgtggagg tcctccaagc attatttgga gttgataata
5581 cttcagctac aaccaagcag aatctctttt ttttggaggt cctcgaagca ttatttggag
5641 ttgataatac ttcagcttca atttggagtt gataatattt cagctagaac ctagtagaat
5701 ctgttttttt cctttggagg tcctcaaagc attattggag ttcataatac tgaagctaga
5761 accaagcaga atctgttttt ttctgaggag tatcggtagc ataaatgtga ttataaacat
5821 agtacacttg atatatggag gcagtgacag ctatttttac aaaatttaaa tctgcaaatg
5881 gattcaacat gtttatgggt tattaaaatt gtctgatttc ttaggttctt tatagtacac
5941 gtgttgaaaa taaatgatta agaattgttt caagaatgca attatttgat cttaaatttt
6001 tatgagttgt taaaatagaa attatttgaa tatcatatat ttgggtaaca aaaggcacaa
6061 gtctgaatgt gtttcttttt ctggaatggc catgcctgcc cactttagaa atacaaatat
6121 cactgggcag cttgaagcag ttgggagcct ccaatgagag caacttgaga gaatgatgtt
6181 gcaagttagt aggagtaaga aatgctgtgt tctccctgtc ttctcttagg tcacatggca
6241 gcctggccta agtgatcgtg aatggtctat aagggaggta gctgggacag ggaggggagt
6301 ttgggctagc caccgtacca cttgtcagcg tgaaaagtaa gattgtaatt gcctgtttag
6361 ttttctgcct catctttgaa agttccacca agctgggaac ctcttgattg tgaggcacaa
6421 atgtaagtac atcagaaaaa aacaaaaaaa ctggctttaa agcaggagct tgtgggcccc
6481 taagccagac ggggactagc ttttggcatt atataattaa gatttttaa atccttaata
6541 agggttttat tttattttta tttatttttt gagacggagt cttgctctgt ggctcaggct
6601 ggagtacagt ggtgcaatct tggctcactg caacctctgc ctcctggctg tgttcaagtg
6661 gttctgcttc agcctcccaa gtagctgggg ttagagcacc ctgtcaccac gccccgctaa
6721 tttttgtatt tctagcagag atgaagtttc actatgttgg ccaggctggg ctcaaactcc
6781 tgacctcaag tgatctgccc gccttggccc cccaaagtgc tgtgattaca ggcgtgagcc
6841 gccacgccca gcctaataag ggttttaaag ataattagtg tgtaggtctg taggcttatg
6901 atggtaacca caagttgtta atggcattgt gaaaagtttt tagttgcgct ttatgggtgg
6961 atgctgaatt acattttgat ttgatactta taaaaagaaa aagtatttct tcagcttaaa
7021 aaattgttta aaagtttgtg atcatattgt ctaccatgta gccagctttc aattatatgt
7081 aagagggact ttttgacatt tacaaataat actttgaggt agatatctga aagcaccagc
7141 acttggaagg tgttcagaag taacaaatta taaaatgagc taacaaacga aaggcaaaat
7201 aaaaccgtaa agcaagcaga tgggaggcgt gttcagtaac ttattcataa tgcatctgaa
7261 atgattgctg tactcaaata tttaacgtta gagtaatagt attttgaatg aaaaccatag
7321 ttgattgtct SEQ ID NO: 4 Human MDM2 Isoform h Amino Acid Sequence (NP_001138811.1)
1 MVRSRQMCNT NMSVPTDGAV TTSQIPASEQ ETIVRPKPLL LKLLKSVGAQ KDTYTMKEVL
61 FYLGQYIMTK RLYDEKQQHI VYCSNDLLGD LFGVPSFSVK EHRKIYTMIY RNLVVVNQQE
121 ENSDELSGER QRKRHKSDSI SLSFDESLAL CVIREICCER SSSSESTGTP SNPDLDAGVS
181 EHSGDWLDQD SYSDQFSVEF EVESLDSEDY SLSEEGQELS DEDDEVYQVT VYQAGESDTD
241 SFEEDPEISL ADYWKCTSCN EMNPPLPSHC NRCWALRENW LPEDKGKDKG EISEKAKLEN
301 STQAEEGFDV PDCKKTIVND SRESCVEEND DKITQASQSQ ESEDYSQPST SSSIIYSSQE TABLE 1-continued

```
 361 DVKEFEREET QDKEESVESS LPLNAIEPCV ICQGRPKNGC IVHGKTGHLM ACFTCAKKLK
 421 KRNKPCPVCR QPIQMIVLTY FP

SEQ ID NO: 5 Human MDM2 Transcript Variant 3 cDNA Sequence
(NM_001145337.2; CDS: 75-1409)
   1 tgtgttcagt ggcgattgga gggtagacct gtgggcacgg acgcacgcca ctttttctct
  61 gctgatccag gcaaatgtgc aataccaaca tgtctgtacc tactgatggt gctgtaacca
 121 cctcacagat tccagcttcg gaacaagaga ccctggttag accaaagcca ttgcttttga
 181 agttattaaa gtctgttggt gcacaaaaag acacttatac tatgaaagag gttctttttt
 241 atcttggcca gtatattatg actaaacgat tatatgatga gaagcaacaa catattgtat
 301 attgttcaaa tgatcttcta ggagatttgt ttggcgtgcc aagcttctct gtgaaagagc
 361 acaggaaaat atataccatg atctacagga acttggtagt agtcaatcag caggaatcat
 421 cggactcagg tacatctgtg agtgagaaca ggtgtcacct tgaaggtggg agtgatcaaa
 481 aggaccttgt acaagagctt caggaagaga aaccttcatc ttcacatttg gtttctagac
 541 catctacctc atctagaagg agagcaatta gtgagacaga agaaaattca gatgaattat
 601 ctggtgaacg acaaagaaaa cgccacaaat ctgatagtat ttccctttcc tttgatgaaa
 661 gcctggctct gtgtgtaata agggagatat gttgtgaaag aagcagtagc agtgaatcta
 721 cagggacgcc atcgaatccg gatcttgatg ctggtgtata tcaagttact gtgtatcagg
 781 caggggagag tgatacagat tcatttgaag aagatcctga aatttcctta gctgactatt
 841 ggaaatgcac ttcatgcaat gaaatgaatc ccccccttcc atcacattgc aacagatgtt
 901 gggcccttcg tgagaattgg cttcctgaag ataaagggaa agataaaggg gaaatctctg
 961 agaaagccaa actggaaaac tcaacacaag ctgaagaggg ctttgatgtt cctgattgta
1021 aaaaaactat agtgaatgat tccagagagt catgtgttga ggaaaatgat gataaaatta
1081 cacaagcttc acaatcacaa gaaagtgaag actattctca gccatcaact tctagtagca
1141 ttatttatag cagccaagaa gatgtgaaag agtttgaaag ggaagaaacc caagacaaag
1201 aagagagtgt ggaatctagt ttgcccctta atgccattga accttgtgtg atttgtcaag
1261 gtcgacctaa aaatggttgc attgtccatg gcaaaacagg acatcttatg gcctgcttta
1321 catgtgcaaa gaagctaaag aaaaggaata agccctgccc agtatgtaga caaccaattc
1381 aaatgattgt gctaacttat ttcccctagt tgacctgtct ataagagaat tatatatttc
1441 taactatata accctaggaa tttagacaac ctgaaattta ttcacatata tcaaagtgag
1501 aaaatgcctc aattcacata gatttcttct ctttagtata attgacctac tttggtagtg
1561 gaatagtgaa tacttactat aatttgactt gaatatgtag ctcatccttt acaccaactc
1621 ctaattttaa ataatttcta ctctgtctta aatgagaagt acttggtttt tttttttctt
1681 aaatatgtat atgacattta aatgtaactt attatttttt ttgagaccga gtcttgctct
1741 gttacccagg ctggagtgca gtggcgtgat cttggctcac tgcaagctct gcctcccggg
1801 ttcgcaccat tctcctgcct cagcctccca attagcttgg cctacagtca tctgccacca
1861 cacctggcta atttttgta ctttagtag agacagggtt tcaccgtgtt agccaggatg
1921 gtctcgatct cctgacctcg tgatccgccc acctcggcct cccaaagtgc tgggattaca
1981 ggcatgagcc accgcgtccg gcctaaatgt cacttagtac ctttgatata aagagaaaat
2041 gtgtgaaaga tttagttttt tgtttttttg tttgtttgtt tgtttgtttg ttttgagatg
2101 agtctctctg tcgcccaggc tggagtgcag tgtcatgatc tagcagtctc cgcttcccgg
2161 gttcaagcca ttctcctggc tcagcctctg gagcagctgg gattacaggc atgcaccacc
2221 atgcccagct aatttttgta tttttagtag agatagggtt tcaccatgtt ggccaggctg
2281 gtcacgaact cctgacctca agtgaggtca cccgcctcgg cctcccgaag tgctgggatt
2341 gcagatgtga gccaccatgt ccagccaaga attagtattt aaattttaga tactcttttt
2401 tttttttttt tttttttttt ttgagacaga gtcttgctcc atcacccatg ctagagtgca
2461 gtggagtgat ctcggctcac tgcaacttcc gccttctggg ttcaagctat tctcctgcct
2521 cagccttcca agtaactggg attacaggca tgtaccacca taccagctga tttttttgta
2581 tttttagtaa agacagggtt tcaccatgtt agccaggctg atcttgaact cctaaactca
2641 agtgatctac tcacctcagc ctcccaaaat gctgggatta cagatgtgag gcacctggcc
2701 tcagattttt gatactctta aaccttctga tccttagttt ctctctccaa aatactcttt
2761 ctaggttaaa aaaaaaaagg ctcttatatt tggtgctatg taaatgaaaa tgtttttttag
2821 gttttcttga tttaacaata gagacagggt ctccctgtgt tgcccaggct ggtctcgaac
2881 tcctgggctc aagagatcct cctgtcttgg cctcgcaaag tgctaagtag gattacaggc
2941 gttagccacc acacccggct gtaaaaatgt acttattctc cagcctcttt tgtataaacc
3001 atagtaaggg atgggagtaa tgatgttatc tgtgaaaata gccaccattt acccgtaaga
3061 caaaacttgt taaagcctcc tgagtctaac ctagattaca tcaggccctt tttcacacac
3121 aaaaaaatcc tttatgggat ttaatggaat ctgttgtttc cccctaagtt gaaaaacaac
3181 tctaagacac tttaaagtac cttcttggcc tgggttacat ggttcccagc ctaggtttca
3241 gacttttgct taaggccagt tttagaaacc cgtgaattca gaaaagttaa ttcagaaatt
3301 tgataaacag aattgttatt taaaaactaa ctggaaagat tgttaagttc tttctgaatt
3361 attcagaaat tatgcatcat tttccttcaa gaatgacagg gtcagcatgt ggaattccaa
3421 gatacctctt gacttcctct caagctccgt gtttggtcag tggaggccca tccgagctca
3481 gcactgagaa gtgttagttt ctttgggacc catctaccct gaccacatca tgatgttcat
3541 ctgcagctgt tgcaaggtgt tcagattgta taaacataaa tgtcacaaaa actttaaaag
3601 aagtgcaatt ctcaaaaggt taggtggact aaagcattct gtaaagcaac tgctaataat
3661 gagcttacag tggatttgaa tttgaaaaat atagtaacaa gcctgtcaaa tatctgcaag
3721 aactatggaa taaaactact gatgcagtga agacagttga aaagatcaaa caaatgccaa
3781 gctatattta taatgaacaa attcaagaaa aaggactacg gaaagttcag gacatcaaag
3841 aagtcaggca aaactcatct tgacccctgt tgcaggcaaa ggaacgcagc tggaagaaaa
3901 gatgatataa cagttaacag gatgcagaca tggcagaggt ttcctaaaaa tctcattatc
3961 tataaccatt tctatattta catttgaaaa tctcctttgg agacttagaa cctctaaatt
4021 attgacttat tttttatata aggtcactcc gatgaaaggt gattacaaaa tcatctacat
4081 tgctgtctac aaaacagata atatggatgt ttgatcgcat ctcattgtta actctttact
4141 gatatgtttg taaatacaga agtgaaatgt ggacataaaa tagttacgct atttggttaa
4201 tggtactaga caacatgtaa ttaatgacat tcaaaaattt atggctagtg atatatataa
4261 agtaaaattt tctttgcagt aaaatatgcc ctttattata gaagggagga tataaggaac
4321 caacagtttg tatgaaaata gctcaaataa tatcttttat tttgatttta atatttctta
4381 ttttggttta ttagtgtctt agaacaaaat ggccttatat aatgaagcct agttatgctg
4441 gactgttttg atctctttta attgttctga cagatagttg gggatgagag ccgaataagg
```

TABLE 1-continued

```
4501 tttgcctgaa ataactgaca ctatataatt tctgctttgg caaatactaa gttctaactt
4561 gtcattcctg gtagaacaag ctttattttt cgagcctagc aatgatctag aagcagatgt
4621 tatctcagtg ccttttgcaa tttgttgtgt gggttttttt tttttaaag ccacacaata
4681 attttggaaa acaatgtatg ggtagaacat gtgtctgtta attgcacaca aaaccacttt
4741 taatgggtac agagttaaat ttgaaggaat aagttctagc tgaagtatta tgaactccaa
4801 ataatgcttt gaggacctcc aaaggtaaaa gtactaatcc ctttggccat ttattgagag
4861 agagagagag agagagtagg gtgactatag ttaatgtatt gaatgttctt gctacaaata
4921 aatgatattt gagctgatgg gtgtgctaat tacactgatt tgatcaatac ccattgtatg
4981 tgaaacagta catacaccat atttacaatt atgtatttaa catttaaaat ttctaatata
5041 agtatctctc aaactgtgga ttaacttctt gatttatatt taaatatgaa tcttaagcaa
5101 aacagtgaaa ataaccatct tgatttagtg tttttctccc atatgtgaat tgtatatact
5161 taggtgaaga caataaaatc aactgaactg taagcttaga ataggactga ggtaattctg
5221 cacagcaact ttactaatgg tacattgttg cttcaaaact ctctctctct ctctctgtct
5281 gtctcaataa atggccaaag ggattagtag tttacctgtg gaggtcctcc aagcattatt
5341 tggagttgat aatacttcag ctacaaccaa gcagaatctc tttttttgg aggtcctcga
5401 agcattattt ggagttgata atacttcagc ttcaatttgg agttgataat atttcagcta
5461 gaacctagta gaatctgttt ttttcctttg gaggtcctca aagcattatt ggagttcata
5521 atactgaagc tagaaccaag cagaatctgt ttttttctga ggagtatcgg tagcataaat
5581 gtgattataa acatagtaca cttgatatat ggaggcagtg acagctattt ttacaaaatt
5641 taaatctgca aatggattca acatgtttat gggttattaa aattgtctga tttcttaggt
5701 tctttatagt acacgtgttg aaaataaatg attaagaatt gtttcaagaa tgcaattatt
5761 tgatcttaaa tttttatgag ttgttaaaat agaaattatt tgaatatcat atatttgggt
5821 aacaaaaggc acaagtctga atgtgtttct ttttctggaa tggccatgcc tgcccacttt
5881 agaaatacaa atatcactgg gcagcttgaa gcagttggga gcctccaatg agagcaactt
5941 gagagaatga tgttgcaagt tagtaggagt aagaaatgct gtgttctccc tgtcttctct
6001 taggtcacat ggcagcctgg cctaagtgat cgtgaatggt ctataaggga ggtagctggg
6061 acagggaggg gagtttgggc tagccaccgt accacttgtc agcgtgaaaa gtaagattgt
6121 aattgcctgt ttagtttttct gcctcatctt tgaaagttcc accaagctgg gaacctcttg
6181 attgtgaggc acaaatgtaa gtacatcaga aaaaaacaaa aaaactggct ttaaagcagg
6241 agcttgtggg cccctaagcc agacggggac tagcttttgg cattatataa ttaagatttt
6301 ttaaatcctt aataagggtt ttattttatt tttatttatt ttttgagacg gagtcttgct
6361 ctgtggctca ggctggagta cagtggtgca atcttggctc actgcaacct ctgcctcctg
6421 gctgtgttca agtggttctg cttcagcctc ccaagtagct ggggttagag caccctgtca
6481 ccacgccccg ctaattttg tatttctagc agagatgaag tttcactatg ttggccaggc
6541 tgggctcaaa ctcctgacct caagtgatct gcccgccttg gccccccaaa gtgctgtgat
6601 tacaggcgtg agccgccacg cccagcctaa taagggtttt aaagataatt agtgtgtagg
6661 tctgtaggct tatgatggta accacaagtt gttaatggca ttgtgaaaag tttttagttg
6721 cgctttatgg gtggatgctg aattacattt tgatttgata cttataaaaa gaaaaagtat
6781 ttcttcagct taaaaaattg tttaaaagtt tgtgatcata ttgtctacca tgtagccagc
6841 tttcaattat atgtaagagg gactttttga catttacaaa taatactttg aggtagatat
6901 ctgaaagcac cagcacttgg aaggtgttca gaagtaacaa attataaaat gagctaacaa
6961 acgaaaggca aaataaaacc gtaaagcaag cagatgggag gcgtgttcag taacttattc
7021 ataatgcatc tgaaatgatt gctgtactca aatatttaac gttagagtaa tagtattttg
7081 aatgaaaacc atagttgatt gtct
```

SEQ ID NO: 6 Human MDM2 Isoform g Amino Acid Sequence (NP_001138809.1)

```
  1 MCNTNMSVPT DGAVTTSQIP ASEQETLVRP KPLLLKLLKS VGAQKDTYTM KEVLFYLGQY
 61 IMTKRLYDEK QQHIVYCSND LLGDLFGVPS FSVKEHRKIY TMIYRNLVVV NQQESSDSGT
121 SYSENRCHLE GGSDQKDLVQ ELQEEKPSSS HLVSRPSTSS RRRAISETEE NSDELSGERQ
181 RKRHKSDSIS LSFDESLALC VIREICCERS SSSESTGTPS NPDLDAGVYQ VTVYQAGESD
241 TDSFEEDPEI SLADYWKCTS CNEMNPPLPS HCNRCWALRE NWLPEDKGKD KGEISEKAKL
301 ENSTQAEEGF DVPDCKKTIV NDSRESCVEE NDDKITQASQ SQESEDYSQP STSSSIIYSS
361 QEDVKEFERE ETQDKEESVE SSLPINAIEP CVICQGRPKN GCIVHGKTGH LMACFTCAKK
421 LKKRNKPCPV CRQPIQMIVL TYFP
```

SEQ ID NO: 7 Human MDM2 Transcript Variant 4 cDNA Sequence (NM_001145340; CDS: 75-962)

```
   1 tgtgttcagt ggcgattgga gggtagacct gtgggcacgg acgcacgcca ctttttctct
  61 gctgatccag gcaaatgtgc aataccaaca tgtctgtacc tactgatggt gctgtaacca
 121 cctcacagat tccagcttcg gaacaagaga ccctggttag accaaagcca ttgcttttga
 181 agttattaaa gtctgttggt gcacaaaaag acacttatac tatgaaagag gatcttgatg
 241 ctggtgtaag tgaacattca ggtgattggt tggatcagga ttcagtttca gatcagttta
 301 gtgtagaatt tgaagttgaa tctctcgact cagaagatta tagccttagt gaagaaggac
 361 aagaactctc agatgaagat gatgaggact attggaaatg cacttcatgc aatgaaatga
 421 atcccccccct tccatcacat tgcaacagat gttgggccct tcgtgagaat tggcttcctg
 481 aagataaagg gaaagataaa ggggaaatct ctgagaaagc caaactggaa aactcaacac
 541 aagctgaaga gggctttgat gttcctgatt gtaaaaaaac tatagtgaat gattccagag
 601 agtcatgtgt tgaggaaaat gatgataaaa ttacacaagc ttcacaatca caagaaagtg
 661 aagactattc tcagccatca acttctagta gcattattta tagcagccaa gaagatgtga
 721 aagagtttga aagggaagaa acccaagaca aagaagagag tgtggaatct agtttgcccc
 781 ttaatgccat tgaaccttgt gtgatttgtc aaggtcgacc taaaaatggt tgcattgtcc
 841 atggcaaaac aggacatctt atggcctgct ttacatgtgc aaagaagcta aagaaaagga
 901 ataagccctg cccagtatgt agacaaccaa ttcaaatgat tgtgctaact tatttcccct
 961 agttgacctg tctataagag aattatatat ttctaactat ataaccctag gaatttagac
1021 aacctgaaat ttattcacat atatcaaagt gagaaaatgc ctcaattcac atagatttct
1081 tctctttagt ataattgacc tactttggta gtggaatagt gaatacttac tataatttga
1141 cttgaatatg tagctcatcc tttacaccaa ctcctaattt taaataattt ctactctgtc
1201 ttaaatgaga agtacttggt ttttttttt cttaaatatg tatatgacat ttaaatgtaa
1261 cttattattt tttttgagac cgagtcttgc tctgttaccc aggctggagt gcagtggcgt
1321 gatcttggct cactgcaagc tctgcctccc gggttcgcac cattctcctg cctcagcctc
```

TABLE 1-continued

| | | | | | | |
|---|---|---|---|---|---|---|
| 1381 | ccaattagct | tggcctacag | tcatctgcca | ccacacctgg | ctaatttttt | gtacttttag |
| 1441 | tagagacagg | gtttcaccgt | gttagccagg | atggtctcga | tctcctgacc | tcgtgatccg |
| 1501 | cccacctcgg | cctcccaaag | tgctgggatt | acaggcatga | gccaccgcgt | ccggcctaaa |
| 1561 | tgtcacttag | tacctttgat | ataaagagaa | aatgtgtgaa | agatttagtt | ttttgttttt |
| 1621 | ttgtttgttt | gtttgtttgt | ttgttttgag | atgagtctct | ctgtcgccca | ggctggagtg |
| 1681 | cagtgtcatg | atctagcagt | ctccgcttcc | cgggttcaag | ccattctcct | ggctcagcct |
| 1741 | ctggagcagc | tgggattaca | ggcatgcacc | accatgccca | gctaattttt | gtatttttag |
| 1801 | tagagatagg | gtttcaccat | gttggccagg | ctggtcacga | actcctgacc | tcaagtgagg |
| 1861 | tcacccgcct | cggcctcccg | aagtgctggg | attgcagatg | tgagccacca | tgtccagcca |
| 1921 | agaattagta | tttaaatttt | agatactctt | tttttttttt | tttttttttt | tttttgagac |
| 1981 | agagtcttgc | tccatcaccc | atgctagagt | gcagtggagt | gatctcggct | cactgcaact |
| 2041 | tccgccttct | gggttcaagc | tattctcctg | cctcagcctt | ccaagtaact | gggattacag |
| 2101 | gcatgtacca | ccataccagc | tgattttttt | gtatttttag | taaagacagg | gtttcaccat |
| 2161 | gttagccagg | ctgatcttga | actcctaaac | tcaagtgatc | tactcacctc | agcctcccaa |
| 2221 | aatgctggga | ttacagatgt | gaggcacctg | gcctcagatt | tttgatactc | ttaaaccttc |
| 2281 | tgatccttag | tttctctctc | caaaatactc | tttctaggtt | aaaaaaaaaa | aggctcttat |
| 2341 | atttggtgct | atgtaaatga | aaatgttttt | taggttttct | tgatttaaca | atagagacag |
| 2401 | ggtctccctg | tgttgcccag | gctggtctcg | aactcctggg | ctcaagagat | cctcctgtct |
| 2461 | tggcctcgca | aagtgctaag | taggattaca | ggcgttagcc | accacacccg | gctgtaaaaa |
| 2521 | tgtacttatt | ctccagcctc | ttttgtataa | accatagtaa | gggatgggag | taatgatgtt |
| 2581 | atctgtgaaa | atagccacca | tttacccgta | agacaaaact | tgttaaagcc | tcctgagtct |
| 2641 | aacctagatt | acatcaggcc | ctttttcaca | cacaaaaaaa | tcctttatgg | gatttaatgg |
| 2701 | aatctgttgt | ttccccctaa | gttgaaaaac | aactctaaga | cactttaaag | taccttcttg |
| 2761 | gcctgggtta | catggttccc | agcctaggtt | tcagactttt | gcttaaggcc | agttttagaa |
| 2821 | acccgtgaat | tcagaaaagt | taattcagaa | atttgataaa | cagaattgtt | atttaaaaac |
| 2881 | taactggaaa | gattgttaag | ttctttctga | attattcaga | aattatgcat | cattttcctt |
| 2941 | caagaatgac | agggtcagca | tgtggaattc | caagatacct | cttgacttcc | tctcaagctc |
| 3001 | cgtgtttggt | cagtggaggc | ccatccgagc | tcagcactga | gaagtgttag | tttctttggg |
| 3061 | acccatctac | cctgaccaca | tcatgatgtt | catctgcagc | tgttgcaagg | tgttcagatt |
| 3121 | gtataaacat | aaatgtcaca | aaaactttaa | aagaagtgca | attctcaaaa | ggttaggtgg |
| 3181 | actaaagcat | tctgtaaagc | aactgctaat | aatgagctta | cagtggattt | gaatttgaaa |
| 3241 | aatatagtaa | caagcctgtc | aaatatctgc | aagaactatg | gaataaaact | actgatgcag |
| 3301 | tgaagacagt | tgaaaagatc | aaacaaatgc | caagctatat | ttataatgaa | caaattcaag |
| 3361 | aaaaaggact | acggaaagtt | caggacatca | aagaagtcag | gcaaaactca | tcttgacccc |
| 3421 | tgttgcaggc | aaaggaacgc | agctggaaga | aaagatgata | taacagttaa | caggatgcag |
| 3481 | acatggcaga | ggtttcctaa | aaatctcatt | atctataacc | atttctatat | ttacatttga |
| 3541 | aaatctcctt | tggagactta | gaacctctaa | attattgact | tattttttat | ataaggtcac |
| 3601 | tccgatgaaa | ggtgattaca | aaatcatcta | cattgctgtc | tacaaaacag | ataatatgga |
| 3661 | tgtttgatcg | catctcattg | ttaactcttt | actgatatgt | ttgtaaatac | agaagtgaaa |
| 3721 | tgtggacata | aaatagttac | gctatttggt | taatggtact | agacaacatg | taattaatga |
| 3781 | cattcaaaaa | tttatggcta | gtgatatata | taaagtaaaa | ttttctttgc | agtaaaatat |
| 3841 | gccctttatt | atagaaggga | ggatataagg | aaccaacagt | ttgtatgaaa | atagctcaaa |
| 3901 | taatatcttt | tattttgatt | ttaatatttc | ttattttggt | ttattagtgt | cttagaacaa |
| 3961 | aatggcctta | tataatgaag | cctagttatg | ctggactgtt | ttgatctctt | ttaattgttc |
| 4021 | tgacagatag | ttggggatga | gagccgaata | aggtttgcct | gaaataactg | acactatata |
| 4081 | atttctgctt | tggcaaatac | taagttctaa | cttgtcattc | ctggtagaac | aagctttatt |
| 4141 | tttcgagcct | agcaatgatc | tagaagcaga | tgttatctca | gtgccttttg | caatttgttg |
| 4201 | tgtgggtttt | tttttttta | aagccacaca | ataattttgg | aaaacaatgt | atgggtagaa |
| 4261 | catgtgtctg | ttaattgcac | acaaaaccac | ttttaatggg | tacagagtta | aatttgaagg |
| 4321 | aataagttct | agctgaagta | ttatgaactc | caaataatgc | tttgaggacc | tccaaaggta |
| 4381 | aaagtactaa | tccctttggc | catttattga | gagagagaga | gagagagagt | agggtgacta |
| 4441 | tagttaatgt | attgaatgtt | cttgctacaa | ataaatgata | tttgagctga | tgggtgtgct |
| 4501 | aattacactg | atttgatcaa | tacccattgt | atgtgaaaca | gtacatacac | catatttaca |
| 4561 | attatgtatt | taacatttaa | aatttctaat | ataagtatct | ctcaaactgt | ggattaactt |
| 4621 | cttgatttat | atttaaatat | gaatcttaag | caaaacagtg | aaaataacca | tcttgattta |
| 4681 | gtgtttttct | cccatatgtg | aattgtatat | acttaggtga | agacaataaa | atcaactgaa |
| 4741 | ctgtaagctt | agaataggac | tgaggtaatt | ctgcacagca | actttactaa | tggtacattg |
| 4801 | ttgcttcaaa | actctctctc | tctctctctg | tctgtctcaa | taaatggcca | aagggattag |
| 4861 | tagtttacct | gtggaggtcc | tccaagcatt | atttggagtt | gataatactt | cagctacaac |
| 4921 | caagcagaat | ctcttttttt | tggaggtcct | cgaagcatta | tttggagttg | ataatacttc |
| 4981 | agcttcaatt | tggagttgat | aatatttcag | ctagaaccta | gtagaatctg | tttttttcct |
| 5041 | ttggaggtcc | tcaaagcatt | attggagttc | ataatactga | agctagaacc | aagcagaatc |
| 5101 | tgtttttttc | tgaggagtat | cggtagcata | aatgtgatta | taaacatagt | acacttgata |
| 5161 | tatggaggca | gtgacagcta | tttttacaaa | atttaaatct | gcaaatggat | tcaacatgtt |
| 5221 | tatgggttat | taaaattgtc | tgatttctta | ggttctttat | agtacacgtg | ttgaaaataa |
| 5281 | atgattaaga | attgtttcaa | gaatgcaatt | atttgatctt | aaatttttat | gagttgttaa |
| 5341 | aatagaaatt | atttgaatat | catatatttg | ggtaacaaaa | ggcacaagtc | tgaatgtgtt |
| 5401 | tctttttctg | gaatggccat | gcctgcccac | tttagaaata | caaatatcac | tgggcagctt |
| 5461 | gaagcagttg | ggagcctcca | atgagagcaa | cttgagagaa | tgatgttgca | agttagtagg |
| 5521 | agtaagaaat | gctgtgttct | ccctgtcttc | tcttaggtca | catggcagcc | tggcctaagt |
| 5581 | gatcgtgaat | ggtctataag | ggaggtagct | gggacaggga | ggggagtttg | ggctagccac |
| 5641 | cgtaccactt | gtcagcgtga | aaagtaagat | tgtaattgcc | tgtttagttt | tctgcctcat |
| 5701 | ctttgaaagt | tccaccaagc | tgggaacctc | ttgattgtga | ggcacaaatg | taagtacatc |
| 5761 | agaaaaaaac | aaaaaaactg | gctttaaagc | aggagcttgt | gggcccctaa | gccagacggg |
| 5821 | gactagcttt | tggcattata | taattaagat | tttttaaatc | cttaataagg | gttttatttt |
| 5881 | atttttattt | atttttttgag | acggagtctt | gctctgtggc | tcaggctgga | gtacagtggt |
| 5941 | gcaatcttgg | ctcactgcaa | cctctgcctc | ctggctgtgt | tcaagtggtt | ctgcttcagc |
| 6001 | ctcccaagta | gctggggtta | gagcaccctg | tcaccacgcc | ccgctaattt | ttgtatttct |
| 6061 | agcagagatg | aagtttcact | atgttggcca | ggctgggctc | aaactcctga | cctcaagtga |
| 6121 | tctgcccgcc | ttggcccccc | aaagtgctgt | gattacaggc | gtgagccgcc | acgcccagcc |

TABLE 1-continued

```
6181 taataagggt tttaaagata attagtgtgt aggtctgtag gcttatgatg gtaaccacaa
6241 gttgttaatg gcattgtgaa aagtttttag ttgcgcttta tgggtggatg ctgaattaca
6301 ttttgatttg atacttataa aaagaaaaag tatttcttca gcttaaaaaa ttgtttaaaa
6361 gtttgtgatc atattgtcta ccatgtagcc agctttcaat tatatgtaag agggactttt
6421 tgacatttac aaataatact ttgaggtaga tatctgaaag caccagcact tggaaggtgt
6481 tcagaagtaa caaattataa aatgagctaa caaacgaaag gcaaaataaa accgtaaagc
6541 aagcagatgg gaggcgtgtt cagtaactta ttcataatgc atctgaaatg attgctgtac
6601 tcaaatattt aacgttagag taatagtatt ttgaatgaaa accatagttg attgtct
```

SEQ ID NO: 8 Human MDM2 Isoform i Amino Acid Sequence (NP_001138812.1)

```
  1 MCNTNMSVPT DGAVTTSQIP ASEQETLVRP KPLLLKLLKS VGAQKDTYTM KEDLDAGVSE
 61 HSGDWLDQDS VSDQFSVEFE VESLDSEDYS LSEEGQELSD EDDEDYWKCT SCNEMNPPLP
121 SHCNRCWALR ENWLPEDKGK DKGEISEKAK LENSTQAEEG FDVPDCKKTI VNDSRESCVE
181 ENDDKITQAS QSQESEDYSQ PSTSSSIIYS SQEDVKEFER EETQDKEESV ESSLPINAIE
241 PCVICQGRPK NGCIVHGKTG HLMACFTCAK KLKKRNKPCP VCRQPIQMIV LTYFP
```

SEQ ID NO: 9 Human MDM2 Transcript Variant 5 cDNA Sequence (NM_001278462.1; CDS: 75-1040)

```
   1 tgtgttcagt ggcgattgga gggtagacct gtgggcacgg acgcacgcca ctttttctct
  61 gctgatccag gcaaatgtgc aataccaaca tgtctgtacc tactgatggt gctgtaacca
 121 cctcacagat tccagcttcg gaacaagaga ccctggttag accaaagcca ttgcttttga
 181 agttattaaa gtctgttggt gcacaaaaag acacttatac tatgaaagag gatcttgatg
 241 ctggtgtaag tgaacattca ggtgattggt tggatcagga ttcagtttca gatcagttta
 301 gtgtagaatt tgaagttgaa tctctcgact cagaagatta tagccttagt gaagaaggac
 361 aagaactctc agatgaagat gatgaggtat atcaagttac tgtgtatcag gcaggggaga
 421 gtgatacaga ttcatttgaa gaagatcctg aaatttcctt agctgactat tggaaatgca
 481 cttcatgcaa tgaaatgaat cccccccttc catcacattg caacagatgt tgggcccttc
 541 gtgagaattg gcttcctgaa gataaaggga aagataaagg ggaaatctct gagaaagcca
 601 aactggaaaa ctcaacacaa gctgaagagg gctttgatgt tcctgattgt aaaaaaacta
 661 tagtgaatga ttccagagag tcatgtgttg aggaaaatga tgataaaatt acacaagctt
 721 cacaatcaca agaaagtgaa gactattctc agccatcaac ttctagtagc attatttata
 781 gcagccaaga agatgtgaaa gagtttgaaa gggaagaaac ccaagacaaa gaagagagtg
 841 tggaatctag tttgcccctt aatgccattg aaccttgtgt gatttgtcaa ggtcgaccta
 901 aaaatggttg cattgtccat ggcaaaacag gacatcttat ggcctgcttt acatgtgcaa
 961 agaagctaaa gaaaaggaat aagccctgcc cagtatgtag acaaccaatt caaatgattg
1021 tgctaactta tttcccctag ttgacctgtc tataagagaa ttatatattt ctaactatat
1081 aaccctagga atttagacaa cctgaaattt attcacatat atcaaagtga gaaaatgcct
1141 caattcacat agatttcttc tctttagtat aattgaccta ctttggtagt ggaatagtga
1201 atacttacta taatttgact tgaatatgta gctcatcctt tacaccaact cctaatttta
1261 aataatttct actctgtctt aaatgagaag tacttggttt tttttttct taaatatgta
1321 tatgacattt aaatgtaact tattattttt tttgagaccg agtcttgctc tgttacccag
1381 gctggagtgc agtggcgtga tcttggctca ctgcaagctc tgcctcccgg gttcgcacca
1441 ttctcctgcc tcagcctccc aattagcttg gcctacagtc atctgccacc acacctggct
1501 aatttttgt acttttagta gagacagggt ttcaccgtgt tagccaggat ggtctcgatc
1561 tcctgacctc gtgatccgcc cacctcggcc tcccaaagtg ctgggattac aggcatgagc
1621 caccgcgtcc ggcctaaatg tcacttagta cctttgatat aaagagaaaa tgtgtgaaag
1681 atttagtttt ttgtttttt gtttgtttgt ttgtttgttt gttttgagat gagtctctct
1741 gtcgcccagg ctggagtgca gtgtcatgat ctagcagtct ccgcttcccg ggttcaagcc
1801 attctcctgg ctcagcctct ggagcagctg ggattacagg catgcaccac catgcccagc
1861 taatttttgt atttttagta gagatagggt ttcaccatgt tggccaggct ggtcacgaac
1921 tcctgacctc aagtgaggtc acccgcctcg gcctcccgaa gtgctgggat tgcagatgtg
1981 agccaccatg tccagccaag aattagtatt taaattttag atactctttt tttttttttt
2041 tttttttttt tttgagacag agtcttgctc catcacccat gctagagtgc agtggagtga
2101 tctcggctca ctgcaacttc cgccttctgg gttcaagcta ttctcctgcc tcagccttcc
2161 aagtaactgg gattacaggc atgtaccacc ataccagctg atttttttgt atttttagta
2221 aagacagggt ttcaccatgt tagccaggct gatcttgaac tcctaaactc aagtgatcta
2281 ctcacctcag cctcccaaaa tgctgggatt acagatgtga ggcacctggc ctcagatttt
2341 tgatactctt aaaccttctg atccttagtt tctctctcca aaatactctt tctaggttaa
2401 aaaaaaaaag gctcttatat ttggtgctat gtaaatgaaa atgtttttta ggttttcttg
2461 atttaacaat agagacaggg tctccctgtg ttgcccaggc tggtctcgaa ctcctgggct
2521 caagagatcc tcctgtcttg gcctcgcaaa gtgctaagta ggattacagg cgttagccac
2581 cacacccggc tgtaaaaatg tacttattct ccagcctctt ttgtataaac catagtaagg
2641 gatgggagta atgatgttat ctgtgaaaat agccaccatt tacccgtaag acaaaacttg
2701 ttaaagcctc ctgagtctaa cctagattac atcaggccct ttttcacaca caaaaaaatc
2761 ctttatggga tttaatggaa tctgttgttt ccccctaagt tgaaaaacaa ctctaagaca
2821 ctttaaagta ccttcttggc ctgggttaca tggttcccag cctaggtttc agacttttgc
2881 ttaaggccag ttttagaaac ccgtgaattc agaaaagtta attcagaaat ttgataaaca
2941 gaattgttat ttaaaaacta actggaaaga ttgttaagtt ctttctgaat tattcagaaa
3001 ttatgcatca ttttccttca agaatgacag ggtcagcatg tggaattcca agatacctct
3061 tgacttcctc tcaagctccg tgtttggtca gtggaggccc atccgagctc agcactgaga
3121 agtgttagtt tctttgggac ccatctaccc tgaccacatc atgatgttca tctgcagctg
3181 ttgcaaggtg ttcagattgt ataaacataa atgtcacaaa aactttaaaa gaagtgcaat
3241 tctcaaaagg ttaggtggac taaagcattc tgtaaagcaa ctgctaataa tgagcttaca
3301 gtggatttga atttgaaaaa tatagtaaca agcctgtcaa atatctgcaa gaactatgga
3361 ataaaactac tgatgcagtg aagacagttg aaaagatcaa acaaatgcca agctatattt
3421 ataatgaaca aattcaagaa aaaggactac ggaaagttca ggacatcaaa gaagtcaggc
3481 aaaactcatc ttgacccctg ttgcaggcaa aggaacgcag ctggaagaaa agatgatata
3541 acagttaaca ggatgcagac atggcagagg tttcctaaaa atctcattat ctataaccat
3601 ttctatattt acatttgaaa atctcctttg gagacttaga acctctaaat tattgactta
3661 tttttatat aaggtcactc cgatgaaagg tgattacaaa atcatctaca ttgctgtcta
```

TABLE 1-continued 3721 caaaacagat aatatggatg tttgatcgca tctcattgtt aactctttac tgatatgttt
3781 gtaaatacag aagtgaaatg tggacataaa atagttacgc tatttggtta atggtactag
3841 acaacatgta attaatgaca ttcaaaaatt tatggctagt gatatatata aagtaaaatt
3901 ttctttgcag taaaatatgc cctttattat agaagggagg atataaggaa ccaacagttt
3961 gtatgaaaat agctcaaata atatctttta ttttgatttt aatatttctt attttggttt
4021 attagtgtct tagaacaaaa tggccttata taatgaagcc tagttatgct ggactgtttt
4081 gatctctttt aattgttctg acagatagtt ggggatgaga gccgaataag gtttgcctga
4141 aataactgac actatataat ttctgctttg gcaaatacta agttctaact tgtcattcct
4201 ggtagaacaa gctttatttt tcgagcctag caatgatcta gaagcagatg ttatctcagt
4261 gccttttgca atttgttgtg tgggtttttt tttttttaaa gccacacaat aattttggaa
4321 aacaatgtat gggtagaaca tgtgtctgtt aattgcacac aaaaccactt ttaatgggta
4381 cagagttaaa tttgaaggaa taagttctag ctgaagtatt atgaactcca aataatgctt
4441 tgaggacctc caaaggtaaa agtactaatc cctttggcca tttattgaga gagagagaga
4501 gagagagtag ggtgactata gttaatgtat tgaatgttct tgctacaaat aaatgatatt
4561 tgagctgatg ggtgtgctaa ttacactgat ttgatcaata cccattgtat gtgaaacagt
4621 acatacacca tatttacaat tatgtattta acatttaaaa tttctaatat aagtatctct
4681 caaactgtgg attaacttct tgatttatat ttaaatatga atcttaagca aaacagtgaa
4741 aataaccatc ttgatttagt gtttttctcc catatgtgaa ttgtatatac ttaggtgaag
4801 acaataaaat caactgaact gtaagcttag aataggactg aggtaattct gcacagcaac
4861 tttactaatg gtacattgtt gcttcaaaac tctctctctc tctctctgtc tgtctcaata
4921 aatggccaaa gggattagta gtttacctgt ggaggtcctc caagcattat ttggagttga
4981 taatacttca gctacaacca agcagaatct cttttttttg gaggtcctcg aagcattatt
5041 tggagttgat aatacttcag cttcaatttg gagttgataa tatttcagct agaacctagt
5101 agaatctgtt tttttccttt ggaggtcctc aaagcattat tggagttcat aatactgaag
5161 ctagaaccaa gcagaatctg tttttttctg aggagtatcg gtagcataaa tgtgattata
5221 aacatagtac acttgatata tggaggcagt gacagctatt tttacaaaat ttaaatctgc
5281 aaatggattc aacatgttta tgggttatta aaattgtctg atttcttagg ttctttatag
5341 tacacgtgtt gaaaataaat gattaagaat tgtttcaaga atgcaattat ttgatcttaa
5401 atttttatga gttgttaaaa tagaaattat ttgaatatca tatatttggg taacaaaagg
5461 cacaagtctg aatgtgtttc tttttctgga atggccatgc ctgcccactt tagaaataca
5521 aatatcactg ggcagcttga agcagttggg agcctccaat gagagcaact tgagagaatg
5581 atgttgcaag ttagtaggag taagaaatgc tgtgttctcc ctgtcttctc ttaggtcaca
5641 tggcagcctg gcctaagtga tcgtgaatgg tctataaggg aggtagctgg gacagggagg
5701 ggagtttggg ctagccaccg taccacttgt cagcgtgaaa agtaagattg taattgcctg
5761 tttagttttc tgcctcatct ttgaaagttc caccaagctg ggaacctctt gattgtgagg
5821 cacaaatgta agtacatcag aaaaaaacaa aaaaactggc tttaaagcag gagcttgtgg
5881 gcccctaagc cagacgggga ctagcttttg gcattatata attaagattt tttaaatcct
5941 taataagggt tttattttat ttttatttat tttttgagac ggagtcttgc tctgtggctc
6001 aggctggagt acagtggtgc aatcttggct cactgcaacc tctgcctcct ggctgtgttc
6061 aagtggttct gcttcagcct cccaagtagc tggggttaga gcaccctgtc accacgcccc
6121 gctaattttt gtatttctag cagagatgaa gtttcactat gttggccagg ctgggctcaa
6181 actcctgacc tcaagtgatc tgcccgcctt ggccccccaa agtgctgtga ttacaggcgt
6241 gagccgccac gcccagccta ataagggttt taaagataat tagtgtgtag gtctgtaggc
6301 ttatgatggt aaccacaagt tgttaatggc attgtgaaaa gtttttagtt gcgctttatg
6361 ggtggatgct gaattacatt ttgatttgat acttataaaa agaaaaagta tttcttcagc
6421 ttaaaaaatt gtttaaaagt ttgtgatcat attgtctacc atgtagccag ctttcaatta
6481 tatgtaagag ggactttttg acatttacaa ataatacttt gaggtagata tctgaaagca
6541 ccagcacttg gaaggtgttc agaagtaaca aattataaaa tgagctaaca aacgaaaggc
6601 aaaataaaac cgtaaagcaa gcagatggga ggcgtgttca gtaacttatt cataatgcat
6661 ctgaaatgat tgctgtactc aaatatttaa cgttagagta atagtatttt gaatgaaaac
6721 catagttgat tgtct SEQ ID NO: 10 Human MDM2 Isoform 1 Amino Acid Sequence (NP_001265391.1)
1 MCNTNMSVPT DGAVTTSQIP ASEQETLVRP KPLLLKLLKS VGAQKDTYTM KEDLDAGVSE
61 HSGDWLDQDS VSDQFSVEFE VESLDSEDYS LSEEGQELSD EDDEVYQVTV YQAGESDTDS
121 FEEDPEISLA DYWKCTSCNE MNPPLPSHCN RCWALRENWL PEDKGKDKGE ISEKAKLENS
181 TQAEEGFDVP DCKKTIVNDS RESCVEENDD KITQASQSQE SEDYSQPSTS SSIIYSSQED
241 VKEFEREETQ DKEESVESSL PLNAIEPCVI CQGRPKNGCI VHGKTGHLMA CFTCAKKLKK
301 RNKPCPVCRQ PIQMIVLTYF P SEQ ID NO: 11 Mouse MDM2 Transcript Variant 1 cDNA Sequence (NM_010786.4; CDS: 295-1764)
1 gttctctccg cggacggtag ggggcgctcg tcacagaact ctgctttgtt aacggggcct
61 ccggggccag cgtagcctag gagcggccgg tgaggagccg ccgccttctc gtcgctcgag
121 ctctggagcg accatggtcg ctcaggcccc ggccgcgggg cctccgcgct ccccgtgaag
181 ggtcggaaga tgcgcgggaa gtagcagccg tctgctgggc gagcgggaga ccgaccggac
241 acccctgggg gaccctctcg gatcaccgcg cttctcctgc gggcctccag gccaatgtgc
301 aataccaaca tgtctgtgtc taccgagggt gctgcaagca cctcacagat tccagcttcg
361 gaacaagaga ctctggttag accaaaacca ttgcttttga agttgttaaa gtccgttgga
421 gcgcaaaacg acacttacac tatgaaagag attatatttt atattggcca gtatattatg
481 actaagaggt tatatgacga gaagcagcag cacattgtgt attgttcaaa tgatctccta
541 ggagatgtgt ttggagtccc gagtttctct gtgaaggagc acaggaaaat atatgcaatg
601 atctacagaa atttagtggc tgtaagtcag caagactctg gcacatcgct gagtgagagc
661 agacgtcagc ctgaaggtgg gagtgatctg aaggatcctt tgcaagcgcc accagaagag
721 aaaccttcat cttctgattt aatttctaga ctgtctacct catctagaag gagatccatt
781 agtgagacag aagagaacac agatgagcta cctggggagc ggcaccggaa gcgccgcagg
841 tccctgtcct ttgatccgag cctgggtctg tgtgagctga gggagatgtg cagcggcggc
901 agcagcagca gtagcagcag cagcagcgag tccacagaga cgccctcgca tcaggatctt
961 gacgatggcg taagtgagca ttctggtgat tgcctggatc aggattcagt ttctgatcag
1021 tttagcgtgg aatttgaagt tgagtctctg gactcggaag attacagcct gagtgacgaa TABLE 1-continued 1081 gggcacgagc tctcagatga ggatgatgag gtctatcggg tcacagtcta tcagacagga
1141 gaaagcgata cagactcttt tgaaggagat cctgagattt ccttagctga ctattggaag
1201 tgtacctcat gcaatgaaat gaatcctccc cttccatcac actgcaaaag atgctggacc
1261 cttcgtgaga actggcttcc agacgataag gggaaagata aagtggaaat ctctgaaaaa
1321 gccaaactgg aaaactcagc tcaggcagaa gaaggcttgg atgtgcctga tggcaaaaag
1381 ctgacagaga atgatgctaa agagccatgt gctgaggagg acagcgagga gaaggccgaa
1441 cagacgcccc tgtcccagga gagtgacgac tattcccaac catcgacttc cagcagcatt
1501 gtttatagca gccaagaaag cgtgaaagag ttgaaggagg aaacgcagga caaagacgag
1561 agtgtggaat ctagcttctc cctgaatgcc atcgaaccat gtgtgatctg ccaggggcgg
1621 cctaaaaatg gctgcattgt tcacggcaag actggacacc tcatgtcatg tttcacgtgt
1681 gcaaagaagc taaaaaaaag aaacaagccc tgcccagtgt gcagacagcc aatccaaatg
1741 attgtgctaa cttacttcaa ctagctgacc tgctcacaaa aatagaattt tatatttcta
1801 actatatgac ccccaaatta gacaacatgg gtattatttt tatacattaa agccagaaaa
1861 ctgtcttagt ccacataaaa ttcacttata atttatcctg gagagtaaat atggtgaata
1921 ttttcttcct ttttagggaa atttcacttg tttattttat atttgtgttt taagtaattt
1981 gcattggctg tttatatttt ccttatattt taaataatct ccgcttggaa ggactttgga
2041 agtgtatgtg agaagtcctt tccatctcct gcagatgatg gtggaccttc ctcatcaagg
2101 gctacagaag tacttgattt ctgttttttt tgttaataat aagaacattt aatttattta
2161 gtgtctttca tgtaaagagt taaagactat gtgaaggatt gtatatttaa gttattgaaa
2221 ttctgaaact gtagtaatct aaaatgtgtg agttgtgggc tgcagagaag actcagccag
2281 taaaggcacc tgctgtgtac acccactgac acacatttga tccttggaac ccccaggaag
2341 agtgaaccag ttccacaaag ttgttccctg atcttcaaat ggatgcacgc atgcacgcac
2401 acacacgcgc gcgtgcgcac acacacacac acacacacac acacacacac acacacacac
2461 acacacacag ttttaaaggc atgaattgca tctggtggta tgtaagtgaa aacacacgcc
2521 ttattttcca gcattttcag ctttttgtca taggggtgtg gcacaagtgt tgcagtttgt
2581 cccaggttga aaagcctgag gctggtagaa gcgccttttt gcctcagctc cgtggttcct
2641 ggtggttgcc tatgtttcag gcctgtactt aggctaggtt tagaaaccag cccattcaga
2701 aagactgaat cagaacatgg ataaagtgaa ctcattctaa gatgactcgt ctatccatgt
2761 agattaatct cctggttcat aataggcctc ttccctttga ttgaagggtc acgtctaagt
2821 atagaaaaca taaaactgta aggtagagga agcgaaggat agctttgtat taatgttgcg
2881 ttaaagcttc agagacaaga acaagaacac tcctcccacg tgacagcatt tgaataggag
2941 gcggtgggtg cggcagcctg ggcagcttca gtcccgattt acaataaagt accttgtgtg
3001 ttattagttc ttaaatgttt atttagaaat ggcattgatg ttatttattt gcaaataaat
3061 ggtttattga agaattgtga aagagatttg tcttacacaa aaaaaaaaaa aaaaaaaaaa
3121 aaaa SEQ ID NO: 12 Mouse MDM2 Isoform 1 Amino Acid Sequence (NP_034916.1)
1 MCNTNMSVST EGAASTSQIP ASEQETLVRP KPLLLKLLKS VGAQNDTYTM KEIIFYIGQY
61 IMTKRLYDEK QQHIVYCSND LLGDVFGVPS FSVKEHRKIY AMIYRNLVAV SQQDSGTSLS
121 ESRRQPEGGS DLKDPLQAPP EEKPSSSDLI SRLSTSSRRR SISETEENTD ELPGERHRKR
181 RRSLSFDPSL GLCELREMCS GGSSSSSSSS SESTETPSHQ DLDDGVSEHS GDOLDQDSVS
241 DQFSVEFEVE SLDSEDYSLS DEGHELSDED DEVYRVTVYQ TGESDTDSFE GDPEISLADY
301 WKCTSCNEMN PPLPSHCKRC WTLRENWLPD DKGKDKVEIS EKAKLENSAQ AEEGLDVPDG
361 KKLTENDAKE PCAEEDSEEK AEQTPLSQES DDYSQPSTSS SIVYSSQESV KELKEETQDK
421 DESVESSFSL NAIEPCVICQ GRPKNGCIVH GKTGHLMSCF TCAKKLKKRN KPCPVCRQPI
481 QMIVLTYFN SEQ ID NO: 13 Mouse MDM2 Transcript Variant 2 cDNA Sequence
(NM_001288586.2 CDS: 357-1679)
1 gttctctccg cggacggtag ggggcgctcg tcacagaact ctgctttgtt aacggggcct
61 ccggggccag cgtagcctag gagcggccgg tgaggagccg ccgccttctc gtcgctcgag
121 ctctggagcg accatggtcg ctcaggcccc ggccgcgggg cctccgcgct ccccgtgaag
181 ggtcggaaga tgcgcgggaa gtagcagccg tctgctgggc gagcgggaga ccgaccggac
241 accccctgggg gaccctctcg gatcaccgcg cttctcctgc gggcctccag gttagaccaa
301 aaccattgct tttgaagttg ttaaagtccg ttggagcgca aaacgacact tacactatga
361 aagagattat attttatatt ggccagtata ttatgactaa gaggttatat gacgagaagc
421 agcagcacat tgtgtattgt tcaaatgatc tcctaggaga tgtgtttgga gtcccgagtt
481 tctctgtgaa ggagcacagg aaaatatatg caatgatcta cagaaattta gtggctgtaa
541 gtcagcaaga ctctggcaca tcgctgagtg agagcagacg tcagcctgaa ggtgggagtg
601 atctgaagga tcctttgcaa gcgccaccag aagagaaacc ttcatcttct gatttaattt
661 ctagactgtc tacctcatct agaaggagat ccattagtga gacagaagag aacacagatg
721 agctacctgg ggagcggcac cggaagcgcc gcaggtccct gtcctttgat ccgagcctgg
781 gtctgtgtga gctgagggag atgtgcagcg gcggcagcag cagcagtagc agcagcagca
841 gcgagtccac agagacgccc tcgcatcagg atcttgacga tggcgtaagt gagcattctg
901 gtgattgcct ggatcaggat tcagtttctg atcagtttag cgtggaattt gaagttgagt
961 ctctggactc ggaagattac agcctgagtg acgaagggca cgagctctca gatgaggatg
1021 atgaggtcta tcgggtcaca gtctatcaga caggagaaag cgatacagac tcttttgaag
1081 gagatcctga gatttcctta gctgactatt ggaagtgtac ctcatgcaat gaaatgaatc
1141 ctccccttcc atcacactgc aaaagatgct ggacccttcg tgagaactgg cttccagacg
1201 ataaggggaa agataaagtg gaaatctctg aaaaagccaa actggaaaac tcagctcagg
1261 cagaagaagg cttggatgtg cctgatggca aaaagctgac agagaatgat gctaaagagc
1321 catgtgctga ggaggacagc gaggagaagg ccgaacagac gcccctgtcc caggagagtg
1381 acgactattc ccaaccatcg acttccagca gcattgttta tagcagccaa gaaagcgtga
1441 aagagttgaa ggaggaaacg caggacaaag acgagagtgt ggaatctagc ttctccctga
1501 atgccatcga accatgtgtg atctgccagg ggcggcctaa aaatggctgc attgttcacg
1561 gcaagactgg acacctcatg tcatgtttca cgtgtgcaaa gaagctaaaa aaaagaaaca
1621 agccctgccc agtgtgcaga cagccaatcc aaatgattgt gctaacttac ttcaactagc
1681 tgacctgctc acaaaaatag aattttatat ttctaactat atgaccccca aattagacaa
1741 catgggtatt atttttatac attaaagcca gaaaactgtc ttagtccaca taaaattcac
1801 ttataattta tcctggagag taaatatggt gaatattttc ttccttttta gggaaatttc TABLE 1-continued 1861 acttgtttat tttatatttg tgttttaagt aatttgcatt ggctgtttat attttcctta
1921 tattttaaat aatctccgct tggaaggact ttggaagtgt atgtgagaag tcctttccat
1981 ctcctgcaga tgatggtgga ccttcctcat caagggctac agaagtactt gatttctgtt
2041 tttttgtta ataataagaa catttaattt atttagtgtc tttcatgtaa agagttaaag
2101 actatgtgaa ggattgtata tttaagttat tgaaattctg aaactgtagt aatctaaaat
2161 gtgtgagttg tgggctgcag agaagactca gccagtaaag gcacctgctg tgtacaccca
2221 ctgacacaca tttgatcctt ggaaccccca ggaagagtga accagttcca caaagttgtt
2281 ccctgatctt caaatggatg cacgcatgca cgcacacaca cgcgcgcgtg cgcacacaca
2341 cacacacaca cacacacaca cacacacaca cacacacaca cacagtttta aaggcatgaa
2401 ttgcatctgg tggtatgtaa gtgaaaacac acgccttatt ttccagcatt ttcagctttt
2461 tgtcataggg gtgtggcaca agtgttgcag tttgtcccag gttgaaaagc ctgaggctgg
2521 tagaagcgcc tttttgcctc agctccgtgg ttcctggtgg ttgcctatgt ttcaggcctg
2581 tacttaggct aggtttagaa accagcccat tcagaaagac tgaatcagaa catggataaa
2641 gtgaactcat tctaagatga ctcgtctatc catgtagatt aatctcctgg ttcataatag
2701 gcctcttccc tttgattgaa gggtcacgtc taagtataga aaacataaaa ctgtaaggta
2761 gaggaagcga aggatagctt tgtattaatg ttgcgttaaa gcttcagaga caagaacaag
2821 aacactcctc ccacgtgaca gcatttgaat aggaggcggt gggtgcggca gcctgggcag
2881 cttcagtccc gatttacaat aaagtacctt gtgtgttatt agttcttaaa tgtttattta
2941 gaaatggcat tgatgttatt tatttgcaaa taaatggttt attgaagaat tgtgaaagag
3001 atttgtctta cacaaaaaaa aaaaaaaaaa aaaaaaaaa SEQ ID NO: 14 Mouse MDM2 Isoform 2 Amino Acid Sequence (NP_001275515.1)
1 MKEIIFYIGQ YIMTKRLYDE KQQHIVYCSN DLLGDVFGVP SFSVKEHRKI YAMIYRNLVA
61 VSQQDSGTSL SESRRQPEGG SDLKDPLQAP PEEKPSSSDL ISRLSTSSRR RSISETEENT
121 DELPGERHRK RRRSLSFDPS LGLCELREMC SGGSSSSSSS SSESTETPSH QDLDDGVSEH
181 SGDCLDQDSV SDQFSVEFEV ESLDSEDYSL SDEGHELSDE DDEVYRVTVY QTGESDTDSF
241 EGDPEISLAD YWKCTSCNEM NPPLPSHCKR CWTLRENWLP DDKGKDKVEI SEKAKLENSA
301 QAEEGLDVPD GKKLTENDAK EPCAEEDSEE KAEQTPLSQE SDDYSQPSTS SSIVYSSQES
361 VKELKEETQD KDESVESSFS LNAIEPCVIC QGRPKNGCIV HGKTGHLMSC FTCAKKLKKR
421 NKPCPVCRQP IQMIVLTYFN SEQ ID NO: 15 Human MDM4 Transcript Variant 1 cDNA Sequence
(NM_002393.4; CDS: 167-1639)
1 gtgtgggagg ccggaagttg cggcttcatt actcgccatt tcaaaatgct gccgaggccc
61 taggatctgt gactgccacc cctcccccca cccgggctcg gcgggggagc gactcatgga
121 gctgccgtaa gttttaccaa cagactgcag tttcttcact accaaaatga catcattttc
181 cacctctgct cagtgttcaa catctgacag tgcttgcagg atctctcctg gacaaatcaa
241 tcaggtacga ccaaaactgc cgcttttgaa gattttgcat gcagcaggtg cgcaaggtga
301 aatgttcact gttaaagagg tcatgcacta tttaggtcag tacataatgg tgaagcaact
361 ttatgatcag caggagcagc atatggtata ttgtggtgga gatcttttgg gagaactact
421 gggacgtcag agcttctccg tgaaagaccc aagccctctc tatgatatgc taagaaagaa
481 tcttgtcact ttagccactg ctactacaga tgctgctcag actctcgctc tcgcacagga
541 tcacagtatg gatattccaa gtcaagacca actgaagcaa agtgcagagg aaagttccac
601 ttccagaaaa agaactacag aagacgatat ccccacactg cctacctcag agcataaatg
661 catacattct agagaagatg aagacttaat tgaaaattta gcccaagatg aaacatctag
721 gctggacctt ggatttgagg agtgggatgt agctggcctg ccttggtggt ttttaggaaa
781 cttgagaagc aactatacac ctagaagtaa tggctcaact gatttacaga caaatcagga
841 tgtgggtact gccattgttt cagatactac agatgacttg tggtttttga atgagtcagt
901 atcagagcag ttaggtgttg gaataaaagt tgaagctgct gatactgaac aaacaagtga
961 agaagtaggg aaagtaagtg acaaaaaggt gattgaagtg ggaaaaaatg atgacctgga
1021 ggactctaag tccttaagtg atgataccga tgtagaggtt acctctgagg atgagtggca
1081 gtgtactgaa tgcaagaaat ttaactctcc aagcaagagg tactgttttc gttgttgggc
1141 cttgaggaag gattggtatt cagattgttc aaagttaacc cattctctct ccacgtctga
1201 tatcactgcc atacctgaaa aggaaaatga aggaaatgat gtccctgatt gtcgaagaac
1261 catttcggct cctgtcgtta gacctaaaga tgcgtatata aagaaagaaa actccaaact
1321 ttttgatccc tgcaactcag tggaattctt ggatttggct cacagttctg aaagccaaga
1381 gaccatctca agcatgggag aacagttaga taacctttct gaacagagaa cagatacaga
1441 aaacatggag gattgccaga atctcttgaa gccatgtagc ttatgtgaga aaagaccacg
1501 agacgggaac attattcatg gaaggacggg ccatcttgtc acttgttttc actgtgccag
1561 aagactaaag aaggctgggg cttcatgccc tatttgcaag aaagagattc agctggttat
1621 taaggttttt atagcataat ggtagtacga acataaaaat gcatttattc cgttcactta
1681 ccacattatt tgaaaatcaa tcctttattt aattttattt ccaacctgtc agagaatgtt
1741 cttaggcatc aaaatccaag gtagctgtaa gaaaaatact ggagctaaca atgaagaaca
1801 gaagtaatct gattagtcaa attattaagt gccatggatt actttatgca gcagtcaggt
1861 acatagttag gtgaacccaa aagaaaaact cttgaaaaca agagatttct tccatgcaca
1921 tttacaatat tgaggtataa ttaacatgat aaagtgtttc cttctaacga gttgtagaaa
1981 tctgagtaac cacccaaaaa agcaatagaa tgtttctgtc accccaaaac actcccttct
2041 gcccctcttc agacagtcct tcagctattt catggctctc accctagttt tttttttttt
2101 tgcacttttt tttttccggg ggtatagggg aggtgtgggg cgacagggtc tgtcttgttc
2161 tgtctcccag gctgaagtgc agtgcagtgg tatgatcatg gctcactgca gccttggttt
2221 cctgggcata agtggtcttc ccacttcagc ctcctgagta gctgagacta tagactagca
2281 taaccacact ggctaatttt ttgtggagat gaagtctcac tatgttgccc aggctggtct
2341 cgaactcctg ggctcaaaca atcctcccgc ctcagccttc caaattgctg ggattatagt
2401 catgaggcac ctagtctggc ccttttgcaa gactttaatc tgaaatctaa atttttaaaa
2461 tttaagtact tacaaaggat atactatcca acatattgca tattatatat gtgctttaaa
2521 gttttttttt ttttttgaga gacggtctca ctttgtcatc caagctggag tgcagtggtg
2581 caaacacggc ccacctcctg ggctcaagtg atcctccagc ctcagcttcc ctcacaggca
2641 ttcactatca ctcccagcta attaaaataa tttgtagacg gtgtctcgtt atgttgccca
2701 ggctggtctc gaactcctgg gtttaagtga ttcccccgcc tcagcctccc aaagtgttgg
2761 gcttacagcc ttgagccact atgcttggct caaagatatt tttatgaaag ccctgggact TABLE 1-continued

| | | | | | | |
|---|---|---|---|---|---|---|
| 2821 | atagatttag | ctgattaaat | ttatagaaaa | agtcctgtca | tataaactgg | caaagtctgt |
| 2881 | tcttaattta | attagccaaa | tcagacttaa | cttccgtcag | aacatgtctt | ggttttaatt |
| 2941 | cagataaaca | cacaaacata | cttctctggc | acagccttca | gaagcatcag | tttttgtttt |
| 3001 | gttttgtttt | gtttttgag | acagggtctt | gctctgtcgc | ccaggctgga | gtgcactggc |
| 3061 | acaatcacag | ttcactgcag | cctcgacctc | ccagatccaa | gcaatcctcc | cacctaagcc |
| 3121 | tcccaagtag | ctgggtctat | aggcgcgtgc | caccaccatg | cccagctgaa | ttttgtattt |
| 3181 | tttgtacaga | cagcatttg | ccatgttgcc | caggctggtc | ccaaacttct | agcctcaagc |
| 3241 | aaccctcctg | cctcagcctc | tcaaagtgct | aggattgcag | tcctgagcta | ctgcccccta |
| 3301 | ccctctttgc | gtcttaggag | tcatttagat | tttttttgat | ccttttgttt | agtgcctctg |
| 3361 | gagctgctta | caccaaggca | atacgccttg | atatactgga | tggttgagag | gcagcctctt |
| 3421 | tttttttttt | tttttttttt | tttttttgga | ggatagggag | tatggctgtt | gtgaaaaggg |
| 3481 | aggtaaagag | aaatggtaga | tctgaagagg | cctcatcaga | gcacatattt | taggacaaca |
| 3541 | catatggaaa | ttggacatct | ttaagttggt | ttccatagag | ctatgcatgt | atccttaccc |
| 3601 | ccatgggaaa | atgttggtgt | gttctcaagg | gtatgcatgt | gtcattttga | agaccaaggc |
| 3661 | cctagaattg | tcaaacttaa | ggatcataaa | aatcatgagg | gttgcttgtt | aaaaatgtcc |
| 3721 | aaacgtgcag | agactgatct | ttgagatctg | gaccaggaat | ttgcatttga | acaagtgttc |
| 3781 | ctggaatctc | tatgcaagtt | ttatacagaa | catacttttg | gaatccttgc | cctagacagg |
| 3841 | ggtgtccaat | cttttggctt | ccctggtcca | caatggaaga | agaattgtct | tggaccacac |
| 3901 | ataaaataca | ctaacactaa | caatagctga | tgagctaaaa | aaaaaaaaaa | aaaaaatcgt |
| 3961 | ggaccgggcg | tagtggctca | cgcctgtaat | cccaacactt | tgggagatca | cctaggtcgg |
| 4021 | gagtttgaga | ccagcctgac | cgacatggag | aaaccccatt | tttactaaaa | atacaaaaaa |
| 4081 | ttagctgggc | atggtggtgc | atgcctgtag | tcccagctac | tcaggaggct | gaggcaggag |
| 4141 | aatcgcttga | acctgagagg | gggagattgc | ggtgagctga | gattgcgcca | ttgcacccca |
| 4201 | gcctgggcaa | caatagcgaa | actgtctcag | aaaaaagaaa | aaaaaaatcg | caaaaagaaa |
| 4261 | aatctcataa | tgtcgttgtt | ggtttttttt | tttttttttg | agacagtctc | actctgttgc |
| 4321 | ccaggctgga | gtgcaatggc | atgatctctg | ctcaccgcaa | cctctgcctc | ccgggttcag |
| 4381 | gtgattctcc | tgcctcagcc | tcccagatag | ctgggactac | aggcacatac | caccatgcct |
| 4441 | ggctaatttt | tgtattttta | gtagagatgg | gggtttcact | gtgttggcca | ggctggtctc |
| 4501 | gaactcctga | cctcatgatc | cacacacctc | ggcctcccaa | agtcctgcga | ttacaggcgt |
| 4561 | gagctaccgc | acccagccaa | gttgtaattt | ttaataaaac | ttaagaagta | aacattttac |
| 4621 | ttatgtttat | aggtatttga | tcctaaattt | gacacatcat | tgcccatgaa | agaatcctct |
| 4681 | taggctgctc | agcttcactc | ttcctgcttg | cccaccgggg | tttttcactg | cttctgttag |
| 4741 | cactaagtac | ttagacgatc | ctaagatatg | tgcttgagcc | gaatttcatc | tttacttgta |
| 4801 | ggaaacttta | aactatttct | tttcttttct | tttttttttt | tttttacttg | agatggagtt |
| 4861 | ttgctcttgt | cgcccaggct | ggagtgcagt | ggagtgatct | cggctcactg | caacctctgc |
| 4921 | ctcccgggtt | caaatgattc | tcctgcctca | gcctcccaag | tagctgggat | tacaggtgtg |
| 4981 | caccaccatg | tctggctaat | tttgtatttt | tagtagagat | ggtttcacca | tgttggtcag |
| 5041 | gctggtctcg | aactcctgac | ctcaggtcat | ccacccacct | cagcctcgca | aagtgctgag |
| 5101 | attacaggca | tgagccacag | cgcccagctt | aaactatttt | cttggtctgt | ttttgatttt |
| 5161 | ctttttttcct | tgccactgcg | gtacagattt | tttttactca | ctgccactaa | actaaagcaa |
| 5221 | ggcatagttt | atatgtgaag | tgttcagagt | ttactgctat | aaggaaactt | ccaaatactg |
| 5281 | acatttacct | tttagctgta | gttattggga | ccatgtgctc | tggttttctg | gagactgcca |
| 5341 | aattgctccc | atttttctgc | atcccacctg | gtttctttct | gcatgtcccc | tttcactttc |
| 5401 | aaacctcttc | atttggatgt | taaattatat | ggtcacctag | ttataggtaa | gccttgttcg |
| 5461 | agttgatatc | ttgattgtga | ggaaggatct | gtgtcattgg | agcttgtttc | tgctgcaacg |
| 5521 | tgctgtagac | tatgaataat | gaaatcacac | cacattacca | tcagatttct | tgttttagtt |
| 5581 | gtcaaattaa | tatttatgat | tgttatcttg | ggcgaaaagt | tcagagcaga | gatgacaaat |
| 5641 | cattagaaca | acgatgaatt | tcagtattac | ggctaaaaag | ttcttctgtc | tgaatattaa |
| 5701 | ctcactctcc | ttccagtgta | cttcacagta | attggtatgc | tttttatttt | aatgcttaaa |
| 5761 | tcaaacttta | taaaaatctt | agaccagatc | tttaatatgg | tatgccattt | ccccagtcta |
| 5821 | ccaatggaat | agtatgggtt | tctaatccta | ggcttgtaca | atggattgga | gttgagccat |
| 5881 | gccagcctcc | acactgccac | taacttctgt | aatgtaagat | tgagtcactg | ccaagcattt |
| 5941 | gaaatatgca | gttgtgtttt | aattataatt | tatgtatagt | tagatgtatg | tagtgcattg |
| 6001 | tgtggtatta | tttggtttgt | aagaatttat | ttttaagggt | caaggtcatt | tgtaacattt |
| 6061 | tgtgtgtgtc | aattcaatgc | aatgttggct | gccttttgaa | gtctttgata | tattggtgaa |
| 6121 | tattcttctg | atctataata | caaagctatg | taatgttacc | tcttgactcg | cttttgaaag |
| 6181 | gaagacaatt | gttaactaga | tatttgagtt | ttttcccctc | agaattatgt | gaatttctga |
| 6241 | tatatggctt | tagatactgt | gaatctgttt | tccatttagt | cagttatctg | cttaaattgt |
| 6301 | tcagaactat | atcctaacga | gcaattagtt | ctgatggttc | tcccagtcat | gagtgtgcat |
| 6361 | gtgtgcaagc | atgttttgat | cctgatgcta | cctttgctaa | aaatggccat | agattaggaa |
| 6421 | ctagctatgt | ttttagaatc | aaagatgaac | cggtaagctg | tctcatgtac | caaacgtgaa |
| 6481 | atttacagtg | tttacaaatg | tctggaattt | tgcactgcca | tagggaatgt | taaggttact |
| 6541 | tggctggaat | ttatcagact | tgtgagtaaa | caagttgaag | tttagcagat | gagggggaat |
| 6601 | attgaggccc | ctaaggctaa | acaaaataat | cagtatctga | gatagtggct | aatgtggctc |
| 6661 | cccaggccta | atttgggaac | agtttttcct | gattgctttg | agaagtactt | tcttttgaca |
| 6721 | gaaattttca | ttctgcttgc | cattgctata | ttctcccttt | ataggagcca | ttggatttct |
| 6781 | ttccttttgt | gggaaatgtc | ccattagcat | tttcagatct | tttgatgtgc | actaatgcca |
| 6841 | ttattggtaa | tgccgttatt | ggtgaataca | gcatagttaa | ataaactgtt | acagtaaatc |
| 6901 | tacacttgga | tttgctgcac | ctctaccaat | agccttttga | atgactgaaa | gtgttaacag |
| 6961 | agaaagaggc | atgtctgcag | aaagagatag | ctaatatttt | ttggtacttt | atctgaaatc |
| 7021 | caagatgctg | cttcccctgc | aggttgtttt | ccttcttacg | atcctcattg | aatcccctct |
| 7081 | gggagcacag | gacagttagt | agaactctcc | atttcttttt | tttttttttt | agacggagtc |
| 7141 | tctctctgtc | gccccggctg | gagtgcagtg | gcgcgatctc | ggctcactgc | aacctccgcc |
| 7201 | tcccgggttc | accccattct | cctgcctcag | cctccctagt | agctgggact | ataggcgccc |
| 7261 | gccaccacgc | ctggctaatt | tttgtatttt | tattggagac | ggggtttcac | cgtcttagcc |
| 7321 | aggatggtct | tgatctcctg | acctcgtgat | ctgcccacct | cagcctccca | aagtactggg |
| 7381 | attacaggcg | tgagccaccg | cgcccggccg | gaactctcca | tttcttaagg | taaagagggt |
| 7441 | caaggatacc | taaaaagggt | caaataatgc | tagaagagca | attcctcttt | cagagcagtt |
| 7501 | gctgtaattt | ggcaaatgct | ttatcgaaga | ttgatattag | gctaggggcg | gtggcttacg |
| 7561 | cctgtaatcc | cagcactttg | ggaggccgag | gtgggtggat | tgcctgagct | caggagttcg |

TABLE 1-continued

```
 7621agaccagtct gaccagtatg gtgaaaccct gtctctacta aaaatacaaa aattagccgg
 7681tcgtggtggc gtgcacctgt agtcccagct acttggcagg ttgagacagg agaatcgctt
 7741gaacctggga ggtggaggtt gcagtgagcc gagactgcac cactgcgctc ccacctgggt
 7801gacagagact ctgtctcaaa aaaaaggaca tttatcatta taacatctta ttagagcccc
 7861taatttctta tctgaaggca ctgttttttt ttttaaacag ttaagtactg atgtcaacag
 7921acaaatattt ctgatcagat agtcccctgt caacagtagc aaatgtggtt tcataaagtg
 7981ggaagaaaac agcattttaa agtaactttt tgggagactg atttgagtaa taataaaact
 8041ctggtctccc ttaagaaaaa aaaacccttc cacctttact gtgtcattta tatcccctta
 8101gttccaaagt taattatctt atttctggat attgctttta taccaaagac ccttatcagc
 8161ccttgtaact acagtatctt tagataagat tcctctttcc agtcagtcct gggaaatgtt
 8221tctgttgcag agttaggcgg tagatgggaa gctgtgatgg cagagctact atctaataaa
 8281gtaacaactc gtagttgagg cttcctttct gtgtgtgatg ggggataggg agttagctcc
 8341cctgttgtct cagcactaag aaattgaggt caggccaggc gcggtggttc actcctgtta
 8401ttccagcact ggggtggcca aagtgggcag attgcttgcg ctctggagct cgagaccagc
 8461ctgggcaaca tggtgaaacc ctgtctctac caaaaataca aaaaaaaagc tgggcatggt
 8521gggtgcatgc ttgtcccagc tactgaggag gctgaggtgg gaggatcgct tgagcctggg
 8581aggtggaggt tgcagtgagc tgagatggca ccactgcaat ccaaggtggg tgacagagac
 8641gctgtctcaa agaaattgag gtcaggcttc cttcttacag aattattttt ttctctgtag
 8701tttgcctcat tttttcactt tcttttcaat gagaatcgaa gtgtttcttt tgggtttttt
 8761tttccccctt ttaaaatcaa caggaaatgt ttcaaaggag ggatgaaatg cttcttggct
 8821tcctcagcac ttggcaaggt agacctcata gcaaccttga atatgacttt ctttagtctc
 8881tagctatgca ctattaagtg cctcttgggt agaggtagag ttaagtattg agtgccagtc
 8941ttgacgtccg tatgcctcag tttttctcat atataaaaag cagtatacat acctaccctt
 9001ttctacctca tcatttgttg tagggattaa atccgggaga gcaattctga agcctataaa
 9061tttccttgaa gagatctaag aacctattat gctcttggtg taccaagctc tggggtatat
 9121attcagaata cctcatgttc tggaagctga gcactagctc cccttaattg cctgcctggc
 9181agagcctgtt tgattactgc aggccctttt acccatgctt ctagtttagg tattctttct
 9241ttgatatgag gctcttgacc agaaaagagt tctttctcta ggtgttctga gagaagtttg
 9301taaatttgga tagtacattc tatcctgata aaaccacctt gctgtggtct tgatgtacaa
 9361aaaaaaaattt tttttttgag acagagtctt actctgtcac ccaggctgga atgcagtggc
 9421gcaatcttgg ttcactgcaa cccccgcctc ctgggttcaa gcgatcctcc tgcctcaacc
 9481tctcaagtag ctgggactac aggcgtgcac caccacacct ggctaatttt gtatttttag
 9541tagagacagg gtttcaccat gttggccagg ctggtcttga actcctgacc tcaggcgatc
 9601tgcccgcctt ggcctcccaa agtactggga ttacaggcgt gagcaactgc tcctggccca
 9661aaacatctct ttctacatac acttgagtag gtggcataaa atgcactgtc aatatataga
 9721aaacatgaaa ttttccaaat atttccgatc agagaatcac aagagcagca aatgtggttt
 9781catcaagtgg gaagaaagca gcaatttaaa ataacttttt gggagactga attgagtaat
 9841aataaaactt cagtctttcg ctaataataa taataataat aataataaca acaacttatt
 9901gaatgtggcc agctcactag atgaggaaag aggaaggcat tttctgcatt cttgcctagt
 9961tttccttata agcaccacta agttaatagc tctgtctttt tggtgtttgc actatgtaat
10021gcttttaata ctttttaatt gtgctttttt atgtattaaa tgtttttcct tttgccaaaa
10081aaaaaaaaaa
```

SEQ ID NO: 16 Human MDM4 Isoform 1 Amino Acid Sequence (NP_002384.2)

```
    1MTSFSTSAQC STSDSACRIS PGQINQVRPK LPLLKILHAA GAQGEMFTVK EVMHYLGQYI
   61MVKQLYDQQE QHMVYCGGDL LGELLGRQSF SVKDPSPLYD MLRKNLVTLA TATTDAAQTL
  121ALAQDHSMDI PSQDQLKQSA EESSTSRKRT TEDDIPTLPT SEHKCIHSRE DEDLIENLAQ
  181DETSRLDLGF EEWDVAGLPW WFLGNLRSNY TPRSNGSTDL QTNQDVGTAI VSDTTDDLWF
  241LNESYSEQLG VGIKVEAADT EQTSEEVGKV SDKKVIEVGK NDDLEDSKSL SDDTDVEVTS
  301EDEWQCTECK KFNSPSKRYC FRCWALRKDW YSDCSKLTHS LSTSDITAIP EKENEGNDVP
  361DCRRTISAPV VRPKDAYIKK ENSKLFDPCN SVEFLDLAHS SESQETISSM GEQLDNLSEQ
  421RTDTENMEDC QNLLKPCSLC EKRPRDGNII HGRTGHLVTC FHCARRLKKA GASCPICKKE
  481IQLVIKVFIA
```

SEQ ID NO: 17 Human MDM4 Transcript Variant 2 cDNA Sequence
(NM_001204171.1; CDS: 167-1489)

```
    1gtgtgggagg ccggaagttg cggcttcatt actcgccatt tcaaaatgct gccgaggccc
   61taggatctgt gactgccacc cctcccccca cccgggctcg gcgggggagc gactcatgga
  121gctgccgtaa gttttaccaa cagactgcag tttcttcact accaaaatga catcattttc
  181cacctctgct cagtgttcaa catctgacag tgcttgcagg atctctcctg gacaaatcaa
  241tcaggtacga ccaaaactgc cgcttttgaa gattttgcat gcagcaggtg cgcaaggtga
  301aatgttcact gttaaagagg tcatgcacta tttaggtcag tacataatgg tgaagcaact
  361ttatgatcag caggagcagc atatggtata ttgtggtgga gatcttttgg gagaactact
  421gggacgtcag agcttctccg tgaaagaccc aagccctctc tatgatatgc taagaaagaa
  481tcttgtcact ttagccactg ctactacaga tgctgctcag actctcgctc tcgcacagga
  541tcacagtatg gatattccaa gtcaagacca actgaagcaa agtgcagagg aaagttccac
  601ttccagaaaa agaactacag aagacgatat ccccacactg cctacctcag agcataaatg
  661catacattct agagaagatg aagacttaat tgaaaattta gcccaagatg aaacatctag
  721gctggacctt ggatttgagg agtgggatgt agctggcctg ccttggtggt tttaggaaa
  781cttgagaagc aactatacac ctagaagtaa tggctcaact gatttacaga caaatcaggt
  841gattgaagtg ggaaaaaatg atgacctgga ggactctaag tccttaagtg atgataccga
  901tgtagaggtt acctctgagg atgagtggca gtgtactgaa tgcaagaaat ttaactctcc
  961aagcaagagg tactgtttc gttgttgggc cttgaggaag gattggtatt cagattgttc
 1021aaagttaacc cattctctct ccacgtctga tatcactgcc atacctgaaa aggaaaatga
 1081aggaaatgat gtccctgatt gtcgaagaac catttcggct cctgtcgtta gacctaaaga
 1141tgcgtatata aagaaagaaa actccaaact tttgatccc tgcaactcag tggaattctt
 1201ggatttggct cacagttctg aaagccaaga gaccatctca agcatgggag aacagttaga
 1261taacctttct gaacagagaa cagatacaga aaacatggag gattgccaga atctcttgaa
 1321gccatgtagc ttatgtgaga aaagaccacg agacgggaac attattcatg gaaggacggg
 1381ccatcttgtc acttgttttc actgtgccag aagactaaag aaggctgggg cttcatgccc
```

TABLE 1-continued

| | | | | | | |
|---|---|---|---|---|---|---|
| 1441 | tatttgcaag | aaagagattc | agctggttat | taaggttttt | atagcataat | ggtagtacga |
| 1501 | acataaaaat | gcatttattc | cgttcactta | ccacattatt | tgaaaatcaa | tcctttattt |
| 1561 | aattttattt | ccaacctgtc | agagaatgtt | cttaggcatc | aaaatccaag | gtagctgtaa |
| 1621 | gaaaaatact | ggagctaaca | atgaagaaca | gaagtaatct | gattagtcaa | attattaagt |
| 1681 | gccatggatt | actttatgca | gcagtcaggt | acatagttag | gtgaacccaa | aagaaaaact |
| 1741 | cttgaaaaca | agagatttct | tccatgcaca | tttacaatat | tgaggtataa | ttaacatgat |
| 1801 | aaagtgtttc | cttctaacga | gttgtagaaa | tctgagtaac | cacccaaaaa | agcaatagaa |
| 1861 | tgtttctgtc | accccaaaac | actcccttct | gcccctcttc | agacagtcct | tcagctattt |
| 1921 | catggctctc | accctagttt | tttttttttt | tgcacttttt | tttttccggg | ggtatagggg |
| 1981 | aggtgtgggg | cgacagggtc | tgtcttgttc | tgtctcccag | gctgaagtgc | agtgcagtgg |
| 2041 | tatgatcatg | gctcactgca | gccttggttt | cctgggcata | agtggtcttc | ccacttcagc |
| 2101 | ctcctgagta | gctgagacta | tagactagca | taaccacact | ggctaatttt | ttgtggagat |
| 2161 | gaagtctcac | tatgttgccc | aggctggtct | cgaactcctg | ggctcaaaca | atcctcccgc |
| 2221 | ctcagccttc | caaattgctg | ggattatagt | catgaggcac | ctagtctggc | ccttttgcaa |
| 2281 | gactttaatc | tgaaatctaa | atttttaaaa | tttaagtact | tacaaaggat | atactatcca |
| 2341 | acatattgca | tattatatat | gtgctttaaa | gttttttttt | ttttttgaga | gacggtctca |
| 2401 | ctttgtcatc | caagctggag | tgcagtggtg | caaacacggc | ccacctcctg | ggctcaagtg |
| 2461 | atcctccagc | ctcagcttcc | ctcacaggca | ttcactatca | ctcccagcta | attaaaataa |
| 2521 | tttgtagacg | gtgtctcgtt | atgttgccca | ggctggtctc | gaactcctgg | gtttaagtga |
| 2581 | ttcccccgcc | tcagcctccc | aaagtgttgg | gcttacagcc | ttgagccact | atgcttggct |
| 2641 | caaagatatt | tttatgaaag | ccctgggact | atagatttag | ctgattaaat | ttatagaaaa |
| 2701 | agtcctgtca | tataaactgg | caaagtctgt | tcttaattta | attagccaaa | tcagacttaa |
| 2761 | cttccgtcag | aacatgtctt | ggttttaatt | cagataaaca | cacaaacata | cttctctggc |
| 2821 | acagccttca | gaagcatcag | tttttgtttt | gttttgtttt | gtttttttgag | acagggtctt |
| 2881 | gctctgtcgc | ccaggctgga | gtgcactggc | acaatcacag | ttcactgcag | cctcgacctc |
| 2941 | ccagatccaa | gcaatcctcc | cacctaagcc | tcccaagtag | ctgggtctat | aggcgcgtgc |
| 3001 | caccaccatg | cccagctgaa | ttttgtattt | tttgtacaga | cagcattttg | ccatgttgcc |
| 3061 | caggctggtc | ccaaacttct | agcctcaagc | aaccctcctg | cctcagcctc | tcaaagtgct |
| 3121 | aggattgcag | tcctgagcta | ctgcccccta | ccctctttgc | gtcttaggag | tcatttagat |
| 3181 | tttttttgat | ccttttgttt | agtgcctctg | gagctgctta | caccaaggca | atacgccttg |
| 3241 | atatactgga | tggttgagag | gcagcctctt | tttttttttt | tttttttttt | ttttttttgga |
| 3301 | ggatagggag | tatggctgtt | gtgaaaaggg | aggtaaagag | aaatggtaga | tctgaagagg |
| 3361 | cctcatcaga | gcacatattt | taggacaaca | catatggaaa | ttggacatct | ttaagttggt |
| 3421 | ttccatagag | ctatgcatgt | atccttaccc | ccatgggaaa | atgttggtgt | gttctcaagg |
| 3481 | gtatgcatgt | gtcattttga | agaccaaggc | cctagaattg | tcaaacttaa | ggatcataaa |
| 3541 | aatcatgagg | gttgcttgtt | aaaaatgtcc | aaacgtgcag | agactgatct | ttgagatctg |
| 3601 | gaccaggaat | ttgcatttga | acaagtgttc | ctggaatctc | tatgcaagtt | ttatacagaa |
| 3661 | catacttttg | gaatccttgc | cctagacagg | ggtgtccaat | cttttggctt | ccctggtcca |
| 3721 | caatggaaga | agaattgtct | tggaccacac | ataaaataca | ctaacactaa | caatagctga |
| 3781 | tgagctaaaa | aaaaaaaaaa | aaaaaatcgt | ggaccgggcg | tagtggctca | cgcctgtaat |
| 3841 | cccaacactt | tgggagatca | cctaggtcgg | gagtttgaga | ccagcctgac | cgacatggag |
| 3901 | aaaccccatt | tttactaaaa | atacaaaaaa | ttagctgggc | atggtggtgc | atgcctgtag |
| 3961 | tcccagctac | tcaggaggct | gaggcaggag | aatcgcttga | acctgagagg | gggagattgc |
| 4021 | ggtgagctga | gattgcgcca | ttgcacccca | gcctgggcaa | caatagcgaa | actgtctcag |
| 4081 | aaaaaagaaa | aaaaaaatcg | caaaaagaaa | aatctcataa | tgtcgttgtt | ggtttttttt |
| 4141 | ttttttttttg | agacagtctc | actctgttgc | ccaggctgga | gtgcaatggc | atgatctctg |
| 4201 | ctcaccgcaa | cctctgcctc | ccgggttcag | gtgattctcc | tgcctcagcc | tcccagatag |
| 4261 | ctgggactac | aggcacatac | caccatgcct | ggctaatttt | tgtattttta | gtagagatgg |
| 4321 | gggtttcact | gtgttggcca | ggctggtctc | gaactcctga | cctcatgatc | cacacacctc |
| 4381 | ggcctcccaa | agtcctgcga | ttacaggcgt | gagctaccgc | acccagccaa | gttgtaattt |
| 4441 | ttaataaaac | ttaagaagta | aacattttac | ttatgtttat | aggtatttga | tcctaaattt |
| 4501 | gacacatcat | tgcccatgaa | agaatcctct | taggctgctc | agcttcactc | ttcctgcttg |
| 4561 | cccaccgggg | tttttcactg | cttctgttag | cactaagtac | ttagacgatc | ctaagatatg |
| 4621 | tgcttgagcc | gaatttcatc | tttacttgta | ggaaacttta | aactatttct | tttcttttct |
| 4681 | tttttttttt | tttttacttg | agatggagtt | ttgctcttgt | cgcccaggct | ggagtgcagt |
| 4741 | ggagtgatct | cggctcactg | caacctctgc | ctcccgggtt | caaatgattc | tcctgcctca |
| 4801 | gcctcccaag | tagctgggat | tacaggtgtg | caccaccatg | tctggctaat | tttgtatttt |
| 4861 | tagtagagat | ggtttcacca | tgttggtcag | gctggtctcg | aactcctgac | ctcaggtcat |
| 4921 | ccacccacct | cagcctcgca | aagtgctgag | attacaggca | tgagccacag | cgcccagctt |
| 4981 | aaactatttt | cttggtctgt | ttttgatttt | ctttttttcct | tgccactgcg | gtacagattt |
| 5041 | tttttactca | ctgccactaa | actaaagcaa | ggcatagttt | atatgtgaag | tgttcagagt |
| 5101 | ttactgctat | aaggaaactt | ccaaatactg | acatttacct | tttagctgta | gttattggga |
| 5161 | ccatgtgctc | tggttttctg | gagactgcca | aattgctccc | atttttctgc | atcccacctg |
| 5221 | gtttctttct | gcatgtcccc | tttcactttc | aaacctcttc | atttggatgt | taaattatat |
| 5281 | ggtcacctag | ttataggtaa | gccttgttcg | agttgatatc | ttgattgtga | ggaaggatct |
| 5341 | gtgtcattgg | agcttgtttc | tgctgcaacg | tgctgtagac | tatgaataat | gaaatcacac |
| 5401 | cacattacca | tcagatttct | tgttttagtt | gtcaaattaa | tatttatgat | tgttatcttg |
| 5461 | ggcgaaaagt | tcagagcaga | gatgacaaat | cattagaaca | acgatgaatt | tcagtattac |
| 5521 | ggctaaaaag | ttcttctgtc | tgaatattaa | ctcactctcc | ttccagtgta | cttcacagta |
| 5581 | attggtatgc | ttttttattt | aatgcttaaa | tcaaacttta | taaaaatctt | agaccagatc |
| 5641 | tttaatatgg | tatgccattt | ccccagtcta | ccaatggaat | agtatgggtt | tctaatccta |
| 5701 | ggcttgtaca | atggattgga | gttgagccat | gccagcctcc | acactgccac | taacttctgt |
| 5761 | aatgtaagat | tgagtcactg | ccaagcattt | gaaatatgca | gttgtgtttt | aattataatt |
| 5821 | tatgtatagt | tagatgtatg | tagtgcattg | tgtggtatta | tttggtttgt | aagaatttat |
| 5881 | ttttaagggt | caaggtcatt | tgtaacattt | tgtgtgtgtc | aattcaatgc | aatgttggct |
| 5941 | gccttttgaa | gtctttgata | tattggtgaa | tattcttctg | atctataata | caaagctatg |
| 6001 | taatgttacc | tcttgactcg | cttttgaaag | gaagacaatt | gttaactaga | tatttgagtt |
| 6061 | ttttcccctc | agaattatgt | gaatttctga | tatatggctt | tagatactgt | gaatctgttt |
| 6121 | tccatttagt | cagttatctg | cttaaattgt | tcagaactat | atcctaacga | gcaattagtt |
| 6181 | ctgatggttc | tcccagtcat | gagtgtgcat | gtgtgcaagc | atgttttgat | cctgatgcta |

TABLE 1-continued

```
6241 cctttgctaa aaatggccat agattaggaa ctagctatgt ttttagaatc aaagatgaac
6301 cggtaagctg tctcatgtac caaacgtgaa atttacagtg tttacaaatg tctggaattt
6361 tgcactgcca tagggaatgt taaggttact tggctggaat ttatcagact tgtgagtaaa
6421 caagttgaag tttagcagat gagggggaat attgaggccc ctaaggctaa acaaaataat
6481 cagtatctga gatagtggct aatgtggctc cccaggccta atttgggaac agtttttcct
6541 gattgctttg agaagtactt tcttttgaca gaaattttca ttctgcttgc cattgctata
6601 ttctcccttt ataggagcca ttggatttct ttccttttgt gggaaatgtc ccattagcat
6661 tttcagatct tttgatgtgc actaatgcca ttattggtaa tgccgttatt ggtgaataca
6721 gcatagttaa ataaactgtt acagtaaatc tacacttgga tttgctgcac ctctaccaat
6781 agccttttga atgactgaaa gtgttaacag agaaagaggc atgtctgcag aaagagatag
6841 ctaatatttt ttggtacttt atctgaaatc caagatgctg cttcccctgc aggttgtttt
6901 ccttcttacg atcctcattg aatcccctct gggagcacag gacagttagt agaactctcc
6961 atttcttttt tttttttttt agacggagtc tctctctgtc gccccggctg gagtgcagtg
7021 gcgcgatctc ggctcactgc aacctccgcc tcccgggttc accccattct cctgcctcag
7081 cctccctagt agctgggact ataggcgccc gccaccacgc ctggctaatt tttgtatttt
7141 tattggagac ggggtttcac cgtcttagcc aggatggtct tgatctcctg acctcgtgat
7201 ctgcccacct cagcctccca aagtactggg attacaggcg tgagccaccg cgcccggccg
7261 gaactctcca tttcttaagg taaagagggt caaggatacc taaaaagggt caaataatgc
7321 tagaagagca attcctcttt cagagcagtt gctgtaattt ggcaaatgct ttatcgaaga
7381 ttgatattag gctaggggcg gtggcttacg cctgtaatcc cagcactttg ggaggccgag
7441 gtgggtggat tgcctgagct caggagttcg agaccagtct gaccagtatg gtgaaacccct
7501 gtctctacta aaaatacaaa aattagccgg tcgtggtggc gtgcacctgt agtcccagct
7561 acttggcagg ttgagacagg agaatcgctt gaacctggga ggtggaggtt gcagtgagcc
7621 gagactgcac cactgcgctc ccacctgggt gacagagact ctgtctcaaa aaaaaggaca
7681 tttatcatta taacatctta ttagagcccc taatttctta tctgaaggca ctgttttttt
7741 ttttaaacag ttaagtactg atgtcaacag acaaatattt ctgatcagat agtcccctgt
7801 caacagtagc aaatgtggtt tcataaagtg ggaagaaaac agcattttaa agtaactttt
7861 tgggagactg atttgagtaa taataaaact ctggtctccc ttaagaaaaa aaaacccttc
7921 cacctttact gtgtcattta tatcccctta gttccaaagt taattatctt atttctggat
7981 attgctttta taccaaagac ccttatcagc ccttgtaact acagtatctt tagataagat
8041 tcctctttcc agtcagtcct gggaaatgtt tctgttgcag agttaggcgg tagatgggaa
8101 gctgtgatgg cagagctact atctaataaa gtaacaactc gtagttgagg cttcctttct
8161 gtgtgtgatg ggggataggg agttagctcc cctgttgtct cagcactaag aaattgaggt
8221 caggccaggc gcggtggttc actcctgtta ttccagcact ggggtggcca aagtgggcag
8281 attgcttgcg ctctggagct cgagaccagc ctgggcaaca tggtgaaacc ctgtctctac
8341 caaaaataca aaaaaaaagc tgggcatggt gggtgcatgc ttgtcccagc tactgaggag
8401 gctgaggtgg gaggatcgct tgagcctggg aggtggaggt tgcagtgagc tgagatggca
8461 ccactgcaat ccaaggtggg tgacagagac gctgtctcaa agaaattgag gtcaggcttc
8521 cttcttacag aattattttt ttctctgtag tttgcctcat tttttcactt tcttttcaat
8581 gagaatcgaa gtgtttcttt tgggtttttt tttccccctt ttaaaatcaa caggaaatgt
8641 ttcaaaggag ggatgaaatg cttcttggct tcctcagcac ttggcaaggt agacctcata
8701 gcaaccttga atatgacttt ctttagtctc tagctatgca ctattaagtg cctcttgggt
8761 agaggtagag ttaagtattg agtgccagtc ttgacgtccg tatgcctcag tttttctcat
8821 atataaaaag cagtatacat acctaccctt ttctacctca tcatttgttg tagggattaa
8881 atccgggaga gcaattctga agcctataaa tttccttgaa gagatctaag aacctattat
8941 gctcttggtg taccaagctc tggggtatat attcagaata cctcatgttc tggaagctga
9001 gcactagctc ccctttattg cctgcctggc agagcctgtt tgattactgc aggccctttt
9061 acccatgctt ctagtttagg tattctttct ttgatatgag gctcttgacc agaaaagagt
9121 tctttctcta ggtgttctga gagaagtttg taaatttgga tagtacattc tatcctgata
9181 aaaccacctt gctgtggtct tgatgtacaa aaaaaaattt tttttttgag acagagtctt
9241 actctgtcac ccaggctgga atgcagtggc gcaatcttgg ttcactgcaa cccccgcctc
9301 ctgggttcaa gcgatcctcc tgcctcaacc tctcaagtag ctgggactac aggcgtgcac
9361 caccacacct ggctaatttt gtatttttag tagagacagg gtttcaccat gttggccagg
9421 ctggtcttga actcctgacc tcaggcgatc tgcccgcctt ggcctcccaa agtactggga
9481 ttacaggcgt gagcaactgc tcctggccca aaacatctct ttctacatac acttgagtag
9541 gtggcataaa atgcactgtc aatatataga aaacatgaaa ttttccaaat atttccgatc
9601 agagaatcac aagagcagca aatgtggttt catcaagtgg gaagaaagca gcaatttaaa
9661 ataacttttt gggagactga attgagtaat aataaaactt cagtctttcg ctaataataa
9721 taataataat aataataaca acaacttatt gaatgtggcc agctcactag atgaggaaag
9781 aggaaggcat tttctgcatt cttgcctagt tttccttata agcaccacta agttaatagc
9841 tctgtctttt tggtgtttgc actatgtaat gcttttaata ctttttaatt gtgctttttt
9901 atgtattaaa tgtttttcct tttgccaaaa aaaaaaaaaa
```

SEQ ID NO: 18 Human MDM4 Isoform 2 Amino Acid Sequence (NP_001191100.1)

```
  1 MTSFSTSAQC STSDSACRIS PGQINQVRPK LPLLKILHAA GAQGEMFTVK EVMHYLGQYI
 61 MVKQLYDQQE QHMVYCGGDL LGELLGRQSF SVKDPSPLYD MLRKNLVTLA TATTDAAQTL
121 ALAQDHSMDI PSQDQLKQSA EESSTSRKRT TEDDIPTLPT SEHKCIHSRE DEDLIENLAQ
181 DETSRLDLGF EEWDVAGLPW WFLGNLRSNY TPRSNGSTDL QTNQVIEVGK NDDLEDSKSL
241 SDDTDVEVTS EDEWQCTECK KFNSPSKRYC FRCWALRKDW YSDCSKLTHS LSTSDITAIP
301 EKENEGNDVP DCRRTISAPV VRPKDAYIKK ENSKLFDPCN SVEFLDLAHS SESQETISSM
361 GEQLDNLSEQ RTDTENMEDC QNLLKPCSLC EKRPRDGNII HGRTGHLVTC FHCARRLKKA
421 GASCPICKKE IQLVIKVFIA
```

SEQ ID NO: 19 Human MDM4 Transcript Variant 3 cDNA Sequence (NM_001204172.1; CDS: 167-661)

```
  1 gtgtgggagg ccggaagttg cggcttcatt actcgccatt tcaaaatgct gccgaggccc
 61 taggatctgt gactgccacc cctcccccca cccgggctcg gcgggggagc gactcatgga
121 gctgccgtaa gttttaccaa cagactgcag tttcttcact accaaaatga catcattttc
181 cacctctgct cagtgttcaa catctgacag tgcttgcagg atctctcctg gacaaatcaa
241 tcaggaaaat gaaggaaatg atgtccctga ttgtcgaaga accatttcgg ctcctgtcgt
```

TABLE 1-continued

| | | | | | | |
|---|---|---|---|---|---|---|
| 301 | tagacctaaa | gatgcgtata | taaagaaaga | aaactccaaa | ctttttgatc | cctgcaactc |
| 361 | agtggaattc | ttggatttgg | ctcacagttc | tgaaagccaa | gagaccatct | caagcatggg |
| 421 | agaacagtta | gataaccttt | ctgaacagag | aacagataca | gaaaacatgg | aggattgcca |
| 481 | gaatctcttg | aagccatgta | gcttatgtga | gaaaagacca | cgagacggga | acattattca |
| 541 | tggaaggacg | ggccatcttg | tcacttgttt | tcactgtgcc | agaagactaa | agaaggctgg |
| 601 | ggcttcatgc | cctatttgca | agaaagagat | tcagctggtt | attaaggttt | ttatagcata |
| 661 | atggtagtac | gaacataaaa | atgcatttat | tccgttcact | taccacatta | tttgaaaatc |
| 721 | aatcctttat | ttaattttat | ttccaacctg | tcagagaatg | ttcttaggca | tcaaaatcca |
| 781 | aggtagctgt | aagaaaaata | ctggagctaa | caatgaagaa | cagaagtaat | ctgattagtc |
| 841 | aaattattaa | gtgccatgga | ttactttatg | cagcagtcag | gtacatagtt | aggtgaaccc |
| 901 | aaaagaaaaa | ctcttgaaaa | caagagattt | cttccatgca | catttacaat | attgaggtat |
| 961 | aattaacatg | ataaagtgtt | tccttctaac | gagttgtaga | aatctgagta | accacccaaa |
| 1021 | aaagcaatag | aatgtttctg | tcaccccaaa | acactccctt | ctgcccctct | tcagacagtc |
| 1081 | cttcagctat | ttcatggctc | tcaccctagt | tttttttttt | tttgcacttt | tttttttccg |
| 1141 | ggggtatagg | ggaggtgtgg | ggcgacaggg | tctgtcttgt | tctgtctccc | aggctgaagt |
| 1201 | gcagtgcagt | ggtatgatca | tggctcactg | cagccttggt | ttcctgggca | taagtggtct |
| 1261 | tcccacttca | gcctcctgag | tagctgagac | tatagactag | cataaccaca | ctggctaatt |
| 1321 | ttttgtggag | atgaagtctc | actatgttgc | ccaggctggt | ctcgaactcc | tgggctcaaa |
| 1381 | caatcctccc | gcctcagcct | tccaaattgc | tgggattata | gtcatgaggc | acctagtctg |
| 1441 | gccctttgc | aagactttaa | tctgaaatct | aaatttttaa | aatttaagta | cttacaaagg |
| 1501 | atatactatc | caacatattg | catattatat | atgtgcttta | aagttttttt | tttttttga |
| 1561 | gagacggtct | cactttgtca | tccaagctgg | agtgcagtgg | tgcaaacacg | gcccacctcc |
| 1621 | tgggctcaag | tgatcctcca | gcctcagctt | ccctcacagg | cattcactat | cactcccagc |
| 1681 | taattaaaat | aatttgtaga | cggtgtctcg | ttatgttgcc | caggctggtc | tcgaactcct |
| 1741 | gggtttaagt | gattcccccg | cctcagcctc | ccaaagtgtt | gggcttacag | ccttgagcca |
| 1801 | ctatgcttgg | ctcaaagata | tttttatgaa | agccctggga | ctatagattt | agctgattaa |
| 1861 | atttatagaa | aaagtcctgt | catataaact | ggcaaagtct | gttcttaatt | taattagcca |
| 1921 | aatcagactt | aacttccgtc | agaacatgtc | ttggttttaa | ttcagataaa | cacacaaaca |
| 1981 | tacttctctg | gcacagcctt | cagaagcatc | agtttttgtt | ttgttttgtt | ttgtttttttg |
| 2041 | agacagggtc | ttgctctgtc | gcccaggctg | gagtgcactg | gcacaatcac | agttcactgc |
| 2101 | agcctcgacc | tcccagatcc | aagcaatcct | cccacctaag | cctcccaagt | agctgggtct |
| 2161 | ataggcgcgt | gccaccacca | tgcccagctg | aattttgtat | tttttgtaca | gacagcattt |
| 2221 | tgccatgttg | cccaggctgg | tcccaaactt | ctagcctcaa | gcaaccctcc | tgcctcagcc |
| 2281 | tctcaaagtg | ctaggattgc | agtcctgagc | tactgccccc | taccctcttt | gcgtcttagg |
| 2341 | agtcatttag | atttttttttg | atccttttgt | ttagtgcctc | tggagctgct | tacaccaagg |
| 2401 | caatacgcct | tgatatactg | gatggttgag | aggcagcctc | tttttttttt | tttttttttt |
| 2461 | tttttttttg | gaggataggg | agtatggctg | ttgtgaaaag | ggaggtaaag | agaaatggta |
| 2521 | gatctgaaga | ggcctcatca | gagcacatat | tttaggacaa | cacatatgga | aattggacat |
| 2581 | ctttaagttg | gtttccatag | agctatgcat | gtatccttac | cccatggga | aaatgttggt |
| 2641 | gtgttctcaa | gggtatgcat | gtgtcatttt | gaagaccaag | gccctagaat | tgtcaaactt |
| 2701 | aaggatcata | aaaatcatga | gggttgcttg | ttaaaaatgt | ccaaacgtgc | agagactgat |
| 2761 | ctttgagatc | tggaccagga | atttgcattt | gaacaagtgt | tcctggaatc | tctatgcaag |
| 2821 | ttttatacag | aacatacttt | tggaatcctt | gccctagaca | ggggtgtcca | atcttttggc |
| 2881 | ttccctggtc | cacaatggaa | gaagaattgt | cttggaccac | acataaaata | cactaacact |
| 2941 | aacaatagct | gatgagctaa | aaaaaaaaaa | aaaaaaaatc | gtggaccggg | cgtagtggct |
| 3001 | cacgcctgta | atcccaacac | tttgggagat | cacctaggtc | gggagtttga | gaccagcctg |
| 3061 | accgacatgg | agaaacccca | tttttactaa | aaatacaaaa | aattagctgg | gcatggtggt |
| 3121 | gcatgcctgt | agtcccagct | actcaggagg | ctgaggcagg | agaatcgctt | gaacctgaga |
| 3181 | gggggagatt | gcggtgagct | gagattgcgc | cattgcaccc | cagcctgggc | aacaatagcg |
| 3241 | aaactgtctc | agaaaaaaga | aaaaaaaaat | cgcaaaaaga | aaaatctcat | aatgtcgttg |
| 3301 | ttggtttttt | tttttttttt | tgagacagtc | tcactctgtt | gcccaggctg | gagtgcaatg |
| 3361 | gcatgatctc | tgctcaccgc | aacctctgcc | tcccgggttc | aggtgattct | cctgcctcag |
| 3421 | cctcccagat | agctgggact | acaggcacat | accaccatgc | ctggctaatt | tttgtatttt |
| 3481 | tagtagagat | gggggtttca | ctgtgttggc | caggctggtc | tcgaactcct | gacctcatga |
| 3541 | tccacacacc | tcggcctccc | aaagtcctgc | gattacaggc | gtgagctacc | gcacccagcc |
| 3601 | aagttgtaat | ttttaataaa | acttaagaag | taaacatttt | acttatgttt | ataggtattt |
| 3661 | gatcctaaat | ttgacacatc | attgcccatg | aaagaatcct | cttaggctgc | tcagcttcac |
| 3721 | tcttcctgct | tgcccaccgg | ggtttttcac | tgcttctgtt | agcactaagt | acttagacga |
| 3781 | tcctaagata | tgtgcttgag | ccgaatttca | tctttacttg | taggaaactt | taaactattt |
| 3841 | cttttctttt | cttttttttt | ttttttact | tgagatggag | ttttgctctt | gtcgcccagg |
| 3901 | ctggagtgca | gtggagtgat | ctcggctcac | tgcaacctct | gcctcccggg | ttcaaatgat |
| 3961 | tctcctgcct | cagcctccca | agtagctggg | attacaggtg | tgcaccacca | tgtctggcta |
| 4021 | attttgtatt | tttagtagag | atggtttcac | catgttggtc | aggctggtct | cgaactcctg |
| 4081 | acctcaggtc | atccacccac | ctcagcctcg | caaagtgctg | agattacagg | catgagccac |
| 4141 | agcgcccagc | ttaaactatt | ttcttggtct | gtttttgatt | ttcttttttc | cttgccactg |
| 4201 | cggtacagat | ttttttttact | cactgccact | aaactaaagc | aaggcatagt | ttatatgtga |
| 4261 | agtgttcaga | gtttactgct | ataaggaaac | ttccaaatac | tgacatttac | cttttagctg |
| 4321 | tagttattgg | gaccatgtgc | tctggttttc | tggagactgc | caaattgctc | ccatttttct |
| 4381 | gcatcccacc | tggtttcttt | ctgcatgtcc | cctttcactt | tcaaacctct | tcatttggat |
| 4441 | gttaaattat | atggtcacct | agttataggt | aagccttgtt | cgagttgata | tcttgattgt |
| 4501 | gaggaaggat | ctgtgtcatt | ggagcttgtt | tctgctgcaa | cgtgctgtag | actatgaata |
| 4561 | atgaaatcac | accacattac | catcagattt | cttgttttag | ttgtcaaatt | aatatttatg |
| 4621 | attgttatct | tgggcgaaaa | gttcagagca | gagatgacaa | atcattagaa | caacgatgaa |
| 4681 | tttcagtatt | acggctaaaa | agttcttctg | tctgaatatt | aactcactct | ccttccagtg |
| 4741 | tacttcacag | taattggtat | gcttttttat | ttaatgctta | aatcaaactt | tataaaaatc |
| 4801 | ttagaccaga | tctttaatat | ggtatgccat | ttccccagtc | taccaatgga | atagtatggg |
| 4861 | tttctaatcc | taggcttgta | caatggattg | gagttgagcc | atgccagcct | ccacactgcc |
| 4921 | actaacttct | gtaatgtaag | attgagtcac | tgccaagcat | ttgaaatatg | cagttgtgtt |
| 4981 | ttaattataa | tttatgtata | gttagatgta | tgtagtgcat | tgtgtggtat | tatttggttt |
| 5041 | gtaagaattt | atttttaagg | gtcaaggtca | tttgtaacat | tttgtgtgtg | tcaattcaat |

TABLE 1-continued 5101 gcaatgttgg ctgccttttg aagtctttga tatattggtg aatattcttc tgatctataa
5161 tacaaagcta tgtaatgtta cctcttgact cgcttttgaa aggaagacaa ttgttaacta
5221 gatatttgag ttttttcccc tcagaattat gtgaatttct gatatatggc tttagatact
5281 gtgaatctgt tttccattta gtcagttatc tgcttaaatt gttcagaact atatcctaac
5341 gagcaattag ttctgatggt tctcccagtc atgagtgtgc atgtgtgcaa gcatgttttg
5401 atcctgatgc tacctttgct aaaaatggcc atagattagg aactagctat gtttttagaa
5461 tcaaagatga accggtaagc tgtctcatgt accaaacgtg aaatttacag tgtttacaaa
5521 tgtctggaat tttgcactgc catagggaat gttaaggtta cttggctgga atttatcaga
5581 cttgtgagta aacaagttga agtttagcag atgaggggga atattgaggc ccctaaggct
5641 aaacaaaata atcagtatct gagatagtgg ctaatgtggc tccccaggcc taatttggga
5701 acagtttttc ctgattgctt tgagaagtac tttcttttga cagaaatttt cattctgctt
5761 gccattgcta tattctccct ttataggagc cattggattt ctttcctttt gtgggaaatg
5821 tcccattagc attttcagat cttttgatgt gcactaatgc cattattggt aatgccgtta
5881 ttggtgaata cagcatagtt aaataaactg ttacagtaaa tctacacttg gatttgctgc
5941 acctctacca atagcctttt gaatgactga aagtgttaac agagaaagag gcatgtctgc
6001 agaaagagat agctaatatt ttttggtact ttatctgaaa tccaagatgc tgcttcccct
6061 gcaggttgtt ttccttctta cgatcctcat tgaatcccct ctgggagcac aggacagtta
6121 gtagaactct ccatttcttt tttttttttt ttagacggag tctctctctg tcgccccggc
6181 tggagtgcag tggcgcgatc tcggctcact gcaacctccg cctcccgggt tcaccccatt
6241 ctcctgcctc agcctcccta gtagctggga ctataggcgc ccgccaccac gcctggctaa
6301 tttttgtatt tttattggag acggggtttc accgtcttag ccaggatggt cttgatctcc
6361 tgacctcgtg atctgcccac ctcagcctcc caaagtactg ggattacagg cgtgagccac
6421 cgcgcccggc cggaactctc catttcttaa ggtaaagagg gtcaaggata cctaaaaagg
6481 gtcaaataat gctagaagag caattcctct ttcagagcag ttgctgtaat ttggcaaatg
6541 ctttatcgaa gattgatatt aggctagggg cggtggctta cgcctgtaat cccagcactt
6601 tgggaggccg aggtgggtgg attgcctgag ctcaggagtt cgagaccagt ctgaccagta
6661 tggtgaaacc ctgtctctac taaaaataca aaaattagcc ggtcgtggtg gcgtgcacct
6721 gtagtcccag ctacttggca ggttgagaca ggagaatcgc ttgaacctgg gaggtggagg
6781 ttgcagtgag ccgagactgc accactgcgc tcccacctgg gtgacagaga ctctgtctca
6841 aaaaaaagga catttatcat tataacatct tattagagcc cctaatttct tatctgaagg
6901 cactgttttt ttttttaaac agttaagtac tgatgtcaac agacaaatat ttctgatcag
6961 atagtcccct gtcaacagta gcaaatgtgg tttcataaag tgggaagaaa acagcatttt
7021 aaagtaactt tttgggagac tgatttgagt aataataaaa ctctggtctc ccttaagaaa
7081 aaaaaaccct tccaccttta ctgtgtcatt tatatcccct tagttccaaa gttaattatc
7141 ttatttctgg atattgcttt tataccaaag acccttatca gcccttgtaa ctacagtatc
7201 tttagataag attcctcttt ccagtcagtc ctgggaaatg tttctgttgc agagttaggc
7261 ggtagatggg aagctgtgat ggcagagcta ctatctaata aagtaacaac tcgtagttga
7321 ggcttccttt ctgtgtgtga tgggggatag ggagttagct cccctgttgt ctcagcacta
7381 agaaattgag gtcaggccag gcgcggtggt tcactcctgt tattccagca ctggggtggc
7441 caaagtgggc agattgcttg cgctctggag ctcgagacca gcctgggcaa catggtgaaa
7501 ccctgtctct accaaaaata caaaaaaaaa gctgggcatg gtgggtgcat gcttgtccca
7561 gctactgagg aggctgaggt gggaggatcg cttgagcctg ggaggtggag gttgcagtga
7621 gctgagatgg caccactgca atccaaggtg ggtgacagag acgctgtctc aaagaaattg
7681 aggtcaggct tccttcttac agaattattt ttttctctgt agtttgcctc attttttcac
7741 tttcttttca atgagaatcg aagtgtttct tttgggtttt tttttccccc ttttaaaatc
7801 aacaggaaat gtttcaaagg agggatgaaa tgcttcttgg cttcctcagc acttggcaag
7861 gtagacctca tagcaacctt gaatatgact ttctttagtc tctagctatg cactattaag
7921 tgcctcttgg gtagaggtag agttaagtat tgagtgccag tcttgacgtc cgtatgcctc
7981 agtttttctc atatataaaa agcagtatac atacctaccc ttttctacct catcatttgt
8041 tgtagggatt aaatccggga gagcaattct gaagcctata aatttccttg aagagatcta
8101 agaacctatt atgctcttgg tgtaccaagc tctggggtat atattcagaa tacctcatgt
8161 tctggaagct gagcactagc tcccctttat tgcctgcctg gcagagcctg tttgattact
8221 gcaggccctt ttacccatgc ttctagttta ggtattcttt ctttgatatg aggctcttga
8281 ccagaaaaga gttctttctc taggtgttct gagagaagtt tgtaaatttg gatagtacat
8341 tctatcctga taaaaccacc ttgctgtggt cttgatgtac aaaaaaaaat tttttttttg
8401 agacagagtc ttactctgtc acccaggctg gaatgcagtg gcgcaatctt ggttcactgc
8461 aacccccgcc tcctgggttc aagcgatcct cctgcctcaa cctctcaagt agctgggact
8521 acaggcgtgc accaccacac ctggctaatt ttgtattttt agtagagaca gggtttcacc
8581 atgttggcca ggctggtctt gaactcctga cctcaggcga tctgcccgcc ttggcctccc
8641 aaagtactgg gattacaggc gtgagcaact gctcctggcc caaaacatct ctttctacat
8701 acacttgagt aggtggcata aaatgcactg tcaatatata gaaaacatga aattttccaa
8761 atatttccga tcagagaatc acaagagcag caaatgtggt ttcatcaagt gggaagaaag
8821 cagcaattta aaataacttt ttgggagact gaattgagta ataataaaac ttcagtcttt
8881 cgctaataat aataataata ataataataa caacaactta ttgaatgtgg ccagctcact
8941 agatgaggaa agaggaaggc attttctgca ttcttgccta gttttcctta taagcaccac
9001 taagttaata gctctgtctt tttggtgttt gcactatgta atgcttttaa tactttttaa
9061 ttgtgctttt ttatgtatta aatgtttttc cttttgccaa aaaaaaaaaa aa SEQ ID NO: 20 Human MDM4 Isoform 3 Amino Acid Sequence (NP_001191101.1)
1 MTSFSTSAQC STSDSACRIS PGQINQENEG NDVPDCRRTI SAPVVRPKDA YIKKENSKLF
61 DPCNSVEFLD LAHSSESQET ISSMGEQLDN LSEQRTDTEN MEDCQNLLKP CSLCEKRPRD
121 GNIIHGRTGH LVTCFHCARR LKKAGASCPI CKKEIQLVIK VFIA SEQ ID NO: 21 Human MDM4 Transcript Variant 4 cDNA Sequence
(NM_001278516.1; CDS: 167-589)
1 gtgtgggagg ccggaagttg cggcttcatt actcgccatt tcaaaatgct gccgaggccc
61 taggatctgt gactgccacc cctcccccca cccgggctcg gcgggggagc gactcatgga
121 gctgccgtaa gttttaccaa cagactgcag tttcttcact accaaaatga catcattttc
181 cacctctgct cagtgttcaa catctgacag tgcttgcagg atctctcctg gacaaatcaa
241 tcaggtacga ccaaaactgc cgcttttgaa gattttgcat gcagcaggtg cgcaaggtga TABLE 1-continued 301 aatgttcact gttaaagagg tcatgcacta tttaggtcag tacataatgg tgaagcaact
361 ttatgatcag caggagcagc atatggtata ttgtggtgga gatcttttgg gagaactact
421 gggacgtcag agcttctccg tgaaagaccc aagccctctc tatgatatgc taagaaagaa
481 tcttgtcact ttagccactg ctactacagc aaagtgcaga ggaaagttcc acttccagaa
541 aaagaactac agaagacgat atccccacac tgcctacctc agagcataaa tgcatacatt
601 ctagagaaga tgaagactta attgaaaatt tagcccaaga tgaaacatct aggctggacc
661 ttggatttga ggagtgggat gtagctggcc tgccttggtg gtttttagga aacttgagaa
721 gcaactatac acctagaagt aatggctcaa ctgatttaca gacaaatcag gatgtgggta
781 ctgccattgt ttcagatact acagatgact tgtggttttt gaatgagtca gtatcagagc
841 agttaggtgt tggaataaaa gttgaagctg ctgatactga acaaacaagt gaagaagtag
901 ggaaagtaag tgacaaaaag gtgattgaag tgggaaaaaa tgatgacctg gaggactcta
961 agtccttaag tgatgatacc gatgtagagg ttacctctga ggatgagtgg cagtgtactg
1021 aatgcaagaa atttaactct ccaagcaaga ggtactgttt tcgttgttgg gccttgagga
1081 aggattggta ttcagattgt tcaaagttaa cccattctct ctccacgtct gatatcactg
1141 ccatacctga aaaggaaaat gaaggaaatg atgtccctga ttgtcgaaga accatttcgg
1201 ctcctgtcgt tagacctaaa gatgcgtata taaagaaaga aaactccaaa ctttttgatc
1261 cctgcaactc agtggaattc ttggatttgg ctcacagttc tgaaagccaa gagaccatct
1321 caagcatggg agaacagtta gataaccttt ctgaacagag aacagataca gaaaacatgg
1381 aggattgcca gaatctcttg aagccatgta gcttatgtga gaaaagacca cgagacggga
1441 acattattca tggaaggacg ggccatcttg tcacttgttt tcactgtgcc agaagactaa
1501 agaaggctgg ggcttcatgc cctatttgca agaaagagat tcagctggtt attaaggttt
1561 ttatagcata atggtagtac gaacataaaa atgcatttat tccgttcact taccacatta
1621 tttgaaaatc aatcctttat ttaattttat ttccaacctg tcagagaatg ttcttaggca
1681 tcaaaatcca aggtagctgt aagaaaaata ctggagctaa caatgaagaa cagaagtaat
1741 ctgattagtc aaattattaa gtgccatgga ttactttatg cagcagtcag gtacatagtt
1801 aggtgaaccc aaaagaaaaa ctcttgaaaa caagagattt cttccatgca catttacaat
1861 attgaggtat aattaacatg ataaagtgtt tccttctaac gagttgtaga aatctgagta
1921 accacccaaa aaagcaatag aatgtttctg tcaccccaaa acactccctt ctgcccctct
1981 tcagacagtc cttcagctat ttcatggctc tcaccctagt tttttttttt tttgcacttt
2041 tttttttccg ggggtatagg ggaggtgtgg ggcgacaggg tctgtcttgt tctgtctccc
2101 aggctgaagt gcagtgcagt ggtatgatca tggctcactg cagccttggt ttcctgggca
2161 taagtggtct tcccacttca gcctcctgag tagctgagac tatagactag cataaccaca
2221 ctggctaatt ttttgtggag atgaagtctc actatgttgc ccaggctggt ctcgaactcc
2281 tgggctcaaa caatcctccc gcctcagcct tccaaattgc tgggattata gtcatgaggc
2341 acctagtctg gccctttttgc aagactttaa tctgaaatct aaatttttaa aatttaagta
2401 cttacaaagg atatactatc caacatattg catattatat atgtgcttta aagttttttt
2461 ttttttttga gagacggtct cactttgtca tccaagctgg agtgcagtgg tgcaaacacg
2521 gcccacctcc tgggctcaag tgatcctcca gcctcagctt ccctcacagg cattcactat
2581 cactcccagc taattaaaat aatttgtaga cggtgtctcg ttatgttgcc caggctggtc
2641 tcgaactcct gggtttaagt gattcccccg cctcagcctc ccaaagtgtt gggcttacag
2701 ccttgagcca ctatgcttgg ctcaaagata tttttatgaa agccctggga ctatagattt
2761 agctgattaa atttatagaa aaagtcctgt catataaact ggcaaagtct gttcttaatt
2821 taattagcca aatcagactt aacttccgtc agaacatgtc ttggttttaa ttcagataaa
2881 cacacaaaca tacttctctg gcacagcctt cagaagcatc agtttttgtt ttgttttgtt
2941 ttgtttttttg agacagggtc ttgctctgtc gcccaggctg gagtgcactg gcacaatcac
3001 agttcactgc agcctcgacc tcccagatcc aagcaatcct cccacctaag cctcccaagt
3061 agctgggtct ataggcgcgt gccaccacca tgcccagctg aattttgtat tttttgtaca
3121 gacagcattt tgccatgttg cccaggctgg tcccaaactt ctagcctcaa gcaaccctcc
3181 tgcctcagcc tctcaaagtg ctaggattgc agtcctgagc tactgccccc taccctcttt
3241 gcgtcttagg agtcatttag attttttttg atccttttgt ttagtgcctc tggagctgct
3301 tacaccaagg caatacgcct tgatatactg gatggttgag aggcagcctc tttttttttt
3361 tttttttttt tttttttttg gaggataggg agtatggctg ttgtgaaaag ggaggtaaag
3421 agaaatggta gatctgaaga ggcctcatca gagcacatat tttaggacaa cacatatgga
3481 aattggacat ctttaagttg gtttccatag agctatgcat gtatccttac ccccatggga
3541 aaatgttggt gtgttctcaa gggtatgcat gtgtcatttt gaagaccaag gccctagaat
3601 tgtcaaactt aaggatcata aaaatcatga gggttgcttg ttaaaaatgt ccaaacgtgc
3661 agagactgat ctttgagatc tggaccagga atttgcattt gaacaagtgt tcctggaatc
3721 tctatgcaag ttttatacag aacatacttt tggaatcctt gccctagaca ggggtgtcca
3781 atcttttggc ttccctggtc cacaatggaa gaagaattgt cttggaccac acataaaata
3841 cactaacact aacaatagct gatgagctaa aaaaaaaaaa aaaaaaaatc gtggaccggg
3901 cgtagtggct cacgcctgta atcccaacac tttgggagat cacctaggtc gggagtttga
3961 gaccagcctg accgacatgg agaaacccca tttttactaa aaatacaaaa aattagctgg
4021 gcatggtggt gcatgcctgt agtcccagct actcaggagg ctgaggcagg agaatcgctt
4081 gaacctgaga gggggagatt gcggtgagct gagattgcgc cattgcaccc cagcctgggc
4141 aacaatagcg aaactgtctc agaaaaaaga aaaaaaaaat cgcaaaaaga aaaatctcat
4201 aatgtcgttg ttggtttttt tttttttttt tgagacagtc tcactctgtt gcccaggctg
4261 gagtgcaatg gcatgatctc tgctcaccgc aacctctgcc tcccgggttc aggtgattct
4321 cctgcctcag cctcccagat agctgggact acaggcacat accaccatgc ctggctaatt
4381 tttgtatttt tagtagagat gggggtttca ctgtgttggc caggctggtc tcgaactcct
4441 gacctcatga tccacacacc tcggcctccc aaagtcctgc gattacaggc gtgagctacc
4501 gcacccagcc aagttgtaat ttttaataaa acttaagaag taaacatttt acttatgttt
4561 ataggtattt gatcctaaat ttgacacatc attgcccatg aaagaatcct cttaggctgc
4621 tcagcttcac tcttcctgct tgcccaccgg ggtttttcac tgcttctgtt agcactaagt
4681 acttagacga tcctaagata tgtgcttgag ccgaatttca tctttacttg taggaaactt
4741 taaactattt cttttctttt cttttttttt tttttttact tgagatggag ttttgctctt
4801 gtcgcccagg ctggagtgca gtggagtgat ctcggctcac tgcaacctct gcctcccggg
4861 ttcaaatgat tctcctgcct cagcctccca agtagctggg attacaggtg tgcaccacca
4921 tgtctggcta attttgtatt tttagtagag atggtttcac catgttggtc aggctggtct
4981 cgaactcctg acctcaggtc atccacccac ctcagcctcg caaagtgctg agattacagg
5041 catgagccac agcgcccagc ttaaactatt ttcttggtct gttttgatt ttcttttttc TABLE 1-continued 5101 cttgccactg cggtacagat tttttttact cactgccact aaactaaagc aaggcatagt
5161 ttatatgtga agtgttcaga gtttactgct ataaggaaac ttccaaatac tgacatttac
5221 cttttagctg tagttattgg gaccatgtgc tctggttttc tggagactgc caaattgctc
5281 ccatttttct gcatcccacc tggtttcttt ctgcatgtcc cctttcactt tcaaacctct
5341 tcatttggat gttaaattat atggtcacct agttataggt aagccttgtt cgagttgata
5401 tcttgattgt gaggaaggat ctgtgtcatt ggagcttgtt tctgctgcaa cgtgctgtag
5461 actatgaata atgaaatcac accacattac catcagattt cttgttttag ttgtcaaatt
5521 aatatttatg attgttatct tgggcgaaaa gttcagagca gagatgacaa atcattagaa
5581 caacgatgaa tttcagtatt acggctaaaa agttcttctg tctgaatatt aactcactct
5641 ccttccagtg tacttcacag taattggtat gctttttat ttaatgctta aatcaaactt
5701 tataaaaatc ttagaccaga tctttaatat ggtatgccat ttccccagtc taccaatgga
5761 atagtatggg tttctaatcc taggcttgta caatggattg gagttgagcc atgccagcct
5821 ccacactgcc actaacttct gtaatgtaag attgagtcac tgccaagcat ttgaaatatg
5881 cagttgtgtt ttaattataa tttatgtata gttagatgta tgtagtgcat tgtgtggtat
5941 tatttggttt gtaagaattt atttttaagg gtcaaggtca tttgtaacat tttgtgtgtg
6001 tcaattcaat gcaatgttgg ctgccttttg aagtctttga tatattggtg aatattcttc
6061 tgatctataa tacaaagcta tgtaatgtta cctcttgact cgcttttgaa aggaagacaa
6121 ttgttaacta gatatttgag tttttccccc tcagaattat gtgaatttct gatatatggc
6181 tttagatact gtgaatctgt tttccattta gtcagttatc tgcttaaatt gttcagaact
6241 atatcctaac gagcaattag ttctgatggt tctcccagtc atgagtgtgc atgtgtgcaa
6301 gcatgttttg atcctgatgc tacctttgct aaaaatggcc atagattagg aactagctat
6361 gtttttagaa tcaaagatga accggtaagc tgtctcatgt accaaacgtg aaatttacag
6421 tgtttacaaa tgtctggaat tttgcactgc catagggaat gttaaggtta cttggctgga
6481 atttatcaga cttgtgagta aacaagttga agtttagcag atgaggggga atattgaggc
6541 ccctaaggct aaacaaaata atcagtatct gagatagtgg ctaatgtggc tccccaggcc
6601 taatttggga acagtttttc ctgattgctt tgagaagtac tttcttttga cagaaatttt
6661 cattctgctt gccattgcta tattctccct ttataggagc cattggattt ctttcctttt
6721 gtgggaaatg tcccattagc attttcagat cttttgatgt gcactaatgc cattattggt
6781 aatgccgtta ttggtgaata cagcatagtt aaataaactg ttacagtaaa tctacacttg
6841 gatttgctgc acctctacca atagcctttt gaatgactga aagtgttaac agagaaagag
6901 gcatgtctgc agaaagagat agctaatatt ttttggtact ttatctgaaa tccaagatgc
6961 tgcttcccct gcaggttgtt ttccttctta cgatcctcat tgaatcccct ctgggagcac
7021 aggacagtta gtagaactct ccatttcttt tttttttttt ttagacggag tctctctctg
7081 tcgccccggc tggagtgcag tggcgcgatc tcggctcact gcaacctccg cctcccgggt
7141 tcaccccatt ctcctgcctc agcctcccta gtagctggga ctataggcgc ccgccaccac
7201 gcctggctaa tttttgtatt tttattggag acggggtttc accgtcttag ccaggatggt
7261 cttgatctcc tgacctcgtg atctgcccac ctcagcctcc caaagtactg ggattacagg
7321 cgtgagccac cgcgcccggc cggaactctc catttcttaa ggtaaagagg gtcaaggata
7381 cctaaaaagg gtcaaataat gctagaagag caattcctct ttcagagcag ttgctgtaat
7441 ttggcaaatg ctttatcgaa gattgatatt aggctagggg cggtggctta cgcctgtaat
7501 cccagcactt tgggaggccg aggtgggtgg attgcctgag ctcaggagtt cgagaccagt
7561 ctgaccagta tggtgaaacc ctgtctctac taaaaataca aaaattagcc ggtcgtggtg
7621 gcgtgcacct gtagtcccag ctacttggca ggttgagaca ggagaatcgc ttgaacctgg
7681 gaggtggagg ttgcagtgag ccgagactgc accactgcgc tcccacctgg gtgacagaga
7741 ctctgtctca aaaaaaagga catttatcat tataacatct tattagagcc cctaatttct
7801 tatctgaagg cactgttttt tttttaaac agttaagtac tgatgtcaac agacaaatat
7861 ttctgatcag atagtcccct gtcaacagta gcaaatgtgg tttcataaag tgggaagaaa
7921 acagcatttt aaagtaactt tttgggagac tgatttgagt aataataaaa ctctggtctc
7981 ccttaagaaa aaaaaaccct tccaccttta ctgtgtcatt tatatcccct tagttccaaa
8041 gttaattatc ttatttctgg atattgcttt tataccaaag acccttatca gcccttgtaa
8101 ctacagtatc tttagataag attcctcttt ccagtcagtc ctgggaaatg tttctgttgc
8161 agagttaggc ggtagatggg aagctgtgat ggcagagcta ctatctaata aagtaacaac
8221 tcgtagttga ggcttccttt ctgtgtgtga tgggggatag ggagttagct cccctgttgt
8281 ctcagcacta agaaattgag gtcaggccag gcgcggtggt tcactcctgt tattccagca
8341 ctggggtggc caaagtgggc agattgcttg cgctctggag ctcgagacca gcctgggcaa
8401 catggtgaaa ccctgtctct accaaaaata caaaaaaaaa gctgggcatg gtgggtgcat
8461 gcttgtccca gctactgagg aggctgaggt gggaggatcg cttgagcctg ggaggtggag
8521 gttgcagtga gctgagatgg caccactgca atccaaggtg ggtgacagag acgctgtctc
8581 aaagaaattg aggtcaggct tccttcttac agaattattt ttttctctgt agtttgcctc
8641 atttttcac tttcttttca atgagaatcg aagtgtttct tttgggtttt tttttccccc
8701 ttttaaaatc aacaggaaat gtttcaaagg agggatgaaa tgcttcttgg cttcctcagc
8761 acttggcaag gtagacctca tagcaacctt gaatatgact ttctttagtc tctagctatg
8821 cactattaag tgcctcttgg gtagaggtag agttaagtat tgagtgccag tcttgacgtc
8881 cgtatgcctc agtttttctc atatataaaa agcagtatac atacctaccc ttttctacct
8941 catcatttgt tgtagggatt aaatccggga gagcaattct gaagcctata aatttccttg
9001 aagagatcta agaacctatt atgctcttgg tgtaccaagc tctggggtat atattcagaa
9061 tacctcatgt tctggaagct gagcactagc tccccttat tgcctgcctg gcagagcctg
9121 tttgattact gcaggccctt ttacccatgc ttctagttta ggtattcttt ctttgatatg
9181 aggctcttga ccagaaaaga gttctttctc taggtgttct gagagaagtt tgtaaatttg
9241 gatagtacat tctatcctga taaaaccacc ttgctgtggt cttgatgtac aaaaaaaaat
9301 tttttttttg agacagagtc ttactctgtc acccaggctg gaatgcagtg gcgcaatctt
9361 ggttcactgc aacccccgcc tcctgggttc aagcgatcct cctgcctcaa cctctcaagt
9421 agctgggact acaggcgtgc accaccacac ctggctaatt ttgtattttt agtagagaca
9481 gggtttcacc atgttggcca ggctggtctt gaactcctga cctcaggcga tctgcccgcc
9541 ttggcctccc aaagtactgg gattacaggc gtgagcaact gctcctggcc caaaacatct
9601 ctttctacat acacttgagt aggtggcata aaatgcactg tcaatatata gaaaacatga
9661 aattttccaa atatttccga tcagagaatc acaagagcag caaatgtggt ttcatcaagt
9721 gggaagaaag cagcaattta aaataacttt ttgggagact gaattgagta ataataaaac
9781 ttcagtcttt cgctaataat aataataata ataataataa caacaactta ttgaatgtgg
9841 ccagctcact agatgaggaa agaggaaggc atttctgca ttcttgccta gttttcctta TABLE 1-continued

```
 9901taagcaccac taagttaata gctctgtctt tttggtgttt gcactatgta atgcttttaa
 9961tactttttaa ttgtgctttt ttatgtatta aatgtttttc cttttgccaa aaaaaaaaaa
10021aa
```

SEQ ID NO: 22 Human MDM4 Isoform 4 Amino Acid Sequence (NP_001265445.1)

```
    1MTSFSTSAQC STSDSACRIS PGQINQVRPK LPLLKILHAA GAQGEMFTVK EVMHYLGQYI
   61MVKQLYDQQE QHMVYCGGDL LGELLGRQSF SVKDPSPLYD MLRKNLVTLA TATTAKCRGK
  121FHFQKKNYRR RYPHTAYLRA
```

SEQ ID NO: 23 Human MDM4 Transcript Variant 5 cDNA Sequence (NM_001278517.1; CDS: 167-1345)

```
    1gtgtgggagg ccggaagttg cggcttcatt actcgccatt tcaaaatgct gccgaggccc
   61taggatctgt gactgccacc cctcccccca cccgggctcg gcgggggagc gactcatgga
  121gctgccgtaa gttttaccaa cagactgcag tttcttcact accaaaatga catcattttc
  181cacctctgct cagtgttcaa catctgacag tgcttgcagg atctctcctg gacaaatcaa
  241tcaggatcac agtatggata ttccaagtca agaccaactg aagcaaagtg cagaggaaag
  301ttccacttcc agaaaaagaa ctacagaaga cgatatcccc acactgccta cctcagagca
  361taaatgcata cattctagag aagatgaaga cttaattgaa aatttagccc aagatgaaac
  421atctaggctg gaccttggat ttgaggagtg ggatgtagct ggcctgcctt ggtggttttt
  481aggaaacttg agaagcaact atacacctag aagtaatggc tcaactgatt tacagacaaa
  541tcaggatgtg ggtactgcca ttgtttcaga tactacagat gacttgtggt ttttgaatga
  601gtcagtatca gagcagttag gtgttggaat aaaagttgaa gctgctgata ctgaacaaac
  661aagtgaagaa gtagggaaag taagtgacaa aaaggtgatt gaagtgggaa aaaatgatga
  721cctggaggac tctaagtcct taagtgatga taccgatgta gaggttacct ctgaggatga
  781gtggcagtgt actgaatgca agaaatttaa ctctccaagc aagaggtact gttttcgttg
  841ttgggccttg aggaaggatt ggtattcaga ttgttcaaag ttaacccatt ctctctccac
  901gtctgatatc actgccatac ctgaaaagga aaatgaagga aatgatgtcc ctgattgtcg
  961aagaaccatt tcggctcctg tcgttagacc taaagatgcg tatataaaga aagaaaactc
 1021caaacttttt gatccctgca actcagtgga attcttggat ttggctcaca gttctgaaag
 1081ccaagagacc atctcaagca tgggagaaca gttagataac ctttctgaac agagaacaga
 1141tacagaaaac atggaggatt gccagaatct cttgaagcca tgtagcttat gtgagaaaag
 1201accacgagac gggaacatta ttcatggaag gacgggccat cttgtcactt gttttcactg
 1261tgccagaaga ctaaagaagg ctggggcttc atgccctatt tgcaagaaag agattcagct
 1321ggttattaag gtttttatag cataatggta gtacgaacat aaaaatgcat ttattccgtt
 1381cacttaccac attatttgaa aatcaatcct ttatttaatt ttatttccaa cctgtcagag
 1441aatgttctta ggcatcaaaa tccaaggtag ctgtaagaaa aatactggag ctaacaatga
 1501agaacagaag taatctgatt agtcaaatta ttaagtgcca tggattactt tatgcagcag
 1561tcaggtacat agttaggtga acccaaaaga aaaactcttg aaaacaagag atttcttcca
 1621tgcacattta caatattgag gtataattaa catgataaag tgtttccttc taacgagttg
 1681tagaaatctg agtaaccacc caaaaaagca atagaatgtt tctgtcaccc caaaacactc
 1741ccttctgccc ctcttcagac agtccttcag ctatttcatg gctctcaccc tagttttttt
 1801tttttttgca cttttttttt tccgggggta tagggggaggt gtggggcgac agggtctgtc
 1861ttgttctgtc tcccaggctg aagtgcagtg cagtggtatg atcatggctc actgcagcct
 1921tggtttcctg ggcataagtg gtcttcccac ttcagcctcc tgagtagctg agactataga
 1981ctagcataac cacactggct aatttttgt ggagatgaag tctcactatg ttgcccaggc
 2041tggtctcgaa ctcctgggct caaacaatcc tcccgcctca gccttccaaa ttgctgggat
 2101tatagtcatg aggcacctag tctggccctt ttgcaagact ttaatctgaa atctaaattt
 2161ttaaaattta agtacttaca aaggatatac tatccaacat attgcatatt atatatgtgc
 2221tttaaagttt tttttttttt ttgagagacg gtctcacttt gtcatccaag ctggagtgca
 2281gtggtgcaaa cacggcccac ctcctgggct caagtgatcc tccagcctca gcttccctca
 2341caggcattca ctatcactcc cagctaatta aaataatttg tagacggtgt ctcgttatgt
 2401tgcccaggct ggtctcgaac tcctgggttt aagtgattcc cccgcctcag cctcccaaag
 2461tgttgggctt acagccttga gccactatgc ttggctcaaa gatattttta tgaaagccct
 2521gggactatag atttagctga ttaaatttat agaaaaagtc ctgtcatata aactggcaaa
 2581gtctgttctt aatttaatta gccaaatcag acttaacttc cgtcagaaca tgtcttggtt
 2641ttaattcaga taaacacaca aacatacttc tctggcacag ccttcagaag catcagtttt
 2701tgttttgttt tgttttgttt tttgagacag ggtcttgctc tgtcgcccag gctggagtgc
 2761actggcacaa tcacagttca ctgcagcctc gacctcccag atccaagcaa tcctcccacc
 2821taagcctccc aagtagctgg gtctataggc gcgtgccacc accatgccca gctgaatttt
 2881gtatttttttg tacagacagc atttgccat gttgcccagg ctggtcccaa acttctagcc
 2941tcaagcaacc ctcctgcctc agcctctcaa agtgctagga ttgcagtcct gagctactgc
 3001cccctaccct ctttgcgtct taggagtcat ttagattttt tttgatcctt ttgtttagtg
 3061cctctggagc tgcttacacc aaggcaatac gccttgatat actggatggt tgagaggcag
 3121cctctttttt tttttttttt tttttttttt tttggaggat agggagtatg gctgttgtga
 3181aaagggaggt aaagagaaat ggtagatctg aagaggcctc atcagagcac atattttagg
 3241acaacacata tggaaattgg acatctttaa gttggtttcc atagagctat gcatgtatcc
 3301ttacccccat gggaaaatgt tggtgtgttc tcaagggtat gcatgtgtca ttttgaagac
 3361caaggcccta gaattgtcaa acttaaggat cataaaaatc atgagggttg cttgttaaaa
 3421atgtccaaac gtgcagagac tgatctttga gatctggacc aggaatttgc atttgaacaa
 3481gtgttcctgg aatctctatg caagttttat acagaacata cttttggaat ccttgcccta
 3541gacaggggtg tccaatcttt tggcttccct ggtccacaat ggaagaagaa ttgtcttgga
 3601ccacacataa aatacactaa cactaacaat agctgatgag ctaaaaaaaa aaaaaaaaaa
 3661aatcgtggac cgggcgtagt ggctcacgcc tgtaatccca acactttggg agatcaccta
 3721ggtcgggagt ttgagaccag cctgaccgac atggagaaac cccattttta ctaaaaatac
 3781aaaaaattag ctgggcatgg tggtgcatgc ctgtagtccc agctactcag gaggctgagg
 3841caggagaatc gcttgaacct gagaggggga gattgcggtg agctgagatt gcgccattgc
 3901accccagcct gggcaacaat agcgaaactg tctcagaaaa aagaaaaaaa aaatcgcaaa
 3961aagaaaaatc tcataatgtc gttgttggtt tttttttttt tttttgagac agtctcactc
 4021tgttgcccag gctggagtgc aatggcatga tctctgctca ccgcaacctc tgcctcccgg
 4081gttcaggtga ttctcctgcc tcagcctccc agatagctgg gactacaggc acataccacc
```

TABLE 1-continued

| | | | | | | |
|---|---|---|---|---|---|---|
| 4141 | atgcctggct | aatttttgta | tttttagtag | agatgggggt | ttcactgtgt | tggccaggct |
| 4201 | ggtctcgaac | tcctgacctc | atgatccaca | cacctcggcc | tcccaaagtc | ctgcgattac |
| 4261 | aggcgtgagc | taccgcaccc | agccaagttg | taatttttaa | taaaacttaa | gaagtaaaca |
| 4321 | ttttacttat | gtttataggt | atttgatcct | aaatttgaca | catcattgcc | catgaaagaa |
| 4381 | tcctcttagg | ctgctcagct | tcactcttcc | tgcttgccca | ccggggtttt | tcactgcttc |
| 4441 | tgttagcact | aagtacttag | acgatcctaa | gatatgtgct | tgagccgaat | ttcatcttta |
| 4501 | cttgtaggaa | actttaaact | atttcttttc | ttttcttttt | tttttttttt | tacttgagat |
| 4561 | ggagttttgc | tcttgtcgcc | caggctggag | tgcagtggag | tgatctcggc | tcactgcaac |
| 4621 | ctctgcctcc | cgggttcaaa | tgattctcct | gcctcagcct | cccaagtagc | tgggattaca |
| 4681 | ggtgtgcacc | accatgtctg | gctaattttg | tatttttagt | agagatggtt | tcaccatgtt |
| 4741 | ggtcaggctg | gtctcgaact | cctgacctca | ggtcatccac | ccacctcagc | ctcgcaaagt |
| 4801 | gctgagatta | caggcatgag | ccacagcgcc | cagcttaaac | tattttcttg | gtctgttttt |
| 4861 | gattttcttt | tttccttgcc | actgcggtac | agattttttt | tactcactgc | cactaaacta |
| 4921 | aagcaaggca | tagtttatat | gtgaagtgtt | cagagtttac | tgctataagg | aaacttccaa |
| 4981 | atactgacat | ttacctttta | gctgtagtta | ttgggaccat | gtgctctggt | tttctggaga |
| 5041 | ctgccaaatt | gctcccattt | ttctgcatcc | cacctggttt | ctttctgcat | gtcccctttc |
| 5101 | actttcaaac | ctcttcattt | ggatgttaaa | ttatatggtc | acctagttat | aggtaagcct |
| 5161 | tgttcgagtt | gatatcttga | ttgtgaggaa | ggatctgtgt | cattggagct | tgtttctgct |
| 5221 | gcaacgtgct | gtagactatg | aataatgaaa | tcacaccaca | ttaccatcag | atttcttgtt |
| 5281 | ttagttgtca | aattaatatt | tatgattgtt | atcttgggcg | aaaagttcag | agcagagatg |
| 5341 | acaaatcatt | agaacaacga | tgaatttcag | tattacggct | aaaaagttct | tctgtctgaa |
| 5401 | tattaactca | ctctccttcc | agtgtacttc | acagtaattg | gtatgctttt | ttatttaatg |
| 5461 | cttaaatcaa | actttataaa | aatcttagac | cagatcttta | atatggtatg | ccatttcccc |
| 5521 | agtctaccaa | tggaatagta | tgggtttcta | atcctaggct | tgtacaatgg | attggagttg |
| 5581 | agccatgcca | gcctccacac | tgccactaac | ttctgtaatg | taagattgag | tcactgccaa |
| 5641 | gcatttgaaa | tatgcagttg | tgttttaatt | ataatttatg | tatagttaga | tgtatgtagt |
| 5701 | gcattgtgtg | gtattatttg | gtttgtaaga | atttattttt | aagggtcaag | gtcatttgta |
| 5761 | acattttgtg | tgtgtcaatt | caatgcaatg | ttggctgcct | tttgaagtct | ttgatatatt |
| 5821 | ggtgaatatt | cttctgatct | ataatacaaa | gctatgtaat | gttacctctt | gactcgcttt |
| 5881 | tgaaaggaag | acaattgtta | actagatatt | tgagtttttt | cccctcagaa | ttatgtgaat |
| 5941 | ttctgatata | tggctttaga | tactgtgaat | ctgttttcca | tttagtcagt | tatctgctta |
| 6001 | aattgttcag | aactatatcc | taacgagcaa | ttagttctga | tggttctccc | agtcatgagt |
| 6061 | gtgcatgtgt | gcaagcatgt | tttgatcctg | atgctacctt | tgctaaaaat | ggccatagat |
| 6121 | taggaactag | ctatgttttt | agaatcaaag | atgaaccggt | aagctgtctc | atgtaccaaa |
| 6181 | cgtgaaattt | acagtgttta | caaatgtctg | gaattttgca | ctgccatagg | gaatgttaag |
| 6241 | gttacttggc | tggaatttat | cagacttgtg | agtaaacaag | ttgaagttta | gcagatgagg |
| 6301 | gggaatattg | aggcccctaa | ggctaaacaa | aataatcagt | atctgagata | gtggctaatg |
| 6361 | tggctcccca | ggcctaattt | gggaacagtt | tttcctgatt | gctttgagaa | gtactttctt |
| 6421 | ttgacagaaa | ttttcattct | gcttgccatt | gctatattct | ccctttatag | gagccattgg |
| 6481 | atttctttcc | ttttgtggga | aatgtcccat | tagcattttc | agatcttttg | atgtgcacta |
| 6541 | atgccattat | tggtaatgcc | gttattggtg | aatacagcat | agttaaataa | actgttacag |
| 6601 | taaatctaca | cttggatttg | ctgcacctct | accaatagcc | ttttgaatga | ctgaaagtgt |
| 6661 | taacagagaa | agaggcatgt | ctgcagaaag | agatagctaa | tattttttgg | tactttatct |
| 6721 | gaaatccaag | atgctgcttc | ccctgcaggt | tgttttcctt | cttacgatcc | tcattgaatc |
| 6781 | ccctctggga | gcacaggaca | gttagtagaa | ctctccattt | cttttttttt | tttttagac |
| 6841 | ggagtctctc | tctgtcgccc | cggctggagt | gcagtggcgc | gatctcggct | cactgcaacc |
| 6901 | tccgcctccc | gggttcaccc | cattctcctg | cctcagcctc | cctagtagct | gggactatag |
| 6961 | gcgcccgcca | ccacgcctgg | ctaattttg | tatttttatt | ggagacgggg | tttcaccgtc |
| 7021 | ttagccagga | tggtcttgat | ctcctgacct | cgtgatctgc | ccacctcagc | ctcccaaagt |
| 7081 | actgggatta | caggcgtgag | ccaccgcgcc | cggccggaac | tctccatttc | ttaaggtaaa |
| 7141 | gagggtcaag | gatacctaaa | aagggtcaaa | taatgctaga | agagcaattc | ctctttcaga |
| 7201 | gcagttgctg | taatttggca | aatgctttat | cgaagattga | tattaggcta | ggggcggtgg |
| 7261 | cttacgcctg | taatcccagc | actttgggag | gccgaggtgg | gtggattgcc | tgagctcagg |
| 7321 | agttcgagac | cagtctgacc | agtatggtga | aaccctgtct | ctactaaaaa | tacaaaaatt |
| 7381 | agccggtcgt | ggtggcgtgc | acctgtagtc | ccagctactt | ggcaggttga | gacaggagaa |
| 7441 | tcgcttgaac | ctgggaggtg | gaggttgcag | tgagccgaga | ctgcaccact | gcgctcccac |
| 7501 | ctgggtgaca | gagactctgt | ctcaaaaaaa | aggacattta | tcattataac | atcttattag |
| 7561 | agcccctaat | ttcttatctg | aaggcactgt | tttttttttt | aaacagttaa | gtactgatgt |
| 7621 | caacagacaa | atatttctga | tcagatagtc | ccctgtcaac | agtagcaaat | gtggtttcat |
| 7681 | aaagtgggaa | gaaaacagca | ttttaaagta | actttttggg | agactgattt | gagtaataat |
| 7741 | aaaactctgg | tctcccttaa | gaaaaaaaaa | cccttccacc | tttactgtgt | catttatatc |
| 7801 | cccttagttc | caaagttaat | tatcttattt | ctggatattg | cttttatacc | aaagaccctt |
| 7861 | atcagccctt | gtaactacag | tatctttaga | taagattcct | ctttccagtc | agtcctggga |
| 7921 | aatgtttctg | ttgcagagtt | aggcggtaga | tgggaagctg | tgatggcaga | gctactatct |
| 7981 | aataaagtaa | caactcgtag | ttgaggcttc | ctttctgtgt | gtgatggggg | atagggagtt |
| 8041 | agctcccctg | ttgtctcagc | actaagaaat | tgaggtcagg | ccaggcgcgg | tggttcactc |
| 8101 | ctgttattcc | agcactgggg | tggccaaagt | gggcagattg | cttgcgctct | ggagctcgag |
| 8161 | accagcctgg | gcaacatggt | gaaaccctgt | ctctaccaaa | aatacaaaaa | aaaagctggg |
| 8221 | catggtgggt | gcatgcttgt | cccagctact | gaggaggctg | aggtgggagg | atcgcttgag |
| 8281 | cctgggaggt | ggaggttgca | gtgagctgag | atggcaccac | tgcaatccaa | ggtgggtgac |
| 8341 | agagacgctg | tctcaaagaa | attgaggtca | ggcttccttc | ttacagaatt | atttttttct |
| 8401 | ctgtagtttg | cctcattttt | tcactttctt | ttcaatgaga | atcgaagtgt | ttcttttggg |
| 8461 | tttttttttc | cccttttaa | aatcaacagg | aaatgtttca | aaggagggat | gaaatgcttc |
| 8521 | ttggcttcct | cagcacttgg | caaggtagac | ctcatagcaa | ccttgaatat | gactttcttt |
| 8581 | agtctctagc | tatgcactat | taagtgcctc | ttgggtagag | gtagagttaa | gtattgagtg |
| 8641 | ccagtcttga | cgtccgtatg | cctcagtttt | tctcatatat | aaaaagcagt | atacatacct |
| 8701 | accctttct | acctcatcat | ttgttgtagg | gattaaatcc | gggagagcaa | ttctgaagcc |
| 8761 | tataaatttc | cttgaagaga | tctaagaacc | tattatgctc | ttggtgtacc | aagctctggg |
| 8821 | gtatatattc | agaatacctc | atgttctgga | agctgagcac | tagctcccct | ttattgcctg |
| 8881 | cctggcagag | cctgtttgat | tactgcaggc | cctttaccc | atgcttctag | tttaggtatt |

TABLE 1-continued

```
8941 ctttctttga tatgaggctc ttgaccagaa aagagttctt tctctaggtg ttctgagaga
9001 agtttgtaaa tttggatagt acattctatc ctgataaaac caccttgctg tggtcttgat
9061 gtacaaaaaa aaatttttt tttgagacag agtcttactc tgtcacccag gctggaatgc
9121 agtggcgcaa tcttggttca ctgcaacccc cgcctcctgg gttcaagcga tcctcctgcc
9181 tcaacctctc aagtagctgg gactacaggc gtgcaccacc acacctggct aattttgtat
9241 ttttagtaga gacagggttt caccatgttg gccaggctgg tcttgaactc ctgacctcag
9301 gcgatctgcc cgccttggcc tcccaaagta ctgggattac aggcgtgagc aactgctcct
9361 ggcccaaaac atctctttct acatacactt gagtaggtgg cataaaatgc actgtcaata
9421 tatagaaaac atgaaatttt ccaaatattt ccgatcagag aatcacaaga gcagcaaatg
9481 tggtttcatc aagtgggaag aaagcagcaa tttaaaataa ctttttggga gactgaattg
9541 agtaataata aaacttcagt ctttcgctaa taataataat aataataata ataacaacaa
9601 cttattgaat gtggccagct cactagatga ggaaagagga aggcattttc tgcattcttg
9661 cctagtttc cttataagca ccactaagtt aatagctctg tctttttggt gtttgcacta
9721 tgtaatgctt ttaatacttt ttaattgtgc ttttttatgt attaaatgtt tttcctttg
9781 ccaaaaaaaa aaaaaa
```

SEQ ID NO: 24 Human MDM4 Isoform 5 Amino Acid Sequence (NP_001265446.1)

```
  1 MTSFSTSAQC STSDSACRIS PGQINQDHSM DIPSQDQLKQ SAEESSTSRK RTTEDDIPTL
 61 PTSEHKCIHS REDEDLIENL AQDETSRLDL GFEEWDVAGL PWWFLGNLRS NYTPRSNGST
121 DLQTNQDVGT AIVSDTTDDL WFLNESYSEQ LGVGIKVEAA DTEQTSEEVG KVSDKKVIEV
181 GKNDDLEDSK SLSDDTDVEV TSEDEWQCTE CKKFNSPSKR YCFRCWALRK DWYSDCSKLT
241 HSLSTSDITA IPEKENEGND VPDCRRTISA PVVRPKDAYI KKENSKLFDP CNSVEFLDLA
301 HSSESQETIS SMGEQLDNLS EQRTDTENME DCQNLLKPCS LCEKRPRDGN IIHGRTGHLV
361 TCFHCARRLK KAGASCPICK KEIQLVIKVF IA
```

SEQ ID NO: 25 Human MDM4 Transcript Variant 6 cDNA Sequence (NM_001278518.1; CDS: 167-517)

```
   1 gtgtgggagg ccggaagttg cggcttcatt actcgccatt tcaaaatgct gccgaggccc
  61 taggatctgt gactgccacc cctcccccca cccgggctcg gcgggggagc gactcatgga
 121 gctgccgtaa gttttaccaa cagactgcag tttcttcact accaaaatga catcattttc
 181 cacctctgct cagtgttcaa catctgacag tgcttgcagg atctctcctg gacaaatcaa
 241 tcaggtacga ccaaaactgc cgcttttgaa gatttgcat gcagcaggtg cgcaaggtga
 301 aatgttcact gttaaagagg tcatgcacta tttaggtcag tacataatgg tgaagcaact
 361 ttatgatcag caggagcagc atatggtata ttgtggtgga gatcttttgg gagaactact
 421 gggacgtcag agcttctccg tgaaagaccc aagccctctc tatgatatgc taagaaagaa
 481 tcttgtcact ttagccactg ctactacagg tgattgaagt gggaaaaaat gatgacctgg
 541 aggactctaa gtccttaagt gatgataccg atgtagaggt tacctctgag gatgagtggc
 601 agtgtactga atgcaagaaa tttaactctc caagcaagag gtactgtttt cgttgttggg
 661 ccttgaggaa ggattggtat tcagattgtt caaagttaac ccattctctc tccacgtctg
 721 atatcactgc catacctgaa aaggaaaatg aaggaaatga tgtccctgat tgtcgaagaa
 781 ccatttcggc tcctgtcgtt agacctaaag atgcgtatat aaagaaagaa aactccaaac
 841 tttttgatcc ctgcaactca gtggaattct tggatttggc tcacagttct gaaagccaag
 901 agaccatctc aagcatggga gaacagttag ataacctttc tgaacagaga acagatacag
 961 aaaacatgga ggattgccag aatctcttga agccatgtag cttatgtgag aaaagaccac
1021 gagacgggaa cattattcat ggaaggacgg gccatcttgt cacttgtttt cactgtgcca
1081 gaagactaaa gaaggctggg gcttcatgcc ctatttgcaa gaaagagatt cagctggtta
1141 ttaaggtttt tatagcataa tggtagtacg aacataaaaa tgcatttatt ccgttcactt
1201 accacattat ttgaaaatca atcctttatt taattttatt tccaacctgt cagagaatgt
1261 tcttaggcat caaaatccaa ggtagctgta agaaaaatac tggagctaac aatgaagaac
1321 agaagtaatc tgattagtca aattattaag tgccatggat tactttatgc agcagtcagg
1381 tacatagtta ggtgaaccca aaagaaaaac tcttgaaaac aagagatttc ttccatgcac
1441 atttacaata ttgaggtata attaacatga taaagtgttt ccttctaacg agttgtagaa
1501 atctgagtaa ccacccaaaa aagcaataga atgtttctgt caccccaaaa cactcccttc
1561 tgcccctctt cagacagtcc ttcagctatt tcatggctct caccctagtt tttttttttt
1621 ttgcactttt ttttttccgg gggtataggg gaggtgtggg gcgacagggt ctgtcttgtt
1681 ctgtctccca ggctgaagtg cagtgcagtg gtatgatcat ggctcactgc agccttggtt
1741 tcctgggcat aagtggtctt cccacttcag cctcctgagt agctgagact atagactagc
1801 ataaccacac tggctaattt tttgtggaga tgaagtctca ctatgttgcc caggctggtc
1861 tcgaactcct gggctcaaac aatcctcccg cctcagcctt ccaaattgct gggattatag
1921 tcatgaggca cctagtctgg ccctttttgca agactttaat ctgaaatcta aatttttaaa
1981 atttaagtac ttacaaagga tatactatcc aacatattgc atattatata tgtgctttaa
2041 agtttttttt tttttttgag agacggtctc actttgtcat ccaagctgga gtgcagtggt
2101 gcaaacacgg cccacctcct gggctcaagt gatcctccag cctcagcttc cctcacaggc
2161 attcactatc actcccagct aattaaaata atttgtagac ggtgtctcgt tatgttgccc
2221 aggctggtct cgaactcctg ggtttaagtg attccccccgc ctcagcctcc caaagtgttg
2281 ggcttacagc cttgagccac tatgcttggc tcaaagatat ttttatgaaa gccctgggac
2341 tatagattta gctgattaaa tttatagaaa aagtcctgtc atataaactg gcaaagtctg
2401 ttcttaattt aattagccaa atcagactta acttccgtca gaacatgtct tggttttaat
2461 tcagataaac acacaaacat acttctctgg cacagccttc agaagcatca gtttttgttt
2521 tgttttgttt tgttttttga gacagggtct tgctctgtcg cccaggctgg agtgcactgg
2581 cacaatcaca gttcactgca gcctcgacct cccagatcca agcaatcctc ccacctaagc
2641 ctcccaagta gctgggtcta taggcgcgtg ccaccaccat gcccagctga attttgtatt
2701 ttttgtacag acagcatttt gccatgttgc ccaggctggt cccaaacttc tagcctcaag
2761 caaccctcct gcctcagcct ctcaaagtgc taggattgca gtcctgagct actgccccct
2821 accctctttg cgtcttagga gtcatttaga tttttttttga tccttttgtt tagtgcctct
2881 ggagctgctt acaccaaggc aatacgcctt gatatactgg atggttgaga ggcagcctct
2941 tttttttttt tttttttttt tttttttttgg aggataggga gtatggctgt tgtgaaaagg
3001 gaggtaaaga gaaatggtag atctgaagag gcctcatcag agcacatatt ttaggacaac
3061 acatatggaa attggacatc tttaagttgg tttccataga gctatgcatg tatccttacc
3121 cccatgggaa aatgttggtg tgttctcaag ggtatgcatg tgtcattttg aagaccaagg
```

TABLE 1-continued

| | | | | | | |
|---|---|---|---|---|---|---|
| 3181 | ccctagaatt | gtcaaactta | aggatcataa | aaatcatgag | ggttgcttgt | taaaaatgtc |
| 3241 | caaacgtgca | gagactgatc | tttgagatct | ggaccaggaa | tttgcatttg | aacaagtgtt |
| 3301 | cctggaatct | ctatgcaagt | tttatacaga | acatactttt | ggaatccttg | ccctagacag |
| 3361 | gggtgtccaa | tcttttggct | tccctggtcc | acaatggaag | aagaattgtc | ttggaccaca |
| 3421 | cataaaatac | actaacacta | acaatagctg | atgagctaaa | aaaaaaaaaa | aaaaaaatcg |
| 3481 | tggaccgggc | gtagtggctc | acgcctgtaa | tcccaacact | ttgggagatc | acctaggtcg |
| 3541 | ggagtttgag | accagcctga | ccgacatgga | gaaaccccat | ttttactaaa | aatacaaaaa |
| 3601 | attagctggg | catggtggtg | catgcctgta | gtcccagcta | ctcaggaggc | tgaggcagga |
| 3661 | gaatcgcttg | aacctgagag | gggagattg | cggtgagctg | agattgcgcc | attgcacccc |
| 3721 | agcctgggca | acaatagcga | aactgtctca | gaaaaaagaa | aaaaaaaatc | gcaaaaagaa |
| 3781 | aaatctcata | atgtcgttgt | tggtttttt | tttttttttt | gagacagtct | cactctgttg |
| 3841 | cccaggctgg | agtgcaatgg | catgatctct | gctcaccgca | acctctgcct | cccgggttca |
| 3901 | ggtgattctc | ctgcctcagc | ctcccagata | gctgggacta | caggcacata | ccaccatgcc |
| 3961 | tggctaattt | ttgtattttt | agtagagatg | gggtttcac | tgtgttggcc | aggctggtct |
| 4021 | cgaactcctg | acctcatgat | ccacacacct | cggcctccca | aagtcctgcg | attacaggcg |
| 4081 | tgagctaccg | cacccagcca | agttgtaatt | tttaataaaa | cttaagaagt | aaacatttta |
| 4141 | cttatgttta | taggtatttg | atcctaaatt | tgacacatca | ttgcccatga | aagaatcctc |
| 4201 | ttaggctgct | cagcttcact | cttcctgctt | gcccaccggg | gtttttcact | gcttctgtta |
| 4261 | gcactaagta | cttagacgat | cctaagatat | gtgcttgagc | cgaatttcat | ctttacttgt |
| 4321 | aggaaacttt | aaactatttc | ttttcttttc | tttttttttt | tttttactt | gagatggagt |
| 4381 | tttgctcttg | tcgcccaggc | tggagtgcag | tggagtgatc | tcggctcact | gcaacctctg |
| 4441 | cctcccgggt | tcaaatgatt | ctcctgcctc | agcctcccaa | gtagctggga | ttacaggtgt |
| 4501 | gcaccaccat | gtctggctaa | ttttgtattt | ttagtagaga | tggtttcacc | atgttggtca |
| 4561 | ggctggtctc | gaactcctga | cctcaggtca | tccacccacc | tcagcctcgc | aaagtgctga |
| 4621 | gattacaggc | atgagccaca | gcgcccagct | taaactattt | tcttggtctg | tttttgattt |
| 4681 | tctttttcc | ttgccactgc | ggtacagatt | ttttttactc | actgccacta | aactaaagca |
| 4741 | aggcatagtt | tatatgtgaa | gtgttcagag | tttactgcta | taaggaaact | tccaaatact |
| 4801 | gacatttacc | ttttagctgt | agttattggg | accatgtgct | ctggttttct | ggagactgcc |
| 4861 | aaattgctcc | catttttctg | catcccacct | ggtttctttc | tgcatgtccc | ctttcacttt |
| 4921 | caaacctctt | catttggatg | ttaaattata | tggtcaccta | gttataggta | agccttgttc |
| 4981 | gagttgatat | cttgattgtg | aggaaggatc | tgtgtcattg | gagcttgttt | ctgctgcaac |
| 5041 | gtgctgtaga | ctatgaataa | tgaaatcaca | ccacattacc | atcagatttc | ttgttttagt |
| 5101 | tgtcaaatta | atatttatga | ttgttatctt | gggcgaaaag | ttcagagcag | agatgacaaa |
| 5161 | tcattagaac | aacgatgaat | ttcagtatta | cggctaaaaa | gttcttctgt | ctgaatatta |
| 5221 | actcactctc | cttccagtgt | acttcacagt | aattggtatg | ctttttatt | taatgcttaa |
| 5281 | atcaaacttt | ataaaaatct | tagaccagat | ctttaatatg | gtatgccatt | tccccagtct |
| 5341 | accaatggaa | tagtatgggt | ttctaatcct | aggcttgtac | aatggattgg | agttgagcca |
| 5401 | tgccagcctc | cacactgcca | ctaacttctg | taatgtaaga | ttgagtcact | gccaagcatt |
| 5461 | tgaaatatgc | agttgtgttt | taattataat | ttatgtatag | ttagatgtat | gtagtgcatt |
| 5521 | gtgtggtatt | atttggtttg | taagaattta | tttttaaggg | tcaaggtcat | ttgtaacatt |
| 5581 | ttgtgtgtgt | caattcaatg | caatgttggc | tgccttttga | agtctttgat | atattggtga |
| 5641 | atattcttct | gatctataat | acaaagctat | gtaatgttac | ctcttgactc | gcttttgaaa |
| 5701 | ggaagacaat | tgttaactag | atatttgagt | tttttcccct | cagaattatg | tgaatttctg |
| 5761 | atatatggct | ttagatactg | tgaatctgtt | ttccatttag | tcagttatct | gcttaaattg |
| 5821 | ttcagaacta | tatcctaacg | agcaattagt | tctgatggtt | ctcccagtca | tgagtgtgca |
| 5881 | tgtgtgcaag | catgttttga | tcctgatgct | acctttgcta | aaaatggcca | tagattagga |
| 5941 | actagctatg | tttttagaat | caaagatgaa | ccggtaagct | gtctcatgta | ccaaacgtga |
| 6001 | aatttacagt | gtttacaaat | gtctggaatt | ttgcactgcc | atagggaatg | ttaaggttac |
| 6061 | ttggctggaa | tttatcagac | ttgtgagtaa | acaagttgaa | gtttagcaga | tgagggggaa |
| 6121 | tattgaggcc | cctaaggcta | aacaaaataa | tcagtatctg | agatagtggc | taatgtggct |
| 6181 | ccccaggcct | aatttgggaa | cagtttttcc | tgattgcttt | gagaagtact | ttcttttgac |
| 6241 | agaaattttc | attctgcttg | ccattgctat | attctccctt | tataggagcc | attggatttc |
| 6301 | tttccttttg | tgggaaatgt | cccattagca | ttttcagatc | ttttgatgtg | cactaatgcc |
| 6361 | attattggta | atgccgttat | tggtgaatac | agcatagtta | aataaactgt | tacagtaaat |
| 6421 | ctacacttgg | atttgctgca | cctctaccaa | tagccttttg | aatgactgaa | agtgttaaca |
| 6481 | gagaaagagg | catgtctgca | gaaagagata | gctaatattt | tttggtactt | tatctgaaat |
| 6541 | ccaagatgct | gcttcccctg | caggttgttt | tccttcttac | gatcctcatt | gaatcccctc |
| 6601 | tgggagcaca | ggacagttag | tagaactctc | catttctttt | tttttttttt | tagacggagt |
| 6661 | ctctctctgt | cgccccggct | ggagtgcagt | ggcgcgatct | cggctcactg | caacctccgc |
| 6721 | ctcccgggtt | caccccattc | tcctgcctca | gcctccctag | tagctgggac | tataggcgcc |
| 6781 | cgccaccacg | cctggctaat | ttttgtattt | ttattggaga | cggggtttca | ccgtcttagc |
| 6841 | caggatggtc | ttgatctcct | gacctcgtga | tctgcccacc | tcagcctccc | aaagtactgg |
| 6901 | gattacaggc | gtgagccacc | gcgcccggcc | ggaactctcc | atttcttaag | gtaaagaggg |
| 6961 | tcaaggatac | ctaaaaaggg | tcaaataatg | ctagaagagc | aattcctctt | tcagagcagt |
| 7021 | tgctgtaatt | tggcaaatgc | tttatcgaag | attgatatta | ggctaggggc | ggtggcttac |
| 7081 | gcctgtaatc | ccagcacttt | gggaggccga | ggtgggtgga | ttgcctgagc | tcaggagttc |
| 7141 | gagaccagtc | tgaccagtat | ggtgaaaccc | tgtctctact | aaaaatacaa | aaattagccg |
| 7201 | gtcgtggtgg | cgtgcacctg | tagtcccagc | tacttggcag | gttgagacag | gagaatcgct |
| 7261 | tgaacctggg | aggtggaggt | tgcagtgagc | cgagactgca | ccactgcgct | cccacctggg |
| 7321 | tgacagagac | tctgtctcaa | aaaaaaggac | atttatcatt | ataacatctt | attagagccc |
| 7381 | ctaatttctt | atctgaaggc | actgtttttt | tttttaaaca | gttaagtact | gatgtcaaca |
| 7441 | gacaaatatt | tctgatcaga | tagtcccctg | tcaacagtag | caaatgtggt | ttcataaagt |
| 7501 | gggaagaaaa | cagcatttta | aagtaacttt | ttgggagact | gatttgagta | ataataaaac |
| 7561 | tctggtctcc | cttaagaaaa | aaaaaccctt | ccacctttac | tgtgtcattt | atatcccctt |
| 7621 | agttccaaag | ttaattatct | tatttctgga | tattgctttt | ataccaaaga | cccttatcag |
| 7681 | cccttgtaac | tacagtatct | ttagataaga | ttcctctttc | cagtcagtcc | tgggaaatgt |
| 7741 | ttctgttgca | gagttaggcg | gtagatggga | agctgtgatg | gcagagctac | tatctaataa |
| 7801 | agtaacaact | cgtagttgag | gcttcctttc | tgtgtgtgat | gggggatagg | gagttagctc |
| 7861 | ccctgttgtc | tcagcactaa | gaaattgagg | tcaggccagg | cgcggtggtt | cactcctgtt |
| 7921 | attccagcac | tggggtggcc | aaagtgggca | gattgcttgc | gctctggagc | tcgagaccag |

TABLE 1-continued

```
7981 cctgggcaac atggtgaaac cctgtctcta ccaaaaatac aaaaaaaaag ctgggcatgg
8041 tgggtgcatg cttgtcccag ctactgagga ggctgaggtg ggaggatcgc ttgagcctgg
8101 gaggtggagg ttgcagtgag ctgagatggc accactgcaa tccaaggtgg gtgacagaga
8161 cgctgtctca aagaaattga ggtcaggctt ccttcttaca gaattatttt tttctctgta
8221 gtttgcctca tttttcact ttcttttcaa tgagaatcga agtgtttctt ttgggttttt
8281 ttttcccct tttaaaatca acaggaaatg tttcaaagga gggatgaaat gcttcttggc
8341 ttcctcagca cttggcaagg tagacctcat agcaaccttg aatatgactt tctttagtct
8401 ctagctatgc actattaagt gcctcttggg tagaggtaga gttaagtatt gagtgccagt
8461 cttgacgtcc gtatgcctca gtttttctca tatataaaaa gcagtataca tacctaccct
8521 tttctacctc atcatttgtt gtagggatta aatccgggag agcaattctg aagcctataa
8581 atttccttga agagatctaa gaacctatta tgctcttggt gtaccaagct ctggggtata
8641 tattcagaat acctcatgtt ctggaagctg agcactagct cccctttatt gcctgcctgg
8701 cagagcctgt ttgattactg caggcccttt tacccatgct tctagtttag gtattctttc
8761 tttgatatga ggctcttgac cagaaaagag ttctttctct aggtgttctg agagaagttt
8821 gtaaatttgg atagtacatt ctatcctgat aaaaccacct tgctgtggtc ttgatgtaca
8881 aaaaaaaatt tttttttga gacagagtct tactctgtca cccaggctgg aatgcagtgg
8941 cgcaatcttg gttcactgca acccccgcct cctgggttca agcgatcctc ctgcctcaac
9001 ctctcaagta gctgggacta caggcgtgca ccaccacacc tggctaattt tgtattttta
9061 gtagagacag ggtttcacca tgttggccag gctggtcttg aactcctgac ctcaggcgat
9121 ctgcccgcct tggcctccca aagtactggg attacaggcg tgagcaactg ctcctggccc
9181 aaaacatctc tttctacata cacttgagta ggtggcataa aatgcactgt caatatatag
9241 aaaacatgaa attttccaaa tatttccgat cagagaatca caagagcagc aaatgtggtt
9301 tcatcaagtg ggaagaaagc agcaatttaa aataacttt tgggagactg aattgagtaa
9361 taataaaact tcagtctttc gctaataata ataataataa taataataac aacaacttat
9421 tgaatgtggc cagctcacta gatgaggaaa gaggaaggca ttttctgcat tcttgcctag
9481 ttttccttat aagcaccact aagttaatag ctctgtcttt ttggtgtttg cactatgtaa
9541 tgcttttaat actttttaat tgtgcttttt tatgtattaa atgtttttcc ttttgccaaa
9601 aaaaaaaaaa a
```

SEQ ID NO: 26 Human MDM4 Isoform 6 Amino Acid Sequence (NP_0012654471)

```
 1 MTSFSTSAQC STSDSACRIS PGQINQVRPK LPLLKILHAA GAQGEMFTVK EVMHYLGQYI
61 MVKQLYDQQE QHMVYCGGDL LGELLGRQSF SVKDPSPLYD MLRKNLVTLA TATTGD
```

SEQ ID NO NO: 27 Human MDM4 Transcript Variant 7 cDNA Sequence (NM_0012785191; CDS: 167-970)

```
   1 gtgtgggagg ccggaagttg cggcttcatt actcgccatt tcaaaatgct gccgaggccc
  61 taggatctgt gactgccacc cctccccca cccgggctcg gcgggggagc gactcatgga
 121 gctgccgtaa gttttaccaa cagactgcag tttcttcact accaaaatga catcattttc
 181 cacctctgct cagtgttcaa catctgacag tgcttgcagg atctctcctg gacaaatcaa
 241 tcaggtacga ccaaaactgc cgcttttgaa gattttgcat gcagcaggtg cgcaaggtga
 301 aatgttcact gttaaagagg tgattgaagt gggaaaaaat gatgacctgg aggactctaa
 361 gtccttaagt gatgataccg atgtagaggt tacctctgag gatgagtggc agtgtactga
 421 atgcaagaaa tttaactctc caagcaagag gtactgtttt cgttgttggg ccttgaggaa
 481 ggattggtat tcagattgtt caaagttaac ccattctctc tccacgtctg atatcactgc
 541 catacctgaa aaggaaaatg aaggaaatga tgtccctgat tgtcgaagaa ccatttcggc
 601 tcctgtcgtt agacctaaag atgcgtatat aaagaaagaa aactccaaac tttttgatcc
 661 ctgcaactca gtggaattct tggatttggc tcacagttct gaaagccaag agaccatctc
 721 aagcatggga gaacagttag ataacctttc tgaacagaga acagatacag aaaacatgga
 781 ggattgccag aatctcttga agccatgtag cttatgtgag aaaagaccac gagacgggaa
 841 cattattcat ggaaggacgg gccatcttgt cacttgtttt cactgtgcca gaagactaaa
 901 gaaggctggg gcttcatgcc ctatttgcaa gaaagagatt cagctggtta ttaaggtttt
 961 tatagcataa tggtagtacg aacataaaaa tgcatttatt ccgttcactt accacattat
1021 ttgaaaatca atcctttatt taattttatt tccaacctgt cagagaatgt tcttaggcat
1081 caaaatccaa ggtagctgta agaaaaatac tggagctaac aatgaagaac agaagtaatc
1141 tgattagtca aattattaag tgccatggat tactttatgc agcagtcagg tacatagtta
1201 ggtgaaccca aaagaaaaac tcttgaaaac aagagatttc ttccatgcac atttacaata
1261 ttgaggtata attaacatga taaagtgttt ccttctaacg agttgtagaa atctgagtaa
1321 ccacccaaaa aagcaataga atgtttctgt caccccaaaa cactcccttc tgcccctctt
1381 cagacagtcc ttcagctatt tcatggctct caccctagtt tttttttttt ttgcactttt
1441 tttttccgg gggtataggg gaggtgtggg gcgacagggt ctgtcttgtt ctgtctccca
1501 ggctgaagtg cagtgcagtg gtatgatcat ggctcactgc agccttggtt tcctgggcat
1561 aagtggtctt cccacttcag cctcctgagt agctgagact atagactagc ataaccacac
1621 tggctaattt tttgtggaga tgaagtctca ctatgttgcc caggctggtc tcgaactcct
1681 gggctcaaac aatcctcccg cctcagcctt ccaaattgct gggattatag tcatgaggca
1741 cctagtctgg cccttttgca agactttaat ctgaaatcta aatttttaaa atttaagtac
1801 ttacaaagga tatactatcc aacatattgc atattatata tgtgctttaa agttttttt
1861 ttttttgag agacggtctc actttgtcat ccaagctgga gtgcagtggt gcaaacacgg
1921 cccacctcct gggctcaagt gatcctccag cctcagcttc cctcacaggc attcactatc
1981 actcccagct aattaaaata atttgtagac ggtgtctcgt tatgttgccc aggctggtct
2041 cgaactcctg ggtttaagtg attcccccgc ctcagcctcc caaagtgttg ggcttacagc
2101 cttgagccac tatgcttggc tcaaagatat ttttatgaaa gccctgggac tatagattta
2161 gctgattaaa tttatagaaa aagtcctgtc atataaactg gcaaagtctg ttcttaattt
2221 aattagccaa atcagactta acttccgtca gaacatgtct tggttttaat tcagataaac
2281 acacaaacat acttctctgg cacagccttc agaagcatca gtttttgttt tgttttgttt
2341 tgttttttga gacagggtct tgctctgtcg cccaggctgg agtgcactgg cacaatcaca
2401 gttcactgca gcctcgacct cccagatcca agcaatcctc ccacctaagc ctcccaagta
2461 gctgggtcta taggcgcgtg ccaccaccat gcccagctga attttgtatt ttttgtacag
2521 acagcatttt gccatgttgc ccaggctggt cccaaacttc tagcctcaag caaccctcct
2581 gcctcagcct ctcaaagtgc taggattgca gtcctgagct actgcccccct accctctttg
2641 cgtcttagga gtcatttaga tttttttga tcctttttgtt tagtgcctct ggagctgctt
```

TABLE 1-continued

```
2701 acaccaaggc aatacgcctt gatatactgg atggttgaga ggcagcctct tttttttttt
2761 tttttttttt ttttttttgg aggataggga gtatggctgt tgtgaaaagg gaggtaaaga
2821 gaaatggtag atctgaagag gcctcatcag agcacatatt ttaggacaac acatatggaa
2881 attggacatc tttaagttgg tttccataga gctatgcatg tatccttacc cccatgggaa
2941 aatgttggtg tgttctcaag ggtatgcatg tgtcattttg aagaccaagg ccctagaatt
3001 gtcaaactta aggatcataa aaatcatgag ggttgcttgt taaaaatgtc caaacgtgca
3061 gagactgatc tttgagatct ggaccaggaa tttgcatttg aacaagtgtt cctggaatct
3121 ctatgcaagt tttatacaga acatactttt ggaatccttg ccctagacag gggtgtccaa
3181 tcttttggct tccctggtcc acaatggaag aagaattgtc ttggaccaca cataaaatac
3241 actaacacta acaatagctg atgagctaaa aaaaaaaaaa aaaaaaatcg tggaccgggc
3301 gtagtggctc acgcctgtaa tcccaacact ttgggagatc acctaggtcg ggagtttgag
3361 accagcctga ccgacatgga gaaaccccat ttttactaaa aatacaaaaa attagctggg
3421 catggtggtg catgcctgta gtcccagcta ctcaggaggc tgaggcagga gaatcgcttg
3481 aacctgagag ggggagattg cggtgagctg agattgcgcc attgcacccc agcctgggca
3541 acaatagcga aactgtctca gaaaaaagaa aaaaaaaatc gcaaaaagaa aaatctcata
3601 atgtcgttgt tggttttttt tttttttttt gagacagtct cactctgttg cccaggctgg
3661 agtgcaatgg catgatctct gctcaccgca acctctgcct cccgggttca ggtgattctc
3721 ctgcctcagc ctcccagata gctgggacta caggcacata ccaccatgcc tggctaattt
3781 ttgtattttt agtagagatg gggggtttcac tgtgttggcc aggctggtct cgaactcctg
3841 acctcatgat ccacacacct cggcctccca aagtcctgcg attacaggcg tgagctaccg
3901 cacccagcca agttgtaatt tttaataaaa cttaagaagt aaacatttta cttatgttta
3961 taggtatttg atcctaaatt tgacacatca ttgcccatga aagaatcctc ttaggctgct
4021 cagcttcact cttcctgctt gcccaccggg gtttttcact gcttctgtta gcactaagta
4081 cttagacgat cctaagatat gtgcttgagc cgaatttcat ctttacttgt aggaaacttt
4141 aaactatttc ttttcttttc tttttttttt tttttactt gagatggagt tttgctcttg
4201 tcgcccaggc tggagtgcag tggagtgatc tcggctcact gcaacctctg cctcccgggt
4261 tcaaatgatt ctcctgcctc agcctcccaa gtagctggga ttacaggtgt gcaccaccat
4321 gtctggctaa ttttgtattt ttagtagaga tggtttcacc atgttggtca ggctggtctc
4381 gaactcctga cctcaggtca tccacccacc tcagcctcgc aaagtgctga gattacaggc
4441 atgagccaca gcgcccagct taaactattt tcttggtctg tttttgattt tcttttttcc
4501 ttgccactgc ggtacagatt ttttttactc actgccacta aactaaagca aggcatagtt
4561 tatatgtgaa gtgttcagag tttactgcta taaggaaact tccaaatact gacatttacc
4621 ttttagctgt agttattggg accatgtgct ctggttttct ggagactgcc aaattgctcc
4681 catttttctg catcccacct ggtttcttc tgcatgtccc ctttcacttt caaacctctt
4741 catttggatg ttaaattata tggtcaccta gttataggta agccttgttc gagttgatat
4801 cttgattgtg aggaaggatc tgtgtcattg gagcttgttt ctgctgcaac gtgctgtaga
4861 ctatgaataa tgaaatcaca ccacattacc atcagatttc ttgttttagt tgtcaaatta
4921 atatttatga ttgttatctt gggcgaaaag ttcagagcag agatgacaaa tcattagaac
4981 aacgatgaat ttcagtatta cggctaaaaa gttcttctgt ctgaatatta actcactctc
5041 cttccagtgt acttcacagt aattggtatg cttttttatt taatgcttaa atcaaacttt
5101 ataaaaatct tagaccagat ctttaatatg gtatgccatt tccccagtct accaatggaa
5161 tagtatgggt ttctaatcct aggcttgtac aatggattgg agttgagcca tgccagcctc
5221 cacactgcca ctaacttctg taatgtaaga ttgagtcact gccaagcatt tgaaatatgc
5281 agttgtgttt taattataat ttatgtatag ttagatgtat gtagtgcatt gtgtggtatt
5341 atttggtttg taagaattta tttttaaggg tcaaggtcat ttgtaacatt ttgtgtgtgt
5401 caattcaatg caatgttggc tgccttttga agtctttgat atattggtga atattcttct
5461 gatctataat acaaagctat gtaatgttac ctcttgactc gcttttgaaa ggaagacaat
5521 tgttaactag atatttgagt tttttcccct cagaattatg tgaatttctg atatatggct
5581 ttagatactg tgaatctgtt ttccatttag tcagttatct gcttaaattg ttcagaacta
5641 tatcctaacg agcaattagt tctgatggtt ctcccagtca tgagtgtgca tgtgtgcaag
5701 catgttttga tcctgatgct acctttgcta aaaatggcca tagattagga actagctatg
5761 tttttagaat caaagatgaa ccggtaagct gtctcatgta ccaaacgtga aatttacagt
5821 gtttacaaat gtctggaatt ttgcactgcc atagggaatg ttaaggttac ttggctggaa
5881 tttatcagac ttgtgagtaa acaagttgaa gtttagcaga tgagggggaa tattgaggcc
5941 cctaaggcta aacaaaataa tcagtatctg agatagtggc taatgtggct ccccaggcct
6001 aatttgggaa cagtttttcc tgattgcttt gagaagtact ttcttttgac agaaattttc
6061 attctgcttg ccattgctat attctccctt tataggagcc attggatttc tttccttttg
6121 tgggaaatgt cccattagca ttttcagatc ttttgatgtg cactaatgcc attattggta
6181 atgccgttat tggtgaatac agcatagtta aataaactgt tacagtaaat ctacacttgg
6241 atttgctgca cctctaccaa tagccttttg aatgactgaa agtgttaaca gagaaagagg
6301 catgtctgca gaaagagata gctaatattt tttggtactt tatctgaaat ccaagatgct
6361 gcttccccctg caggttgttt tccttcttac gatcctcatt gaatcccctc tgggagcaca
6421 ggacagttag tagaactctc catttctttt tttttttttt tagacggagt ctctctctgt
6481 cgccccggct ggagtgcagt ggcgcgatct cggctcactg caacctccgc ctcccgggtt
6541 caccccattc tcctgcctca gcctccctag tagctgggac tataggcgcc cgccaccacg
6601 cctggctaat ttttgtattt ttattggaga cggggtttca ccgtcttagc caggatggtc
6661 ttgatctcct gacctcgtga tctgcccacc tcagcctccc aaagtactgg gattacaggc
6721 gtgagccacc gcgcccggcc ggaactctcc atttcttaag gtaaagaggg tcaaggatac
6781 ctaaaaaggg tcaaataatg ctagaagagc aattcctctt tcagagcagt tgctgtaatt
6841 tggcaaatgc tttatcgaag attgatatta ggctaggggc ggtggcttac gcctgtaatc
6901 ccagcacttt gggaggccga ggtgggtgga ttgcctgagc tcaggagttc gagaccagtc
6961 tgaccagtat ggtgaaaccc tgtctctact aaaaatacaa aaattagccg gtcgtggtgg
7021 cgtgcacctg tagtcccagc tacttggcag gttgagacag gagaatcgct tgaacctggg
7081 aggtggaggt tgcagtgagc cgagactgca ccactgcgct cccacctggg tgacagagac
7141 tctgtctcaa aaaaaaggac atttatcatt ataacatctt attagagccc ctaatttctt
7201 atctgaaggc actgtttttt tttttaaaca gttaagtact gatgtcaaca gacaaatatt
7261 tctgatcaga tagtcccctg tcaacagtag caaatgtggt ttcataaagt gggaagaaaa
7321 cagcatttta aagtaacttt ttgggagact gatttgagta ataataaaac tctggtctcc
7381 cttaagaaaa aaaaaccctt ccacctttac tgtgtcattt atatcccctt agttccaaag
7441 ttaattatct tatttctgga tattgctttt ataccaaaga cccttatcag cccttgtaac
```

TABLE 1-continued

```
7501 tacagtatct ttagataaga ttcctctttc cagtcagtcc tgggaaatgt ttctgttgca
7561 gagttaggcg gtagatggga agctgtgatg gcagagctac tatctaataa agtaacaact
7621 cgtagttgag gcttcctttc tgtgtgtgat gggggatagg gagttagctc ccctgttgtc
7681 tcagcactaa gaaattgagg tcaggccagg cgcggtggtt cactcctgtt attccagcac
7741 tggggtggcc aaagtgggca gattgcttgc gctctggagc tcgagaccag cctgggcaac
7801 atggtgaaac cctgtctcta ccaaaaatac aaaaaaaaag ctgggcatgg tgggtgcatg
7861 cttgtcccag ctactgagga ggctgaggtg ggaggatcgc ttgagcctgg gaggtggagg
7921 ttgcagtgag ctgagatggc accactgcaa tccaaggtgg gtgacagaga cgctgtctca
7981 aagaaattga ggtcaggctt ccttcttaca gaattatttt tttctctgta gtttgcctca
8041 ttttttcact ttcttttcaa tgagaatcga agtgtttctt ttgggttttt ttttcccccct
8101 tttaaaatca acaggaaatg tttcaaagga gggatgaaat gcttcttggc ttcctcagca
8161 cttggcaagg tagacctcat agcaaccttg aatatgactt tctttagtct ctagctatgc
8221 actattaagt gcctcttggg tagaggtaga gttaagtatt gagtgccagt cttgacgtcc
8281 gtatgcctca gtttttctca tatataaaaa gcagtataca tacctaccct tttctacctc
8341 atcatttgtt gtagggatta aatccgggag agcaattctg aagcctataa atttccttga
8401 agagatctaa gaacctatta tgctcttggt gtaccaagct ctggggtata tattcagaat
8461 acctcatgtt ctggaagctg agcactagct cccctttatt gcctgcctgg cagagcctgt
8521 ttgattactg caggcccttt tacccatgct tctagtttag gtattctttc tttgatatga
8581 ggctcttgac cagaaaagag ttctttctct aggtgttctg agagaagttt gtaaatttgg
8641 atagtacatt ctatcctgat aaaaccacct tgctgtggtc ttgatgtaca aaaaaaaatt
8701 tttttttga gacagagtct tactctgtca cccaggctgg aatgcagtgg cgcaatcttg
8761 gttcactgca accccgcct cctgggttca agcgatcctc ctgcctcaac ctctcaagta
8821 gctgggacta caggcgtgca ccaccacacc tggctaattt tgtattttta gtagagacag
8881 ggtttcacca tgttggccag gctggtcttg aactcctgac ctcaggcgat ctgcccgcct
8941 tggcctccca aagtactggg attacaggcg tgagcaactg ctcctggccc aaaacatctc
9001 tttctacata cacttgagta ggtggcataa aatgcactgt caatatatag aaaacatgaa
9061 attttccaaa tatttccgat cagagaatca caagagcagc aaatgtggtt tcatcaagtg
9121 ggaagaaagc agcaatttaa aataactttt tgggagactg aattgagtaa taataaaact
9181 tcagtctttc gctaataata ataataataa taataataac aacaacttat tgaatgtggc
9241 cagctcacta gatgaggaaa gaggaaggca ttttctgcat tcttgcctag ttttccttat
9301 aagcaccact aagttaatag ctctgtcttt ttggtgtttg cactatgtaa tgcttttaat
9361 actttttaat tgtgcttttt tatgtattaa atgtttttcc ttttgccaaa aaaaaaaaaa
9421 a
```

SEQ ID NO: 28 Human MDM4 Isoform 7 Amino Acid Sequence (NP_001265448.1)

```
  1 MTSFSTSAQC STSDSACRIS PGQINQVRPK LPLLKILHAA GAQGEMFTVK EVIEVGKNDD
 61 LEDSKSLSDD TDVEVTSEDE WQCTECKKFN SPSKRYCFRC WALRKDWYSD CSKLTHSLST
121 SDITAIPEKE NEGNDVPDCR RTISAPVVRP KDAYIKKENS KLFDPCNSVE FLDLAHSSES
181 QETISSMGEQ LDNLSEQRTD TENMEDCQNL LKPCSLCEKR PRDGNIIHGR TGHLVTCFHC
241 ARRLKKAGAS CPICKKEIQL VIKVFIA
```

SEQ ID NO: 29 Mouse MDM4 Transcript Variant 1 cDNA Sequence (NM_001302801.1; CDS: 200-1672)

```
   1 tctatggttc ccccggcctc cccggaagct cttgcgaacg ctgggtttga gaggccggaa
  61 gtggtgctgc cgttgctcgc agtttcaaaa tgcagtgcag gccttagggt ctccggctgc
 121 cacccctccc ccagctagga gggggagcga ctcatggagc ggccgtaagt ttgctaactg
 181 tggagtcttc actgccaaaa tgacatcaca ttccacctcg gcccagtgtt cagcatctga
 241 cagtgcttgc agaatttctt cggaacaaat tagtcagcag gtgcggccaa aactgcagct
 301 tttgaagatt ttgcatgcag caggtgcgca gggggaagta ttcaccatga aagaggtaat
 361 gcactatcta ggccagtata taatggtgaa gcagctctat gatcaacagg agcaacatat
 421 ggtatactgt ggtggagatc ttttgggaga tctacttgga tgtcagagct tttctgtgaa
 481 agatccaagc cctctctatg acatgctaag aaagaatctt gttacatcag cttctattaa
 541 cacagatgct gctcagactc tcgctctcgc acaggatcac actatggatt ttccaagtca
 601 agaccgactg aagcacggtg caacagaata ctccaatccc agaaaaagaa ctgaagaaga
 661 ggatactcac acactgccta cctcacgaca taaatgcaga gactccagag cagatgaaga
 721 cttgatagaa catttatctc aagatgagac atctaggctt gaccttgatt ttgaggagtg
 781 ggacgttgct ggcctgcctt ggtggtttct agggaatttg agaaacaact gtattcctaa
 841 aagtaatggc tcaactgatt tacagacaaa tcaggatata ggtactgcca ttgtttcaga
 901 cactacggat gatttgtggt ttttaaatga gaccgtgtca gagcaattag gtgttggaat
 961 aaaagttgaa gctgctaatt ctgagcaaac aagtgaagta gggaaaacaa gtaacaagaa
1021 gacggtggag gtgggaaagg atgatgatct tgaggactcc aggtccttga gcgatgatac
1081 tgacgtggaa cttacctctg aggatgagtg gcagtgtacg gaatgcaaga agtttaattc
1141 tccaagcaag aggtactgtt ttcgttgctg ggccttgaga aaggattggt attcggattg
1201 ttctaaatta actcattccc tatctacatc taatattact gccatacctg aaaagaagga
1261 caatgaagga attgatgttc ccgattgtag gagaaccatt tcagctcctg ttgttaggcc
1321 taaagatgga tatttaaagg aggaaaagcc caggtttgac ccttgcaact cagtgggatt
1381 tttggatttg gctcatagtt ctgaaagcca ggagatcatc tcaagcgcga gagaacaaac
1441 agatattttt tctgagcaga aagctgaaac agaaagtatg gaagatttcc agaatgtctt
1501 gaagccgtgt agcttatgtg aaaaaaggcc tcgggatggg aacattattc atgggaagac
1561 gagccatctg acgacatgtt tccactgtgc caggagactg aagaagtctg gggcttcgtg
1621 tcctgcttgt aagaaagaga ttcagttggt tattaaagtt tttatagcat agttgagtca
1681 gtcacagaga aatactagga ggaccaggtc atttatcaaa aaaatcagta ttcttagagg
1741 caggggcaga agatcaccaa ttttgatgcc agtctgggcc atataatgag atcttagtct
1801 taaaaggatc agtattgagc atcttttata aatgtgaccc attgcatatg tttatttgta
1861 taagcatata tgaactttta gctaagtttt gagggtttca ttagtgagaa gatactttgt
1921 tcttccaaat tgtgaaccca gagggaataa tatcaataca aacatagcaa tgcattcttt
1981 tattcacttc caaattattg caagaataat acattagttg atttattctc taccctggtg
2041 ttatgtaatg ttcttgaggc atcaaaatct aaagcattta ttaaatactg gggctaacac
2101 tgaagaggac atatccagtc agtcgctcat tgtgtagtca aggatgacct taaattcctg
2161 atagctgtct ctaccaccta tgtgctcata ggctcatagg ccgccccact agcccatctg
```

TABLE 1-continued

| | | | | | | |
|---|---|---|---|---|---|---|
| 2221 | aaatctctta | gttttaggtc | aggtaacaca | ggtgtacatc | tctccacagc | cttattatca |
| 2281 | gttccaaaaa | ggaaaggcac | agactttgtt | gcccacactt | tgcatttgtc | tctcaagctg |
| 2341 | gctgggtgtt | ttgtgttttg | tgctctgcag | ctgttcacat | tctgaggcag | tggcctatga |
| 2401 | taaggcttga | acagtagaga | ggaggaatgt | agcagctgtg | aaaggagggg | aacaaattga |
| 2461 | tctcttcaat | tctgcttagt | cattttagac | cacatcaact | tagtataata | tcaatatatg |
| 2521 | aactgaagat | cttcacgctg | aatcccgtat | gcctgttctg | tgtccactga | acacatggcc |
| 2581 | atcttgatgt | ttccccaggg | acatgagaac | atcattttaa | agaccaagtc | cctagaacta |
| 2641 | ttgagcttga | gggcaatcta | gctgtcttgg | cttttcctat | ggctcctgct | gttagaaagg |
| 2701 | gggagatgca | tggtatccag | tccccttaat | gtcattatgt | ccctgctgga | ctgggaccac |
| 2761 | tggggctcct | ctaattacta | ctaagaggag | ctatgttagc | tttatcttgc | attgatccca |
| 2821 | tgttccctgt | ctgtcccatg | ctctaccatt | agacccaact | ttaccaaatt | ctcactggat |
| 2881 | cagttatcat | agttactctt | taattttgat | gacaaagcac | caatgcaaaa | tataaaagaa |
| 2941 | agcatttaat | ggggtttgct | tttgagaggg | ttagaatcca | tgatggcagg | cagggacagc |
| 3001 | tgagagctca | catcttgatc | tgcaagtaga | atgcagagaa | aaagagagcc | ctggaaaacc |
| 3061 | ccagggcctg | cccccccagt | gtcgtaattg | gtctaccttt | tccaccgact | ggggtccaag |
| 3121 | tattcaaact | taagagcctg | tggtttatat | tctcatgtaa | accaccacat | tccatgaaaa |
| 3181 | gaattactaa | ttactgtgct | gcagaaccag | tattaggcgt | tctggacacc | tcttctatca |
| 3241 | aagaaattac | ttttcactcc | aggcttaggc | aaattcttag | gacaagggta | gaaggcagcc |
| 3301 | acattctttg | tcaaacataa | ccagaataag | tctttagcca | gttgttaata | gttgttctac |
| 3361 | cctgcagcct | cttgatctag | gcttcctctc | agtactaact | gtcttttagg | ctccaactgg |
| 3421 | acccattaag | ctctgtttac | agccttgaac | cctttcttag | tccaaagtct | tacacattcc |
| 3481 | tccaaaaaaa | ccacatggtc | aggtctttca | cagcaaagat | ccacttcctg | gtagtagctt |
| 3541 | ctgtgtcttg | gctactctaa | aattgctatg | acaaaacatc | ccgaccaagg | cagaatgtac |
| 3601 | aagaaagcat | tgagtttatg | gtttcagagg | tatttagttc | atgatagaac | agttgagagc |
| 3661 | ttacatcttg | atctgtaagt | aggaggcaga | gagagaaccc | aggggatggc | atggactttt |
| 3721 | gaaacctcca | agccttcacc | ttgtgacaga | cctccccaac | agagccacat | ctcctaatcc |
| 3781 | tttccaagta | gttcctccaa | ctggggacca | aatactccag | catgagcata | ggggagcatt |
| 3841 | ctcattcaca | ccaccagttt | gccgaggaac | tttcctagcc | atggcttgtc | attcattgct |
| 3901 | cccagttgat | aatttcacta | tttgtagcaa | actcagtggc | caagtccttg | ctattatggg |
| 3961 | tcttctgctt | gtattgaaaa | tactgcagct | cctgttgggg | ttgctgtgca | gtctctctga |
| 4021 | gggactgata | acagacttgt | atatccatat | ctccatggca | gtgagaaacg | gtagcttaga |
| 4081 | ggtaatccta | gaagccatca | ctcacagtcc | ctgcttgaga | ataggctatg | atatgtctag |
| 4141 | ccctggactt | tagtcatttc | ctagacatgg | acctgctggg | tggaattggg | tcattatgat |
| 4201 | gtttaattcc | aagcactgca | ttcaaaatag | gatacatgat | atagtatgtc | agcttcattc |
| 4261 | taacgtttct | cctaatcttt | tggggcagag | tcttgctgtt | tcaccatgac | tggcctgggc |
| 4321 | cttaccctac | atctcaggct | ggcctcagct | ttgcagtgac | cttcctgctt | ttgcctctcg |
| 4381 | agtgctggaa | ttctaggcat | gtaatgacta | aatttcttat | tttgcttttt | atttaagttt |
| 4441 | ttgttactct | atcttggaca | aaaagtgcag | agcagaggtg | tcggattact | aggaaagtct |
| 4501 | ccagggcttc | gctgttactg | tgttccccac | agggacttcc | tggttgttga | cgtgcttctg |
| 4561 | tttactactg | tgtcagatga | gcgactcaga | gctcggcttc | agataggtgt | gactgccgcc |
| 4621 | ctcgcccatt | taggatgtag | tagatttatg | attgagggct | ggaacgggta | gattacattg |
| 4681 | taccgccaag | catttgtgac | tgtgtggata | tatattcatt | atttatgtat | atttaggtgt |
| 4741 | gtgtgatact | ttgcatggtt | tgaaagaatc | tattctgaaa | gccaggatca | tttgtaacct |
| 4801 | ttgtgtgtca | gttcaatgta | atgttggggc | ctttgaaaag | ttgattgaga | aattggggat |
| 4861 | cattcccagt | tctccgatgt | tacttgttta | gtcctcttta | gaaagaaaga | cacttttgga |
| 4921 | ccagctgttt | cgctgttttg | ttctgtttcc | atgatattct | gtgaacctcc | atggctttag |
| 4981 | atactgtgac | tgttattttc | ctttttgccc | aaattgttga | ttcagtctaa | agaatactat |
| 5041 | tttttgatgc | ctcttacaat | tcatgcatgt | gcacactata | gattgatgct | acctttgcta |
| 5101 | aaaatgtctt | aagataaaga | actagctctt | tagaacctgc | acttcaaaga | taaacctgga |
| 5161 | agctgtcctg | tgccaaaagt | aaagtgtaca | atgtttacag | atgggtggaa | ttttgcactg |
| 5221 | ccatagggaa | cggtgagctc | gcatcacggg | gttccttaga | tgtatgggta | gatagttgca |
| 5281 | gttgagctta | tgagaggaac | tgtggagccc | tctaaggcta | agctgctaat | gagtatccaa |
| 5341 | gacaggtggt | tggtgaacgt | gactccctag | acctagctgg | ggtcttctgt | tgacagctct |
| 5401 | tcatggtttg | cagacactat | atgttttctt | tagaggagct | gccagctctc | ccctcttgtg |
| 5461 | aaagactgtc | ttgtagacat | tttgagatct | tttgatgtaa | tgtgcaatcc | caagtaatgc |
| 5521 | cattattggt | gaatgtagca | ttgttaaact | tttattgtaa | attatctctg | atcttacctt |
| 5581 | gatagcctta | gggtttttttg | tttttgtttt | tttttgttat | gttttcagag | acagagtctc |
| 5641 | gctatttggt | ttacctagaa | tttgctttat | gattaggctg | tccccaaact | cacagatgtc |
| 5701 | tgcctttcta | ccaccacgcc | catgtaactg | atgttaccaa | aaatgatctc | atatccatgg |
| 5761 | tgttgcttat | gtgtctttgc | ataggcgcct | ccttcagtcc | catctaggag | cacagcacag |
| 5821 | tagaagtcca | tttcttaagt | gggcagagtc | agagataagc | taagagggca | agtagttgct |
| 5881 | tcagtggttt | ttagagcttg | gcaaacgctt | tactgaagat | tagcattgtg | ttgtgacact |
| 5941 | tgagggccaa | tacgagcatt | taatttgtta | cctaaaggtg | ctttgtgttc | ttaaacagca |
| 6001 | agtatttgat | gtgtgtaaac | atttcccttc | attctccctc | cctcctcacc | gtttttatgg |
| 6061 | tctcctattt | ctgagttagc | tgcatttgga | cattgctttt | atgccagagg | ccatctgtca |
| 6121 | ccttggatgt | ttagaagtac | agtgtactta | tgtagggtcc | tccttgagcc | tgtcctgagc |
| 6181 | agtgttgtgg | ttacagaatt | gcctacgagc | tccaacagag | aggtggggaa | gctgggaggg |
| 6241 | cacagctgtc | tggcttcctt | tgtggaggtg | ttggtttgtt | tgaacactaa | ggaatttgag |
| 6301 | gttaatcttc | cccctcttcc | tgcccatagt | tttcacttcc | ctttcagtaa | gaacgacccc |
| 6361 | ctaaaagaaa | acaggaggag | atgcagcgct | ttaggccgcc | ttagccagca | gcttgtgtcc |
| 6421 | tactctggaa | gttgtaacct | acagtttttc | tcacctgtaa | agccaacaca | cacagctacc |
| 6481 | cgtttctacc | tcagtttgat | gtggcgacta | tggaggaaca | actcttaaaa | gctctgactg |
| 6541 | ccttgaagat | ggaggaagct | agtggtcttg | gtcgactgtg | ctctgaggtt | tatattgaga |
| 6601 | atcctttatt | ctggaagtga | gtgcggttct | cctgaccgcc | tgctcagtag | aacctgtgtt |
| 6661 | gcctgcttta | agtctctgcc | cacctgcctg | tcctttcctt | gacactaggc | tcttgattag |
| 6721 | gaagagttgt | ctccagatgc | tttgagaagc | acatgtaaat | ctagatagca | cattctaccc |
| 6781 | tgatggaact | tccttgcttg | tcttgctgta | taggaattca | ttctgtatac | acttgagtgg |
| 6841 | gtggcatgag | atgctcgact | tgtgtgtcga | gaggcagtgt | catgacattc | ccagtctggt |
| 6901 | acttgccagt | gcagaagcaa | atgaggggta | ataaactgag | aagaagggca | gcttactaac |
| 6961 | gaggccagag | ggaaatgttt | ccgtgtgtcc | ttatgtaact | ttttacagtg | ccactaagtt |

TABLE 1-continued

```
7021 aatagccctg tacatgggtg tttgcactat gtaatgcttt taatgcggtt ttattgtgtt
7081 tttgtgtgat taaacagttt tcatttcatt gtgttttgtc attattggaa ataggtaatt
7141 ttgcttatgt acagctaacc cattttctgt tatctttggc atgatttggg gaagtgatta
7201 aaagtcattg gcagcttttc cct
```

SEQ ID NO: 30 Mouse MDM4 Isoform 1 Amino Acid Sequence (NP_001289730.1)

```
  1 MTSHSTSAQC SASDSACRIS SEQISQQVRP KLQLLKILHA AGAQGEVFTM KEVMHYLGQY
 61 IMVKQLYDQQ EQHMVYCGGD LLGDLLGCQS FSVKDPSPLY DMLRKNLVTS ASINTDAAQT
121 LALAQDHTMD FPSQDRLKHG ATEYSNPRKR TEEEDTHTLP TSRHKCRDSR ADEDLIEHLS
181 QDETSRLDLD FEEWDVAGLP WWFLGNLRNN CIPKSNGSTD LQTNQDIGTA IVSDTTDDLW
241 FLNETVSEQL GVGIKVEAAN SEQTSEVGKT SNKKTVEVGK DDDLEDSRSL SDDTDVELTS
301 EDEWQCTECK KFNSPSKRYC FRCWALRKDW YSDCSKLTHS LSTSNITAIP EKKDNEGIDV
361 PDCRRTISAP VVRPKDGYLK EEKPRFDPCN SVGFLDLAHS SESQEIISSA REQTDIFSEQ
421 KAETESMEDF QNVLKPCSLC EKRPRDGNII HGKTSHLTTC FHCARRLKKS GASCPACKKE
481 IQLVIKVFIA
```

SEQ ID NO: 31 Mouse MDM4 Transcript Variant 2 cDNA Sequence (NM_001302802.1; CDS: 84-1556)

```
   1 gggtgggttt gtggtggtgg tttaaggcag cagtggtcaa agaagaaaca aagtttgcta
  61 actgtggagt cttcactgcc aaaatgacat cacattccac ctcggcccag tgttcagcat
 121 ctgacagtgc ttgcagaatt tcttcggaac aaattagtca gcaggtgcgg ccaaaactgc
 181 agcttttgaa gattttgcat gcagcaggtg cgcaggggga agtattcacc atgaaagagg
 241 taatgcacta tctaggccag tatataatgg tgaagcagct ctatgatcaa caggagcaac
 301 atatggtata ctgtggtgga gatcttttgg gagatctact tggatgtcag agcttttctg
 361 tgaaagatcc aagccctctc tatgacatgc taagaaagaa tcttgttaca tcagcttcta
 421 ttaacacaga tgctgctcag actctcgctc tcgcacagga tcacactatg gattttccaa
 481 gtcaagaccg actgaagcac ggtgcaacag aatactccaa tcccagaaaa agaactgaag
 541 aagaggatac tcacacactg cctacctcac gacataaatg cagagactcc agagcagatg
 601 aagacttgat agaacattta tctcaagatg agacatctag gcttgacctt gattttgagg
 661 agtgggacgt tgctggcctg ccttggtggt ttctagggaa tttgagaaac aactgtattc
 721 ctaaaagtaa tggctcaact gatttacaga caaatcagga tataggtact gccattgttt
 781 cagacactac ggatgatttg tggtttttaa atgagaccgt gtcagagcaa ttaggtgttg
 841 gaataaaagt tgaagctgct aattctgagc aaacaagtga agtagggaaa acaagtaaca
 901 agaagacggt ggaggtggga aaggatgatg atcttgagga ctccaggtcc ttgagcgatg
 961 atactgacgt ggaacttacc tctgaggatg agtggcagtg tacggaatgc aagaagttta
1021 attctccaag caagaggtac tgttttcgtt gctgggcctt gagaaaggat tggtattcgg
1081 attgttctaa attaactcat tccctatcta catctaatat tactgccata cctgaaaaga
1141 aggacaatga aggaattgat gttcccgatt gtaggagaac catttcagct cctgttgtta
1201 ggcctaaaga tggatattta aaggaggaaa agcccaggtt tgacccttgc aactcagtgg
1261 gatttttgga tttggctcat agttctgaaa gccaggagat catctcaagc gcgagagaac
1321 aaacagatat tttttctgag cagaaagctg aaacagaaag tatggaagat ttccagaatg
1381 tcttgaagcc gtgtagctta tgtgaaaaaa ggcctcggga tgggaacatt attcatggga
1441 agacgagcca tctgacgaca tgtttccact gtgccaggag actgaagaag tctggggctt
1501 cgtgtcctgc ttgtaagaaa gagattcagt tggttattaa agtttttata gcatagttga
1561 gtcagtcaca gagaaatact aggaggacca ggtcatttat caaaaaaatc agtattctta
1621 gaggcagggg cagaagatca ccaattttga tgccagtctg ggccatataa tgagatctta
1681 gtcttaaaag gatcagtatt gagcatcttt tataaatgtg acccattgca tatgtttatt
1741 tgtataagca tatatgaact tttagctaag ttttgagggt ttcattagtg agaagatact
1801 ttgttcttcc aaattgtgaa cccagaggga ataatatcaa tacaaacata gcaatgcatt
1861 cttttattca cttccaaatt attgcaagaa taatacatta gttgatttat tctctaccct
1921 ggtgttatgt aatgttcttg aggcatcaaa atctaaagca tttattaaat actggggcta
1981 acactgaaga ggacatatcc agtcagtcgc tcattgtgta gtcaaggatg accttaaatt
2041 cctgatagct gtctctacca cctatgtgct catacgctca taggccgccc cactagccca
2101 tctgaaatct cttagtttta ggtcaggtaa cacaggtgta catctctcca cagccttatt
2161 atcagttcca aaaaggaaag gcacagactt tgttgcccac actttgcatt tgtctctcaa
2221 gctggctggg tgttttgtgt tttgtgctct gcagctgttc acattctgag gcagtggcct
2281 atgataaggc ttgaacagta gagaggagga atgtagcagc tgtgaaagga ggggaacaaa
2341 ttgatctctt caattctgct tagtcatttt agaccacatc aacttagtat aatatcaata
2401 tatgaactga agatcttcac gctgaatccc gtatgcctgt tctgtgtcca ctgaacacat
2461 ggccatcttg atgtttcccc agggacatga gaacatcatt ttaaagacca agtccctaga
2521 actattgagc ttgagggcaa tctagctgtc ttggcttttc ctatggctcc tgctgttaga
2581 aagggggaga tgcatggtat ccagtcccct taatgtcatt atgtccctgc tggactggga
2641 ccactggggc tcctctaatt actactaaga ggagctatgt tagctttatc ttgcattgat
2701 cccatgttcc ctgtctgtcc catgctctac cattagaccc aactttacca aattctcact
2761 ggatcagtta tcatagttac tctttaattt tgatgacaaa gcaccaatgc aaaatataaa
2821 agaaagcatt taatggggtt tgcttttgag agggttagaa tccatgatgg caggcaggga
2881 cagctgagag ctcacatctt gatctgcaag tagaatgcag agaaaaagag agccctggaa
2941 aaccccaggg cctgcccccc cagtgtcgta attggtctac cttttccacc gactggggtc
3001 caagtattca aacttaagag cctgtggttt atattctcat gtaaaccacc acattccatg
3061 aaaagaatta ctaattactg tgctgcagaa ccagtattag gcgttctgga cacctcttct
3121 atcaaagaaa ttacttttca ctccaggctt aggcaaattc ttaggacaag ggtagaaggc
3181 agccacattc tttgtcaaac ataaccagaa taagtcttta gccagttgtt aatagttgtt
3241 ctaccctgca gcctcttgat ctaggcttcc tctcagtact aactgtcttt taggctccaa
3301 ctggacccat taagctctgt ttacagcctt gaaccctttc ttagtccaaa gtcttacaca
3361 ttcctccaaa aaaaccacat ggtcaggtct ttcacagcaa agatccactt cctggtagta
3421 gcttctgtgt cttggctact ctaaaattgc tatgacaaaa catcccgacc aaggcagaat
3481 gtacaagaaa gcattgagtt tatggtttca gaggtattta gttcatgata gaacagttga
3541 gagcttacat cttgatctgt aagtaggagg cagagagaga acccagggga tggcatggac
3601 ttttgaaacc tccaagcctt caccttgtga cagacctccc caacagagcc acatctccta
3661 atcctttcca agtagttcct ccaactgggg accaaatact ccagcatgag catagggag
```

TABLE 1-continued 3721 cattctcatt cacaccacca gtttgccgag gaactttcct agccatggct tgtcattcat
3781 tgctcccagt tgataatttc actatttgta gcaaactcag tggccaagtc cttgctatta
3841 tgggtcttct gcttgtattg aaaatactgc agctcctgtt ggggttgctg tgcagtctct
3901 ctgagggact gataacagac ttgtatatcc atatctccat ggcagtgaga aacggtagct
3961 tagaggtaat cctagaagcc atcactcaca gtccctgctt gagaataggc tatgatatgt
4021 ctagccctgg actttagtca tttcctagac atggacctgc tgggtggaat tgggtcatta
4081 tgatgtttaa ttccaagcac tgcattcaaa ataggataca tgatatagta tgtcagcttc
4141 attctaacgt ttctcctaat cttttggggc agagtcttgc tgtttcacca tgactggcct
4201 gggccttacc ctacatctca ggctggcctc agctttgcag tgaccttcct gcttttgcct
4261 ctcgagtgct ggaattctag gcatgtaatg actaaatttc ttattttgct ttttatttaa
4321 gtttttgtta ctctatcttg gacaaaaagt gcagagcaga ggtgtcggat tactaggaaa
4381 gtctccaggg cttcgctgtt actgtgttcc ccacagggac ttcctggttg ttgacgtgct
4441 tctgtttact actgtgtcag atgagcgact cagagctcgg cttcagatag gtgtgactgc
4501 cgccctcgcc catttaggat gtagtagatt tatgattgag ggctggaacg ggtagattac
4561 attgtaccgc caagcatttg tgactgtgtg gatatatatt cattatttat gtatatttag
4621 gtgtgtgtga tactttgcat ggtttgaaag aatctattct gaaagccagg atcatttgta
4681 acctttgtgt gtcagttcaa tgtaatgttg gggcctttga aaagttgatt gagaaattgg
4741 ggatcattcc cagttctccg atgttacttg tttagtcctc tttagaaaga aagacacttt
4801 tggaccagct gtttcgctgt tttgttctgt ttccatgata ttctgtgaac ctccatggct
4861 ttagatactg tgactgttat tttccttttt gcccaaattg ttgattcagt ctaaagaata
4921 ctattttttg atgcctctta caattcatgc atgtgcacac tatagattga tgctaccttt
4981 gctaaaaatg tcttaagata aagaactagc tctttagaac ctgcacttca aagataaacc
5041 tggaagctgt cctgtgccaa aagtaaagtg tacaatgttt acagatgggt ggaattttgc
5101 actgccatag ggaacggtga gctcgcatca cggggttcct tagatgtatg ggtagatagt
5161 tgcagttgag cttatgagag gaactgtgga gccctctaag gctaagctgc taatgagtat
5221 ccaagacagg tggttggtga acgtgactcc ctagacctag ctggggtctt ctgttgacag
5281 ctcttcatgg tttgcagaca ctatatgttt tctttagagg agctgccagc tctcccctct
5341 tgtgaaagac tgtcttgtag acattttgag atcttttgat gtaatgtgca atcccaagta
5401 atgccattat tggtgaatgt agcattgtta aacttttatt gtaaattatc tctgatctta
5461 ccttgatagc cttagggttt tttgttttttg tttttttttg ttatgttttc agagacagag
5521 tctcgctatt tggtttacct agaatttgct ttatgattag gctgtcccca aactcacaga
5581 tgtctgcctt tctaccacca cgcccatgta actgatgtta ccaaaaatga tctcatatcc
5641 atggtgttgc ttatgtgtct ttgcataggc gcctccttca gtcccatcta ggagcacagc
5701 acagtagaag tccatttctt aagtgggcag agtcagagat aagctaagag ggcaagtagt
5761 tgcttcagtg gtttttagag cttggcaaac gctttactga agattagcat tgtgttgtga
5821 cacttgaggg ccaatacgag catttaattt gttacctaaa ggtgctttgt gttcttaaac
5881 agcaagtatt tgatgtgtgt aaacatttcc cttcattctc cctccctcct caccgttttt
5941 atggtctcct atttctgagt tagctgcatt tggacattgc ttttatgcca gaggccatct
6001 gtcaccttgg atgtttagaa gtacagtgta cttatgtagg gtcctccttg agcctgtcct
6061 gagcagtgtt gtggttacag aattgcctac gagctccaac agagaggtgg ggaagctggg
6121 agggcacagc tgtctggctt cctttgtgga ggtgttggtt tgtttgaaca ctaaggaatt
6181 tgaggttaat cttccccctc ttcctgccca tagttttcac ttccctttca gtaagaacga
6241 ccccctaaaa gaaaacagga ggagatgcag cgctttaggc cgccttagcc agcagcttgt
6301 gtcctactct ggaagttgta acctacagtt tttctcacct gtaaagccaa cacacacagc
6361 tacccgtttc tacctcagtt tgatgtggcg actatggagg aacaactctt aaaagctctg
6421 actgccttga agatggagga agctagtggt cttggtcgac tgtgctctga ggtttatatt
6481 gagaatcctt tattctggaa gtgagtgcgg ttctcctgac cgcctgctca gtagaacctg
6541 tgttgcctgc tttaagtctc tgcccacctg cctgtccttt ccttgacact aggctcttga
6601 ttaggaagag ttgtctccag atgctttgag aagcacatgt aaatctagat agcacattct
6661 accctgatgg aacttccttg cttgtcttgc tgtataggaa ttcattctgt atacacttga
6721 gtgggtggca tgagatgctc gacttgtgtg tcgagaggca gtgtcatgac attcccagtc
6781 tggtacttgc cagtgcagaa gcaaatgagg ggtaataaac tgagaagaag ggcagcttac
6841 taacgaggcc agagggaaat gtttccgtgt gtccttatgt aactttttac agtgccacta
6901 agttaatagc cctgtacatg ggtgtttgca ctatgtaatg cttttaatgc ggttttattg
6961 tgtttttgtg tgattaaaca gttttcattt cattgtgttt tgtcattatt ggaaataggt
7021 aattttgctt atgtacagct aacccatttt ctgttatctt tggcatgatt tggggaagtg
7081 attaaaagtc attggcagct tttccct SEQ ID NO: 32 Mouse MDM4 Isoform 2 Amino Acid Sequence (NP_001289731.1)
1 MTSHSTSAQC SASDSACRIS SEQISQQVRP KLQLLKILHA AGAQGEVFTM KEVMHYLGQY
61 IMVKQLYDQQ EQHMVYCGGD LLGDLLGCQS FSVKDPSPLY DMLRKNLVTS ASINTDAAQT
121 LALAQDHTMD FPSQDRLKHG ATEYSNPRKR TEEEDTHTLP TSRHKCRDSR ADEDLIEHLS
181 QDETSRLDLD FEEWDVAGLP WWFLGNLRNN CIPKSNGSTD LQTNQDIGTA IVSDTTDDLW
241 FLNETVSEQL GVGIKVEAAN SEQTSEVGKT SNKKTVEVGK DDDLEDSRSL SDDTDVELTS
301 EDEWQCTECK KFNSPSKRYC FRCWALRKDW YSDCSKLTHS LSTSNITAIP EKKDNEGIDV
361 PDCRRTISAP VVRPKDGYLK EEKPRFDPCN SVGFLDLAHS SESQEIISSA REQTDIFSEQ
421 KAETESMEDF QNVLKPCSLC EKRPRDGNII HGKTSHLTTC FHCARRLKKS GASCPACKKE
481 IQLVIKVFIA SEQ ID NO: 33 Mouse MDM4 Transcript Variant 3 cDNA Sequence
(NM_001302803.1; CDS: 200-1669)
1 tctatggttc ccccggcctc cccggaagct cttgcgaacg ctgggtttga gaggccggaa
61 gtggtgctgc cgttgctcgc agtttcaaaa tgcagtgcag gccttagggt ctccggctgc
121 cacccctccc ccagctagga gggggagcga ctcatggagc ggccgtaagt ttgctaactg
181 tggagtcttc actgccaaaa tgacatcaca ttccacctcg gcccagtgtt cagcatctga
241 cagtgcttgc agaatttctt cggaacaaat tagtcaggtg cggccaaaac tgcagctttt
301 gaagattttg catgcagcag gtgcgcaggg ggaagtattc accatgaaag aggtaatgca
361 ctatctaggc cagtatataa tggtgaagca gctctatgat caacaggagc aacatatggt
421 atactgtggt ggagatcttt tgggagatct acttggatgt cagagctttt ctgtgaaaga
481 tccaagccct ctctatgaca tgctaagaaa gaatcttgtt acatcagctt ctattaacac TABLE 1-continued

| | | | | | | |
|---|---|---|---|---|---|---|
| 541 | agatgctgct | cagactctcg | ctctcgcaca | ggatcacact | atggattttc | caagtcaaga |
| 601 | ccgactgaag | cacggtgcaa | cagaatactc | caatcccaga | aaaagaactg | aagaagagga |
| 661 | tactcacaca | ctgcctacct | cacgacataa | atgcagagac | tccagagcag | atgaagactt |
| 721 | gatagaacat | ttatctcaag | atgagacatc | taggcttgac | cttgattttg | aggagtggga |
| 781 | cgttgctggc | ctgccttggt | ggtttctagg | gaatttgaga | aacaactgta | ttcctaaaag |
| 841 | taatggctca | actgatttac | agacaaatca | ggatataggt | actgccattg | tttcagacac |
| 901 | tacggatgat | ttgtggtttt | taaatgagac | cgtgtcagag | caattaggtg | ttggaataaa |
| 961 | agttgaagct | gctaattctg | agcaaacaag | tgaagtaggg | aaaacaagta | acaagaagac |
| 1021 | ggtggaggtg | ggaaaggatg | atgatcttga | ggactccagg | tccttgagcg | atgatactga |
| 1081 | cgtggaactt | acctctgagg | atgagtggca | gtgtacggaa | tgcaagaagt | ttaattctcc |
| 1141 | aagcaagagg | tactgttttc | gttgctgggc | cttgagaaag | gattggtatt | cggattgttc |
| 1201 | taaattaact | cattccctat | ctacatctaa | tattactgcc | atacctgaaa | agaaggacaa |
| 1261 | tgaaggaatt | gatgttcccg | attgtaggag | aaccatttca | gctcctgttg | ttaggcctaa |
| 1321 | agatggatat | ttaaaggagg | aaaagcccag | gtttgaccct | tgcaactcag | tgggattttt |
| 1381 | ggatttggct | catagttctg | aaagccagga | gatcatctca | agcgcgagag | aacaaacaga |
| 1441 | tattttttct | gagcagaaag | ctgaaacaga | aagtatggaa | gatttccaga | atgtcttgaa |
| 1501 | gccgtgtagc | ttatgtgaaa | aaaggcctcg | ggatgggaac | attattcatg | ggaagacgag |
| 1561 | ccatctgacg | acatgtttcc | actgtgccag | gagactgaag | aagtctgggg | cttcgtgtcc |
| 1621 | tgcttgtaag | aaagagattc | agttggttat | taaagttttt | atagcatagt | tgagtcagtc |
| 1681 | acagagaaat | actaggagga | ccaggtcatt | tatcaaaaaa | atcagtattc | ttagaggcag |
| 1741 | gggcagaaga | tcaccaattt | tgatgccagt | ctgggccata | taatgagatc | ttagtcttaa |
| 1801 | aaggatcagt | attgagcatc | ttttataaat | gtgacccatt | gcatatgttt | atttgtataa |
| 1861 | gcatatatga | acttttagct | aagttttgag | ggtttcatta | gtgagaagat | actttgttct |
| 1921 | tccaaattgt | gaacccagag | ggaataatat | caatacaaac | atagcaatgc | attcttttat |
| 1981 | tcacttccaa | attattgcaa | gaataataca | ttagttgatt | tattctctac | cctggtgtta |
| 2041 | tgtaatgttc | ttgaggcatc | aaaatctaaa | gcatttatta | aatactgggg | ctaacactga |
| 2101 | agaggacata | tccagtcagt | cgctcattgt | gtagtcaagg | atgaccttaa | attcctgata |
| 2161 | gctgtctcta | ccacctatgt | gctcataggc | tcataggccg | ccccactagc | ccatctgaaa |
| 2221 | tctcttagtt | ttaggtcagg | taacacaggt | gtacatctct | ccacagcctt | attatcagtt |
| 2281 | ccaaaaagga | aaggcacaga | ctttgttgcc | cacactttgc | atttgtctct | caagctggct |
| 2341 | gggtgttttg | tgttttgtgc | tctgcagctg | ttcacattct | gaggcagtgg | cctatgataa |
| 2401 | ggcttgaaca | gtagagagga | ggaatgtagc | agctgtgaaa | ggaggggaac | aaattgatct |
| 2461 | cttcaattct | gcttagtcat | tttagaccac | atcaacttag | tataatatca | atatatgaac |
| 2521 | tgaagatctt | cacgctgaat | cccgtatgcc | tgttctgtgt | ccactgaaca | catggccatc |
| 2581 | ttgatgtttc | cccagggaca | tgagaacatc | attttaaaga | ccaagtccct | agaactattg |
| 2641 | agcttgaggg | caatctagct | gtcttggctt | ttcctatggc | tcctgctgtt | agaaaggggg |
| 2701 | agatgcatgg | tatccagtcc | ccttaatgtc | attatgtccc | tgctggactg | ggaccactgg |
| 2761 | ggctcctcta | attactacta | agaggagcta | tgttagcttt | atcttgcatt | gatcccatgt |
| 2821 | tccctgtctg | tcccatgctc | taccattaga | cccaacttta | ccaaattctc | actggatcag |
| 2881 | ttatcatagt | tactctttaa | ttttgatgac | aaagcaccaa | tgcaaaatat | aaaagaaagc |
| 2941 | atttaatggg | gtttgctttt | gagagggtta | gaatccatga | tggcaggcag | ggacagctga |
| 3001 | gagctcacat | cttgatctgc | aagtagaatg | cagagaaaaa | gagagccctg | gaaaacccca |
| 3061 | gggcctgccc | ccccagtgtc | gtaattggtc | taccttttcc | accgactggg | gtccaagtat |
| 3121 | tcaaacttaa | gagcctgtgg | tttatattct | catgtaaacc | accacattcc | atgaaaagaa |
| 3181 | ttactaatta | ctgtgctgca | gaaccagtat | taggcgttct | ggacacctct | tctatcaaag |
| 3241 | aaattacttt | tcactccagg | cttaggcaaa | ttcttaggac | aagggtagaa | ggcagccaca |
| 3301 | ttctttgtca | aacataacca | gaataagtct | ttagccagtt | gttaatagtt | gttctaccct |
| 3361 | gcagcctctt | gatctaggct | tcctctcagt | actaactgtc | ttttaggctc | caactggacc |
| 3421 | cattaagctc | tgtttacagc | cttgaaccct | ttcttagtcc | aaagtcttac | acattcctcc |
| 3481 | aaaaaaacca | catggtcagg | tctttcacag | caaagatcca | cttcctggta | gtagcttctg |
| 3541 | tgtcttggct | actctaaaat | tgctatgaca | aaacatcccg | accaaggcag | aatgtacaag |
| 3601 | aaagcattga | gtttatggtt | tcagaggtat | ttagttcatg | atagaacagt | tgagagctta |
| 3661 | catcttgatc | tgtaagtagg | aggcagagag | agaacccagg | ggatggcatg | gacttttgaa |
| 3721 | acctccaagc | cttcaccttg | tgacagacct | ccccaacaga | gccacatctc | ctaatccttt |
| 3781 | ccaagtagtt | cctccaactg | gggaccaaat | actccagcat | gagcataggg | gagcattctc |
| 3841 | attcacacca | ccagtttgcc | gaggaacttt | cctagccatg | gcttgtcatt | cattgctccc |
| 3901 | agttgataat | ttcactattt | gtagcaaact | cagtggccaa | gtccttgcta | ttatgggtct |
| 3961 | tctgcttgta | ttgaaaatac | tgcagctcct | gttggggttg | ctgtgcagtc | tctctgaggg |
| 4021 | actgataaca | gacttgtata | tccatatctc | catggcagtg | agaaacggta | gcttagaggt |
| 4081 | aatcctagaa | gccatcactc | acagtccctg | cttgagaata | ggctatgata | tgtctagccc |
| 4141 | tggactttag | tcatttccta | gacatggacc | tgctgggtgg | aattgggtca | ttatgatgtt |
| 4201 | taattccaag | cactgcattc | aaaataggat | acatgatata | gtatgtcagc | ttcattctaa |
| 4261 | cgtttctcct | aatcttttgg | ggcagagtct | tgctgtttca | ccatgactgg | cctgggcctt |
| 4321 | accctacatc | tcaggctggc | ctcagctttg | cagtgacctt | cctgcttttg | cctctcgagt |
| 4381 | gctggaattc | taggcatgta | atgactaaat | ttcttatttt | gctttttatt | taagtttttg |
| 4441 | ttactctatc | ttggacaaaa | agtgcagagc | agaggtgtcg | gattactagg | aaagtctcca |
| 4501 | gggcttcgct | gttactgtgt | tccccacagg | gacttcctgg | ttgttgacgt | gcttctgttt |
| 4561 | actactgtgt | cagatgagcg | actcagagct | cggcttcaga | taggtgtgac | tgccgccctc |
| 4621 | gcccatttag | gatgtagtag | atttatgatt | gagggctgga | acgggtagat | tacattgtac |
| 4681 | cgccaagcat | ttgtgactgt | gtggatatat | attcattatt | tatgtatatt | taggtgtgtg |
| 4741 | tgatactttg | catggtttga | aagaatctat | tctgaaagcc | aggatcattt | gtaacctttg |
| 4801 | tgtgtcagtt | caatgtaatg | ttggggcctt | tgaaaagttg | attgagaaat | tggggatcat |
| 4861 | tcccagttct | ccgatgttac | ttgtttagtc | ctctttagaa | agaaagacac | ttttggacca |
| 4921 | gctgtttcgc | tgttttgttc | tgtttccatg | atattctgtg | aacctccatg | gctttagata |
| 4981 | ctgtgactgt | tattttcctt | tttgcccaaa | ttgttgattc | agtctaaaga | atactatttt |
| 5041 | ttgatgcctc | ttacaattca | tgcatgtgca | cactatagat | tgatgctacc | tttgctaaaa |
| 5101 | atgtcttaag | ataaagaact | agctctttag | aacctgcact | tcaaagataa | acctggaagc |
| 5161 | tgtcctgtgc | caaaagtaaa | gtgtacaatg | tttacagatg | ggtggaattt | tgcactgcca |
| 5221 | tagggaacgg | tgagctcgca | tcacggggtt | ccttagatgt | atgggtagat | agttgcagtt |
| 5281 | gagcttatga | gaggaactgt | ggagccctct | aaggctaagc | tgctaatgag | tatccaagac |

TABLE 1-continued

```
5341 aggtggttgg tgaacgtgac tccctagacc tagctggggt cttctgttga cagctcttca
5401 tggtttgcag acactatatg ttttctttag aggagctgcc agctctcccc tcttgtgaaa
5461 gactgtcttg tagacatttt gagatctttt gatgtaatgt gcaatcccaa gtaatgccat
5521 tattggtgaa tgtagcattg ttaaactttt attgtaaatt atctctgatc ttaccttgat
5581 agccttaggg tttttttgttt ttgttttttt ttgttatgtt ttcagagaca gagtctcgct
5641 atttggttta cctagaattt gctttatgat taggctgtcc ccaaactcac agatgtctgc
5701 ctttctacca ccacgcccat gtaactgatg ttaccaaaaa tgatctcata tccatggtgt
5761 tgcttatgtg tctttgcata ggcgcctcct tcagtcccat ctaggagcac agcacagtag
5821 aagtccattt cttaagtggg cagagtcaga gataagctaa gagggcaagt agttgcttca
5881 gtggtttttta gagcttggca aacgctttac tgaagattag cattgtgttg tgacacttga
5941 gggccaatac gagcatttaa tttgttacct aaaggtgctt tgtgttctta aacagcaagt
6001 atttgatgtg tgtaaacatt tcccttcatt ctccctccct cctcaccgtt tttatggtct
6061 cctatttctg agttagctgc atttggacat tgcttttatg ccagaggcca tctgtcacct
6121 tggatgttta gaagtacagt gtacttatgt agggtcctcc ttgagcctgt cctgagcagt
6181 gttgtggtta cagaattgcc tacgagctcc aacagagagg tggggaagct gggagggcac
6241 agctgtctgg cttcctttgt ggaggtgttg gtttgtttga acactaagga atttgaggtt
6301 aatcttcccc ctcttcctgc ccatagtttt cacttccctt tcagtaagaa cgacccccta
6361 aaagaaaaca ggaggagatg cagcgcttta ggccgcctta gccagcagct tgtgtcctac
6421 tctggaagtt gtaacctaca gtttttctca cctgtaaagc caacacacac agctacccgt
6481 ttctacctca gtttgatgtg gcgactatgg aggaacaact cttaaaagct ctgactgcct
6541 tgaagatgga ggaagctagt ggtcttggtc gactgtgctc tgaggtttat attgagaatc
6601 ctttattctg gaagtgagtg cggttctcct gaccgcctgc tcagtagaac ctgtgttgcc
6661 tgctttaagt ctctgcccac ctgcctgtcc tttccttgac actaggctct tgattaggaa
6721 gagttgtctc cagatgcttt gagaagcaca tgtaaatcta gatagcacat tctaccctga
6781 tggaacttcc ttgcttgtct tgctgtatag gaattcattc tgtatacact tgagtgggtg
6841 gcatgagatg ctcgacttgt gtgtcgagag gcagtgtcat gacattccca gtctggtact
6901 tgccagtgca gaagcaaatg aggggtaata aactgagaag aagggcagct tactaacgag
6961 gccagaggga aatgtttccg tgtgtcctta tgtaactttt tacagtgcca ctaagttaat
7021 agccctgtac atgggtgttt gcactatgta atgcttttaa tgcggtttta ttgtgttttt
7081 gtgtgattaa acagttttca tttcattgtg ttttgtcatt attggaaata ggtaattttg
7141 cttatgtaca gctaacccat tttctgttat ctttggcatg atttggggaa gtgattaaaa
7201 gtcattggca gcttttccct
```

SEQ ID NO: 34 Mouse MDM4 Isoform 3 Amino Acid Sequence (NP_001289732.1)

```
  1 MTSHSTSAQC SASDSACRIS SEQISQVRPK LQLLKILHAA GAQGEVFTMK EVMHYLGQYI
 61 MVKQLYDQQE QHMVYCGGDL LGDLLGCQSF SVKDPSPLYD MLRKNLVTSA SINTDAAQTL
121 ALAQDHTMDF PSQDRLKHGA TEYSNPRKRT EEEDTHTLPT SRHKCRDSRA DEDLIEHLSQ
181 DETSRLDLDF EEWDVAGLPW WFLGNLRNNC IPKSNGSTDL QTNQDIGTAI VSDTTDDLWF
241 LNETVSEQLG VGIKVEAANS EQTSEVGKTS NKKTVEVGKD DDLEDSRSLS DDTDVELTSE
301 DEWQCTECKK FNSPSKRYCF RCWALRKDWY SDCSKLTHSL STSNITAIPE KKDNEGIDVP
361 DCRRTISAPV VRPKDGYLKE EKPRFDPCNS VGFLDLAHSS ESQEIISSAR EQTDIFSEQK
421 AETESMEDFQ NVLKPCSLCE KRPRDGNIIH GKTSHLTTCF HCARRLKKSG ASCPACKKEI
481 QLVIKVFIA
```

SEQ ID NO: 35 Mouse MDM4 Transcript Variant 4 cDNA Sequence
(NM_001302804.1; CDS: 555-1643)

```
   1 tctatggttc ccccggcctc cccggaagct cttgcgaacg ctgggtttga gaggccggaa
  61 gtggtgctgc cgttgctcgc agtttcaaaa tgcagtgcag gccttagggt ctccggctgc
 121 cacccctccc ccagctagga gggggagcga ctcatggagc ggccgtaagt ttgctaactg
 181 tggagtcttc actgccaaaa tgacatcaca ttccacctcg gcccagtgtt cagcatctga
 241 cagtgcttgc agaatttctt cggaacaaat tagtcagcag gtgcggccaa aactgcagct
 301 tttgaagatt ttgcatgcag caggtgcgca gggggaagta ttcaccatga aagaggtaat
 361 gcactatcta ggccagtata taatggtgaa gcagctctat gatcaacagg agcaacatat
 421 ggtatactgt ggtggagatc ttttgggaga tctacttgga tgtcagagct tttctgtgaa
 481 agatccaagc cctctctatg acatgctaag aaagaatctt gttacatcag cttctattaa
 541 cacaggatca cactatggat tttccaagtc aagaccgact gaagcacggt gcaacagaat
 601 actccaatcc cagaaaaaga actgaagaag aggatactca cacactgcct acctcacgac
 661 ataaatgcag agactccaga gcagatgaag acttgataga acatttatct caagatgaga
 721 catctaggct tgaccttgat tttgaggagt gggacgttgc tggcctgcct tggtggtttc
 781 tagggaattt gagaaacaac tgtattccta aaagtaatgg ctcaactgat ttacagacaa
 841 atcaggatat aggtactgcc attgtttcag acactacgga tgatttgtgg tttttaaatg
 901 agaccgtgtc agagcaatta ggtgttggaa taaaagttga agctgctaat tctgagcaaa
 961 caagtgaagt agggaaaaca agtaacaaga agacggtgga ggtgggaaag gatgatgatc
1021 ttgaggactc caggtccttg agcgatgata ctgacgtgga acttacctct gaggatgagt
1081 ggcagtgtac ggaatgcaag aagtttaatt ctccaagcaa gaggtactgt tttcgttgct
1141 gggccttgag aaaggattgg tattcggatt gttctaaatt aactcattcc ctatctacat
1201 ctaatattac tgccatacct gaaaagaagg acaatgaagg aattgatgtt cccgattgta
1261 ggagaaccat ttcagctcct gttgttaggc ctaaagatgg atatttaaag gaggaaaagc
1321 ccaggtttga cccttgcaac tcagtgggat ttttggattt ggctcatagt tctgaaagcc
1381 aggagatcat ctcaagcgcg agagaacaaa cagatatttt ttctgagcag aaagctgaaa
1441 cagaaagtat ggaagatttc cagaatgtct tgaagccgtg tagcttatgt gaaaaaaggc
1501 ctcgggatgg gaacattatt catgggaaga cgagccatct gacgacatgt ttccactgtg
1561 ccaggagact gaagaagtct ggggcttcgt gtcctgcttg taagaaagag attcagttgg
1621 ttattaaagt tttatagca tagttgagtc agtcacagag aaatactagg aggaccaggt
1681 catttatcaa aaaaatcagt attcttagag gcaggggcag aagatcacca attttgatgc
1741 cagtctgggc catataatga gatcttagtc ttaaaaggat cagtattgag catcttttat
1801 aaatgtgacc cattgcatat gtttatttgt ataagcatat atgaactttt agctaagttt
1861 tgagggtttc attagtgaga agatactttg ttcttccaaa ttgtgaaccc agagggaata
1921 atatcaatac aaacatagca atgcattctt ttattcactt ccaaattatt gcaagaataa
1981 tacattagtt gatttattct ctaccctggt gttatgtaat gttcttgagg catcaaaatc
```

TABLE 1-continued

| | | | | | | |
|---|---|---|---|---|---|---|
| 2041 | taaagcattt | attaaatact | ggggctaaca | ctgaagagga | catatccagt | cagtcgctca |
| 2101 | ttgtgtagtc | aaggatgacc | ttaaattcct | gatagctgtc | tctaccacct | atgtgctcat |
| 2161 | aggctcatag | gccgccccac | tagcccatct | gaaatctctt | agttttaggt | caggtaacac |
| 2221 | aggtgtacat | ctctccacag | ccttattatc | agttccaaaa | aggaaaggca | cagactttgt |
| 2281 | tgcccacact | ttgcatttgt | ctctcaagct | ggctgggtgt | tttgtgtttt | gtgctctgca |
| 2341 | gctgttcaca | ttctgaggca | gtggcctatg | ataaggcttg | aacagtagag | aggaggaatg |
| 2401 | tagcagctgt | gaaaggaggg | gaacaaattg | atctcttcaa | ttctgcttag | tcattttaga |
| 2461 | ccacatcaac | ttagtataat | atcaatatat | gaactgaaga | tcttcacgct | gaatcccgta |
| 2521 | tgcctgttct | gtgtccactg | aacacatggc | catcttgatg | tttccccagg | gacatgagaa |
| 2581 | catcatttta | aagaccaagt | ccctagaact | attgagcttg | agggcaatct | agctgtcttg |
| 2641 | gcttttccta | tggctcctgc | tgttagaaag | ggggagatgc | atggtatcca | gtccccttaa |
| 2701 | tgtcattatg | tccctgctgg | actgggacca | ctggggctcc | tctaattact | actaagagga |
| 2761 | gctatgttag | ctttatcttg | cattgatccc | atgttccctg | tctgtcccat | gctctaccat |
| 2821 | tagacccaac | tttaccaaat | tctcactgga | tcagttatca | tagttactct | ttaattttga |
| 2881 | tgacaaagca | ccaatgcaaa | atataaaaga | aagcatttaa | tggggtttgc | ttttgagagg |
| 2941 | gttagaatcc | atgatggcag | gcagggacag | ctgagagctc | acatcttgat | ctgcaagtag |
| 3001 | aatgcagaga | aaaagagagc | cctggaaaac | cccagggcct | gcccccccag | tgtcgtaatt |
| 3061 | ggtctacctt | ttccaccgac | tggggtccaa | gtattcaaac | ttaagagcct | gtggtttata |
| 3121 | ttctcatgta | aaccaccaca | ttccatgaaa | agaattacta | attactgtgc | tgcagaacca |
| 3181 | gtattaggcg | ttctggacac | ctcttctatc | aaagaaatta | cttttcactc | caggcttagg |
| 3241 | caaattctta | ggacaagggt | agaaggcagc | cacattcttt | gtcaaacata | accagaataa |
| 3301 | gtctttagcc | agttgttaat | agttgttcta | ccctgcagcc | tcttgatcta | ggcttcctct |
| 3361 | cagtactaac | tgtcttttag | gctccaactg | gacccattaa | gctctgttta | cagccttgaa |
| 3421 | ccctttctta | gtccaaagtc | ttacacattc | ctccaaaaaa | accacatggt | caggtctttc |
| 3481 | acagcaaaga | tccacttcct | ggtagtagct | tctgtgtctt | ggctactcta | aaattgctat |
| 3541 | gacaaaacat | cccgaccaag | gcagaatgta | caagaaagca | ttgagtttat | ggtttcagag |
| 3601 | gtatttagtt | catgatagaa | cagttgagag | cttacatctt | gatctgtaag | taggaggcag |
| 3661 | agagagaacc | caggggatgg | catggacttt | tgaaacctcc | aagccttcac | cttgtgacag |
| 3721 | acctccccaa | cagagccaca | tctcctaatc | ctttccaagt | agttcctcca | actggggacc |
| 3781 | aaatactcca | gcatgagcat | aggggagcat | tctcattcac | accaccagtt | tgccgaggaa |
| 3841 | ctttcctagc | catggcttgt | cattcattgc | tcccagttga | taatttcact | atttgtagca |
| 3901 | aactcagtgg | ccaagtcctt | gctattatgg | gtcttctgct | tgtattgaaa | atactgcagc |
| 3961 | tcctgttggg | gttgctgtgc | agtctctctg | agggactgat | aacagacttg | tatatccata |
| 4021 | tctccatggc | agtgagaaac | ggtagcttag | aggtaatcct | agaagccatc | actcacagtc |
| 4081 | cctgcttgag | aataggctat | gatatgtcta | gccctggact | ttagtcattt | cctagacatg |
| 4141 | gacctgctgg | gtggaattgg | gtcattatga | tgtttaattc | caagcactgc | attcaaaata |
| 4201 | ggatacatga | tatagtatgt | cagcttcatt | ctaacgtttc | tcctaatctt | ttggggcaga |
| 4261 | gtcttgctgt | ttcaccatga | ctggcctggg | ccttacccta | catctcaggc | tggcctcagc |
| 4321 | tttgcagtga | ccttcctgct | tttgcctctc | gagtgctgga | attctaggca | tgtaatgact |
| 4381 | aaatttctta | ttttgctttt | tatttaagtt | tttgttactc | tatcttggac | aaaaagtgca |
| 4441 | gagcagaggt | gtcggattac | taggaaagtc | tccagggctt | cgctgttact | gtgttcccca |
| 4501 | cagggacttc | ctggttgttg | acgtgcttct | gtttactact | gtgtcagatg | agcgactcag |
| 4561 | agctcggctt | cagataggtg | tgactgccgc | cctcgcccat | ttaggatgta | gtagatttat |
| 4621 | gattgagggc | tggaacgggt | agattacatt | gtaccgccaa | gcatttgtga | ctgtgtggat |
| 4681 | atatattcat | tatttatgta | tatttaggtg | tgtgtgatac | tttgcatggt | ttgaaagaat |
| 4741 | ctattctgaa | agccaggatc | atttgtaacc | tttgtgtgtc | agttcaatgt | aatgttgggg |
| 4801 | cctttgaaaa | gttgattgag | aaattgggga | tcattcccag | ttctccgatg | ttacttgttt |
| 4861 | agtcctcttt | agaaagaaag | acacttttgg | accagctgtt | tcgctgtttt | gttctgtttc |
| 4921 | catgatattc | tgtgaacctc | catggcttta | gatactgtga | ctgttatttt | ccttttttgcc |
| 4981 | caaattgttg | attcagtcta | aagaatacta | tttttgatg | cctcttacaa | ttcatgcatg |
| 5041 | tgcacactat | agattgatgc | tacctttgct | aaaaatgtct | taagataaag | aactagctct |
| 5101 | ttagaacctg | cacttcaaag | ataaacctgg | aagctgtcct | gtgccaaaag | taaagtgtac |
| 5161 | aatgtttaca | gatgggtgga | attttgcact | gccataggga | acggtgagct | cgcatcacgg |
| 5221 | ggttccttag | atgtatgggt | agatagttgc | agttgagctt | atgagaggaa | ctgtggagcc |
| 5281 | ctctaaggct | aagctgctaa | tgagtatcca | agacaggtgg | ttggtgaacg | tgactcccta |
| 5341 | gacctagctg | gggtcttctg | ttgacagctc | ttcatggttt | gcagacacta | tatgttttct |
| 5401 | ttagaggagc | tgccagctct | cccctcttgt | gaaagactgt | cttgtagaca | ttttgagatc |
| 5461 | ttttgatgta | atgtgcaatc | ccaagtaatg | ccattattgg | tgaatgtagc | attgttaaac |
| 5521 | ttttattgta | aattatctct | gatcttacct | tgatagcctt | agggtttttt | gtttttgttt |
| 5581 | tttttgtta | tgttttcaga | gacagagtct | cgctatttgg | tttacctaga | atttgcttta |
| 5641 | tgattaggct | gtccccaaac | tcacagatgt | ctgcctttct | accaccacgc | ccatgtaact |
| 5701 | gatgttacca | aaaatgatct | catatccatg | gtgttgctta | tgtgtctttg | cataggcgcc |
| 5761 | tccttcagtc | ccatctagga | gcacagcaca | gtagaagtcc | atttcttaag | tgggcagagt |
| 5821 | cagagataag | ctaagagggc | aagtagttgc | ttcagtggtt | tttagagctt | ggcaaacgct |
| 5881 | ttactgaaga | ttagcattgt | gttgtgacac | ttgagggcca | atacgagcat | ttaatttgtt |
| 5941 | acctaaaggt | gctttgtgtt | cttaaacagc | aagtatttga | tgtgtgtaaa | catttccctt |
| 6001 | cattctccct | ccctcctcac | cgtttttatg | gtctcctatt | tctgagttag | ctgcatttgg |
| 6061 | acattgcttt | tatgccagag | gccatctgtc | accttggatg | tttagaagta | cagtgtactt |
| 6121 | atgtagggtc | ctccttgagc | ctgtcctgag | cagtgttgtg | gttacagaat | tgcctacgag |
| 6181 | ctccaacaga | gaggtgggga | agctgggagg | gcacagctgt | ctggcttcct | ttgtggaggt |
| 6241 | gttggtttgt | ttgaacacta | aggaatttga | ggttaatctt | ccccctcttc | ctgcccatag |
| 6301 | ttttcacttc | cctttcagta | agaacgaccc | cctaaaagaa | aacaggagga | gatgcagcgc |
| 6361 | tttaggccgc | cttagccagc | agcttgtgtc | ctactctgga | agttgtaacc | tacagttttt |
| 6421 | ctcacctgta | aagccaacac | acacagctac | ccgtttctac | ctcagtttga | tgtggcgact |
| 6481 | atggaggaac | aactcttaaa | agctctgact | gccttgaaga | tggaggaagc | tagtggtctt |
| 6541 | ggtcgactgt | gctctgaggt | ttatattgag | aatcctttat | tctggaagtg | agtgcggttc |
| 6601 | tcctgaccgc | ctgctcagta | gaacctgtgt | tgcctgcttt | aagtctctgc | ccacctgcct |
| 6661 | gtcctttcct | tgacactagg | ctcttgatta | ggaagagttg | tctccagatg | ctttgagaag |
| 6721 | cacatgtaaa | tctagatagc | acattctacc | ctgatggaac | ttccttgctt | gtcttgctgt |
| 6781 | ataggaattc | attctgtata | cacttgagtg | ggtggcatga | gatgctcgac | ttgtgtgtcg |

TABLE 1-continued

```
6841 agaggcagtg tcatgacatt cccagtctgg tacttgccag tgcagaagca aatgaggggt
6901 aataaactga gaagaagggc agcttactaa cgaggccaga gggaaatgtt tccgtgtgtc
6961 cttatgtaac tttttacagt gccactaagt taatagccct gtacatgggt gtttgcacta
7021 tgtaatgctt ttaatgcggt tttattgtgt ttttgtgtga ttaaacagtt ttcatttcat
7081 tgtgttttgt cattattgga aataggtaat tttgcttatg tacagctaac ccattttctg
7141 ttatctttgg catgatttgg ggaagtgatt aaaagtcatt ggcagctttt ccct
```

SEQ ID NO: 36 Mouse MDM4 Isoform 4 Amino Acid Sequence (NP_001289733.1)

```
  1 MDFPSQDRLK HGATEYSNPR KRTEEEDTHT LPTSRHKCRD SRADEDLIEH LSQDETSRLD
 61 LDFEEWDVAG LPWWFLGNLR NNCIPKSNGS TDLQTNQDIG TAIVSDTTDD LWFLNETVSE
121 QLGVGIKVEA ANSEQTSEVG KTSNKKTVEV GKDDDLEDSR SLSDDTDVEL TSEDEWQCTE
181 CKKFNSPSKR YCFRCWALRK DWYSDCSKLT HSLSTSNITA IPEKKDNEGI DVPDCRRTIS
241 APVVRPKDGY LKEEKPRFDP CNSVGFLDLA HSSESQEIIS SAREQTDIFS EQKAETESME
301 DFQNVLKPCS LCEKRPRDGN IIHGKTSHLT TCFHCARRLK KSGASCPACK KEIQLVIKVF
361 IA
```

SEQ ID NO: 37 Mouse MDM4 Transcript Variant 5 cDNA Sequence (NM_008575.4; CDS: 278-1747)

```
   1 tctatggttc ccccggcctc cccggaagct cttgcgaacg ctgggtttga gaggccggaa
  61 gtggtgctgc cgttgctcgc agtttcaaaa tgcagtgcag gccttagggt ctccggctgc
 121 cacccctccc ccagctagga gggggagcga ctcatggagc ggccgtaagg attcacctga
 181 gggacacttg gctggtttag tttttagctt ctgtgctgga tttgagaatt gagaatttca
 241 gttcagtttt gctaactgtg gagtcttcac tgccaaaatg acatcacatt ccacctcggc
 301 ccagtgttca gcatctgaca gtgcttgcag aatttcttcg gaacaaatta gtcaggtgcg
 361 gccaaaactg cagcttttga agattttgca tgcagcaggt gcgcaggggg aagtattcac
 421 catgaaagag gtaatgcact atctaggcca gtatataatg gtgaagcagc tctatgatca
 481 acaggagcaa catatggtat actgtggtgg agatcttttg ggagatctac ttggatgtca
 541 gagcttttct gtgaaagatc caagccctct ctatgacatg ctaagaaaga atcttgttac
 601 atcagcttct attaacacag atgctgctca gactctcgct ctcgcacagg atcacactat
 661 ggattttcca agtcaagacc gactgaagca cggtgcaaca gaatactcca atcccagaaa
 721 aagaactgaa gaagaggata ctcacacact gcctacctca cgacataaat gcagagactc
 781 cagagcagat gaagacttga tagaacattt atctcaagat gagacatcta ggcttgacct
 841 tgattttgag gagtgggacg ttgctggcct gccttggtgg tttctaggga atttgagaaa
 901 caactgtatt cctaaaagta atggctcaac tgatttacag acaaatcagg atataggtac
 961 tgccattgtt tcagacacta cggatgattt gtggttttta aatgagaccg tgtcagagca
1021 attaggtgtt ggaataaaag ttgaagctgc taattctgag caaacaagtg aagtagggaa
1081 aacaagtaac aagaagacgg tggaggtggg aaaggatgat gatcttgagg actccaggtc
1141 cttgagcgat gatactgacg tggaacttac ctctgaggat gagtggcagt gtacggaatg
1201 caagaagttt aattctccaa gcaagaggta ctgttttcgt tgctgggcct tgagaaagga
1261 ttggtattcg gattgttcta aattaactca ttccctatct acatctaata ttactgccat
1321 acctgaaaag aaggacaatg aaggaattga tgttcccgat tgtaggagaa ccatttcagc
1381 tcctgttgtt aggcctaaag atggatattt aaaggaggaa aagcccaggt ttgacccttg
1441 caactcagtg ggatttttgg atttggctca tagttctgaa agccaggaga tcatctcaag
1501 cgcgagagaa caaacagata tttttctga gcagaaagct gaaacagaaa gtatggaaga
1561 tttccagaat gtcttgaagc cgtgtagctt atgtgaaaaa aggcctcggg atgggaacat
1621 tattcatggg aagacgagcc atctgacgac atgtttccac tgtgccagga gactgaagaa
1681 gtctggggct tcgtgtcctg cttgtaagaa agagattcag ttggttatta aagtttttat
1741 agcatagttg agtcagtcac agagaaatac taggaggacc aggtcattta tcaaaaaaat
1801 cagtattctt agaggcaggg gcagaagatc accaattttg atgccagtct gggccatata
1861 atgagatctt agtcttaaaa ggatcagtat tgagcatctt ttataaatgt gacccattgc
1921 atatgtttat ttgtataagc atatatgaac ttttagctaa gttttgaggg tttcattagt
1981 gagaagatac tttgttcttc caaattgtga acccagaggg aataatatca atacaaacat
2041 agcaatgcat tcttttattc acttccaaat tattgcaaga ataatacatt agttgattta
2101 ttctctaccc tggtgttatg taatgttctt gaggcatcaa aatctaaagc atttattaaa
2161 tactggggct aacactgaag aggacatatc cagtcagtcg ctcattgtgt agtcaaggat
2221 gaccttaaat tcctgatagc tgtctctacc acctatgtgc tcataggctc ataggccgcc
2281 ccactagccc atctgaaatc tcttagtttt aggtcaggta acacaggtgt acatctctcc
2341 acagccttat tatcagttcc aaaaaggaaa ggcacagact ttgttgccca cactttgcat
2401 ttgtctctca agctggctgg gtgttttgtg ttttgtgctc tgcagctgtt cacattctga
2461 ggcagtggcc tatgataagg cttgaacagt agagaggagg aatgtagcag ctgtgaaagg
2521 aggggaacaa attgatctct tcaattctgc ttagtcattt tagaccacat caacttagta
2581 taatatcaat atatgaactg aagatcttca cgctgaatcc cgtatgcctg ttctgtgtcc
2641 actgaacaca tggccatctt gatgtttccc cagggacatg agaacatcat tttaaagacc
2701 aagtccctag aactattgag cttgagggca atctagctgt cttggctttt cctatggctc
2761 ctgctgttag aaagggggag atgcatggta tccagtcccc ttaatgtcat tatgtccctg
2821 ctggactggg accactgggg ctcctctaat tactactaag aggagctatg ttagctttat
2881 cttgcattga tcccatgttc cctgtctgtc ccatgctcta ccattagacc caactttacc
2941 aaattctcac tggatcagtt atcatagtta ctctttaatt ttgatgacaa agcaccaatg
3001 caaaatataa aagaaagcat ttaatggggt ttgcttttga gagggttaga atccatgatg
3061 gcaggcaggg acagctgaga gctcacatct tgatctgcaa gtagaatgca gagaaaaaga
3121 gagccctgga aaaccccagg gcctgccccc ccagtgtcgt aattggtcta ccttttccac
3181 cgactggggt ccaagtattc aaacttaaga gcctgtggtt tatattctca tgtaaaccac
3241 cacattccat gaaaagaatt actaattact gtgctgcaga accagtatta ggcgttctgg
3301 acacctcttc tatcaaagaa attacttttc actccaggct taggcaaatt cttaggacaa
3361 gggtagaagg cagccacatt ctttgtcaaa cataaccaga ataagtcttt agccagttgt
3421 taatagttgt tctaccctgc agcctcttga tctaggcttc ctctcagtac taactgtctt
3481 ttaggctcca actggaccca ttaagctctg tttacagcct tgaacccttt cttagtccaa
3541 agtcttacac attcctccaa aaaaaccaca tggtcaggtc tttcacagca aagatccact
3601 tcctggtagt agcttctgtg tcttggctac tctaaaattg ctatgacaaa acatcccgac
3661 caaggcagaa tgtacaagaa agcattgagt ttatggtttc agaggtattt agttcatgat
```

TABLE 1-continued 3721 agaacagttg agagcttaca tcttgatctg taagtaggag gcagagagag aacccagggg
3781 atggcatgga cttttgaaac ctccaagcct tcaccttgtg acagacctcc ccaacagagc
3841 cacatctcct aatcctttcc aagtagttcc tccaactggg gaccaaatac tccagcatga
3901 gcatagggga gcattctcat tcacaccacc agtttgccga ggaactttcc tagccatggc
3961 ttgtcattca ttgctcccag ttgataattt cactatttgt agcaaactca gtggccaagt
4021 ccttgctatt atgggtcttc tgcttgtatt gaaaatactg cagctcctgt tggggttgct
4081 gtgcagtctc tctgagggac tgataacaga cttgtatatc catatctcca tggcagtgag
4141 aaacggtagc ttagaggtaa tcctagaagc catcactcac agtccctgct tgagaatagg
4201 ctatgatatg tctagccctg gactttagtc atttcctaga catggacctg ctgggtggaa
4261 ttgggtcatt atgatgttta attccaagca ctgcattcaa aataggatac atgatatagt
4321 atgtcagctt cattctaacg tttctcctaa tcttttgggg cagagtcttg ctgtttcacc
4381 atgactggcc tgggccttac cctacatctc aggctggcct cagctttgca gtgaccttcc
4441 tgcttttgcc tctcgagtgc tggaattcta ggcatgtaat gactaaattt cttattttgc
4501 tttttattta agtttttgtt actctatctt ggacaaaaag tgcagagcag aggtgtcgga
4561 ttactaggaa agtctccagg gcttcgctgt tactgtgttc cccacaggga cttcctggtt
4621 gttgacgtgc ttctgtttac tactgtgtca gatgagcgac tcagagctcg gcttcagata
4681 ggtgtgactg ccgccctcgc ccatttagga tgtagtagat ttatgattga gggctggaac
4741 gggtagatta cattgtaccg ccaagcattt gtgactgtgt ggatatatat tcattattta
4801 tgtatattta ggtgtgtgtg atactttgca tggtttgaaa gaatctattc tgaaagccag
4861 gatcatttgt aacctttgtg tgtcagttca atgtaatgtt ggggcctttg aaaagttgat
4921 tgagaaattg gggatcattc ccagttctcc gatgttactt gtttagtcct ctttagaaag
4981 aaagacactt ttggaccagc tgtttcgctg ttttgttctg tttccatgat attctgtgaa
5041 cctccatggc tttagatact gtgactgtta ttttcctttt tgcccaaatt gttgattcag
5101 tctaaagaat actatttttt gatgcctctt acaattcatg catgtgcaca ctatagattg
5161 atgctacctt tgctaaaaat gtcttaagat aaagaactag ctctttagaa cctgcacttc
5221 aaagataaac ctggaagctg tcctgtgcca aaagtaaagt gtacaatgtt tacagatggg
5281 tggaattttg cactgccata gggaacggtg agctcgcatc acggggttcc ttagatgtat
5341 gggtagatag ttgcagttga gcttatgaga ggaactgtgg agccctctaa ggctaagctg
5401 ctaatgagta tccaagacag gtggttggtg aacgtgactc cctagaccta gctggggtct
5461 tctgttgaca gctcttcatg gtttgcagac actatatgtt ttctttagag gagctgccag
5521 ctctcccctc ttgtgaaaga ctgtcttgta gacattttga gatcttttga tgtaatgtgc
5581 aatcccaagt aatgccatta ttggtgaatg tagcattgtt aaacttttat tgtaaattat
5641 ctctgatctt accttgatag ccttagggtt ttttgttttt gttttttttt gttatgtttt
5701 cagagacaga gtctcgctat ttggtttacc tagaatttgc tttatgatta ggctgtcccc
5761 aaactcacag atgtctgcct ttctaccacc acgcccatgt aactgatgtt accaaaaatg
5821 atctcatatc catggtgttg cttatgtgtc tttgcatagg cgcctccttc agtcccatct
5881 aggagcacag cacagtagaa gtccatttct taagtgggca gagtcagaga taagctaaga
5941 gggcaagtag ttgcttcagt ggtttttaga gcttggcaaa cgctttactg aagattagca
6001 ttgtgttgtg acacttgagg gccaatacga gcatttaatt tgttacctaa aggtgctttg
6061 tgttcttaaa cagcaagtat ttgatgtgtg taaacatttc ccttcattct ccctccctcc
6121 tcaccgtttt tatggtctcc tatttctgag ttagctgcat ttggacattg cttttatgcc
6181 agaggccatc tgtcaccttg gatgtttaga agtacagtgt acttatgtag ggtcctcctt
6241 gagcctgtcc tgagcagtgt tgtggttaca gaattgccta cgagctccaa cagagaggtg
6301 gggaagctgg gagggcacag ctgtctggct tcctttgtgg aggtgttggt ttgtttgaac
6361 actaaggaat ttgaggttaa tcttccccct cttcctgccc atagttttca cttccctttc
6421 agtaagaacg accccctaaa agaaaacagg aggagatgca gcgctttagg ccgccttagc
6481 cagcagcttg tgtcctactc tggaagttgt aacctacagt ttttctcacc tgtaaagcca
6541 acacacacag ctacccgttt ctacctcagt ttgatgtggc gactatggag gaacaactct
6601 taaaagctct gactgccttg aagatggagg aagctagtgg tcttggtcga ctgtgctctg
6661 aggtttatat tgagaatcct ttattctgga agtgagtgcg gttctcctga ccgcctgctc
6721 agtagaacct gtgttgcctg ctttaagtct ctgcccacct gcctgtcctt tccttgacac
6781 taggctcttg attaggaaga gttgtctcca gatgctttga gaagcacatg taaatctaga
6841 tagcacattc taccctgatg gaacttcctt gcttgtcttg ctgtatagga attcattctg
6901 tatacacttg agtgggtggc atgagatgct cgacttgtgt gtcgagaggc agtgtcatga
6961 cattcccagt ctggtacttg ccagtgcaga agcaaatgag gggtaataaa ctgagaagaa
7021 gggcagctta ctaacgaggc cagagggaaa tgtttccgtg tgtccttatg taacttttta
7081 cagtgccact aagttaatag ccctgtacat gggtgtttgc actatgtaat gcttttaatg
7141 cggttttatt gtgtttttgt gtgattaaac agttttcatt tcattgtgtt ttgtcattat
7201 tggaaatagg taattttgct tatgtacagc taacccattt tctgttatct ttggcatgat
7261 ttggggaagt gattaaaagt cattggcagc ttttccct SEQ ID NO: 38 Mouse MDM4 Isoform 5 Amino Acid Sequence (NP_032601.2)
1 MTSHSTSAQC SASDSACRIS SEQISQVRPK LQLLKILHAA GAQGEVFTMK EVMHYLGQYI
61 MVKQLYDQQE QHMVYCGGDL LGDLLGCQSF SVKDPSPLYD MLRKNLVTSA SINTDAAQTL
121 ALAQDHTMDF PSQDRLKHGA TEYSNPRKRT EEEDTHTLPT SRHKCRDSRA DEDLIEHLSQ
181 DETSRLDLDF EEWDVAGLPW WFLGNLRNNC IPKSNGSTDL QTNQDIGTAI VSDTTDDLWF
241 LNETVSEQLG VGIKVEAANS EQTSEVGKTS NKKTVEVGKD DDLEDSRSLS DDTDVELTSE
301 DEWQCTECKK FNSPSKRYCF RCWALRKDWY SDCSKLTHSL STSNITAIPE KKDNEGIDVP
361 DCRRTISAPV VRPKDGYLKE EKPRFDPCNS VGFLDLAHSS ESQEIISSAR EQTDIFSEQK
421 AETESMEDFQ NVLKPCSLCE KRPRDGNIIH GKTSHLTTCF HCARRLKKSG ASCPACKKEI
481 QLVIKVFIA SEQ ID NO: 39 Human LIG4 Isoform 1 Amino Acid Sequence (NP_002303.2, NP_996820.1, NP_001091738.1, NP_001339527.1, NP_001339528.1, NP_001339529.1, NP_001339530.1, NP_001339531.1, NP_001339532.1)
1 MAASQTSQTV ASHVPFADLC STLERIQKSK GRAEKIRHFR EFLDSWRKFH DALHKNHKDV
61 TDSFYPAMRL ILPQLERERM AYGIKETMLA KLYIELLNLP RDGKDALKLL NYRTPTGTHG
121 DAGDFAMIAY FVLKPRCLQK GSLTIQQVND LLDSIASNNS AKRKDLIKKS LLQLITQSSA
181 LEQKWLIRMI IKDLKLGVSQ QTIFSVFHND AAELHNVTTD LEKVCRQLHD PSVGLSDISI
241 TLFSAFKPML AAIADIEHIE KDMKHQSFYI ETKLDGERMQ MHKDGDVYKY FSRNGYNYTD TABLE 1-continued

```
301 QFGASPTEGS LTPFIHNAFK ADIQICILDG EMMAYNPNTQ TFMQKGTKFD IKRMVEDSDL
361 QTCYCVFDVL MVNNKKLGHE TLRKRYEILS SIFTPIPGRI EIVQKTQAHT KNEVIDALNE
421 AIDKREEGIM VKQPLSIYKP DKRGEGWLKI KPEYVSGLMD ELDILIVGGY WGKGSRGGMM
481 SHFLCAVAEK PPPGEKPSVF HTLSRVGSGC TMKELYDLGL KLAKYWKPFH RKAPPSSILC
541 GTEKPEVYIE PCNSVIVQIK AAEIVPSDMY KTGCTLRFPR IEKIRDDKEW HECMTLDDLE
601 QLRGKASGKL ASKHLYIGGD DEPQEKKRKA APKMKKVIGI IEHLKAPNLT NVNKISNIFE
661 DVEFCVMSGT DSQPKPDLEN RIAEFGGYIV QNPGPDTYCV IAGSENIRVK NIILSNKHDV
721 VKPAWLLECF KTKSFVPWQP RFMIHMCPST KEHFAREYDC YGDSYFIDTD LNQLKEVFSG
781 IKNSNEQTPE EMASLIADLE YRYSWDCSPL SMFRRHTVYL DSYAVINDLS TKNEGTRLAI
841 KALELRFHGA KVVSCLAEGV SHVIIGEDHS RVADFKAFRR TFKRKFKILK ESWVTDSIDK
901 CELQEENQYL I
```

SEQ ID NO: 40 Human LIG4 Isoform 2 Amino Acid Sequence (NP_001317524.1)

```
  1 MRLILPQLER ERMAYGIKET MLAKLYIELL NLPRDGKDAL KLLNYRTPTG THGDAGDFAM
 61 IAYFVLKPRC LQKGSLTIQQ VNDLLDSIAS NNSAKRKDLI KKSLLQLITQ SSALEQKWLI
121 RMIIKDLKLG VSQQTIFSVF HNDAAELHNV TTDLEKVCRQ LHDPSVGLSD ISITLFSAFK
181 PMLAAIADIE HIEKDMKHQS FYIETKLDGE RMQMHKDGDV YKYFSRNGYN YTDQFGASPT
241 EGSLTPFIHN AFKADIQICI LDGEMMAYNP NTQTFMQKGT KFDIKRMVED SDLQTCYCVF
301 DVLMVNNKKL GHETLRKRYE ILSSIFTPIP GRIEIVQKTQ AHTKNEVIDA LNEAIDKREE
361 GIMVKQPLSI YKPDKRGEGW LKIKPEYVSG LMDELDILIV GGYWGKGSRG GMMSHFLCAV
421 AEKPPPGEKP SVFHTLSRVG SGCTMKELYD LGLKLAKYWK PFHRKAPPSS ILCGTEKPEV
481 YIEPCNSVIV QIKAAEIVPS DMYKTGCTLR FPRIEKIRDD KEWHECMTLD DLEQLRGKAS
541 GKLASKHLYI GGDDEPQEKK RKAAPKMKKV IGIIEHLKAP NITNVNKISN IFEDVEFCVM
601 SGTDSQPKPD LENRIAEFGG YIVQNPGPDT YCVIAGSENI RVKNIILSNK HDVVKPAWLL
661 ECFKTKSFVP WQPRFMIHMC PSTKEHFARE YDCYGDSYFI DTDLNQLKEV FSGIKNSNEQ
721 TPEEMASLIA DLEYRYSWDC SPLSMFRRHT VYLDSYAVIN DLSTKNEGTR LAIKALELRF
781 HGAKVVSCLA EGVSHVIIGE DHSRVADFKA FRRTFKRKFK ILKESWVTDS IDKCELQEEN
841 QYLI
```

SEQ ID NO: 41 Human LIG4 isoform 3 Amino Acid Sequence (NP_001339533.1)

```
  1 MATPQETIKI SFYSWDSLVH RGNGACPRPD LCSTLERIQK SKGRAEKIRH FREFLDSWRK
 61 FHDALHKNHK DVTDSFYPAM RLILPQLERE RMAYGIKETM LAKLYIELLN LPRDGKDALK
121 LLNYRTPTGT HGDAGDFAMI AYFVLKPRCL QKGSLTIQQV NDLLDSIASN NSAKRKDLIK
181 KSLLQLITQS SALEQKWLIR MIIKDLKLGV SQQTIFSVFH NDAAELHNVT TDLEKVCRQL
241 HDPSVGLSDI SITLFSAFKP MLAAIADIEH IEKDMKHQSF YIETKLDGER MQMHKDGDVY
301 KYFSRNGYNY TDQFGASPTE GSLTPFIHNA FKADIQICIL DGEMMAYNPN TQTFMQKGTK
361 FDIKRMVEDS DLQTCYCVFD VLMVNNKKLG HETLRKRYEI LSSIFTPIPG RIEIVQKTQA
421 HTKNEVIDAL NEAIDKREEG IMVKQPLSIY KPDKRGEGWL KIKPEYVSGL MDELDILIVG
481 GYWGKGSRGG MMSHFLCAVA EKPPPGEKPS VFHTLSRVGS GCTMKELYDL GLKLAKYWKP
541 FHRKAPPSSI LCGTEKPEVY IEPCNSVIVQ IKAAEIVPSD MYKTGCTLRF PRIEKIRDDK
601 EWHECMTLDD LEQLRGKASG KLASKHLYIG GDDEPQEKKR KAAPKMKKVI GIIEHLKAPN
661 LTNVNKISNI FEDVEFCVMS GTDSQPKPDL ENRIAEFGGY IVQNPGPDTY CVIAGSENIR
721 VKNIILSNKH DVVKPAWLLE CFKTKSFVPW QPRFMIHMCP STKEHFAREY DCYGDSYFID
781 TDLNQLKEVF SGIKNSNEQT PEEMASLIAD LEYRYSWDCS PLSMFRRHTV YLDSYAVIND
841 LSTKNEGTRL AIKALELRFH GAKVVSCLAE GVSHVIIGED HSRVADFKAF RRTFKRKFKI
901 LKESWVTDSI DKCELQEENQ YLI
```

SEQ ID NO: 42 Human LIG4 Transcript Variant 1 cDNA Sequence (NM_002312.3; CDS: 274-3009)

```
   1 ccacagcgct gtagactgcg ccgcattaga agcctggcct cctgatgctg tgctcttcat
  61 ctagacccaa gccccaggtc gtgggacgat ttctcccgtt tttgactccc tggaactgta
 121 ttgcctgctt tacctgcgta catgttgatt ctttctcatg gcaaccccgc aggaaaccat
 181 caagatctca ttttacagct gggattctct ggttcacaga ggtaacggag cttgcccgag
 241 gccagttaaa cgagaagatt catcaccgct ttgatggctg cctcacaaac ttcacaaact
 301 gttgcatctc acgttccttt tgcagatttg tgttcaactt tagaacgaat acagaaaagt
 361 aaaggacgtg cagaaaaaat cagacacttc agggaatttt tagattcttg gagaaaattt
 421 catgatgctc ttcataagaa ccacaaagat gtcacagact ctttttatcc agcaatgaga
 481 ctaattcttc ctcagctaga aagagagaga atggcctatg gaattaaaga aactatgctt
 541 gctaagcttt atattgagtt gcttaattta cctagagatg gaaaagatgc cctcaaactt
 601 ttaaactaca gaacacccac tggaactcat ggagatgctg gagactttgc aatgattgca
 661 tattttgtgt tgaagccaag atgtttacag aaaggaagtt taaccataca gcaagtaaac
 721 gacctttttag actcaattgc cagcaataat tctgctaaaa gaaaagacct aataaaaaag
 781 agccttcttc aacttataac tcagagttca gcacttgagc aaaagtggct tatacggatg
 841 atcataaagg atttaaagct tggtgttagt cagcaaacta tcttttctgt ttttcataat
 901 gatgctgctg agttgcataa tgtcactaca gatctggaaa aagtctgtag gcaactgcat
 961 gatccttctg taggactcag tgatatttct atcactttat tttctgcatt taaaccaatg
1021 ctagctgcta ttgcagatat tgagcacatt gagaaggata tgaaacatca gagtttctac
1081 atagaaacca agctagatgg tgaacgtatg caaatgcaca aagatggaga tgtatataaa
1141 tacttctctc gaaatggata taactacact gatcagtttg gtgcttctcc tactgaaggt
1201 tctcttaccc cattcattca taatgcattc aaagcagata tacaaatctg tattcttgat
1261 ggtgagatga tggcctataa tcctaataca caaactttca tgcaaaaggg aactaagttt
1321 gatattaaaa gaatggtaga ggattctgat ctgcaaactt gttattgtgt ttttgatgta
1381 ttgatggtta ataataaaaa gctagggcat gagactctga gaaagaggta tgagattctt
1441 agtagtattt ttacaccaat tccaggtaga atagaaatag tgcagaaaac acaagctcat
1501 actaagaatg aagtaattga tgcattgaat gaagcaatag ataaaagaga agagggaatt
1561 atggtaaaac aacctctatc catctacaag ccagacaaaa gaggtgaagg gtggttaaaa
1621 attaaaccag agtatgtcag tggactaatg gatgaattgg acattttaat tgttggagga
1681 tattggggta aaggatcacg gggtggaatg atgtctcatt ttctgtgtgc agtagcagag
1741 aagcccccctc ctggtgagaa gccatctgtg tttcatactc tctctcgtgt tgggtctggc
1801 tgcaccatga aagaactgta tgatctgggt ttgaaattgg ccaagtattg gaagcctttt
```

TABLE 1-continued 1861 catagaaaag ctccaccaag cagcatttta tgtggaacag agaagccaga agtatacatt
1921 gaaccttgta attctgtcat tgttcagatt aaagcagcag agatcgtacc cagtgatatg
1981 tataaaactg gctgcacctt gcgttttcca cgaattgaaa agataagaga tgacaaggag
2041 tggcatgagt gcatgaccct ggacgaccta gaacaactta gggggaaggc atctggtaag
2101 ctcgcatcta aacaccttta tataggtggt gatgatgaac cacaagaaaa aaagcggaaa
2161 gctgccccaa agatgaagaa agttattgga attattgagc acttaaaagc acctaacctt
2221 actaacgtta acaaaatttc taatatattt gaagatgtag agttttgtgt tatgagtgga
2281 acagatagcc agccaaagcc tgacctggag aacagaattg cagaatttgg tggttatata
2341 gtacaaaatc caggcccaga cacgtactgt gtaattgcag ggtctgagaa catcagagtg
2401 aaaaacataa ttttgtcaaa taaacatgat gttgtcaagc ctgcatggct tttagaatgt
2461 tttaagacca aaagctttgt accatggcag cctcgcttta tgattcatat gtgcccatca
2521 accaaagaac attttgcccg tgaatatgat tgctatggtg atagttattt cattgataca
2581 gacttgaacc aactgaagga agtattctca ggaattaaaa attctaacga gcagactcct
2641 gaagaaatgg cttctctgat tgctgattta gaatatcggt attcctggga ttgctctcct
2701 ctcagtatgt ttcgacgcca caccgtttat ttggactcgt atgctgttat taatgacctg
2761 agtaccaaaa atgaggggac aaggttagct attaaagcct tggagcttcg gtttcatgga
2821 gcaaaagtag tttcttgttt agctgaggga gtgtctcatg taataattgg ggaagatcat
2881 agtcgtgttg cagattttaa agcttttaga agaactttta agagaaagtt taaaatccta
2941 aaagaaagtt gggtaactga ttcaatagac aagtgtgaat tacaagaaga aaaccagtat
3001 ttgatttaaa gctaggtttc ctagtgagga aagcctctga tctggcagac tcattgcagc
3061 aggtggtaat gataaaatac taaactacat tttatttttg tatcttaaaa atctatgcct
3121 aaaaagtatc attacatata ggaaaacaat aattttaact tttaaggttg aaaagacaat
3181 agcccaaagc caagaaagaa aaattatctt gaatgtagta ttcaatgatt ttttatgatc
3241 aaggtgaaat aaacagtcta aagaagaggt gtttttataa tatccatata gaaatctaga
3301 atttttactt agatactaat aaaatacatt tagaaacttt taaagtcatg aaaaagcatt
3361 aaccttctaa acagtatatt ctaaaaagtc aaaacgttaa caatagtttt tatctaataa
3421 aagcactgca agaaaatagg gtagaattgt tacagctgga cttgtaaaaa tatgtctttt
3481 tactcagggt ttaaaatgtc ccatttaaat atgaaatgta aacaaatttg tttttttaagg
3541 ttaaggccaa atgtaacaat aaaaccctgt cgatggtttt agctaaatta gaggaagttg
3601 tatgagactt aatgatctaa aaacttaaaa ttgaattggt ttgattaaaa ataaagcttg
3661 caattttaaa agtagctcac atttaatttc ttgtgtgaaa tagaacatgc tttaaaggaa
3721 gtatttttat gtgaatttgc attccagtat aaatagtatt cacaaaaaag attttcctag
3781 attttatcta ttgaataggt gtcaatatgg catgcatatt gtaactttca ttagaaataa
3841 gttgctttga cttttaaaaa tgacatagtt agattattta aagtcaatgt atatagtata
3901 tattatgtat ggatttatat accaaatttt ggaatacagc ctatctcatg accatattga
3961 aatgtacgga atttgatcca tgcgatacta tgtgtgcatt atttgaaagt tattggaaat
4021 tttattcaaa ccgtggaaca aatgtatgtg attttgttat acttcttaat ttaaataaaa
4081 tatttaatgc actattaaaa aaaaaaaaaa aaaaa SEQ ID NO: 43 Human LIG4 Transcript Variant 2 cDNA Sequence (NM_206937.1; CDS: 153-2888)

1 cttctggcgc cagcttccgg cttagcggct gagcttcagg cttgacgtca ggaaaccatc
61 aagatctcat tttacagctg ggattctctg gttcacagag gtaacggagc ttgcccgagg
121 ccagttaaac gagaagattc atcaccgctt tgatggctgc ctcacaaact tcacaaactg
181 ttgcatctca cgttcctttt gcagatttgt gttcaacttt agaacgaata cagaaaagta
241 aaggacgtgc agaaaaaatc agacacttca gggaattttt agattcttgg agaaaatttc
301 atgatgctct tcataagaac cacaaagatg tcacagactc tttttatcca gcaatgagac
361 taattcttcc tcagctagaa agagagagaa tggcctatgg aattaaagaa actatgcttg
421 ctaagcttta tattgagttg cttaatttac ctagagatgg aaaagatgcc ctcaaacttt
481 taaactacag aacacccact ggaactcatg gagatgctgg agactttgca atgattgcat
541 attttgtgtt gaagccaaga tgtttacaga aaggaagttt aaccatacag caagtaaacg
601 accttttaga ctcaattgcc agcaataatt ctgctaaaag aaaagaccta ataaaaaaga
661 gccttcttca acttataact cagagttcag cacttgagca aaagtggctt atacggatga
721 tcataaagga tttaaagctt ggtgttagtc agcaaactat cttttctgtt tttcataatg
781 atgctgctga gttgcataat gtcactacag atctggaaaa agtctgtagg caactgcatg
841 atccttctgt aggactcagt gatatttcta tcactttatt ttctgcattt aaaccaatgc
901 tagctgctat tgcagatatt gagcacattg agaaggatat gaaacatcag agtttctaca
961 tagaaaccaa gctagatggt gaacgtatgc aaatgcacaa agatggagat gtatataaat
1021 acttctctcg aaatggatat aactacactg atcagtttgg tgcttctcct actgaaggtt
1081 ctcttacccc attcattcat aatgcattca aagcagatat acaaatctgt attcttgatg
1141 gtgagatgat ggcctataat cctaatacac aaactttcat gcaaaaggga actaagtttg
1201 atattaaaag aatggtagag gattctgatc tgcaaacttg ttattgtgtt tttgatgtat
1261 tgatggttaa taataaaaag ctagggcatg agactctgag aaagaggtat gagattctta
1321 gtagtatttt tacaccaatt ccaggtagaa tagaaatagt gcagaaaaca caagctcata
1381 ctaagaatga agtaattgat gcattgaatg aagcaataga taaaagagaa gagggaatta
1441 tggtaaaaca acctctatcc atctacaagc cagacaaaag aggtgaaggg tggttaaaaa
1501 ttaaaccaga gtatgtcagt ggactaatgg atgaattgga cattttaatt gttggaggat
1561 attggggtaa aggatcacgg ggtggaatga tgtctcattt tctgtgtgca gtagcagaga
1621 agccccctcc tggtgagaag ccatctgtgt ttcatactct ctctcgtgtt gggtctggct
1681 gcaccatgaa agaactgtat gatctgggtt tgaaattggc caagtattgg aagccttttc
1741 atagaaaagc tccaccaagc agcattttat gtggaacaga gaagccagaa gtatacattg
1801 aaccttgtaa ttctgtcatt gttcagatta aagcagcaga gatcgtaccc agtgatatgt
1861 ataaaactgg ctgcaccttg cgttttccac gaattgaaaa gataagagat gacaaggagt
1921 ggcatgagtg catgaccctg gacgacctag aacaacttag ggggaaggca tctggtaagc
1981 tcgcatctaa acacctttat ataggtggtg atgatgaacc acaagaaaaa aagcggaaag
2041 ctgccccaaa gatgaagaaa gttattggaa ttattgagca cttaaaagca cctaacctta
2101 ctaacgttaa caaaatttct aatatatttg aagatgtaga gttttgtgtt atgagtggaa
2161 cagatagcca gccaaagcct gacctggaga acagaattgc agaatttggt ggttatatag
2221 tacaaaatcc aggcccagac acgtactgtg taattgcagg gtctgagaac atcagagtga
2281 aaaacataat tttgtcaaat aaacatgatg ttgtcaagcc tgcatggctt ttagaatgtt TABLE 1-continued

```
2341 ttaagaccaa aagctttgta ccatggcagc ctcgctttat gattcatatg tgcccatcaa
2401 ccaaagaaca ttttgcccgt gaatatgatt gctatggtga tagttatttc attgatacag
2461 acttgaacca actgaaggaa gtattctcag gaattaaaaa ttctaacgag cagactcctg
2521 aagaaatggc ttctctgatt gctgatttag aatatcggta ttcctgggat tgctctcctc
2581 tcagtatgtt tcgacgccac accgtttatt tggactcgta tgctgttatt aatgacctga
2641 gtaccaaaaa tgaggggaca aggttagcta ttaaagcctt ggagcttcgg tttcatggag
2701 caaaagtagt ttcttgttta gctgagggag tgtctcatgt aataattggg gaagatcata
2761 gtcgtgttgc agattttaaa gcttttagaa gaacttttaa gagaaagttt aaaatcctaa
2821 aagaaagttg ggtaactgat tcaatagaca agtgtgaatt acaagaagaa aaccagtatt
2881 tgatttaaag ctaggtttcc tagtgaggaa agcctctgat ctggcagact cattgcagca
2941 ggtggtaatg ataaaatact aaactacatt ttatttttgt atcttaaaaa tctatgccta
3001 aaaagtatca ttacatatag gaaaacaata attttaactt ttaaggttga aaagacaata
3061 gcccaaagcc aagaaagaaa aattatcttg aatgtagtat tcaatgattt tttatgatca
3121 aggtgaaata aacagtctaa agaagaggtg tttttataat atccatatag aaatctagaa
3181 tttttactta gatactaata aaatacattt agaaactttt aaagtcatga aaaagcatta
3241 accttctaaa cagtatattc taaaaagtca aaacgttaac aatagttttt atctaataaa
3301 agcactgcaa gaaaataggg tagaattgtt acagctggac ttgtaaaaat atgtcttttt
3361 actcagggtt taaaatgtcc catttaaata tgaaatgtaa acaaatttgt tttttaaggt
3421 taaggccaaa tgtaacaata aaaccctgtc gatggtttta gctaaattag aggaagttgt
3481 atgagactta atgatctaaa aacttaaaat tgaattggtt tgattaaaaa taaagcttgc
3541 aattttaaaa gtagctcaca tttaatttct tgtgtgaaat agaacatgct ttaaaggaag
3601 tatttttatg tgaatttgca ttccagtata aatagtattc acaaaaaaga ttttcctaga
3661 ttttatctat tgaataggtg tcaatatggc atgcatattg taactttcat tagaaataag
3721 ttgctttgac ttttaaaaat gacatagtta gattatttaa agtcaatgta tatagtatat
3781 attatgtatg gatttatata ccaaattttg gaatacagcc tatctcatga ccatattgaa
3841 atgtacggaa tttgatccat gcgatactat gtgtgcatta tttgaaagtt attggaaatt
3901 ttattcaaac cgtggaacaa atgtatgtga ttttgttata cttcttaatt taaataaaat
3961 atttaatgca ctattaaaaa aaaaaaaaaa aaaa
```

SEQ ID NO: 123 Human LIG4 Transcript Variant 3 cDNA Sequence
(NM_001098268.1; CDS: 236-2971)

```
   1 gccagtgagc ccccgcgacg gtggcccgga cggaaaagat acctcggcgg cgtgggcccg
  61 gctccctgct ccaggaccta gggatcttgg ccttccaccc tcctccgagc accaggactc
 121 cctccagttc cgtacccgag gcctccgtgg tgaagaggtg ccggacccga tgagctcggg
 181 agtccaccat cgctctgcaa gccgcagtta aacgagaaga ttcatcaccg ctttgatggc
 241 tgcctcacaa acttcacaaa ctgttgcatc tcacgttcct tttgcagatt tgtgttcaac
 301 tttagaacga atacagaaaa gtaaaggacg tgcagaaaaa atcagacact tcagggaatt
 361 tttagattct tggagaaaat ttcatgatgc tcttcataag aaccacaaag atgtcacaga
 421 ctcttttat ccagcaatga gactaattct tcctcagcta gaaagagaga gaatggccta
 481 tggaattaaa gaaactatgc ttgctaagct ttatattgag ttgcttaatt tacctagaga
 541 tggaaaagat gccctcaaac ttttaaacta cagaacaccc actggaactc atggagatgc
 601 tggagacttt gcaatgattg catattttgt gttgaagcca agatgtttac agaaaggaag
 661 tttaaccata cagcaagtaa acgacctttt agactcaatt gccagcaata attctgctaa
 721 aagaaaagac ctaataaaaa agagccttct tcaacttata actcagagtt cagcacttga
 781 gcaaaagtgg cttatacgga tgatcataaa ggatttaaag cttggtgtta gtcagcaaac
 841 tatcttttct gtttttcata atgatgctgc tgagttgcat aatgtcacta cagatctgga
 901 aaaagtctgt aggcaactgc atgatccttc tgtaggactc agtgatattt ctatcacttt
 961 atttctgca tttaaaccaa tgctagctgc tattgcagat attgagcaca ttgagaagga
1021 tatgaaacat cagagtttct acatagaaac caagctagat ggtgaacgta tgcaaatgca
1081 caaagatgga gatgtatata aatacttctc tcgaaatgga tataactaca ctgatcagtt
1141 tggtgcttct cctactgaag gttctcttac ccattcatt cataatgcat tcaaagcaga
1201 tatacaaatc tgtattcttg atggtgagat gatggcctat aatcctaata cacaaacttt
1261 catgcaaaag ggaactaagt ttgatattaa aagaatggta gaggattctg atctgcaaac
1321 ttgttattgt gtttttgatg tattgatggt taataataaa aagctagggc atgagactct
1381 gagaaagagg tatgagattc ttagtagtat ttttacacca attccaggta gaatagaaat
1441 agtgcagaaa acacaagctc atactaagaa tgaagtaatt gatgcattga atgaagcaat
1501 agataaaaga gaagagggaa ttatggtaaa acaacctcta tccatctaca agccagacaa
1561 aagaggtgaa gggtggttaa aaattaaacc agagtatgtc agtggactaa tggatgaatt
1621 ggacatttta attgttggag gatattgggg taaaggatca cggggtggaa tgatgtctca
1681 ttttctgtgt gcagtagcag agaagccccc tcctggtgag aagccatctg tgtttcatac
1741 tctctctcgt gttgggtctg gctgcaccat gaaagaactg tatgatctgg gtttgaaatt
1801 ggccaagtat tggaagcctt ttcatagaaa agctccacca agcagcattt tatgtggaac
1861 agagaagcca gaagtataca ttgaaccttg taattctgtc attgttcaga ttaaagcagc
1921 agagatcgta cccagtgata tgtataaaac tggctgcacc ttgcgttttc cacgaattga
1981 aaagataaga gatgacaagg agtggcatga gtgcatgacc ctggacgacc tagaacaact
2041 taggggggaag gcatctggta agctcgcatc taaacacctt tatataggtg gtgatgatga
2101 accacaagaa aaaaagcgga agctgcccc aaagatgaag aaagttattg gaattattga
2161 gcacttaaaa gcacctaacc ttactaacgt taacaaaatt tctaatatat ttgaagatgt
2221 agagttttgt gttatgagtg gaacagatag ccagccaaag cctgacctgg agaacagaat
2281 tgcagaattt ggtggttata tagtacaaaa tccaggccca gacacgtact gtgtaattgc
2341 agggtctgag aacatcagag tgaaaaacat aattttgtca aataaacatg atgttgtcaa
2401 gcctgcatgg cttttagaat gttttaagac caaaagcttt gtaccatggc agcctcgctt
2461 tatgattcat atgtgcccat caaccaaaga acattttgcc cgtgaatatg attgctatgg
2521 tgatagttat ttcattgata cagacttgaa ccaactgaag gaagtattct caggaattaa
2581 aaattctaac gagcagactc ctgaagaaat ggcttctctg attgctgatt tagaatatcg
2641 gtattcctgg gattgctctc ctctcagtat gtttcgacgc cacaccgttt atttggactc
2701 gtatgctgtt attaatgacc tgagtaccaa aaatgagggg acaaggttag ctattaaagc
2761 cttggagctt cggtttcatg gagcaaaagt agtttcttgt ttagctgagg gagtgtctca
2821 tgtaataatt ggggaagatc atagtcgtgt tgcagatttt aaagctttta gaagaacttt
2881 taagagaaag tttaaaatcc taaaagaaag ttgggtaact gattcaatag acaagtgtga
```

TABLE 1-continued

```
2941 attacaagaa gaaaaccagt atttgattta aagctaggtt tcctagtgag gaaagcctct
3001 gatctggcag actcattgca gcaggtggta atgataaaat actaaactac attttatttt
3061 tgtatcttaa aaatctatgc ctaaaaagta tcattacata taggaaaaca ataattttaa
3121 cttttaaggt tgaaaagaca atagcccaaa gccaagaaag aaaaattatc ttgaatgtag
3181 tattcaatga tttttatga tcaaggtgaa ataaacagtc taaagaagag gtgtttttat
3241 aatatccata tagaaatcta gaatttttac ttagatacta ataaaataca tttagaaact
3301 tttaaagtca tgaaaaagca ttaaccttct aaacagtata ttctaaaaag tcaaaacgtt
3361 aacaatagtt tttatctaat aaaagcactg caagaaaata gggtagaatt gttacagctg
3421 gacttgtaaa aatatgtctt tttactcagg gtttaaaatg tcccatttaa atatgaaatg
3481 taaacaaatt tgttttttaa ggttaaggcc aaatgtaaca ataaaaccct gtcgatggtt
3541 ttagctaaat tagaggaagt tgtatgagac ttaatgatct aaaaacttaa aattgaattg
3601 gtttgattaa aaataaagct tgcaatttta aaagtagctc acatttaatt tcttgtgtga
3661 aatagaacat gctttaaagg aagtattttt atgtgaattt gcattccagt ataaatagta
3721 ttcacaaaaa agattttcct agattttatc tattgaatag gtgtcaatat ggcatgcata
3781 ttgtaacttt cattagaaat aagttgcttt gacttttaaa aatgacatag ttagattatt
3841 taaagtcaat gtatatagta tatattatgt atggatttat ataccaaatt ttggaataca
3901 gcctatctca tgaccatatt gaaatgtacg gaatttgatc catgcgatac tatgtgtgca
3961 ttatttgaaa gttattggaa attttattca aaccgtggaa caaatgtatg tgattttgtt
4021 atacttctta atttaaataa aatatttaat gcactattaa aaaaaaaaaa aaaaaaa
```

SEQ ID NO: 44 Human LIG4 Transcript Variant 4 cDNA Sequence
(NM_001330595.1; CDS: 274-2808)

```
   1 cttctggcgc cagcttccgg cttagcggct gagcttcagg cttgacgtca ggaaaccatc
  61 aagatctcat tttacagctg ggattctctg gttcacagag gtaacggagc ttgcccgagg
 121 ccagatttgt gttcaacttt agaacgaata cagaaaagta aaggacgtgc agaaaaaatc
 181 agacacttca gggaattttt agattcttgg agaaaatttc atgatgctct tcataagaac
 241 cacaaagatg tcacagactc tttttatcca gcaatgagac taattcttcc tcagctagaa
 301 agagagagaa tggcctatgg aattaaagaa actatgcttg ctaagcttta tattgagttg
 361 cttaatttac ctagagatgg aaaagatgcc ctcaaacttt taaactacag aacacccact
 421 ggaactcatg gagatgctgg agactttgca atgattgcat attttgtgtt gaagccaaga
 481 tgtttacaga aaggaagttt aaccatacag caagtaaacg accttttaga ctcaattgcc
 541 agcaataatt ctgctaaaag aaaagaccta ataaaaaaga gccttcttca acttataact
 601 cagagttcag cacttgagca aaagtggctt atacggatga tcataaagga tttaaagctt
 661 ggtgttagtc agcaaactat cttttctgtt tttcataatg atgctgctga gttgcataat
 721 gtcactacag atctggaaaa agtctgtagg caactgcatg atccttctgt aggactcagt
 781 gatatttcta tcactttatt ttctgcattt aaaccaatgc tagctgctat tgcagatatt
 841 gagcacattg agaaggatat gaaacatcag agtttctaca tagaaaccaa gctagatggt
 901 gaacgtatgc aaatgcacaa agatggagat gtatataaat acttctctcg aaatggatat
 961 aactacactg atcagtttgg tgcttctcct actgaaggtt ctcttacccc attcattcat
1021 aatgcattca aagcagatat acaaatctgt attcttgatg gtgagatgat ggcctataat
1081 cctaatacac aaactttcat gcaaaaggga actaagtttg atattaaaag aatggtagag
1141 gattctgatc tgcaaacttg ttattgtgtt tttgatgtat tgatggttaa taataaaaag
1201 ctagggcatg agactctgag aaagaggtat gagattctta gtagtatttt tacaccaatt
1261 ccaggtagaa tagaaatagt gcagaaaaca caagctcata ctaagaatga agtaattgat
1321 gcattgaatg aagcaataga taaaagagaa gagggaatta tggtaaaaca acctctatcc
1381 atctacaagc cagacaaaag aggtgaaggg tggttaaaaa ttaaaccaga gtatgtcagt
1441 ggactaatgg atgaattgga cattttaatt gttggaggat attggggtaa aggatcacgg
1501 ggtggaatga tgtctcattt tctgtgtgca gtagcagaga agcccccctcc tggtgagaag
1561 ccatctgtgt ttcatactct ctctcgtgtt gggtctggct gcaccatgaa agaactgtat
1621 gatctgggtt tgaaattggc caagtattgg aagccttttc atagaaaagc tccaccaagc
1681 agcattttat gtggaacaga gaagccagaa gtatacattg aaccttgtaa ttctgtcatt
1741 gttcagatta aagcagcaga gatcgtaccc agtgatatgt ataaaactgg ctgcaccttg
1801 cgttttccac gaattgaaaa gataagagat gacaaggagt ggcatgagtg catgaccctg
1861 gacgacctag aacaacttag gggaaggca tctggtaagc tcgcatctaa acacctttat
1921 ataggtggtg atgatgaacc acaagaaaaa aagcggaaag ctgccccaaa gatgaagaaa
1981 gttattggaa ttattgagca cttaaaagca cctaacctta ctaacgttaa caaaatttct
2041 aatatatttg aagatgtaga gttttgtgtt atgagtggaa cagatagcca gccaaagcct
2101 gacctggaga acagaattgc agaatttggt ggttatatag tacaaaatcc aggcccagac
2161 acgtactgtg taattgcagg gtctgagaac atcagagtga aaaacataat tttgtcaaat
2221 aaacatgatg ttgtcaagcc tgcatggctt ttagaatgtt ttaagaccaa aagctttgta
2281 ccatggcagc ctcgctttat gattcatatg tgcccatcaa ccaaagaaca ttttgcccgt
2341 gaatatgatt gctatggtga tagttatttc attgatacag acttgaacca actgaaggaa
2401 gtattctcag gaattaaaaa ttctaacgag cagactcctg aagaaatggc ttctctgatt
2461 gctgatttag aatatcggta ttcctgggat tgctctcctc tcagtatgtt tcgacgccac
2521 accgtttatt tggactcgta tgctgttatt aatgacctga gtaccaaaaa tgaggggaca
2581 aggttagcta ttaaagcctt ggagcttcgg tttcatggag caaaagtagt ttcttgttta
2641 gctgagggag tgtctcatgt aataattggg gaagatcata gtcgtgttgc agattttaaa
2701 gcttttagaa gaacttttaa gagaaagttt aaaatcctaa aagaaagttg ggtaactgat
2761 tcaatagaca agtgtgaatt acaagaagaa aaccagtatt tgatttaaag ctaggtttcc
2821 tagtgaggaa agcctctgat ctggcagact cattgcagca ggtggtaatg ataaaatact
2881 aaactacatt ttatttttgt atcttaaaaa tctatgccta aaaagtatca ttacatatag
2941 gaaaacaata attttaactt ttaaggttga aaagacaata gcccaaagcc aagaaagaaa
3001 aattatcttg aatgtagtat tcaatgattt tttatgatca aggtgaaata aacagtctaa
3061 agaagaggtg tttttataat atccatatag aaatctagaa tttttactta gatactaata
3121 aaatacattt agaaactttt aaagtcatga aaaagcatta accttctaaa cagtatattc
3181 taaaaagtca aaacgttaac aatagttttt atctaataaa agcactgcaa gaaaataggg
3241 tagaattgtt acagctggac ttgtaaaaat atgtcttttt actcagggtt taaaatgtcc
3301 catttaaata tgaaatgtaa acaaatttgt tttttaaggt taaggccaaa tgtaacaata
3361 aaaccctgtc gatggtttta gctaaattag aggaagttgt atgagactta atgatctaaa
3421 aacttaaaat tgaattggtt tgattaaaaa taaagcttgc aattttaaaa gtagctcaca
```

TABLE 1-continued

```
3481 tttaatttct tgtgtgaaat agaacatgct ttaaaggaag tatttttatg tgaatttgca
3541 ttccagtata aatagtattc acaaaaaaga ttttcctaga ttttatctat tgaataggtg
3601 tcaatatggc atgcatattg taactttcat tagaaataag ttgctttgac ttttaaaaat
3661 gacatagtta gattatttaa agtcaatgta tatagtatat attatgtatg gatttatata
3721 ccaaattttg gaatacagcc tatctcatga ccatattgaa atgtacggaa tttgatccat
3781 gcgatactat gtgtgcatta tttgaaagtt attggaaatt ttattcaaac cgtggaacaa
3841 atgtatgtga ttttgttata cttcttaatt taaataaaat atttaatgca ctattaaaaa
3901 aaaaaaaaaa aaaa
```

SEQ ID NO: 45 Human LIG4 Transcript Variant 5 cDNA Sequence
(NM_001352598.1; CDS: 653-3388)

```
   1 gccagtgagc ccccgcgacg gtggcccgga cggaaaagat acctcggcgg cgtgggcccg
  61 gctccctgct ccaggaccta gggatcttgg ccttccaccc tcctccgagc accaggactc
 121 cctccagttc cgtacccgag gcctccgtgg tgaagaggtg ccggacccga tgagctcggg
 181 agtccaccat cgctctgcaa gccgcagaga gcatctgctg ccgaggccaa taggagccgt
 241 gtgtactcaa gaccctaacc aggatcctgc aggtcccgcc tccgcagccc cacggggctg
 301 ccggcccccc cacctcccat cgcgagcctg gctgcgccgg cgtgcttgag cccggtgact
 361 gcaaggcccc gggtctcccc tgcgcctgcg cggcgagcag ctggcggaac cggcatcttc
 421 tggcgccagc ttccggctta gcggctgagc ttcaggcttg acgtcagacc caagccccag
 481 gtcgtgggac gatttctccc gtttttgact ccctggaact gtattgcctg ctttacctgc
 541 gtacatgttg attctttctc atggcaaccc cgcaggaaac catcaagatc tcattttaca
 601 gctgggattc tctggttcac agagttaaac gagaagattc atcaccgctt tgatggctgc
 661 ctcacaaact tcacaaactg ttgcatctca cgttcctttt gcagatttgt gttcaacttt
 721 agaacgaata cagaaaagta aaggacgtgc agaaaaaatc agacacttca gggaattttt
 781 agattcttgg agaaaatttc atgatgctct tcataagaac cacaaagatg tcacagactc
 841 tttttatcca gcaatgagac taattcttcc tcagctagaa agagagagaa tggcctatgg
 901 aattaaagaa actatgcttg ctaagcttta tattgagttg cttaatttac ctagagatgg
 961 aaaagatgcc ctcaaacttt taaactacag aacacccact ggaactcatg gagatgctgg
1021 agactttgca atgattgcat attttgtgtt gaagccaaga tgtttacaga aaggaagttt
1081 aaccatacag caagtaaacg accttttaga ctcaattgcc agcaataatt ctgctaaaag
1141 aaaagaccta ataaaaaaga gccttcttca acttataact cagagttcag cacttgagca
1201 aaagtggctt atacggatga tcataaagga tttaaagctt ggtgttagtc agcaaactat
1261 ctttttctgtt tttcataatg atgctgctga gttgcataat gtcactacag atctggaaaa
1321 agtctgtagg caactgcatg atccttctgt aggactcagt gatatttcta tcactttatt
1381 ttctgcattt aaaccaatgc tagctgctat tgcagatatt gagcacattg agaaggatat
1441 gaaacatcag agtttctaca tagaaaccaa gctagatggt gaacgtatgc aaatgcacaa
1501 agatggagat gtatataaat acttctctcg aaatggatat aactacactg atcagtttgg
1561 tgcttctcct actgaaggtt ctcttacccc attcattcat aatgcattca aagcagatat
1621 acaaatctgt attcttgatg gtgagatgat ggcctataat cctaatacac aaactttcat
1681 gcaaaaggga actaagtttg atattaaaag aatggtagag gattctgatc tgcaaacttg
1741 ttattgtgtt tttgatgtat tgatggttaa taataaaaag ctagggcatg agactctgag
1801 aaagaggtat gagattctta gtagtatttt tacaccaatt ccaggtagaa tagaaatagt
1861 gcagaaaaca caagctcata ctaagaatga agtaattgat gcattgaatg aagcaataga
1921 taaaagagaa gagggaatta tggtaaaaca acctctatcc atctacaagc cagacaaaag
1981 aggtgaaggg tggttaaaaa ttaaaccaga gtatgtcagt ggactaatgg atgaattgga
2041 cattttaatt gttggaggat attggggtaa aggatcacgg ggtggaatga tgtctcattt
2101 tctgtgtgca gtagcagaga agccccctcc tggtgagaag ccatctgtgt ttcatactct
2161 ctctcgtgtt gggtctggct gcaccatgaa agaactgtat gatctgggtt tgaaattggc
2221 caagtattgg aagcctttttc atagaaaagc tccaccaagc agcattttat gtggaacaga
2281 gaagccagaa gtatacattg aaccttgtaa ttctgtcatt gttcagatta aagcagcaga
2341 gatcgtaccc agtgatatgt ataaaactgg ctgcaccttg cgttttccac gaattgaaaa
2401 gataagagat gacaaggagt ggcatgagtg catgaccctg gacgacctag aacaacttag
2461 ggggaaggca tctggtaagc tcgcatctaa acacctttat ataggtggtg atgatgaacc
2521 acaagaaaaa aagcggaaag ctgccccaaa gatgaagaaa gttattggaa ttattgagca
2581 cttaaaagca cctaacctta ctaacgttaa caaaatttct aatatatttg aagatgtaga
2641 gtttttgtgtt atgagtggaa cagatagcca gccaaagcct gacctggaga acagaattgc
2701 agaatttggt ggttatatag tacaaaatcc aggcccagac acgtactgtg taattgcagg
2761 gtctgagaac atcagagtga aaaacataat tttgtcaaat aaacatgatg ttgtcaagcc
2821 tgcatggctt ttagaatgtt ttaagaccaa aagctttgta ccatggcagc ctcgctttat
2881 gattcatatg tgcccatcaa ccaaagaaca ttttgcccgt gaatatgatt gctatggtga
2941 tagttatttc attgatacag acttgaacca actgaaggaa gtattctcag gaattaaaaa
3001 ttctaacgag cagactcctg aagaaatggc ttctctgatt gctgatttag aatatcggta
3061 ttcctgggat tgctctcctc tcagtatgtt tcgacgccac accgtttatt tggactcgta
3121 tgctgttatt aatgacctga gtaccaaaaa tgagggggaca aggttagcta ttaaagcctt
3181 ggagcttcgg tttcatggag caaaagtagt ttcttgttta gctgagggag tgtctcatgt
3241 aataattggg gaagatcata gtcgtgttgc agattttaaa gcttttagaa gaacttttaa
3301 gagaaagttt aaaatcctaa aagaaagttg ggtaactgat tcaatagaca agtgtgaatt
3361 acaagaagaa aaccagtatt tgatttaaag ctaggtttcc tagtgaggaa agcctctgat
3421 ctggcagact cattgcagca ggtggtaatg ataaaatact aaactacatt ttattttttgt
3481 atcttaaaaa tctatgccta aaaagtatca ttacatatag gaaaacaata attttaactt
3541 ttaaggttga aaagacaata gcccaaagcc aagaaagaaa aattatcttg aatgtagtat
3601 tcaatgattt tttatgatca aggtgaaata aacagtctaa agaagaggtg tttttataat
3661 atccatatag aaatctagaa tttttactta gatactaata aaatacattt agaaactttt
3721 aaagtcatga aaaagcatta accttctaaa cagtatattc taaaaagtca aaacgttaac
3781 aatagttttt atctaataaa agcactgcaa gaaaataggg tagaattgtt acagctggac
3841 ttgtaaaaat atgtcttttt actcagggtt taaaatgtcc catttaaata tgaaatgtaa
3901 acaaatttgt tttttaaggt taaggccaaa tgtaacaata aaaccctgtc gatggtttta
3961 gctaaattag aggaagttgt atgagactta atgatctaaa aacttaaaat tgaattggtt
4021 tgattaaaaa taaagcttgc aattttaaaa gtagctcaca tttaatttct tgtgtgaaat
4081 agaacatgct ttaaaggaag tatttttatg tgaatttgca ttccagtata aatagtattc
```

TABLE 1-continued 4141 acaaaaaaga ttttcctaga ttttatctat tgaataggtg tcaatatggc atgcatattg
4201 taactttcat tagaaataag ttgctttgac ttttaaaaat gacatagtta gattatttaa
4261 agtcaatgta tatagtatat attatgtatg gatttatata ccaaattttg gaatacagcc
4321 tatctcatga ccatattgaa atgtacggaa tttgatccat gcgatactat gtgtgcatta
4381 tttgaaagtt attggaaatt ttattcaaac cgtggaacaa atgtatgtga ttttgttata
4441 cttcttaatt taaataaaat atttaatgca ctattaaaa SEQ ID NO: 46 Human LIG4 Transcript Variant 6 cDNA Sequence
(NM_001352599.1; CDS: 677-3412)
1 gccagtgagc ccccgcgacg gtggcccgga cggaaaagat acctcggcgg cgtgggcccg
61 gctccctgct ccaggaccta gggatcttgg ccttccaccc tcctccgagc accaggactc
121 cctccagttc cgtacccgag gcctccgtgg tgaagaggtg ccggacccga tgagctcggg
181 agtccaccat cgctctgcaa gccgcagaga gcatctgctg ccgaggccaa taggagccgt
241 gtgtactcaa gaccctaacc aggatcctgc aggtcccgcc tccgcagccc cacggggctg
301 ccggcccccc cacctcccat cgcgagcctg gctgcgccgg cgtgcttgag cccggtgact
361 gcaaggcccc gggtctcccc tgcgcctgcg cggcgagcag ctggcggaac cggcatcttc
421 tggcgccagc ttccggctta gcggctgagc ttcaggcttg acgtcagacc caagccccag
481 gtcgtgggac gatttctccc gtttttgact ccctggaact gtattgcctg ctttacctgc
541 gtacatgttg attctttctc atggcaaccc cgcaggaaac catcaagatc tcattttaca
601 gctgggattc tctggttcac agaggtaacg gagcttgccc gaggccagtt aaacgagaag
661 attcatcacc gctttgatgg ctgcctcaca aacttcacaa actgttgcat ctcacgttcc
721 ttttgcagat ttgtgttcaa ctttagaacg aatacagaaa agtaaaggac gtgcagaaaa
781 aatcagacac ttcagggaat ttttagattc ttggagaaaa tttcatgatg ctcttcataa
841 gaaccacaaa gatgtcacag actcttttta tccagcaatg agactaattc ttcctcagct
901 agaaagagag agaatggcct atggaattaa agaaactatg cttgctaagc tttatattga
961 gttgcttaat ttacctagag atggaaaaga tgccctcaaa cttttaaact acagaacacc
1021 cactggaact catggagatg ctggagactt tgcaatgatt gcatattttg tgttgaagcc
1081 aagatgttta cagaaaggaa gtttaaccat acagcaagta aacgaccttt tagactcaat
1141 tgccagcaat aattctgcta aaagaaaaga cctaataaaa aagagccttc ttcaacttat
1201 aactcagagt tcagcacttg agcaaaagtg gcttatacgg atgatcataa aggatttaaa
1261 gcttggtgtt agtcagcaaa ctatcttttc tgtttttcat aatgatgctg ctgagttgca
1321 taatgtcact acagatctgg aaaaagtctg taggcaactg catgatcctt ctgtaggact
1381 cagtgatatt tctatcactt tattttctgc atttaaacca atgctagctg ctattgcaga
1441 tattgagcac attgagaagg atatgaaaca tcagagtttc tacatagaaa ccaagctaga
1501 tggtgaacgt atgcaaatgc acaaagatgg agatgtatat aaatacttct ctcgaaatgg
1561 atataactac actgatcagt ttggtgcttc tcctactgaa ggttctctta ccccattcat
1621 tcataatgca ttcaaagcag atatacaaat ctgtattctt gatggtgaga tgatggccta
1681 taatcctaat acacaaactt tcatgcaaaa gggaactaag tttgatatta aaagaatggt
1741 agaggattct gatctgcaaa cttgttattg tgtttttgat gtattgatgg ttaataataa
1801 aaagctaggg catgagactc tgagaaagag gtatgagatt cttagtagta tttttacacc
1861 aattccaggt agaatagaaa tagtgcagaa aacacaagct catactaaga atgaagtaat
1921 tgatgcattg aatgaagcaa tagataaaag agaagaggga attatggtaa aacaacctct
1981 atccatctac aagccagaca aaagaggtga agggtggtta aaaattaaac cagagtatgt
2041 cagtggacta atggatgaat tggacatttt aattgttgga ggatattggg gtaaaggatc
2101 acggggtgga atgatgtctc attttctgtg tgcagtagca gagaagcccc ctcctggtga
2161 gaagccatct gtgtttcata ctctctctcg tgttgggtct ggctgcacca tgaaagaact
2221 gtatgatctg ggtttgaaat tggccaagta ttggaagcct tttcatagaa aagctccacc
2281 aagcagcatt ttatgtggaa cagagaagcc agaagtatac attgaacctt gtaattctgt
2341 cattgttcag attaaagcag cagagatcgt acccagtgat atgtataaaa ctggctgcac
2401 cttgcgtttt ccacgaattg aaaagataag agatgacaag gagtggcatg agtgcatgac
2461 cctggacgac ctagaacaac ttaggggaa ggcatctggt aagctcgcat ctaaacacct
2521 ttatataggt ggtgatgatg aaccacaaga aaaaaagcgg aaagctgccc caaagatgaa
2581 gaaagttatt ggaattattg agcacttaaa agcacctaac cttactaacg ttaacaaaat
2641 ttctaatata tttgaagatg tagagttttg tgttatgagt ggaacagata gccagccaaa
2701 gcctgacctg gagaacagaa ttgcagaatt tggtggttat atagtacaaa atccaggccc
2761 agacacgtac tgtgtaattg cagggtctga gaacatcaga gtgaaaaaca taattttgtc
2821 aaataaacat gatgttgtca agcctgcatg gcttttagaa tgttttaaga ccaaaagctt
2881 tgtaccatgg cagcctcgct ttatgattca tatgtgccca tcaaccaaag aacattttgc
2941 ccgtgaatat gattgctatg gtgatagtta tttcattgat acagacttga accaactgaa
3001 ggaagtattc tcaggaatta aaaattctaa cgagcagact cctgaagaaa tggcttctct
3061 gattgctgat ttagaatatc ggtattcctg ggattgctct cctctcagta tgtttcgacg
3121 ccacaccgtt tatttggact cgtatgctgt tattaatgac ctgagtacca aaaatgaggg
3181 gacaaggtta gctattaaag ccttggagct tcggtttcat ggagcaaaag tagtttcttg
3241 tttagctgag ggagtgtctc atgtaataat tggggaagat catagtcgtg ttgcagattt
3301 taaagctttt agaagaactt ttaagagaaa gtttaaaatc ctaaaagaaa gttgggtaac
3361 tgattcaata gacaagtgtg aattacaaga agaaaaccag tatttgattt aaagctaggt
3421 ttcctagtga ggaaagcctc tgatctggca gactcattgc agcaggtggt aatgataaaa
3481 tactaaacta cattttattt ttgtatctta aaaatctatg cctaaaaagt atcattacat
3541 ataggaaaac aataatttta acttttaagg ttgaaaagac aatagcccaa agccaagaaa
3601 gaaaaattat cttgaatgta gtattcaatg atttttatg atcaaggtga aataaacagt
3661 ctaaagaaga ggtgttttta taatatccat atagaaatct agaattttta cttagatact
3721 aataaaatac atttagaaac ttttaaagtc atgaaaaagc attaaccttc taaacagtat
3781 attctaaaaa gtcaaaacgt taacaatagt ttttatctaa taaaagcact gcaagaaaat
3841 agggtagaat tgttacagct ggacttgtaa aaatatgtct ttttactcag ggtttaaaat
3901 gtcccattta aatatgaaat gtaaacaaat ttgtttttta aggttaaggc caaatgtaac
3961 aataaaaccc tgtcgatggt tttagctaaa ttagaggaag ttgtatgaga cttaatgatc
4021 taaaaactta aaattgaatt ggtttgatta aaaataaagc ttgcaatttt aaaagtagct
4081 cacatttaat ttcttgtgtg aaatagaaca tgctttaaag gaagtatttt tatgtgaatt
4141 tgcattccag tataaatagt attcacaaaa aagattttcc tagattttat ctattgaata
4201 ggtgtcaata tggcatgcat attgtaactt tcattagaaa taagttgctt tgacttttaa TABLE 1-continued 4261 aaatgacata gttagattat ttaaagtcaa tgtatatagt atatattatg tatggattta
4321 tataccaaat tttggaatac agcctatctc atgaccatat tgaaatgtac ggaatttgat
4381 ccatgcgata ctatgtgtgc attatttgaa agttattgga aattttattc aaaccgtgga
4441 acaaatgtat gtgattttgt tatacttctt aatttaaata aaatatttaa tgcactatta
4501 aaa SEQ ID NO: 47 Human LIG4 Transcript Variant 7 cDNA Sequence
(NM_001352600.1; CDS: 569-3304)
1 gccagtgagc ccccgcgacg gtggcccgga cggaaaagat acctcggcgg cgtgggcccg
61 gctccctgct ccaggaccta gggatcttgg ccttccaccc tcctccgagc accaggactc
121 cctccagttc cgtacccgag gcctccgtgg tgaagaggtg ccggacccga tgagctcggg
181 agtccaccat cgctctgcaa gccgcagaga gcatctgctg ccgaggccaa taggagccgt
241 gtgtactcaa gaccctaacc aggatcctgc aggtcccgcc tccgcagccc cacggggctg
301 ccggcccccc cacctcccat cgcgagcctg gctgcgccgg cgtgcttgag cccggtgact
361 gcaaggcccc gggtctcccc tgcgcctgcg cggcgagcag ctggcggaac cggcatcttc
421 tggcgccagc ttccggctta gcggctgagc ttcaggcttg acgtcaggaa accatcaaga
481 tctcatttta cagctgggat tctctggttc acagaggtaa cggagcttgc ccgaggccag
541 ttaaacgaga agattcatca ccgctttgat ggctgcctca caaacttcac aaactgttgc
601 atctcacgtt ccttttgcag atttgtgttc aactttagaa cgaatacaga aaagtaaagg
661 acgtgcagaa aaaatcagac acttcaggga atttttagat tcttggagaa aatttcatga
721 tgctcttcat aagaaccaca aagatgtcac agactctttt tatccagcaa tgagactaat
781 tcttcctcag ctagaaagag agagaatggc ctatggaatt aaagaaacta tgcttgctaa
841 gctttatatt gagttgctta atttacctag agatggaaaa gatgccctca aacttttaaa
901 ctacagaaca cccactggaa ctcatggaga tgctggagac tttgcaatga ttgcatattt
961 tgtgttgaag ccaagatgtt tacagaaagg aagtttaacc atacagcaag taaacgacct
1021 tttagactca attgccagca ataattctgc taaaagaaaa gacctaataa aaaagagcct
1081 tcttcaactt ataactcaga gttcagcact tgagcaaaag tggcttatac ggatgatcat
1141 aaaggattta aagcttggtg ttagtcagca aactatcttt tctgtttttc ataatgatgc
1201 tgctgagttg cataatgtca ctacagatct ggaaaaagtc tgtaggcaac tgcatgatcc
1261 ttctgtagga ctcagtgata tttctatcac tttattttct gcatttaaac caatgctagc
1321 tgctattgca gatattgagc acattgagaa ggatatgaaa catcagagtt tctacataga
1381 aaccaagcta gatggtgaac gtatgcaaat gcacaaagat ggagatgtat ataaatactt
1441 ctctcgaaat ggatataact acactgatca gtttggtgct tctcctactg aaggttctct
1501 taccccattc attcataatg cattcaaagc agatatacaa atctgtattc ttgatggtga
1561 gatgatggcc tataatccta atacacaaac tttcatgcaa aagggaacta agtttgatat
1621 taaaagaatg gtagaggatt ctgatctgca aacttgttat tgtgtttttg atgtattgat
1681 ggttaataat aaaaagctag ggcatgagac tctgagaaag aggtatgaga ttcttagtag
1741 tatttttaca ccaattccag gtagaataga aatagtgcag aaaacacaag ctcatactaa
1801 gaatgaagta attgatgcat tgaatgaagc aatagataaa agagaagagg gaattatggt
1861 aaaacaacct ctatccatct acaagccaga caaaagaggt gaagggtggt taaaaattaa
1921 accagagtat gtcagtggac taatggatga attggacatt ttaattgttg gaggatattg
1981 gggtaaagga tcacggggtg gaatgatgtc tcattttctg tgtgcagtag cagagaagcc
2041 ccctcctggt gagaagccat ctgtgtttca tactctctct cgtgttgggt ctggctgcac
2101 catgaaagaa ctgtatgatc tgggtttgaa attggccaag tattggaagc cttttcatag
2161 aaaagctcca ccaagcagca ttttatgtgg aacagagaag ccagaagtat acattgaacc
2221 ttgtaattct gtcattgttc agattaaagc agcagagatc gtacccagtg atatgtataa
2281 aactggctgc accttgcgtt ttccacgaat tgaaaagata agagatgaca aggagtggca
2341 tgagtgcatg accctggacg acctagaaca acttaggggg aaggcatctg gtaagctcgc
2401 atctaaacac ctttatatag gtggtgatga tgaaccacaa gaaaaaaagc ggaaagctgc
2461 cccaaagatg aagaaagtta ttggaattat tgagcactta aaagcaccta accttactaa
2521 cgttaacaaa atttctaata tatttgaaga tgtagagttt tgtgttatga gtggaacaga
2581 tagccagcca aagcctgacc tggagaacag aattgcagaa tttggtggtt atatagtaca
2641 aaatccaggc ccagacacgt actgtgtaat tgcagggtct gagaacatca gagtgaaaaa
2701 cataattttg tcaaataaac atgatgttgt caagcctgca tggcttttag aatgttttaa
2761 gaccaaaagc tttgtaccat ggcagcctcg ctttatgatt catatgtgcc catcaaccaa
2821 agaacatttt gcccgtgaat atgattgcta tggtgatagt tatttcattg atacagactt
2881 gaaccaactg aaggaagtat tctcaggaat taaaaattct aacgagcaga ctcctgaaga
2941 aatggcttct ctgattgctg atttagaata tcggtattcc tgggattgct ctcctctcag
3001 tatgtttcga cgccacaccg tttatttgga ctcgtatgct gttattaatg acctgagtac
3061 caaaaatgag gggacaaggt tagctattaa agccttggag cttcggtttc atggagcaaa
3121 agtagtttct tgtttagctg agggagtgtc tcatgtaata attggggaag atcatagtcg
3181 tgttgcagat tttaaagctt ttagaagaac ttttaagaga aagtttaaaa tcctaaaaga
3241 aagttgggta actgattcaa tagacaagtg tgaattacaa gaagaaaacc agtatttgat
3301 ttaaagctag gtttcctagt gaggaaagcc tctgatctgg cagactcatt gcagcaggtg
3361 gtaatgataa aatactaaac tacattttat ttttgtatct taaaaatcta tgcctaaaaa
3421 gtatcattac atataggaaa acaataattt taacttttaa ggttgaaaag acaatagccc
3481 aaagccaaga aagaaaaatt atcttgaatg tagtattcaa tgatttttta tgatcaaggt
3541 gaaataaaca gtctaaagaa gaggtgtttt tataatatcc atatagaaat ctagaatttt
3601 tacttagata ctaataaaat acatttagaa acttttaaag tcatgaaaaa gcattaacct
3661 tctaaacagt atattctaaa aagtcaaaac gttaacaata gtttttatct aataaaagca
3721 ctgcaagaaa atagggtaga attgttacag ctggacttgt aaaaatatgt ctttttactc
3781 agggtttaaa atgtcccatt taaatatgaa atgtaaacaa atttgttttt taaggttaag
3841 gccaaatgta acaataaaac cctgtcgatg gttttagcta aattagagga agttgtatga
3901 gacttaatga tctaaaaact taaaattgaa ttggtttgat taaaaataaa gcttgcaatt
3961 ttaaaagtag ctcacattta atttcttgtg tgaaatagaa catgctttaa aggaagtatt
4021 tttatgtgaa tttgcattcc agtataaata gtattcacaa aaaagatttt cctagatttt
4081 atctattgaa taggtgtcaa tatggcatgc atattgtaac tttcattaga aataagttgc
4141 tttgactttt aaaaatgaca tagttagatt atttaaagtc aatgtatata gtatatatta
4201 tgtatggatt tatataccaa attttggaat acagcctatc tcatgaccat attgaaatgt
4261 acggaatttg atccatgcga tactatgtgt gcattatttg aaagttattg gaaattttat TABLE 1-continued

```
4321 tcaaaccgtg gaacaaatgt atgtgatttt gttatacttc ttaatttaaa taaaatattt
4381 aatgcactat taaaa
```

SEQ ID NO: 48 Human LIG4 Transcript Variant 8 cDNA Sequence
(NM_001352601.1; CDS: 288-3023)

```
   1 gacggtgtgg ggggagtcaa gtggaaggtg tggtccagca ggcggcgaga agtctgtggg
  61 gcaacagacc gggggaagac ccaagcccca ggtcgtggga cgatttctcc cgtttttgac
 121 tccctggaac tgtattgcct gctttacctg cgtacatgtt gattctttct catggcaacc
 181 ccgcaggaaa ccatcaagat ctcattttac agctgggatt ctctggttca cagaggtaac
 241 ggagcttgcc cgaggccagt taaacgagaa gattcatcac cgctttgatg gctgcctcac
 301 aaacttcaca aactgttgca tctcacgttc cttttgcaga tttgtgttca actttagaac
 361 gaatacagaa aagtaaagga cgtgcagaaa aaatcagaca cttcagggaa tttttagatt
 421 cttggagaaa atttcatgat gctcttcata agaaccacaa agatgtcaca gactcttttt
 481 atccagcaat gagactaatt cttcctcagc tagaaagaga gagaatggcc tatggaatta
 541 aagaaactat gcttgctaag ctttatattg agttgcttaa tttacctaga gatggaaaag
 601 atgccctcaa acttttaaac tacagaacac ccactggaac tcatggagat gctggagact
 661 ttgcaatgat tgcatatttt gtgttgaagc caagatgttt acagaaagga agtttaacca
 721 tacagcaagt aaacgacctt ttagactcaa ttgccagcaa taattctgct aaaagaaaag
 781 acctaataaa aaagagcctt cttcaactta taactcagag ttcagcactt gagcaaaagt
 841 ggcttatacg gatgatcata aaggatttaa agcttggtgt tagtcagcaa actatctttt
 901 ctgtttttca taatgatgct gctgagttgc ataatgtcac tacagatctg gaaaaagtct
 961 gtaggcaact gcatgatcct tctgtaggac tcagtgatat ttctatcact ttattttctg
1021 catttaaacc aatgctagct gctattgcag atattgagca cattgagaag gatatgaaac
1081 atcagagttt ctacatagaa accaagctag atggtgaacg tatgcaaatg cacaaagatg
1141 gagatgtata taaatacttc tctcgaaatg gatataacta cactgatcag tttggtgctt
1201 ctcctactga aggttctctt accccattca ttcataatgc attcaaagca gatatacaaa
1261 tctgtattct tgatggtgag atgatggcct ataatcctaa tacacaaact ttcatgcaaa
1321 agggaactaa gtttgatatt aaaagaatgg tagaggattc tgatctgcaa acttgttatt
1381 gtgtttttga tgtattgatg gttaataata aaaagctagg gcatgagact ctgagaaaga
1441 ggtatgagat tcttagtagt atttttacac caattccagg tagaatagaa atagtgcaga
1501 aaacacaagc tcatactaag aatgaagtaa ttgatgcatt gaatgaagca atagataaaa
1561 gagaagaggg aattatggta aaacaacctc tatccatcta caagccagac aaaagaggtg
1621 aagggtggtt aaaaattaaa ccagagtatg tcagtggact aatggatgaa ttggacattt
1681 taattgttgg aggatattgg ggtaaaggat cacggggtgg aatgatgtct cattttctgt
1741 gtgcagtagc agagaagccc cctcctggtg agaagccatc tgtgtttcat actctctctc
1801 gtgttgggtc tggctgcacc atgaaagaac tgtatgatct gggtttgaaa ttggccaagt
1861 attggaagcc ttttcataga aaagctccac caagcagcat tttatgtgga acagagaagc
1921 cagaagtata cattgaacct tgtaattctg tcattgttca gattaaagca gcagagatcg
1981 tacccagtga tatgtataaa actggctgca ccttgcgttt tccacgaatt gaaaagataa
2041 gagatgacaa ggagtggcat gagtgcatga ccctggacga cctagaacaa cttaggggga
2101 aggcatctgg taagctcgca tctaaacacc tttatatagg tggtgatgat gaaccacaag
2161 aaaaaaagcg gaaagctgcc ccaaagatga agaaagttat tggaattatt gagcacttaa
2221 aagcacctaa ccttactaac gttaacaaaa tttctaatat atttgaagat gtagagtttt
2281 gtgttatgag tggaacagat agccagccaa agcctgacct ggagaacaga attgcagaat
2341 ttggtggtta tatagtacaa aatccaggcc cagacacgta ctgtgtaatt gcagggtctg
2401 agaacatcag agtgaaaaac ataattttgt caaataaaca tgatgttgtc aagcctgcat
2461 ggcttttaga atgttttaag accaaaagct ttgtaccatg gcagcctcgc tttatgattc
2521 atatgtgccc atcaaccaaa gaacattttg cccgtgaata tgattgctat ggtgatagtt
2581 atttcattga tacagacttg aaccaactga aggaagtatt ctcaggaatt aaaaattcta
2641 acgagcagac tcctgaagaa atggcttctc tgattgctga tttagaatat cggtattcct
2701 gggattgctc tcctctcagt atgtttcgac gccacaccgt ttatttggac tcgtatgctg
2761 ttattaatga cctgagtacc aaaaatgagg ggacaaggtt agctattaaa gccttggagc
2821 ttcggtttca tggagcaaaa gtagtttctt gtttagctga gggagtgtct catgtaataa
2881 ttggggaaga tcatagtcgt gttgcagatt ttaaagcttt tagaagaact tttaagagaa
2941 agtttaaaat cctaaaagaa agttgggtaa ctgattcaat agacaagtgt gaattacaag
3001 aagaaaacca gtatttgatt taaagctagg tttcctagtg aggaaagcct ctgatctggc
3061 agactcattg cagcaggtgg taatgataaa atactaaact acattttatt tttgtatctt
3121 aaaaatctat gcctaaaaag tatcattaca tataggaaaa caataatttt aactttttaag
3181 gttgaaaaga caatagccca aagccaagaa agaaaaatta tcttgaatgt agtattcaat
3241 gatttttat gatcaaggtg aaataaacag tctaaagaag aggtgttttt ataatatcca
3301 tatagaaatc tagaattttt acttagatac taataaaata catttagaaa cttttaaagt
3361 catgaaaaag cattaacctt ctaaacagta tattctaaaa agtcaaaacg ttaacaatag
3421 tttttatcta ataaaagcac tgcaagaaaa tagggtagaa ttgttacagc tggacttgta
3481 aaaatatgtc tttttactca gggtttaaaa tgtcccattt aaatatgaaa tgtaaacaaa
3541 tttgtttttt aaggttaagg ccaaatgtaa caataaaacc ctgtcgatgg ttttagctaa
3601 attagaggaa gttgtatgag acttaatgat ctaaaaactt aaaattgaat tggtttgatt
3661 aaaaataaag cttgcaattt taaaagtagc tcacatttaa tttcttgtgt gaaatagaac
3721 atgctttaaa ggaagtattt ttatgtgaat ttgcattcca gtataaatag tattcacaaa
3781 aaagattttc ctagatttta tctattgaat aggtgtcaat atggcatgca tattgtaact
3841 ttcattagaa ataagttgct ttgactttta aaaatgacat agttagatta tttaaagtca
3901 atgtatatag tatatattat gtatggattt atataccaaa ttttggaata cagcctatct
3961 catgaccata ttgaaatgta cggaatttga tccatgcgat actatgtgtg cattatttga
4021 aagttattgg aaattttatt caaaccgtgg aacaaatgta tgtgattttg ttatacttct
4081 taatttaaat aaaatattta atgcactatt aaaa
```

SEQ ID NO: 49 Human LIG4 Transcript Variant 9 cDNA Sequence
(NM_001352602.1; CDS: 180-2915)

```
   1 gacggtgtgg ggggagtcaa gtggaaggtg tggtccagca ggcggcgaga agtctgtggg
  61 gcaacagacc gggggaagga aaccatcaag atctcatttt acagctggga ttctctggtt
 121 cacagaggta acggagcttg cccgaggcca gttaaacgag aagattcatc accgctttga
```

TABLE 1-continued 181 tggctgcctc acaaacttca caaactgttg catctcacgt tcctttttgca gatttgtgtt
241 caactttaga acgaatacag aaaagtaaag gacgtgcaga aaaaatcaga cacttcaggg
301 aatttttaga ttcttggaga aaatttcatg atgctcttca taagaaccac aaagatgtca
361 cagactcttt ttatccagca atgagactaa ttcttcctca gctagaaaga gagagaatgg
421 cctatggaat taaagaaact atgcttgcta agctttatat tgagttgctt aatttaccta
481 gagatggaaa agatgccctc aaacttttaa actacagaac acccactgga actcatggag
541 atgctggaga ctttgcaatg attgcatatt ttgtgttgaa gccaagatgt ttacagaaag
601 gaagtttaac catacagcaa gtaaacgacc ttttagactc aattgccagc aataattctg
661 ctaaaagaaa agacctaata aaaaagagcc ttcttcaact tataactcag agttcagcac
721 ttgagcaaaa gtggcttata cggatgatca taaaggattt aaagcttggt gttagtcagc
781 aaactatctt ttctgttttt cataatgatg ctgctgagtt gcataatgtc actacagatc
841 tggaaaaagt ctgtaggcaa ctgcatgatc cttctgtagg actcagtgat atttctatca
901 ctttatttc tgcatttaaa ccaatgctag ctgctattgc agatattgag cacattgaga
961 aggatatgaa acatcagagt ttctacatag aaaccaagct agatggtgaa cgtatgcaaa
1021 tgcacaaaga tggagatgta tataaatact tctctcgaaa tggatataac tacactgatc
1081 agtttggtgc ttctcctact gaaggttctc ttaccccatt cattcataat gcattcaaag
1141 cagatataca aatctgtatt cttgatggtg agatgatggc ctataatcct aatacacaaa
1201 ctttcatgca aaagggaact aagtttgata ttaaaagaat ggtagaggat tctgatctgc
1261 aaacttgtta ttgtgttttt gatgtattga tggttaataa taaaaagcta gggcatgaga
1321 ctctgagaaa gaggtatgag attcttagta gtatttttac accaattcca ggtagaatag
1381 aaatagtgca gaaaacacaa gctcatacta agaatgaagt aattgatgca ttgaatgaag
1441 caatagataa aagagaagag ggaattatgg taaaacaacc tctatccatc tacaagccag
1501 acaaaagagg tgaagggtgg ttaaaaatta aaccagagta tgtcagtgga ctaatggatg
1561 aattggacat tttaattgtt ggaggatatt ggggtaaagg atcacggggt ggaatgatgt
1621 ctcattttct gtgtgcagta gcagagaagc cccctcctgg tgagaagcca tctgtgtttc
1681 atactctctc tcgtgttggg tctggctgca ccatgaaaga actgtatgat ctgggtttga
1741 aattggccaa gtattggaag ccttttcata gaaaagctcc accaagcagc attttatgtg
1801 gaacagagaa gccagaagta tacattgaac cttgtaattc tgtcattgtt cagattaaag
1861 cagcagagat cgtacccagt gatatgtata aaactggctg caccttgcgt tttccacgaa
1921 ttgaaaagat aagagatgac aaggagtggc atgagtgcat gaccctggac gacctagaac
1981 aacttagggg gaaggcatct ggtaagctcg catctaaaca cctttatata ggtggtgatg
2041 atgaaccaca agaaaaaaag cggaaagctg ccccaaagat gaagaaagtt attggaatta
2101 ttgagcactt aaaagcacct aaccttacta acgttaacaa aatttctaat atatttgaag
2161 atgtagagtt ttgtgttatg agtggaacag atagccagcc aaagcctgac ctggagaaca
2221 gaattgcaga atttggtggt tatatagtac aaaatccagg cccagacacg tactgtgtaa
2281 ttgcagggtc tgagaacatc agagtgaaaa acataatttt gtcaaataaa catgatgttg
2341 tcaagcctgc atggctttta gaatgtttta agaccaaaag ctttgtacca tggcagcctc
2401 gctttatgat tcatatgtgc ccatcaacca aagaacattt tgcccgtgaa tatgattgct
2461 atggtgatag ttatttcatt gatacagact tgaaccaact gaaggaagta ttctcaggaa
2521 ttaaaaattc taacgagcag actcctgaag aaatggcttc tctgattgct gatttagaat
2581 atcggtattc ctgggattgc tctcctctca gtatgtttcg acgccacacc gtttatttgg
2641 actcgtatgc tgttattaat gacctgagta ccaaaaatga ggggacaagg ttagctatta
2701 aagccttgga gcttcggttt catggagcaa aagtagtttc ttgtttagct gagggagtgt
2761 ctcatgtaat aattggggaa gatcatagtc gtgttgcaga ttttaaagct tttagaagaa
2821 cttttaagag aaagtttaaa atcctaaaag aaagttgggt aactgattca atagacaagt
2881 gtgaattaca agaagaaaac cagtatttga tttaaagcta ggtttcctag tgaggaaagc
2941 ctctgatctg gcagactcat tgcagcaggt ggtaatgata aaatactaaa ctacatttta
3001 tttttgtatc ttaaaaatct atgcctaaaa agtatcatta catataggaa aacaataatt
3061 ttaactttta aggttgaaaa gacaatagcc caaagccaag aaagaaaaat tatcttgaat
3121 gtagtattca atgatttttt atgatcaagg tgaaataaac agtctaaaga agaggtgttt
3181 ttataatatc catatagaaa tctagaattt ttacttagat actaataaaa tacatttaga
3241 aacttttaaa gtcatgaaaa agcattaacc ttctaaacag tatattctaa aaagtcaaaa
3301 cgttaacaat agtttttatc taataaaagc actgcaagaa aatagggtag aattgttaca
3361 gctggacttg taaaaatatg tctttttact cagggtttaa aatgtcccat ttaaatatga
3421 aatgtaaaca aatttgtttt ttaaggttaa ggccaaatgt aacaataaaa ccctgtcgat
3481 ggttttagct aaattagagg aagttgtatg agacttaatg atctaaaaac ttaaaattga
3541 attggtttga ttaaaaataa agcttgcaat tttaaaagta gctcacattt aatttcttgt
3601 gtgaaataga acatgcttta aaggaagtat ttttatgtga atttgcattc cagtataaat
3661 agtattcaca aaaaagattt tcctagattt tatctattga ataggtgtca atatggcatg
3721 catattgtaa ctttcattag aaataagttg ctttgacttt taaaaatgac atagttagat
3781 tatttaaagt caatgtatat agtatatatt atgtatggat ttatatacca aattttggaa
3841 tacagcctat ctcatgacca tattgaaatg tacggaattt gatccatgcg atactatgtg
3901 tgcattattt gaaagttatt ggaaatttta ttcaaaccgt ggaacaaatg tatgtgattt
3961 tgttatactt cttaatttaa ataaaatatt taatgcacta ttaaaa SEQ ID NO: 50 Human LIG4 Transcript Variant 10 cDNA Sequence
(NM_001352603.1; CDS: 129-2864)
1 ggggtatctg tgggacgtca ggttggggaa accatcaaga tctcatttta cagctgggat
61 tctctggttc acagaggtaa cggagcttgc ccgaggccag ttaaacgaga agattcatca
121 ccgctttgat ggctgcctca caaacttcac aaactgttgc atctcacgtt ccttttgcag
181 atttgtgttc aactttagaa cgaatacaga aaagtaaagg acgtgcagaa aaaatcagac
241 acttcaggga atttttagat tcttggagaa aatttcatga tgctcttcat aagaaccaca
301 aagatgtcac agactctttt tatccagcaa tgagactaat tcttcctcag ctagaaagag
361 agagaatggc ctatggaatt aaagaaacta tgcttgctaa gctttatatt gagttgctta
421 atttacctag agatggaaaa gatgccctca aacttttaaa ctacagaaca cccactggaa
481 ctcatggaga tgctggagac tttgcaatga ttgcatattt tgtgttgaag ccaagatgtt
541 tacagaaagg aagtttaacc atacagcaag taaacgacct tttagactca attgccagca
601 ataattctgc taaaagaaaa gacctaataa aaaagagcct tcttcaactt ataactcaga
661 gttcagcact tgagcaaaag tggcttatac ggatgatcat aaaggattta aagcttggtg
721 ttagtcagca aactatcttt tctgtttttc ataatgatgc tgctgagttg cataatgtca TABLE 1-continued

```
 781 ctacagatct ggaaaaagtc tgtaggcaac tgcatgatcc ttctgtagga ctcagtgata
 841 tttctatcac tttattttct gcatttaaac caatgctagc tgctattgca gatattgagc
 901 acattgagaa ggatatgaaa catcagagtt tctacataga aaccaagcta gatggtgaac
 961 gtatgcaaat gcacaaagat ggagatgtat ataaatactt ctctcgaaat ggatataact
1021 acactgatca gtttggtgct tctcctactg aaggttctct taccccattc attcataatg
1081 cattcaaagc agatatacaa atctgtattc ttgatggtga gatgatggcc tataatccta
1141 atacacaaac tttcatgcaa aagggaacta agtttgatat taaaagaatg gtagaggatt
1201 ctgatctgca aacttgttat tgtgtttttg atgtattgat ggttaataat aaaaagctag
1261 ggcatgagac tctgagaaag aggtatgaga ttcttagtag tatttttaca ccaattccag
1321 gtagaataga aatagtgcag aaaacacaag ctcatactaa gaatgaagta attgatgcat
1381 tgaatgaagc aatagataaa agagaagagg gaattatggt aaaacaacct ctatccatct
1441 acaagccaga caaaagaggt gaagggtggt taaaaattaa accagagtat gtcagtggac
1501 taatggatga attggacatt ttaattgttg gaggatattg ggtaaagga tcacggggtg
1561 gaatgatgtc tcattttctg tgtgcagtag cagagaagcc ccctcctggt gagaagccat
1621 ctgtgtttca tactctctct cgtgttgggt ctggctgcac catgaaagaa ctgtatgatc
1681 tgggtttgaa attggccaag tattggaagc cttttcatag aaaagctcca ccaagcagca
1741 ttttatgtgg aacagagaag ccagaagtat acattgaacc ttgtaattct gtcattgttc
1801 agattaaagc agcagagatc gtacccagtg atatgtataa aactggctgc accttgcgtt
1861 ttccacgaat tgaaaagata agagatgaca aggagtggca tgagtgcatg accctggacg
1921 acctagaaca acttaggggg aaggcatctg gtaagctcgc atctaaacac ctttatatag
1981 gtggtgatga tgaaccacaa gaaaaaaagc ggaaagctgc cccaaagatg aagaaagtta
2041 ttggaattat tgagcactta aaagcaccta accttactaa cgttaacaaa atttctaata
2101 tatttgaaga tgtagagttt tgtgttatga gtggaacaga tagccagcca aagcctgacc
2161 tggagaacag aattgcagaa tttggtggtt atatagtaca aaatccaggc ccagacacgt
2221 actgtgtaat tgcagggtct gagaacatca gagtgaaaaa cataattttg tcaaataaac
2281 atgatgttgt caagcctgca tggcttttag aatgttttaa gaccaaaagc tttgtaccat
2341 ggcagcctcg ctttatgatt catatgtgcc catcaaccaa agaacatttt gcccgtgaat
2401 atgattgcta tggtgatagt tatttcattg atacagactt gaaccaactg aaggaagtat
2461 tctcaggaat taaaaattct aacgagcaga ctcctgaaga aatggcttct ctgattgctg
2521 atttagaata tcggtattcc tgggattgct ctcctctcag tatgtttcga cgccacaccg
2581 tttatttgga ctcgtatgct gttattaatg acctgagtac caaaaatgag gggacaaggt
2641 tagctattaa agccttggag cttcggtttc atggagcaaa agtagtttct tgtttagctg
2701 agggagtgtc tcatgtaata attggggaag atcatagtcg tgttgcagat tttaaagctt
2761 ttagaagaac ttttaagaga aagtttaaaa tcctaaaaga aagttgggta actgattcaa
2821 tagacaagtg tgaattacaa gaagaaaacc agtatttgat ttaaagctag gtttcctagt
2881 gaggaaagcc tctgatctgg cagactcatt gcagcaggtg gtaatgataa aatactaaac
2941 tacattttat ttttgtatct taaaaatcta tgcctaaaaa gtatcattac atataggaaa
3001 acaataattt taactttttaa ggttgaaaag acaatagccc aaagccaaga aagaaaaatt
3061 atcttgaatg tagtattcaa tgattttta tgatcaaggt gaaataaaca gtctaaagaa
3121 gaggtgtttt tataatatcc atatagaaat ctagaatttt tacttagata ctaataaaat
3181 acatttagaa acttttaaag tcatgaaaaa gcattaacct tctaaacagt atattctaaa
3241 aagtcaaaac gttaacaata gtttttatct aataaaagca ctgcaagaaa atagggtaga
3301 attgttacag ctggacttgt aaaaatatgt ctttttactc agggtttaaa atgtcccatt
3361 taaatatgaa atgtaaacaa atttgttttt taaggttaag gccaaatgta acaataaaac
3421 cctgtcgatg gttttagcta aattagagga agttgtatga gacttaatga tctaaaaact
3481 taaaattgaa ttggtttgat taaaaataaa gcttgcaatt ttaaaagtag ctcacattta
3541 atttcttgtg tgaaatagaa catgctttaa aggaagtatt tttatgtgaa tttgcattcc
3601 agtataaata gtattcacaa aaaagatttt cctagatttt atctattgaa taggtgtcaa
3661 tatggcatgc atattgtaac tttcattaga aataagttgc tttgactttt aaaaatgaca
3721 tagttagatt atttaaagtc aatgtatata gtatatatta tgtatggatt tatataccaa
3781 attttggaat acagcctatc tcatgaccat attgaaatgt acggaatttg atccatgcga
3841 tactatgtgt gcattatttg aaagttattg gaaattttat tcaaaccgtg gaacaaatgt
3901 atgtgatttt gttatacttc ttaatttaaa taaaatattt aatgcactat taaaa
```

SEQ ID NO: 51 Human LIG4 Transcript Variant 11 cDNA Sequence
(NM_001352604.1; CDS: 172-2943)

```
   1 gacggtgtgg ggggagtcaa gtggaaggtg tggtccagca ggcggcgaga agtctgtggg
  61 gcaacagacc gggggaagac ccaagcccca ggtcgtggga cgatttctcc cgtttttgac
 121 tccctggaac tgtattgcct gctttacctg cgtacatgtt gattctttct catggcaacc
 181 ccgcaggaaa ccatcaagat ctcattttac agctgggatt ctctggttca cagaggtaac
 241 ggagcttgcc cgaggccaga tttgtgttca actttagaac gaatacagaa aagtaaagga
 301 cgtgcagaaa aaatcagaca cttcagggaa tttttagatt cttggagaaa atttcatgat
 361 gctcttcata agaaccacaa agatgtcaca gactcttttt atccagcaat gagactaatt
 421 cttcctcagc tagaaagaga gagaatggcc tatggaatta aagaaactat gcttgctaag
 481 ctttatattg agttgcttaa tttacctaga gatggaaaag atgccctcaa acttttaaac
 541 tacagaacac ccactggaac tcatggagat gctggagact ttgcaatgat tgcatatttt
 601 gtgttgaagc caagatgttt acagaaagga agtttaacca tacagcaagt aaacgacctt
 661 ttagactcaa ttgccagcaa taattctgct aaaagaaaag acctaataaa aaagagcctt
 721 cttcaactta taactcagag ttcagcactt gagcaaaagt ggcttatacg gatgatcata
 781 aaggatttaa agcttggtgt tagtcagcaa actatctttt ctgtttttca taatgatgct
 841 gctgagttgc ataatgtcac tacagatctg gaaaaagtct gtaggcaact gcatgatcct
 901 tctgtaggac tcagtgatat ttctatcact ttattttctg catttaaacc aatgctagct
 961 gctattgcag atattgagca cattgagaag gatatgaaac atcagagttt ctacatagaa
1021 accaagctag atggtgaacg tatgcaaatg cacaaagatg gagatgtata taaatacttc
1081 tctcgaaatg gatataacta cactgatcag tttggtgctt ctcctactga aggttctctt
1141 accccattca ttcataatgc attcaaagca gatatacaaa tctgtattct tgatggtgag
1201 atgatggcct ataatcctaa tacacaaact ttcatgcaaa agggaactaa gtttgatatt
1261 aaaagaatgg tagaggattc tgatctgcaa acttgttatt gtgtttttga tgtattgatg
1321 gttaataata aaaagctagg gcatgagact ctgagaaaga ggtatgagat tcttagtagt
1381 atttttacac caattccagg tagaatagaa atagtgcaga aaacacaagc tcatactaag
```

TABLE 1-continued

```
1441 aatgaagtaa ttgatgcatt gaatgaagca atagataaaa gagaagaggg aattatggta
1501 aaacaacctc tatccatcta caagccagac aaaagaggtg aagggtggtt aaaaattaaa
1561 ccagagtatg tcagtggact aatggatgaa ttggacattt taattgttgg aggatattgg
1621 ggtaaaggat cacggggtgg aatgatgtct cattttctgt gtgcagtagc agagaagccc
1681 cctcctggtg agaagccatc tgtgtttcat actctctctc gtgttgggtc tggctgcacc
1741 atgaaagaac tgtatgatct gggtttgaaa ttggccaagt attggaagcc ttttcataga
1801 aaagctccac caagcagcat tttatgtgga acagagaagc cagaagtata cattgaacct
1861 tgtaattctg tcattgttca gattaaagca gcagagatcg tacccagtga tatgtataaa
1921 actggctgca ccttgcgttt tccacgaatt gaaaagataa gagatgacaa ggagtggcat
1981 gagtgcatga ccctggacga cctagaacaa cttaggggga aggcatctgg taagctcgca
2041 tctaaacacc tttatatagg tggtgatgat gaaccacaag aaaaaaagcg gaaagctgcc
2101 ccaaagatga agaaagttat tggaattatt gagcacttaa aagcacctaa ccttactaac
2161 gttaacaaaa tttctaatat atttgaagat gtagagtttt gtgttatgag tggaacagat
2221 agccagccaa agcctgacct ggagaacaga attgcagaat ttggtggtta tatagtacaa
2281 aatccaggcc cagacacgta ctgtgtaatt gcagggtctg agaacatcag agtgaaaaac
2341 ataattttgt caaataaaca tgatgttgtc aagcctgcat ggcttttaga atgttttaag
2401 accaaaagct ttgtaccatg gcagcctcgc tttatgattc atatgtgccc atcaaccaaa
2461 gaacattttg cccgtgaata tgattgctat ggtgatagtt atttcattga tacagacttg
2521 aaccaactga aggaagtatt ctcaggaatt aaaaattcta acgagcagac tcctgaagaa
2581 atggcttctc tgattgctga tttagaatat cggtattcct gggattgctc tcctctcagt
2641 atgtttcgac gccacaccgt ttatttggac tcgtatgctg ttattaatga cctgagtacc
2701 aaaaatgagg ggacaaggtt agctattaaa gccttggagc ttcggtttca tggagcaaaa
2761 gtagtttctt gtttagctga gggagtgtct catgtaataa ttggggaaga tcatagtcgt
2821 gttgcagatt ttaaagcttt tagaagaact tttaagagaa agtttaaaat cctaaaagaa
2881 agttgggtaa ctgattcaat agacaagtgt gaattacaag aagaaaacca gtatttgatt
2941 taaagctagg tttcctagtg aggaaagcct ctgatctggc agactcattg cagcaggtgg
3001 taatgataaa atactaaact acattttatt tttgtatctt aaaaatctat gcctaaaaag
3061 tatcattaca tataggaaaa caataatttt aacttttaag gttgaaaaga caatagccca
3121 aagccaagaa agaaaaatta tcttgaatgt agtattcaat gatttttat gatcaaggtg
3181 aaataaacag tctaaagaag aggtgttttt ataatatcca tatagaaatc tagaattttt
3241 acttagatac taataaaata catttagaaa cttttaaagt catgaaaaag cattaacctt
3301 ctaaacagta tattctaaaa agtcaaaacg ttaacaatag tttttatcta ataaaagcac
3361 tgcaagaaaa tagggtagaa ttgttacagc tggacttgta aaaatatgtc tttttactca
3421 gggtttaaaa tgtcccattt aaatatgaaa tgtaaacaaa tttgtttttt aaggttaagg
3481 ccaaatgtaa caataaaacc ctgtcgatgg ttttagctaa attagaggaa gttgtatgag
3541 acttaatgat ctaaaaactt aaaattgaat tggtttgatt aaaaataaag cttgcaattt
3601 taaaagtagc tcacatttaa tttcttgtgt gaaatagaac atgctttaaa ggaagtattt
3661 ttatgtgaat ttgcattcca gtataaatag tattcacaaa aaagatttc ctagatttta
3721 tctattgaat aggtgtcaat atggcatgca tattgtaact ttcattagaa ataagttgct
3781 ttgactttta aaaatgacat agttagatta tttaaagtca atgtatatag tatatattat
3841 gtatggattt atataccaaa ttttggaata cagcctatct catgaccata ttgaaatgta
3901 cggaatttga tccatgcgat actatgtgtg cattatttga aagttattgg aaattttatt
3961 caaaccgtgg aacaaatgta tgtgattttg ttatacttct taatttaaat aaaatattta
4021 atgcactatt aaaa
```

SEQ ID NO: 52 Mouse LIG4 cDNA Sequence (NM_176953.3; CDS: 323-3058)

```
   1 ggggcaacct ctgctaagca agtggtgtgg cgggttggag gaggcaggga ggttcttggt
  61 cctagggagg ctgcgtcctt cccgtgcttt gtcccagcgt caccacccgc cttccacggt
 121 gcagccggct cgctggggac tgatttcagg tggcagccac cgggtgaaga aatcgtgtcc
 181 tgatgcttag ttgtatccgc acgctgccct gcccccctgcc acctagctac ctgggacctg
 241 cgcgctcccc cagctccttc attcggcagg gttggggttc acgggctgct tagttcaaac
 301 cggaggattt gttgtcgctt ctatggcttc ctcacaaact tcacaaactg ttgcagctca
 361 tgtccccttt gcagacttat gttccacact agaacggata cagaaaggta aagaccgtgc
 421 agaaaaaatc aggcacttca aggagttttt ggattcgtgg agaaaatttc atgatgccct
 481 tcataagaac agaaaggacg ttacagactc tttttaccct gcaatgagac tcattctccc
 541 ccagttagaa agagagagga tggcttatgg aatcaaagaa accatgctcg ctaagctcta
 601 catcgaattg ctgaacttac cacgagaagg caaggatgcc cagaagctcc tcaattaccg
 661 aacccccagt ggagctcgca cggatgctgg ggactttgcc atgattgcat actttgtttt
 721 gaagccaagg tgcttacaga aaggaagctt aaccatacag caggtaaatg aactcttaga
 781 cttagttgcc agcaataact ctggcaaaaa aaaagaccta gtgaaaaaga gccttcttca
 841 gttaataacc cagagttcag cactggagca aaaatggctg attcgcatga ttatcaaaga
 901 cttaaagctt ggcatcagtc agcaaacaat attttccatt ttccacaatg atgcagttga
 961 gttgcacaac gtcaccacag atctggaaaa ggtctgcagg cagctgcatg acccctctgt
1021 agggcttagt gacatctcta tcactctgtt ttctgccttt aagccaatgc tagctgctgt
1081 agcagacgtg gagcgtgtgg agaaggacat gaagcagcag agtttctaca tcgaaactaa
1141 gcttgatggt gagcgcatgc agatgcacaa agatggcgcg ctgtaccggt acttctccag
1201 aaacggttac aactataccg accagtttgg tgaatctcca caggaaggct ctctcacccc
1261 atttattcac aatgcgttcg ggacagatgt gcaagcgtgc atccttgacg gtgagatgat
1321 ggcctacaac ccaacaacac agactttcat gcagaagggg gtcaagtttg atatcaaaag
1381 gatggtggaa gattctggcc tacagacttg ttactctgtt tttgacgtac tgatggttaa
1441 taagaagaag ctagggcgcg agactcttag gaagaggtat gagatcctta gtagcacttt
1501 cacacccata caaggccgca tagaaatagt gcagaaaact caagctcata caaagaagga
1561 agtagtggat gcattaaatg atgccataga caagagagaa gaggggatca tggttaaaca
1621 ccctctgtcc atttacaagc cagacaaaag aggtgaaggg tggctaaaga ttaaaccaga
1681 gtacgtcagt ggactaatgg atgaattaga cgtcctaatt gtggggggct actggggtaa
1741 aggttcacga ggtggcatga tgtctcactt tttgtgtgca gtggcagaga caccacctcc
1801 tggtgacagg ccatctgtat tccacactct gtgccgtgtt gggtctggtt acaccatgaa
1861 agaactctat gacctgggct tgaaattggc aaaatactgg aagccttttc ataagaaatc
1921 tccaccaagt agcattctgt gtggtacaga gaagccggaa gtgtacatag agcctcagaa
1981 ctctgtcatt gttcagatca aggcagctga gatcgtcccc agtgacatgt acaagactgg
```

TABLE 1-continued

```
2041 ctccaccctg cgcttcccac gcatcgaaaa gatcagagat gacaaagagt ggcacgaatg
2101 tatgacactg ggtgacttgg agcagctgag ggggaaagca tctgggaagc ttgccacgaa
2161 acaccttcat gtaggtgatg atgatgaacc tagagaaaaa aggcggaagc ccatctccaa
2221 gacgaagaaa gccattagaa tcattgaaca cttaaaagca cccaaccttt ctaacgtaaa
2281 caaagtttcc aatgtatttg aagatgttga gttttgtgtt atgagtggat tagatggtta
2341 tccaaaggct gacctagaga acagaattgc agaattcggt ggttatatag tacagaatcc
2401 aggcccggat acatactgtg ttattgcagg ttctgagaac gttagagtga aaaacattat
2461 ttcttcagat aaaaatgatg ttgtcaagcc cgagtggctt ttagagtgtt ttaagacaaa
2521 aacatgcgtg ccgtggcaac ctcgctttat gattcacatg tgcccgtcga caaagcagca
2581 ttttgcccgt gagtatgact gctatggtga tagctatttt gttgacacag atttggatca
2641 attgaaagaa gtgtttctag gaattaaacc cagtgagcag cagactcctg aagaaatggc
2701 ccctgtgatt gctgacttag aatgtcgtta ttcctgggac cactctcctc tcagtatgtt
2761 tcgacattac accatttatt tggacttgta tgctgttatt aatgacttga gttccagaat
2821 tgaagccacg agattaggta ttacagccct tgagctgcgg tttcatggag caaaggtggt
2881 ttcctgctta tctgaagggg tatctcatgt tatcattggg gaggatcaga gacgagttac
2941 tgactttaaa atattcagaa gaatgcttaa gaaaaagttt aaaatcctgc aagaaagttg
3001 ggtgtccgat tcagtagaca agggcgaact gcaggaggaa aaccagtatt tgctttagag
3061 cttgctggcc cggcgggggg gggggaagaa gaagtgttat tgtcagacaa cagcagacag
3121 tgatgatgaa atagccagta gccttcattg tatctcctaa tacttcaaaa ggattattga
3181 tcagaacgca ataattttca agtagaaagg aaactaaatg ggccaaagca aaaaaaaaaa
3241 aaccaaaaaa aataaaacaa acaaaaaaaa ccaacccttt tcctaacacg acttataact
3301 atggcttcaa gaagtgcttg tatggtatcc atactgaagc tatccatact taaagtgtat
3361 ttgaaacctt ttagaaacat caccactatt gactttctag acaaaatttt ccagacttaa
3421 aaattaaagt ttttagctaa taaaagtatt ataccaataa aaaaaatcag aattgttaaa
3481 gttagactta taaaaataag catttttatt tgcgggctca aatacccccct ataagcatga
3541 catattaagc ataaagagtt tttaaggttc atcaaatgtt ttttgataat gtgggggaag
3601 ttgagagaga atcatctaaa caccaaacac ttaagatatt aattttattg aaaaaaatcc
3661 ttgcaacttt taagttagct gagacttaat tttggtgaag actttaatgt ttcatggaga
3721 aatgtttgag tgaatttaca ctccagcatt gacagtgttt acagaacttg tctcctatcg
3781 atgatccatt gcgtagctgt ccatacagtg aacactttca ttagagactg ggtgctctgg
3841 cttttagaga tggcttttat gactatgttg aagtcacagt catgtgtgga ttgtatctgt
3901 tgagaattgt acttccatgg cagtactgaa atggagggat gtgggacctt aagtgatggg
3961 tataaactat ttaagtaatt agacttgttg aagtgattga agaaacattt gtgattattg
4021 taacttaaat aaaattatta aatattgtaa cttaaataaa attattgaat atttaatgta
4081 a
```

SEQ ID NO: 53 Mouse LIG4 Amino Acid Sequence (NP_795927.2)

```
  1 MASSQTSQTV AAHVPFADLC STLERIQKGK DRAEKIRHFK EFLDSWRKFH DALHKNRKDV
 61 TDSFYPAMRL ILPQLERERM AYGIKETMLA KLYIELLNLP REGKDAQKLL NYRTPSGART
121 DAGDFAMIAY FVLKPRCLQK GSLTIQQVNE LLDLVASNNS GKKKDLVKKS LLQLITQSSA
181 LEQKWLIRMI IKDLKLGISQ QTIFSIFHND AVELHNVTTD LEKVCRQLHD PSVGLSDISI
241 TLFSAFKPML AAVADVERVE KDMKQQSFYI ETKLDGERMQ MHKDGALYRY FSRNGYNYTD
301 QFGESPQEGS LTPFIHNAFG TDVQACILDG EMMAYNPTTQ TFMQKGVKFD IKRMVEDSGL
361 QTCYSVFDVL MVNKKKLGRE TLRKRYEILS STFTPIQGRI EIVQKTQAHT KKEVVDALND
421 AIDKREEGIM VKHPLSIYKP DKRGEGWLKI KPEYVSGLMD ELDVLIVGGY WGKGSRGGMM
481 SHFLCAVAET PPPGDRPSVF HTICRVGSGY TMKELYDLGL KLAKYWKPFH KKSPPSSILC
541 GTEKPEVYIE PQNSVIVQIK AAEIVPSDMY KTGSTLRFPR IEKIRDDKEW HECMTLGDLE
601 QLRGKASGKL ATKHLHVGDD DEPREKRRKP ISKTKKAIRI IEHLKAPNLS NVNKVSNVFE
661 DVEFCVMSGL DGYPKADLEN RIAEFGGYIV QNPGPDTYCV IAGSENVRVK NIISSDKNDV
721 VKPEWLLECF KTKTCVPWQP RFMIHMCPST KQHFAREYDC YGDSYFVDTD LDQLKEVFLG
781 IKPSEQQTPE EMAPVIADLE CRYSWDHSPL SMFRHYTIYL DLYAVINDLS SRIEATRLGI
841 TALELRFHGA KVVSCLSEGV SHVIIGEDQR RVTDFKIFRR MLKKKFKILQ ESWVSDSVDK
901 GELQEENQYL L
```

SEQ ID NO: 54 Human PUM3 cDNA Sequence (NM_014878.4; CDS: 97-2043)

```
   1 ggcccggggg cggagcaagg caaggaagcg gaagcggaga ggcggtcggg atccgctgcg
  61 cgagctgtct cggtcccacg tgtgcgagtt gctacgatgg aagttaaagg gaaaaagcaa
 121 ttcacaggaa agagtacaaa gacagcacaa gaaaaaaaca gatttcataa aaatagtgat
 181 tctggttctt caaagacatt tccaacaagg aaagttgcta aagaaggtgg acctaaagtc
 241 acatctagga actttgagaa aagtatcaca aaacttggga aaaagggtgt aaagcagttc
 301 aagaataagc agcaagggga caaatcacca aagaacaaat tccagccggc aaataaattc
 361 aacaagaaga gaaaattcca gccagatggt agaagcgatg aatcagcagc caagaagccc
 421 aaatgggatg acttcaaaaa gaagaagaaa gaactgaagc aaagcagaca actcagtgat
 481 aaaaccaact atgacattgt tgttcgggca aagcagatgt gggagatttt aagaagaaaa
 541 gactgtgaca aagaaaaaag agtaaagtta atgagtgatt tgcagaagtt gattcaaggg
 601 aaaattaaaa ctattgcatt tgcacacgat tcaactcgtg tgatccagtg ttacattcag
 661 tatggtaatg aagaacagag aaaacaggct tttgaagaat tgcgagatga tttggttgag
 721 ttaagtaaag ccaaatattc gagaaatatt gttaagaaat ttctcatgta tggaagtaaa
 781 ccacagattg cagagataat cagaagtttt aaaggccacg tgaggaagat gctgcggcat
 841 gcggaagcat cagccatcgt ggagtacgca tacaatgaca aagccatttt ggagcagagg
 901 aacatgctga cggaagagct ctatgggaac acatttcagc tttacaagtc agcagatcac
 961 cgaactctgg acaaagtgtt agaggtacag ccagaaaaat tagaacttat tatggatgaa
1021 atgaaacaga ttctaactcc aatggcccaa aaggaagctg tgattaagca ctcattggtg
1081 cataaagtat tcttggactt ttttacctat gcacccccca aactcagatc agaaatgatt
1141 gaagccatcc gcgaagcggt ggtctacctg gcacacacac acgatggcgc cagagtggcc
1201 atgcactgcc tgtggcatgg cacgcccaag gacaggaaag tgattgtgaa aacaatgaag
1261 acttatgttg aaaaggtggc taatggccaa tactcccatt tggttttact ggcggcattt
1321 gattgtattg atgatactaa gcttgtgaag cagataatca tatcagaaat tatcagttca
1381 ttgcctagca tagtaaatga caaatatgga aggaaggtcc tattgtactt actaagcccc
1441 agagatcctg cacatacagt acgagaaatc attgaagttc tgcaaaaagg agatggaaat
```

TABLE 1-continued

```
1501 gcacacagta agaaagatac agaggtccgc agacgggagc tcctagaatc catttctcca
1561 gctttgttaa gctacctgca agaacacgcc caagaagtgg tgctagataa gtctgcgtgt
1621 gtgttggtgt ctgacattct gggatctgcc actggagacg ttcagcctac catgaatgcc
1681 atcgccagct tggcagcaac aggactgcat cctggtggca aggacggaga gcttcacatt
1741 gcagaacatc ctgcaggaca tctagttctg aagtggttaa tagagcaaga taaaaagatg
1801 aaagaaaatg ggagagaagg ttgttttgca aaaacacttg tagagcatgt tggtatgaag
1861 aacctgaagt cctgggctag tgtaaatcga ggtgccatta ttctttctag cctcctccag
1921 agttgtgacc tggaagttgc aaacaaagtc aaagctgcac tgaaaagctt gattcctaca
1981 ttggaaaaaa ccaaaagcac cagcaaagga atagaaattc tacttgaaaa actgagcaca
2041 taggtggaaa gagttaagag caagatggaa tgattttttc tgttctctgt tctgtttccc
2101 aatgcagaaa agaaggggta gggtccacca tactggtaat tggggtactc tgtatatgtg
2161 tttcttcttt gtatacgaat ctatttatat aaattgtttt tttaaatggt ctttttttaaa
2221 aaaaaaaaaa aa
```

SEQ ID NO: 55 Human PUM3 Amino Acid Sequence (NP_055693.4)

```
  1 MEVKGKKQFT GKSTKTAQEK NRFHKNSDSG SSKTFPTRKV AKEGGPKVTS RNFEKSITKL
 61 GKKGVKQFKN KQQGDKSPKN KFQPANKFNK KRKFQPDGRS DESAAKKPKW DDFKKKKKEL
121 KQSRQLSDKT NYDIVVRAKQ MWEILRRKDC DKEKRVKLMS DLQKLIQGKI KTIAFAHDST
181 RVIQCYIQYG NEEQRKQAFE ELRDDLVELS KAKYSRNIVK KFLMYGSKPQ IAEIIRSFKG
241 HVRKMLRHAE ASAIVEYAYN DKAILEQRNM LTEELYGNTF QLYKSADHRT LDKVLEVQPE
301 KLELIMDEMK QILTPMAQKE AVIKHSLVHK VFLDFFTYAP PKLRSEMIEA IREAVVYLAH
361 THDGARVAMH CLWHGTPKDR KVIVKTMKTY VEKVANGQYS HLVLLAAFDC IDDTKLVKQI
421 IISEIISSLP SIVNDKYGRK VLLYLLSPRD PAHTVREIIE VLQKGDGNAH SKKDTEVRRR
481 ELLESISPAL LSYLQEHAQE VVLDKSACVL VSDILGSATG DVQPTMNAIA SLAATGLHPG
541 GKDGELHIAE HPAGHLVLKW LIEQDKKMKE NGREGCFAKT LVEHVGMKNL KSWASVNRGA
601 IILSSLLQSC DLEVANKVKA ALKSLIPTLE KTKSTSKGIE ILLEKLST
```

SEQ ID NO: 56 Mouse PUM3 cDNA Sequence (NM_177474.5; CDS: 125-2071)

```
   1 agtaccagga cgtaacgcta caatcagcgg atccggggcg gggcagaacg cggaagcgga
  61 agcggaagcg gcggggggtg gtggcggaac tctgcgagtt tctgccccac gtgtgcgaag
 121 tactatgatg gaagtcaaag ggaagaaaaa gtttacagga aagagtccac agacatcaca
 181 aggaaagaat aaatttcata agaacagtga gtctagttct tcaaagacat tcccaaggaa
 241 agctgttaag gaaggcggac ctaaagtcac atctaagaac tttgagaaag gtgccacaaa
 301 acctggcaag aaaggtgtga agcagttcaa gaacaagcca caaggggggca aaggaccgaa
 361 ggacaaattt cagaaggcaa ataaattcag caagaagcgg aaattccagc cagatggtga
 421 aagtgatgaa tcaggagcca agaaacccaa gtgggatgac ttcaaaaaga agaagaaaga
 481 gctgaagcag agcaggcagc tcagtgacaa gaccaactat gacatcgtgg ttcgagcaaa
 541 gcacatttgg gagagcttga gaagaaaaga ttgtgacaag gaaaaacggg tgaagctcat
 601 gagtgatttg cagaagttga ttcaagggaa aattaaaact atcgcctttg cacatgactc
 661 gacgcgcgtg atccagtgct tcattcagta tgggaacgag gagcagagga agcaggcttt
 721 ccaagagttg caaggcgact tggttgaatt aagtaaagcc aaatattcca ggaatatcgt
 781 taagaaattt ctcatgtatg gaagtaagcc acaagttgcg gagataatca gaagttttaa
 841 aggtcatgtg aggaagatgc tgcggcattc ggaggcatcg gccattgtgg agtacgcata
 901 caacgacaaa gccattttgg aacagaggaa catgctgaca gaggagctct atgggaacac
 961 gtttcagctt tacaagtcag cagatcaccc aacgctggac aaggtgctgg agctgcagcc
1021 agcaaagcta gagcttatca tggacgagat gaagcagatt ctgacaccga tggcccaaaa
1081 ggaagctgtg attaagcact cactcgttca taaagtattc ttggactttt ttacctacgc
1141 acccccaaaa cctcgatcag aactaattga agccatccgg gaagcagtgg tgtacctggc
1201 ccacacacac gatggcgcca gagtggccat gcactgcctg tggcacggca cacccaagga
1261 caggaaagtg atcgtgaaaa cgatgaagac gtatgtggag aaggttgcca atggccagta
1321 ctctcacttg gttctcctgg cagcgtttga ctgtattgat gatactaagc ttgtgaagca
1381 gataatcata tcagaaatca tcagttcctt gcccagcata gttaatgaca aatacggaag
1441 gaaagtcctc ttgtacttga tgagccccag agaccccgcc cacacggtgc ccgagctcat
1501 cgagcttctg cagaagggtg atggcaacgc gcacagcaag aaggacactg caatccgccg
1561 gcgtgagctc ttggagtcca tctctccagc tttgctgagc tacctgcaag gacacactca
1621 agaggtggtg ctggataagt ctgcatgtgt gctggtgtct gacatgctgg gatctgctac
1681 tggagatgtt cagcctgcta tggatgccat cgccagtttg gcagcagcag aactgcatcc
1741 tggtggcaag gacggagagc ttcatgttgc tgagcatcct gcaggacatc tggttctcaa
1801 atggttacta gagcaagata aaaagatgaa agaaagcgga aaggaaggtt gttttgcaaa
1861 aaccccttgta gagcgtgttg gtatgaagaa cctcaagtcc tgggccagca tcaaccgagg
1921 tgccattatt ctttccagcc ttcttcagag ttgtgaccaa gaagttgtaa acaaagtcaa
1981 aggtggactg aaacccctga ttcctacctt ggaaaaaaac aaaagcagca gcagaggcat
2041 ccagaccctg cttgagaagc tgactgcgta ggcagcagga tgagcaagcg ggaacccgct
2101 tcccagagga gaaggtggaa tctctcatac tcacaactgg acgctctgtg catgcatttg
2161 ttaaaggacc tatttatata aaattgtttc taaaagagac ctttggttta atgtcaactg
2221 tctgatctgt gagactgagt actacacagt atggcagtga tctgtgggcc caggtgtgtg
2281 ctctgtggtt gaatggctta atttaggaaa ggagacagct atgatctgag aaggtttcct
2341 ggtgtaggtg aactttagag ggatgttata acaaaagaat taaggacatg aagttcaaac
2401 agagtgtgta tagtggagca ggaaagtggt ctgaactccg ggaagcctgt ggccagggca
2461 gcctgcactg gggacagctg cttcctcagc tgccgtgcag actgagttcc atcaggtttg
2521 tttggaagct gctctggtca gtccagcaca tggagggaag tgtgctagag gaatcaggag
2581 atgatgggtc ctcgcttgaa gtcagcgttg ctgggaaagt ctgatctttg tatttgggcc
2641 ttcagggtaa ataccttcca aggagaatga ggacattgtc ccatgaacaa tccctaaaat
2701 agtcagagcc catagtgtga ctaaaagggg gaactgtaga ggattgagtg taggtagtat
2761 gtttggactt taaaaataca gctggctttc agcggcaaaa ctggagatct gtagaccatg
2821 agaacttgtg tagcaggcgt ttttagtaca gaggcctgtc cttgctgctc tgcatgtctg
2881 atatatacta aggcggccat ctgaccctct gaggaattgt ctgtgcctta cctgtcccaa
2941 cttaaggttc caggactact aatgcagctt ctaggactct cctgccctct cgtgctgggg
3001 tgtagtaagc cctttcccag gcatgacacc tgccactgtt ggctggatcc tctaggcatg
3061 gagtgaggag gagagtgggg aaagacagtt tgatttgctt ctgtgtggct aacataccat
```

TABLE 1-continued

```
3121 gactcgagtt ttcgttctcc gtataaagga ccgtttagag agatgagagt cgggtgctaa
3181 catgtttaat ctttaaaagt gaaaaacacg tacataactt gaaaggtgct tttgtgcagc
3241 ttgtagaaaa agcagctgtt tcctctgtag ttctaattca cgctctccat aatgacttga
3301 gttcttagct ctggtgaatt tctaaacatg tagtatgaag tcccgagtac ctaaaacgta
3361 tatattcaaa tacacaataa agagcatgtt tattttttgt tttttaaggc aggatcttgc
3421 tatgtagctc tgactgtttt gaaatttatt gtgtagacca aactggcctc aaactcacag
3481 agatctgcct gcctctgtct ccctggtgct gcgattaaag atgtgggcca ccacatccag
3541 ctgaggacac agttaaaaaa aaaaaaaaaa aaaaaaaaaa aaaaaaaaaa aaaaaa

SEQ ID NO: 57 Mouse PUM3 Amino Acid Sequence (NP_803425.1)
   1 MMEVKGKKKF TGKSPQTSQG KNKFHKNSES SSSKTFPRKA VKEGGPKVTS KNFEKGATKP
  61 GKKGVKQFKN KPQGGKGPKD KFQKANKFSK KRKFQPDGES DESGAKKPKW DDFKKKKKEL
 121 KQSRQLSDKT NYDIVVRAKH IWESLRRKDC DKEKRVKLMS DLQKLIQGKI KTIAFANDST
 181 RVIQCFIQYG NEEQRKGAFQ ELQGDLVELS KAKYSRNIVK KFLMYGSKPQ VAEIIRSFKG
 241 HVRKMLRHSE ASAIVEYAYN DKAILEQRNM LTEELYGNTF QLYKSADHPT LDKVLELQPA
 301 KLELIMDEMK QILTPMAQKE AVIKHSLVHK VFLDFFTYAP PKPRSELIEA IREAVVYLAH
 361 THDGARVAMH CLWHGTPKDR KVIVKTMKTY VEKVANGQYS HLVLLAAFDC IDDTKLVKQI
 421 IISEIISSLP SIVNDKYGRK VLLYLMSPRD PAHTVPELIE LLQKGDGNAH SKKDTAIRRR
 481 ELLESISPAL LSYLQGHTQE VVLDKSACVL VSDMLGSATG DVQPAMDAIA SLAAAELHPG
 541 GKDGELHVAE HPAGHLVLKW LLEQDKKMKE SGKEGCFAKT LVERVGMKNL KSWASINRGA
 601 IILSSLLQSC DQEVVNKVKG GLKPLIPTLE KNKSSSRGIQ TLLEKLTA

SEQ ID NO: 58 Human UBE2D3 Isoform 1 Amino Acid Sequence (NP_003331.1,
NP_871615.1, NP_871616.1, NP_871617.1, NP_871618.1, NP_871619.1, NP_871620.1)
   1 MALKRINKEL SDLARDPPAQ CSAGPVGDDM FHWQATIMGP NDSPYQGGVF FLTIHFPTDY
  61 PFKPPKVAFT TRIYHPNINS NGSICLDILR SQWSPALTIS KVLLSICSLL CDPNPDDPLV
 121 PEIARIYKTD RDKYNRISRE WTQKYAM

SEQ ID NO: 59 Human UBE2D3 Isoform 2 Amino Acid Sequence (NP_871621.1)
   1 MALKRINKEL SDLARDPPAQ CSAGPVGDDM FHWQATIMGP NDSPYQGGVF FLTIHFPTDY
  61 PFKPPKVAFT TRIYHPNINS NGSICLDILR SQWSPALTIS KVLLSICSLL CDPNPDDPLV
 121 PEIARIYKTD RDKYNRLARE WTEKYAML

SEQ ID NO: 60 Human UBE2D3 isoform 3 Amino Acid Sequence (NP_871622.1)
   1 MLSNRKCLSK ELSDLARDPP AQCSAGPVGD DMFHWQATIM GPNDSPYQGG VFFLTIHFPT
  61 DYPFKPPKVA FTTRIYHPNI NSNGSICLDI LRSQWSPALT ISKVLLSICS LLCDPNPDDP
 121 LVPEIARIYK TDRDKYNRIS REWTQKYAM

SEQ ID NO: 61 Human UBE2D3 isoform 4 Amino Acid Sequence
(NP_001287724.1)
   1 MFHWQATIMG PNDSPYQGGV FFLTIHFPTD YPFKPPKVAF TTRIYHPNIN SNGSICLDIL
  61 RSQWSPALTI SKVLLSICSL LCDPNPDDPL VPEIARIYKT DRDKYNRISR EWTQKYAM

SEQ ID NO: 62 Human UBE2D3 Transcript Variant 1 cDNA Sequence
(NM_003340.6; CDS: 486-929)
   1 accaagtgag gaaactgggg gacgctgtgg ggaggggcgt ggggctggat cgcgcagcgg
  61 ctgcttcctt taccttcctc ccatggtctc cttccggttc tcgatgcttc tctgagccta
 121 agggtttccg ccactcgttc accctccccc cagctcatga tcctcctccc tcccccgccc
 181 tcctggtcca atctccgatc tgtttagtaa gaaggtgctg ttccgagaag aaggaaaagg
 241 gcttgacacg tattcactcg gccccggacg tgggaagcaa gccgtctggc ttcggcctca
 301 catcggtctt gtgctcggga cggcggcgtt ggcggactga tccgcggcgg tgaagaggcg
 361 cctgtgtctg gcagagctgg tgtgagacga gacaatcctg ccccgccgcc gggataatca
 421 agagttttgg ccggaccttt gagcatacac cgagagagtg aggagccaga cgacaagcac
 481 acactatggc gctgaaacgg attaataagg aacttagtga tttggcccgt gaccctccag
 541 cacaatgttc tgcaggtcca gttggggatg atatgtttca ttggcaagcc acaattatgg
 601 gacctaatga cagcccatat caaggcggtg tattcttttt gacaattcat tttcctacag
 661 actacccctt caaaccacct aaggttgcat ttacaacaag aatttatcat ccaaatatta
 721 acagtaatgg cagcatttgt ctcgatattc taagatcaca gtggtcgcct gctttaacaa
 781 tttctaaagt tcttttatcc atttgttcac tgctatgtga tccaaaccca gatgaccccc
 841 tagtgccaga gattgcacgg atctataaaa cagacagaga taagtacaac agaatatctc
 901 gggaatggac tcagaagtat gccatgtgat gctaccttaa agtcagaata acctgcatta
 961 tagctggaat aaactttaaa ttactgttcc ttttttgatt ttcttatccg gctgctcccc
1021 tatcagacct catctttttt aatttttattt tttgtttacc tccctccatt cattcacatg
1081 ctcatctgag aagacttaag ttcttccagc tttggacaat aactgctttt agaaactgta
1141 aagtagttac aagagaacag ttgcccaaga ctcagaattt ttaaaaaaaa aaatggagca
1201 tgtgtattat gtggccaatg tcttcactct aacttggtta tgagactaaa accattcctc
1261 actgctctaa catgctgaag aaatcatctg agggggaggg agatggatgc tcagttgtca
1321 catcaaagga tacagcatta ttctagcagc atccattctt gtttaagcct tccactgtta
1381 gagatttgag gttacatgat atgctttatg ctcataactg atgtggctgg agaattggta
1441 ttgaatttat agcatcagca gaacagaaaa tgtgatgtat tttatgcatg tcaataaagg
1501 aatgacctgt tcttgttcta cagagaatgg aaattggaag tcaaacaccc tttgtattcc
1561 aaaatagggt ctcaaacatt ttgtaatttt catttaaatt gttaggaggc ttggagctat
1621 tagttaatct atcttccaat acactgttta atatagcact gaataaatga tgcaagttgt
1681 caatggatga gtgatcaact aatagctctg ctagtaattg atttattttt cttcaataaa
1741 gttgcataaa ccaatgagtt agctgcctgg attaatcagt atgggaaaca atcttttgta
1801 aatgcaaagc tgttttttgt atatactgtt gggatttgct tcattgtttg acatcaaatg
1861 atgatgtaaa gttcgaaaga gtgaatattt tgccatgttc agttaaagtg cacagtctgt
1921 tacaggttga cacattgctt gacctgattt atgcagaatt aataagctat ttggatagtg
1981 tagctttaat gtgctgcaca tgatactggc agccctagag ttcatagatg gacttttggg
2041 acccagcagt tttgaaatgt gtttatggag tttaagaaat ttattttcca ggtgcagccc
```

TABLE 1-continued 2101 ctgtctaact gaaatttctc ttcaccttgt acacttgaca gctgaaaaaa aacaacatgg
2161 gagtaataat gggtcaaaat ttgcaaaata aagtactgtt ttggtgtggg agttgtcatg
2221 aggctgtgtt gaagtgactt atctatgtgg gatattgagt atccattgaa atggatttgt
2281 tcagccattt acattaatga gcatttaaat gcaacagata tcatttcagg tgacttaaca
2341 tgaatgaata aaagtcaatg ctattggatt gtttttgtt tgacaagtgc tatctgtgcc
2401 actgatttaa cttctgtagt aacaagggca ttaccattct tcacctttcc taattctgat
2461 cccatagttt tacattttc ctgtttattt tgattttgtt cactgcttta tttcttaaag
2521 ttctagcaca tctgtgactc ctccacttcc acatttttgc actgcttaca cttacgtgca
2581 atcttattcc ttgtctgcac acacatgtgg aaagctagaa ataaatgtta aaacttactt
2641 tttataaaca ttttaatatg tagtttggac atgatttatt gacttaaggt tcttctctaa
2701 actggaagtg aaatgcatgc cttctgaaga tgttctggct ttgttaattc tgtaatcatt
2761 tcattgggga aaaaaccagc tacgcagttt ttccaatgag tgaatttttt cattttgtgt
2821 tttgcttaaa acggctcctt cagggtagat gtcatactgc ataacttttt tggattcaaa
2881 ttatgaatga gaaattagtt aacattctgc tccacaaggt aagaaaaact gctctttggc
2941 tctattttca aaattacttc tgagatgcat atagtctcaa aataacagct ttagtaggca
3001 tatcacttct tgaaagccaa acatgagtgt aagacacttt tatgaaacac ggtggatccc
3061 taactggctt tcaaattgac ctttatagcc ttagacaacc cttaggtatt tacggagatg
3121 acttctttga ttgtcataac aattagtgga tgtgtccagt tctctgtatc tttgacttga
3181 tgctttatac atcatttcat ttgttgcttc taagggaata agccatagag gcttctccag
3241 gtttaaaaga acagtaaagt acctggaaaa ccaacatttt tgaatgtatg gacactggac
3301 atgagatatg tacaatgaaa tcttaaaaga atctaagaat ttgccctctt tgccccactc
3361 cacccagtaa tttgacatta ctagtgccat gtataggacc caactgagta ttagaatcag
3421 ttttgactat gtctttgtat ttcctaaatc ttttaatgca taaaccgaat tagggtccag
3481 ttggcctgtt aatggtaaat ttacatttta aatgactcag tttgtttttc ctgggcgagt
3541 ttgcaatgtg ataatcagat tttttaaaac tgattaattt gctttcttgt gtgggtgtac
3601 tcacatttta aagtatgaac cacagttaac tagtggtctc aggggtagtg aaacactcac
3661 tttttttttt gtttgttttt ttttgtttgt tgaaatggct tagttgaagt atacttaagg
3721 tactgatcat gctgtgttag taatttgggc ggggaggggg gtaactcagc catgttttgt
3781 gttggcataa caaaactgtt aatgattgtt gattacactt ttaagtgaat ttgtctttta
3841 tgaggaaccc agtgcaagtc actaaatatt gtctaatagt gacatctgca taagacttgt
3901 aatagctgaa gttaattgag cttaaaggaa ttgttaccat taaagtctgt gtttaaagac
3961 aaaaaaaaaa aaaaaa SEQ ID NO: 63 Human UBE2D3 Transcript Variant 2 cDNA Sequence
(NM_181886.3; CDS: 694-1137)

1 accaagtgag gaaactgggg gacgctgtgg ggagggggcgt ggggctggat cgcgcagcgg
61 ctgcttcctt taccttcctc ccatggtctc cttccggttc tcgatgcttc tctgagccta
121 agggtttccg ccactcgttc accctccccc cagctcatga tcctcctccc tcccccgccc
181 tcctggtcca atctccgatc tgtttagtaa gaaggtgctg ttccgagaag aaggaaaagg
241 gcttgacacg tattcactcg gccccggacg tgggaagcaa gccgtctggc ttcggcctca
301 catcggtctt gtgctcggga cggcggcgtt ggcggactga tccgcggcgg tgaagagagg
361 ccgggaagtt aaacttgtag ccaccacctc cgctcttccc gtcaccctcg cccccacttc
421 gggccgaaag cacggtacag aggctgttgg tggctttgcc acgccacccc acccaccccg
481 gatcgcggct gtcttaaggg acctggattc atcaggggct cttcggggcc tgtgcgagtg
541 ctgatctgct ccgtttttgc aaaaggcgcc tgtgtctggc agagctggtg tgagacgaga
601 caatcctgcc ccgccgccgg gataatcaag agttttggcc ggacctttga gcatacaccg
661 agagagtgag gagccagacg acaagcacac actatggcgc tgaaacggat taataaggaa
721 cttagtgatt tggcccgtga ccctccagca caatgttctg caggtccagt tggggatgat
781 atgtttcatt ggcaagccac aattatggga cctaatgaca gcccatatca aggcggtgta
841 ttctttttga caattcattt tcctacagac taccccttca aaccacctaa ggttgcattt
901 acaacaagaa tttatcatcc aaatattaac agtaatggca gcatttgtct cgatattcta
961 agatcacagt ggtcgcctgc tttaacaatt tctaaagttc ttttatccat ttgttcactg
1021 ctatgtgatc caaacccaga tgacccccta gtgccagaga ttgcacggat ctataaaaca
1081 gacagagata agtacaacag aatatctcgg gaatggactc agaagtatgc catgtgatgc
1141 taccttaaag tcagaataac ctgcattata gctggaataa actttaaatt actgttcctt
1201 ttttgatttt cttatccggc tgctccccta tcagacctca tcttttttaa ttttattttt
1261 tgtttacctc cctccattca ttcacatgct catctgagaa gacttaagtt cttccagctt
1321 tggacaataa ctgcttttag aaactgtaaa gtagttacaa gagaacagtt gcccaagact
1381 cagaattttt aaaaaaaaaa atggagcatg tgtattatgt ggccaatgtc ttcactctaa
1441 cttggttatg agactaaaac cattcctcac tgctctaaca tgctgaagaa atcatctgag
1501 ggggagggag atggatgctc agttgtcaca tcaaaggata cagcattatt ctagcagcat
1561 ccattcttgt ttaagccttc cactgttaga gatttgaggt tacatgatat gctttatgct
1621 cataactgat gtggctggag aattggtatt gaatttatag catcagcaga acagaaaatg
1681 tgatgtattt tatgcatgtc aataaaggaa tgacctgttc ttgttctaca gagaatggaa
1741 attggaagtc aaacaccctt tgtattccaa aatagggtct caaacatttt gtaattttca
1801 tttaaattgt taggaggctt ggagctatta gttaatctat cttccaatac actgtttaat
1861 atagcactga ataaatgatg caagttgtca atggatgagt gatcaactaa tagctctgct
1921 agtaattgat ttatttttct tcaataaagt tgcataaacc aatgagttag ctgcctggat
1981 taatcagtat gggaaacaat cttttgtaaa tgcaaagctg ttttttgtat atactgttgg
2041 gatttgcttc attgtttgac atcaaatgat gatgtaaagt tcgaaagagt gaatattttg
2101 ccatgttcag ttaaagtgca cagtctgtta caggttgaca cattgcttga cctgatttat
2161 gcagaattaa taagctattt ggatagtgta gctttaatgt gctgcacatg atactggcag
2221 ccctagagtt catagatgga cttttgggac ccagcagttt tgaaatgtgt ttatggagtt
2281 taagaaattt attttccagg tgcagcccct gtctaactga aatttctctt caccttgtac
2341 acttgacagc tgaaaaaaaa caacatggga gtaataatgg gtcaaaattt gcaaaataaa
2401 gtactgtttt ggtgtgggag ttgtcatgag gctgtgttga agtgacttat ctatgtggga
2461 tattgagtat ccattgaaat ggatttgttc agccatttac attaatgagc atttaaatgc
2521 aacagatatc atttcaggtg acttaacatg aatgaataaa agtcaatgct attggattgt
2581 tttttgtttg acaagtgcta tctgtgccac tgatttaact tctgtagtaa caagggcatt
2641 accattcttc acctttccta attctgatcc catagtttta cattttcct gtttattttg TABLE 1-continued 2701 attttgttca ctgctttatt tcttaaagtt ctagcacatc tgtgactcct ccacttccac
2761 atttttgcac tgcttacact tacgtgcaat cttattcctt gtctgcacac acatgtggaa
2821 agctagaaat aaatgttaaa acttactttt tataaacatt ttaatatgta gtttggacat
2881 gatttattga cttaaggttc ttctctaaac tggaagtgaa atgcatgcct tctgaagatg
2941 ttctggcttt gttaattctg taatcatttc attggggaaa aaaccagcta cgcagttttt
3001 ccaatgagtg aatttttttca ttttgtgttt tgcttaaaac ggctccttca gggtagatgt
3061 catactgcat aacttttttg gattcaaatt atgaatgaga aattagttaa cattctgctc
3121 cacaaggtaa gaaaaactgc tctttggctc tattttcaaa attacttctg agatgcatat
3181 agtctcaaaa taacagcttt agtaggcata tcacttcttg aaagccaaac atgagtgtaa
3241 gacactttta tgaaacacgg tggatcccta actggctttc aaattgacct ttatagcctt
3301 agacaaccct taggtattta cggagatgac ttctttgatt gtcataacaa ttagtggatg
3361 tgtccagttc tctgtatctt tgacttgatg ctttatacat catttcattt gttgcttcta
3421 agggaataag ccatagaggc ttctccaggt ttaaaagaac agtaaagtac ctggaaaacc
3481 aacatttttg aatgtatgga cactggacat gagatatgta caatgaaatc ttaaaagaat
3541 ctaagaattt gccctctttg ccccactcca cccagtaatt tgacattact agtgccatgt
3601 ataggaccca actgagtatt agaatcagtt ttgactatgt ctttgtattt cctaaatctt
3661 ttaatgcata aaccgaatta gggtccagtt ggcctgttaa tggtaaattt acattttaaa
3721 tgactcagtt tgtttttcct gggcgagttt gcaatgtgat aatcagattt tttaaaactg
3781 attaatttgc tttcttgtgt gggtgtactc acattttaaa gtatgaacca cagttaacta
3841 gtggtctcag gggtagtgaa acactcactt ttttttttgt ttgttttttt ttgtttgttg
3901 aaatggctta gttgaagtat acttaaggta ctgatcatgc tgtgttagta atttgggcgg
3961 ggaggggggt aactcagcca tgttttgtgt tggcataaca aaactgttaa tgattgttga
4021 ttacactttt aagtgaattt gtcttttatg aggaacccag tgcaagtcac taaatattgt
4081 ctaatagtga catctgcata agacttgtaa tagctgaagt taattgagct taaaggaatt
4141 gttaccatta aagtctgtgt ttaaagacaa aaaaaaaaaa aaaa SEQ ID NO: 64 Human UBE2D3 Transcript Variant 3 cDNA Sequence
(NM_181887.2; CDS: 464-907)

1 gtagttccgt cagagcggac atcttgtggc tgtgtcgtgc gcgtgagccc cgtagggccg
61 gggaggcacc agctgccgcg cggggaggag gccgaggccg cagcttgagg gaggccccgg
121 cccctctagg ccgggaagtt aaacttgtag ccaccacctc cgctcttccc gtcaccctcg
181 cccccacttc gggccgaaag cacggtacag aggctgttgg tggctttgcc acgccacccc
241 acccaccccg gatcgcggct gtcttaaggg acctggattc atcaggggct cttcggggcc
301 tgtgcgagtg ctgatctgct ccgtttttgc aaaaggcgcc tgtgtctggc agagctggtg
361 tgagacgaga caatcctgcc ccgccgccgg gataatcaag agttttggcc ggacctttga
421 gcatacaccg agagagtgag gagccagacg acaagcacac actatggcgc tgaaacggat
481 taataaggaa cttagtgatt tggcccgtga ccctccagca caatgttctg caggtccagt
541 tggggatgat atgtttcatt ggcaagccac aattatggga cctaatgaca gcccatatca
601 aggcggtgta ttctttttga caattcattt tcctacagac taccccttca aaccacctaa
661 ggttgcattt acaacaagaa tttatcatcc aaatattaac agtaatggca gcatttgtct
721 cgatattcta agatcacagt ggtcgcctgc tttaacaatt tctaaagttc ttttatccat
781 ttgttcactg ctatgtgatc caaacccaga tgaccccctta gtgccagaga ttgcacggat
841 ctataaaaca gacagagata agtacaacag aatatctcgg gaatggactc agaagtatgc
901 catgtgatgc taccttaaag tcagaataac ctgcattata gctggaataa actttaaatt
961 actgttcctt ttttgatttt cttatccggc tgctccccta tcagacctca tcttttttaa
1021 ttttattttt tgtttacctc cctccattca ttcacatgct catctgagaa gacttaagtt
1081 cttccagctt tggacaataa ctgcttttag aaactgtaaa gtagttacaa gagaacagtt
1141 gcccaagact cagaattttt aaaaaaaaaa atggagcatg tgtattatgt ggccaatgtc
1201 ttcactctaa cttggttatg agactaaaac cattcctcac tgctctaaca tgctgaagaa
1261 atcatctgag ggggagggag atggatgctc agttgtcaca tcaaaggata cagcattatt
1321 ctagcagcat ccattcttgt ttaagccttc cactgttaga gatttgaggt tacatgatat
1381 gctttatgct cataactgat gtggctggag aattggtatt gaatttatag catcagcaga
1441 acagaaaatg tgatgtattt tatgcatgtc aataaaggaa tgacctgttc ttgttctaca
1501 gagaatggaa attggaagtc aaacaccctt tgtattccaa aatagggtct caaacatttt
1561 gtaattttca tttaaattgt taggaggctt ggagctatta gttaatctat cttccaatac
1621 actgtttaat atagcactga ataaatgatg caagttgtca atggatgagt gatcaactaa
1681 tagctctgct agtaattgat ttatttttct tcaataaagt tgcataaacc aatgagttag
1741 ctgcctggat taatcagtat gggaaacaat cttttgtaaa tgcaaagctg ttttttgtat
1801 atactgttgg gatttgcttc attgtttgac atcaaatgat gatgtaaagt tcgaaagagt
1861 gaatattttg ccatgttcag ttaaagtgca cagtctgtta caggttgaca cattgcttga
1921 cctgatttat gcagaattaa taagctattt ggatagtgta gctttaatgt gctgcacatg
1981 atactggcag ccctagagtt catagatgga cttttgggac ccagcagttt tgaaatgtgt
2041 ttatggagtt taagaaattt attttccagg tgcagcccct gtctaactga aatttctctt
2101 caccttgtac acttgacagc tgaaaaaaaa caacatggga gtaataatgg gtcaaaattt
2161 gcaaaataaa gtactgtttt ggtgtgggag ttgtcatgag gctgtgttga agtgacttat
2221 ctatgtggga tattgagtat ccattgaaat ggatttgttc agccatttac attaatgagc
2281 atttaaatgc aacagatatc atttcaggtg acttaacatg aatgaataaa agtcaatgct
2341 attggattgt tttttgtttg acaagtgcta tctgtgccac tgatttaact tctgtagtaa
2401 caagggcatt accattcttc acctttccta attctgatcc catagtttta catttttcct
2461 gtttattttg attttgttca ctgctttatt tcttaaagtt ctagcacatc tgtgactcct
2521 ccacttccac atttttgcac tgcttacact tacgtgcaat cttattcctt gtctgcacac
2581 acatgtggaa agctagaaat aaatgttaaa acttactttt tataaacatt ttaatatgta
2641 gtttggacat gatttattga cttaaggttc ttctctaaac tggaagtgaa atgcatgcct
2701 tctgaagatg ttctggcttt gttaattctg taatcatttc attggggaaa aaaccagcta
2761 cgcagttttt ccaatgagtg aatttttttca ttttgtgttt tgcttaaaac ggctccttca
2821 gggtagatgt catactgcat aacttttttg gattcaaatt atgaatgaga aattagttaa
2881 cattctgctc cacaaggtaa gaaaaactgc tctttggctc tattttcaaa attacttctg
2941 agatgcatat agtctcaaaa taacagcttt agtaggcata tcacttcttg aaagccaaac
3001 atgagtgtaa gacactttta tgaaacacgg tggatcccta actggctttc aaattgacct
3061 ttatagcctt agacaaccct taggtattta cggagatgac ttctttgatt gtcataacaa TABLE 1-continued

```
3121 ttagtggatg tgtccagttc tctgtatctt tgacttgatg ctttatacat catttcattt
3181 gttgcttcta agggaataag ccatagaggc ttctccaggt ttaaaagaac agtaaagtac
3241 ctggaaaacc aacatttttg aatgtatgga cactggacat gagatatgta caatgaaatc
3301 ttaaaagaat ctaagaattt gccctctttg ccccactcca cccagtaatt tgacattact
3361 agtgccatgt ataggaccca actgagtatt agaatcagtt ttgactatgt ctttgtattt
3421 cctaaatctt ttaatgcata aaccgaatta gggtccagtt ggcctgttaa tggtaaattt
3481 acattttaaa tgactcagtt tgtttttcct gggcgagttt gcaatgtgat aatcagattt
3541 tttaaaactg attaatttgc tttcttgtgt gggtgtactc acattttaaa gtatgaacca
3601 cagttaacta gtggtctcag gggtagtgaa acactcactt tttttttgt ttgtttttt
3661 ttgtttgttg aaatggctta gttgaagtat acttaaggta ctgatcatgc tgtgttagta
3721 atttgggcgg ggaggggggt aactcagcca tgttttgtgt tggcataaca aaactgttaa
3781 tgattgttga ttacactttt aagtgaattt gtcttttatg aggaacccag tgcaagtcac
3841 taaatattgt ctaatagtga catctgcata agacttgtaa tagctgaagt taattgagct
3901 taaaggaatt gttaccatta aagtctgtgt ttaaagacaa aaaaaaaaaa aaaa
```

SEQ ID NO: 65 Human UBE2D3 Transcript Variant 4 cDNA Sequence
(NM_181888.3; CDS: 343-786)

```
   1 accaagtgag gaaactgggg gacgctgtgg ggaggggcgt ggggctggat cgcgcagcgg
  61 ctgcttcctt taccttcctc ccatggtctc cttccggttc tcgatgcttc tctgagccta
 121 agggtttccg ccactcgttc accctccccc cagctcatga tcctcctccc tcccccgccc
 181 tcctggtcca atctccgatc tgtttagtaa gaaggcgcct gtgtctggca gagctggtgt
 241 gagacgagac aatcctgccc cgccgccggg ataatcaaga gttttggccg gacctttgag
 301 catacaccga gagagtgagg agccagacga caagcacaca ctatggcgct gaaacggatt
 361 aataaggaac ttagtgattt ggcccgtgac cctccagcac aatgttctgc aggtccagtt
 421 ggggatgata tgtttcattg gcaagccaca attatgggac ctaatgacag cccatatcaa
 481 ggcggtgtat tctttttgac aattcatttt cctacagact accccttcaa accacctaag
 541 gttgcattta caacaagaat ttatcatcca aatattaaca gtaatggcag catttgtctc
 601 gatattctaa gatcacagtg gtcgcctgct ttaacaattt ctaaagttct tttatccatt
 661 tgttcactgc tatgtgatcc aaacccagat gacccccctag tgccagagat tgcacggatc
 721 tataaaacag acagagataa gtacaacaga atatctcggg aatggactca gaagtatgcc
 781 atgtgatgct accttaaagt cagaataacc tgcattatag ctggaataaa ctttaaatta
 841 ctgttccttt tttgatttc ttatccggct gctcccctat cagacctcat ctttttaat
 901 tttatttttt gtttacctcc ctccattcat tcacatgctc atctgagaag acttaagttc
 961 ttccagcttt ggacaataac tgcttttaga aactgtaaag tagttacaag agaacagttg
1021 cccaagactc agaattttta aaaaaaaaaa tggagcatgt gtattatgtg gccaatgtct
1081 tcactctaac ttggttatga gactaaaacc attcctcact gctctaacat gctgaagaaa
1141 tcatctgagg gggagggaga tggatgctca gttgtcacat caaaggatac agcattattc
1201 tagcagcatc cattcttgtt taagccttcc actgttagag atttgaggtt acatgatatg
1261 ctttatgctc ataactgatg tggctggaga attggtattg aatttatagc atcagcagaa
1321 cagaaaatgt gatgtatttt atgcatgtca ataaaggaat gacctgttct tgttctacag
1381 agaatggaaa ttggaagtca aacacccttt gtattccaaa atagggtctc aaacattttg
1441 taattttcat ttaaattgtt aggaggcttg gagctattag ttaatctatc ttccaataca
1501 ctgtttaata tagcactgaa taaatgatgc aagttgtcaa tggatgagtg atcaactaat
1561 agctctgcta gtaattgatt tatttttctt caataaagtt gcataaacca atgagttagc
1621 tgcctggatt aatcagtatg ggaaacaatc ttttgtaaat gcaaagctgt tttttgtata
1681 tactgttggg atttgcttca ttgtttgaca tcaaatgatg atgtaaagtt cgaaagagtg
1741 aatattttgc catgttcagt taaagtgcac agtctgttac aggttgacac attgcttgac
1801 ctgatttatg cagaattaat aagctatttg gatagtgtag ctttaatgtg ctgcacatga
1861 tactggcagc cctagagttc atagatggac ttttgggacc cagcagtttt gaaatgtgtt
1921 tatggagttt aagaaattta ttttccaggt gcagcccctg tctaactgaa atttctcttc
1981 accttgtaca cttgacagct gaaaaaaaac aacatgggag taataatggg tcaaaatttg
2041 caaaataaag tactgttttg gtgtgggagt tgtcatgagg ctgtgttgaa gtgacttatc
2101 tatgtgggat attgagtatc cattgaaatg gatttgttca gccatttaca ttaatgagca
2161 tttaaatgca acagatatca tttcaggtga cttaacatga atgaataaaa gtcaatgcta
2221 ttggattgtt ttttgtttga caagtgctat ctgtgccact gatttaactt ctgtagtaac
2281 aagggcatta ccattcttca cctttcctaa ttctgatccc atagttttac atttttcctg
2341 tttattttga ttttgttcac tgctttattt cttaaagttc tagcacatct gtgactcctc
2401 cacttccaca tttttgcact gcttacactt acgtgcaatc ttattccttg tctgcacaca
2461 catgtggaaa gctagaaata aatgttaaaa cttacttttt ataaacattt taatatgtag
2521 tttggacatg atttattgac ttaaggttct tctctaaact ggaagtgaaa tgcatgcctt
2581 ctgaagatgt tctggctttg ttaattctgt aatcatttca ttggggaaaa aaccagctac
2641 gcagtttttc caatgagtga attttttcat tttgtgtttt gcttaaaacg gctccttcag
2701 ggtagatgtc atactgcata actttttgg attcaaatta tgaatgagaa attagttaac
2761 attctgctcc acaaggtaag aaaaactgct ctttggctct attttcaaaa ttacttctga
2821 gatgcatata gtctcaaaat aacagcttta gtaggcatat cacttcttga aagccaaaca
2881 tgagtgtaag acactttat gaaacacggt ggatccctaa ctggctttca aattgacctt
2941 tatagcctta gacaaccctt aggtatttac ggagatgact tctttgattg tcataacaat
3001 tagtggatgt gtccagttct ctgtatcttt gacttgatgc tttatacatc atttcatttg
3061 ttgcttctaa gggaataagc catagaggct tctccaggtt taaaagaaca gtaaagtacc
3121 tggaaaacca acatttttga atgtatggac actggacatg agatatgtac aatgaaatct
3181 taaaagaatc taagaatttg ccctctttgc cccactccac ccagtaattt gacattacta
3241 gtgccatgta taggacccaa ctgagtatta gaatcagttt tgactatgtc tttgtatttc
3301 ctaaatcttt taatgcataa accgaattag ggtccagttg gcctgttaat ggtaaattta
3361 cattttaaat gactcagttt gtttttcctg ggcgagtttg caatgtgata atcagatttt
3421 ttaaaactga ttaatttgct ttcttgtgtg ggtgtactca cattttaaag tatgaaccac
3481 agttaactag tggtctcagg ggtagtgaaa cactcacttt ttttttgtt tgttttttt
3541 tgtttgttga aatggcttag ttgaagtata cttaaggtac tgatcatgct gtgttagtaa
3601 tttgggcggg gagggggta actcagccat gttttgtgtt ggcataacaa aactgttaat
3661 gattgttgat tacactttta agtgaatttg tcttttatga ggaacccagt gcaagtcact
```

TABLE 1-continued 3721 aaatattgtc taatagtgac atctgcataa gacttgtaat agctgaagtt aattgagctt
3781 aaaggaattg ttaccattaa agtctgtgtt taaagacaaa aaaaaaaaaa aaa SEQ ID NO: 66 Human UBE2D3 Transcript Variant 5 cDNA Sequence
(NM_181889.2 CDS: 366-809)
1 tggggaattc catttcctct accaaccacc ggcataagca ttcaggggcg ttgctttcct
61 ggcagtggcc cgccccagtt cgagccggtg ccttactgcg tctcgcgaga acttatgcat
121 tttggaggcg gaaccccgtc aggaaaagcg cacaaaactg ctcttaagtc attgcagagc
181 taccgcttcg gttagccagc cacgaagttc tcgcgagagt cgtctcctcg ataccaagcg
241 cctgtgtctg gcagagctgg tgtgagacga gacaatcctg ccccgccgcc gggataatca
301 agagtttgg ccggaccttt gagcatacac cgagagagtg aggagccaga cgacaagcac
361 acactatggc gctgaaacgg attaataagg aacttagtga tttggcccgt gaccctccag
421 cacaatgttc tgcaggtcca gttggggatg atatgtttca ttggcaagcc acaattatgg
481 gacctaatga cagcccatat caaggcggtg tattcttttt gacaattcat tttcctacag
541 actacccctt caaaccacct aaggttgcat ttacaacaag aatttatcat ccaaatatta
601 acagtaatgg cagcatttgt ctcgatattc taagatcaca gtggtcgcct gctttaacaa
661 tttctaaagt tcttttatcc atttgttcac tgctatgtga tccaaaccca gatgaccccc
721 tagtgccaga gattgcacgg atctataaaa cagacagaga taagtacaac agaatatctc
781 gggaatggac tcagaagtat gccatgtgat gctaccttaa agtcagaata acctgcatta
841 tagctggaat aaactttaaa ttactgttcc ttttttgatt ttcttatccg gctgctcccc
901 tatcagacct catctttttt aattttattt tttgtttacc tccctccatt cattcacatg
961 ctcatctgag aagacttaag ttcttccagc tttggacaat aactgctttt agaaactgta
1021 aagtagttac aagagaacag ttgcccaaga ctcagaattt ttaaaaaaaa aaatggagca
1081 tgtgtattat gtggccaatg tcttcactct aacttggtta tgagactaaa accattcctc
1141 actgctctaa catgctgaag aaatcatctg agggggaggg agatggatgc tcagttgtca
1201 catcaaagga tacagcatta ttctagcagc atccattctt gtttaagcct tccactgtta
1261 gagatttgag gttacatgat atgctttatg ctcataactg atgtggctgg agaattggta
1321 ttgaatttat agcatcagca gaacagaaaa tgtgatgtat tttatgcatg tcaataaagg
1381 aatgacctgt tcttgttcta cagagaatgg aaattggaag tcaaacaccc tttgtattcc
1441 aaaatagggt ctcaaacatt ttgtaatttt catttaaatt gttaggaggc ttggagctat
1501 tagttaatct atcttccaat acactgttta atatagcact gaataaatga tgcaagttgt
1561 caatggatga gtgatcaact aatagctctg ctagtaattg atttattttt cttcaataaa
1621 gttgcataaa ccaatgagtt agctgcctgg attaatcagt atgggaaaca atcttttgta
1681 aatgcaaagc tgttttttgt atatactgtt gggatttgct tcattgtttg acatcaaatg
1741 atgatgtaaa gttcgaaaga gtgaatattt tgccatgttc agttaaagtg cacagtctgt
1801 tacaggttga cacattgctt gacctgattt atgcagaatt aataagctat ttggatagtg
1861 tagctttaat gtgctgcaca tgatactggc agccctagag ttcatagatg gacttttggg
1921 acccagcagt tttgaaatgt gtttatggag tttaagaaat ttattttcca ggtgcagccc
1981 ctgtctaact gaaatttctc ttcaccttgt acacttgaca gctgaaaaaa aacaacatgg
2041 gagtaataat gggtcaaaat ttgcaaaata aagtactgtt ttggtgtggg agttgtcatg
2101 aggctgtgtt gaagtgactt atctatgtgg gatattgagt atccattgaa atggatttgt
2161 tcagccattt acattaatga gcatttaaat gcaacagata tcatttcagg tgacttaaca
2221 tgaatgaata aaagtcaatg ctattggatt gttttttgtt tgacaagtgc tatctgtgcc
2281 actgatttaa cttctgtagt aacaagggca ttaccattct tcacctttcc taattctgat
2341 cccatagttt tacatttttc ctgtttattt tgattttgtt cactgcttta tttcttaaag
2401 ttctagcaca tctgtgactc ctccacttcc acatttttgc actgcttaca cttacgtgca
2461 atcttattcc ttgtctgcac acacatgtgg aaagctagaa ataaatgtta aaacttactt
2521 tttataaaca ttttaatatg tagtttggac atgatttatt gacttaaggt tcttctctaa
2581 actggaagtg aaatgcatgc cttctgaaga tgttctggct ttgttaattc tgtaatcatt
2641 tcattgggga aaaaaccagc tacgcagttt ttccaatgag tgaatttttt cattttgtgt
2701 tttgcttaaa acggctcctt cagggtagat gtcatactgc ataacttttt tggattcaaa
2761 ttatgaatga gaaattagtt aacattctgc tccacaaggt aagaaaaact gctctttggc
2821 tctattttca aaattacttc tgagatgcat atagtctcaa aataacagct ttagtaggca
2881 tatcacttct tgaaagccaa acatgagtgt aagacacttt tatgaaacac ggtggatccc
2941 taactggctt tcaaattgac ctttatagcc ttagacaacc cttaggtatt tacggagatg
3001 acttctttga ttgtcataac aattagtgga tgtgtccagt tctctgtatc tttgacttga
3061 tgctttatac atcatttcat ttgttgcttc taagggaata agccatagag gcttctccag
3121 gtttaaaaga acagtaaagt acctggaaaa ccaacatttt tgaatgtatg gacactggac
3181 atgagatatg tacaatgaaa tcttaaaaga atctaagaat ttgccctctt tgccccactc
3241 cacccagtaa tttgacatta ctagtgccat gtataggacc caactgagta ttagaatcag
3301 ttttgactat gtctttgtat ttcctaaatc ttttaatgca taaaccgaat tagggtccag
3361 ttggcctgtt aatggtaaat ttacatttta aatgactcag tttgtttttc ctgggcgagt
3421 ttgcaatgtg ataatcagat tttttaaaac tgattaattt gctttcttgt gtgggtgtac
3481 tcacatttta aagtatgaac cacagttaac tagtggtctc aggggtagtg aaacactcac
3541 tttttttttt gtttgttttt ttttgtttgt tgaaatggct tagttgaagt atacttaagg
3601 tactgatcat gctgtgttag taatttgggc ggggaggggg gtaactcagc catgttttgt
3661 gttggcataa caaaactgtt aatgattgtt gattacactt ttaagtgaat ttgtctttta
3721 tgaggaaccc agtgcaagtc actaaatatt gtctaatagt gacatctgca taagacttgt
3781 aatagctgaa gttaattgag cttaaaggaa ttgttaccat taaagtctgt gtttaaagac
3841 aaaaaaaaaa aaaaaa SEQ ID NO: 67 Human UBE2D3 Transcript Variant 6 cDNA Sequence
(NM_181890.2)
1 ggcggactgc cgaggcgcgg gaactggcgg gtagcgaggc cctcctcgga atctcgtgtg
61 aaggtggccc tcctcttggg cctttaacgt ctgtagatgc tggagaccag cagaaaggat
121 actgtgtgcg atgagataag catgtgagaa tgctttctaa ccgaaagtgc ctttcaaaag
181 cgcctgtgtc tggcagagct ggtgtgagac gagacaatcc tgccccgccg ccgggataat
241 caagagtttt ggccggacct ttgagcatac accgagagag tgaggagcca gacgacaagc
301 acacactatg gcgctgaaac ggattaataa ggaacttagt gatttggccc gtgaccctcc
361 agcacaatgt tctgcaggtc cagttgggga tgatatgttt cattggcaag ccacaattat TABLE 1-continued 421 gggacctaat gacagcccat atcaaggcgg tgtattcttt ttgacaattc attttcctac
481 agactacccc ttcaaaccac ctaaggttgc atttacaaca agaatttatc atccaaatat
541 taacagtaat ggcagcattt gtctcgatat tctaagatca cagtggtcgc ctgctttaac
601 aatttctaaa gttcttttat ccatttgttc actgctatgt gatccaaacc cagatgaccc
661 cctagtgcca gagattgcac ggatctataa aacagacaga gataagtaca acagaatatc
721 tcgggaatgg actcagaagt atgccatgtg atgctacctt aaagtcagaa taacctgcat
781 tatagctgga ataaacttta aattactgtt cctttttga ttttcttatc cggctgctcc
841 cctatcagac ctcatctttt ttaattttat tttttgttta cctccctcca ttcattcaca
901 tgctcatctg agaagactta agttcttcca gctttggaca ataactgctt ttagaaactg
961 taaagtagtt acaagagaac agttgcccaa gactcagaat ttttaaaaaa aaaaatggag
1021 catgtgtatt atgtggccaa tgtcttcact ctaacttggt tatgagacta aaaccattcc
1081 tcactgctct aacatgctga agaaatcatc tgagggggag ggagatggat gctcagttgt
1141 cacatcaaag gatacagcat tattctagca gcatccattc ttgtttaagc cttccactgt
1201 tagagatttg aggttacatg atatgcttta tgctcataac tgatgtggct ggagaattgg
1261 tattgaattt atagcatcag cagaacagaa aatgtgatgt attttatgca tgtcaataaa
1321 ggaatgacct gttcttgttc tacagagaat ggaaattgga agtcaaacac cctttgtatt
1381 ccaaaatagg gtctcaaaca ttttgtaatt ttcatttaaa ttgttaggag gcttggagct
1441 attagttaat ctatcttcca atacactgtt taatatagca ctgaataaat gatgcaagtt
1501 gtcaatggat gagtgatcaa ctaatagctc tgctagtaat tgatttattt ttcttcaata
1561 aagttgcata aaccaatgag ttagctgcct ggattaatca gtatgggaaa caatcttttg
1621 taaatgcaaa gctgtttttt gtatatactg ttgggatttg cttcattgtt tgacatcaaa
1681 tgatgatgta aagttcgaaa gagtgaatat tttgccatgt tcagttaaag tgcacagtct
1741 gttacaggtt gacacattgc ttgacctgat ttatgcagaa ttaataagct atttggatag
1801 tgtagcttta atgtgctgca catgatactg gcagccctag agttcataga tggacttttg
1861 ggacccagca gttttgaaat gtgtttatgg agtttaagaa atttattttc caggtgcagc
1921 ccctgtctaa ctgaaatttc tcttcacctt gtacacttga cagctgaaaa aaaacaacat
1981 gggagtaata atgggtcaaa atttgcaaaa taaagtactg ttttggtgtg ggagttgtca
2041 tgaggctgtg ttgaagtgac ttatctatgt gggatattga gtatccattg aaatggattt
2101 gttcagccat ttacattaat gagcatttaa atgcaacaga tatcatttca ggtgacttaa
2161 catgaatgaa taaaagtcaa tgctattgga ttgttttttg tttgacaagt gctatctgtg
2221 ccactgattt aacttctgta gtaacaaggg cattaccatt cttcaccttt cctaattctg
2281 atcccatagt tttacatttt tcctgtttat tttgattttg ttcactgctt tatttcttaa
2341 agttctagca catctgtgac tcctccactt ccacattttt gcactgctta cacttacgtg
2401 caatcttatt ccttgtctgc acacacatgt ggaaagctag aaataaatgt taaaacttac
2461 tttttataaa cattttaata tgtagtttgg acatgattta ttgacttaag gttcttctct
2521 aaactggaag tgaaatgcat gccttctgaa gatgttctgg ctttgttaat tctgtaatca
2581 tttcattggg gaaaaaacca gctacgcagt ttttccaatg agtgaatttt ttcattttgt
2641 gttttgctta aaacggctcc ttcagggtag atgtcatact gcataacttt tttggattca
2701 aattatgaat gagaaattag ttaacattct gctccacaag gtaagaaaaa ctgctctttg
2761 gctctatttt caaaattact tctgagatgc atatagtctc aaaataacag ctttagtagg
2821 catatcactt cttgaaagcc aaacatgagt gtaagacact tttatgaaac acggtggatc
2881 cctaactggc tttcaaattg acctttatag ccttagacaa cccttaggta tttacggaga
2941 tgacttcttt gattgtcata acaattagtg gatgtgtcca gttctctgta tctttgactt
3001 gatgctttat acatcatttc atttgttgct tctaagggaa taagccatag aggcttctcc
3061 aggtttaaaa gaacagtaaa gtacctggaa aaccaacatt tttgaatgta tggacactgg
3121 acatgagata tgtacaatga aatcttaaaa gaatctaaga atttgccctc tttgccccac
3181 tccacccagt aatttgacat tactagtgcc atgtatagga cccaactgag tattagaatc
3241 agttttgact atgtctttgt atttcctaaa tcttttaatg cataaaccga attagggtcc
3301 agttggcctg ttaatggtaa atttacattt taaatgactc agtttgtttt tcctgggcga
3361 gtttgcaatg tgataatcag attttttaaa actgattaat ttgctttctt gtgtgggtgt
3421 actcacattt taaagtatga accacagtta actagtggtc tcaggggtag tgaaacactc
3481 acttttttt ttgtttgttt tttttgttt gttgaaatgg cttagttgaa gtatacttaa
3541 ggtactgatc atgctgtgtt agtaatttgg gcggggaggg gggtaactca gccatgtttt
3601 gtgttggcat aacaaaactg ttaatgattg ttgattacac ttttaagtga atttgtcttt
3661 tatgaggaac ccagtgcaag tcactaaata ttgtctaata gtgacatctg cataagactt
3721 gtaatagctg aagttaattg agcttaaagg aattgttacc attaaagtct gtgtttaaag
3781 acaaaaaaaa aaaaaaaa SEQ ID NO: 68 Human UBE2D3 Transcript Variant 7 cDNA Sequence
(NM_181891.2; CDS: 651-1094)
1 accaagtgag gaaactgggg gacgctgtgg ggaggggcgt ggggctggat cgcgcagcgg
61 ctgcttcctt taccttcctc ccatggtctc cttccggttc tcgatgcttc tctgagccta
121 agggtttccg ccactcgttc accctccccc cagctcatga tcctcctccc tcccccgccc
181 tcctggtcca atctccgatc tgtttagtaa gaaggtgctg ttccgagaag aaggaaaagg
241 gcttgacacg tattcactcg gccccggacg tgggaagcaa gccgtctggc ttcggcctca
301 catcggtctt gtgctcggga cggcggcgtt ggcggactga tccgcggcgg tgaagaggca
361 ggaggagggg gaggggcgga gcgtggcagc tggcagtagt tccgtcagag cggacatctt
421 gtggctgtgt cgtgcgcgtg agccccgtag ggccggggag gcaccagctg ccgcgcgggg
481 aggaggccga ggccgcagct tgagggaggc cccggcccct ctgcgcctgt gtctggcaga
541 gctggtgtga gacgagacaa tcctgccccg ccgccgggat aatcaagagt tttggccgga
601 cctttgagca tacaccgaga gagtgaggag ccagacgaca agcacacact atggcgctga
661 aacggattaa taaggaactt agtgatttgg cccgtgaccc tccagcacaa tgttctgcag
721 gtccagttgg ggatgatatg tttcattggc aagccacaat tatgggacct aatgacagcc
781 catatcaagg cggtgtattc tttttgacaa ttcattttcc tacagactac cccttcaaac
841 cacctaaggt tgcatttaca acaagaattt atcatccaaa tattaacagt aatggcagca
901 tttgtctcga tattctaaga tcacagtggt cgcctgcttt aacaatttct aaagttcttt
961 tatccatttg ttcactgcta tgtgatccaa acccagatga ccccctagtg ccagagattg
1021 cacggatcta taaaacagac agagataagt acaacagaat atctcgggaa tggactcaga
1081 agtatgccat gtgatgctac cttaaagtca gaataacctg cattatagct ggaataaact
1141 ttaaattact gttccttttt tgattttctt atccggctgc tcccctatca gacctcatct TABLE 1-continued

```
1201 tttttaattt tatttttgt ttacctccct ccattcattc acatgctcat ctgagaagac
1261 ttaagttctt ccagctttgg acaataactg cttttagaaa ctgtaaagta gttacaagag
1321 aacagttgcc caagactcag aatttttaaa aaaaaaaatg gagcatgtgt attatgtggc
1381 caatgtcttc actctaactt ggttatgaga ctaaaaccat tcctcactgc tctaacatgc
1441 tgaagaaatc atctgagggg gagggagatg gatgctcagt tgtcacatca aaggatacag
1501 cattattcta gcagcatcca ttcttgttta agccttccac tgttagagat ttgaggttac
1561 atgatatgct ttatgctcat aactgatgtg gctggagaat tggtattgaa tttatagcat
1621 cagcagaaca gaaaatgtga tgtattttat gcatgtcaat aaaggaatga cctgttcttg
1681 ttctacagag aatggaaatt ggaagtcaaa caccctttgt attccaaaat agggtctcaa
1741 acattttgta attttcattt aaattgttag gaggcttgga gctattagtt aatctatctt
1801 ccaatacact gtttaatata gcactgaata aatgatgcaa gttgtcaatg gatgagtgat
1861 caactaatag ctctgctagt aattgattta tttttcttca ataaagttgc ataaaccaat
1921 gagttagctg cctggattaa tcagtatggg aaacaatctt ttgtaaatgc aaagctgttt
1981 tttgtatata ctgttgggat ttgcttcatt gtttgacatc aaatgatgat gtaaagttcg
2041 aaagagtgaa tattttgcca tgttcagtta aagtgcacag tctgttacag gttgacacat
2101 tgcttgacct gatttatgca gaattaataa gctatttgga tagtgtagct ttaatgtgct
2161 gcacatgata ctggcagccc tagagttcat agatggactt ttgggaccca gcagttttga
2221 aatgtgttta tggagtttaa gaaatttatt ttccaggtgc agcccctgtc taactgaaat
2281 ttctcttcac cttgtacact tgacagctga aaaaaaacaa catgggagta ataatgggtc
2341 aaaatttgca aaataaagta ctgttttggt gtgggagttg tcatgaggct gtgttgaagt
2401 gacttatcta tgtgggatat tgagtatcca ttgaaatgga tttgttcagc catttacatt
2461 aatgagcatt taaatgcaac agatatcatt tcaggtgact taacatgaat gaataaaagt
2521 caatgctatt ggattgtttt ttgtttgaca agtgctatct gtgccactga tttaacttct
2581 gtagtaacaa gggcattacc attcttcacc tttcctaatt ctgatcccat agttttacat
2641 ttttcctgtt tattttgatt ttgttcactg ctttatttct taaagttcta gcacatctgt
2701 gactcctcca cttccacatt tttgcactgc ttacacttac gtgcaatctt attccttgtc
2761 tgcacacaca tgtggaaagc tagaaataaa tgttaaaact tactttttat aaacatttta
2821 atatgtagtt tggacatgat ttattgactt aaggttcttc tctaaactgg aagtgaaatg
2881 catgccttct gaagatgttc tggctttgtt aattctgtaa tcatttcatt ggggaaaaaa
2941 ccagctacgc agtttttcca atgagtgaat tttttcattt tgtgttttgc ttaaaacggc
3001 tccttcaggg tagatgtcat actgcataac tttttggat tcaaattatg aatgagaaat
3061 tagttaacat tctgctccac aaggtaagaa aaactgctct ttggctctat tttcaaaatt
3121 acttctgaga tgcatatagt ctcaaaataa cagctttagt aggcatatca cttcttgaaa
3181 gccaaacatg agtgtaagac acttttatga aacacggtgg atccctaact ggctttcaaa
3241 ttgaccttta tagccttaga caacccttag gtatttacgg agatgacttc tttgattgtc
3301 ataacaatta gtggatgtgt ccagttctct gtatctttga cttgatgctt tatacatcat
3361 ttcatttgtt gcttctaagg gaataagcca tagaggcttc tccaggttta aaagaacagt
3421 aaagtacctg gaaaaccaac atttttgaat gtatggacac tggacatgag atatgtacaa
3481 tgaaatctta aaagaatcta agaatttgcc ctctttgccc cactccaccc agtaatttga
3541 cattactagt gccatgtata ggacccaact gagtattaga atcagttttg actatgtctt
3601 tgtatttcct aaatctttta atgcataaac cgaattaggg tccagttggc ctgttaatgg
3661 taaatttaca ttttaaatga ctcagtttgt ttttcctggg cgagtttgca atgtgataat
3721 cagatttttt aaaactgatt aatttgcttt cttgtgtggg tgtactcaca ttttaaagta
3781 tgaaccacag ttaactagtg gtctcagggg tagtgaaaca ctcacttttt tttttgtttg
3841 tttttttttg tttgttgaaa tggcttagtt gaagtatact taaggtactg atcatgctgt
3901 gttagtaatt tgggcgggga ggggggtaac tcagccatgt tttgtgttgg cataacaaaa
3961 ctgttaatga ttgttgatta cacttttaag tgaatttgtc ttttatgagg aacccagtgc
4021 aagtcactaa atattgtcta atagtgacat ctgcataaga cttgtaatag ctgaagttaa
4081 ttgagcttaa aggaattgtt accattaaag tctgtgttta aagacaaaaa aaaaaaaaaa
4141 a
```

SEQ ID NO: 69 Human UBE2D3 Transcript Variant 8 cDNA Sequence (NM_181892.3; CDS: 676-1122)

```
   1 gggcgcgcgc gggagcgcgc tggaaggcgg agtgagtgta cggtggcgtc aggggtgaca
  61 cagaatagct cgctgcgagg atagcaatac acatcaagtc tcccttcctt tatttccttc
 121 cttttcccgg ccgcaccttt ggacagaaac cgaaagcagc ccggcgtccg tccggagtct
 181 tatgcttccc cctcccccct tgcctttctt tgccctagtg acgccggtat agcgccgact
 241 aggccccggc tcctcctctg ctgggctccg gaccctgccc cgcacccacc cctttctcct
 301 acgcctcttc ctctcccacc cgggtctctt cctttctaga ggccgggaag ttaaacttgt
 361 agccaccacc tccgctcttc ccgtcaccct cgccccccact tcgggccgaa agcacggtac
 421 agaggctgtt ggtggctttg ccacgccacc ccacccaccc cggatcgcgg ctgtcttaag
 481 ggacctggat tcatcagggg ctcttcgggg cctgtgcgag tgctgatctg ctccgttttt
 541 gcaaaaggcg cctgtgtctg gcagagctgg tgtgagacga gacaatcctg ccccgccgcc
 601 gggataatca agagttttgg ccggaccttt gagcatacac cgagagagtg aggagccaga
 661 cgacaagcac acactatggc gctgaaacgg attaataagg aacttagtga tttggcccgt
 721 gaccctccag cacaatgttc tgcaggtcca gttggggatg atatgtttca ttggcaagcc
 781 acaattatgg gacctaatga cagcccatat caaggcggtg tattcttttt gacaattcat
 841 tttcctacag actacccctt caaaccacct aaggttgcat ttacaacaag aatttatcat
 901 ccaaatatta acagtaatgg cagcatttgt ctcgatattc taagatcaca gtggtcgcct
 961 gctttaacaa tttctaaagt tcttttatcc atttgttcac tgctatgtga tccaaaccca
1021 gatgaccccc tagtgccaga gattgcacgg atctataaaa cagacagaga taagtacaat
1081 aggttagcaa gagagtggac agagaaatac gctatgttgt agggtacaac agaatatctc
1141 gggaatggac tcagaagtat gccatgtgat gctaccttaa agtcagaata acctgcatta
1201 tagctggaat aaactttaaa ttactgttcc tttttgatt ttcttatccg gctgctcccc
1261 tatcagacct catctttttt aattttattt tttgtttacc tccctccatt cattcacatg
1321 ctcatctgag aagacttaag ttcttccagc tttggacaat aactgctttt agaaactgta
1381 aagtagttac aagagaacag ttgcccaaga ctcagaattt ttaaaaaaaa aaatggagca
1441 tgtgtattat gtggccaatg tcttcactct aacttggtta tgagactaaa accattcctc
1501 actgctctaa catgctgaag aaatcatctg agggggaggg agatggatgc tcagttgtca
1561 catcaaagga tacagcatta ttctagcagc atccattctt gtttaagcct tccactgtta
```

TABLE 1-continued

```
1621 gagatttgag gttacatgat atgctttatg ctcataactg atgtggctgg agaattggta
1681 ttgaatttat agcatcagca gaacagaaaa tgtgatgtat tttatgcatg tcaataaagg
1741 aatgacctgt tcttgttcta cagagaatgg aaattggaag tcaaacaccc tttgtattcc
1801 aaaatagggt ctcaaacatt ttgtaatttt catttaaatt gttaggaggc ttggagctat
1861 tagttaatct atcttccaat acactgttta atatagcact gaataaatga tgcaagttgt
1921 caatggatga gtgatcaact aatagctctg ctagtaattg atttattttt cttcaataaa
1981 gttgcataaa ccaatgagtt agctgcctgg attaatcagt atgggaaaca atcttttgta
2041 aatgcaaagc tgttttttgt atatactgtt gggatttgct tcattgtttg acatcaaatg
2101 atgatgtaaa gttcgaaaga gtgaatattt tgccatgttc agttaaagtg cacagtctgt
2161 tacaggttga cacattgctt gacctgattt atgcagaatt aataagctat ttggatagtg
2221 tagctttaat gtgctgcaca tgatactggc agccctagag ttcatagatg gacttttggg
2281 acccagcagt tttgaaatgt gtttatggag tttaagaaat ttattttcca ggtgcagccc
2341 ctgtctaact gaaatttctc ttcaccttgt acacttgaca gctgaaaaaa aacaacatgg
2401 gagtaataat gggtcaaaat ttgcaaaata aagtactgtt ttggtgtggg agttgtcatg
2461 aggctgtgtt gaagtgactt atctatgtgg gatattgagt atccattgaa atggatttgt
2521 tcagccattt acattaatga gcatttaaat gcaacagata tcatttcagg tgacttaaca
2581 tgaatgaata aaagtcaatg ctattggatt gtttttgtt tgacaagtgc tatctgtgcc
2641 actgatttaa cttctgtagt aacaagggca ttaccattct tcacctttcc taattctgat
2701 cccatagttt tacatttttc ctgtttattt tgattttgtt cactgcttta tttcttaaag
2761 ttctagcaca tctgtgactc ctccacttcc acatttttgc actgcttaca cttacgtgca
2821 atcttattcc ttgtctgcac acacatgtgg aaagctagaa ataaatgtta aaacttactt
2881 tttataaaca ttttaatatg tagtttggac atgatttatt gacttaaggt tcttctctaa
2941 actggaagtg aaatgcatgc cttctgaaga tgttctggct ttgttaattc tgtaatcatt
3001 tcattgggga aaaaaccagc tacgcagttt ttccaatgag tgaatttttt cattttgtgt
3061 tttgcttaaa acggctcctt cagggtagat gtcatactgc ataacttttt tggattcaaa
3121 ttatgaatga gaaattagtt aacattctgc tccacaaggt aagaaaaact gctctttggc
3181 tctattttca aaattacttc tgagatgcat atagtctcaa aataacagct ttagtaggca
3241 tatcacttct tgaaagccaa acatgagtgt aagacacttt tatgaaacac ggtggatccc
3301 taactggctt tcaaattgac ctttatagcc ttagacaacc cttaggtatt tacggagatg
3361 acttctttga ttgtcataac aattagtgga tgtgtccagt tctctgtatc tttgacttga
3421 tgctttatac atcatttcat ttgttgcttc taagggaata agccatagag gcttctccag
3481 gtttaaaaga acagtaaagt acctggaaaa ccaacatttt tgaatgtatg gacactggac
3541 atgagatatg tacaatgaaa tcttaaaaga atctaagaat ttgccctctt tgccccactc
3601 cacccagtaa tttgacatta ctagtgccat gtataggacc caactgagta ttagaatcag
3661 ttttgactat gtctttgtat ttcctaaatc ttttaatgca taaaccgaat tagggtccag
3721 ttggcctgtt aatggtaaat ttacatttta aatgactcag tttgtttttc ctgggcgagt
3781 ttgcaatgtg ataatcagat tttttaaaac tgattaattt gctttcttgt gtgggtgtac
3841 tcacatttta aagtatgaac cacagttaac tagtggtctc aggggtagtg aaacactcac
3901 tttttttttt gtttgttttt ttttgtttgt tgaaatggct tagttgaagt atacttaagg
3961 tactgatcat gctgtgttag taatttgggc ggggaggggg gtaactcagc catgttttgt
4021 gttggcataa caaaactgtt aatgattgtt gattacactt ttaagtgaat ttgtctttta
4081 tgaggaaccc agtgcaagtc actaaatatt gtctaatagt gacatctgca taagacttgt
4141 aatagctgaa gttaattgag cttaaaggaa ttgttaccat taaagtctgt gtttaaagac
4201 aaaaaaaaaa aaaaaa
```

SEQ ID NO: 70 Human UBE2D3 Transcript Variant 9 cDNA Sequence
(NM_181893.2 CDS: 150-599)

```
   1 ggcggactgc cgaggcgcgg gaactggcgg gtagcgaggc cctcctcgga atctcgtgtg
  61 aaggtggccc tcctcttggg cctttaacgt ctgtagatgc tggagaccag cagaaaggat
 121 actgtgtgcg atgagataag catgtgagaa tgctttctaa ccgaaagtgc ctttcaaaag
 181 aacttagtga tttggcccgt gaccctccag cacaatgttc tgcaggtcca gttggggatg
 241 atatgtttca ttggcaagcc acaattatgg gacctaatga cagcccatat caaggcggtg
 301 tattcttttt gacaattcat tttcctacag actacccctt caaaccacct aaggttgcat
 361 ttacaacaag aatttatcat ccaaatatta acagtaatgg cagcatttgt ctcgatattc
 421 taagatcaca gtggtcgcct gctttaacaa tttctaaagt tcttttatcc atttgttcac
 481 tgctatgtga tccaaaccca gatgaccccc tagtgccaga gattgcacgg atctataaaa
 541 cagacagaga taagtacaac agaatatctc gggaatggac tcagaagtat gccatgtgat
 601 gctaccttaa agtcagaata acctgcatta tagctggaat aaactttaaa ttactgttcc
 661 tttttgatt ttcttatccg gctgctcccc tatcagacct catcttttt aattttattt
 721 tttgtttacc tccctccatt cattcacatg ctcatctgag aagacttaag ttcttccagc
 781 tttggacaat aactgctttt agaaactgta aagtagttac aagagaacag ttgcccaaga
 841 ctcagaattt ttaaaaaaaa aaatggagca tgtgtattat gtggccaatg tcttcactct
 901 aacttggtta tgagactaaa accattcctc actgctctaa catgctgaag aaatcatctg
 961 agggggaggg agatggatgc tcagttgtca catcaaagga tacagcatta ttctagcagc
1021 atccattctt gtttaagcct tccactgtta gagatttgag gttacatgat atgctttatg
1081 ctcataactg atgtggctgg agaattggta ttgaatttat agcatcagca gaacagaaaa
1141 tgtgatgtat tttatgcatg tcaataaagg aatgacctgt tcttgttcta cagagaatgg
1201 aaattggaag tcaaacaccc tttgtattcc aaaatagggt ctcaaacatt ttgtaatttt
1261 catttaaatt gttaggaggc ttggagctat tagttaatct atcttccaat acactgttta
1321 atatagcact gaataaatga tgcaagttgt caatggatga gtgatcaact aatagctctg
1381 ctagtaattg atttattttt cttcaataaa gttgcataaa ccaatgagtt agctgcctgg
1441 attaatcagt atgggaaaca atcttttgta aatgcaaagc tgttttttgt atatactgtt
1501 gggatttgct tcattgtttg acatcaaatg atgatgtaaa gttcgaaaga gtgaatattt
1561 tgccatgttc agttaaagtg cacagtctgt tacaggttga cacattgctt gacctgattt
1621 atgcagaatt aataagctat ttggatagtg tagctttaat gtgctgcaca tgatactggc
1681 agccctagag ttcatagatg gacttttggg acccagcagt tttgaaatgt gtttatggag
1741 tttaagaaat ttattttcca ggtgcagccc ctgtctaact gaaatttctc ttcaccttgt
1801 acacttgaca gctgaaaaaa aacaacatgg gagtaataat gggtcaaaat ttgcaaaata
1861 aagtactgtt ttggtgtggg agttgtcatg aggctgtgtt gaagtgactt atctatgtgg
1921 gatattgagt atccattgaa atggatttgt tcagccattt acattaatga gcatttaaat
```

TABLE 1-continued

```
1981 gcaacagata tcatttcagg tgacttaaca tgaatgaata aaagtcaatg ctattggatt
2041 gttttttgtt tgacaagtgc tatctgtgcc actgatttaa cttctgtagt aacaagggca
2101 ttaccattct tcacctttcc taattctgat cccatagttt tacatttttc ctgtttattt
2161 tgattttgtt cactgcttta tttcttaaag ttctagcaca tctgtgactc ctccacttcc
2221 acatttttgc actgcttaca cttacgtgca atcttattcc ttgtctgcac acacatgtgg
2281 aaagctagaa ataaatgtta aaacttactt tttataaaca ttttaatatg tagtttggac
2341 atgatttatt gacttaaggt tcttctctaa actggaagtg aaatgcatgc cttctgaaga
2401 tgttctggct ttgttaattc tgtaatcatt tcattgggga aaaaaccagc tacgcagttt
2461 ttccaatgag tgaatttttt cattttgtgt tttgcttaaa acggctcctt cagggtagat
2521 gtcatactgc ataacttttt tggattcaaa ttatgaatga gaaattagtt aacattctgc
2581 tccacaaggt aagaaaaact gctctttggc tctattttca aaattacttc tgagatgcat
2641 atagtctcaa aataacagct ttagtaggca tatcacttct tgaaagccaa acatgagtgt
2701 aagacacttt tatgaaacac ggtggatccc taactggctt tcaaattgac ctttatagcc
2761 ttagacaacc cttaggtatt tacggagatg acttctttga ttgtcataac aattagtgga
2821 tgtgtccagt tctctgtatc tttgacttga tgctttatac atcatttcat ttgttgcttc
2881 taagggaata agccatagag gcttctccag gtttaaaaga acagtaaagt acctggaaaa
2941 ccaacatttt tgaatgtatg gacactggac atgagatatg tacaatgaaa tcttaaaaga
3001 atctaagaat ttgccctctt tgccccactc cacccagtaa tttgacatta ctagtgccat
3061 gtataggacc caactgagta ttagaatcag ttttgactat gtctttgtat ttcctaaatc
3121 ttttaatgca taaaccgaat tagggtccag ttggcctgtt aatggtaaat ttacatttta
3181 aatgactcag tttgttttc ctgggcgagt ttgcaatgtg ataatcagat tttttaaaac
3241 tgattaattt gctttcttgt gtgggtgtac tcacatttta aagtatgaac cacagttaac
3301 tagtggtctc aggggtagtg aaacactcac ttttttttt gtttgttttt ttttgtttgt
3361 tgaaatggct tagttgaagt atacttaagg tactgatcat gctgtgttag taatttgggc
3421 ggggaggggg gtaactcagc catgttttgt gttggcataa caaaactgtt aatgattgtt
3481 gattacactt ttaagtgaat ttgtctttta tgaggaaccc agtgcaagtc actaaatatt
3541 gtctaatagt gacatctgca taagacttgt aatagctgaa gttaattgag cttaaaggaa
3601 ttgttaccat taaagtctgt gtttaaagac aaaaaaaaaa aaaaaa
```

SEQ ID NO: 71 Human UBE2D3 Transcript Variant 10 cDNA Sequence (NM_001300795.1; CDS: 266-622)

```
   1 agttgcagct tttcacccga agctatttat ccgagggaca ccgggaactg atgtaaaagg
  61 cattctggaa gctccctttt ccttttggct ggagagtggg ggtggataag gggtgcgatg
 121 gcaagggtgg agtgtttaca gctaacttga aaaaaatgtc atggaataaa ttcagcctta
 181 ctagaaaaat tgtggagtgt cggaacttag tgatttggcc cgtgaccctc cagcacaatg
 241 ttctgcaggt ccagttgggg atgatatgtt tcattggcaa gccacaatta tgggacctaa
 301 tgacagccca tatcaaggcg gtgtattctt tttgacaatt cattttccta cagactaccc
 361 cttcaaacca cctaaggttg catttacaac aagaatttat catccaaata ttaacagtaa
 421 tggcagcatt tgtctcgata ttctaagatc acagtggtcg cctgctttaa caatttctaa
 481 agttctttta tccatttgtt cactgctatg tgatccaaac ccagatgacc ccctagtgcc
 541 agagattgca cggatctata aaacagacag agataagtac aacagaatat ctcgggaatg
 601 gactcagaag tatgccatgt gatgctacct taaagtcaga ataacctgca ttatagctgg
 661 aataaacttt aaattactgt tcctttttg atttcttat ccggctgctc ccctatcaga
 721 cctcatcttt tttaatttta ttttttgttt acctccctcc attcattcac atgctcatct
 781 gagaagactt aagttcttcc agctttggac aataactgct tttagaaact gtaaagtagt
 841 tacaagagaa cagttgccca agactcagaa tttttaaaaa aaaaaatgga gcatgtgtat
 901 tatgtggcca atgtcttcac tctaacttgg ttatgagact aaaaccattc ctcactgctc
 961 taacatgctg aagaaatcat ctgaggggga gggagatgga tgctcagttg tcacatcaaa
1021 ggatacagca ttattctagc agcatccatt cttgtttaag ccttccactg ttagagattt
1081 gaggttacat gatatgcttt atgctcataa ctgatgtggc tggagaattg gtattgaatt
1141 tatagcatca gcagaacaga aaatgtgatg tattttatgc atgtcaataa aggaatgacc
1201 tgttcttgtt ctacagagaa tggaaattgg aagtcaaaca ccctttgtat tccaaaatag
1261 ggtctcaaac attttgtaat tttcatttaa attgttagga ggcttggagc tattagttaa
1321 tctatcttcc aatacactgt ttaatatagc actgaataaa tgatgcaagt tgtcaatgga
1381 tgagtgatca actaatagct ctgctagtaa ttgatttatt tttcttcaat aaagttgcat
1441 aaaccaatga gttagctgcc tggattaatc agtatgggaa acaatctttt gtaaatgcaa
1501 agctgttttt tgtatatact gttgggattt gcttcattgt ttgacatcaa atgatgatgt
1561 aaagttcgaa agagtgaata ttttgccatg ttcagttaaa gtgcacagtc tgttacaggt
1621 tgacacattg cttgacctga tttatgcaga attaataagc tatttggata gtgtagcttt
1681 aatgtgctgc acatgatact ggcagcccta gagttcatag atggactttt gggacccagc
1741 agttttgaaa tgtgtttatg gagtttaaga aatttatttt ccaggtgcag cccctgtcta
1801 actgaaattt ctcttcacct tgtacacttg acagctgaaa aaaaacaaca tgggagtaat
1861 aatgggtcaa aatttgcaaa ataaagtact gttttggtgt gggagttgtc atgaggctgt
1921 gttgaagtga cttatctatg tgggatattg agtatccatt gaaatggatt tgttcagcca
1981 tttacattaa tgagcattta aatgcaacag atatcatttc aggtgactta acatgaatga
2041 ataaaagtca atgctattgg attgtttttt gtttgacaag tgctatctgt gccactgatt
2101 taacttctgt agtaacaagg gcattaccat tcttcacctt tcctaattct gatcccatag
2161 ttttacattt ttcctgttta ttttgatttt gttcactgct ttatttctta aagttctagc
2221 acatctgtga ctcctccact tccacatttt tgcactgctt acacttacgt gcaatcttat
2281 tccttgtctg cacacacatg tggaaagcta gaaataaatg ttaaaactta ctttttataa
2341 acattttaat atgtagtttg gacatgattt attgacttaa ggttcttctc taaactggaa
2401 gtgaaatgca tgccttctga agatgttctg gctttgttaa ttctgtaatc atttcattgg
2461 ggaaaaaacc agctacgcag tttttccaat gagtgaattt tttcattttg tgttttgctt
2521 aaaacggctc cttcagggta gatgtcatac tgcataactt ttttggattc aaattatgaa
2581 tgagaaatta gttaacattc tgctccacaa ggtaagaaaa actgctcttt ggctctattt
2641 tcaaaattac ttctgagatg catatagtct caaaataaca gctttagtag gcatatcact
2701 tcttgaaagc caaacatgag tgtaagacac ttttatgaaa cacggtggat ccctaactgg
2761 ctttcaaatt gacctttata gccttagaca acccttaggt atttacggag atgacttctt
2821 tgattgtcat aacaattagt ggatgtgtcc agttctctgt atctttgact tgatgcttta
2881 tacatcattt catttgttgc ttctaaggga ataagccata gaggcttctc caggtttaaa
```

TABLE 1-continued

```
2941 agaacagtaa agtacctgga aaaccaacat ttttgaatgt atggacactg gacatgagat
3001 atgtacaatg aaatcttaaa agaatctaag aatttgccct ctttgcccca ctccacccag
3061 taatttgaca ttactagtgc catgtatagg acccaactga gtattagaat cagttttgac
3121 tatgtctttg tatttcctaa atcttttaat gcataaaccg aattagggtc cagttggcct
3181 gttaatggta aatttacatt ttaaatgact cagtttgttt ttcctgggcg agtttgcaat
3241 gtgataatca gatttttaa aactgattaa tttgcttttct tgtgtgggtg tactcacatt
3301 ttaaagtatg aaccacagtt aactagtggt ctcaggggta gtgaaacact cacttttttt
3361 tttgtttgtt ttttttgtt tgttgaaatg gcttagttga agtatactta aggtactgat
3421 catgctgtgt tagtaatttg ggcggggagg ggggtaactc agccatgttt tgtgttggca
3481 taacaaaact gttaatgatt gttgattaca cttttaagtg aatttgtctt ttatgaggaa
3541 cccagtgcaa gtcactaaat attgtctaat agtgacatct gcataagact tgtaatagct
3601 gaagttaatt gagcttaaag gaattgttac cattaaagtc tgtgtttaaa gacaaaaaaa
3661 aaaaaaaaa
```

SEQ ID NO: 72 Mouse UBE2D3 Transcript Variant 2 cDNA Sequence
(NM_001356594.1; CDS: 253-696)

```
   1 ggatttgggg gcgggtcccg agccaggaag agagcacaaa actgccctta agtcattgca
  61 gacccggagc tgctgcgagc ctgccacgag gttctcgcga gatccgccac ctccatccca
 121 agcgcctgtg tctggcagag ccggtgtgag aagaagagac aacccttccc cgccgccggg
 181 ataatcaaga attttggccg gacctttgag tacacctcgg gatagtgagg agcccggcga
 241 aaagcacaga ctatggcgct gaaacggatt aataaggaac ttagtgattt ggcccgtgac
 301 cctccagcac aatgttctgc aggtccagtt ggagatgaca tgtttcattg gcaagccaca
 361 attatgggac ctaatgacag cccatatcaa ggtggtgtat tctttttgac aattcatttt
 421 cctacagact accccttcaa accacctaag gttgcattta caacaagaat ttatcatcca
 481 aatattaaca gtaatggcag catttgtctt gatattctaa gatcacagtg gtctcctgct
 541 ttaactattt ctaaagttct tttatccatt tgttcactgc tatgtgatcc aaacccagac
 601 gacccccctag tgccagagat tgcacggatc tataaaacag acagagataa gtacaacaga
 661 atatctcggg aatggactca gaagtatgcc atgtgatgct accttacagt cagaataacc
 721 tgcattatag ctggaataaa ctttaaatta ctgttccttt tttgattttc ttatccggct
 781 gctcccctat cagacctcat cttttttaat tttattttt gtttacctcc ctccattcat
 841 tcacatgctc atctgagaag acttaagttc ttccagcttt ggacaataac tgcttttaga
 901 aactgtaaag tagttacacg agaacagttg cccaagattc agaaattttt ttaaaaactg
 961 gagcatgtgt attatgtggc caatgtcttc actctaactt ggttatgaga ctaaaccaat
1021 cctcactgct ctaacatgct gaagaagcca tctgaggggg agggagatgg atgctcagct
1081 gtcacatcaa aggaagcagc attattctag cagcatccgt tcttgtttaa accttccact
1141 gttagaggtt tgaggttaca tgatatactt tatgctcata actgatgtgg ctggagaatt
1201 ggtattgaat tatagcatca gcagaacaga aaatgtgatg tattttatgc atgtcaataa
1261 aggaatgacc tgttcttgtt ctacagagaa tggaaattgg aagtcaaaca ccctttgtat
1321 tccaaaatag ggtctcaaaa cattttgtaa ttttcattta aattgttagg aggcttggag
1381 ctattagtta atctatcttc caatactgtt taatatagca ctgaataaat gatgcgagtt
1441 gtcaatggat gagtgatcaa ctaatagctc tcctagtaat tgatttattt ttcttcaata
1501 aagttgcata aaccaatgag ttagctgcct ggattaatca gtatgggaaa caatcctttg
1561 taaatgcaaa gctgttttttg tatatactgt tgggatttgc ttcattgttt gacatcaaat
1621 gatgatgtaa agttcaaaag agtgaatata ttgccatgtt cagttaaaat gcacagtctg
1681 ttacaggttg acacattgct tgacctgatt tatgcagaat taataagcta ttcaaatagt
1741 gtagctttaa tacgctgcac atgattctgg cagccctaga gttcataaat ggacttggga
1801 ctcagcagtt ttgaaacgtg tatatggagt ttaagaaatt tattttccag gtgcatcccc
1861 ttctaactaa aatttcttc atcttgtaca cttaacagct gaaaaagata tatatatata
1921 taaaacttgg gagtaataat gggtcaaaat ttacaaaata aagtactgtt ttggtgtggg
1981 agttgtcatg aggctgtgtt gaagtgactt aactgtggga tattgactat ccattgagat
2041 ggatttgttc agccatttac attaatgagc atttaaatgc aacagatcat ttcgggtgac
2101 ttaacatgaa tgaataaaaa agtcaatgct attggattgt ttgacaagtg ctatctgtgc
2161 cactaaatct tatgtagtaa taagggcatt accatttttc acccaagttc tgaacctgta
2221 gtttgacacc tttttctagc tttgatttct ccattgcttt cttagtcttg tatttgattt
2281 ctagcacatg tgatgttcac ttccatattt tgcactgctt atatttacgt gcaatcttat
2341 tccttgtccg cacacagatg tggaaagcta gaaataaatg taaaagctta atttttttata
2401 aacatttaaa tatgtaattt ggacatgatt tgttacttaa ggttctttaa actggaagtg
2461 aagtgcatgc cttctgaaga tgttctggct ttattctgta ataagtattt acattggaaa
2521 ataccaattt cgctatacag tttttttttcc acacacccat tttaccttttt gcttaaattg
2581 tgggttcttc agggttaatg tcacgctaat taataaaact tttgggttca aatcaagtgt
2641 tcccacaagg gtaagaacag tattctttga ctcttaaaaa gtcctttctg agacctgtac
2701 tcaaaacagc tttattaggc ctgtgtcgtg aaagccagat atgacaaaca tttttacaaa
2761 gcagtggatc tctagttggc tttcaaattc ctcccatcta ccacctttgg tatttacaga
2821 gatgacgtcc ttaaaccatt gtcagaatta atgggtatgt ccagttctct ttatctttga
2881 cttgatgctt tatacaacat ttcatatgtc gcttctaagg gaataagcca tagaggcttc
2941 tccaggttta agagaacaga gtacctggaa aaccaacatt ctgaatgtat agacactgga
3001 ctggacttga ggtcacctat gatgaggttt ttaaaagaat ctaagaattt gctctctacc
3061 cttcccagta gtgtgtggca tcactagtgc tgggtatagg actaaagtga gtattaggtt
3121 gaatattgtt gtagagtatt tgtgtgtcct atacctctta atgcataaat tcctaaattt
3181 aaacatgtct ttagagtcca gttggcctgt caatggtgaa tttccttttg atttttttctt
3241 gggcaggttt gcaatgtgat aatcagattt tttttaact gattatagat tgtttccttg
3301 tgtgggtgta ctcacattta aaagtatgaa ccacggttaa ctagtggtct caggggtagt
3361 gaaacactca ctttttattt actgggttag ttgaagtatt cttaagacac tgatcatgct
3421 gtgttcgtga tttgggggggt gggtaatact aaaattagtc atgttttgtg ttcacataac
3481 aaaactgttc aatgactgtt ggttacactt ttaagtgaat ttgtctccta ttttatgagg
3541 aacccaatgc aagtcactaa atgtcttaat agtgacatct gcataagact tgtaatagct
3601 aaagttaatt gagcttaaag gaattgttac cattaaagtc tgtgtttaaa cacactttgg
3661 tcttactcag
```

TABLE 1-continued

SEQ ID NO: 73 Mouse UBE2D3 Isoform 1 Amino Acid Sequence
(NP_001343523.1)
1 MALKRINKEL SDLARDPPAQ CSAGPVGDDM FHWQATIMGP NDSPYQGGVF FLTIHFPTDY
61 PFKPPKVAFT TRIYHPNINS NGSICLDILR SQWSPALTIS KVLLSICSLL CDPNPDDPLV
121 PEIARIYKTD RDKYNRISRE WTQKYAM SEQ ID NO: 74 Mouse UBE2D3 Transcript Variant 3 cDNA Sequence
(NM_001356595.1; CDS: 249-692)
1 cacgaggttc tcgcgagatc cgccacctcc atcccaagtg aggaaacggg gggccactca
61 gggaggggcg tggggcctcg accgcgcagc tgccgcttcc attaccttcc tcctaaggcg
121 cctgtgtctg gcagagccgg tgtgagaaga agagacaacc cttccccgcc gccgggataa
181 tcaagaattt tggccggacc tttgagtaca cctcgggata gtgaggagcc cggcgaaaag
241 cacagactat ggcgctgaaa cggattaata aggaacttag tgatttggcc cgtgaccctc
301 cagcacaatg ttctgcaggt ccagttggag atgacatgtt tcattggcaa gccacaatta
361 tgggacctaa tgacagccca tatcaaggtg gtgtattctt tttgacaatt cattttccta
421 cagactaccc cttcaaacca cctaaggttg catttacaac aagaatttat catccaaata
481 ttaacagtaa tggcagcatt tgtcttgata ttctaagatc acagtggtct cctgctttaa
541 ctatttctaa agttctttta tccatttgtt cactgctatg tgatccaaac ccagacgacc
601 ccctagtgcc agagattgca cggatctata aaacagacag agataagtac aacagaatat
661 ctcgggaatg gactcagaag tatgccatgt gatgctacct tacagtcaga ataacctgca
721 ttatagctgg aataaacttt aaattactgt tcctttttg atttcttat ccggctgctc
781 ccctatcaga cctcatcttt tttaatttta tttttgttt acctccctcc attcattcac
841 atgctcatct gagaagactt aagttcttcc agctttggac aataactgct tttagaaact
901 gtaaagtagt tacacgagaa cagttgccca agattcagaa atttttttaa aaactggagc
961 atgtgtatta tgtggccaat gtcttcactc taacttggtt atgagactaa accaatcctc
1021 actgctctaa catgctgaag aagccatctg agggggaggg agatggatgc tcagctgtca
1081 catcaaagga agcagcatta ttctagcagc atccgttctt gtttaaacct tccactgtta
1141 gaggtttgag gttacatgat atactttatg ctcataactg atgtggctgg agaattggta
1201 ttgaattata gcatcagcag aacagaaaat gtgatgtatt ttatgcatgt caataaagga
1261 atgacctgtt cttgttctac agagaatgga aattggaagt caaacaccct ttgtattcca
1321 aaatagggtc tcaaaacatt ttgtaatttt catttaaatt gttaggaggc ttggagctat
1381 tagttaatct atcttccaat actgtttaat atagcactga ataaatgatg cgagttgtca
1441 atggatgagt gatcaactaa tagctctcct agtaattgat ttatttttct tcaataaagt
1501 tgcataaacc aatgagttag ctgcctggat taatcagtat gggaaacaat cctttgtaaa
1561 tgcaaagctg tttttgtata tactgttggg atttgcttca ttgtttgaca tcaaatgatg
1621 atgtaaagtt caaaagagtg aatatattgc catgttcagt taaaatgcac agtctgttac
1681 aggttgacac attgcttgac ctgatttatg cagaattaat aagctattca aatagtgtag
1741 ctttaatacg ctgcacatga ttctggcagc cctagagttc ataaatggac ttgggactca
1801 gcagttttga aacgtgtata tggagtttaa gaaatttatt ttccaggtgc atccccttct
1861 aactaaaatt ttcttcatct tgtacactta acagctgaaa aagatatata tatatataaa
1921 acttgggagt aataatgggt caaaatttac aaaataaagt actgttttgg tgtgggagtt
1981 gtcatgaggc tgtgttgaag tgacttaact gtgggatatt gactatccat tgagatggat
2041 ttgttcagcc atttacatta atgagcattt aaatgcaaca gatcatttcg ggtgacttaa
2101 catgaatgaa taaaaaagtc aatgctattg gattgtttga caagtgctat ctgtgccact
2161 aaatcttatg tagtaataag ggcattacca tttttcaccc aagttctgaa cctgtagttt
2221 gacacctttt tctagctttg atttctccat tgctttctta gtcttgtatt tgatttctag
2281 cacatgtgat gttcacttcc atattttgca ctgcttatat ttacgtgcaa tcttattcct
2341 tgtccgcaca cagatgtgga aagctagaaa taaatgtaaa agcttaattt tttataaaca
2401 tttaaatatg taatttggac atgatttgtt acttaaggtt ctttaaactg gaagtgaagt
2461 gcatgccttc tgaagatgtt ctggctttat tctgtaataa gtatttacat tggaaaatac
2521 caatttcgct atacagtttt ttttccacac acccatttta ccttttgctt aaattgtggg
2581 ttcttcaggg ttaatgtcac gctaattaat aaaacttttg ggttcaaatc aagtgttccc
2641 acaagggtaa gaacagtatt ctttgactct taaaaagtcc tttctgagac ctgtactcaa
2701 aacagcttta ttaggcctgt gtcgtgaaag ccagatatga caaacatttt tacaaagcag
2761 tggatctcta gttggctttc aaattcctcc catctaccac ctttggtatt tacagagatg
2821 acgtccttaa accattgtca gaattaatgg gtatgtccag ttctctttat ctttgacttg
2881 atgctttata caacatttca tatgtcgctt ctaagggaat aagccataga ggcttctcca
2941 ggtttaagag aacagagtac ctggaaaacc aacattctga atgtatagac actggactgg
3001 acttgaggtc acctatgatg aggtttttaa aagaatctaa gaatttgctc tctacccttc
3061 ccagtagtgt gtggcatcac tagtgctggg tataggacta aagtgagtat taggttgaat
3121 attgttgtag agtatttgtg tgtcctatac ctcttaatgc ataaattcct aaatttaaac
3181 atgtctttag agtccagttg gcctgtcaat ggtgaatttc cttttgattt tttcttgggc
3241 aggtttgcaa tgtgataatc agattttttt ttaactgatt atagattgtt tccttgtgtg
3301 ggtgtactca catttaaaag tatgaaccac ggttaactag tggtctcagg ggtagtgaaa
3361 cactcacttt ttatttactg ggttagttga agtattctta agacactgat catgctgtgt
3421 tcgtgatttg gggggtgggt aatactaaaa ttagtcatgt tttgtgttca cataacaaaa
3481 ctgttcaatg actgttggtt acacttttaa gtgaatttgt ctcctatttt atgaggaacc
3541 caatgcaagt cactaaatgt cttaatagtg acatctgcat aagacttgta atagctaaag
3601 ttaattgagc ttaaaggaat tgttaccatt aaagtctgtg tttaaacaca ctttggtctt
3661 actcag SEQ ID NO: 75 Mouse UBE2D3 Isoform 1 Amino Acid Sequence
(NP_001343524.1)
1 MALKRINKEL SDLARDPPAQ CSAGPVGDDM FHWQATIMGP NDSPYQGGVF FLTIHFPTDY
61 PFKPPKVAFT TRIYHPNINS NGSICLDILR SQWSPALTIS KVLLSICSLL CDPNPDDPLV
121 PEIARIYKTD RDKYNRISRE WTQKYAM TABLE 1-continued SEQ ID NO: 76 Mouse UBE2D3 Transcript Variant 1 cDNA Sequence
(NM_0013565961; CDS: 351-794)

```
   1 actcgcctac cctcccctc agcccatgac ccgcctccgt cccccgccct cccggcccga
  61 cctccgatcg ctttagcgag aaggtgctgt tccgacaggg agacggcaag cgggcggcac
 121 gtccactcgg cccgagcgag ggaagcaaac cgctcccccc tgaacccctc ggctcgcccc
 181 gcgctcgcga cggcggcgtt ggcggacgga tacgcggcgg cgcctgtgtc tggcagagcc
 241 ggtgtgagaa gaagagacaa cccttccccg ccgccgggat aatcaagaat tttggccgga
 301 cctttgagta cacctcggga tagtgaggag cccggcgaaa agcacagact atggcgctga
 361 aacggattaa taaggaactt agtgatttgg cccgtgaccc tccagcacaa tgttctgcag
 421 gtccagttgg agatgacatg tttcattggc aagccacaat tatgggacct aatgacagcc
 481 catatcaagg tggtgtattc tttttgacaa ttcattttcc tacagactac cccttcaaac
 541 cacctaaggt tgcatttaca acaagaattt atcatccaaa tattaacagt aatggcagca
 601 tttgtcttga tattctaaga tcacagtggt ctcctgcttt aactatttct aaagttcttt
 661 tatccatttg ttcactgcta tgtgatccaa acccagacga ccccctagtg ccagagattg
 721 cacggatcta taaaacagac agagataagt acaacagaat atctcgggaa tggactcaga
 781 agtatgccat gtgatgctac cttacagtca gaataacctg cattatagct ggaataaact
 841 ttaaattact gttccttttt tgattttctt atccggctgc tcccctatca gacctcatct
 901 tttttaattt tattttttgt ttacctccct ccattcattc acatgctcat ctgagaagac
 961 ttaagttctt ccagctttgg acaataactg cttttagaaa ctgtaaagta gttacacgag
1021 aacagttgcc caagattcag aaatttttt aaaaactgga gcatgtgtat tatgtggcca
1081 atgtcttcac tctaacttgg ttatgagact aaaccaatcc tcactgctct aacatgctga
1141 agaagccatc tgagggggag ggagatggat gctcagctgt cacatcaaag gaagcagcat
1201 tattctagca gcatccgttc ttgtttaaac cttccactgt tagaggtttg aggttacatg
1261 atatacttta tgctcataac tgatgtggct ggagaattgg tattgaatta tagcatcagc
1321 agaacagaaa atgtgatgta ttttatgcat gtcaataaag gaatgacctg ttcttgttct
1381 acagagaatg gaaattggaa gtcaaacacc ctttgtattc caaaataggg tctcaaaaca
1441 ttttgtaatt ttcatttaaa ttgttaggag gcttggagct attagttaat ctatcttcca
1501 atactgttta atatagcact gaataaatga tgcgagttgt caatggatga gtgatcaact
1561 aatagctctc ctagtaattg atttattttt cttcaataaa gttgcataaa ccaatgagtt
1621 agctgcctgg attaatcagt atgggaaaca atcctttgta aatgcaaagc tgtttttgta
1681 tatactgttg ggatttgctt cattgtttga catcaaatga tgatgtaaag ttcaaaagag
1741 tgaatatatt gccatgttca gttaaaatgc acagtctgtt acaggttgac acattgcttg
1801 acctgattta tgcagaatta ataagctatt caaatagtgt agctttaata cgctgcacat
1861 gattctggca gccctagagt tcataaatgg acttgggact cagcagtttt gaaacgtgta
1921 tatggagttt aagaaattta ttttccaggt gcatcccctt ctaactaaaa ttttcttcat
1981 cttgtacact taacagctga aaaagatata tatatatata aaacttggga gtaataatgg
2041 gtcaaaattt acaaaataaa gtactgtttt ggtgtgggag ttgtcatgag gctgtgttga
2101 agtgacttaa ctgtgggata ttgactatcc attgagatgg atttgttcag ccatttacat
2161 taatgagcat ttaaatgcaa cagatcattt cgggtgactt aacatgaatg aataaaaaag
2221 tcaatgctat tggattgttt gacaagtgct atctgtgcca ctaaatctta tgtagtaata
2281 agggcattac catttttcac ccaagttctg aacctgtagt ttgacacctt tttctagctt
2341 tgatttctcc attgctttct tagtcttgta tttgatttct agcacatgtg atgttcactt
2401 ccatatttg cactgcttat atttacgtgc aatcttattc cttgtccgca cacagatgtg
2461 gaaagctaga aataaatgta aaagcttaat tttttataaa catttaaata tgtaatttgg
2521 acatgatttg ttacttaagg ttctttaaac tggaagtgaa gtgcatgcct tctgaagatg
2581 ttctggcttt attctgtaat aagtatttac attggaaaat accaatttcg ctatacagtt
2641 ttttttccac acacccattt taccttttgc ttaaattgtg ggttcttcag ggttaatgtc
2701 acgctaatta ataaaacttt tgggttcaaa tcaagtgttc ccacaagggt aagaacagta
2761 ttctttgact cttaaaaagt cctttctgag acctgtactc aaaacagctt tattaggcct
2821 gtgtcgtgaa agccagatat gacaaacatt tttacaaagc agtggatctc tagttggctt
2881 tcaaattcct cccatctacc acctttggta tttacagaga tgacgtcctt aaaccattgt
2941 cagaattaat gggtatgtcc agttctcttt atctttgact tgatgcttta tacaacattt
3001 catatgtcgc ttctaaggga ataagccata gaggcttctc caggtttaag agaacagagt
3061 acctggaaaa ccaacattct gaatgtatag acactggact ggacttgagg tcacctatga
3121 tgaggttttt aaaagaatct aagaatttgc tctctaccct tcccagtagt gtgtggcatc
3181 actagtgctg ggtataggac taaagtgagt attaggttga atattgttgt agagtatttg
3241 tgtgtcctat acctcttaat gcataaattc ctaaatttaa acatgtcttt agagtccagt
3301 tggcctgtca atggtgaatt tccttttgat tttttcttgg gcaggtttgc aatgtgataa
3361 tcagattttt ttttaactga ttatagattg tttccttgtg tgggtgtact cacatttaaa
3421 agtatgaacc acggttaact agtggtctca ggggtagtga aacactcact ttttatttac
3481 tgggttagtt gaagtattct taagacactg atcatgctgt gttcgtgatt tggggggtgg
3541 gtaatactaa aattagtcat gttttgtgtt cacataacaa aactgttcaa tgactgttgg
3601 ttacactttt aagtgaattt gtctcctatt ttatgaggaa cccaatgcaa gtcactaaat
3661 gtcttaatag tgacatctgc ataagacttg taatagctaa agttaattga gcttaaagga
3721 attgttacca ttaaagtctg tgtttaaaca cactttggtc ttactcag
```

SEQ ID NO: 77 Mouse UBE2D3 Isoform 1 Amino Acid Sequence
(NP_001343525.1)

```
   1 MALKRINKEL SDLARDPPAQ CSAGPVGDDM FHWQATIMGP NDSPYQGGVF FLTIHFPTDY
  61 PFKPPKVAFT TRIYHPNINS NGSICLDILR SQWSPALTIS KVLLSICSLL CDPNPDDPLV
 121 PEIARIYKTD RDKYNRISRE WTQKYAM
```

SEQ ID NO: 78 Mouse UBE2D3 Transcript Variant 5 cDNA Sequence
(NM_001356597.1; CDS: 650-1093)

```
   1 gcgctgcgag gcggagagta cggtggtgtc aggggcgacc cagaacagcc ctcgccgtgg
  61 ggacgggagc gcacccgggg cccattgcct tgtgctggct cgctgtccct tggagccgaa
 121 accgaaagga gcccggcgtc ggtccggagc cgcccgctcc cctccccctt gcctttctct
 181 gcccgagtga cgccggccta gcgccgacta ggccccggct cctcctctgc ccggctctgg
 241 accctgcccc gcacccaccc ctttctcctc cgcctcttcc tctcccaccc ggggctcgtc
```

TABLE 1-continued

```
 301 ttcctttcaa gaggccggga agttaaactt gtaaccacct ctcggcgctt cccgtcaccc
 361 tctcgccctc tctggggcga agcgcggatc tcggtagctg gtggctccgc caccccgccc
 421 cgccctgccg ggatcgcggc ggttttcagg gttctggagt cagcagggtt tctccgaggc
 481 cctggcgagt cgctgacctg ctccgttttt gcaaaaaggc gcctgtgtct ggcagagccg
 541 gtgtgagaag aagagacaac ccttccccgc cgcccgggata atcaagaatt ttggccggac
 601 ctttgagtac acctcgggat agtgaggagc ccggcgaaaa gcacagacta tggcgctgaa
 661 acggattaat aaggaactta gtgatttggc ccgtgaccct ccagcacaat gttctgcagg
 721 tccagttgga gatgacatgt ttcattggca agccacaatt atgggaccta atgacagccc
 781 atatcaaggt ggtgtattct ttttgacaat tcattttcct acagactacc ccttcaaacc
 841 acctaaggtt gcatttacaa caagaattta tcatccaaat attaacagta atggcagcat
 901 ttgtcttgat attctaagat cacagtggtc tcctgcttta actatttcta aagttctttt
 961 atccatttgt tcactgctat gtgatccaaa cccagacgac cccctagtgc cagagattgc
1021 acggatctat aaaacagaca gagataagta caacagaata tctcgggaat ggactcagaa
1081 gtatgccatg tgatgctacc ttacagtcag aataacctgc attatagctg gaataaactt
1141 taaattactg ttcctttttt gattttctta tccggctgct cccctatcag acctcatctt
1201 ttttaatttt attttttgtt tacctccctc cattcattca catgctcatc tgagaagact
1261 taagttcttc cagctttgga caataactgc ttttagaaac tgtaaagtag ttacacgaga
1321 acagttgccc aagattcaga aatttttta aaaactggag catgtgtatt atgtggccaa
1381 tgtcttcact ctaacttggt tatgagacta aaccaatcct cactgctcta acatgctgaa
1441 gaagccatct gagggggagg gagatggatg ctcagctgtc acatcaaagg aagcagcatt
1501 attctagcag catccgttct tgtttaaacc ttccactgtt agaggtttga ggttacatga
1561 tatactttat gctcataact gatgtggctg gagaattggt attgaattat agcatcagca
1621 gaacagaaaa tgtgatgtat tttatgcatg tcaataaagg aatgacctgt tcttgttcta
1681 cagagaatgg aaattggaag tcaaacaccc tttgtattcc aaaatagggt ctcaaaacat
1741 tttgtaattt tcatttaaat tgttaggagg cttggagcta ttagttaatc tatcttccaa
1801 tactgtttaa tatagcactg aataaatgat gcgagttgtc aatggatgag tgatcaacta
1861 atagctctcc tagtaattga tttattttc ttcaataaag ttgcataaac caatgagtta
1921 gctgcctgga ttaatcagta tgggaaacaa tcctttgtaa atgcaaagct gtttttgtat
1981 atactgttgg gatttgcttc attgtttgac atcaaatgat gatgtaaagt tcaaaagagt
2041 gaatatattg ccatgttcag ttaaaatgca cagtctgtta caggttgaca cattgcttga
2101 cctgatttat gcagaattaa taagctattc aaatagtgta gctttaatac gctgcacatg
2161 attctggcag ccctagagtt cataaatgga cttgggactc agcagttttg aaacgtgtat
2221 atggagttta agaaatttat tttccaggtg catccccttc taactaaaat tttcttcatc
2281 ttgtacactt aacagctgaa aaagatatat atatatataa aacttgggag taataatggg
2341 tcaaaattta caaaataaag tactgttttg gtgtgggagt tgtcatgagg ctgtgttgaa
2401 gtgacttaac tgtgggatat tgactatcca ttgagatgga tttgttcagc catttacatt
2461 aatgagcatt taaatgcaac agatcatttc gggtgactta acatgaatga ataaaaaagt
2521 caatgctatt ggattgtttg acaagtgcta tctgtgccac taaatcttat gtagtaataa
2581 gggcattacc atttttcacc caagttctga acctgtagtt tgacaccttt ttctagcttt
2641 gatttctcca ttgctttctt agtcttgtat ttgatttcta gcacatgtga tgttcacttc
2701 catattttgc actgcttata tttacgtgca atcttattcc ttgtccgcac acagatgtgg
2761 aaagctagaa ataaatgtaa aagcttaatt ttttataaac atttaaatat gtaatttgga
2821 catgatttgt tacttaaggt tctttaaact ggaagtgaag tgcatgcctt ctgaagatgt
2881 tctggcttta ttctgtaata agtatttaca ttggaaaata ccaatttcgc tatacagttt
2941 tttttccaca cacccatttt accttttgct taaattgtgg gttcttcagg gttaatgtca
3001 cgctaattaa taaaactttt gggttcaaat caagtgttcc cacaagggta agaacagtat
3061 tctttgactc ttaaaaagtc ctttctgaga cctgtactca aaacagcttt attaggcctg
3121 tgtcgtgaaa gccagatatg acaaacattt ttacaaagca gtggatctct agttggcttt
3181 caaattcctc ccatctacca cctttggtat ttacagagat gacgtcctta aaccattgtc
3241 agaattaatg ggtatgtcca gttctcttta tctttgactt gatgctttat acaacatttc
3301 atatgtcgct tctaagggaa taagccatag aggcttctcc aggtttaaga gaacagagta
3361 cctggaaaac caacattctg aatgtataga cactggactg gacttgaggt cacctatgat
3421 gaggttttta aaagaatcta agaatttgct ctctaccctt cccagtagtg tgtggcatca
3481 ctagtgctgg gtataggact aaagtgagta ttaggttgaa tattgttgta gagtatttgt
3541 gtgtcctata cctcttaatg cataaattcc taaatttaaa catgtcttta gagtccagtt
3601 ggcctgtcaa tggtgaattt ccttttgatt ttttcttggg caggtttgca atgtgataat
3661 cagatttttt tttaactgat tatagattgt ttccttgtgt gggtgtactc acatttaaaa
3721 gtatgaacca cggttaacta gtggtctcag gggtagtgaa acactcactt tttatttact
3781 gggttagttg aagtattctt aagacactga tcatgctgtg ttcgtgattt gggggggtggg
3841 taatactaaa attagtcatg ttttgtgttc acataacaaa actgttcaat gactgttggt
3901 tacactttta agtgaatttg tctcctattt tatgaggaac ccaatgcaag tcactaaatg
3961 tcttaatagt gacatctgca taagacttgt aatagctaaa gttaattgag cttaaaggaa
4021 ttgttaccat taaagtctgt gtttaaacac actttggtct tactcag
```

SEQ ID NO: 79 Mouse UBE2D3 Isoform 1 Amino Acid Sequence
(NP_001343526.1)

```
  1 MALKRINKEL SDLARDPPAQ CSAGPVGDDM FHWQATIMGP NDSPYQGGVF FLTIHFPTDY
 61 PFKPPKVAFT TRIYHPNINS NGSICLDILR SQWSPALTIS KVLLSICSLL CDPNPDDPLV
121 PEIARIYKTD RDKYNRISRE WTQKYAM
```

SEQ ID NO: 80 Mouse UBE2D3 Transcript Variant 6 cDNA Sequence
(NM_001356598.1; CDS: 448-783)

```
  1 gaataggcgg ggggaggggc ggagcgtggc agctggcagt agttccgtca gagcggacat
 61 cttgtggctg tgccgtgcgc gtgagccccg tagggccggg gaggcaccag ctgccgcgcg
121 gggaggaggc cgaggccgca gctcgaggga ggccccggcc ctctgcgcct gtgtctggca
181 gagccggtgt gagaagaaga gacaaccctt ccccgccgcc gggataatca agaattttgg
241 ccggaccttt gagtacacct cgggatagtg aggagcccgg cgaaaagcac agactatggc
301 gctgaaacgg attaataagg aacttagtga tttggcccgt gaccctccag cacaatgttc
361 tgcaggtcca gttggagatg acatgtttca ttggcaagcc acaattatgg gacctctcaa
421 tgaaagtgag caagcacctg ctgtgtgatg aggataaaga atgacagccc atatcaaggt
```

TABLE 1-continued

```
 481 ggtgtattct ttttgacaat tcattttcct acagactacc ccttcaaacc acctaaggtt
 541 gcatttacaa caagaattta tcatccaaat attaacagta atggcagcat ttgtcttgat
 601 attctaagat cacagtggtc tcctgcttta actatttcta aagttctttt atccatttgt
 661 tcactgctat gtgatccaaa cccagacgac cccctagtgc cagagattgc acggatctat
 721 aaaacagaca gagataagta caacagaata tctcgggaat ggactcagaa gtatgccatg
 781 tgatgctacc ttacagtcag aataacctgc attatagctg gaataaactt taaattactg
 841 ttcctttttt gattttctta tccggctgct cccctatcag acctcatctt ttttaatttt
 901 atttttttgtt tacctccctc cattcattca catgctcatc tgagaagact taagttcttc
 961 cagctttgga caataactgc ttttagaaac tgtaaagtag ttacacgaga acagttgccc
1021 aagattcaga aattttttta aaaactggag catgtgtatt atgtggccaa tgtcttcact
1081 ctaacttggt tatgagacta aaccaatcct cactgctcta acatgctgaa gaagccatct
1141 gagggggagg gagatggatg ctcagctgtc acatcaaagg aagcagcatt attctagcag
1201 catccgttct tgtttaaacc ttccactgtt agaggtttga ggttacatga tatactttat
1261 gctcataact gatgtggctg gagaattggt attgaattat agcatcagca gaacagaaaa
1321 tgtgatgtat tttatgcatg tcaataaagg aatgacctgt tcttgttcta cagagaatgg
1381 aaattggaag tcaaacaccc tttgtattcc aaaatagggt ctcaaaacat tttgtaattt
1441 tcatttaaat tgttaggagg cttggagcta ttagttaatc tatcttccaa tactgtttaa
1501 tatagcactg aataaatgat gcgagttgtc aatggatgag tgatcaacta atagctctcc
1561 tagtaattga tttatttttc ttcaataaag ttgcataaac caatgagtta gctgcctgga
1621 ttaatcagta tgggaaacaa tcctttgtaa atgcaaagct gtttttgtat atactgttgg
1681 gatttgcttc attgtttgac atcaaatgat gatgtaaagt tcaaaagagt gaatatattg
1741 ccatgttcag ttaaaatgca cagtctgtta caggttgaca cattgcttga cctgatttat
1801 gcagaattaa taagctattc aaatagtgta gctttaatac gctgcacatg attctggcag
1861 ccctagagtt cataaatgga cttgggactc agcagttttg aaacgtgtat atggagttta
1921 agaaatttat tttccaggtg catccccttc taactaaaat tttcttcatc ttgtacactt
1981 aacagctgaa aaagatatat atatatataa aacttgggag taataatggg tcaaaattta
2041 caaaataaag tactgttttg gtgtgggagt tgtcatgagg ctgtgttgaa gtgacttaac
2101 tgtgggatat tgactatcca ttgagatgga tttgttcagc catttacatt aatgagcatt
2161 taaatgcaac agatcatttc gggtgactta acatgaatga ataaaaaagt caatgctatt
2221 ggattgtttg acaagtgcta tctgtgccac taaatcttat gtagtaataa gggcattacc
2281 atttttcacc caagttctga acctgtagtt tgacaccttt ttctagcttt gatttctcca
2341 ttgctttctt agtcttgtat ttgatttcta gcacatgtga tgttcacttc catattttgc
2401 actgcttata tttacgtgca atcttattcc ttgtccgcac acagatgtgg aaagctagaa
2461 ataaatgtaa aagcttaatt ttttataaac atttaaatat gtaatttgga catgatttgt
2521 tacttaaggt tctttaaact ggaagtgaag tgcatgcctt ctgaagatgt tctggcttta
2581 ttctgtaata agtatttaca ttggaaaata ccaatttcgc tatacagttt tttttccaca
2641 cacccatttt accttttgct taaattgtgg gttcttcagg gttaatgtca cgctaattaa
2701 taaaactttt gggttcaaat caagtgttcc cacaagggta agaacagtat tctttgactc
2761 ttaaaaagtc ctttctgaga cctgtactca aaacagcttt attaggcctg tgtcgtgaaa
2821 gccagatatg acaaacattt ttacaaagca gtggatctct agttggcttt caaattcctc
2881 ccatctacca cctttggtat ttacagagat gacgtcctta aaccattgtc agaattaatg
2941 ggtatgtcca gttctcttta tctttgactt gatgctttat acaacatttc atatgtcgct
3001 tctaagggaa taagccatag aggcttctcc aggtttaaga gaacagagta cctggaaaac
3061 caacattctg aatgtataga cactggactg gacttgaggt cacctatgat gaggttttta
3121 aaagaatcta agaatttgct ctctaccctt cccagtagtg tgtggcatca ctagtgctgg
3181 gtataggact aaagtgagta ttaggttgaa tattgttgta gagtatttgt gtgtcctata
3241 cctcttaatg cataaattcc taaatttaaa catgtcttta gagtccagtt ggcctgtcaa
3301 tggtgaattt cctttttgatt ttttcttggg caggtttgca atgtgataat cagatttttt
3361 tttaactgat tatagattgt ttccttgtgt gggtgtactc acatttaaaa gtatgaacca
3421 cggttaacta gtggtctcag gggtagtgaa acactcactt tttatttact gggttagttg
3481 aagtattctt aagacactga tcatgctgtg ttcgtgattt ggggggtggg taatactaaa
3541 attagtcatg ttttgtgttc acataacaaa actgttcaat gactgttggt tacactttta
3601 agtgaatttg tctcctattt tatgaggaac ccaatgcaag tcactaaatg tcttaatagt
3661 gacatctgca taagacttgt aatagctaaa gttaattgag cttaaaggaa ttgttaccat
3721 taaagtctgt gtttaaacac actttggtct tactcag
```

SEQ ID NO: 81 Mouse UBE2D3 Isoform 2 Amino Acid Sequence (NP_001343527.1)

```
 1 MRIKNDSPYQ GGVFFLTIHF PTDYPFKPPK VAFTTRIYHP NINSNGSICL DILRSQWSPA
61 LTISKVLLSI CSLLCDPNPD DPLVPEIARI YKTDRDKYNR ISREWTQKYA M
```

SEQ ID NO: 82 Mouse UBE2D3 Transcript Variant 1 cDNA Sequence (NM_025356.5 CDS: 296-739)

```
  1 gaataggcgg ggggaggggc ggagcgtggc agctggcagt agttccgtca gagcggacat
 61 cttgtggctg tgccgtgcgc gtgagccccg tagggccggg gaggcaccag ctgccgcgcg
121 gggaggaggc cgaggccgca gctcgaggga ggccccggcc ctctgcgcct gtgtctggca
181 gagccggtgt gagaagaaga gacaaccctt ccccgccgcc gggataatca agaattttgg
241 ccggaccttt gagtacacct cgggatagtg aggagcccgg cgaaaagcac agactatggc
301 gctgaaacgg attaataagg aacttagtga tttggcccgt gaccctccag cacaatgttc
361 tgcaggtcca gttggagatg acatgtttca ttggcaagcc acaattatgg gacctaatga
421 cagcccatat caaggtggtg tattcttttt gacaattcat ttttcctacag actacccctt
481 caaaccacct aaggttgcat ttacaacaag aatttatcat ccaaatatta acagtaatgg
541 cagcatttgt cttgatattc taagatcaca gtggtctcct gctttaacta tttctaaagt
601 tcttttatcc atttgttcac tgctatgtga tccaaaccca gacgaccccc tagtgccaga
661 gattgcacgg atctataaaa cagacagaga taagtacaac agaatatctc gggaatggac
721 tcagaagtat gccatgtgat gctaccttac agtcagaata acctgcatta tagctggaat
781 aaactttaaa ttactgttcc tttttgatt ttcttatccg gctgctcccc tatcagacct
841 catctttttt aattttattt tttgtttacc tccctccatt cattcacatg ctcatctgag
901 aagacttaag ttcttccagc tttggacaat aactgctttt agaaactgta aagtagttac
961 acgagaacag ttgcccaaga ttcagaaatt tttttaaaaa ctggagcatg tgtattatgt
```

TABLE 1-continued

```
1021 ggccaatgtc ttcactctaa cttggttatg agactaaacc aatcctcact gctctaacat
1081 gctgaagaag ccatctgagg gggagggaga tggatgctca gctgtcacat caaaggaagc
1141 agcattattc tagcagcatc cgttcttgtt taaaccttcc actgttagag gtttgaggtt
1201 acatgatata ctttatgctc ataactgatg tggctggaga attggtattg aattatagca
1261 tcagcagaac agaaaatgtg atgtatttta tgcatgtcaa taaaggaatg acctgttctt
1321 gttctacaga gaatggaaat tggaagtcaa acaccctttg tattccaaaa tagggtctca
1381 aaacattttg taattttcat ttaaattgtt aggaggcttg gagctattag ttaatctatc
1441 ttccaatact gtttaatata gcactgaata aatgatgcga gttgtcaatg gatgagtgat
1501 caactaatag ctctcctagt aattgattta tttttcttca ataaagttgc ataaaccaat
1561 gagttagctg cctggattaa tcagtatggg aaacaatcct ttgtaaatgc aaagctgttt
1621 ttgtatatac tgttgggatt tgcttcattg tttgacatca aatgatgatg taaagttcaa
1681 aagagtgaat atattgccat gttcagttaa aatgcacagt ctgttacagg ttgacacatt
1741 gcttgacctg atttatgcag aattaataag ctattcaaat agtgtagctt taatacgctg
1801 cacatgattc tggcagccct agagttcata aatggacttg ggactcagca gttttgaaac
1861 gtgtatatgg agtttaagaa atttattttc caggtgcatc cccttctaac taaaattttc
1921 ttcatcttgt acacttaaca gctgaaaaag atatatatat atataaaact tgggagtaat
1981 aatgggtcaa aatttacaaa ataaagtact gttttggtgt gggagttgtc atgaggctgt
2041 gttgaagtga cttaactgtg ggatattgac tatccattga gatggatttg ttcagccatt
2101 tacattaatg agcatttaaa tgcaacagat catttcgggt gacttaacat gaatgaataa
2161 aaaagtcaat gctattggat tgtttgacaa gtgctatctg tgccactaaa tcttatgtag
2221 taataagggc attaccattt ttcacccaag ttctgaacct gtagtttgac acctttttct
2281 agctttgatt tctccattgc tttcttagtc ttgtatttga tttctagcac atgtgatgtt
2341 cacttccata ttttgcactg cttatattta cgtgcaatct tattccttgt ccgcacacag
2401 atgtggaaag ctagaaataa atgtaaaagc ttaatttttt ataaacattt aaatatgtaa
2461 tttggacatg atttgttact taaggttctt taaactggaa gtgaagtgca tgccttctga
2521 agatgttctg gctttattct gtaataagta tttacattgg aaaataccaa tttcgctata
2581 cagttttttt tccacacacc cattttacct tttgcttaaa ttgtgggttc ttcagggtta
2641 atgtcacgct aattaataaa acttttgggt tcaaatcaag tgttcccaca agggtaagaa
2701 cagtattctt tgactcttaa aaagtccttt ctgagacctg tactcaaaac agctttatta
2761 ggcctgtgtc gtgaaagcca gatatgacaa acatttttac aaagcagtgg atctctagtt
2821 ggctttcaaa ttcctcccat ctaccacctt tggtatttac agagatgacg tccttaaacc
2881 attgtcagaa ttaatgggta tgtccagttc tctttatctt tgacttgatg ctttatacaa
2941 catttcatat gtcgcttcta agggaataag ccatagaggc ttctccaggt ttaagagaac
3001 agagtacctg gaaaaccaac attctgaatg tatagacact ggactggact tgaggtcacc
3061 tatgatgagg tttttaaaag aatctaagaa tttgctctct acccttccca gtagtgtgtg
3121 gcatcactag tgctgggtat aggactaaag tgagtattag gttgaatatt gttgtagagt
3181 atttgtgtgt cctatacctc ttaatgcata aattcctaaa tttaaacatg tctttagagt
3241 ccagttggcc tgtcaatggt gaatttcctt ttgatttttt cttgggcagg tttgcaatgt
3301 gataatcaga tttttttta actgattata gattgtttcc ttgtgtgggt gtactcacat
3361 ttaaaagtat gaaccacggt taactagtgg tctcaggggt agtgaaacac tcacttttta
3421 tttactgggt tagttgaagt attcttaaga cactgatcat gctgtgttcg tgatttgggg
3481 ggtgggtaat actaaaatta gtcatgtttt gtgttcacat aacaaaactg ttcaatgact
3541 gttggttaca cttttaagtg aatttgtctc ctattttatg aggaacccaa tgcaagtcac
3601 taaatgtctt aatagtgaca tctgcataag acttgtaata gctaaagtta attgagctta
3661 aaggaattgt taccattaaa gtctgtgttt aaacacactt tggtcttact cag
```

SEQ ID NO: 83 Mouse UBE2D3 Isoform 2 Amino Acid Sequence (NP_079632.1)

```
 1 MRIKNDSPYQ GGVFFLTIHF PTDYPFKPPK VAFTTRIYHP NINSNGSICL DILRSQWSPA
61 LTISKVLLSI CSLLCDPNPD DPLVPEIARI YKTDRDKYNR ISREWTQKYA M
```

SEQ ID NO: 84 Human PPM1D cDNA Sequence (NM_003620.3; CDS: 233-2050)

```
   1 ggggaagcgc agtgcgcagg cgcaactgcc tggctctgct cgctccggcg ctccggccca
  61 gctctcgcgg acaagtccag acatcgcgcg cccccccttc tccgggtccg cccccctccc
 121 cttctcggcg tcgtcgaaga taaacaatag ttggccggcg agcgcctagt gtgtctcccg
 181 ccgccggatt cggcgggctg cgtgggaccg gcgggatccc ggccagccgg ccatggcggg
 241 gctgtactcg ctgggagtga gcgtcttctc cgaccagggc gggaggaagt acatggagga
 301 cgttactcaa atcgttgtgg agcccgaacc gacggctgaa gaaaagccct cgccgcggcg
 361 gtcgctgtct cagccgttgc ctccgcggcc gtcgccggcc gcccttcccg gcggcgaagt
 421 ctcggggaaa ggcccagcgg tggcagcccg agaggctcgc gaccctctcc cggacgccgg
 481 ggcctcgccg gcacctagcc gctgctgccg ccgccgttcc tccgtggcct ttttcgccgt
 541 gtgcgacggg cacggcgggc gggaggcggc acagtttgcc cgggagcact tgtggggttt
 601 catcaagaag cagaagggtt tcacctcgtc cgagccggct aaggtttgcg ctgccatccg
 661 caaaggcttt ctcgcttgtc accttgccat gtggaagaaa ctggcggaat ggccaaagac
 721 tatgacgggt cttcctagca catcagggac aactgccagt gtggtcatca ttcggggcat
 781 gaagatgtat gtagctcacg taggtgactc agggggtggtt cttggaattc aggatgaccc
 841 gaaggatgac tttgtcagag ctgtggaggt gacacaggac cataagccag aacttcccaa
 901 ggaaagagaa cgaatcgaag gacttggtgg gagtgtaatg aacaagtctg gggtgaatcg
 961 tgtagtttgg aaacgacctc gactcactca caatggacct gttagaagga gcacagttat
1021 tgaccagatt ccttttctgg cagtagcaag agcacttggt gatttgtgga gctatgattt
1081 cttcagtggt gaatttgtgg tgtcacctga accagacaca agtgtccaca ctcttgaccc
1141 tcagaagcac aagtatatta tattggggag tgatggactt tggaatatga ttccaccaca
1201 agatgccatc tcaatgtgcc aggaccaaga ggagaaaaaa tacctgatgg gtgagcatgg
1261 acaatcttgt gccaaaatgc ttgtgaatcg agcattgggc cgctggaggc agcgtatgct
1321 ccgagcagat aacactagtg ccatagtaat ctgcatctct ccagaagtgg acaatcaggg
1381 aaactttacc aatgaagatg agttatacct gaacctgact gacagccctt cctataatag
1441 tcaagaaacc tgtgtgatga ctccttcccc atgttctaca ccaccagtca agtcactgga
1501 ggaggatcca tggccaaggg tgaattctaa ggaccatata cctgccctgg ttcgtagcaa
1561 tgccttctca gagaattttt tagaggtttc agctgagata gctcgagaga atgtccaagg
1621 tgtagtcata ccctcaaaag atccagaacc acttgaagaa aattgcgcta aagccctgac
1681 tttaaggata catgattctt tgaataatag ccttccaatt ggccttgtgc ctactaattc
```

TABLE 1-continued 1741 aacaaacact gtcatggacc aaaaaaattt gaagatgtca actcctggcc aaatgaaagc
1801 ccaagaaatt gaaagaaccc ctccaacaaa ctttaaaagg acattagaag agtccaattc
1861 tggccccctg atgaagaagc atagacgaaa tggcttaagt cgaagtagtg gtgctcagcc
1921 tgcaagtctc cccacaacct cacagcgaaa gaactctgtt aaactcacca tgcgacgcag
1981 acttaggggc cagaagaaaa ttggaaatcc tttacttcat caacacagga aaactgtttg
2041 tgtttgctga aatgcatctg ggaaatgagg tttttccaaa cttaggatat aagagggctt
2101 tttaaatttg gtgccgatgt tgaacttttt ttaaggggag aaaattaaaa gaaatataca
2161 gtttgacttt ttggaattca gcagttttat cctggccttg tacttgcttg tattgtaaat
2221 gtggattttg tagatgttag ggtataagtt gctgtaaaat ttgtgtaaat ttgtatccac
2281 acaaattcag tctctgaata cacagtattc agagtctctg atacacagta attgtgacaa
2341 tagggctaaa tgtttaaaga aatcaaaaga atctattaga ttttagaaaa acatttaaac
2401 tttttaaaat acttattaaa aaatttgtat aagccacttg tcttgaaaac tgtgcaactt
2461 tttaaagtaa attattaagc agactggaaa agtgatgtat tttcatagtg acctgtgttt
2521 cacttaatgt ttcttagagc caagtgtctt ttaaacatta tttttattt ctgatttcat
2581 aattcagaac taaatttttc atagaagtgt tgagccatgc tacagttagt cttgtcccaa
2641 ttaaaatact atgcagtatc tcttacatca gtagcatttt tctaaaacct tagtcatcag
2701 atatgcttac taaatcttca gcatagaagg aagtgtgttt gcctaaaaca atctaaaaca
2761 attcccttct ttttcatccc agaccaatgg cattattagg tcttaaagta gttactccct
2821 tctcgtgttt gcttaaaata tgtgaagttt tccttgctat ttcaataaca gatggtgctg
2881 ctaattccca acatttctta aattatttta tatcatacag ttttcattga ttatatgggt
2941 atatattcat ctaataaatc agtgaactgt tcctcatgtt gctgaatttg tagttgttgg
3001 tttattttaa tggtatgtac aagttgagta tcccttatcc aaaatgcttg ggaccagaag
3061 tgtttcagat tttttaaaat tttggaatat ttgctttata ctgagctttt gagtgttccc
3121 aatctgaaat tcaaaatgct ctaatgagca tttcctttga gcatcatgcc tgctctgaaa
3181 aagtttctga ttctggagca ttttggattt tggattttca gattagggat gcttaacctg
3241 gattaacatt ctgttgtgcc atgatcatgc tttacagtga gtgtatttta tttatttatt
3301 attttgtttg tttgtttgag atggagtctc actctgtcat ccaggctaga gtgcagtggc
3361 gtgatctcgg ctgactgcaa cctctgcctc ccgggttcaa gtgattctcc tgcctcaatc
3421 tctctcccca gaagctggga ttacaggtgt gtgccaccac acccggctaa tttttttttt
3481 tttttttgag atggagtcta gctctgtcat ccaggctgga gtgcagtggt gtgatctcgg
3541 ctccctgcaa cctctgcctt ctgggttcct gcgattctcc tgcctcagcc tcctgagtag
3601 ctgagattac aggcacgcgc cactgtgccc agccaatttt tgtattttta gtagagatgg
3661 ggtttcacat gtcagtcatg ctggtcttga tctcctgacc tcgtgatcca cccgcctcga
3721 cctcccaaag tactgggatt acaggcgtga gccaccgcat ccggcctgag ttttatgctt
3781 tcaatgtatt tcttacattt cagttcaagt gattttcatg tctcagcctc ctgagtagct
3841 ggaactacag gtgcgtgcca ccatgcctgg ctaagttttg tatttttagt agagatgggt
3901 tttcatcatg ttggccaaga tggtcttgat ctcttgacct catgatccac cagcctaggc
3961 ctcccaaagt gctgggatta caggtgtgag ccaccgtgcc cagccaacta tgccattatt
4021 taaccatgtc cacacattct ggttattttc aatattttgc agaagataat tcttgatcgg
4081 tgtgtcttat gccacaagga ttaaaatatg tattcattgc tacaaaacaa tatctcgaaa
4141 tttagcagtt taaaacaaca aatattatct ccagtttctg agcctcagaa atctgagagt
4201 ggtttagctg ggtgatagtc tcgtggtttt ggtcaagcta ccaaccaggg ctacaatctt
4261 tcgaaggtgt cattggggct agaagatctg cttcccgcaa gactcacagc tgttggcagg
4321 agacctcagt ttgttgccac atgttcccct ccagagggcc tctcacaaca tggcagttat
4381 ttgtccccag agcaagcaac accggagggc aaggaagaag ccatgatgtt ttttgtaacc
4441 tagcctctga aagtgtcata ccaattctgt attttgttgg tcacacagac caagtcaact
4501 acaacgtggg agactcctac acaaggcatg aattctagga ggtgggcatt tttaagtgtc
4561 atctggaagg aggctgtcac aacctggaag ttaaaagcat tgatattctg aaatacagcg
4621 tgtataacat tgttttagta gggtgtgcaa tagttatgtt ttggtaatag cattaatgaa
4681 caatgttatt ttcatcttcc agacatctgg aagattgctc tagtggagta aaacatctta
4741 atgtattttg tccctaaata aactatctca ctaacaaaaa aaaaaaaaaa SEQ ID NO: 85 Human PPM1D Amino Acid Sequence (NP_003611.1)
1 MAGLYSLGVS VFSDQGGRKY MEDVTQIVVE PEPTAEEKPS PRRSLSQPLP PRPSPAALPG
61 GEVSGKGPAV AAREARDPLP DAGASPAPSR CCRRRSSVAF FAVCDGHGGR EAAQFAREHL
121 WGFIKKQKGF TSSEPAKVCA AIRKGFLACH LAMWKKLAEW PKTMTGLPST SGTTASVVII
181 RGMKMYVAHV GDSGVVLGIQ DDPKDDFVRA VEVTQDHKPE LPKERERIEG LGGSVMNKSG
241 VNRVVWKRPR LTHNGPVRRS TVIDQIPFLA VARALGDLWS YDFFSGEFVV SPEPDTSVHT
301 LDPQKHKYII LGSDGLWNMI PPGDAISMCQ DQEEKKYLMG EHGQSCAKML VNRALGRWRQ
361 RMLRADNTSA IVICISPEVD NQGNFTNEDE LYLNITDSPS YNSQETCVMT PSPCSTPPVK
421 SLEEDPWPRV NSKDHIPALV RSNAFSENFL EVSAEIAREN VQGVVIPSKD PEPLEENCAK
481 ALTLRIHDSL NNSLPIGLVP TNSTNTVMDQ KNLKMSTPGQ MKAQEIERTP PTNFKRTLEE
541 SNSGPLMKKH RRNGLSRSSG AQPASLPTTS QRKNSVKLTM RRRLRGQKKI GNPLLHQHRK
601 TVCVC SEQ ID NO: 86 Mouse PPM1D cDNA Sequence (NM_016910.3; CDS: 220-2016)
1 cgcagctgct cggctcctct cgcccgcgac tcgaccggcc cagctctcgc ggacaagtcc
61 cgacatcacg cgcccccccc caccgccgcg gggaccgcct cctcttcact ctcggcttcg
121 tcgaagataa acaatagttg gccggcgagc ggcgagtgtg tctcccgcct cggaattcgg
181 cgggctgcgt gggaacggcg ggatcccggg cagccggcca tggcggggct gtactcgctg
241 ggagtgagcg tcttctcgga ccagggcggg aggaagtaca tggaggacgt aactcagatc
301 gtggtggagc ccgagccggc tgcggaggac aagccggcgc cggtaccgcg gcgggcgctc
361 gggttgccgg cgacccccac tctcgccggc gtcgggccat cggaaaaagg cccggcggcg
421 gcccgcgacc ctgccccgga cgccgcggcc tcgctacccg ctggccgctg ctgtcgccgc
481 cgctcttcgg tggccttctt tgcagtgtgc gacgggcacg gcggtcggga ggcggcacag
541 tttgcccggg agcacttgtg gggtttcatc aagaagcaga aaggcttcac ctcgtccgag
601 cccgccaagg tgtgcgctgc catccgcaaa ggtttcctcg cctgtcacct cgccatgtgg
661 aagaaactgg cagaatggcc aaagactatg acaggtcttc ccagcacgtc cgggacaact
721 gccagtgtgg ttataatacg gggcatgaag atgtatgtag cgcatgtagg tgactctggg
781 gtggtccttg gaattcagga tgacccaaag gatgattttg tgagagctgt ggaggtgaca TABLE 1-continued

```
 841 caagatcaca agccagaact tcccaaggaa agagaaagaa tcgaaggact tggcggcagt
 901 gtgatgaaca agtctggagt gaaccgagta gtttggaaaa ggccccggct cactcacagt
 961 ggacctgtca gaaggagcac agtcattgac cagattcctt ttctggctgt agcaagagcg
1021 cttggtgact tgtggagcta tgatttcttc agtggtaagt ttgtggtgtc acctgaacca
1081 gacaccagtg tccacactct tgacccccgg aagcacaagt atattatcct gggaagtgat
1141 ggactttgga atatggttcc acctcaagat gccatctcca tgtgccaaga ccaagaggag
1201 aaaaaatact tgatgggtga gcaaggacag tcctgtgcca aaatgcttgt gaatcgagca
1261 cttggccgct ggaggcagcg tatgcttcgg gcagataaca caagtgccat cgtaatctgc
1321 atctctccag aagtagacaa ccaagggaac ttcaccaatg aagatgagct ctttctgaac
1381 ctgactgata gccctactta caacagccag gagacctgtg tgatgacttc ttctccaagt
1441 tctacaccac caatcaagtc accggaagaa gatgcatggc caaggctgag ctctaaggac
1501 catatacctg cccttgttcg cagtaatgcc ttctcagaga agtttttaga ggtcccagct
1561 gagatagcta gagggaatat ccagactgta gtgatgacct caaaagactc agagacactt
1621 gaagaaaatt gccccaaagc cctgacttta aggattcatg attctttgaa taatactctg
1681 tcagttggcc tcattccaac caattcaaca aatactatca tggaccaaaa aaacttaaag
1741 atgtcaactc caggtcaaat gaaagctcaa gaagttgaaa gaacccctcc agccaatttt
1801 aaaaggacat tagaagaatc caactctggc cccccttatga agaagcaccg acgaaatggc
1861 ttaagtcgaa gtagcggggc ccaggcttcc agtctcccta cagcatccca gcgcaggcac
1921 tctgtcaaac tgaccctgag gcgcagactc aggggccaga ggaagatggg aaatcctctt
1981 ctccaccagc accggaaaac agtgtgtgtg tgctgagatg ggcctgggaa gtgggggtct
2041 ccctacctac gactgagggc tttttaaact tggtgcgaag ttgaactttt ttaaggggat
2101 aaaataaaga gaatacagtt tgactttttg gaatttaaca gttttatttt ggccttgtac
2161 ttgcctgtat tataatgtga attttgtaga tgtagggaat aagttgctgt aaaatgtgtg
2221 taaatttgta tcctttacac aagtttagtc tcttactctg acacatagta attgtgacag
2281 cagggctaat gttgaagaaa agtcagaaga atctttaaga ttttaaaaat gtctttaaag
2341 tttttaaaat gcttactaca tacttatata caccccttgt gaagaacaca tgacttttta
2401 aagaaaatta ctaagcaaac tggaaaagtg aagtattttc atagtgatct gtgctccact
2461 taatgtttcc cagggaccat tagtgtcttt ttaaaattac attttatttc acatttcata
2521 attcagaagt aaacctttca taggaaaaat actgagctgt gctaatgtag ctgattttag
2581 tctccttgtc ccacttacac tatgcagtat ctcctaactt cagtgcactc tgctagaaca
2641 gtacatttgc tgtatttact gaaatctctg gcacagaagg aagtgtgttt gcctcacaca
2701 ccatttgtcc cagaccagtg gcattaggcc atatattctc ttctagtgtt tgcttaaaat
2761 atgtgaagtt tttcttgcta tttcaataac aaatggtgct gctaacaccc aacatttcct
2821 aaattatttt ctatcataca gttttcattg gttatatgag tatgtctacc caataaatca
2881 ctgaatttat gttgaaaaaa aaaaaaaaaa a
```

SEQ ID NO: 87 Mouse PPM1D Amino Acid Sequence (NP_058606.3)

```
  1 MAGLYSLGVS VFSDQGGRKY MEDVTQIVVE PEPAAEDKPA PVPRRALGLP ATPTLAGVGP
 61 SEKGPAAARD PAPDAAASLP AGRCCRRRSS VAFFAVCDGH GGREAAQFAR EHLWGFIKKQ
121 KGFTSSEPAK VCAAIRKGFL ACHLAMWKKL AEWPKTMTGL PSTSGTTASV VIIRGMKMYV
181 AHVGDSGVVL GIQDDPKDDF VRAVEVTQDH KPELPKERER IEGLGGSVMN KSGVNRVVWK
241 RPRLTHSGPV RRSTVIDQIP FLAVARALGD LWSYDFFSGK FVVSPEPDTS VHTLDPRKHK
301 YIILGSDGLW NMVPPQDAIS MCQDQEEKKY LMGEQGQSCA KMLVNRALGR WRQRMLRADN
361 TSAIVICISP EVDNQGNFTN EDELFLNITD SPTYNSQETC VMTSSPSSTP PIKSPEEDAW
421 PRLSSKDHIP ALVRSNAFSE KFLEVPAEIA RGNIQTVVMT SKDSETLEEN CPKALTLRIH
481 DSLNNTLSVG LIPTNSTNTI MDQKNLKMST PGQMKAQEVE RTPPANFKRT LEESNSGPLM
541 KKHRRNGLSR SSGAQASSLP TASQRRHSVK LTLRRRLRGQ RKMGNPLLHQ HRKTVCVC
```

SEQ ID NO: 88 Human PPM1D cDNA Sequence (NM_177983.2; CDS: 262-1902)

```
   1 agttgctaag gaaatgactg cccgcagcgc ctggccccgc cgcgcaggcc gggcggggtc
  61 tggagcggcg ccgtttccgc ttccgctccc tcacagctcc cgtcccgtta ccgcctcctg
 121 gccggcctcg cgcctttcac cggcaccttg cgtcggtcgc gccgcggggc ctgctcctgc
 181 cgcgcgcacc cccggggctt cggctccggc acgggtcgcg cccagctttc ctgcacctga
 241 ggccgccggc cagccgccgc catgggtgcc tacctctccc agcccaacac ggtgaagtgc
 301 tccggggacg gggtcggcgc cccgcgcctg ccgctgccct acggcttctc cgccatgcaa
 361 ggctggcgcg tctccatgga ggatgctcac aactgtattc ctgagctgga cagtgagaca
 421 gccatgtttt ctgtctacga tggacatgga ggggaggaag ttgccttgta ctgtgccaaa
 481 tatcttcctg atatcatcaa agatcagaag gcctacaagg aaggcaagct acagaaggct
 541 ttagaagatg ccttcttggc tattgacgcc aaattgacca ctgaagaagt cattaaagag
 601 ctggcacaga ttgcagggcg acccactgag gatgaagatg aaaaagaaaa agtagctgat
 661 gaagatgatg tggacaatga ggaggctgca ctgctgcatg aagaggctac catgactatt
 721 gaagagctgc tgacacgcta cggcagaac tgtcacaagg gccctcccca cagcaaatct
 781 ggaggtggga caggcgagga accagggtcc cagggcctca atggggaggc aggacctgag
 841 gactcaacta gggaaactcc ttcacaagaa aatggcccca cagccaaggc ctacacaggc
 901 ttttcctcca actcggaacg tggactgag gcaggccaag ttggtgagcc tggcattccc
 961 actggtgagg ctgggccttc ctgctcttca gcctctgaca agctgcctcg agttgctaag
1021 tccaagttct ttgaggacag tgaggatgag tcagatgagg cggaggaaga agaggaagac
1081 agtgaggaat gcagcgagga agaggatggc tacagcagtg aggaggcaga gaatgaggaa
1141 gatgaggatg acaccgagga ggctgaagag gacgatgaag aagaagaaga agagatgatg
1201 gtgccaggga tggaaggcaa agaggagcct ggctctgaca gtggtacaac agcggtggtg
1261 gccctgatac gagggaagca gttgattgta gccaacgcag gagactctcg ctgtgtggta
1321 tctgaggctg gcaaagcttt agacatgtcc tatgatcaca aaccagagga tgaagtagaa
1381 ctagcacgca tcaagaatgc tggtggcaag gtcaccatgg atgggcgagt caacgggggc
1441 ctcaacctct ccagagccat tggggaccac ttctataaga gaaacaagaa cctgccacct
1501 gaggaacaga tgatttcagc ccttcctgac atcaaggtgc tgactctcac tgacgaccat
1561 gaattcatgg tcattgcctg tgatggcatc tggaatgtga tgagcagcca ggaagttgta
1621 gatttcattc aatcaaagat cagccagcgt gatgaaaatg gggagcttcg gttattgtca
1681 tccattgtgg aagagctgct ggatcagtgc ctggcaccag acacttctgg ggatggtaca
1741 gggtgtgaca acatgacctg catcatcatt tgcttcaagc cccgaaacac agcagagctc
1801 cagccagaga gtggcaagcg aaaactagag gaggtgctct ctactgaggg ggctgaagaa
```

TABLE 1-continued

```
1861 aatggcaaca gcgacaagaa gaagaaggcc aagcgagact agcagtcatc cagacccctg
1921 cccacctaga ctgttttctg agccctccgg acctgagact gagttttgtc tttttccttt
1981 agccttagca gtgggtatga ggtgtgcagg gggagctggg tggcttcact ccgcccattc
2041 caaagagggc tctccctcca cactgcagcc gggagcctct gctgtccttc ccagccgcct
2101 ctgctcctcg ggctcatcac cggttctgtg cctgtgctct gttgtgttgg agggaaggac
2161 tggcggttct ggtttttact ctgtgaactt tatttaagga cattcttttt tattggcggc
2221 tccatggccc tcggccgctt gcacccgctc tctgttgtac actttcaatc aacacttttt
2281 cagactaaag gccaaaacct aa
```

SEQ ID NO: 89 Human PPM1D Amino Acid Sequence (NP_817092.1)

```
  1 MGAYLSQPNT VKCSGDGVGA PRLPLPYGFS AMQGWRVSME DAHNCIPELD SETAMFSVYD
 61 GHGGEEVALY CAKYLPDIIK DQKAYKEGKL QKALEDAFLA IDAKLTTEEV IKELAQIAGR
121 PTEDEDEKEK VADEDDVDNE EAALLHEEAT MTIEELLTRY GQNCHKGPPH SKSGGGTGEE
181 PGSQGLNGEA GPEDSTRETP SQENGPTAKA YTGFSSNSER GTEAGQVGEP GIPTGEAGPS
241 CSSASDKLPR VAKSKFFEDS EDESDEAEEE EEDSEECSEE EDGYSSEEAE NEEDEDDTEE
301 AEEDDEEEEE EMMVPGMEGK EEPGSDSGTT AVVALIRGKQ LIVANAGDSR CVVSEAGKAL
361 DMSYDHKPED EVELARIKNA GGKVTMDGRV NGGLNLSRAI GDHFYKRNKN LPPEEQMISA
421 LPDIKVLTLT DDHEFMVIAC DGIWNVMSSQ EVVDFIQSKI SQRDENGELR LLSSIVEELL
481 DQCLAPDTSG DGTGCDNMTC IIICFKPRNT AELQPESGKR KLEEVLSTEG AEENGNSDKK
541 KKAKRD
```

SEQ ID NO: 90 Mouse PPM1D cDNA Sequence (NM_008014.3; CDS: 124-1752)

```
   1 cttgcgtcga ctgcgcagcc gggcccgctc cttgccacgc gcgcccccag gggccccggc
  61 tccggcgccg gcaagggtcg cgtcccgctt acctgttcct caggtagcca gccatccgcc
 121 gccatgggtg cctacctctc tcagcccaac acggtgaagt gctccgggga cggggttggc
 181 gccccgcggc tcccgctgcc ctacggcttc tccgccatgc aaggctggcg cgtctccatg
 241 gaggatgctc acaactgtat tcctgagctg gacaatgaga cagccatgtt ttctgtctac
 301 gatggacatg gaggggaaga ggttgccttg tactgtgcca aatatcttcc tgatattatc
 361 aaagatcaga aggcctacaa ggaaggcaag cttcagaagg ctttacaaga tgccttcttg
 421 gctattgatg ccaagctgac cacagaggaa gtcattaagg aactggccca gattgcaggg
 481 agacccactg aagatgagga tgataaagac aaagtagcag atgaggatga tgtggacaat
 541 gaggaggctg cattgttgca tgaagaggct accatgacta ttgaagagct gctgacgcga
 601 tatgggcaga actgtcagaa ggtccctccc cacaccaaat ctggaattgg gacaggcgat
 661 gaaccagggc cccagggcct caatggggag gctggacctg aggacccatc tagggaaact
 721 ccttcccagg aaaatggccc cacagccaaa ggccacacag gcttttcctc caactcggaa
 781 catgggactg aggcaggcca aattagtgag cccggtactg ctaccggtga ggctggacct
 841 tcctgctctt cagcctctga caagctgcct cgagttgcta agtccaagtt ctttgaggac
 901 agtgaagatg aatcagatga ggtggaggaa gaggaggatg acagtgagga atgtagtgag
 961 gacgaggacg gctacagcag tgaggaggca gagaacgagg aagacgagga tgacacggag
1021 gaggctgaag aggatgatga tgaagagatg atggtccctg gaatggaagg caaagaagag
1081 cctggttctg acagtggcac aacagcggtg gtggctctga tcagagggaa gcagttgatt
1141 gtggccaatg caggagactc tcgctgtgtg gtgtccgagg ctggcaaagc tttagatatg
1201 tcctatgacc acaaaccaga ggatgaagtg gagctggcac gcatcaagaa tgctggtggc
1261 aaggtcacca tggatggacg agtcaatgga ggcctcaacc tctccagggc cattggagac
1321 cacttctaca agagaaacaa aaacttgcca ccccaggaac agatgatttc tgcccttcct
1381 gacatcaagg tgctgactct cactgatgac catgaattca tggtcattgc ttgtgacggc
1441 atctggaatg tgatgagcag ccaggaggtt gtagacttta ttcaatcaaa gatcagtcaa
1501 cgtgatgaaa acggggagct tcggttattg tcatccattg tggaagagct gctggatcag
1561 tgcctggcgc cagacacttc tggggatggt acagggtgtg acaacatgac gtgcatcatc
1621 atttgcttca agccccgaaa cacagtagag cttcaggcag agagtggcaa gaggaaactg
1681 gaggaggcac tgtccacgga gggggctgaa gacaccggca acagtgacaa aaagaaggcc
1741 aagagggact agtggtcaac cggaccctgc ccatgtggac tgttttctga gcccttggac
1801 ccgagactga gttttgtcct tgtcctttag ccttagcagt gggtatgagg tgtgcagggg
1861 gctgggtggc tttcctcagc ccattacaaa gagggccccc caccccccc acgcggcagc
1921 ctgggaggct ctgctgtcct cttaagcctc cttactctcc ttgggctcat cgactatcgg
1981 ttctgtgcct gtgctctgtt gtgttggagg gaaggactgg tagttctgat ttttactctg
2041 tgaacacttt atttaaggac attctttttt attggcggct ctgtgacccc tagccgcttg
2101 cacccgctct ctgttgtaca ctttcaagca acactttttc agactaaagg ccaaacaaaa
2161 gctaa
```

SEQ ID NO: 91 Mouse PPM1D Amino Acid Sequence (NP_032040.1)

```
  1 MGAYLSQPNT VKCSGDGVGA PRLPLPYGFS AMQGWRVSME DAHNCIPELD NETAMFSVYD
 61 GHGGEEVALY CAKYLPDIIK DQKAYKEGKL QKALQDAFLA IDAKLTTEEV IKELAQIAGR
121 PTEDEDDKDK VADEDDVDNE EAALLHEEAT MTIEELLTRY GQNCQKVPPH TKSGIGTGDE
181 PGPQGLNGEA GPEDPSRETP SQENGPTAKG HTGFSSNSEH GTEAGQISEP GTATGEAGPS
241 CSSASDKLPR VAKSKFFEDS EDESDEVEEE EDDSEECSED EDGYSSEEAE NEEDEDDTEE
301 AEEDDDEEMM VPGMEGKEEP GSDSGTTAVV ALIRGKQLIV ANAGDSRCVV SEAGKALDMS
361 YDHKPEDEVE LARIKNAGGK VTMDGRVNGG LNLSRAIGDH FYKRNKNLPP QEQMISALPD
```

TABLE 1-continued

| | | | | | | |
|---|---|---|---|---|---|---|
| 421 | IKVLTLTDDH | EFMVIACDGI | WNVMSSQEVV | DFIQSKISQR | DENGELRLLS | SIVEELLDQC |
| 481 | LAPDTSGDGT | GCDNMTCIII | CFKPRNTVEL | QAESGKRKLE | EALSTEGAED | TGNSDKKKAK |
| 541 | RD | | | | | |

* The nucleic acid and polypeptide sequences of the biomarkers of the present invention listed in Table 1 have been submitted at GenBank under the unique identifier provided herein and each such uniquely identified sequence submitted at GenBank is hereby incorporated in its entirety by reference.
* Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.
* Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

TABLE 2

TP53
Dephosphorylated human TP53 at Ser 15 or at corresponding phosphorylable amino acid in an ortholog thereof SEQ ID NO: 92 Human TP53 Isoform a Amino Acid Sequence (NP_000537.3, NP_001119584.1)

```
   1 MEEPQSDPSV EPPLSQETFS DLWKLLPENN VLSPLPSQAM DDLMLSPDDI EQWFTEDPGP
  61 DEAPRMPEAA PPVAPAPAAP TPAAPAPAPS WPLSSSVPSQ KTYQGSYGFR LGFLHSGTAK
 121 SVTCTYSPAL NKMFCQLAKT CPVQLWVDST PPPGTRVRAM AIYKQSQHMT EVVRRCPHHE
 181 RCSDSDGLAP PQHLIRVEGN LRVEYLDDRN TFRHSVVVPY EPPEVGSDCT TIHYNYMCNS
 241 SCMGGMNRRP ILTIITLEDS SGNLLGRNSF EVRVCACPGR DRRTEEENLR KKGEPHHELP
 301 PGSTKRALPN NTSSSPQPKK KPLDGEYFTL QIRGRERFEM FRELNEALEL KDAQAGKEPG
 361 GSRAHSSHLK SKKGQSTSRH KKLMFKTEGP DSD
```

SEQ ID NO: 93 Human TP53 transcript variant 1 cDNA sequence (NM_000546.5, CDS: 203-1384)

```
   1 gatgggattg gggttttccc ctcccatgtg ctcaagactg gcgctaaaag ttttgagctt
  61 ctcaaaagtc tagagccacc gtccagggag caggtagctg ctgggctccg gggacacttt
 121 gcgttcgggc tgggagcgtg ctttccacga cggtgacacg cttccctgga ttggcagcca
 181 gactgccttc cgggtcactg ccatggagga gccgcagtca gatcctagcg tcgagccccc
 241 tctgagtcag gaaacatttt cagacctatg gaaactactt cctgaaaaca acgttctgtc
 301 ccccttgccg tcccaagcaa tggatgattt gatgctgtcc ccggacgata ttgaacaatg
 361 gttcactgaa gacccaggtc cagatgaagc tcccagaatg ccagaggctg ctccccccgt
 421 ggcccctgca ccagcagctc ctacaccggc ggcccctgca ccagccccct cctggcccct
 481 gtcatcttct gtcccttccc agaaaaccta ccagggcagc tacggtttcc gtctgggctt
 541 cttgcattct gggacagcca agtctgtgac ttgcacgtac tcccctgccc tcaacaagat
 601 gttttgccaa ctggccaaga cctgccctgt gcagctgtgg gttgattcca caccccccgcc
 661 cggcacccgc gtccgcgcca tggccatcta caagcagtca cagcacatga cggaggttgt
 721 gaggcgctgc ccccaccatg agcgctgctc agatagcgat ggtctggccc ctcctcagca
 781 tcttatccga gtggaaggaa atttgcgtgt ggagtatttg gatgacagaa acacttttcg
 841 acatagtgtg gtggtgccct atgagccgcc tgaggttggc tctgactgta ccaccatcca
 901 ctacaactac atgtgtaaca gttcctgcat gggcggcatg aaccggaggc ccatcctcac
 961 catcatcaca ctggaagact ccagtggtaa tctactggga cggaacagct ttgaggtgcg
1021 tgtttgtgcc tgtcctggga gagaccggcg cacagaggaa gagaatctcc gcaagaaagg
1081 ggagcctcac cacgagctgc ccccagggag cactaagcga gcactgccca acaacaccag
1141 ctcctctccc cagccaaaga agaaaccact ggatggagaa tatttcaccc ttcagatccg
1201 tgggcgtgag cgcttcgaga tgttccgaga gctgaatgag gccttggaac tcaaggatgc
1261 ccaggctggg aaggagccag gggggagcag ggctcactcc agccacctga agtccaaaaa
1321 gggtcagtct acctcccgcc ataaaaaact catgttcaag acagaagggc ctgactcaga
1381 ctgacattct ccacttcttg ttccccactg acagcctccc acccccatct ctccctcccc
1441 tgccattttg ggttttgggt ctttgaaccc ttgcttgcaa taggtgtgcg tcagaagcac
1501 ccaggacttc catttgcttt gtcccggggc tccactgaac aagttggcct gcactggtgt
1561 tttgttgtgg ggaggaggat ggggagtagg acataccagc ttagatttta aggtttttac
1621 tgtgagggat gtttgggaga tgtaagaaat gttcttgcag ttaagggtta gtttacaatc
1681 agccacattc taggtagggg cccacttcac cgtactaacc agggaagctg tccctcactg
1741 ttgaattttc tctaacttca aggcccatat ctgtgaaatg ctggcatttg cacctacctc
1801 acagagtgca ttgtgagggt taatgaaata atgtacatct ggccttgaaa ccacctttta
1861 ttacatgggg tctagaactt gacccccttg agggtgcttg ttccctctcc ctgttggtcg
1921 gtgggttggt agtttctaca gttgggcagc tggttaggta gagggagttg tcaagtctct
1981 gctggcccag ccaaaccctg tctgacaacc tcttggtgaa ccttagtacc taaaaggaaa
2041 tctcacccca tcccacaccc tggaggattt catctcttgt atatgatgat ctggatccac
2101 caagacttgt tttatgctca gggtcaattt cttttttctt tttttttttt tttttttctt
2161 ttctttgaga ctgggtctcg ctttgttgcc caggctggag tggagtggcg tgatcttggc
2221 ttactgcagc ctttgcctcc ccggctcgag cagtcctgcc tcagcctccg gagtagctgg
2281 gaccacaggt tcatgccacc atggccagcc aacttttgca tgttttgtag agatggggtc
2341 tcacagtgtt gcccaggctg gtctcaaact cctgggctca ggcgatccac ctgtctcagc
2401 ctcccagagt gctgggatta caattgtgag ccaccacgtc cagctggaag ggtcaacatc
2461 ttttacattc tgcaagcaca tctgcatttt caccccaccc ttcccctcct tctccctttt
2521 tatatcccat ttttatatcg atctcttatt ttacaataaa actttgctgc cacctgtgtg
```

TABLE 2-continued

| TP53 Dephosphorylated human TP53 at Ser 15 or at corresponding phosphorylable amino acid in an ortholog thereof |
|---|

2581 tctgaggggt g

SEQ ID NO: 94 Human TP53 transcript variant 2 cDNA sequence
(NM_001126112.2; CDS: 200-1381)

```
   1 gatgggattg gggttttccc ctcccatgtg ctcaagactg gcgctaaaag ttttgagctt
  61 ctcaaaagtc tagagccacc gtccagggag caggtagctg ctgggctccg gggacacttt
 121 gcgttcgggc tgggagcgtg ctttccacga cggtgacacg cttccctgga ttggccagac
 181 tgccttccgg gtcactgcca tggaggagcc gcagtcagat cctagcgtcg agccccctct
 241 gagtcaggaa acattttcag acctatggaa actacttcct gaaaacaacg ttctgtcccc
 301 cttgccgtcc caagcaatgg atgatttgat gctgtccccg gacgatattg aacaatggtt
 361 cactgaagac ccaggtccag atgaagctcc cagaatgcca gaggctgctc cccccgtggc
 421 ccctgcacca gcagctccta caccggcggc ccctgcacca gccccctcct ggcccctgtc
 481 atcttctgtc ccttcccaga aaacctacca gggcagctac ggtttccgtc tgggcttctt
 541 gcattctggg acagccaagt ctgtgacttg cacgtactcc cctgccctca acaagatgtt
 601 ttgccaactg gccaagacct gccctgtgca gctgtgggtt gattccacac ccccgcccgg
 661 cacccgcgtc cgcgccatgg ccatctacaa gcagtcacag cacatgacgg aggttgtgag
 721 gcgctgcccc caccatgagc gctgctcaga tagcgatggt ctggcccctc ctcagcatct
 781 tatccgagtg gaaggaaatt tgcgtgtgga gtatttggat gacagaaaca cttttcgaca
 841 tagtgtggtg gtgccctatg agccgcctga ggttggctct gactgtacca ccatccacta
 901 caactacatg tgtaacagtt cctgcatggg cggcatgaac cggaggccca tcctcaccat
 961 catcacactg gaagactcca gtggtaatct actgggacgg aacagctttg aggtgcgtgt
1021 ttgtgcctgt cctgggagag accggcgcac agaggaagag aatctccgca agaaagggga
1081 gcctcaccac gagctgcccc cagggagcac taagcgagca ctgcccaaca acaccagctc
1141 ctctccccag ccaaagaaga aaccactgga tggagaatat ttcacccttc agatccgtgg
1201 gcgtgagcgc ttcgagatgt tccgagagct gaatgaggcc ttggaactca aggatgccca
1261 ggctgggaag gagccagggg ggagcagggc tcactccagc cacctgaagt ccaaaaaggg
1321 tcagtctacc tcccgccata aaaaactcat gttcaagaca gaagggcctg actcagactg
1381 acattctcca cttcttgttc cccactgaca gcctcccacc cccatctctc cctcccctgc
1441 cattttgggt tttgggtctt tgaacccttg cttgcaatag gtgtgcgtca gaagcaccca
1501 ggacttccat ttgctttgtc ccggggctcc actgaacaag ttggcctgca ctggtgtttt
1561 gttgtgggga ggaggatggg gagtaggaca taccagctta gattttaagg tttttactgt
1621 gagggatgtt tgggagatgt aagaaatgtt cttgcagtta agggttagtt tacaatcagc
1681 cacattctag gtaggggccc acttcaccgt actaaccagg gaagctgtcc ctcactgttg
1741 aattttctct aacttcaagg cccatatctg tgaaatgctg gcatttgcac ctacctcaca
1801 gagtgcattg tgagggttaa tgaaataatg tacatctggc cttgaaacca ccttttatta
1861 catggggtct agaacttgac cccttgagg gtgcttgttc cctctccctg ttggtcggtg
1921 ggttggtagt ttctacagtt gggcagctgg ttaggtagag ggagttgtca agtctctgct
1981 ggcccagcca aaccctgtct gacaacctct tggtgaacct tagtacctaa aaggaaatct
2041 caccccatcc cacaccctgg aggatttcat ctcttgtata tgatgatctg gatccaccaa
2101 gacttgtttt atgctcaggg tcaatttctt ttttcttttt tttttttttt tttctttttc
2161 tttgagactg ggtctcgctt tgttgcccag gctggagtgg agtggcgtga tcttggctta
2221 ctgcagcctt tgcctccccg gctcgagcag tcctgcctca gcctccggag tagctgggac
2281 cacaggttca tgccaccatg gccagccaac ttttgcatgt tttgtagaga tggggtctca
2341 cagtgttgcc caggctggtc tcaaactcct gggctcaggc gatccacctg tctcagcctc
2401 ccagagtgct gggattacaa ttgtgagcca ccacgtccag ctggaagggt caacatcttt
2461 tacattctgc aagcacatct gcattttcac cccacccttc ccctccttct ccctttttat
2521 atcccatttt tatatcgatc tcttatttta caataaaact ttgctgccac ctgtgtgtct
2581 gaggggtg
```

SEQ ID NO: 95 Human TP53 isoform b Amino Acid Sequence (NP_001119586.1)

```
  1 MEEPQSDPSV EPPLSQETFS DLWKLLPENN VLSPLPSQAM DDLMLSPDDI EQWFTEDPGP
 61 DEAPRMPEAA PPVAPAPAAP TPAAPAPAPS WPLSSSVPSQ KTYQGSYGFR LGFLHSGTAK
121 SVTCTYSPAL NKMFCQLAKT CPVQLWVDST PPPGTRVRAM AIYKQSQHMT EVVRRCPHHE
181 RCSDSDGLAP PQHLIRVEGN LRVEYLDDRN TFRHSVVVPY EPPEVGSDCT TIHYNYMCNS
241 SCMGGMNRRP ILTIITLEDS SGNLLGRNSF EVRVCACPGR DRRTEEENLR KKGEPHHELP
301 PGSTKRALPN NTSSSPQPKK KPLDGEYFTL QDQTSFQKEN C
```

SEQ ID NO: 96 Human TP53 transcript variant 3 cDNA sequence
NM_001126114.2 CDS: 203-1228)

```
  1 gatgggattg gggttttccc ctcccatgtg ctcaagactg gcgctaaaag ttttgagctt
 61 ctcaaaagtc tagagccacc gtccagggag caggtagctg ctgggctccg gggacacttt
121 gcgttcgggc tgggagcgtg ctttccacga cggtgacacg cttccctgga ttggcagcca
181 gactgccttc cgggtcactg ccatggagga gccgcagtca gatcctagcg tcgagccccc
241 tctgagtcag gaaacatttt cagacctatg gaaactactt cctgaaaaca acgttctgtc
301 cccttgccg tcccaagcaa tggatgattt gatgctgtcc ccggacgata ttgaacaatg
361 gttcactgaa gacccaggtc cagatgaagc tcccagaatg ccagaggctg ctccccccgt
421 ggcccctgca ccagcagctc ctacaccggc ggcccctgca ccagcccct cctggcccct
481 gtcatcttct gtcccttccc agaaaaccta ccagggcagc tacggtttcc gtctgggctt
541 cttgcattct gggacagcca agtctgtgac ttgcacgtac tcccctgccc tcaacaagat
601 gttttgccaa ctggccaaga cctgccctgt gcagctgtgg gttgattcca cacccccgcc
661 cggcacccgc gtccgcgcca tggccatcta caagcagtca cagcacatga cggaggttgt
721 gaggcgctgc ccccaccatg agcgctgctc agatagcgat ggtctggccc ctcctcagca
781 tcttatccga gtggaaggaa atttgcgtgt ggagtatttg gatgacagaa acacttttcg
841 acatagtgtg gtggtgccct atgagccgcc tgaggttggc tctgactgta ccaccatcca
901 ctacaactac atgtgtaaca gttcctgcat gggcggcatg aaccggaggc ccatcctcac
961 catcatcaca ctggaagact ccagtggtaa tctactggga cggaacagct ttgaggtgcg
```

TABLE 2-continued

TP53
Dephosphorylated human TP53 at Ser 15 or at corresponding phosphorylable amino acid in an ortholog thereof 1021 tgtttgtgcc tgtcctggga gagaccggcg cacagaggaa gagaatctcc gcaagaaagg
1081 ggagcctcac cacgagctgc ccccagggag cactaagcga gcactgccca acaacaccag
1141 ctcctctccc cagccaaaga agaaaccact ggatggagaa tatttcaccc ttcaggacca
1201 gaccagcttt caaaaagaaa attgttaaag agagcatgaa aatggttcta tgactttgcc
1261 tgatacagat gctacttgac ttacgatggt gttacttcct gataaactcg tcgtaagttg
1321 aaaatattat ccgtgggcgt gagcgcttcg agatgttccg agagctgaat gaggccttgg
1381 aactcaagga tgcccaggct gggaaggagc caggggggag cagggctcac tccagccacc
1441 tgaagtccaa aaagggtcag tctacctccc gccataaaaa actcatgttc aagacagaag
1501 ggcctgactc agactgacat tctccacttc ttgttcccca ctgacagcct cccaccccca
1561 tctctccctc ccctgccatt ttgggttttg ggtctttgaa cccttgcttg caataggtgt
1621 gcgtcagaag cacccaggac ttccatttgc tttgtcccgg ggctccactg aacaagttgg
1681 cctgcactgg tgttttgttg tggggaggag gatggggagt aggacatacc agcttagatt
1741 ttaaggtttt tactgtgagg gatgtttggg agatgtaaga aatgttcttg cagttaaggg
1801 ttagtttaca atcagccaca ttctaggtag gggcccactt caccgtacta accagggaag
1861 ctgtccctca ctgttgaatt ttctctaact tcaaggccca tatctgtgaa atgctggcat
1921 ttgcacctac ctcacagagt gcattgtgag ggttaatgaa ataatgtaca tctggccttg
1981 aaaccacctt ttattacatg gggtctagaa cttgaccccc ttgagggtgc ttgttccctc
2041 tccctgttgg tcggtgggtt ggtagtttct acagttgggc agctggttag gtagagggag
2101 ttgtcaagtc tctgctggcc cagccaaacc ctgtctgaca acctcttggt gaaccttagt
2161 acctaaaagg aaatctcacc ccatcccaca ccctggagga tttcatctct tgtatatgat
2221 gatctggatc caccaagact tgttttatgc tcagggtcaa tttctttttt cttttttttt
2281 tttttttttc tttttctttg agactgggtc tcgctttgtt gcccaggctg gagtggagtg
2341 gcgtgatctt ggcttactgc agcctttgcc tccccggctc gagcagtcct gcctcagcct
2401 ccggagtagc tgggaccaca ggttcatgcc accatggcca gccaactttt gcatgttttg
2461 tagagatggg gtctcacagt gttgcccagg ctggtctcaa actcctgggc tcaggcgatc
2521 cacctgtctc agcctcccag agtgctggga ttacaattgt gagccaccac gtccagctgg
2581 aagggtcaac atcttttaca ttctgcaagc acatctgcat tttcacccca cccttcccct
2641 ccttctccct ttttatatcc catttttata tcgatctctt attttacaat aaaactttgc
2701 tgccacctgt gtgtctgagg ggtg SEQ ID NO: 97 Human TP53 isoform c Amino Acid Sequence (NP_001119585.1)
1 MEEPQSDPSV EPPLSQETFS DLWKLLPENN VLSPLPSQAM DDLMLSPDDI EQWFTEDPGP
61 DEAPRMPEAA PPVAPAPAAP TPAAPAPAPS WPLSSSVPSQ KTYQGSYGFR LGFLHSGTAK
121 SVTCTYSPAL NKMFCQLAKT CPVQLWVDST PPPGTRVRAM AIYKQSQHMT EVVRRCPHHE
181 RCSDSDGLAP PQHLIRVEGN LRVEYLDDRN TFRHSVVVPY EPPEVGSDCT TIHYNYMCNS
241 SCMGGMNRRP ILTIITLEDS SGNLLGRNSF EVRVCACPGR DRRTEEENLR KKGEPHHELP
301 PGSTKRALPN NTSSSPQPKK KPLDGEYFTL QMLLDLRWCY FLINSS SEQ ID NO: 98 Human TP53 transcript variant 4 cDNA sequence
NM_001126113.2 CDS: 203-1243)
1 gatgggattg gggttttccc ctcccatgtg ctcaagactg gcgctaaaag ttttgagctt
61 ctcaaaagtc tagagccacc gtccagggag caggtagctg ctgggctccg gggacacttt
121 gcgttcgggc tgggagcgtg ctttccacga cggtgacacg cttccctgga ttggcagcca
181 gactgccttc cgggtcactg ccatggagga gccgcagtca gatcctagcg tcgagccccc
241 tctgagtcag gaaacatttt cagacctatg gaaactactt cctgaaaaca acgttctgtc
301 ccccttgccg tcccaagcaa tggatgattt gatgctgtcc ccggacgata ttgaacaatg
361 gttcactgaa gacccaggtc cagatgaagc tcccagaatg ccagaggctg ctccccccgt
421 ggcccctgca ccagcagctc ctacaccggc ggcccctgca ccagccccct cctggcccct
481 gtcatcttct gtcccttccc agaaaaccta ccagggcagc tacggtttcc gtctgggctt
541 cttgcattct gggacagcca agtctgtgac ttgcacgtac tcccctgccc tcaacaagat
601 gttttgccaa ctggccaaga cctgccctgt gcagctgtgg gttgattcca cacccccgcc
661 cggcacccgc gtccgcgcca tggccatcta caagcagtca cagcacatga cggaggttgt
721 gaggcgctgc ccccaccatg agcgctgctc agatagcgat ggtctggccc ctcctcagca
781 tcttatccga gtggaaggaa atttgcgtgt ggagtatttg gatgacagaa acacttttcg
841 acatagtgtg gtggtgccct atgagccgcc tgaggttggc tctgactgta ccaccatcca
901 ctacaactac atgtgtaaca gttcctgcat gggcggcatg aaccggaggc ccatcctcac
961 catcatcaca ctggaagact ccagtggtaa tctactggga cggaacagct ttgaggtgcg
1021 tgtttgtgcc tgtcctggga gagaccggcg cacagaggaa gagaatctcc gcaagaaagg
1081 ggagcctcac cacgagctgc ccccagggag cactaagcga gcactgccca acaacaccag
1141 ctcctctccc cagccaaaga agaaaccact ggatggagaa tatttcaccc ttcagatgct
1201 acttgactta cgatggtgtt acttcctgat aaactcgtcg taagttgaaa atattatccg
1261 tgggcgtgag cgcttcgaga tgttccgaga gctgaatgag gccttggaac tcaaggatgc
1321 ccaggctggg aaggagccag gggggagcag ggctcactcc agccacctga agtccaaaaa
1381 gggtcagtct acctcccgcc ataaaaaact catgttcaag acagaagggc ctgactcaga
1441 ctgacattct ccacttcttg ttccccactg acagcctccc acccccatct ctccctcccc
1501 tgccattttg ggttttgggt ctttgaaccc ttgcttgcaa taggtgtgcg tcagaagcac
1561 ccaggacttc catttgcttt gtcccggggc tccactgaac aagttggcct gcactggtgt
1621 tttgttgtgg ggaggaggat ggggagtagg acataccagc ttagatttta aggtttttac
1681 tgtgagggat gtttgggaga tgtaagaaat gttcttgcag ttaagggtta gtttacaatc
1741 agccacattc taggtagggg cccacttcac cgtactaacc agggaagctg tccctcactg
1801 ttgaattttc tctaacttca aggcccatat ctgtgaaatg ctggcatttg cacctacctc
1861 acagagtgca ttgtgagggt taatgaaata atgtacatct ggccttgaaa ccacctttta
1921 ttacatgggg tctagaactt gacccccttg agggtgcttg ttccctctcc ctgttggtcg
1981 gtgggttggt agtttctaca gttgggcagc tggttaggta gagggagttg tcaagtctct
2041 gctggcccag ccaaaccctg tctgacaacc tcttggtgaa ccttagtacc taaaaggaaa
2101 tctcacccca tcccacaccc tggaggattt catctcttgt atatgatgat ctggatccac TABLE 2-continued TP53
Dephosphorylated human TP53 at Ser 15 or at corresponding phosphorylable amino acid in an ortholog thereof 2161 caagacttgt tttatgctca gggtcaattt ctttttttctt ttttttttt tttttttcttt
2221 ttctttgaga ctgggtctcg ctttgttgcc caggctggag tggagtggcg tgatcttggc
2281 ttactgcagc ctttgcctcc ccggctcgag cagtcctgcc tcagcctccg gagtagctgg
2341 gaccacaggt tcatgccacc atggccagcc aacttttgca tgttttgtag agatggggtc
2401 tcacagtgtt gcccaggctg gtctcaaact cctgggctca ggcgatccac ctgtctcagc
2461 ctcccagagt gctgggatta caattgtgag ccaccacgtc cagctggaag ggtcaacatc
2521 ttttacattc tgcaagcaca tctgcatttt caccccaccc ttcccctcct tctccctttt
2581 tatatcccat ttttatatcg atctcttatt ttacaataaa actttgctgc cacctgtgtg
2641 tctgaggggt g SEQ ID NO: 99 Human TP53 isoform d Amino Acid Sequence (NP_001119587.1)
1 MFCQLAKTCP VQLWVDSTPP PGTRVRAMAI YKQSQHMTEV VRRCPHHERC SDSDGLAPPQ
61 HLIRVEGNLR VEYLDDRNTF RHSVVVPYEP PEVGSDCTTI HYNYMCNSSC MGGMNRRPIL
121 TIITLEDSSG NLLGRNSFEV RVCACPGRDR RTEEENLRKK GEPHHELPPG STKRALPNNT
181 SSSPQPKKKP LDGEYFTLQI RGRERFEMFR ELNEALELKD AQAGKEPGGS RAHSSHLKSK
241 KGQSTSRHKK LMFKTEGPDS D SEQ ID NO: 100 Human TP53 transcript variant 5 cDNA sequence (NM_001126115.1; CDS: 279-1064)
1 tgaggccagg agatggaggc tgcagtgagc tgtgatcaca ccactgtgct ccagcctgag
61 tgacagagca agaccctatc tcaaaaaaaa aaaaaaaaaa gaaaagctcc tgaggtgtag
121 acgccaactc tctctagctc gctagtgggt tgcaggaggt gcttacgcat gtttgtttct
181 ttgctgccgt cttccagttg ctttatctgt tcacttgtgc cctgactttc aactctgtct
241 ccttcctctt cctacagtac tcccctgccc tcaacaagat gttttgccaa ctggccaaga
301 cctgccctgt gcagctgtgg gttgattcca cacccccgcc cggcacccgc gtccgcgcca
361 tggccatcta caagcagtca cagcacatga cggaggttgt gaggcgctgc ccccaccatg
421 agcgctgctc agatagcgat ggtctggccc ctcctcagca tcttatccga gtggaaggaa
481 atttgcgtgt ggagtatttg gatgacagaa acacttttcg acatagtgtg gtggtgccct
541 atgagccgcc tgaggttggc tctgactgta ccaccatcca ctacaactac atgtgtaaca
601 gttcctgcat gggcggcatg aaccggaggc ccatcctcac catcatcaca ctggaagact
661 ccagtggtaa tctactggga cggaacagct ttgaggtgcg tgtttgtgcc tgtcctggga
721 gagaccggcg cacagaggaa gagaatctcc gcaagaaagg ggagcctcac cacgagctgc
781 ccccagggag cactaagcga gcactgccca acaacaccag ctcctctccc cagccaaaga
841 agaaaccact ggatggagaa tatttcaccc ttcagatccg tgggcgtgag cgcttcgaga
901 tgttccgaga gctgaatgag gccttggaac tcaaggatgc ccaggctggg aaggagccag
961 gggggagcag ggctcactcc agccacctga agtccaaaaa gggtcagtct acctcccgcc
1021 ataaaaaact catgttcaag acagaagggc ctgactcaga ctgacattct ccacttcttg
1081 ttccccactg acagcctccc acccccatct ctccctcccc tgccattttg ggttttgggt
1141 ctttgaaccc ttgcttgcaa taggtgtgcg tcagaagcac ccaggacttc catttgcttt
1201 gtcccggggc tccactgaac aagttggcct gcactggtgt tttgttgtgg ggaggaggat
1261 ggggagtagg acataccagc ttagatttta aggtttttac tgtgagggat gtttgggaga
1321 tgtaagaaat gttcttgcag ttaagggtta gtttacaatc agccacattc taggtagggg
1381 cccacttcac cgtactaacc agggaagctg tccctcactg ttgaattttc tctaacttca
1441 aggcccatat ctgtgaaatg ctggcatttg cacctacctc acagagtgca ttgtgagggt
1501 taatgaaata atgtacatct ggccttgaaa ccacctttta ttacatgggg tctagaactt
1561 gacccccttg agggtgcttg ttccctctcc ctgttggtcg gtgggttggt agtttctaca
1621 gttgggcagc tggttaggta gagggagttg tcaagtctct gctggcccag ccaaaccctg
1681 tctgacaacc tcttggtgaa ccttagtacc taaaaggaaa tctcacccca tcccacaccc
1741 tggaggattt catctcttgt atatgatgat ctggatccac caagacttgt tttatgctca
1801 gggtcaattt ctttttttctt ttttttttt tttttttcttt ttctttgaga ctgggtctcg
1861 ctttgttgcc caggctggag tggagtggcg tgatcttggc ttactgcagc ctttgcctcc
1921 ccggctcgag cagtcctgcc tcagcctccg gagtagctgg gaccacaggt tcatgccacc
1981 atggccagcc aacttttgca tgttttgtag agatggggtc tcacagtgtt gcccaggctg
2041 gtctcaaact cctgggctca ggcgatccac ctgtctcagc ctcccagagt gctgggatta
2101 caattgtgag ccaccacgtc cagctggaag ggtcaacatc ttttacattc tgcaagcaca
2161 tctgcatttt caccccaccc ttcccctcct tctccctttt tatatcccat ttttatatcg
2221 atctcttatt ttacaataaa actttgctgc cacctgtgtg tctgaggggt g SEQ ID NO: 101 Human TP53 isoform e Amino Acid Sequence (NP_001119588.1)
1 MFCQLAKTCP VQLWVDSTPP PGTRVRAMAI YKQSQHMTEV VRRCPHHERC SDSDGLAPPQ
61 HLIRVEGNLR VEYLDDRNTF RHSVVVPYEP PEVGSDCTTI HYNYMCNSSC MGGMNRRPIL
121 TIITLEDSSG NLLGRNSFEV RVCACPGRDR RTEEENLRKK GEPHHELPPG STKRALPNNT
181 SSSPQPKKKP LDGEYFTLQD QTSFQKENC SEQ ID NO: 102 Human TP53 transcript variant 6 cDNA sequence NM_001126116.1; CDS: 279-908)
1 tgaggccagg agatggaggc tgcagtgagc tgtgatcaca ccactgtgct ccagcctgag
61 tgacagagca agaccctatc tcaaaaaaaa aaaaaaaaaa gaaaagctcc tgaggtgtag
121 acgccaactc tctctagctc gctagtgggt tgcaggaggt gcttacgcat gtttgtttct
181 ttgctgccgt cttccagttg ctttatctgt tcacttgtgc cctgactttc aactctgtct
241 ccttcctctt cctacagtac tcccctgccc tcaacaagat gttttgccaa ctggccaaga
301 cctgccctgt gcagctgtgg gttgattcca cacccccgcc cggcacccgc gtccgcgcca
361 tggccatcta caagcagtca cagcacatga cggaggttgt gaggcgctgc ccccaccatg
421 agcgctgctc agatagcgat ggtctggccc ctcctcagca tcttatccga gtggaaggaa
481 atttgcgtgt ggagtatttg gatgacagaa acacttttcg acatagtgtg gtggtgccct
541 atgagccgcc tgaggttggc tctgactgta ccaccatcca ctacaactac atgtgtaaca TABLE 2-continued TP53
Dephosphorylated human TP53 at Ser 15 or at corresponding phosphorylable amino acid in an ortholog thereof 601 gttcctgcat gggcggcatg aaccggaggc ccatcctcac catcatcaca ctggaagact
661 ccagtggtaa tctactggga cggaacagct ttgaggtgcg tgtttgtgcc tgtcctggga
721 gagaccggcg cacagaggaa gagaatctcc gcaagaaagg ggagcctcac cacgagctgc
781 ccccagggag cactaagcga gcactgccca acaacaccag ctcctctccc cagccaaaga
841 agaaaccact ggatggagaa tatttcaccc ttcaggacca gaccagcttt caaaaagaaa
901 attgttaaag agagcatgaa aatggttcta tgactttgcc tgatacagat gctacttgac
961 ttacgatggt gttacttcct gataaactcg tcgtaagttg aaaatattat ccgtgggcgt
1021 gagcgcttcg agatgttccg agagctgaat gaggccttgg aactcaagga tgcccaggct
1081 gggaaggagc caggggggag cagggctcac tccagccacc tgaagtccaa aaagggtcag
1141 tctacctccc gccataaaaa actcatgttc aagacagaag ggcctgactc agactgacat
1201 tctccacttc ttgttcccca ctgacagcct cccaccccca tctctccctc ccctgccatt
1261 ttgggttttg ggtctttgaa cccttgcttg caataggtgt gcgtcagaag cacccaggac
1321 ttccatttgc tttgtcccgg ggctccactg aacaagttgg cctgcactgg tgttttgttg
1381 tggggaggag gatggggagt aggacatacc agcttagatt ttaaggtttt tactgtgagg
1441 gatgtttggg agatgtaaga aatgttcttg cagttaaggg ttagtttaca atcagccaca
1501 ttctaggtag ggcccactt caccgtacta accagggaag ctgtccctca ctgttgaatt
1561 ttctctaact tcaaggccca tatctgtgaa atgctggcat ttgcacctac ctcacagagt
1621 gcattgtgag ggttaatgaa ataatgtaca tctggccttg aaaccacctt ttattacatg
1681 gggtctagaa cttgaccccc ttgagggtgc ttgttccctc tccctgttgg tcggtgggtt
1741 ggtagtttct acagttgggc agctggttag gtagagggag ttgtcaagtc tctgctggcc
1801 cagccaaacc ctgtctgaca acctcttggt gaaccttagt acctaaaagg aaatctcacc
1861 ccatcccaca ccctggagga tttcatctct tgtatatgat gatctggatc caccaagact
1921 tgttttatgc tcagggtcaa tttctttttt cttttttttt tttttttttc tttttctttg
1981 agactgggtc tcgctttgtt gcccaggctg gagtggagtg gcgtgatctt ggcttactgc
2041 agcctttgcc tccccggctc gagcagtcct gcctcagcct ccggagtagc tgggaccaca
2101 ggttcatgcc accatggcca gccaactttt gcatgttttg tagagatggg gtctcacagt
2161 gttgcccagg ctggtctcaa actcctgggc tcaggcgatc cacctgtctc agcctcccag
2221 agtgctggga ttacaattgt gagccaccac gtccagctgg aagggtcaac atcttttaca
2281 ttctgcaagc acatctgcat tttcacccca cccttcccct ccttctccct ttttatatcc
2341 catttttata tcgatctctt attttacaat aaaactttgc tgccacctgt gtgtctgagg
2401 ggtg SEQ ID NO: 103 Human TP53 isoform f Amino Acid Sequence (NP_001119589.1)
1 MFCQLAKTCP VQLWVDSTPP PGTRVRAMAI YKQSQHMTEV VRRCPHHERC SDSDGLAPPQ
61 HLIRVEGNLR VEYLDDRNTF RHSVVVPYEP PEVGSDCTTI HYNYMCNSSC MGGMNRRPIL
121 TIITLEDSSG NLLGRNSFEV RVCACPGRDR RTEEENLRKK GEPHHELPPG STKRALPNNT
181 SSSPQPKKKP LDGEYFTLQM LLDLRWCYFL INSS SEQ ID NO: 104 Human TP53 transcript variant 7 cDNA sequence
NM_001126117.1; CDS: 279-923)
1 tgaggccagg agatggaggc tgcagtgagc tgtgatcaca ccactgtgct ccagcctgag
61 tgacagagca agaccctatc tcaaaaaaaa aaaaaaaaaa gaaaagctcc tgaggtgtag
121 acgccaactc tctctagctc gctagtgggt tgcaggaggt gcttacgcat gtttgtttct
181 ttgctgccgt cttccagttg ctttatctgt tcacttgtgc cctgactttc aactctgtct
241 ccttcctctt cctacagtac tcccctgccc tcaacaagat gttttgccaa ctggccaaga
301 cctgccctgt gcagctgtgg gttgattcca cacccccgcc cggcacccgc gtccgcgcca
361 tggccatcta caagcagtca cagcacatga cggaggttgt gaggcgctgc ccccaccatg
421 agcgctgctc agatagcgat ggtctggccc ctcctcagca tcttatccga gtggaaggaa
481 atttgcgtgt ggagtatttg gatgacagaa acacttttcg acatagtgtg gtggtgccct
541 atgagccgcc tgaggttggc tctgactgta ccaccatcca ctacaactac atgtgtaaca
601 gttcctgcat gggcggcatg aaccggaggc ccatcctcac catcatcaca ctggaagact
661 ccagtggtaa tctactggga cggaacagct ttgaggtgcg tgtttgtgcc tgtcctggga
721 gagaccggcg cacagaggaa gagaatctcc gcaagaaagg ggagcctcac cacgagctgc
781 ccccagggag cactaagcga gcactgccca acaacaccag ctcctctccc cagccaaaga
841 agaaaccact ggatggagaa tatttcaccc ttcagatgct acttgactta cgatggtgtt
901 acttcctgat aaactcgtcg taagttgaaa atattatccg tgggcgtgag cgcttcgaga
961 tgttccgaga gctgaatgag gccttggaac tcaaggatgc ccaggctggg aaggagccag
1021 gggggagcag ggctcactcc agccacctga agtccaaaaa gggtcagtct acctcccgcc
1081 ataaaaaact catgttcaag acagaagggc ctgactcaga ctgacattct ccacttcttg
1141 ttccccactg acagcctccc acccccatct ctccctcccc tgccattttg ggttttgggt
1201 ctttgaaccc ttgcttgcaa taggtgtgcg tcagaagcac ccaggacttc catttgcttt
1261 gtcccggggc tccactgaac aagttggcct gcactggtgt tttgttgtgg ggaggaggat
1321 ggggagtagg acataccagc ttagatttta aggtttttac tgtgagggat gtttgggaga
1381 tgtaagaaat gttcttgcag ttaagggtta gtttacaatc agccacattc taggtagggg
1441 cccacttcac cgtactaacc agggaagctg tccctcactg ttgaattttc tctaacttca
1501 aggcccatat ctgtgaaatg ctggcatttg cacctacctc acagagtgca ttgtgagggt
1561 taatgaaata atgtacatct ggccttgaaa ccacctttta ttacatgggg tctagaactt
1621 gacccccttg agggtgcttg ttccctctcc ctgttggtcg gtgggttggt agtttctaca
1681 gttgggcagc tggttaggta gagggagttg tcaagtctct gctggcccag ccaaaccctg
1741 tctgacaacc tcttggtgaa ccttagtacc taaaaggaaa tctcacccca tcccacaccc
1801 tggaggattt catctcttgt atatgatgat ctggatccac caagacttgt tttatgctca
1861 gggtcaattt ctttttctt tttttttttt ttttttcttt ttctttgaga ctgggtctcg
1921 ctttgttgcc caggctggag tggagtggcg tgatcttggc ttactgcagc ctttgcctcc
1981 ccggctcgag cagtcctgcc tcagcctccg gagtagctgg gaccacaggt tcatgccacc
2041 atggccagcc aacttttgca tgttttgtag agatggggtc tcacagtgtt gcccaggctg
2101 gtctcaaact cctgggctca ggcgatccac ctgtctcagc ctcccagagt gctgggatta TABLE 2-continued TP53
Dephosphorylated human TP53 at Ser 15 or at corresponding phosphorylable amino acid in an ortholog thereof 2161 caattgtgag ccaccacgtc cagctggaag ggtcaacatc ttttacattc tgcaagcaca
2221 tctgcatttt caccccaccc ttcccctcct tctccctttt tatatcccat ttttatatcg
2281 atctcttatt ttacaataaa actttgctgc cacctgtgtg tctgaggggt g SEQ ID NO: 105 Human TP53 isoform g Amino Acid Sequence (NP_001119590.1, NP_001263689.1, and NP_001263690.1)
1 MDDLMLSPDD IEQWFTEDPG PDEAPRMPEA APPVAPAPAA PTPAAPAPAP SWPLSSSVPS
61 QKTYQGSYGF RLGFLHSGTA KSVTCTYSPA LNKMFCQLAK TCPVQLWVDS TPPPGTRVRA
121 MAIYKQSQHM TEVVRRCPHH ERCSDSDGLA PPQHLIRVEG NLRVEYLDDR NTFRHSVVVP
181 YEPPEVGSDC TTIHYNYMCN SSCMGGMNRR PILTIITLED SSGNLLGRNS FEVRVCACPG
241 RDRRTEEENL RKKGEPHHEL PPGSTKRALP NNTSSSPQPK KKPLDGEYFT LQIRGRERFE
301 MFRELNEALE LKDAQAGKEP GGSRAHSSHL KSKKGQSTSR HKKLMFKTEG PDSD SEQ ID NO: 106 Human TP53 transcript variant 8 cDNA sequence (NM_001126118.1; CDS: 437-1501)
1 gatgggattg gggttttccc ctcccatgtg ctcaagactg gcgctaaaag ttttgagctt
61 ctcaaaagtc tagagccacc gtccagggag caggtagctg ctgggctccg gggacacttt
121 gcgttcgggc tgggagcgtg ctttccacga cggtgacacg cttccctgga ttggcagcca
181 gactgccttc cgggtcactg ccatggagga gccgcagtca gatcctagcg tcgagccccc
241 tctgagtcag gaaacatttt cagacctatg gaaactgtga gtggatccat tggaagggca
301 ggcccaccac ccccacccca accccagccc cctagcagag acctgtggga agcgaaaatt
361 ccatgggact gactttctgc tcttgtcttt cagacttcct gaaaacaacg ttctgtcccc
421 cttgccgtcc caagcaatgg atgatttgat gctgtccccg gacgatattg aacaatggtt
481 cactgaagac ccaggtccag atgaagctcc cagaatgcca gaggctgctc cccccgtggc
541 ccctgcacca gcagctccta caccggcggc ccctgcacca gccccctcct ggcccctgtc
601 atcttctgtc ccttcccaga aaacctacca gggcagctac ggtttccgtc tgggcttctt
661 gcattctggg acagccaagt ctgtgacttg cacgtactcc cctgccctca acaagatgtt
721 ttgccaactg gccaagacct gccctgtgca gctgtgggtt gattccacac ccccgcccgg
781 cacccgcgtc cgcgccatgg ccatctacaa gcagtcacag cacatgacgg aggttgtgag
841 gcgctgcccc caccatgagc gctgctcaga tagcgatggt ctggcccctc ctcagcatct
901 tatccgagtg gaaggaaatt tgcgtgtgga gtatttggat gacagaaaca cttttcgaca
961 tagtgtggtg gtgccctatg agccgcctga ggttggctct gactgtacca ccatccacta
1021 caactacatg tgtaacagtt cctgcatggg cggcatgaac cggaggccca tcctcaccat
1081 catcacactg gaagactcca gtggtaatct actgggacgg aacagctttg aggtgcgtgt
1141 ttgtgcctgt cctgggagag accggcgcac agaggaagag aatctccgca agaaagggga
1201 gcctcaccac gagctgcccc cagggagcac taagcgagca ctgcccaaca acaccagctc
1261 ctctccccag ccaaagaaga aaccactgga tggagaatat ttcacccttc agatccgtgg
1321 gcgtgagcgc ttcgagatgt tccgagagct gaatgaggcc ttggaactca aggatgccca
1381 ggctgggaag gagccagggg ggagcagggc tcactccagc cacctgaagt ccaaaaaggg
1441 tcagtctacc tcccgccata aaaaactcat gttcaagaca gaagggcctg actcagactg
1501 acattctcca cttcttgttc cccactgaca gcctcccacc cccatctctc cctcccctgc
1561 cattttgggt tttgggtctt tgaacccttg cttgcaatag gtgtgcgtca gaagcaccca
1621 ggacttccat ttgctttgtc ccggggctcc actgaacaag ttggcctgca ctggtgtttt
1681 gttgtgggga ggaggatggg gagtaggaca taccagctta gattttaagg tttttactgt
1741 gagggatgtt tgggagatgt aagaaatgtt cttgcagtta agggttagtt tacaatcagc
1801 cacattctag gtaggggccc acttcaccgt actaaccagg gaagctgtcc ctcactgttg
1861 aattttctct aacttcaagg cccatatctg tgaaatgctg gcatttgcac ctacctcaca
1921 gagtgcattg tgagggttaa tgaaataatg tacatctggc cttgaaacca ccttttatta
1981 catggggtct agaacttgac ccccttgagg gtgcttgttc cctctccctg ttggtcggtg
2041 ggttggtagt ttctacagtt gggcagctgg ttaggtagag ggagttgtca agtctctgct
2101 ggcccagcca aaccctgtct gacaacctct tggtgaacct tagtacctaa aaggaaatct
2161 caccccatcc cacaccctgg aggatttcat ctcttgtata tgatgatctg gatccaccaa
2221 gacttgtttt atgctcaggg tcaatttctt ttttcttttt tttttttttt tttctttttc
2281 tttgagactg ggtctcgctt tgttgcccag gctggagtgg agtggcgtga tcttggctta
2341 ctgcagcctt tgcctccccg gctcgagcag tcctgcctca gcctccggag tagctgggac
2401 cacaggttca tgccaccatg gccagccaac ttttgcatgt tttgtagaga tggggtctca
2461 cagtgttgcc caggctggtc tcaaactcct gggctcaggc gatccacctg tctcagcctc
2521 ccagagtgct gggattacaa ttgtgagcca ccacgtccag ctggaagggt caacatcttt
2581 tacattctgc aagcacatct gcattttcac cccacccttc ccctccttct ccctttttat
2641 atcccatttt tatatcgatc tcttatttta caataaaact ttgctgccac ctgtgtgtct
2701 gaggggtg SEQ ID NO: 107 Human TP53 transcript variant 1 cDNA Sequence (NM_001276760.1; CDS: 320-1384)
1 gatgggattg gggttttccc ctcccatgtg ctcaagactg gcgctaaaag ttttgagctt
61 ctcaaaagtc tagagccacc gtccagggag caggtagctg ctgggctccg gggacacttt
121 gcgttcgggc tgggagcgtg ctttccacga cggtgacacg cttccctgga ttggcagcca
181 gactgccttc cgggtcactg ccatggagga gccgcagtca gatcctagcg tcgagccccc
241 tctgagtcag gaaacatttt cagacctatg gaaactactt cctgaaaaca acgttctgtc
301 ccccttgccg tcccaagcaa tggatgattt gatgctgtcc ccggacgata ttgaacaatg
361 gttcactgaa gacccaggtc cagatgaagc tcccagaatg ccagaggctg ctccccccgt
421 ggcccctgca ccagcagctc ctacaccggc ggcccctgca ccagccccct cctggcccct
481 gtcatcttct gtcccttccc agaaaaccta ccagggcagc tacggtttcc gtctgggctt
541 cttgcattct gggacagcca agtctgtgac ttgcacgtac tcccctgccc tcaacaagat
601 gttttgccaa ctggccaaga cctgccctgt gcagctgtgg gttgattcca cacccccgcc
661 cggcacccgc gtccgcgcca tggccatcta caagcagtca cagcacatga cggaggttgt TABLE 2-continued TP53
Dephosphorylated human TP53 at Ser 15 or at corresponding phosphorylable amino acid in an ortholog thereof

```
 721 gaggcgctgc ccccaccatg agcgctgctc agatagcgat ggtctggccc ctcctcagca
 781 tcttatccga gtggaaggaa atttgcgtgt ggagtatttg gatgacagaa acacttttcg
 841 acatagtgtg gtggtgccct atgagccgcc tgaggttggc tctgactgta ccaccatcca
 901 ctacaactac atgtgtaaca gttcctgcat gggcggcatg aaccggaggc ccatcctcac
 961 catcatcaca ctggaagact ccagtggtaa tctactggga cggaacagct ttgaggtgcg
1021 tgtttgtgcc tgtcctggga gagaccggcg cacagaggaa gagaatctcc gcaagaaagg
1081 ggagcctcac cacgagctgc ccccagggag cactaagcga gcactgccca acaacaccag
1141 ctcctctccc cagccaaaga agaaaccact ggatggagaa tatttcaccc ttcagatccg
1201 tgggcgtgag cgcttcgaga tgttccgaga gctgaatgag gccttggaac tcaaggatgc
1261 ccaggctggg aaggagccag gggggagcag ggctcactcc agccacctga agtccaaaaa
1321 gggtcagtct acctcccgcc ataaaaaact catgttcaag acagaagggc ctgactcaga
1381 ctgacattct ccacttcttg ttccccactg acagcctccc acccccatct ctccctcccc
1441 tgccattttg ggttttgggt ctttgaaccc ttgcttgcaa taggtgtgcg tcagaagcac
1501 ccaggacttc catttgcttt gtcccggggc tccactgaac aagttggcct gcactggtgt
1561 tttgttgtgg ggaggaggat ggggagtagg acataccagc ttagatttta aggtttttac
1621 tgtgagggat gtttgggaga tgtaagaaat gttcttgcag ttaagggtta gtttacaatc
1681 agccacattc taggtagggg cccacttcac cgtactaacc agggaagctg tccctcactg
1741 ttgaattttc tctaacttca aggcccatat ctgtgaaatg ctggcatttg cacctacctc
1801 acagagtgca ttgtgagggt taatgaaata atgtacatct ggccttgaaa ccaccttta
1861 ttacatgggg tctagaactt gacccccttg agggtgcttg ttccctctcc ctgttggtcg
1921 gtgggttggt agtttctaca gttgggcagc tggttaggta gagggagttg tcaagtctct
1981 gctggcccag ccaaaccctg tctgacaacc tcttggtgaa ccttagtacc taaaaggaaa
2041 tctcacccca tcccacaccc tggaggattt catctcttgt atatgatgat ctggatccac
2101 caagacttgt tttatgctca gggtcaattt cttttttctt tttttttttt tttttctttt
2161 ttctttgaga ctgggtctcg ctttgttgcc caggctggag tggagtggcg tgatcttggc
2221 ttactgcagc ctttgcctcc ccggctcgag cagtcctgcc tcagcctccg gagtagctgg
2281 gaccacaggt tcatgccacc atggccagcc aacttttgca tgtttttgtag agatggggtc
2341 tcacagtgtt gcccaggctg gtctcaaact cctgggctca ggcgatccac ctgtctcagc
2401 ctcccagagt gctgggatta caattgtgag ccaccacgtc cagctggaag ggtcaacatc
2461 ttttacattc tgcaagcaca tctgcatttt caccccaccc ttcccctcct tctccctttt
2521 tatatcccat ttttatatcg atctcttatt ttacaataaa actttgctgc cacctgtgtg
2581 tctgaggggt g
```

SEQ ID NO: 108 Human TP53 transcript variant 2 cDNA Sequence
(NM_001276761.1; CDS: 317-1381)

```
   1 gatgggattg gggttttccc ctcccatgtg ctcaagactg gcgctaaaag ttttgagctt
  61 ctcaaaagtc tagagccacc gtccagggag caggtagctg ctgggctccg gggacacttt
 121 gcgttcgggc tgggagcgtg ctttccacga cggtgacacg cttccctgga ttggccagac
 181 tgccttccgg gtcactgcca tggaggagcc gcagtcagat cctagcgtcg agccccctct
 241 gagtcaggaa acattttcag acctatggaa actacttcct gaaaacaacg ttctgtcccc
 301 cttgccgtcc caagcaatgg atgatttgat gctgtccccg gacgatattg aacaatggtt
 361 cactgaagac ccaggtccag atgaagctcc cagaatgcca gaggctgctc cccccgtggc
 421 ccctgcacca gcagctccta caccggcggc ccctgcacca gccccctcct ggcccctgtc
 481 atcttctgtc ccttcccaga aaacctacca gggcagctac ggtttccgtc tgggcttctt
 541 gcattctggg acagccaagt ctgtgacttg cacgtactcc cctgccctca acaagatgtt
 601 ttgccaactg gccaagacct gccctgtgca gctgtgggtt gattccacac ccccgcccgg
 661 cacccgcgtc cgcgccatgg ccatctacaa gcagtcacag cacatgacgg aggttgtgag
 721 gcgctgcccc caccatgagc gctgctcaga tagcgatggt ctggcccctc ctcagcatct
 781 tatccgagtg gaaggaaatt tgcgtgtgga gtatttggat gacagaaaca cttttcgaca
 841 tagtgtggtg gtgccctatg agccgcctga ggttggctct gactgtacca ccatccacta
 901 caactacatg tgtaacagtt cctgcatggg cggcatgaac cggaggccca tcctcaccat
 961 catcacactg gaagactcca gtggtaatct actgggacgg aacagctttg aggtgcgtgt
1021 ttgtgcctgt cctgggagag accggcgcac agaggaagag aatctccgca agaaagggga
1081 gcctcaccac gagctgcccc cagggagcac taagcgagca ctgcccaaca acaccagctc
1141 ctctccccag ccaaagaaga aaccactgga tggagaatat ttcacccttc agatccgtgg
1201 gcgtgagcgc ttcgagatgt tccgagagct gaatgaggcc ttggaactca aggatgccca
1261 ggctgggaag gagccagggg ggagcagggc tcactccagc cacctgaagt ccaaaaaggg
1321 tcagtctacc tcccgccata aaaaactcat gttcaagaca gaagggcctg actcagactg
1381 acattctcca cttcttgttc cccactgaca gcctcccacc cccatctctc cctcccctgc
1441 cattttgggt tttgggtctt tgaacccttg cttgcaatag gtgtgcgtca gaagcaccca
1501 ggacttccat ttgctttgtc ccggggctcc actgaacaag ttggcctgca ctggtgtttt
1561 gttgtgggga ggaggatggg gagtaggaca taccagctta gattttaagg tttttactgt
1621 gagggatgtt tgggagatgt aagaaatgtt cttgcagtta agggttagtt tacaatcagc
1681 cacattctag gtaggggccc acttcaccgt actaaccagg gaagctgtcc ctcactgttg
1741 aattttctct aacttcaagg cccatatctg tgaaatgctg gcatttgcac ctacctcaca
1801 gagtgcattg tgagggttaa tgaaataatg tacatctggc cttgaaacca ccttttatta
1861 catggggtct agaacttgac ccccttgagg gtgcttgttc cctctccctg ttggtcggtg
1921 ggttggtagt ttctacagtt gggcagctgg ttaggtagag ggagttgtca agtctctgct
1981 ggcccagcca aaccctgtct gacaacctct tggtgaacct tagtacctaa aaggaaatct
2041 caccccatcc cacaccctgg aggatttcat ctcttgtata tgatgatctg gatccaccaa
2101 gacttgtttt atgctcaggg tcaatttctt ttttcttttt tttttttttt tttcttttttc
2161 tttgagactg ggtctcgctt tgttgcccag gctggagtgg agtggcgtga tcttggctta
2221 ctgcagcctt tgcctccccg gctcgagcag tcctgcctca gcctccggag tagctgggac
2281 cacaggttca tgccaccatg gccagccaac ttttgcatgt tttgtagaga tggggtctca
2341 cagtgttgcc caggctggtc tcaaactcct gggctcaggc gatccacctg tctcagcctc
2401 ccagagtgct gggattacaa ttgtgagcca ccacgtccag ctggaagggt caacatcttt
```

TABLE 2-continued

| TP53 Dephosphorylated human TP53 at Ser 15 or at corresponding phosphorylable amino acid in an ortholog thereof |
|---|
| 2461 tacattctgc aagcacatct gcattttcac cccacccttc ccctccttct ccctttttat<br>2521 atcccatttt tatatcgatc tcttatttta caataaaact ttgctgccac ctgtgtgtct<br>2581 gaggggtg |
| SEQ ID NO: 109 Human TP53 isoform h Amino Acid Sequence (NP_001263624.1)<br>1 MDDLMLSPDD IEQWFTEDPG PDEAPRMPEA APPVAPAPAA PTPAAPAPAP SWPLSSSVPS<br>61 QKTYQGSYGF RLGFLHSGTA KSVTCTYSPA LNKMFCQLAK TCPVQLWVDS TPPPGTRVRA<br>121 MAIYKQSQHM TEVVRRCPHH ERCSDSDGLA PPQHLIRVEG NLRVEYLDDR NTFRHSVVVP<br>181 YEPPEVGSDC TTIHYNYMCN SSCMGGMNRR PILTIITLED SSGNLLGRNS FEVRVCACPG<br>241 RDRRTEEENL RKKGEPHHEL PPGSTKRALP NNTSSSPQPK KKPLDGEYFT LQMLLDLRWC<br>301 YFLINSS |
| SEQ ID NO: 110 Human TP53 transcript variant 4 cDNA Sequence (NM_001276695.1; CDS: 320-1243)<br>1 gatgggattg gggttttccc ctcccatgtg ctcaagactg gcgctaaaag ttttgagctt<br>61 ctcaaaagtc tagagccacc gtccagggag caggtagctg ctgggctccg gggacacttt<br>121 gcgttcgggc tgggagcgtg ctttccacga cggtgacacg cttccctgga ttggcagcca<br>181 gactgccttc cgggtcactg ccatggagga gccgcagtca gatcctagcg tcgagccccc<br>241 tctgagtcag gaaacatttt cagacctatg gaaactactt cctgaaaaca acgttctgtc<br>301 cccttgccg tcccaagcaa tggatgattt gatgctgtcc ccggacgata ttgaacaatg<br>361 gttcactgaa gacccaggtc cagatgaagc tcccagaatg ccagaggctg ctccccccgt<br>421 ggcccctgca ccagcagctc ctacaccggc ggcccctgca ccagcccct cctggcccct<br>481 gtcatcttct gtcccttccc agaaaaccta ccagggcagc tacggtttcc gtctgggctt<br>541 cttgcattct gggacagcca agtctgtgac ttgcacgtac tcccctgccc tcaacaagat<br>601 gttttgccaa ctggccaaga cctgccctgt gcagctgtgg gttgattcca cacccccgcc<br>661 cggcacccgc gtccgcgcca tggccatcta caagcagtca cagcacatga cggaggttgt<br>721 gaggcgctgc ccccaccatg agcgctgctc agatagcgat ggtctggccc ctcctcagca<br>781 tcttatccga gtggaaggaa atttgcgtgt ggagtatttg gatgacagaa acacttttcg<br>841 acatagtgtg gtggtgccct atgagccgcc tgaggttggc tctgactgta ccaccatcca<br>901 ctacaactac atgtgtaaca gttcctgcat gggcggcatg aaccggaggc ccatcctcac<br>961 catcatcaca ctggaagact ccagtggtaa tctactggga cggaacagct ttgaggtgcg<br>1021 tgtttgtgcc tgtcctggga gagaccggcg cacagaggaa gagaatctcc gcaagaaagg<br>1081 ggagcctcac cacgagctgc ccccagggag cactaagcga gcactgccca acaacaccag<br>1141 ctcctctccc cagccaaaga agaaaccact ggatggagaa tatttcaccc ttcagatgct<br>1201 acttgactta cgatggtgtt acttcctgat aaactcgtcg taagttgaaa atattatccg<br>1261 tgggcgtgag cgcttcgaga tgttccgaga gctgaatgag gccttggaac tcaaggatgc<br>1321 ccaggctggg aaggagccag gggggagcag ggctcactcc agccacctga agtccaaaaa<br>1381 gggtcagtct acctcccgcc ataaaaaact catgttcaag acagaagggc ctgactcaga<br>1441 ctgacattct ccacttcttg ttccccactg acagcctccc acccccatct ctccctcccc<br>1501 tgccattttg ggttttgggt ctttgaaccc ttgcttgcaa taggtgtgcg tcagaagcac<br>1561 ccaggacttc catttgcttt gtcccggggc tccactgaac aagttggcct gcactggtgt<br>1621 tttgttgtgg ggaggaggat ggggagtagg acataccagc ttagatttta aggtttttac<br>1681 tgtgagggat gtttgggaga tgtaagaaat gttcttgcag ttaagggtta gtttacaatc<br>1741 agccacattc taggtagggg cccacttcac cgtactaacc agggaagctg tccctcactg<br>1801 ttgaattttc tctaacttca aggcccatat ctgtgaaatg ctggcatttg cacctacctc<br>1861 acagagtgca ttgtgagggt taatgaaata atgtacatct ggccttgaaa ccacctttta<br>1921 ttacatgggg tctagaactt gaccccccttg agggtgcttg ttccctctcc ctgttggtcg<br>1981 gtgggttggt agtttctaca gttgggcagc tggttaggta gagggagttg tcaagtctct<br>2041 gctggcccag ccaaaccctg tctgacaacc tcttggtgaa ccttagtacc taaaaggaaa<br>2101 tctcacccca tcccacaccc tggaggattt catctcttgt atatgatgat ctggatccac<br>2161 caagacttgt tttatgctca gggtcaattt ctttttctt ttttttttt tttttcttt<br>2221 ttctttgaga ctgggtctcg ctttgttgcc caggctggag tggagtggcg tgatcttggc<br>2281 ttactgcagc ctttgcctcc ccggctcgag cagtcctgcc tcagcctccg gagtagctgg<br>2341 gaccacaggt tcatgccacc atggccagcc aacttttgca tgttttgtag agatggggtc<br>2401 tcacagtgtt gcccaggctg gtctcaaact cctgggctca ggcgatccac ctgtctcagc<br>2461 ctcccagagt gctgggatta caattgtgag ccaccacgtc cagctggaag ggtcaacatc<br>2521 ttttacattc tgcaagcaca tctgcatttt caccccaccc ttcccctcct tctccctttt<br>2581 tatatcccat ttttatatcg atctcttatt ttacaataaa actttgctgc cacctgtgtg<br>2641 tctgaggggt g |
| SEQ ID NO: 111 Human TP53 isoform i Amino Acid Sequence (NP_001263625.1)<br>1 MDDLMLSPDD IEQWFTEDPG PDEAPRMPEA APPVAPAPAA PTPAAPAPAP SWPLSSSVPS<br>61 QKTYQGSYGF RLGFLHSGTA KSVTCTYSPA LNKMFCQLAK TCPVQLWVDS TPPPGTRVRA<br>121 MAIYKQSQHM TEVVRRCPHH ERCSDSDGLA PPQHLIRVEG NLRVEYLDDR NTFRHSVVVP<br>181 YEPPEVGSDC TTIHYNYMCN SSCMGGMNRR PILTIITLED SSGNLLGRNS FEVRVCACPG<br>241 RDRRTEEENL RKKGEPHHEL PPGSTKRALP NNTSSSPQPK KKPLDGEYFT LQDQTSFQKE<br>301 NC |
| SEQ ID NO: 112 Human TP53 transcript variant 3 cDNA sequence (NM_001276696.1; CDS: 320-1228)<br>1 gatgggattg gggttttccc ctcccatgtg ctcaagactg gcgctaaaag ttttgagctt<br>61 ctcaaaagtc tagagccacc gtccagggag caggtagctg ctgggctccg gggacacttt<br>121 gcgttcgggc tgggagcgtg ctttccacga cggtgacacg cttccctgga ttggcagcca<br>181 gactgccttc cgggtcactg ccatggagga gccgcagtca gatcctagcg tcgagccccc<br>241 tctgagtcag gaaacatttt cagacctatg gaaactactt cctgaaaaca acgttctgtc<br>301 cccttgccg tcccaagcaa tggatgattt gatgctgtcc ccggacgata ttgaacaatg |

TABLE 2-continued

TP53
Dephosphorylated human TP53 at Ser 15 or at corresponding phosphorylable amino acid in an ortholog thereof

```
 361 gttcactgaa gacccaggtc cagatgaagc tcccagaatg ccagaggctg ctccccccgt
 421 ggcccctgca ccagcagctc ctacaccggc ggcccctgca ccagccccct cctggcccct
 481 gtcatcttct gtcccttccc agaaaaccta ccagggcagc tacggtttcc gtctgggctt
 541 cttgcattct gggacagcca agtctgtgac ttgcacgtac tcccctgccc tcaacaagat
 601 gttttgccaa ctggccaaga cctgccctgt gcagctgtgg gttgattcca caccccgcc
 661 cggcacccgc gtccgcgcca tggccatcta caagcagtca cagcacatga cggaggttgt
 721 gaggcgctgc ccccaccatg agcgctgctc agatagcgat ggtctggccc ctcctcagca
 781 tcttatccga gtggaaggaa atttgcgtgt ggagtatttg gatgacagaa acacttttcg
 841 acatagtgtg gtggtgccct atgagccgcc tgaggttggc tctgactgta ccaccatcca
 901 ctacaactac atgtgtaaca gttcctgcat gggcggcatg aaccggaggc ccatcctcac
 961 catcatcaca ctggaagact ccagtggtaa tctactggga cggaacagct ttgaggtgcg
1021 tgtttgtgcc tgtcctggga gagaccggcg cacagaggaa gagaatctcc gcaagaaagg
1081 ggagcctcac cacgagctgc ccccagggag cactaagcga gcactgccca acaacaccag
1141 ctcctctccc cagccaaaga agaaaccact ggatggagaa tatttcaccc ttcaggacca
1201 gaccagcttt caaaaagaaa attgttaaag agagcatgaa aatggttcta tgactttgcc
1261 tgatacagat gctacttgac ttacgatggt gttacttcct gataaactcg tcgtaagttg
1321 aaaatattat ccgtgggcgt gagcgcttcg agatgttccg agagctgaat gaggccttgg
1381 aactcaagga tgcccaggct gggaaggagc caggggggag cagggctcac tccagccacc
1441 tgaagtccaa aaagggtcag tctacctccc gccataaaaa actcatgttc aagacagaag
1501 ggcctgactc agactgacat tctccacttc ttgttcccca ctgacagcct cccaccccca
1561 tctctccctc ccctgccatt ttgggttttg ggtctttgaa cccttgcttg caataggtgt
1621 gcgtcagaag cacccaggac ttccatttgc tttgtcccgg ggctccactg aacaagttgg
1681 cctgcactgg tgttttgttg tggggaggag gatggggagt aggacatacc agcttagatt
1741 ttaaggtttt tactgtgagg gatgtttggg agatgtaaga aatgttcttg cagttaaggg
1801 ttagtttaca atcagccaca ttctaggtag gggcccactt caccgtacta accagggaag
1861 ctgtccctca ctgttgaatt ttctctaact tcaaggccca tatctgtgaa atgctggcat
1921 ttgcacctac ctcacagagt gcattgtgag ggttaatgaa ataatgtaca tctggccttg
1981 aaaccacctt ttattacatg gggtctagaa cttgaccccc ttgagggtgc ttgttccctc
2041 tccctgttgg tcggtgggtt ggtagtttct acagttgggc agctggttag gtagagggag
2101 ttgtcaagtc tctgctggcc cagccaaacc ctgtctgaca acctcttggt gaaccttagt
2161 acctaaaagg aaatctcacc ccatcccaca ccctggagga tttcatctct tgtatatgat
2221 gatctggatc caccaagact tgttttatgc tcagggtcaa tttctttttt cttttttttt
2281 tttttttttc tttttctttg agactgggtc tcgctttgtt gcccaggctg gagtggagtg
2341 gcgtgatctt ggcttactgc agcctttgcc tccccggctc gagcagtcct gcctcagcct
2401 ccggagtagc tgggaccaca ggttcatgcc accatggcca gccaactttt gcatgttttg
2461 tagagatggg gtctcacagt gttgcccagg ctggtctcaa actcctgggc tcaggcgatc
2521 cacctgtctc agcctcccag agtgctggga ttacaattgt gagccaccac gtccagctgg
2581 aagggtcaac atcttttaca ttctgcaagc acatctgcat tttcacccca cccttcccct
2641 ccttctccct ttttatatcc cattttata tcgatctctt attttacaat aaaactttgc
2701 tgccacctgt gtgtctgagg ggtg
```

SEQ ID NO: 113 Human TP53 isoform j Amino Acid Sequence (NP_001263626.1)

```
  1 MAIYKQSQHM TEVVRRCPHH ERCSDSDGLA PPQHLIRVEG NLRVEYLDDR NTFRHSVVVP
 61 YEPPEVGSDC TTIHYNYMCN SSCMGGMNRR PILTIITLED SSGNLLGRNS FEVRVCACPG
121 RDRRTEEENL RKKGEPHHEL PPGSTKRALP NNTSSSPQPK KKPLDGEYFT LQIRGRERFE
181 MFRELNEALE LKDAQAGKEP GGSRAHSSHL KSKKGQSTSR HKKLMFKTEG PDSD
```

SEQ ID NO: 114 Human TP53 transcript variant 5 cDNA sequence NM_001276697.1; CDS: 360-1064)

```
   1 tgaggccagg agatggaggc tgcagtgagc tgtgatcaca ccactgtgct ccagcctgag
  61 tgacagagca agaccctatc tcaaaaaaaa aaaaaaaaaa gaaaagctcc tgaggtgtag
 121 acgccaactc tctctagctc gctagtgggt tgcaggaggt gcttacgcat gtttgtttct
 181 ttgctgccgt cttccagttg ctttatctgt tcacttgtgc cctgactttc aactctgtct
 241 ccttcctctt cctacagtac tcccctgccc tcaacaagat gttttgccaa ctggccaaga
 301 cctgccctgt gcagctgtgg gttgattcca caccccgcc cggcacccgc gtccgcgcca
 361 tggccatcta caagcagtca cagcacatga cggaggttgt gaggcgctgc ccccaccatg
 421 agcgctgctc agatagcgat ggtctggccc ctcctcagca tcttatccga gtggaaggaa
 481 atttgcgtgt ggagtatttg gatgacagaa acacttttcg acatagtgtg gtggtgccct
 541 atgagccgcc tgaggttggc tctgactgta ccaccatcca ctacaactac atgtgtaaca
 601 gttcctgcat gggcggcatg aaccggaggc ccatcctcac catcatcaca ctggaagact
 661 ccagtggtaa tctactggga cggaacagct ttgaggtgcg tgtttgtgcc tgtcctggga
 721 gagaccggcg cacagaggaa gagaatctcc gcaagaaagg ggagcctcac cacgagctgc
 781 ccccagggag cactaagcga gcactgccca acaacaccag ctcctctccc cagccaaaga
 841 agaaaccact ggatggagaa tatttcaccc ttcagatccg tgggcgtgag cgcttcgaga
 901 tgttccgaga gctgaatgag gccttggaac tcaaggatgc ccaggctggg aaggagccag
 961 gggggagcag ggctcactcc agccacctga agtccaaaaa gggtcagtct acctcccgcc
1021 ataaaaaact catgttcaag acagaagggc ctgactcaga ctgacattct ccacttcttg
1081 ttccccactg acagcctccc acccccatct ctccctcccc tgccattttg ggttttgggt
1141 ctttgaaccc ttgcttgcaa taggtgtgcg tcagaagcac ccaggacttc catttgcttt
1201 gtcccggggc tccactgaac aagttggcct gcactggtgt tttgttgtgg ggaggaggat
1261 ggggagtagg acataccagc ttagatttta aggtttttac tgtgagggat gtttgggaga
1321 tgtaagaaat gttcttgcag ttaagggtta gtttacaatc agccacattc taggtagggg
1381 cccacttcac cgtactaacc agggaagctg tccctcactg ttgaattttc tctaacttca
1441 aggcccatat ctgtgaaatg ctggcatttg cacctacctc acagagtgca ttgtgagggt
1501 taatgaaata atgtacatct ggccttgaaa ccacctttta ttacatgggg tctagaactt
1561 gacccccttg agggtgcttg ttccctctcc ctgttggtcg gtgggttggt agtttctaca
```

TABLE 2-continued

TP53
Dephosphorylated human TP53 at Ser 15 or at corresponding phosphorylable amino acid in an ortholog thereof 1621 gttgggcagc tggttaggta gagggagttg tcaagtctct gctggcccag ccaaaccctg
1681 tctgacaacc tcttggtgaa ccttagtacc taaaaggaaa tctcacccca tcccacaccc
1741 tggaggattt catctcttgt atatgatgat ctggatccac caagacttgt tttatgctca
1801 gggtcaattt cttttttctt tttttttttt tttttctttt ttctttgaga ctgggtctcg
1861 ctttgttgcc caggctggag tggagtggcg tgatcttggc ttactgcagc ctttgcctcc
1921 ccggctcgag cagtcctgcc tcagcctccg gagtagctgg gaccacaggt tcatgccacc
1981 atggccagcc aacttttgca tgttttgtag agatggggtc tcacagtgtt gcccaggctg
2041 gtctcaaact cctgggctca ggcgatccac ctgtctcagc ctcccagagt gctgggatta
2101 caattgtgag ccaccacgtc cagctggaag ggtcaacatc ttttacattc tgcaagcaca
2161 tctgcatttt caccccaccc ttcccctcct tctccctttt tatatcccat ttttatatcg
2221 atctcttatt ttacaataaa actttgctgc cacctgtgtg tctgaggggt g SEQ ID NO: 115 Human TP53 isoform k Amino Acid Sequence (NP_001263627.1)
1 MAIYKQSQHM TEVVRRCPHH ERCSDSDGLA PPQHLIRVEG NLRVEYLDDR NTFRHSVVVP
61 YEPPEVGSDC TTIHYNYMCN SSCMGGMNRR PILTIITLED SSGNLLGRNS FEVRVCACPG
121 RDRRTEEENL RKKGEPHHEL PPGSTKRALP NNTSSSPQPK KKPLDGEYFT LQDQTSFQKE
181 NC SEQ ID NO: 116 Human TP53 transcript variant 6 cDNA sequence
(NM_001276698.1; CDS: 360-908)
1 tgaggccagg agatggaggc tgcagtgagc tgtgatcaca ccactgtgct ccagcctgag
61 tgacagagca agaccctatc tcaaaaaaaa aaaaaaaaaa gaaaagctcc tgaggtgtag
121 acgccaactc tctctagctc gctagtgggt tgcaggaggt gcttacgcat gtttgtttct
181 ttgctgccgt cttccagttg ctttatctgt tcacttgtgc cctgactttc aactctgtct
241 ccttcctctt cctacagtac tcccctgccc tcaacaagat gttttgccaa ctggccaaga
301 cctgccctgt gcagctgtgg gttgattcca cacccccgcc cggcacccgc gtccgcgcca
361 tggccatcta caagcagtca cagcacatga cggaggttgt gaggcgctgc ccccaccatg
421 agcgctgctc agatagcgat ggtctggccc ctcctcagca tcttatccga gtggaaggaa
481 atttgcgtgt ggagtatttg gatgacagaa acacttttcg acatagtgtg gtggtgccct
541 atgagccgcc tgaggttggc tctgactgta ccaccatcca ctacaactac atgtgtaaca
601 gttcctgcat gggcggcatg aaccggaggc ccatcctcac catcatcaca ctggaagact
661 ccagtggtaa tctactggga cggaacagct ttgaggtgcg tgtttgtgcc tgtcctggga
721 gagaccggcg cacagaggaa gagaatctcc gcaagaaagg ggagcctcac cacgagctgc
781 ccccagggag cactaagcga gcactgccca acaacaccag ctcctctccc cagccaaaga
841 agaaaccact ggatggagaa tatttcaccc ttcaggacca gaccagcttt caaaaagaaa
901 attgttaaag agagcatgaa aatggttcta tgactttgcc tgatacagat gctacttgac
961 ttacgatggt gttacttcct gataaactcg tcgtaagttg aaaatattat ccgtgggcgt
1021 gagcgcttcg agatgttccg agagctgaat gaggccttgg aactcaagga tgcccaggct
1081 gggaaggagc caggggggag cagggctcac tccagccacc tgaagtccaa aaagggtcag
1141 tctacctccc gccataaaaa actcatgttc aagacagaag ggcctgactc agactgacat
1201 tctccacttc ttgttcccca ctgacagcct cccaccccca tctctccctc ccctgccatt
1261 ttgggttttg ggtctttgaa cccttgcttg caataggtgt gcgtcagaag cacccaggac
1321 ttccatttgc tttgtcccgg ggctccactg aacaagttgg cctgcactgg tgttttgttg
1381 tggggaggag gatggggagt aggacatacc agcttagatt ttaaggtttt tactgtgagg
1441 gatgtttggg agatgtaaga aatgttcttg cagttaaggg ttagtttaca atcagccaca
1501 ttctaggtag gggcccactt caccgtacta accagggaag ctgtccctca ctgttgaatt
1561 ttctctaact tcaaggccca tatctgtgaa atgctggcat ttgcacctac ctcacagagt
1621 gcattgtgag ggttaatgaa ataatgtaca tctggccttg aaaccacctt ttattacatg
1681 gggtctagaa cttgaccccc ttgagggtgc ttgttccctc tccctgttgg tcggtgggtt
1741 ggtagtttct acagttgggc agctggttag gtagagggag ttgtcaagtc tctgctggcc
1801 cagccaaacc ctgtctgaca acctcttggt gaaccttagt acctaaaagg aaatctcacc
1861 ccatcccaca ccctggagga tttcatctct tgtatatgat gatctggatc caccaagact
1921 tgttttatgc tcagggtcaa tttctttttt cttttttttt tttttttttc tttttctttg
1981 agactgggtc tcgctttgtt gcccaggctg gagtggagtg gcgtgatctt ggcttactgc
2041 agcctttgcc tccccggctc gagcagtcct gcctcagcct ccggagtagc tgggaccaca
2101 ggttcatgcc accatggcca gccaactttt gcatgttttg tagagatggg gtctcacagt
2161 gttgcccagg ctggtctcaa actcctgggc tcaggcgatc cacctgtctc agcctcccag
2221 agtgctggga ttacaattgt gagccaccac gtccagctgg aagggtcaac atcttttaca
2281 ttctgcaagc acatctgcat tttcacccca cccttcccct ccttctccct ttttatatcc
2341 catttttata tcgatctctt attttacaat aaaactttgc tgccacctgt gtgtctgagg
2401 ggtg SEQ ID NO: 117 Human TP53 isoform 1 Amino Acid Sequence (NP_001263628.1)
1 MAIYKQSQHM TEVVRRCPHH ERCSDSDGLA PPQHLIRVEG NLRVEYLDDR NTFRHSVVVP
61 YEPPEVGSDC TTIHYNYMCN SSCMGGMNRR PILTIITLED SSGNLLGRNS FEVRVCACPG
121 RDRRTEEENL RKKGEPHHEL PPGSTKRALP NNTSSSPQPK KKPLDGEYFT LQMLLDLRWC
181 YFLINSS SEQ ID NO: 118 Human TP53 transcript variant 7 cDNA sequence
NM_001276699.1; CDS: 360-923)
1 tgaggccagg agatggaggc tgcagtgagc tgtgatcaca ccactgtgct ccagcctgag
61 tgacagagca agaccctatc tcaaaaaaaa aaaaaaaaaa gaaaagctcc tgaggtgtag
121 acgccaactc tctctagctc gctagtgggt tgcaggaggt gcttacgcat gtttgtttct
181 ttgctgccgt cttccagttg ctttatctgt tcacttgtgc cctgactttc aactctgtct
241 ccttcctctt cctacagtac tcccctgccc tcaacaagat gttttgccaa ctggccaaga
301 cctgccctgt gcagctgtgg gttgattcca cacccccgcc cggcacccgc gtccgcgcca TABLE 2-continued TP53
Dephosphorylated human TP53 at Ser 15 or at corresponding phosphorylable amino acid in an ortholog thereof 361 tggccatcta caagcagtca cagcacatga cggaggttgt gaggcgctgc ccccaccatg
421 agcgctgctc agatagcgat ggtctggccc ctcctcagca tcttatccga gtggaaggaa
481 atttgcgtgt ggagtatttg gatgacagaa acacttttcg acatagtgtg gtggtgccct
541 atgagccgcc tgaggttggc tctgactgta ccaccatcca ctacaactac atgtgtaaca
601 gttcctgcat gggcggcatg aaccggaggc ccatcctcac catcatcaca ctggaagact
661 ccagtggtaa tctactggga cggaacagct ttgaggtgcg tgtttgtgcc tgtcctggga
721 gagaccggcg cacagaggaa gagaatctcc gcaagaaagg ggagcctcac cacgagctgc
781 ccccagggag cactaagcga gcactgccca acaacaccag ctcctctccc cagccaaaga
841 agaaaccact ggatggagaa tatttcaccc ttcagatgct acttgactta cgatggtgtt
901 acttcctgat aaactcgtcg taagttgaaa atattatccg tgggcgtgag cgcttcgaga
961 tgttccgaga gctgaatgag gccttggaac tcaaggatgc ccaggctggg aaggagccag
1021 gggggagcag ggctcactcc agccacctga agtccaaaaa gggtcagtct acctcccgcc
1081 ataaaaaact catgttcaag acagaagggc ctgactcaga ctgacattct ccacttcttg
1141 ttccccactg acagcctccc acccccatct ctccctcccc tgccattttg ggttttgggt
1201 ctttgaaccc ttgcttgcaa taggtgtgcg tcagaagcac ccaggacttc catttgcttt
1261 gtcccggggc tccactgaac aagttggcct gcactggtgt tttgttgtgg ggaggaggat
1321 ggggagtagg acataccagc ttagatttta aggtttttac tgtgagggat gtttgggaga
1381 tgtaagaaat gttcttgcag ttaagggtta gtttacaatc agccacattc taggtagggg
1441 cccacttcac cgtactaacc agggaagctg tccctcactg ttgaattttc tctaacttca
1501 aggcccatat ctgtgaaatg ctggcatttg cacctacctc acagagtgca ttgtgagggt
1561 taatgaaata atgtacatct ggccttgaaa ccacctttta ttacatgggg tctagaactt
1621 gacccccttg agggtgcttg ttccctctcc ctgttggtcg gtgggttggt agtttctaca
1681 gttgggcagc tggttaggta gagggagttg tcaagtctct gctggcccag ccaaaccctg
1741 tctgacaacc tcttggtgaa ccttagtacc taaaaggaaa tctcacccca tcccacaccc
1801 tggaggattt catctcttgt atatgatgat ctggatccac caagacttgt tttatgctca
1861 gggtcaattt cttttttctt tttttttttt tttttctttt ttctttgaga ctgggtctcg
1921 ctttgttgcc caggctggag tggagtggcg tgatcttggc ttactgcagc ctttgcctcc
1981 ccggctcgag cagtcctgcc tcagcctccg gagtagctgg gaccacaggt tcatgccacc
2041 atggccagcc aacttttgca tgttttgtag agatggggtc tcacagtgtt gcccaggctg
2101 gtctcaaact cctgggctca ggcgatccac ctgtctcagc ctcccagagt gctgggatta
2161 caattgtgag ccaccacgtc cagctggaag ggtcaacatc ttttacattc tgcaagcaca
2221 tctgcatttt caccccaccc ttcccctcct tctccctttt tatatcccat ttttatatcg
2281 atctcttatt ttacaataaa actttgctgc cacctgtgtg tctgaggggt g SEQ ID NO: 119 Mouse TP53 isoform b Amino Acid Sequence (NP_001120705.1)
1 MTAMEESQSD ISLELPLSQE TFSGLWKLLP PEDILPSPHC MDDLLLPQDV EEFFEGPSEA
61 LRVSGAPAAQ DPVTETPGPV APAPATPWPL SSFVPSQKTY QGNYGFHLGF LQSGTAKSVM
121 CTYSPPLNKL FCQLAKTCPV QLWVSATPPA GSRVRAMAIY KKSQHMTEVV RRCPHHERCS
181 DGDGLAPPQH LIRVEGNLYP EYLEDRQTFR HSVVVPYEPP EAGSEYTTIH YKYMCNSSCM
241 GGMNRRPILT IITLEDSSGN LLGRDSFEVR VCACPGRDRR TEEENFRKKE VLCPELPPGS
301 AKRALPTCTS ASPPQKKKPL DGEYFTLKIR GRKRFEMFRE LNEALELKDA HATEESGDSR
361 AHSSLQPRAF QALIKEESPN C SEQ ID NO: 120 Mouse TP53 transcript variant 2 cDNA sequence
NM_001127233.1; CDS: 158-1303)
1 tttcccctcc cacgtgctca ccctggctaa agttctgtag cttcagttca ttgggaccat
61 cctggctgta ggtagcgact acagttaggg ggcacctagc attcaggccc tcatcctcct
121 ccttcccagc agggtgtcac gcttctccga agactggatg actgccatgg aggagtcaca
181 gtcggatatc agcctcgagc tccctctgag ccaggagaca ttttcaggct tatggaaact
241 acttcctcca gaagatatcc tgccatcacc tcactgcatg gacgatctgt tgctgcccca
301 ggatgttgag gagttttttg aaggcccaag tgaagccctc cgagtgtcag gagctcctgc
361 agcacaggac cctgtcaccg agacccctgg gccagtggcc cctgccccag ccactccatg
421 gcccctgtca tcttttgtcc cttctcaaaa aacttaccag ggcaactatg gcttccacct
481 gggcttcctg cagtctggga cagccaagtc tgttatgtgc acgtactctc ctcccctcaa
541 taagctattc tgccagctgg cgaagacgtg ccctgtgcag ttgtgggtca gcgccacacc
601 tccagctggg agccgtgtcc gcgccatggc catctacaag aagtcacagc acatgacgga
661 ggtcgtgaga cgctgccccc accatgagcg ctgctccgat ggtgatggcc tggctcctcc
721 ccagcatctt atccgggtgg aaggaaattt gtatcccgag tatctggaag acaggcagac
781 ttttcgccac agcgtggtgg taccttatga gccacccgag gccggctctg agtataccac
841 catccactac aagtacatgt gtaatagctc ctgcatgggg ggcatgaacc gccgacctat
901 ccttaccatc atcacactgg aagactccag tgggaacctt ctgggacggg acagctttga
961 ggttcgtgtt tgtgcctgcc ctgggagaga ccgccgtaca gaagaagaaa atttccgcaa
1021 aaaggaagtc ctttgccctg aactgccccc agggagcgca aagagagcgc tgcccacctg
1081 cacaagcgcc tctcccccgc aaaagaaaaa accacttgat ggagagtatt tcaccctcaa
1141 gatccgcggg cgtaaacgct tcgagatgtt ccgggagctg aatgaggcct tagagttaaa
1201 ggatgcccat gctacagagg agtctggaga cagcagggct cactccagcc tccagcctag
1261 agccttccaa gccttgatca aggaggaaag cccaaactgc tagctcccat cacttcatcc
1321 ctcccctttt ctgtcttcct atagctacct gaagaccaag aagggccagt ctacttcccg
1381 ccataaaaaa acaatggtca agaaagtggg gcctgactca gactgactgc ctctgcatcc
1441 cgtccccatc accagcctcc ccctctcctt gctgtcttat gacttcaggg ctgagacaca
1501 atcctcccgg tcccttctgc tgcctttttt accttgtagc tagggctcag ccccctctct
1561 gagtagtggt tcctggccca agttggggaa taggttgata gttgtcaggt ctctgctggc
1621 ccagcgaaat tctatccagc cagttgttgg accctggcac ctacaatgaa atctcaccct
1681 accccacacc ctgtaagatt ctatcttggg ccctcatagg gtccatatcc tccagggcct
1741 actttccttc cattctgcaa agcctgtctg catttatcca ccccccaccc tgtctccctc
1801 tttttttttt ttttacccct ttttatatat caatttccta ttttacaata aaattttgtt TABLE 2-continued TP53
Dephosphorylated human TP53 at Ser 15 or at corresponding phosphorylable amino acid in an ortholog thereof 1861 atcacttaaa aaaaaaa SEQ ID NO: 121 Mouse TP53 isoform a Amino Acid Sequence (NP_035770.2)
1 MTAMEESQSD ISLELPLSQE TFSGLWKLLP PEDILPSPHC MDDLLLPQDV EEFFEGPSEA
61 LRVSGAPAAQ DPVTETPGPV APAPATPWPL SSFVPSQKTY QGNYGFHLGF LQSGTAKSVM
121 CTYSPPLNKL FCQLAKTCPV QLWVSATPPA GSRVRAMAIY KKSQHMTEVV RRCPHHERCS
181 DGDGLAPPQH LIRVEGNLYP EYLEDRQTFR HSVVVPYEPP EAGSEYTTIH YKYMCNSSCM
241 GGMNRRPILT IITLEDSSGN LLGRDSFEVR VCACPGRDRR TEEENFRKKE VLCPELPPGS
301 AKRALPTCTS ASPPQKKKPL DGEYFTLKIR GRKRFEMFRE LNEALELKDA HATEESGDSR
361 AHSSYLKTKK GQSTSRHKKT MVKKVGPDSD SEQ ID NO: 122 Mouse TP53 transcript variant 1 cDNA sequence (NM_011640.3; CDS: 158-1330)
1 tttcccctcc cacgtgctca ccctggctaa agttctgtag cttcagttca ttgggaccat
61 cctggctgta ggtagcgact acagttaggg ggcacctagc attcaggccc tcatcctcct
121 ccttcccagc agggtgtcac gcttctccga agactggatg actgccatgg aggagtcaca
181 gtcggatatc agcctcgagc tccctctgag ccaggagaca ttttcaggct tatggaaact
241 acttcctcca gaagatatcc tgccatcacc tcactgcatg gacgatctgt tgctgcccca
301 ggatgttgag gagtttttg aaggcccaag tgaagccctc cgagtgtcag gagctcctgc
361 agcacaggac cctgtcaccg agacccctgg gccagtggcc cctgccccag ccactccatg
421 gcccctgtca tcttttgtcc cttctcaaaa aacttaccag ggcaactatg gcttccacct
481 gggcttcctg cagtctggga cagccaagtc tgttatgtgc acgtactctc ctcccctcaa
541 taagctattc tgccagctgg cgaagacgtg ccctgtgcag ttgtgggtca gcgccacacc
601 tccagctggg agccgtgtcc gcgccatggc catctacaag aagtcacagc acatgacgga
661 ggtcgtgaga cgctgccccc accatgagcg ctgctccgat ggtgatggcc tggctcctcc
721 ccagcatctt atccgggtgg aaggaaattt gtatcccgag tatctggaag acaggcagac
781 ttttcgccac agcgtggtgg taccttatga gccacccgag gccggctctg agtataccac
841 catccactac aagtacatgt gtaatagctc ctgcatgggg ggcatgaacc gccgacctat
901 ccttaccatc atcacactgg aagactccag tgggaacctt ctgggacggg acagctttga
961 ggttcgtgtt tgtgcctgcc ctgggagaga ccgccgtaca gaagaagaaa atttccgcaa
1021 aaaggaagtc ctttgccctg aactgccccc agggagcgca aagagagcgc tgcccacctg
1081 cacaagcgcc tctcccccgc aaaagaaaaa accacttgat ggagagtatt tcaccctcaa
1141 gatccgcggg cgtaaacgct tcgagatgtt ccgggagctg aatgaggcct tagagttaaa
1201 ggatgcccat gctacagagg agtctggaga cagcagggct cactccagct acctgaagac
1261 caagaagggc cagtctactt cccgccataa aaaaacaatg gtcaagaaag tggggcctga
1321 ctcagactga ctgcctctgc atcccgtccc catcaccagc ctccccctct ccttgctgtc
1381 ttatgacttc agggctgaga cacaatcctc ccggtccctt ctgctgcctt ttttaccttg
1441 tagctagggc tcagccccct ctctgagtag tggttcctgg cccaagttgg ggaataggtt
1501 gatagttgtc aggtctctgc tggcccagcg aaattctatc cagccagttg ttggaccctg
1561 gcacctacaa tgaaatctca ccctacccca caccctgtaa gattctatct tgggccctca
1621 tagggtccat atcctccagg gcctactttc cttccattct gcaaagcctg tctgcattta
1681 tccacccccc accctgtctc cctcttttt ttttttttac cccttttat atatcaattt
1741 cctattttac aataaaattt tgttatcact taaaaaaaaa a

* The nucleic acid and polypeptide sequences of the biomarkers of the present invention listed in Table 2 have been submitted at GenBank under the unique identifier provided herein and each such uniquely identified sequence submitted at GenBank is hereby incorporated in its entirety by reference.
* Included in Table 2 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 2, or a portion thereof. Such nucleic acid molecules can have a function of the full-length nucleic acid as described further herein.
* Included in Table 2 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 2, or a portion thereof. Such polypeptides can have a function of the full-length polypeptide as described further herein.

TABLE 3

| Reported Target | Compound ID | Structure | Reference |
|---|---|---|---|
| USP2 & USP7 | NSC632839 | 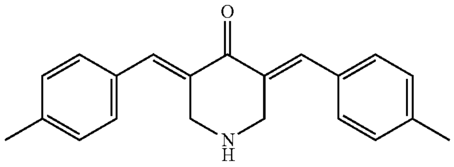<br>O=C(/C(CNC/1)=C/C2=CC=C(C)C=C2)C1=C\C3=CC=C(C)C=C3 | Nicholson B, et al. Protein Sci, 2008, 17(6), 1035-1043. |

TABLE 3-continued

| Reported Target | Compound ID | Structure | Reference |
|---|---|---|---|
| USP7 | HBX19818 | 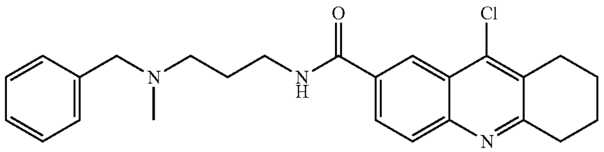 CN(CCCNC(C1=CC=C(N=C(CCCC2)C2=C3C1)C3=C1)=O)CC4=CC=CC=C4 | Reverdy, C., Conrath, S., Lopez, R., Planquette, C., Atmanene, C., Collura, V., Harpon, J., Battaglia, V., Vivat, V., Sippl, W., and Colland, F. (2012) *Chemistry & biology* 19, 467-477 |
| | HBX41108 | 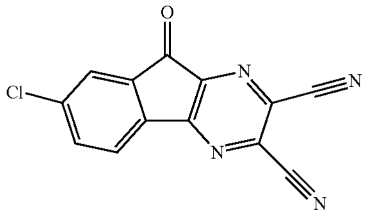 O=C1C2=CC(C1)=CC=C2C3=C1N=C(C#N)C(C#N)=N3 | Colombo, M., et al. (2010). "Synthesis and biological evaluation of 9-oxo-9H-indeno[1,2-b]pyrazine-2,3-dicarbonitrile analogues as potential inhibitors of deubiquitinating enzymes." ChemMedChem 5(4): 552-558. |
| | Spongiacidin A | 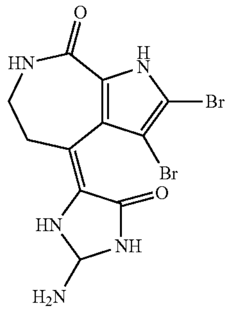 O=C1NC(N)N/C1=C(C2=C3NC(Br)=C2Br)\CCNC3=O | Yamaguchi, M., et al. (2013). "Spongiacidin C, a pyrrole alkaloid from the marine sponge *Stylissa massa*, functions as a USP7 inhibitor." Bioorg Med Chem Lett 23(13): 3884-3886. |
| | Petroquinones | 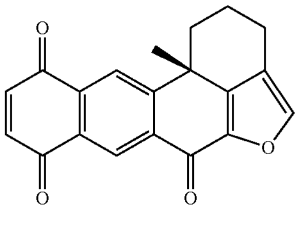 O=C(C1=C2[C@@]3(C)CCCC2=CO1)C(C3=C4)=CC5=C4C(C=CC5=O)=O | Tanokashira, N., et. al. (2016). "Petroquinones: trimeric and dimeric xestoquinone derivatives isolated from the marine sponge *Petrosia alfiani*." *Tetrahedron* 72(35): 5530-5540. |
| | Compound 2 | 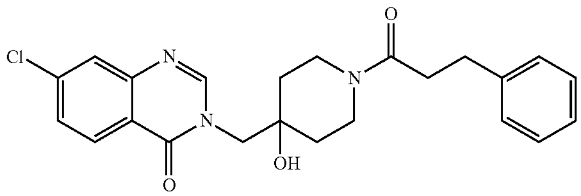 O=C1N(CC2(O)CCN(C(CCC3=CC=CC=C3)=O)CC2)C=NC4=CC(C1)=CC=C41 | Compound 2 - WO2013030218; Analogs - WO20160185785, WO20160185786, WO2016126926, WO2016126929, WO2016126935. |

TABLE 3-continued

| Reported Target | Compound ID | Structure | Reference |
| --- | --- | --- | --- |
| USP7 & USP8 | HY50736/ Compound 16 | 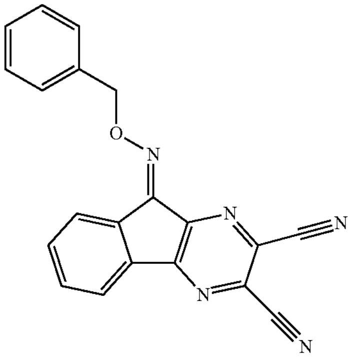<br>N#CC1═NC2═C(N═C1C#N)/C(C3═CC═CC═C32)═N/OCC4═CC═CC═C4 | Colombo, M., et al. (2010). "Synthesis and biological evaluation of 9-oxo-9H-indeno[1,2-b]pyrazine-2,3-dicarbonitrile analogues as potential inhibitors of deubiquitinating enzymes." ChemMedChem 5(4): 552-558. |
| | HY-50737A | 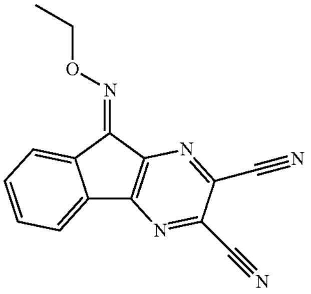<br>CCO/N═C1C2═CC═CC═C2C3═C\1N═C(C#N)C(C#N)═N3 | Colombo, M., et al. (2010). "Synthesis and biological evaluation of 9-oxo-9H-indeno[1,2-b]pyrazine-2,3-dicarbonitrile analogues as potential inhibitors of deubiquitinating enzymes." ChemMedChem 5(4): 552-558. |
| USP7 & USP47 | P5091 | 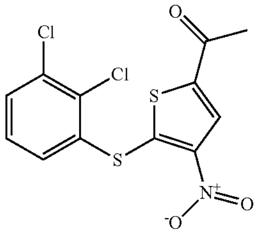<br>ClC1═C(Cl)C═CC═C1SC2═C([N+]([O-])═O)C═C(C(C)═O)S2 | Chauhan D, et al. Cancer Cell, 2012, 22(3), 345-358. |
| | P22077 | 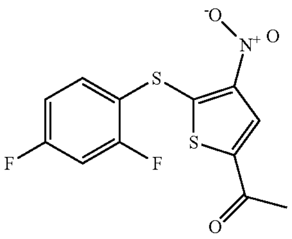<br>FC1═CC═C(SC2═C([N+]([O-])═O)C═C(C(C)═O)S2)C(F)═C1 | Tian X, et al. Assay Drug Dev Technol, 2011, 9(2), 165-173. Ritorto, M. S. et al. Screening of DUB activity and specificity by MALDI-TOF mass spectrometry. Nature communications 5, 4763, doi: 10.1038/ncomms 5763 (2014). |

TABLE 3-continued

| Reported Target | Compound ID | Structure | Reference |
|---|---|---|---|
| | 1247825-37-1 | 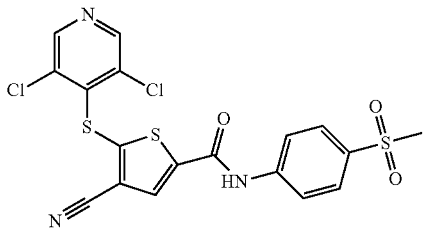 O=C(NC1=CC=C(S(=O)(C)=O)C=C1)C2=CC(C#N)=C(SC3=C(C1)C=NC=C3C1)S2 | Weinstock, J., Wu, J., Cao, P., Kingsbury, W. D., McDermott, J. L., Kodrasov, M. P., McKelvey, D. M., Suresh Kumar, K. G., Goldenberg, S. J., Mattern, M. R., and Nicholson, B. (2012) *ACS medicinal chemistry* letters 3, 789-792 |

II. Subjects

In one embodiment, the subject for whom cancer treatment is administered or who is predicted likelihood of efficacy of an anti-cancer therapy (e.g., therapy with at least one agent that inhibits at least one biomarker listed in Table 1) is determined, is a mammal (e.g., mouse, rat, primate, non-human mammal, domestic animal such as dog, cat, cow, horse), and is preferably a human.

In another embodiment of the methods encompassed by the present invention, the subject has not undergone treatment, such as chemotherapy, radiation therapy, targeted therapy, and/or anti-cancer therapy (e.g., therapy with at least one agent that inhibits at least one biomarker listed in Table 1). In still another embodiment, the subject has undergone treatment, such as chemotherapy, radiation therapy, targeted therapy, and/or anti-cancer therapy (e.g., therapy with at least one agent that inhibits at least one biomarker listed in Table 1).

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient. In some embodiments, the subject has metastatic cancer, such as newly diagnosed metastatic cancer, and/or relapsed cancer.

The methods encompassed by the present invention can be used to determine the responsiveness to anti-cancer therapy (e.g., therapy with at least one agent that inhibits at least one biomarker listed in Table 1) of different cancers in subjects such as those described above. In one embodiment, the cancers is Ewing sarcoma.

III. Sample Collection, Preparation and Separation

In some embodiments, biomarker presence, absence, amount, and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples, such as the normal copy number, amount, or activity of a biomarker in the cell or tissue type of a member of the same species as from which the test sample was obtained or a non-diseased cell or tissue from the subject from which the test samples was obtained. As described herein, a "pre-determined" biomarker amount and/or activity measurement(s) may be a biomarker amount and/or activity measurement(s) used to, by way of example only, evaluate a subject that may be selected for treatment, evaluate a response to an anti-cancer therapy (e.g., therapy with at least one agent that inhibits at least one biomarker listed in Table 1), and/or evaluate a response to a combination anti-cancer therapy (e.g., therapy with at least one agent that inhibits at least one biomarker listed in Table 1 plus immunoinhibitory inhibitor therapy). A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., biomarker expression normalized to the expression of a housekeeping gene, or gene expression at various time points).

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments encompassed by the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. “Body fluids” refer to fluids that are excreted or secreted from the body as well as fluids that are normally not (e.g., amniotic fluid, aqueous humor, bile, blood and blood plasma, cerebrospinal fluid, cerumen and earwax, cowper’s fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the biomarker amount and/or activity measurements of the subject obtained over time can be conveniently compared with each other, as well as with those of normal controls during the monitoring period, thereby providing the subject’s own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect encompassed by the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 KB, 3 KB, 2 kB, 1 KB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule encompassed by the present invention can be isolated using standard molecular biology techniques and the sequence information in the database records described herein. Using all or a portion of such nucleic acid sequences, nucleic acid molecules encompassed by the present invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, NY, 1989).

A nucleic acid molecule encompassed by the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule encompassed by the present invention can be prepared by standard synthetic techniques, e.g., using an automated DNA synthesizer.

Moreover, a nucleic acid molecule encompassed by the present invention can comprise only a portion of a nucleic acid sequence, wherein the full length nucleic acid sequence comprises a marker encompassed by the present invention or which encodes a polypeptide corresponding to a marker encompassed by the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers encompassed by the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker encompassed by the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope encompassed by the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker encompassed by the present invention or to a nucleic acid molecule encoding a protein corresponding to a marker encompassed by the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule encompassed by the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect encompassed by the present invention pertains to nucleic acid molecules encoding a polypeptide encompassed by the present invention that contain changes in amino acid residues that are not essential for activity. Such polypeptides differ in amino acid sequence from the naturally-occurring proteins which correspond to the markers encompassed by the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids encompassed by the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid encompassed by the present invention, e.g., complementary to the coding strand of a double-stranded cDNA molecule corresponding to a marker encompassed by the present invention or complementary to an mRNA sequence corresponding to a marker encompassed by the present invention. Accordingly, an antisense nucleic acid molecule encompassed by the present invention can hydrogen bond to (i.e. anneal with) a sense nucleic acid encompassed by the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide encompassed by the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules encompassed by the present invention are typically administered to a subject or generated in situ such that they hybridize with or bind to cellular mRNA and/or genomic DNA encoding a polypeptide corresponding to a selected marker encompassed by the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules encompassed by the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule encompassed by the present invention can be an a-anomeric nucleic acid molecule. An a-anomeric nucleic acid molecule forms specific double-stranded hybrids with complementary RNA in which, contrary to the usual a-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215: 327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker encompassed by the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide encompassed by the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6 (6): 569-84; Helene (1992) *Ann. N.Y. Acad. Sci.* 660:27-36; and Maher (1992) *Bioassays* 14 (12): 807-15.

In various embodiments, the nucleic acid molecules encompassed by the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675. PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., SI nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24 (17): 3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24 (17): 3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect encompassed by the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker encompassed by the present invention are produced by recombinant DNA techniques. Alternative to recombinant expression, a polypeptide corresponding to a marker encompassed by the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein encompassed by the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide encompassed by the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=#of identical positions/total #of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.*

215:403-410. BLAST nucleotide searches can be performed with the NBLAST program, score=100, wordlength=12 to obtain nucleotide sequences homologous to a nucleic acid molecules encompassed by the present invention. BLAST protein searches can be performed with the XBLAST program, score=50, wordlength=3 to obtain amino acid sequences homologous to a protein molecules encompassed by the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the National Center for Biotechnology Information (NCBI) website at ncbi.nlm.nih.gov. Another preferred, non-limiting example of a mathematical algorithm utilized for the comparison of sequences is the algorithm of Myers and Miller, (1988) *Comput Appl Biosci*, 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a biomarker protein. As used herein, a "chimeric protein" or "fusion protein" comprises all or part (preferably a biologically active part) of a polypeptide corresponding to a marker encompassed by the present invention operably linked to a heterologous polypeptide (i.e., a polypeptide other than the polypeptide corresponding to the marker). Within the fusion protein, the term "operably linked" is intended to indicate that the polypeptide encompassed by the present invention and the heterologous polypeptide are fused in-frame to each other. The heterologous polypeptide can be fused to the amino-terminus or the carboxyl-terminus of the polypeptide encompassed by the present invention.

One useful fusion protein is a GST fusion protein in which a polypeptide corresponding to a marker encompassed by the present invention is fused to the carboxyl terminus of GST sequences. Such fusion proteins can facilitate the purification of a recombinant polypeptide encompassed by the present invention.

In another embodiment, the fusion protein contains a heterologous signal sequence, immunoglobulin fusion protein, toxin, or other useful protein sequence. Chimeric and fusion proteins encompassed by the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide encompassed by the present invention can be cloned into such an expression vector such that the fusion moiety is linked in-frame to the polypeptide encompassed by the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein encompassed by the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides encompassed by the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker encompassed by the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein encompassed by the present invention (Arkin and Yourvan, 1992, *Proc. Natl. Acad. Sci. USA* 89:7811-7815; Delgrave et al., 1993, *Protein Engineering* 6 (3): 327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors encompassed by the present invention comprise a nucleic acid encompassed by the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors encompassed by the present invention can be introduced into host cells to thereby produce proteins or peptides, including fusion proteins or peptides, encoded by nucleic acids as described herein.

The recombinant expression vectors for use in the invention can be designed for expression of a polypeptide corresponding to a marker encompassed by the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In Gene Expression Technology: Methods in Enzymology vol. 185, Academic Press, San Diego, CA, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, CA, 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences encompassed by the present invention can be carried out by standard DNA synthesis techniques.

In another embodiment, the expression vector is a yeast expression vector. Examples of vectors for expression in yeast *S. cerevisiae* include pYepSecl (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid encompassed by the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the a-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide encompassed by the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1 (1)).

Another aspect encompassed by the present invention pertains to host cells into which a recombinant expression vector encompassed by the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

A. Methods for Detection of Copy Number and/or Genomic Nucleic Acid Mutations

Methods of evaluating the copy number and/or genomic nucleic acid status (e.g., mutations) of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. In some embodiments, the increased copy number of at least one biomarker listed in Table 1 is predictive of better outcome of therapy with at least one agent that inhibits at least one biomarker listed in Table 1. A copy number of at least 3, 4, 5, 6, 7, 8, 9, or 10 of at least one biomarker listed in Table 1 is predictive of likely responsive to therapy with at least one agent that inhibits at least one biomarker listed in Table 1.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152:649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3:1227-1234; Pinkel (1988) *Proc. Natl. Acad. Sci. USA* 85:9138-9142; EPO Pub. No. 430,402; Methods in Molecular Biology, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20:207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods encompassed by the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4:560, Landegren, et al. (1988) *Science* 241:1077, and Barringer et al. (1990) *Gene* 89:117), transcription amplification (Kwoh, et al. (1989) *Proc. Natl. Acad. Sci. USA* 86:1173), self-sustained sequence replication (Guatelli, et al. (1990) *Proc. Nat. Acad. Sci. USA* 87:1874), dot PCR, and linker adapter PCR, etc.

Loss of heterozygosity (LOH) and major copy proportion (MCP) mapping (Wang, Z. C., et al. (2004) *Cancer Res* 64 (1): 64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Biomarker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278:1481; Emmert-Buck et al. (1996) Science 274:998; Fend et al. (1999) Am. J. Path. 154:61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope encompassed by the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4:80-84 (1994). Real time PCR may also be used.

Other known amplification methods which can be utilized herein include but are not limited to the so-called "NASBA" or "3SR" technique described in PNAS USA 87:1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42:9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos: 6,618,6796; 6,379,897; 6,664,377; 6,451,536; 548,257; US20030157485 and Schena et al. (1995) *Science* 20, 467-470; Gerhold et al. (1999) Trends In Biochem. Sci. 24, 168-173; and Lennon et al. (2000) Drug Discovery Today 5, 59-65, which are herein incorporated by reference in their entirety). Serial Analysis of Gene Expression (SAGE) can also be performed (See for example U.S. patent application No. 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an anti-cancer therapy (e.g., therapy with at least one agent that inhibits at least one biomarker listed in Table 1). Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}I$, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}I$, $^{121}I$), carbon ($^{14}C$), sulphur ($^{35}S$), tritium ($^{3}H$), indium ($^{112}$ In), and technetium ($^{99}mTc$), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$ M, $10^{-9}$M, $10^{-10}$ M, $10^{-11}$ M, or $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F (ab') 2 fragments, respectively. Other proteases with the requisite substrate specificity can also be used to generate Fab or F(ab')2 fragments. Antibodies can also be produced in a variety of truncated forms using antibody genes in which one or more stop codons have been introduced upstream of the natural stop site. For example, a chimeric gene encoding a F (ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10:1455-1460 (1992), regarding primatized antibody, and Ladner et al., U.S. Pat. No. 4,946,778 and Bird, R. E. et al., Science, 242:423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify sequences or agents that affect translation of biomarkers or biomarker-related genes.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in a biomarker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of anti-cancer therapy (e.g., therapy with at least one agent that inhibits at least one biomarker listed in Table 1) is predicted according to biomarker presence, absence, amount and/or activity associated with a cancer (e.g., cancer) in a subject according to the methods described herein. In one embodiment, such anti-cancer therapy (e.g., therapy with at least one agent that inhibits at least one biomarker listed in Table 1) or combinations of therapies (e.g., anti-PD-1 and anti-immunoinhibitory therapies) can be administered to a desired subject or once a subject is indicated as being a likely responder to anti-cancer therapy (e.g., therapy with at least one agent that inhibits at least one biomarker listed in Table 1). In another embodiment, such anti-cancer therapy (e.g., therapy with at least one agent that inhibits at least one biomarker listed in Table 1) can be avoided once a subject is indicated as not being a likely responder to the anti-cancer therapy (e.g., therapy with at least one agent that inhibits at least one biomarker listed in Table 1) and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with or without anti-cancer therapy (e.g., therapy with at least one agent that inhibits at least one biomarker listed in Table 1).

The TP53 pathway and targets that are dependencies thereof, as well as exemplary agents useful for inhibiting the targets or other biomarkers described herein, have been described above.

The compositions described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

The term "targeted therapy" refers to administration of agents that selectively interact with a chosen biomolecule to thereby treat cancer. For example, targeted therepy regarding the inhibition of immune checkpoint inhibitor is useful in combination with the methods encompassed by the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Inhibition of one or more immune checkpoint inhibitors can block or otherwise neutralize inhibitory signaling to thereby upregulate an immune response in order to more efficaciously treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" referes to administration of agents that do not selectively interact with a chosen biomolecule yet treat cancer. Representative examples of untargeted therapies include, without limitation, chemotherapy, gene therapy, and radiation therapy.

In one embodiment, mitochondrial cofactor therapy is useful. For example, vitamin E is known to block cell death via ferroptosis such that mitochondrial cofactor therapy can alleviate or improve any toxicity associated with ISC biosynthesis pathway inhibition. Mitochondrial cofactor therapies are well known in the art and include, for example, coenzyme Q10 (ubiquinone), riboflavin, thiamin, niacin, vitamin K (phylloquinone and menadione), creatine, carnitine, and other antioxidants such as ascorbic acid and lipoic acid (see, for example, Marriage et al. (2003) *J. Am. Diet. Assoc.* 103:1029-1038 and Parikh et al. (2009) *Curr. Treat. Options Neurol.* 11:414-430).

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6 (5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of.beta.-nicotinamide adenine dinucleotide (NAD+) into nicotinamide and poly-ADP-ribose (PAR). Both poly(ADP-ribose) and PARP have been linked to regulation of transcription, cell proliferation, genomic stability, and carcinogenesis (Bouchard V. J. et.al. Experimental Hematology, Volume 31, Number 6, June 2003, pp. 446-454 (9); Herceg Z.; Wang Z.-Q. Mutation Research/Fundamental and Molecular Mechanisms of Mutagenesis, Volume 477, Number 1, 2 Jun. 2001, pp. 97-110 (14)). Poly(ADP-ribose) polymerase 1 (PARPI) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) *Nature* 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide (CO2) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium: yttrium-aluminum-garnet (Nd: YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-cancer therapy (e.g., therapy with at least one agent that inhibits at least one biomarker listed in Table 1) may vary according to the particular inhibitor agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods encompassed by the present invention is a factor in determining optimal treatment doses and schedules.

Any means for the introduction of a polynucleotide into mammals, human or non-human, or cells thereof may be adapted to the practice of this invention for the delivery of the various constructs encompassed by the present invention into the intended recipient. In one embodiment encompassed by the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment encompassed by the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide encompassed by the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth,; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clincal Efficacy

Clinical efficacy can be measured by any method known in the art. For example, the response to an anti-cancer therapy (e.g., therapy with at least one agent that inhibits at least one biomarker listed in Table 1), relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular therapeutic regimen is at least 25%, 30%, 35%, 40%, 45%, 50%, 55%, 60%, 65%, 70%, 75%, 80%, 85%, or more.

Additional criteria for evaluating the response to anti-cancer therapy (e.g., therapy with at least one agent that inhibits at least one biomarker listed in Table 1) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular therapeutic regimen can be administered to a population of subjects and the outcome can be correlated to biomarker measurements that were determined prior to administration of any anti-cancer therapy (e.g., therapy with at least one agent that inhibits at least one biomarker listed in Table 1). The outcome measurement may be pathologic response to therapy given in the neoadjuvant setting. Alternatively, outcome measures, such as overall survival and disease-free survival can be monitored over a period of time for subjects following anti-cancer therapy (e.g., therapy with at least one agent that inhibits at least one biomarker listed in Table 1) for whom biomarker measurement values are known. In certain embodiments, the same doses of agents are administered to each subject. In related embodiments, the doses administered are standard doses known in the art for therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-cancer therapy (e.g., therapy with at least one agent that inhibits at least one biomarker listed in Table 1) can be determined using methods such as those described in the Examples section.

5. Further Uses and Methods Encompassed by the Present Invention

The compositions described herein can be used in a variety of diagnostic, prognostic, and therapeutic applications regarding biomarkers described herein, such as those listed in Table 1.

a. Screening Methods

One aspect encompassed by the present invention relates to screening assays, including non-cell based assays. In one embodiment, the assays provide a method for identifying whether a cancer is likely to respond to anti-cancer therapy (e.g., therapy with at least one agent that inhibits at least one biomarker listed in Table 1) and/or whether an agent can inhibit the growth of or kill a cancer cell that is unlikely to respond to anti-cancer therapy (e.g., therapy with at least one agent that inhibits at least one biomarker listed in Table 1).

In one embodiment, the invention relates to assays for screening test agents which bind to, or modulate the biological activity of, at least one biomarker listed in Table 1. In one embodiment, a method for identifying such an agent entails determining the ability of the agent to modulate, e.g. inhibit, the at least one biomarker listed in Table 1.

In one embodiment, an assay is a cell-free or cell-based assay, comprising contacting at least one biomarker listed in Table 1, with a test agent, and determining the ability of the test agent to modulate (e.g. inhibit) the enzymatic activity of the biomarker, such as by measuring direct binding of substrates or by measuring indirect parameters as described below.

In another embodiment, an assay is a cell-free or cell-based assay, comprising contacting at least one biomarker listed in Table 1, with a test agent, and determining the ability of the test agent to modulate the ability of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies encompassed by the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within a pathway.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect encompassed by the present invention relates to diagnostic assays for determining the presence, absence, amount, and/or activity level of a biomarker described herein, such as those listed in Table 1, in the context of a biological sample (e.g., blood, serum, cells, or tissue) to thereby determine whether an individual afflicted with a cancer is likely to respond to anti-cancer therapy (e.g., therapy with at least one agent that inhibits at least one biomarker listed in Table 1), whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those listed in Table 1.

Another aspect encompassed by the present invention pertains to monitoring the influence of agents (e.g., drugs, compounds, and small nucleic acid-based molecules) on the expression or activity of a biomarker listed in Table 1. These and other agents are described in further detail in the following sections.

The ordinarily skilled artisan will also appreciate that, in certain embodiments, the methods encompassed by the present invention implement a computer program and computer system. For example, a computer program can be used to perform the algorithms described herein. A computer system can also store and manipulate data generated by the methods encompassed by the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part encompassed by the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods encompassed by the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to anti-cancer therapy (e.g., therapy with at least one agent that inhibits at least one biomarker listed in Table 1). In some embodiments, the present invention is useful for classifying a sample (e.g., from a subject) as associated with or at risk for responding to or not responding to anti-cancer therapy (e.g., therapy with at least one agent that inhibits at least one biomarker listed in Table 1) using a statistical algorithm and/or empirical data (e.g., the amount or activity of a biomarker listed in Table 1).

An exemplary method for detecting the amount or activity of a biomarker listed in Table 1, and thus useful for classifying whether a sample is likely or unlikely to respond to anti-cancer therapy (e.g., therapy with at least one agent that inhibits at least one biomarker listed in Table 1) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-cancer therapy (e.g., therapy with at least one agent that inhibits at least one biomarker listed in Table 1) responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method encompassed by the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to anti-cancer therapy (e.g., therapy with at least one agent that inhibits at least one biomarker listed in Table 1), a biological sample from the subject during remission, or a biological sample from the subject during treatment for developing a cancer progressing despite anti-cancer therapy (e.g., therapy with at least one agent that inhibits at least one biomarker listed in Table 1).

d. Prognostic Assays

The diagnostic methods described herein can furthermore be utilized to identify subjects having or at risk of developing a cancer that is likely or unlikely to be responsive to anti-cancer therapy (e.g., therapy with at least one agent that inhibits at least one biomarker listed in Table 1). The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

Another aspect encompassed by the present invention pertains to methods of modulating the expression or activity of one or more biomarkers described herein (e.g., those listed in Table 1 and the Examples or fragments thereof) for therapeutic purposes. The biomarkers encompassed by the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Modulatory methods encompassed by the present invention involve contacting a cell with one or more biomarkers encompassed by the present invention, including one or more biomarkers encompassed by the present invention, including one or more biomarkers listed in Table 1, Table 2, and the Examples, or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers encompassed by the present invention, including one or more biomarkers encompassed by the present invention, including one or more biomarkers listed in Table 1 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 μg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers encompassed by the present invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers encompassed by the present invention listed in Table 1 or 2 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or down-regulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions encompassed by the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods encompassed by the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods encompassed by the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions encompassed by the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents encompassed by the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods encompassed by the present invention so as to obtain an amount of the active ingredient, which is effective to achieve the desired therapeutic response for a particular subject, composition, and mode of administration, without being toxic to the subject.

The nucleic acid molecules encompassed by the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit encompassed by the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments encompassed by the present invention are described in the following Examples. The present invention is further illustrated by the following examples which should not be construed as further limiting.

EXAMPLES

Example 1: Materials and Methods for Examples 2-11 a. CRISPR-Cas9 Screening

The CRISPR-Cas9 screen was performed using the Broad Institute's GeCKO library (Sanjana et al. (2014) *Nat. Methods* 11:783-784; Aguirre et al. (2016) *Cancer Discov.* 6:914-929). Thirty-three cancer cell lines (including nine Ewing sarcoma lines) were screened with the GeCKO library, which contains ~95,000 guides and an average of six guides per gene (Sanjana et al. (2014) *Nat. Methods* 11:783-784; Aguirre et al. (2016) *Cancer Discov.* 6:914-929). The library contains ~1,000 negative control guides that do not target any location in the reference genome. The library also included guides with more than one perfect match in the reference genome allowing us to computationally correct for the previously described cutting toxicity associated with multiple Cas9 cuts in the genome (Aguirre et al. (2016) *Cancer Discov.* 6:914-929).

Cancer cell lines were transduced with Cas9 using a lentiviral system (Aguirre et al. (2016) *Cancer Discov.* 6:914-929). Cell lines that met quality control criteria, including Cas9 activity measured using a GFP reporter, and other parameters, were then screened with the CRISPR library. A pool of guides was transduced into a population of cells. The cells were cultured for ~21 days in vitro, and at the end of the assay, barcodes for each guide were sequenced for each cell line in replicate. Reads per kilobase were calculated for each replicate and then the log 2 fold change compared with the initial plasmid pool was calculated for each guide. Samples with poor replicate reproducibility, as well as guides that have low representation in the initial plasmid pool, were removed from the analysis. Next, the guides from multiple replicates for each sample were used to collapse the data into gene scores using the CERES algorithm (Meyers et al. (2017) *Nat. Genet.* 49:1779-1784), which models the cutting effect of each guide correcting for multiple cuts in the genome to produce a score that reflects the effect of disruption of the gene. After the dependency scores were calculated using the CERES algorithm, the scores for each cell line were scaled so that mean of negative controls was 0 and the mean of a subset of positive controls was-1.

For all of the analyses, the data were filtered and only the set of genetic dependencies with variable dependency scores that had standard deviations two sigma above the mean standard deviation across all genes were used. This resulted in 705 dependencies. Pearson correlations were then computed between the dependency gene score for TP53 and all other variable dependencies in the screen. The top eight anti-correlated genes were used for subsequent analysis.

b. Cell Lines and Chemical Compounds

Cell lines were obtained from the American Type Culture Collection (ATCC), except for VH-64 and WE-68, which were provided by J. Sonnemann (Universitatsklinikum Jena, Jena, Germany); TC138 and CHLA258, which were purchased from the COG Cell Line and Xenograft Repository; and SJSA-X, which was provided by G. Wahl (The Salk Institute for Biological Studies, La Jolla, CA). Cell line identity was confirmed by Short Tandem Repeat (STR) profiling. ATSP-7041 and ATSP-7342 were synthesized according to established methods (Bird et al. (2011) *Curr. Protoc. Chem. Biol.* 3:99-117; Chang et al. (2013) *Proc. Natl. Acad. Sci. U.S.A.* 110: E3445-E3454). XL-188 was synthesized according to established methods (Lamberto et al. (2017) *Cell Chem. Biol.* 24:1490-1500). RG7388 (ApexBio Technology), GSK2830371 (Selleck Chemicals), P5091 (Sigma-Aldrich), doxorubicin (Cell Signaling), etoposide (Selleck Chemicals), and vincristine (Selleck Chemicals) were solubilized in DMSO.

c. Lentivirus Production and Transduction

Lentivirus was produced by transfecting HEK-293T cells with the pLentiV2 vector (Addgene plasmid 52961) and the packaging plasmids pCMV8.9 and pCMV-VSVG according to the FuGENER 6 (Roche) protocol. For lentiviral transduction, Ewing sarcoma cells were incubated with 2 ml of virus and 8 μg/ml of polybrene (Sigma-Aldrich). Cells were selected in puromycin (Sigma-Aldrich) 48 h after infection for single knockout experiments. For dual knockout experiments, PPM1D, USP7, and MDM4 sgRNA sequences were cloned into a LentiV2 vector with a blasticidin selection marker (Addgene plasmid 83480).

d. sgRNA Sequences sgRNAs were designed using the Broad Institute's sgRNA designer tool. The following sequences were used as control or to target the respective genes: control sgRNA, 5'-GTAGCGAACGTGTCCGGCGT-3' (SEQ ID NO: 125); sgMDM2 2: 5'-AGTTACTGTGTATCAGGCAG-3' (SEQ ID NO: 126); sgMDM2 5: 5'-AGACACTTATACTATGAAAG-3' (SEQ ID NO: 127); sgMDM4 4: 5'-AGATGTTGAACACTGAGCAG-3' (SEQ ID NO: 128); sgMDM4 6: 5'-AAGAATTCCACTGAGTTGCA-3' (SEQ ID NO: 129); sgUSP7 1: 5'-AGATGTATGATCCCAAAACG-3' (SEQ ID NO: 130); sgUSP7 2: 5'-ACCATACCCAAATTATTC CG-3' (SEQ ID NO: 131); sgPPMID 1: 5'-CTGAAGAAAAGCCCTCGCCG-3' (SEQ ID NO: 132); sgPPMID 2: 5'-CAGGTGATTTGTGGAGCTAT-3' (SEQ ID NO: 133); sgTP53 1: 5'-GCTTGTAGATGGCCATGGCG-3' (SEQ ID NO: 134); sgTP53 2: 5'-TCCTCAGCATCTTATCCGAG-3' (SEQ ID NO: 135); sgTP53 4: 5'-GCAGTCACAGCACATGACGG-3' (SEQ ID NO: 136); and sgTP53 5: 5'-GTAGTGGTAATCTACTGGGA-3' (SEQ ID NO: 137).

e. Protein Extraction and Immunoblotting

Whole-cell lysates were extracted in cell lysis buffer (Cell Signaling) supplemented with EDTA-free protease inhibitors and PhosSTOP™ phosphatase inhibitors (Roche). Western immunoblotting was performed using standard techniques. Primary antibodies used included anti-MDM2 (ab178938; Abcam), anti-MDM2 (86934; Cell Signaling), anti-MDM4 (A300-287A; Bethyl Laboratories), anti-p53 (2527S; Cell Signaling), anti-p21 (2946S; Cell Signaling), anti-Vinculin (18058; Abcam), anti-Wip1 (A300-664A; Bethyl Laboratories), anti-pSer15-p53 (9284; Cell Signaling), anti-USP7 (A300-033A; Bethyl Laboratories), and anti-Tubulin (cp06; CalBiochem).

f. Cell Viability Assays

Cell viability was assessed using the CellTiter-Glo® Luminescent Cell Viability Assay (Promega). Viability assays were performed after Ewing sarcoma cell lines were infected with sgRNAs targeting TP53, MDM2, MDM4, PPM1D, or USP7 or treated with ATSP-7041, ATSP-7342, GSK2830371, P5091, XL-188, or vehicle control.

g. Immunoprecipitation Experiments

Five million TC32 cells were treated with either 10 μM RG7388 or vehicle control for 4 h. Cells were lysed in buffer A (150 mM NaCl, 50 mM Tris, and 0.5% NP-40, pH 7.4) and combined with anti-MDM4 antibody (A300-287A; Bethyl Laboratories) in the presence of 20 μM RG7388, ATSP-7041, or vehicle control in a total volume of 1 ml, rotating at 4° C. for 16 h. Subsequently, 50 μl washed Protein AG beads (sc-2003; Santa Cruz) were added and the mixture was incubated for 1 h rotating at 4° C. Beads were washed three times in buffer A, and protein complexes were eluted by boiling in NuPage® LDS Sample Buffer (NP0007; Invitrogen) supplemented with DTT. Samples were analyzed by Western blot with antibodies against p53 DO-1 (sc-126; Santa Cruz) and MDM4 (A300-287A; Bethyl Laboratories).

h. Annexin V Staining

Ewing sarcoma cells lines were assessed for induction of cell death after 2 days (d) of treatment with ATSP-7041 or P5091, or after 3 d of treatment with GSK2830371. Cell death was measured using flow cytometric analysis of Annexin V staining according to the manufacturer's instructions (eBioscience). Data analysis was completed using Flowjo 7.6 software (Treestar).

i. Quantitative PCR

RNA was extracted from cells with the RNeasy® kit and on-column DNA digestion (Qiagen). cDNA was prepared using M-MLV reverse transcription (ThermoFisher Scientific). TaqMan™ Gene Expression Master Mix (Applied Biosystems) was used per the manufacturer's protocol. TaqMan™ probes included RPL13A (Hs04194366_g1; ThermoFisher Scientific), CDKNIA (Hs00355782_m1; Thermo Fisher Scientific), and MDM2 (Hs01066930_m1; ThermoFisher Scientific). Data were collected in triplicate and analyzed using the ΔΔCT method.

j. Ewing Sarcoma Xenograft Studies

For anti-tumor efficacy studies, tumor xenografts were established in 15 nude female mice by implanting three million TC32 cells into the right flank. Animals were randomized to either 20 d of treatment with 30 mg/kg q.o.d. IV ATSP-7041 (n=8) or vehicle (n=7) for a total of 10 doses. Treatment was started when tumors reached 100-200 mm3. Tumor volumes were measured with calipers twice a week. For PDX studies, tumor fragments were implanted into the right flank of nude female mice by minor surgery. After tumor engraftment, studies were performed as described for TC32 xenograft studies.

For pharmacodynamics studies, tumor xenografts were established in six nude female mice by implanting three million TC32 cells or PDX tumor fragments into the right flank. Animals were randomized to either ATSP-7041 (n=3) or vehicle treatment (n=3). Mice were treated with three doses of 30 mg/kg ATSP-7041 IV or vehicle and were sacrificed 8 h after the third dose. Tumor tissue was flash frozen for protein or RNA extraction using standard methods.

For in vivo studies, ATSP-7041 was prepared using the following protocol: mPEG-DSPE (Nanocs) was dissolved in chloroform and dried by a rotary evaporator. ATSP-7041 was dissolved in 1 M NaOH and diluted 100-fold in 10 mM histidine-buffered saline to a final concentration of 3 mg/ml. This mixture was added to the dried lipid film to a final mPEG-DSPE concentration of 50 mg/ml and final pH 7. The film was rehydrated by brief sonication and heating in a 50° C. water bath. The mixture was then subjected to five freeze-thaw cycles in liquid nitrogen and 40° C. water, respectively, and the solution passed 10 times through an Avanti Mini-Extruder Set (Avanti Polar Lipids) equipped with a 800-nm filter (Whatman).

All animal studies were conducted under the auspices of protocols approved by the Dana-Farber Cancer Institute Animal Care and Use Committee.

k. Drug Synergy Analysis Chou-Talalay Combination Index for Loewe Additivity

Loewe Additivity is a dose-effect approach that estimates the effect of combining two drugs based on the concentration of each individual drug that produces the same quantitative effect (Goldoni and Johansson (2007) *Toxicol. In Vitro* 21:759-769). Chou and Talalay (Chou (2006) *Pharmacol. Rev.* 58:621-681; Chou (2010) *Cancer Res.* 70:440-446) showed that Loewe equations are valid for enzyme inhibitors with similar mechanisms of action, either competitive or noncompetitive toward the substrate. They introduced the combination index (CI) scores to estimate the interaction between the two drugs. If CI<1, the drugs have a synergistic effect, and if CI>1, the drugs have an antagonistic effect. CI=1 means the drugs have an additive effect.

Example 2: Genome-Scale CRISPR-Cas9 Screening Distinguishes Between TP53 Wild Type and TP53 Mutant Cell Lines To identify new therapeutic targets for TP53 wild-type Ewing sarcoma, data from a genome-scale CRISPR-Cas9 screen of 33 cancer cell lines, including nine Ewing sarcoma cell lines (Aguirre et al. (2016) *Cancer Discov.* 6:914-929), were analyzed. It was determined that targeting TP53 in this genome-scale screen provided a proliferative advantage in wild-type TP53 cell lines (indicated by positive scores) and very little to no effect in mutant TP53 cell lines (FIG. 1A). p53 mutation status was assigned by mining published data from several large studies (Barretina et al. (2012) *Nature* 483:603-607; Cancer Cell Line Encyclopedia Consortium (2015) *Nature* 528:84-87; Klijn et al. (2015) *Nat. Biotechnol.* 33:306-312), a curated list of mutations (Edlund et al. (2012) *Proc. Natl. Acad. Sci. U.S.A.* 109:9551-9556), and a literature search for cell lines for which no information was available from other sources (FIG. 11). The response to TP53 disruption was consistent with the annotated mutation status in 97% of cell lines, including all of the Ewing sarcoma cell lines in this screen.

Example 3: Regulators of p53 are Anti-Correlated with TP53 Dependency Scores

Figure 2A:
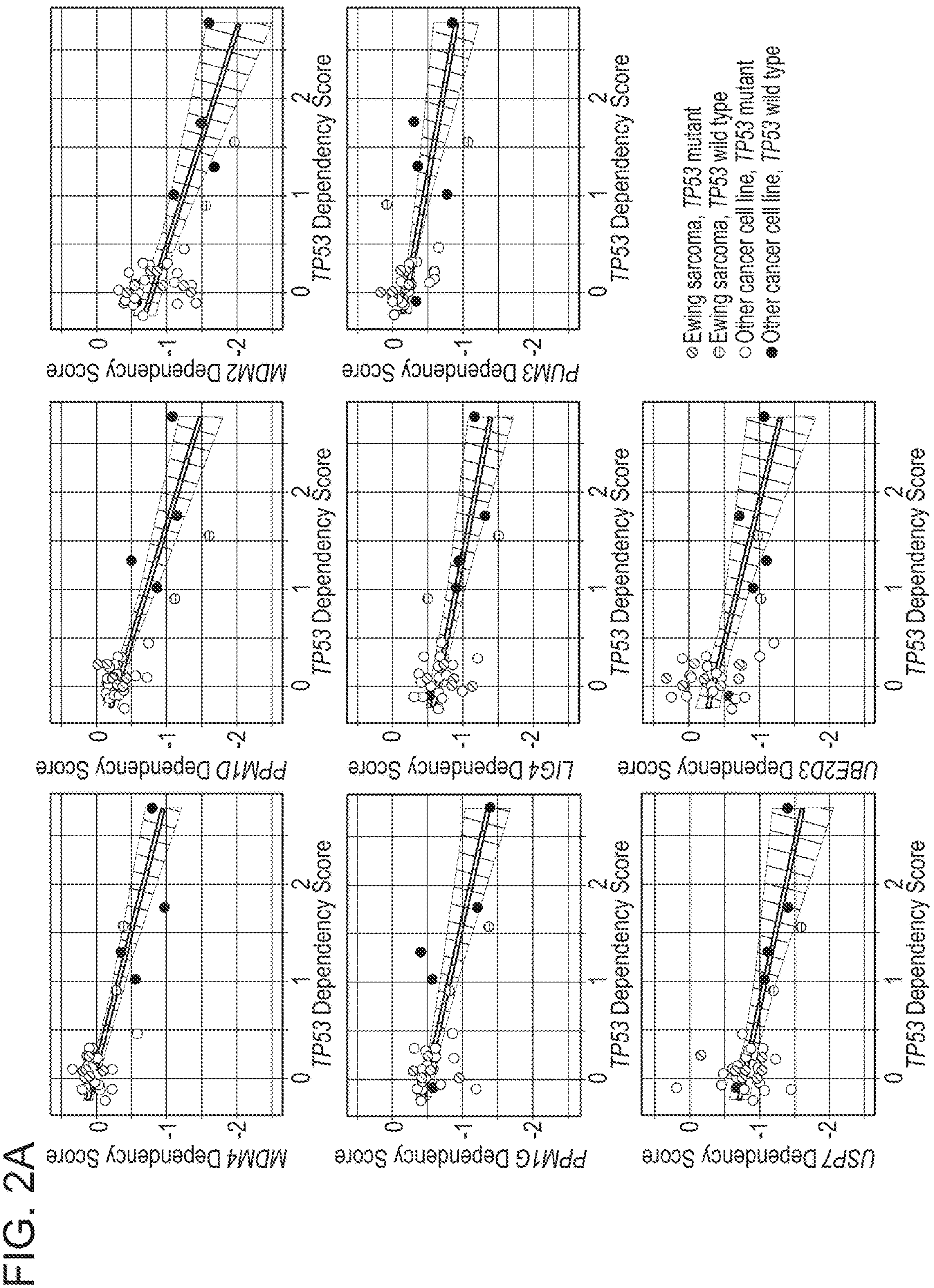
FIG. 2A-FIG. 2B show the correlation of TP53 dependency with top scoring genes.
Figure 2B:
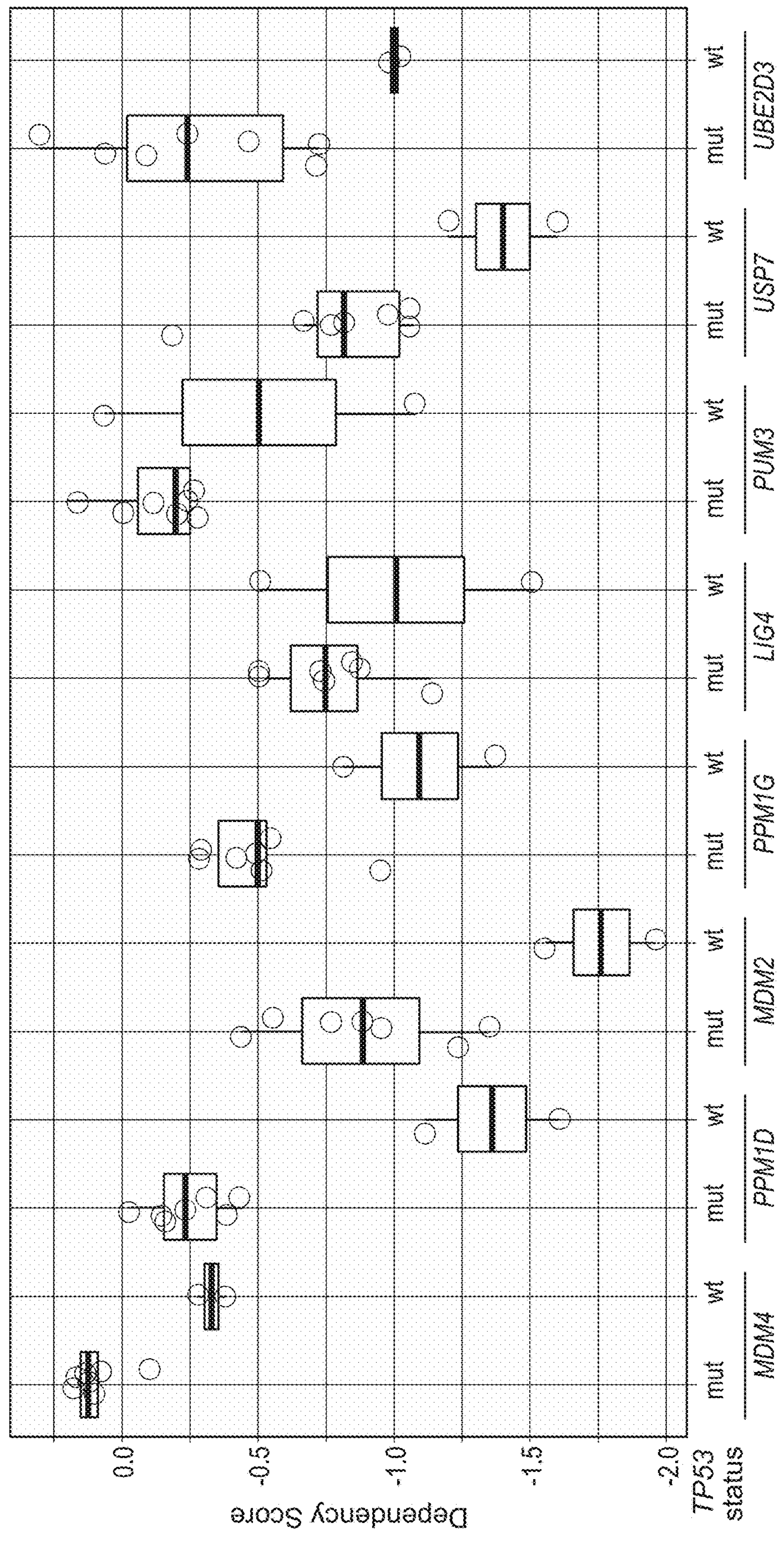

To identify targets in TP53 wild-type cell lines, it was hypothesized that cell lines with the greatest proliferative advantage upon TP53 suppression (presumably due to the presence of a functional p53 pathway) would also be dependent on negative regulators of TP53. The top eight variable genetic dependencies that were anti-correlated to TP53 dependency scores in all 33 cancer cell lines in the screen included MDM2, MDM4, USP7, and PPM1D, as well as other genes with known roles in p53 regulation (FIG. 1B) and with p53 interaction in the Search Tool for the Retrieval of Interacting Genes/Proteins (STRING) database (FIG. 1C; Szklarczyk et al. (2015) *Nucl. Acids Res.* 43: D447-D452). Prioritizing translatable targets, the druggable dependencies MDM2, MDM4, USP7, and PPM1D, which have inhibitors in preclinical or clinical evaluation, were focused upon. In Ewing sarcoma, MDM2, MDM4, USP7, and PPM1D were preferential dependencies in the TP53 wild-type cell lines (FIGS. 1D and 2A-2B).

MDM2 is an E3 ubiquitin ligase that marks p53 for degradation by the proteasome (Wade et al. (2013) *Nat. Rev. Cancer.* 13:83-96). MDM4, a structural homologue of MDM2, inhibits p53 by binding to and sequestering its transactivation domain (Wade et al. (2013) *Nat. Rev. Cancer.* 13:83-96). USP7 has been implicated in several cellular processes, including deubiquitination of MDM2, which leads to a decrease in p53 (Nicholson and Kumar (2011) *Cell Biochem. Biophys.* 60:61-68). PPM1D encodes for the serine-phosphatase Wip1 that dephosphorylates and inactivates p53 and other proteins involved in cell stress and DNA damage (Zhu and Bulavin (2012) *Prog. Mol. Biol. Transl. Sci.* 106:307-325).

With an eye toward clinical translation, MDM2 and MDM4, both of which can be targeted simultaneously with a dual inhibitor currently in clinical trials for adults with TP53 wild-type cancers (Chang et al. (2013) *Proc. Natl. Acad. Sci. U.S.A.* 110: E3445-E3454; Meric-Bernstam et al. (2017) *J. Clin. Oncol.* 35:2505-2505), were focused upon.

Example 4: Genetic Disruption of MDM2 and MDM4 has a Selective Cytotoxic Effect in TP53 Wild-Type Ewing Sarcoma Cell Lines It was sought to validate the dependencies on MDM2 and MDM4 by CRISPR-Cas9 in two TP53 wild-type cell lines (TC32 and TC138) and two TP53 mutant cell lines (A673 and EWS502).

Figure 3A:
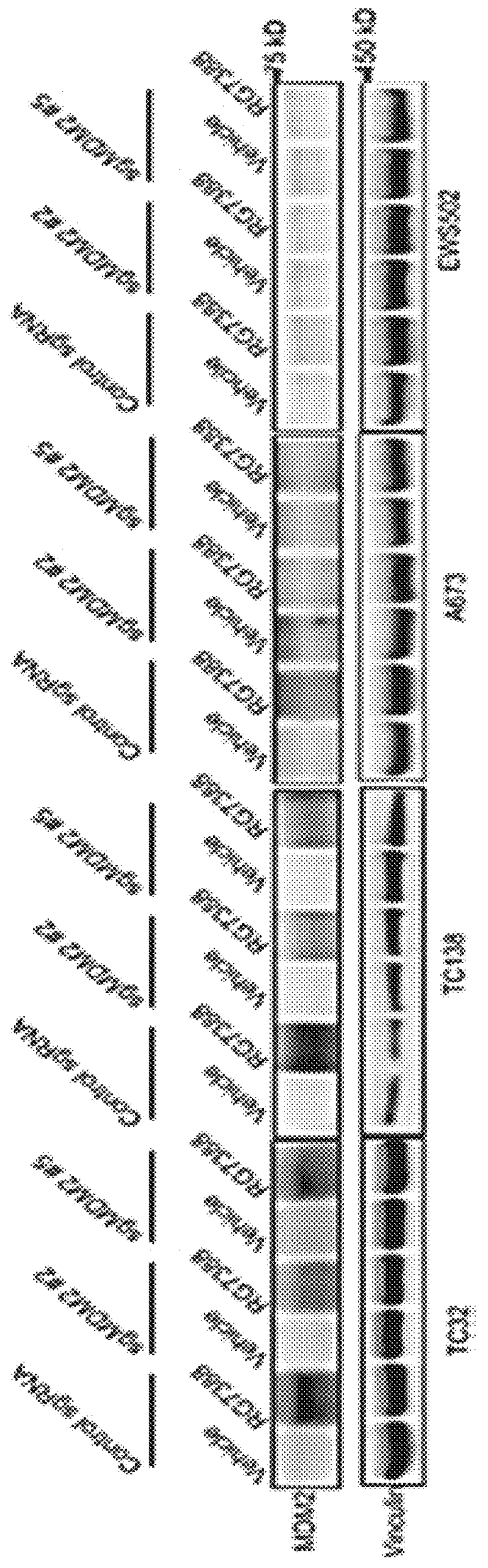
FIG. 3A-FIG. 3F show validation of MDM2 and MDM4 as dependencies in TP53 wild-type Ewing sarcoma. Western blots (FIG. 3A) demonstrate abrogation of the observed increase in MDM2 protein levels upon RG7388 treatment (1 μM; 4 h) in TP53 wild-type cell lines TC32 and TC138 cells infected with sgRNAs targeting MDM2 compared with a nontargeting control sgRNA and no response to RG7388 treatment in TP53 mutated cell lines A673 and EWS502. Western blots (FIG. 3B) demonstrate decreased protein levels of MDM2 with sgRNAs targeting MDM2 compared with a control guide in the SJSA-X cell line.
Figure 3B:
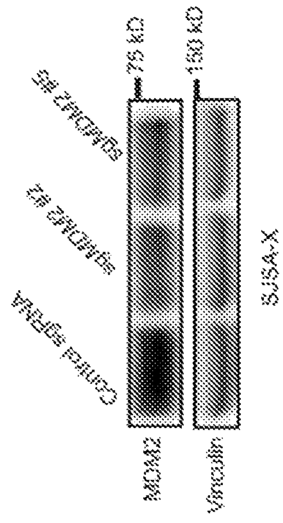
Figure 3C:
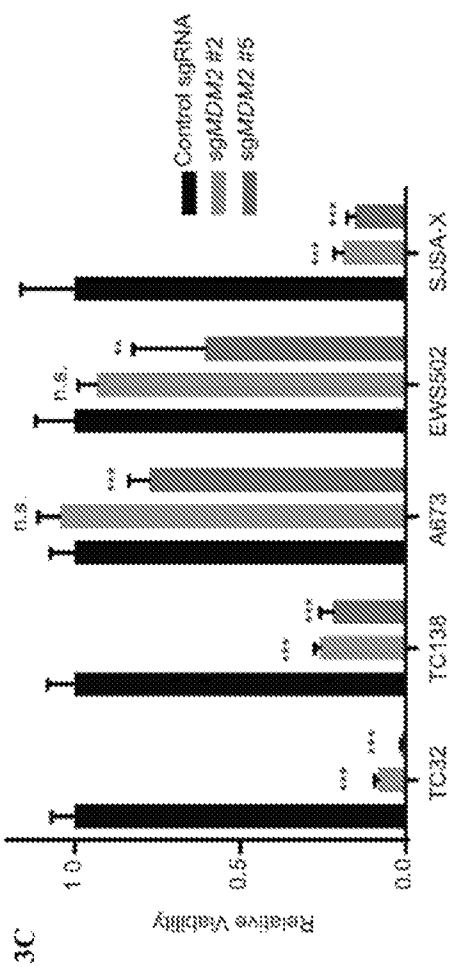

To genetically disrupt MDM2, the Ewing sarcoma cell lines were infected with MDM2 sgRNAs and then treated with the MDM2 inhibitor RG7388, which causes an up-regulation of MDM2 through a negative feedback mechanism in response to elevated p53 levels (Ding et al. (2013) *J. Med. Chem.* 56:5979-5983). TP53 wild-type cells infected with sgRNAs targeting MDM2 exhibited a weaker increase in MDM2 protein levels compared with cells infected with the control sgRNA, which is consistent with MDM2 knock-out in a population of cells in the pool (FIG. 3A). Given the disrupted p53-MDM2 axis in the TP53 mutant lines, there was no increase in MDM2 protein following RG7388 treatment of A673 and EWS502 cells, irrespective of infection with MDM2 or control sgRNAs (FIG. 3A). To further validate the on-target activity of the sgRNAs, the osteosarcoma cell line, SJSA-X, which is engineered to overexpress MDM4 in the context of endogenously elevated MDM2 levels (Wade et al. (2008) *Cell Cycle* 7:1973-1982), was infected with sgRNAs targeting MDM2. Knockout was confirmed by Western blot (FIG. 3B) and selectively impaired the viability of TP53 wild-type Ewing sarcoma and SJSA-X cells, with little to no effect on the TP53 mutant cell lines (FIG. 3C), consistent with the CRISPR-Cas9 screening results.

Figure 3D:
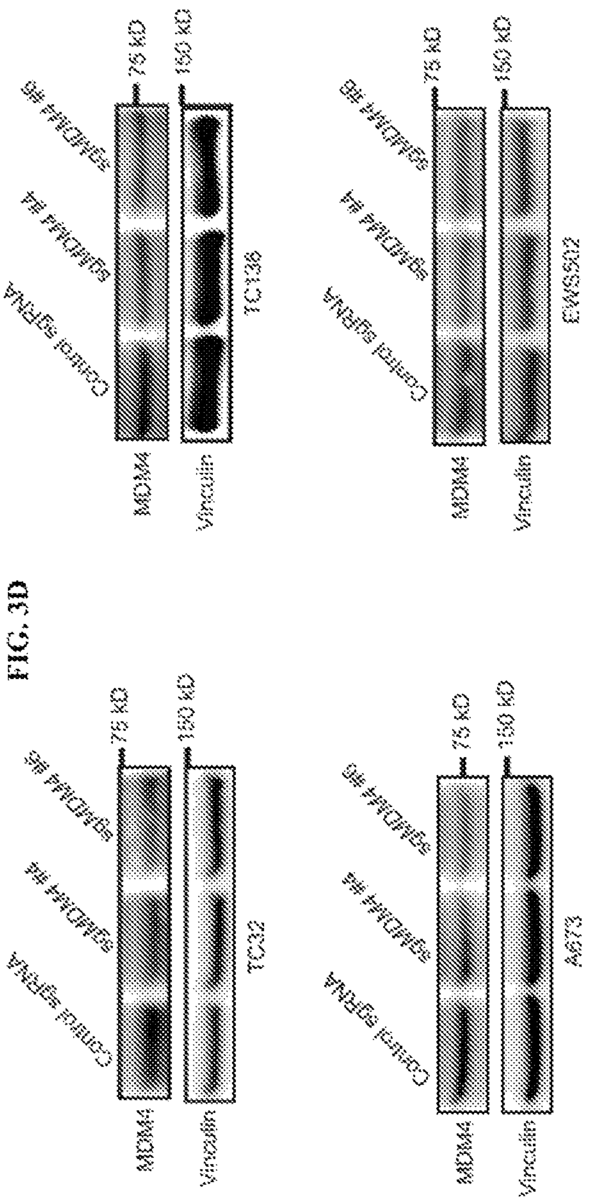
Figure 3E:
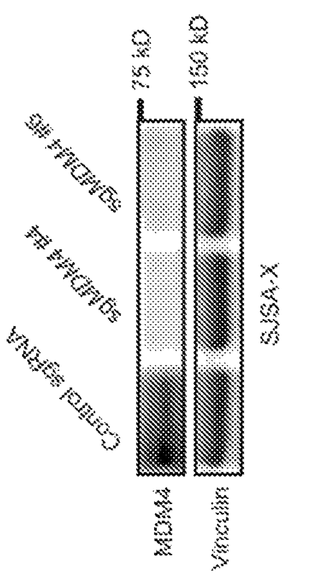
Figure 3F:
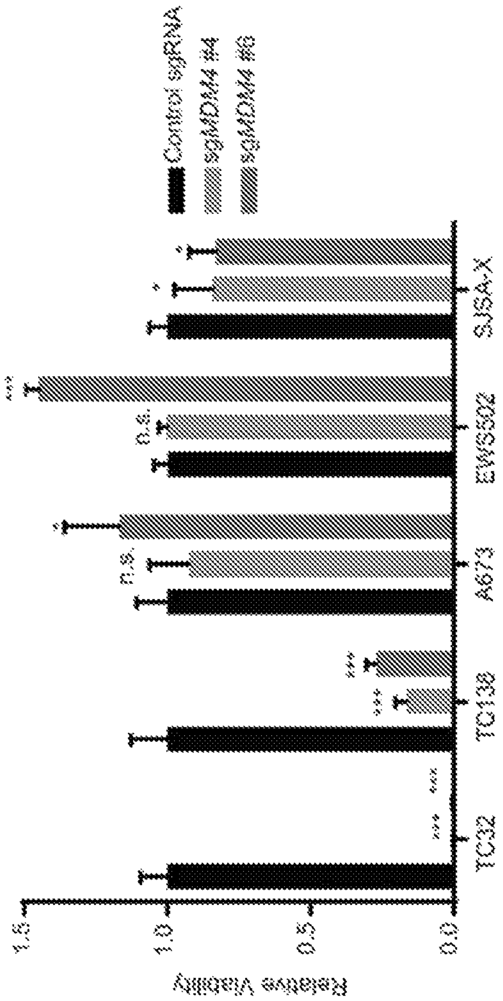

Similarly, MDM4 was disrupted next by CRISPR-Cas9 in Ewing sarcoma cell lines (FIG. 3D) an demonstrated MDM4 knockout in two TP53 mutant cell lines and SJSA-X cells (FIG. 3E). As predicted by the screen, and consistent with the MDM2 findings (FIG. 3C), loss of MDM4 impaired the viability of TP53 wildtype Ewing sarcoma cell lines in a strikingly selective fashion, while SJSA-X, a cell line engineered to overexpress MDM4, does not depend on the gene as previously reported (FIG. 3F; Wade et al. (2008) *Cell Cycle* 7:1973-1982).

Example 5: Chemical Inhibition of MDM2/MDM4 Reduces Viability of TP53 Wild-Type Ewing Sarcoma ATSP-7041 is a stapled peptide, dual inhibitor of MDM2 and MDM4 (Chang et al. (2013) *Proc. Natl. Acad. Sci. U.S.A.* 110: E3445-E3454). Modeled after the p53 transactivation a-helix, stapled p53 peptides engage the p53 binding domain of MDM2 and MDM4 with high affinity and respectively block the degradation and sequestration of p53 (Bernal et al. (2010) *Cancer Cell* 18:411-422).

Figure 4B:
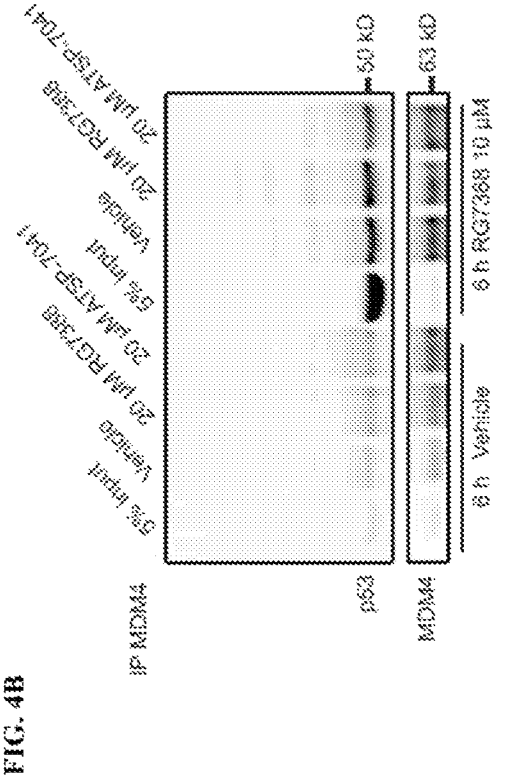
FIG. 4A-FIG. 4F show that ATSP-7041 reactivates the p53 pathway to induce cell death in TP53 wild-type Ewing sarcoma cell lines. Western blots (FIG. 4A) show increased protein levels of MDM2, p53, and p21 after ATSP-7041 treatment at the indicated time and concentrations in TP53 wild-type Ewing sarcoma cell lines.
Figure 4A:
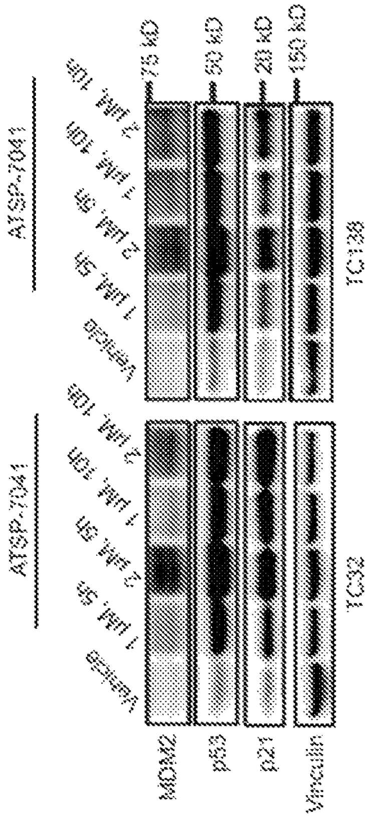

Concentration-dependent increases in MDM2, p53, and p21 protein levels were observed after ATSP-7041 treatment of TP53 wild-type Ewing sarcoma cell lines (FIG. 4A). To verify the mechanism of action of ATSP-7041 in Ewing sarcoma, immunoprecipitation experiments were performed. TC32 cells were pre-treated with the MDM2 inhibitor RG7388 to increase p53 protein levels and then cell lysates were treated with vehicle, ATSP-7041 or RG7388, followed by MDM4 immunoprecipitation and p53 and MDM4 Western blot analysis. Whereas RG7388 was unable to dissociate the inhibitory p53-MDM4 complexes formed in response to selective inhibition of MDM2 in Ewing sarcoma cells, ATSP-7041 exposure decreased the level of p53-MDM4 interaction (FIG. 4B), consistent with the mechanism reported for other cancer cell lines (Bernal et al. (2010) *Cancer Cell* 18:411-422; Chang et al. (2013) *Proc. Natl. Acad. Sci. U.S.A.* 110: E3445-E3454).

Figure 4C:
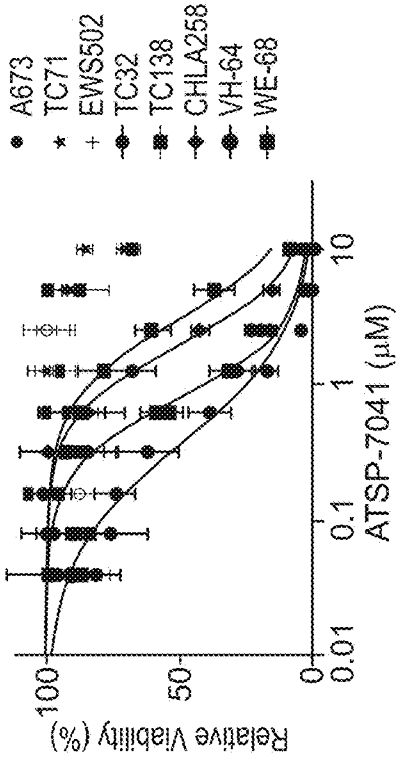
Figure 4D:
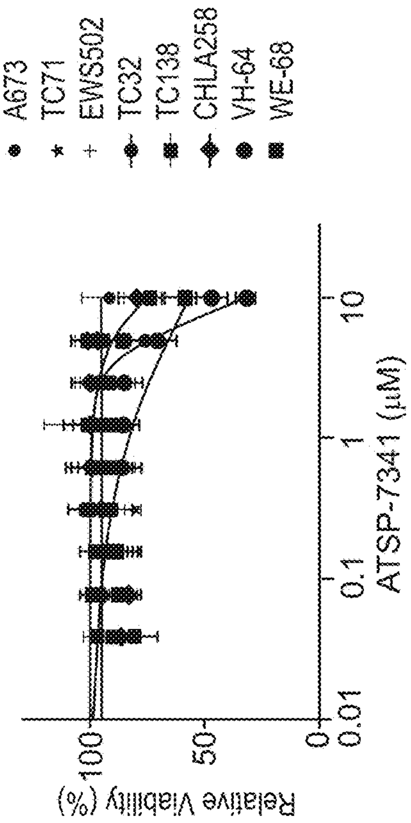
Figure 4E:
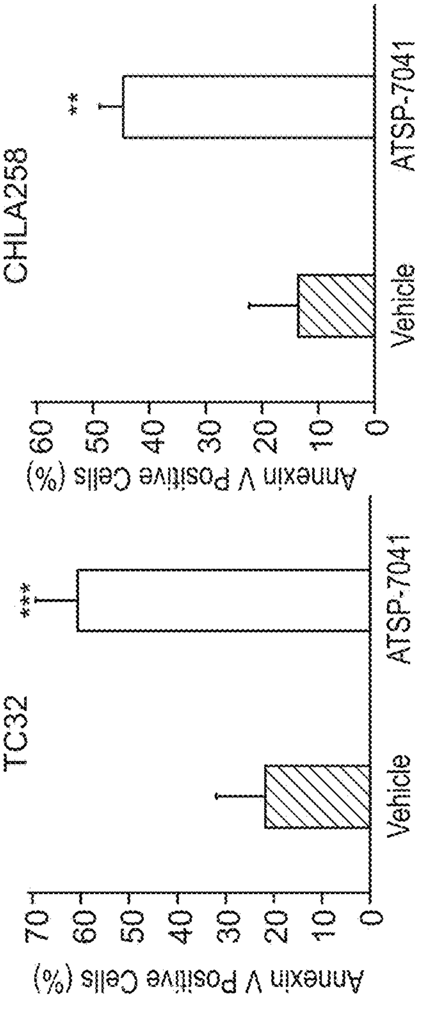

ATSP-7041 selectively reduced the viability of five TP53 wildtype Ewing sarcoma cell lines at low micromolar concentrations (FIG. 4C), whereas TP53 mutated Ewing sarcoma cell lines were resistant, mirroring the results of our genetic perturbation studies. ATSP-7342, a negative control stapled peptide that bears an inactivating F19A point mutation and thus exhibits impaired MDM2/MDM4 binding activity (Chang et al. (2013) *Proc. Natl. Acad. Sci. U.S.A.* 110: E3445-E3454), was essentially ineffective at these concentrations (FIG. 4D). Annexin V staining likewise demonstrated induction of cell death at the corresponding concentrations of ATSP-7041 in TP53 wild-type Ewing sarcoma cell lines (FIG. 4E).

Figure 4F:
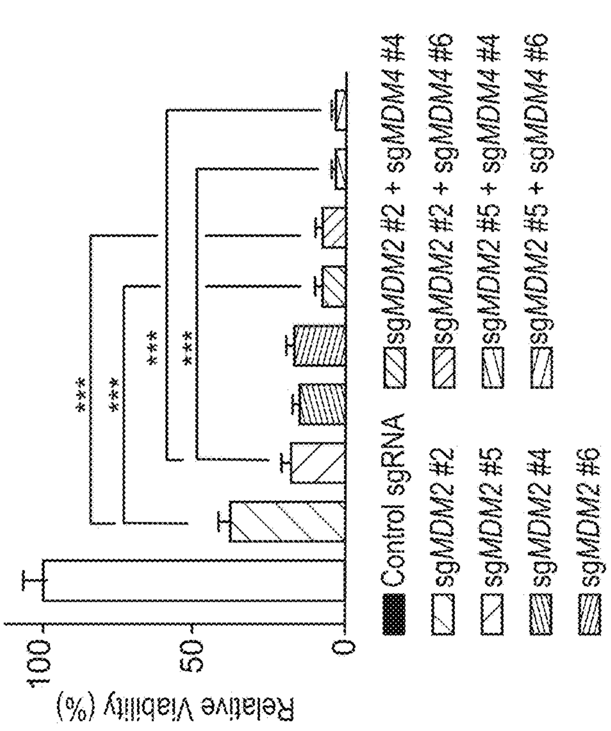

To study a genetic model of ATSP-7041 that allows for the comparison of MDM2/4 dual inhibition to MDM2 inhibition alone, dual-knockout experiments were performed with CRISPR-Cas9 constructs targeting MDM2 and MDM4. TC32 cells were infected with CRI SPR-Cas9 constructs either targeting MDM2 alone, MDM4 alone, or one construct each for targeting MDM2 and MDM4 simultaneously. Overall, knockout of both MDM2 and MDM4 decreased viability more effectively than loss of either alone at this time point (FIG. 4F), validating the potential therapeutic benefit of dual inhibition of MDM2 and MDM4 over inhibiting MDM2 alone.

Figure 5A:
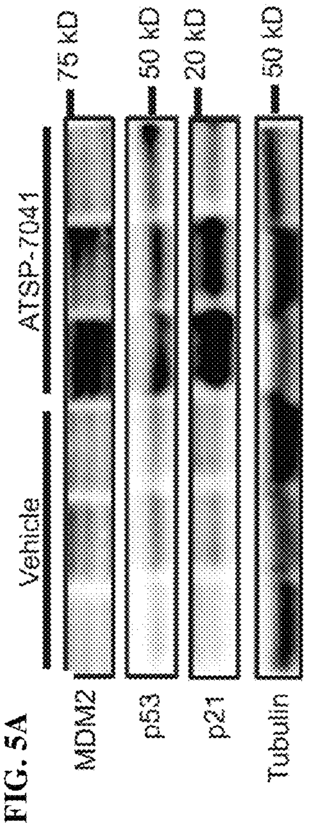
FIG. 5A-FIG. 5I show that ATSP-7041 shows anti-tumor efficacy in Ewing sarcoma models in vivo. Western blot results (FIG. 5A) show an increase of MDM2, p53, and p21 protein levels in TC32 xenograft tumor tissues after ATSP-7041 treatment in vivo. After tumor engraftment, mice were treated with three doses of 30 mg/kg q.o.d. ATSP-7041 or vehicle and sacrificed 8 h after the last dose. Each lane represents an individual mouse tumor.
Figure 5B:
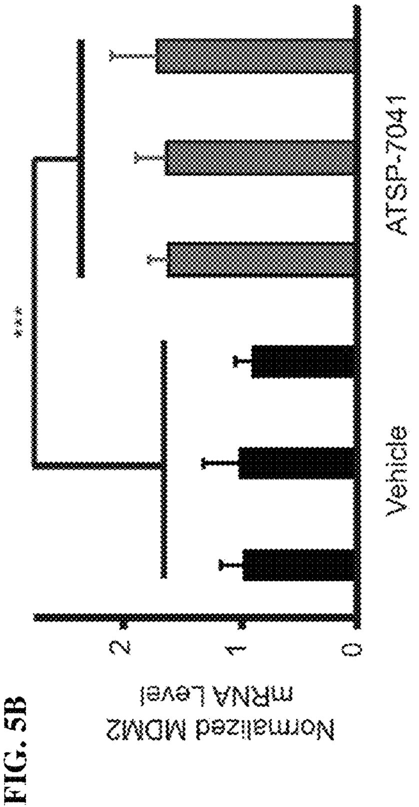
Figure 5C:
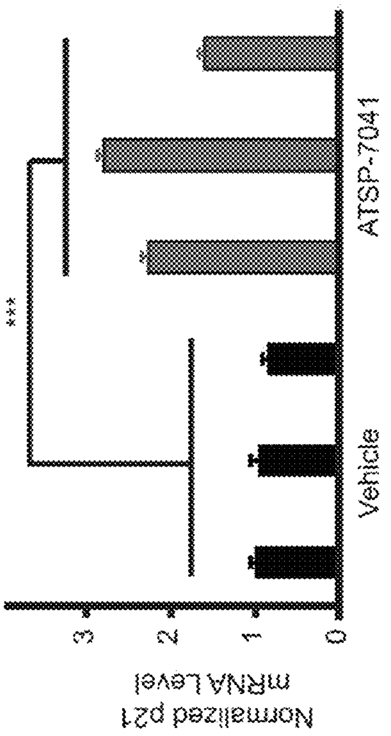
Figure 5D:
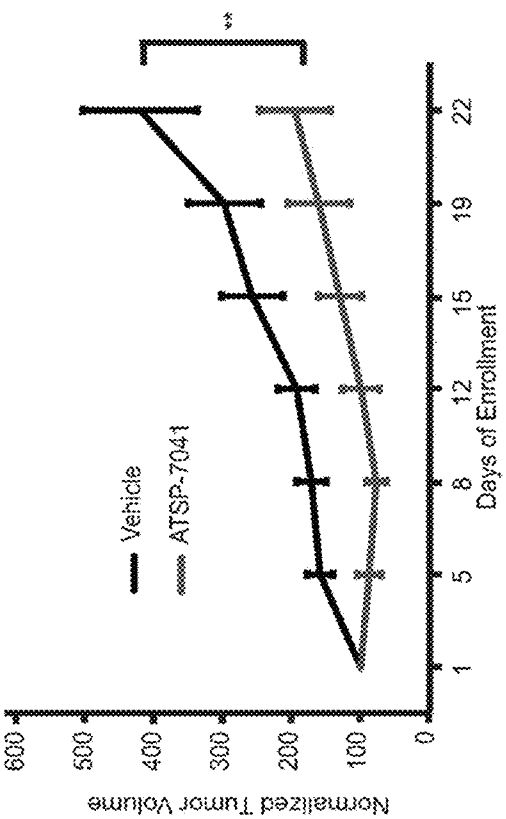

Example 6: ATSP-7041 Reactivates the p53 Transcriptional Pathway and Suppresses Ewing Sarcoma Growth In Vivo It was next sought to evaluate the activity of ATSP-7041 Ewing sarcoma in vivo. TC32 Ewing sarcoma cells were implanted subcutaneously in nude mice. Following tumor engraftment with tumor volumes >100 cubed millimeters (mm3), mice were dosed with 30 mg/kg IV ATSP-7041 or vehicle every other day for 6 d. Eight hours (8 h) after the last dose, mice were sacrificed and tumors were collected for comparative analysis of p53 pathway reactivation. It was found that ATSP-7041 treatment led to both an increase in MDM2, p53, and p21 protein levels (FIG. 5A) and MDM2 and p21 mRNA levels (FIGS. 5B-5C) in tumor tissue. After validating the on-mechanism activity of ATSP-7041 in vivo, it was next sought to assess anti-tumor efficacy. Treatment of TC32 Ewing sarcoma xenografted mice with 30 mg/kg ATSP-7041 or vehicle IV every other day for 20 d significantly suppressed tumor growth, sustaining a reduction in tumor progression throughout the 22-d evaluation period (FIG. 5D).

Figure 5E:
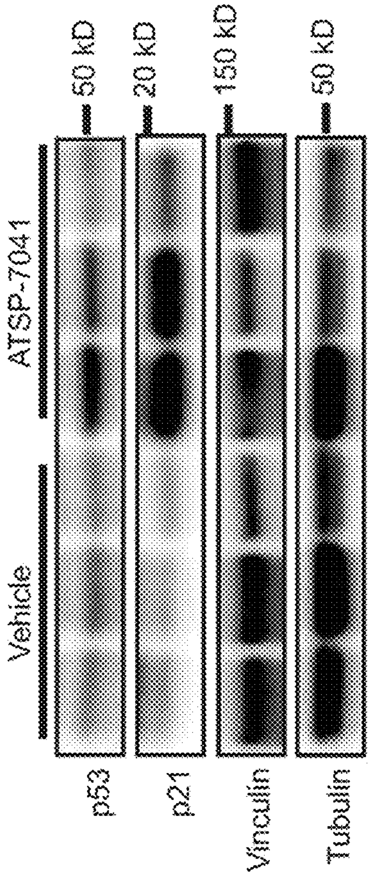
Figure 5F:
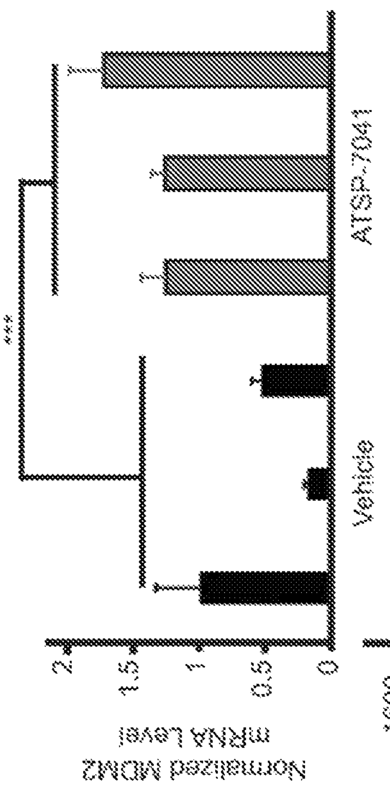
Figure 5G:
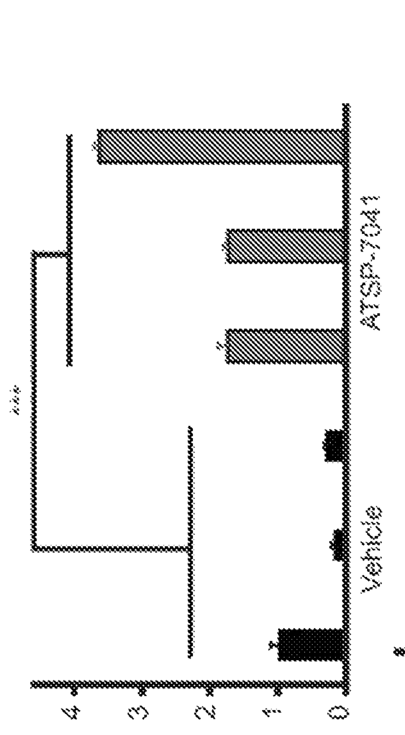
Figure 5H:
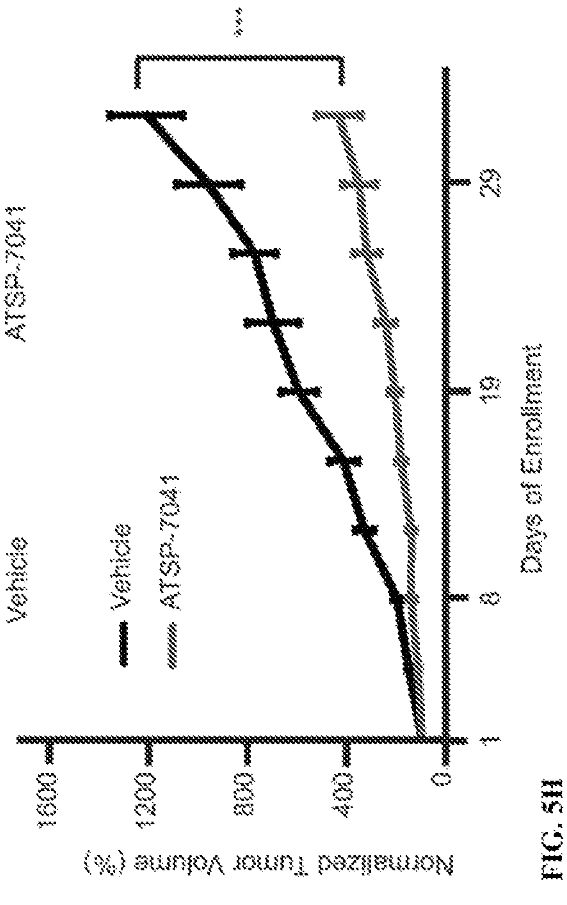
Figure 5I:
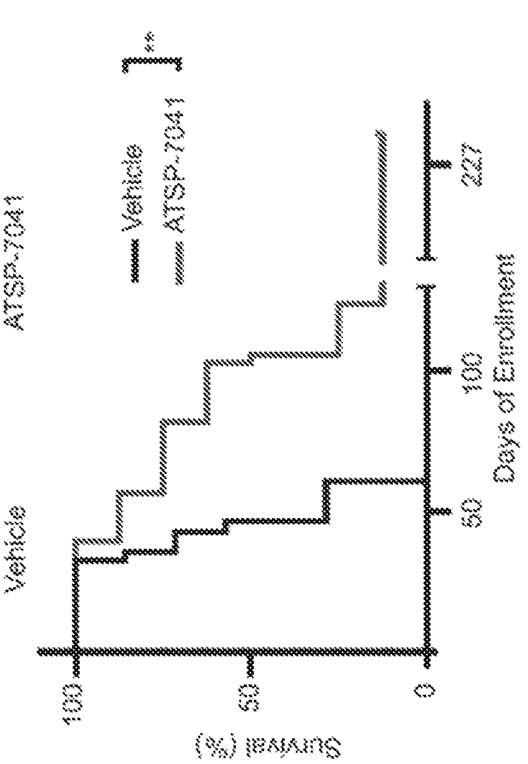

To test ATSP-7041 in a model that more closely recapitulates patient tumors, a patient-derived xenograft (PDX) model of Ewing sarcoma (HSJD-ES-002), which was derived from a tumor resected from the fibula of a 12-yr-old patient at diagnosis (Ordonez et al. (2015) *Oncotarget* 6:18875-18890), was studied. In vivo treatment of mice bearing HSJD-ES-002 tumors with ATSP-7041 increased intratumoral p53 and p21 protein levels (FIG. 5E) and increased MDM2 and p21 mRNA levels (FIGS. 5F-5G). Tumor growth was slowed significantly after 10 doses of ATSP-7041 (FIG. 5H). Survival of mice was significantly extended, and, remarkably, one mouse treated with ATSP-7041 was cured of disease, showing complete tumor regression without recurrence over the observed time frame of 227 d (FIG. 5I).

Example 7: Genetic Disruption of USP7 and PPM1D is Selectively Cytotoxic to Ewing Sarcoma Lines Bearing Wild-Type TP53

Figures 6A, 6B:
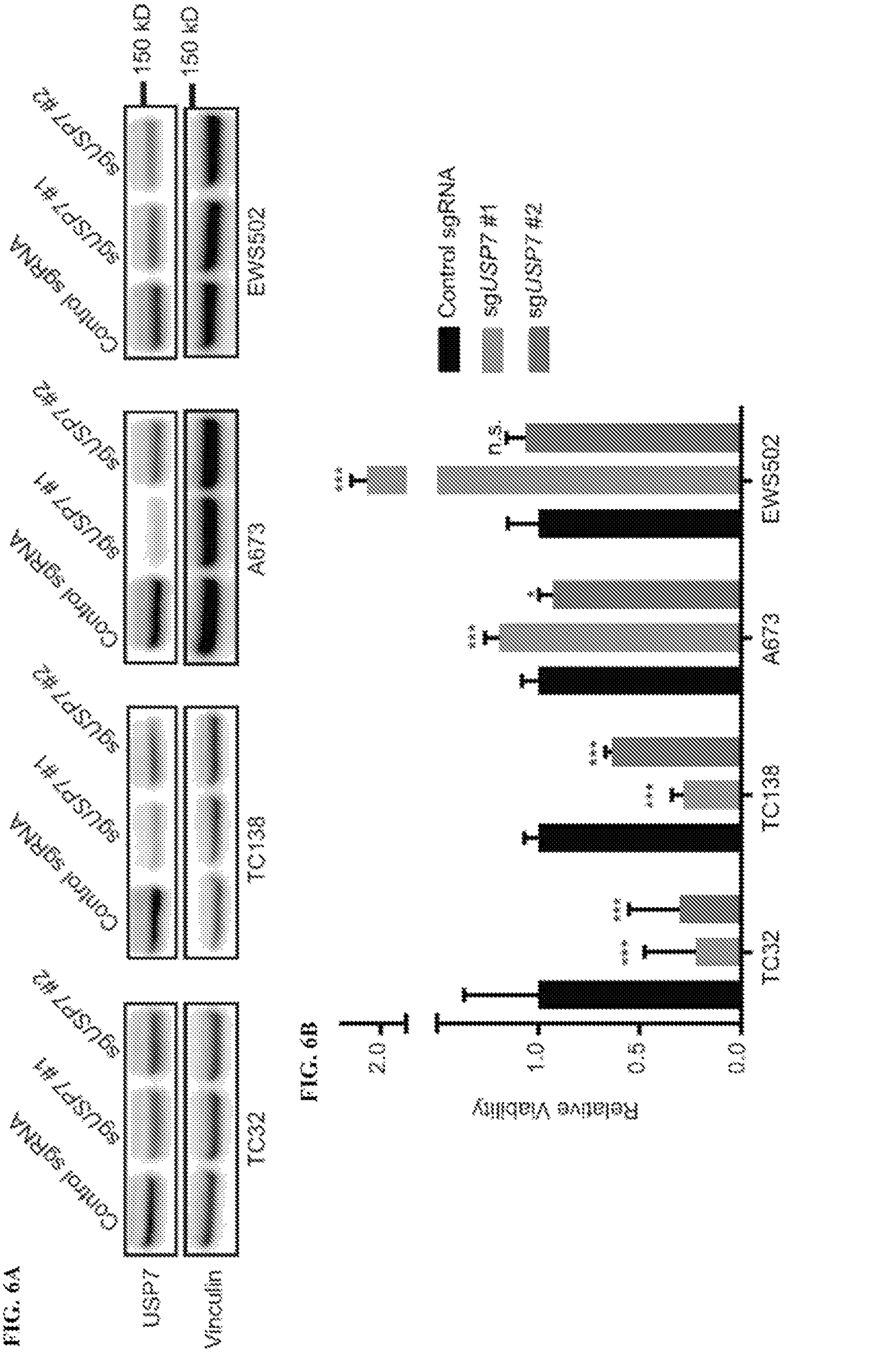
FIG. 6A-FIG. 6D show validation of PPM1D and USP7 as dependencies in TP53 wild-type Ewing sarcoma. Western blots (FIG. 6A) show decreased protein levels of USP7 after infection with sgRNAs targeting USP7 compared with control sgRNAs.

After validating MDM2 and MDM4 as gene dependencies in TP53 wild-type Ewing sarcoma, USP7 and PPM1D were evaluated. USP7 was disrupted by CRISPR-Cas9 in TC32, TC138, A673, and EWS502 cells (FIG. 6A), and reduced viability of TP53 wild type compared with mutant Ewing sarcoma cell lines was observed (FIG. 6B).

Figure 6C:
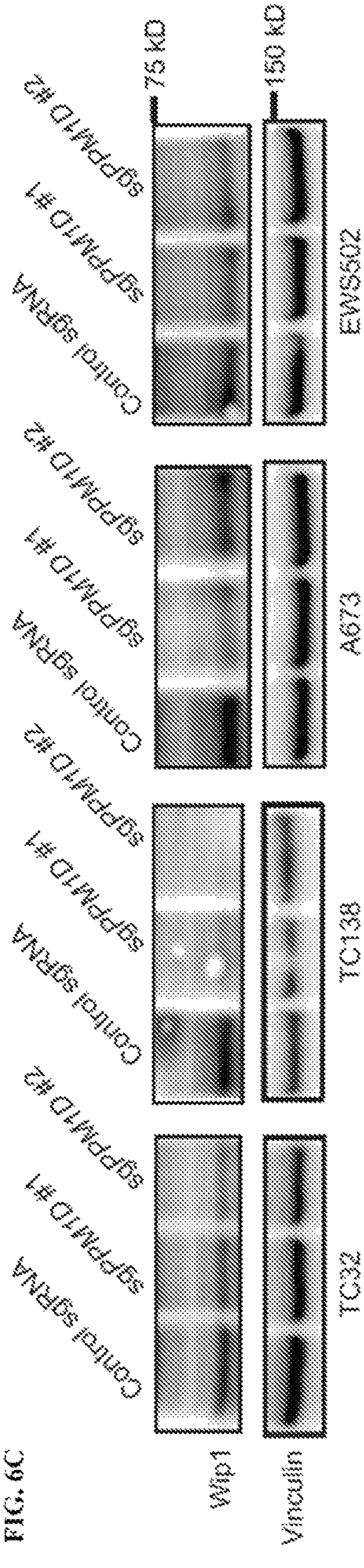
Figure 6D:
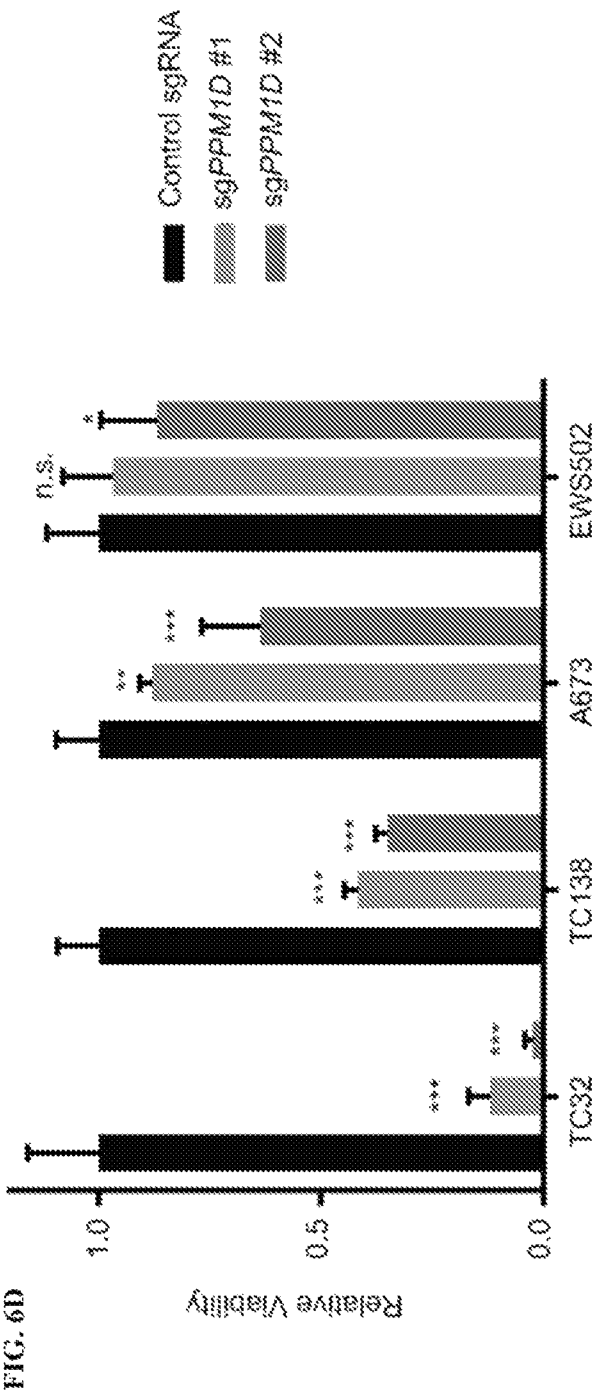

Similarly, the disruption of PPM1D by CRISPR-Cas9 in TC32, TC138, A673, and EWS502 led to reduced protein levels of Wip1 (FIG. 6C) and a decrease in viability of the TP53 wild type compared with the TP53 mutant Ewing sarcoma cell lines (FIG. 6D).

Figure 7A:
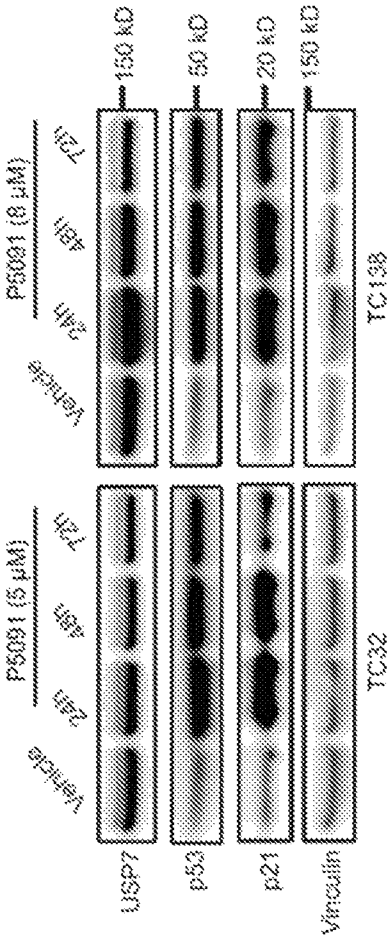
FIG. 7A-FIG. 7F show that GSK2830371 and P5091 reduce viability and induce cell death in TP53 wild-type Ewing sarcoma cell lines. Western blots (FIG. 7A) show an increase in p53 and p21 protein levels with P5091 treatment in TP53 wild-type Ewing sarcoma cell lines.
Figure 7B:
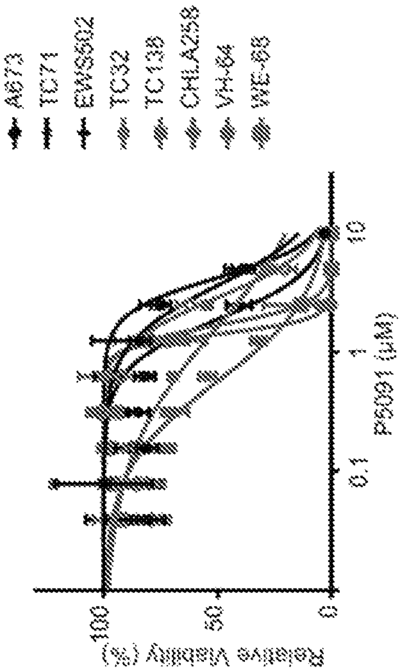
Figure 7C:
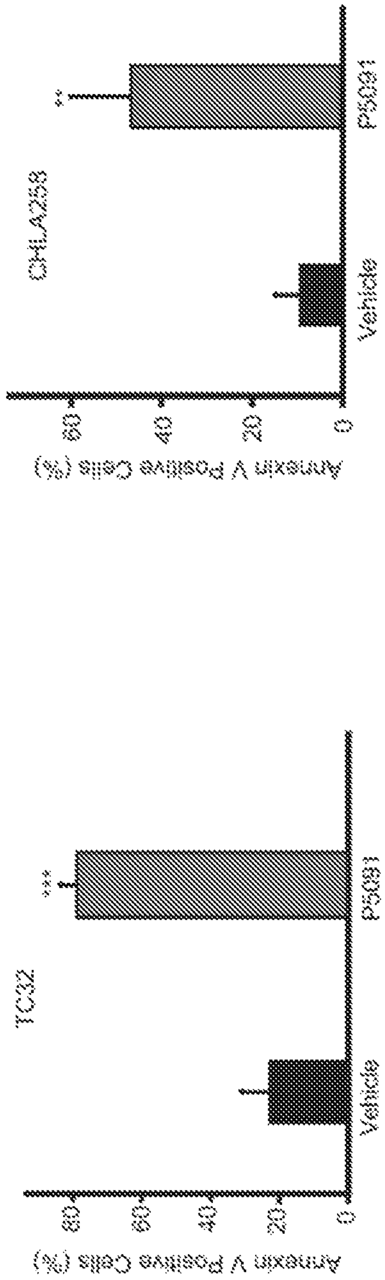

Example 8: Chemical Inhibition of USP7 and Wip1 Impairs the Viability of TP53 Wild-Type Ewing Sarcoma Cells Given the selective effects of genetic disruption of USP7 and PPM1D on the viability of wild-type TP53 Ewing sarcoma, the pharmacologic activities of their respective small inhibitors, P5091 (Chauhan et al. (2012) *Cancer Cell* 22:345-358) and GSK2830371 (Gilmartin et al. (2014) *Nat. Chem. Biol.* 10:181-187), were tested. P5091 increased p53 and p21 protein levels in a time-dependent fashion in the wild-type TP53 cells, TC32 and TC138 (FIG. 7A). The inhibitor appeared to be relatively more cytotoxic to a subset of TP53 wild-type Ewing sarcoma lines compared with TP53 mutant cells (FIG. 7B). Annexin V staining likewise demonstrated P5091-induced cell death in TP53 wildtype Ewing sarcoma cell lines (FIG. 7C).

Figure 7D:
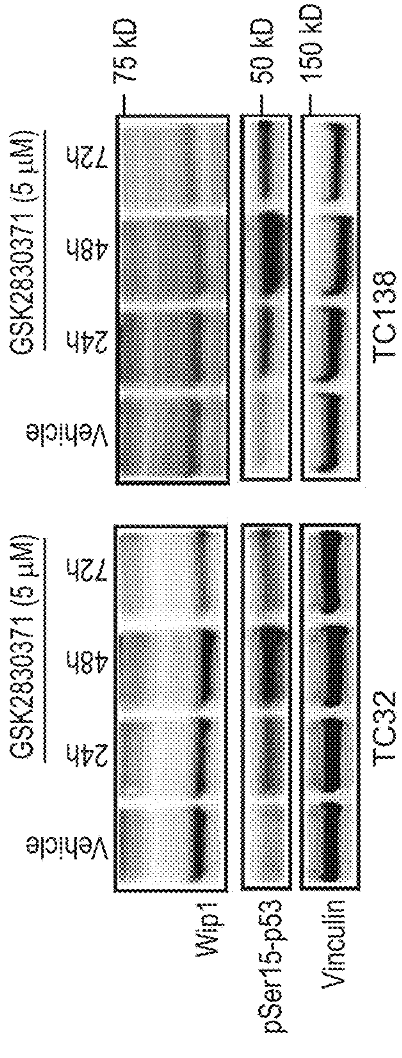
Figure 7E:
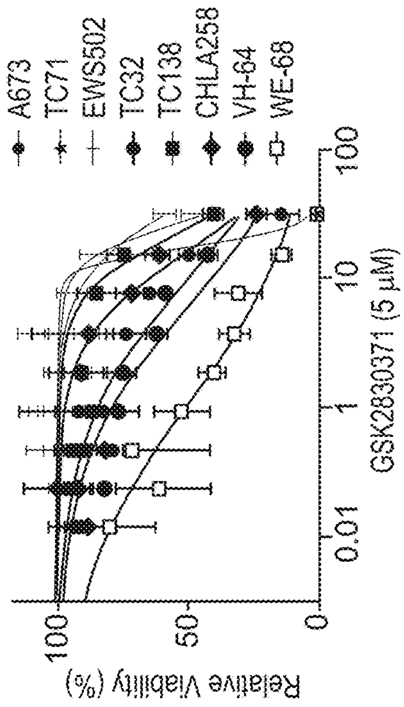
Figure 7F:
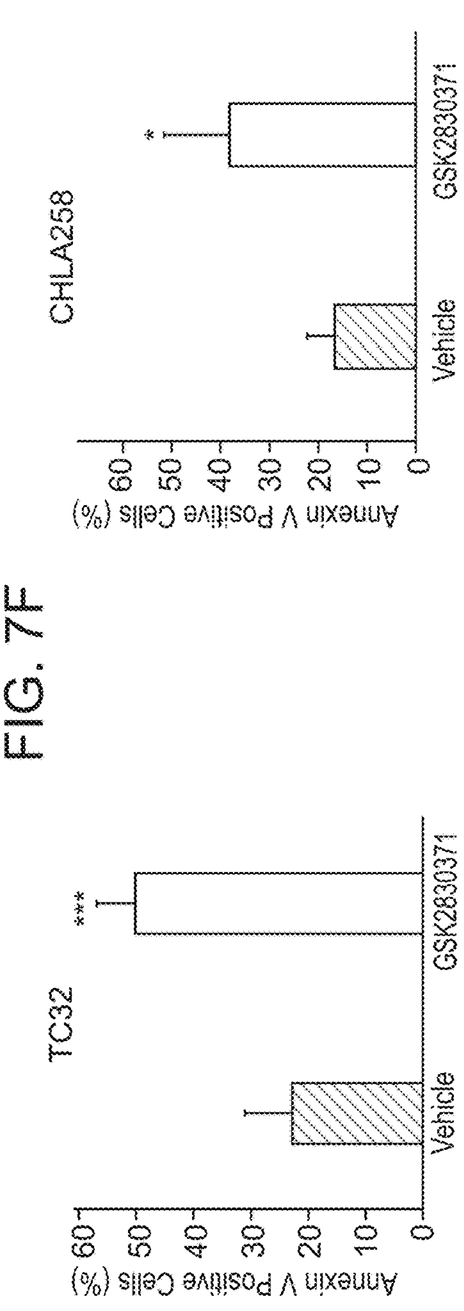

GSK2830371 reduced the protein levels of Wip1 in a time-dependent manner and triggered a surge in phosphorylation of Serine 15 of p53, the primary p53 dephosphorylation target site of Wip1 (FIG. 7D). There was a notable increase in susceptibility of TP53 wild-type Ewing sarcoma cell lines to micromolar concentrations of GSK2830371, as compared with the TP53 mutated cell lines (FIG. 7E). GSK2830371-induced cell death in TP53 wild-type Ewing sarcoma cell lines was likewise observed by Annexin V staining (FIG. 7F).

Example 9: ATSP-7041 Synergizes with Chemical Inhibition of USP7 and Wip1

Figure 8A:
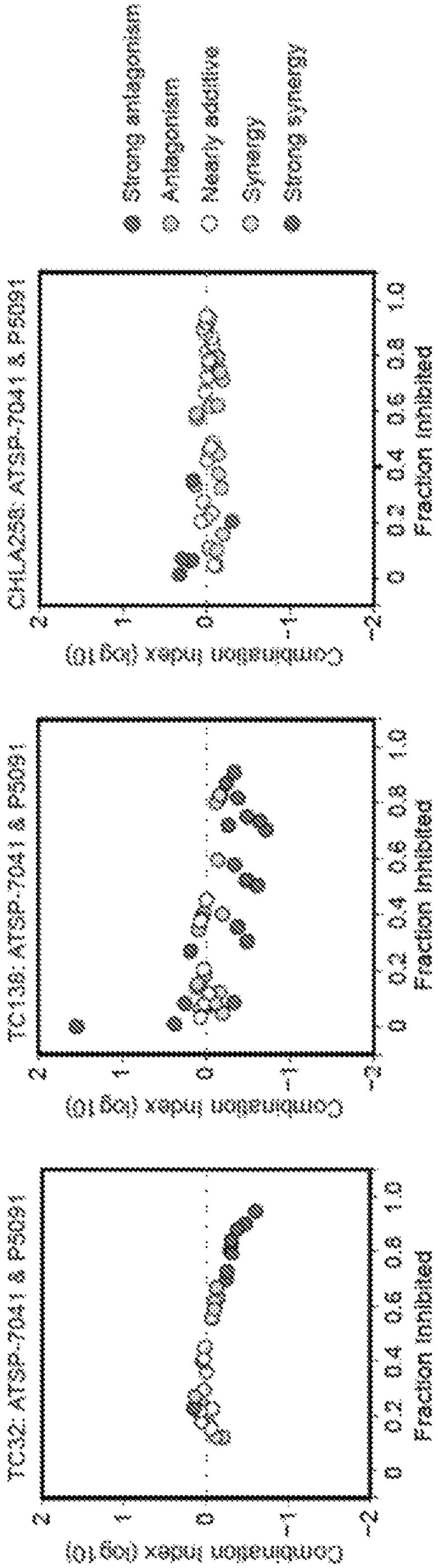
FIG. 8A-FIG. 8D show that ATSP-7041 synergizes with GSK2830371 and P5091.
Figure 8B:
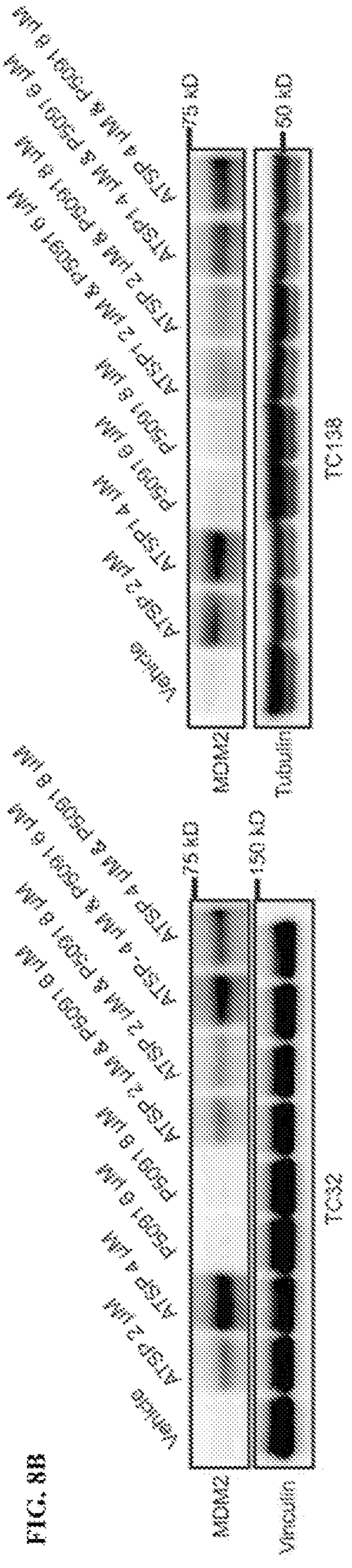

Given the promising single-agent activity of GSK2830371 and P5091 in reactivating the p53 pathway, the therapeutic potential of combining these molecules with ATSP-7041 was evaluated. Because MDM2, MDM4, USP7, and PPM1D all scored as top dependencies in TP53 wild-type Ewing sarcoma, it was reasoned that chemically inhibiting these proteins in combination could provide the most effective mechanism to trigger p53-mediated cell death in Ewing sarcoma. Indeed, it was found that the combination of ATSP-7041 with P5091 exhibited synergy in TC32 and TC138 and additivity in CHLA258 cells as assessed by the Chou-Talalay combination index for Loewe additivity model (FIG. 8A; Chou (2006) *Pharmacol. Rev.* 58:621-681; Chou (2010) *Cancer Res.* 70:440-446). It was hypothesized that the heightened therapeutic response could be due to synergistic action on the p53 axis. Western blot analysis revealed that P5091 decreased the level of MDM2 protein that is otherwise induced by ATSP-7041 as a result of the surge in p53 and counter-up-regulation of MDM2 (FIG. 8B). These data indicate that pharmacologic blockade of USP7 can counteract the natural up-regulation of MDM2 in response to elevated p53 levels, thereby maximizing the p53 response to ATSP-7041.

Figure 8C:
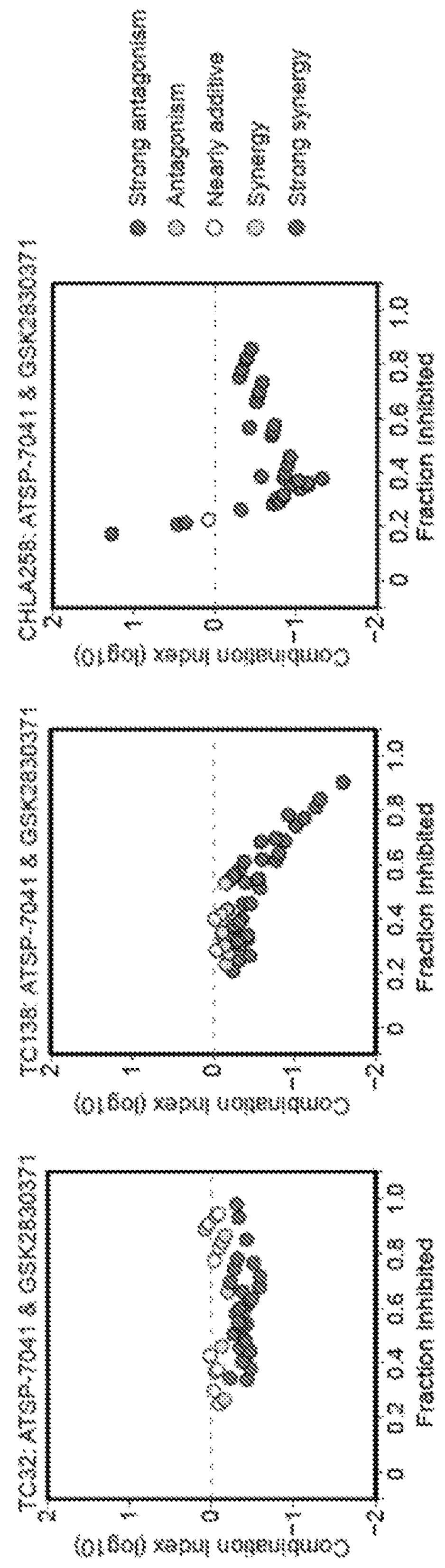
Figure 8D:
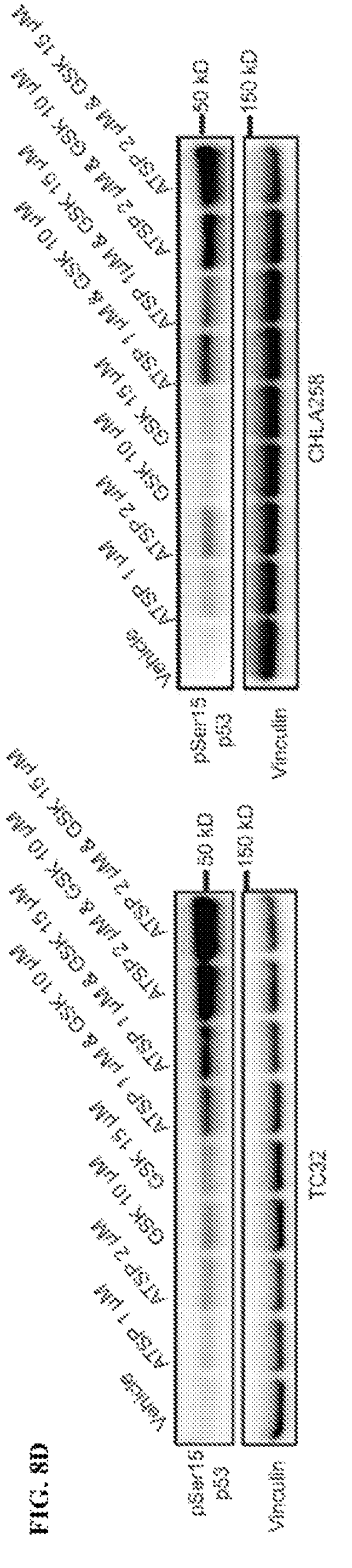

The combination of ATSP-7041 with GSK2830371 exhibited strong synergy across a broad concentration range in TC32, TC138, and CHLA258 cells (FIG. 8C). Western blot assays revealed that the combination of ATSP-7041 and GSK2830371 increased the phosphorylation of p53 at Serine 15 in two Ewing sarcoma cell lines (FIG. 8D). These data indicate that phosphorylation of p53 underlies the synergism of these two drugs and provides mechanistic evidence that Wip1 acts as a phosphatase of p53 in Ewing sarcoma.

After MDM2, MDM4, USP7, and PPM1D were identified as co-dependencies in the CRISPR-Cas9 screen, the combination of pharmacologic inhibitors targeting these proteins yielded synergistic cytotoxicity, indicating that a subset of correlated genetic dependencies predicts the synergy of inhibitor combinations.

Figure 9A:
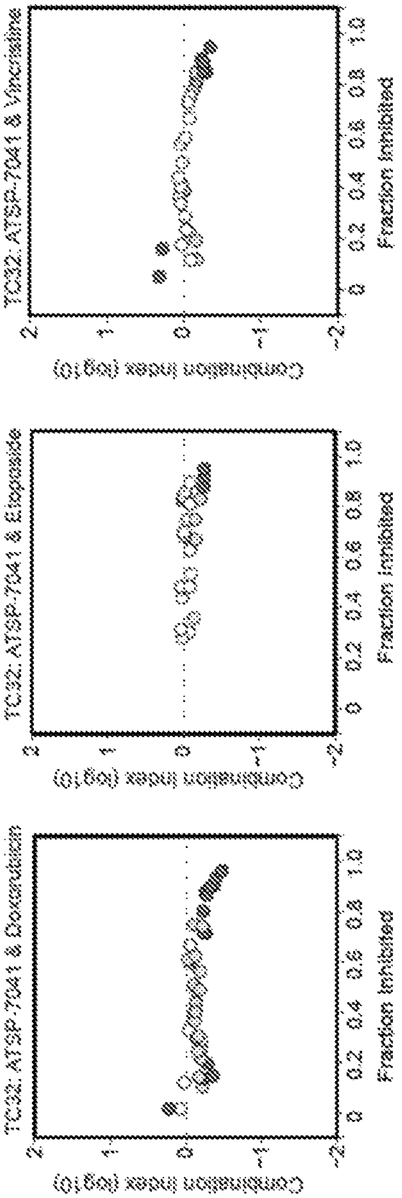
FIG. 9A-FIG. 9F show that ATSP-7041 synergizes with chemotherapy agents.
Figure 9B:
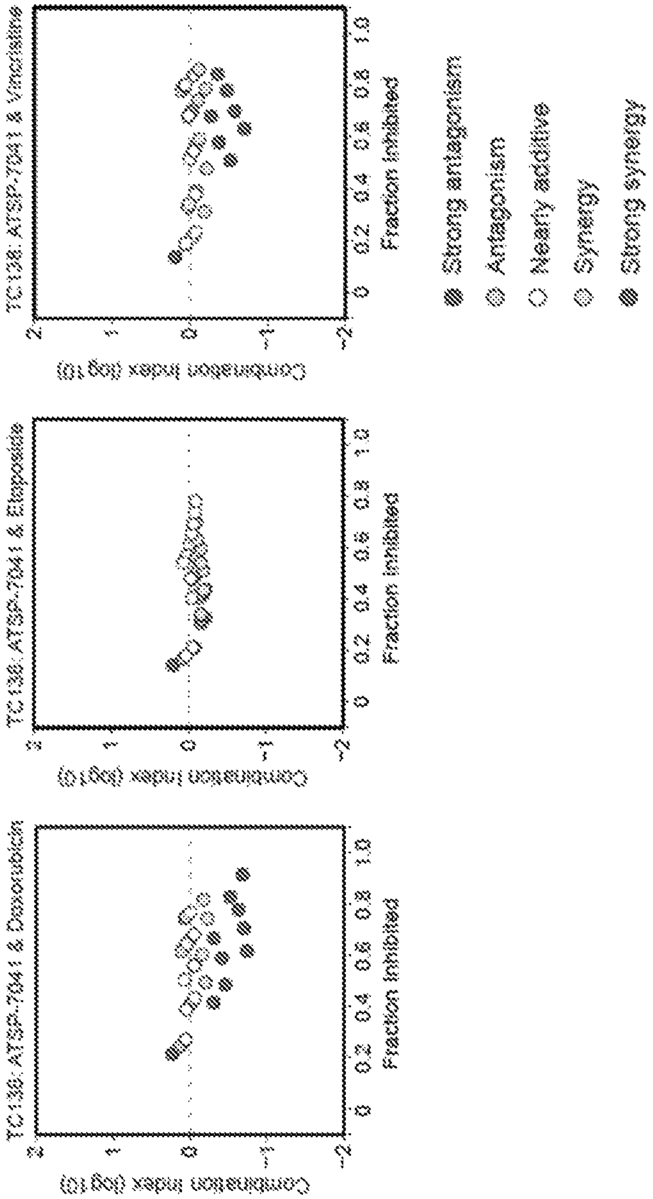
Figure 9C:
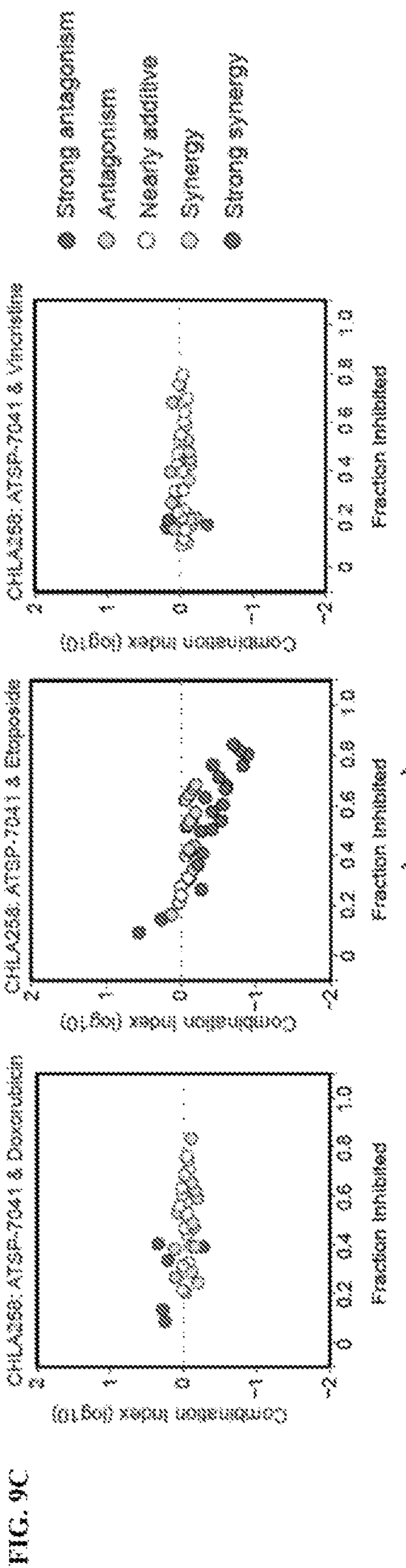

Example 10: ATSP-7041 Synergizes with Standard of Care Chemotherapeutics in Ewing Sarcoma Since an MDM2/4 dual inhibitor stapled peptide is currently in Phase 1 and Phase 2 testing in adult cancers bearing wild-type TP53, it was sought to test for synergistic activity of ATSP-7041 with approved treatment regimens for Ewing sarcoma. Thus, ATSP-7041 was combined with doxorubicin, etoposide, or vincristine, three drugs used clinically in the treatment of Ewing sarcoma (Gaspar et al. (2015) *J. Clin. Oncol.* 33:3036-3046). All drug combinations demonstrated additivity or synergy at several concentrations, as assessed by the Chou-Talalay combination index for Loewe additivity model (FIGS. 9A-9C).

Figure 9D:
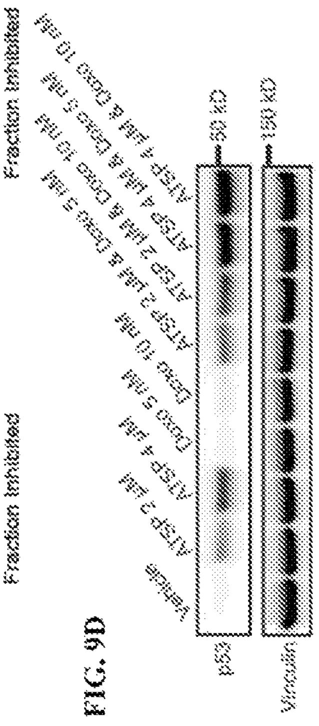
Figure 9E:
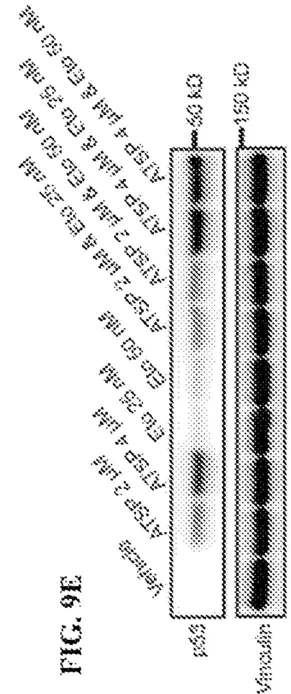
Figure 9F:
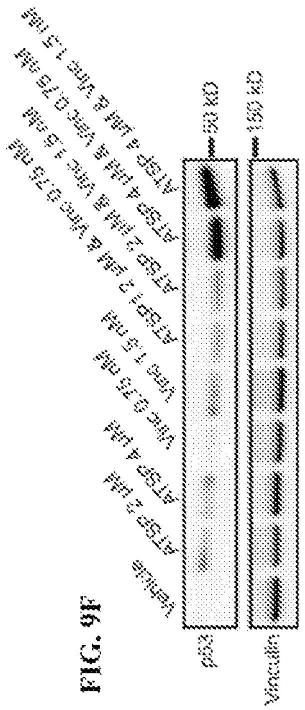

As cytotoxic chemotherapeutic agents are well known to induce pro-apoptotic signals in cancer cells, the effect of combining ATSP-7041 and chemotherapy agents on p53 protein levels was investigated. Combination treatments of ATSP-7041 with etoposide, doxorubicin, or vincristine greatly increased p53 protein levels in Ewing sarcoma cells, indicating that the synergy observed is due to synergistic action on the p53 pathway axis (FIGS. 9D-9F). Based on these data, it is believed that adding a stapled peptide dual inhibitor of MDM2/MDM4 to chemotherapy regimens is beneficial for patients with TP53 wild-type Ewing sarcoma.

Figure 10A:
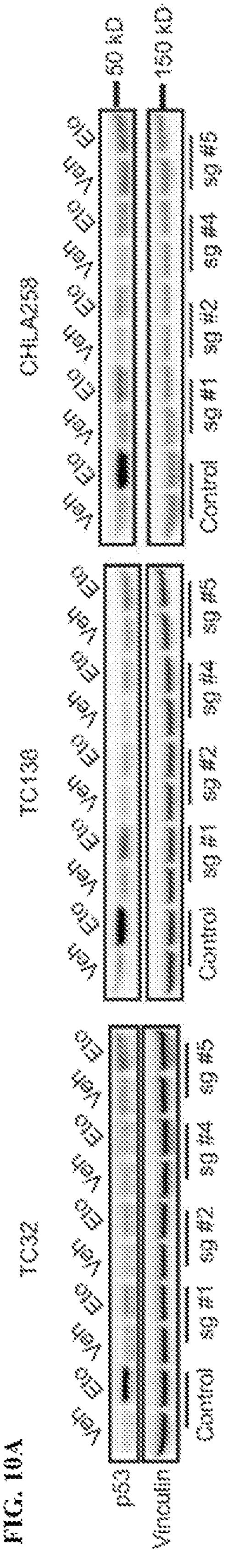
FIG. 10A-FIG. 10I show that loss of PPM1D and USP7 is rescued by concurrent TP53 loss. Western blots (FIG. 10A) show attenuated increase of p53 protein levels in TC32, TC138, and CHLA258 cells infected with sgRNAs targeting TP53 after etoposide treatment (Control, control sgRNA; sg #1, sgTP53 1; sg #2, sgTP53 2; sg #4, sgTP53 4; sg #5, sgTP53 5). Cells were treated with vehicle or 50 μM etoposide for one hour (Veh, vehicle; Eto, etoposide).
Figure 10B:
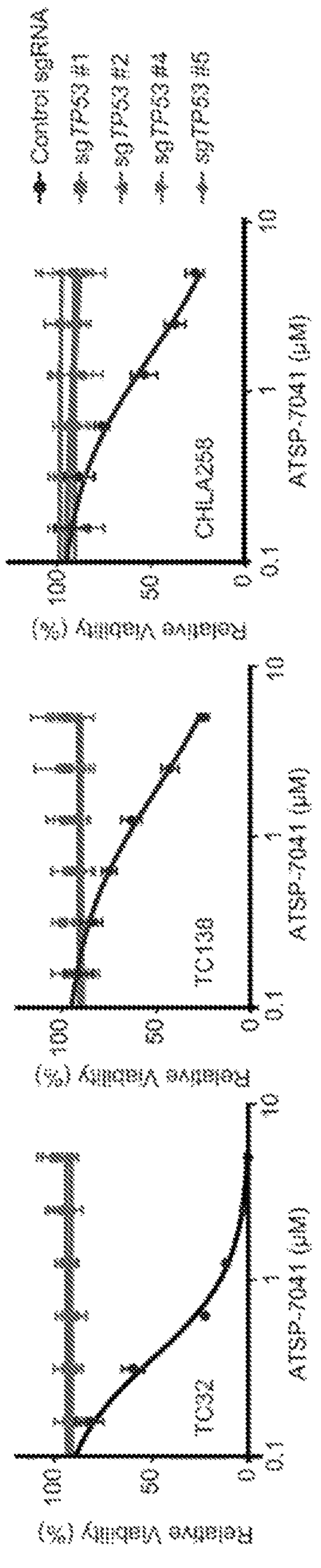
Figure 10C:
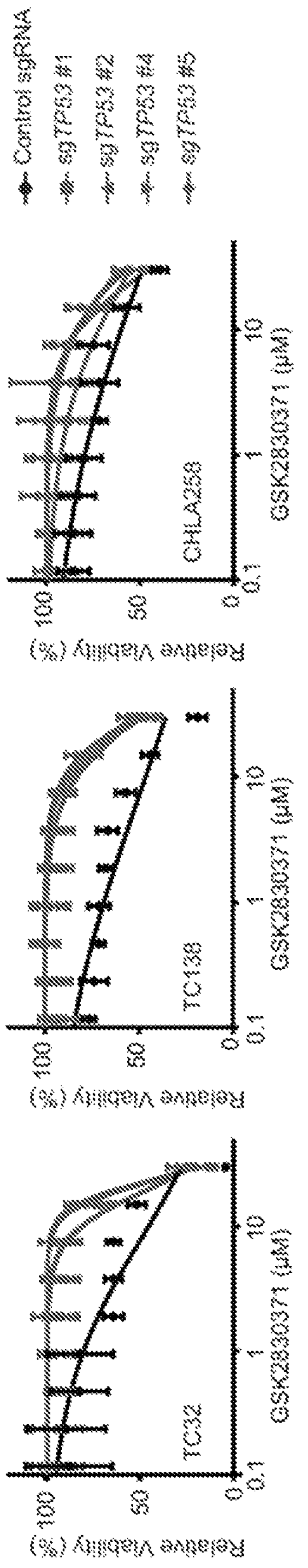

Example 11: Loss of TP53 Rescues the Effects of MDM2, MDM4, PPM1D, and USP7 Inhibition While these data indicate that TP53 wild-type Ewing sarcoma cancer cell lines are more sensitive to loss of MDM2, MDM4, PPM1D, and USP7 than TP53 mutated ones, isogenic cell lines with TP53 loss were generated to more definitively support this hypothesis. Three TP53 wild-type cell lines were infected with CRISPR-Cas9 constructs targeting TP53, and loss of TP53 was demonstrated by diminished increases of p53 protein levels in response to etoposide treatment (FIG. 10A). Treatment of TP53 knockout cells revealed that loss of TP53 fully rescues the cytotoxic effect of ATSP-7041, indicating on-target activity of the drug (FIG. 10B) and the dependency on intact p53 for response to MDM2/MDM4 inhibition. Similarly, the Wip1 inhibitor, GSK2830371, was less effective in TP53 knockout cells than control cells, which indicates on-target activity of GSK2830371 (FIG. 10C).

Figure 10D:
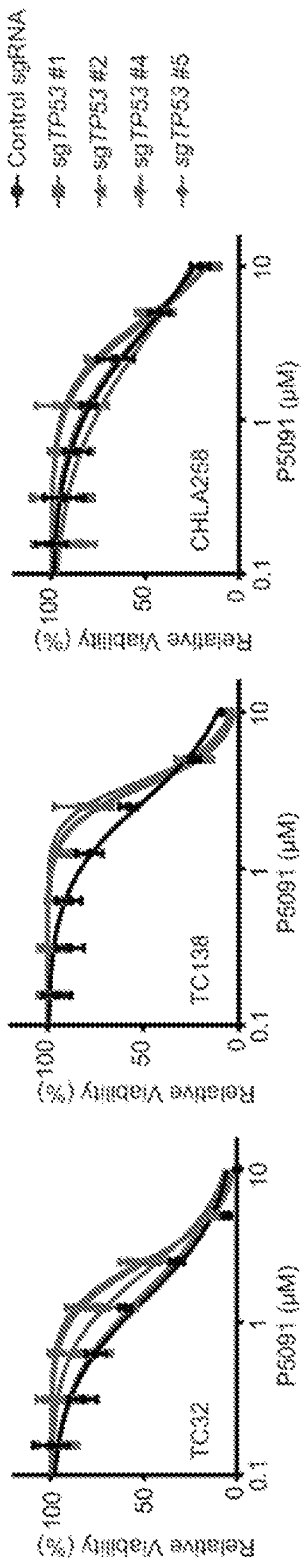
Figures 10E, 10F, 10G, 10H, 10I:
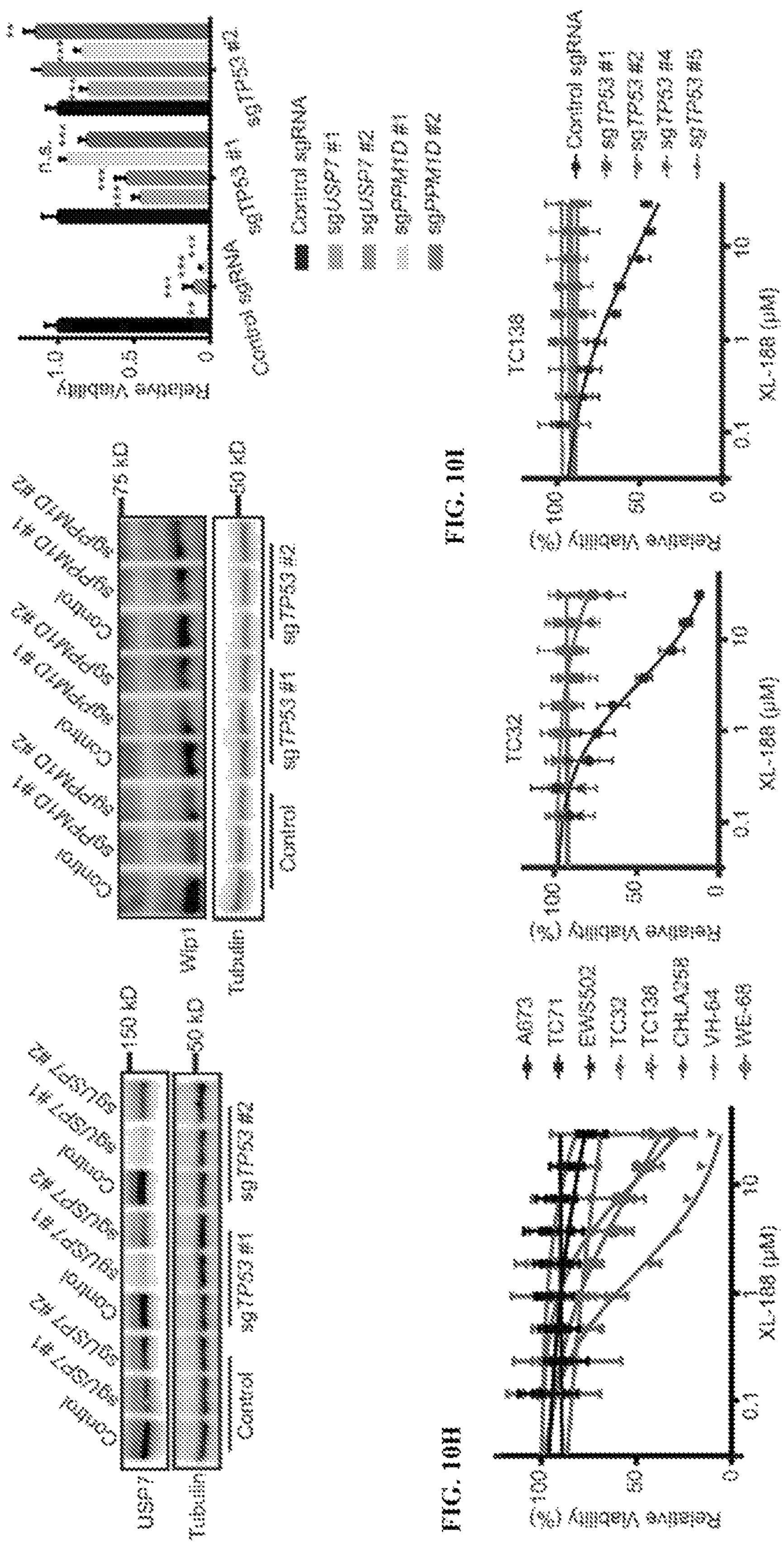

TP53 knockout, however, did not rescue cells from the effects of P5091, indicative of either a p53 independent mechanism or the possibility of an off-target effect(s) of the molecule (FIG. 10D). To address this question, both genetic and chemical analyses were undertaken. First, TP53 knockout cells were infected with CRISPR-Cas9 constructs targeting USP7. The concurrent loss of TP53 effectively rescued the cytotoxic effect of USP7 knockout, as also observed for PPM1D knockout (FIGS. 10E-10G).

Several new USP7 inhibitors have been described in recent publications. Highly selective XL-188 (Lamberto et al. (2017) *Cell Chem. Biol.* 24:1490-1500) was chosen to examine the effect of a more refined USP7 inhibitor on Ewing sarcoma susceptibility. XL-188 reduced viability predominantly in TP53 wild-type Ewing sarcoma cell lines, with an especially robust effect observed in TC32 cells (FIG. 10H). Strikingly, TP53 knockout completely reversed the cytotoxic effect of XL-188 (FIG. 10I), supporting the requirement of functional p53 for the observed response to USP7 inhibition in Ewing sarcoma. Collectively, these data validate the hypothesis that in Ewing sarcoma, MDM2, MDM4, PPM1D, and USP7 dependencies are both mediated by functional p53 and exert their cytotoxic effects, singly and in combination, by reactivating the p53 tumor suppressor pathway.

TP53 is a potent tumor suppressor gene critical to cellular homeostasis (Lane (1992) *Nature* 358:15-16). Loss of p53, either by genetic deletion, mutation, or protein interaction-based suppression, is a key oncogenic event in tumorigenesis (Hanahan and Weinberg (2011) *Cell* 144:646-674). Whereas TP53 is mutated in ~50% of human tumors (Leroy et al. (2014) *Hum. Mutat.* 35:672-688), a large subset of pediatric cancers exhibit a low frequency of TP53 mutations (Malkin et al. (1994) *Cancer Res.* 54:2077-2079; Kato et al. (1996) *Cancer Lett.* 106:75-82; Hendy et al. (2009) *Hematol.* 14:335-340; Hof et al. (2011) *J. Clin. Oncol.* 29:3185-3193; Ognjanovic et al. (2012) *Sarcoma* 2012:492086), implicating negative regulation of p53 through protein interactions as a pathogenic mechanism. Indeed, several recent studies indicate that the TP5 mutation rate in Ewing sarcoma is very low (Brohl et al. (2014) *PLOS Genet.* 10: e1004475; Crompton et al. (2014) *Cancer Discov.* 4:1326-1341; Tirode et al. (2014) *Cancer Discov.* 4:1342-1353). Given the urgent need for new therapeutic approaches to treat Ewing sarcoma, it was sought to identify drug targets in the context of TP53 wild-type disease.

To discover druggable candidates in TP53 wild-type Ewing sarcoma, data of a previously published CRISPR-Cas9 screen (Aguirre et al. (2016) *Cancer Discov.* 6:914-929) was used. The large number of heterogeneous cell lines with diverse molecular features allowed for analysis of disease-specific dependencies or dependencies correlated with specific gene mutations. Here, the data set was analyzed to study the difference between TP53 wild-type and TP53 mutated cell lines. As expected, cell lines with functional p53 proliferate faster upon TP53 knockout (leading to a positive dependency score), while cell lines with mutated TP53 show little to no effect. The data were leveraged from 33 cancer cell lines and MDM2, MDM4, PPM1D, and USP7 were identified as anti-correlated with TP53 dependency scores in Ewing sarcoma and across all cancer cell lines in the dataset. A similar approach was recently used in the context of acute myeloid leukemia (Wang et al. (2017) *Cell* 168:890-903).

Each of the proteins, MDM2, MDM4, Wip1, and USP7, has been implicated in p53 regulation. MDM2 is an E3 ubiquitin ligase that targets p53 for degradation and is induced by p53 in a negative feedback loop. MDM2-deficient murine embryos are nonviable, a phenotype that can be rescued by concurrent TP53 loss (Wade et al. (2013) *Nat. Rev. Cancer.* 13:83-96). In cancer, MDM2 can act as an oncogene whose overexpression promotes malignancy by inhibiting the tumor suppressor function of p53 (Wade et al. (2013) *Nat. Rev. Cancer.* 13:83-96). Indeed, MDM2 was found to be amplified in Ewing sarcoma patient samples, highlighting the importance of the gene in this disease (Ladanyi et al. (1995) *J. Pathol.* 175:211-217). MDM4 is a structural homologue of MDM2 that inhibits p53 by binding and blocking its transactivation domain. Similar to MDM2, MDM4 deficiency is embryonic lethal in mice and can be rescued by TP53 loss (Wade et al. (2013) *Nat. Rev. Cancer.* 13:83-96). The MDM4 gene is located on chromosome 1q, which is found to have copy number gains in a subset of patient Ewing sarcoma samples (Crompton et al. (2014) *Cancer Discov.* 4:1326-1341). One study reported that 50% of Ewing sarcoma tumors contained greater than threefold amplification of MDM4 (Ito et al. (2011) *Clin. Cancer Res.* 17:416-426). PPM1D encodes the phosphatase wild-type p53-induced phosphatase 1 (Wip1) that has several functions as an anti-apoptotic regulator, including dephosphorylation of p53 at serine 15 and deactivation. Wip1 has also been suggested to target ataxia telangiectasia mutated (ATM), ataxia telangiectasia and Rad3 related (ATR), checkpoint kinase 1 (CHK1), and checkpoint kinase 2 (CHK2), as well as MDM2 and MDM4 (Lu et al. (2007) *Cancer Cell* 12:342-354; Zhu and Bulavin (2012) *Prog. Mol. Biol. Transl. Sci.* 106:307-325). High Wip1 levels or PPM1D amplification have been found to correlate with poor prognosis in a variety of cancer types (Saito-Ohara et al. (2003) *Cancer Res.* 63:1876-1883; Castellino et al. (2008) *J. Neurooncol.* 86:245-256; Tan et al. (2009) *Clin. Cancer Res.* 15:2269-2280; Lambros et al. (2010) *Mod. Pathol.* 23:1334-1345; Ma et al. (2014) *Mol. Med. Rep.* 10:191-194; Peng et al. (2014) *Exp. Ther. Med.* 8:430-434; Xu et al. (2016) *Front. Med.* 10:52-60; Zhao et al. (2016) *Oncol. Lett.* 11:2365-2370). USP7 is a deubiquitinating enzyme involved in a variety of cellular processes and is implicated in the regulation of MDM2, MDM4, and p53, as well as several other targets (Nicholson and Kumar (2011) *Cell Biochem. Biophys.* 60:61-68). Prior studies have targeted MDM2 in Ewing sarcoma and found anti-tumor efficacy in vitro and in vivo (Pishas et al. (2011) *Clin. Cancer Res.* 17:494-504; Sonnemann et al. (2011) *Eur. J. Cancer* 47:1432-1441; Carol et al. (2013) *Pediatr. Blood Cancer* 60:633-641). MDM2 inhibition by RG7112 and RG7388 is being investigated in clinical trials with single agents or combination treatments for several malignancies. While early clinical trials testing RG7112 in patients with leukemia (Andreeff et al. (2016) *Clin. Cancer Res.* 22:868-876) and advanced solid tumors (Patnaik et al. (2015) *Cancer Chemother. Pharmacol.* 76:587-595) have shown promise, coexpression of MDM4 can cause resistance (Hu et al. (2006) *J. Biol. Chem.* 281:33030-33035; Patton et al. (2006) *Cancer Res.* 66:3169-3176; Wade et al. (2008) *Cell Cycle* 7:1973-1982; Chapeau et al. (2017) *Proc. Natl. Acad. Sci. U.S.A.* 114:3151-3156). In addition, the observation described herein that alternative negative regulators can coexist to thwart wildtype TP53 signaling indicates that inhibitory strategies beyond selective MDM2 targeting may be required to achieve maximal reactivation of p53. The notion of dual targeting of MDM2 and MDM4 is further supported by dual-knockout experiments of MDM2 and MDM4 presented herein, where it is demonstrated that loss of both MDM2 and MDM4 decreases viability of Ewing sarcoma cells more effectively than loss of either target alone. Of course, these latter experiments must be interpreted within the technical limitations of dual knockout of two strong dependencies, where adequate protein was unable to obtained for confirmation of equivalent knockout across these conditions because of the rapid onset of cell death.

Because MDM4 overexpression has been established as a mechanism of resistance to MDM2 inhibitors, the development of MDM4 inhibitors has been of special interest (Bernal et al. (2010) *Cancer Cell* 18:411-422). Whereas a putative small molecule MDM4 inhibitor, XI-006, has been reported previously (Wang et al. (2011) *Mol. Cancer Ther.* 10:69-79), TP53 mutational status was not a biomarker for XI-006 sensitivity in Ewing sarcoma and breast cancer models (Pishas et al. (2015) *Sci. Rep.* 5:11465), suggesting potential off-target effects. ATSP-7041 is a mechanistically validated stapled peptide inhibitor of both MDM2 and MDM4 (Chang et al. (2013) *Proc. Natl. Acad. Sci. U.S.A.* 110: E3445-E3454; Wachter et al. (2017) *Oncogene* 36:2184-2190). The ATSP-7041 derivative, ALRN-6924, is the first clinical grade stapled peptide to target an intracellular protein interaction in human cancer, prompting its advancement to clinical testing. ALRN-6924 is currently in phase 2 evaluation for TP53 wild-type solid tumors, lymphomas, and peripheral T cell lymphomas in adults (NCT02264613), and in phase 1 evaluation for acute myeloid leukemia as a single agent and for myelodysplastic syndromes in combination with cytarabine (NCT02909972). Thus, stapled p53 peptides offer the unique opportunity to target two of the highest scoring dependencies in TP53 wild-type Ewing sarcoma cell lines simultaneously. It has been demonstrated herein that both MDM2 and MDM4 are strong dependencies in Ewing sarcoma. The potential of ATSP-7041 is shown by its ability to decrease tumor growth in two different Ewing sarcoma models, including a study with an aggressive PDX model, where tumor progression was slowed in all mice, and one out of eight mice achieved complete and sustained remission of disease. Thus, it is believed that a dual MDM2/MDM4 inhibitory strategyis the most effective and rapidly translatable approach to reactivate p53 in patients with Ewing sarcoma.

As single agent therapies rarely cure cancer, it was sought to identify agents that could be used in combination with ATSP-7041. To evaluate the most readily translatable combinations, ATSP-7041 was combined with standard-of-care Ewing sarcoma cytotoxic chemotherapeutics. Additivity or synergy with doxorubicin, etoposide, and vincristine, was observed. The combination of ATSP-7041 with chemotherapeutic agents has been shown herein to induce a stronger p53 response than these agents achieve individually. This provides mechanistic data supporting the addition of ATSP-7041 or other p53 reactivating agents to chemotherapy regimens. The synergistic induction of pro-apoptotic signals in cancer cells might allow for reduced doses of chemotherapy, thereby decreasing adverse effects. The data support this notion and provides preclinical support for additional testing of ATSP-7041 with cytotoxic chemotherapy regimens in TP53 wildtype Ewing sarcoma models.

Furthermore, the combination of ATSP-7041 with the Wip1 inhibitor GSK2830371, and the USP7 inhibitor P5091, strongly synergizes in TP53 wild-type Ewing sarcoma cell lines. These results support the hypothesis that inhibiting several members of the p53 regulatory network could be therapeutically beneficial (Pechackova et al. (2016) *Oncotarget* 7:14458-14475; Sriraman et al. (2016) *Oncotarget* 7:31623-31638). For example, in the case of ATSP-7041 and P0591 treatment, the addition of P0951 suppresses the feedback up-regulation of MDM2. The combination of ATSP-7041 with GSK2830371 increases the level of pSer15 on p53 more than with either molecule alone.

The results described herein also highlight the potential of genetic screening approaches to predict synergistic drug combinations, as MDM2, MDM4, PPM1D, and USP7 were highly correlated dependencies in the analysis of the CRI SPR-Cas9 screen. Since it has been demonstrated herein that inhibitors of these targets have synergistic anti-cancer activity, it is believed that systematic analysis of correlated dependencies in genetic screens can inform new, effective, and potentially rapidly translatable drug combinations. Additionally, these results indicate that analysis of genetic screens for biomarker-specific dependencies (in this case TP53 status) can reveal proteins involved in the homeostasis of that biomarker (in this case MDM2, MDM4, Wip1, and USP7). This method is believed to be applicable to a wide variety of clinical contexts.

USP7 has received increasing attention as a target in cancer and recent publications report new, selective inhibitors of the enzyme (Kategaya et al. (2017) *Nature* 550:534-538; Lamberto et al. (2017) *Cell Chem. Biol.* 24:1490-1500: Turnbull et al. (2017) *Nature* 550:481-486; Gavory et al. (2018) *Nat. Chem. Biol.* 14:118-125). A series of p53-independent molecular targets and functions of USP7 have been proposed in different cancer types, recent examples of which include regulation of RAD18 in DNA damage response in hematologic malignancies Agathanggelou et al. (2017) *Blood* 130:156-166), regulation of wingless-type MMTV integration site (Wnt) family signaling in colorectal cancer (An et al. (2017) *Biochem. Pharmacol.* 131:29-39), Geminin deregulation in breast cancer (Hernandez-Perez et al. (2017) *Oncogene* 36:4802-4809), regulation of the Sonic Hedgehog pathway in medulloblastomas (Zhan et al. (2017) *Biochem. Biophys. Res. Commun.* 484:429-434), and stabilization of MYCN in neuroblastoma (Tavana et al. (2016) *Nat. Med.* 22:1180-1186). It is demonstrated herein that in Ewing sarcoma a key target of USP7 is the p53 pathway, as demonstrated by TP53 knockout experiments and the notable synergism of ATSP-7041 and P5091. The identified role of USP7 in Ewing sarcoma is distinct from that reported in other cancer types and warrants further exploration in this disease. Given the superior selectivity of the small-molecule inhibitor XL-188, as compared with previous generation molecules such as P5091, the clinical translation of these USP7 findings is believed to be achievable.

The results described herein also indicate a p53-dependent mechanism for Wip1 in Ewing sarcoma. While the phosphatase has been shown to target a variety of proteins in different disease contexts, it appears to act through p53 in Ewing sarcoma, as indicated by TP53 knockout experiments and the synergistic elevation of phosphorylated p53 at serine 15 when GSK2830371 was combined with ATSP-7041. This finding advances the understanding of Wip1 activity in Ewing sarcoma and warrants further evaluation of Wip1 as a drug target in this disease.

Overall, CRISPR-Cas9 screening data was used to identify dependencies specific for TP53 wild-type cancers, including Ewing sarcoma, and it was discovered that at least four p53 regulators (e.g., MDM2, MDM4, PPM1D, and USP7) were top hits. Validation of these targets using genetic and pharmacologic approaches confirmed their dependencies in Ewing sarcoma via a p53-dependent mechanism of action. The in vivo activity of ATSP-7041 was further determined in two mouse models of Ewing sarcoma and synergistic combinations for clinical translation were determined, such as by using standard cytotoxic drugs and small molecule inhibitors of Wip1 and USP7.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments encompassed by the present invention described herein. Such equivalents are intended to be encompassed by the following claims.

What is claimed is:

1. A method of treating a subject afflicted with Ewing sarcoma, wherein cancer cells of the Ewing sarcoma encode intact tumor-suppressor 53 (p53), comprising administering to the subject i) a mouse double minute 2 (MDM2) inhibitor, wherein the MDM2 inhibitor is ATSP-7041, and ii) a ubiquitin specific peptidase 7 (USP7) inhibitor or a protein phosphatase, Mg2+/Mn2+-dependent 1D (PPM1D) inhibitor, wherein the USP7 inhibitor is P5091 or the PPM1D inhibitor is GSK2830371, thereby treating the subject afflicted with Ewing sarcoma.

2. The method of claim 1, wherein i) and ii) are administered in a pharmaceutically acceptable formulation.

3. The method of claim 1, wherein the p53 is wild-type p53.

4. The method of claim 1, wherein the Ewing sarcoma is metastatic and/or relapsed.

5. The method of claim 1, wherein the subject is a mammal.

6. The method of claim 5, wherein the mammal is an animal model of Ewing sarcoma.

7. The method of claim 5, wherein the mammal is a human.

8. The method of claim 1, further comprising administering one or more additional anti-cancer agents.

9. The method of claim 8, wherein the additional anti-cancer agent comprises a chemotherapeutic agent.

10. A method of inhibiting hyperproliferative growth of Ewing sarcoma cancer cells, wherein the Ewing sarcoma cancer cells encode intact tumor-suppressor 53 (p53), comprising contacting the Ewing sarcoma cancer cells with i) a mouse double minute 2 (MDM2) inhibitor, wherein the MDM2 inhibitor is ATSP-7041, and ii) a ubiquitin specific peptidase 7 (USP7) inhibitor or a protein phosphatase, Mg2+/Mn2+-dependent 1D (PPM1D) inhibitor, wherein the USP7 inhibitor is P5091 or the PPM1D inhibitor is GSK2830371, thereby inhibiting hyperproliferative growth of the Ewing sarcoma cancer cells.

11. The method of claim 10, wherein i) and ii) are administered in a pharmaceutically acceptable formulation.

12. The method of claim 10, wherein the p53 is wild-type p53.

13. The method of claim 10, wherein the Ewing sarcoma cells are from a metastatic and/or relapsed Ewing sarcoma tumor.

14. The method of claim 10, wherein the Ewing sarcoma cells are from a mammal.

15. The method of claim 14, wherein the mammal is an animal model of Ewing sarcoma.

16. The method of claim 14, wherein the mammal is a human.

17. The method of claim 10, further comprising contacting the Ewing sarcoma cells with one or more additional anti-cancer agents.

18. The method of claim 17, wherein the additional anti-cancer agent comprises a chemotherapeutic agent.

* * * * *